US011098040B2

(12) United States Patent
Jiang et al.

(10) Patent No.: US 11,098,040 B2
(45) Date of Patent: Aug. 24, 2021

(54) COMPOUNDS AND METHODS OF USE

(71) Applicant: Ferro Therapeutics, Inc., Palo Alto, CA (US)

(72) Inventors: Chun Jiang, Hillsborough, CA (US); Ruihong Chen, Burlingame, CA (US); Anjali Pandey, Fremont, CA (US); Biswajit Kalita, Bangalore (IN); Athisayamani Jeyaraj Duraiswamy, Bangalore (IN)

(73) Assignee: Ferro Therapeutics, Inc., Palo Alto, CA (US)

( * ) Notice: Subject to any disclaimer, the term of this patent is extended or adjusted under 35 U.S.C. 154(b) by 0 days.

(21) Appl. No.: 16/287,805

(22) Filed: Feb. 27, 2019

(65) Prior Publication Data

US 2019/0263802 A1 Aug. 29, 2019

Related U.S. Application Data

(60) Provisional application No. 62/636,614, filed on Feb. 28, 2018.

(51) Int. Cl.

| | |
|---|---|
| ***C07D 471/04*** | (2006.01) |
| ***A61P 35/00*** | (2006.01) |
| ***C07D 217/04*** | (2006.01) |
| ***C07D 217/26*** | (2006.01) |
| ***C07D 495/04*** | (2006.01) |
| ***C07D 217/14*** | (2006.01) |
| *A61K 47/40* | (2006.01) |
| *A61K 45/06* | (2006.01) |

(52) U.S. Cl.

CPC ............ *C07D 471/04* (2013.01); *A61P 35/00* (2018.01); *C07D 217/04* (2013.01); *C07D 217/14* (2013.01); *C07D 217/26* (2013.01); *C07D 495/04* (2013.01); *A61K 45/06* (2013.01); *A61K 47/40* (2013.01)

(58) Field of Classification Search

CPC ............................... C07D 471/04; A61P 35/00

See application file for complete search history.

(56) References Cited

U.S. PATENT DOCUMENTS

| | | | | |
|---|---|---|---|---|
| 9,695,133 | B2 * | 7/2017 | Stockwell ............ | C07D 403/06 |
| 10,519,148 | B2 | 12/2019 | Guan et al. | |
| 2003/0225092 | A1 | 12/2003 | Orme et al. | |
| 2010/0081654 | A1 | 4/2010 | Stockwell et al. | |
| 2016/0332974 | A1 | 11/2016 | Stockwell et al. | |
| 2020/0138829 | A1 | 5/2020 | Chen et al. | |

FOREIGN PATENT DOCUMENTS

| | | | |
|---|---|---|---|
| CN | 109796424 | A | 5/2019 |
| FR | 2916200 | A1 | 11/2008 |
| WO | WO 97/03985 | A1 | 2/1997 |
| WO | WO 01/94347 | A1 | 12/2001 |
| WO | WO 02/28858 | A2 | 4/2002 |
| WO | WO 02/38563 | A2 | 5/2002 |
| WO | WO 2007/016361 | A2 | 2/2007 |
| WO | WO 2008/044144 | A2 | 4/2008 |
| WO | WO 2008/103470 | A2 | 8/2008 |
| WO | WO 2011/063223 | A1 | 5/2011 |
| WO | WO 2014/011973 | A2 | 1/2014 |
| WO | WO 2016/196201 | A1 | 1/2014 |
| WO | WO 2015/051149 | A1 | 4/2015 |
| WO | WO 2016/099452 | A1 | 6/2016 |
| WO | WO 2017/080338 | A1 | 5/2017 |
| WO | WO 2017/120455 | A1 | 7/2017 |
| WO | WO 2018/118711 | A1 | 7/2017 |
| WO | WO 2017/136688 | A1 | 8/2017 |
| WO | WO 2018/218087 | A1 | 11/2018 |
| WO | WO 2019/016772 | A2 | 1/2019 |
| WO | WO 2019/106434 | A1 | 6/2019 |
| WO | WO 2019/113004 | A1 | 6/2019 |
| WO | WO 2020/176757 | A1 | 9/2020 |

OTHER PUBLICATIONS

Beghyn et al.: "Drug-to-Genome-to-Drug, Step 2: Reversing Selectivity in a Series of Antiplasmodial Compounds", Journal of Medicinal Chemistry, vol. 55 No. 3, Jan. 24, 2012 (Jan. 24, 2012), pp. 1274-1286, XP055576643.

Chauhan et al.; "A Diversity Oriented Synthesis of Natural Product Inspired Molecular Libraries" Organic a& Biomolecular Chemistry, vol. 15, No. 43, Jan. 1, 2017, pp. 9108-9120, XP055601193.

Chen et al.: "Diastereoselective Synthesis of Bridged Polycyclic Alkaloids via Tandem Acylation/Intramolecular Diels-Alder Reaction", Journal Of Organic Chemistry, vol. 78, No. 19, Sep. 5, 2013, pp. 9738-9747, XP055601468.

Database Caplus [Online] Chemical Abstracts Service, Columbus, Ohio, US; 1987, Misztal, Stanislaw; Boksa, Jan; Chojnacka-Wojcik, Ewa; Tatarczynska, Ewa; Lewandowska, Anna: "Synthesis and pharmacological properties of some 2-substituted 1-(3-pyridyl)-1,2,3,4-tetrahydro-beta-carb olines", XP002792598. Database Accession No. 1987:568626. Compound RN: 110785-17-6 and 110785-18-7.

Database Caplus [Online] Chemical Abstracts Service, Columbus, Ohio, US; 1989, Misztal, Stanislaw; Boska, Jan; Chojnacka-Wojcik, Ewa; Tatarczynska, Ewa; Russeva, S.: "Synthesis and pharmacological properties of some 2-(3-aminopropionyi)- and 2-(3-aminopropyl)-1-(3-pyridy1)-1,2,3,4-te trahydro-beta-carbolines", XP002792597. Database Accession No. 1989:107998. Compound RN: 119464-22-1.

(Continued)

*Primary Examiner* — Golam M Shameem

(74) *Attorney, Agent, or Firm* — Sheppard Mullin Richter & Hampton LLP

(57) ABSTRACT

This present disclosure relates to compounds with ferroptosis inducing activity, a method of treating a subject with cancer with the compounds, and combination treatments with a second therapeutic agent.

26 Claims, No Drawings

(56) References Cited

OTHER PUBLICATIONS

Database Caplus [Online] Chemical Abstracts Service, Columbus, Ohio, US; 2000, You, Ye Cheng et al.; "Application of DDQ in the synthesis of .beta.-carboline alkaloid", XP002790284. Database Accession No. 2000:3379953. Compound RN: 284037-15-6.
Database Caplus [Online] Chmical Abstracts Service, Columbus, OH, US; Dec. 29, 1991 Misztal, Stanislaw; Dukat, Malgorzata; Mokrosz, Jerzy L.: "Structure and spectral properties of beta-carbolines. Part 3. Synthesis and stereochemistry of 1,2,3,4,6,7,9,10,15b,15c-decahydropyrido [1', 2':1', 2']pyrazino [4', 3':1]pyrido [3,4-b] indoles", XP002792596. Database Accession No. 1991:62055. Compoubd RB: 131652-89-6.
Database Registry [Online] Chemical Abstracts Service, Columbus, Ohio, US; May 10, 2001, XP002792592. Database Accession No. 335118-40-6.
Database Registry [Online] Chemical Abstracts Service, Columbus, Ohio, US; May 10, 2001, XP002792593. Database Accession No. 335118-29-1.
Database Registry [Online] Chemical Abstracts Service, Columbus, Ohio, US; May 10, 2001, XP002792594. Database Accession No. 335118-04-2.
Database Registry [Online] Chemical Abstracts Service, Columbus, Ohio, US; May 10, 2001. XP002792595. Database Accession No. 335117-90-3.
Database Registry [Online] Chemical. Abstracts Service, Columbus, Ohio, US; May 22, 2001, XP002792599. Database Accession No. 337315-27-2.
Database Registry [Online] Chemical Abstracts Service, Columbus, Ohio, US; Sep. 3, 2008, XP002792591. Database Accession No. 1045914-84-8.
Daugan et al.: "The Discovery of Tadalafil: A Novel and Highly Selective PDE5 Inhibitor. 2: 2,3,6,7,12,12a-hexahydropyrazino[1'2':1,61pyrido[3,4-b]indole-1,4-dione Analogues", Journal of American Chemical Society, US, vol, 46, No. 21, Jan. 1, 2003, pp. 4533-4542, XP008052656, ISSN: 0022-2623.
Desai et al.: "How hydrogen bonds impact P-glycoprotein transport and permeability", Bioorganic & Medicinal Chemistry Letters, vol. 22, issue 21, Nov. 1, 2012, pp. 6540-6548.
Eaton et al.: "Targeting a Therapy-Resistant Cancer Cell State Using Masked Electrophiles as GPX4 Inhibitors", Jul. 24, 2018, https://www.biorxiv.org/content/10.1101/376764v3.
Eaton, et al. Selective covalent targeting of GPX4 using masked nitrile-oxide electrophiles. Natural Chemical Biology. May 2020; 16:497-506.
El-Gamil et al.: "Design of Novel [beta]-Carboline Derivatives with Pendant 5-Bromothienyl and Their Evaluation as Phosphodiesterase-5 Inhibitors", Archiv Der Pharmazie, vol. 346, No. 1, Jan. 1, 2013, pp. 23-33, XP055601459.
Hangauer et al,: "Drug-tolerant persister cancer cells are vulnerable to GPX4 inhibition", Nature International Journal of Science, vol. 551, Nov. 9, 2017, pp. 247-250.
International Search Report and Written Opinion dated Jul. 17, 2019 for PCT/US2019/019854. 34 pages.
Jiang et al: "Synthesis and Sar of Tetracycylic Pyrroloquinolones As Phosphodiesterase 5 Inhibitors", Bioorganic & Medicinal Chemi, Pergamon, GB, vol. 12, No. 6, Mar. 15, 2004 (Mar. 15, 2004), pp. 1505-1515, XP008105689.
Lemaire et al., Alternative Synthesis of the PDE5 Inhibitor RWJ387273 (R290629), Synlett, vol. 20007, No. 5, Mar. 1, 2007, pp. 0709-0712, XP055577124.
Lonsdale et. al.: "Expanding the Armory: Predicating and Tuning Covalent Warhead Reactivity", Journal of Chemical Information and Modeling, Nov. 13, 2017. Retrieved from the Internet: URL: http://pubs.acs.org, retrieved on Nov. 15, 2017.
Misztal et al.: "Structure and Spectral Properties of p-Carbolines. Part 4. Synthesis of the New Ring System", J.Chem. Soc. Perkin Trans, Jan. 1, 1991, XP055601572.
Ooko et al.: [Abstract] "Artemisinin derivatives induce iron-dependent cell death (ferroptosis) in tumor cells", Internation Journal of Phytotherapy & Phytopharmacology, vol. 22, Issue 11, Oct. 15, 2015, pp. 1045-1054.
Roh et al.: [Abstract] "Induction of ferroptotic cell death for overcoming cisplatin resistance of head and neck cancer",Cancer Letters, vol. 381, Issue1 , pp. 96-103,Oct. 10, 2016.
St. Jean Jr. et al.: "Mitigating Heterocycle Metabolism in Drug Discovery", Journal of Medicinal Chemistry, Apr. 25, 2012: Retrieved from the Internet; URL: https://pubs.acs.org/sharingguidelines, retrieved Oct. 15, 2018.
Sugita, et al. Novel Phorbol Analogs Which Bind to Protein Kinase C (PKC) without Activation. Chem Pharm. Bull. 1996; 44(2):463-465.
Viswanathan et al.: Dependency of a therapy-resistant state of cancer cells on a lipid peroxidase pathway, Nature International Journal of Science, vol. 547. Jul. 27, 2017, pp. 453-457.
Wada, et al. Dramatic Switching of Protein Kinase C Agonist/Antagonist Activity by Modifying the 12-Ester Side Chain of Phorbol Esters. J. Am. Chem, Soc. 2002, 124, 10658-10659.
Yang et al.: "Regulation of Ferroptotic Cancer Cell Death by GPX4", Cell, vol. 156, Jan. 16, 2014, pp. 317-331.
Zheng et al.: "S1 Supporting Information Discovery of Furyl/Thienyl [beta]-Carboline Derivatives as Potent and Selective PDES Inhibitors with Excellent Vasorelaxant Effect" , Sep. 15, 2018 (Sep. 15, 2018), pp. S1-S170, XP055601535, Retrieved from the Internet: URL: https://ars.els-cdn.com/content/image/1-s2.0-S0223523418308006-mmcl.pdf, retrieved on Jul. 2, 2019.
Zheng et al: "Discovery of furyl/thienyl [beta]-carboline derivatives as potent and selective PDE5 inhibitors with excellent vasorelaxant effect" , European Journal Of Medicinal Chemistry, vol. 158, Sep. 15, 2018; pp. 767-788, XP055601520.

* cited by examiner

COMPOUNDS AND METHODS OF USE

CROSS REFERENCE TO RELATED APPLICATIONS

This application claims benefit to U.S. Provisional Application No. 62/636,614, filed Feb. 28, 2018, the entirety of which is hereby incorporated by reference.

BACKGROUND

Radiation and drug therapy represent two of the most common types of cancer treatments. Some types of radiation therapy uses focused, high-energy photon beams to destroy cancer cells. Photon radiation include X-rays and gamma rays. Radiation therapy can also employ particle radiation, which includes electron, proton, and neutron beams. Radiation can be used as a curative therapy for a number of cancer types, or used in combination with other treatments, for example prior to surgery or chemotherapy to reduce initial tumor burden and to destroy any remaining cancer cell after such therapy. Radiation therapy works by damaging the DNA of cancer cells, either by direct or indirect ionization of the atoms that make up the DNA chain. Indirect ionization occurs through the generation of reactive oxygen species (ROS), particularly hydroxyl radicals, which then damage the DNA. However, the mechanisms by which DNA damage ultimately leads to cell death appears to be complex, acting through a multitude of cellular signaling pathways that regulate different cell death processes. These processes include apoptosis, mitotic catastrophe, necrosis, senescence, and autophagy. Various genes and intracellular pathways have been reported to be involved in the different types of radiation induced cell death. Apoptosis has been associated with cellular components ATM, p53, Bax, Cytochrome c and Caspases, while mitotic catastrophe appears to implicate cellular components p53, Caspases, and Cytochrome c. Necrosis has been associated with TNF (alpha), PAR, JNK and Caspases while senescence is associated with, among others, cellular components MYC, INK4A, ARF, p53 and p21. With autophagy, the cellular molecules PI3K, Akt and mTOR may be to be involved.

Chemotherapy can target different components of the cellular machinery and can have synergistic therapeutic effects when used in combination with radiation therapy. Chemotherapy can be nonspecific, hormonal or targeted. Nonspecific chemotherapeutic agents are generally cytotoxic agents that typically affect cell division, and include, among others, classes of agents such as alkylating agents, antimetabolites, anti-microtubule agents, topoisomerase inhibitors, cytotoxic antibiotics, and platinum-based coordination complexes. Hormone-based cancer therapy is used to treat hormone sensitive cancers (e.g., prostate cancer and breast cancer) by targeting the endocrine system using specific hormones or drugs that inhibit the production or activity of such hormones (hormone antagonists). Hormonal chemotherapeutic agents include, among others, aromatase inhibitors, GnRH analogues, selective estrogen receptor modulators, antiandrogens, estrogens, and progestogens. Targeted chemotherapy attempts to overcome the non-discriminate killing of noncancerous cells by traditional cytotoxic chemotherapeutic agents by acting on specific cellular targets. Types of targeted chemotherapeutic agents include antiangiogenesis agents, apoptosis inducing agents, differentiation agents, and signal transduction inhibitors. Some forms of targeted therapy use traditional non-specific cytotoxic agents but formulated for specific delivery to cancer cells or delivered in such a way to localize the drug to the tumor site. However, most chemotherapy, whether non-specific or targeted, ultimately involve cell death processes that are also implicated in radiation induced killing of cancer cells. Desirable are other chemotherapeutic agents that, either indirectly or directly, induce killing of cancer cells.

SUMMARY

The present disclosure relates to compounds having ferroptosis inducing activity, and methods of using the compounds for treatment of cancer. In certain embodiments, provided herein is a compound of formula (I):

(I)

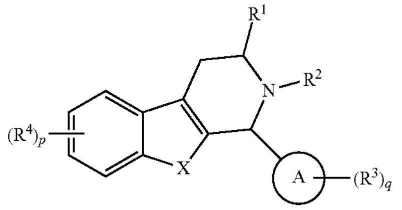

or a tautomer, stereoisomer, mixture of stereoisomers, isotopically enriched analog, or pharmaceutically acceptable salt thereof, wherein:

ring A is $C_4$-$C_{10}$cycloalkyl, heterocyclyl, aryl, or heteroaryl;

X is $NR^5$, O or S;

p is 0, 1, 2 or 3;

q is 0, 1, 2 or 3;

$R^1$ is $C_1$-$C_6$alkyl, $C_2$-$C_6$alkenyl, $C_2$-$C_6$alkynyl, $C_1$-$C_6$haloalkyl, $C_3$-$C_{10}$cycloalkyl, —CN, —OH, —$C(O)OR^6$, —$C(O)N(R^7)_2$, —$OC(O)R^6$, —$S(O)_2R^8$, —$S(O)_2N(R^7)_2$, —$S(O)N(R^7)_2$, —$S(O)R^8$, —$NH_2$, —$NHR^8$, —$N(R^8)_2$, —$NO_2$, —$OR^8$, —$C_1$-$C_6$alkyl-OH, —$C_1$-$C_6$alkyl-OR, or —$Si(R^{15})_3$;

$R^2$ is —$C(O)R^9$;

each $R^3$ is independently halo, —CN, —OH, —OR, —$NH_2$, —$NHR^8$, —$N(R^8)_2$, —$S(O)_2R^8$, —$S(O)R^8$, —$S(O)_2N(R^7)_2$, —$S(O)N(R^7)_2$, —$NO_2$, —$Si(R^{12})_3$, —$SF_5$, —$C(O)OR^6$, —$C(O)N(R^7)_2$, —$NR^{12}C(O)R^8$, —$NR^{12}C(O)OR^8$, —$OC(O)N(R^7)_2$, —$OC(O)R^8$, —$C(O)R^6$, —$OC(O)CHR^8N(R^{12})_2$, $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_{10}$cycloalkyl, —$C_2$-$C_6$alkenyl$C_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, $C_1$-$C_6$alkylheteroaryl, or —$C_2$-$C_6$alkenylheteroaryl; wherein each $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_{10}$cycloalkyl, —$C_2$-$C_6$alkenyl$C_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, $C_1$-$C_6$alkylheteroaryl, or —$C_2$-$C_6$alkenylheteroaryl of $R^3$ is independently optionally substituted with one to three $R^{10}$;

each $R^4$ is independently halo, —CN, —OH, —OR, —$NH_2$, —$NHR^8$, —$N(R^8)_2$, —$S(O)_2R^8$, —$S(O)R^8$, —$S(O)_2N(R^7)_2$, —$S(O)N(R^7)_2$, —$NO_2$, —$Si(R^{15})_3$, —$C(O)OR^6$, —$C(O)N(R^7)_2$, —$NR^{12}C(O)R^8$, —$OC(O)R^8$, —$C(O)R^6$, —$NR^{12}C(O)OR^8$, —$OC(O)N(R^7)_2$, —$OC(O)CHR^8N(R^{12})_2$, $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_{10}$cycloalkyl, —$C_2$-$C_6$alkenyl$C_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, $C_1$-$C_6$alkylheteroaryl, or —$C_2$-$C_6$alkenylheteroaryl; wherein each $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_{10}$cycloalkyl, —$C_2$-$C_6$alkenyl$C_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, $C_1$-$C_6$alkylheteroaryl, or —$C_2$-$C_6$alkenylheteroaryl of $R^4$ is optionally independently optionally substituted with one to three $R^{10}$;

$R^5$ is hydrogen or $C_1$-$C_6$alkyl;

each $R^6$ is independently hydrogen, $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_{10}$cycloalkyl, —$C_2$-$C_6$alkenyl$C_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, $C_1$-$C_6$alkylheteroaryl, or —$C_2$-$C_6$alkenylheteroaryl; wherein each $R^6$ is independently further substituted with one to three $R^{11}$;

each $R^7$ is independently hydrogen, $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_6$cycloalkyl, —$C_2$-$C_6$alkenyl$C_3$-$C_6$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, —$C_1$-$C_6$alkylheteroaryl, —$C_2$-$C_6$alkenylheteroaryl, or two $R^7$ together with the nitrogen atom to which they are attached, form a 4 to 7 membered heterocyclyl; wherein each $R^7$ or ring formed thereby is independently further substituted with one to three $R^{11}$;

each $R^8$ is independently $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_{10}$cycloalkyl, —$C_2$-$C_6$alkenyl$C_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, —$C_1$-$C_6$alkylheteroaryl, or —$C_2$-$C_6$alkenylheteroaryl; wherein each $R^8$ is independently further substituted with one to three $R^{11}$;

$R^9$ is —$C_1$-$C_2$haloalkyl, —$C_2$-$C_3$alkenyl, —$C_2$-$C_3$haloalkenyl, $C_2$alkynyl, or —$CH_2OS(O)_2$-phenyl, wherein the $C_1$-$C_2$alkylhalo and —$C_2$-$C_3$alkenylhalo are optionally substituted with one or two —$CH_3$, and the $C_2$alkynyl and phenyl are optionally substituted with one —$CH_3$;

each $R^{10}$ is independently halo, —CN, —$OR^{12}$, —$NO_2$, —$N(R^{12})_2$, —$S(O)R^{13}$, —$S(O)_2R^{13}$, —$S(O)N(R^{12})_2$, —$S(O)_2N(R^{12})_2$, —$Si(R^{12})_3$, —$C(O)R^{12}$, —$C(O)OR^{12}$, —$C(O)N(R^{12})_2$, —$NR^{12}C(O)R^{12}$, —$OC(O)R^{12}$, —$OC(O)OR^{12}$, —$OC(O)N(R^{12})_2$, —$NR^{12}C(O)OR^{12}$, —$OC(O)CHR^{12}N(R^{12})_2$, $C_1$-$C_6$alkyl, $C_1$-$C_6$haloalkyl, $C_2$-$C_6$alkenyl, $C_2$-$C_6$alkynyl, $C_3$-$C_{10}$cycloalkyl, heterocyclyl, aryl, or heteroaryl, wherein each $C_1$-$C_6$alkyl, $C_1$-$C_6$haloalkyl, $C_2$-$C_6$alkenyl, $C_2$-$C_6$alkynyl, $C_3$-$C_{10}$cycloalkyl, heterocyclyl, aryl, or heteroaryl of $R^{10}$ is optionally independently substituted with one to three $R^{11}$;

each $R^{11}$ is independently halo, —CN, —$OR^{12}$, —$NO_2$, —$N(R^{12})_2$, —$S(O)R^{13}$, —$S(O)_2R^{13}$, —$S(O)N(R^{12})_2$, —$S(O)_2N(R^{12})_2$, —$Si(R^{12})_3$, —$C(O)R^{12}$, —$C(O)OR^{12}$, —$C(O)N(R^{12})_2$, —$NR^{12}C(O)R^{12}$, —$OC(O)R^{12}$, —$OC(O)OR^{12}$, —$OC(O)N(R^{12})_2$, —$NR^{12}C(O)OR^{12}$, —$OC(O)CHR^{12}N(R^{12})_2$, $C_1$-$C_6$alkyl, $C_1$-$C_6$haloalkyl, $C_2$-$C_6$alkenyl, $C_2$-$C_6$alkynyl, $C_3$-$C_{10}$cycloalkyl, heterocyclyl, aryl, or heteroaryl;

each $R^{12}$ is independently hydrogen, $C_1$-$C_6$alkyl or $C_3$-$C_{10}$cycloalkyl;

each $R^{13}$ is independently $C_1$-$C_6$alkyl or $C_3$-$C_{10}$cycloalkyl, and each $R^{15}$ is independently $C_1$-$C_6$alkyl, $C_2$-$C_6$alkenyl, aryl, heteroaryl, —$C_1$-$C_6$alkylaryl, —$C_2$-$C_6$alkenylaryl, —$C_1$-$C_6$alkylheteroaryl, and —$C_2$-$C_6$alkenylheteroaryl.

In certain embodiments, the compounds are used in a method of inhibiting GPX4 in a cell, comprising contacting a cell with an effective amount of the compound described herein to inhibit GPX4 in the cell. In certain embodiments, the cell is a cancer cell.

In certain embodiments, the compounds are used in a method of treating cancer in a subject, comprising administering to a subject having cancer a therapeutically effective amount of the ferroptosis inducing compounds. Various cancers for treatment with the compounds include, but aren't limited to, adrenocortical cancer, anal cancer, biliary cancer, bladder cancer, bone cancer, gliomas, astrocytoma, neuroblastoma, breast cancer, cervical cancer, colon cancer, endometrial cancer, esophageal cancer, head and neck cancer, intestinal cancer, liver cancer, lung cancer, oral cancer, ovarian cancer, pancreatic cancer, renal cancer, prostate cancer, salivary gland cancer, skin cancer, stomach cancer, testicular cancer, throat cancer, thyroid cancer, uterine cancer, vaginal cancer, sarcoma, and soft tissue carcinomas. In certain embodiments, the compound is used to treat pancreatic cancer.

In certain embodiments, provided is a method for treating a cancer in a patient in need thereof, comprising administering an effective amount of a compound or composition provided herein. In certain embodiments, the cancer is renal cell carcinoma (RCC), pancreatic cancer, lung cancer, breast cancer, or prostate cancer. In certain embodiments, provided is a method for treating renal cell carcinoma (RCC) in a patient in need thereof, comprising administering an effective amount of a compound or composition provided herein. In certain embodiments, provided is a method for treating pancreatic cancer in a patient in need thereof, comprising administering an effective amount of a compound or composition provided herein. In certain embodiments, provided is a method for treating lung cancer in a patient in need thereof, comprising administering an effective amount of a compound or composition provided herein.

In certain embodiments, provided is a method for treating breast cancer in a patient in need thereof, comprising administering an effective amount of a compound or composition provided herein. In certain embodiments, provided is a method for treating prostate cancer in a patient in need thereof, comprising administering an effective amount of a compound or composition provided herein.

In certain embodiments, provided is a method for treating a malignant solid tumor in a patient in need thereof, comprising administering an effective amount of a compound or composition provided herein to the patient. In certain embodiments, the malignant solid tumor is a sarcoma, carcinoma, or lymphoma.

In certain embodiments, the cancer for treatment is a hematologic cancer, for example, acute lymphoblastic leukemia (ALL), acute myeloid leukemia (AML), lymphoma (e.g., Hodgkin's lymphoma, Non-Hodgkin's lymphoma, Burkitt's lymphoma), chronic lymphocytic leukemia (CLL), chronic myelogenous leukemia (CML), Hairy Cell chronic myelogenous leukemia (CML), and multiple myeloma.

In certain embodiments, the compounds herein are used to treat cancers resistant to or previously treated with a chemotherapeutic agent or ionizing radiation. In certain embodiments, the cancer for treatment determined to have, or identified as having, resistance to a chemotherapeutic agent or ionizing radiation. In certain embodiments, the cancer selected for treatment with the ferroptosis inducer is identified as being previously treated with a chemotherapeutic agent or ionizing radiation. In certain embodiments, the cancer selected for treatment has been previously treated with or is resistant to a chemotherapeutic agent selected from alkylating agents, antibiotic agents, antimetabolic agents (e.g., folate antagonists, purine analogs, pyrimidine analogs, etc.), topoisomerase inhibiting agents, anti-microtubule agents, aromatase inhibitors, antiangiogenic agents, differentiation inducing agents, cell growth arrest inducing agents, apoptosis inducing agents, cytotoxic agents, biologic agents (e.g., monoclonal antibodies), kinase inhibitors and inhibitors of growth factors and their receptors. In certain embodiments, the cancer selected for treatment has been previously treated with or is resistant to ionizing radiation.

In certain embodiments, the cancer selected for treatment with the compounds are determined to have or identified as having an activating or oncogenic RAS activity. In certain embodiments, the activating or oncogenic RAS activity is an activating or oncogenic RAS mutations. In certain embodiments, the activating or oncogenic RAS activity is an activating or activating K-RAS activity, particularly an activating or oncogenic K-RAS mutation. In certain embodiments, the activating or oncogenic RAS activity is an activating or activating N-RAS activity, particularly an activating or oncogenic N-RAS mutation. In certain embodiments, the activating or oncogenic RAS activity is an activating or activating H-RAS activity, particularly an activating or oncogenic H-RAS mutation.

In certain embodiments, the compounds are used in combination with a second therapeutic agent, such as platinating agents, alkylating agents, antibiotic agents, antimetabolic agents (e.g., folate antagonists, purine analogs, pyrimidine analogs, etc.), topoisomerase I inhibiting agents, topoisomerase II inhibiting agents, anti-microtubule agents, aromatase inhibitors, antiangiogenic agents, differentiation inducing agents, cell growth arrest inducing agents, apoptosis inducing agents, cytotoxic agents, agents affecting cell bioenergetics, biologic agents, e.g., monoclonal antibodies, kinase inhibitors and inhibitors of growth factors and their receptors.

In certain embodiments of the combination treatment, the second therapeutic agent can be administered prior to, concurrently with, or subsequent to the administration of the compounds herein. In certain embodiments, the compound and the second therapeutic agent can be provided as a single composition where appropriate for ease of administration and enhance compliance with the combination treatment regimen. In certain embodiments, the use of the compound in combination with a second therapeutic agent is used to treat a cancer resistant to or previously treated with a chemotherapeutic agent or ionizing radiation, as further described herein.

DETAILED DESCRIPTION

As used in this specification and the appended claims, the singular forms "a," "an" and "the" include plural referents unless the context clearly indicates otherwise. Thus, for example, reference to "a protein" includes more than one protein, and reference to "a compound" refers to more than one compound.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

It is to be understood that both the foregoing general description, including the drawings, and the following detailed description are exemplary and explanatory only and are not restrictive of this disclosure. The section headings used herein are for organizational purposes only and not to be construed as limiting the subject matter described.

1. Definitions

In reference to the present disclosure, the technical and scientific terms used in the descriptions herein will have the meanings commonly understood by one of ordinary skill in the art, unless specifically defined otherwise. Accordingly, the following terms are intended to have the meanings as described below.

"Ferroptosis" refers to a form of cell death understood in the art as involving generation of reactive oxygen species mediated by iron, and characterized by, in part, lipid peroxidation.

"Ferroptosis inducer" or "ferroptosis activator" refers to an agent which induces, promotes or activates ferroptosis.

"K-RAS" refers to Kirsten rat sarcoma viral oncogene homolog, a small GTPase and a member of the RAS family of proteins involved in signal transduction. Exemplary human K-RAS nucleic acid and protein sequences are provided in GenBank Nos. M54968.1 and AAB414942.1, respectively. "K-RAS" as used herein encompasses variants, including orthologs and interspecies homologs, of the human K-RAS protein.

"Mutant K-RAS polypeptide," "mutant K-RAS protein" and "mutant K-RAS" are used interchangeably and refer to a K-RAS polypeptide comprising at least one K-RAS mutation as compared to the corresponding wild-type K-RAS sequence. Certain exemplary mutant K-RAS polypeptides include, but are not limited to, allelic variants, splice variants, derivative variants, substitution variants, deletion variants, insertion variants, and fusion polypeptides.

"N-RAS" refers to Neuroblastoma RAS Viral (V-RAS) oncogene homolog, a small GTPase and a member of the RAS family of proteins involved in signal transduction. Exemplary human N-RAS nucleic acid and protein sequences are provided in NCBI Accession No. NP_002515 and GenBank Accession No. X02751, respectively. "N-RAS" as used herein encompasses variants, including orthologs and interspecies homologs of the human N-RAS protein.

"Mutant N-RAS polypeptide," "mutant N-RAS protein" and "mutant N-RAS" are used interchangeably and refer to an N-RAS polypeptide comprising at least one N-RAS mutation as compared to the corresponding wild-type N-RAS sequence. Certain exemplary mutant N-RAS polypeptides include, but are not limited to, allelic variants, splice variants, derivative variants, substitution variants, deletion variants, insertion variants, and fusion polypeptides.

"H-RAS" refers to Harvey Rat Sarcoma viral oncogene homolog, a small GTPase and a member of the RAS family of proteins involved in signal transduction. Exemplary human H-RAS nucleic acid and protein sequences are provided in NCBI Accession No. P01112 and GenBank Accession No. NM_176795, respectively. "H-RAS" as used herein encompasses variants, including orthologs and interspecies homologs of the human H-RAS protein.

"Mutant H-RAS polypeptide," "mutant H-RAS protein" and "mutant H-RAS" are used interchangeably and refer to an H-RAS polypeptide comprising at least one H-RAS mutation as compared to the corresponding wild-type H-RAS sequence. Certain exemplary mutant H-RAS polypeptides include, but are not limited to, allelic variants, splice variants, derivative variants, substitution variants, deletion variants, insertion variants, and fusion polypeptides.

"Activating K-RAS" refers to a form of K-RAS that has increased activity compared to wild-type K-RAS. The activation of K-RAS activity can result from a mutation or in certain embodiments, overexpression of the K-RAS protein.

"Activating N-RAS" refers to a form of N-RAS that has increased activity compared to wild-type N-RAS. The activation of N-RAS activity can result from a mutation, or in certain embodiments, overexpression of the N-RAS protein.

"Activating H-RAS" refers to a form of H-RAS that has increased activity compared to wild-type H-RAS. The activation of H-RAS activity can result from a mutation, or in certain embodiments, overexpression of the H-RAS protein.

"Mutation" or "mutant" refers to an amino acid or polynucleotide sequence which has been altered by substitution, insertion, and/or deletion. In certain embodiments, a mutant or variant sequence can have increased, decreased, or substantially similar activities or properties in comparison to the parental sequence.

"Identified" or "determined" refers to analyzing for, detection of, or carrying out a process for the presence or absence of one or more specified characteristics.

"Wild-type" or "naturally occurring" refers to the form found in nature. For example, a naturally occurring or wild-type polypeptide or polynucleotide sequence is a sequence present in an organism that can be isolated from a source in nature and which has not been intentionally modified by human manipulation.

"Control" or "control sample" or "control group" refers to a sample or group that is compared to another sample or group, where generally the control sample or group are the same as a comparison group except for one or more factors being compared.

"Selecting" refers to the process of determining that a subject will receive an agent to treat the occurrence of a condition. Selecting can be based on an individual susceptibility to a particular disease or condition due to, for example, presence of an identifying cellular, physiological or environment factor or factors. In certain embodiments, selecting can be based on determining or identifying whether that subject will be responsive to an agent, for example as assessed by identifying the presence of a biomarker and/or drug target marker that makes the subject sensitive, insensitive, responsive, or unresponsive to an agent or treatment.

"Biological sample" refers to any sample including a biomolecule, such as a protein, a peptide, a nucleic acid, a lipid, a carbohydrate or a combination thereof, that is obtained from an organism, particularly a mammal. Examples of mammals include humans; veterinary animals like cats, dogs, horses, cattle, and swine; and laboratory animals like mice, rats and primates. In certain embodiments, a human subject in the clinical setting is referred to as a patient. Biological samples include tissue samples (such as tissue sections and needle biopsies of tissue), cell samples (for example, cytological smears such as Pap or blood smears or samples of cells obtained by microdissection), or cell fractions, fragments or organelles (such as obtained by lysing cells and separating their components by centrifugation or otherwise). Other examples of biological samples include blood, serum, urine, semen, fecal matter, cerebrospinal fluid, interstitial fluid, mucous, tears, sweat, pus, biopsied tissue (for example, obtained by a surgical biopsy or a needle biopsy), nipple aspirates, milk, vaginal fluid, saliva, swabs (such as buccal swabs), or any material containing biomolecules that is derived from a first biological sample. In certain embodiments, the biological sample is a "cell free sample," such as cell free or extracellular polynucleotides, and cell free or extracellular proteins. In certain embodiments, cell free DNA or cfDNA refers to extracellular DNA obtained from blood, particularly the serum.

"Subject" as used herein refers to a mammal, for example a dog, a cat, a horse, or a rabbit. In certain embodiments, the subject is a non-human primate, for example a monkey, chimpanzee, or gorilla. In certain embodiments, the subject is a human, sometimes referred to herein as a patient.

"Treating" or "treatment" of a disease, disorder, or syndrome, as used herein, includes (i) preventing the disease, disorder, or syndrome from occurring in a subject, i.e. causing the clinical symptoms of the disease, disorder, or syndrome not to develop in an animal that may be exposed to or predisposed to the disease, disorder, or syndrome but does not yet experience or display symptoms of the disease, disorder, or syndrome; (ii) inhibiting the disease, disorder, or syndrome, i.e., arresting its development; and (iii) relieving the disease, disorder, or syndrome, i.e., causing regression of the disease, disorder, or syndrome. As is known in the art, adjustments for systemic versus localized delivery, age, body weight, general health, sex, diet, time of administration, drug interaction and the severity of the condition may be necessary, and will be ascertainable with routine experimentation by one of ordinary skill in the art, particularly in view of the guidance provided in the present disclosure.

"Therapeutically effective amount" refers to that amount which, when administered to an animal (e.g., human) for treating a disease, is sufficient to effect such treatment for the disease, disorder, or condition. In certain embodiments, the treatment provides a therapeutic benefit such as amelioration of symptoms or slowing of disease progression. For example, a therapeutically effective amount may be an amount sufficient to decrease a symptom of a disease or condition of as described herein.

"Alkyl" refers to a straight or branched chain hydrocarbon group of 1 to 20 carbon atoms ($C_1$-$C_{20}$ or $C_{1-20}$), e.g., 1 to 12 carbon atoms ($C_1$-$C_{12}$ or $C_{1-12}$), or 1 to 8 carbon atoms ($C_1$-$C_8$ or $C_{1-8}$). Exemplary "alkyl" includes, but are not limited to, methyl, ethyl, n-propyl, i-propyl, n-butyl, s-butyl, t-butyl, n-pentyl, and s-pentyl, and the like.

"Alkenyl" refers to a straight or branched chain hydrocarbon group of 2 to 20 carbon atoms ($C_2$-$C_{20}$ or $C_{2-20}$), e.g., 2 to 12 carbon atoms ($C_2$-$C_{12}$ or $C_{2-12}$), or 2 to 8 carbon atoms ($C_2$-$C_8$ or $C_{2-8}$), having at least one double bond. Exemplary "alkenyl" includes, but are not limited to, vinyl ethenyl, allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl and 5-hexenyl, and the like.

"Alkynyl" refers to a straight or branched chain hydrocarbon group of 2 to 12 carbon atoms ($C_2$-$C_{12}$ or $C_{2-12}$), e.g., 2 to 8 carbon atoms ($C_2$-$C_8$ or $C_{2-8}$), containing at least one triple bond. Exemplary "alkynyl" includes ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl, and the like.

"Alkylene," "alkenylene" and "alkynylene" refers to a straight or branched chain divalent hydrocarbon radical of the corresponding alkyl, alkenyl, and alkynyl, respectively. The "alkylene," "alkenylene" and "alkynylene" may be optionally substituted, for example with alkyl, alkyloxy, hydroxyl, carbonyl, carboxyl, halo, nitro, and the like. In certain embodiments, "alkyl," "alkenyl," and "alkynyl" can represent the corresponding "alkylene," "alkenylene" and "alkynylene," such as, by way of example and not limitation, cycloalkylalkyl-, heterocycloalkylalkyl-, arylalkyl-, heteroarylalkyl-, cycloalkylalkenyl-, heterocycloalkylalkenyl-, arylalkenyl-, heteroarylalkenyl-, cycloalkylalkynyl-, heterocycloalkylalkynyl-, arylalkynyl-, heteroarylalkynyl-, and the like, wherein the cycloalkyl, heterocycloalkyl, aryl, and heteroaryl group is connected, as a substituent via the corresponding alkylene, alkenylene, or alkynylene group.

"Aliphatic" refers to an organic compound characterized by substituted or unsubstituted, straight or branched, and/or cyclic chain arrangements of constituent carbon atoms. Aliphatic compounds do not contain aromatic rings as part of the molecular structure of the compounds. Aliphatic compound can have 1-20 ($C_1$-$C_{20}$ or $C_{1-20}$) carbon atoms, 1-12 ($C_1$-$C_{12}$ or $C_{1-12}$) carbon atoms, or 1-8 ($C_1$-$C_8$ or $C_{1-8}$) carbon atoms.

"Lower" in reference to substituents refers to a group having between one and six carbon atoms.

"Alkylhalo" or "haloalkyl" refers to a straight or branched chain hydrocarbon group of 1 to 20 carbon atoms ($C_1$-$C_{20}$ or $C_{1-20}$), e.g., 1 to 12 carbon atoms ($C_1$-$C_{12}$ or $C_{1-12}$), or 1 to 8 carbon atoms ($C_1$-$C_8$ or $C_{1-8}$) wherein one or more (e.g., one to three, or one) hydrogen atom is replaced by a halogen (e.g., Cl, F, etc.). In certain embodiments, the term "alkylhalo" refers to an alkyl group as defined herein, wherein one hydrogen atom is replaced by a halogen (e.g., Cl, F, etc.). In certain embodiments, the term "alkylhalo" refers to an alkylchloride.

"Alkenylhalo" or "haloalkenyl" refers to a straight or branched chain hydrocarbon group of 2 to 20 carbon atoms ($C_2$-$C_{20}$ or $C_{2-20}$), e.g., 2 to 12 carbon atoms ($C_2$-$C_{12}$ or $C_{2-12}$), or 2 to 8 carbon atoms ($C_2$-$C_8$ or $C_{2-8}$), having at least one double bond, wherein one or more (e.g., one to three, or one) hydrogen atom is replaced by a halogen (e.g., Cl, F, etc.). In certain embodiments, the term "alkenylhalo" refers to an alkenyl group as defined herein, wherein one hydrogen atom is replaced by a halogen (e.g., Cl, F, etc.). In certain embodiments, the term "alkenylhalo" refers to an alkenylchloride.

"Cycloalkyl" refers to any stable monocyclic or polycyclic system which consists of carbon atoms, any ring of which being saturated. "Cycloalkenyl" refers to any stable monocyclic or polycyclic system which consists of carbon atoms, with at least one ring thereof being partially unsaturated. Examples of cycloalkyls include, but are not limited to, cyclopropyl, cyclobutyl, cyclopentyl, cyclohexyl, cycloheptyl, cyclooctyl, bicycloalkyls and tricycloalkyls (e.g., adamantyl).

"Heterocycloalkyl" or "heterocyclyl" refers to a substituted or unsubstituted 4 to 14 membered, mono- or polycyclic (e.g., bicyclic), non-aromatic hydrocarbon ring, wherein 1 to 3 carbon atoms are replaced by a heteroatom. Heteroatoms and/or heteroatomic groups which can replace the carbon atoms include, but are not limited to, —O—, —S—, —S—O—, —$NR^{40}$—, —PH—, —C(O)—, —S(O)—, —$S(O)_2$—, —$S(O)NR^{40}$—, —$S(O)_2NR^{40}$—, and the like, including combinations thereof, where each $R^{40}$ is independently hydrogen or lower alkyl. Examples include thiazolidinyl, thiadiazolyl, triazinyl, morpholinyl, pyrrolidinonyl, pyrrolidinyl, piperidinyl, piperazinyl, 2,3-dihydrofuranyl, dihydropyranyl, hydantoinyl, valerolactamyl, oxiranyl, oxetanyl, tetrahydrofuranyl, tetrahydropyranyl, dihydropyridinyl, tetrahydropyridinyl, tetrahydropyrimidinyl, tetrahydrothiophenyl, tetrahydrothiopyranyl, and the like. In certain embodiments, the "heterocycloalkyl" or "heterocyclyl" is a substituted or unsubstituted 4 to 7 membered monocyclic ring, wherein 1 to 3 carbon atoms are replaced by a heteroatom as described above.

In certain embodiments, the "heterocycloalkyl" or "heterocyclyl" is a substituted or unsubstituted 4 to 10, or 4 to 9, or 5 to 9, or 5 to 7, or 5 to 6 membered mono- or polycyclic (e.g., bicyclic) ring, wherein 1 to 3 carbon atoms are replaced by a heteroatom as described above. In certain embodiments, when the "heterocycloalkyl" or "heterocyclyl" is a substituted or unsubstituted bicyclic ring, one ring may be aromatic, provided at least one ring is non-aromatic, regardless of the point of attachment to the remainder of the molecule (e.g., indolinyl, isoindolinyl, and the like).

"Carbocycle," "carbocyclyl," and "carbocyclic," as used herein, refer to a non-aromatic saturated or unsaturated ring in which each atom of the ring is carbon. The ring may be monocyclic, bicyclic, tricyclic, or even of higher order. Thus, the terms "carbocycle," "carbocyclyl," and "carbocyclic," encompass fused, bridged and spirocyclic systems. Preferably a carbocycle ring contains from 3 to 14 atoms, including 3 to 8 or 5 to 7 atoms, such as for example, 5 or 6 atoms.

"Aryl" refers to a 6 to 14-membered, mono- or bi-carbocyclic ring, wherein the monocyclic ring is aromatic and at least one of the rings in the bicyclic ring is aromatic. Unless stated otherwise, the valency of the group may be located on any atom of any ring within the radical, valency rules permitting. Examples of "aryl" groups include phenyl, naphthyl, indenyl, biphenyl, phenanthrenyl, naphthacenyl, and the like.

"Heteroaryl" means an aromatic heterocyclic ring, including monocyclic and polycyclic (e.g., bicyclic) ring systems, where at least one carbon atom of one or both of the rings is replaced with a heteroatom independently selected from nitrogen, oxygen, and sulfur, or at least two carbon atoms of one or both of the rings are replaced with a heteroatom independently selected from nitrogen, oxygen, and sulfur. In certain embodiments, the heteroaryl can be a 5 to 6 membered monocyclic, or 7 to 11 membered bicyclic ring systems. Examples of "heteroaryl" groups include pyrrolyl, pyrazolyl, imidazolyl, pyrazinyl, oxazolyl, isoxazolyl, thiazolyl, furyl, thienyl, pyridyl, pyrimidyl, benzothiazolyl, purinyl, benzimidazolyl, indolyl, isoquinolyl, quinoxalinyl, quinolyl, and the like.

"Bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In certain embodiments, a bridged bicyclic group has 5-12 ring members and 0-4 heteroatoms independently selected from nitrogen, oxygen, and sulfur. Such bridged bicyclic groups include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bridged bicyclics include, but are not limited to:

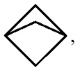, 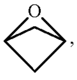, 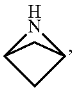, 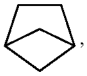, 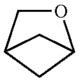,

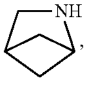, 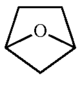, 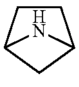, 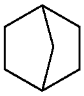,

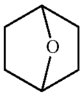, 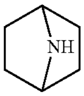, 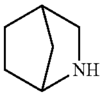, 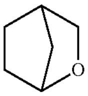,

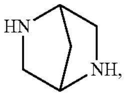, 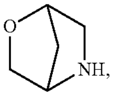, 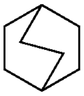, 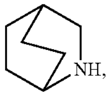,

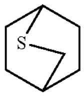, 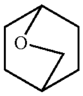, and 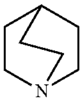.

"Fused ring" refers a ring system with two or more rings having at least one bond and two atoms in common. A "fused aryl" and a "fused heteroaryl" refer to ring systems having at least one aryl and heteroaryl, respectively, that share at least one bond and two atoms in common with another ring.

"Carbonyl" refers to —C(O)—. The carbonyl group may be further substituted with a variety of substituents to form different carbonyl groups including acids, acid halides, aldehydes, amides, esters, and ketones. For example, an —C(O)$R^{41}$, wherein $R^{41}$ is an alkyl is referred to as an alkylcarbonyl. In certain embodiments, $R^{41}$ is selected from an optionally substituted alkyl, cycloalkyl, cycloalkylalkyl, heterocycloalkyl, heterocycloalkylalkyl, aryl, arylalkyl, heteroaryl, and heteroarylalkyl.

"Halogen" or "halo" refers to fluorine, chlorine, bromine and iodine.

"Hydroxy" refers to —OH.

"Oxy" refer to group —O—, which may have various substituents to form different oxy groups, including ethers and esters. In certain embodiments, the oxy group is an —O$R^{42}$, wherein $R^{42}$ is selected from an optionally substituted alkyl, cycloalkyl, cycloalkylalkyl, heterocycloalkyl, heterocycloalkylalkyl, aryl, arylalkyl, heteroaryl, and heteroarylalkyl.

"Acyl" refers to —C(O)$R^{43}$, where $R^{43}$ is hydrogen, or an optionally substituted alkyl, heteroalkyl, cycloalkyl, cycloalkylalkyl, heterocycloalkyl, heterocycloalkylalkyl, aryl, arylalkyl, heteroaryl, or heteroarylalkyl as defined herein. Exemplary acyl groups include, but are not limited to, formyl, acetyl, cyclohexylcarbonyl, cyclohexylmethylcarbonyl, benzoyl, benzylcarbonyl, and the like.

"Alkyloxy" or "alkoxy" refers to —O$R^{44}$, wherein $R^{44}$ is an optionally substituted alkyl.

"Aryloxy" refers to —O$R^{45}$, wherein $R^{45}$ is an optionally substituted aryl.

"Carboxy" refers to —COO— or COOM, wherein M is H or a counterion (e.g., a cation, such as Nat, $Ca^{2+}$, $Mg^{2+}$, etc.).

"Carbamoyl" refers to —C(O)N$R^{46}R^{46}$, wherein each $R^{46}$ is independently selected from H or an optionally substituted alkyl, cycloalkyl, cycloalkylalkyl, heterocycloalkyl, heterocylcoalkylalkyl, aryl, arylalkyl, heteroaryl, or heteroarylalkyl.

"Cyano" refers to —CN.

"Ester" refers to a group such as —C(═O)O$R^{47}$, alternatively illustrated as —C(O)O$R^{47}$, wherein $R^{47}$ is selected from an optionally substituted alkyl, cycloalkyl, cycloalkylalkyl, heterocycloalkyl, heterocyclolalkylalkyl, aryl, arylalkyl, heteroaryl, and heteroarylalkyl.

"Thiol" refers to —SH.

"Sulfanyl" refers to —S$R^{48}$, wherein $R^{48}$ is selected from an optionally substituted alkyl, cycloalkyl, cycloalkylalkyl, heterocycloalkyl, heterocycloalkylalkyl, aryl, arylalkyl, heteroaryl, and heteroarylalkyl. For example, —S$R^{48}$, wherein $R^{48}$ is an alkyl is an alkylsulfanyl.

"Sulfonyl" refers to —$S(O)_2$—, which may have various substituents to form different sulfonyl groups including sulfonic acids, sulfonamides, sulfonate esters, and sulfones. For example, —$S(O)_2R^{49}$ wherein $R^{49}$ is an alkyl refers to an alkylsulfonyl. In certain embodiments of —$S(O)_2R^{49}$, $R^{49}$ is selected from an optionally substituted alkyl, cycloalkyl, cycloalkylalkyl, heterocycloalkyl, heterocycloalkylalkyl, aryl, arylalkyl, heteroaryl, and heteroarylalkyl.

"Sulfinyl" refers to —S(O)—, which may have various substituents to form different sulfinyl groups including sulfinic acids, sulfinamides, and sulfinyl esters. For example, —S(O)$R^{50}$, wherein $R^{50}$ is an alkyl refers to an alkylsulfinyl. In certain embodiments of —S(O)$R^{50}$, $R^{50}$ is selected from an optionally substituted alkyl, cycloalkyl, cycloalkylalkyl, heterocycloalkyl, heterocycloalkylalkyl, aryl, arylalkyl, heteroaryl, and heteroarylalkyl.

"Silyl" refers to Si, which may have various substituents, for example —Si$R^{51}R^{51}R^{51}$, where each $R^{51}$ is independently selected from alkyl, cycloalkyl, cycloalkylalkyl, heterocycloalkyl, heterocycloalkylalkyl, aryl, arylalkyl, heteroaryl, and heteroarylalkyl. As defined herein, any heterocycloalkyl or heteroaryl group present in a silyl group has from 1 to 3 heteroatoms selected independently from O, N, and S.

"Amino" or "amine" refers to the group —N$R^{52}R^{52}$ or —N+$R^{52}R^{52}R^{52}$, wherein each $R^{52}$ is independently selected from hydrogen and an optionally substituted alkyl, cycloalkyl, heterocycloalkyl, alkyloxy, aryl, heteroaryl, heteroarylalkyl, acyl, alkyloxycarbonyl, sulfanyl, sulfinyl, sulfonyl, and the like. Exemplary amino groups include, but are not limited to, dimethylamino, diethylamino, trimethylammonium, triethylammonium, methylysulfonylamino, furanyl-oxy-sulfamino, and the like.

"Amide" refers to a group such as, —C(═O)N$R^{53}R^{53}$, wherein each $R^{53}$ is independently selected from H and an optionally substituted alkyl, cycloalkyl, cycloalkylalkyl, heterocycloalkyl, heterocycloalkylalkyl, aryl, arylalkyl, heteroaryl, and heteroarylalkyl.

"Sulfonamide" refers to —$S(O)_2NR^{54}R^{54}$, wherein each $R^{54}$ is independently selected from H and an optionally substituted alkyl, heteroalkyl, heteroaryl, heterocycle, alkenyl, alkynyl, arylalkyl, heteroarylalkyl, heterocyclylalkyl, -alkylenecarbonyl-, or alkylene-O—C(O)—$OR^{55}$, where $R^{55}$ is selected from H, alkyl, heteroalkyl, cycloalkyl, heterocyclyl, aryl, heteroaryl, alkenyl, alkynyl, arylalkyl, heterocycloalkyl, heteroarylalkyl, amino, and sulfinyl.

"Adamantyl" refers to a compound of structural formula:

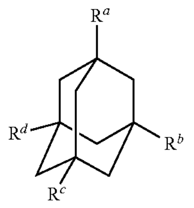

where optional substitutions can be present on one or more of $R^a$, Rb, $R^c$, and $R^d$. Adamantyl includes substituted adamantyl, e.g., 1- or 2-adamantyl, substituted by one or more substituents, including alkyl, halo, OH, $NH_2$, and alkoxy. Exemplary derivatives include methyladamatane, haloadamantane, hydroxyadamantane, and aminoadamantane (e.g., amantadine).

"N-protecting group" as used herein refers to those groups intended to protect a nitrogen atom against undesirable reactions during synthetic procedures. Exemplary N-protecting groups include, but is not limited to, acyl groups such acetyl and t-butylacetyl, pivaloyl, alkoxycarbonyl groups such as methyloxycarbonyl and t-butyloxycarbonyl (Boc), aryloxycarbonyl groups such as benzyloxycarbonyl (Cbz) and fluorenylmethoxycarbonyl (Fmoc and aroyl groups such as benzoyl. N-protecting groups are described in Greene's Protective Groups in Organic Synthesis, 5th Edition, P. G. M. Wuts, ed., Wiley (2014).

"Optional" or "optionally" refers to a described event or circumstance may or may not occur, and that the description includes instances where the event or circumstance occurs and instances where the event or circumstance does not. For example, "optionally substituted alkyl" refers to an alkyl group that may or may not be substituted and that the description encompasses both substituted alkyl group and unsubstituted alkyl group.

"Substituted" as used herein means one or more hydrogen atoms of the group is replaced with a substituent atom or group commonly used in pharmaceutical chemistry. Each substituent can be the same or different. Examples of suitable substituents include, but are not limited to, alkyl, alkenyl, alkynyl, cycloalkyl, aryl, arylalkyl, heterocycloalkyl, heteroaryl, —$OR^{56}$ (e.g., hydroxyl, alkyloxy (e.g., methoxy, ethoxy, and propoxy), aryloxy, heteroaryloxy, arylalkyloxy, ether, ester, carbamate, etc.), hydroxyalkyl, alkyloxycarbonyl, alkyloxyalkyloxy, perhaloalkyl, alkyloxyalkyl, $SR^{56}$ (e.g., thiol, alkylthio, arylthio, heteroarylthio, arylalkylthio, etc.), $S^+R^{56}{}_2$, $S(O)R^{56}$, $SO_2R^{56}$, $NR^{56}R^{57}$ (e.g., primary amine (i.e., $NH_2$), secondary amine, tertiary amine, amide, carbamate, urea, etc.), hydrazide, halo, nitrile, nitro, sulfide, sulfoxide, sulfone, sulfonamide, thiol, carboxy, aldehyde, keto, carboxylic acid, ester, amide, imine, and imide, including seleno and thio derivatives thereof, wherein each $R^{56}$ and $R^{57}$ are independently alkyl, alkenyl, alkynyl, heteroalkyl, cycloalkyl, cycloalkylalkyl, heterocycloalkyl, heterocycloalkylalkyl, aryl, arylalkyl, heteroaryl, or heteroarylalkyl, and wherein each of the substituents can be optionally further substituted. In embodiments in which a functional group with an aromatic carbon ring is substituted, such substitutions will typically number less than about 10 substitutions, more preferably about 1 to 5, with about 1 or 2 substitutions being preferred.

"Pharmaceutically acceptable salt" is meant to include salts of the active compounds which are prepared with relatively nontoxic acids or bases, depending on the particular substituents found on the compounds described herein. When compounds as disclosed herein contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds as disclosed herein contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, phosphoric, partially neutralized phosphoric acids, sulfuric, partially neutralized sulfuric, hydroiodic, or phosphorous acids and the like, as well as the salts derived from relatively nontoxic organic acids like acetic, propionic, isobutyric, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present disclosure may contain both basic and acidic functionalities that allow the compounds to be converted into either base or acid addition salts. Lists of suitable salts are found in Remington's Pharmaceutical Sciences, 17th Ed., Mack Publishing Company, Easton, Pa., (1985) and Journal of Pharmaceutical Science, 66:2 (1977), each of which is incorporated herein by reference in its entirety.

"Pharmaceutically acceptable carrier" or "pharmaceutically acceptable excipient" refers to an excipient, carrier or adjuvant that can be administered to a subject, together with at least one therapeutic agent, and which does not destroy the pharmacological activity thereof and is generally safe, nontoxic and neither biologically nor otherwise undesirable when administered in doses sufficient to deliver a therapeutic amount of the agent.

Any compound or structure given herein, is also intended to represent unlabeled forms as well as isotopically labeled forms of the compounds. These forms of compounds may also be referred to as "isotopically enriched analogs." Isotopically labeled compounds have structures depicted herein, except that one or more atoms are replaced by an atom having a selected atomic mass or mass number.

Examples of isotopes that can be incorporated into the disclosed compounds include isotopes of hydrogen, carbon, nitrogen, oxygen, phosphorous, fluorine, chlorine and iodine, such as $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. Various isotopically labeled compounds of the present disclosure, for example those into which radioactive isotopes such as $^3H$, $^{13}C$ and $^{14}C$ are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The term "isotopically enriched analogs" includes "deuterated analogs" of compounds described herein in which one or more hydrogens is/are replaced by deuterium, such as a hydrogen on a carbon atom. Such compounds exhibit increased resistance to metabolism and are thus useful for increasing the half-life of any compound when administered to a mammal, e.g., a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}F$, $^{3}H$, $^{11}C$ labeled compound may be useful for PET or SPECT or other imaging studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in a compound described herein.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen," the position is understood to have hydrogen at its natural abundance isotopic composition. Accordingly, in the compounds of this disclosure any atom specifically designated as a deuterium (D) is meant to represent deuterium.

Some of the compounds exist as tautomers. Tautomers are in equilibrium with one another. For example, amide containing compounds may exist in equilibrium with imidic acid tautomers. Regardless of which tautomer is shown and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

The compounds as disclosed herein, or their pharmaceutically acceptable salts include an asymmetric center and may thus give rise to enantiomers, diastereomers, and other stereoisomeric forms that may be defined, in terms of absolute stereochemistry, as (R)- or (S)- or, as (D)- or (L)- for amino acids. The present disclosure is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers.

A "stereoisomer" refers to a compound made up of the same atoms bonded by the same bonds but having different three-dimensional structures, which are not interchangeable. The present disclosure contemplates various stereoisomers and mixtures thereof and includes "enantiomers," which refers to two stereoisomers whose molecules are non-superimposable mirror images of one another.

"Diastereomers" are stereoisomers that have at least two asymmetric atoms, but which are not mirror-images of each other.

Relative centers of the compounds as depicted herein are indicated graphically using the "thick bond" style (bold or parallel lines) and absolute stereochemistry is depicted using wedge bonds (bold or parallel lines).

"Prodrugs" means any compound which releases an active parent drug according to a structure described herein in vivo when such prodrug is administered to a mammalian subject. Prodrugs of a compound described herein are prepared by modifying functional groups present in the compound described herein in such a way that the modifications may be cleaved in vivo to release the parent compound. Prodrugs include compounds described herein wherein a hydroxy, amino, carboxyl, or sulfhydryl group in a compound described herein is bonded to any group that may be cleaved in vivo to regenerate the free hydroxy, amino, or sulfhydryl group, respectively. Examples of prodrugs include, but are not limited to esters (e.g., acetate, formate and benzoate derivatives), amides, guanidines, carbamates (e.g., N,N-dimethylaminocarbonyl) of hydroxy functional groups in compounds described herein and the like. Specific prodrugs may include, but are not limited to, compounds provided herein where a solubility-enhancing moiety has been appended thereto. For example, a compound may be modified to include a polyethylene glycol group (e.g., $-(OCH_2CH_2)_u-OH$, where u is from about 2 to about 6, or more) at or off a suitable functional group (e.g., an ester, amide, sulfonyl, or sulfonamide moiety) on $R^1$, $R^3$ or $R^4$, such as in Example 189 (below):

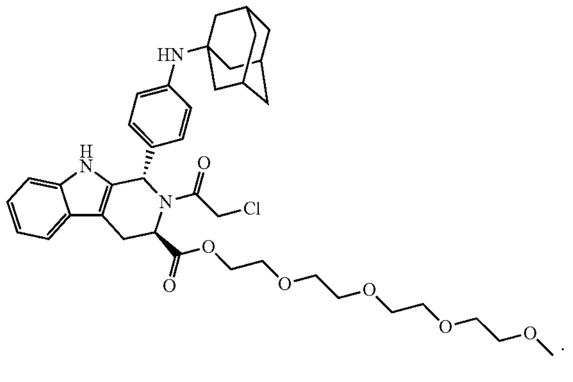 [SMILES: COCCOCCOCCOCCOC(=O)[C@H]1Cc2c([nH]c3ccccc23)[C@H](c2ccc(NC34CC5CC(CC(C5)C3)C4)cc2)N1C(=O)CCl]

Preparation, selection and use of prodrugs is discussed in T. Higuchi and V. Stella, "Pro-drugs as Novel Delivery Systems," Vol. 14 of the A.C.S. Symposium Series; "Design of Prodrugs," ed. H. Bundgaard, Elsevier, 1985; and in Bioreversible Carriers in Drug Design, ed. Edward B. Roche, American Pharmaceutical Association and Pergamon Press, 1987, each of which are hereby incorporated by reference in their entirety.

2. Compounds

Cell death is crucial for normal development, homeostasis and the prevention of proliferative diseases such as cancer (Fuchs and Steller, 2011, Cell 147(4):742-58; Thompson, C. B., 1995, Science. 1995 267(5203):1456-62). Programmed cell death (PCD) can take different forms, such as apoptosis, mitotic catastrophe, necrosis, senescence, and autophagy. While each of these processes ultimately lead to cell death, the pathways and mechanisms appear to be unique, both at the molecular and cellular level.

Ferroptosis have been identified as another cellular pathway that can lead to the death of cells. Ferroptosis does not display the classical features of apoptosis, such as mitochondrial cytochrome c release, caspase activation and chromatin fragmentation (Dolma et al., 2003, Cancer Cell, 2003, 3(3):285-96; Yagoda et al., 2007, Nature. 447(7146):864-8; Yang and Stockwell, 2008, Chem Biol. 15(3):234-45). Ferroptosis does not appear to be sensitive to inhibitors of caspases, cathepsin or calpain proteases, RIPK1 (necrostatin-1), cyclophilin D (cyclosporin A) or lysosomal function/autophagy that are involved in forms of apoptosis, necrosis and autophagic cell death. Ferroptosis is characterized by increased levels of intracellular reactive oxygen species (ROS) and is prevented by iron chelation or genetic inhibition of cellular iron uptake. Addition of iron, but not by other divalent transition metal ions can potentiate ferroptosis. Cellular components implicated in and regulating ferroptosis include, among others, cysteine-glutamate antiporter (system $X^-_c$), glutathione peroxidase 4 (GPX4), p53, and cargo receptor NCOA4. The inactivation or inhibition of some of these molecules, for example system $X^-_c$ or GPX4, leads to iron-dependent cell death (see, e.g., Gao et al., 2016, Cell Res. 26:1021-1032). A distinctive morphological feature of ferroptosis is reduction in mitochondrial size and increased membrane density. The prevention of cell death by iron chelation has been suggested to be a rare phenomenon, having only a limited number of triggers that can induce this iron-dependent cell death mechanism (see, e.g., Wolpaw et al., 2011, Proc Natl Acad Sci USA. 108(39):E771-E780). This suggests that ferroptosis might not be subject to the significant selection pressures for accumulation of mutations that inactivate other cell death pathways in cancer cells, thereby affording an alternative pathway for inducing cell death in cancer cells, bypassing mutations that inactivate or attenuate other cell death pathways.

RSL3, a compound of the following structure;

RSL3 (K601)

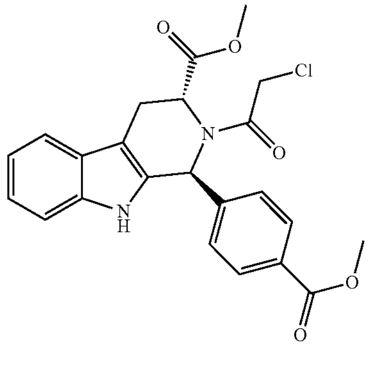

was identified in a synthetic lethal screen of oncogenic RAS (Yang et al., 2008, Chemistry & Biology 15:234-245). The RSL3 compound, also denoted as K601 in the present disclosure, binds to and inactivates glutathione peroxidases (GPXs), unlike another ferroptosis inducer, erastin, which inactivates GPX4 by depletion of glutathione (Yang et al., 2014, 156(1-2):317-33). The RSL3 compound displays growth inhibiting properties against various cancer cell lines. Other compounds similar to RSL3 are described in US patent publication US2010-0081654. However, RSL3 may be rapidly hydrolyzed under biological conditions, and its poor pharmacokinetic properties may disadvantage its use as a therapeutic (see, e.g., Hangauer et al., 2017, Nature 551(7679):247-250). In addition, based on analysis of the crystal structure of GPX4, the enzyme is suggested to have a round molecular surface with no apparent druggable pockets, and while the enzyme has a catalytic site, its active site in considered insufficient to accommodate small molecules. See, e.g., Sakamoto et al., 2016, Biochem Biophy Res Commun. 482(2):195-201.

Studies have shown that lipophilic antioxidants, such as ferrostatin, can rescue cells from GPX4 inhibition-induced ferroptosis. For instance, mesenchymal state GPX4-knockout cells can survive in the presence of ferrostatin, however, when the supply of ferrostatin is terminated, these cells undergo ferroptosis (see, e.g., Viswanathan et al., Nature 547:453-7, 2017). Accordingly, the ability of a molecule to induce ferroptotic cancer cell death, and that such ability is admonished by the addition of ferrostatin, is clear indication that the molecule is a GPX4 inhibitor. In view of the foregoing, the present disclosure provides compounds with GPX4 inhibiting activity, and in certain embodiments, compounds having altered or enhanced stability (e.g., metabolic stability) and/or enhanced activity or other characteristics as compared to other GPX4 inhibitors. In certain embodiments, the compounds described herein are selective for GPX4 over other GPXs.

In certain embodiments, provided herein is a compound of formula (I):

(I)

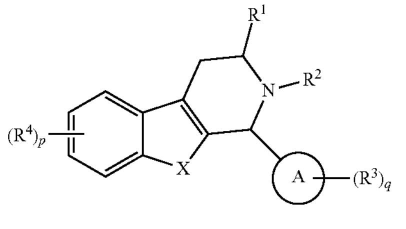

or a tautomer, stereoisomer, mixture of stereoisomers, isotopically enriched analog, or pharmaceutically acceptable salt thereof, wherein:

ring A is $C_4$-$C_{10}$cycloalkyl, heterocyclyl, aryl, or heteroaryl;

X is $NR^5$, O or S;

p is 0, 1, 2 or 3;

q is 0, 1, 2 or 3;

$R^1$ is $C_1$-$C_6$alkyl, $C_2$-$C_6$alkenyl, $C_2$-$C_6$alkynyl, $C_1$-$C_6$haloalkyl, $C_3$-$C_{10}$cycloalkyl, —CN, —OH, —C(O)OR$^6$, —C(O)N(R$^7$)$_2$, —OC(O)R$^6$, —S(O)$_2$R$^8$, —S(O)$_2$N(R$^7$)$_2$, —S(O)N(R$^7$)$_2$, —S(O)R$^8$, —NH$_2$, —NHR$^8$, —N(R$^8$)$_2$, —NO$_2$, —OR$^8$, —$C_1$-$C_6$alkyl-OH, —$C_1$-$C_6$alkyl-OR, or —Si(R$^{15}$)$_3$;

$R^2$ is —C(O)R$^9$;

each $R^3$ is independently halo, —CN, —OH, —OR, —NH$_2$, —NHR$^8$, —N(R$^8$)$_2$, —S(O)$_2$R$^8$, —S(O)R$^8$, —S(O)$_2$N(R$^7$)$_2$, —S(O)N(R$^7$)$_2$, —NO$_2$, —Si(R$^{12}$)$_3$, —$SF_5$, —$C(O)OR^6$, —$C(O)N(R^7)_2$, —$NR^{12}C(O)R$, —$NR^{12}C(O)OR^8$, —$OC(O)N(R^7)_2$, —$OC(O)R^8$, —$C(O)R^6$, —$OC(O)CHR^8N(R^{12})_2$, $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_{10}$cycloalkyl, —$C_2$-$C_6$alkenyl$C_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, $C_1$-$C_6$alkylheteroaryl, or —$C_2$-$C_6$alkenylheteroaryl; wherein each $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_{10}$cycloalkyl, —$C_2$-$C_6$alkenyl$C_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, $C_1$-$C_6$alkylheteroaryl, or —$C_2$-$C_6$alkenylheteroaryl of $R^3$ is independently optionally substituted with one to three $R^{10}$;

each $R^4$ is independently halo, —CN, —OH, —OR, —$NH_2$, —$NHR^8$, —$N(R^8)_2$, —$S(O)_2R^8$, —$S(O)R^8$, —$S(O)_2N(R^7)_2$, —$S(O)N(R^7)_2$, —$NO_2$, —$Si(R^{15})_3$, —$C(O)OR^6$, —$C(O)N(R^7)_2$, —$NR^{12}C(O)R^8$, —$OC(O)R^8$, —$C(O)R^6$, —$NR^{12}C(O)OR^8$, —$OC(O)N(R^7)_2$, —$OC(O)CHR^8N(R^{12})_2$, $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_{10}$cycloalkyl, —$C_2$-$C_6$alkenyl$C_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, $C_1$-$C_6$alkylheteroaryl, or —$C_2$-$C_6$alkenylheteroaryl; wherein each $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_{10}$cycloalkyl, —$C_2$-$C_6$alkenyl$C_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, $C_1$-$C_6$alkylheteroaryl, or —$C_2$-$C_6$alkenylheteroaryl of $R^4$ is optionally independently optionally substituted with one to three $R^{10}$;

$R^5$ is hydrogen or $C_1$-$C_6$alkyl;

each $R^6$ is independently hydrogen, $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_{10}$cycloalkyl, —$C_2$-$C_6$alkenyl$C_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, $C_1$-$C_6$alkylheteroaryl, or —$C_2$-$C_6$alkenylheteroaryl; wherein each $R^6$ is independently further substituted with one to three $R^{11}$;

each $R^7$ is independently hydrogen, $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_6$cycloalkyl, —$C_2$-$C_6$alkenyl$C_3$-$C_6$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, —$C_1$-$C_6$alkylheteroaryl, —$C_2$-$C_6$alkenylheteroaryl, or two $R^7$ together with the nitrogen atom to which they are attached, form a 4 to 7 membered heterocyclyl; wherein each $R^7$ or ring formed thereby is independently further substituted with one to three $R^{11}$;

each $R^8$ is independently $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_{10}$cycloalkyl, —$C_2$-$C_6$alkenyl$C_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, —$C_1$-$C_6$alkylheteroaryl, or —$C_2$-$C_6$alkenylheteroaryl; wherein each $R^8$ is independently further substituted with one to three $R^{11}$;

$R^9$ is —$C_1$-$C_2$haloalkyl, —$C_2$-$C_3$alkenyl, —$C_2$-$C_3$haloalkenyl, $C_2$alkynyl, or —$CH_2OS(O)_2$-phenyl, wherein the $C_1$-$C_2$alkylhalo and —$C_2$-$C_3$alkenylhalo are optionally substituted with one or two —$CH_3$, and the $C_2$alkynyl and phenyl are optionally substituted with one —$CH_3$;

each $R^{10}$ is independently halo, —CN, —$OR^{12}$, —$NO_2$, —$N(R^{12})_2$, —$S(O)R^{13}$, —$S(O)_2R^{13}$, —$S(O)N(R^{12})_2$, —$S(O)_2N(R^{12})_2$, —$Si(R^{12})_3$, —$C(O)R^{12}$, —$C(O)OR^{12}$, —$C(O)N(R^{12})_2$, —$NR^{12}C(O)R^{12}$, —$OC(O)R^{12}$, —$OC(O)OR^{12}$, —$OC(O)N(R^{12})_2$, —$NR^{12}C(O)OR^{12}$, —$OC(O)CHR^{12}N(R^{12})_2$, $C_1$-$C_6$alkyl, $C_1$-$C_6$haloalkyl, $C_2$-$C_6$alkenyl, $C_2$-$C_6$alkynyl, $C_3$-$C_{10}$cycloalkyl, heterocyclyl, aryl, or heteroaryl, wherein each $C_1$-$C_6$alkyl, $C_1$-$C_6$haloalkyl, $C_2$-$C_6$alkenyl, $C_2$-$C_6$alkynyl, $C_3$-$C_{10}$cycloalkyl, heterocyclyl, aryl, or heteroaryl of $R^{10}$ is optionally independently substituted with one to three $R^{11}$;

each $R^{11}$ is independently halo, —CN, —$OR^{12}$, —$NO_2$, —$N(R^{12})_2$, —$S(O)R^{13}$, —$S(O)_2R^{13}$, —$S(O)N(R^{12})_2$, —$S(O)_2N(R^{12})_2$, —$Si(R^{12})_3$, —$C(O)R^{12}$, —$C(O)OR^{12}$, —$C(O)N(R^{12})_2$, —$NR^{12}C(O)R^{12}$, —$OC(O)R^{12}$, —$OC(O)OR^{12}$, —$OC(O)N(R^{12})_2$, —$NR^{12}C(O)OR^{12}$, —$OC(O)CHR^{12}N(R^{12})_2$, $C_1$-$C_6$alkyl, $C_1$-$C_6$haloalkyl, $C_2$-$C_6$alkenyl, $C_2$-$C_6$alkynyl, $C_3$-$C_{10}$cycloalkyl, heterocyclyl, aryl, or heteroaryl;

each $R^{12}$ is independently hydrogen, $C_1$-$C_6$alkyl or $C_3$-$C_{10}$cycloalkyl;

each $R^{13}$ is independently $C_1$-$C_6$alkyl or $C_3$-$C_{10}$cycloalkyl; and each $R^{15}$ is independently $C_1$-$C_6$alkyl, $C_2$-$C_6$alkenyl, aryl, heteroaryl, —$C_1$-$C_6$alkylaryl, —$C_2$-$C_6$alkenylaryl, —$C_1$-$C_6$alkylheteroaryl, and —$C_2$-$C_6$alkenylheteroaryl.

In certain embodiments, when X is $NR^5$, then $R^9$ is $C_2$alkynyl.

In certain embodiments, when X is $NR^5$, and $R^9$ is —$C_1$-$C_2$haloalkyl, —$C_2$-$C_3$alkenyl, —$C_2$-$C_3$haloalkenyl, or —$CH_2OS(O)_2$-phenyl, wherein the $C_1$-$C_2$alkylhalo and —$C_2$-$C_3$alkenylhalo are optionally substituted with one or two —$CH_3$, and the phenyl is optionally substituted with —$CH_3$, then $R^1$ is other than —$C(O)OR^6$ and —$C(O)N(R^7)_2$.

In certain embodiments, when X is $NR^5$, then (i) $R^9$ is $C_2$alkynyl; or (ii) $R^9$ is —$C_1$-$C_2$haloalkyl, —$C_2$-$C_3$alkenyl, —$C_2$-$C_3$haloalkenyl, or —$CH_2OS(O)_2$-phenyl, wherein the $C_1$-$C_2$alkylhalo and —$C_2$-$C_3$alkenylhalo are optionally substituted with one or two —$CH_3$, and the phenyl is optionally substituted with —$CH_3$, and $R^1$ is other than —$C(O)OR^6$ and —$C(O)N(R^7)_2$.

In certain embodiments, when X is NH, $R^1$ is —$C(O)OR^6$, $R^2$ is —$C(O)CH_2Cl$ or $C(O)CH_2F$, q is 1, p is 0, and ring A with the $R^3$ is

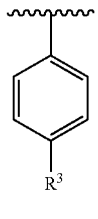
;

$R^3$; then (i) $R^3$ and $R^6$ are not simultaneously —$NO_2$ and —$CH_3$, respectively, and (ii) when $R^6$ is —$CH_3$, then $R^3$ is other than H, halo, and —$NO_2$.

In certain embodiments, when X is NH, $R^1$ is —C(O)O$R^6$, $R^2$ is —C(O)$CH_2$Cl or C(O)$CH_2$F, q is 1, p is 0, ring A with the $R^3$ is

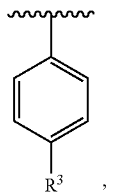

, $R^3$, and $R^3$ is —C(O)O$R^6$; then both $R^6$ are not simultaneously (i) —$CH_3$;

(ii) —$CH_3$ and $C_2$-$C_6$alkynyl, respectively; or (iii) —$CH_2CH_3$ and —$CH_3$, respectively.

In certain embodiments, when X is NH, $R^1$ is —C(O)O$CH_3$, $R^2$ is —C(O)$CH_2$Cl or —C(O)$CH_2$F, q is 1, p is 0, and $R^3$ is H; then ring A is other than phenyl.

In certain embodiments, and when X is NH, $R^1$ is —C(O)N$(R^7)_2$, wherein $R^7$ are H, $R^2$ is —C(O)$CH_2$Cl or —C(O)$CH_2$F, q is 0, or 1, p is 0, and ring A is phenyl; then q is not 0, or when q is 1, $R^3$ is other than halo.

In certain embodiments, the compound is not:

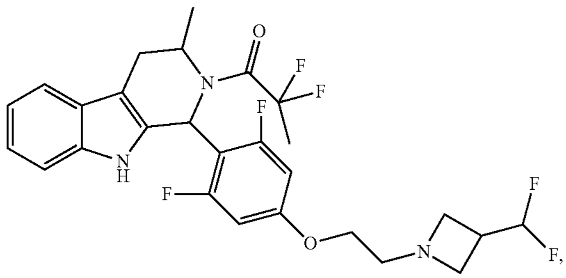

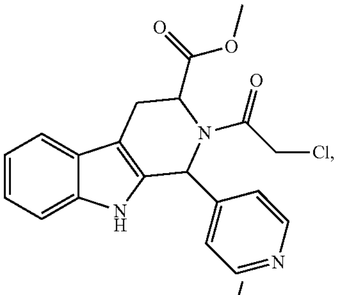

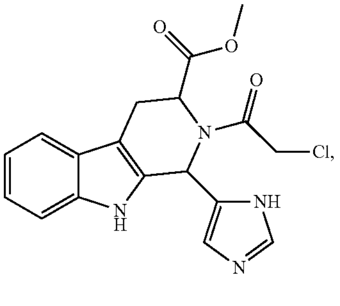

-continued

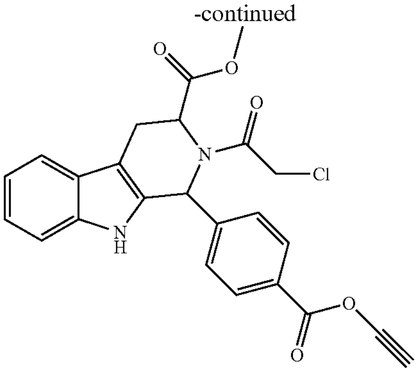

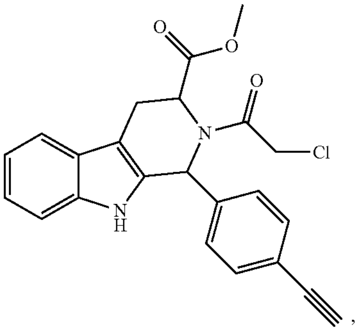

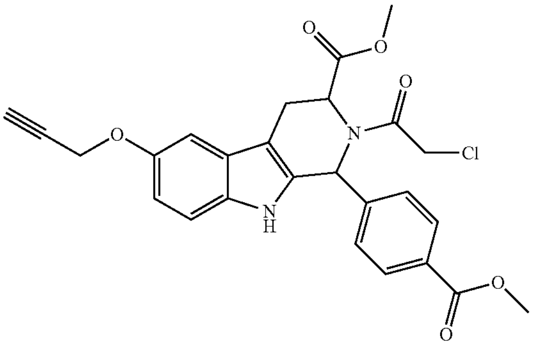

, or

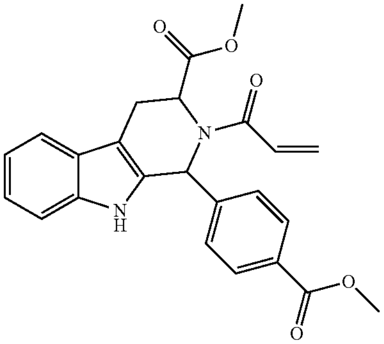

, or a tautomer, stereoisomer, mixture of stereoisomers, isotopically enriched analog, or pharmaceutically acceptable salt thereof.

Also provided herein is a compound of formula (I'), or a tautomer, stereoisomer, mixture of stereoisomers, isotopically enriched analog, or pharmaceutically acceptable salt thereof:

(I')

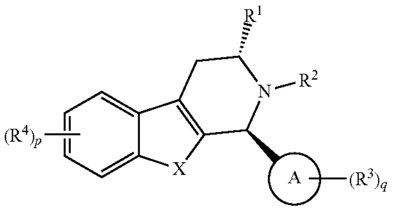

where each of ring A, p, q, $R^1$, $R^3$, $R^4$ and $R^9$ are as defined herein.

Also provided herein is a compound of formula (II), or a tautomer, stereoisomer, mixture of stereoisomers, isotopically enriched analog, or pharmaceutically acceptable salt thereof:

(II)

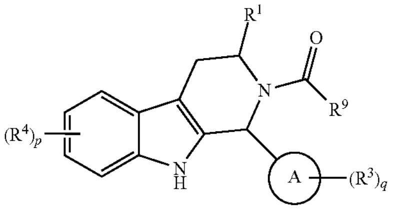

where each of ring A, p, q, $R^1$, $R^3$, $R^4$ and $R^9$ are as defined herein.

Also provided herein is a compound of formula (II'), or a tautomer, isotopically enriched analog, or pharmaceutically acceptable salt thereof:

(II')

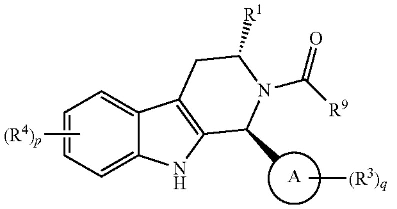

where each of ring A, p, q, $R^1$, $R^3$, $R^4$ and $R^9$ are as defined herein.

In certain embodiments, $R^9$ is $C_2$alkynyl. In certain embodiments, X is $NR^5$, and $R^9$ is $C_2$alkynyl.

Also provided herein is a compound of formula (III), or a tautomer, stereoisomer, mixture of stereoisomers, isotopically enriched analog, or pharmaceutically acceptable salt thereof:

(III)

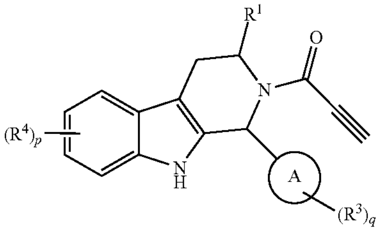

where each of ring A, p, q, $R^1$, $R^3$, and $R^4$ are as defined herein.

Also provided herein is a compound of formula (III'), or a tautomer, isotopically enriched analog, or pharmaceutically acceptable salt thereof:

(III')

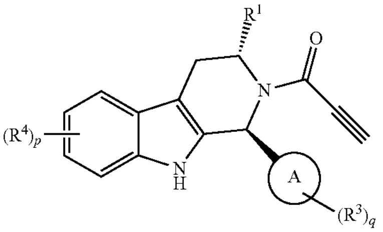

where each of ring A, p, q, $R^1$, $R^3$, and $R^4$ are as defined herein.

Also provided herein is a compound of formula (IIIa), or a tautomer, stereoisomer, mixture of stereoisomers, isotopically enriched analog, or pharmaceutically acceptable salt thereof:

(IIIa)

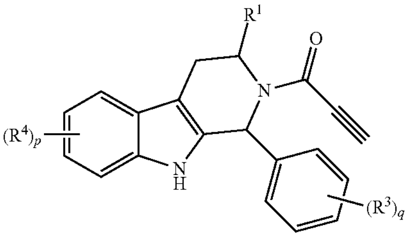

where each of p, q, $R^1$, $R^3$, and $R^4$ are as defined herein.

Also provided herein is a compound of formula (IIIa'), or a tautomer, isotopically enriched analog, or pharmaceutically acceptable salt thereof:

(IIIa')

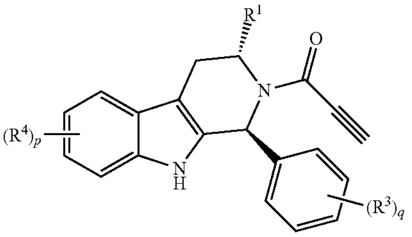

where each of p, q, $R^1$, $R^3$, and $R^4$ are as defined herein.

Also provided herein is a compound of formula (IIIb), or a tautomer, stereoisomer, mixture of stereoisomers, isotopically enriched analog, or pharmaceutically acceptable salt thereof:

(IIIb)

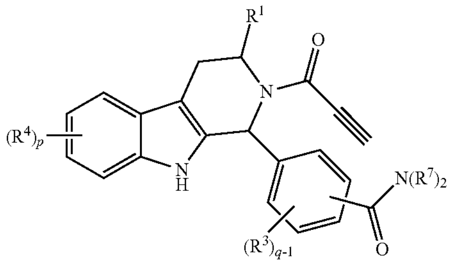

where each of p, q, $R^1$, $R^3$, $R^4$, and $R^7$ are as defined herein.

Also provided herein is a compound of formula (IIIb'), or a tautomer, isotopically enriched analog, or pharmaceutically acceptable salt thereof:

(IIIb')

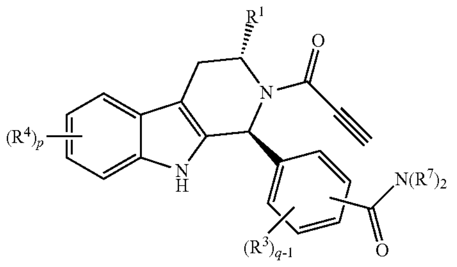

where each of p, q, $R^1$, $R^3$, $R^4$, and $R^7$ are as defined herein.

Also provided herein is a compound of formula (IIIc), or a tautomer, stereoisomer, mixture of stereoisomers, isotopically enriched analog, or pharmaceutically acceptable salt thereof:

(IIIc)

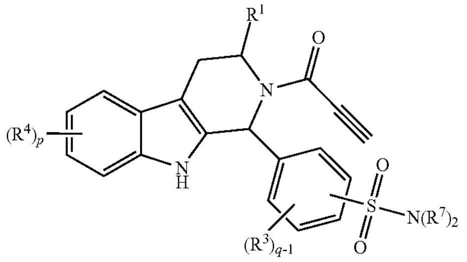

where each of p, q, $R^1$, $R^3$, $R^4$, and $R^7$ are as defined herein.

Also provided herein is a compound of formula (IIIc'), or a tautomer, isotopically enriched analog, or pharmaceutically acceptable salt thereof:

(IIIc')

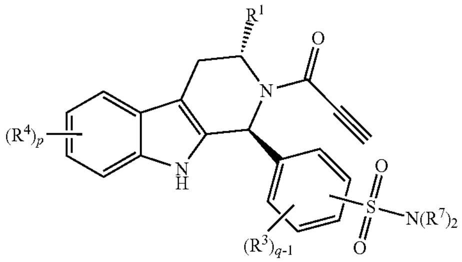

where each of p, q, $R^1$, $R^3$, $R^4$, and $R^7$ are as defined herein.

In certain embodiments of formula (IIIb), (IIIb'), IIIc) or (IIIc'), the two $R^{11}$ groups together with the nitrogen atom to which they are attached form a 4 to 7 membered heterocyclyl, wherein the heterocyclyl formed by the two $R^{11}$ groups is optionally substituted with a 4- to 6-membered heterocyclyl or —$N(C_1-C_6alkyl)_2$, wherein the 4- to 6-membered heterocyclyl when containing 2 or more N atoms is optionally substituted with an N-protecting group. In certain embodiments, the 4 to 7 membered heterocyclyl is selected from azetidinyl, pyrrolidinyl, piperidinyl, pyrazolidinyl, isoxazolidinyl, oxazolidinyl, thiazolidinyl, imidazolidinyl, piperazinyl, morpholinyl, thiomorpholinyl, 1,3-oxazinanyl, 1,3-thiazinanyl, dihydropyridinyl, tetrahydropyranyl, 1,3-tetrahydropyrimidinyl, dihydropyrimidinyl, azepanyl and 1,4-diazepanyl. In certain embodiments, the 4- to 6-membered heterocyclyl, when present as a substituent, is selected from azetidinyl, oxetanyl, thietanyl, piperidinyl, 1,2,3,6-tetrahydropyridinyl, pyranyl, dioxanyl, 1,3-dioxolanyl, dihydropyranyl, dihydrothienyl, dihydrofuranyl, imidazolinyl, pyrrolidinyl, piperidinyl, pyrazolidinyl, isoxazolidinyl, oxazolidinyl, thiazolidinyl, piperazinyl, morpholinyl, thiomorpholinyl, 1,3-oxazinanyl, 1,3-thiazinanyl, dihydropyridinyl, 1,3-tetrahydropyrimidinyl, and dihydropyrimidinyl. In certain embodiments, the N-protecting group when present is t-Boc.

Also provided herein is a compound of formula (IIId), or a tautomer, stereoisomer, mixture of stereoisomers, isotopically enriched analog, or pharmaceutically acceptable salt thereof:

(IIId)

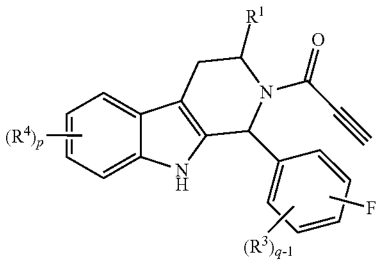

where each of p, q, $R^1$, $R^3$, and $R^4$ are as defined herein.

Also provided herein is a compound of formula (IIId'), or a tautomer, isotopically enriched analog, or pharmaceutically acceptable salt thereof:

(IIId')

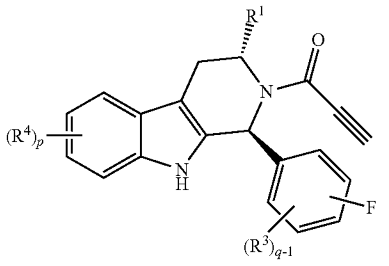

where each of p, q, $R^1$, $R^3$, and $R^4$ are as defined herein.

In certain embodiments, $R^1$ is $C_1$-$C_6$alkyl, $C_2$-$C_6$alkenyl, $C_2$-$C_6$alkynyl, $C_1$-$C_6$haloalkyl, $C_3$-$C_{10}$cycloalkyl, —CN, —C(O)$OR^6$, —C(O)N($R^7$)$_2$, —$NH_2$, —$NHR^8$, —N($R^8$)$_2$, —OH, —$OR^8$, —$C_1$-$C_6$alkyl-OH or —$C_1$-$C_6$alkyl-$OR^8$. In certain embodiments, $R^1$ is $C_1$-$C_6$alkyl, $C_2$-$C_6$alkenyl, $C_2$-$C_6$alkynyl, $C_1$-$C_6$haloalkyl, —C(O)$OR^6$, —C(O)N($R^7$)$_2$, —$NH_2$, —$NHR^8$, —N($R^8$)$_2$, —OH, —$OR^8$, —$C_1$-$C_6$alkyl-OH or —$C_1$-$C_6$alkyl-$OR^8$.

In certain embodiments, $R^1$ is $C_1$-$C_6$alkyl, $C_2$-$C_6$alkenyl, $C_2$-$C_6$alkynyl, $C_1$-$C_6$haloalkyl, —CN, $C_3$-$C_{10}$cycloalkyl, —$NH_2$, —$NHR^8$, —N($R^8$)$_2$, —OH, —$OR^8$, —$C_1$-$C_6$alkyl-OH or —$C_1$-$C_6$alkyl-$OR^8$. In certain embodiments, $R^1$ is $C_1$-$C_6$alkyl, $C_2$-$C_6$alkenyl, $C_2$-$C_6$alkynyl, $C_1$-$C_6$haloalkyl, —$NH_2$, —$NHR^8$, —N($R^8$)$_2$, —OH, —$OR^8$, —$C_1$-$C_6$alkyl-OH or —$C_1$-$C_6$alkyl-$OR^8$.

In certain embodiments, $R^1$ is —C(O)$OR^6$ or —C(O)N($R^7$)$_2$. In certain embodiments, $R^1$ is $C_1$-$C_6$alkyl. In certain embodiments, $R^1$ is $C_3$-$C_{10}$cycloalkyl.

Also provided herein is a compound of formula (IV), or a tautomer, stereoisomer, mixture of stereoisomers, isotopically enriched analog, or pharmaceutically acceptable salt thereof:

(IV)

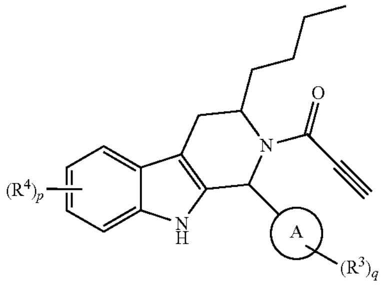

where each of ring A, p, q, $R^3$, and $R^4$ are as defined herein.

Also provided herein is a compound of formula (IV'), or a tautomer, stereoisomer, mixture of stereoisomers, isotopically enriched analog, or pharmaceutically acceptable salt thereof:

(IV')

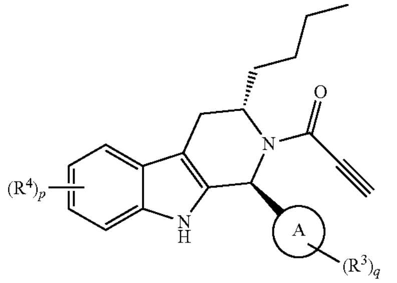

where each of ring A, p, q, $R^3$, and $R^4$ are as defined herein.

Also provided herein is a compound of formula (IVa), or a tautomer, stereoisomer, mixture of stereoisomers, isotopically enriched analog, or pharmaceutically acceptable salt thereof:

(IVa)

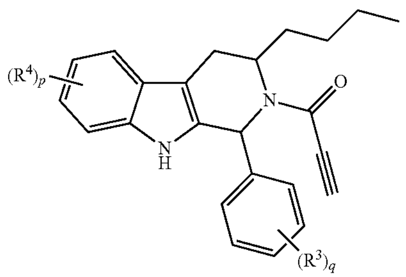

where each of ring A, p, q, $R^3$, and $R^4$ are as defined herein.

Also provided herein is a compound of formula (IVa'), or a tautomer, stereoisomer, mixture of stereoisomers, isotopically enriched analog, or pharmaceutically acceptable salt thereof:

(IVa')

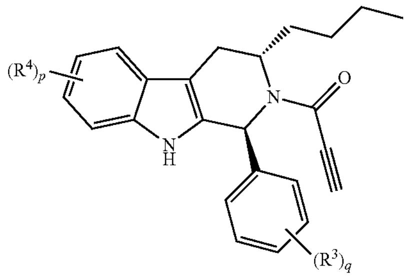

where each of ring A, p, q, $R^3$, and $R^4$ are as defined herein.

In certain embodiments, p is 1, 2 or 3. In certain embodiments, p is 1. In certain embodiments, p is 2. In certain embodiments, p is 3.

In certain embodiments, p is 0. In certain embodiments, p is 0 or 1. In certain embodiments, p is 1 or 2.

In certain embodiments, q is 1, 2 or 3. In certain embodiments, q is 1. In certain embodiments, q is 2. In certain embodiments, q is 3. In certain embodiments, q is 0.

In certain embodiments, X is $NR^5$ or S.

In certain embodiments, $R^1$ is $C_1$-$C_6$alkyl, $C_1$-$C_6$haloalkyl, $C_3$-$C_{10}$cycloalkyl, —CN, —C(O)$OR^6$, —C(O)$N(R^7)_2$, —$C_1$-$C_6$alkyl-OH or —$C_1$-$C_6$alkyl-$OR^8$.

In certain embodiments, at least one $R^3$ is halo, —$NH_2$, —$NHR^8$, —$N(R^8)_2$, —$S(O)_2R^8$, —$S(O)R^8$, —$S(O)_2N(R^7)_2$, —$S(O)N(R^7)_2$, —$NO_2$, —$Si(R^{12})_3$, —$SF_5$, —C(O)$OR^6$, —C(O)$N(R^7)_2$, —$NR^{12}C(O)R^8$, —$NR^{12}C(O)OR^8$, —OC(O)$R^8$, —C(O)$R^6$, or —OC(O)$CHR^8N(R^{12})_2$.

In certain embodiments, at least one $R^3$ is halo.

In certain embodiments, at least one $R^3$ is —$NHR^8$. In certain embodiments, at least one $R^3$ is —$N(R^8)_2$. In certain embodiments, q is 2, and one $R^3$ is halo and the other $R^3$ is —$N(R^8)_2$. In certain embodiments, q is 3, and two $R^3$ are independently halo and one $R^3$ is —$N(R^8)_2$.

In certain embodiments, at least one $R^3$ is —C(O)$OR^6$ or —C(O)$R^6$.

In certain embodiments, at least one $R^3$ is —$S(O)_2N(R^7)_2$, —$S(O)N(R^7)_2$, or —C(O)$N(R^7)_2$.

In certain embodiments, at least one $R^3$ is —$S(O)_2R^8$, —$S(O)R^8$, —$NR^{12}C(O)R^8$, —$NR^{12}C(O)OR^8$, —OC(O)$R^8$, or —OC(O)$CHR^8N(R^{12})_2$.

In certain embodiments, each $R^3$ is independently halo, —CN, —OR, —$NHR^8$, —$S(O)_2R^8$, —$S(O)_2N(R^7)_2$, —$NO_2$, —$Si(R^{12})_3$, —$SF_5$, —C(O)$OR^6$, —C(O)$N(R^7)_2$, —$NR^{12}C(O)R^8$, —$NR^{12}C(O)OR^8$, —OC(O)$R^8$, —OC(O)$CHR^8N(R^{12})_2$, $C_1$-$C_6$alkyl, $C_3$-$C_{10}$cycloalkyl, heterocyclyl, heteroaryl, or —$C_1$-$C_6$alkylheterocyclyl; wherein each $C_1$-$C_6$alkyl, $C_3$-$C_{10}$cycloalkyl, heterocyclyl, heteroaryl, or —$C_1$-$C_6$alkylheterocyclyl of $R^3$ is independently optionally substituted with one to three $R^{10}$.

In certain embodiments, each $R^3$ is independently halo, —CN, —$OR^8$, —$NHR^8$, —$S(O)_2R^8$, —$S(O)_2N(R^7)_2$, —$NO_2$, —$Si(R^{12})_3$, —$SF_5$, —C(O)$OR^6$, —C(O)$N(R^7)_2$, —$NR^{12}C(O)R^8$, —$NR^{12}C(O)OR^8$, —OC(O)$R^8$, —OC(O)$CHR^8N(R^{12})_2$, $C_1$-$C_6$alkyl, $C_3$-$C_{10}$cycloalkyl, heterocyclyl, heteroaryl, or —$C_1$-$C_6$alkylheterocyclyl; wherein each $C_1$-$C_6$alkyl, $C_3$-$C_{10}$cycloalkyl, heterocyclyl, heteroaryl, or —$C_1$-$C_6$alkylheterocyclyl is independently optionally substituted with one to three substituents independently selected from —$OR^{12}$, —$N(R^{12})_2$, —$S(O)_2R^{13}$, —OC(O)$CHR^{12}N(R^{12})_2$, and $C_1$-$C_6$alkyl optionally substituted with one to three halo, —$OR^{12}$, —$N(R^{12})_2$, —$Si(R^{12})_3$, —C(O)$OR^{12}$, —$NR^{12}C(O)OR^{12}$, —OC(O)$CHR^{12}N(R^{12})_2$, $C_1$-$C_6$alkyl, or heterocyclyl; wherein each $R^{12}$ is independently hydrogen, $C_1$-$C_6$alkyl or $C_3$-$C_{10}$cycloalkyl; and each $R^{13}$ is independently $C_1$-$C_6$alkyl or $C_3$-$C_{10}$cycloalkyl.

In certain embodiments, each $R^4$ is independently halo, —CN, —OH, —$OR^8$, —$NH_2$, —$NHR^8$, —$N(R^8)_2$, —$S(O)_2R^8$, —$S(O)R^8$, —$S(O)_2N(R^7)_2$, —$S(O)N(R^7)_2$, —$NO_2$, —$Si(R^{15})_3$, —C(O)$OR^6$, —C(O)$N(R^7)_2$, —$NR^{12}C(O)R$, —OC(O)$R^8$, —C(O)$R^6$, $C_1$-$C_6$alkyl, $C_2$-$C_6$alkenyl, $C_2$-$C_6$alkynyl, or $C_3$-$C_{10}$cycloalkyl; wherein each $C_1$-$C_6$alkyl, $C_2$-$C_6$alkenyl, $C_2$-$C_6$alkynyl, or $C_3$-$C_{10}$cycloalkyl of $R^4$ is independently optionally substituted with one to three $R^{10}$. In certain embodiments, each $R^4$ is independently halo, —CN, —OH, —$OR^8$, $C_1$-$C_6$alkyl, $C_2$-$C_6$alkynyl, or $C_3$-$C_{10}$cycloalkyl; wherein each $C_1$-$C_6$alkyl, $C_2$-$C_6$alkynyl, or $C_3$-$C_{10}$cycloalkyl of $R^4$ is independently optionally substituted with one to three $R^{10}$.

In certain embodiments, each $R^4$ is independently halo, —CN, —OH, —$OR^8$, $C_1$-$C_6$alkyl, or $C_2$-$C_6$alkynyl; wherein the $C_1$-$C_6$alkyl of $R^4$ is optionally substituted with one to three $R^{10}$.

In certain embodiments, each $R^4$ is independently halo, —CN, —OH, —$OR^8$, $C_1$-$C_6$alkyl, $C_2$-$C_6$alkynyl; wherein the $C_1$-$C_6$alkyl of $R^4$ is optionally substituted with one to three substituents independently selected from —$OR^{12}$, —$N(R^{12})_2$, —$S(O)_2R^{13}$, —OC(O)$CHR^{12}N(R^{12})_2$, and $C_1$-$C_6$alkyl optionally substituted with one to three halo, —$OR^{12}$, —$N(R^{12})_2$, —$Si(R^{12})_3$, —C(O)$OR^{12}$, —$NR^{12}C(O)OR^{12}$, —OC(O)$CHR^{12}N(R^{12})_2$, $C_1$-$C_6$alkyl, or heterocyclyl; wherein each $R^{12}$ is independently hydrogen, $C_1$-$C_6$alkyl or $C_3$-$C_{10}$cycloalkyl; and each $R^{13}$ is independently $C_1$-$C_6$alkyl or $C_3$-$C_{10}$cycloalkyl.

In certain embodiments, each $R^6$ is independently hydrogen, $C_1$-$C_6$alkyl, $C_2$-$C_6$alkenyl, or —$C_1$-$C_6$alkyl$C_3$-$C_{10}$cycloalkyl; wherein each $R^6$ is independently further substituted with one to three $R^{11}$.

In certain embodiments, each $R^6$ is independently hydrogen, $C_1$-$C_6$alkyl, $C_2$-$C_6$alkenyl, or —$C_1$-$C_6$alkyl$C_3$-$C_{10}$cycloalkyl; wherein each $R^6$ is independently further substituted with one to three halo, —$OR^{12}$, —$N(R^{12})_2$, —$Si(R^{12})_3$, —C(O)$OR^{12}$, —$NR^{12}C(O)OR^{12}$, —OC(O)$CHR^{12}N(R^{12})_2$, $C_1$-$C_6$alkyl, or heterocyclyl; wherein each $R^{12}$ is independently hydrogen, $C_1$-$C_6$alkyl or $C_3$-$C_{10}$cycloalkyl.

In certain embodiments, each $R^7$ is independently hydrogen, $C_1$-$C_6$alkyl, $C_3$-$C_{10}$cycloalkyl, heterocyclyl, heteroaryl, —$C_1$-$C_6$alkyl$C_3$-$C_6$cycloalkyl, —$C_1$-$C_6$alkylheterocyclyl, or two $R^7$ together with the nitrogen atom to which they are attached, form a 4 to 7 membered heterocyclyl; wherein each $R^7$ or ring formed thereby is independently further substituted with one to three $R^{11}$.

In certain embodiments, each $R^7$ is independently hydrogen, $C_1$-$C_6$alkyl, $C_3$-$C_{10}$cycloalkyl, heterocyclyl, heteroaryl, —$C_1$-$C_6$alkyl$C_3$-$C_6$cycloalkyl, —$C_1$-$C_6$alkylheterocyclyl, or two $R^7$ together with the nitrogen atom to which they are attached, form a 4 to 7 membered heterocyclyl; wherein each $R^7$ or ring formed thereby is independently further substituted with one to three halo, —$OR^{12}$, —$N(R^{12})_2$, —$Si(R^{12})_3$, —C(O)$OR^{12}$, —$NR^{12}C(O)OR^{12}$, —OC(O)$CHR^{12}N(R^{12})_2$, $C_1$-$C_6$alkyl, or heterocyclyl; wherein each $R^{12}$ is independently hydrogen, $C_1$-$C_6$alkyl or $C_3$-$C_{10}$cycloalkyl.

In certain embodiments, each $R^8$ is independently $C_1$-$C_6$alkyl, $C_2$-$C_6$alkynyl, $C_3$-$C_{10}$cycloalkyl, —$C_1$-$C_6$alkyl$C_3$-$C_{10}$cycloalkyl, or —$C_1$-$C_6$alkylaryl; wherein each $R^8$ is independently further substituted with one to three $R^{11}$.

In certain embodiments, each $R^8$ is independently $C_1$-$C_6$alkyl, $C_2$-$C_6$alkynyl, $C_3$-$C_{10}$cycloalkyl, —$C_1$-$C_6$alkyl$C_3$-$C_{10}$cycloalkyl, or —$C_1$-$C_6$alkylaryl; wherein each $R^8$ is independently further substituted with one to three halo, —$OR^{12}$, —$N(R^{12})_2$, —$Si(R^{12})_3$, —C(O)$OR^{12}$, —$NR^{12}C(O)OR^{12}$, —OC(O)$CHR^{12}N(R^{12})_2$, $C_1$-$C_6$alkyl, or heterocyclyl; wherein each $R^{12}$ is independently hydrogen, $C_1$-$C_6$alkyl or $C_3$-$C_{10}$cycloalkyl.

In certain embodiments, each $R^{10}$ is independently —$OR^{12}$, —$N(R^{12})_2$, —$S(O)_2R^{13}$, —OC(O)$CHR^{12}N(R^{12})_2$, or $C_1$-$C_6$alkyl, wherein the $C_1$-$C_6$alkyl, of $R^{10}$ is optionally independently substituted with one to three $R^{11}$;

each $R^{11}$ is independently halo, —$OR^{12}$, —$N(R^{12})_2$, —$Si(R^{12})_3$, —C(O)$OR^{12}$, —$NR^{12}C(O)OR^{12}$, —OC(O)$CHR^{12}N(R^{12})_2$, $C_1$-$C_6$alkyl, or heterocyclyl;

each $R^{12}$ is independently hydrogen, $C_1$-$C_6$alkyl or $C_3$-$C_{10}$cycloalkyl; and each $R^{13}$ is independently $C_1$-$C_6$alkyl or $C_3$-$C_{10}$cycloalkyl.

In certain embodiments, ring A is $C_4$-$C_{10}$cycloalkyl, heterocyclyl, aryl, or heteroaryl;

X is $NR^5$ or S;

p is 0, 1, 2 or 3;

q is 0, 1, 2 or 3;

$R^1$ is $C_1$-$C_6$alkyl, $C_1$-$C_6$haloalkyl, $C_3$-$C_{10}$cycloalkyl, —CN, —C(O)OR$^6$, —C(O)N($R^7$)$_2$, —$C_1$-$C_6$alkyl-OH or —$C_1$-$C_6$alkyl-OR$^8$;

$R^2$ is —C(O)R$^9$;

each $R^3$ is independently halo, —CN, —OR, —NHR$^8$, —S(O)$_2$R$^8$, —S(O)$_2$N($R^7$)$_2$, —NO$_2$, —Si($R^{12}$)$_3$, —SF$_5$, —C(O)OR$^6$, —C(O)N($R^7$)$_2$, —NR$^{12}$C(O)R$^8$, —NR$^{12}$C(O)OR$^8$, —OC(O)R$^8$, —OC(O)CHR$^8$ N($R^{12}$)$_2$, $C_1$-$C_6$alkyl, $C_3$-$C_{10}$cycloalkyl, heterocyclyl, heteroaryl, or —$C_1$-$C_6$alkylheterocyclyl; wherein each $C_1$-$C_6$alkyl, $C_3$-$C_{10}$cycloalkyl, heterocyclyl, heteroaryl, or —$C_1$-$C_6$alkylheterocyclyl of $R^3$ is independently optionally substituted with one to three $R^{10}$;

each $R^4$ is independently halo, —CN, —OH, —OR, $C_1$-$C_6$alkyl, or $C_2$-$C_6$alkynyl; wherein the $C_1$-$C_6$alkyl of $R^4$ is optionally independently optionally substituted with one to three $R^{10}$;

$R^5$ is hydrogen or $C_1$-$C_6$alkyl;

each $R^6$ is independently hydrogen, $C_1$-$C_6$alkyl, $C_2$-$C_6$alkenyl, or —$C_1$-$C_6$alkyl$C_3$-$C_{10}$cycloalkyl; wherein each $R^6$ is independently further substituted with one to three $R^{11}$;

each $R^7$ is independently hydrogen, $C_1$-$C_6$alkyl, $C_3$-$C_{10}$cycloalkyl, heterocyclyl, heteroaryl, —$C_1$-$C_6$alkyl$C_3$-$C_6$cycloalkyl, —$C_1$-$C_6$alkylheterocyclyl, or two $R^7$ together with the nitrogen atom to which they are attached, form a 4 to 7 membered heterocyclyl; wherein each $R^7$ or ring formed thereby is independently further substituted with one to three $R^{11}$;

each $R^8$ is independently $C_1$-$C_6$alkyl, $C_2$-$C_6$alkynyl, $C_3$-$C_{10}$cycloalkyl, —$C_1$-$C_6$alkyl$C_3$-$C_{10}$cycloalkyl, or —$C_1$-$C_6$alkylaryl; wherein each $R^8$ is independently further substituted with one to three $R^{11}$;

$R^9$ is —$C_1$-$C_2$haloalkyl, —$C_2$-$C_3$alkenyl, —$C_2$-$C_3$haloalkenyl, $C_2$alkynyl, or —CH$_2$OS(O)$_2$-phenyl, wherein the $C_1$-$C_2$alkylhalo and —$C_2$-$C_3$alkenylhalo are optionally substituted with one or two —CH$_3$, and the $C_2$alkynyl and phenyl are optionally substituted with one —CH$_3$;

each $R^{10}$ is independently —OR$^{12}$, —N($R^{12}$)$_2$, —S(O)$_2$R$^{13}$, —OC(O)CHR$^{12}$N($R^{12}$)$_2$, or $C_1$-$C_6$alkyl, wherein the $C_1$-$C_6$alkyl, of $R^{10}$ is optionally independently substituted with one to three $R^{11}$;

each $R^{11}$ is independently halo, —OR$^{12}$, —N($R^{12}$)$_2$, —Si($R^{12}$)$_3$, —C(O)OR$^{12}$, —NR$^{12}$C(O)OR$^{12}$, —OC(O)CHR$^{12}$N($R^{12}$)$_2$, $C_1$-$C_6$alkyl, or heterocyclyl;

each $R^{12}$ is independently hydrogen, $C_1$-$C_6$alkyl or $C_3$-$C_{10}$cycloalkyl; and each $R^{13}$ is independently $C_1$-$C_6$alkyl or $C_3$-$C_{10}$cycloalkyl.

In certain embodiments, each $R^{15}$ is independently $C_1$-$C_6$alkyl.

In certain embodiments, the compound has a structure of formula (V):

(V)

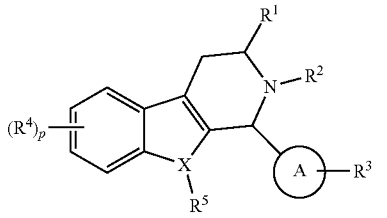

or an enantiomer or pharmaceutically acceptable salt thereof, wherein:

X is N, O or S;

A is a 4 to 7 membered cycloalkyl, 4 to 7 membered heterocyclyl, aryl, heteroaryl, or bridged bicyclic ring having 0-2 heteroatoms independently selected from nitrogen, oxygen, and sulfur;

$R^1$ is H, $C_1$-$C_6$alkyl, —$C_1$-$C_6$alkylhalo, —C(O)OR$^6$, —C(O)N($R^7$)$_2$, —OC(O)R$^6$, —SO$_2$R$^8$, —SOR$^8$, NO$_2$, —OR, —$C_1$-$C_6$alkyl-OR$^{12}$, or —Si($R^{15}$)$_3$;

$R^2$ is —C(O)R$^9$;

$R^3$ is H, halo, —C(O)OR$^{10}$, —C(O)N($R^{11}$)$_2$, —OC(O)R$^{10}$, —$C_0$-$C_6$alkyl$C_3$-$C_8$cycloalkyl, —$C_0$-$C_6$alkylheterocyclyl, —N($R^{11}$)$_2$, —SO$_2$R$^8$, —SOR$^8$, —NO$_2$ or —Si($R^{15}$)$_3$;

$R^4$ is independently halo, CN, —NH$_2$, —SO$_2$, $C_1$-$C_8$alkyl, —OR$^{12}$, —$C_1$-$C_6$alkyl-OR$^{12}$, —$C_1$-$C_6$alkyl-NR$^{12}$ or —OC(O)R$^{12}$;

$R^5$ is H, $C_1$-$C_6$alkyl, or is absent when X is S or O;

p is 0, 1, 2 or 3;

$R^6$ is $C_1$-$C_6$alkyl, $C_3$-$C_6$alkyl, $C_2$-$C_6$alkenyl, $C_2$-$C_6$alkynyl, $C_3$-$C_6$cycloalkyl, heterocyclyl, aryl, heteroaryl, $C_3$-$C_6$cycloalkyl$C_1$-$C_6$alkyl-, $C_3$-$C_6$cycloalkyl$C_2$-$C_6$alkenyl-, heterocyclyl$C_1$-$C_6$alkyl-, heterocyclyl$C_2$-$C_6$alkenyl-, aryl$C_1$-$C_6$alkyl-, aryl$C_2$-$C_6$alkenyl-, heteroaryl$C_1$-$C_6$alkyl-, heteroaryl$C_2$-$C_6$alkenyl-, ($R^{11}$)$_2$N$C_1$-$C_6$alkyl-, or ($R^{11}$)$_2$N$C_2$-$C_6$alkenyl-;

each $R^7$ is independently H, $C_1$-$C_6$alkyl, $C_2$-$C_6$alkenyl, $C_3$-$C_6$cycloalkyl, heterocyclyl, aryl, heteroaryl, $C_3$-$C_6$cycloalkyl$C_1$-$C_6$alkyl-, $C_3$-$C_6$cycloalkyl$C_2$-$C_6$alkenyl-, heterocyclyl$C_1$-$C_6$alkyl-, heterocyclyl$C_2$-$C_6$alkenyl-, aryl$C_1$-$C_6$alkyl-, aryl$C_2$-$C_6$alkenyl-, heteroaryl$C_1$-$C_6$alkyl-, heteroaryl$C_2$-$C_6$alkenyl-, ($R^{11}$)$_2$N$C_1$-$C_6$alkyl-, ($R^{11}$)$_2$N$C_2$-$C_6$alkenyl-, $R^{12}$O—$C_1$-$C_6$alkyl-, or $R^{12}$O(O)C—$C_1$-$C_6$alkyl-, or two $R^7$ together with the nitrogen atom to which they are attached form a 4 to 7 membered heterocyclyl, wherein the heterocyclyl formed by the two $R^7$ groups is optionally substituted with OH, halo, $C_1$-$C_6$alkyl, a 4- to 6-membered heterocyclyl, or ($R^{11}$)$_2$N—, wherein the 4- to 6-membered heterocyclyl when containing 2 or more N atoms is optionally substituted with an N-protecting group;

each $R^8$ is independently $C_1$-$C_6$alkyl, $C_3$-$C_6$alkyl, $C_2$-$C_6$alkenyl, $C_2$-$C_6$alkynyl, $C_3$-$C_6$cycloalkyl, heterocyclyl, aryl, heteroaryl, $C_3$-$C_6$cycloalkyl$C_1$-$C_6$alkyl-, $C_3$-$C_6$cycloalkyl$C_2$-$C_6$alkenyl-, heterocyclyl$C_1$-$C_6$alkyl-, heterocyclyl$C_2$-$C_6$alkenyl-, aryl$C_1$-$C_6$alkyl-, aryl$C_2$-$C_6$alkenyl-, heteroaryl$C_1$-$C_6$alkyl-, heteroaryl$C_2$-$C_6$alkenyl-, adamantyl, adamantyl$C_1$-$C_6$aliphatic-, ($R^{11}$)$_2$N$C_1$-$C_6$alkyl-, ($R^{11}$)$_2$N—, $R^{14}$$C_0$-$C_6$alkyl-;

$R^9$ is —$C_1$-$C_2$alkylhalo, —$C_2$-$C_3$alkenylhalo, or $C_2$alkynyl, wherein the $C_1$-$C_2$alkyl is optionally substituted with one or two halo, one or two —$CH_3$, or one or up to all H is replaced with deuterium;

$R^{10}$ is $C_1$-$C_6$alkyl, $C_2$-$C_6$alkyl, $C_2$-$C_6$alkenyl, $C_2$-$C_6$alkynyl, $C_3$-$C_6$cycloalkyl, heterocyclyl, aryl, heteroaryl, $C_3$-$C_6$cycloalkyl$C_1$-$C_6$alkyl-, $C_3$-$C_6$cycloalkyl$C_2$-$C_6$alkenyl-, heterocyclyl$C_1$-$C_6$alkyl-, heterocyclyl$C_2$-$C_6$alkenyl-, aryl$C_1$-$C_6$alkyl-, aryl$C_2$-$C_6$alkenyl-, heteroaryl$C_1$-$C_6$alkyl-, heteroaryl$C_2$-$C_6$alkenyl-, adamantyl, adamantyl$C_1$-$C_6$aliphatic-, $(R^{11})_2NC_1$-$C_6$alkyl-, $(R^{11})_2NC_2$-$C_6$alkenyl-, $R^{13}(NH_2)CH$—, $R^{14}C_0$-$C_6$alkyl-, or $(R^{15})_3SiC_0$-$C_6$alkyl-;

each $R^{11}$ is independently H, $C_1$-$C_6$alkyl, $C_2$-$C_6$alkenyl, $C_3$-$C_6$cycloalkyl, heterocyclyl, aryl, heteroaryl, $C_3$-$C_6$cycloalkyl$C_1$-$C_6$alkyl-, $C_3$-$C_6$cycloalkyl$C_2$-$C_6$alkenyl-, heterocyclyl$C_1$-$C_6$alkyl-, heterocyclyl$C_2$-$C_6$alkenyl-, aryl$C_1$-$C_6$alkyl-, aryl$C_2$-$C_6$alkenyl-, heteroaryl$C_1$-$C_6$alkyl-, heteroaryl$C_2$-$C_6$alkenyl-, adamantyl, adamantyl$C_1$-$C_6$aliphatic-, $R^{12}O$—$C_1$-$C_6$alkyl-, $(R^{11})_2NC_1$-$C_6$alkyl-, $(R^{11})_2NC_2$-$C_6$alkenyl-, $R^{12}O(O)C$—$C_1$-$C_6$alkyl-, $R^{13}(NH_2)CH$—, $R^{14}C_0$-$C_6$alkyl-, $(R^{15})_3SiC_0$- $C_6$alkyl-, or an N-protecting group; or two $R^{11}$ together with the nitrogen atom to which they are attached form a 4 to 7 membered heterocyclyl, wherein the heterocyclyl formed by the two $R^{11}$ groups has optionally 0, 1 or 2 additional heteroatoms selected from nitrogen, oxygen, and sulfur, and the heterocyclyl is optionally substituted with OH, halo, $C_1$-$C_6$alkyl, $C_1$-$C_6$alkyl-O(O)C—, $(R^{11})_2N$—, or a 4- to 6-membered heterocyclyl, wherein the 4- to 6-membered heterocyclyl is optionally substituted with OH, halo, —$NH_2$, or $C_1$-$C_6$alkyl, or when containing 2 or more N atoms is optionally substituted with an N-protecting group;

each $R^{12}$ is independently H or $C_1$-$C_6$alkyl;

each $R^{13}$ is independently H, $C_1$-$C_6$alkyl, $C_3$-$C_6$cycloalkyl, heterocyclyl, aryl, heteroaryl, $C_3$-$C_6$cycloalkyl$C_1$-$C_6$alkyl-, $C_3$-$C_6$cycloalkyl$C_2$-$C_6$alkenyl-, heterocyclyl$C_1$-$C_6$alkyl-, heterocyclyl$C_2$-$C_6$alkenyl-, aryl$C_1$-$C_6$alkyl-, aryl$C_2$-$C_6$alkenyl-, heteroaryl$C_1$-$C_6$alkyl-, heteroaryl$C_2$-$C_6$alkenyl-, adamantyl, adamantyl$C_1$-$C_6$aliphatic-, or an N protecting group;

$R^{14}$ is a bridged bicyclic ring having 0-2 heteroatoms independently selected from nitrogen, oxygen, and sulfur; and each $R^{15}$ is independently $C_1$-$C_6$alkyl, $C_2$-$C_6$alkenyl, aryl, heteroaryl, aryl$C_1$-$C_6$alkyl-, aryl$C_2$-$C_6$alkenyl-, heteroaryl$C_1$-$C_6$alkyl-, and heteroaryl$C_2$-$C_6$alkenyl-;

wherein the $C_1$-$C_6$alkyl, —$C_3$-$C_6$cycloalkyl, heterocyclyl, aryl, heteroaryl, or bridged bicyclic ring, by itself or attached to another moiety, are independently optionally substituted with 1-3 substituents selected from the group consisting of OH, halo, —$NH_2$, $C_1$-$C_6$alkyl, $C_1$-$C_6$alkyl-O—, $R^{12}O$—$C_1$-$C_6$alkyl(O)C—, and $R^{12}O(O)C$—.

Also provided herein is a compound of formula (V):

(V)

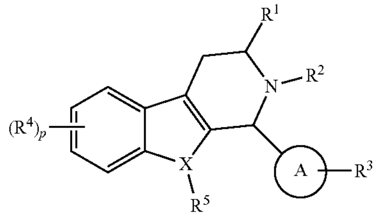

or an enantiomer or pharmaceutically acceptable salt thereof, wherein:

X is N, O or S;

A is a 4 to 7 membered cycloalkyl, 4 to 7 membered heterocyclyl, aryl, heteroaryl, or bridged bicyclic ring having 0-2 heteroatoms independently selected from nitrogen, oxygen, and sulfur;

$R^1$ is H, $C_1$-$C_6$alkyl, —$C_1$-$C_6$alkylhalo, —$C(O)OR^6$, —$C(O)N(R^7)_2$, —$OC(O)R^6$, —$SO_2R^8$, —$SOR^8$, $NO_2$, —OR, —$C_1$-$C_6$alkyl-$OR^{12}$, or —$Si(R^{15})$—;

$R^2$ is —$C(O)R^9$;

$R^3$ is H, halo, —$C(O)OR^{10}$, —$C(O)N(R^{11})_2$, —$OC(O)R^{10}$, —$C_0$-$C_6$alkyl$C_3$-$C_8$cycloalkyl, —$C_0$-$C_6$alkylheterocyclyl, —$N(R^{11})_2$, —$SO_2R^8$, —$SOR^8$, —$NO_2$ or —$Si(R^{15})_3$;

$R^4$ is independently halo, CN, —$NH_2$, —$SO_2$, $C_1$-$C_8$alkyl, —$OR^{12}$, —$C_1$-$C_6$alkyl-$OR^{12}$, —$C_1$-$C_6$alkyl-$NR^{12}$ or —$OC(O)R^{12}$;

$R^5$ is H, $C_1$-$C_6$alkyl, or is absent when X is S or O;

p is 0, 1, 2 or 3;

$R^6$ is $C_1$-$C_6$alkyl, $C_3$-$C_6$alkyl, $C_2$-$C_6$alkenyl, $C_2$-$C_6$alkynyl, $C_3$-$C_6$cycloalkyl, heterocyclyl, aryl, heteroaryl, $C_3$-$C_6$cycloalkyl$C_1$-$C_6$alkyl-, $C_3$-$C_6$cycloalkyl$C_2$-$C_6$alkenyl-, heterocyclyl$C_1$-$C_6$alkyl-, heterocyclyl$C_2$-$C_6$alkenyl-, aryl$C_1$-$C_6$alkyl-, aryl$C_2$-$C_6$alkenyl-, heteroaryl$C_1$-$C_6$alkyl-, heteroaryl$C_2$-$C_6$alkenyl-, $(R^{11})_2NC_1$-$C_6$alkyl-, or $(R^{11})_2NC_2$-$C_6$alkenyl-;

each $R^7$ is independently H, $C_1$-$C_6$alkyl, $C_2$-$C_6$alkenyl, $C_3$-$C_6$cycloalkyl, heterocyclyl, aryl, heteroaryl, $C_3$-$C_6$cycloalkyl$C_1$-$C_6$alkyl-, $C_3$-$C_6$cycloalkyl$C_2$-$C_6$alkenyl-, heterocyclyl$C_1$-$C_6$alkyl-, heterocyclyl$C_2$-$C_6$alkenyl-, aryl$C_1$-$C_6$alkyl-, aryl$C_2$-$C_6$alkenyl-, heteroaryl$C_1$-$C_6$alkyl-, heteroaryl$C_2$-$C_6$alkenyl-, $(R^{11})_2NC_1$-$C_6$alkyl-, $(R^{11})_2NC_2$-$C_6$alkenyl-, $R^{12}O$—$C_1$-$C_6$alkyl-, or $R^{12}O(O)C$—$C_1$-$C_6$alkyl-, or two $R^7$ together with the nitrogen atom to which they are attached form a 4 to 7 membered heterocyclyl, wherein the heterocyclyl formed by the two $R^7$ groups is optionally substituted with OH, halo, $C_1$-$C_6$alkyl, a 4- to 6-membered heterocyclyl, or $(R^{11})_2N$—, wherein the 4- to 6-membered heterocyclyl when containing 2 or more N atoms is optionally substituted with an N-protecting group;

each $R^8$ is independently $C_1$-$C_6$alkyl, $C_3$-$C_6$alkyl, $C_2$-$C_6$alkenyl, $C_2$-$C_6$alkynyl, $C_3$-$C_6$cycloalkyl, heterocyclyl, aryl, heteroaryl, $C_3$-$C_6$cycloalkyl$C_1$-$C_6$alkyl-, $C_3$-$C_6$cycloalkyl$C_2$-$C_6$alkenyl-, heterocyclyl$C_1$-$C_6$alkyl-, heterocyclyl$C_2$-$C_6$alkenyl-, aryl$C_1$-$C_6$alkyl-, aryl$C_2$-$C_6$alkenyl-, heteroaryl$C_1$-$C_6$alkyl-, heteroaryl$C_2$-$C_6$alkenyl-, adamantyl, adamantyl$C_1$-$C_6$aliphatic-, $(R^{11})_2NC_1$-$C_6$alkyl-, $(R^{11})_2N$—, or $R^{14}C_0$-$C_6$alkyl-;

$R^9$ is —$C_1$-$C_2$alkylhalo, —$C_2$-$C_3$alkenylhalo, or $C_2$alkynyl, wherein the $C_1$-$C_2$alkyl is optionally substituted with one or two halo, one or two —$CH_3$, or one or up to all H is replaced with deuterium;

$R^{10}$ is $C_1$-$C_6$alkyl, $C_2$-$C_6$alkyl, $C_2$-$C_6$alkenyl, $C_2$-$C_6$alkynyl, $C_3$-$C_6$cycloalkyl, heterocyclyl, aryl, heteroaryl, $C_3$-$C_6$cycloalkyl$C_1$-$C_6$alkyl-, $C_3$-$C_6$cycloalkyl$C_2$-$C_6$alkenyl-, heterocyclyl$C_1$-$C_6$alkyl-, heterocyclyl$C_2$-$C_6$alkenyl-, aryl$C_1$-$C_6$alkyl-, aryl$C_2$-$C_6$alkenyl-, heteroaryl$C_1$-$C_6$alkyl-, heteroaryl$C_2$-$C_6$alkenyl-, adamantyl, adamantyl$C_1$-

$C_6$aliphatic-, $(R^{11})_2NC_1$-$C_6$alkyl-, $(R^{11})_2NC_2$-$C_6$alkenyl-, $R^{13}(NH_2)CH$—, $R^{14}C_0$-$C_6$alkyl- or $(R^{15})_3SiC_0$-$C_6$alkyl;

each $R^{11}$ is independently H, $C_1$-$C_6$alkyl, $C_2$-$C_6$alkenyl, $C_3$-$C_6$cycloalkyl, heterocyclyl, aryl, heteroaryl, $C_3$-$C_6$cycloalkyl$C_1$-$C_6$alkyl-, $C_3$-$C_6$cycloalkyl$C_2$-$C_6$alkenyl-, heterocyclyl$C_1$-$C_6$alkyl-, heterocyclyl$C_2$-$C_6$alkenyl-, aryl$C_1$-$C_6$alkyl-, aryl$C_2$-$C_6$alkenyl-, heteroaryl$C_1$-$C_6$alkyl-, heteroaryl$C_2$-$C_6$alkenyl-, adamantyl, adamantyl$C_1$-$C_6$aliphatic-, $R^{12}O$—$C_1$-$C_6$alkyl-, $(R^{16})_2NC_1$-$C_6$alkyl-, $(R^{16})_2NC_2$-$C_6$alkenyl-, $R^{12}O(O)C$—$C_1$-$C_6$alkyl-, $R^{13}(NH_2)CH$—, $R^{14}C_0$-$C_6$alkyl-, $(R^{15})_3SiC_0$- $C_6$alkyl-, or an N-protecting group; or two $R^{11}$ together with the nitrogen atom to which they are attached form a 4 to 7 membered heterocyclyl, wherein the heterocyclyl formed by the two $R^{11}$ groups has optionally 0, 1 or 2 additional heteroatoms selected from nitrogen, oxygen, and sulfur, and the heterocyclyl is optionally substituted with OH, halo, $C_1$-$C_6$alkyl, $C_1$-$C_6$alkyl-O(O)C—, $(R^{16})_2N$—, or a 4- to 6-membered heterocyclyl, wherein the 4- to 6-membered heterocyclyl is optionally substituted with OH, halo, —$NH_2$, or $C_1$-$C_6$alkyl, or when containing 2 or more N atoms is optionally substituted with an N-protecting group;

each $R^{12}$ is independently H or $C_1$-$C_6$alkyl;

each $R^{13}$ is independently H, $C_1$-$C_6$alkyl, $C_3$-$C_6$cycloalkyl, heterocyclyl, aryl, heteroaryl, $C_3$-$C_6$cycloalkyl$C_1$-$C_6$alkyl-, $C_3$-$C_6$cycloalkyl$C_2$-$C_6$alkenyl-, heterocyclyl$C_1$-$C_6$alkyl-, heterocyclyl$C_2$-$C_6$alkenyl-, aryl$C_1$-$C_6$alkyl-, aryl$C_2$-$C_6$alkenyl-, heteroaryl$C_1$-$C_6$alkyl-, heteroaryl$C_2$-$C_6$alkenyl-, adamantyl, adamantyl$C_1$-$C_6$aliphatic-, or an N protecting group;

$R^{14}$ is a bridged bicyclic ring having 0-2 heteroatoms independently selected from nitrogen, oxygen, and sulfur; and each $R^{15}$ is independently $C_1$-$C_6$alkyl, $C_2$-$C_6$alkenyl, aryl, heteroaryl, aryl$C_1$-$C_6$alkyl-, aryl$C_2$-$C_6$alkenyl-, heteroaryl$C_1$-$C_6$alkyl-, and heteroaryl$C_2$-$C_6$alkenyl-;

wherein the $C_1$-$C_6$alkyl, —$C_3$-$C_6$cycloalkyl, heterocyclyl, aryl, heteroaryl, or bridged bicyclic ring, by itself or attached to another moiety, are independently optionally substituted with 1-3 substituents selected from the group consisting of OH, halo, —$NH_2$, $C_1$-$C_6$alkyl, $C_1$-$C_6$alkyl-O—, $R^{12}O$—$C_1$-$C_6$alkyl(O)C—, and $R^{12}O(O)C$—;

each $R^{16}$ is independently H, $C_1$-$C_6$alkyl, $C_2$-$C_6$alkenyl, $C_3$-$C_6$cycloalkyl, heterocyclyl, aryl, heteroaryl, $C_3$-$C_6$cycloalkyl$C_1$-$C_6$alkyl-, $C_3$-$C_6$cycloalkyl$C_2$-$C_6$alkenyl-, heterocyclyl$C_1$-$C_6$alkyl-, heterocyclyl$C_2$-$C_6$alkenyl-, aryl$C_1$-$C_6$alkyl-, aryl$C_2$-$C_6$alkenyl-, heteroaryl$C_1$-$C_6$alkyl-, heteroaryl$C_2$-$C_6$alkenyl-, adamantyl, adamantyl$C_1$-$C_6$aliphatic-, $R^{12}O$—$C_1$-$C_6$alkyl-, $(R^{13})_2NC_1$-$C_6$alkyl-, $(R^{13})_2NC_2$-$C_6$alkenyl-, $R^{12}O(O)C$—$C_1$-$C_6$alkyl-, $R^{13}(NH_2)CH$—, $R^{14}C_0$-$C_6$alkyl-, $(R^{15})_3SiC_0$- $C_6$alkyl-, or an N-protecting group; or two $R^{16}$ together with the nitrogen atom to which they are attached form a 4 to 7 membered heterocyclyl, wherein the heterocyclyl formed by the two $R^{16}$ groups has optionally 0, 1 or 2 additional heteroatoms selected from nitrogen, oxygen, and sulfur, and the heterocyclyl is optionally substituted with OH, halo, $C_1$-$C_6$alkyl, $C_1$-$C_6$alkyl-O(O)C—, $(R^{13})_2N$—, or a 4- to 6-membered heterocyclyl, wherein the 4- to 6-membered heterocyclyl is optionally substituted with OH, halo, —$NH_2$, or $C_1$-$C_6$alkyl, or when containing 2 or more N atoms is optionally substituted with an N-protecting group;

with the proviso that:

(a) when

X is N;

$R^1$ is —C(O)$OR^6$ $R^2$ is —C(O)$CH_2$Cl or C(O)$CH_2$F;

A with the $R^3$ is

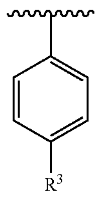

;

p is 0; and $R^5$ is H;

then (i) $R^3$ and $R^6$ are not simultaneously-$NO_2$ and —$CH_3$, respectively, and (ii) when $R^6$ is —$CH_3$, then $R^3$ is other than H, halo, and —$NO_2$; and (b) when X is N;

$R^1$ is —C(O)$OR^6$ $R^2$ is —C(O)$CH_2$Cl or C(O)$CH_2$F;

A with the $R^3$ is

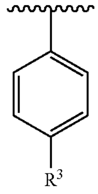

;

$R^3$ is —C(O)$OR^{10}$;

p is 0; and $R^5$ is H;

then $R^6$ and $R^{10}$ are not simultaneously (i) —$CH_3$;

(ii) —$CH_3$ and $C_2$-$C_6$alkynyl, respectively; and (iii) —$CH_2CH_3$ and —$CH_3$, respectively; and (c) when X is N;

$R^1$ is —C(O)$OR^6$, wherein $R^6$ is —$CH_3$;

$R^2$ is —C(O)$CH_2$Cl or —C(O)$CH_2$F;

p is 0;

$R^3$ is H; and $R^5$ is H;

then ring A is other than phenyl; and (d) when

X is N;

$R^1$ is —C(O)$N(R^7)_2$, wherein $R^7$ are H;

$R^2$ is —C(O)$CH_2$Cl or —C(O)$CH_2$F;

p is 0;

$R^5$ is H; and ring A is phenyl;

then $R^3$ is other than H or halo.

In certain embodiments, the compound has a structure of formula (V):

(V)

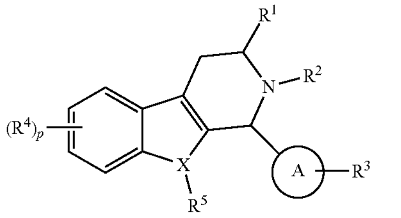

or an enantiomer or pharmaceutically acceptable salt thereof, wherein:

X is N, O or S;

ring A is a 4 to 7 membered cycloalkyl, 4 to 7 membered heterocyclyl, aryl, heteroaryl, or bridged bicyclic ring having 0-2 heteroatoms independently selected from nitrogen, oxygen, and sulfur;

$R^1$ is H, $C_1$-$C_6$alkyl, —$C_1$-$C_6$alkylhalo, —C(O)OR$^6$, —C(O)N(R$^7$)$_2$, —OC(O)R$^6$, —SO$_2$R$^8$, —SOR$^8$, NO$_2$, —OR$^8$, —$C_1$-$C_6$alkyl-OR$^{12}$, or —Si(R$^{15}$)—;

$R^2$ is —C(O)R$^9$;

$R^3$ is H, halo, —C(O)OR$^{10}$, —C(O)N(R$^{11}$)$_2$, —OC(O)R$^{10}$, —$C_0$-$C_6$alkylC$_3$-C$_8$cycloalkyl, —$C_0$-$C_6$alkylheterocyclyl, —N(R$^{11}$)$_2$, —SO$_2$R$^8$, —SOR$^8$, —NO$_2$ or —Si(R$^{15}$)$_3$;

$R^4$ is independently halo, CN, —NH$_2$, —SO$_2$, $C_1$-$C_8$alkyl, —OR$^{12}$, —$C_1$-$C_6$alkyl-OR$^{12}$, —$C_1$-$C_6$alkyl-NR$^{12}$ or —OC(O)R$^{12}$;

$R^5$ is H, $C_1$-$C_6$alkyl, or is absent when X is S or O;

p is 0, 1, 2 or 3;

$R^6$ is $C_1$-$C_6$alkyl, $C_3$-$C_6$alkyl, $C_2$-$C_6$alkenyl, $C_2$-$C_6$alkynyl, $C_3$-$C_6$cycloalkyl, heterocyclyl, aryl, heteroaryl, $C_3$-$C_6$cycloalkylC$_1$-$C_6$alkyl-, $C_3$-$C_6$cycloalkylC$_2$-$C_6$alkenyl-, heterocyclylC$_1$-$C_6$alkyl-, heterocyclylC$_2$-$C_6$alkenyl-, arylC$_1$-$C_6$alkyl-, arylC$_2$-$C_6$alkenyl-, heteroarylC$_1$-$C_6$alkyl-, heteroarylC$_2$-$C_6$alkenyl-, (R$^{11}$)$_2$NC$_1$-$C_6$alkyl-, or (R$^{11}$)$_2$NC$_2$-$C_6$alkenyl-;

each $R^7$ is independently H, $C_1$-$C_6$alkyl, $C_2$-$C_6$alkenyl, $C_3$-$C_6$cycloalkyl, heterocyclyl, aryl, heteroaryl, $C_3$-$C_6$cycloalkylC$_1$-$C_6$alkyl-, $C_3$-$C_6$cycloalkylC$_2$-$C_6$alkenyl-, heterocyclylC$_1$-$C_6$alkyl-, heterocyclylC$_2$-$C_6$alkenyl-, arylC$_1$-$C_6$alkyl-, arylC$_2$-$C_6$alkenyl-, heteroarylC$_1$-$C_6$alkyl-, heteroarylC$_2$-$C_6$alkenyl-, (R$^{11}$)$_2$NC$_1$-$C_6$alkyl-, (R$^{11}$)$_2$NC$_2$-$C_6$alkenyl-, R$^{12}$O—$C_1$-$C_6$alkyl-, or R$^{12}$O(O)C—$C_1$-$C_6$alkyl-, or two $R^7$ together with the nitrogen atom to which they are attached form a 4 to 7 membered heterocyclyl, wherein the heterocyclyl formed by the two $R^7$ groups is optionally substituted with OH, halo, $C_1$-$C_6$alkyl, a 4- to 6-membered heterocyclyl, or (R$^{11}$)$_2$N—, wherein the 4- to 6-membered heterocyclyl when containing 2 or more N atoms is optionally substituted with an N-protecting group;

each $R^8$ is independently $C_1$-$C_6$alkyl, $C_3$-$C_6$alkyl, $C_2$-$C_6$alkenyl, $C_2$-$C_6$alkynyl, $C_3$-$C_6$cycloalkyl, heterocyclyl, aryl, heteroaryl, $C_3$-$C_6$cycloalkylC$_1$-$C_6$alkyl-, $C_3$-$C_6$cycloalkylC$_2$-$C_6$alkenyl-, heterocyclylC$_1$-$C_6$alkyl-, heterocyclylC$_2$-$C_6$alkenyl-, arylC$_1$-$C_6$alkyl-, arylC$_2$-$C_6$alkenyl-, heteroarylC$_1$-$C_6$alkyl-, heteroarylC$_2$-$C_6$alkenyl-, adamantyl, adamantylC$_1$-$C_6$aliphatic-, (R$^{11}$)$_2$NC$_1$-$C_6$alkyl-, (R$^{11}$)$_2$N—, or R$^{14}$C$_0$-$C_6$alkyl-;

$R^9$ is —$C_1$-$C_2$alkylhalo, —$C_2$-$C_3$alkenylhalo, or $C_2$alkynyl, wherein the $C_1$-$C_2$alkyl is optionally substituted with one or two halo, one or two —CH$_3$, or one or up to all H is replaced with deuterium;

$R^{10}$ is $C_1$-$C_6$alkyl, $C_2$-$C_6$alkyl, $C_2$-$C_6$alkenyl, $C_2$-$C_6$alkynyl, $C_3$-$C_6$cycloalkyl, heterocyclyl, aryl, heteroaryl, $C_3$-$C_6$cycloalkylC$_1$-$C_6$alkyl-, $C_3$-$C_6$cycloalkylC$_2$-$C_6$alkenyl-, heterocyclylC$_1$-$C_6$alkyl-, heterocyclylC$_2$-$C_6$alkenyl-, arylC$_1$-$C_6$alkyl-, arylC$_2$-$C_6$alkenyl-, heteroarylC$_1$-$C_6$alkyl-, heteroarylC$_2$-$C_6$alkenyl-, adamantyl, adamantylC$_1$-$C_6$aliphatic-, (R$^{11}$)$_2$NC$_1$-$C_6$alkyl-, (R$^{11}$)$_2$NC$_2$-$C_6$alkenyl-, R$^{13}$(NH$_2$)CH—, R$^{14}$C$_0$-$C_6$alkyl- or (R$^{15}$)$_3$SiC$_0$-$C_6$alkyl;

each $R^{11}$ is independently H, $C_1$-$C_6$alkyl, $C_2$-$C_6$alkenyl, $C_3$-$C_6$cycloalkyl, heterocyclyl, aryl, heteroaryl, $C_3$-$C_6$cycloalkylC$_1$-$C_6$alkyl-, $C_3$-$C_6$cycloalkylC$_2$-$C_6$alkenyl-, heterocyclylC$_1$-$C_6$alkyl-, heterocyclylC$_2$-$C_6$alkenyl-, arylC$_1$-$C_6$alkyl-, arylC$_2$-$C_6$alkenyl-, heteroarylC$_1$-$C_6$alkyl-, heteroarylC$_2$-$C_6$alkenyl-, adamantyl, adamantylC$_1$-$C_6$aliphatic-, R$^{12}$O—$C_1$-$C_6$alkyl-, (R$^{11}$)$_2$NC$_1$-$C_6$alkyl-, (R$^{11}$)$_2$NC$_2$-$C_6$alkenyl-, R$^{12}$O(O)C—$C_1$-$C_6$alkyl-, R$^{13}$(NH$_2$)CH—, R$^{14}$C$_0$-$C_6$alkyl-, (R$^{15}$)$_3$SiC$_0$- $C_6$alkyl-, or an N-protecting group; or two $R^{11}$ together with the nitrogen atom to which they are attached form a 4 to 7 membered heterocyclyl, wherein the heterocyclyl formed by the two $R^{11}$ groups has optionally 0, 1 or 2 additional heteroatoms selected from nitrogen, oxygen, and sulfur, and the heterocyclyl is optionally substituted with OH, halo, $C_1$-$C_6$alkyl, $C_1$-$C_6$alkyl-O(O)C—, (R$^{11}$)$_2$N—, or a 4- to 6-membered heterocyclyl, wherein the 4- to 6-membered heterocyclyl is optionally substituted with OH, halo, —NH$_2$, or $C_1$-$C_6$alkyl, or when containing 2 or more N atoms is optionally substituted with an N-protecting group;

each $R^{12}$ is independently H or $C_1$-$C_6$alkyl;

each $R^{13}$ is independently H, $C_1$-$C_6$alkyl, $C_3$-$C_6$cycloalkyl, heterocyclyl, aryl, heteroaryl, $C_3$-$C_6$cycloalkylC$_1$-$C_6$alkyl-, $C_3$-$C_6$cycloalkylC$_2$-$C_6$alkenyl-, heterocyclylC$_1$-$C_6$alkyl-, heterocyclylC$_2$-$C_6$alkenyl-, arylC$_1$-$C_6$alkyl-, arylC$_2$-$C_6$alkenyl-, heteroarylC$_1$-$C_6$alkyl-, heteroarylC$_2$-$C_6$alkenyl-, adamantyl, adamantylC$_1$-$C_6$aliphatic-, or an N protecting group;

$R^{14}$ is a bridged bicyclic ring having 0-2 heteroatoms independently selected from nitrogen, oxygen, and sulfur; and each $R^{15}$ is independently $C_1$-$C_6$alkyl, $C_2$-$C_6$alkenyl, aryl, heteroaryl, arylC$_1$-$C_6$alkyl-, arylC$_2$-$C_6$alkenyl-, heteroarylC$_1$-$C_6$alkyl-, and heteroarylC$_2$-$C_6$alkenyl-;

wherein the $C_1$-$C_6$alkyl, —$C_3$-$C_6$cycloalkyl, heterocyclyl, aryl, heteroaryl, or bridged bicyclic ring, by itself or attached to another moiety, are independently optionally substituted with 1-3 substituents selected from the group consisting of OH, halo, —NH$_2$, $C_1$-$C_6$alkyl, $C_1$-$C_6$alkyl-O—, R$^{12}$O—$C_1$-$C_6$alkyl(O)C—, and R$^{12}$O(O)C—;

with the proviso that:

(a) when

X is N;

$R^1$ is —C(O)OR$^6$ $R^2$ is —C(O)CH$_2$Cl or C(O)CH$_2$F;

A with the $R^3$ is

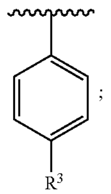

p is 0; and $R^5$ is H;

then (i) $R^3$ and $R^6$ are not simultaneously-$NO_2$ and —$CH_3$, respectively, and (ii) when $R^6$ is —$CH_3$, then $R^3$ is other than H, halo, and —$NO_2$; and (b) when X is N;

$R^1$ is —C(O)$OR^6$ $R^2$ is —C(O)$CH_2$Cl or C(O)$CH_2$F;

A with the $R^3$ is

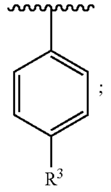

$R^3$ is —C(O)$OR^{10}$;

p is 0; and $R^5$ is H;

then $R^6$ and $R^{10}$ are not simultaneously (i) —$CH_3$;

(ii) —$CH_3$ and $C_2$-$C_6$alkynyl, respectively; and (iii) —$CH_2CH_3$ and —$CH_3$, respectively; and (c) when X is N;

$R^1$ is —C(O)$OR^6$, wherein $R^6$ is —$CH_3$;

$R^2$ is —C(O)$CH_2$Cl or —C(O)$CH_2$F;

p is 0;

$R^3$ is H; and $R^5$ is H;

then ring A is other than phenyl; and (d) when

X is N;

$R^1$ is —C(O)N($R^7$)$_2$, wherein $R^7$ are H;

$R^2$ is —C(O)$CH_2$Cl or —C(O)$CH_2$F;

p is 0;

$R^5$ is H; and ring A is phenyl;

then $R^3$ is other than H or halo.

In certain embodiments, ring A is aryl or heteroaryl. In certain embodiments, ring A is a monocyclic aryl or monocyclic heteroaryl. In certain embodiments, ring A is heterocyclyl. In certain embodiments, ring A is a 4 to 7 membered heterocyclyl. In certain embodiments, ring A is aryl. In certain embodiments, ring A is phenyl. In certain embodiments, ring A is heteroaryl. In certain embodiments, ring A is pyridyl. In certain embodiments, ring A is phenyl, pyridyl, piperidynyl, piperazinyl, or morpholinyl.

In certain embodiments, ring A is aryl or heteroaryl, each of which is substituted by one to three $R^3$. In certain embodiments, ring A is aryl or heteroaryl, each of which is substituted by one to three $R^3$, where at least one $R^3$ is $C_3$-$C_{10}$cycloalkyl, heterocyclyl, aryl, or heteroaryl; wherein each $C_3$-$C_{10}$cycloalkyl, heterocyclyl, aryl, and heteroaryl of $R^3$ is optionally substituted with one to three $R^{10}$.

In certain embodiments, ring A is aryl or heteroaryl, each of which is substituted by two or three $R^3$. In certain embodiments, ring A is aryl or heteroaryl, each of which is substituted by two or three $R^3$; wherein at least one $R^3$ is halo.

In certain embodiments, ring A is:

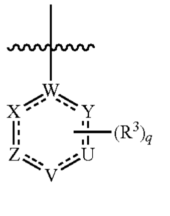

wherein 0 to 3 of U, V, W, X, Y, and Z is independently N, S, or O, and each ------ independently represents a single or double bond, which comply with valency requirements based on U, V, W, X, Y and Z.

In certain embodiments, ring A is:

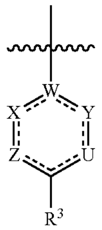

or

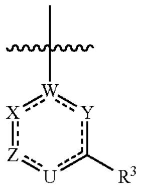

wherein 1 to 3 of U, W, X, Y, and Z is N, S, or O, and ------ represents a single or double bond, which comply with valency requirements based on U, W, X, Y and Z.

In certain embodiments, ring A is cyclohexyl. In certain embodiments, ring A is $C_4$-$C_{10}$cycloalkyl, substituted with one to three $R^3$. In certain embodiments, ring A is a $C_4$-$C_7$cycloalkyl, substituted with one to three $R^3$. In certain embodiments, ring A is bicyclo[1.1.1]pentanyl, substituted with one to three $R^3$. In certain embodiments, ring A is selected from cyclobutyl, cyclopentyl, cyclohexyl, and cycloheptyl, wherein each is substituted with one to three $R^3$.

In certain embodiments, ring A is cyclohexyl. In certain embodiments, ring A is $C_4$-$C_{10}$cycloalkyl. In certain embodiments, ring A is a $C_4$-$C_7$cycloalkyl. In certain embodiments, ring A is bicyclo[1.1.1]pentanyl. In certain embodiments, ring A is selected from cyclobutyl, cyclopentyl, cyclohexyl, and cycloheptyl.

In certain embodiments, ring A is:

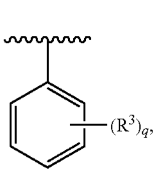
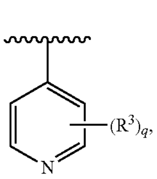
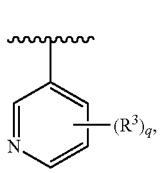
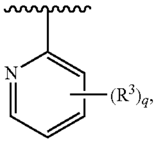
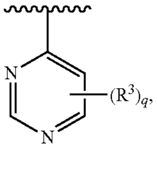
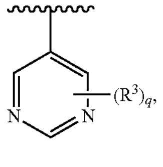

-continued

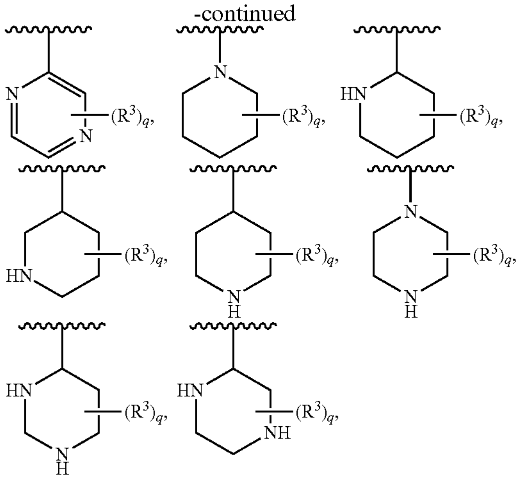

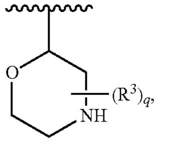

or

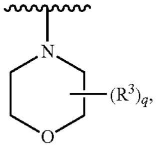

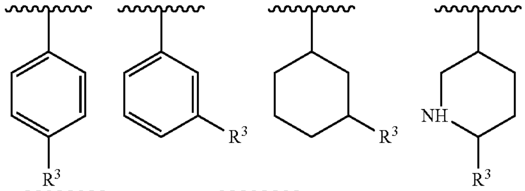

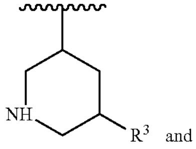

and

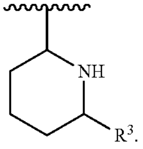

where q and each $R^3$ is independently as defined herein.

In certain embodiments, ring A is selected from:

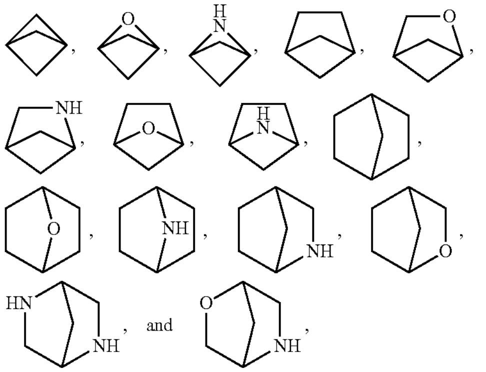

In certain embodiments, ring A is a bridged bicyclic ring selected from:

wherein each is substituted with one to three $R^3$. In certain embodiments, ring A is a bridged bicyclic ring selected from:

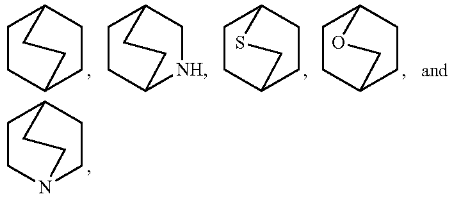

wherein each $R^3$ is attached to a carbon atom on the bridged bicyclic ring.

In certain embodiments, ring A is a bridged bicyclic ring selected from:

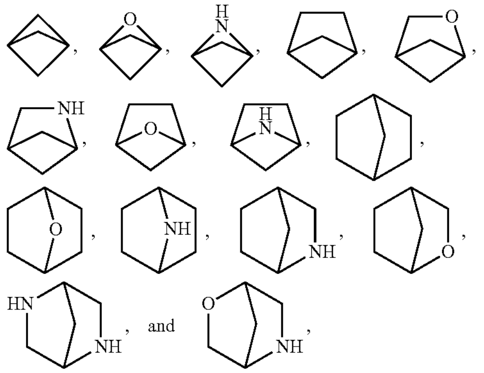

and wherein $R^3$ is attached to a carbon atom on the bridged bicyclic ring. In certain embodiments, ring A is a bridged bicyclic ring selected from:

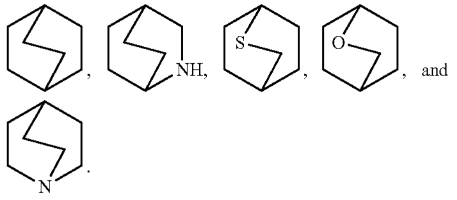

In certain embodiments, ring A is:

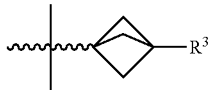

or

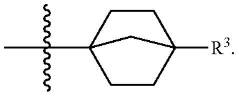

In certain embodiments, at least one $R^3$ is —$NH_2$, —$NHR^8$, —$N(R^8)_2$, —$S(O)_2R^8$, —$S(O)R^8$, —$S(O)_2N(R^7)_2$, —$S(O)N(R^7)_2$, —$NO_2$, —$Si(R^{12})_3$, —$SF_5$, —$C(O)OR^6$, —$C(O)N(R^7)_2$, —$NR^{12}C(O)R^8$, —$NR^{12}C(O)OR^8$, —OC(O)R, —$C(O)R^6$, or —$OC(O)CHR^8N(R^{12})_2$.

In certain embodiments, at least one $R^3$ is —$NHR^8$ or —$N(R)_2$.

In certain embodiments, at least one $R^3$ is —$C(O)OR^6$ or —$C(O)R^6$.

In certain embodiments, at least one $R^3$ is —$S(O)_2N(R^7)_2$, —$S(O)N(R^7)_2$, or —$C(O)N(R^7)_2$.

In certain embodiments, at least one $R^3$ is —$S(O)_2R^8$, —$S(O)R^8$, —$NR^{12}C(O)R^8$, —$NR^{12}C(O)OR^8$, —OC(O)R, or —$OC(O)CHR^8N(R^{12})_2$.

In certain embodiments, the compound of formula (V) has the stereochemical structure (V'):

(V')

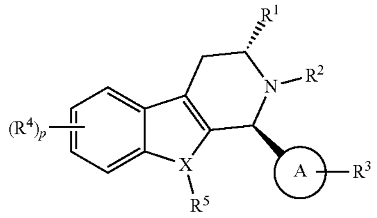

or an enantiomer or a pharmaceutically acceptable salt thereof.

In certain embodiments, each of the compounds described herein can have the stereochemical structure depicted for formula (V').

In certain embodiments, the compound has a structure of formula (Va):

(Va)

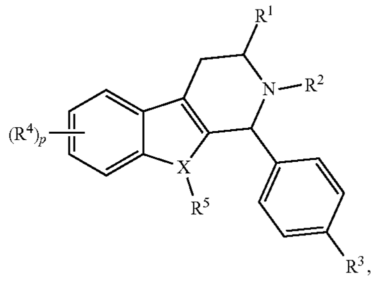

or an enantiomer or pharmaceutically acceptable salt thereof, wherein:

X is N, O or S;

$R^1$ is H, $C_1$-$C_6$alkyl, —$C_1$-$C_6$alkylhalo, —C(O)O$R^6$, —C(O)N($R^7$)$_2$, —OC(O)$R^6$, —$SO_2R^8$, —SO$R^8$, $NO_2$, —O$R^8$, —$C_1$-$C_6$alkyl-O$R^{12}$, or —Si($R^{15}$)$_3$;

$R^2$ is —C(O)$R^9$;

$R^3$ is —C(O)O$R^{10}$, —C(O)N($R^{11}$)$_2$, —OC(O)$R^{10}$, —$C_0$-$C_6$alkyl$C_3$-$C_8$cycloalkyl, —$C_0$-$C_6$alkylheterocyclyl, —N($R^{11}$)$_2$, —$SO_2R^8$, —SO$R^8$, —$NO_2$ or —Si($R^{15}$)$_3$;

$R^4$ is independently halo, CN, —$NH_2$, —$SO_2$, $C_1$-$C_8$alkyl, —O$R^{12}$, —$C_1$-$C_6$alkyl-O$R^{12}$, —$C_1$-$C_6$alkyl-N$R^{12}$ or —OC(O)$R^{12}$;

$R^5$ is H, $C_1$-$C_6$alkyl, or is absent when X is S or O;

p is 0, 1, 2 or 3;

$R^6$ is $C_1$-$C_6$alkyl, $C_3$-$C_6$alkyl, $C_2$-$C_6$alkenyl, $C_2$-$C_6$alkynyl, $C_3$-$C_6$cycloalkyl, heterocyclyl, aryl, heteroaryl, $C_3$-$C_6$cycloalkyl$C_1$-$C_6$alkyl-, $C_3$-$C_6$cycloalkyl$C_2$-$C_6$alkenyl-, heterocyclyl$C_1$-$C_6$alkyl-, heterocyclyl$C_2$-$C_6$alkenyl-, aryl$C_1$-$C_6$alkyl-, aryl$C_2$-$C_6$alkenyl-, heteroaryl$C_1$-$C_6$alkyl-, heteroaryl$C_2$-$C_6$alkenyl-, ($R^{11}$)$_2$N$C_1$-$C_6$alkyl-, or ($R^{11}$)$_2$N$C_2$-$C_6$alkenyl-;

each $R^7$ is independently H, $C_1$-$C_6$alkyl, $C_2$-$C_6$alkenyl, $C_3$-$C_6$cycloalkyl, heterocyclyl, aryl, heteroaryl, $C_3$-$C_6$cycloalkyl$C_1$-$C_6$alkyl-, $C_3$-$C_6$cycloalkyl$C_2$-$C_6$alkenyl-, heterocyclyl$C_1$-$C_6$alkyl-, heterocyclyl$C_2$-$C_6$alkenyl-, aryl$C_1$-$C_6$alkyl-, aryl$C_2$-$C_6$alkenyl-, heteroaryl$C_1$-$C_6$alkyl-, heteroaryl$C_2$-$C_6$alkenyl-, ($R^{11}$)$_2$N$C_1$-$C_6$alkyl-, ($R^{11}$)$_2$N$C_2$-$C_6$alkenyl-, $R^{12}$O—$C_1$-$C_6$alkyl-, or $R^{12}$O(O)C—$C_1$-$C_6$alkyl-, or two $R^7$ together with the nitrogen atom to which they are attached form a 4 to 7 membered heterocyclyl, wherein the heterocyclyl formed by the two $R^7$ groups is optionally substituted with OH, halo, $C_1$-$C_6$alkyl, a 4- to 6-membered heterocyclyl, or ($R^{11}$)$_2$N—, wherein the 4- to 6-membered heterocyclyl when containing 2 or more N atoms is optionally substituted with an N-protecting group;

each $R^8$ is independently $C_1$-$C_6$alkyl, $C_3$-$C_6$alkyl, $C_2$-$C_6$alkenyl, $C_2$-$C_6$alkynyl, $C_3$-$C_6$cycloalkyl, heterocyclyl, aryl, heteroaryl, $C_3$-$C_6$cycloalkyl$C_1$-$C_6$alkyl-, $C_3$-$C_6$cycloalkyl$C_2$-$C_6$alkenyl-, heterocyclyl$C_1$-$C_6$alkyl-, heterocyclyl$C_2$-$C_6$alkenyl-, aryl$C_1$-$C_6$alkyl-, aryl$C_2$-$C_6$alkenyl-, heteroaryl$C_1$-$C_6$alkyl-, heteroaryl$C_2$-$C_6$alkenyl-, adamantyl, adamantyl$C_1$-$C_6$aliphatic-, ($R^{11}$)$_2$N$C_1$-$C_6$alkyl-, ($R^{11}$)$_2$N—, or $R^{14}C_0$-$C_6$alkyl-;

$R^9$ is —$C_1$-$C_2$alkylhalo, —$C_2$-$C_3$alkenylhalo, or $C_2$alkynyl, wherein the $C_1$-$C_2$alkyl is optionally substituted with one or two halo, one or two —$CH_3$, or one or up to all H is replaced with deuterium;

$R^{10}$ is $C_1$-$C_6$alkyl, $C_2$-$C_6$alkyl, $C_2$-$C_6$alkenyl, $C_2$-$C_6$alkynyl, $C_3$-$C_6$cycloalkyl, heterocyclyl, aryl, heteroaryl, $C_3$-$C_6$cycloalkyl$C_1$-$C_6$alkyl-, $C_3$-$C_6$cycloalkyl$C_2$-$C_6$alkenyl-, heterocyclyl$C_1$-$C_6$alkyl-, heterocyclyl$C_2$-$C_6$alkenyl-, aryl$C_1$-$C_6$alkyl-, aryl$C_2$-$C_6$alkenyl-, heteroaryl$C_1$-$C_6$alkyl-, heteroaryl$C_2$-$C_6$alkenyl-, adamantyl, adamantyl$C_1$-$C_6$aliphatic-, ($R^{11}$)$_2$N$C_1$-$C_6$alkyl-, ($R^{11}$)$_2$N$C_2$-$C_6$alkenyl-, $R^{13}$($NH_2$)CH—, $R^{14}C_0$-$C_6$alkyl-, or ($R^{15}$)$_3$Si$C_0$-$C_6$alkyl-;

each $R^{11}$ is independently H, $C_1$-$C_6$alkyl, $C_2$-$C_6$alkenyl, $C_3$-$C_6$cycloalkyl, heterocyclyl, aryl, heteroaryl, $C_3$-$C_6$cycloalkyl$C_1$-$C_6$alkyl-, $C_3$-$C_6$cycloalkyl$C_2$-$C_6$alkenyl-, heterocyclyl$C_1$-$C_6$alkyl-, heterocyclyl$C_2$-$C_6$alkenyl-, aryl$C_1$-$C_6$alkyl-, aryl$C_2$-$C_6$alkenyl-, heteroaryl$C_1$-$C_6$alkyl-, heteroaryl$C_2$-$C_6$alkenyl-, adamantyl, adamantyl$C_1$-$C_6$aliphatic-, $R^{12}$O—$C_1$-$C_6$alkyl-, ($R^{11}$)$_2$N$C_1$-$C_6$alkyl-, ($R^{11}$)$_2$N$C_2$-$C_6$alkenyl-, $R^{12}$O(O)C—$C_1$-$C_6$alkyl-, $R^{13}$($NH_2$)CH—, $R^{14}C_0$-$C_6$alkyl-, ($R^{15}$)$_3$Si$C_0$- $C_6$alkyl-, or an N-protecting group; or two $R^{11}$ together with the nitrogen atom to which they are attached form a 4 to 7 membered heterocyclyl, wherein the heterocyclyl formed by the two $R^{11}$ groups has optionally 0, 1 or 2 additional heteroatoms selected from nitrogen, oxygen, and sulfur, and the heterocyclyl is optionally substituted with OH, halo, $C_1$-$C_6$alkyl, $C_1$-$C_6$alkyl-O(O)C—, ($R^{11}$)$_2$N—, or a 4- to 6-membered heterocyclyl, wherein the 4- to 6-membered heterocyclyl is optionally substituted with OH, halo, —$NH_2$, or $C_1$-$C_6$alkyl, or when containing 2 or more N atoms is optionally substituted with an N-protecting group;

each $R^{12}$ is independently H or $C_1$-$C_6$alkyl;

each $R^{13}$ is independently H, $C_1$-$C_6$alkyl, $C_3$-$C_6$cycloalkyl, heterocyclyl, aryl, heteroaryl, $C_3$-$C_6$cycloalkyl$C_1$-$C_6$alkyl-, $C_3$-$C_6$cycloalkyl$C_2$-$C_6$alkenyl-, heterocyclyl$C_1$-$C_6$alkyl-, heterocyclyl$C_2$-$C_6$alkenyl-, aryl$C_1$-$C_6$alkyl-, aryl$C_2$-$C_6$alkenyl-, heteroaryl$C_1$-$C_6$alkyl-, heteroaryl$C_2$-$C_6$alkenyl-, adamantyl, adamantyl$C_1$-$C_6$aliphatic-, or an N protecting group;

$R^{14}$ is a bridged bicyclic ring having 0-2 heteroatoms independently selected from nitrogen, oxygen, and sulfur; and each $R^{15}$ is independently $C_1$-$C_6$alkyl, $C_2$-$C_6$alkenyl, aryl, heteroaryl, aryl$C_1$-$C_6$alkyl-, aryl$C_2$-$C_6$alkenyl-, heteroaryl$C_1$-$C_6$alkyl-, and heteroaryl$C_2$-$C_6$alkenyl-;

wherein the $C_1$-$C_6$alkyl, —$C_3$-$C_6$cycloalkyl, heterocyclyl, aryl, heteroaryl, or bridged bicyclic ring, by itself or attached to another moiety, are independently optionally substituted with 1-3 substituents selected from the group consisting of OH, halo, —$NH_2$, $C_1$-$C_6$alkyl, $C_1$-$C_6$alkyl-O—, $R^{12}$O—$C_1$-$C_6$alkyl(O)C—, and $R^{12}$O(O)C—;

with the proviso that:

(a) when

X is N;

$R^1$ is —C(O)$OR^6$ $R^2$ is —C(O)$CH_2$Cl or —C(O)$CH_2$F;

p is 0; and $R^5$ is H;

then (i) $R^3$ and $R^6$ are not simultaneously-$NO_2$ and —$CH_3$, respectively;

(b) when

X is N;

$R^1$ is —C(O)$OR^6$ $R^2$ is —C(O)$CH_2$Cl or —C(O)$CH_2$F;

$R^3$ is —C(O)$OR^{10}$;

p is 0; and $R^5$ is H;

then $R^6$ and $R^{10}$ are not simultaneously (i) —$CH_3$;

(ii) —$CH_3$ and $C_2$-$C_6$alkynyl, respectively; and (iii) —$CH_2CH_3$ and —$CH_3$, respectively.

In certain embodiments, the compound of structural formula (Va) has the following stereochemical structure (Va'):

(Va')

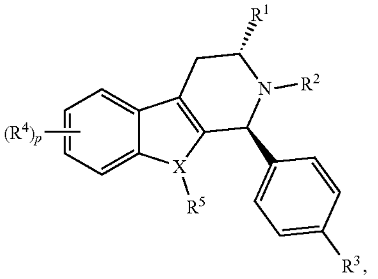

or an enantiomer or a pharmaceutically acceptable salt thereof.

In certain embodiments, the aryl, when used alone or as part of a larger moiety, e.g., aryl$C_1$-$C_6$alkyl, is selected from phenyl, naphthyl, and biphenyl.

In certain embodiments, the heteroaryl, when used alone or as part of a larger moiety, e.g., heteroaryl$C_1$-$C_6$alkyl, is selected from furanyl, imidazolyl, benzimidazolyl, isoxazolyl, oxazolyl, pyrrolyl, pyridyl, pyrimidinyl, pyridazinyl, thiazolyl, thienyl, 3-thienyl, benzofuryl, indolyl, pyrazolyl, isothiazolyl, oxadiazolylpurinyl, pyrazinyl, and quinolinyl.

In certain embodiments, the 4 to 7-membered heterocyclyl is selected from azetidinyl, pyrrolidinyl, piperidinyl, pyrazolidinyl, isoxazolidinyl, oxazolidinyl, thiazolidinyl, imidazolidinyl, piperazinyl, morpholinyl, thiomorpholinyl, 1,3-oxazinanyl, 1,3-thiazinanyl, dihydropyridinyl, 1,3-tetrahydropyrimidinyl, dihydropyrimidinyl, azepanyl and 1,4-diazepanyl.

In certain embodiments, the 4 to 6-membered heterocyclyl when present is selected from azetidinyl, oxetanyl, thietanyl, piperidinyl, 1,2,3,6-tetrahydropyridinyl, pyranyl, tetrahydropyranyl, dioxanyl, 1,3-dioxolanyl, dihydropyranyl, dihydrothienyl, dihydrofuranyl, imidazolinyl, pyrrolidinyl, piperidinyl, pyrazolidinyl, isoxazolidinyl, oxazolidinyl, thiazolidinyl, piperazinyl, morpholinyl, thiomorpholinyl, 1,3-oxazinanyl, 1,3-thiazinanyl, dihydropyridinyl, 1,3-tetrahydropyrimidinyl, and dihydropyrimidinyl.

In certain embodiments, $R^4$ is halo. In certain embodiments, $R^4$ is Br, Cl, or F, and p is 1 or 2.

In certain embodiments, $R^9$ is —$C_1$-$C_2$alkylhalo. In certain embodiments, $R^9$ is —$C_1$-$C_2$alkylCl or —$C_1$-$C_2$alkylF. In certain embodiments, $R^9$ is —$CH_2CH_2$Cl. In certain embodiments, $R^9$ is —$CD_2CD_2$Cl. In certain embodiments, $R^9$ is —$CH_2$Cl or —$CH_2$F. In certain embodiments, $R^9$ is —$CH_2$Cl. In certain embodiments, $R^9$ is —$CD_2$Cl or —$CD_2$F. In certain embodiments, $R^9$ is —$CD_2$Cl.

In certain embodiments, $R^1$ is —C(O)$OR^6$, wherein $R^6$ is a $C_1$-$C_6$alkyl, $C_1$-$C_4$alkyl, or $C_3$-$C_6$alkyl. In certain embodiments, the $R^6$ of —C(O)$OR^6$ is methyl, ethyl, n-propyl, n-butyl, isopropyl, t-butyl, pentyl, or hexyl.

In certain embodiments, $R^3$ is —C(O)$OR^{10}$, wherein $R^{10}$ is a $C_1$-$C_6$alkyl, $C_1$-$C_4$alkyl, or $C_3$-$C_6$alkyl.

In certain embodiments, the $R^{10}$ of —C(O)$OR^{10}$ is methyl, ethyl, n-propyl, n-butyl, isopropyl, t-butyl, pentyl, or hexyl.

As noted for the compounds of formula (Va) and (Va'), when $R^1$ is —C(O)$OR^6$, $R^2$ is —C(O)$CH_2$Cl; and $R^3$ is —C(O)$OR^{10}$, then $R^6$ and $R^{10}$ are not simultaneously: (i) —$CH_3$, (ii) —$CH_3$ and $C_2$-$C_6$alkynyl respectively; and (iii) —$CH_2CH_3$ and —$CH_3$, respectively.

In certain embodiments, the compound has the following structural formula (Vb):

(Vb)

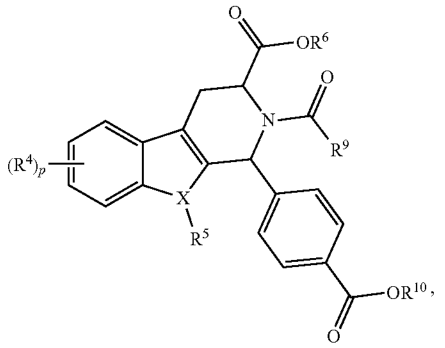

or an enantiomer or pharmaceutically acceptable salt thereof, wherein:

X is N, O or S;

$R^4$ is independently halo, CN, —$NH_2$, —$SO_2$, $C_1$-$C_8$alkyl, —$OR^{12}$, —$C_1$-$C_6$alkyl-$OR^{12}$, —$C_1$-$C_6$alkyl-$NR^{12}$ or —OC(O)$R^{12}$;

$R^5$ is H, $C_1$-$C_6$alkyl, or is absent when X is S or O;

p is 0, 1, 2 or 3;

$R^6$ is $C_1$-$C_6$alkyl, $C_3$-$C_6$alkyl, $C_2$-$C_6$alkenyl, $C_2$-$C_6$alkynyl, $C_3$-$C_6$cycloalkyl, heterocyclyl, aryl, heteroaryl, $C_3$-$C_6$cycloalkyl$C_1$-$C_6$alkyl-, $C_3$-$C_6$cycloalkyl$C_2$-$C_6$alkenyl-, heterocyclyl$C_1$-$C_6$alkyl-, heterocyclyl$C_2$-$C_6$alkenyl-, aryl$C_1$-$C_6$alkyl-, aryl$C_2$-$C_6$alkenyl-, heteroaryl$C_1$-$C_6$alkyl-, heteroaryl$C_2$-$C_6$alkenyl-, $(R^{11})_2$N$C_1$-$C_6$alkyl-, or $(R^{11})_2$N$C_2$-$C_6$alkenyl-;

$R^9$ is —$C_1$-$C_2$alkylhalo, —$C_2$-$C_3$alkenylhalo, or $C_2$alkynyl, wherein the $C_1$-$C_2$alkyl is optionally substituted with one or two halo, one or two —$CH_3$, or one or up to all H is replaced with deuterium;

$R^{10}$ is $C_1$-$C_6$alkyl, $C_2$-$C_6$alkyl, $C_2$-$C_6$alkenyl, $C_2$-$C_6$alkynyl, $C_3$-$C_6$cycloalkyl, heterocyclyl, aryl, heteroaryl, $C_3$-$C_6$cycloalkyl$C_1$-$C_6$alkyl-, $C_3$-$C_6$cycloalkyl$C_2$-$C_6$alkenyl-, heterocyclyl$C_1$-$C_6$alkyl-, heterocyclyl$C_2$-$C_6$alkenyl-, aryl$C_1$-$C_6$alkyl-, aryl$C_2$-$C_6$alkenyl-, heteroaryl$C_1$-$C_6$alkyl-, heteroaryl$C_2$-$C_6$alkenyl-, adamantyl, adamantyl$C_1$-$C_6$aliphatic-, $(R^{11})_2NC_1$-$C_6$alkyl-, $(R^{11})_2NC_2$-$C_6$alkenyl-, $R^{13}(NH_2)CH$—, $R^{14}C_0$-$C_6$alkyl-, or $(R^{15})_3SiC_0$-$C_6$alkyl-;

each $R^{11}$ is independently H, $C_1$-$C_6$alkyl, $C_2$-$C_6$alkenyl, $C_3$-$C_6$cycloalkyl, heterocyclyl, aryl, heteroaryl, $C_3$-$C_6$cycloalkyl$C_1$-$C_6$alkyl-, $C_3$-$C_6$cycloalkyl$C_2$-$C_6$alkenyl-, heterocyclyl$C_1$-$C_6$alkyl-, heterocyclyl$C_2$-$C_6$alkenyl-, aryl$C_1$-$C_6$alkyl-, aryl$C_2$-$C_6$alkenyl-, heteroaryl$C_1$-$C_6$alkyl-, heteroaryl$C_2$-$C_6$alkenyl-, adamantyl, adamantyl$C_1$-$C_6$aliphatic-, $R^{12}O$—$C_1$-$C_6$alkyl-, $(R^{11})_2NC_1$-$C_6$alkyl-, $(R^{11})_2NC_2$-$C_6$alkenyl-, $R^2O(O)C$—$C_1$-$C_6$alkyl-, $R^{13}(NH_2)CH$—, $R^{14}C_0$-$C_6$alkyl-, $(R^{15})_3SiC_0$- $C_6$alkyl-, or an N-protecting group; or two $R^{11}$ together with the nitrogen atom to which they are attached form a 4 to 7 membered heterocyclyl, wherein the heterocyclyl formed by the two $R^{11}$ groups has optionally 0, 1 or 2 additional heteroatoms selected from nitrogen, oxygen, and sulfur, and the heterocyclyl is optionally substituted with OH, halo, $C_1$-$C_6$alkyl, $C_1$-$C_6$alkyl-O(O)C—, $(R^{11})_2N$—, or a 4- to 6-membered heterocyclyl, wherein the 4- to 6-membered heterocyclyl is optionally substituted with OH, halo, —$NH_2$, or $C_1$-$C_6$alkyl, or when containing 2 or more N atoms is optionally substituted with an N-protecting group;

each $R^{12}$ is independently H or $C_1$-$C_6$alkyl;

each $R^{13}$ is independently H, $C_1$-$C_6$alkyl, $C_3$-$C_6$cycloalkyl, heterocyclyl, aryl, heteroaryl, $C_3$-$C_6$cycloalkyl$C_1$-$C_6$alkyl-, $C_3$-$C_6$cycloalkyl$C_2$-$C_6$alkenyl-, heterocyclyl$C_1$-$C_6$alkyl-, heterocyclyl$C_2$-$C_6$alkenyl-, aryl$C_1$-$C_6$alkyl-, aryl$C_2$-$C_6$alkenyl-, heteroaryl$C_1$-$C_6$alkyl-, heteroaryl$C_2$-$C_6$alkenyl-, adamantyl, adamantyl$C_1$-$C_6$aliphatic-, or an N protecting group;

$R^{14}$ is a bridged bicyclic ring having 0-2 heteroatoms independently selected from nitrogen, oxygen, and sulfur; and each $R^{15}$ is independently $C_1$-$C_6$alkyl, $C_2$-$C_6$alkenyl, aryl, heteroaryl, aryl$C_1$-$C_6$alkyl-, aryl$C_2$-$C_6$alkenyl-, heteroaryl$C_1$-$C_6$alkyl-, and heteroaryl$C_2$-$C_6$alkenyl-;

wherein the $C_1$-$C_6$alkyl, —$C_3$-$C_6$cycloalkyl, heterocyclyl, aryl, heteroaryl, or bridged bicyclic ring, by itself or attached to another moiety, are independently optionally substituted with 1-3 substituents selected from the group consisting of OH, halo, —$NH_2$, $C_1$-$C_6$alkyl, $C_1$-$C_6$alkyl-O—, $R^{12}O$—$C_1$-$C_6$alkyl(O)C—, and $R^{12}O(O)C$—;

with the proviso that when

X is N;

$R^9$ is —$CH_2Cl$, —$CH_2F$, —$CD_2Cl$, or —$CD_2F$;

p is 0; and $R^5$ is H, then $R^6$ and $R^{10}$ are not simultaneously (i) —$CH_3$;

(ii) —$CH_3$ and $C_2$-$C_6$alkynyl, respectively; and (iii) —$CH_2CH_3$ and —$CH_3$, respectively.

In certain embodiments, the compound of structural formula (Vb) has the following stereochemical structure (Vb');

(Vb')

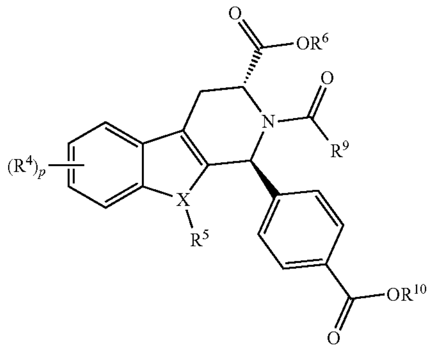

or an enantiomer or pharmaceutically acceptable salt thereof.

In certain embodiments of the compound of formula (Vb) or (Vb'),

X is N, O or S;

$R^4$ is independently halo, CN, —$NH_2$, —$SO_2$, $C_1$-$C_8$alkyl, —$OR^{12}$, —$C_1$-$C_6$alkyl-$OR^{12}$, —$C_1$-$C_6$alkyl-$NR^{12}$ or —$OC(O)R^{12}$;

$R^5$ is H, $C_1$-$C_6$alkyl, or is absent when X is S or O;

$R^6$ is $C_1$-$C_6$alkyl;

$R^9$ is —$C_1$-$C_2$alkylCl, wherein optionally one or up to all H in —$C_1$-$C_2$alkyl is replaced with deuterium;

$R^{10}$ is $C_2$-$C_6$alkyl, $C_3$-$C_6$cycloalkyl, or $C_3$-$C_6$cycloalkyl$C_1$-$C_6$alkyl-;

$R^{12}$ is H or $C_1$-$C_6$alkyl; and p is 0, 1, 2 or 3.

In certain embodiments of the compound of formula (Vb) or (Vb'), X is N. In certain embodiments of formula (Vb) or (Vb'), $R^4$ is halo or absent. In certain embodiments, $R^4$ is Br, Cl, or F, and p is 1 or 2. In certain embodiments of formula (Vb) or (Vb'), $R^6$ is $C_3$-$C_6$alkyl. In certain embodiments of formula (Vb) or (Vb'), $R^{10}$ is $C_3$-$C_6$alkyl. In certain embodiments of formula (Vb) or (Vb'), X is N, $R^4$ is halo or absent, and $R^6$ is $C_3$-$C_6$alkyl. In certain embodiments of formula (Vb) or (Vb'), X is N, $R^4$ is halo or absent, and $R^{10}$ is $C_3$-$C_6$alkyl.

In certain embodiments of the compound of formula (Vb) or (Vb'), or an enantiomer or pharmaceutically acceptable salt thereof, X is N, O or S;

$R^4$ is independently halo, CN, —$NH_2$, —$SO_2$, $C_1$-$C_8$alkyl, —$OR^{12}$, —$C_1$-$C_6$alkyl-$OR^{12}$, —$C_1$-$C_6$alkyl-$NR^{12}$ or —$OC(O)R^{12}$;

$R^5$ is H, $C_1$-$C_6$alkyl, or is absent when X is S or O;

$R^6$ is $C_3$-$C_6$alkyl;

$R^9$ is —$C_1$-$C_2$alkylCl, wherein optionally one or up to all H in —$C_1$-$C_2$alkyl is replaced with deuterium;

$R^{10}$ is $C_1$-$C_6$alkyl;

$R^{12}$ is H or $C_1$-$C_6$alkyl; and p is 0, 1, 2 or 3.

In certain embodiments of the compound of formula (Vb) and (Vb'), $R^6$ is t-butyl and $R^{10}$ is $C_1$-$C_6$alkyl.

In certain embodiments of the compound of formula (Vb) and (Vb'), $R^6$ is $C_3$-$C_6$alkyl; and $R^{10}$ is —$CH_3$. In certain embodiments, $R^6$ is t-butyl.

In certain embodiments, $R^{10}$ is t-butyl.

In certain embodiments of the compound of formula (Vb) or (Vb'), or an enantiomer or pharmaceutically acceptable salt thereof, X is N, O or S;

$R^4$ is independently halo, CN, —$NH_2$, —$SO_2$, $C_1$-$C_8$alkyl, —$OR^{12}$, —$C_1$-$C_6$alkyl-$OR^{12}$, —$C_1$-$C_6$alkyl-$NR^{12}$ or —$OC(O)R^{12}$;

$R^5$ is H, $C_1$-$C_6$alkyl, or is absent when X is S or O;

$R^6$ is $C_1$-$C_6$alkyl;

$R^9$ is —$C_1$-$C_2$alkylCl, wherein optionally one or up to all H in —$C_1$-$C_2$alkyl is replaced with deuterium;

$R^{10}$ is $C_3$-$C_6$alkyl;

$R^{12}$ is H or $C_1$-$C_6$alkyl; and p is 0, 1, 2 or 3.

In certain embodiments of the compound of formula (Vb) and (Vb'), $R^6$ is $C_1$-$C_6$alkyl and $R^{10}$ is t-butyl.

In certain embodiments of the compound of formula (Vb) and (Vb'), $R^6$ is —$CH_3$; and $R^{10}$ is $C_3$-$C_6$alkyl. In certain embodiments, $R^6$ is —$CH_3$ and $R^{10}$ is t-butyl.

In certain embodiments of the compound of formula (Vb) and (Vb'), $R^6$ is ethyl; and $R^{10}$ is t-butyl.

In certain embodiments of the compound of structural formula (Vb) or (Vb'), or an enantiomer or pharmaceutically acceptable salt thereof, X is N, O or S;

$R^4$ is independently halo, CN, —$NH_2$, —$SO_2$, $C_1$-$C_8$alkyl, —$OR^{12}$, —$C_1$-$C_6$alkyl-$OR^{12}$, —$C_1$-$C_6$alkyl-$NR^{12}$ or —$OC(O)R^{12}$;

$R^5$ is H, $C_1$-$C_6$alkyl, or is absent when X is S or O;

$R^6$ is $C_1$-$C_6$alkyl;

$R^9$ is —$C_1$-$C_2$alkylCl, wherein optionally one or up to all H in —$C_1$-$C_2$alkyl is replaced with deuterium; and $R^{10}$ is adamantyl or adamantyl$C_1$-$C_6$aliphatic-;

$R^{12}$ is H or $C_1$-$C_6$alkyl; and p is 0, 1, 2 or 3.

In certain embodiments, the adamantyl is selected from the following:

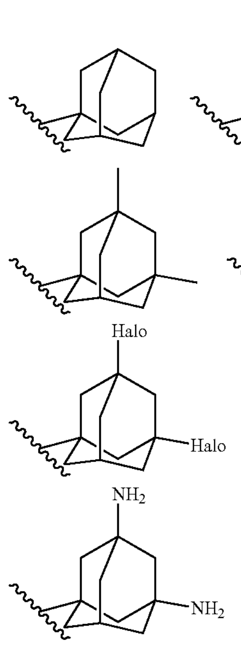

In certain embodiments of the compound of formula (V), (V'), (Va), (Va'), (Vb), and (Vb'), $R^6$ is methyl, ethyl, n-propyl, n-butyl, isopropyl, t-butyl, pentyl, or hexyl; and $R^{10}$ is adamantyl$C_1$-$C_6$aliphatic-.

In certain embodiments of the compound of formula (Vb) or (Vb'), X is N. In certain embodiments of the compound of formula (Vb) or (Vb'), X is N; and $R^5$ is H.

In certain embodiments of the compound of formula (Vb) or (Vb'), $R^4$ is halo. In certain embodiments of formula (Vb) or (Vb'), p is 0.

In certain embodiments of the compound of formula (V), (V'), (Va) or (Va'), $R^1$ is —$C(O)N(R^7)_2$ or —$OC(O)R^6$; and $R^3$ is —$C(O)OR^{10}$. In certain embodiments, $R^1$ is —$C(O)N(R^7)_2$.

In certain embodiments of the compound of formula (V), (V'), (Va) or (Va'), $R^1$ is —$C(O)OR^6$; and $R^3$ is —$C(O)N(R^{11})_2$, or —$OC(O)R^{10}$. In certain embodiments, $R^3$ is —$C(O)N(R^{11})_2$.

In certain embodiments, the compound has the following structural formula (Vc):

(Vc)

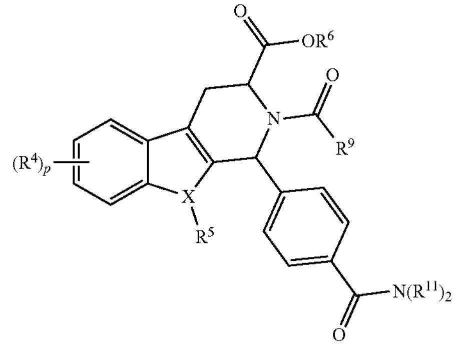

or an enantiomer or pharmaceutically acceptable salt thereof, wherein:

X is N, O or S;

$R^4$ is independently halo, CN, —$NH_2$, —$SO_2$, $C_1$-$C_8$alkyl, —$OR^{12}$, —$C_1$-$C_6$alkyl-$OR^{12}$, —$C_1$-$C_6$alkyl-$NR^{12}$ or —$OC(O)R^{12}$;

$R^5$ is H, $C_1$-$C_6$alkyl, or is absent when X is S or O;

p is 0, 1, 2 or 3;

each $R^6$ is independently $C_1$-$C_6$alkyl, $C_3$-$C_6$alkyl, $C_2$-$C_6$alkenyl, $C_2$-$C_6$alkynyl, $C_3$-$C_6$cycloalkyl, heterocyclyl, aryl, heteroaryl, $C_3$-$C_6$cycloalkyl$C_1$-$C_6$alkyl-, $C_3$-$C_6$cycloalkyl$C_2$-$C_6$alkenyl-, heterocyclyl$C_1$-$C_6$alkyl-, heterocyclyl$C_2$-$C_6$alkenyl-, aryl$C_1$-$C_6$alkyl-, aryl$C_2$-$C_6$alkenyl-, heteroaryl$C_1$-$C_6$alkyl-, heteroaryl$C_2$-$C_6$alkenyl-, $(R^{11})_2NC_1$-$C_6$alkyl-, or $(R^{11})_2NC_2$-$C_6$alkenyl-;

$R^9$ is —$C_1$-$C_2$alkylhalo, —$C_2$-$C_3$alkenylhalo, or $C_2$alkynyl, wherein the $C_1$-$C_2$alkyl is optionally substituted with one or two halo, one or two —$CH_3$, or one or up to all H in —$C_1$-$C_2$alkyl is replaced with deuterium;

each $R^{11}$ is independently H, $C_1$-$C_6$alkyl, $C_2$-$C_6$alkenyl, $C_3$-$C_6$cycloalkyl, heterocyclyl, aryl, heteroaryl, $C_3$-$C_6$cycloalkyl$C_1$-$C_6$alkyl-, $C_3$-$C_6$cycloalkyl$C_2$-$C_6$alkenyl-, heterocyclyl$C_1$-$C_6$alkyl-, heterocyclyl$C_2$-$C_6$alkenyl-, aryl$C_1$-$C_6$alkyl-, aryl$C_2$-$C_6$alkenyl-, heteroaryl$C_1$-$C_6$alkyl-, heteroaryl$C_2$-$C_6$alkenyl-, adamantyl, adamantyl$C_1$-$C_6$aliphatic-, $R^{12}O$—$C_1$-$C_6$alkyl-, $(R^{11})_2NC_1$-$C_6$alkyl-, $(R^{11})_2NC_2$-$C_6$alkenyl-, $R^{12}O(O)C$—$C_1$-$C_6$alkyl-, $R^{13}(NH_2)CH$—, $R^{14}C_0$-$C_6$alkyl-, $(R^{15})_3SiC_0$- $C_6$alkyl-, or an N-protecting group; or two $R^{11}$ together with the nitrogen atom to which they are attached form a 4 to 7 membered heterocyclyl, wherein the heterocyclyl formed by the two $R^{11}$ groups has optionally 0, 1 or 2 additional heteroatoms selected from nitrogen, oxygen, and sulfur, and the heterocyclyl is optionally substituted with OH, halo, $C_1$-$C_6$alkyl, $C_1$-$C_6$alkyl-O(O)C—, $(R^{11})_2N$—, or a 4- to 6-membered heterocyclyl, wherein the 4- to 6-membered heterocyclyl is optionally substituted with OH, halo, —$NH_2$, or $C_1$-$C_6$alkyl, or when containing 2 or more N atoms is optionally substituted with an N-protecting group;

each $R^{12}$ is independently H or $C_1$-$C_6$alkyl;

each $R^{13}$ is independently H, $C_1$-$C_6$alkyl, $C_3$-$C_6$cycloalkyl, heterocyclyl, aryl, heteroaryl, $C_3$-$C_6$cycloalkyl$C_1$-$C_6$alkyl-, $C_3$-$C_6$cycloalkyl$C_2$-$C_6$alkenyl-, heterocyclyl$C_1$-$C_6$alkyl-, heterocyclyl$C_2$-$C_6$alkenyl-, aryl$C_1$-$C_6$alkyl-, aryl$C_2$-$C_6$alkenyl-, heteroaryl$C_1$-$C_6$alkyl-, heteroaryl$C_2$-$C_6$alkenyl-, adamantyl, adamantyl$C_1$-$C_6$aliphatic-, or an N protecting group;

$R^{14}$ is a bridged bicyclic ring having 0-2 heteroatoms independently selected from nitrogen, oxygen, and sulfur; and each $R^{15}$ is independently $C_1$-$C_6$alkyl, $C_2$-$C_6$alkenyl, aryl, heteroaryl, aryl$C_1$-$C_6$alkyl-, aryl$C_2$-$C_6$alkenyl-, heteroaryl$C_1$-$C_6$alkyl-, and heteroaryl$C_2$-$C_6$alkenyl-;

wherein the $C_1$-$C_6$alkyl, —$C_3$-$C_6$cycloalkyl, heterocyclyl, aryl, heteroaryl, or bridged bicyclic ring, by itself or attached to another moiety, are independently optionally substituted with 1-3 substituents selected from the group consisting of OH, halo, —$NH_2$, $C_1$-$C_6$alkyl, $C_1$-$C_6$alkyl-O—, $R^{12}$O—$C_1$-$C_6$alkyl(O)C—, and $R^{12}$O(O)C—.

In certain embodiments, the compound has the following structural formula (Vd):

(Vd)

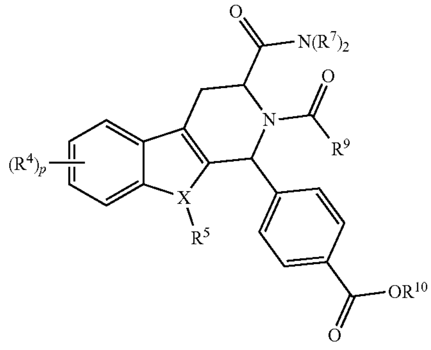

or an enantiomer or pharmaceutically acceptable salt thereof, wherein:

X is N, O or S;

$R^4$ is independently halo, CN, —$NH_2$, —$SO_2$, $C_1$-$C_8$alkyl, —$OR^{12}$, —$C_1$-$C_6$alkyl-$OR^{12}$, —$C_1$-$C_6$alkyl-$NR^{12}$ or —OC(O)$R^{12}$;

$R^5$ is H, $C_1$-$C_6$alkyl, or is absent when X is S or O;

p is 0, 1, 2 or 3;

each $R^7$ is independently H, $C_1$-$C_6$alkyl, $C_2$-$C_6$alkenyl, $C_3$-$C_6$cycloalkyl, heterocyclyl, aryl, heteroaryl, $C_3$-$C_6$cycloalkyl$C_1$-$C_6$alkyl-, $C_3$-$C_6$cycloalkyl$C_2$-$C_6$alkenyl-, heterocyclyl$C_1$-$C_6$alkyl-, heterocyclyl$C_2$-$C_6$alkenyl-, aryl$C_1$-$C_6$alkyl-, aryl$C_2$-$C_6$alkenyl-, heteroaryl$C_1$-$C_6$alkyl-, heteroaryl$C_2$-$C_6$alkenyl-, $(R^{11})_2NC_1$-$C_6$alkyl-, $(R^{11})_2NC_2$-$C_6$alkenyl-, $R^{12}$O—$C_1$-$C_6$alkyl-, or $R^{12}$O(O)C—$C_1$-$C_6$alkyl-, or two $R^7$ together with the nitrogen atom to which they are attached form a 4 to 7 membered heterocyclyl, wherein the heterocyclyl formed by the two $R^7$ groups is optionally substituted with OH, halo, $C_1$-$C_6$alkyl, a 4- to 6-membered heterocyclyl, or $(R^{11})_2N$—, wherein the 4- to 6-membered heterocyclyl when containing 2 or more N atoms is optionally substituted with an N-protecting group;

$R^9$ is —$C_1$-$C_2$alkylhalo, —$C_2$-$C_3$alkenylhalo, or $C_2$alkynyl, wherein the $C_1$-$C_2$alkyl is optionally substituted with one or two halo, one or two —$CH_3$, or one or up to all H in —$C_1$-$C_2$alkyl is replaced with deuterium;

$R^{10}$ is $C_1$-$C_6$alkyl, $C_2$-$C_6$alkyl, $C_2$-$C_6$alkenyl, $C_2$-$C_6$alkynyl, $C_3$-$C_6$cycloalkyl, heterocyclyl, aryl, heteroaryl, $C_3$-$C_6$cycloalkyl$C_1$-$C_6$alkyl-, $C_3$-$C_6$cycloalkyl$C_2$-$C_6$alkenyl-, heterocyclyl$C_1$-$C_6$alkyl-, heterocyclyl$C_2$-$C_6$alkenyl-, aryl$C_1$-$C_6$alkyl-, aryl$C_2$-$C_6$alkenyl-, heteroaryl$C_1$-$C_6$alkyl-, heteroaryl$C_2$-$C_6$alkenyl-, adamantyl, adamantyl$C_1$-$C_6$aliphatic-, $(R^{11})_2NC_1$-$C_6$alkyl-, $(R^{11})_2NC_2$-$C_6$alkenyl-, $R^{13}(NH_2)$CH—, $R^{14}C_0$-$C_6$alkyl-, $(R^{15})_3SiC_0$-$C_6$alkyl-;

each $R^{11}$ is independently H, $C_1$-$C_6$alkyl, $C_2$-$C_6$alkenyl, $C_3$-$C_6$cycloalkyl, heterocyclyl, aryl, heteroaryl, $C_3$-$C_6$cycloalkyl$C_1$-$C_6$alkyl-, $C_3$-$C_6$cycloalkyl$C_2$-$C_6$alkenyl-, heterocyclyl$C_1$-$C_6$alkyl-, heterocyclyl$C_2$-$C_6$alkenyl-, aryl$C_1$-$C_6$alkyl-, aryl$C_2$-$C_6$alkenyl-, heteroaryl$C_1$-$C_6$alkyl-, heteroaryl$C_2$-$C_6$alkenyl-, adamantyl, adamantyl$C_1$-$C_6$aliphatic-, $R^{12}$O—$C_1$-$C_6$alkyl-, $(R^{11})_2NC_1$-$C_6$alkyl-, $(R^{11})_2NC_2$-$C_6$alkenyl-, $R^{12}$O(O)C—$C_1$-$C_6$alkyl-, $R^{13}(NH_2)$CH—, $R^{14}C_0$-$C_6$alkyl-, $(R^{15})_3SiC_0$- $C_6$alkyl-, or an N-protecting group; or two $R^{11}$ together with the nitrogen atom to which they are attached form a 4 to 7 membered heterocyclyl, wherein the heterocyclyl formed by the two $R^{11}$ groups has optionally 0, 1 or 2 additional heteroatoms selected from nitrogen, oxygen, and sulfur, and the heterocyclyl is optionally substituted with OH, halo, $C_1$-$C_6$alkyl, $C_1$-$C_6$alkyl-O(O)C—, $(R^{11})_2N$—, or a 4- to 6-membered heterocyclyl, wherein the 4- to 6-membered heterocyclyl is optionally substituted with OH, halo, —$NH_2$, or $C_1$-$C_6$alkyl, or when containing 2 or more N atoms is optionally substituted with an N-protecting group;

each $R^{12}$ is independently H or $C_1$-$C_6$alkyl;

each $R^{13}$ is independently H, $C_1$-$C_6$alkyl, $C_3$-$C_6$cycloalkyl, heterocyclyl, aryl, heteroaryl, $C_3$-$C_6$cycloalkyl$C_1$-$C_6$alkyl-, $C_3$-$C_6$cycloalkyl$C_2$-$C_6$alkenyl-, heterocyclyl$C_1$-$C_6$alkyl-, heterocyclyl$C_2$-$C_6$alkenyl-, aryl$C_1$-$C_6$alkyl-, aryl$C_2$-$C_6$alkenyl-, heteroaryl$C_1$-$C_6$alkyl-, heteroaryl$C_2$-$C_6$alkenyl-, adamantyl, adamantyl$C_1$-$C_6$aliphatic-, or an N protecting group;

$R^{14}$ is a bridged bicyclic ring having 0-2 heteroatoms independently selected from nitrogen, oxygen, and sulfur; and each $R^{15}$ is independently $C_1$-$C_6$alkyl, $C_2$-$C_6$alkenyl, aryl, heteroaryl, aryl$C_1$-$C_6$alkyl-, aryl$C_2$-$C_6$alkenyl-, heteroaryl$C_1$-$C_6$alkyl-, and heteroaryl$C_2$-$C_6$alkenyl-;

wherein the $C_1$-$C_6$alkyl, —$C_3$-$C_6$cycloalkyl, heterocyclyl, aryl, heteroaryl, or bridged bicyclic ring, by itself or attached to another moiety, are independently optionally substituted with 1-3 substituents selected from the group consisting of OH, halo, —$NH_2$, $C_1$-$C_6$alkyl, $C_1$-$C_6$alkyl-O—, $R^{12}$O—$C_1$-$C_6$alkyl(O)C—, and $R^{12}$O(O)C—.

In certain embodiments, the compound of formula (Vc) and (Vd) has the following stereochemical structure (Vc') and (Vd'), respectively:

(Vc')

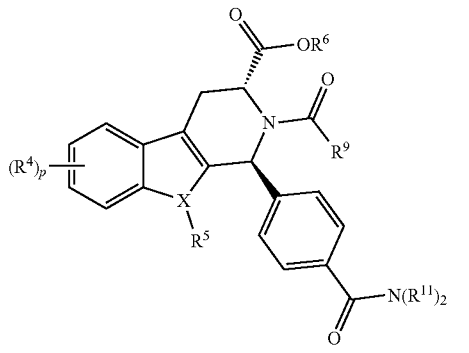

(Vd')

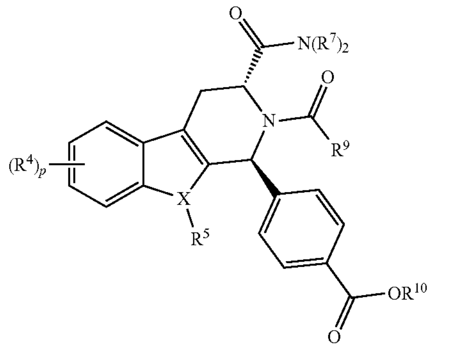

or an enantiomer or pharmaceutically acceptable salt thereof.

In certain embodiments of the compound of formula (Vc) or (Vc'), or an enantiomer or pharmaceutically acceptable salt thereof, X is N, O or S;

$R^4$ is independently halo, CN, —$NH_2$, —$SO_2$, $C_1$-$C_8$alkyl, —$OR^{12}$, —$C_1$-$C_6$alkyl-$OR^{12}$, —$C_1$-$C_6$alkyl-$NR^{12}$ or —OC(O)$R^{12}$;

$R^5$ is H, $C_1$-$C_6$alkyl, or is absent when X is S or O;

$R^6$ is $C_1$-$C_6$ alkyl;

$R^9$ is —$C_1$-$C_2$alkylCl, wherein optionally one or up to all H in —$C_1$-$C_2$alkyl is replaced with deuterium;

$R^{11}$ are as defined for formula (V) above;

$R^{12}$ is H or $C_1$-$C_6$alkyl; and p is 0, 1, 2 or 3.

In certain embodiments of the compound of formula (Vc) and (Vc'), each $R^{11}$ is a $C_1$-$C_6$alkyl. In certain embodiments of the compound of formula (Vc) and (Vc'), each $R^{11}$ is —$CH_3$. In certain embodiments of the compound of formula (Vc) and (Vc'), one of $R^{11}$ is $R^{12}$O(O)C—$C_1$-$C_6$alkyl- or $R^{12}$O—$C_1$-$C_6$alkyl-, wherein the $C_1$-$C_6$ alkyl is optionally substituted with $C_1$-$C_6$alkyl or —$NH_2$, and $R^{12}$ is H or $C_1$-$C_6$alkyl.

In certain embodiments of formula (Vc) and (Vc'), the two $R^{11}$ group together with the nitrogen atom to which they are attached form a 4 to 7 membered heterocyclyl, wherein the heterocyclyl formed by the two $R^{11}$ groups is optionally substituted with a 4- to 6-membered heterocyclyl or —N($C_1$-$C_6$alkyl)$_2$, wherein the 4- to 6-membered heterocyclyl when containing 2 or more N atoms is optionally substituted with an N-protecting group. In certain embodiments, the 4 to 7 membered heterocyclyl is selected from azetidinyl, pyrrolidinyl, piperidinyl, pyrazolidinyl, isoxazolidinyl, oxazolidinyl, thiazolidinyl, imidazolidinyl, piperazinyl, morpholinyl, thiomorpholinyl, 1,3-oxazinanyl, 1,3-thiazinanyl, dihydropyridinyl, tetrahydropyranyl, 1,3-tetrahydropyrimidinyl, dihydropyrimidinyl, azepanyl and 1,4-diazepanyl. In certain embodiments, the 4- to 6-membered heterocyclyl, when present as a substituent, is selected from azetidinyl, oxetanyl, thietanyl, piperidinyl, 1,2,3,6-tetrahydropyridinyl, pyranyl, dioxanyl, 1,3-dioxolanyl, dihydropyranyl, dihydrothienyl, dihydrofuranyl, imidazolinyl, pyrrolidinyl, piperidinyl, pyrazolidinyl, isoxazolidinyl, oxazolidinyl, thiazolidinyl, piperazinyl, morpholinyl, thiomorpholinyl, 1,3-oxazinanyl, 1,3-thiazinanyl, dihydropyridinyl, 1,3-tetrahydropyrimidinyl, and dihydropyrimidinyl. In certain embodiments, the N-protecting group when present is t-Boc.

In certain embodiments of the compound of formula (Vd) or (Vd'), or an enantiomer or pharmaceutically acceptable salt thereof, X is N, O or S;

$R^4$ is independently halo, CN, —$NH_2$, —$SO_2$, $C_1$-$C_8$alkyl, —$OR^{12}$, —$C_1$-$C_6$alkyl-$OR^{12}$, —$C_1$-$C_6$alkyl-$NR^{12}$ or —OC(O)$R^{12}$;

$R^5$ is H, $C_1$-$C_6$alkyl, or is absent when X is S or O;

$R^7$ is as defined for formula (V) above;

$R^9$ is —$C_1$-$C_2$alkylCl, wherein optionally one or up to all H in —$C_1$-$C_2$alkyl is replaced with deuterium;

$R^{10}$ is $C_1$-$C_6$alkyl;

$R^{12}$ is H or $C_1$-$C_6$alkyl; and p is 0, 1, 2 or 3.

In certain embodiments of the compound of formula (Vd) and (Vd'), each $R^7$ is a H or $C_1$-$C_6$alkyl. In certain embodiments of the compound of formula (Vd) and (Vd'), $R^7$ is $C_1$-$C_6$alkyl. In certain embodiments of the compound of formula (Vd) and (Vd'), $R^7$ is $C_1$-$C_6$alkyl and $R^{10}$ is $C_1$-$C_6$alkyl. In certain embodiments of the compound of formula (Vd), $R^7$ is $R^{12}$O(O)C—$C_1$-$C_6$alkyl-, wherein $C_1$-$C_6$ alkyl is optionally substituted with $C_1$-$C_6$alkyl or $NH_2$, and each $R^{12}$ is independently H or $C_1$-$C_6$alkyl.

In certain embodiments of the compound of formula (Vd) or (Vd'), or an enantiomer or pharmaceutically acceptable salt thereof, X is N, O or S;

$R^4$ is independently halo, CN, —$NH_2$, —$SO_2$, $C_1$-$C_8$alkyl, —$OR^{12}$, —$C_1$-$C_6$alkyl-$OR^{12}$, —$C_1$-$C_6$alkyl-$NR^2$ or —OC(O)$R^{12}$;

$R^5$ is H, $C_1$-$C_6$alkyl, or is absent when X is S or O;

$R^7$ is $C_1$-$C_6$alkyl;

$R^9$ is —$C_1$-$C_2$alkylCl, wherein optionally one or up to all H in —$C_1$-$C_2$alkyl is replaced with deuterium;

$R^{10}$ is $C_1$-$C_6$alkyl;

$R^{12}$ is H or $C_1$-$C_6$alkyl; and p is 0, 1, 2 or 3.

In certain embodiments of the compound of formula (Vd) or (Vd'), or an enantiomer or pharmaceutically acceptable salt thereof, $R^{10}$ is t-butyl.

In certain embodiments of the compound of formula (Vc), (Vc'), (Vd), and (Vd'), X is N. In certain embodiments of the compound of formula (Vc), (Vc'), (Vd), and (Vd'), X is N; and $R^5$ is H.

In certain embodiments of the compound of formula (Vc), (Vc'), (Vd), and (Vd'), $R^4$ is halo. In certain embodiments of formula (Vc), (Vc'), (Vd), and (Vd'), p is 0.

In certain embodiments, the compound has the formula:

(Ve)

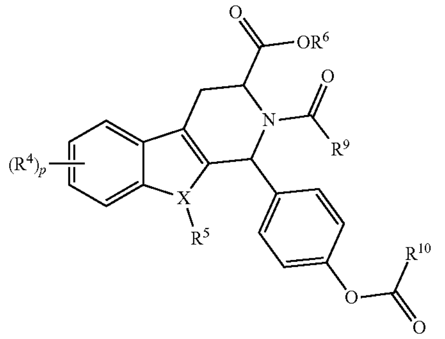

or (Vf)

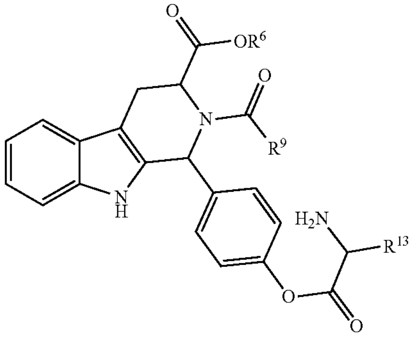

or an enantiomer or pharmaceutically acceptable salt thereof, wherein:

X is N, O or S;

$R^4$ is independently halo, CN, —$NH_2$, —$SO_2$, $C_1$-$C_8$alkyl, —$OR^{12}$, —$C_1$-$C_6$alkyl-$OR^{12}$, —$C_1$-$C_6$alkyl-$NR^{12}$ or —OC(O)$R^{12}$;

$R^5$ is H, $C_1$-$C_6$alkyl, or is absent when X is S or O;

p is 0, 1, 2 or 3;

$R^6$ is $C_1$-$C_6$alkyl, $C_3$-$C_6$alkyl, $C_2$-$C_6$alkenyl, $C_2$-$C_6$alkynyl, $C_3$-$C_6$cycloalkyl, heterocyclyl, aryl, heteroaryl, $C_3$-$C_6$cycloalkyl$C_1$-$C_6$alkyl-, $C_3$-$C_6$cycloalkyl$C_2$-$C_6$alkenyl-, heterocyclyl$C_1$-$C_6$alkyl-, heterocyclyl$C_2$-$C_6$alkenyl-, aryl$C_1$-$C_6$alkyl-, aryl$C_2$-$C_6$alkenyl-, heteroaryl$C_1$-$C_6$alkyl-, heteroaryl$C_2$-$C_6$alkenyl-, $(R^{11})_2NC_1$-$C_6$alkyl-, or $(R^{11})_2NC_2$-$C_6$alkenyl-;

$R^9$ is —$C_1$-$C_2$alkylhalo, —$C_2$-$C_3$alkenylhalo, or $C_2$alkynyl, wherein the $C_1$-$C_2$alkyl is optionally substituted with one or two halo, one or two —$CH_3$, or one or up to all H in —$C_1$-$C_2$alkyl is replaced with deuterium;

$R^{10}$ is $C_1$-$C_6$alkyl, $C_2$-$C_6$alkyl, $C_2$-$C_6$alkenyl, $C_2$-$C_6$alkynyl, $C_3$-$C_6$cycloalkyl, heterocyclyl, aryl, heteroaryl, $C_3$-$C_6$cycloalkyl$C_1$-$C_6$alkyl-, $C_3$-$C_6$cycloalkyl$C_2$-$C_6$alkenyl-, heterocyclyl$C_1$-$C_6$alkyl-, heterocyclyl$C_2$-$C_6$alkenyl-, aryl$C_1$-$C_6$alkyl-, aryl$C_2$-$C_6$alkenyl-, heteroaryl$C_1$-$C_6$alkyl-, heteroaryl$C_2$-$C_6$alkenyl-, adamantyl, adamantyl$C_1$-$C_6$aliphatic-, $(R^{11})_2NC_1$-$C_6$alkyl-, $(R^{11})_2NC_2$-$C_6$alkenyl-, $R^{13}(NH_2)CH$—, $R^{14}C_0$-$C_6$alkyl- or $(R^{15})_3SiC_0$-$C_6$alkyl-;

each $R^{11}$ is independently H, $C_1$-$C_6$alkyl, $C_2$-$C_6$alkenyl, $C_3$-$C_6$cycloalkyl, heterocyclyl, aryl, heteroaryl, $C_3$-$C_6$cycloalkyl$C_1$-$C_6$alkyl-, $C_3$-$C_6$cycloalkyl$C_2$-$C_6$alkenyl-, heterocyclyl$C_1$-$C_6$alkyl-, heterocyclyl$C_2$-$C_6$alkenyl-, aryl$C_1$-$C_6$alkyl-, aryl$C_2$-$C_6$alkenyl-, heteroaryl$C_1$-$C_6$alkyl-, heteroaryl$C_2$-$C_6$alkenyl-, adamantyl, adamantyl$C_1$-$C_6$aliphatic-, $R^{12}O$—$C_1$-$C_6$alkyl-, $(R^{11})_2NC_1$-$C_6$alkyl-, $(R^{11})_2NC_2$-$C_6$alkenyl-, $R^2O(O)C$—$C_1$-$C_6$alkyl-, $R^{13}(NH_2)CH$—, $R^{14}C_0$-$C_6$alkyl-, $(R^{15})_3SiC_0$- $C_6$alkyl-, or an N-protecting group; or two $R^{11}$ together with the nitrogen atom to which they are attached form a 4 to 7 membered heterocyclyl, wherein the heterocyclyl formed by the two $R^{11}$ groups has optionally 0, 1 or 2 additional heteroatoms selected from nitrogen, oxygen, and sulfur, and the heterocyclyl is optionally substituted with OH, halo, $C_1$-$C_6$alkyl, $C_1$-$C_6$alkyl-O(O)C—, $(R^{11})_2N$—, or a 4- to 6-membered heterocyclyl, wherein the 4- to 6-membered heterocyclyl is optionally substituted with OH, halo, —$NH_2$, or $C_1$-$C_6$alkyl, or when containing 2 or more N atoms is optionally substituted with an N-protecting group;

each $R^{12}$ is independently H or $C_1$-$C_6$alkyl;

each $R^{13}$ is independently H, $C_1$-$C_6$alkyl, $C_3$-$C_6$cycloalkyl, heterocyclyl, aryl, heteroaryl, $C_3$-$C_6$cycloalkyl$C_1$-$C_6$alkyl-, $C_3$-$C_6$cycloalkyl$C_2$-$C_6$alkenyl-, heterocyclyl$C_1$-$C_6$alkyl-, heterocyclyl$C_2$-$C_6$alkenyl-, aryl$C_1$-$C_6$alkyl-, aryl$C_2$-$C_6$alkenyl-, heteroaryl$C_1$-$C_6$alkyl-, heteroaryl$C_2$-$C_6$alkenyl-, adamantyl, adamantyl$C_1$-$C_6$aliphatic-, or an N protecting group;

$R^{14}$ is a bridged bicyclic ring having 0-2 heteroatoms independently selected from nitrogen, oxygen, and sulfur; and each $R^{15}$ is independently $C_1$-$C_6$alkyl, $C_2$-$C_6$alkenyl, aryl, heteroaryl, aryl$C_1$-$C_6$alkyl-, aryl$C_2$-$C_6$alkenyl-, heteroaryl$C_1$-$C_6$alkyl-, and heteroaryl$C_2$-$C_6$alkenyl-;

wherein the $C_1$-$C_6$alkyl, —$C_3$-$C_6$cycloalkyl, heterocyclyl, aryl, heteroaryl, or bridged bicyclic ring, by itself or attached to another moiety, are independently optionally substituted with 1-3 substituents selected from the group consisting of OH, halo, —$NH_2$, $C_1$-$C_6$alkyl, $C_1$-$C_6$alkyl-O—, $R^{12}O$—$C_1$-$C_6$alkyl(O)C—, and $R^{12}O$(O)C—.

In certain embodiments, the compound of formula (Ve) or (Vf) has the following stereochemical structure (Ve') and (Vf'), respectively:

(Ve')

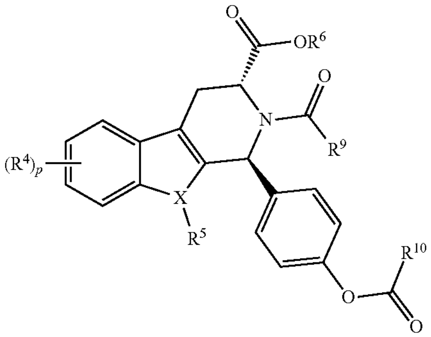

-continued (Vf')

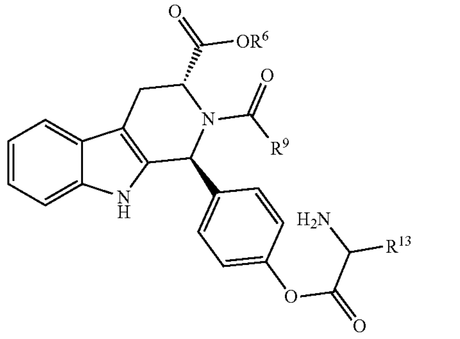

or an enantiomer or pharmaceutically acceptable salt thereof.

In certain embodiments, the compound of formula (Ve), (Ve'), (Vf) and (Vf'), or an enantiomer or pharmaceutically acceptable salt thereof, X is N, O or S;

$R^4$ is independently halo, CN, —$NH_2$, —$SO_2$, $C_1$-$C_8$alkyl, —$OR^{12}$, —$C_1$-$C_6$alkyl-$OR^{12}$, —$C_1$-$C_6$alkyl-$NR^{12}$ or —$OC(O)R^{12}$;

$R^5$ is H, $C_1$-$C_6$alkyl, or is absent when X is S or O;

$R^6$ is $C_1$-$C_6$alkyl;

$R^9$ is —$C_1$-$C_2$alkylCl, wherein optionally one or up to all H in —$C_1$-$C_2$alkyl is replaced with deuterium; and $R^{10}$, $R^{12}$ and $R^{13}$ are as defined for the compound of formula (Ve) or (Vf), above.

In certain embodiments of the compound of formula (Ve) or (Ve'), $R^6$ is methyl, ethyl, n-propyl, n-butyl, isopropyl, t-butyl, pentyl, or hexyl. In certain embodiments of the compound of formula (Ve) or (Ve'), $R^6$ is t-butyl. In certain embodiments of the compound of formula (Ve) or (Ve'), $R^{10}$ is a $C_1$-$C_6$alkyl.

In certain embodiments of the compound of formula (Vf) or (Vf), $R^{13}$ is a $C_1$-$C_6$alkyl, $C_3$-$C_6$cycloalkyl$C_1$-$C_6$alkyl-, $C_3$-$C_6$cycloalkyl$C_2$-$C_6$alkenyl-, heterocyclyl$C_1$-$C_6$alkyl-, heterocyclyl$C_2$-$C_6$alkenyl-, aryl$C_1$-$C_6$alkyl-, aryl$C_2$-$C_6$alkenyl-, heteroaryl$C_1$-$C_6$alkyl-, or heteroaryl$C_2$-$C_6$alkenyl-, wherein the $C_3$-$C_6$cycloalkyl, heterocyclyl, aryl, and heteroaryl are optionally substituted with 1-3 substituents selected from the group consisting of OH, halo, $C_1$-$C_6$alkyl, and $C_1$-$C_6$alkyl-O—, $HOCH_2(O)C$—, $R^{12}O(O)C$—, wherein $R^{12}$ is as defined for formula (V).

In certain embodiments of the compound of formula (Ve), (Ve'), (Vf) or (Vf), $R^6$ is t-butyl.

In certain embodiments of the compound of formula (Ve), (Ve'), (Vf) or (Vf) above, the aryl when present is selected from phenyl and naphthyl. In certain embodiments of the compound of (Ve), (Ve'), (Vf) or (Vf) above, the heteroaryl when present is selected from furanyl, imidazolyl, benzimidazolyl, isoxazolyl, oxazolyl, pyrrolyl, pyridyl, pyrimidinyl, pyridazinyl, thiazolyl, thienyl, 3-thienyl, benzofuryl, indolyl, pyrazolyl, isothiazolyl, oxadiazolylpurinyl, pyrazinyl, and quinolinyl. In certain embodiments of the compound of formula (Ve), (Ve'), (Vf) or (Vf') above, the heterocyclyl when present is selected from azetidinyl, pyrrolidinyl, piperidinyl, pyrazolidinyl, isoxazolidinyl, oxazolidinyl, thiazolidinyl, imidazolidinyl, piperazinyl, morpholinyl, thiomorpholinyl, 1,3-oxazinanyl, 1,3-thiazinanyl, dihydropyridinyl, 1,3-tetrahydropyrimidinyl, dihydropyrimidinyl, azepanyl and 1,4-diazepanyl.

In certain embodiments of the compound of formula (Ve), (Ve'), (Vf), and (Vf'), X is N. In certain embodiments of the compound of formula (Ve), (Ve'), (Vf), and (Vf'), X is N; and $R^5$ is H.

In certain embodiments of the compound of formula (Ve), (Ve'), (Vf), and (Vf'), $R^4$ is halo. In certain embodiments of formula (Ve), (Ve'), (Vf), and (Vf'), p is 0.

In certain embodiments, the compound has the following structural formula (Vg):

(Vg)

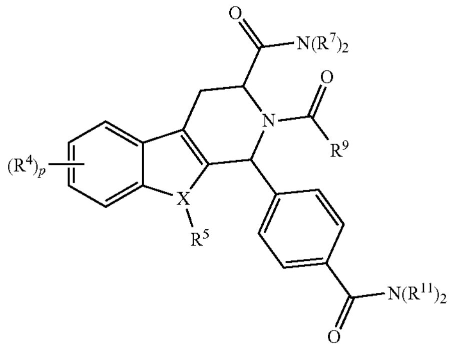

or an enantiomer or pharmaceutically acceptable salt thereof, wherein:

X is N, O or S;

$R^4$ is independently halo, CN, —$NH_2$, —$SO_2$, $C_1$-$C_8$alkyl, —$OR^{12}$, —$C_1$-$C_6$alkyl-$OR^{12}$, —$C_1$-$C_6$alkyl-$NR^{12}$ or —$OC(O)R^{12}$;

$R^5$ is H, $C_1$-$C_6$alkyl, or is absent when X is S or O;

p is 0, 1, 2 or 3;

each $R^7$ is independently H, $C_1$-$C_6$alkyl, $C_2$-$C_6$alkenyl, $C_3$-$C_6$cycloalkyl, heterocyclyl, aryl, heteroaryl, $C_3$-$C_6$cycloalkyl$C_1$-$C_6$alkyl-, $C_3$-$C_6$cycloalkyl$C_2$-$C_6$alkenyl-, heterocyclyl$C_1$-$C_6$alkyl-, heterocyclyl$C_2$-$C_6$alkenyl-, aryl$C_1$-$C_6$alkyl-, aryl$C_2$-$C_6$alkenyl-, heteroaryl$C_1$-$C_6$alkyl-, heteroaryl$C_2$-$C_6$alkenyl-, $(R^{11})_2NC_1$-$C_6$alkyl-, $(R^{11})_2NC_2$-$C_6$alkenyl-, $R^{12}O$—$C_1$-$C_6$alkyl-, or $R^{12}O(O)C$—$C_1$-$C_6$alkyl-, or two $R^7$ together with the nitrogen atom to which they are attached form a 4 to 7 membered heterocyclyl, wherein the heterocyclyl formed by the two $R^7$ groups is optionally substituted with OH, halo, $C_1$-$C_6$alkyl, a 4- to 6-membered heterocyclyl, or $(R^{11})_2N$—, wherein the 4- to 6-membered heterocyclyl when containing 2 or more N atoms is optionally substituted with an N-protecting group;

$R^9$ is —$C_1$-$C_2$alkylhalo, —$C_2$-$C_3$alkenylhalo, or $C_2$alkynyl, wherein the $C_1$-$C_2$alkyl is optionally substituted with one or two halo, one or two —$CH_3$, or one or up to all H in —$C_1$-$C_2$alkyl is replaced with deuterium;

each $R^{11}$ is independently H, $C_1$-$C_6$alkyl, $C_2$-$C_6$alkenyl, $C_3$-$C_6$cycloalkyl, heterocyclyl, aryl, heteroaryl, $C_3$-$C_6$cycloalkyl$C_1$-$C_6$alkyl-, $C_3$-$C_6$cycloalkyl$C_2$-$C_6$alkenyl-, heterocyclyl$C_1$-$C_6$alkyl-, heterocyclyl$C_2$-$C_6$alkenyl-, aryl$C_1$-$C_6$alkyl-, aryl$C_2$-$C_6$alkenyl-, heteroaryl$C_1$-$C_6$alkyl-, heteroaryl$C_2$-$C_6$alkenyl-, adamantyl, adamantyl$C_1$-$C_6$aliphatic-, $R^{12}O$—$C_1$-$C_6$alkyl-, $(R^{11})_2NC_1$-$C_6$alkyl-, $(R^{11})_2NC_2$-$C_6$alkenyl-, $R^{12}O(O)C$—$C_1$-$C_6$alkyl-, $R^{13}(NH_2)CH$—, $R^{14}C_0$-$C_6$alkyl-, $(R^{15})_3SiC_0$- $C_6$alkyl-, or an N-protecting group; or two $R^{11}$ together with the nitrogen atom to which they are attached form a 4 to 7 membered heterocyclyl, wherein the heterocyclyl formed by the two $R^{11}$ groups has optionally 0, 1 or 2 additional heteroatoms selected from nitrogen, oxygen, and sulfur, and the heterocyclyl is optionally substituted with OH, halo, $C_1$-$C_6$alkyl, $C_1$-$C_6$alkyl-O(O)C—, $(R^{11})_2N$—, or a 4- to 6-membered heterocyclyl, wherein the 4- to 6-membered heterocyclyl is optionally substituted with OH, halo, —$NH_2$, or $C_1$-$C_6$alkyl, or when containing 2 or more N atoms is optionally substituted with an N-protecting group;

each $R^{12}$ is independently H or $C_1$-$C_6$alkyl;

each $R^{13}$ is independently H, $C_1$-$C_6$alkyl, $C_3$-$C_6$cycloalkyl, heterocyclyl, aryl, heteroaryl, $C_3$-$C_6$cycloalkyl$C_1$-$C_6$alkyl-, $C_3$-$C_6$cycloalkyl$C_2$-$C_6$alkenyl-, heterocyclyl$C_1$-$C_6$alkyl-, heterocyclyl$C_2$-$C_6$alkenyl-, aryl$C_1$-$C_6$alkyl-, aryl$C_2$-$C_6$alkenyl-, heteroaryl$C_1$-$C_6$alkyl-, heteroaryl$C_2$-$C_6$alkenyl-, adamantyl, adamantyl$C_1$-$C_6$aliphatic-, or an N protecting group;

$R^{14}$ is a bridged bicyclic ring having 0-2 heteroatoms independently selected from nitrogen, oxygen, and sulfur; and each $R^{15}$ is independently $C_1$-$C_6$alkyl, $C_2$-$C_6$alkenyl, aryl, heteroaryl, aryl$C_1$-$C_6$alkyl-, aryl$C_2$-$C_6$alkenyl-, heteroaryl$C_1$-$C_6$alkyl-, and heteroaryl$C_2$-$C_6$alkenyl-;

wherein the $C_1$-$C_6$alkyl, —$C_3$-$C_6$cycloalkyl, heterocyclyl, aryl, heteroaryl, or bridged bicyclic ring, by itself or attached to another moiety, are independently optionally substituted with 1-3 substituents selected from the group consisting of OH, halo, —$NH_2$, $C_1$-$C_6$alkyl, $C_1$-$C_6$alkyl-O—, $R^{12}$O—$C_1$-$C_6$alkyl(O)C—, and $R^{12}$O(O)C—.

In certain embodiments, the compound of formula (Vg) has the following stereochemical structure (Vg'):

(Vg')

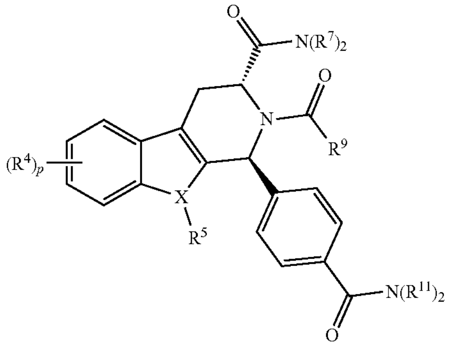

or an enantiomer or pharmaceutically acceptable salt thereof.

In certain embodiments of the compound of formula (Vg) and (Vg'), X is N. In certain embodiments of the compound of formula (Vg) and (Vg'), X is N; and $R^5$ is H.

In certain embodiments of the compound of formula (Vg) and (Vg'), $R^4$ is halo. In certain embodiments of formula (Vg) and (Vg'), p is 0.

In certain embodiments, the compound has the following structural formula (Vh):

(Vh)

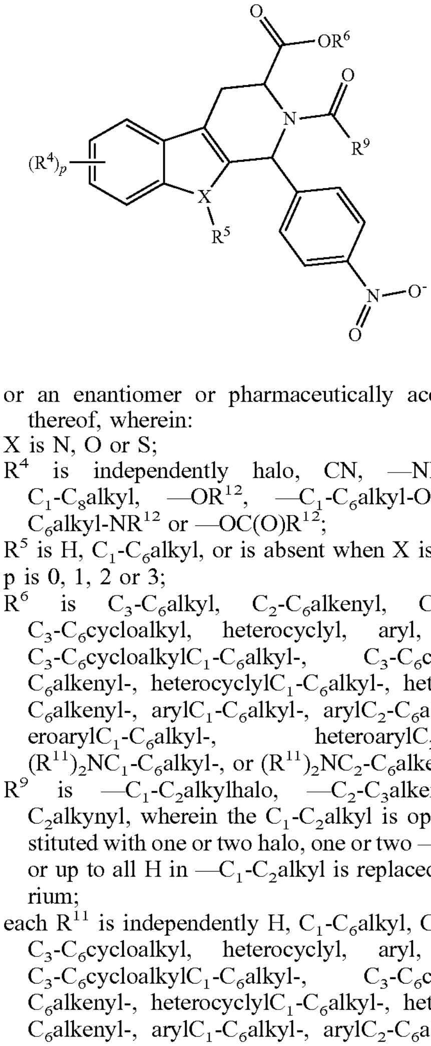

or an enantiomer or pharmaceutically acceptable salt thereof, wherein:

X is N, O or S;

$R^4$ is independently halo, CN, —$NH_2$, —$SO_2$, $C_1$-$C_8$alkyl, —$OR^{12}$, —$C_1$-$C_6$alkyl-$OR^{12}$, —$C_1$-$C_6$alkyl-$NR^{12}$ or —OC(O)$R^{12}$;

$R^5$ is H, $C_1$-$C_6$alkyl, or is absent when X is S or O;

p is 0, 1, 2 or 3;

$R^6$ is $C_3$-$C_6$alkyl, $C_2$-$C_6$alkenyl, $C_2$-$C_6$alkynyl, $C_3$-$C_6$cycloalkyl, heterocyclyl, aryl, heteroaryl, $C_3$-$C_6$cycloalkyl$C_1$-$C_6$alkyl-, $C_3$-$C_6$cycloalkyl$C_2$-$C_6$alkenyl-, heterocyclyl$C_1$-$C_6$alkyl-, heterocyclyl$C_2$-$C_6$alkenyl-, aryl$C_1$-$C_6$alkyl-, aryl$C_2$-$C_6$alkenyl-, heteroaryl$C_1$-$C_6$alkyl-, heteroaryl$C_2$-$C_6$alkenyl-, $(R^{11})_2NC_1$-$C_6$alkyl-, or $(R^{11})_2NC_2$-$C_6$alkenyl-;

$R^9$ is —$C_1$-$C_2$alkylhalo, —$C_2$-$C_3$alkenylhalo, or $C_2$alkynyl, wherein the $C_1$-$C_2$alkyl is optionally substituted with one or two halo, one or two —$CH_3$, or one or up to all H in —$C_1$-$C_2$alkyl is replaced with deuterium;

each $R^{11}$ is independently H, $C_1$-$C_6$alkyl, $C_2$-$C_6$alkenyl, $C_3$-$C_6$cycloalkyl, heterocyclyl, aryl, heteroaryl, $C_3$-$C_6$cycloalkyl$C_1$-$C_6$alkyl-, $C_3$-$C_6$cycloalkyl$C_2$-$C_6$alkenyl-, heterocyclyl$C_1$-$C_6$alkyl-, heterocyclyl$C_2$-$C_6$alkenyl-, aryl$C_1$-$C_6$alkyl-, aryl$C_2$-$C_6$alkenyl-, heteroaryl$C_1$-$C_6$alkyl-, heteroaryl$C_2$-$C_6$alkenyl-, adamantyl, adamantyl$C_1$-$C_6$aliphatic-, $R^{12}$O—$C_1$-$C_6$alkyl-, $(R^{11})_2NC_1$-$C_6$alkyl-, $(R^{11})_2NC_2$-$C_6$alkenyl-, $R^{12}$O(O)C—$C_1$-$C_6$alkyl-, $R^{13}(NH_2)CH$—, $R^{14}C_0$-$C_6$alkyl-, $(R^{15})_3SiC_0$- $C_6$alkyl-, or an N-protecting group; or two $R^{11}$ together with the nitrogen atom to which they are attached form a 4 to 7 membered heterocyclyl, wherein the heterocyclyl formed by the two $R^{11}$ groups has optionally 0, 1 or 2 additional heteroatoms selected from nitrogen, oxygen, and sulfur, and the heterocyclyl is optionally substituted with OH, halo, $C_1$-$C_6$alkyl, $C_1$-$C_6$alkyl-O(O)C—, $(R^{11})_2N$—, or a 4- to 6-membered heterocyclyl, wherein the 4- to 6-membered heterocyclyl is optionally substituted with OH, halo, —$NH_2$, or $C_1$-$C_6$alkyl, or when containing 2 or more N atoms is optionally substituted with an N-protecting group;

each $R^{12}$ is independently H or $C_1$-$C_6$alkyl;

each $R^{13}$ is independently H, $C_1$-$C_6$alkyl, $C_3$-$C_6$cycloalkyl, heterocyclyl, aryl, heteroaryl, $C_3$-$C_6$cycloalkyl$C_1$-$C_6$alkyl-, $C_3$-$C_6$cycloalkyl$C_2$-$C_6$alkenyl-, heterocyclyl$C_1$-$C_6$alkyl-, heterocyclyl$C_2$-$C_6$alkenyl-, aryl$C_1$-$C_6$alkyl-, aryl$C_2$-$C_6$alkenyl-, heteroaryl$C_1$-$C_6$alkyl-, heteroaryl$C_2$-$C_6$alkenyl-, adamantyl, adamantyl$C_1$-$C_6$aliphatic-, or an N protecting group;

$R^{14}$ is a bridged bicyclic ring having 0-2 heteroatoms independently selected from nitrogen, oxygen, and sulfur; and each $R^{15}$ is independently $C_1$-$C_6$alkyl, $C_2$-$C_6$alkenyl, aryl, heteroaryl, aryl$C_1$-$C_6$alkyl-, aryl$C_2$-$C_6$alkenyl-, heteroaryl$C_1$-$C_6$alkyl-, and heteroaryl$C_2$-$C_6$alkenyl-;

wherein the $C_1$-$C_6$alkyl, —$C_3$-$C_6$cycloalkyl, heterocyclyl, aryl, heteroaryl, or bridged bicyclic ring, by itself or attached to another moiety, are independently optionally substituted with 1-3 substituents selected from the group consisting of OH, halo, —$NH_2$, $C_1$-$C_6$alkyl, $C_1$-$C_6$alkyl-O—, $R^{12}$O—$C_1$-$C_6$alkyl(O)C—, and $R^{12}$O(O)C—.

In certain embodiments, the compound of formula (Vh) has the following stereochemical structure (Vh'):

(Vh')

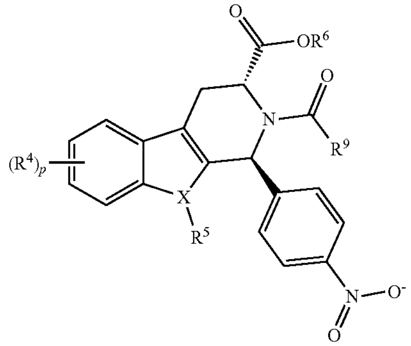

or an enantiomer or pharmaceutically acceptable salt thereof.

In certain embodiments of the compound of structural formula (Vh) or (Vh'), or an enantiomer or pharmaceutically acceptable salt thereof, X is N, O or S;

$R^4$ is independently halo, CN, —$NH_2$, —$SO_2$, $C_1$-$C_8$alkyl, —$OR^{12}$, —$C_1$-$C_6$alkyl-$OR^{12}$, —$C_1$-$C_6$alkyl-$NR^{12}$ or —OC(O)$R^{12}$;

$R^5$ is H, $C_1$-$C_6$alkyl, or is absent when X is S or O;

$R^6$ is $C_3$-$C_6$alkyl;

$R^9$ is —$C_1$-$C_2$alkylhalo, wherein optionally one or up to all H in —$C_1$-$C_2$alkyl is replaced with deuterium;

$R^{12}$ is H or $C_1$-$C_6$alkyl; and p is 0, 1, 2 or 3.

In certain embodiments, $R^6$ is t-butyl.

In certain embodiments of the compound of formula (Vh) and (Vh'), X is N. In certain embodiments of the compound of formula (Vh) and (Vh'), X is N; and $R^5$ is H.

In certain embodiments of the compound of formula (Vh) and (Vh'), $R^4$ is halo. In certain embodiments of formula (Vh) and (Vh'), p is 0.

In certain embodiments, the compound has the structural formula (Vi):

(Vi)

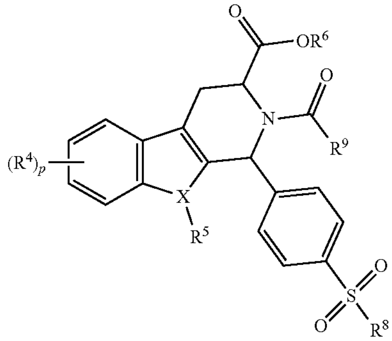

or an enantiomer or pharmaceutically acceptable salt thereof, wherein:

X is N, O or S;

$R^4$ is independently halo, CN, —$NH_2$, —$SO_2$, $C_1$-$C_8$alkyl, —$OR^{12}$, —$C_1$-$C_6$alkyl-$OR^{12}$, —$C_1$-$C_6$alkyl-$NR^{12}$ or —OC(O)$R^{12}$;

$R^5$ is H, $C_1$-$C_6$alkyl, or is absent when X is S or O;

p is 0, 1, 2 or 3;

$R^6$ is $C_1$-$C_6$alkyl, $C_3$-$C_6$alkyl, $C_2$-$C_6$alkenyl, $C_2$-$C_6$alkynyl, $C_3$-$C_6$cycloalkyl, heterocyclyl, aryl, heteroaryl, $C_3$-$C_6$cycloalkyl$C_1$-$C_6$alkyl-, $C_3$-$C_6$cycloalkyl$C_2$-$C_6$alkenyl-, heterocyclyl$C_1$-$C_6$alkyl-, heterocyclyl$C_2$-$C_6$alkenyl-, aryl$C_1$-$C_6$alkyl-, aryl$C_2$-$C_6$alkenyl-, heteroaryl$C_1$-$C_6$alkyl-, heteroaryl$C_2$-$C_6$alkenyl-, $(R^{11})_2NC_1$-$C_6$alkyl-, or $(R^{11})_2NC_2$-$C_6$alkenyl-;

$R^8$ is $C_1$-$C_6$alkyl, $C_3$-$C_6$alkyl, $C_2$-$C_6$alkenyl, $C_2$-$C_6$alkynyl, $C_3$-$C_6$cycloalkyl, heterocyclyl, aryl, heteroaryl, $C_3$-$C_6$cycloalkyl$C_1$-$C_6$alkyl-, $C_3$-$C_6$cycloalkyl$C_2$-$C_6$alkenyl-, heterocyclyl$C_1$-$C_6$alkyl-, heterocyclyl$C_2$-$C_6$alkenyl-, aryl$C_1$-$C_6$alkyl-, aryl$C_2$-$C_6$alkenyl-, heteroaryl$C_1$-$C_6$alkyl-, heteroaryl$C_2$-$C_6$alkenyl-, adamantyl, adamantyl$C_1$-$C_6$aliphatic-, $(R^{11})_2NC_1$-$C_6$alkyl-, or $(R^{11})_2N$—;

$R^9$ is —$C_1$-$C_2$alkylhalo, —$C_2$-$C_3$alkenylhalo, or $C_2$alkynyl, wherein the $C_1$-$C_2$alkyl is optionally substituted with one or two halo, one or two —$CH_3$, or one or up to all H in —$C_1$-$C_2$alkyl is replaced with deuterium;

each $R^{11}$ is independently H, $C_1$-$C_6$alkyl, $C_2$-$C_6$alkenyl, $C_3$-$C_6$cycloalkyl, heterocyclyl, aryl, heteroaryl, $C_3$-$C_6$cycloalkyl$C_1$-$C_6$alkyl-, $C_3$-$C_6$cycloalkyl$C_2$-$C_6$alkenyl-, heterocyclyl$C_1$-$C_6$alkyl-, heterocyclyl$C_2$-$C_6$alkenyl-, aryl$C_1$-$C_6$alkyl-, aryl$C_2$-$C_6$alkenyl-, heteroaryl$C_1$-$C_6$alkyl-, heteroaryl$C_2$-$C_6$alkenyl-, adamantyl, adamantyl$C_1$-$C_6$aliphatic-, $R^{12}$O—$C_1$-$C_6$alkyl-, $(R^{11})_2NC_1$-$C_6$alkyl-, $(R^{11})_2NC_2$-$C_6$alkenyl-, $R^{12}$O(O)C—$C_1$-$C_6$alkyl-, $R^{13}(NH_2)$CH—, $R^{14}C_0$-$C_6$alkyl-, $(R^{15})_3SiC_0$- $C_6$alkyl-, or an N-protecting group; or two $R^{11}$ together with the nitrogen atom to which they are attached form a 4 to 7 membered heterocyclyl, wherein the heterocyclyl formed by the two $R^{11}$ groups has optionally 0, 1 or 2 additional heteroatoms selected from nitrogen, oxygen, and sulfur, and the heterocyclyl is optionally substituted with OH, halo, $C_1$-$C_6$alkyl, $C_1$-$C_6$alkyl-O(O)C—, $(R^{11})_2N$—, or a 4- to 6-membered heterocyclyl, wherein the 4- to 6-membered heterocyclyl is optionally substituted with OH, halo, —$NH_2$, or $C_1$-$C_6$alkyl, or when containing 2 or more N atoms is optionally substituted with an N-protecting group;

each $R^{12}$ is independently H or $C_1$-$C_6$alkyl;

each $R^{13}$ is independently H, $C_1$-$C_6$alkyl, $C_3$-$C_6$cycloalkyl, heterocyclyl, aryl, heteroaryl, $C_3$-$C_6$cycloalkyl$C_1$-$C_6$alkyl-, $C_3$-$C_6$cycloalkyl$C_2$-$C_6$alkenyl-, heterocyclyl$C_1$-$C_6$alkyl-, heterocyclyl$C_2$-$C_6$alkenyl-, aryl$C_1$-$C_6$alkyl-, aryl$C_2$-$C_6$alkenyl-, heteroaryl$C_1$-$C_6$alkyl-, heteroaryl$C_2$-$C_6$alkenyl-, adamantyl, adamantyl$C_1$-$C_6$aliphatic-, or an N protecting group;

$R^{14}$ is a bridged bicyclic ring having 0-2 heteroatoms independently selected from nitrogen, oxygen, and sulfur; and each $R^{15}$ is independently $C_1$-$C_6$alkyl, $C_2$-$C_6$alkenyl, aryl, heteroaryl, aryl$C_1$-$C_6$alkyl-, aryl$C_2$-$C_6$alkenyl-, heteroaryl$C_1$-$C_6$alkyl-, and heteroaryl$C_2$-$C_6$alkenyl-;

wherein the $C_1$-$C_6$alkyl, —$C_3$-$C_6$cycloalkyl, heterocyclyl, aryl, heteroaryl, bridged bicyclic ring, by itself or attached to another moiety, are independently optionally substituted with 1-3 substituents selected from the group consisting of OH, halo, —$NH_2$, $C_1$-$C_6$alkyl, $C_1$-$C_6$alkyl-O—, $R^{12}$O—$C_1$-$C_6$alkyl(O)C—, and $R^{12}$O(O)C—.

In certain embodiments, the compound of formula (Vi) has the following stereochemical structure (Vi'):

(Vi')

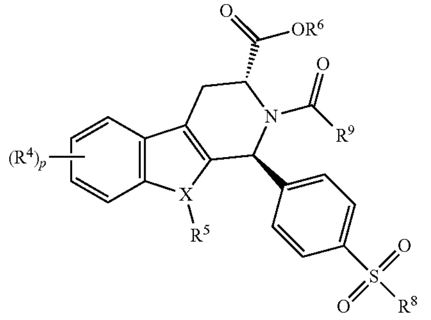

or an enantiomer or pharmaceutically acceptable salt thereof. In certain embodiments of the compound, or an enantiomer or pharmaceutically acceptable salt thereof, of structural formula (Vi) or (Vi'):

$R^6$ is $C_1$-$C_6$alkyl, $C_3$-$C_6$alkyl, $C_3$-$C_6$cycloalkyl, heterocyclyl, aryl, heteroaryl, $C_3$-$C_6$cycloalkyl$C_1$-$C_6$alkyl-, heterocyclyl$C_1$-$C_6$alkyl-, aryl$C_1$-$C_6$alkyl-, or heteroaryl$C_1$-$C_6$alkyl-;

$R^8$ is $C_1$-$C_6$alkyl, $C_3$-$C_6$alkyl, $C_2$-$C_6$alkenyl, $C_2$-$C_6$alkynyl, $C_3$-$C_6$cycloalkyl, heterocyclyl, aryl, heteroaryl, $C_3$-$C_6$cycloalkyl$C_1$-$C_6$alkyl-, $C_3$-$C_6$cycloalkyl$C_2$-$C_6$alkenyl-, heterocyclyl$C_1$-$C_6$alkyl-, heterocyclyl$C_2$-$C_6$alkenyl-, aryl$C_1$-$C_6$alkyl-, aryl$C_2$-$C_6$alkenyl-, heteroaryl$C_1$-$C_6$alkyl-, heteroaryl$C_2$-$C_6$alkenyl-, adamantyl, adamantyl$C_1$-$C_6$aliphatic-, $(R^{11})_2NC_1$-$C_6$alkyl-, or $(R^{11})_2N$—;

$R^9$ is —$C_1$-$C_2$alkylhalo, —$C_2$-$C_3$alkenylhalo, or $C_2$alkynyl, wherein the $C_1$-$C_2$alkyl is optionally substituted with one or two halo, one or two —$CH_3$, or one or up to all H in —$C_1$-$C_2$alkyl is replaced with deuterium;

each $R^{11}$ is independently H, $C_1$-$C_6$alkyl, $C_2$-$C_6$alkenyl, $C_3$-$C_6$cycloalkyl, heterocyclyl, aryl, heteroaryl, $C_3$-$C_6$cycloalkyl$C_1$-$C_6$alkyl-, $C_3$-$C_6$cycloalkyl$C_2$-$C_6$alkenyl-, heterocyclyl$C_1$-$C_6$alkyl-, heterocyclyl$C_2$-$C_6$alkenyl-, aryl$C_1$-$C_6$alkyl-, aryl$C_2$-$C_6$alkenyl-, heteroaryl$C_1$-$C_6$alkyl-, heteroaryl$C_2$-$C_6$alkenyl-, adamantyl, adamantyl$C_1$-$C_6$aliphatic-, $R^{12}$O—$C_1$-$C_6$alkyl-, or $(R^{11})_2NC_1$-$C_6$alkyl-; or two $R^{11}$ together with the nitrogen atom to which they are attached form a 4 to 7 membered heterocyclyl, wherein the heterocyclyl formed by the two $R^{11}$ groups is optionally substituted with OH, halo, $C_1$-$C_6$alkyl, a 4- to 6-membered heterocyclyl, or $(R^{11})_2N$—, wherein the 4- to 6-membered heterocyclyl is optionally substituted with OH, halo, or $C_1$-$C_6$alkyl, or when containing 2 or more N atoms is optionally substituted with an N-protecting group;

each $R^{12}$ is independently H or $C_1$-$C_6$alkyl; and wherein the $C_1$-$C_6$alkyl, $C_3$-$C_6$cycloalkyl, heterocyclyl, aryl, and heteroaryl, by itself or as part of larger moiety are independently optionally substituted with 1-3 substituents selected from the group consisting of OH, halo, $C_1$-$C_6$alkyl, $C_1$-$C_6$alkyl-O—, $R^{12}$O—$C_1$-$C_6$alkyl(O)C—, and $R^{12}$O(O)C—.

In certain embodiments of the compound of formula (Vi) and (Vi'),

X is N, O or S;

$R^4$ is independently halo, CN, —$NH_2$, —$SO_2$, $C_1$-$C_8$alkyl, —$OR^{12}$, —$C_1$-$C_6$alkyl-$OR^{12}$, —$C_1$-$C_6$alkyl-$NR^{12}$ or —OC(O)$R^{12}$;

$R^5$ is H, $C_1$-$C_6$alkyl, or is absent when X is S or O;

p is 0, 1, 2 or 3;

$R^6$ is $C_1$-$C_6$alkyl;

$R^8$ is $(R^{11})_2N$—;

$R^9$ is —$C_1$-$C_2$alkylhalo, wherein optionally one or up to all H in —$C_1$-$C_2$alkyl is replaced with deuterium;

each $R^{11}$ is independently H, $C_1$-$C_6$alkyl, adamantyl, or adamantyl$C_1$-$C_6$aliphatic-; and $R^{12}$ is H or $C_1$-$C_6$alkyl.

In certain embodiments of the compound of formula (Vi) and (Vi'),

X is N, O or S;

$R^4$ is independently halo or $C_1$-$C_8$alkyl;

$R^5$ is H, $C_1$-$C_6$alkyl, or is absent when X is S or O;

p is 0, 1, 2 or 3;

$R^6$ is $C_1$-$C_6$alkyl;

$R^8$ is $(R^{11})_2N$—;

$R^9$ is —$C_1$-$C_2$alkylhalo, wherein optionally one or up to all H in —$C_1$-$C_2$alkyl is replaced with deuterium; and $R^{11}$ is H, and adamantyl or adamantyl$C_1$-$C_6$aliphatic-.

In certain embodiments of the compound of formula (Vi) and (Vi'),

X is N, O or S;

$R^4$ is independently halo or $C_1$-$C_8$alkyl;

$R^5$ is H, $C_1$-$C_6$alkyl, or is absent when X is S or O;

p is 0, 1, 2 or 3;

$R^6$ is $C_1$-$C_6$alkyl;

$R^8$ is $(R^{11})_2N$—;

$R^9$ is —$C_1$-$C_2$alkylhalo, wherein optionally one or up to all H in —$C_1$-$C_2$alkyl is replaced with deuterium; and two $R^{11}$ together with the nitrogen atom to which they are attached form a 4 to 7 membered heterocyclyl, wherein the heterocyclyl formed by the two $R^{11}$ groups is optionally substituted with OH, halo, $C_1$-$C_6$alkyl, a 4- to 6-membered heterocyclyl, or $(R^{11})_2N$—, wherein the 4- to 6-membered heterocyclyl is optionally substituted with OH, halo, or $C_1$-$C_6$alkyl, or when containing 2 or more N atoms is optionally substituted with an N-protecting group.

In certain embodiments of the compound of formula (Vi) and (Vi'), X is N. In certain embodiments of the compound of formula (Vi) and (Vi'), X is N; and $R^5$ is H.

In certain embodiments of the compound of formula (Vi) and (Vi'), $R^4$ is halo. In certain embodiments of formula (Vi) and (Vi'), p is 0.

In certain embodiments, the compound has the structural formula (Vj):

(Vj)

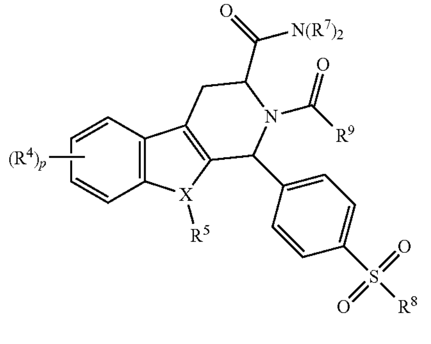

or an enantiomer or pharmaceutically acceptable salt thereof, wherein:

X is N, O or S;

$R^4$ is independently halo, CN, —$NH_2$, —$SO_2$, $C_1$-$C_8$alkyl, —$OR^{12}$, —$C_1$-$C_6$alkyl-$OR^{12}$, —$C_1$-$C_6$alkyl-$NR^{12}$ or —$OC(O)R^{12}$;

$R^5$ is H, $C_1$-$C_6$alkyl, or is absent when X is S or O;

p is 0, 1, 2 or 3;

each $R^7$ is independently H, $C_1$-$C_6$alkyl, $C_2$-$C_6$alkenyl, $C_3$-$C_6$cycloalkyl, heterocyclyl, aryl, heteroaryl, $C_3$-$C_6$cycloalkyl$C_1$-$C_6$alkyl-, $C_3$-$C_6$cycloalkyl$C_2$-$C_6$alkenyl-, heterocyclyl$C_1$-$C_6$alkyl-, heterocyclyl$C_2$-$C_6$alkenyl-, aryl$C_1$-$C_6$alkyl-, aryl$C_2$-$C_6$alkenyl-, heteroaryl$C_1$-$C_6$alkyl-, heteroaryl$C_2$-$C_6$alkenyl-, $(R^{11})_2NC_1$-$C_6$alkyl-, $(R^{11})_2NC_2$-$C_6$alkenyl-, $R^{12}O$—$C_1$-$C_6$alkyl-, or $R^{12}O(O)C$—$C_1$-$C_6$alkyl-, or two $R^7$ together with the nitrogen atom to which they are attached form a 4 to 7 membered heterocyclyl, wherein the heterocyclyl formed by the two $R^7$ groups is optionally substituted with OH, halo, $C_1$-$C_6$alkyl, a 4- to 6-membered heterocyclyl, or $(R^{11})_2N$—, wherein the 4- to 6-membered heterocyclyl when containing 2 or more N atoms is optionally substituted with an N-protecting group;

$R^8$ is independently $C_1$-$C_6$alkyl, $C_3$-$C_6$alkyl, $C_2$-$C_6$alkenyl, $C_2$-$C_6$alkynyl, $C_3$-$C_6$cycloalkyl, heterocyclyl, aryl, heteroaryl, $C_3$-$C_6$cycloalkyl$C_1$-$C_6$alkyl-, $C_3$-$C_6$cycloalkyl$C_2$-$C_6$alkenyl-, heterocyclyl$C_1$-$C_6$alkyl-, heterocyclyl$C_2$-$C_6$alkenyl-, aryl$C_1$-$C_6$alkyl-, aryl$C_2$-$C_6$alkenyl-, heteroaryl$C_1$-$C_6$alkyl-, heteroaryl$C_2$-$C_6$alkenyl-, adamantyl, adamantyl$C_1$-$C_6$aliphatic-, $(R^{11})_2NC_1$-$C_6$alkyl-, or $(R^{11})_2N$—;

$R^9$ is —$C_1$-$C_2$alkylhalo, —$C_2$-$C_3$alkenylhalo, or $C_2$alkynyl, wherein the $C_1$-$C_2$alkyl is optionally substituted with one or two halo, one or two —$CH_3$, or one or up to all H in —$C_1$-$C_2$alkyl is replaced with deuterium;

each $R^{11}$ is independently H, $C_1$-$C_6$alkyl, $C_2$-$C_6$alkenyl, $C_3$-$C_6$cycloalkyl, heterocyclyl, aryl, heteroaryl, $C_3$-$C_6$cycloalkyl$C_1$-$C_6$alkyl-, $C_3$-$C_6$cycloalkyl$C_2$-$C_6$alkenyl-, heterocyclyl$C_1$-$C_6$alkyl-, heterocyclyl$C_2$-$C_6$alkenyl-, aryl$C_1$-$C_6$alkyl-, aryl$C_2$-$C_6$alkenyl-, heteroaryl$C_1$-$C_6$alkyl-, heteroaryl$C_2$-$C_6$alkenyl-, adamantyl, adamantyl$C_1$-$C_6$aliphatic-, $R^{12}O$—$C_1$-$C_6$alkyl-, $(R^{11})_2NC_1$-$C_6$alkyl-, $(R^{11})_2NC_2$-$C_6$alkenyl-, $R^2O(O)C$—$C_1$-$C_6$alkyl-, $R^{13}(NH_2)CH$—, $R^{14}C_0$-$C_6$alkyl-, $(R^{15})_3SiC_0$- $C_6$alkyl-, or an N-protecting group; or two $R^{11}$ together with the nitrogen atom to which they are attached form a 4 to 7 membered heterocyclyl, wherein the heterocyclyl formed by the two $R^{11}$ groups has optionally 0, 1 or 2 additional heteroatoms selected from nitrogen, oxygen, and sulfur, and the heterocyclyl is optionally substituted with OH, halo, $C_1$-$C_6$alkyl, $C_1$-$C_6$alkyl-O(O)C—, $(R^{11})_2N$—, or a 4- to 6-membered heterocyclyl, wherein the 4- to 6-membered heterocyclyl is optionally substituted with OH, halo, —$NH_2$, or $C_1$-$C_6$alkyl, or when containing 2 or more N atoms is optionally substituted with an N-protecting group;

each $R^{12}$ is independently H or $C_1$-$C_6$alkyl;

each $R^{13}$ is independently H, $C_1$-$C_6$alkyl, $C_3$-$C_6$cycloalkyl, heterocyclyl, aryl, heteroaryl, $C_3$-$C_6$cycloalkyl$C_1$-$C_6$alkyl-, $C_3$-$C_6$cycloalkyl$C_2$-$C_6$alkenyl-, heterocyclyl$C_1$-$C_6$alkyl-, heterocyclyl$C_2$-$C_6$alkenyl-, aryl$C_1$-$C_6$alkyl-, aryl$C_2$-$C_6$alkenyl-, heteroaryl$C_1$-$C_6$alkyl-, heteroaryl$C_2$-$C_6$alkenyl-, adamantyl, adamantyl$C_1$-$C_6$aliphatic-, or an N protecting group;

$R^{14}$ is a bridged bicyclic ring having 0-2 heteroatoms independently selected from nitrogen, oxygen, and sulfur; and each $R^{15}$ is independently $C_1$-$C_6$alkyl, $C_2$-$C_6$alkenyl, aryl, heteroaryl, aryl$C_1$-$C_6$alkyl-, aryl$C_2$-$C_6$alkenyl-, heteroaryl$C_1$-$C_6$alkyl-, and heteroaryl$C_2$-$C_6$alkenyl-;

wherein the $C_1$-$C_6$alkyl, —$C_3$-$C_6$cycloalkyl, heterocyclyl, aryl, heteroaryl, or bridged bicyclic ring, by itself or attached to another moiety, are independently optionally substituted with 1-3 substituents selected from the group consisting of OH, halo, —$NH_2$, $C_1$-$C_6$alkyl, $C_1$-$C_6$alkyl-O—, $R^{12}O$—$C_1$-$C_6$alkyl(O)C—, and $R^{12}O(O)C$—.

In certain embodiments, the compound of formula (Vj) has the following stereochemical structure (Vj'):

(Vj')

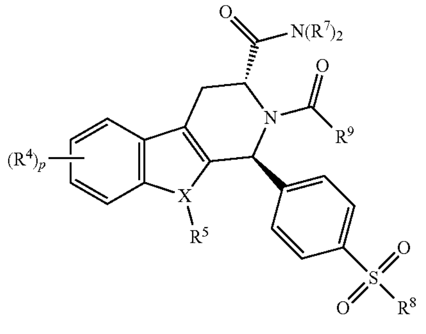

or an enantiomer or pharmaceutically acceptable salt thereof.

In certain embodiments of the compound of formula (Vj) and (Vj'), X is N. In certain embodiments of the compound of formula (Vj) and (Vj'), X is N; and $R^5$ is H.

In certain embodiments of the compound of formula (Vj) and (Vj'), $R^4$ is halo. In certain embodiments of formula (Vj) and (Vj'), p is 0.

In certain embodiments, the compound has the structural formula (Vk):

(Vk)

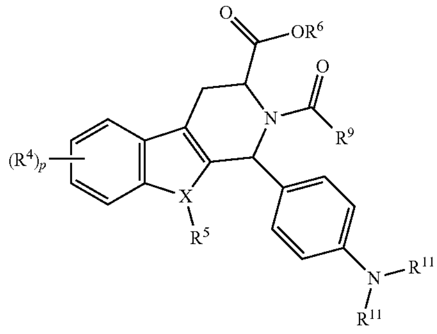

or an enantiomer or pharmaceutically acceptable salt thereof, wherein:

X is N, O or S;

$R^4$ is independently halo, CN, —$NH_2$, —$SO_2$, $C_1$-$C_8$alkyl, —$OR^{12}$, —$C_1$-$C_6$alkyl-$OR^{12}$, —$C_1$-$C_6$alkyl-$NR^{12}$ or —OC(O)$R^{12}$;

$R^5$ is H, $C_1$-$C_6$alkyl, or is absent when X is S or O;

p is 0, 1, 2 or 3;

$R^6$ is $C_1$-$C_6$alkyl, $C_3$-$C_6$alkyl, $C_2$-$C_6$alkenyl, $C_2$-$C_6$alkynyl, $C_3$-$C_6$cycloalkyl, heterocyclyl, aryl, heteroaryl, $C_3$-$C_6$cycloalkyl$C_1$-$C_6$alkyl-, $C_3$-$C_6$cycloalkyl$C_2$-$C_6$alkenyl-, heterocyclyl$C_1$-$C_6$alkyl-, heterocyclyl$C_2$-$C_6$alkenyl-, aryl$C_1$-$C_6$alkyl-, aryl$C_2$-$C_6$alkenyl-, heteroaryl$C_1$-$C_6$alkyl-, heteroaryl$C_2$-$C_6$alkenyl-, $(R^{11})_2NC_1$-$C_6$alkyl-, or $(R^{11})_2NC_2$-$C_6$alkenyl-;

$R^9$ is —$C_1$-$C_2$alkylhalo, —$C_2$-$C_3$alkenylhalo, or $C_2$alkynyl, wherein the $C_1$-$C_2$alkyl is optionally substituted with one or two halo, one or two —$CH_3$, or one or up to all H in —$C_1$-$C_2$alkyl is replaced with deuterium;

each $R^{11}$ is independently H, $C_1$-$C_6$alkyl, $C_2$-$C_6$alkenyl, $C_3$-$C_6$cycloalkyl, heterocyclyl, aryl, heteroaryl, $C_3$-$C_6$cycloalkyl$C_1$-$C_6$alkyl-, $C_3$-$C_6$cycloalkyl$C_2$-$C_6$alkenyl-, heterocyclyl$C_1$-$C_6$alkyl-, heterocyclyl$C_2$-$C_6$alkenyl-, aryl$C_1$-$C_6$alkyl-, aryl$C_2$-$C_6$alkenyl-, heteroaryl$C_1$-$C_6$alkyl-, heteroaryl$C_2$-$C_6$alkenyl-, adamantyl, adamantyl$C_1$-$C_6$aliphatic-, $R^{12}$O—$C_1$-$C_6$alkyl-, $(R^{11})_2NC_1$-$C_6$alkyl-, $(R^{11})_2NC_2$-$C_6$alkenyl-, $R^{12}$O(O)C—$C_1$-$C_6$alkyl-, $R^{13}(NH_2)$CH—, $R^{14}C_0$-$C_6$alkyl-, $(R^{15})_3SiC_0$- $C_6$alkyl-, or an N-protecting group; or two $R^{11}$ together with the nitrogen atom to which they are attached form a 4 to 7 membered heterocyclyl, wherein the heterocyclyl formed by the two $R^{11}$ groups has optionally 0, 1 or 2 additional heteroatoms selected from nitrogen, oxygen, and sulfur, and the heterocyclyl is optionally substituted with OH, halo, $C_1$-$C_6$alkyl, $C_1$-$C_6$alkyl-O(O)C—, $(R^{11})_2$N—, or a 4- to 6-membered heterocyclyl, wherein the 4- to 6-membered heterocyclyl is optionally substituted with OH, halo, —$NH_2$, or $C_1$-$C_6$alkyl, or when containing 2 or more N atoms is optionally substituted with an N-protecting group;

each $R^{12}$ is independently H or $C_1$-$C_6$alkyl;

each $R^{13}$ is independently H, $C_1$-$C_6$alkyl, $C_3$-$C_6$cycloalkyl, heterocyclyl, aryl, heteroaryl, $C_3$-$C_6$cycloalkyl$C_1$-$C_6$alkyl-, $C_3$-$C_6$cycloalkyl$C_2$-$C_6$alkenyl-, heterocyclyl$C_1$-$C_6$alkyl-, heterocyclyl$C_2$-$C_6$alkenyl-, aryl$C_1$-$C_6$alkyl-, aryl$C_2$-$C_6$alkenyl-, heteroaryl$C_1$-$C_6$alkyl-, heteroaryl$C_2$-$C_6$alkenyl-, adamantyl, adamantyl$C_1$-$C_6$aliphatic-, or an N protecting group;

$R^{14}$ is a bridged bicyclic ring having 0-2 heteroatoms independently selected from nitrogen, oxygen, and sulfur; and each $R^{15}$ is independently $C_1$-$C_6$alkyl, $C_2$-$C_6$alkenyl, aryl, heteroaryl, aryl$C_1$-$C_6$alkyl-, aryl$C_2$-$C_6$alkenyl-, heteroaryl$C_1$-$C_6$alkyl-, and heteroaryl$C_2$-$C_6$alkenyl-;

wherein the $C_1$-$C_6$alkyl, —$C_3$-$C_6$cycloalkyl, heterocyclyl, aryl, heteroaryl, or bridged bicyclic ring, by itself or attached to another moiety, are independently optionally substituted with 1-3 substituents selected from the group consisting of OH, halo, —$NH_2$, $C_1$-$C_6$alkyl, $C_1$-$C_6$alkyl-O—, $R^{12}$O—$C_1$-$C_6$alkyl(O)C—, and $R^{12}$O(O)C—.

In certain embodiments of the compound of formula (Vk), $R^6$ is $C_1$-$C_6$alkyl, $C_3$-$C_6$alkyl, $C_2$-$C_6$alkenyl, or $C_2$-$C_6$alkynyl. In certain embodiments of the compound of formula (Vk), $R^6$ is $C_1$-$C_6$alkyl.

In certain embodiments, $R^6$ is methyl, ethyl, n-propyl, n-butyl, isopropyl, t-butyl, pentyl, or hexyl. In certain embodiments of the compound of formula (Vk), $R^6$ is $C_3$-$C_6$alkyl, such as t-butyl.

In certain embodiments of the compound of formula (Vk), one of $R^{11}$ is H and the other of $R^{11}$ is $C_1$-$C_6$alkyl, $C_2$-$C_6$alkenyl, $C_3$-$C_6$cycloalkyl, heterocyclyl, aryl, heteroaryl, $C_3$-$C_6$cycloalkyl$C_1$-$C_6$alkyl-, $C_3$-$C_6$cycloalkyl$C_2$-$C_6$alkenyl-, heterocyclyl$C_1$-$C_6$alkyl-, heterocyclyl$C_2$-$C_6$alkenyl-, aryl$C_1$-$C_6$alkyl-, aryl$C_2$-$C_6$alkenyl-, heteroaryl$C_1$-$C_6$alkyl-, heteroaryl$C_2$-$C_6$alkenyl-, adamantyl, adamantyl$C_1$-$C_6$aliphatic-, $R^{12}$O—$C_1$-$C_6$alkyl-, $(R^{11})_2NC_1$-$C_6$alkyl-, $(R^{11})_2NC_2$-$C_6$alkenyl-, $R^{12}$O(O)C—$C_1$-$C_6$alkyl-, $R^{13}(NH_2)$CH—, $R^{14}C_0$-$C_6$alkyl-, $(R^{15})_3SiC_0$-$C_6$alkyl-, or an N-protecting group.

In certain embodiments of the compound of formula (Vk), one of $R^{11}$ is H and the other of $R^{11}$ is $C_3$-$C_6$cycloalkyl, heterocyclyl, aryl, heteroaryl, $C_3$-$C_6$cycloalkyl$C_1$-$C_6$alkyl-, $C_3$-$C_6$cycloalkyl$C_2$-$C_6$alkenyl-, heterocyclyl$C_1$-$C_6$alkyl-, heterocyclyl$C_2$-$C_6$alkenyl-, aryl$C_1$-$C_6$alkyl-, aryl$C_2$-$C_6$alkenyl-, heteroaryl$C_1$-$C_6$alkyl-, heteroaryl$C_2$-$C_6$alkenyl-, adamantyl, adamantyl$C_1$-$C_6$aliphatic- or an N-protecting group.

In certain embodiments of the compound of formula (Vk), $R^4$ is halo or absent. In certain embodiments, $R^4$ is Br, Cl, or F.

In certain embodiments, the compound of formula (Vk) has the following stereochemical structure (Vk'):

(Vk')

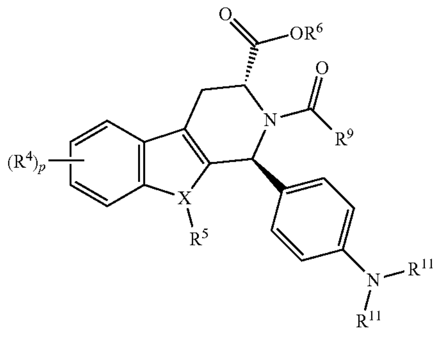

or an enantiomer or pharmaceutically acceptable salt thereof.

In certain embodiments, the compound has the structural formula (Vm):

(Vm)

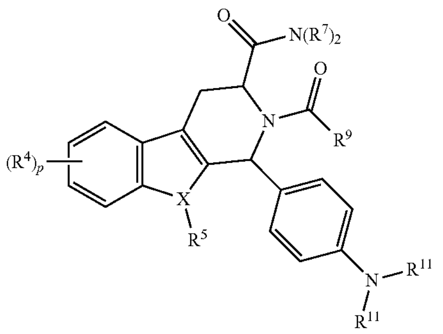

or an enantiomer or pharmaceutically acceptable salt thereof, wherein:

X is N, O or S;

$R^4$ is independently halo, CN, —$NH_2$, —$SO_2$, $C_1$-$C_8$alkyl, —$OR^{12}$, —$C_1$-$C_6$alkyl-$OR^{12}$, —$C_1$-$C_6$alkyl-$NR^{12}$ or —$OC(O)R^{12}$;

$R^5$ is H, $C_1$-$C_6$alkyl, or is absent when X is S or O;

p is 0, 1, 2 or 3;

each $R^7$ is independently H, $C_1$-$C_6$alkyl, $C_2$-$C_6$alkenyl, $C_3$-$C_6$cycloalkyl, heterocyclyl, aryl, heteroaryl, $C_3$-$C_6$cycloalkyl$C_1$-$C_6$alkyl-, $C_3$-$C_6$cycloalkyl$C_2$-$C_6$alkenyl-, heterocyclyl$C_1$-$C_6$alkyl-, heterocyclyl$C_2$-$C_6$alkenyl-, aryl$C_1$-$C_6$alkyl-, aryl$C_2$-$C_6$alkenyl-, heteroaryl$C_1$-$C_6$alkyl-, heteroaryl$C_2$-$C_6$alkenyl-, $(R^{11})_2NC_1$-$C_6$alkyl-, $(R^{11})_2NC_2$-$C_6$alkenyl-, $R^{12}O$—$C_1$-$C_6$alkyl-, or $R^{12}O(O)C$—$C_1$-$C_6$alkyl-, or two $R^7$ together with the nitrogen atom to which they are attached form a 4 to 7 membered heterocyclyl, wherein the heterocyclyl formed by the two $R^7$ groups is optionally substituted with OH, halo, $C_1$-$C_6$alkyl, a 4- to 6-membered heterocyclyl, or $(R^{11})_2N$—, wherein the 4- to 6-membered heterocyclyl when containing 2 or more N atoms is optionally substituted with an N-protecting group;

$R^9$ is —$C_1$-$C_2$alkylhalo, —$C_2$-$C_3$alkenylhalo, or $C_2$alkynyl, wherein the $C_1$-$C_2$alkyl is optionally substituted with one or two halo, one or two —$CH_3$, or one or up to all H in —$C_1$-$C_2$alkyl is replaced with deuterium;

each $R^{11}$ is independently H, $C_1$-$C_6$alkyl, $C_2$-$C_6$alkenyl, $C_3$-$C_6$cycloalkyl, heterocyclyl, aryl, heteroaryl, $C_3$-$C_6$cycloalkyl$C_1$-$C_6$alkyl-, $C_3$-$C_6$cycloalkyl$C_2$-$C_6$alkenyl-, heterocyclyl$C_1$-$C_6$alkyl-, heterocyclyl$C_2$-$C_6$alkenyl-, aryl$C_1$-$C_6$alkyl-, aryl$C_2$-$C_6$alkenyl-, heteroaryl$C_1$-$C_6$alkyl-, heteroaryl$C_2$-$C_6$alkenyl-, adamantyl, adamantyl$C_1$-$C_6$aliphatic-, $R^{12}O$—$C_1$-$C_6$alkyl-, $(R^{11})_2NC_1$-$C_6$alkyl-, $(R^{11})_2NC_2$-$C_6$alkenyl-, $R^{12}(O)C$—$C_1$-$C_6$alkyl-, $R^{13}(NH_2)CH$—, $R^{14}C_0$-$C_6$alkyl-, $(R^{15})_3SiC_0$- $C_6$alkyl-, or an N-protecting group; or two $R^{11}$ together with the nitrogen atom to which they are attached form a 4 to 7 membered heterocyclyl, wherein the heterocyclyl formed by the two $R^{11}$ groups has optionally 0, 1 or 2 additional heteroatoms selected from nitrogen, oxygen, and sulfur, and the heterocyclyl is optionally substituted with OH, halo, $C_1$-$C_6$alkyl, $C_1$-$C_6$alkyl-O(O)C—, $(R^{11})_2N$—, or a 4- to 6-membered heterocyclyl, wherein the 4- to 6-membered heterocyclyl is optionally substituted with OH, halo, —$NH_2$, or $C_1$-$C_6$alkyl, or when containing 2 or more N atoms is optionally substituted with an N-protecting group;

each $R^{12}$ is independently H or $C_1$-$C_6$alkyl;

each $R^{13}$ is independently H, $C_1$-$C_6$alkyl, $C_3$-$C_6$cycloalkyl, heterocyclyl, aryl, heteroaryl, $C_3$-$C_6$cycloalkyl$C_1$-$C_6$alkyl-, $C_3$-$C_6$cycloalkyl$C_2$-$C_6$alkenyl-, heterocyclyl$C_1$-$C_6$alkyl-, heterocyclyl$C_2$-$C_6$alkenyl-, aryl$C_1$-$C_6$alkyl-, aryl$C_2$-$C_6$alkenyl-, heteroaryl$C_1$-$C_6$alkyl-, heteroaryl$C_2$-$C_6$alkenyl-, adamantyl, adamantyl$C_1$-$C_6$aliphatic-, or an N protecting group;

$R^{14}$ is a bridged bicyclic ring having 0-2 heteroatoms independently selected from nitrogen, oxygen, and sulfur; and each $R^{15}$ is independently $C_1$-$C_6$alkyl, $C_2$-$C_6$alkenyl, aryl, heteroaryl, aryl$C_1$-$C_6$alkyl-, aryl$C_2$-$C_6$alkenyl-, heteroaryl$C_1$-$C_6$alkyl-, and heteroaryl$C_2$-$C_6$alkenyl-;

wherein the $C_1$-$C_6$alkyl, —$C_3$-$C_6$cycloalkyl, heterocyclyl, aryl, heteroaryl, or bridged bicyclic ring, by itself or attached to another moiety, are independently optionally substituted with 1-3 substituents selected from the group consisting of OH, halo, —$NH_2$, $C_1$-$C_6$alkyl, $C_1$-$C_6$alkyl-O—, $R^{12}O$—$C_1$-$C_6$alkyl(O)C—, and $R^2O$(O)C—.

In certain embodiments of the compound of formula (Vm), each $R^7$ is independently H, $C_1$-$C_6$alkyl. In certain embodiments, each $R^7$ is $C_1$-$C_6$alkyl. In certain embodiments, wherein $R^7$ is an alkyl, $R^7$ is methyl, ethyl, n-propyl, n-butyl, isopropyl, t-butyl, pentyl, or hexyl.

In certain embodiments of the compound of formula (Vm), one of $R^{11}$ is H and the other of $R^{11}$ is $C_1$-$C_6$alkyl, $C_2$-$C_6$alkenyl, $C_3$-$C_6$cycloalkyl, heterocyclyl, aryl, heteroaryl, $C_3$-$C_6$cycloalkyl$C_1$-$C_6$alkyl-, $C_3$-$C_6$cycloalkyl$C_2$-$C_6$alkenyl-, heterocyclyl$C_1$-$C_6$alkyl-, heterocyclyl$C_2$-$C_6$alkenyl-, aryl$C_1$-$C_6$alkyl-, aryl$C_2$-$C_6$alkenyl-, heteroaryl$C_1$-$C_6$alkyl-, heteroaryl$C_2$-$C_6$alkenyl-, adamantyl, adamantyl$C_1$-$C_6$aliphatic-, $R^{12}O$—$C_1$-$C_6$alkyl-, $(R^{11})_2NC_1$-$C_6$alkyl-, $(R^{11})_2NC_2$-$C_6$alkenyl-, $R^{12}O(O)C$—$C_1$-$C_6$alkyl-, $R^{13}(NH_2)CH$—, $R^{14}C_0$-$C_6$alkyl-, $(R^{15})_3SiC_0$-$C_6$alkyl-, or an N-protecting group.

In certain embodiments of the compound of formula (Vm), one of $R^{11}$ is H and the other of $R^{11}$ is $C_3$-$C_6$cycloalkyl, heterocyclyl, aryl, heteroaryl, $C_3$-$C_6$cycloalkyl$C_1$-$C_6$alkyl-, $C_3$-$C_6$cycloalkyl$C_2$-$C_6$alkenyl-, heterocyclyl$C_1$-$C_6$alkyl-, heterocyclyl$C_2$-$C_6$alkenyl-, aryl$C_1$-$C_6$alkyl-, aryl$C_2$-$C_6$alkenyl-, heteroaryl$C_1$-$C_6$alkyl-, heteroaryl$C_2$-$C_6$alkenyl-, adamantyl, adamantyl$C_1$-$C_6$aliphatic- or an N-protecting group.

In certain embodiments of the compound of formula (Vm), $R^4$ is halo or absent. In certain embodiments, $R^4$ is Br, Cl, or F.

In certain embodiments, the compound of formula (Vm) has the following stereochemical structure (Vm'):

(Vm')

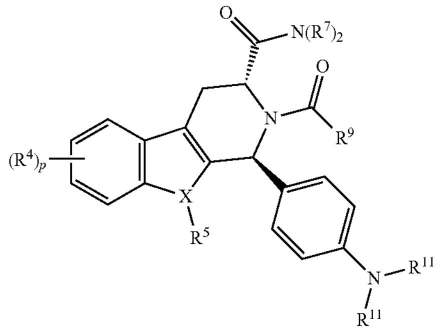

or an enantiomer or pharmaceutically acceptable salt thereof.

In certain embodiments, the compound has a structure of formula (Vn):

(Vn)

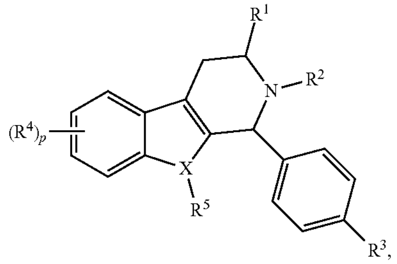

or an enantiomer or pharmaceutically acceptable salt thereof, wherein:

X is N, O or S;

$R^1$ is $C_1$-$C_6$alkyl, —$C_1$-$C_6$alkylhalo or —$C_1$-$C_6$alkyl-$OR^{12}$;

$R^2$ is —C(O)$R^9$;

$R^3$ is —C(O)O$R^{10}$, —C(O)N($R^{11}$)$_2$, —OC(O)$R^{10}$, —$C_0$-$C_6$alkyl$C_3$-$C_8$cycloalkyl, —$C_0$-$C_6$alkylheterocyclyl, —N($R^{11}$)$_2$, —$SO_2R^8$, —SO$R^8$, —$NO_2$ or —Si($R^{15}$)$_3$;

$R^4$ is independently halo, CN, —$NH_2$, —$SO_2$, $C_1$-$C_8$alkyl, —O$R^{12}$, —$C_1$-$C_6$alkyl-O$R^{12}$, —$C_1$-$C_6$alkyl-N$R^{12}$ or —OC(O)$R^{12}$;

$R^5$ is H, $C_1$-$C_6$alkyl, or is absent when X is S or O;

p is 0, 1, 2 or 3;

$R^8$ is independently $C_1$-$C_6$alkyl, $C_3$-$C_6$alkyl, $C_2$-$C_6$alkenyl, $C_2$-$C_6$alkynyl, $C_3$-$C_6$cycloalkyl, heterocyclyl, aryl, heteroaryl, $C_3$-$C_6$cycloalkyl$C_1$-$C_6$alkyl-, $C_3$-$C_6$cycloalkyl$C_2$-$C_6$alkenyl-, heterocyclyl$C_1$-$C_6$alkyl-, heterocyclyl$C_2$-$C_6$alkenyl-, aryl$C_1$-$C_6$alkyl-, aryl$C_2$-$C_6$alkenyl-, heteroaryl$C_1$-$C_6$alkyl-, heteroaryl$C_2$-$C_6$alkenyl-, adamantyl, adamantyl$C_1$-$C_6$aliphatic-, ($R^{11}$)$_2$N$C_1$-$C_6$alkyl-, ($R^{11}$)$_2$N—, or $R^{14}C_0$-$C_6$alkyl-;

$R^9$ is —$C_1$-$C_2$alkylhalo, —$C_2$-$C_3$alkenylhalo, or $C_2$alkynyl, wherein the $C_1$-$C_2$alkyl is optionally substituted with one or two halo, one or two —$CH_3$, or one or up to all H is replaced with deuterium;

$R^{10}$ is $C_1$-$C_6$alkyl, $C_2$-$C_6$alkyl, $C_2$-$C_6$alkenyl, $C_2$-$C_6$alkynyl, $C_3$-$C_6$cycloalkyl, heterocyclyl, aryl, heteroaryl, $C_3$-$C_6$cycloalkyl$C_1$-$C_6$alkyl-, $C_3$-$C_6$cycloalkyl$C_2$-$C_6$alkenyl-, heterocyclyl$C_1$-$C_6$alkyl-, heterocyclyl$C_2$-$C_6$alkenyl-, aryl$C_1$-$C_6$alkyl-, aryl$C_2$-$C_6$alkenyl-, heteroaryl$C_1$-$C_6$alkyl-, heteroaryl$C_2$-$C_6$alkenyl-, adamantyl, adamantyl$C_1$-$C_6$aliphatic-, ($R^{11}$)$_2$N$C_1$-$C_6$alkyl-, ($R^{11}$)$_2$N$C_2$-$C_6$alkenyl-, $R^{13}$($NH_2$)CH—, $R^{14}C_0$-$C_6$alkyl-, or ($R^{15}$)$_3$Si$C_0$-$C_6$alkyl-;

each $R^{11}$ is independently H, $C_1$-$C_6$alkyl, $C_2$-$C_6$alkenyl, $C_3$-$C_6$cycloalkyl, heterocyclyl, aryl, heteroaryl, $C_3$-$C_6$cycloalkyl$C_1$-$C_6$alkyl-, $C_3$-$C_6$cycloalkyl$C_2$-$C_6$alkenyl-, heterocyclyl$C_1$-$C_6$alkyl-, heterocyclyl$C_2$-$C_6$alkenyl-, aryl$C_1$-$C_6$alkyl-, aryl$C_2$-$C_6$alkenyl-, heteroaryl$C_1$-$C_6$alkyl-, heteroaryl$C_2$-$C_6$alkenyl-, adamantyl, adamantyl$C_1$-$C_6$aliphatic-, $R^{12}$O—$C_1$-$C_6$alkyl-, ($R^{11}$)$_2$N$C_1$-$C_6$alkyl-, ($R^{11}$)$_2$N$C_2$-$C_6$alkenyl-, $R^2$O(O)C—$C_1$-$C_6$alkyl-, $R^{13}$($NH_2$)CH—, $R^{14}C_0$-$C_6$alkyl-, ($R^{15}$)$_3$Si$C_0$- $C_6$alkyl-, or an N-protecting group; or two $R^{11}$ together with the nitrogen atom to which they are attached form a 4 to 7 membered heterocyclyl, wherein the heterocyclyl formed by the two $R^{11}$ groups has optionally 0, 1 or 2 additional heteroatoms selected from nitrogen, oxygen, and sulfur, and the heterocyclyl is optionally substituted with OH, halo, $C_1$-$C_6$alkyl, $C_1$-$C_6$alkyl-O(O)C—, ($R^{11}$)$_2$N—, or a 4- to 6-membered heterocyclyl, wherein the 4- to 6-membered heterocyclyl is optionally substituted with OH, halo, —$NH_2$, or $C_1$-$C_6$alkyl, or when containing 2 or more N atoms is optionally substituted with an N-protecting group;

each $R^{12}$ is independently H or $C_1$-$C_6$alkyl;

each $R^{13}$ is independently H, $C_1$-$C_6$alkyl, $C_3$-$C_6$cycloalkyl, heterocyclyl, aryl, heteroaryl, $C_3$-$C_6$cycloalkyl$C_1$-$C_6$alkyl-, $C_3$-$C_6$cycloalkyl$C_2$-$C_6$alkenyl-, heterocyclyl$C_1$-$C_6$alkyl-, heterocyclyl$C_2$-$C_6$alkenyl-, aryl$C_1$-$C_6$alkyl-, aryl$C_2$-$C_6$alkenyl-, heteroaryl$C_1$-$C_6$alkyl-, heteroaryl$C_2$-$C_6$alkenyl-, adamantyl, adamantyl$C_1$-$C_6$aliphatic-, or an N protecting group;

$R^{14}$ is a bridged bicyclic ring having 0-2 heteroatoms independently selected from nitrogen, oxygen, and sulfur; and each $R^{15}$ is independently $C_1$-$C_6$alkyl, $C_2$-$C_6$alkenyl, aryl, heteroaryl, aryl$C_1$-$C_6$alkyl-, aryl$C_2$-$C_6$alkenyl-, heteroaryl$C_1$-$C_6$alkyl-, and heteroaryl$C_2$-$C_6$alkenyl-;

wherein the $C_1$-$C_6$alkyl, —$C_3$-$C_6$cycloalkyl, heterocyclyl, aryl, heteroaryl, or bridged bicyclic ring, by itself or attached to another moiety, are independently optionally substituted with 1-3 substituents selected from the group consisting of OH, halo, —$NH_2$, $C_1$-$C_6$alkyl, $C_1$-$C_6$alkyl-O—, $R^{12}$O—$C_1$-$C_6$alkyl(O)C—, and $R^{12}$O(O)C—.

In certain embodiments, the compound has a structure of formula (Vp):

(Vp)

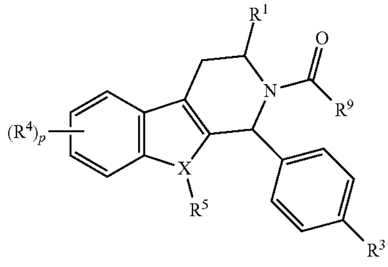

or an enantiomer or pharmaceutically acceptable salt thereof, wherein:

X is N, O or S;

$R^1$ is $C_1$-$C_6$alkyl, —$C_1$-$C_6$alkylhalo or —$C_1$-$C_6$alkyl-$OR^{12}$;

$R^3$ is —$C_0$-$C_6$alkyl$C_3$-$C_8$cycloalkyl or —$C_0$-$C_6$alkylheterocyclyl;

$R^4$ is independently halo, CN, —$NH_2$, —$SO_2$, $C_1$-$C_8$alkyl, —$OR^{12}$, —$C_1$-$C_6$alkyl-$OR^{12}$, —$C_1$-$C_6$alkyl-$NR^{12}$ or —$OC(O)R^{12}$;

$R^5$ is H, $C_1$-$C_6$alkyl, or is absent when X is S or O;

p is 0, 1, 2 or 3;

$R^9$ is —$C_1$-$C_2$alkylhalo, —$C_2$-$C_3$alkenylhalo, or $C_2$alkynyl, wherein the $C_1$-$C_2$alkyl is optionally substituted with one or two halo, one or two —$CH_3$, or one or up to all H is replaced with deuterium;

$R^{12}$ is independently H or $C_1$-$C_6$alkyl;

wherein the $C_0$-$C_6$alkyl or —$C_3$-$C_8$cycloalkyl are independently optionally substituted with 1-3 substituents selected from the group consisting of OH, halo, —$NH_2$, $C_1$-$C_6$alkyl, $C_1$-$C_6$alkyl-O—, $R^{12}$O—$C_1$-$C_6$alkyl(O)C—, and $R^{12}$O(O)C—.

In certain embodiments, the compound of formula (Vn) and (Vp) have the following stereochemical structure (Vn'):

(Vn')

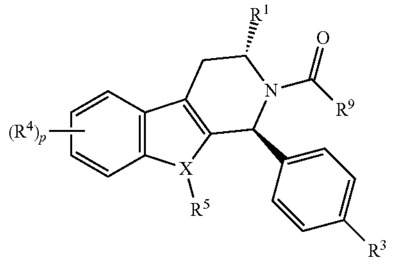

or an enantiomer or pharmaceutically acceptable salt thereof.

In certain embodiments of the compounds of formula (Vn), (Vp) and (Vn'), $R^9$ is —$C_1$-$C_2$alkylhalo. In certain embodiments, $R^9$ is —$C_1$-$C_2$alkylCl or —$C_1$-$C_2$alkylF. In certain embodiments, $R^9$ is —$CH_2CH_2Cl$. In certain embodiments, $R^9$ is —$CD_2CD_2Cl$. In certain embodiments, $R^9$ is —$CH_2Cl$ or —$CH_2F$.

In certain embodiments, $R^9$ is —$CH_2Cl$. In certain embodiments, $R^9$ is —$CD_2Cl$ or —$CD_2F$. In certain embodiments, $R^9$ is-$CD_2Cl$.

In certain embodiments of the compounds of formula (Va), (Vn), (Vp) and (Vn'), the $C_3$-$C_8$cycloalkyl group of the —$C_0$-$C_6$alkyl$C_3$-$C_8$cycloalkyl is cyclopropyl, cyclobutyl, cyclopentyl, cyclohexyl, cycloheptyl, or cyclooctyl. In certain embodiments, the $C_3$-$C_8$cycloalkyl is cyclopropyl, cyclobutyl, cyclopentyl, or cyclohexyl.

In certain embodiments of the compounds of formula (Va), (Vn), (Vp) and (Vn'), the heterocyclyl group of the —$C_0$-$C_6$alkylheterocyclyl is a 4-7 membered heterocyclic ring containing 1, 2 or 3 heteroatoms selected from S, N, and O, wherein the heterocyclic ring is optionally substituted with 1, 2 or 3 substituents selected from OH, halo, —$NH_2$, and $C_1$-$C_6$alkyl, or when containing 2 or more N atoms is optionally substituted with an N-protecting group. In certain embodiments the heterocyclic ring is selected from azetidinyl, pyrrolidinyl, piperidinyl, pyrazolidinyl, isoxazolidinyl, oxazolidinyl, thiazolidinyl, imidazolidinyl, tetrahydropyranyl, piperazinyl, morpholinyl, thiomorpholinyl, 1,3-oxazinanyl, 1,3-thiazinanyl, dihydropyridinyl, 1,3-tetrahydropyrimidinyl, dihydropyrimidinyl, azepanyl and 1,4- diazepanyl. In certain embodiments, the heterocycloalkyl is tetrahydropyranyl, piperidinyl, piperazinyl, or morpholinyl.

In certain embodiments, the compound is selected from the group consisting of the compounds of Table 1.

TABLE 1

| No. | Structure |
|---|---|
| 1 | 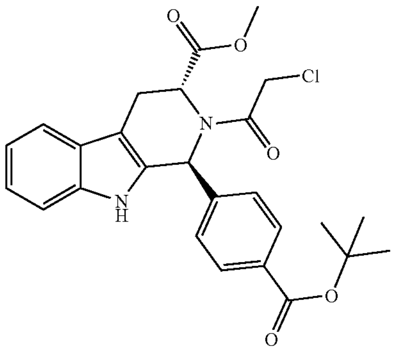 [SMILES: COC(=O)[C@H]1Cc2c([nH]c3ccccc23)[C@H](c2ccc(C(=O)OC(C)(C)C)cc2)N1C(=O)CCl] |
| 2 | 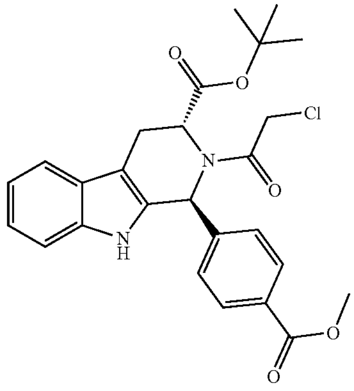 [SMILES: COC(=O)c1ccc([C@H]2c3[nH]c4ccccc4c3C[C@H](C(=O)OC(C)(C)C)N2C(=O)CCl)cc1] |
| 3 | 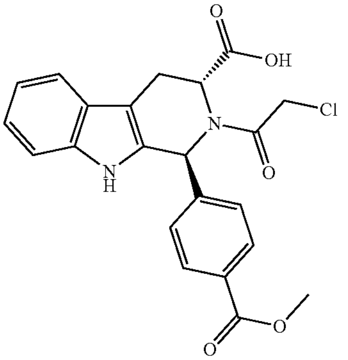 [SMILES: COC(=O)c1ccc([C@H]2c3[nH]c4ccccc4c3C[C@H](C(=O)O)N2C(=O)CCl)cc1] |
| 4 | 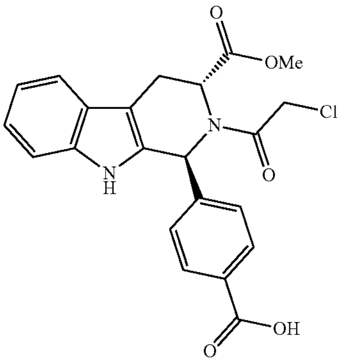 [SMILES: COC(=O)[C@H]1Cc2c([nH]c3ccccc23)[C@H](c2ccc(C(=O)O)cc2)N1C(=O)CCl] |

TABLE 1-continued
| No. | Structure |
| --- | --- |
| 5 | 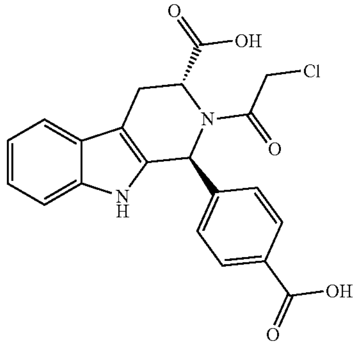 [SMILES: O=C(O)c1ccc([C@H]2c3[nH]c4ccccc4c3C[C@H](C(=O)O)N2C(=O)CCl)cc1] |
| 6 | 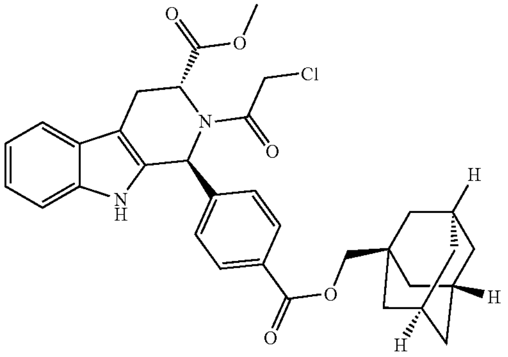 [SMILES: COC(=O)[C@H]1Cc2c([nH]c3ccccc23)[C@H](c2ccc(C(=O)OC[C@]34C[C@H]5C[C@H](C[C@H](C5)C3)C4)cc2)N1C(=O)CCl] |
| 7 | 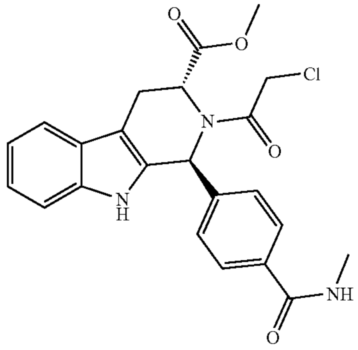 [SMILES: CNC(=O)c1ccc([C@H]2c3[nH]c4ccccc4c3C[C@H](C(=O)OC)N2C(=O)CCl)cc1] |
| 8 | 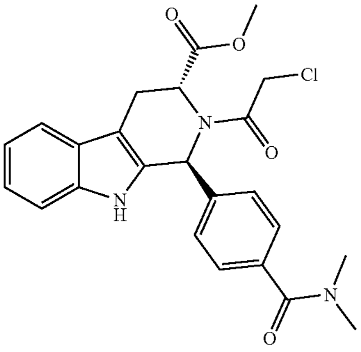 [SMILES: COC(=O)[C@H]1Cc2c([nH]c3ccccc23)[C@H](c2ccc(C(=O)N(C)C)cc2)N1C(=O)CCl] |
TABLE 1-continued
| No. | Structure |
| --- | --- |
| 9 | 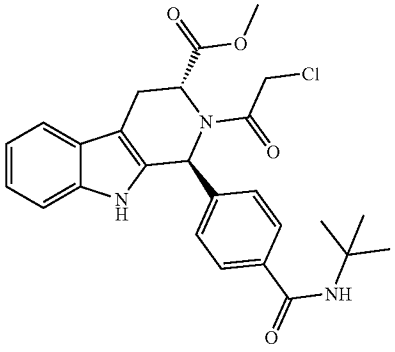 [SMILES: COC(=O)[C@H]1Cc2c([nH]c3ccccc23)[C@H](c2ccc(C(=O)NC(C)(C)C)cc2)N1C(=O)CCl] |
| 10 | 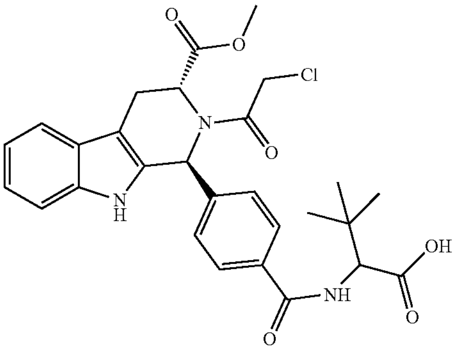 [SMILES: COC(=O)[C@H]1Cc2c([nH]c3ccccc23)[C@H](c2ccc(C(=O)NC(C(=O)O)C(C)(C)C)cc2)N1C(=O)CCl] |
| 11 | 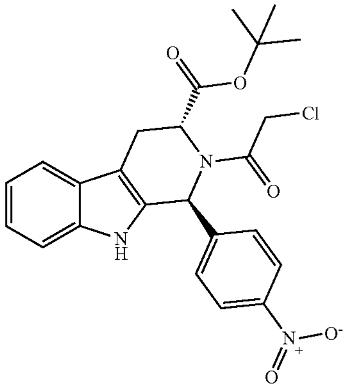 |
| 12 | 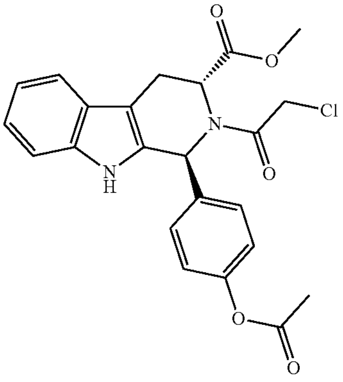 [SMILES: COC(=O)[C@H]1Cc2c([nH]c3ccccc23)[C@H](c2ccc(OC(C)=O)cc2)N1C(=O)CCl] |

TABLE 1-continued
| No. | Structure |
|---|---|
| 13 | 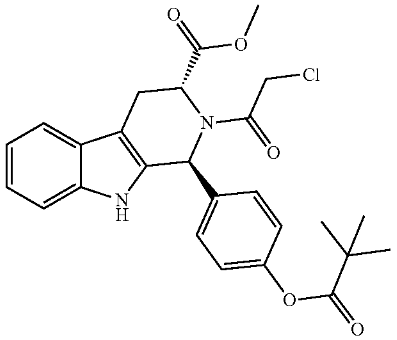 [SMILES: COC(=O)[C@H]1Cc2c([nH]c3ccccc23)[C@H](c2ccc(OC(=O)C(C)(C)C)cc2)N1C(=O)CCl] |
| 14 | 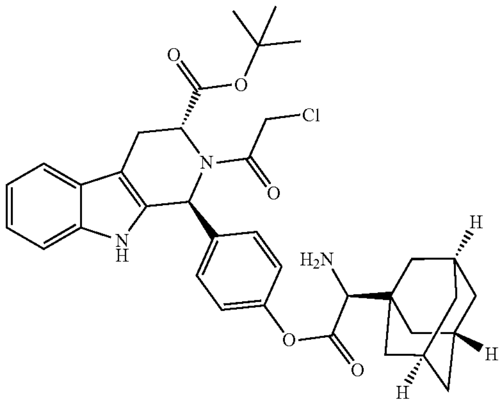 [SMILES: CC(C)(C)OC(=O)[C@H]1Cc2c([nH]c3ccccc23)[C@H](c2ccc(OC(=O)[C@@H](N)C34C[C@H]5C[C@@H](C3)C[C@@H](C4)C5)cc2)N1C(=O)CCl] |
| 15 | 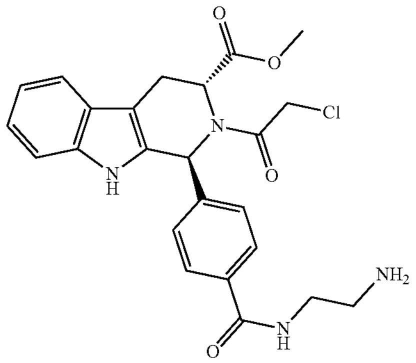 [SMILES: COC(=O)[C@H]1Cc2c([nH]c3ccccc23)[C@H](c2ccc(C(=O)NCCN)cc2)N1C(=O)CCl] |
| 16 | 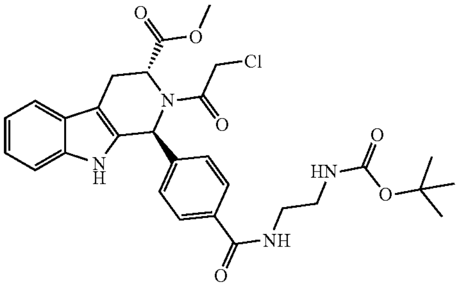 [SMILES: COC(=O)[C@H]1Cc2c([nH]c3ccccc23)[C@H](c2ccc(C(=O)NCCNC(=O)OC(C)(C)C)cc2)N1C(=O)CCl] |
TABLE 1-continued
| No. | Structure |
|---|---|
| 17 | 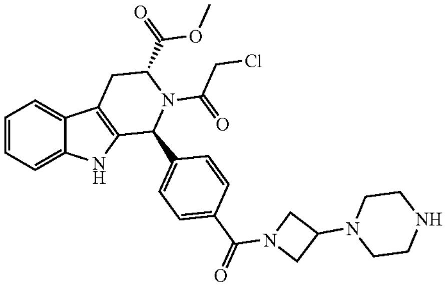 [SMILES: COC(=O)[C@H]1Cc2c([nH]c3ccccc23)[C@H](c2ccc(C(=O)N3CC(N4CCNCC4)C3)cc2)N1C(=O)CCl] |
| 18 | 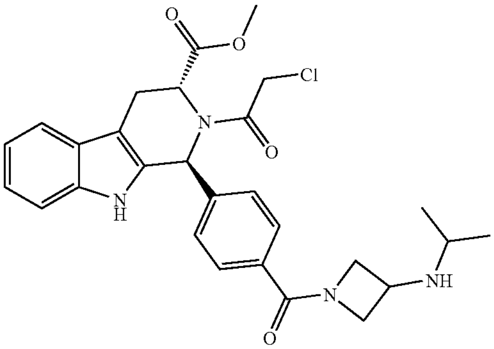 [SMILES: COC(=O)[C@H]1Cc2c([nH]c3ccccc23)[C@H](c2ccc(C(=O)N3CC(NC(C)C)C3)cc2)N1C(=O)CCl] |
| 19 | 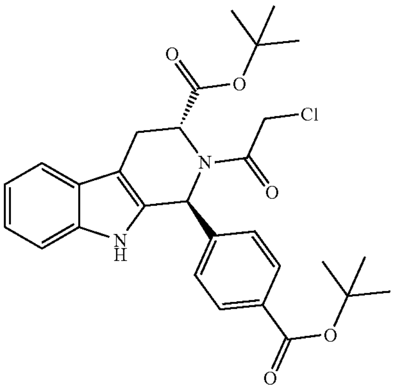 [SMILES: CC(C)(C)OC(=O)c1ccc([C@H]2c3[nH]c4ccccc4c3C[C@H](C(=O)OC(C)(C)C)N2C(=O)CCl)cc1] |
| 20 | 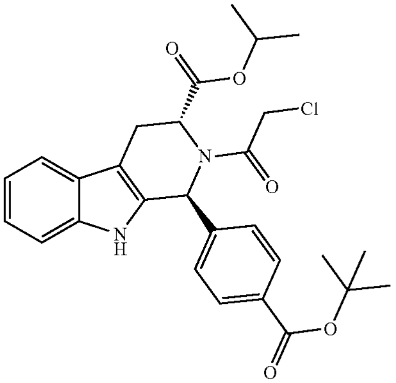 [SMILES: CC(C)OC(=O)[C@H]1Cc2c([nH]c3ccccc23)[C@H](c2ccc(C(=O)OC(C)(C)C)cc2)N1C(=O)CCl] |

TABLE 1-continued
| No. | Structure |
|---|---|
| 21 | 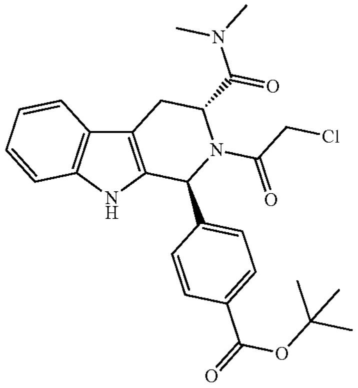 [SMILES: CN(C)C(=O)[C@H]1Cc2c([nH]c3ccccc23)[C@H](c2ccc(C(=O)OC(C)(C)C)cc2)N1C(=O)CCl] |
| 22 | 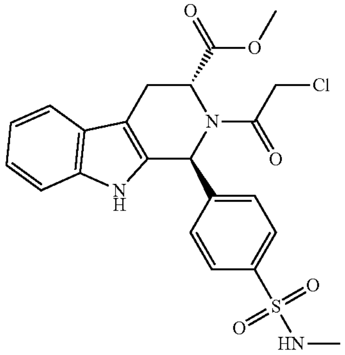 [SMILES: CNS(=O)(=O)c1ccc([C@H]2c3[nH]c4ccccc4c3C[C@H](C(=O)OC)N2C(=O)CCl)cc1] |
| 23 | 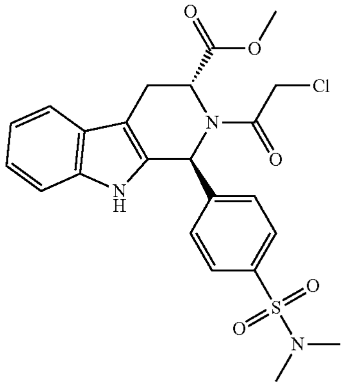 [SMILES: COC(=O)[C@H]1Cc2c([nH]c3ccccc23)[C@H](c2ccc(S(=O)(=O)N(C)C)cc2)N1C(=O)CCl] |
| 24 | 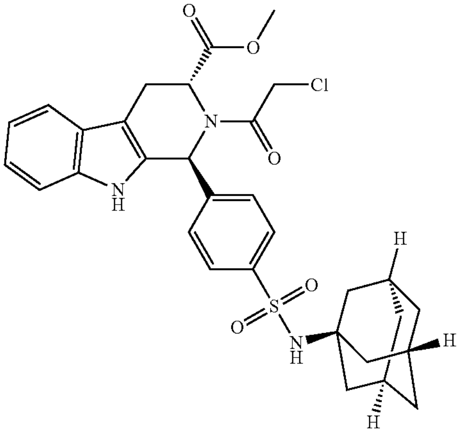 [SMILES: COC(=O)[C@H]1Cc2c([nH]c3ccccc23)[C@H](c2ccc(S(=O)(=O)N[C@]34C[C@H]5C[C@H](C[C@H](C5)C3)C4)cc2)N1C(=O)CCl] |
TABLE 1-continued
| No. | Structure |
|---|---|
| 25 | 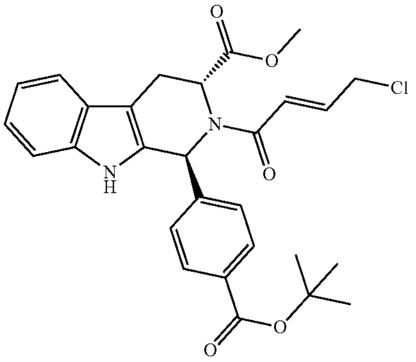 [SMILES: COC(=O)[C@H]1Cc2c([nH]c3ccccc23)[C@H](c2ccc(C(=O)OC(C)(C)C)cc2)N1C(=O)/C=C/CCl] |
| 26 | 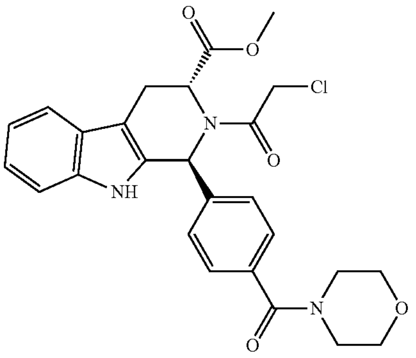 [SMILES: COC(=O)[C@H]1Cc2c([nH]c3ccccc23)[C@H](c2ccc(C(=O)N3CCOCC3)cc2)N1C(=O)CCl] |
| 27 | 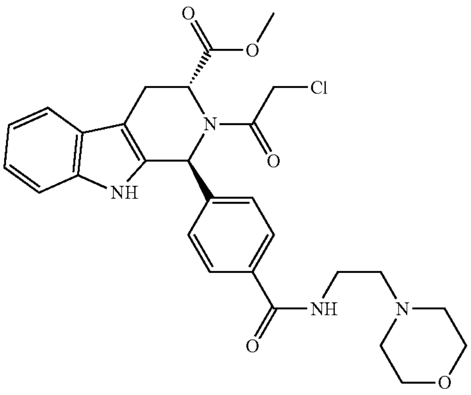 [SMILES: COC(=O)[C@H]1Cc2c([nH]c3ccccc23)[C@H](c2ccc(C(=O)NCCN3CCOCC3)cc2)N1C(=O)CCl] |
| 28 | 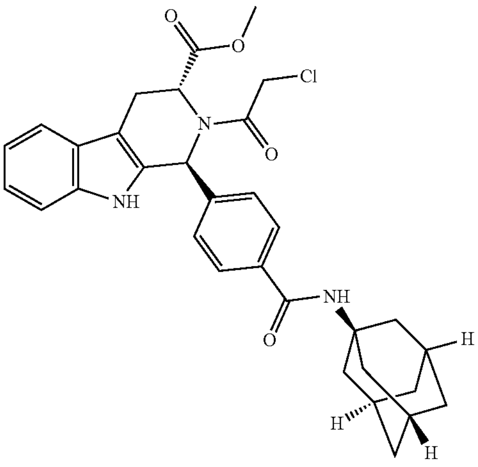 [SMILES: COC(=O)[C@H]1Cc2c([nH]c3ccccc23)[C@H](c2ccc(C(=O)N[C@]34CC5C[C@H](C[C@H](C5)C3)C4)cc2)N1C(=O)CCl] |

TABLE 1-continued
| No. | Structure |
|---|---|
| 29 | 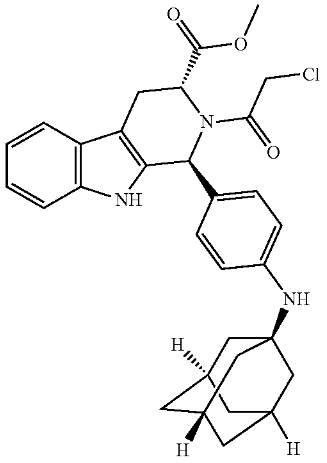 [SMILES: COC(=O)[C@H]1Cc2c([nH]c3ccccc23)[C@H](c2ccc(N[C@]34CC5C[C@H](C[C@H](C5)C3)C4)cc2)N1C(=O)CCl] |
| 30 | 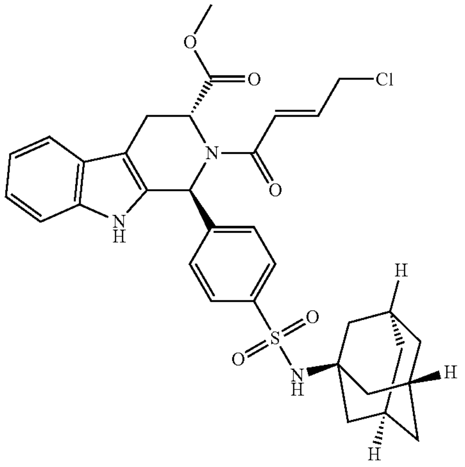 [SMILES: COC(=O)[C@H]1Cc2c([nH]c3ccccc23)[C@H](c2ccc(S(=O)(=O)N[C@]34C[C@H]5C[C@H](C[C@H](C5)C3)C4)cc2)N1C(=O)/C=C/CCl] |
| 31 | 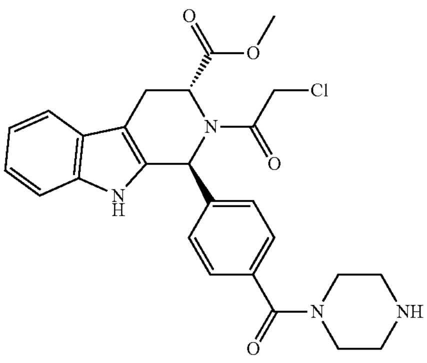 [SMILES: COC(=O)[C@H]1Cc2c([nH]c3ccccc23)[C@H](c2ccc(C(=O)N3CCNCC3)cc2)N1C(=O)CCl] |
TABLE 1-continued
| No. | Structure |
|---|---|
| 32 | 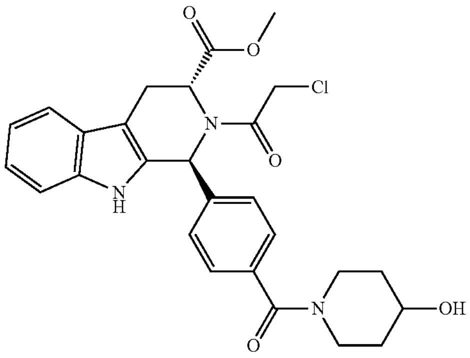 [SMILES: COC(=O)[C@H]1Cc2c([nH]c3ccccc23)[C@H](c2ccc(C(=O)N3CCC(O)CC3)cc2)N1C(=O)CCl] |
| 33 | 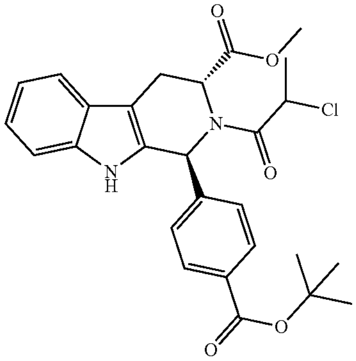 [SMILES: COC(=O)[C@H]1Cc2c([nH]c3ccccc23)[C@H](c2ccc(C(=O)OC(C)(C)C)cc2)N1C(=O)C(C)Cl] |
| 34 | 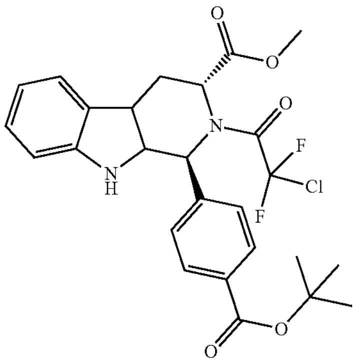 [SMILES: COC(=O)[C@H]1CC2c3ccccc3NC2[C@H](c2ccc(C(=O)OC(C)(C)C)cc2)N1C(=O)C(F)(F)Cl] |
| 35 | 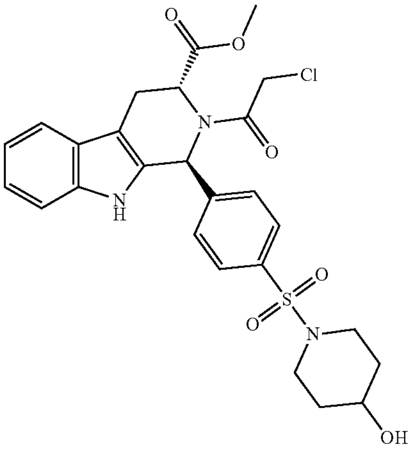 [SMILES: COC(=O)[C@H]1Cc2c([nH]c3ccccc23)[C@H](c2ccc(S(=O)(=O)N3CCC(O)CC3)cc2)N1C(=O)CCl] |

TABLE 1-continued
| No. | Structure |
|---|---|
| 36 | 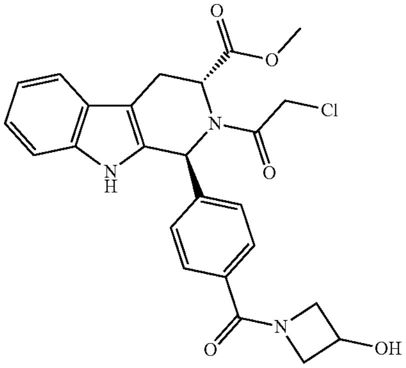 [SMILES: COC(=O)[C@H]1Cc2c([nH]c3ccccc23)[C@H](c2ccc(C(=O)N3CC(O)C3)cc2)N1C(=O)CCl] |
| 37 | 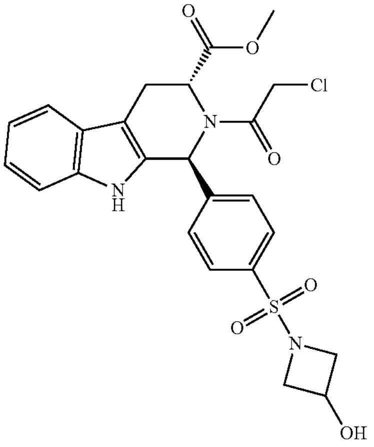 [SMILES: COC(=O)[C@H]1Cc2c([nH]c3ccccc23)[C@H](c2ccc(S(=O)(=O)N3CC(O)C3)cc2)N1C(=O)CCl] |
| 38 | 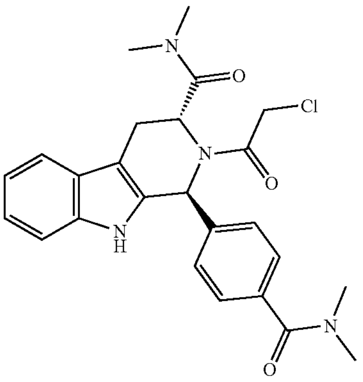 [SMILES: CN(C)C(=O)c1ccc([C@H]2c3[nH]c4ccccc4c3C[C@H](C(=O)N(C)C)N2C(=O)CCl)cc1] |
TABLE 1-continued
| No. | Structure |
|---|---|
| 39 | 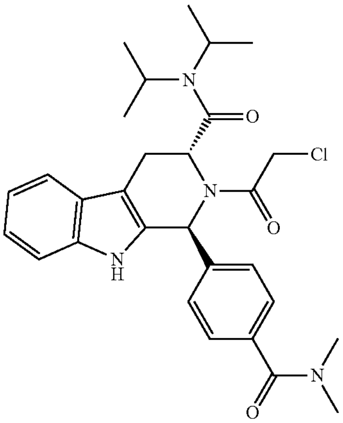 [SMILES: CC(C)N(C(=O)[C@H]1Cc2c([nH]c3ccccc23)[C@H](c2ccc(C(=O)N(C)C)cc2)N1C(=O)CCl)C(C)C] |
| 40 | 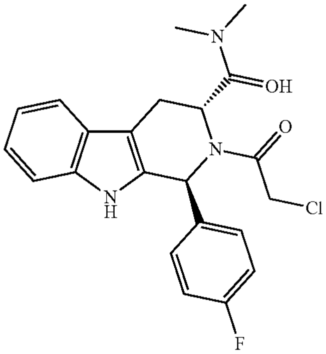 [SMILES: CN(C)C(=O)[C@H]1Cc2c([nH]c3ccccc23)[C@H](c2ccc(F)cc2)N1C(=O)CCl] |
| 41 | 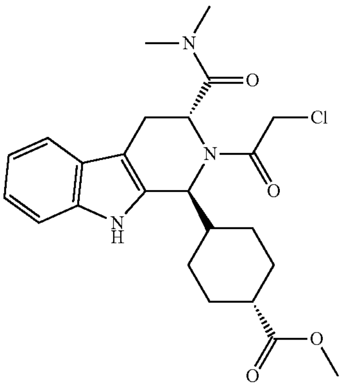 |

TABLE 1-continued
| No. | Structure |
|---|---|
| 42 | 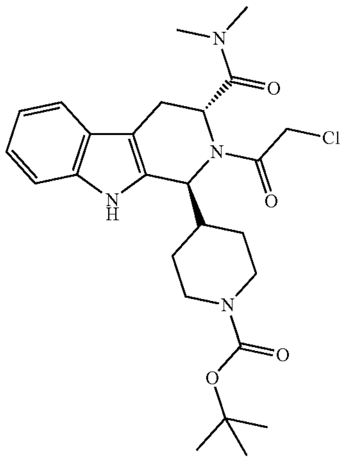 [SMILES: CN(C)C(=O)[C@H]1Cc2c([nH]c3ccccc23)[C@H](C2CCN(C(=O)OC(C)(C)C)CC2)N1C(=O)CCl] |
| 43 | 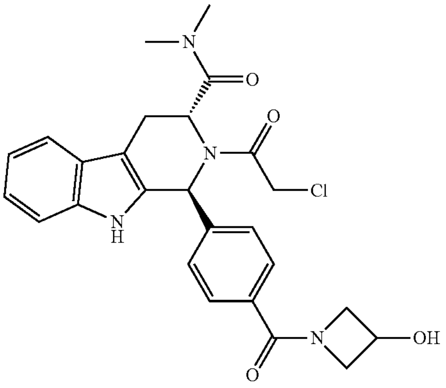 [SMILES: CN(C)C(=O)[C@H]1Cc2c([nH]c3ccccc23)[C@H](c2ccc(C(=O)N3CC(O)C3)cc2)N1C(=O)CCl] |
| 44 | 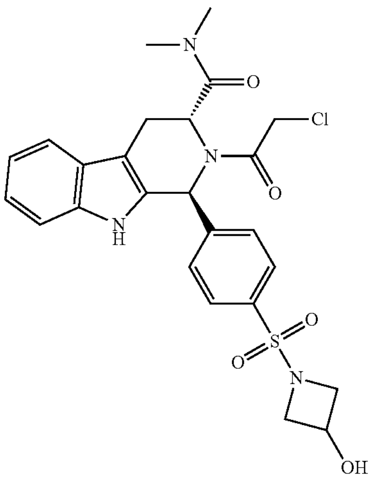 [SMILES: CN(C)C(=O)[C@H]1Cc2c([nH]c3ccccc23)[C@H](c2ccc(S(=O)(=O)N3CC(O)C3)cc2)N1C(=O)CCl] |
TABLE 1-continued
| No. | Structure |
|---|---|
| 45 | 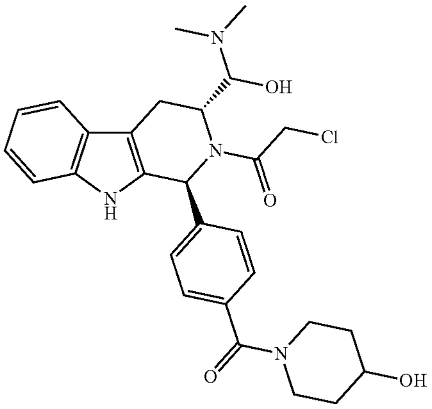 [SMILES: CN(C)C(O)[C@H]1Cc2c([nH]c3ccccc23)[C@H](c2ccc(C(=O)N3CCC(O)CC3)cc2)N1C(=O)CCl] |
| 46 | 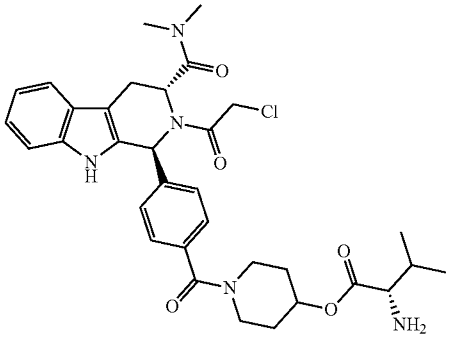 [SMILES: CC(C)[C@H](N)C(=O)OC1CCN(C(=O)c2ccc([C@H]3c4[nH]c5ccccc5c4C[C@H](C(=O)N(C)C)N3C(=O)CCl)cc2)CC1] |
| 47 | 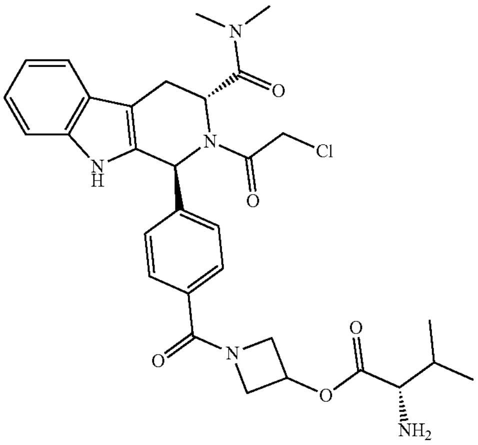 [SMILES: CC(C)[C@H](N)C(=O)OC1CN(C(=O)c2ccc([C@H]3c4[nH]c5ccccc5c4C[C@H](C(=O)N(C)C)N3C(=O)CCl)cc2)C1] |

TABLE 1-continued
| No. | Structure |
| --- | --- |
| 48 | 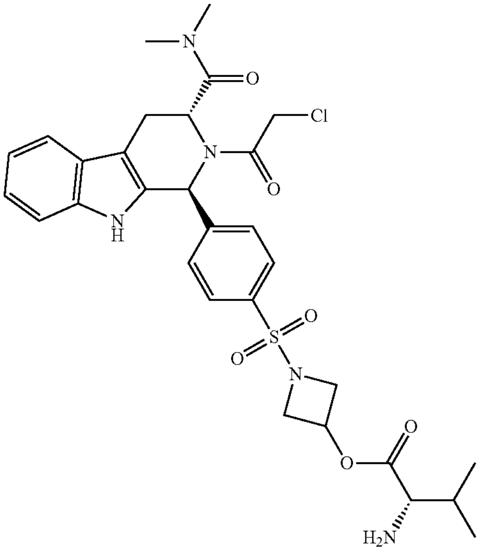 [SMILES: CC(C)[C@H](N)C(=O)OC1CN(S(=O)(=O)c2ccc([C@H]3c4[nH]c5ccccc5c4C[C@H](C(=O)N(C)C)N3C(=O)CCl)cc2)C1] |
| 49 | 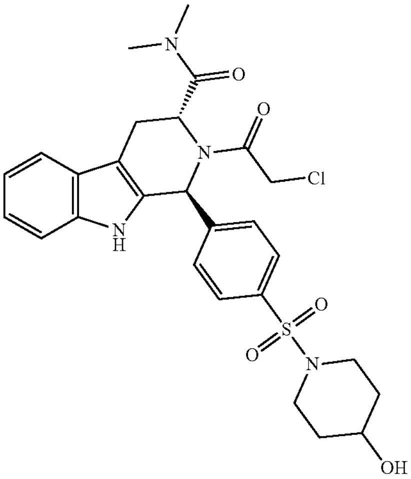 [SMILES: CN(C)C(=O)[C@H]1Cc2c([nH]c3ccccc23)[C@H](c2ccc(S(=O)(=O)N3CCC(O)CC3)cc2)N1C(=O)CCl] |
| 50 | 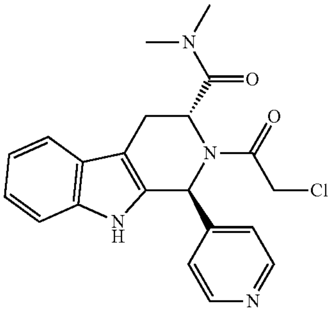 [SMILES: CN(C)C(=O)[C@H]1Cc2c([nH]c3ccccc23)[C@H](c2ccncc2)N1C(=O)CCl] |
TABLE 1-continued
| No. | Structure |
| --- | --- |
| 51 | 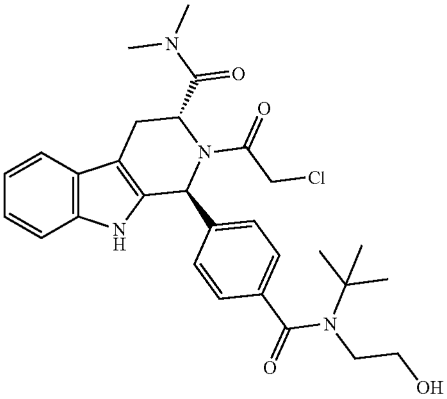 [SMILES: CN(C)C(=O)[C@H]1Cc2c([nH]c3ccccc23)[C@H](c2ccc(C(=O)N(CCO)C(C)(C)C)cc2)N1C(=O)CCl] |
| 52 | 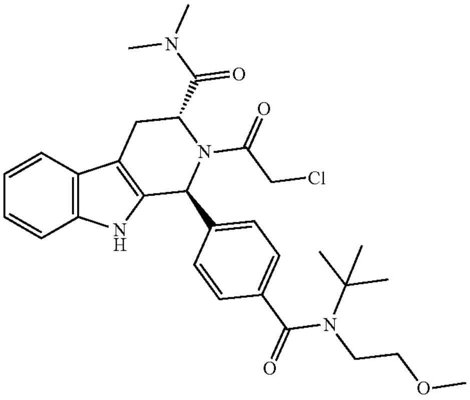 [SMILES: COCCN(C(=O)c1ccc([C@H]2c3[nH]c4ccccc4c3C[C@H](C(=O)N(C)C)N2C(=O)CCl)cc1)C(C)(C)C] |
| 53 | 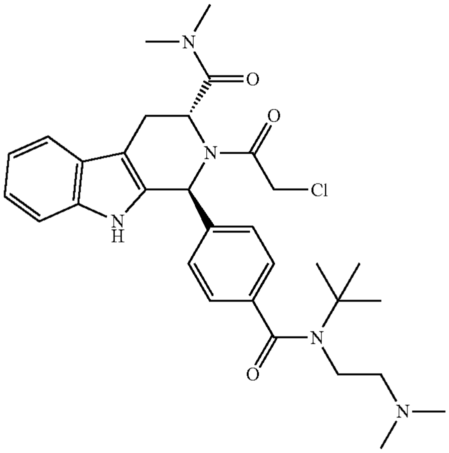 [SMILES: CN(C)CCN(C(=O)c1ccc([C@H]2c3[nH]c4ccccc4c3C[C@H](C(=O)N(C)C)N2C(=O)CCl)cc1)C(C)(C)C] |
| 54 | 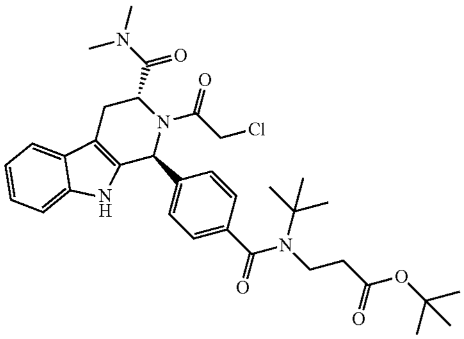 [SMILES: CN(C)C(=O)[C@H]1Cc2c([nH]c3ccccc23)[C@H](c2ccc(C(=O)N(CCC(=O)OC(C)(C)C)C(C)(C)C)cc2)N1C(=O)CCl] |

TABLE 1-continued
| No. | Structure |
| --- | --- |
| 55 | 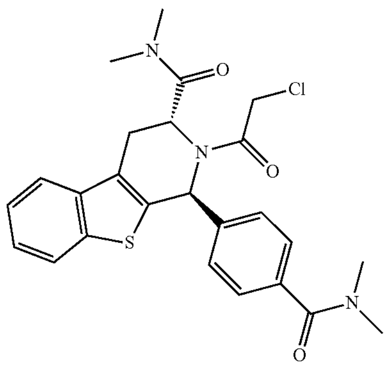 [SMILES: CN(C)C(=O)c1ccc([C@H]2c3sc4ccccc4c3C[C@H](C(=O)N(C)C)N2C(=O)CCl)cc1] |
| 56 | 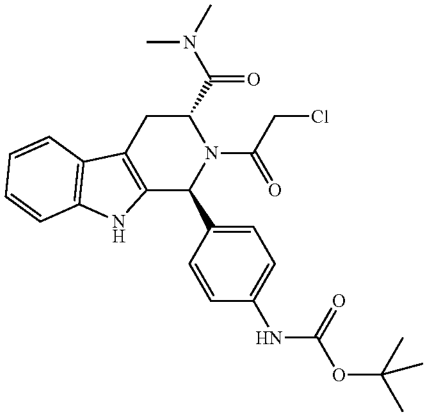 [SMILES: CN(C)C(=O)[C@H]1Cc2c([nH]c3ccccc23)[C@H](c2ccc(NC(=O)OC(C)(C)C)cc2)N1C(=O)CCl] |
| 57 | 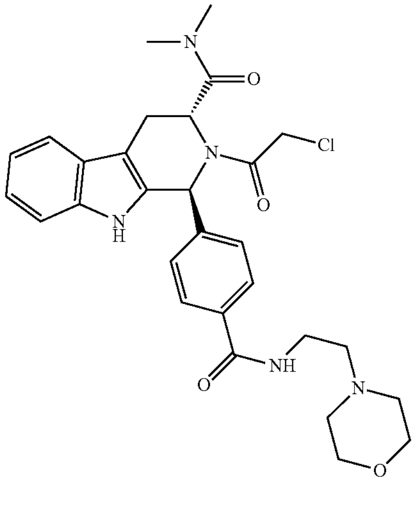 [SMILES: CN(C)C(=O)[C@H]1Cc2c([nH]c3ccccc23)[C@H](c2ccc(C(=O)NCCN3CCOCC3)cc2)N1C(=O)CCl] |
TABLE 1-continued
| No. | Structure |
| --- | --- |
| 58 | 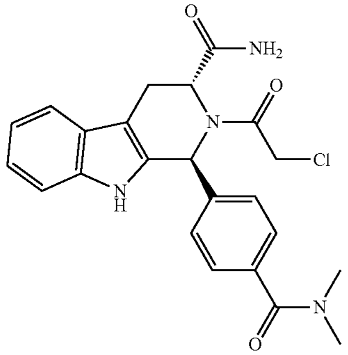 [SMILES: CN(C)C(=O)c1ccc([C@H]2c3[nH]c4ccccc4c3C[C@H](C(N)=O)N2C(=O)CCl)cc1] |
| 59 | 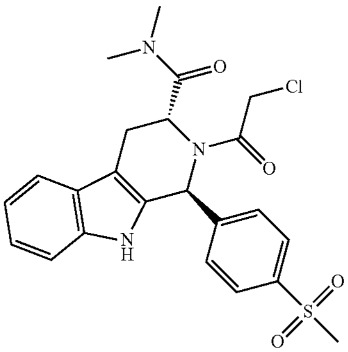 [SMILES: CN(C)C(=O)[C@H]1Cc2c([nH]c3ccccc23)[C@H](c2ccc(S(C)(=O)=O)cc2)N1C(=O)CCl] |
| 60 | 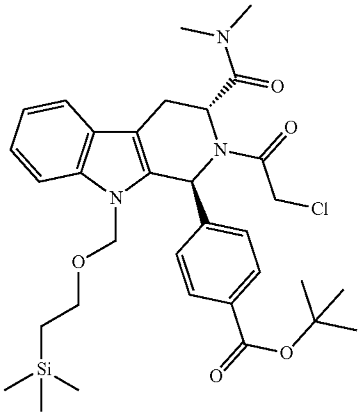 [SMILES: CN(C)C(=O)[C@H]1Cc2c(n(COCC[Si](C)(C)C)c3ccccc23)[C@H](c2ccc(C(=O)OC(C)(C)C)cc2)N1C(=O)CCl] |
| 61 | 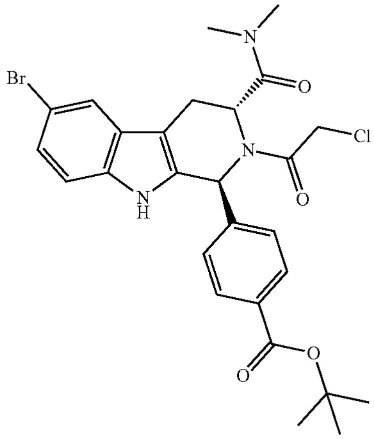 [SMILES: CN(C)C(=O)[C@H]1Cc2c([nH]c3ccc(Br)cc23)[C@H](c2ccc(C(=O)OC(C)(C)C)cc2)N1C(=O)CCl] |

TABLE 1-continued
| No. | Structure |
|---|---|
| 62 | 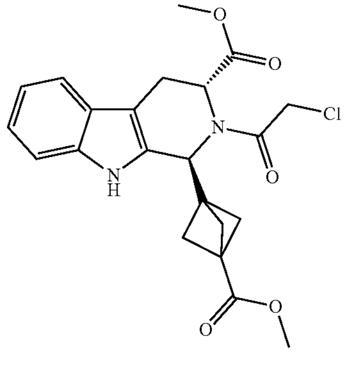 [SMILES: COC(=O)[C@H]1Cc2c([nH]c3ccccc23)[C@H](C23CC(C(=O)OC)(C2)C3)N1C(=O)CCl] |
| 63 | 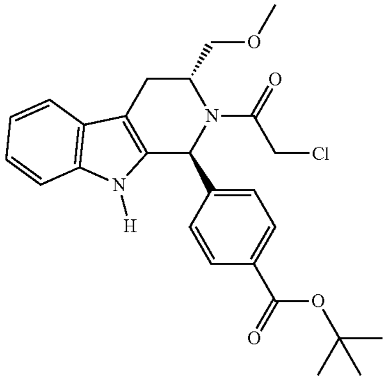 [SMILES: COC[C@H]1Cc2c([nH]c3ccccc23)[C@H](c2ccc(C(=O)OC(C)(C)C)cc2)N1C(=O)CCl] |
| 64 | 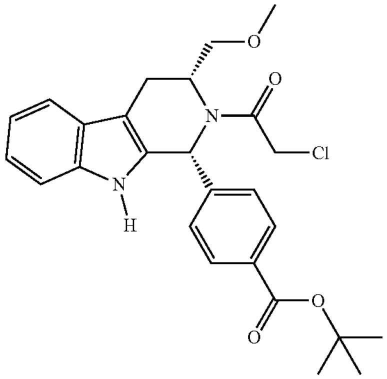 [SMILES: COC[C@H]1Cc2c([nH]c3ccccc23)[C@@H](c2ccc(C(=O)OC(C)(C)C)cc2)N1C(=O)CCl] |
| 65 | 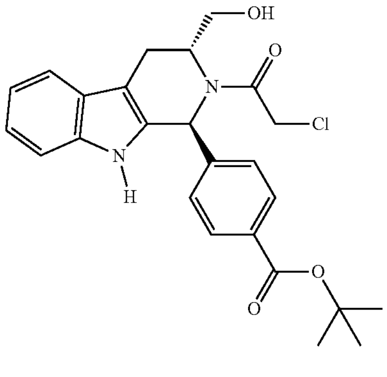 [SMILES: CC(C)(C)OC(=O)c1ccc([C@H]2c3[nH]c4ccccc4c3C[C@H](CO)N2C(=O)CCl)cc1] |
TABLE 1-continued
| No. | Structure |
|---|---|
| 66 | 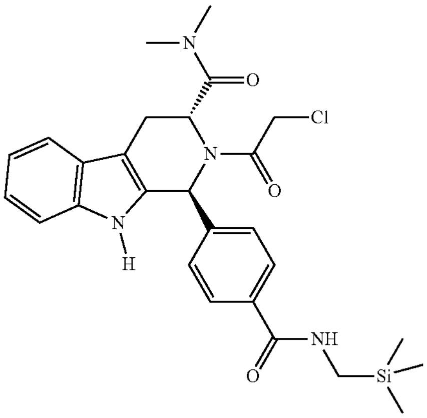 [SMILES: CN(C)C(=O)[C@H]1Cc2c([nH]c3ccccc23)[C@H](c2ccc(C(=O)NC[Si](C)(C)C)cc2)N1C(=O)CCl] |
| 67 | 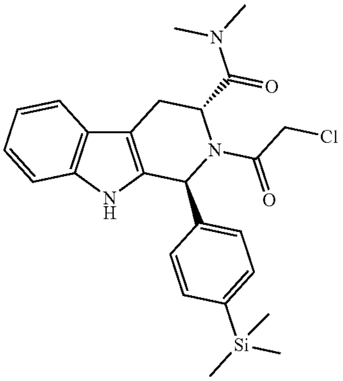 [SMILES: CN(C)C(=O)[C@H]1Cc2c([nH]c3ccccc23)[C@H](c2ccc([Si](C)(C)C)cc2)N1C(=O)CCl] |
| 68 | 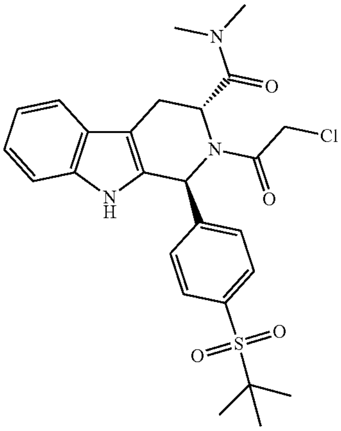 [SMILES: CN(C)C(=O)[C@H]1Cc2c([nH]c3ccccc23)[C@H](c2ccc(S(=O)(=O)C(C)(C)C)cc2)N1C(=O)CCl] |

TABLE 1-continued
| No. | Structure |
|---|---|
| 69 | 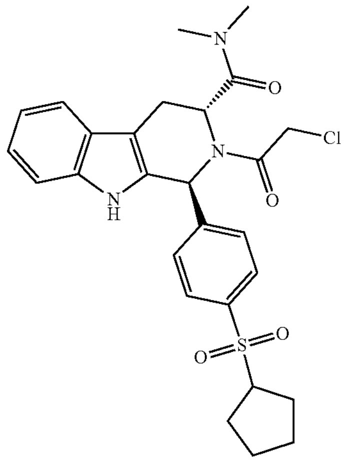 [SMILES: CN(C)C(=O)[C@H]1Cc2c([nH]c3ccccc23)[C@H](c2ccc(S(=O)(=O)C3CCCC3)cc2)N1C(=O)CCl] |
| 70 | 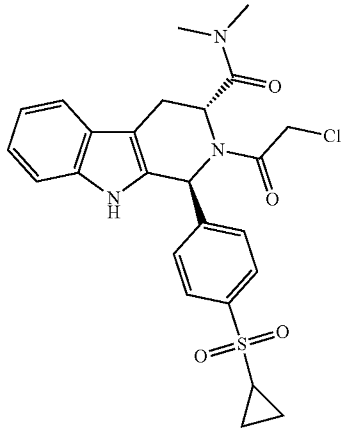 [SMILES: CN(C)C(=O)[C@H]1Cc2c([nH]c3ccccc23)[C@H](c2ccc(S(=O)(=O)C3CC3)cc2)N1C(=O)CCl] |
| 71 | 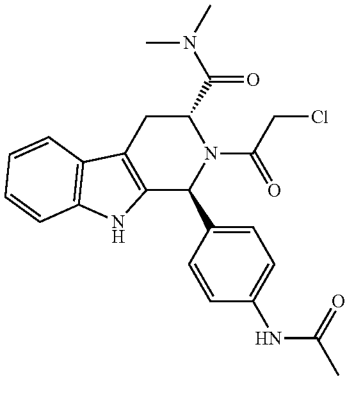 [SMILES: CC(=O)Nc1ccc([C@H]2c3[nH]c4ccccc4c3C[C@H](C(=O)N(C)C)N2C(=O)CCl)cc1] |
| 72 | 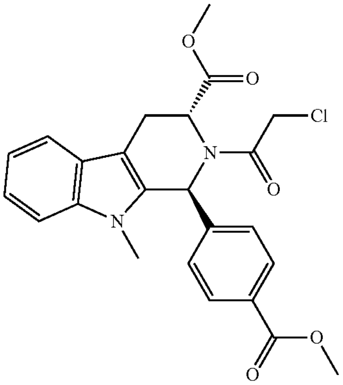 [SMILES: COC(=O)c1ccc([C@H]2c3c(c4ccccc4n3C)C[C@H](C(=O)OC)N2C(=O)CCl)cc1] |
| 73 | 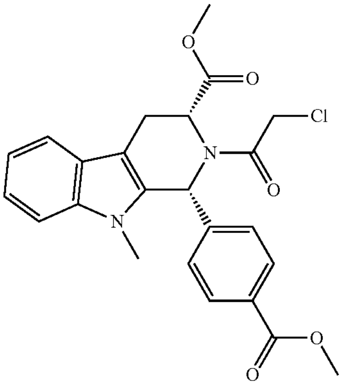 [SMILES: COC(=O)c1ccc([C@@H]2c3c(c4ccccc4n3C)C[C@H](C(=O)OC)N2C(=O)CCl)cc1] |
| 74 | 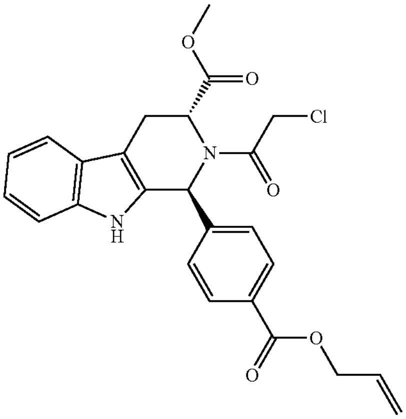 [SMILES: C=CCOC(=O)c1ccc([C@H]2c3[nH]c4ccccc4c3C[C@H](C(=O)OC)N2C(=O)CCl)cc1] |
| 75 | 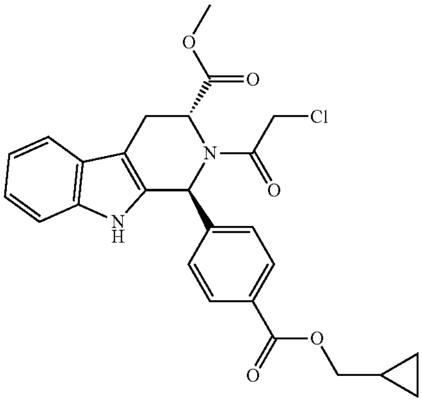 [SMILES: COC(=O)[C@H]1Cc2c([nH]c3ccccc23)[C@H](c2ccc(C(=O)OCC3CC3)cc2)N1C(=O)CCl] |

TABLE 1-continued
| No. | Structure |
| --- | --- |
| 76 | 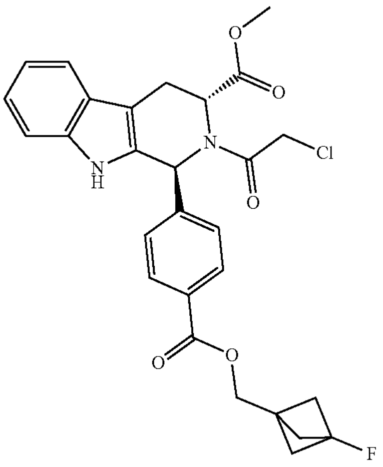 [SMILES: COC(=O)[C@H]1Cc2c([nH]c3ccccc23)[C@H](c2ccc(C(=O)OCC34CC(F)(C3)C4)cc2)N1C(=O)CCl] |
| 77 | 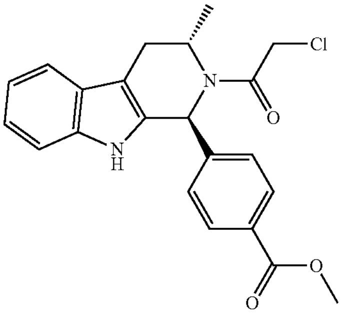 [SMILES: COC(=O)c1ccc([C@H]2c3[nH]c4ccccc4c3C[C@H](C)N2C(=O)CCl)cc1] |
| 78 | 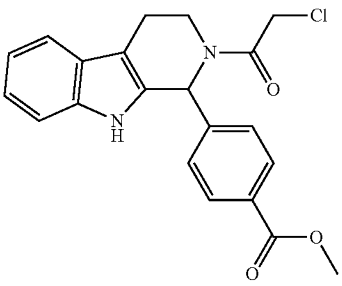 [SMILES: COC(=O)c1ccc(C2c3[nH]c4ccccc4c3CCN2C(=O)CCl)cc1] |
| 79 | 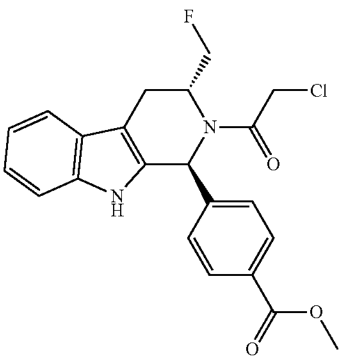 [SMILES: COC(=O)c1ccc([C@H]2c3[nH]c4ccccc4c3C[C@H](CF)N2C(=O)CCl)cc1] |
TABLE 1-continued
| No. | Structure |
| --- | --- |
| 80 | 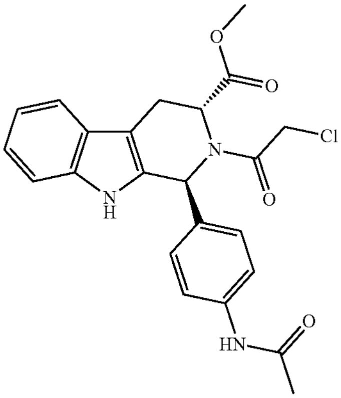 [SMILES: COC(=O)[C@H]1Cc2c([nH]c3ccccc23)[C@H](c2ccc(NC(C)=O)cc2)N1C(=O)CCl] |
| 81 | 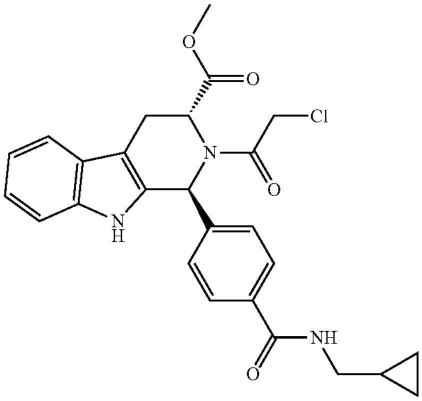 [SMILES: COC(=O)[C@H]1Cc2c([nH]c3ccccc23)[C@H](c2ccc(C(=O)NCC3CC3)cc2)N1C(=O)CCl] |
| 82 | 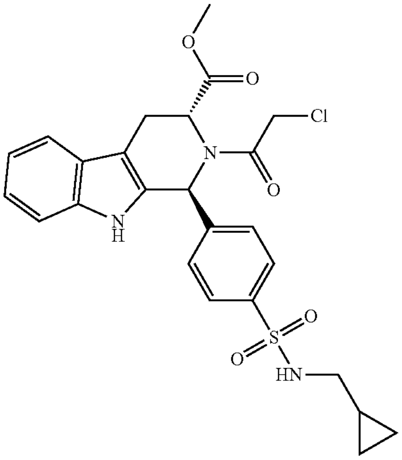 [SMILES: COC(=O)[C@H]1Cc2c([nH]c3ccccc23)[C@H](c2ccc(S(=O)(=O)NCC3CC3)cc2)N1C(=O)CCl] |

TABLE 1-continued
| No. | Structure |
| --- | --- |
| 83 | 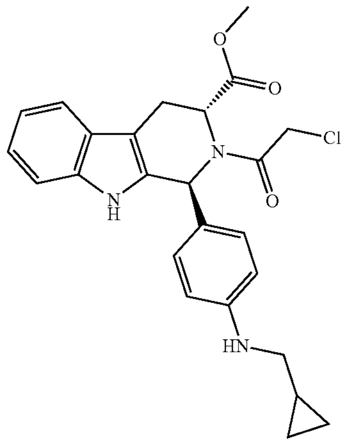 [SMILES: COC(=O)[C@H]1Cc2c([nH]c3ccccc23)[C@H](c2ccc(NCC3CC3)cc2)N1C(=O)CCl] |
| 84 | 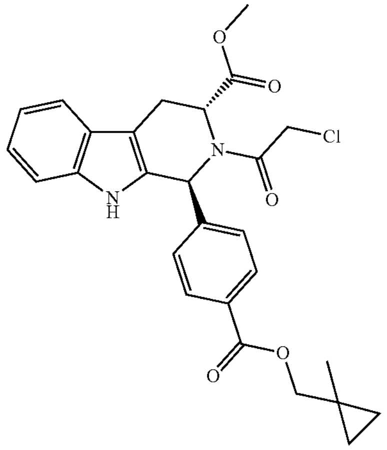 [SMILES: COC(=O)[C@H]1Cc2c([nH]c3ccccc23)[C@H](c2ccc(C(=O)OCC3(C)CC3)cc2)N1C(=O)CCl] |
| 85 | 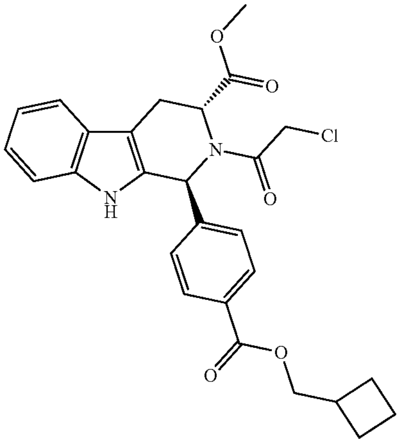 [SMILES: COC(=O)[C@H]1Cc2c([nH]c3ccccc23)[C@H](c2ccc(C(=O)OCC3CCC3)cc2)N1C(=O)CCl] |
TABLE 1-continued
| No. | Structure |
| --- | --- |
| 86 | 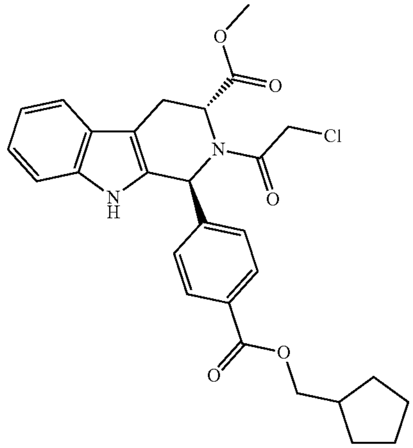 [SMILES: COC(=O)[C@H]1Cc2c([nH]c3ccccc23)[C@H](c2ccc(C(=O)OCC3CCCC3)cc2)N1C(=O)CCl] |
| 87 | 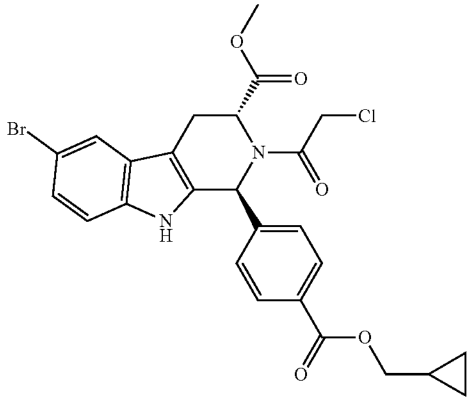 [SMILES: COC(=O)[C@H]1Cc2c([nH]c3ccc(Br)cc23)[C@H](c2ccc(C(=O)OCC3CC3)cc2)N1C(=O)CCl] |
| 88 | 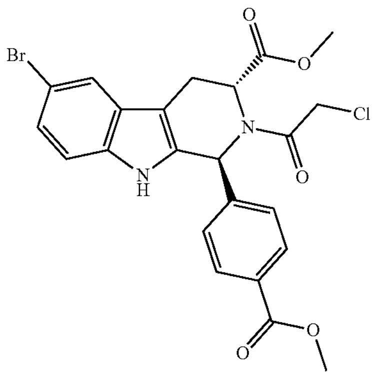 [SMILES: COC(=O)c1ccc([C@H]2c3[nH]c4ccc(Br)cc4c3C[C@H](C(=O)OC)N2C(=O)CCl)cc1] |

TABLE 1-continued
| No. | Structure |
| --- | --- |
| 89 | 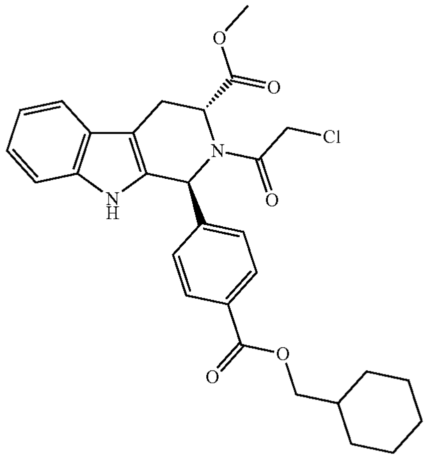 [SMILES: COC(=O)[C@H]1Cc2c([nH]c3ccccc23)[C@H](c2ccc(C(=O)OCC3CCCCC3)cc2)N1C(=O)CCl] |
| 90 | 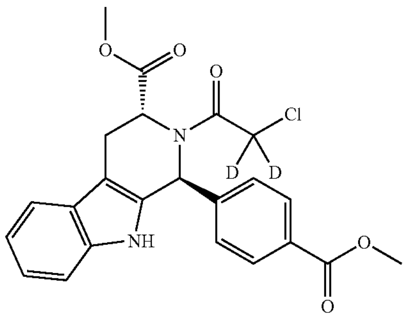 [SMILES: [2H]C([2H])(Cl)C(=O)N1[C@@H](c2ccc(C(=O)OC)cc2)c2[nH]c3ccccc3c2C[C@@H]1C(=O)OC] |
| 91 | 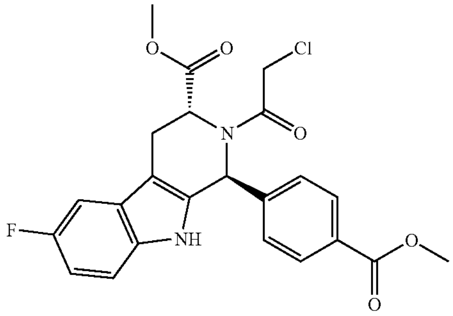 [SMILES: COC(=O)c1ccc([C@H]2c3[nH]c4ccc(F)cc4c3C[C@H](C(=O)OC)N2C(=O)CCl)cc1] |
| 92 | 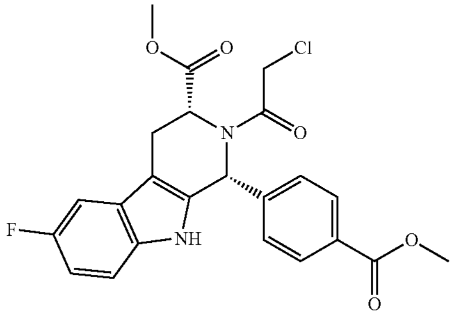 [SMILES: COC(=O)c1ccc([C@@H]2c3[nH]c4ccc(F)cc4c3C[C@H](C(=O)OC)N2C(=O)CCl)cc1] |
TABLE 1-continued
| No. | Structure |
| --- | --- |
| 93 | 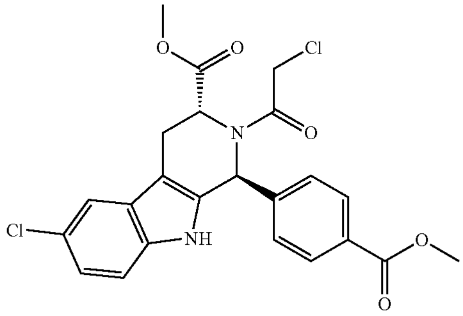 [SMILES: COC(=O)c1ccc([C@H]2c3[nH]c4ccc(Cl)cc4c3C[C@H](C(=O)OC)N2C(=O)CCl)cc1] |
| 94 | 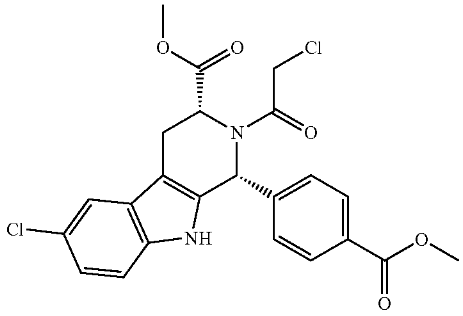 [SMILES: COC(=O)c1ccc([C@@H]2c3[nH]c4ccc(Cl)cc4c3C[C@H](C(=O)OC)N2C(=O)CCl)cc1] |
| 95 | 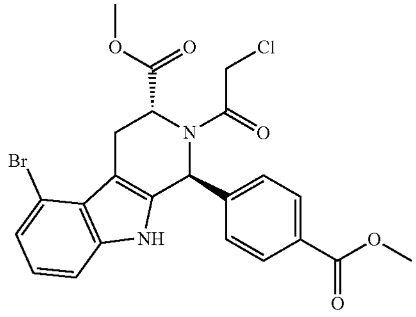 [SMILES: COC(=O)c1ccc([C@H]2c3[nH]c4cccc(Br)c4c3C[C@H](C(=O)OC)N2C(=O)CCl)cc1] |
| 96 | 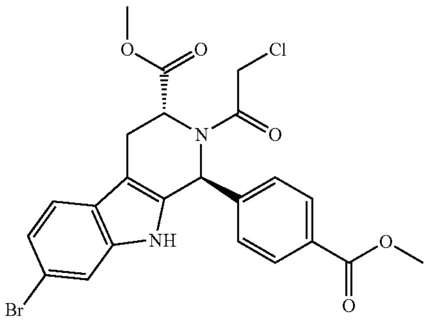 [SMILES: COC(=O)c1ccc([C@H]2c3[nH]c4cc(Br)ccc4c3C[C@H](C(=O)OC)N2C(=O)CCl)cc1] |
| 97 | 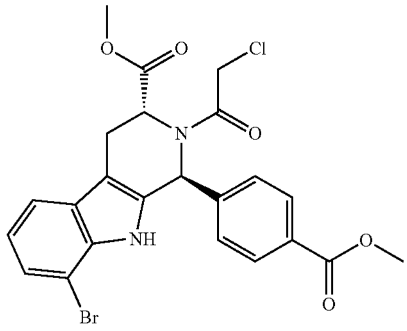 [SMILES: COC(=O)c1ccc([C@H]2c3[nH]c4c(Br)cccc4c3C[C@H](C(=O)OC)N2C(=O)CCl)cc1] |

TABLE 1-continued
| No. | Structure |
| --- | --- |
| 98 | 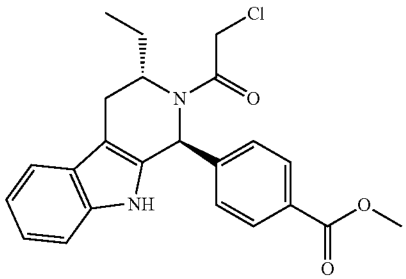 [SMILES: CC[C@H]1Cc2c([nH]c3ccccc23)[C@H](c2ccc(C(=O)OC)cc2)N1C(=O)CCl] |
| 99 | 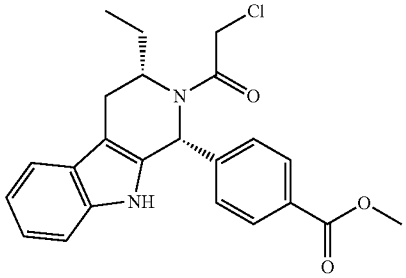 [SMILES: CC[C@H]1Cc2c([nH]c3ccccc23)[C@@H](c2ccc(C(=O)OC)cc2)N1C(=O)CCl] |
| 100 | 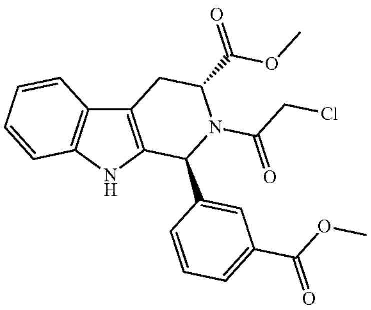 [SMILES: COC(=O)c1cccc([C@H]2c3[nH]c4ccccc4c3C[C@H](C(=O)OC)N2C(=O)CCl)c1] |
| 101 | 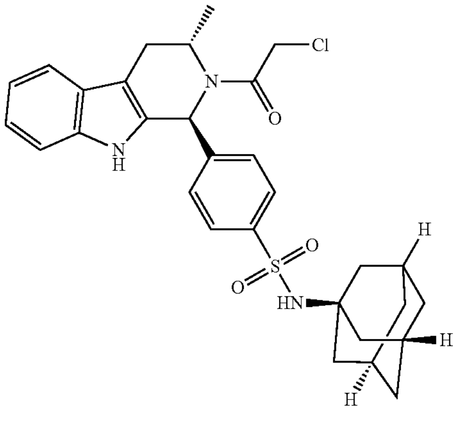 [SMILES: C[C@H]1Cc2c([nH]c3ccccc23)[C@H](c2ccc(S(=O)(=O)N[C@]34CC5C[C@H](C[C@H](C5)C3)C4)cc2)N1C(=O)CCl] |
TABLE 1-continued
| No. | Structure |
| --- | --- |
| 102 | 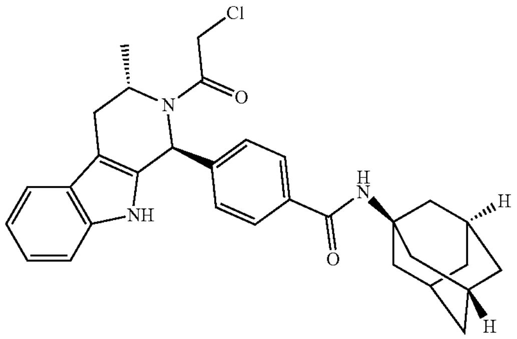 [SMILES: C[C@H]1Cc2c([nH]c3ccccc23)[C@H](c2ccc(C(=O)N[C@]34CC5C[C@H](C[C@H](C5)C3)C4)cc2)N1C(=O)CCl] |
| 103 | 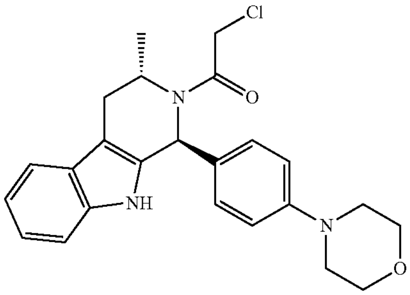 [SMILES: C[C@H]1Cc2c([nH]c3ccccc23)[C@H](c2ccc(N3CCOCC3)cc2)N1C(=O)CCl] |
| 104 | 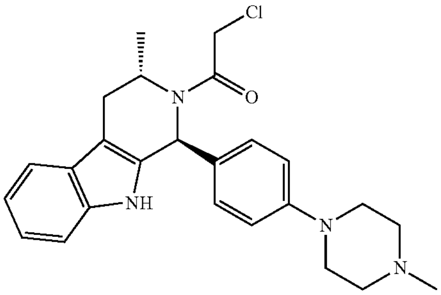 [SMILES: C[C@H]1Cc2c([nH]c3ccccc23)[C@H](c2ccc(N3CCN(C)CC3)cc2)N1C(=O)CCl] |
| 105 | 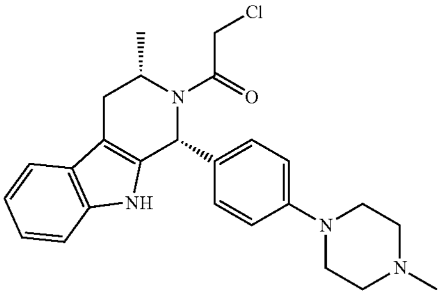 [SMILES: C[C@H]1Cc2c([nH]c3ccccc23)[C@@H](c2ccc(N3CCN(C)CC3)cc2)N1C(=O)CCl] |
| 106 | 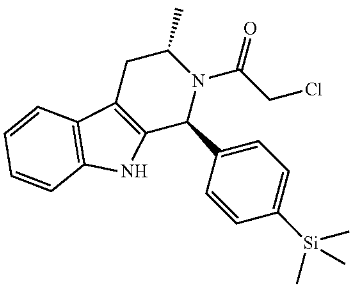 [SMILES: C[C@H]1Cc2c([nH]c3ccccc23)[C@H](c2ccc([Si](C)(C)C)cc2)N1C(=O)CCl] |

TABLE 1-continued
| No. | Structure |
|---|---|
| 107 | 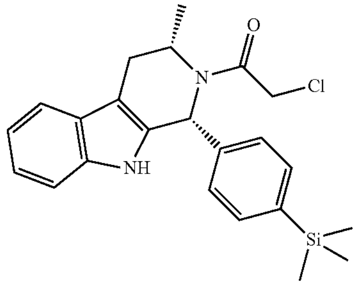 [SMILES: C[C@H]1Cc2c([nH]c3ccccc23)[C@@H](c2ccc([Si](C)(C)C)cc2)N1C(=O)CCl] |
| 108 | 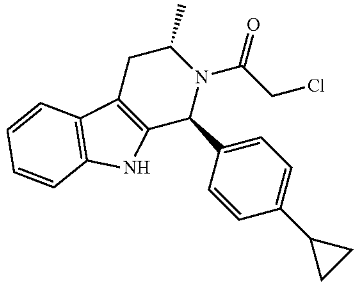 [SMILES: C[C@H]1Cc2c([nH]c3ccccc23)[C@H](c2ccc(C3CC3)cc2)N1C(=O)CCl] |
| 109 | 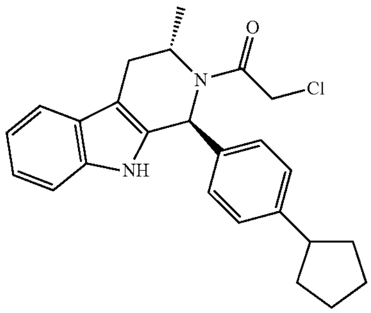 [SMILES: C[C@H]1Cc2c([nH]c3ccccc23)[C@H](c2ccc(C3CCCC3)cc2)N1C(=O)CCl] |
| 110 | 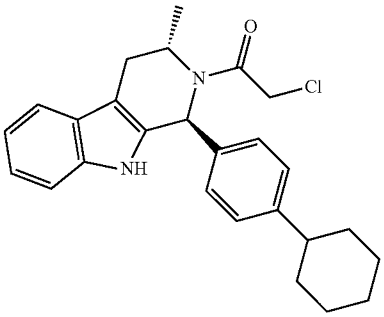 [SMILES: C[C@H]1Cc2c([nH]c3ccccc23)[C@H](c2ccc(C3CCCCC3)cc2)N1C(=O)CCl] |
| 111 | 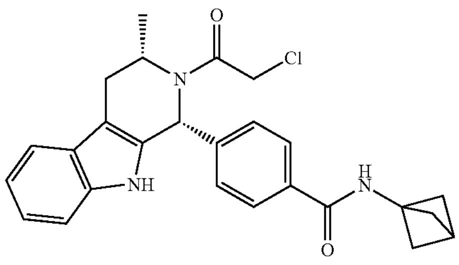 [SMILES: C[C@H]1Cc2c([nH]c3ccccc23)[C@@H](c2ccc(C(=O)NC34CC(C3)C4)cc2)N1C(=O)CCl] |
TABLE 1-continued
| No. | Structure |
|---|---|
| 112 | 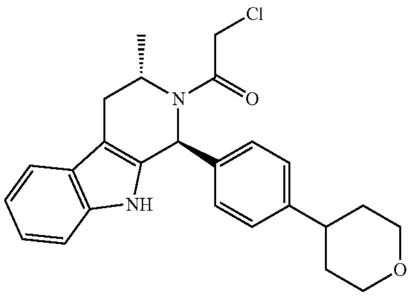 |
| 113 | 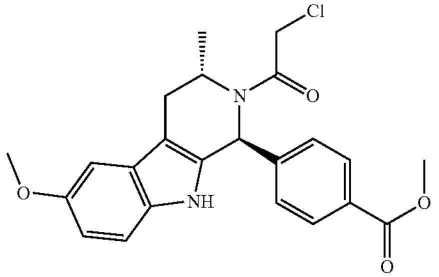 |
| 114 | 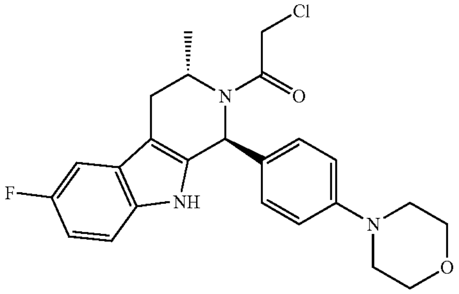 [SMILES: C[C@H]1Cc2c([nH]c3ccc(F)cc23)[C@H](c2ccc(N3CCOCC3)cc2)N1C(=O)CCl] |
| 115 | 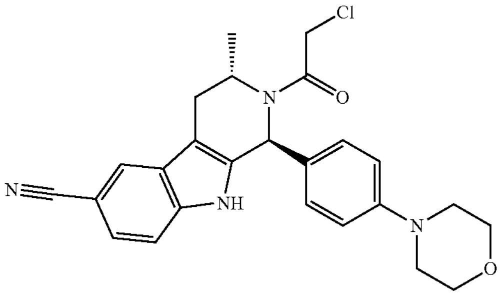 [SMILES: C[C@H]1Cc2c([nH]c3ccc(C#N)cc23)[C@H](c2ccc(N3CCOCC3)cc2)N1C(=O)CCl] |
| 116 | 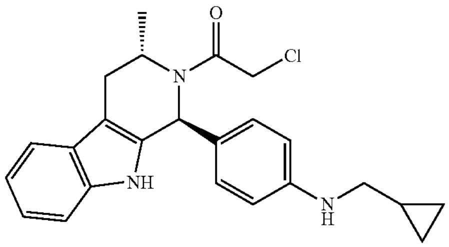 [SMILES: C[C@H]1Cc2c([nH]c3ccccc23)[C@H](c2ccc(NCC3CC3)cc2)N1C(=O)CCl] |

TABLE 1-continued
| No. | Structure |
| --- | --- |
| 117 | 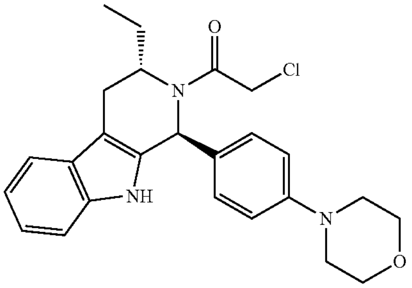 [SMILES: CC[C@H]1Cc2c([nH]c3ccccc23)[C@H](c2ccc(N3CCOCC3)cc2)N1C(=O)CCl] |
| 118 | 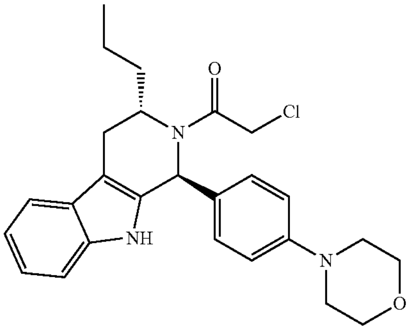 [SMILES: CCC[C@H]1Cc2c([nH]c3ccccc23)[C@H](c2ccc(N3CCOCC3)cc2)N1C(=O)CCl] |
| 119 | 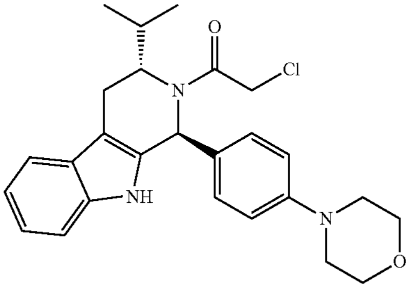 [SMILES: CC(C)[C@H]1Cc2c([nH]c3ccccc23)[C@H](c2ccc(N3CCOCC3)cc2)N1C(=O)CCl] |
| 120 | 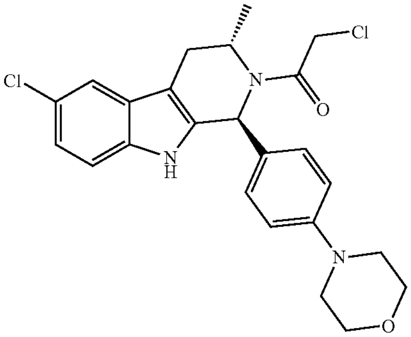 [SMILES: C[C@H]1Cc2c([nH]c3ccc(Cl)cc23)[C@H](c2ccc(N3CCOCC3)cc2)N1C(=O)CCl] |
| 121 | 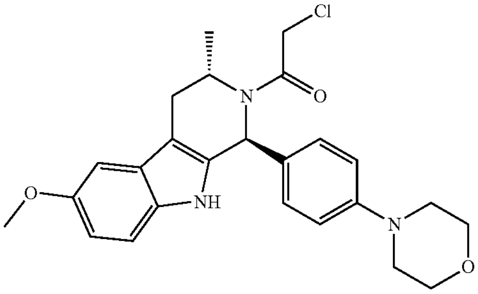 [SMILES: COc1ccc2[nH]c3c(c2c1)C[C@H](C)N(C(=O)CCl)[C@H]3c1ccc(N2CCOCC2)cc1] |
TABLE 1-continued
| No. | Structure |
| --- | --- |
| 122 | 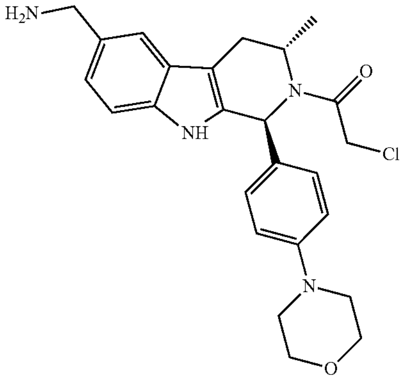 [SMILES: C[C@H]1Cc2c([nH]c3ccc(CN)cc23)[C@H](c2ccc(N3CCOCC3)cc2)N1C(=O)CCl] |
| 123 | 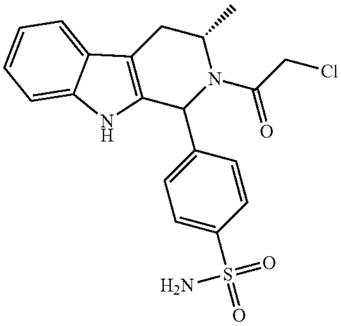 [SMILES: C[C@H]1Cc2c([nH]c3ccccc23)C(c2ccc(S(N)(=O)=O)cc2)N1C(=O)CCl] |
| 124 | 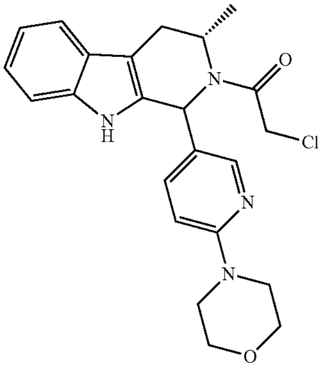 [SMILES: C[C@H]1Cc2c([nH]c3ccccc23)C(c2ccc(N3CCOCC3)nc2)N1C(=O)CCl] |
| 125 | 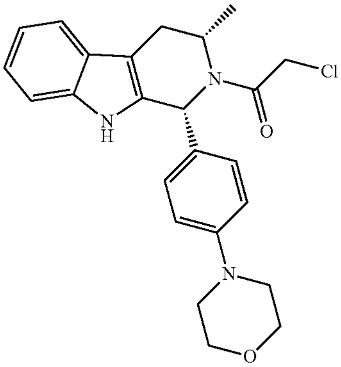 [SMILES: C[C@H]1Cc2c([nH]c3ccccc23)[C@@H](c2ccc(N3CCOCC3)cc2)N1C(=O)CCl] |

TABLE 1-continued
| No. | Structure |
|---|---|
| 127 | 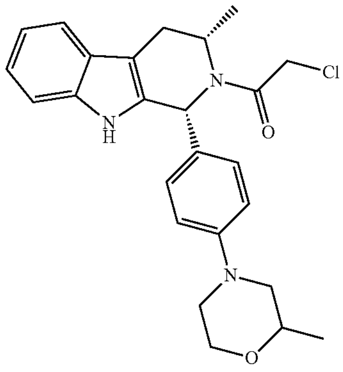 [SMILES: CC1CN(c2ccc([C@@H]3c4[nH]c5ccccc5c4C[C@H](C)N3C(=O)CCl)cc2)CCO1] |
| 128 | 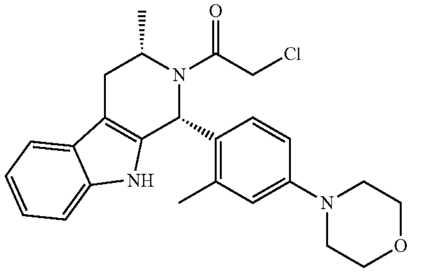 [SMILES: Cc1cc(N2CCOCC2)ccc1[C@@H]1c2[nH]c3ccccc3c2C[C@H](C)N1C(=O)CCl] |
| 129 | 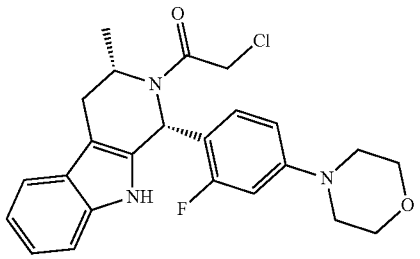 [SMILES: C[C@H]1Cc2c([nH]c3ccccc23)[C@@H](c2ccc(N3CCOCC3)cc2F)N1C(=O)CCl] |
| 130 | 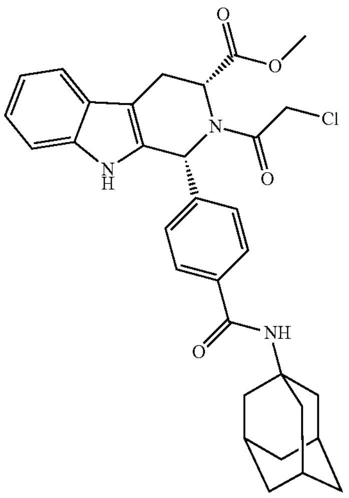 [SMILES: COC(=O)[C@H]1Cc2c([nH]c3ccccc23)[C@@H](c2ccc(C(=O)NC34CC5CC(CC(C5)C3)C4)cc2)N1C(=O)CCl] |
TABLE 1-continued
| No. | Structure |
|---|---|
| 132 | 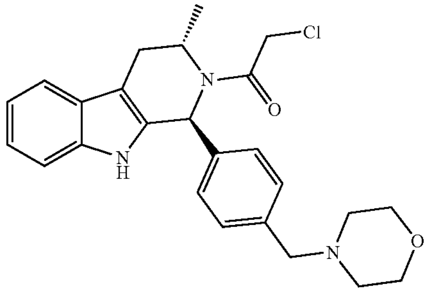 [SMILES: C[C@H]1Cc2c([nH]c3ccccc23)[C@H](c2ccc(CN3CCOCC3)cc2)N1C(=O)CCl] |
| 133 | 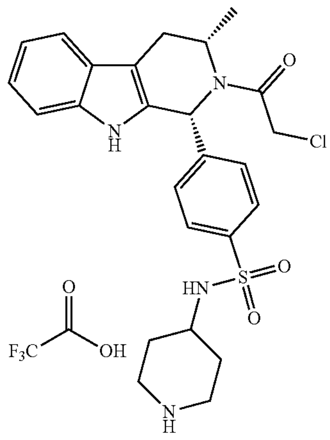 |
| 134 | 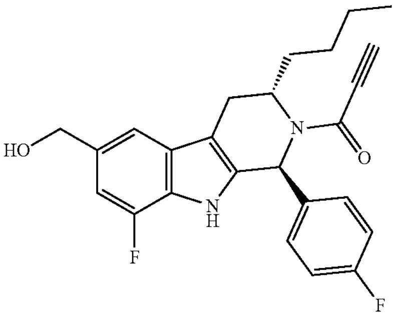 [SMILES: C#CC(=O)N1[C@@H](CCCC)Cc2c([nH]c3c(F)cc(CO)cc23)[C@@H]1c1ccc(F)cc1] |
| 135 | 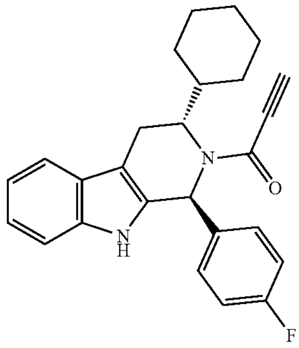 [SMILES: C#CC(=O)N1[C@@H](c2ccc(F)cc2)c2[nH]c3ccccc3c2C[C@@H]1C1CCCCC1] |

TABLE 1-continued
| No. | Structure |
|---|---|
| 136 | 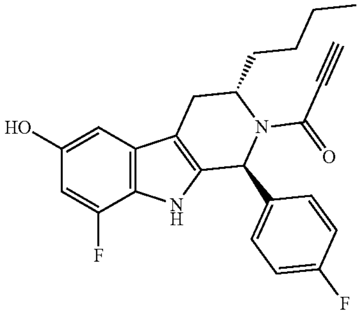 [SMILES: C#CC(=O)N1[C@@H](CCCC)Cc2c([nH]c3c(F)cc(O)cc23)[C@@H]1c1ccc(F)cc1] |
| 137 | 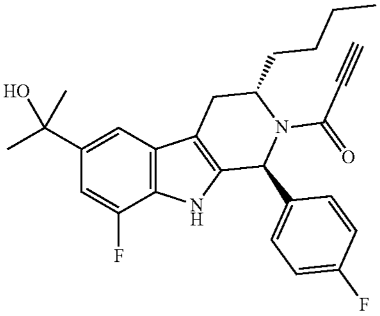 [SMILES: C#CC(=O)N1[C@@H](CCCC)Cc2c([nH]c3c(F)cc(C(C)(C)O)cc23)[C@@H]1c1ccc(F)cc1] |
| 138 | 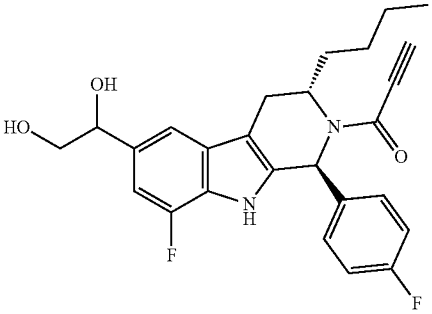 [SMILES: C#CC(=O)N1[C@@H](CCCC)Cc2c([nH]c3c(F)cc(C(O)CO)cc23)[C@@H]1c1ccc(F)cc1] |
| 139 | 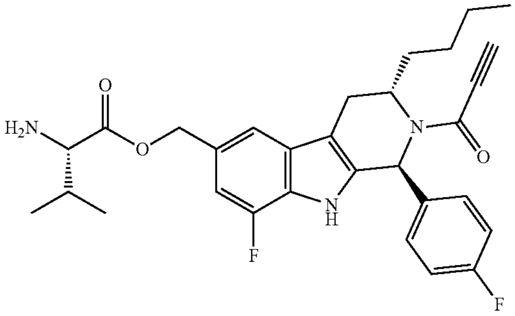 [SMILES: C#CC(=O)N1[C@@H](CCCC)Cc2c([nH]c3c(F)cc(COC(=O)[C@@H](N)C(C)C)cc23)[C@@H]1c1ccc(F)cc1] |
| 140 | 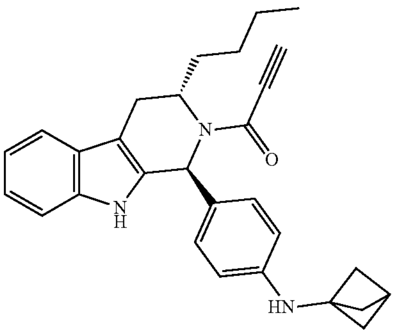 [SMILES: C#CC(=O)N1[C@@H](CCCC)Cc2c([nH]c3ccccc23)[C@@H]1c1ccc(NC23CC(C2)C3)cc1] |
TABLE 1-continued
| No. | Structure |
|---|---|
| 141 | 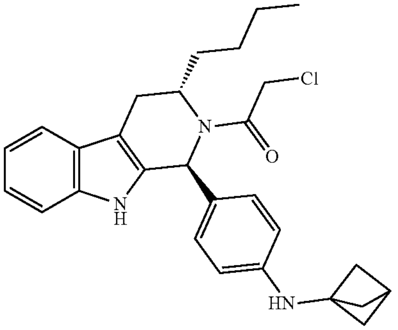 [SMILES: CCCC[C@H]1Cc2c([nH]c3ccccc23)[C@H](c2ccc(NC34CC(C3)C4)cc2)N1C(=O)CCl] |
| 142 | 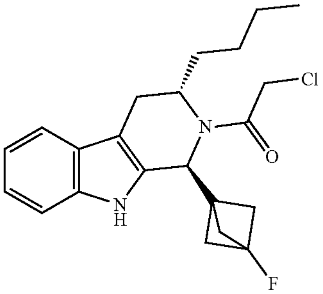 [SMILES: CCCC[C@H]1Cc2c([nH]c3ccccc23)[C@H](C23CC(F)(C2)C3)N1C(=O)CCl] |
| 143 | 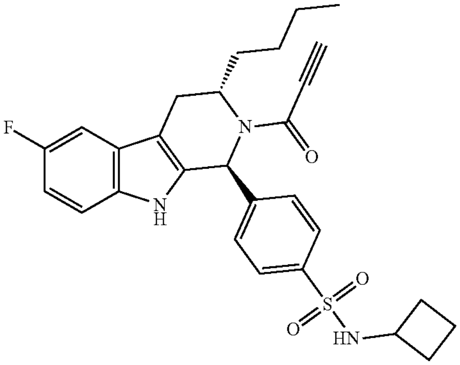 [SMILES: C#CC(=O)N1[C@@H](CCCC)Cc2c([nH]c3ccc(F)cc23)[C@@H]1c1ccc(S(=O)(=O)NC2CCC2)cc1] |
| 144 | 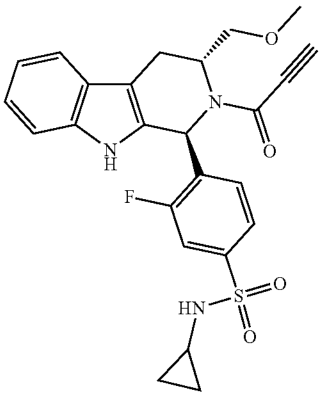 [SMILES: C#CC(=O)N1[C@@H](COC)Cc2c([nH]c3ccccc23)[C@@H]1c1ccc(S(=O)(=O)NC2CC2)cc1F] |

TABLE 1-continued
| No. | Structure |
|---|---|
| 145 | 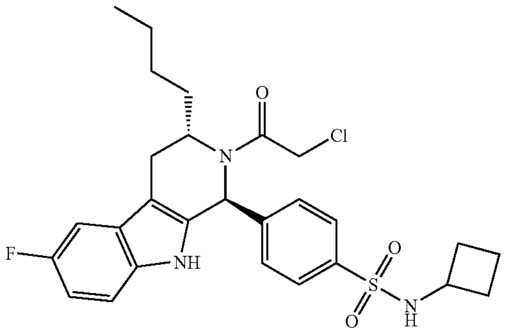 [SMILES: CCCC[C@H]1Cc2c([nH]c3ccc(F)cc23)[C@H](c2ccc(S(=O)(=O)NC3CCC3)cc2)N1C(=O)CCl] |
| 146 | 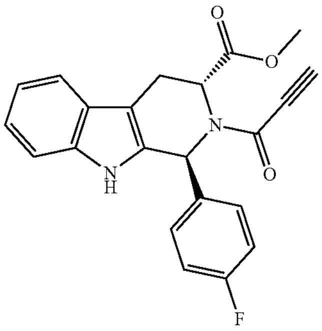 [SMILES: C#CC(=O)N1[C@@H](c2ccc(F)cc2)c2[nH]c3ccccc3c2C[C@@H]1C(=O)OC] |
| 147 | 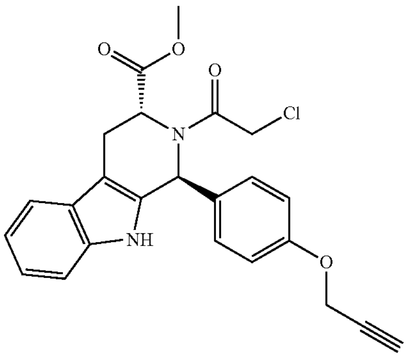 [SMILES: C#CCOc1ccc([C@H]2c3[nH]c4ccccc4c3C[C@H](C(=O)OC)N2C(=O)CCl)cc1] |
| 148 | 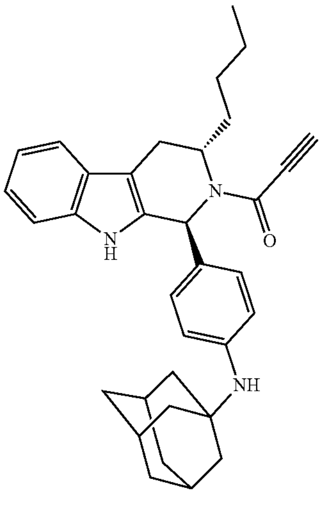 [SMILES: C#CC(=O)N1[C@@H](CCCC)Cc2c([nH]c3ccccc23)[C@@H]1c1ccc(NC23CC4CC(CC(C4)C2)C3)cc1] |
TABLE 1-continued
| No. | Structure |
|---|---|
| 149 | 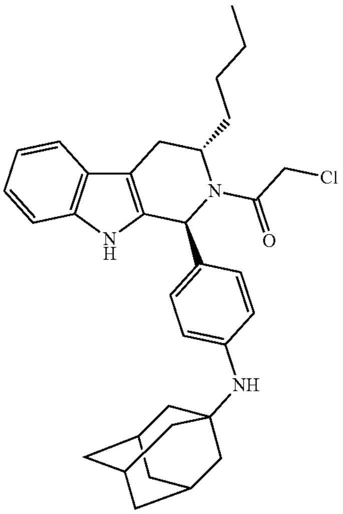 [SMILES: CCCC[C@H]1Cc2c([nH]c3ccccc23)[C@H](c2ccc(NC34CC5CC(CC(C5)C3)C4)cc2)N1C(=O)CCl] |
| 150 | 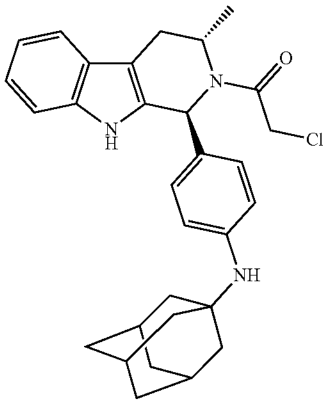 [SMILES: C[C@H]1Cc2c([nH]c3ccccc23)[C@H](c2ccc(NC34CC5CC(CC(C5)C3)C4)cc2)N1C(=O)CCl] |
| 151 | 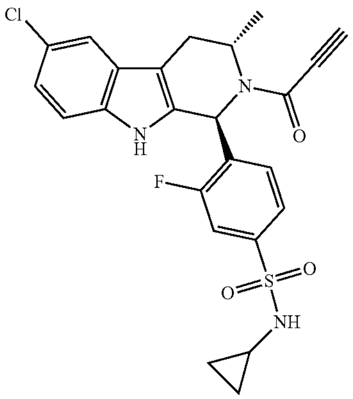 [SMILES: C#CC(=O)N1[C@@H](c2ccc(S(=O)(=O)NC3CC3)cc2F)c2[nH]c3ccc(Cl)cc3c2C[C@@H]1C] |

| No. | Structure |
| --- | --- |
| 152 | 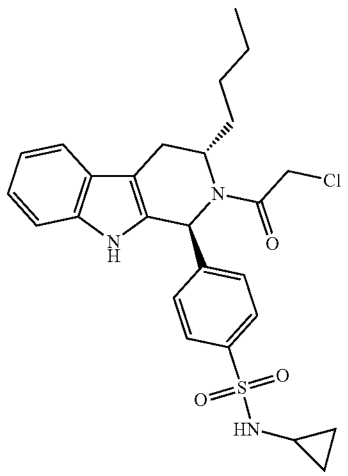 [SMILES: CCCC[C@H]1Cc2c([nH]c3ccccc23)[C@H](c2ccc(S(=O)(=O)NC3CC3)cc2)N1C(=O)CCl] |
| 153 | 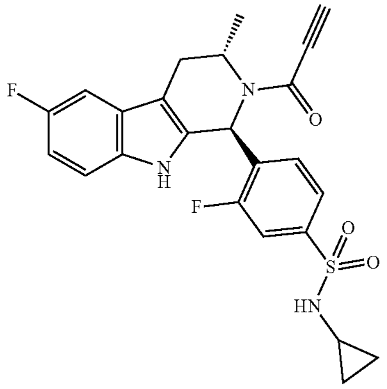 [SMILES: C#CC(=O)N1[C@@H](c2ccc(S(=O)(=O)NC3CC3)cc2F)c2[nH]c3ccc(F)cc3c2C[C@@H]1C] |
| 154 | 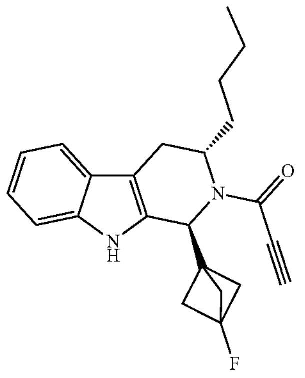 [SMILES: C#CC(=O)N1[C@@H](CCCC)Cc2c([nH]c3ccccc23)[C@@H]1C12CC(F)(C1)C2] |
| No. | Structure |
| --- | --- |
| 155 | 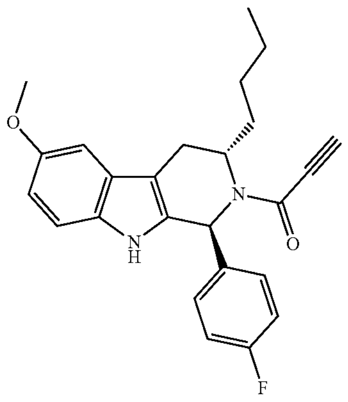 [SMILES: C#CC(=O)N1[C@@H](CCCC)Cc2c([nH]c3ccc(OC)cc23)[C@@H]1c1ccc(F)cc1] |
| 156 | 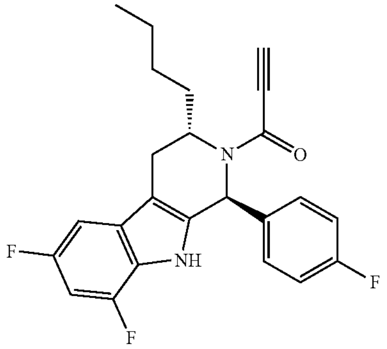 [SMILES: C#CC(=O)N1[C@@H](CCCC)Cc2c([nH]c3c(F)cc(F)cc23)[C@@H]1c1ccc(F)cc1] |
| 157 | 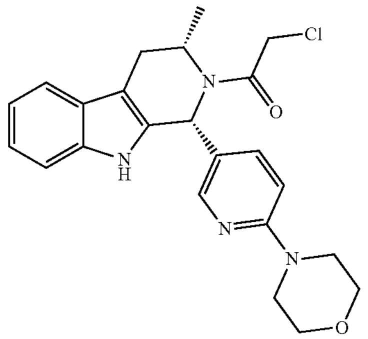 [SMILES: C[C@H]1Cc2c([nH]c3ccccc23)[C@@H](c2ccc(N3CCOCC3)nc2)N1C(=O)CCl] |
| 158 | 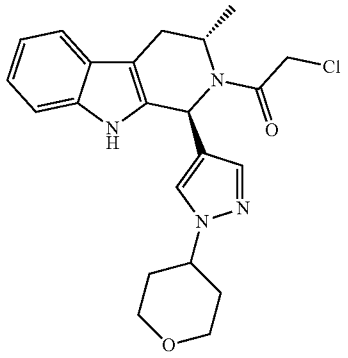 [SMILES: C[C@H]1Cc2c([nH]c3ccccc23)[C@H](c2cnn(C3CCOCC3)c2)N1C(=O)CCl] |

TABLE 1-continued
| No. | Structure |
| --- | --- |
| 159 | 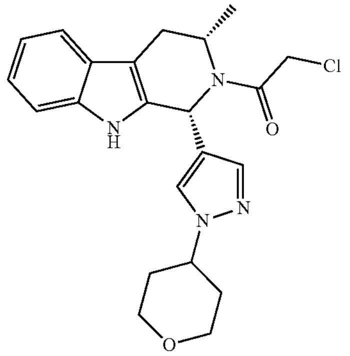 [SMILES: C[C@H]1Cc2c([nH]c3ccccc23)[C@@H](c2cnn(C3CCOCC3)c2)N1C(=O)CCl] |
| 160 | 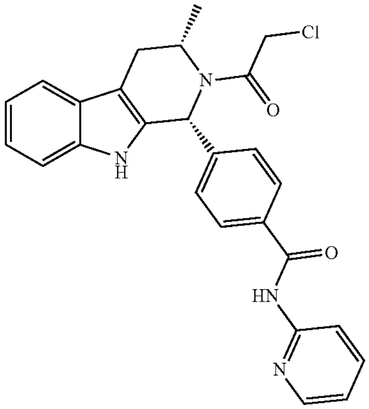 [SMILES: C[C@H]1Cc2c([nH]c3ccccc23)[C@@H](c2ccc(C(=O)Nc3ccccn3)cc2)N1C(=O)CCl] |
| 161 | 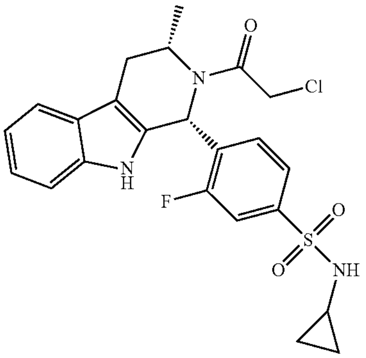 [SMILES: C[C@H]1Cc2c([nH]c3ccccc23)[C@@H](c2ccc(S(=O)(=O)NC3CC3)cc2F)N1C(=O)CCl] |
| 162 | 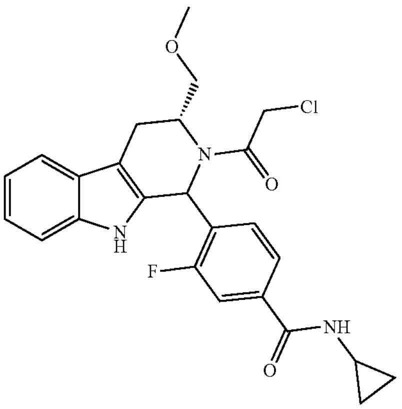 [SMILES: COC[C@H]1Cc2c([nH]c3ccccc23)C(c2ccc(C(=O)NC3CC3)cc2F)N1C(=O)CCl] |
TABLE 1-continued
| No. | Structure |
| --- | --- |
| 163 | 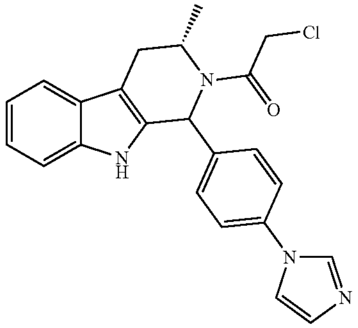 [SMILES: C[C@H]1Cc2c([nH]c3ccccc23)C(c2ccc(-n3ccnc3)cc2)N1C(=O)CCl] |
| 164 | 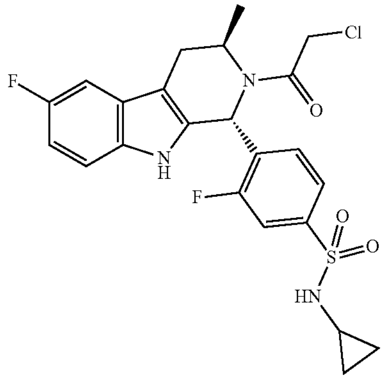 [SMILES: C[C@@H]1Cc2c([nH]c3ccc(F)cc23)[C@@H](c2ccc(S(=O)(=O)NC3CC3)cc2F)N1C(=O)CCl] |
| 165 | 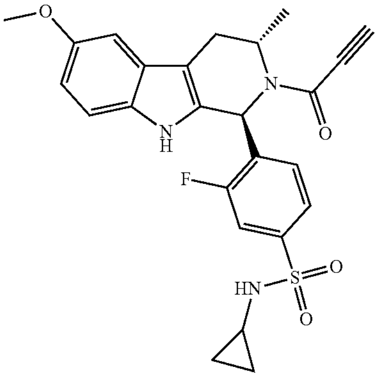 [SMILES: C#CC(=O)N1[C@@H](c2ccc(S(=O)(=O)NC3CC3)cc2F)c2[nH]c3ccc(OC)cc3c2C[C@@H]1C] |
| 166 | 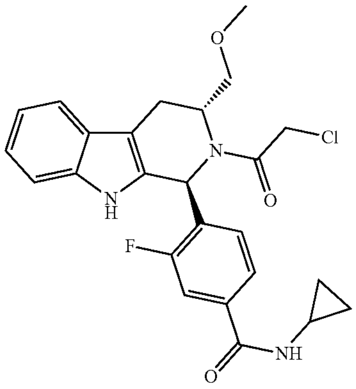 [SMILES: COC[C@H]1Cc2c([nH]c3ccccc23)[C@H](c2ccc(C(=O)NC3CC3)cc2F)N1C(=O)CCl] |

TABLE 1-continued
| No. | Structure |
|---|---|
| 167 | 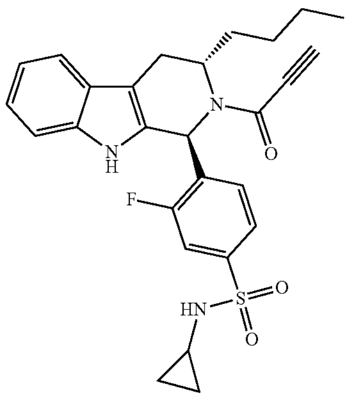 [SMILES: C#CC(=O)N1[C@@H](CCCC)Cc2c([nH]c3ccccc23)[C@@H]1c1ccc(S(=O)(=O)NC2CC2)cc1F] |
| 168 | 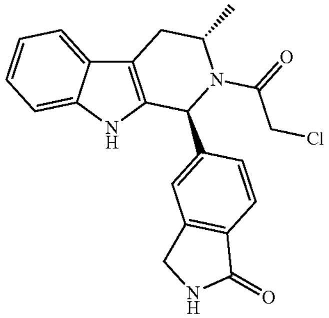 [SMILES: C[C@H]1Cc2c([nH]c3ccccc23)[C@H](c2ccc3c(c2)CNC3=O)N1C(=O)CCl] |
| 169 | 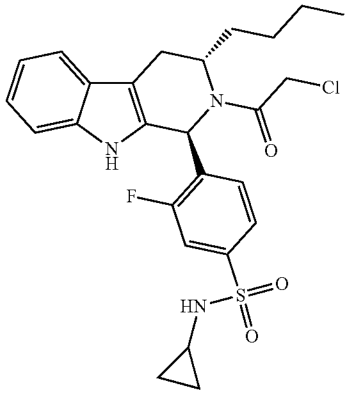 [SMILES: CCCC[C@H]1Cc2c([nH]c3ccccc23)[C@H](c2ccc(S(=O)(=O)NC3CC3)cc2F)N1C(=O)CCl] |
| 170 | 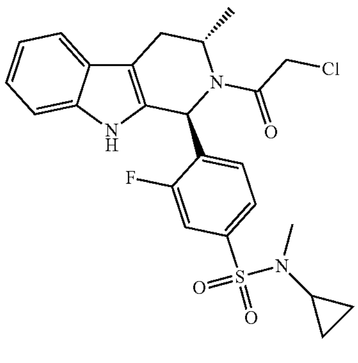 [SMILES: C[C@H]1Cc2c([nH]c3ccccc23)[C@H](c2ccc(S(=O)(=O)N(C)C3CC3)cc2F)N1C(=O)CCl] |
TABLE 1-continued
| No. | Structure |
|---|---|
| 171 | 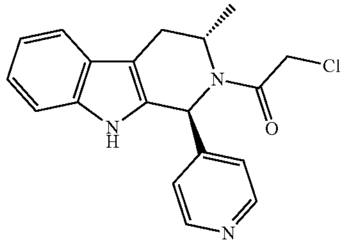 [SMILES: C[C@H]1Cc2c([nH]c3ccccc23)[C@H](c2ccncc2)N1C(=O)CCl] |
| 172 | 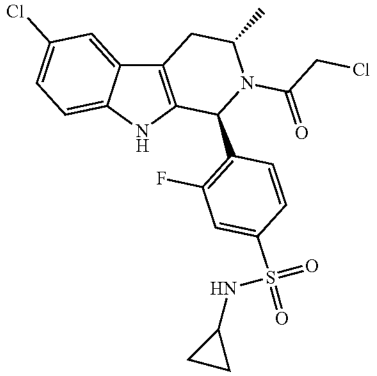 [SMILES: C[C@H]1Cc2c([nH]c3ccc(Cl)cc23)[C@H](c2ccc(S(=O)(=O)NC3CC3)cc2F)N1C(=O)CCl] |
| 173 | 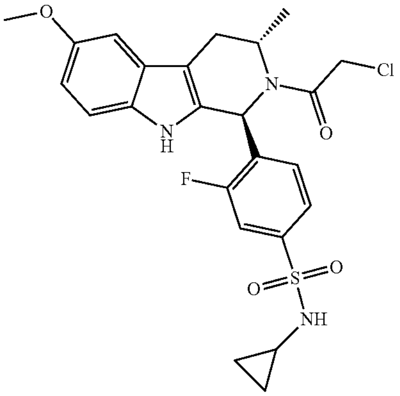 [SMILES: COc1ccc2[nH]c3c(c2c1)C[C@H](C)N(C(=O)CCl)[C@H]3c1ccc(S(=O)(=O)NC2CC2)cc1F] |
| 174 | 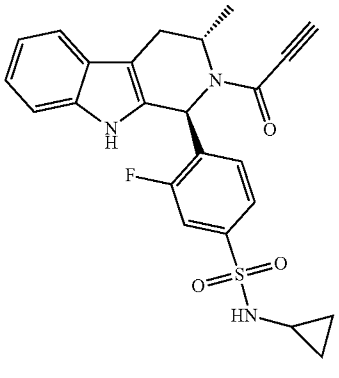 [SMILES: C#CC(=O)N1[C@@H](c2ccc(S(=O)(=O)NC3CC3)cc2F)c2[nH]c3ccccc3c2C[C@@H]1C] |

TABLE 1-continued
| No. | Structure |
|---|---|
| 175 | 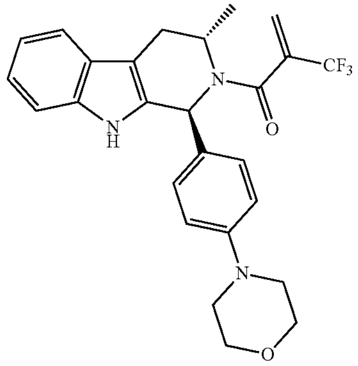 [SMILES: C=C(C(=O)N1[C@@H](c2ccc(N3CCOCC3)cc2)c2[nH]c3ccccc3c2C[C@@H]1C)C(F)(F)F] |
| 176 | 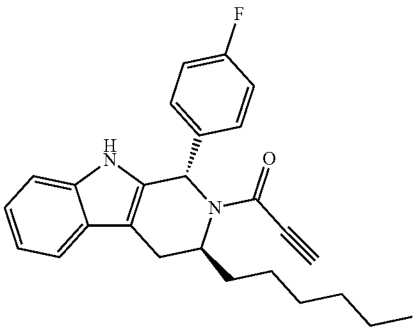 [SMILES: C#CC(=O)N1[C@@H](CCCCCC)Cc2c([nH]c3ccccc23)[C@@H]1c1ccc(F)cc1] |
| 177 | 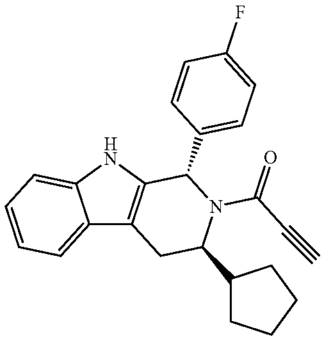 [SMILES: C#CC(=O)N1[C@@H](c2ccc(F)cc2)c2[nH]c3ccccc3c2C[C@@H]1C1CCCC1] |
| 178 | 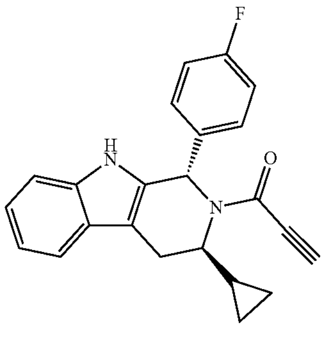 [SMILES: C#CC(=O)N1[C@@H](c2ccc(F)cc2)c2[nH]c3ccccc3c2C[C@@H]1C1CC1] |
| 179 | 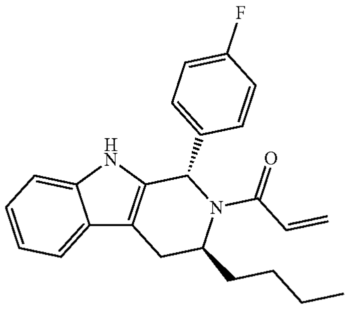 [SMILES: C=CC(=O)N1[C@@H](CCCC)Cc2c([nH]c3ccccc23)[C@@H]1c1ccc(F)cc1] |
| 180 | 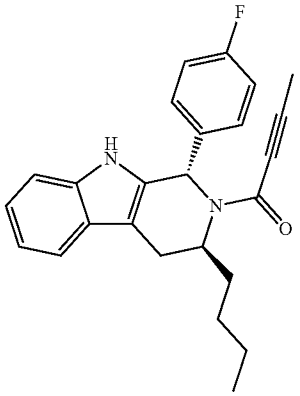 [SMILES: CC#CC(=O)N1[C@@H](CCCC)Cc2c([nH]c3ccccc23)[C@@H]1c1ccc(F)cc1] |
| 181 | 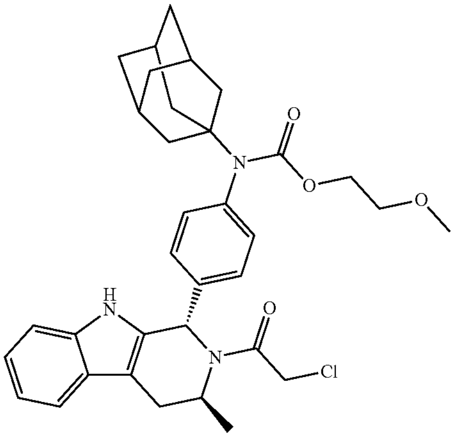 [SMILES: COCCOC(=O)N(c1ccc([C@H]2c3[nH]c4ccccc4c3C[C@H](C)N2C(=O)CCl)cc1)C12CC3CC(CC(C3)C1)C2] |
| 182 | 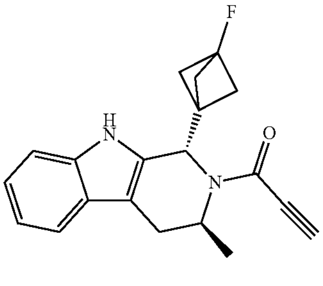 [SMILES: C#CC(=O)N1[C@@H](C)Cc2c([nH]c3ccccc23)[C@@H]1C12CC(F)(C1)C2] |

TABLE 1-continued
| No. | Structure |
|---|---|
| 183 | 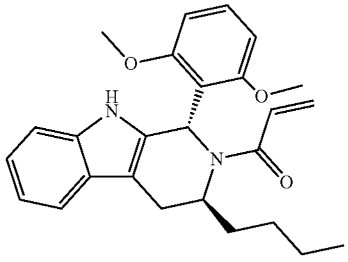 [SMILES: C=CC(=O)N1[C@@H](CCCC)Cc2c([nH]c3ccccc23)[C@@H]1c1c(OC)cccc1OC] |
| 184 | 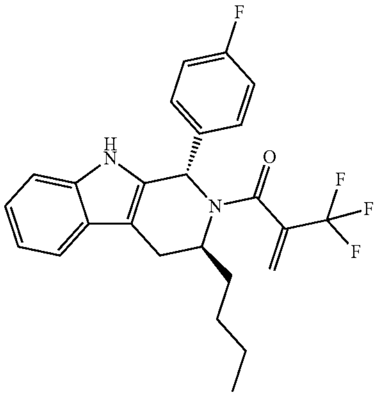 [SMILES: C=C(C(=O)N1[C@@H](CCCC)Cc2c([nH]c3ccccc23)[C@@H]1c1ccc(F)cc1)C(F)(F)F] |
| 185 | 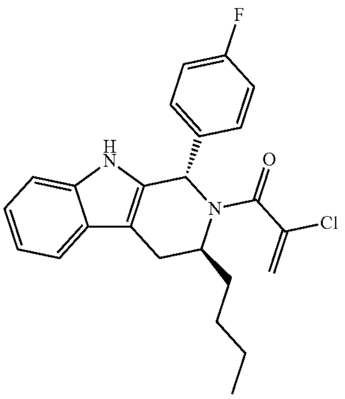 [SMILES: C=C(Cl)C(=O)N1[C@@H](CCCC)Cc2c([nH]c3ccccc23)[C@@H]1c1ccc(F)cc1] |
| 186 | 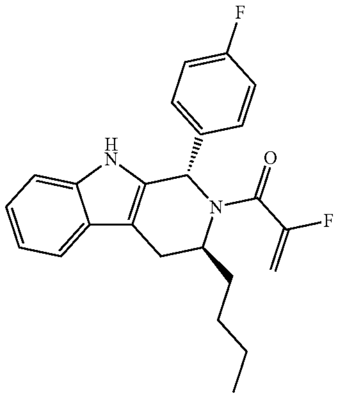 [SMILES: C=C(F)C(=O)N1[C@@H](CCCC)Cc2c([nH]c3ccccc23)[C@@H]1c1ccc(F)cc1] |
TABLE 1-continued
| No. | Structure |
|---|---|
| 187 | 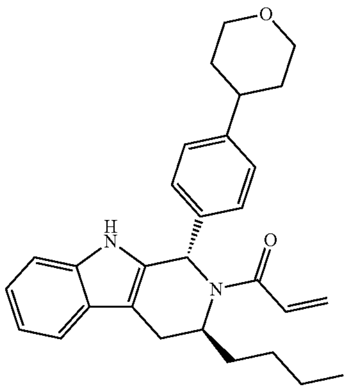 [SMILES: C=CC(=O)N1[C@@H](CCCC)Cc2c([nH]c3ccccc23)[C@@H]1c1ccc(C2CCOCC2)cc1] |
| 188 | 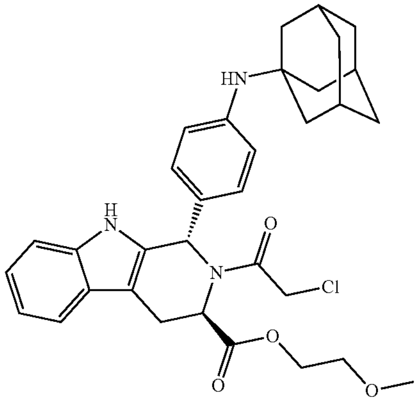 [SMILES: COCCOC(=O)[C@H]1Cc2c([nH]c3ccccc23)[C@H](c2ccc(NC34CC5CC(CC(C5)C3)C4)cc2)N1C(=O)CCl] |
| 189 | 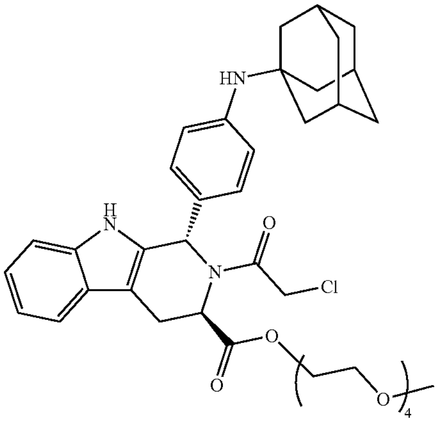 |
| 190 | 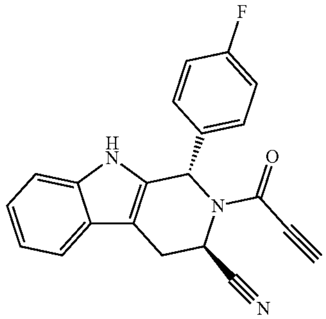 [SMILES: C#CC(=O)N1[C@@H](c2ccc(F)cc2)c2[nH]c3ccccc3c2C[C@@H]1C#N] |

TABLE 1-continued
| No. | Structure |
| --- | --- |
| 191 | 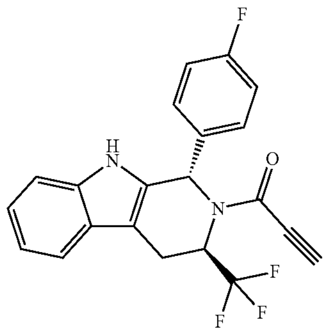 [SMILES: C#CC(=O)N1[C@@H](c2ccc(F)cc2)c2[nH]c3ccccc3c2C[C@@H]1C(F)(F)F] |
| 192 | 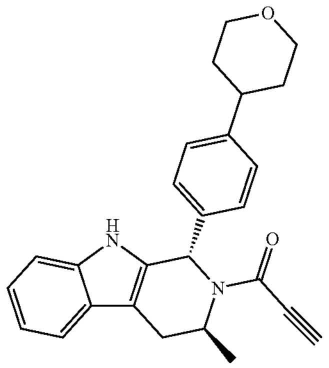 |
| 193 | 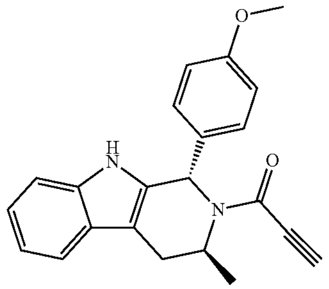 [SMILES: C#CC(=O)N1[C@@H](c2ccc(OC)cc2)c2[nH]c3ccccc3c2C[C@@H]1C] |
| 194 | 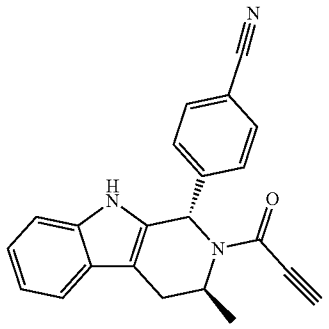 [SMILES: C#CC(=O)N1[C@@H](c2ccc(C#N)cc2)c2[nH]c3ccccc3c2C[C@@H]1C] |
| 195 | 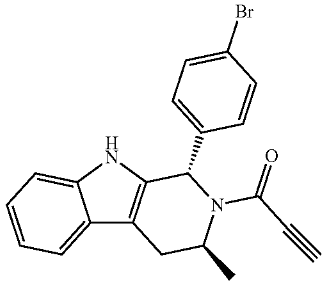 [SMILES: C#CC(=O)N1[C@@H](c2ccc(Br)cc2)c2[nH]c3ccccc3c2C[C@@H]1C] |
| 196 | 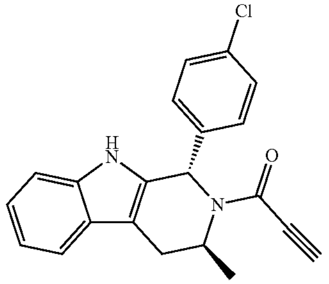 [SMILES: C#CC(=O)N1[C@@H](c2ccc(Cl)cc2)c2[nH]c3ccccc3c2C[C@@H]1C] |
| 197 | 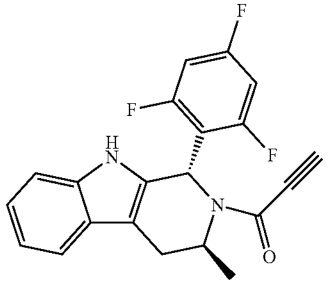 [SMILES: C#CC(=O)N1[C@@H](c2c(F)cc(F)cc2F)c2[nH]c3ccccc3c2C[C@@H]1C] |
| 198 | 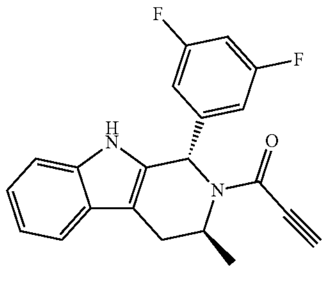 [SMILES: C#CC(=O)N1[C@@H](c2cc(F)cc(F)c2)c2[nH]c3ccccc3c2C[C@@H]1C] |
| 199 | 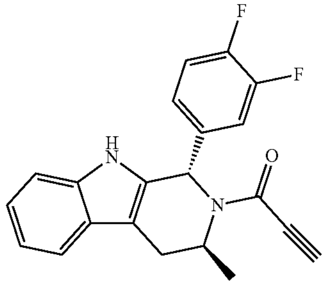 [SMILES: C#CC(=O)N1[C@@H](c2ccc(F)c(F)c2)c2[nH]c3ccccc3c2C[C@@H]1C] |

TABLE 1-continued
| No. | Structure |
| --- | --- |
| 200 | 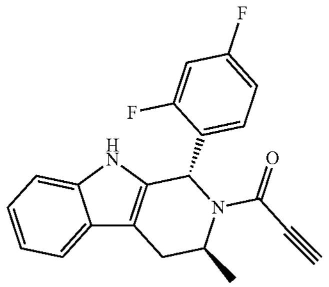 [SMILES: C#CC(=O)N1[C@@H](c2ccc(F)cc2F)c2[nH]c3ccccc3c2C[C@@H]1C] |
| 201 | 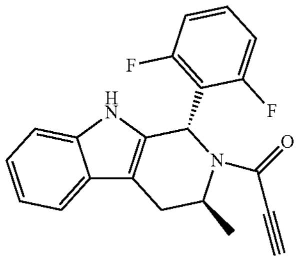 [SMILES: C#CC(=O)N1[C@@H](c2c(F)cccc2F)c2[nH]c3ccccc3c2C[C@@H]1C] |
| 202 | 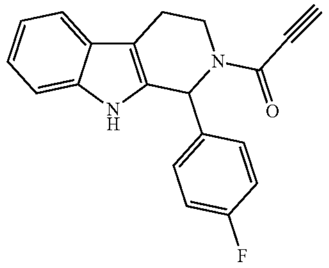 [SMILES: C#CC(=O)N1CCc2c([nH]c3ccccc23)C1c1ccc(F)cc1] |
| 204 | 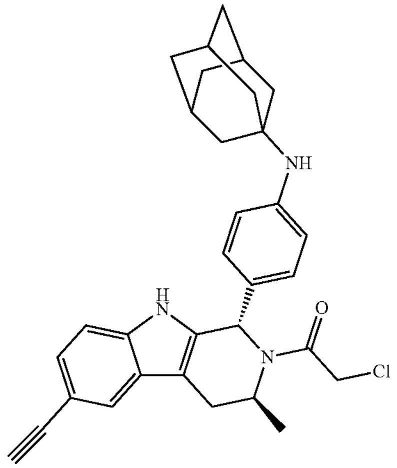 [SMILES: C#Cc1ccc2[nH]c3c(c2c1)C[C@H](C)N(C(=O)CCl)[C@H]3c1ccc(NC23CC4CC(CC(C4)C2)C3)cc1] |
| 205 | 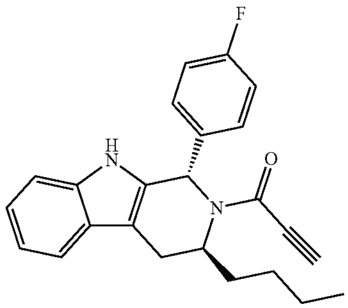 [SMILES: C#CC(=O)N1[C@@H](CCCC)Cc2c([nH]c3ccccc23)[C@@H]1c1ccc(F)cc1] |
TABLE 1-continued
| No. | Structure |
| --- | --- |
| 206 | 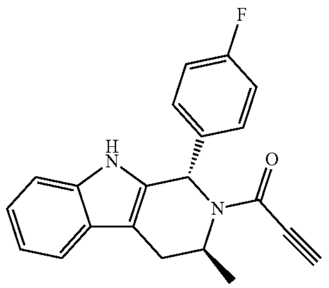 [SMILES: C#CC(=O)N1[C@@H](c2ccc(F)cc2)c2[nH]c3ccccc3c2C[C@@H]1C] |
| 207 | 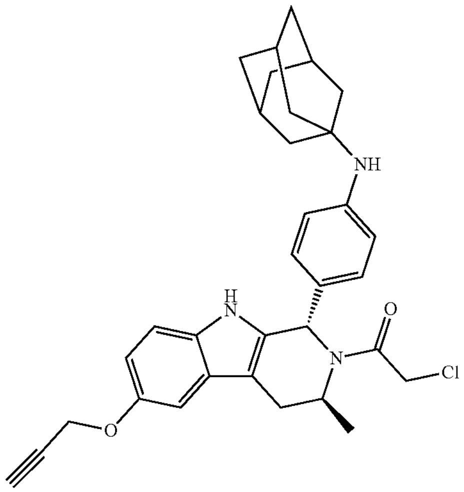 [SMILES: C#CCOc1ccc2[nH]c3c(c2c1)C[C@H](C)N(C(=O)CCl)[C@H]3c1ccc(NC23CC4CC(CC(C4)C2)C3)cc1] |
| 208 | 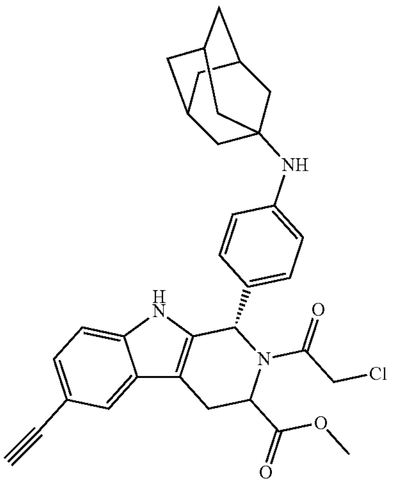 [SMILES: C#Cc1ccc2[nH]c3c(c2c1)CC(C(=O)OC)N(C(=O)CCl)[C@H]3c1ccc(NC23CC4CC(CC(C4)C2)C3)cc1] |

TABLE 1-continued
| No. | Structure |
|---|---|
| 209 | 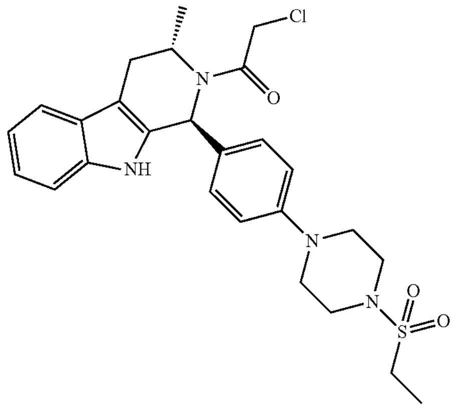 [SMILES: CCS(=O)(=O)N1CCN(c2ccc([C@H]3c4[nH]c5ccccc5c4C[C@H](C)N3C(=O)CCl)cc2)CC1] |
| 210 | 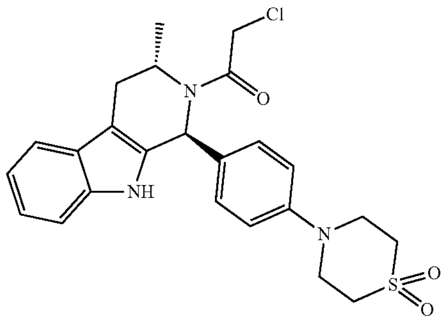 [SMILES: C[C@H]1Cc2c([nH]c3ccccc23)[C@H](c2ccc(N3CCS(=O)(=O)CC3)cc2)N1C(=O)CCl] |
| 211 | 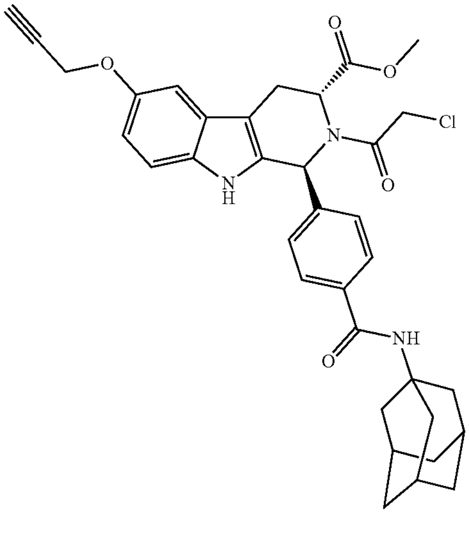 [SMILES: C#CCOc1ccc2[nH]c3c(c2c1)C[C@H](C(=O)OC)N(C(=O)CCl)[C@H]3c1ccc(C(=O)NC23CC4CC(CC(C4)C2)C3)cc1] |
| 212 | 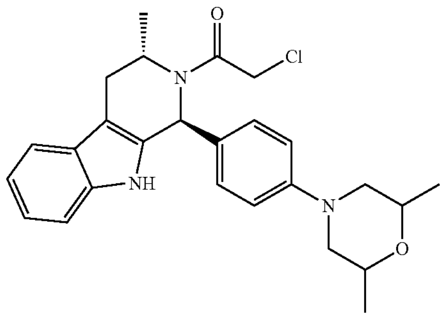 [SMILES: CC1CN(c2ccc([C@H]3c4[nH]c5ccccc5c4C[C@H](C)N3C(=O)CCl)cc2)CC(C)O1] |
TABLE 1-continued
| No. | Structure |
|---|---|
| 213 | 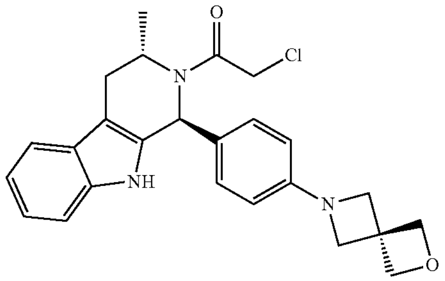 |
| 214 | 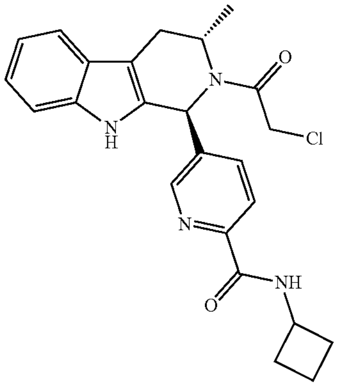 [SMILES: C[C@H]1Cc2c([nH]c3ccccc23)[C@H](c2ccc(C(=O)NC3CCC3)nc2)N1C(=O)CCl] |
| 215 | 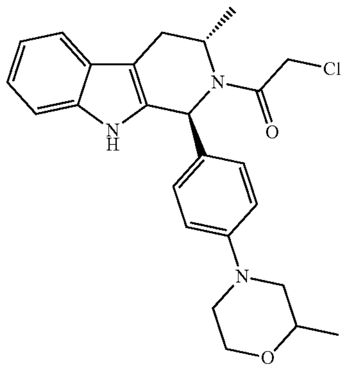 [SMILES: CC1CN(c2ccc([C@H]3c4[nH]c5ccccc5c4C[C@H](C)N3C(=O)CCl)cc2)CCO1] |
| 216 | 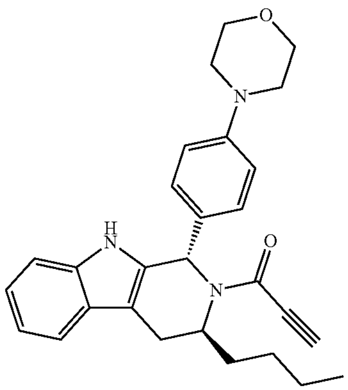 [SMILES: C#CC(=O)N1[C@@H](CCCC)Cc2c([nH]c3ccccc23)[C@@H]1c1ccc(N2CCOCC2)cc1] |

TABLE 1-continued
| No. | Structure |
| --- | --- |
| 217 | 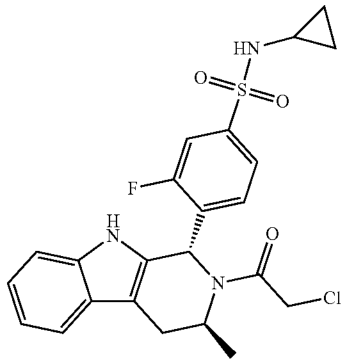 [SMILES: C[C@H]1Cc2c([nH]c3ccccc23)[C@H](c2ccc(S(=O)(=O)NC3CC3)cc2F)N1C(=O)CCl] |
| 218 | 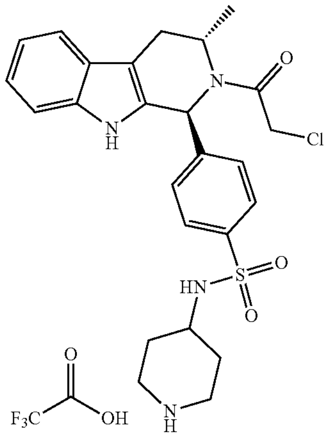 |
| 219 | 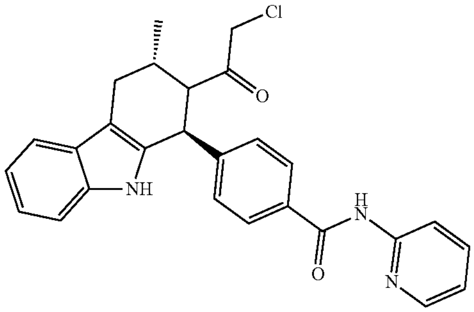 [SMILES: C[C@H]1Cc2c([nH]c3ccccc23)[C@H](c2ccc(C(=O)Nc3ccccn3)cc2)C1C(=O)CCl] |
| 220 | 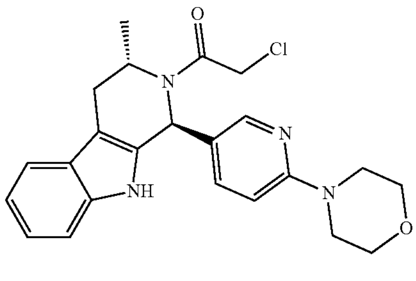 [SMILES: C[C@H]1Cc2c([nH]c3ccccc23)[C@H](c2ccc(N3CCOCC3)nc2)N1C(=O)CCl] |
| 221 | 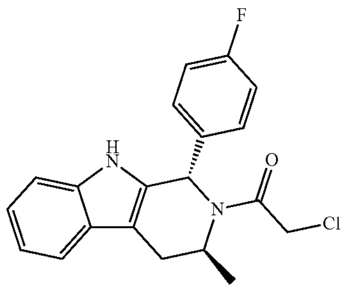 [SMILES: C[C@H]1Cc2c([nH]c3ccccc23)[C@H](c2ccc(F)cc2)N1C(=O)CCl] |
| 222 | 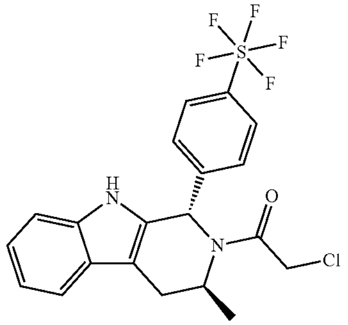 [SMILES: C[C@H]1Cc2c([nH]c3ccccc23)[C@H](c2ccc(S(F)(F)(F)(F)F)cc2)N1C(=O)CCl] |
| 223 | 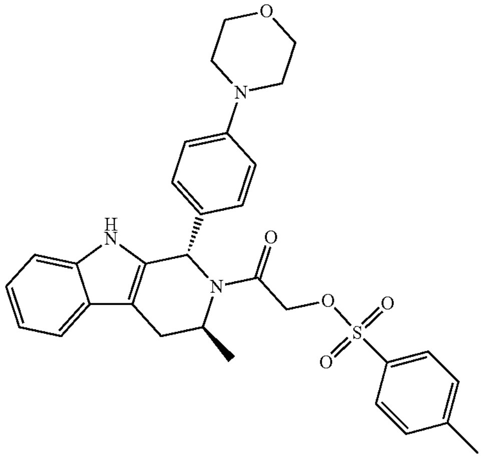 [SMILES: Cc1ccc(S(=O)(=O)OCC(=O)N2[C@@H](c3ccc(N4CCOCC4)cc3)c3[nH]c4ccccc4c3C[C@@H]2C)cc1] |
| 224 | 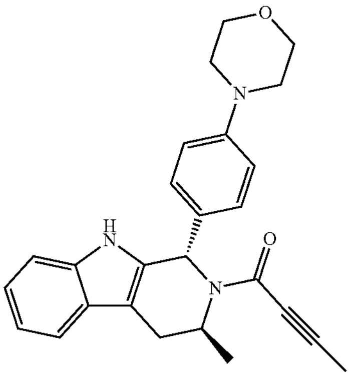 [SMILES: CC#CC(=O)N1[C@@H](c2ccc(N3CCOCC3)cc2)c2[nH]c3ccccc3c2C[C@@H]1C] |

TABLE 1-continued
| No. | Structure |
|---|---|
| 225 | 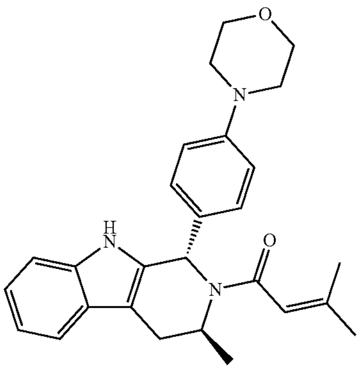 [SMILES: CC(C)=CC(=O)N1[C@@H](c2ccc(N3CCOCC3)cc2)c2[nH]c3ccccc3c2C[C@@H]1C] |
| 226 | 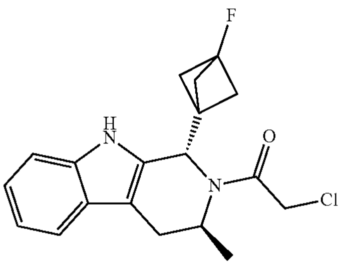 [SMILES: C[C@H]1Cc2c([nH]c3ccccc23)[C@H](C23CC(F)(C2)C3)N1C(=O)CCl] |
| 227 | 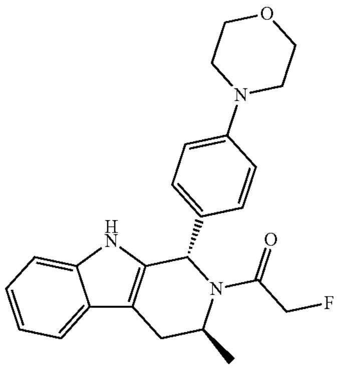 [SMILES: C[C@H]1Cc2c([nH]c3ccccc23)[C@H](c2ccc(N3CCOCC3)cc2)N1C(=O)CF] |
| 228 | 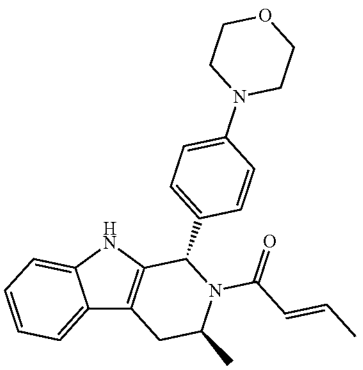 [SMILES: C/C=C/C(=O)N1[C@@H](c2ccc(N3CCOCC3)cc2)c2[nH]c3ccccc3c2C[C@@H]1C] |
TABLE 1-continued
| No. | Structure |
|---|---|
| 229 | 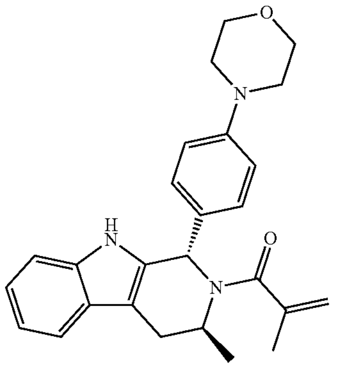 [SMILES: C=C(C)C(=O)N1[C@@H](c2ccc(N3CCOCC3)cc2)c2[nH]c3ccccc3c2C[C@@H]1C] |
| 230 | 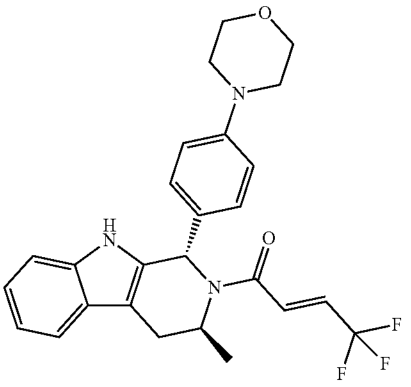 [SMILES: C[C@H]1Cc2c([nH]c3ccccc23)[C@H](c2ccc(N3CCOCC3)cc2)N1C(=O)/C=C/C(F)(F)F] |
| 231 | 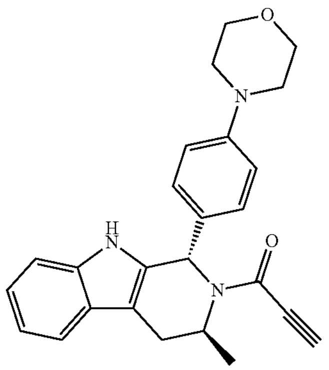 [SMILES: C#CC(=O)N1[C@@H](c2ccc(N3CCOCC3)cc2)c2[nH]c3ccccc3c2C[C@@H]1C] |
| 232 | 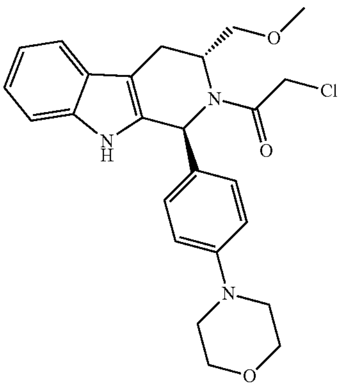 [SMILES: COC[C@H]1Cc2c([nH]c3ccccc23)[C@H](c2ccc(N3CCOCC3)cc2)N1C(=O)CCl] |

TABLE 1-continued
| No. | Structure |
|---|---|
| 233 | 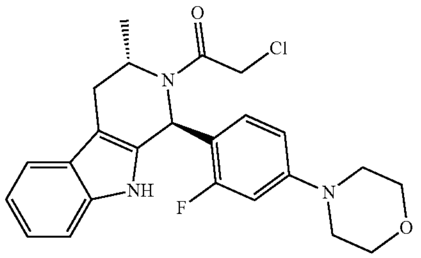 [SMILES: C[C@H]1Cc2c([nH]c3ccccc23)[C@H](c2ccc(N3CCOCC3)cc2F)N1C(=O)CCl] |
| 234 | 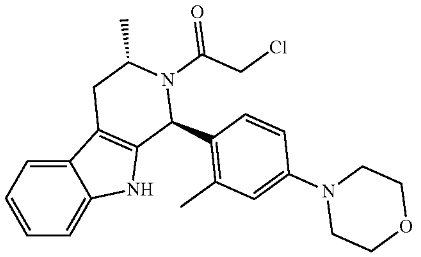 [SMILES: Cc1cc(N2CCOCC2)ccc1[C@H]1c2[nH]c3ccccc3c2C[C@H](C)N1C(=O)CCl] |
| 235 | 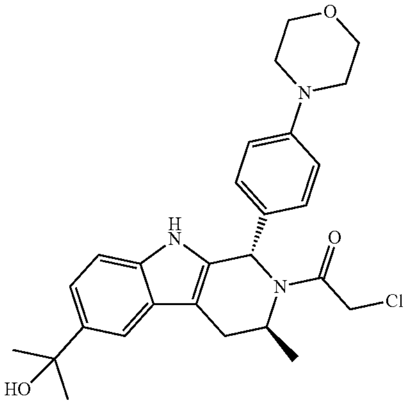 [SMILES: C[C@H]1Cc2c([nH]c3ccc(C(C)(C)O)cc23)[C@H](c2ccc(N3CCOCC3)cc2)N1C(=O)CCl] |
| 236 | 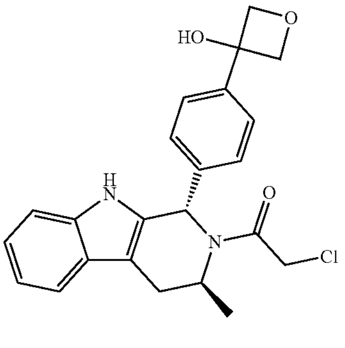 [SMILES: C[C@H]1Cc2c([nH]c3ccccc23)[C@H](c2ccc(C3(O)COC3)cc2)N1C(=O)CCl] |
TABLE 1-continued
| No. | Structure |
|---|---|
| 237 | 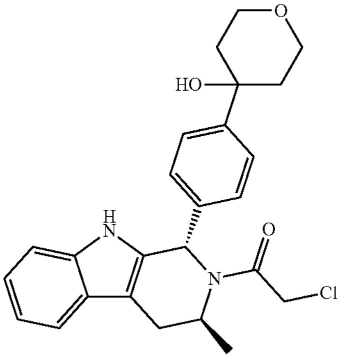 [SMILES: C[C@H]1Cc2c([nH]c3ccccc23)[C@H](c2ccc(C3(O)CCOCC3)cc2)N1C(=O)CCl] |
| 238 | 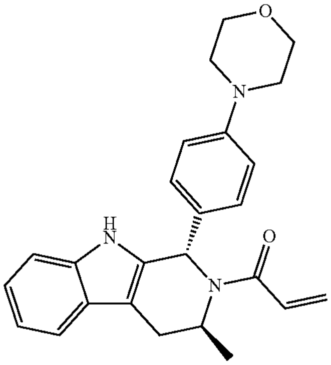 [SMILES: C=CC(=O)N1[C@@H](c2ccc(N3CCOCC3)cc2)c2[nH]c3ccccc3c2C[C@@H]1C] |
| 239 | 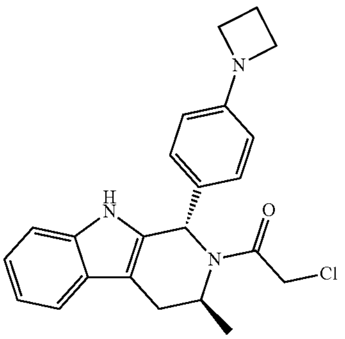 [SMILES: C[C@H]1Cc2c([nH]c3ccccc23)[C@H](c2ccc(N3CCC3)cc2)N1C(=O)CCl] |
| 240 | 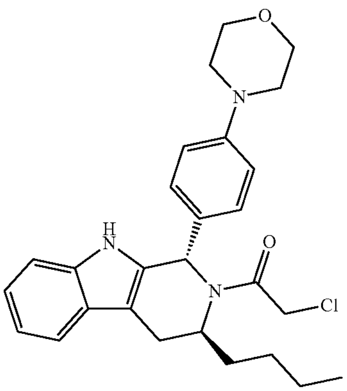 [SMILES: CCCC[C@H]1Cc2c([nH]c3ccccc23)[C@H](c2ccc(N3CCOCC3)cc2)N1C(=O)CCl] |

TABLE 1-continued
| No. | Structure |
| --- | --- |
| 241 | 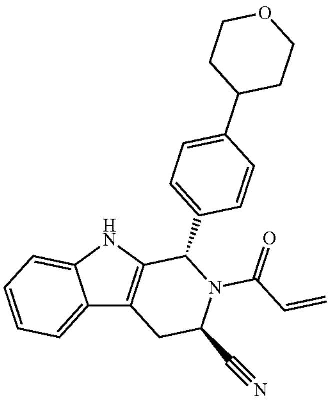 [SMILES: C=CC(=O)N1[C@@H](c2ccc(C3CCOCC3)cc2)c2[nH]c3ccccc3c2C[C@@H]1C#N] |
| 242 | 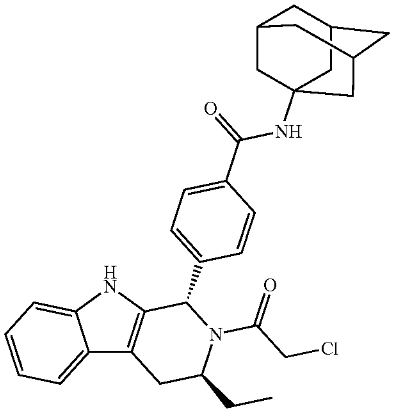 [SMILES: CC[C@H]1Cc2c([nH]c3ccccc23)[C@H](c2ccc(C(=O)NC34CC5CC(CC(C5)C3)C4)cc2)N1C(=O)CCl] |
| 243 | 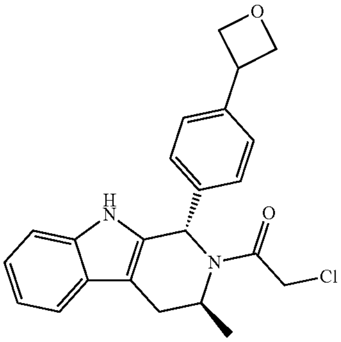 [SMILES: C[C@H]1Cc2c([nH]c3ccccc23)[C@H](c2ccc(C3COC3)cc2)N1C(=O)CCl] |
| 244 | 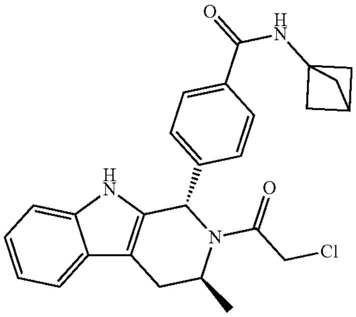 [SMILES: C[C@H]1Cc2c([nH]c3ccccc23)[C@H](c2ccc(C(=O)NC34CC(C3)C4)cc2)N1C(=O)CCl] |
TABLE 1-continued
| No. | Structure |
| --- | --- |
| 245 | 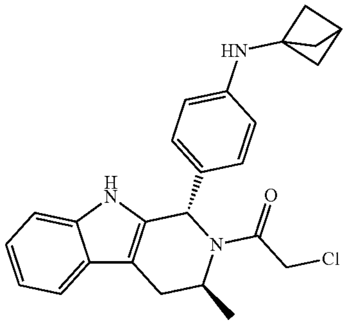 [SMILES: C[C@H]1Cc2c([nH]c3ccccc23)[C@H](c2ccc(NC34CC(C3)C4)cc2)N1C(=O)CCl] |
| 246 | 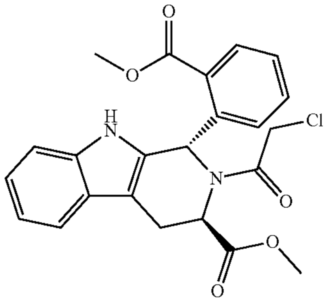 [SMILES: COC(=O)c1ccccc1[C@H]1c2[nH]c3ccccc3c2C[C@H](C(=O)OC)N1C(=O)CCl] |
| 247 | 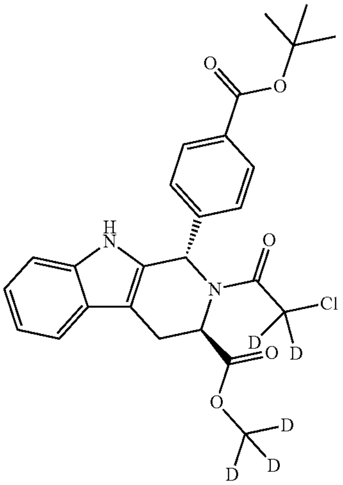 [SMILES: [2H]C([2H])([2H])OC(=O)[C@H]1Cc2c([nH]c3ccccc23)[C@H](c2ccc(C(=O)OC(C)(C)C)cc2)N1C(=O)C([2H])([2H])Cl] |
| 249 | 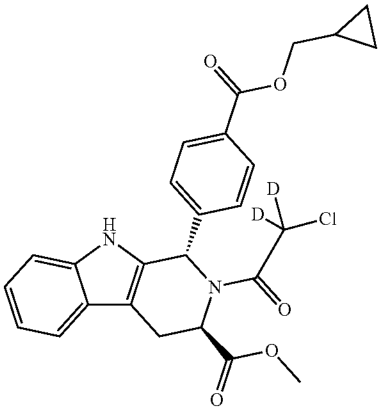 [SMILES: [2H]C([2H])(Cl)C(=O)N1[C@@H](c2ccc(C(=O)OCC3CC3)cc2)c2[nH]c3ccccc3c2C[C@@H]1C(=O)OC] |

| No. | Structure |
|---|---|
| 250 | 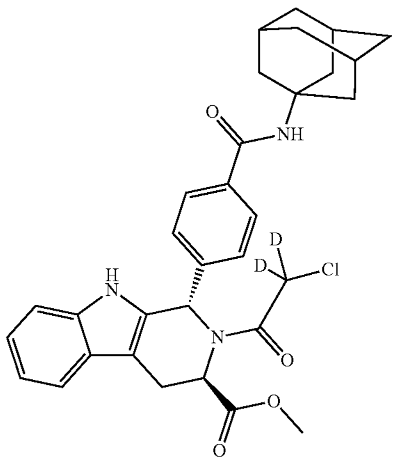 [SMILES: [2H]C([2H])(Cl)C(=O)N1[C@@H](c2ccc(C(=O)NC34CC5CC(CC(C5)C3)C4)cc2)c2[nH]c3ccccc3c2C[C@@H]1C(=O)OC] |
| 251 | 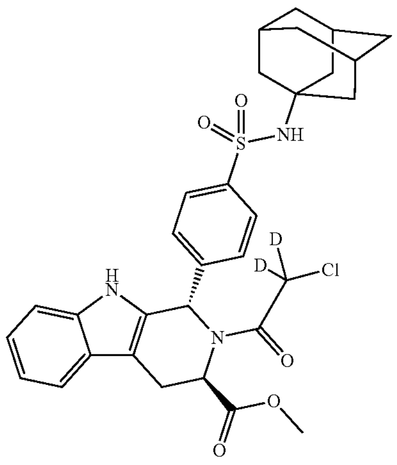 [SMILES: [2H]C([2H])(Cl)C(=O)N1[C@@H](c2ccc(S(=O)(=O)NC34CC5CC(CC(C5)C3)C4)cc2)c2[nH]c3ccccc3c2C[C@@H]1C(=O)OC] |
| 257 | 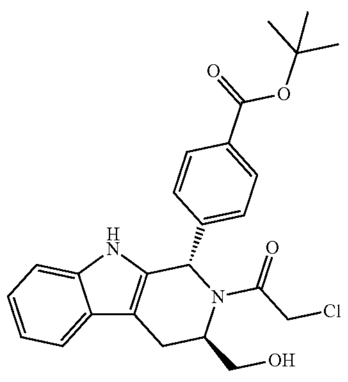 [SMILES: CC(C)(C)OC(=O)c1ccc([C@H]2c3[nH]c4ccccc4c3C[C@H](CO)N2C(=O)CCl)cc1] |
| No. | Structure |
|---|---|
| 258 | 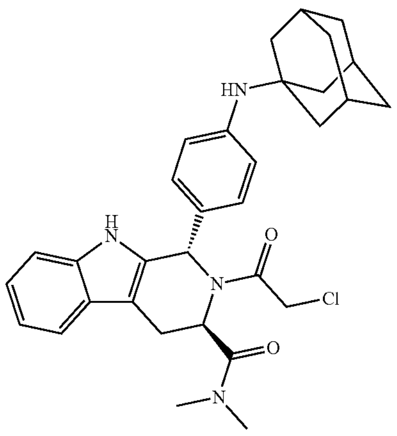 [SMILES: CN(C)C(=O)[C@H]1Cc2c([nH]c3ccccc23)[C@H](c2ccc(NC34CC5CC(CC(C5)C3)C4)cc2)N1C(=O)CCl] |
| 259 | 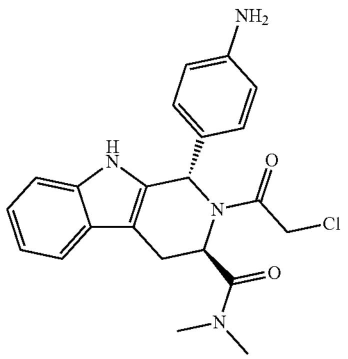 [SMILES: CN(C)C(=O)[C@H]1Cc2c([nH]c3ccccc23)[C@H](c2ccc(N)cc2)N1C(=O)CCl] |
| 260 | 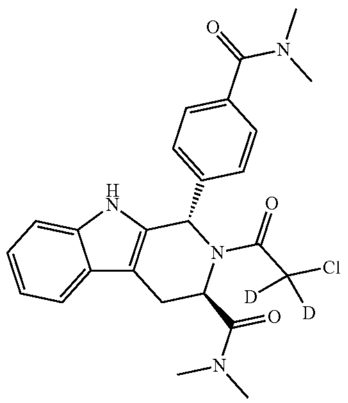 [SMILES: [2H]C([2H])(Cl)C(=O)N1[C@@H](c2ccc(C(=O)N(C)C)cc2)c2[nH]c3ccccc3c2C[C@@H]1C(=O)N(C)C] |

TABLE 1-continued
| No. | Structure |
|---|---|
| 261 | 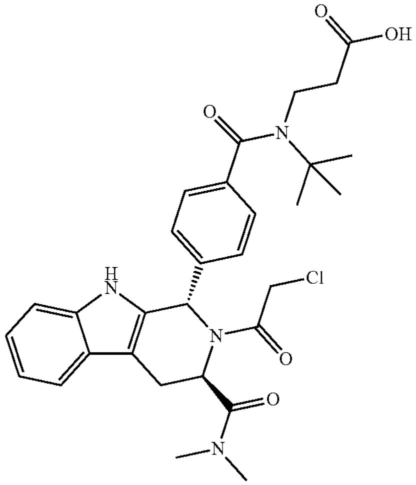 [SMILES: CN(C)C(=O)[C@H]1Cc2c([nH]c3ccccc23)[C@H](c2ccc(C(=O)N(CCC(=O)O)C(C)(C)C)cc2)N1C(=O)CCl] |
| 262 | 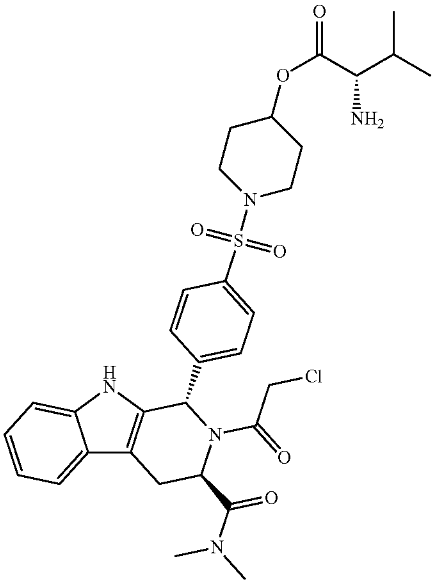 [SMILES: CC(C)[C@H](N)C(=O)OC1CCN(S(=O)(=O)c2ccc([C@H]3c4[nH]c5ccccc5c4C[C@H](C(=O)N(C)C)N3C(=O)CCl)cc2)CC1] |
| 263 | 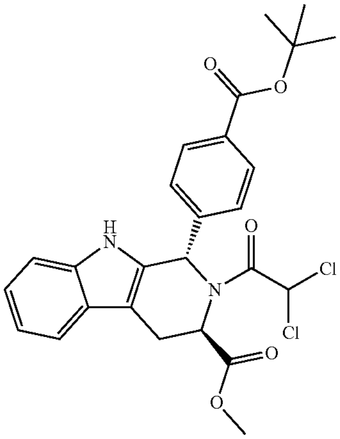 [SMILES: COC(=O)[C@H]1Cc2c([nH]c3ccccc23)[C@H](c2ccc(C(=O)OC(C)(C)C)cc2)N1C(=O)C(Cl)Cl] |
TABLE 1-continued
| No. | Structure |
|---|---|
| 264 | 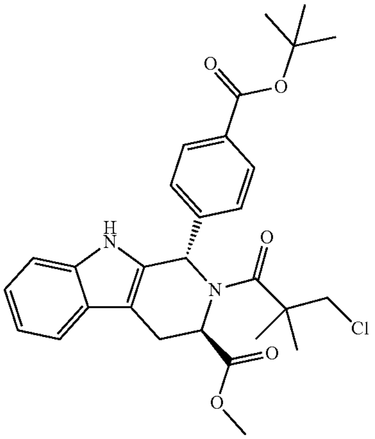 [SMILES: COC(=O)[C@H]1Cc2c([nH]c3ccccc23)[C@H](c2ccc(C(=O)OC(C)(C)C)cc2)N1C(=O)C(C)(C)CCl] |
| 265 | 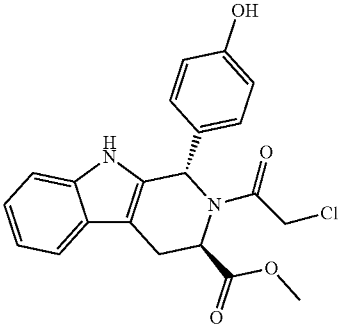 [SMILES: COC(=O)[C@H]1Cc2c([nH]c3ccccc23)[C@H](c2ccc(O)cc2)N1C(=O)CCl] |
| 266 | 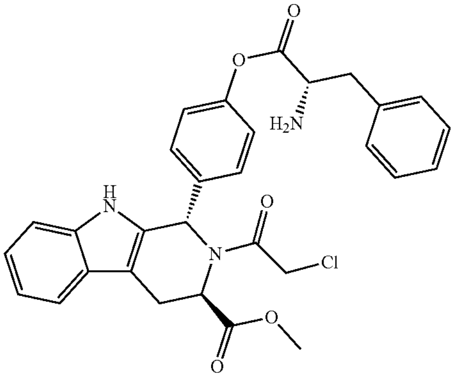 [SMILES: COC(=O)[C@H]1Cc2c([nH]c3ccccc23)[C@H](c2ccc(OC(=O)[C@@H](N)Cc3ccccc3)cc2)N1C(=O)CCl] |
| 268 | 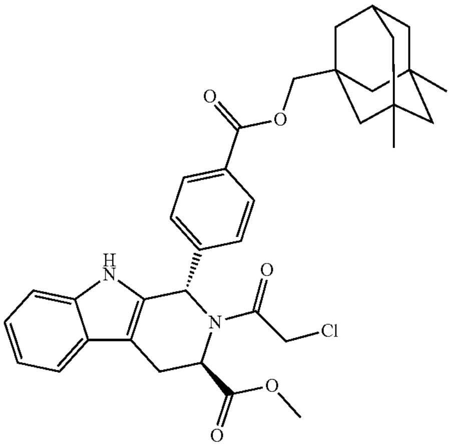 [SMILES: COC(=O)[C@H]1Cc2c([nH]c3ccccc23)[C@H](c2ccc(C(=O)OCC34CC5CC(C)(CC(C)(C5)C3)C4)cc2)N1C(=O)CCl] |

TABLE 1-continued
| No. | Structure |
|---|---|
| 269 | 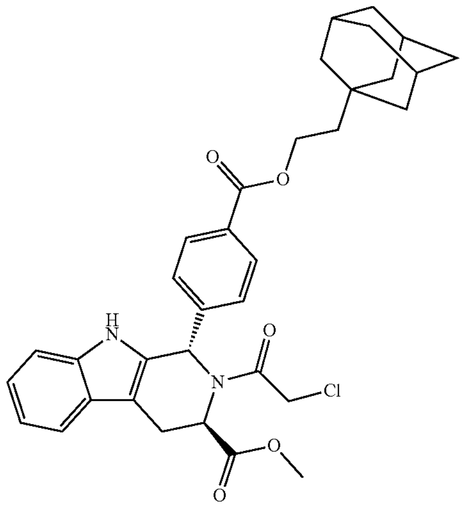 [SMILES: COC(=O)[C@H]1Cc2c([nH]c3ccccc23)[C@H](c2ccc(C(=O)OCCC34CC5CC(CC(C5)C3)C4)cc2)N1C(=O)CCl] |
| 270 | 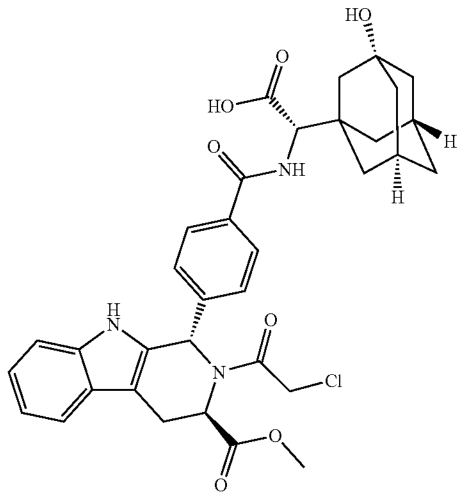 [SMILES: COC(=O)[C@H]1Cc2c([nH]c3ccccc23)[C@H](c2ccc(C(=O)N[C@H](C(=O)O)C34C[C@H]5C[C@@H](C3)C[C@](O)(C5)C4)cc2)N1C(=O)CCl] |
| 271 | 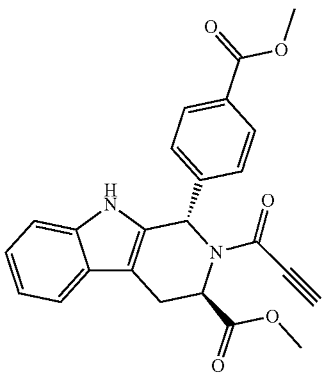 [SMILES: C#CC(=O)N1[C@@H](c2ccc(C(=O)OC)cc2)c2[nH]c3ccccc3c2C[C@@H]1C(=O)OC] |
TABLE 1-continued
| No. | Structure |
|---|---|
| 272 | 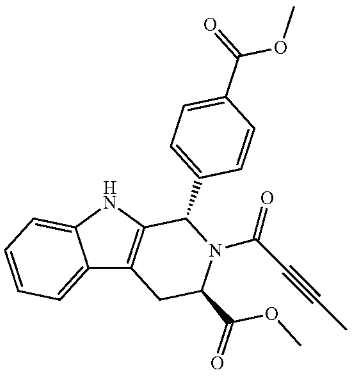 [SMILES: CC#CC(=O)N1[C@@H](c2ccc(C(=O)OC)cc2)c2[nH]c3ccccc3c2C[C@@H]1C(=O)OC] |
| 273 | 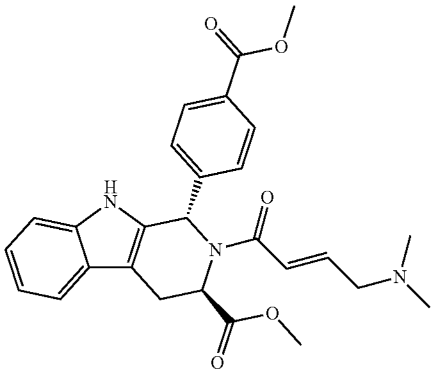 [SMILES: COC(=O)c1ccc([C@H]2c3[nH]c4ccccc4c3C[C@H](C(=O)OC)N2C(=O)/C=C/CN(C)C)cc1] |
| 274 | 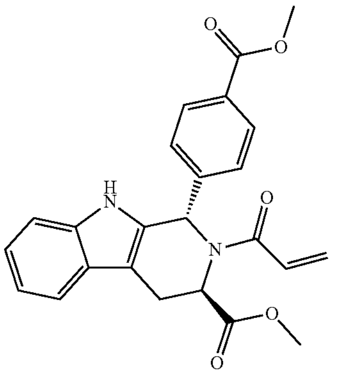 [SMILES: C=CC(=O)N1[C@@H](c2ccc(C(=O)OC)cc2)c2[nH]c3ccccc3c2C[C@@H]1C(=O)OC] |
| 275 | 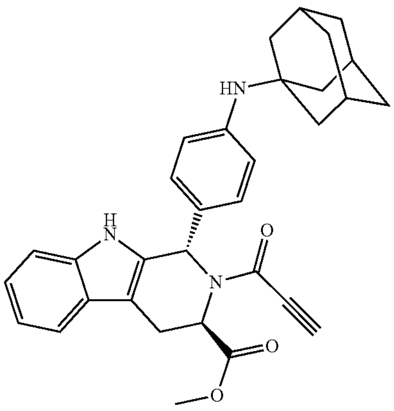 [SMILES: C#CC(=O)N1[C@@H](c2ccc(NC34CC5CC(CC(C5)C3)C4)cc2)c2[nH]c3ccccc3c2C[C@@H]1C(=O)OC] |

TABLE 1-continued
| No. | Structure |
| --- | --- |
| 276 | 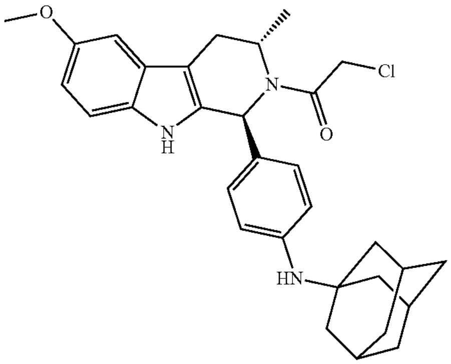 [SMILES: COc1ccc2[nH]c3c(c2c1)C[C@H](C)N(C(=O)CCl)[C@H]3c1ccc(NC23CC4CC(CC(C4)C2)C3)cc1] |
| 277 | 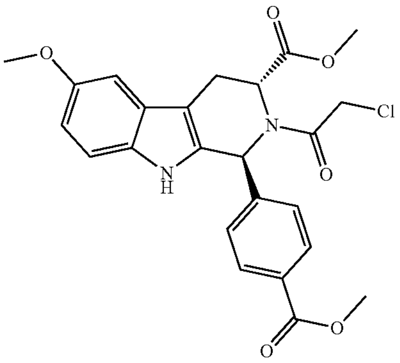 [SMILES: COC(=O)c1ccc([C@H]2c3[nH]c4ccc(OC)cc4c3C[C@H](C(=O)OC)N2C(=O)CCl)cc1] |
| 278 | 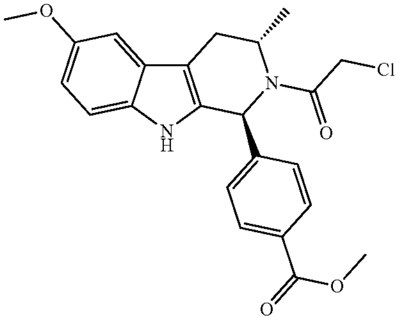 [SMILES: COC(=O)c1ccc([C@H]2c3[nH]c4ccc(OC)cc4c3C[C@H](C)N2C(=O)CCl)cc1] |
| 279 | 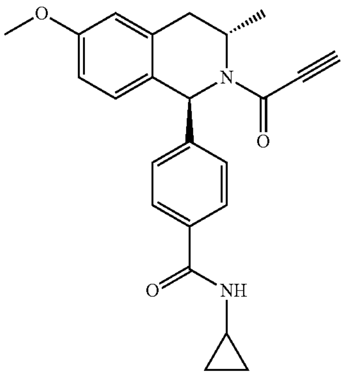 [SMILES: C#CC(=O)N1[C@@H](c2ccc(C(=O)NC3CC3)cc2)c2ccc(OC)cc2C[C@@H]1C] |
TABLE 1-continued
| No. | Structure |
| --- | --- |
| 280 | 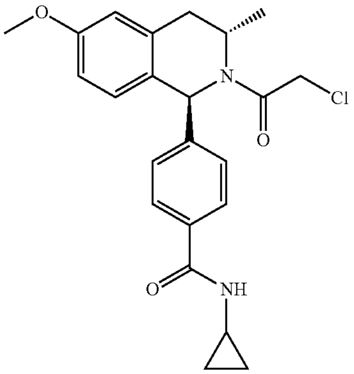 [SMILES: COc1ccc2c(c1)C[C@H](C)N(C(=O)CCl)[C@H]2c1ccc(C(=O)NC2CC2)cc1] |
| 281 | 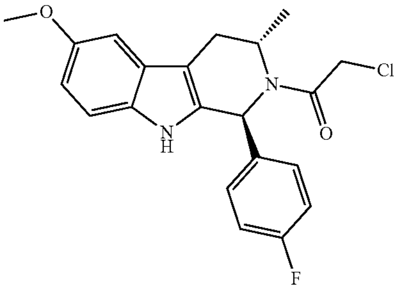 [SMILES: COc1ccc2[nH]c3c(c2c1)C[C@H](C)N(C(=O)CCl)[C@H]3c1ccc(F)cc1] |
| 282 | 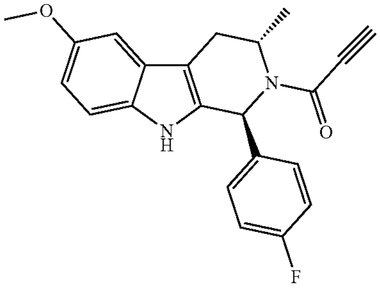 [SMILES: C#CC(=O)N1[C@@H](c2ccc(F)cc2)c2[nH]c3ccc(OC)cc3c2C[C@@H]1C] |
| 283 | 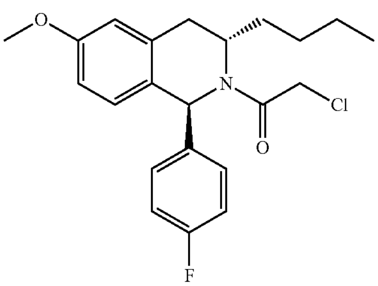 [SMILES: CCCC[C@H]1Cc2cc(OC)ccc2[C@H](c2ccc(F)cc2)N1C(=O)CCl] |

TABLE 1-continued
| No. | Structure |
| --- | --- |
| 284 | 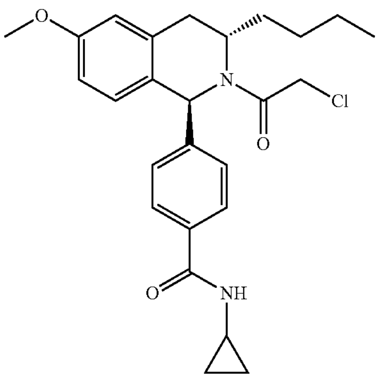 [SMILES: CCCC[C@H]1Cc2cc(OC)ccc2[C@H](c2ccc(C(=O)NC3CC3)cc2)N1C(=O)CCl] |
| 285 | 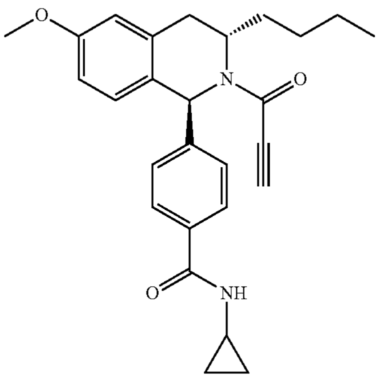 [SMILES: C#CC(=O)N1[C@@H](CCCC)Cc2cc(OC)ccc2[C@@H]1c1ccc(C(=O)NC2CC2)cc1] |
| 286 | 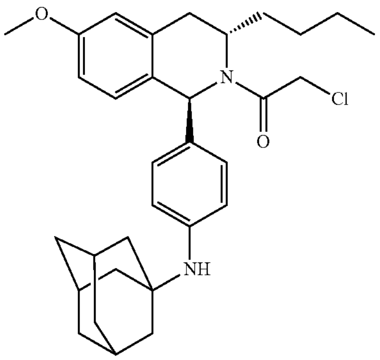 [SMILES: CCCC[C@H]1Cc2cc(OC)ccc2[C@H](c2ccc(NC34CC5CC(CC(C5)C3)C4)cc2)N1C(=O)CCl] |
| 287 | 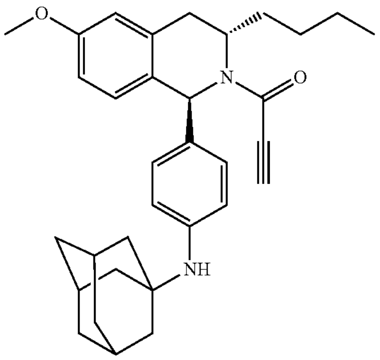 [SMILES: C#CC(=O)N1[C@@H](CCCC)Cc2cc(OC)ccc2[C@@H]1c1ccc(NC23CC4CC(CC(C4)C2)C3)cc1] |
TABLE 1-continued
| No. | Structure |
| --- | --- |
| 288 | 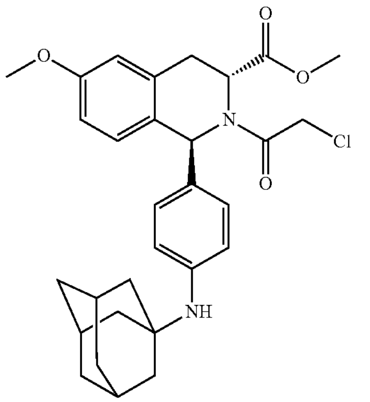 [SMILES: COC(=O)[C@H]1Cc2cc(OC)ccc2[C@H](c2ccc(NC34CC5CC(CC(C5)C3)C4)cc2)N1C(=O)CCl] |
| 290 | 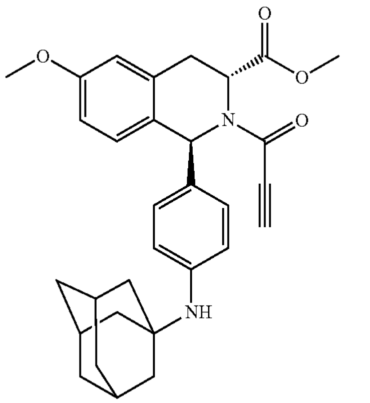 |
| 291 | 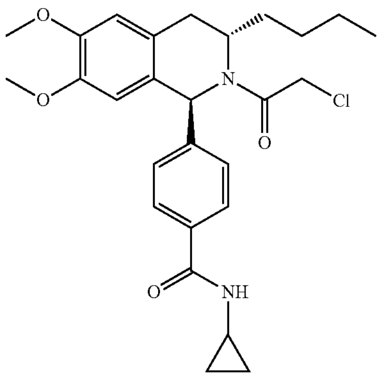 [SMILES: CCCC[C@H]1Cc2cc(OC)c(OC)cc2[C@H](c2ccc(C(=O)NC3CC3)cc2)N1C(=O)CCl] |
| 292 | 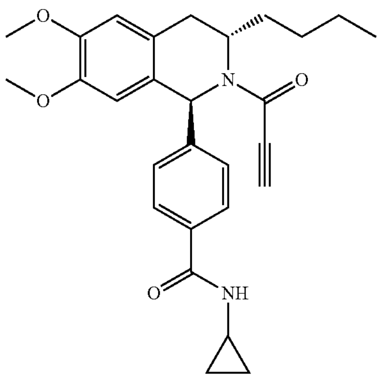 [SMILES: C#CC(=O)N1[C@@H](CCCC)Cc2cc(OC)c(OC)cc2[C@@H]1c1ccc(C(=O)NC2CC2)cc1] |

TABLE 1-continued

| No. | Structure |
| --- | --- |
| 293 | 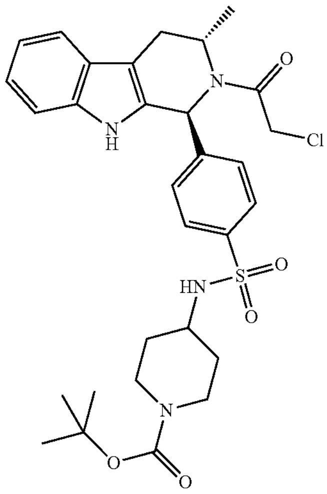 [SMILES: C[C@H]1Cc2c([nH]c3ccccc23)[C@H](c2ccc(S(=O)(=O)NC3CCN(C(=O)OC(C)(C)C)CC3)cc2)N1C(=O)CCl] |

or an enantiomer or pharmaceutically acceptable salt thereof.

3. Methods of Preparation

The compounds of the present disclosure can be synthesized in view of the guidance provided herein, incorporating known chemical reactions and related procedures such as separation and purification. Representative methods and procedures for preparation of the compounds in this disclosure are described below and in the Examples. Acronyms are abbreviations are used per convention which can be found in literature and scientific journals.

It is understood that the starting materials and reaction conditions may be varied, the sequence of the reactions altered, and additional steps employed to produce compounds encompassed by the present disclosure, as demonstrated by the following examples. General references for known chemical reactions useful for synthesizing the disclosed compounds are available (see, e.g., Smith and March, March's Advanced Organic Chemistry: Reactions, Mechanisms, and Structure, Fifth Edition, Wiley Interscience, 2001; or Carey and Sundberg, Advanced Organic Chemistry, Part B. Reaction and Synthesis; Fifth Edition, Springer, 2007; or Li, J. J. Name Reactions, A Collection of Detailed Mechanisms and Synthetic Applications; Fifth Edition, Springer, 2014).

Starting materials can be obtained from commercial sources or prepared by know reactions and literature methods such as scientific journals, which are known to those skilled in the art.

In certain embodiments, synthesis of the compounds can use the following schemes. For example, compounds of Formula (I) can be prepared according to the general syntheses outlined below in Scheme 1, where suitable reagents can be purchased form commercial sources or synthesized via known methods or methods adapted from the examples provided herein. In Scheme 1, each of ring A, X, $R^1$, $R^2$, $R^3$, $R^4$, p, and q are independently as defined herein, and LG is a leaving group (e.g., halo).

Scheme 1

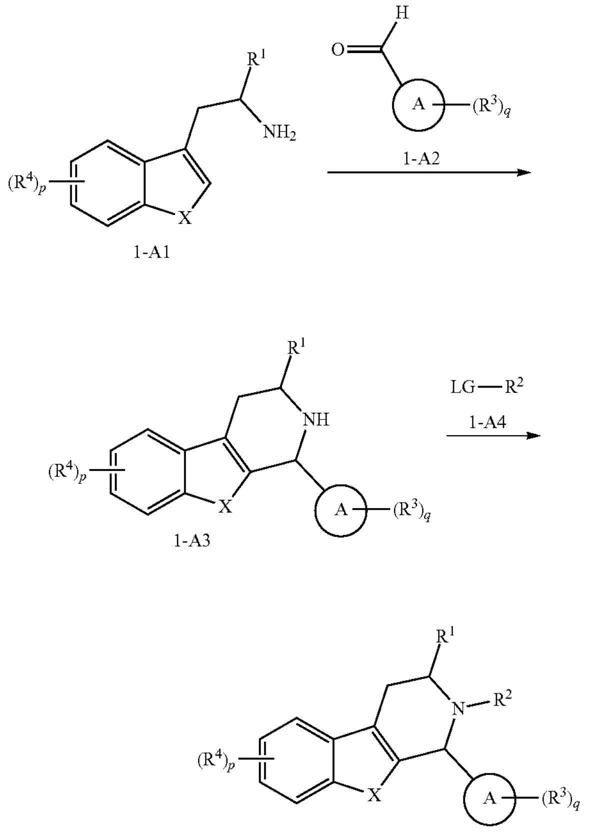

1-A1

1-A3

(I)

In Scheme 1, compound 1-A3 can be provided by cyclizing an amine 1-A1 with aldehyde 1-A2. Compounds of formula (I) can then be provided by coupling 1-A3 with 1-A4 under reaction conditions suitable to provide compounds of formula (I). Further exemplary syntheses are shown in the schemes below.

For synthesis of compounds described herein having esters at $R^1$ and $R^3$, an exemplary synthesis is shown in Scheme 1A.

Scheme 1A

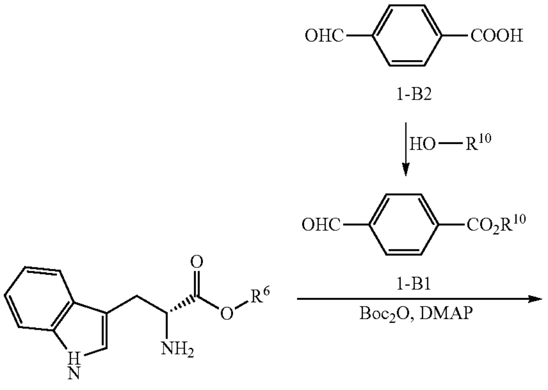

1-A

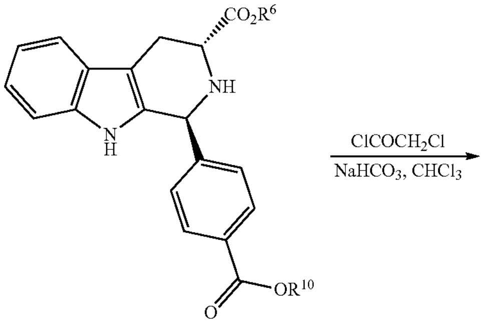

1-4

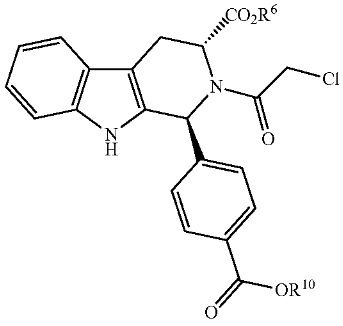

I-E

In certain embodiments, $R^6$ and $R^{10}$ are alkyl groups. Use of different alcohols HO—$R^{10}$ in the reaction with 1-B2 can yield different alkyl 4-formylbenzoate compound (1-B1) for the cyclization reaction with compound 1-A to yield compound 1-4. Reaction with 2-chloroacetyl chloride results in compound I-E, where esters are present at both $R^1$ and $R^3$.

In certain embodiments, synthesis of compounds with other esters at $R^3$ can use the synthesis shown in Scheme 1B starting from compound I-E*:

Scheme 1B

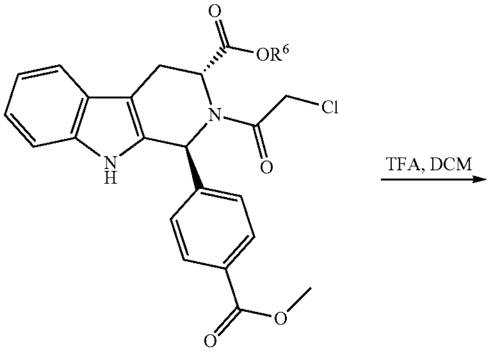

I-E*

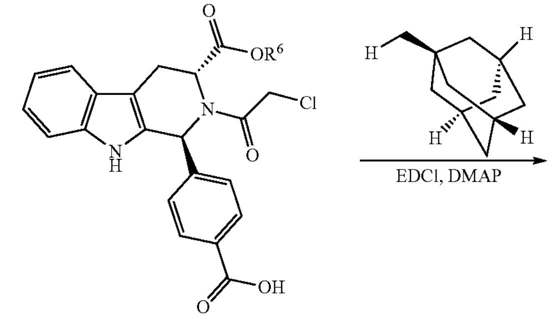

1-5

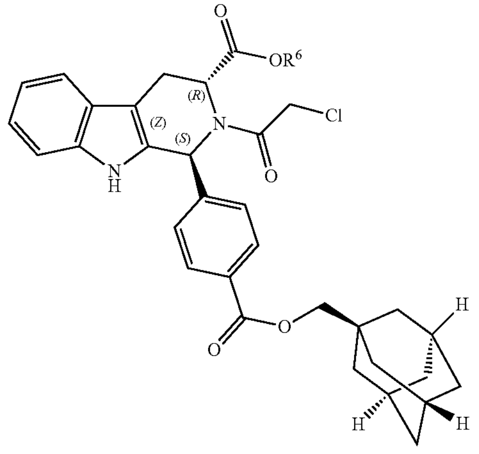

In certain embodiments, the compound 1-5 can also be used for synthesis of amides at $R^3$ as shown in Scheme 1C.

Scheme 1C

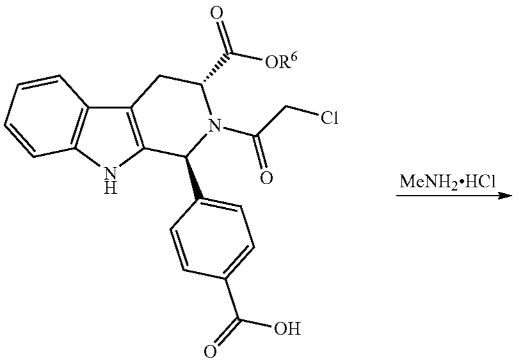

1-5

-continued

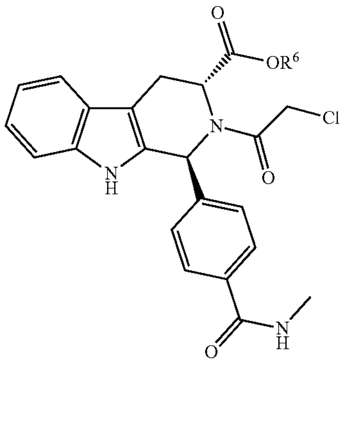

Use of different alkylamino groups can be used to introduce different alkyl substituted amides, for example $NH(CH_3)_2$, or $NH_2$-t-butyl as shown in Scheme 1D Scheme 1D

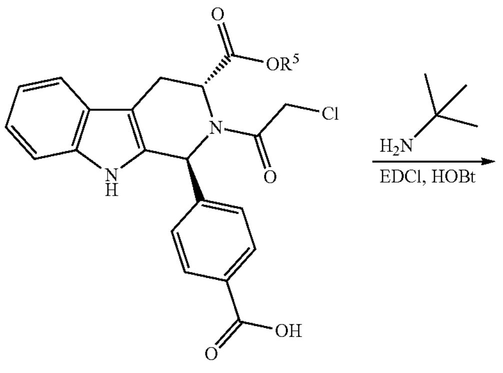

1-5

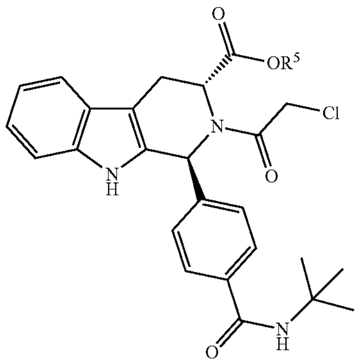

Synthesis of reverse esters at the $R^3$ position can use the synthetic route of Scheme 1, but replacing the alkyl 4-formylbenzoate with a substituted starting material, e.g., 4-formylphenyl acetate) as shown in Scheme 1E:

Scheme IE

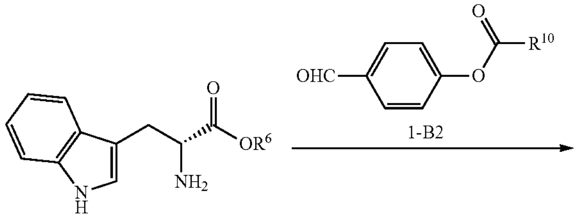

1-A

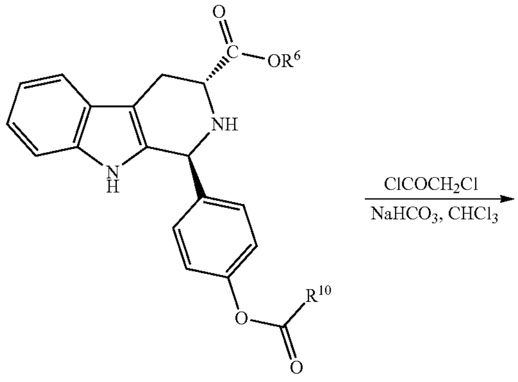

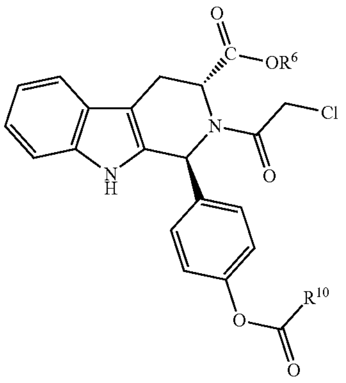

I-RE

The substituted 4-formylphenyl acetate compound, for example 4-formyl t-butylacetate, can be prepared as below, and the resulting product 1-B3 coupled to compound 1-A having a methyl ester as shown in Scheme 1F:

Scheme 1F

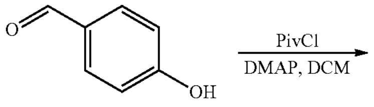

1-B3a

-continued

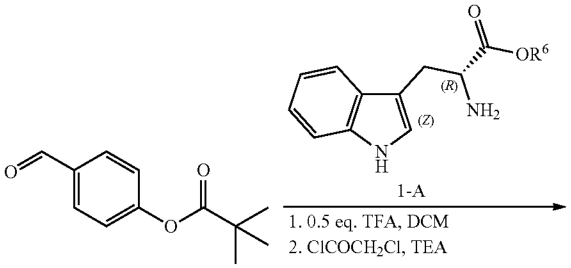

1-B3

1-A

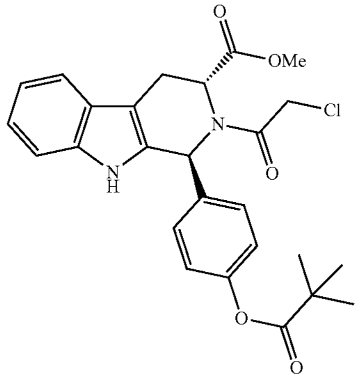

For synthesis of compounds in which ring A is phenyl substituted with a sulfonyl group, for example a sulfonamide, the synthetic route of Scheme 1G can be used.

Scheme 1G

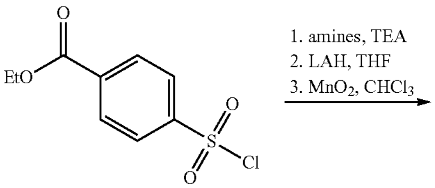

1-S1

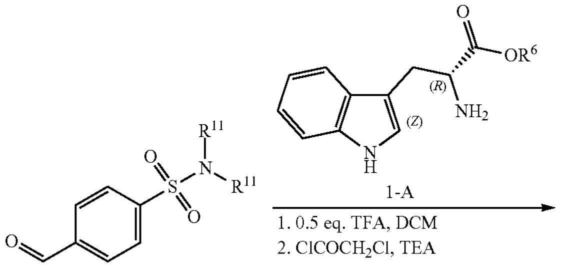

1-A

1-SA1

-continued

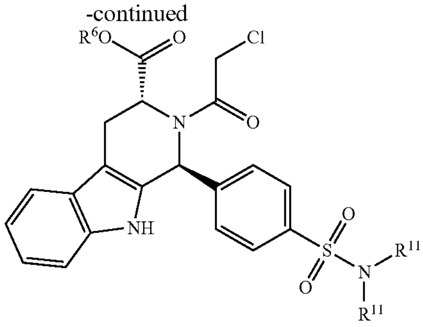

IV-S

In Scheme 1G, the ethyl 4-(chlorosulfonyl)benzoate is reacted with an amine $NH(R^{11})_2$ to form compound 1-SA1, N-substituted 4-formyl benzenesulfonamide. Compound 1-SA1 is coupled to compound 1-A and then reacted with 2 chloroacetyl acetate as shown in Scheme 1A above to form compound IV-S. A similar method can be used to provide compounds where $R^3$ is —$SO_2$-alkyl, and the like.

For synthesis of compounds in which $R^1$ is cycloalkyl, for example a cyclohexyl, a synthetic route according to Scheme 1H can be used:

Scheme 1H

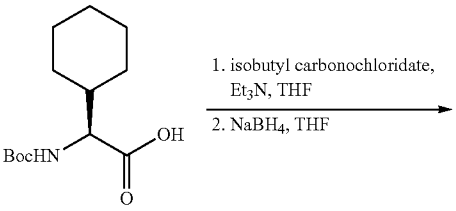

5-1

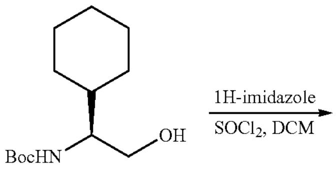

5-2

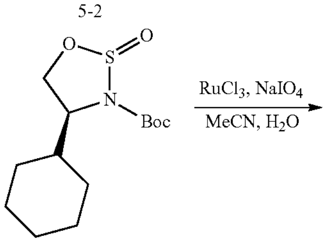

5-3

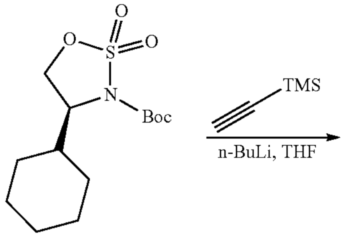

5-4

-continued

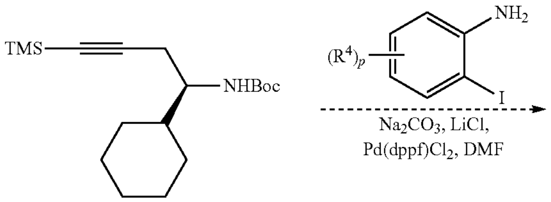

5-5

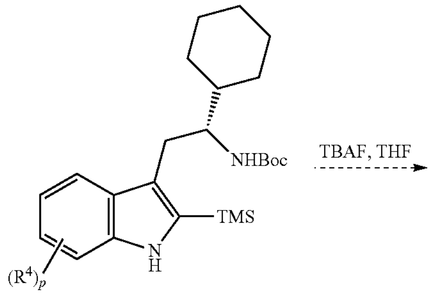

5-6

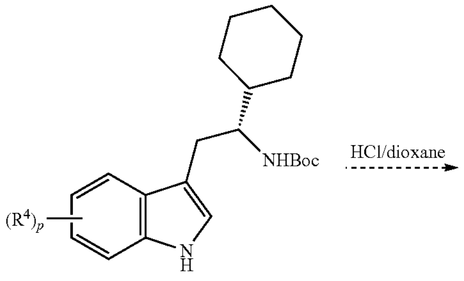

5-7

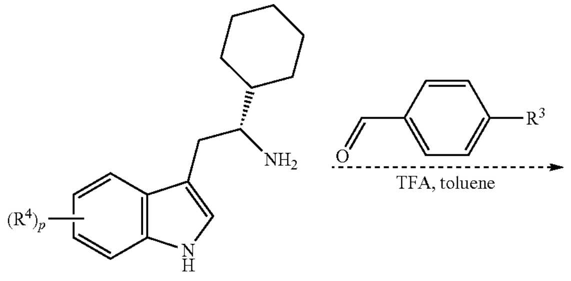

5-8

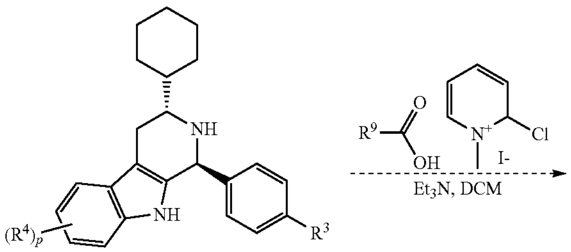

5-9

-continued

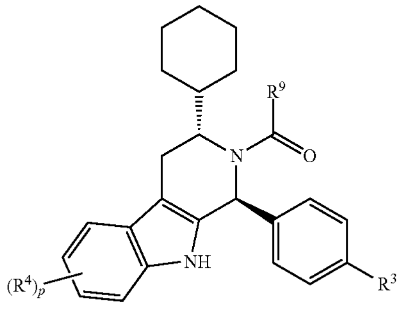

5-10

In Scheme 1H, compound 5-1 is reduced, cyclized and oxidized to provide compound 5-4. Compound 5-4 is reacted with ethynyltrimethylsilane to provide the alkyne 5-5. Cyclization with an optionally substituted 2-iodoaniline provides compound 5-6, which can then be deprotected and coupled with an optionally substituted benzaldehyde provides compound 5-9, which upon reaction with a desired acid, yields compound 5-10.

For the synthesis of compounds having various $R^4$ substituents, a synthetic route as in Scheme 1I can be used.

Scheme 1I

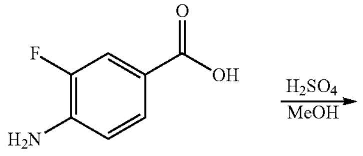

6-1

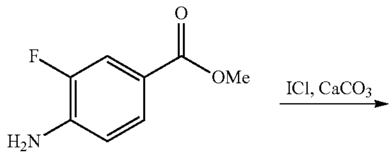

6-2

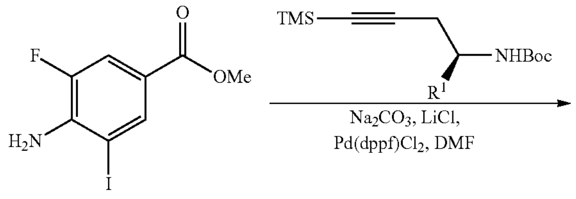

6-3

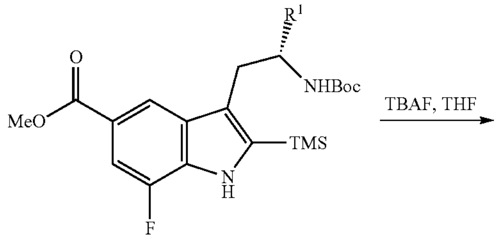

6-4

-continued

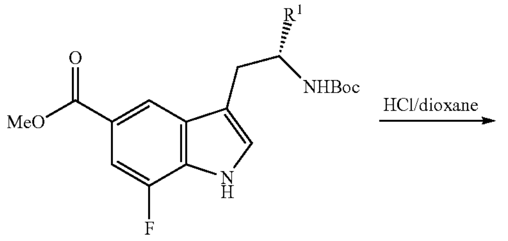

6-5

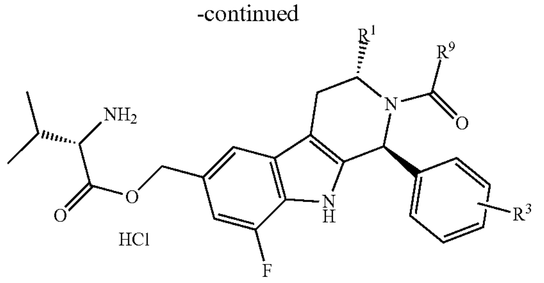

6-11

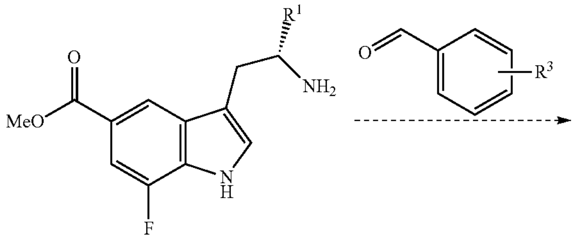

6-6

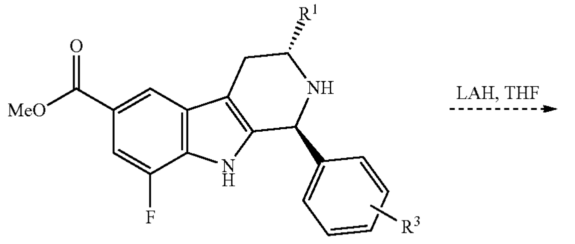

6-7

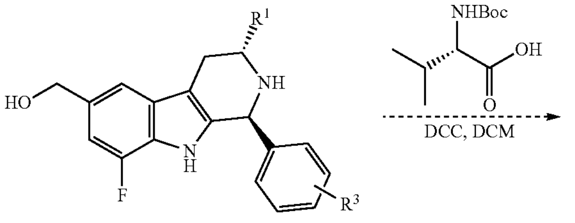

6-8

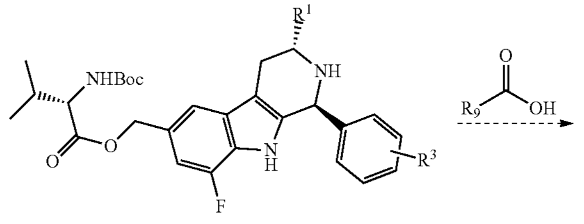

6-9

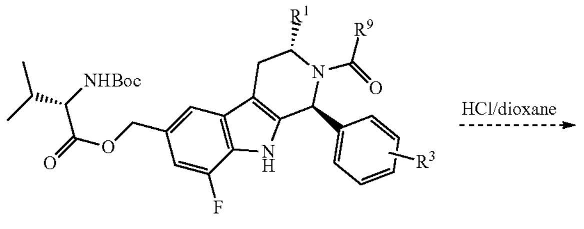

6-10

In Scheme 11, compound 6-1 can be functionalized via the corresponding ester 6-2, to provide compound 6-3, which can then be converted to a protected indole 6-4. Deprotection provides compound 6-6, which can then be coupled with an optionally substituted benzaldehyde to provide compound 6-7.

Reduction of the ester yields compound 6-8, which can then be coupled with an acid moiety (e.g., an amino acid, such as valine) to give compound 6-9. Reaction of compound 6-9 with a suitable acid provides compound 6-10, which can be optionally reacted with an acid to provide the corresponding salt, as in compound 6-11.

Other compounds of the disclosure can be synthesized using the synthetic routes above and adapting chemical synthetic procedures available to the skilled artisan. Exemplary methods of synthesis are provided in the Examples. It is to be understood that each of the Procedures describing synthesis of exemplary compounds are part of the specification, and thus incorporated herein into the Detailed Description of this disclosure.

4. Methods of Use

In certain embodiments, the compounds described herein are used in a method of treating cancer. In certain embodiments, the method of treating cancer comprises administering to a subject in need thereof a therapeutically effective amount any of the compounds described herein.

In certain embodiments, the compounds can be used as monotherapy, or as further provided below, in a combination therapy with one or more therapeutic treatments, particularly in combination with one or more chemotherapeutic agents. In certain embodiments, the compounds are used in combination with a second therapeutic agent, where the compounds are used at levels that sensitizes the cancer or cancer cell to the second therapeutic agent, for example at levels of the compound that do not cause significant cell death. In certain embodiments, the compounds can be used in combination with radiation therapy, either to sensitize the cells to radiation therapy or as an adjunct to radiation therapy (e.g., at doses sufficient to activate cell death pathway).

In certain embodiments, provided is a method for treating a cancer in a patient in need thereof, comprising administering an effective amount of a compound or composition provided herein.

In certain embodiments, provided is a method for treating a malignant solid tumor in a patient in need thereof, comprising administering an effective amount of a compound or composition provided herein to the patient. In certain embodiments, the malignant solid tumor is a carcinoma. In certain embodiments, the malignant solid tumor is a lymphoma. In certain embodiments, the malignant solid tumor is a sarcoma.

In certain embodiments, the cancer for treatment with the compound can be selected from, among others, adrenocortical cancer, anal cancer, biliary cancer, bladder cancer, bone cancer (e.g., osteosarcoma), brain cancer (e.g., gliomas, astrocytoma, neuroblastoma, etc.), breast cancer, cervical cancer, colon cancer, endometrial cancer, esophageal cancer, head and neck cancer, hematologic cancer (e.g., leukemia and lymphoma), intestinal cancer (small intestine), liver cancer, lung cancer (e.g., bronchial cancer, small cell lung cancer, non-small cell lung cancer, etc.), oral cancer, ovarian cancer, pancreatic cancer, renal cancer, prostate cancer, salivary gland cancer, skin cancer (e.g., basal cell carcinoma, melanoma), stomach cancer, testicular cancer, throat cancer, thyroid cancer, uterine cancer, vaginal cancer, sarcoma, and soft tissue carcinomas. In certain embodiments, the cancer is renal cell carcinoma (RCC). In certain embodiments, the cancer is pancreatic cancer. In certain embodiments, the cancer is lung cancer. In certain embodiments, the cancer is breast cancer. In certain embodiments, the cancer is prostate cancer.

In certain embodiments, the cancer for treatment with the compound is pancreatic cancer. In certain embodiments, the pancreatic cancer for treatment with the compounds is pancreatic adenocarcinoma or metastatic pancreatic cancer. In certain embodiments, the cancer for treatment with the compounds is stage 1, stage II, stage III, or stage IV pancreatic adenocarcinoma.

In certain embodiments, the cancer for treatment with the compounds is lung cancer. In certain embodiments, the lung cancer for treatment with the compounds is small cell lung cancer or non-small cell lung cancer. In certain embodiments, the non-small cell lung cancer for treatment with the compounds is an adenocarcinoma, squamous cell carcinoma, or large cell carcinoma. In certain embodiments, the lung cancer for treatment with the compounds is metastatic lung cancer.

In certain embodiments, the cancer for treatment with the compounds is a hematologic cancer. In certain embodiments, the hematologic cancer is selected from acute lymphoblastic leukemia (ALL), acute myeloid leukemia (AML), lymphoma (e.g., Hodgkin's lymphoma, Non-Hodgkin's lymphoma, Burkitt's lymphoma), chronic lymphocytic leukemia (CLL), chronic myelogenous leukemia (CML), Hairy Cell chronic myelogenous leukemia (CML), and multiple myeloma.

In certain embodiments, the cancer for treatment with the compounds is a leukemia selected from acute lymphoblastic leukemia (ALL), acute myeloid leukemia (AML), chronic lymphocytic leukemia (CLL), chronic myelogenous leukemia (CML), Hairy Cell chronic myelogenous leukemia (CML), and multiple myeloma.

In certain embodiments, the cancer for treatment with the compound is a lymphoma selected from Hodgkin's lymphoma, Non-Hodgkin's lymphoma, and Burkitt's lymphoma.

In certain embodiments, the cancer for treatment with the compound is a cancer characterized by mesenchymal features or mesenchymal phenotype. In some cancers, gain of mesenchymal features is associated with migratory (e.g., intravasation) and invasiveness of cancers. Mesenchymal features can include, among others, enhanced migratory capacity, invasiveness, elevated resistance to apoptosis, and increased production of extracellular matrix (ECM) components. In addition to these physiological characteristics, the mesenchymal features can include expression of certain biomarkers, including among others, E-cadherin, N-cadherin, integrins, FSP-1, α-SMA, vimentin, β-catenin, collagen I, collagen II, collagen III, collagen IV, fibronectin, laminin 5, SNAIL-1, SNAIL-2, Twist-1, Twist-2, and Lef-1. In certain embodiments, the cancer selected for treatment with the compounds herein include, among others, breast cancer, lung cancer, head and neck cancer, prostate cancer, and colon cancer. In certain embodiments, the mesenchymal features can be inherent to the cancer type or induced by or selected for by treatment of cancers with chemotherapy and/or radiation therapy.

In certain embodiments, the cancer for treatment with the compound is identified as having or determined to have an activating or oncogenic RAS activity. In certain embodiments, the RAS is K-RAS, H-RAS or N-RAS. In certain embodiments, the activating or oncogenic RAS is an activating or oncogenic RAS mutation.

In certain embodiments, the cancer for treatment with the compounds is identified as having or determined to have an activating or oncogenic K-RAS mutation. In certain embodiments, the cancer selected for treatment is identified as having or determined to have an activating or oncogenic mutation in human K-RAS at one or more of codon 5, codon 9, codon 12, codon 13, codon 14, codon 18, codon 19, codon 22, codon 23, codon 24, codon 26, codon 33, codon 36, codon 57, codon 59, codon 61, codon 62, codon 63, codon 64, codon 68, codon 74, codon 84, codon 92, codon 35, codon 97, codon 110, codon 115, codon 117, codon 118, codon 119, codon 135, codon 138, codon 140, codon 146, codon 147, codon 153, codon 156, codon 160, codon 164, codon 171, codon 176, codon 185, and codon 188.

In certain embodiments, the activating or oncogenic K-RAS mutation can be a mutation in which codon 5 is K5E; codon 9 is V91; codon 12 is G12A, G12C, G12D, G12F, G12R, G12S, G12V, or G12Y; codon 13 is G13C, G13D, or G13V; codon 14 is V14I or V14L; codon 18 is A18D; codon 19 is L19F; codon 22 is Q22K; codon 23 is L23R; codon 24 is I24N; codon 26 is N26K; codon 33 is D33E; codon 36 is I36L or I36M; codon 57 is D57N; codon 59 is A59E, A59G, or A59T; codon 61 is Q61H, Q61K, Q61L, or Q61R; codon 62 is E62G or E62K; codon 63 is E63K; codon 64 is Y64D, Y64H, or Y64N; codon 68 is R68S; codon 74 is T74P; codon 84 is I84T; codon 92 is D92Y; codon 97 is R97I; codon 110 is P110H or P110S; codon 115 is G115E; codon 117 is K117N; codon 118 is C118S; codon 119 is D119N; codon 135 is R135T; codon 138 is G138V; codon 140 is P140H; codon 146 is A146T or A146V; codon 147 is K147N; codon 153 is D153N; codon 156 is F156L; codon 160 is V160A; codon 164 is R164Q; codon 171 is I117M; codon 176 is K176Q; codon 185 is C185R or C185S; and codon 188 is M188V.

In certain embodiments, the cancer for treatment with the compound is identified as having or determined to have an oncogenic or activating K-RAS mutations at codon 12, codon 13 and/or codon 61.

In certain embodiments, the oncogenic or activating K-RAS mutation at codon 12 is G12A, G12C, G12D, G12F, G12R, G12S, G12V, or G12Y; at codon 13 is G13C, G13D, or G13V; and at codon 61 is Q61H, Q61K, Q61L, or Q61R. In certain embodiments, the oncogenic or activating K-RAS mutation is a combination of oncogenic or activating K-RAS mutations at codon 12 and codon 13; codon 12 and codon 61; codon 13 and 61; or codon 12, codon 13 and codon 61.

In certain embodiments, the cancer for treatment with the compounds is identified as having or determined to have an activating or oncogenic N-RAS mutation. In certain embodiments, the cancer is identified as having or determined to have an activating or oncogenic mutation in human N-RAS at one or more of codon 12, codon 13 and codon 61. In certain embodiments, the activating or oncogenic N-RAS mutation at codon 12 is G12A, G12C, G12D, G12R, G12S, or G12V. In certain embodiments, the activating or oncogenic N-RAS mutation at codon 13 is G13A, G13C, G13D, G13R, G13S, or G13V. In certain embodiments, the activating or oncogenic N-RAS mutation at codon 61 is Q61E, Q61H, Q61K, Q61L, Q61P, or Q61R. In certain embodiments, the oncogenic or activating N-RAS mutation is a combination of activating or oncogenic N-RAS mutations at codon 12 and codon 13; codon 12 and codon 61; codon 13 and 61; or codon 12, codon 13 and codon 61.

In certain embodiments, the cancer for treatment with the compounds is identified as having or determined to have an activating or oncogenic H-RAS mutation. In certain embodiments, the cancer selected for treatment is identified as having an activating or oncogenic mutation in human H-RAS at one or more of codon 12, codon 13 and codon 61. In certain embodiments, the activating or oncogenic H-RAS mutation at codon 12 is G12A, G12C, G12D, G12R, G12S, or G12V. In certain embodiments, the activating or oncogenic H-RAS mutation at codon 13 is G13A, G13C, G13D, G13R, G13S, or G13V. In certain embodiments, the activating or oncogenic H-RAS mutation at codon 61 is Q61E, Q61H, Q61K, Q61L, Q61P, or Q61R. In certain embodiments, the oncogenic or activating H-RAS mutation is a combination of activating or oncogenic H-RAS mutations at codon 12 and codon 13; codon 12 and codon 61; codon 13 and 61; or codon 12, codon 13 and codon 61.

In certain embodiments, the cancer for treatment with the compounds can be a cancer having prevalence (e.g., at least about 10% or more, or about 15% or more of the cancers), of an activating or oncogenic RAS mutation, such as biliary tract cancer, cervical cancer, endometrial cancer, pancreatic cancer, lung cancer, colorectal cancer, head and neck cancer, stomach (gastric) cancer, hematologic cancer (e.g., leukemia, lymphomas, etc.), ovarian cancer, prostate cancer, salivary gland cancer, skin cancer, small intestinal cancer, thyroid cancer, aerodigestive tract, urinary tract cancer, and bladder cancer.

In certain embodiments, the compounds can be used to treat a cancer that is refractory to one or more other chemotherapeutic agents, particularly cytotoxic chemotherapeutic agents; or treat a cancer resistant to radiation treatment. In certain embodiments, the compounds are used to treat cancers that have developed tolerance to chemotherapeutic agents activating other cell death pathways, such as apoptosis, mitotic catastrophe, necrosis, senescence and/or autophagy.

In certain embodiments, the cancer for treatment with the compounds is identified as being refractory or resistant to chemotherapy. In certain embodiments, the cancer is refractory or resistant to one or more of alkylating agents, anticancer antibiotic agents, antimetabolic agents (e.g., folate antagonists, purine analogs, pyrimidine analogs, etc.), topoisomerase inhibiting agents, anti-microtubule agents (e.g., taxanes, *vinca* alkaloids), hormonal agents (e.g., aromatase inhibitors), plant-derived agents and their synthetic derivatives, anti-angiogenic agents, differentiation inducing agents, cell growth arrest inducing agents, apoptosis inducing agents, cytotoxic agents, agents affecting cell bioenergetics i.e., affecting cellular ATP levels and molecules/activities regulating these levels, biologic agents, e.g., monoclonal antibodies, kinase inhibitors and inhibitors of growth factors and their receptors.

In certain embodiments, the cancer for treatment with the compounds is a cancer identified as being refractory or resistant to one or more of afatinib, afuresertib, alectinib, alisertib, alvocidib, amsacrine, amonafide, amuvatinib, axitinib, azacitidine, azathioprine, bafetinib, barasertib, bendamustine, bleomycin, bosutinib, bortezomib, busulfan, cabozantinib, camptothecin, canertinib, capecitabine, cabazitaxel, carboplatin, carmustine, cenisertib, ceritinib, chlorambucil, cisplatin, cladribine, clofarabine, crenolanib, crizotinib, cyclophosphamide, cytarabine, dabrafenib, dacarbazine, dacomitinib, dactinomycin, danusertib, dasatinib, daunorubicin, decitabine, dinaciclib, docetaxel, dovitinib, doxorubicin, epirubicin, epitinib, eribulin mesylate, errlotinib, etirinotecan, etoposide, everolimus, exemestane, floxuridine, fludarabine, fluorouracil, gefitinib, gemcitabine, hydroxyurea, ibrutinib, icotinib, idarubicin, ifosfamide, imatinib, imetelstat, ipatasertib, irinotecan, ixabepilone, lapatinib, lenalidomide, lestaurtinib, lomustine, lucitanib, masitinib, mechlorethamine, melphalan, mercaptopurine, methotrexate, midostaurin, mitomycin, mitoxantrone, mubritinib, nelarabine, neratinib, nilotinib, nintedanib, omacetaxine mepesuccinate, orantinib, oxaliplatin, paclitaxel, palbociclib, palifosfamide tris, pazopanib, pelitinib, pemetrexed, pentostatin, plicamycin, ponatinib, poziotinib, pralatrexate, procarbazine, quizartinib, raltitrexed, regorafenib, ruxolitinib, seliciclib, sorafenib, streptozocin, sulfatinib, sunitinib, tamoxifen, tandutinib, temozolomide, temsirolimus, teniposide, theliatinib, thioguanine, thiotepa, topotecan, uramustine, valrubicin, vandetanib, vemurafenib (Zelborae), vincristine, vinblastine, vinorelbine, and vindesine.

In certain embodiments, the cancer for treatment with the compound is identified as being refractory or resistant to one or more chemotherapeutics agents selected from cyclophosphamide, chlorambucil, melphalan, mechlorethamine, ifosfamide, busulfan, lomustine, streptozocin, temozolomide, dacarbazine, cisplatin, carboplatin, oxaliplatin, procarbazine, uramustine, methotrexate, pemetrexed, fludarabine, cytarabine, fluorouracil, floxuridine, gemcitabine, capecitabine, vinblastine, vincristine, vinorelbine, etoposide, paclitaxel, docetaxel, doxorubicin, daunorubicin, epirubicin, idarubicin, mitoxantrone, bleomycin, mitomycin, hydroxyurea, topotecan, irinotecan, amsacrine, teniposide, and erlotinib.

In certain embodiments, the cancer for treatment with the compounds is a cancer resistant to ionizing radiation therapy. The radioresistance of the cancer can be inherent or as a result of radiation therapy. In certain embodiments, the cancers for treatment with the compounds is, among others, a radioresistant adrenocortical cancer, anal cancer, biliary cancer, bladder cancer, bone cancer (e.g., osteosarcoma), brain cancer (e.g., gliomas, astrocytoma, neuroblastoma, etc.), breast cancer, cervical cancer, colon cancer, endometrial cancer, esophageal cancer, head and neck cancer, hematologic cancer (e.g., leukemia and lymphoma), intestinal cancer (small intestine), liver cancer, lung cancer (e.g., bronchial cancer, small cell lung cancer, non-small cell lung cancer, etc.), oral cancer, ovarian cancer, pancreatic cancer, renal cancer, prostate cancer, salivary gland cancer, skin cancer (e.g., basal cell carcinoma, melanoma), stomach cancer, testicular cancer, throat cancer, thyroid cancer, uterine cancer, or vaginal cancer. In certain embodiments, the cancer is pancreatic cancer, breast cancer, glioblastoma, advanced non-small-cell lung cancer, bladder cancer, sarcoma, or soft tissue carcinoma.

5. Combination Treatments

In certain embodiments, the compounds described herein are used in combination with one or more of other (e.g., second therapeutic agent) therapeutic treatments for cancer.

In certain embodiments, a subject with cancer is treated with a combination of a compound described herein and radiation therapy. In certain embodiments, the method comprises administering to a subject with cancer a therapeutically effective amount of a compound of the disclosure, and adjunctively treating the subject with an effective amount of radiation therapy. In certain embodiments, the compound is administered to the subject in need thereof prior to, concurrently with, or subsequent to the treatment with radiation.

In certain embodiments, the method comprises administering an effective amount of a compound described herein to a subject with cancer to sensitize the cancer to radiation treatment, and administering a therapeutically effective amount of radiation therapy to treat the cancer. In certain embodiments, an effective amount of X-ray and gamma ray is administered to the subject. In certain embodiments, an effective amount of particle radiation is administered to the subject, where the particle radiation is selected from electron beam, proton beam, and neutron beam radiation. In certain embodiments, the radiation therapy is fractionated.

In certain embodiments, a subject with cancer is administered a therapeutically effective amount of a compound described herein, or a first pharmaceutical composition thereof, and adjunctively administered a therapeutically effective amount of a second chemotherapeutic agent, or a second pharmaceutical composition thereof.

In certain embodiments, the second chemotherapeutic agent is selected from an platinating agent, alkylating agent, anti-cancer antibiotic agent, antimetabolic agent (e.g., folate antagonists, purine analogs, pyrimidine analogs, etc.), topoisomerase I inhibiting agent, topoisomerase II inhibiting agent antimicrotubule agent (e.g., taxanes, *vinca* alkaloids), hormonal agent (e.g., aromatase inhibitors), plant-derived agent and synthetic derivatives thereof, anti-angiogenic agent, differentiation inducing agent, cell growth arrest inducing agent, apoptosis inducing agent, cytotoxic agent, agent affecting cell bioenergetics, i.e., affecting cellular ATP levels and molecules/activities regulating these levels, anticancer biologic agent (e.g., monoclonal antibodies), kinase inhibitors and inhibitors of growth factors and their receptors.

In certain embodiments, the second chemotherapeutic agent is an angiogenesis inhibitor, such as but not limited to, an inhibitor of soluble VEGFR-1, NRP-1, angiopoietin 2, TSP-1, TSP-2, angiostatin and related molecules, endostatin, vasostatin, calreticulin, platelet factor-4, TIMP, CDAI, Meth-1, Meth-2, IFN-α, IFN-β, IFN-γ, CXCL10, IL-4, IL-12, IL-18, prothrombin (kringle domain-2), antithrombin III fragment, prolactin, VEGI, SPARC, osteopontin, maspin, canstatin (a fragment of COL4A2), or proliferin-related protein. In certain embodiments, the angiogenesis inhibitor is bevacizumab (Avastin), itraconazole, carboxyamidotriazole, TNP-470 (an analog of fumagillin), CM101, IFN-c, IL-12, platelet factor-4, suramin, SU5416, thrombospondin, a VEGFR antagonist, an angiostatic steroid plus heparin, cartilage-derived angiogenesis inhibitory factor (CDAI), a matrix metalloproteinase inhibitor, angiostatin, endostatin, 2-methoxyestradiol, tecogalan, tetrathiomolybdate, thalidomide, thrombospondin, prolactin, a cVB3 inhibitor, linomide, ramucirumab, tasquinimod, ranibizumab, sorafenib (Nexavar), sunitinib (Sutent), pazopanib (Votrient), or everolimus (Afinitor).

In certain embodiments, the second chemotherapeutic agent is a cyclin-dependent kinase (CDK) inhibitor (e.g., a CDK4/CDK6 inhibitor). Examples include, but are not limited to, palbociclib (Ibrance), Ribociclib (optionally further in combination with letrozole), abemaciclib (LY2835219; Verzenio), P1446A-05, and Trilaciclib (G1T28).

In certain embodiments, the second chemotherapeutic agent is a Bruton's tyrosine kinase (BTK) inhibitor, such as but not limited to, Ibrutinib (PCI-32765), acalabrutinib, ONO-4059 (GS-4059), spebrutinib (AVL-292, CC-292), BGB-3111, and HM71224.

In certain embodiments, the second chemotherapeutic agent is a BRAF inhibitor. Examples include, but are not limited to, BAY43-9006 (Sorafenib, Nexavar), PLX-4032 (Vemurafenib), GDC-0879, PLX-4720, dabrafenib and LGX818.

In certain embodiments, the second chemotherapeutic agent is a EGFR inhibitor. Examples include, but are not limited to, gefitinib, erlotinib, afatinib, brigatinib, icotinib, cetuximab, osimertinib, panitumumab, brigatinib, lapatinib, cimaVax-EGF, and veristrat.

In certain embodiments, the second chemotherapeutic agent is a human epidermal growth factor receptor 2 (HER2) inhibitor. Examples include, but are not limited to, trastuzumab, pertuzumab (optionally further in combination with trastuzumab), margetuximab, and NeuVax In certain embodiments, disclosed herein is a method of increasing a subject's responsiveness to an immunotherapeutic or immunogenic chemotherapeutic agent, the method comprising administering to the subject in need thereof an effective amount of a compound described herein and an effective amount of an immunotherapeutic agent and/or an immunogenic chemotherapeutic agent. In certain embodiments, the method further includes administering to the subject a lipoxygenase inhibitor. In certain embodiments, the subject has a tumor whose cellular microenvironment is stromal cell rich. In certain embodiments, the administration of compound described herein results in killing one or more stromal cells in the tumor cells' microenvironment. In certain embodiments, the administration of an effective amount of an immunotherapeutic agent and/or an immunogenic chemotherapeutic agent results in killing one or more tumor cells. Also provided herein is a combination comprising a compound described herein and an immunotherapeutic agent, lipoxygenase inhibitor, or immunogenic chemotherapeutic agent. In certain embodiments, the immunotherapeutic agent is selected from a CTLA4, PDL1 or PD1 inhibitor. In certain embodiments, the immunotherapeutic agent can be selected from CTLA4 inhibitor such as ipilimumab, a PD1 inhibitor such as pembrolizumab or nivolumab or a PDL1 inhibitor such as atezolizumab or durvalumab. In certain embodiments, the immunotherapeutic agent is pembrolizumab. In other embodiments, the immunogenic chemotherapeutic agent is a compound selected from anthracycline, doxorubicin, cyclophosphamide, paclitaxel, docetaxel, cisplatin, oxaliplatin or carboplatin. In certain embodiments, provided herein is a combination comprising a compound described herein and a lipoxygenase inhibitor. In certain embodiments, the lipoxygenase inhibitor is selected from PD147176 and/or ML351. In certain embodiments, the lipoxygenase inhibitor may be a 15-lipoxygenase inhibitor (see, e.g., Sadeghian et al., Expert Opinion on Therapeutic Patents, 2015, 26:1, 65-88).

In certain embodiments, the second chemotherapeutic agent is selected from an alkylating agent, including, but not limiting to, adozelesin, altretamine, bendamustine, bizelesin, busulfan, carboplatin, carboquone, carmofur, carmustine, chlorambucil, cisplatin, cyclophosphamide, dacarbazine, estramustine, etoglucid, fotemustine, hepsulfam, ifosfamide, improsulfan, irofulven, lomustine, mannosulfan, mechlorethamine, melphalan, mitobronitol, nedaplatin, nimustine, oxaliplatin, piposulfan, prednimustine, procarbazine, ranimustine, satraplatin, semustine, streptozocin, temozolomide, thiotepa, treosulfan, triaziquone, triethylenemelamine, triplatin tetranitrate, trofosphamide, and uramustine; an antibiotic, including, but not limiting to, aclarubicin, amrubicin, bleomycin, dactinomycin, daunorubicin, doxorubicin, elsamitrucin, epirubicin, idarubicin, menogaril, mitomycin, neocarzinostatin, pentostatin, pirarubicin, plicamycin, valrubicin, and zorubicin; an antimetabolite, including, but not limiting to, aminopterin, azacitidine, azathioprine, capecitabine, cladribine, clofarabine, cytarabine, decitabine, floxuridine, fludarabine, 5-fluorouracil, gemcitabine, hydroxyurea, mercaptopurine, methotrexate, nelarabine, pemetrexed, raltitrexed, tegafur-uracil, thioguanine, trimethoprim, trimetrexate, and vidarabine; an immunotherapy, an antibody therapy, including, but not limiting to, alemtuzumab, bevacizumab, cetuximab, galiximab, gemtuzumab, panitumumab, pertuzumab, rituximab, brentuximab, tositumomab, trastuzumab, 90 Y ibritumomab tiuxetan, ipilimumab, tremelimumab and anti-CTLA-4 antibodies; a hormone or hormone antagonist, including, but not limiting to, anastrozole, androgens, buserelin, diethylstilbestrol, exemestane, flutamide, fulvestrant, goserelin, idoxifene, letrozole, leuprolide, magestrol, raloxifene, tamoxifen, and toremifene; a taxane, including, but not limiting to, DJ-927, docetaxel, TPI 287, larotaxel, ortataxel, paclitaxel, DHA-paclitaxel, and tesetaxel; a retinoid, including, but not limiting to, alitretinoin, bexarotene, fenretinide, isotretinoin, and tretinoin; an alkaloid, including, but not limiting to, demecolcine, homoharringtonine, vinblastine, vincristine, vindesine, vinflunine, and vinorelbine; an antiangiogenic agent, including, but not limiting to, AE-941 (GW786034, Neovastat), ABT-510, 2-methoxyestradiol, lenalidomide, and thalidomide; a topoisomerase inhibitor, including, but not limiting to, amsacrine, belotecan, edotecarin, etoposide, etoposide phosphate, exatecan, irinotecan (also active metabolite SN-38 (7-ethyl-10-hydroxy-camptothecin)), lucanthone, mitoxantrone, pixantrone, rubitecan, teniposide, topotecan, and 9-aminocamptothecin; a kinase inhibitor, including, but not liming to, axitinib (AG 013736), dasatinib (BMS 354825), erlotinib, gefitinib, flavopiridol, imatinib mesylate, lapatinib, motesanib diphosphate (AMG 706), nilotinib (AMN107), seliciclib, sorafenib, sunitinib malate, AEE-788, BMS-599626, UCN-01 (7-hydroxystaurosporine), vemurafenib, dabrafenib, selumetinib, paradox breakers (such as PLX8394 or PLX7904), LGX818, BGB-283, pexidartinib (PLX3397) and vatalanib; a targeted signal transduction inhibitor including, but not limiting to bortezomib, geldanamycin, and rapamycin; a biological response modifier, including, but not limiting to, imiquimod, interferon-α, and interleukin-2; and other chemotherapeutics, including, but not limiting to 3-AP (3-amino-2-carboxyaldehyde thiosemicarbazone), altrasentan, aminoglutethimide, anagrelide, asparaginase, bryostatin-1, cilengitide, elesclomol, eribulin mesylate (E7389), ixabepilone, lonidamine, masoprocol, mitoguanazone, oblimersen, sulindac, testolactone, tiazofurin, mTOR inhibitors (e.g. sirolimus, temsirolimus, everolimus, deforolimus, INK28, AZD8055, PI3K inhibitors (e.g. BEZ235, GDC-0941, XL147, XL765, BMK120), cyclin dependent kinase (CDK) inhibitors (e.g., a CDK4 inhibitor or a CDK6 inhibitor, such as Palbociclib (PD-0332991), Ribocyclib (LEE011), Abemaciclib (LY2835219), P1446A-05, Abemaciclib (LY2835219), Trilaciclib (G1T28), etc.), AKT inhibitors, Hsp90 inhibitors (e.g. geldanamycin, radicicol, tanespimycin), farnesyltransferase inhibitors (e.g. tipifarnib), Aromatase inhibitors (anastrozole letrozole exemestane); an MEK inhibitor including, but are not limited to, AS703026, AZD6244 (Selumetinib), AZD8330, BIX 02188, CI-1040 (PD184352), GSK1120212 (also known as trametinib or JTP-74057), cobimetinib, PD0325901, PD318088, PD98059, RDEA119(BAY 869766), TAK-733 and U0126-EtOH; tyrosine kinase inhibitors, including, but are not limited to, AEE788, AG-1478 (Tyrphostin AG-1478), AG-490, Apatinib (YN968D1), AV-412, AV-951(Tivozanib), Axitinib, AZD8931, BIBF1120 (Vargatef), BIBW2992 (Afatinib), BMS794833, BMS-599626, Brivanib (BMS-540215), Brivanib alaninate (BMS-582664), Cediranib (AZD2171), Chrysophanic acid (Chrysophanol), Crenolanib (CP-868569), CUDC-101, CYC116, Dovitinib Dilactic acid (TK1258 Dilactic acid), E7080, Erlotinib Hydrochloride (Tarceva, CP-358774, OSI-774, NSC-718781), Foretinib (GSK1363089, XL880), Gefitinib (ZD-1839 or Iressa), Imatinib (Gleevec), Imatinib Mesylate, Ki8751, KRN 633, Lapatinib (Tykerb), Linifanib (ABT-869), Masitinib (Masivet, AB1010), MGCD-265, Motesanib (AMG-706), MP-470, Mubritinib (TAK 165), Neratinib (HKI-272), NVP-BHG712, OSI-420 (Desmethyl Erlotinib, CP-473420), OSI-930, Pazopanib HCl, PD-153035 HCl, PD173074, Pelitinib (EKB-569), PF299804, Ponatinib (AP24534), PP121, RAF265 (CHIR-265), Raf265 derivative, Regorafenib (BAY 73-4506), Sorafenib Tosylate (Nexavar), Sunitinib Malate (Sutent), Telatinib (BAY 57-9352), TSU-68 (SU6668), Vandetanib (Zactima), Vatalanib dihydrochloride (PTK787), WZ3146, WZ4002, WZ8040, quizartinib, Cabozantinib, XL647, EGFR siRNA, FLT4 siRNA, KDR siRNA, Antidiabetic agents such as metformin, PPAR agonists (rosiglitazone, pioglitazone, bezafibrate, ciprofibrate, clofibrate, gemfibrozil, fenofibrate, indeglitazar), DPP4 inhibitors (sitagliptin, vildagliptin, saxagliptin, dutogliptin, gemigliptin, alogliptin) or an EGFR inhibitor, including, but not limited to, AEE-788, AP-26113, BIBW-2992 (Tovok), CI-1033, GW-572016, Iressa, LY2874455, RO-5323441, Tarceva (Erlotinib, OSI-774), CUDC-101 and WZ4002.

In certain embodiments, the second chemotherapeutic agent is selected from afatinib, afuresertib, alectinib, alisertib, alvocidib, amsacrine, amonafide, amuvatinib, axitinib, azacitidine, azathioprine, bafetinib, barasertib, bendamustine, bleomycin, bosutinib, bortezomib, busulfan, cabozantinib, camptothecin, canertinib, capecitabine, cabazitaxel, carboplatin, carmustine, cenisertib, ceritinib, chlorambucil, cisplatin, cladribine, clofarabine, crenolanib, crizotinib, cyclophosphamide, cytarabine, dabrafenib, dacarbazine, dacomitinib, dactinomycin, danusertib, dasatinib, daunorubicin, decitabine, dinaciclib, docetaxel, dovitinib, doxorubicin, epirubicin, epitinib, eribulin mesylate, errlotinib, etirinotecan, etoposide, everolimus, exemestane, floxuridine, fludarabine, fluorouracil, gefitinib, gemcitabine, hydroxyurea, ibrutinib, icotinib, idarubicin, idelalisib, ifosfamide, imatinib, imetelstat, ipatasertib, irinotecan, ixabepilone, lapatinib, lenalidomide, lestaurtinib, lomustine, lucitanib, masitinib, mechlorethamine, melphalan, mercaptopurine, methotrexate, midostaurin, mitomycin, mitoxantrone, mubritinib, nelarabine, neratinib, nilotinib, nintedanib, omacetaxine mepesuccinate, olaparib, orantinib, oxaliplatin, paclitaxel, palbociclib, palifosfamide tris, pazopanib, pelitinib, pemetrexed, pentostatin, plicamycin, ponatinib, poziotinib, pralatrexate, procarbazine, quizartinib, raltitrexed, regorafenib, ruxolitinib, seliciclib, sorafenib, streptozocin, sulfatinib, sunitinib, tamoxifen, tandutinib, temozolomide, temsirolimus, teniposide, theliatinib, thioguanine, thiotepa, topotecan, uramustine, valrubicin, vandetanib, vemurafenib (Zelboraf), vincristine, vinblastine, vinorelbine, vindesine, and the like. In certain embodiments, the compounds herein are administered prior to, concurrently with, or subsequent to the treatment with the chemotherapeutic agent.

In certain embodiments, the method of treating a cancer comprises administering a therapeutically effective amount of a compound described herein and a therapeutically effective amount a biologic agent used to treat cancer. In certain embodiments, the biologic agent is selected from anti-BAFF (e.g., belimumab); anti-CCR4 (e.g., mogamulizumab); anti-CD19/CD3 (e.g., blinatumomab); anti-CD20 (e.g., obinutuzumab, rituximab, ibritumomab tiuxetan, ofatumumab, tositumomab); anti-CD22 (e.g., moxetumomab pasudotox); anti-CD30 (e.g., brentuximab vedotin); anti-CD33 (e.g., gemtuzumab); anti-CD37 (e.g., otlertuzumab); anti-CD38 (e.g., daratumumab); anti-CD52 (e.g., alemtuzumab); anti-CD56 (e.g., lorvotuzumab mertansine); anti-CD74 (e.g., milatuzumab); anti-CD105; anti-CD248 (TEM1) (e.g., ontuxizumab); anti-CTLA4 (e.g., tremelimumab, ipilimumab); anti-EGFL7 (e.g., parsatuzumab); anti-EGFR (HER1/ERBB1) (e.g., panitumumab, nimotuzumab, necitumumab, cetuximab, imgatuzumab, futuximab); anti-FZD7 (e.g., vantictumab); anti-HER2 (ERBB2/neu) (e.g., margetuximab, pertuzumab, ado-trastuzumab emtansine, trastuzumab); anti-HER3 (ERBB3); anti-HGF (e.g., rilotumumab, ficlatuzumab); anti-IGF-1R (e.g., ganitumab, figitumumab, cixutumumab, dalotuzumab); anti-IGF-2R; anti-KIR (e.g., lirilumab, onartuzumab); anti-MMP9; anti-PD-1 (e.g., nivolumab, pidilizumab, lambrolizumab); anti-PD-L1 (e.g. Atezolizumab); anti-PDGFRa (e.g., ramucirumab, tovetumab); anti-PD-L2; anti-PIGF (e.g., ziv-aflibercept); anti-RANKL (e.g., denosumab); anti-TNFRSF 9 (CD 137/4-1 BB) (e.g., urelumab); anti-TRAIL-RI/DR4,R2/D5 (e.g., dulanermin); anti-TRAIL-R1/D4 (e.g., mapatumumab); anti-TRAIL-R2/D5 (e.g., conatumumab, lexatumumab, apomab); anti-VEGFA (e.g., bevacizumab, ziv-aflibercept); anti-VEGFB (e.g., ziv-aflibercept); and anti-VEGFR2 (e.g., ramucirumab).

For the methods herein, mutations in K-RAS, N-RAS, and H-RAS can be identified using various techniques available to the skilled artisan. In various embodiments, the presence or absence of a mutation can be determined by known DNA or RNA detection methods, for example, DNA sequencing, oligonucleotide hybridization, polymerase chain reaction (PCR) amplification with primers specific to the mutation, or protein detection methods, for example, immunoassays or biochemical assays to identify a mutated protein, such as mutated K-RAS, N-RAS and H-RAS. In certain embodiments, the nucleic acid or RNA in a sample can be detected by any suitable methods or techniques of detecting gene sequences. Such methods include, but are not limited to, PCR, reverse transcriptase-PCR (RT-PCR), in situ PCR, in situ hybridization, Southern blot, Northern blot, sequence analysis, microarray analysis, or other DNA/RNA hybridization platforms (see, e.g., Taso et al., 2010, Lung Cancer 68(1):51-7). In certain embodiments, detection of mutations can use samples obtained non-invasively, such as cell free nucleic acid (e.g., cfDNA) from blood.

In certain embodiments, mutations can be detected using various Next-Gen sequencing (NGS) techniques, particularly high-throughput NGS techniques. Exemplary NGS techniques include, among others, Polony sequencing (see, e.g., Shendure et al., 2005, Science 309(5741):1728-32), lonTorrent sequencing (see, e.g., Rusk, N., 2011, Nat Meth 8(1):44-44), pyrosequencing (see, e.g., Marguiles et al., 2005, Nature 437(7057):376-380), reversible dye sequencing with colony sequencing (Bentley et al., 2008, Nature 456(7218):53-59; Illumina, CA, USA), sequencing by ligation (e.g., SOLid systems of Applied Biosystems; Valouev et al., 2008, Genome Res. 18(7):1051-1063), high throughput rolling circle "nanoball" sequencing (see, e.g., Drmanac et al., 2010, Science 327 (5961):78-81; Porreca, G. J., 2010, Nature Biotech. 28 (1):43-44), and zero-mode wave guide based sequencing (see, e.g., Chin et al., 2013, Nat Methods 10(6):563-569); all publications incorporated herein by reference. In certain embodiments, massively parallel sequencing of target genes, such as genes encoding K-RAS, N-RAS, H-RAS.

In certain embodiments, detection of point mutations in target nucleic acids can be accomplished by molecular cloning of the target nucleic acid molecules and sequencing the nucleic acid molecules using available techniques. Alternatively, amplification techniques such as PCR can be used to amplify target nucleic acid sequences directly from a genomic DNA preparation from a tumor tissue, cell sample, or cell free sample (e.g., cell free plasma from blood). The nucleic acid sequence of the amplified molecules can then be determined to identify mutations. Design and selection of appropriate primers are within the abilities of one of ordinary skill in the art. Other methods of detecting mutations that can be used include, among others, ligase chain reaction, allele-specific PCR restriction fragment length polymorphism, single stranded conformation polymorphism analysis, mismatch detection proteins (e.g., GRIN2A or TRRAP), RNase protection (e.g., Winter et al., 1985, Proc. Natl. Acad. Sci. USA 82:7575-7579), enzymatic or chemical cleavage (Cotton et al., 1988, Proc. Natl. Acad. Sci. USA 85: 4397; Shenk et al., 1975, Proc. Natl. Acad. Sci. USA 72:989).

In certain embodiments, mutations in nucleic acid molecules can also be detected by screening for alterations of the corresponding protein. For example, monoclonal antibodies immunoreactive with a target gene product can be used to screen a tissue, for example an antibody that is known to bind to a particular mutated position of the gene product (protein). For example, a suitable antibody may be one that binds to a deleted exon or that binds to a conformational epitope comprising a deleted portion of the target protein. Lack of cognate antigen would indicate a mutation. Such immunological assays can be accomplished using any convenient format known in the art, such as Western blot, immunohistochemical assay and ELISA. For example, antibody-based detection of K-ras mutations is described in Elisabah et al., 2013, J Egypt Natl Cancer Inst. 25(1):51-6).

The expression of mRNA or proteins, such as expression of RAS, can use standard techniques available to the skilled artisan, including some of the methods described above. For example, the mRNA encoding a protein of interest can be detected by hybridization with nucleic acid probes, reverse transcription, polymerase chain reaction, and combinations thereof (e.g., RT-qPCR). In certain embodiments, chip-based or bead-based microarrays containing nucleic acid probes hybridizing to the target sequence can be used. In certain embodiments, mRNA expression can be detected directly in the target cells, such as by in-situ hybridization.

In certain embodiments, the protein products can be detected directly. Direct detection can use a binding agent that binds specifically to the protein, such as antibodies or target-interacting proteins or small molecule reagents that bind specifically with the protein target of interest (see, e.g., Current Protocols in Immunology, Coligan et al., eds., John Wiley & Sons (updates to 2015); Immunoassays: A Practical Approach, Gosling, ed., Oxford University Press (2000)). In certain embodiments, the protein product can be detected by immunological methods, including, by way of example, enzyme immunoassays, enzyme-linked immunoassays, fluorescence polarization immunoassay, and chemiluminescence assay.

Biological sample for the method herein include any samples are amenable to analysis herein, such as tissue or biopsy samples containing cancer cells, or any biological fluids that contain the material of interests (e.g., DNA), such as blood, plasma, saliva, tissue swabs, and intestinal fluids. In certain embodiments, exosomes extruded by cancer cells and obtained from blood or other body fluids can be used to detect nucleic acids and proteins produced by the cancer cells.

General biological, biochemical, immunological and molecular biological methods applicable to the present disclosure are described in Sambrook et al., Molecular Cloning: A Laboratory Manual $2^{nd}$ Ed. (1989) Cold Spring Harbor Laboratory Press, Cold Spring Harbor, N.Y.; Current Protocols in Molecular Biology, Ausubel et al., ed., John Wiley & Sons (2015); Current Protocols in Immunology, Coligan, J E ed., John Wiley & Sons (2015); and Methods in Enzymology, Vol. 200, Abelson et al., ed., Academic Press (1991). All publications are incorporated herein by reference.

6. Formulations and Administration

In certain embodiments, the pharmaceutical compositions of the therapeutic agents can be formulated by standard techniques using one or more physiologically acceptable carriers or excipients. Suitable pharmaceutical carriers are described herein and in Remington: The Science and Practice of Pharmacy, $21^{st}$ Ed. (2005). The therapeutic compounds and their physiologically acceptable salts, hydrates and solvates can be formulated for administration by any suitable route, including, among others, topically, nasally, orally, parenterally, rectally or by inhalation. In certain embodiments, the administration of the pharmaceutical composition may be made by intradermal, subdermal, intravenous, intramuscular, intranasal, intracerebral, intratracheal, intraarterial, intraperitoneal, intravesical, intrapleural, intracoronary or intratumoral injection, with a syringe or other devices. Transdermal administration is also contemplated, as are inhalation or aerosol administration. Tablets, capsules, and solutions can be administered orally, rectally or vaginally.

For oral administration, a pharmaceutical composition can take the form of, for example, a tablet or a capsule prepared by conventional means with a pharmaceutically acceptable excipient. Tablets and capsules comprising the active ingredient can be prepared together with excipients such as: (a) diluents or fillers, e.g., lactose, dextrose, sucrose, mannitol, sorbitol, cellulose (e.g., ethyl cellulose, microcrystalline cellulose), glycine, pectin, polyacrylates and/or calcium hydrogen phosphate, calcium sulfate; (b) lubricants, e.g., silica, talcum, stearic acid, its magnesium or calcium salt, metallic stearates, colloidal silicon dioxide, hydrogenated vegetable oil, corn starch, sodium benzoate, sodium acetate and/or polyethyleneglycol; (c) binders, e.g., magnesium aluminum silicate, starch paste, gelatin, tragacanth, methylcellulose, sodium carboxymethylcellulose, polyvinylpyrrolidone and/or hydroxypropyl methylcellulose; (d) disintegrants, e.g., starches (including potato starch or sodium starch), glycolate, agar, alginic acid or its sodium salt, or effervescent mixtures; (e) wetting agents, e.g., sodium lauryl sulphate, and/or (f) absorbents, colorants, flavors and sweeteners. The compositions are prepared according to conventional mixing, granulating or coating methods.

In certain embodiments, the carrier is a cyclodextrin, such as to enhance solubility and/or bioavailability of the compounds herein. In certain embodiments, the cyclodextrin for use in the pharmaceutical compositions can be selected from α-cyclodextrin, β-cyclodextrin, γ-cyclodextrin, derivatives thereof, and combinations thereof. In certain embodiments, the cyclodextrin is selected from β-cyclodextrin, γ-cyclodextrin, derivatives thereof, and combinations thereof.

In certain embodiments, the compounds can be formulated with a cyclodextrin or derivative thereof selected from carboxyalkyl cyclodextrin, hydroxyalkyl cyclodextrin, sulfoalkylether cyclodextrin, and an alkyl cyclodextrin. In various embodiments, the alkyl group in the cyclodextrin is methyl, ethyl, propyl, butyl, or pentyl.

In certain embodiments, the cyclodextrin is α-cyclodextrin or a derivative thereof. In certain embodiments, the α-cyclodextrin or derivative thereof is selected from carboxyalkyl-α-cyclodextrin, hydroxyalkyl-α-cyclodextrin, sulfoalkylether-α-cyclodextrin, alkyl-α-cyclodextrin, and combinations thereof. In certain embodiments, the alkyl group in the α-cyclodextrin derivative is methyl, ethyl, propyl, butyl, or pentyl.

In certain embodiments, the cyclodextrin is β-cyclodextrin or a derivative thereof. In certain embodiments, the β-cyclodextrin or derivative thereof is selected from carboxyalkyl-β-cyclodextrin, hydroxyalkyl-β-cyclodextrin, sulfoalkylether-β-cyclodextrin, alkyl-β-cyclodextrin, and combinations thereof. In certain embodiments, the alkyl group in the β-cyclodextrin derivative is methyl, ethyl, propyl, butyl, or pentyl.

In certain embodiments, the β-cyclodextrin or a derivative thereof is hydroxyalkyl-β-cyclodextrin or sulfoalkylether-β-cyclodextrin. In certain embodiments, the hydroxyalkyl-β-cyclodextrin is hydroxypropyl-β-cyclodextrin. In certain embodiments, the sulfoalkylether-β-cyclodextrin is sulfobutylether-β-cyclodextrin. In certain embodiments, β-cyclodextrin or a derivative thereof is alkyl-β-cyclodextrin, or methyl-β-cyclodextrin. In certain embodiments using methyl-β-cyclodextrin, the β-cyclodextrin is randomly methylated β-cyclodextrin.

In certain embodiments, the cyclodextrin is γ-cyclodextrin or a derivative thereof. In certain embodiments, the γ-cyclodextrin or derivative thereof is selected from carboxyalkyl-γ-cyclodextrin, hydroxyalkyl-γ-cyclodextrin, sulfoalkylether-γ-cyclodextrin, and alkyl-γ-cyclodextrin. In certain embodiments, the alkyl group in the γ-cyclodextrin derivative is methyl, ethyl, propyl, butyl, or pentyl. In certain embodiments, the γ-cyclodextrin or derivative thereof is hydroxyalkyl-γ-cyclodextrin or sulfoalkylether-γ-cyclodextrin. In certain embodiments, the hydroxyalkyl-γ-cyclodextrin is hydroxypropyl-γ-cyclodextrin.

When used in a formulation with the compound of the present disclosure, the cyclodextrin can be present at about 0.1 w/v to about 30% w/v, about 0.1 w/v to about 20% w/v, about 0.5% w/v to about 10% w/v, or about 1% w/v to about 5% w/v. In certain embodiments, the cyclodextrin is present at about 0.1% w/v, about 0.2% w/v, about 0.5% w/v, about 1% w/v, about 2% w/v, about 3% w/v, about 4% w/v, about 5% w/v, about 6% w/v, about 7% w/v, about 8% w/v, about 9% w/v, about 10% w/v, about 12% w/v, about 14% w/v, about 16% w/v, about 18% w/v, about 20% w/v, about 25% w/v, or about 30% w/v or more.

Tablets may be either film coated or enteric coated according to methods known in the art. Liquid preparations for oral administration can take the form of, for example, solutions, syrups, or suspensions, or they can be presented as a dry product for reconstitution with water or other suitable vehicle before use. Such liquid preparations can be prepared by conventional means with pharmaceutically acceptable carriers and additives, for example, suspending agents, e.g., sorbitol syrup, cellulose derivatives, or hydrogenated edible fats; emulsifying agents, for example, lecithin or acacia; non-aqueous vehicles, for example, almond oil, oily esters, ethyl alcohol, or fractionated vegetable oils; and preservatives, for example, methyl or propyl-p-hydroxybenzoates or sorbic acid. The preparations can also contain buffer salts, flavoring, coloring, and/or sweetening agents as appropriate. If desired, preparations for oral administration can be suitably formulated to give controlled release of the active compound.

The therapeutic agents can be formulated for parenteral administration, for example by bolus injection or continuous infusion. Formulations for injection can be presented in unit dosage form, for example, in ampoules or in multi-dose containers, with an optionally added preservative. Injectable compositions can be aqueous isotonic solutions or suspensions. In certain embodiments for parenteral administration, the therapeutic agents can be prepared with a surfactant, such as Cremaphor, or lipophilic solvents, such as triglycerides or liposomes. The compositions may be sterilized and/or contain adjuvants, such as preserving, stabilizing, wetting or emulsifying agents, solution promoters, salts for regulating the osmotic pressure and/or buffers. Alternatively, the therapeutic agent can be in powder form for reconstitution with a suitable vehicle, for example, sterile pyrogen-free water, before use. In addition, they may also contain other therapeutically effective substances.

For administration by inhalation, the therapeutic agent may be conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compound and a suitable powder base, for example, lactose or starch.

Suitable formulations for transdermal application include an effective amount of a therapeutic agent with a carrier. Preferred carriers include absorbable pharmacologically acceptable solvents to assist passage through the skin of the subject. For example, transdermal devices are in the form of a bandage or patch comprising a backing member, a reservoir containing the therapeutic agent optionally with carriers, optionally a rate controlling barrier to deliver the compound to the skin of the host at a controlled and predetermined rate over a prolonged period of time, and a means to secure the device to the skin. Matrix transdermal formulations may also be used.

Suitable formulations for topical application, e.g., to the skin and eyes, are preferably aqueous solutions, ointments, creams or gels well-known in the art. The formulations may contain solubilizers, stabilizers, tonicity enhancing agents, buffers and preservatives.

In certain embodiments, the therapeutic agent can also be formulated as a rectal composition, for example, suppositories or retention enemas, for example, containing conventional suppository bases, for example, cocoa butter or other glycerides, or gel forming agents, such as carbomers.

In certain embodiments, the therapeutic agent can be formulated as a depot preparation. Such long-acting formulations can be administered by implantation (for example, subcutaneously or intramuscularly) or by intramuscular injection. The therapeutic agent can be formulated with suitable polymeric or hydrophobic materials (for example as an emulsion in an acceptable oil), ion exchange resins, biodegradable polymers, or as sparingly soluble derivatives, for example, as a sparingly soluble salt.

The pharmaceutical compositions can, if desired, be presented in a pack or dispenser device that can contain one or more unit dosage forms containing the active ingredient. The pack can, for example, comprise metal or plastic foil, for example, a blister pack. The pack or dispenser device can be accompanied by instructions for administration.

7. Effective Amount and Dosing

In certain embodiments, a pharmaceutical composition of the therapeutic agent is administered to a subject, preferably a human, at a therapeutically effective dose to prevent, treat, or control a condition or disease as described herein. The pharmaceutical composition is administered to a subject in an amount sufficient to elicit an effective therapeutic response in the subject. An effective therapeutic response is a response that at least partially arrests or slows the symptoms or complications of the condition or disease. An amount adequate to accomplish this is defined as "therapeutically effective dose" or "therapeutically effective amount." The dosage of therapeutic agents can take into consideration, among others, the species of warm-blooded animal (mammal), the body weight, age, condition being treated, the severity of the condition being treated, the form of administration, route of administration. The size of the dose also will be determined by the existence, nature, and extent of any adverse effects that accompany the administration of a particular therapeutic compound in a particular subject.

In certain embodiments, a suitable dosage of the compounds of the disclosure or a composition thereof is from about 1 ng/kg to about 1000 mg/kg, from 0.01 mg/kg to 900 mg/kg, 0.1 mg/kg to 800 mg/kg, from about 1 mg/kg to about 700 mg/kg, from about 2 mg/kg to about 500 mg/kg, from about 3 mg/kg to about 400 mg/kg, 4 mg/kg to about 300 mg/kg, or from about 5 mg/kg to about 200 mg/kg. In certain embodiments, the suitable dosages of the compound can be about 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 125 mg/kg, 150 mg/kg, 175 mg/kg, 200 mg/kg, 250 mg/kg, 300 mg/kg, 400 mg/kg, 500 mg/kg, 600 mg/kg, 700 mg/kg, 800 mg/kg, 900 mg/kg, or 1000 mg/kg. In certain embodiments, the dose of the compound can be administered once per day or divided into subdoses and administered in multiple doses, e.g., twice, three times, or four times per day.

In certain embodiments, the compounds can be administered with one or more of a second therapeutic agent, sequentially or concurrently, either by the same route or by different routes of administration. When administered sequentially, the time between administrations is selected to benefit, among others, the therapeutic efficacy and/or safety of the combination treatment. In certain embodiments, the compounds herein can be administered first followed by a second therapeutic agent, or alternatively, the second therapeutic agent administered first followed by the compounds of the present disclosure. By way of example and not limitation, the time between administrations is about 1 hr, about 2 hr, about 4 hr, about 6 hr, about 12 hr, about 16 hr or about 20 hr. In certain embodiments, the time between administrations is about 1, about 2, about 3, about 4, about 5, about 6, or about 7 more days. In certain embodiments, the time between administrations is about 1 week, 2 weeks, 3 weeks, or 4 weeks or more. In certain embodiments, the time between administrations is about 1 month or 2 months or more.

When administered concurrently, the compound can be administered separately at the same time as the second therapeutic agent, by the same or different routes, or administered in a single composition by the same route. In certain embodiments, the amount and frequency of administration of the second therapeutic agent can used standard dosages and standard administration frequencies used for the particular therapeutic agent. See, e.g., Physicians' Desk Reference, 70th Ed., PDR Network, 2015; incorporated herein by reference.

In certain embodiments where the compounds of the present disclosure is administered in combination with a second therapeutic agent, the dose of the second therapeutic agent is administered at a therapeutically effective dose. In certain embodiments, a suitable dose can be from about 1 ng/kg to about 1000 mg/kg, from about 0.01 mg/kg to about 900 mg/kg, from about 0.1 mg/kg to about 800 mg/kg, from about 1 mg/kg to about 700 mg/kg, from about 2 mg/kg to about 500 mg/kg, from about 3 mg/kg to about 400 mg/kg, from about 4 mg/kg to about 300 mg/kg, or from about 5 mg/kg to about 200 mg/kg. In certain embodiments, the suitable dosages of the second therapeutic agent can be about 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 125 mg/kg, 150 mg/kg, 175 mg/kg, 200 mg/kg, 250 mg/kg, 300 mg/kg, 400 mg/kg, 500 mg/kg, 600 mg/kg, 700 mg/kg, 800 mg/kg, 900 mg/kg, or 1000 mg/kg. In certain embodiments, guidance for dosages of the second therapeutic agent is provided in Physicians' Desk Reference, $70^{th}$ Ed, PDR Network (2015), incorporated herein by reference.

It to be understood that optimum dosages, toxicity, and therapeutic efficacy of such therapeutic agents may vary depending on the relative potency of individual therapeutic agent and can be determined by standard pharmaceutical procedures in cell cultures or experimental animals, for example, by determining the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio, $LD_{50}/ED_{50}$. Therapeutic agents or combinations thereof that exhibit large therapeutic indices are preferred. While certain agents that exhibit toxic side effects can be used, care should be used to design a delivery system that targets such agents to the site of affected tissue to minimize potential damage to normal cells and, thereby, reduce side effects.

The data obtained from, for example, cell culture assays and animal studies can be used to formulate a dosage range for use in humans. The dosage of such small molecule compounds lies preferably within a range of circulating concentrations that include the $ED_{50}$ with little or no toxicity. The dosage can vary within this range depending upon the dosage form employed and the route of administration. For any compounds used in the methods disclosed herein, the therapeutically effective dose can be estimated initially from cell culture assays. A dose can be formulated in animal models to achieve a circulating plasma concentration range that includes the $IC_{50}$ (the concentration of the test compound that achieves a half-maximal inhibition of symptoms) as determined in cell culture. Such information can be used to more accurately determine useful doses in humans. Levels in plasma can be measured, for example, by high performance liquid chromatography (HPLC).

The following examples are provided to further illustrate the methods of the present disclosure, and the compounds and compositions for use in the methods. The examples described are illustrative only and are not intended to limit the scope of the invention(s) in any way. The disclosures of all articles and references mentioned in this application, including patents, are incorporated herein by reference in their entirety.

Synthetic Examples

Scheme AA: Synthesis of Compound K601

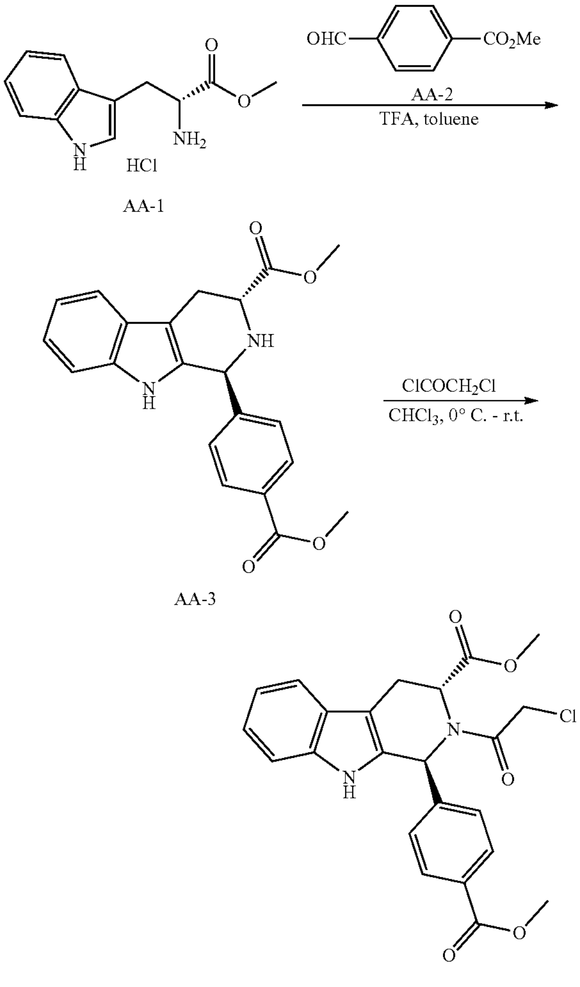

AA-1

AA-3

K601

A solution of AA-1 (8.50 g, 33.37 mmol, 1.00 eq, HCl) in toluene (100.00 mL) was mixed with TEA (4.05 g, 40.04 mmol, 5.55 mL, 1.20 eq) and stirred at 20° C. for 18 h. The completion of reaction was detected by TLC. The reaction mixture was filtered, and the filtrate concentrated under reduced pressure to give free form of AA-1.

To a solution of free state of AA-1 (5.52 g, 25.29 mmol, 1.00 eq) and AA-2 (4.57 g, 27.82 mmol, 1.10 eq) in toluene (80.00 mL) were added TFA (7.70 g, 67.52 mmol, 5.00 mL, 2.67 eq) and 4A molecular sieves (0.2 g). The reaction mixture was stirred at 120° C. for 4 h, while maintaining gentle reflux, to give a yellow mixture. The completion of reaction was detected by TLC. The mixture was diluted with $H_2O$ (100 mL) and 30% NaOH aq. added until solution reached pH 7 and then extracted with EtOAc (50 mL). The combined organic layers were dried over $Na_2SO_4$, and concentrated under reduced pressure to give AA-3. About half of the product (4.5 g) was directly used for the next step. The rest was purified, and then used for the next step.

To a solution of AA-3 (4.50 g, 12.35 mmol, 1.00 eq) and $NaHCO_3$ (1.25 g, 14.82 mmol, 576.40 μL, 1.20 eq) in $CHCl_3$ (50.00 mL) was added slowly 2-chloroacetyl chloride (3.35 g, 29.64 mmol, 2.36 mL, 2.40 eq) at 0° C. The mixture was stirred at 20° C. for 4 h to give a black mixture. The completion of reaction was detected by TLC. The reaction mixture was diluted with DCM (20 mL), washed with a saturated solution of $NaHCO_3$ and brine (10 mL each) in sequence. The organic layer was dried over $Na_2SO_4$, concentrated under reduced pressure. The product was purified by column chromatography ($SiO_2$, Petroleum ether/Ethyl acetate=10/1 to 4:1) to give K601. LC-MS (m/z): 441.1 $[M+H]^+$. $^1H$ NMR (400 MHz, DMSO, T=80° C.) δ 10.80 (s, 1H), 7.88-7.86 (m, 2H), 7.60-7.58 (m, 2H), 7.47 (d, J=7.5 Hz, 1H), 7.26 (d, J=8.0 Hz, 1H), 7.06-7.02 (m, 1H), 7.01-6.96 (m, 1H), 6.19 (s, 1H), 5.27 (s, 1H), 4.60 (d, J=13.8 Hz, 1H), 4.27-4.24 (m, 1H), 3.82 (s, 3H), 3.54 (s, 3H), 3.49-3.48 (m, 1H), 3.36-3.32 (m, 1H).

Scheme AB: Synthesis of Compound 1 and Compound 4

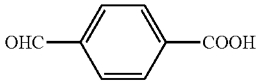

AB-2

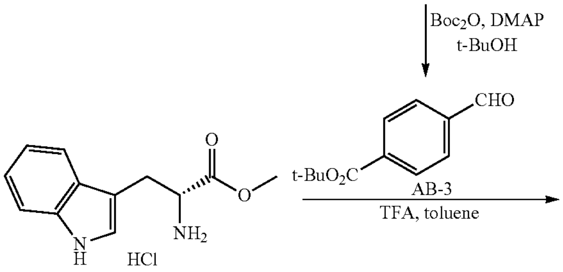

AA-1

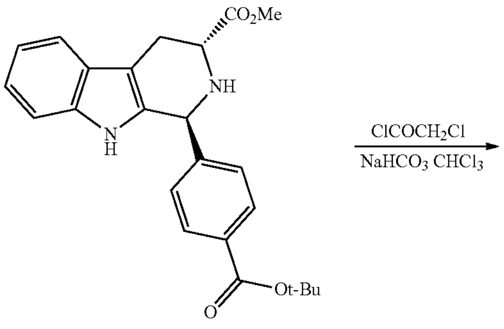

AB-4

-continued

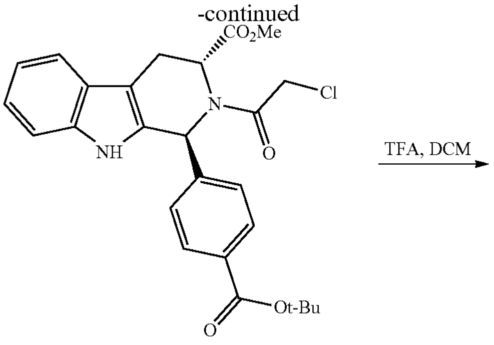

Compound 1

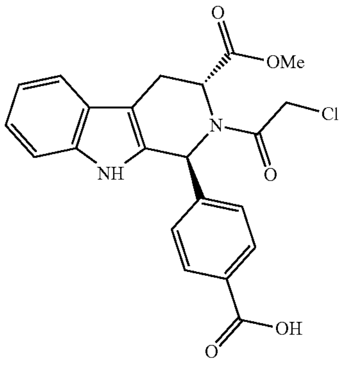

Compound 4

Preparation of Compound AB-3

A solution of AA-1 (5 g, 19.63 mmol, 1 eq, HCl) in toluene (50 mL) was added TEA (2.38 g, 23.56 mmol, 3.28 mL, 1.2 eq), and the mixture stirred at 20° C. for 1 h to give a yellow mixture. The completion of reaction was detected by TLC. The reaction mixture was filtered and the filtrate concentrated under reduced pressure to give a free state of AA-1.

To prepare AB-3, a solution of AB-2 (10 g, 66.61 mmol, 1 eq) in tert-butyl alcohol (200 mL) were added tert-butoxycarbonyl tert-butyl carbonate (15.26 g, 69.94 mmol, 16.07 mL, 1.05 eq) and DMAP (406.87 mg, 3.33 mmol, 0.05 eq). The mixture was stirred at 30° C. for 14 h to give a white mixture. TLC (PE/EtOAc=1/1, SiO2) showed the reaction was completed. The reaction solution was diluted with DCM (300 mL), washed with HCl (1 M 200 mL), then washed with sat. aqu. $NaHCO_3$ (200 mL). The organic layer was dried over anhydrous $Na_2SO_4$, filtered, and concentrated under reduced pressure to give the crude product. The residue was purified by column chromatography ($SiO_2$, Petroleum ether/Ethyl acetate=0/1 to 10:1) to give AB-3.

To a cooled solution (0° C.) of AA-1 (1 g, 4.58 mmol, 1 eq) in DCM (30 mL) were added AB-3 (1.13 g, 5.50 mmol, 1.2 eq) and TFA (783.64 mg, 6.87 mmol, 508.86 μL, 1.5 eq). The mixture was stirred at 20° C. for 24 h to give a yellow solution. Completion of reaction was analyzed by TLC. The reaction solution was diluted with $H_2O$ (8 mL), neutralized with sat. aqu. $NaHCO_3$, and extracted with DCM (10 mL×3). The combined organic layers were dried over anhydrous $Na_2SO_4$, filtered, and concentrated under reduced pressure. The residue was purified by column chromatography ($SiO_2$, Petroleum ether/Ethyl acetate=10/1 to 5:1) to give AB-4.

Preparation of Compound 1

A solution of 601-4A (35 mg, 86.11 μmol, 1 eq) and $NaHCO_3$ (8.68 mg, 103.33 μmol, 4.02 μL, 1.2 eq) in $CHCl_3$ (1 mL) was added 2-chloroacetyl chloride (23.34 mg, 206.66 μmol, 16.44 μL, 2.4 eq) at 0° C. The mixture was stirred at 20° C. for 14 h to give a green solution. LCMS showed the desired MS. The reaction solution was diluted with DCM (10 mL), washed with saturated aqueous $NaHCO_3$ (20 mL) and extracted with DCM (10 mL×3). The combined organic layers were dried over anhydrous $Na_2SO_4$, filtered, and concentrated under reduced pressure. The residue was purified by preparative TLC ($SiO_2$, PE:EA=2:1) to give Compound 1. LC-MS (m/z): 505.0 [M+Na]+. 1H NMR (400 MHz, $CDCl_3$) δ 8.10-7.70 (m, 3H), 7.53-7.51 (m, 1H), 7.38-7.26 (m, 2H), 7.20-7.14 (m, 1H), 7.12-7.10 (m, 2H), 6.23-6.10 (m, 1H), 5.26 (s, 1H), 4.11-3.28 (m, 7H), 1.61-1.55 (m, 9H).

Preparation of Compound 4

A solution of Compound 1 (40 mg, 82.82 μmol, 1 eq) in DCM (1 mL) was mixed with TFA (154.00 mg, 1.35 mmol, 0.1 mL, 16.31 eq). The mixture was stirred at 20° C. for 12 h to give a black solution. LCMS showed the desired MS. The reaction solution was concentrated under $N_2$. The residue was purified by preparative HPLC (column: Phenomenex Gemini 150×25 mm×10 μm; mobile phase: [water (0.05% HCl)-ACN]; B %: 38%-68%, 10 min) to give Compound 4. LC-MS (m/z): 426.9 [M+Na]+. $^1H$ NMR (400 MHz, DMSO) δ 10.93 (s, 1H), 7.82-7.80 (m, 2H), 7.53-7.46 (m, 3H), 7.23-7.21 (m, 1H), 7.04-6.96 (m, 2H), 6.02 (s, 1H), 5.39 (s, 1H), 4.74-4.71 (m, 1H), 4.44-4.40 (m, 1H), 3.59-3.51 (m, 5H).

Procedure AC: Synthesis of Compound 2 and Compound 3

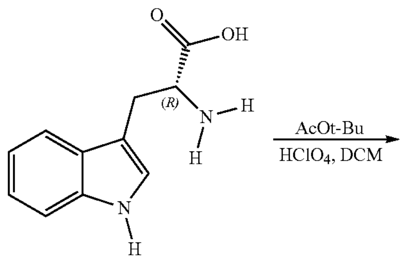

AC-1

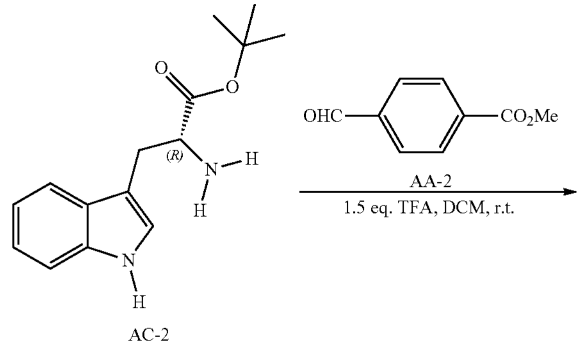

AC-2

-continued

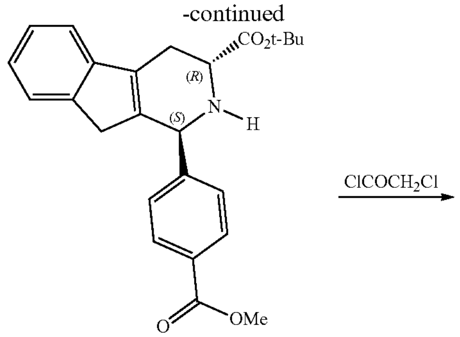

AC-4

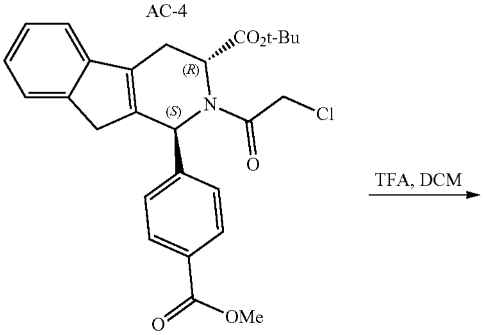

Compound 2

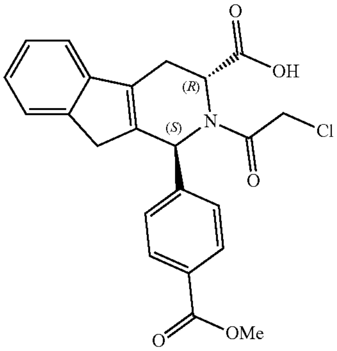

Compound 3

A solution of AC-1 was reacted with Ac-t-butyl in presence of HC1O4 in DCM until completion of reaction to form AC-2, as shown in the scheme above.

To a cooled solution (0° C.) of AC-2 (200 mg, 768.25 μmol, 1 eq) in DCM (1.5 mL) were added AA-2 (151.34 mg, 921.90 μmol, 1.2 eq) and TFA (131.40 mg, 1.15 mmol, 85.32 μL, 1.5 eq). The mixture was stirred at 20° C. for 16 h to give a red solution. The completion of reaction was detected by TLC and LCMS. The reaction solution was diluted with $H_2O$ (10 mL), neutralized with sat. aq. $NaHCO_3$ until pH 7, and extracted with DCM (10 mL×3). The combined organic layers were dried over anhydrous $Na_2SO_4$, filtered, and concentrated under reduced pressure. The residue was purified by preparative TLC ($SiO_2$, PE:EA=3:1) to give AC-4.

Preparation of Compound 2

To a solution of AC-4 (80 mg, 196.81 μmol, 1 eq) and $NaHCO_3$ (19.84 mg, 236.18 μmol, 9.19 μL, 1.2 eq) in $CHCl_3$ (1 mL) was added 2-chloroacetyl chloride (53.35 mg, 472.36 μmol, 37.57 μL, 2.4 eq) at 0° C. The mixture was stirred at 20° C. for 14 h to give a black solution.

The completion of reaction was detected by TLC. The reaction solution was diluted with DCM (10 mL), washed with sat. aqu. $NaHCO_3$ (10 mL), extracted with DCM (10 mL×3). The combined organic layers were dried over anhydrous $Na_2SO_4$, filtered, and concentrated under reduced pressure. The residue was purified by preparative TLC ($SiO_2$, PE:EA=2:1) to give Compound 2. LC-MS (m/z): 483.1[M+H]$^+$. $^1$H NMR (400 MHz, $CDCl_3$) δ 8.00-7.92 (m, 2H), 7.77 (s, 1H), 7.53-7.51 (m, 1H), 7.42 (s, 2H), 7.24-7.16 (m, 1H), 7.15-7.10 (m, 2H), 6.21-6.09 (m, 1H), 5.30-5.10 (m, 1H), 4.17-4.11 (m, 1H), 4.07-3.98 (m, 1H), 3.86 (s, 3H), 3.73-3.65 (m, 1H), 3.49-3.39 (m, 1H), 1.25-1.21 (m, 9H).

Preparation of Compound 3

To a solution of Compound 2 (35 mg, 72.47 μmol, 1 eq) in DCM (1 mL) was added TFA (154.00 mg, 1.35 mmol, 0.1 mL, 18.64 eq). The reaction solution was stirred at 20° C. for 14 h to give a black solution. The completion of reaction was detected by LCMS. The reaction solution was diluted with DCM (10 mL), and then concentrated under reduced pressure. The residue was purified by preparative HPLC (column: Phenomenex Gemini 150×25 mm×10 μm; mobile phase: [water (0.1% TFA)-ACN]; B %: 40%-70%, 10 min) to give Compound 4. LC-MS (m/z): 426.9[M+H]$^+$. $^1$H NMR (400 MHz, DMSO) δ 10.95 (s, 1H), 7.85-7.82 (m, 2H), 7.57-7.54 (m, 2H), 7.48-7.46 (m, 1H), 7.24-7.21 (m, 1H), 7.04-6.94 (m, 3H), 6.02 (s, 1H), 5.29 (s, 1H), 4.74-7.71 (m, 1H), 4.36-4.32 (m, 1H), 3.80 (s, 4H), 3.59-3.55 (m, 1H).

Procedure AD: Synthesis of Compound 273

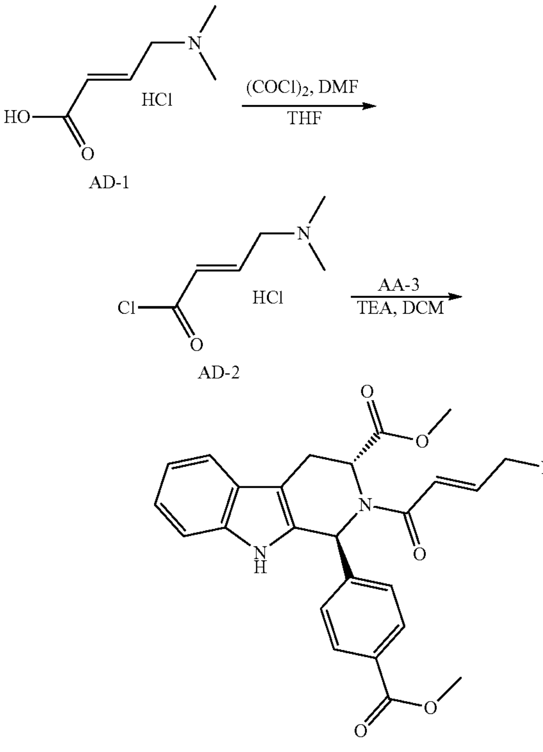

AD-1

AD-2

273

To a solution of AD-1 (200 mg, 1.21 mmol, 1 eq, HCl) in THF (8 mL) were added DMF (31.67 mg, 433.23 μmol, 33.33 μL, 3.59e-1 eq) and oxalyl dichloride (145.61 mg, 1.15 mmol, 100.42 μL, 0.95 eq) at 0° C. with ice-bath. The reaction solution was stirred at 20° C. for 2 h to give orange mixture. The reaction was completed as detected by TLC. The reaction solution was concentrated under reduced pressure to give AD-2. The product was used for the next step without further purification.

Preparation of Compound 273

To a solution of AA-3 (50 mg, 137.21 μmol, 1 eq) and TEA (83.31 mg, 823.28 μmol, 114.59 μL, 6 eq) in DCM (1 mL) was added AD-2 (101.02 mg, 548.85 μmol, 4 eq, HCl). The mixture was stirred at 20° C. for 12 h to give black solution. The reaction was completed as detected by LCMS. The reaction solution was diluted with $H_2O$ (30 mL), extracted with DCM (20 mL×3). The combined organic layers were dried over $Na_2SO_4$ and concentrated under reduced pressure. The product was purified by prep-HPLC (column: Phenomenex Gemini 150×25 mm×10 μm; mobile phase: [water (0.1% TFA)-ACN]; B %: 25%-55%, 10 min) to give compound 273. LC-MS (m/z): 476.1 [M+H]$^+$. $^1$H NMR (400 MHz, DMSO) δ 11.23-10.92 (m, 1H), 9.84 (m, 1H), 7.93-7.95 (m, 1H), 7.82-7.84 (m, 1H), 7.65-7.67 (m, 1H), 7.55-7.57 (m, 1H), 7.47-7.49 (m, 1H), 7.35-7.20 (m, 1H), 7.12-6.92 (m, 3H), 6.51-6.55 (m, 1H), 6.13 (s, 1H), 5.64 (s, 1H), 5.04 (s, 1H), 3.86 (s, 1H), 3.79-3.82 (m, 4H), 3.55 (s, 1H), 3.49 (s, 3H), 2.82-2.69 (m, 5H), 2.66-2.67 (m, 2H).

Procedure AE: Synthesis of Compound 6

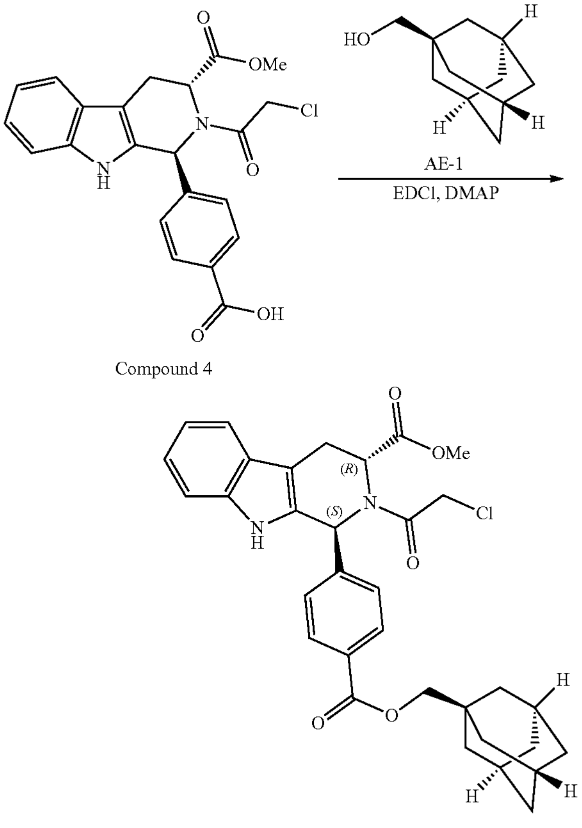

Compound 4

Compound 6

To a solution of Compound 4 (25 mg, 58.57 μmol, 1 eq; see Procedure AA) and AE-1 (9.74 mg, 58.57 μmol, 1 eq) in DCM (1 mL) were added EDCI (22.46 mg, 117.14 μmol, 2 eq) and DMAP (14.31 mg, 117.14 μmol, 2 eq). The mixture was stirred at 20° C. for 14 h to give a yellow solution. The completion of reaction was detected by LCMS. The reaction solution was diluted with $H_2O$ (10 mL) and extracted with DCM (10 mL×3). The combined organic layers were dried over anhydrous $Na_2SO_4$, filtered, and concentrated under reduced pressure. The residue was purified by preparative HPLC (column: Phenomenex Gemini 150×25 mm×10 μm; mobile phase: [water (0.05% HCl)-ACN]; B %: 80%-90%, 10 min) to give Compound 6. LC-MS (m/z): 575.1[M+H]$^+$. $^1$H NMR (400 MHz, DMSO) δ 11.22-11.04 (m, 1H), 7.96-7.83 (m, 2H), 7.69-7.56 (m, 2H), 7.48-7.46 (M, 1H), 7.32-7.21 (m, 1H), 7.04-6.94 (m, 2H), 6.03 (s, 1H), 5.41 (s, 1H), 4.75-4.71 (m, 1H), 4.44-4.41 (m, 1H), 3.83 (s, 3H), 1.94 (s, 3H), 1.75-1.60 (m, 6H), 1.55 (s, 5H), 1.46-1.39 (m, 1H), 1.23 (s, 3H).

Procedure AF: Synthesis of Compound 7

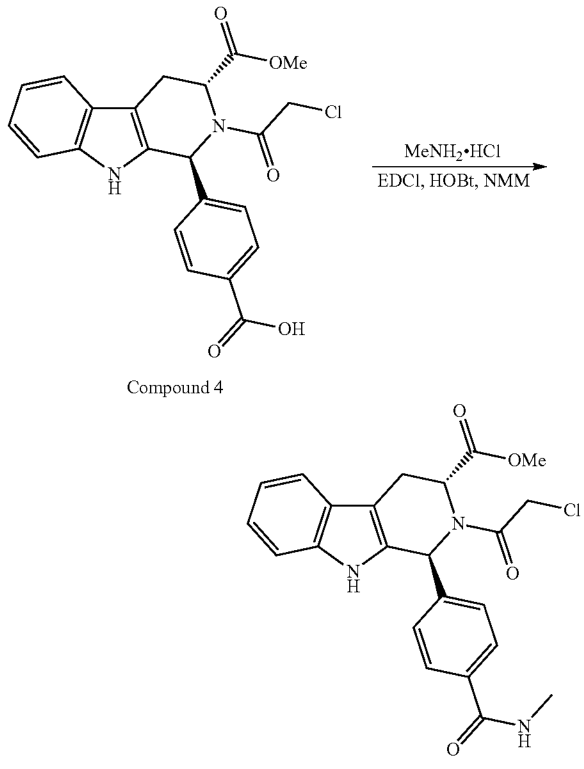

Compound 4

Compound 7

Preparation of Compound 7

To a solution Compound 4 (100 mg, 234.27 μmol, 1 eq; see Procedure AA), methanamine (31.64 mg, 468.55 μmol, 2 eq, HCl), EDCI (67.37 mg, 351.41 μmol, 1.5 eq) and HOBt (31.66 mg, 234.27 μmol, 1 eq) in DMF (1 mL) was added NMM (94.79 mg, 937.10 μmol, 103.03 μL, 4 eq) at 0° C. The mixture was stirred at 20° C. for 16 h to give a yellow solution. The completion of reaction was detected by LCMS. The reaction solution was diluted with EA (20 mL), washed with 1N HCl (15 mL), washed with sat. aqu. $NaHCO_3$ (20 mL) and then with brine (15 mL). The organic layer was dried over anhydrous $Na_2SO_4$, filtered, and concentrated under reduced pressure. The residue was purified by preparative HPLC (column: Phenomenex Gemini 150×25 mm×10 μm; mobile phase: [water (0.05% HCl)-ACN]; B %: 25%-55%, 7 min) to give Compound 7. LC-MS (m/z): 462.0[M+Na]$^+$. $^1$H NMR (400 MHz, DMSO-$d_6$) δ=11.12-10.94 (m, 1H), 8.43-8.31 (m, 1H), 7.82-7.67 (m, 2H), 7.60-7.41 (m, 3H), 7.34-7.21 (m, 1H), 7.04-6.94 (m, 2H), 6.01 (s, 1H), 5.39 (s, 1H), 4.97-4.71 (m, 1H), 4.44-4.09 (m, 1H), 3.58-3.38 (m, 5H), 2.83-2.70 (m, 3H).

Scheme AG: Synthesis of Compound 8

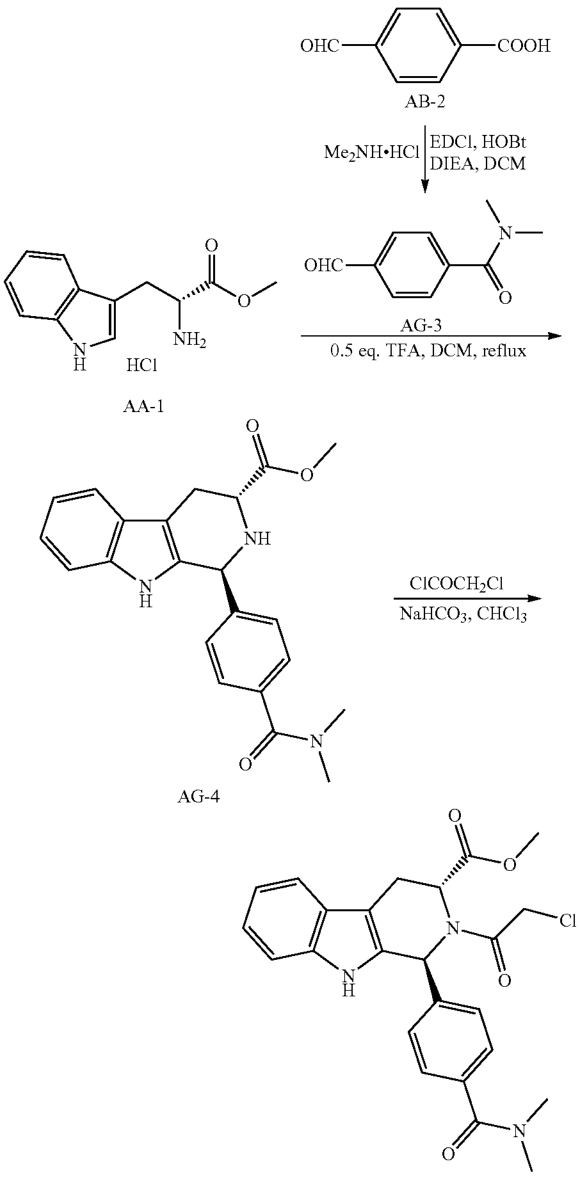

AB-2

AA-1

AG-3

AG-4

Compound 8

To a solution of AB-2 (1 g, 6.66 mmol, 1 eq), EDCI (1.53 g, 7.99 mmol, 1.2 eq), HOBt (900.03 mg, 6.66 mmol, 1 eq) and DIEA (3.44 g, 26.64 mmol, 4.64 mL, 4 eq) in DCM (15 mL) was added N-methylmethanamine (814.73 mg, 9.99 mmol, 915.43 μL, 1.5 eq, HCl) at 0° C. The mixture was stirred at 20° C. for 12 h to give a red solution. The completion of reaction was detected by TLC and LCMS. The reaction solution was diluted with DCM (40 mL), then washed with sat. aqu. $NaHCO_3$ (30 mL) and brine (30 mL).

The organic layer was dried over anhydrous $Na_2SO_4$, filtered, and concentrated under reduced pressure. The residue was purified by column chromatography ($SiO_2$, Petroleum ether/Ethyl acetate=10/1 to 1:1) to give AG-3.

To a solution of AA-1 (10 g, 39.26 mmol, 1 eq, HCl) in toluene (200 mL) was added TEA (4.77 g, 47.11 mmol, 6.56 mL, 1.2 eq), and the mixture stirred at 20° C. for 1 h to give a yellow mixture. The completion of reaction was detected by TLC. The reaction mixture was filtered and filtrate concentrated under reduced pressure to give a free form of AG-1.

To a solution of AG-1 (923.75 mg, 4.23 mmol, 1 eq) and AG-3 (900 mg, 5.08 mmol, 1.2 eq) in DCM (10 mL) was added TFA (482.60 mg, 4.23 mmol, 313.38 μL, 1 eq) at 0° C. The mixture was stirred at 40° C. for 12 h to give a yellow solution. LCMS showed AG-1 remained; the reaction solution was stirred at 40° C. for another 24 h. The completion of reaction was detected by LCMS. The reaction solution was diluted with DCM (30 mL), then washed with sat. aqu. $NaHCO_3$ (15 mL) and brine (15 mL). The organic layer was dried over anhydrous $Na_2SO_4$, filtered, and concentrated under reduced pressure. The residue was purified by column chromatography ($SiO_2$, Petroleum ether/Ethyl acetate=10/1 to 1:2) to give AG-4.

Preparation of Compound 8

To a solution of AG-4 (100 mg, 264.95 μmol, 1 eq) and $NaHCO_3$ (44.51 mg, 529.89 μmol, 20.61 μL, 2 eq) in CHCl3 (1 mL) was added 2-chloroacetyl chloride (59.85 mg, 529.89 μmol, 42.15 μL, 2 eq) at 0° C. The mixture was stirred at 20° C. for 3 h to give a yellow suspension. The completion of reaction was detected by LCMS. The reaction solution was diluted with DCM (15 mL), washed with sat. aqu. $NaHCO_3$ (20 mL) and brine, and then extracted with DCM (10 mL×2). The combined organic layers were dried over anhydrous $Na_2SO_4$, filtered, and concentrated under reduced pressure. The residue was purified by preparative HPLC (column: Phenomenex Gemini 150×25 mm×10 μm; mobile phase: [water (0.05% HCl)-ACN]; B %: 32%-62%, 10 min) to give Compound 8. LC-MS (m/z): 475.9 $[M+Na]^+$. $^1H$ NMR (400 MHz, $CDCl_3$) δ 8.82 (s, 1H), 7.53-7.50 (m, 1H), 7.48-7.32 (m, 2H), 7.26 (s, 3H), 7.11-7.07 (m, 2H), 6.22-5.97 (m, 1H), 5.20-5.07 (m, 1H), 4.13-3.72 (m, 2H), 3.65 (s, 3H), 3.46-3.24 (m, 1H), 3.24-2.73 (m, 6H).

Procedure AH: Synthesis of Compound 9

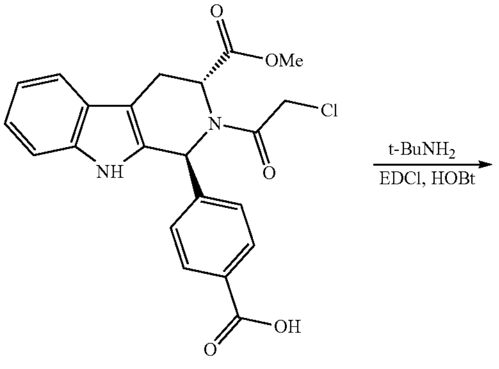

Compound 4

-continued

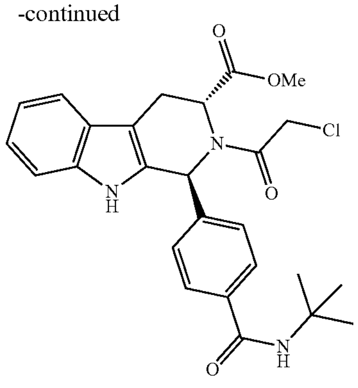

Compound 9

Preparation of Compound 9

To a solution of Compound 4 (100 mg, 234.27 μmol, 1 eq), EDCI (44.91 mg, 234.27 μmol, 1 eq) and HOBt (63.31 mg, 468.55 μmol, 2 eq) in DMF (1 mL) was added 2-methylpropan-2-amine-(34.27 mg, 468.55 μmol, 49.24 μL, 2 eq) at 0° C. The mixture was stirred at 20° C. for 12 h to give a red solution. The completion of reaction was detected by LCMS. The reaction solution was diluted with EA (10 mL), washed with 1N HCl (10 mL), then washed with sat. aqu. $NaHCO_3$ (15 mL) and brine. The organic layer was dried over anhydrous $Na_2SO_4$, filtered, and then concentrated under reduced pressure. The residue was purified by prep-HPLC (column: Phenomenex Gemini 150×25 mm×10 μm; mobile phase: [water (0.05% HCl)-ACN]; B %: 40%-70%, 10 min) to give Compound 9. LC-MS (m/z): 504.1[M+Na]+. $^1H$ NMR (400 MHz, MeOD) δ 7.73 (s, 1H), 7.61-7.59 (m, 2H), 7.47-7.44 (m, 2H), 7.26-7.17 (m, 1H), 7.06-6.99 (m, 2H), 6.08 (s, 1H), 5.40 (s, 1H), 4.54-4.44 (m, 1H), 4.24-4.02 (m, 1H), 3.74-3.48 (m, 5H), 1.43-1.41 (m, 9H).

Procedure AI: Synthesis of Compound 10

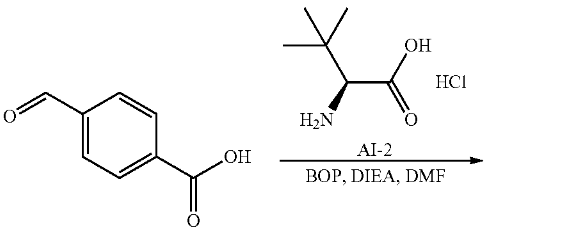

AI-1

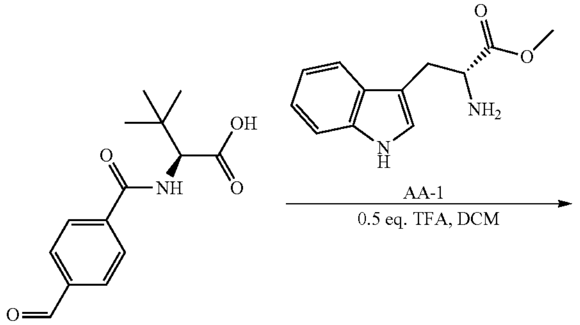

AI-3

-continued

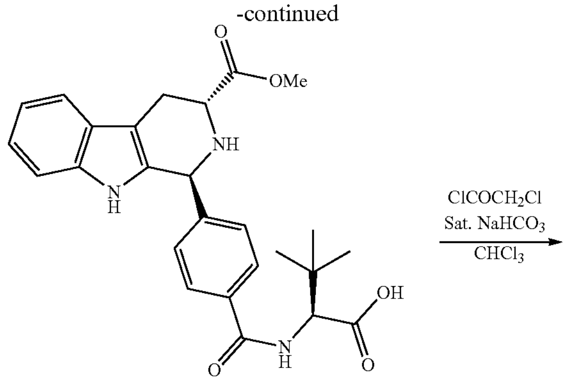

AI-5

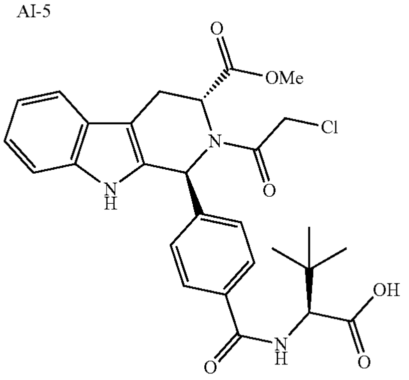

Compound 10

To a solution of AI-1 (500 mg, 3.33 mmol, 1 eq) in DMF (5 mL) were added AI-2 (546.01 mg, 3.26 mmol, 9.78e-1 eq, HCl), DIEA (1.29 g, 9.99 mmol, 1.74 mL, 3 eq) and BOP (1.77 g, 4.00 mmol, 1.2 eq). The mixture was stirred at 20° C. for 16 h to give a yellow solution. LCMS and TLC (eluting with: PE/EtOAc=1/1) showed the reaction was completed. The reaction mixture was quenched with $H_2O$ (20 mL) and extracted with MTBE (30 mL×3). The organic layers were dried over $Na_2SO_4$ and concentrated to give the crude product. The product was purified by a flash column (eluting with: PE/EtOAc=5% to 50%) to give AI-3.

To a solution of AA-1 (240 mg, 1.10 mmol, 1 eq) in DCM (5 mL) were added AI-3 (289.52 mg, 1.10 mmol, 1 eq) and TFA (62.69 mg, 549.82 μmol, 40.71 μL, 0.5 eq). The mixture was stirred at 50° C. for 12 h to give a yellow solution. LCMS and TLC (eluting with: 100% EtOAc) showed the reaction was completed. The reaction mixture was quenched with $H_2O$ (20 mL) and extracted with DCM (30 mL×3). The organic layers were dried over $Na_2SO_4$ and concentrated to give the crude product. The crude product was purified by a flash column (eluting with: 100% EtOAc) to give AI-5.

Preparation of Compound 10

To a solution of AI-5 (80 mg, 172.59 μmol, 1 eq) in THF (2 mL) were added Sat. $NaHCO_3$ (172.59 μmol, 1 mL, 1 eq) and 2-chloroacetyl chloride (58.48 mg, 517.77 μmol, 41.18 μL, 3 eq). The mixture was stirred at 20° C. for 12 h to give a yellow solution. LCMS showed no desired mass was found, and AI-5 remained. $CHCl_3$ (3 mL) and Sat. $NaHCO_3$ (2 mL) were added, then 0.03 mL 2-chloroacetyl chloride was added dropwise. The mixture was stirred at 20° C. for 12 h again. LCMS showed the reaction was completed. The reaction mixture was quenched with HCl (12N, 1 mL). The mixture was stirred at 20° C. for 0.5 h. LCMS showed the reaction was completed. The mixture was extracted with DCM (20 mL×3). The organic layers were dried over $Na_2SO_4$ and concentrated to give the crude product. The product was purified by preparative HPLC (column: Phenomenex Gemini 150×25 mm×10 μm; mobile phase: [water (0.1% TFA)-ACN]; B %: 43%-73%, 10 min) to give two products (peak 2 and peak 1, i.e., Compound 10). NOE showed peak 2 was the cis-isomer, and peak 1 was the trans-isomer. LC-MS (m/z): 540.0 [M+H]+. $^1$H NMR (400 MHz, MeOD): δ 7.84-7.47 (m, 5H), 7.22-7.01 (m, 3H), 7.51-7.35 (m, 2H), 6.39-6.11 (m, 1H), 5.42 (s, 1H), 4.56-4.47 (m, 2H), 4.27-4.07 (m, 1H), 3.76-3.33 (m, 5H), 1.09 (s, 9H).

Procedure AJ: Synthesis of Compound 11

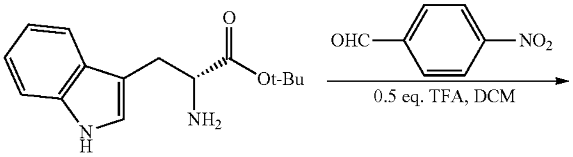

AJ-1

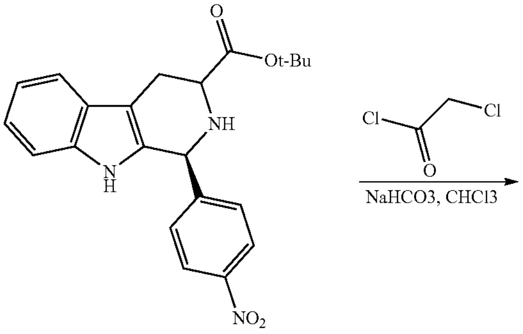

AJ-2

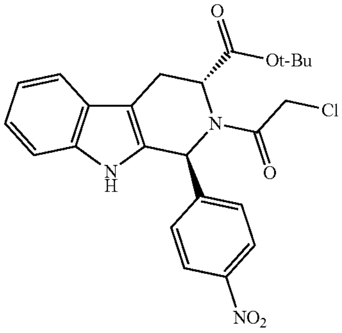

Compound 11

To a solution of AJ-1 (0.5 g, 1.92 mmol, 1 eq) and 4-nitrobenzaldehyde (348.18 mg, 2.30 mmol, 1.2 eq) in DCM (15 mL) was added dropwise TFA (109.49 mg, 960.00 μmol, 71.10 μL, 0.5 eq) at 0° C. The reaction solution was heated to 40° C. in a sealed tube for 16 h to give a brown solution. TLC (PE/EtOAc=2/1, $SiO_2$) showed that two new spots were formed. The reaction solution was washed with sat. aqueous $NaHCO_3$ solution (5 mL), dried over anhydrous $Na_2SO_4$, filtered, and concentrated under reduced pressure to give the crude product. The crude product was purified by combi flash (PE/EtOAc=10/1 to 2/1) to give AJ-2.

Preparation of Compound 11

To a mixture of AJ-2 (50 mg, 127.09 μmol, 1 eq) and $NaHCO_3$ (12.81 mg, 152.50 μmol, 5.93 μL, 1.2 eq) in $CHCl_3$ (0.5 mL) was added dropwise a solution of 2-chloroacetyl chloride (35.88 mg, 317.71 μmol, 25.27 μL, 2.5 eq) in $CHCl_3$ (0.5 mL) at 0° C. The mixture was stirred at 15° C. for 16 h to give a brown solution. LCMS showed the desired MS. The mixture was filtered and the filtrate was concentrated under reduced pressure. The residue was directly purified by preparative HPLC (column: Phenomenex Gemini 150×25 mm×10 μm; mobile phase: [water (0.1% TFA)-ACN]; B %: 55%-85%, 10 min) to give Compound 11. LC-MS (m/z): 470.1 $[M+H]^+$. $^1H$ NMR (400 MHz, $CDCl_3$) δ 8.13 (d, J=8.3 Hz, 2H), 7.73 (brs, 1H), 7.58-7.45 (m, 3H), 7.24-7.19 (m, 1H), 7.19-7.10 (m, 2H), 6.13 (s, 1H), 5.12 (dd, J=2.6, 4.9 Hz, 1H), 4.17 (d, J=12.8 Hz, 1H), 4.06 (d, J=12.8 Hz, 1H), 3.70 (d, J=15.8 Hz, 1H), 3.41 (dd, J=4.6, 15.2 Hz, 1H), 1.21 (s, 9H).

Procedure AK: Synthesis of Compound 12

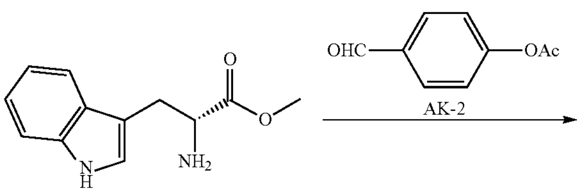

AA-1

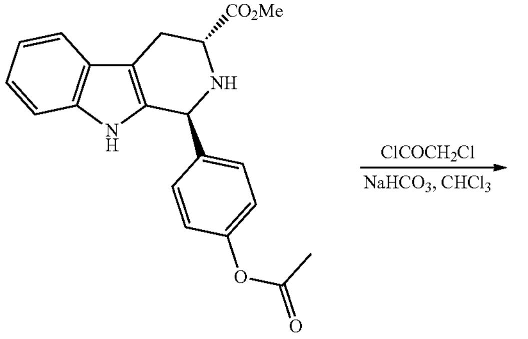

AK-3

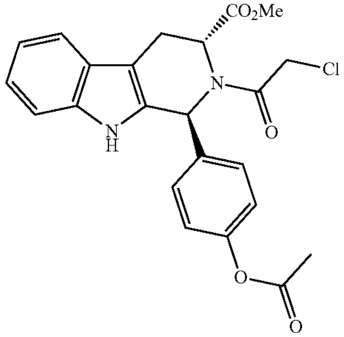

Compound 12

To a solution of AA-1 (500 mg, 2.29 mmol, 1 eq) and AK-2 (394.88 mg, 2.41 mmol, 1.05 eq) in DCM (7 mL) was added dropwise TFA (261.21 mg, 2.29 mmol, 169.62 μL, 1 eq) at 0° C. The reaction solution was heated to 40° C. in a sealed tube for 16 h to give a brown solution. TLC (PE/EtOAc=1/1, SiO2) showed that four new spots were formed. The reaction solution was washed with sat. aqueous $NaHCO_3$ solution (5 mL), dried over anhydrous $Na_2SO_4$, filtered, and concentrated under reduced pressure to give the crude product. The crude product was purified by combi flash (PE/EtOAc=10/1 to 1/1) to give AK-3.

Preparation of Compound 12

To a mixture of AK-3 (50 mg, 137.21 μmol, 1 eq) and $NaHCO_3$ (13.83 mg, 164.66 μmol, 6.40 μL, 1.2 eq) in $CHCl_3$ (0.5 mL) was added dropwise a solution of 2-chloroacetyl chloride (38.74 mg, 343.04 μmol, 27.28 μL, 2.5 eq) in $CHCl_3$ (0.5 mL) at 0° C. The mixture was stirred at 15° C. for 2 h to give a brown solution. LCMS showed the desired MS. The mixture was filtered and the filtrate concentrated under reduced pressure. The residue was directly purified by combi flash (PE/EtOAc=5/1 to 2/1) to give Compound 12. LC-MS (m/z): 441.0 [M+H]+. $^1H$ NMR (400 MHz, $CDCl_3$) δ 8.11-7.80 (m, 1H), 7.58-7.50 (m, 1H), 7.46-6.85 (m, 7H), 6.30-5.97 (m, 1H), 5.15 (brs, 1H), 4.17-4.07 (m, 1H), 4.07-3.84 (m, 1H), 3.77-3.09 (m, 5H), 2.27 (s, 3H).

Procedure AL: Synthesis of Compound 13 and 13a

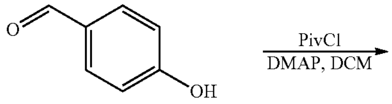

AL-1

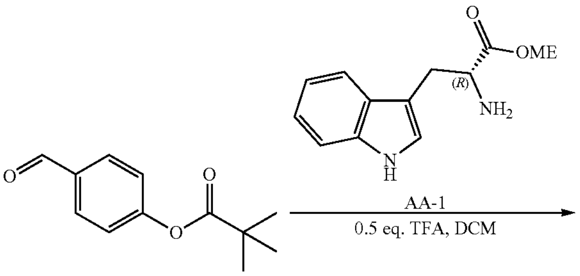

AL-2

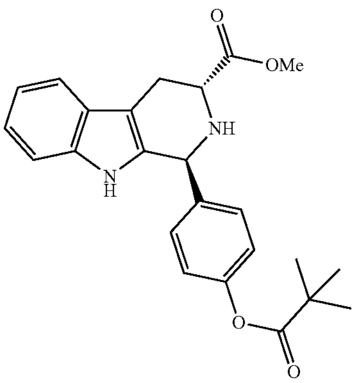

AL-3

-continued

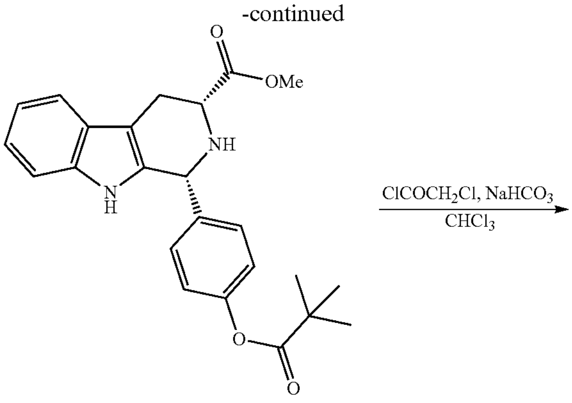

AL-3a

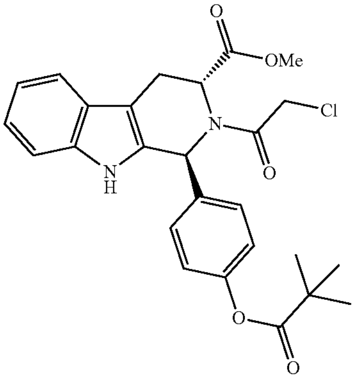

Compound 13

+

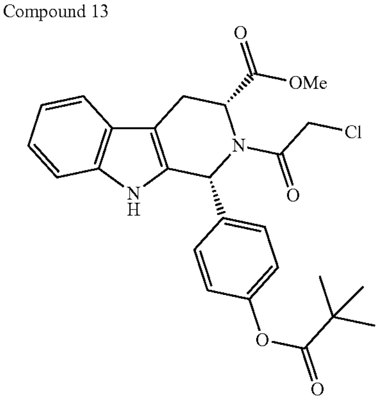

Compound 13a

To a solution of AL-1 (1.5 g, 12.28 mmol, 1 eq) in DCM (20 mL) were added DMAP (4.50 g, 36.85 mmol, 3 eq) and 2,2-dimethylpropanoyl chloride (2.22 g, 18.42 mmol, 2.27 mL, 1.5 eq). The mixture was stirred at 20° C. for 12 h to give a yellow suspension. LCMS and TLC (eluting with: PE/EtOAc=5/1) showed the reaction was completed. The reaction mixture was quenched with $H_2O$ (20 mL) and extracted with DCM (30 mL×3). The organic layers were dried over $Na_2SO_4$ and concentrated to give the crude product. The crude product was purified by flash column chromatography (eluting with: PE/EtOAc=100% PE to 20%) to give AL-2.

To a solution of AA-1 (500 mg, 2.29 mmol, 1 eq) in DCM (5 mL) were added AL-2 and TFA (770.00 mg, 6.75 mmol, 500.00 μL, 2.95 eq). The mixture was stirred at 20° C. for 24 h to give a yellow solution. LCMS and TLC showed the reaction was completed. The reaction mixture was quenched with Sat. $NaHCO_3$ (15 mL) and extracted with MBTE (20 mL×3). The organic layers were dried over $Na_2SO_4$ and concentrated to give the crude product. The crude product was purified by flash column chromatography (eluting with: PE/EtOAc=100% PE to 20%) to give AL-3a and AL-3.

Preparation of Compound 13

To a solution of AL-3 (30 mg, 73.81 μmol, 1 eq) in $CHCl_3$ (2 mL) was added $NaHCO_3$ (31.00 mg, 369.03 μmol, 14.35 μL, 5 eq), followed by 2-chloroacetyl chloride (10.00 mg, 88.57 μmol, 7.04 μL, 1.2 eq) added dropwise at 0° C. The mixture was stirred at 20° C. for 12 h to give a yellow solution. LCMS showed the reaction was completed. The reaction was quenched with $H_2O$ (10 mL) and extracted with DCM (20 mL×3). The organic layers were dried over $Na_2SO_4$ and concentrated to give the crude product. The crude product was purified by preparative HPLC (column: Phenomenex Gemini 150×25 mm×10 μm; mobile phase: [water (0.1% TFA)-ACN]; B %: 60%-90%, 8.8 min) to give Compound 13.

Preparation of Compound 13a

To a solution of AL-3a (30.00 mg, 73.81 μmol, 1 eq) in $CHCl_3$ (2 mL) was added $NaHCO_3$ (31.00 mg, 369.03 μmol, 14.35 μL, 5 eq), followed by 2-chloroacetyl chloride (10.00 mg, 88.57 μmol, 7.04 μL, 1.2 eq) added dropwise at 0° C. The mixture was stirred at 20° C. for 12 h to give a yellow solution. LCMS showed the reaction was completed. The reaction mixture was then quenched with $H_2O$ (20 mL). The mixture was extracted with DCM (20 mL×3). The organic layers were dried over $Na_2SO_4$ and concentrated to give the crude product. The crude product was purified by preparative HPLC (column: Phenomenex Gemini 150×25 mm×10 μm; mobile phase: [water (0.1% TFA)-ACN]; B %: 60%-90%, 8.8 min) to give Compound 13. 40.4 mg was prepared. LC-MS (m/z): 431.0$[M+H]^+$. $^1H$ NMR (400 MHz, $CD_3OD$) δ 8.01-7.99 (m, 1H), 7.91-7.89 (m, 1H), 7.54-7.53 (m, 1H), 7.48-7.42 (m, 1H), 7.19-7.02 (m, 1H), 6.99-3.97 (m, 2H), 6.58-6.08 (m, 1H), 5.76-5.03 (m, 1H), 3.86-3.83 (m, 3H), 3.68-3.45 (m, 5H), 2.14-2.03 (m, 3H).

Procedure AM: Synthesis of Compound 14

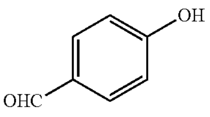

AM-1

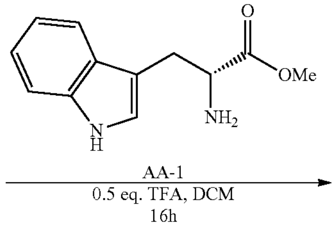

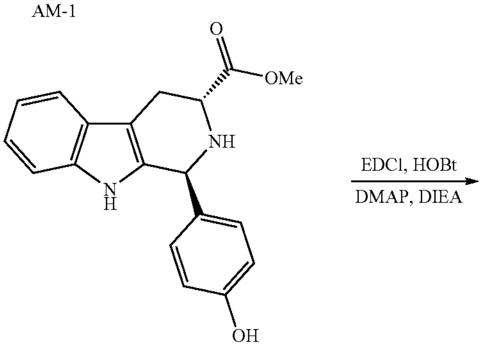

AM-3

-continued

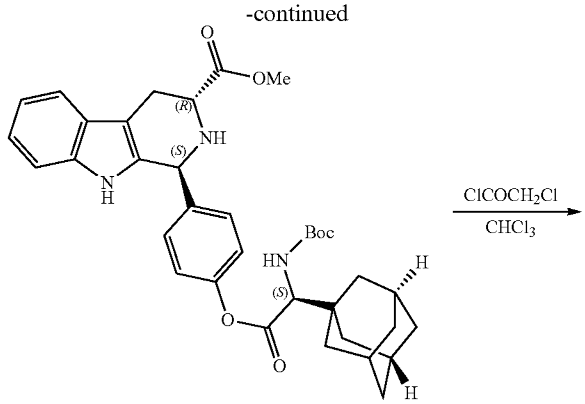

AM-4

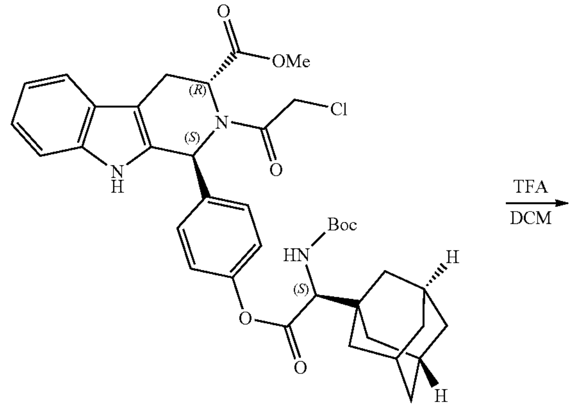

AM-5

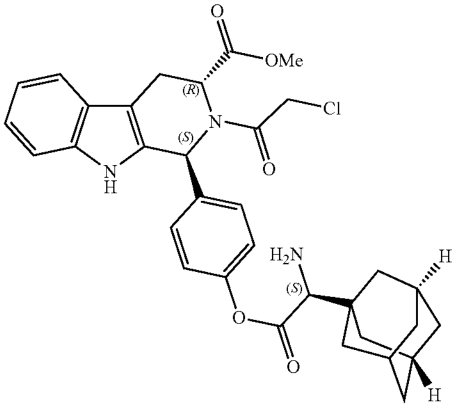

Compound 14

To a solution of AA-1 (800 mg, 3.67 mmol, 1 eq) in DCM (20 mL) were added AM-1 (447.64 mg, 3.67 mmol, 1 eq) and TFA (208.98 mg, 1.83 mmol, 135.70 μL, 0.5 eq). The mixture was stirred at 50° C. for 12 h to give a yellow solution. LCMS showed desired mass was found; however AA-1 and AM-1 remained. Thus, the mixture was stirred at 50° C. for an additional 16 h. LCMS and TLC (eluting with: PE/EtOAc=1/1) showed the reaction was completed. The reaction mixture was quenched with Sat. $NaHCO_3$ (20 mL) and extracted with DCM (30 mL×3). The organic layers were dried over $Na_2SO_4$ and concentrated to give the crude product. The crude product was purified by flash chromatography (eluting with: PE/EtOAc=100% PE to 30%) to give AM-3 and the cis-isomer.

To a solution of AM-3 (50 mg, 155.11 μmol, 1 eq) in DCM (3 mL) were added (2S)-2-(1-adamantyl)-2-(tert-butoxycarbonylamino)acetic acid (57.59 mg, 186.13 μmol, 1.2 eq), DMAP (1.89 mg, 15.51 μmol, 0.1 eq), DIEA (60.14 mg, 465.32 μmol, 81.05 μL, 3 eq), HOBt (23.05 mg, 170.62 μmol, 1.1 eq) and EDCI (35.68 mg, 186.13 μmol, 1.2 eq). The mixture was stirred at 20° C. for 12 h to give a yellow solution. LCMS and TLC (eluting with: PE/EtOAc=1/1) showed the reaction was completed. The mixture was quenched with $H_2O$ (10 mL) and extracted with DCM (20 mL×3). The organic layers were dried over $Na_2SO_4$ and concentrated to give the crude product. The crude product was purified by preparative TLC (eluting with: PE/EtOAc=1/1) to give AM-4.

To a solution of AM-4 (110 mg, 179.23 μmol, 1 eq) in CHCl3 (3 mL) were added $NaHCO_3$ (150.56 mg, 1.79 mmol, 69.71 μL, 10 eq) and 2-chloroacetyl chloride (60.73 mg, 537.68 μmol, 42.77 μL, 3 eq). The mixture was stirred at 20° C. for 2 h to give a yellow suspension. LCMS showed the reaction was completed. The reaction mixture was quenched with $H_2O$ (10 mL) and extracted with DCM (20 mL). The organic layers were dried over $Na_2SO_4$ and concentrated to give AM-5.

Preparation of Compound 14

To a solution of AM-5 (50 mg, 81.47 μmol, 1 eq) in DCM (3 mL) was added TFA (462.00 mg, 4.05 mmol, 0.3 mL, 49.74 eq). The mixture was stirred at 20° C. for 1 h to give a yellow solution. LCMS showed the reaction was completed. The reaction mixture was concentrated to give the crude product. The crude product was purified by preparative HPLC (column: Phenomenex Gemini 150×25 mm×10 μm; mobile phase: [water (0.1% TFA)-ACN]; B %: 33%-63%, 10 min) to give Compound 14. LC-MS (m/z): 612.1 [M+Na]+. $^1H$ NMR (400 MHz, MeOD): δ9.16 (s, 1H), 7.55-7.51 (m, 3H), 7.26-7.06 (m, 5H), 6.08-5.23 (m, 1H), 4.45-4.41 (m, 1H), 4.24-4.21 (m, 1H), 3.85 (brs, 1H), 3.66-3.47 (m, 5H), 2.07-1.83 (m, 4H), 1.80-1.68 (m, 12H).

Procedure AN: Synthesis of Compound 15

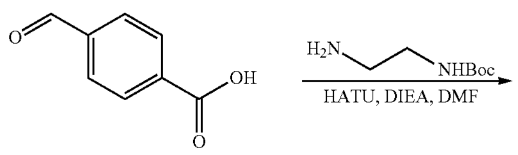

AN-1

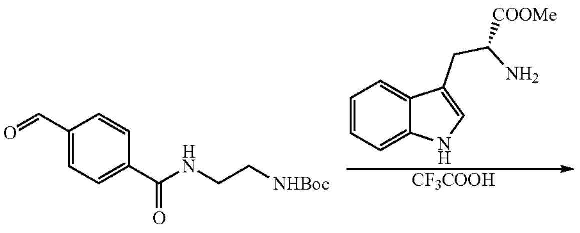

AN-2

-continued

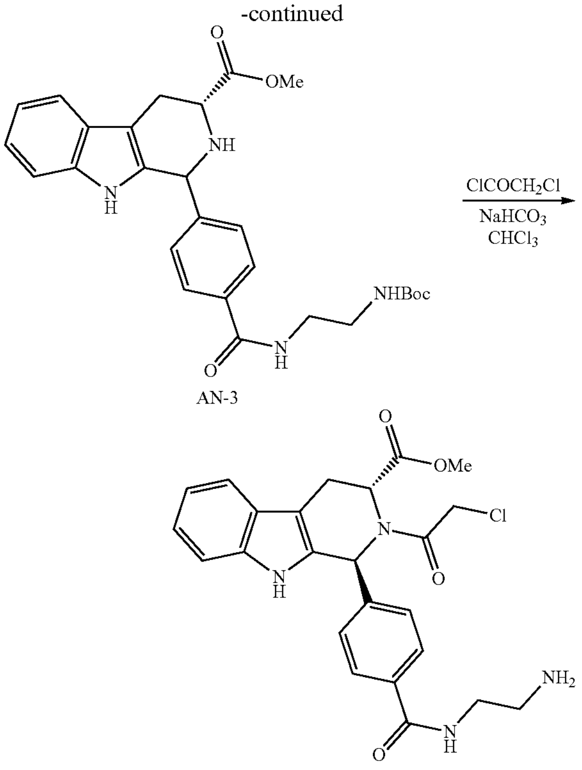

AN-3

Compound 15

To a solution of compound AN-1 (1 g, 6.66 mmol, 1 eq) in DMF (30 mL), DIEA (1.29 g, 9.99 mmol, 1.74 mL, 1.5 eq) was added with stirring at 20° C. for 30 min, then tert-butyl N-(2-aminoethyl) carbamate (1.81 g, 11.32 mmol, 1.78 mL, 1.7 eq) was added with stirring at 20° C. for 12 h to give a yellow solution. TLC (eluting with: PE/EtOAc=1/1) showed the reaction was completed. The reaction mixture was partitioned between water (30 mL) and EtOAc (40 mL), and the aqueous layers extracted with EtOAc (30 mL×2). The combined organic layers were washed with brine (30 mL), dried over sodium sulfate, and concentrated to give the crude product. The crude product was purified by silica gel chromatography (eluting with: PE/EtOAc=3/1-1/1) to give AN-2.

To a solution of compound AN-2 (2.2 g, 7.53 mmol, 1 eq) and methyl (2R)-2-amino-3-(1H-indol-3-yl)propanoate (1.81 g, 8.28 mmol, 1.1 eq) in DCM (25 mL) was added dropwise TFA (858.11 mg, 7.53 mmol, 557.21 μL, 1 eq). The reaction mixture was stirred at 20° C. for 24 h to give a yellow solution. TLC (eluting with: PE/EtOAc=5/1) showed the reaction was completed. The reaction mixture was partitioned between water (20 mL) and DCM (20 mL), and the aqueous layer extracted with DCM (20 mL). The combined organic layers were washed with saturated sodium bicarbonate solution (20 mL), dried over sodium sulfate and concentrated to give the crude product. The crude product was purified by a flash column (eluting with: EA:MeOH=10:1) to give AN-3.

Preparation of Compound 15

To a solution of compound AN-3 (1.00 g, 2.03 mmol, 1 eq) in $CHCl_3$ (15 mL) was added $NaHCO_3$ (341.10 mg, 4.06 mmol, 157.92 μL, 2 eq). Then 2-chloroacetyl chloride (343.94 mg, 3.05 mmol, 42.21 μL, 1.5 eq) was added dropwise at 0° C. The reaction mixture was stirred at 20° C. for 6 h to give a yellow suspension. LCMS and TLC (eluting with: EA/MeOH=20/1) showed the reaction was completed. The reaction mixture was quenched with Sat. $NaHCO_3$ (15 mL) and extracted with DCM (20 mL×3). The organic layers were dried over $Na_2SO_4$ and concentrated to give the crude product. The crude product was purified by preparative HPLC (column: Phenomenex Gemini 150×25 mm×10 μm; mobile phase: [water (0.05% HCl)-ACN]; B %: 18%-38%, 10 min) to give Compound 15. LC-MS (m/z): 469.0 $[M+H]^+$. $^1H$ NMR (400 MHz, DMSO-$d_6$) δ: 2.87-3.04 (m, 2H), 3.46-3.61 (m, 7H), 4.09 (d, J=12.80 Hz, 1H), 4.42 (d, J=13.80 Hz, 1H), 4.75 (d, J=13.80 Hz, 1H), 4.96 (s, 1H), 5.41 (s, 1H), 6.03 (s, 1H), 6.40 (s, 1H), 6.93-7.09 (m, 2H), 7.23 (d, J=8.03 Hz, 1H), 7.46-7.54 (m, 2H), 7.77 (d, J=7.78 Hz, 1H), 7.91 (s, 3H), 8.54-8.78 (m, 1H), 8.54-8.78 (m, 1H), 10.99 (s, 1H). 11.16 (s, 1H).

Procedure AO: Synthesis of Compound 19

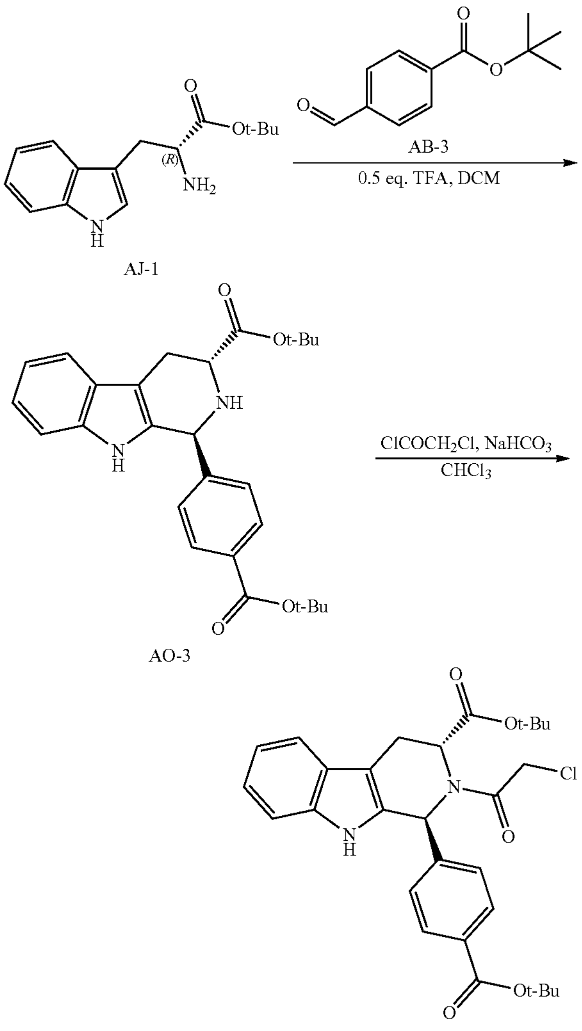

AB-3

AJ-1

AO-3

Compound 19

To a solution of AJ-1 (300 mg, 1.15 mmol, 1 eq) in THF (5 mL) were added AB-3 (237.66 mg, 1.15 mmol, 1 eq) and TFA (65.70 mg, 576.19 μmol, 42.66 μL, 0.5 eq). The mixture was stirred at 50° C. for 3 h to give a yellow solution. LCMS and TLC (eluting with: PE/EtOAc=2/1) showed the reaction was completed. The reaction mixture was quenched with Sat. $NaHCO_3$ (10 mL) and extracted with DCM (20 mL×3). The organic layers were dried over $Na_2SO_4$ and concentrated to give the crude product. The crude product was purified by a flash column (eluting with: PE/EtOAc=100% PE to 20%) to give AO-3 and tert-butyl (1R,3R)-1-(4-tert-butoxycarbonylphenyl)-2,3,4,9-tetrahydro-1H-pyrido[3,4-b]indole-3-carboxylate.

Preparation of Compound 19

To a solution of AO-3 (42 mg, 93.63 μmol, 1 eq) in $CHCl_3$ (3 mL) were added $NaHCO_3$ (7.87 mg, 93.63 μmol, 3.64 μL, 1 eq) and 2-chloroacetyl chloride (52.88 mg, 468.17 μmol, 37.24 μL, 5 eq). The mixture was stirred at 20° C. for 2 h to give a yellow suspension. LCMS showed that the reaction was completed. The reaction mixture was filtered, and the filtrate washed with DCM (10 mL) and concentrated to give the crude product. The product was purified by preparative HPLC (column: Phenomenex Gemini 150×25 mm×10 m; mobile phase: [water (0.1% TFA)-ACN]; B %: 70%-95%, 8.8 min) to give Compound 19. LC-MS (m/z): 525.0 $[M+H]^+$. $^1H$ NMR (400 MHz, MeOD): δ 7.99-7.85 (m, 2H), 7.64-7.48 (m, 3H), 7.25-7.23 (m, 1H), 7.07-7.01 (m, 2H), 6.01 (s, 1H), 5.27-5.18 (m, 2H), 4.50-4.24 (m, 1H), 3.98-3.49 (m, 5H), 1.65 (s, 9H), 1.26 (s, 9H).

Procedure AP: Synthesis of Compound 21 and Compound 21a

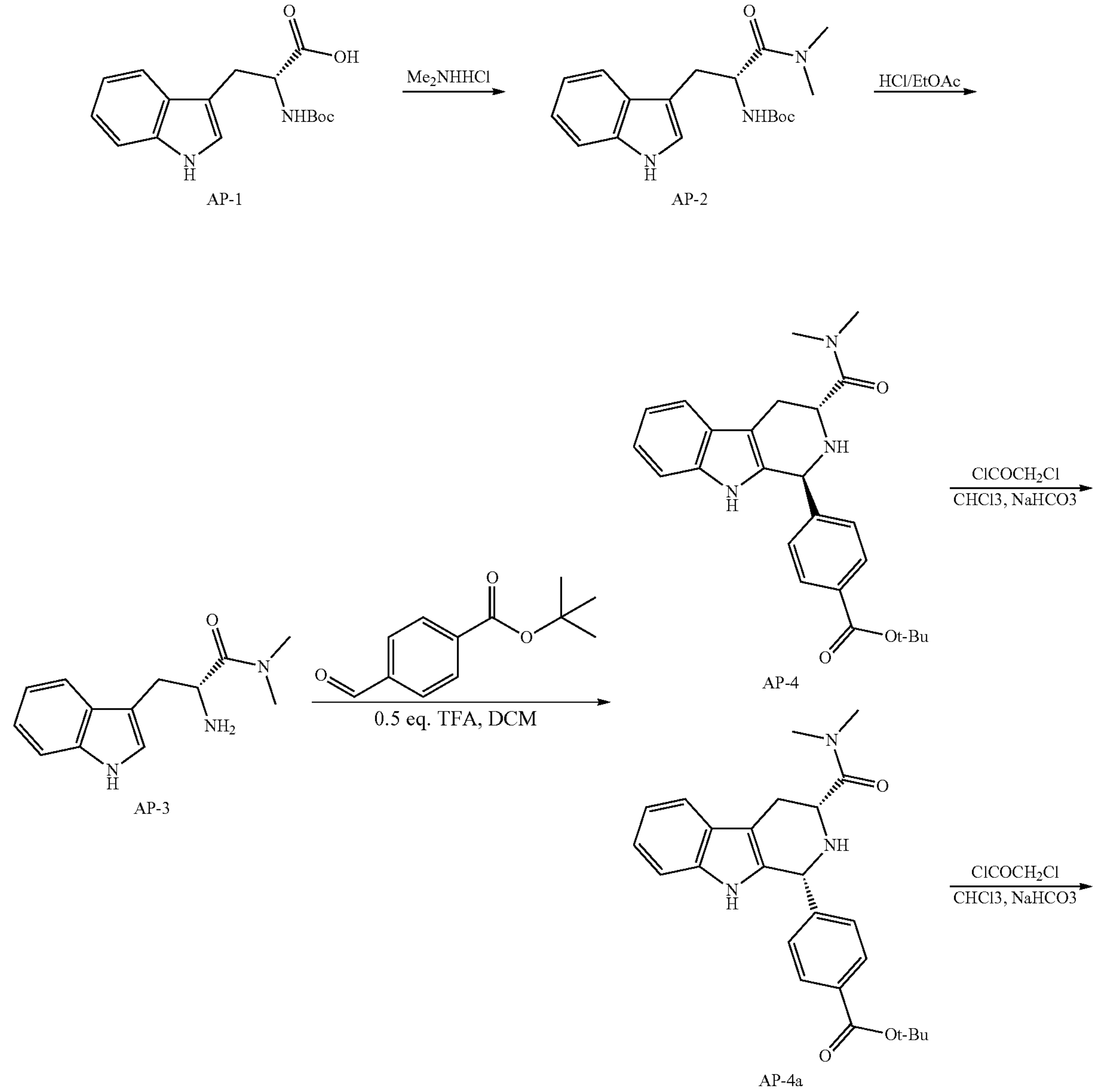

AP-1

AP-2

AP-3

AP-4

AP-4a

-continued

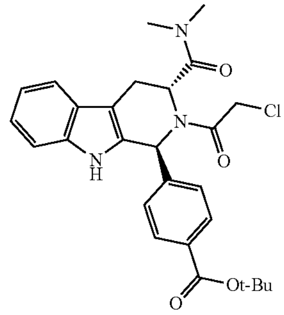

Compound 21

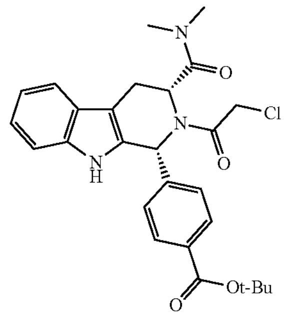

Compound 21a

To a solution of AP-1 (1 g, 3.29 mmol, 1 eq) in THF (25 mL) were added $Me_2NH$ (321.53 mg, 3.94 mmol, 361.27 µL, 1.2 eq, HCl), DMAP (40.14 mg, 328.58 µmol, 0.1 eq), DIEA (1.27 g, 9.86 mmol, 1.72 mL, 3 eq), HOBt (443.99 mg, 3.29 mmol, 1 eq) and EDCI (755.87 mg, 3.94 mmol, 1.2 eq). The mixture was stirred at 25° C. for 16 h to give a yellow solution. LCMS showed that the reaction was completed. To the mixture was added $H_2O$ (10 mL) and then extracted with MTBE (10 mL×3). The organic layers were combined and dried over $Na_2SO_4$, filtered, and then concentrated. The residue was purified by column chromatography ($SiO_2$, Petroleum ether/Ethyl acetate=I/O to 1:1) to give AP-2.

A solution of AP-2 (592 mg, 1.79 mmol, 1 eq) in HCl/EtOAc (4 M, 10 mL, 22.39 eq) was stirred at 25° C. for 2 h to give a yellow solution. LCMS showed that the reaction was completed. The mixture was concentrated to give a residue, which was then diluted with saturated $NaHCO_3$ aq. (10 mL) and DCM (10 mL). The mixture was stirred for 10 min and then extracted with DCM (5 mL×3). The organic layers were combined and dried over $Na_2SO_4$, filtered and the concentrated to give AP-3.

To a solution of AP-3 (100 mg, 432.35 µmol, 1 eq) in DCM (5 mL) were added tert-butyl 4-formylbenzoate (89.17 mg, 432.35 µmol, 1 eq) and TFA (24.65 mg, 216.18 µmol, 16.01 µL, 0.5 eq). The mixture was heated at 50° C. for 16 h to give a yellow solution. LCMS and TLC (eluting with: EtOAc:PE=1:2) showed that the reaction was completed. The mixture was adjusted to pH 8 with saturated $NaHCO_3$ and then extracted with DCM (5 mL×3). The organic layers were combined, dried over $Na_2SO_4$ and concentrated to give the crude product. The product was purified by preparative TLC ($SiO_2$, PE: EtOAc=1:2) by collecting the spot with higher polarity. It was confirmed by NMR and NOE as AP-4a (cis-isomer). This isomer is the major product and was used in the next step before confirmation by NOE.

To a solution of AP-4a (30.00 mg, 71.51 µmol, 1 eq) in DCM (2 mL) were added 2-chloroacetyl chloride (40.38 mg, 357.55 µmol, 28.44 µL, 5 eq) and $NaHCO_3$ (60.07 mg, 715.11 µmol, 27.81 µL, 10 eq). The mixture was stirred at 25° C. for 16 h to give a yellow solution. LCMS showed that the reaction was completed. The reaction mixture was filtered and the filtrate concentrated to give the crude product. The product was purified by preparative HPLC (column: Phenomenex Gemini 150×25 mm×10 m; mobile phase: [water (0.1% TFA)-ACN]; B %: 55%-85%, 10 min) to give Compound 21a.

To a solution of AP-3 (100 mg, 432.35 µmol, 1 eq) in DCM (5 mL) were added tert-butyl 4-formylbenzoate (89.17 mg, 432.35 µmol, 1 eq) and TFA (24.65 mg, 216.18 µmol, 16.01 µL, 0.5 eq). The mixture was heated at 50° C. for 16 h to give a yellow solution. LCMS and TLC (eluting with: EtOAc:PE=1:2) showed that the reaction was completed. The mixture was adjusted to pH 8 with saturated $NaHCO_3$ and extracted with DCM (5 mL×3). The organic layers were combined and dried over $Na_2SO_4$ and then concentrated to give the crude product. The product was purified by preparative TLC ($SiO_2$, PE: EtOAc=1:2) to give AP-4.

Preparation of Compound 21

To a solution of AP-4 (48 mg, 114.42 µmol, 1 eq) in DCM (2 mL) were added 2-chloroacetyl chloride (64.61 mg, 572.09 µmol, 45.50 µL, 5 eq) and $NaHCO_3$ (96.12 mg, 1.14 mmol, 44.50 µL, 10 eq). The mixture was stirred at 25° C. for 16 h to give a yellow solution. LCMS showed that the reaction was completed. The reaction mixture was filtered, and the filtrate concentrated to give the crude product. The crude product was purified by preparative HPLC (column: Phenomenex Gemini 150×25 mm×10 µm; mobile phase: [water (0.1% TFA)-ACN]; B %: 55%-85%, 10 min) to give Compound 21. LC-MS (m/z):496.0 $[M]^+$. $^1H$ NMR (400 MHz, $CDCl_3$) δ=8.49-8.20 (m, 1H), 8.05-7.83 (m, 2H), 7.52-7.37 (m, 3H), 7.08-6.79 (m, 3H), 6.45 (brs, 1H), 5.86 (brs, 1H), 3.48-3.28 (m, 2H), 3.19-2.95 (m, 2H), 2.94-2.82 (m, 4H), 1.56 (s, 9H).

Procedure AQ: Synthesis of Compound 24

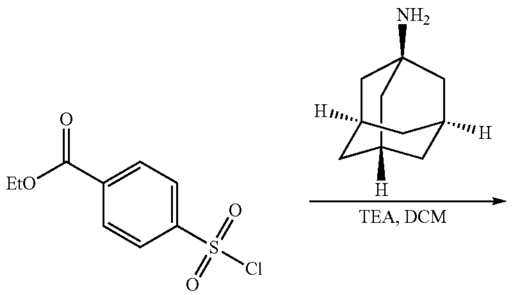

AQ-1

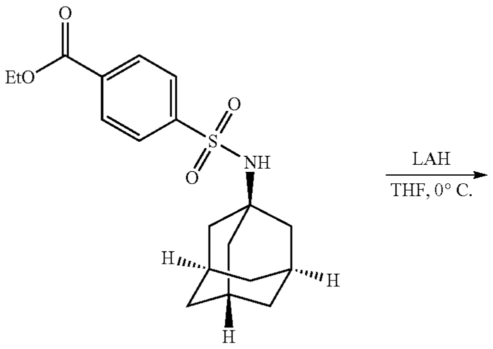

AQ-2

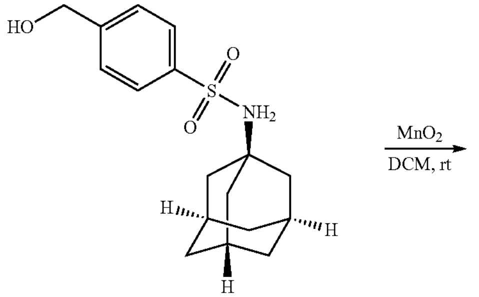

AQ-3

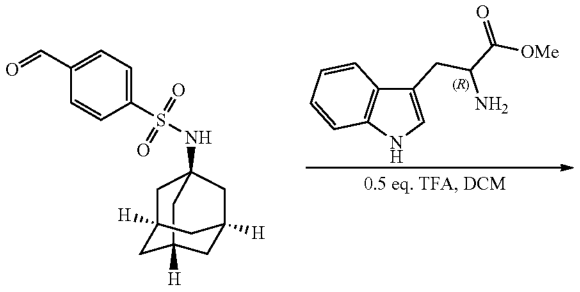

AQ-4

-continued

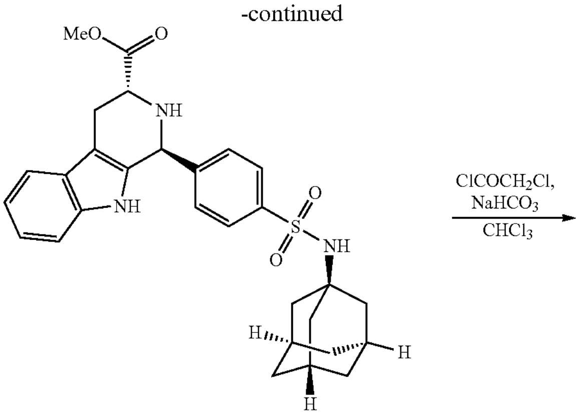

AQ-5

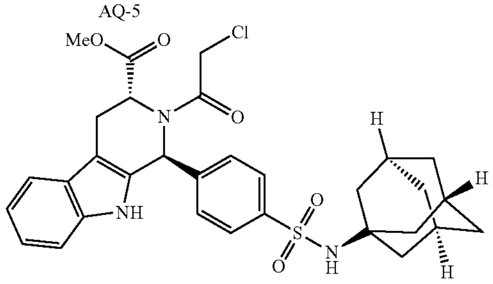

Compound 24

A solution of adamantan-1-amine (1 g, 6.61 mmol, 1.05 eq) and TEA (955.76 mg, 9.45 mmol, 1.31 mL, 1.5 eq) in DCM (30 mL) was mixed with ethyl 4-chlorosulfonylbenzoate (1.57 g, 6.30 mmol, 1 eq) in portions at 15° C. The reaction mixture was stirred at 15° C. for 16 h to give a white suspension. TLC (PE/EtOAc=3/1, $SiO_2$) showed that the reaction was completed. The reaction mixture was diluted with 0.2 N HCl solution (10 mL) and separated. The organic layer was washed with brine (5 mL), dried over $Na_2SO_4$, filtered, and concentrated under reduced pressure to give the crude product. The crude product was diluted with a mixed solvent of PE (30 mL) and EtOAc (10 mL) and stirred at 0° C. for 10 minutes. The product was collected by filtration, and dried in vacuo to give AQ-2.

To a suspension of $LiAlH_4$ (75.18 mg, 1.98 mmol, 1.2 eq) in THF (6 mL) was added dropwise a solution of AQ-2 (0.6 g, 1.65 mmol, 1 eq) in THF (6 mL) at 0° C. The reaction solution was stirred at 15° C. for 2 h to give a white suspension. TLC (PE/EtOAc=2/1, $SiO_2$) showed that the reaction was completed. To the mixture was added 75 μL water, 75 μL 15% NaOH solution, 225 μL water at 0° C., and stirred at 15° C. for 10 minutes before filtration. The filtrate was concentrated under reduced pressure to give AQ-3.

To a solution of AQ-3 (334 mg, 1.04 mmol, 1 eq) in $CHCl_3$ (15 mL) was added $MnO_2$ (100 mg, 1.15 mmol, 1.11 eq). The mixture was stirred at 15° C. for 16 h to give a dark suspension. TLC (PE/EtOAc=2/1, $SiO_2$) showed a new spot, but a significant amount of starting material remained. The reaction mixture was filtered through a pad of Celite, and the filtrate concentrated under reduced pressure to give the crude product. The crude product was purified by Combi flash (PE/EtOAc=10/1 to 1/1) to give AQ-4 and recovered starting material.

To a solution of methyl D-tryptophanate (43.05 mg, 197.23 μmol, 1 eq) and AQ-4 (63 mg, 197.23 μmol, 1 eq) in DCM (3 mL) was added TFA (11.24 mg, 98.62 μmol, 7.30 μL, 0.5 eq) at 0° C. The reaction solution was stirred at 40° C. for 16 h to give a clear solution. TLC (PE/EtOAc=1/1, $SiO_2$) showed that the aldehyde was consumed, and two new spots were observed. The reaction solution was washed with sat. aqu. $NaHCO_3$ solution (1 mL), dried over $Na_2SO_4$, filtered, and concentrated under reduced pressure to give the crude product. The crude product was purified by Combi flash (PE/EtOAc=3/1 to 1/1) to give a less polar compound and a more polar compound. For the more polar compound, NOE showed it was the desired product.

Preparation of Compound 24

To a solution of AQ-5 (30 mg, 57.73 μmol, 1 eq) in $CHCl_3$ (0.5 mL) was added $NaHCO_3$ (10 mg, 119.03 μmol, 4.63 μL, 2.06 eq) followed by dropwise addition of a solution of 2-chloroacetyl chloride (16.30 mg, 144.33 μmol, 11.48 μL, 2.5 eq) in $CHCl_3$ (0.5 mL) at 0° C. The reaction mixture was stirred at 15° C. for 2 h to give a brown suspension. TLC (PE/EtOAc=1/1, $SiO_2$) showed that the reaction was completed. The reaction mixture was filtered, and the filtrate concentrated and directly purified by Combi flash (PE/EtOAc=3/1 to 1/1) to give Compound 24. LC-MS (m/z): 618.0 $[M+Na]^+$. $^1H$ NMR (400 MHz, $CDCl_3$) δ 7.92-7.72 (m, 2H), 7.54 (d, J=7.8 Hz, 1H), 7.51-7.35 (m, 2H), 7.26-7.21 (m, 1H), 7.20-7.07 (m, 2H), 6.33-6.08 (m, 1H), 5.29-5.04 (m, 1H), 4.52-4.34 (m, 1H), 4.21-3.91 (m, 2H), 3.65 (s, 4H), 3.53-3.20 (m, 1H), 2.03-1.95 (m, 3H), 1.80-1.74 (m, 6H), 1.61-1.50 (m, 6H).

A similar synthetic scheme was used to synthesize Compound 23 and Compound 23a by reacting AQ-1 with dimethylamine hydrochloride. Compound 35 and Compound 37 were also synthesized by a similar process.

Compound 23

LC-MS (m/z): 489.9 $[M+H]^+$. $^1H$ NMR (400 MHz, MeOD): δ 7.79-7.67 (m, 4H), 7.50-7.48 (m, 1H), 7.24-7.01 (m, 3H), 6.15 (s, 1H), 5.43 (s, 1H), 4.58-4.45 (m, 1H), 4.30-4.27 (m, 1H), 3.77-3.49 (m, 5H), 2.64 (s, 6H).

Compound 23a: LC-MS (m/z): 490.1 $[M+H]^+$. $^1H$ NMR (400 MHz, MeOD): δ 7.74-7.72 (m, 2H), 7.59-7.57 (m, 1H), 7.48-7.46 (m, 2H), 7.32-7.30 (m, 1H), 7.16-7.04 (m, 2H), 5.25-5.24 (m, 1H), 4.74-4.64 (m, 2H), 4.41-4.38 (m, 1H), 3.70-3.66 (m, 1H), 3.24-3.18 (m, 1H), 3.08 (s, 6H), 2.69 (s, 6H).

Compound 35

(LC-MS (m/z):568.0 $[M+Na]^+$. $^1H$ NMR (400 MHz, METHANOL-$d_4$) δ 7.78 (d, J=5.5 Hz, 1H), 7.73-7.63 (m, 3H), 7.48 (d, J=7.8 Hz, 1H), 7.23 (d, J=7.5 Hz, 1H), 7.13-7.00 (m, 2H), 6.14 (s, 1H), 5.43 (brs, 1H), 4.71-4.52 (m, 5H), 4.28 (d, J=13.3 Hz, 1H), 3.75 (d, J=15.3 Hz, 1H), 3.67-3.56 (m, 4H), 3.56-3.37 (m, 2H), 2.82-2.66 (m, 2H), 1.85 (ddd, J=3.1, 6.2, 9.7 Hz, 2H), 1.61-1.49 (m, 2H).

Compound 37

LC-MS (m/z): 517.9 $[M+H]^+$. $^1H$ NMR (400 MHz, MeOD) δ ppm 3.47-3.78 (m, 7H), 3.90-3.91 (br d, J=6.02 Hz, 2H), 4.27-4.58 (m, 3H), 5.44 (br s, 1H), 6.17 (s, 1H), 7.00-7.09 (m, 2H), 7.23-7.25 (d, J=8.03 Hz, 1H), 7.70-7.88 (m, 4H).

Procedure AR: Synthesis of Compound 26

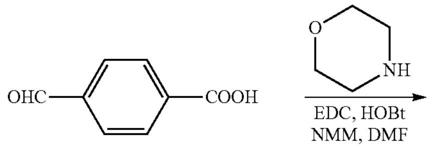

AB-2

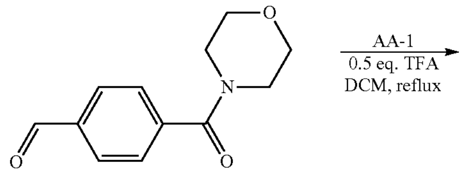

AR-2

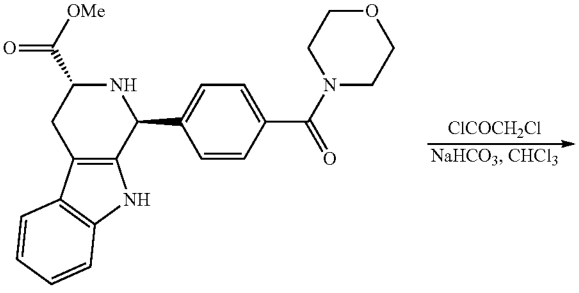

AR-4

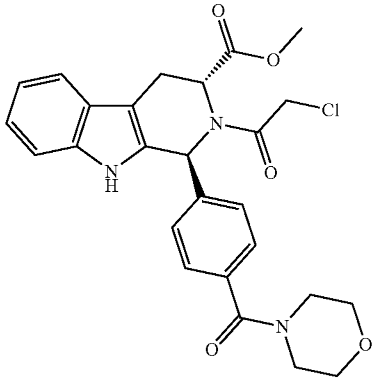

Compound 26

A solution of AB-2 (500 mg, 3.33 mmol, 1 eq) in DMF (8 mL) was mixed with morpholine (348.18 mg, 4.00 mmol, 351.69 μL, 1.2 eq), HOBt (495.02 mg, 3.66 mmol, 1.1 eq) and EDCI (766.14 mg, 4.00 mmol, 1.2 eq), and stirred at 30° C. for 16 h to give a yellow suspension. LCMS showed that the reaction was completed. The reaction mixture was diluted with $H_2O$ (30 mL) and then extracted with MTBE (5 mL×3). The organic layers were combined, dried over $Na_2SO_4$, filtered and then concentrated to give crude product. The residue was purified by column chromatography ($SiO_2$, Petroleum ether/Ethyl acetate=I/O to 1:1) to give AR-2.

To a solution of AA-1 (177.20 mg, 811.91 μmol, 1 eq) in DCM (5 mL) were added AR-2 (178 mg, 811.91 μmol, 1 eq) and TFA (46.29 mg, 405.96 μmol, 30.06 μL, 0.5 eq). The mixture was stirred at 50° C. for 16 h to give a yellow suspension. LCMS showed that R1 remained. The mixture was adjusted to pH 8 with saturated $NaHCO_3$, and extracted with DCM (5 mL×3). The organic layers were combined, dried over $Na_2SO_4$, and then concentrated to give the crude product. The residue was purified by preparative TLC ($SiO_2$, PE:EtOAc=0:1) to give AR-4.

Preparation of Compound 26

To a solution of AR-4 (46 mg, 109.66 μmol, 1 eq) in $CHCl_3$ (2 mL) were added $NaHCO_3$ (92.12 mg, 1.10 mmol, 42.65 μL, 10 eq) and 2-chloroacetyl chloride (61.93 mg, 548.31 μmol, 43.61 μL, 5 eq). The mixture was stirred at 25° C. for 16 h to give a yellow suspension. LCMS showed that the reaction was completed. The reaction mixture was filtered, and the filtrate concentrated to give the crude product. The crude product was purified by preparative HPLC (column: Phenomenex Gemini 150x25 mmx10 μm; mobile phase: [water (0.1% TFA)-ACN]; B %: 45%-55%, 10 min) to give Compound 26. LC-MS (m/z):496.0 $[M+H]^+$. $^1H$ NMR (400 MHz, $CDCl_3$) δ=8.32 (br s, 1H), 7.53 (br d, J=7.5 Hz, 1H), 7.49-7.35 (m, 2H), 7.35-7.28 (m, 2H), 7.16-7.09 (m, 2H), 6.28-6.12 (m, 1H), 6.02 (br s, 1H), 5.27-5.11 (m, 1H), 4.19-4.01 (m, 1H), 3.86-3.69 (m, 4H), 3.66 (s, 5H), 3.64-3.57 (m, 2H), 3.57-3.38 (m, 3H).

Procedure AS: Synthesis of Compound 28

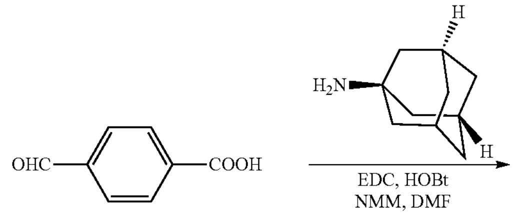

AB-2

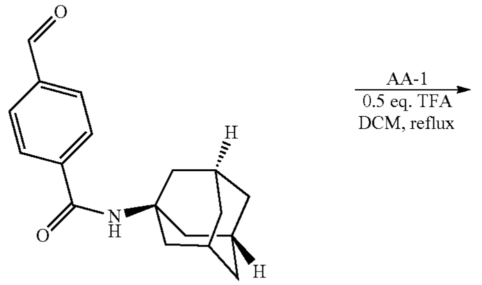

AS-2

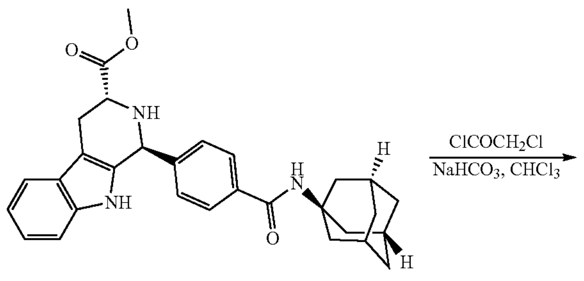

AS-4

-continued

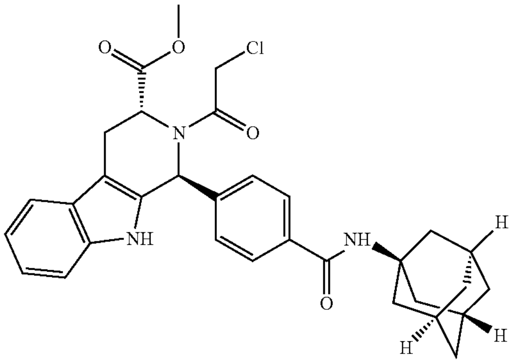

Compound 28

To a solution of AB-2 (500 mg, 3.33 mmol, 1 eq), EDCI (702.29 mg, 3.66 mmol, 1.1 eq), HOBt (450.02 mg, 3.33 mmol, 1 eq) and NMM (842.16 mg, 8.33 mmol, 915.39 μL, 2.5 eq) in DMF (10 mL) was added adamantan-1-amine (503.72 mg, 3.33 mmol, 1 eq) at 0° C. The mixture was stirred at 20° C. for 16 h to give yellow solution. Completion of the reaction was detected by TLC. The reaction solution was diluted with EA (20 mL), washed with 1N HCl (15 mL), washed with sat. aqu. $NaHCO_3$ (20 mL) and brine (20 mL), and extracted with EA (10 mLx3). The organic layers were combined and dried over anhydrous $Na_2SO_4$, filtered, and concentrated under reduced pressure. The residue was purified by column chromatography ($SiO_2$, Petroleum ether/Ethyl acetate=10/1 to 1:1) to give AS-2.

To a solution of AA-1 (500 mg, 2.29 mmol, 1 eq) and AS-2 (775.71 mg, 2.74 mmol, 1.2 eq) in DCM (10 mL) was added TFA (130.06 mg, 1.14 mmol, 84.45 μL, 0.5 eq) at 0° C. The mixture was stirred at 40° C. for 24 h to give yellow mixture. Completion of the reaction was detected by TLC. The reaction solution was diluted with DCM (40 mL), then washed with sat. aqu. $NaHCO_3$ (40 mL) and brine (40 mL). The organic layer was dried over anhydrous $Na_2SO_4$, filtered, and concentrated under reduced pressure. The residue was purified by column chromatography ($SiO_2$, Petroleum ether/Ethyl acetate=10/1 to 2:1) to give AS-4.

Preparation of Compound 28

To a solution of AS-4 (150 mg, 310.17 μmol, 1 eq) and $NaHCO_3$ (52.11 mg, 620.35 μmol, 24.13 μL, 2 eq) in $CHCl_3$ (1 mL) was added 2-chloroacetyl chloride (84.08 mg, 744.42 μmol, 59.21 μL, 2.4 eq) at 0° C. The mixture was stirred at 25° C. for 3 h to give a yellow solution. Completion of the reaction was detected by TLC. The reaction solution was diluted with DCM (15 mL), washed with sat. aqu. $NaHCO_3$ (15 mL) and brine (15 mL). The organic layer was dried over anhydrous $Na_2SO_4$, filtered, and concentrated under reduced pressure. The residue was purified by preparative TLC ($SiO_2$, PE:EA=1:1) to give Compound 28. LC-MS (m/z): 560.1$[M+H]^+$. $^1H$ NMR (400 MHz, $CDCl_3$) δ 8.65-8.47 (m, 1H), 7.60-7.39 (m, 4H), 7.26-7.07 (m, 4H), 6.20-6.05 (m, 1H), 5.77-5.68 (m, 1H), 5.23- 5.09 (m, 1H), 4.12-3.82 (m, 2H), 3.64 (s, 3H), 3.50-3.22 (m, 1H), 2.20-2.00 (m, 8H), 1.70 (s, 7H).

Procedure AT: Synthesis of Compound 29

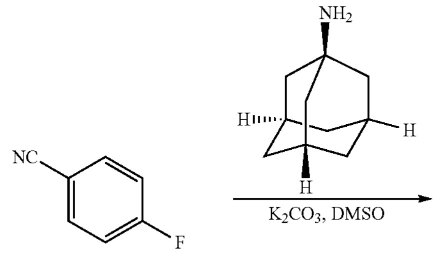

AT-1

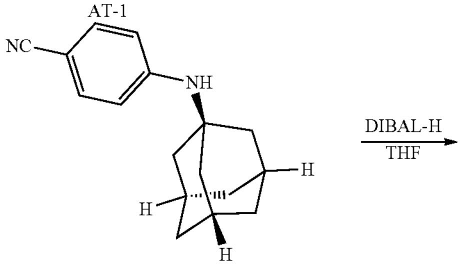

AT-2

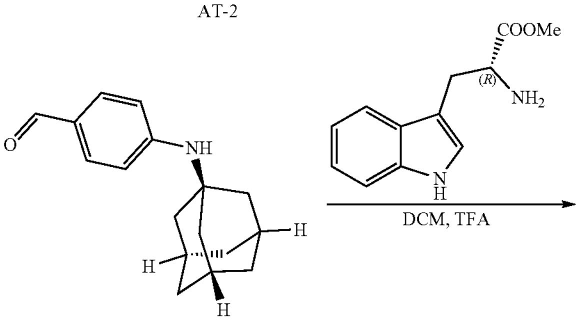

AT-3

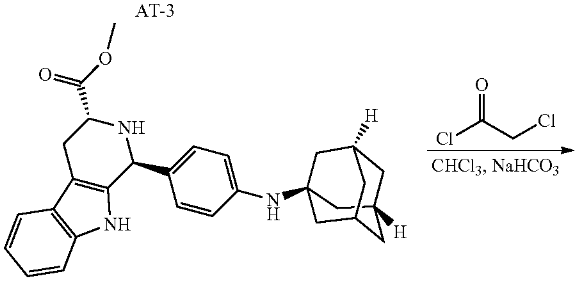

AT-4

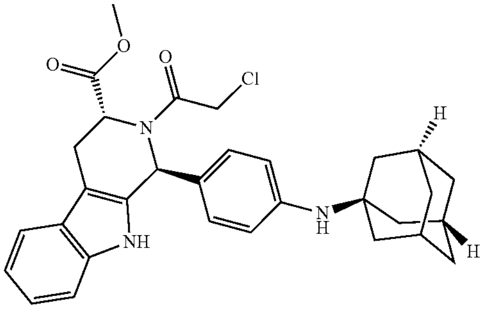

Compound 29

A solution of compound AT-1 (1.2 g, 9.91 mmol, 1.5 eq) and adamantan-1-amine (999.06 mg, 6.61 mmol, 1 eq) in DMSO (30 mL) was mixed with $K_2CO_3$ (1.83 g, 13.21 mmol, 2 eq). The reaction mixture was stirred at 120° C. for 16 h to give a suspension. TLC (eluting with: PE/EtOAc=3/1) showed that the reaction was completed. The reaction mixture was partitioned between with water (20 mL) and EtOAc (30 mL), and the aqueous layers extracted with EtOAc (20 mL×2). The organic layers were combined and washed with brine (30 mL), dried over sodium sulfate, and concentrated to give the crude product. The crude product was purified by silica gel chromatography (eluting with: PE/EtOAc=20/1-10/1) to give AT-2.

To a solution of compound AT-2 340 mg, 1.35 mmol, 1 eq) in THF (15 mL) was added dropwise DIBAL-H (228.31 mg, 1.62 mmol, 1.2 eq) at 0° C., and the reaction mixture stirred at 0° C. for 3 h to give a yellow solution. TLC (eluting with: PE/EtOAc=3/1) showed that the reaction was completed. The reaction mixture was partitioned between water (20 mL) and EtOAc (20 mL), and the aqueous layer extracted with EtOAc (20 mL). The organic layers were combined and washed with brine (20 mL), dried over sodium sulfate, and concentrated to give the crude product. The crude product was used in the next step without further purification.

A solution of AT-3 (390 mg, 1.53 mmol, 1 eq) and methyl (2R)-2-amino-3-(1H-indol-3-yl) propanoate (400.00 mg, 1.83 mmol, 1.2 eq) in DCM (15 mL) was mixed with TFA (174.15 mg, 1.53 mmol, 113.08 μL, 1 eq), and the reaction mixture stirred at 20° C. to for 16 h to give dark red solution. LCMS and TLC (eluting with: PE/EA=3/1) showed that the reaction was completed. The reaction mixture was quenched with Sat. $NaHCO_3$ (15 mL), extracted with DCM (20 mL×3). The organic layers dried over $Na_2SO_4$, concentrated to give a crude product, and then purified by flash column chromatography (eluting with: PE/EA=10/1-4/1) to give AT-4.

Preparation of Compound 29

To a solution of AT-4 (50 mg, 109.75 μmol, 1 eq) and $Et_3N$ (33.32 mg, 329.24 μmol, 45.83 μL, 3 eq) in DCM (2 mL) was added dropwise 2-chloroacetyl chloride (24.79 mg, 219.50 μmol, 17.46 μL, 2 eq) at 0° C. The reaction mixture was stirred at 0° C. for 2 h to give a yellow suspension. LCMS and TLC (eluting with: PE:EA=1/1) showed that the reaction was completed. The reaction mixture was quenched with Sat. $NaHCO_3$ (15 mL) and extracted with DCM (20 mL×3). The organic layers were dried over $Na_2SO_4$, concentrated to give a crude product, and then purified by preparative HPLC (column: Phenomenex Gemini 150×25 mm×10 μm; mobile phase: [water (0.1% TFA)-ACN]; B %: 40%-90%, 9.5 min) to give Compound 29. LC-MS (m/z): 532.1 $[M+H]^+$. $^1H$ NMR (400 MHz, DMSO-$d_6$) δ: 1.80 (s, 9H), 2.10 (s, 6H), 3.50-3.59 (m, 3H), 4.27 (s, 1H), 4.42 (d, J=11.80 Hz, 1H), 4.72 (d, J=13.55 Hz, 1H), 5.39 (s, 1H), 6.05 (s, 1H), 6.93-7.02 (m, 2H), 7.05 (s, 2H), 7.25 (s, 4H), 7.49 (d, J=7.53 Hz, 2H), 7.56 (s, 2H), 10.69 (s, 2H), 11.01 (s, 1H).

Procedure AU: Synthesis of Compound 31

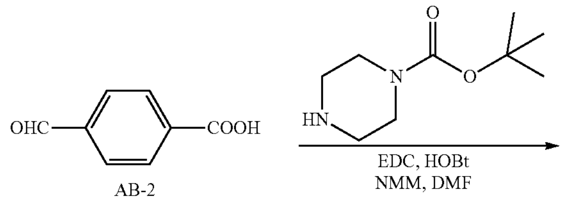

AB-2

-continued

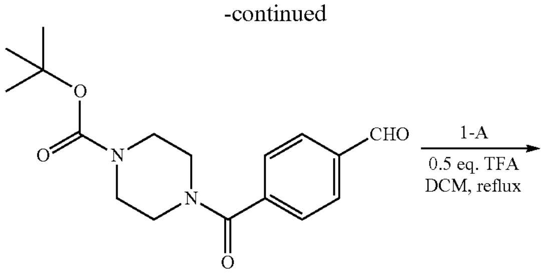

AU-2

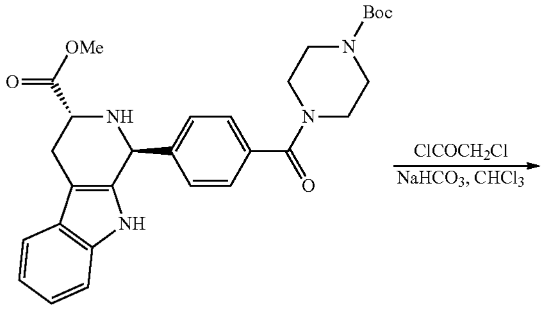

AU-4

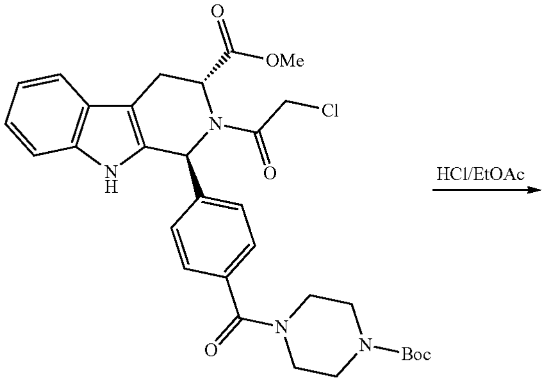

AU-5

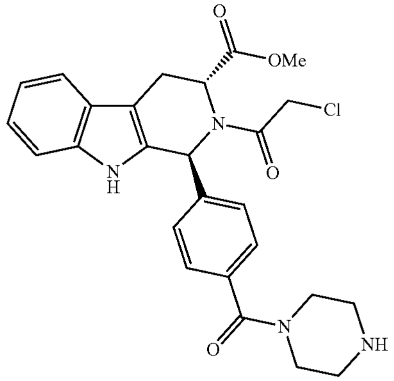

Compound 31

To a solution of AB-2 (1 g, 6.66 mmol, 1 eq) in DMF (20 mL) were added tert-butyl piperazine-1-carboxylate (1.49 g, 7.99 mmol, 1.2 eq), NMM (2.02 g, 19.98 mmol, 2.20 mL, 3 eq), HOBt (990.04 mg, 7.33 mmol, 1.1 eq) and EDCI (2.55 g, 13.32 mmol, 2 eq). The mixture was stirred at 25° C. for 16 h to give a yellow solution. LCMS showed that the reaction was completed. The reaction mixture was diluted with $H_2O$ (50 mL), and extracted with MTBE (20 mL×3). The organic layers were combined and dried over $Na_2SO_4$, filtered, and then concentrated to give a crude product. The residue was purified by column chromatography ($SiO_2$, Petroleum ether/Ethyl acetate=I/O to 1:1) to give AU-2.

To a solution of AU-2 (200 mg, 628.20 μmol, 1 eq) in DCM (5 mL) were added 1-A (137.11 mg, 628.20 μmol, 1 eq) and TFA (35.81 mg, 314.10 μmol, 23.26 μL, 0.5 eq). The mixture was stirred at 50° C. for 16 h to give a yellow solution. LCMS showed that the reaction was completed. The mixture was adjusted to pH 8 with saturated $NaHCO_3$ and extracted with DCM (5 mL×3). The organic layers were combined, dried over $Na_2SO_4$, and concentrated the crude product. The residue was purified by preparative TLC ($SiO_2$, EtOAc:PE=4:1) to give AU-4.

To a solution of AU-4 (80 mg, 154.26 μmol, 1 eq) in $CHCl_3$ (2 mL) were added $NaHCO_3$ (129.59 mg, 1.54 mmol, 59.99 μL, 10 eq) and 2-chloroacetyl chloride (87.11 mg, 771.30 μmol, 61.35 μL, 5 eq). The mixture was stirred at 25° C. for 16 h to give a yellow solution. LCMS showed that the reaction was completed. The mixture was filtered and concentrated to give the crude product. The crude product was purified by preparative HPLC (column: Phenomenex Gemini 150×25 mm×10 m; mobile phase: [water (0.1% TFA)-ACN]; B %: 50%-80%, 8 min) to give AU-5.

Preparation of Compound 31

To a solution of AU-5 (80 mg, 134.43 μmol, 1 eq) in HCl/EtOAc (4 M, 10 mL, 297.54 eq) was stirred at 25° C. to give a yellow solution. LCMS showed that the reaction was completed. The reaction solution was concentrated to give the crude product, and. crude product purified by preparative HPLC (column: Phenomenex Gemini 150×25 mm×10 m; mobile phase: [water (0.05% HCl)-ACN]; B %: 20%-50%, 7 min) to give Compound 31. LC-MS (m/z): 495.0 [M+H]. $^1H$ NMR (400 MHz, DMSO-$d_6$) δ 7.53-7.45 (m, 3H), 7.36 (br d, J=8.0 Hz, 2H), 7.24 (br d, J=7.8 Hz, 1H), 7.07-6.95 (m, 2H), 6.05 (s, 1H), 5.41 (br s, 1H), 4.73 (s, 1H), 4.44 (s, 1H), 3.80-3.53 (m, 6H), 3.50 (s, 4H), 3.30-3.02 (m, 4H).

A similar scheme was used to synthesize Compound 32 and Compound 32a.

Compound 32

LC-MS (m/z): 510.0 $[M+H]^+$. $^1H$ NMR (400 MHz, MeOD) δ 7.57-7.55 (m, 1H), 7.51-7.44 (m, 4H), 7.30-7.26 (m, 1H), 7.18-7.14 (m, 1H), 7.11-7.07 (m, 1H), 5.93 (s, 1H), 5.14-5.10 (m, 1H), 4.40-4.37 (m, 1H), 4.23-4.21 (m, 2H), 3.92-3.83 (m, 5H), 3.64-3.57 (m, 1H), 3.53-3.47 (m, 1H), 3.39 (s, 1H), 3.27-3.25 (m, 1H), 2.04-1.67 (m, 4H).

Compound 32a: LC-MS (m/z): 510.0 $[M+H]^+$. $^1H$ NMR (400 MHz, DMSO) δ 7.84-7.54 (m, 5H), 7.29-7.27 (m, 1H), 7.13-7.10 (m, 1H), 7.06-7.03 (m, 1H), 5.97 (s, 1H), 5.06-5.03 (m, 1H), 4.76 (s, 1H), 4.41 (s, 2H), 3.94-3.73 (m, 4H), 3.49 (s, 3H), 1.94-1.89 (m, 2H), 1.75-1.47 (m, 2H).

Procedure AV: Synthesis of Compound 38

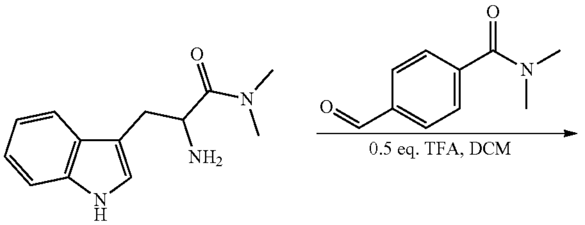

AV-1

-continued

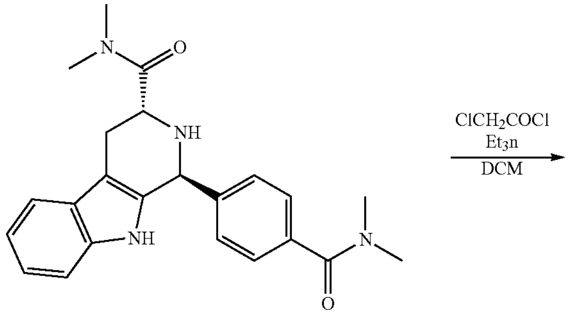

AV-2

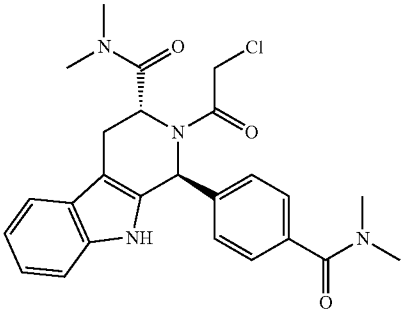

Compound 38

To a solution of AV-1 (500 mg, 2.16 mmol, 1 eq) and 4-formyl-N,N-dimethyl-benzamide (574.59 mg, 3.24 mmol, 1.5 eq) in DCM (20 mL) was added TFA (246.49 mg, 2.16 mmol, 160.06 μL, 1 eq) at 20° C., and the reaction mixture stirred at 40° C. for 16 h. TLC (eluting with: PE/EtOAc=1/1) showed that the reaction was completed. The reaction mixture was partitioned between water (10 mL) and DCM (10 mL), and the aqueous layer extracted with DCM (10 mL×2). The organic layers were combined and concentrated. The crude product was purified by preparative HPLC (column: Phenomenex Gemini 150×25 mm×10 μm; mobile phase: [water (0.05% HCl)-ACN]; B %: 4%-34%, 6.5 min) to give AV-2.

Preparation of Compound 38

To a solution of AV-2 (130 mg, 332.93 μmol, 1 eq) and Et3N (101.07 mg, 998.78 μmol, 139.02 μL, 3 eq) in DCM (2 mL) was added dropwise 2-chloroacetyl chloride (75.20 mg, 665.85 μmol, 52.96 μL, 2 eq) at 0° C. The reaction mixture was stirred at 20° C. for 16 h. TLC (eluting with: PE/EtOAc=2/1) showed that the reaction was completed. The reaction mixture was quenched with Sat. $NaHCO_3$ (15 mL) and extracted with DCM (20 mL×3). The organic layers were dried over $Na_2SO_4$ and concentrated to give a crude product. The crude product was purified by preparative TLC (DCM/MeOH=10/1) to afford Compound 38. LC-MS (m/z): 467.0 [M+H]+. 1H NMR (400 MHz, $CDCl_3$) δ: 2.87 (s, 3H), 2.93 (s, 3H), 3.09 (s, 5H), 3.37 (t, J=4.64 Hz, 2H), 3.90 (s, 1H), 4.11-4.19 (m, 1H), 5.70 (s, 1H), 6.39 (s, 1H), 7.07 (s, 2H), 7.35-7.49 (m, 5H), 8.20 (s, 1H).

Procedure AW: Synthesis of Compound 39

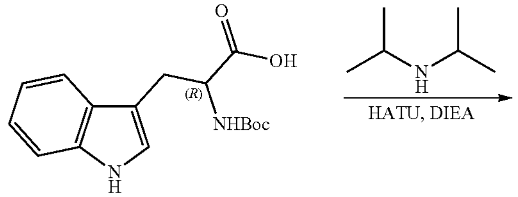

AW-1

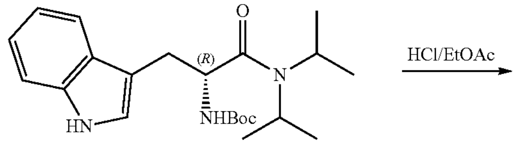

AW-2

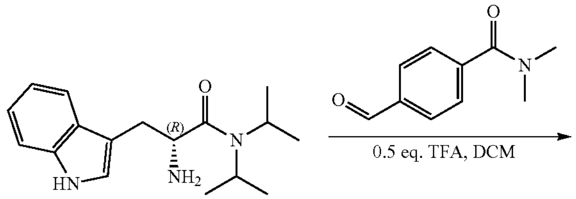

AW-3

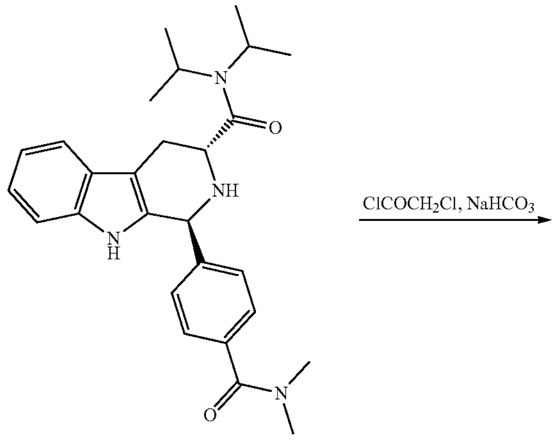

AW-4

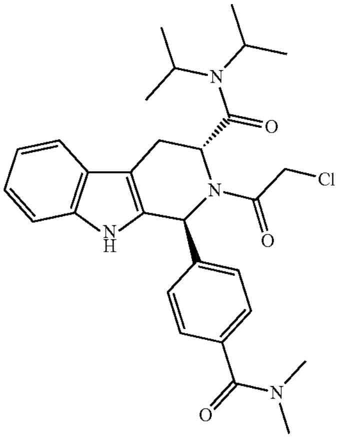

Compound 39

To a solution of AW-1 (1 g, 3.29 mmol, 1 eq) in DMF (10 mL) were added HATU (1.87 g, 4.93 mmol, 1.5 eq) and DIEA (849.33 mg, 6.57 mmol, 1.14 mL, 2 eq) at 0° C. The mixture was stirred at 0° C. for 30 min, and then N-isopropylpropan-2-amine (398.99 mg, 3.94 mmol, 557.24 μL, 1.2 eq) was added. The mixture was stirred at 20° C. for 15.5 h to give a brown solution. LCMS showed that the reaction was completed. The mixture was diluted with $H_2O$ (50 mL) and then extracted with MTBE (10 mL×3). The organic layers were combined and dried over $Na_2SO_4$, filtered and concentrated. The residue was purified by column chromatography ($SiO_2$, Petroleum ether/Ethyl acetate=I/O to 5:1) to give AW-2.

A solution of tert-butyl AW-2 (675 mg, 1.74 mmol, 1 eq) was added HCl/EtOAc (4 M, 10 mL, 22.96 eq) and stirred at 25° C. for 16 h to give a brown solution. LCMS showed that the reaction was completed. The mixture was concentrated and the resulting residue diluted with MTBE (10 mL) and Sat. $NaHCO_3$ aq. (20 mL). The mixture was stirred 30 min and extracted with MTBE (10 mL×3). The organic layers were combined and dried over $Na_2SO_4$, the filtered and concentrated to give AW-3.

To a solution of AW-3 (150 mg, 521.92 μmol, 1 eq) in DCM (5 mL) were added 4-formyl-N, N-dimethyl-benzamide (92.48 mg, 521.92 μmol, 1 eq) and TFA (29.76 mg, 260.96 μmol, 19.32 μL, 0.5 eq), and the mixture heated to reflux for 16 h to give a brown suspension. LCMS showed the compound AW-3 was not completely consumed. The mixture was adjusted to pH 8 with saturated $NaHCO_3$ and extracted with DCM (5 mL×3). The organic layers were combined, dried over $Na_2SO_4$ and concentrated to a crude product. The residue was purified by preparative TLC ($SiO_2$, EtOAc:PE=1:0) to give AW-4.

Preparation of Compound 39

To a solution of AW-4 (32 mg, 71.66 μmol, 1 eq) in $CHCl_3$ (2 mL) were added $NaHCO_3$ (60.19 mg, 716.55 μmol, 27.87 μL, 10 eq) and 2-chloroacetyl chloride (40.46 mg, 358.28 μmol, 28.50 μL, 5 eq). The mixture was stirred at 25° C. for 16 h to give a yellow suspension. LCMS showed that the reaction was completed. The mixture was filtered, concentrated to give a crude product, and the crude product purified by preparative HPLC (column: Phenomenex Gemini 150×25 mm×10 μm; mobile phase: [water (0.1% TFA)-ACN]; B %: 45%-75%, 7.8 min) to give Compound 39. LC-MS (m/z):523.0 [M+H]+. 1H NMR (400 MHz, METHANOL-d4) δ=7.65-7.20 (m, 6H), 7.09-6.97 (m, 2H), 6.46-6.38 (m, 1H), 5.64-5.29 (m, 1H), 4.51 (brs, 1H), 4.24 (d, J=13.6 Hz, 1H), 3.95-3.56 (m, 1H), 3.43-3.33 (m, 2H), 3.06 (s, 3H), 2.96 (s, 3H), 1.35-0.75 (m, 12H).

Procedure AX: Synthesis of Compound 40a

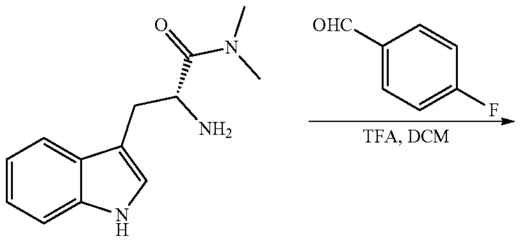

AX-1

-continued

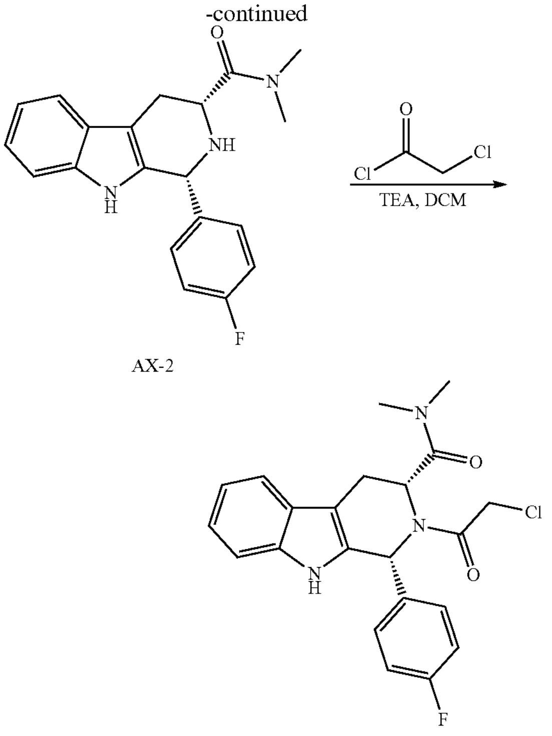

AX-2

Compound 40a

To a solution of AX-1 (200 mg, 864.70 μmol, 1 eq) and 4-fluorobenzaldehyde (107.32 mg, 864.70 μmol, 90.95 μL, 1 eq) in DCM (3 mL) was added TFA (49.30 mg, 432.35 μmol, 32.01 μL, 0.5 eq) at 20° C., and the solution stirred at 20° C. for 16 h to give a brown solution. TLC (quenched with DCM and water, eluting with: PE/EtOAc=0/1) indicated that the reaction was completed. The reaction solution was diluted with DCM (20 mL), washed with saturate sodium bicarbonate solution (20 mL×3). The organic layer was dried over anhydrous $Na_2SO_4$ and concentrated under reduced pressure.

Preparation of Compound 40a

To a solution of AX-2 (140 mg, 414.95 μmol, 1 eq) and 2-chloroacetyl chloride (46.87 mg, 414.95 μmol, 33.00 μL, 1 eq) in DCM (5 mL) was added TEA (83.98 mg, 829.90 μmol, 115.51 μL, 2 eq) at 0° C. The mixture was stirred at 0° C. to 25° C. for 16 h to give a yellow solution. LCMS and (eluting with: PE/EtOAc=0/1) showed that the reaction was completed. The reaction solution was diluted with DCM (10 mL), washed with saturate sodium bicarbonate solution (10 mL×3). The organic layer was dried over anhydrous $Na_2SO_4$, concentrated under reduced pressure. The residue was purified by column chromatography (SiO2, 0% to 40% EtOAc in petroleum ether). The product was not pure and it was combined and purified by preparative HPLC (column: Xtimate C18 150×25 mm×5 μm; mobile phase: [water (0.05% HCl)-ACN]; B %: 36%-66%, 9.5 min) to give Compound 40a. LC-MS (m/z): 413.9$[M]^+$. $^1H$ NMR (400 MHz, $CD_3OD$) δ 8.01-7.99 (m, 1H), 7.91-7.89 (m, 1H), 7.54-7.53 (m, 1H), 7.48-7.42 (m, 1H), 7.19-7.02 (m, 1H), 6.99-3.97 (m, 2H), 6.58-6.08 (m, 1H), 5.76- 5.03 (m, 1H), 3.86-3.83 (m, 3H), 3.68-3.45 (m, 5H), 2.14-2.03 (m, 3H).

Procedure AY: Synthesis of Compound 45

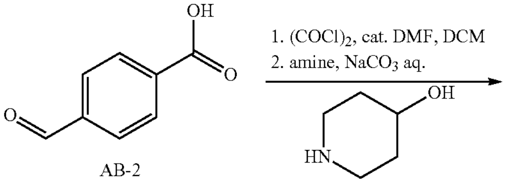

AB-2

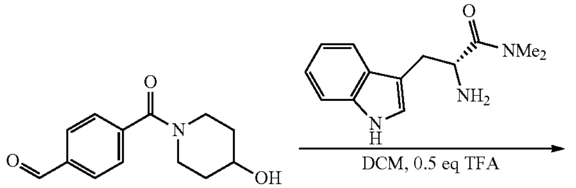

AY-2

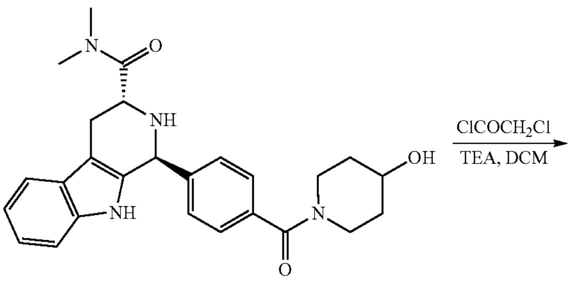

AY-3

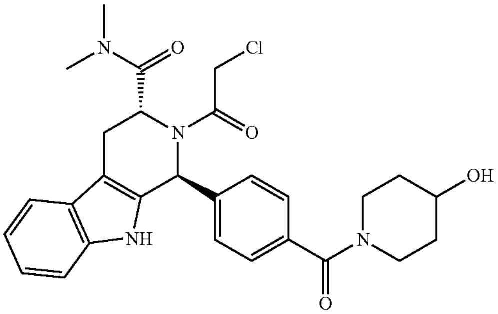

Compound 45

Preparation of Compound AY-2

To a solution of AB-2 (1 g, 6.66 mmol, 1 eq) in DCM (10 mL) was added DMF (38.00 mg, 519.88 μmol, 0.04 mL, 7.81e-2 eq) and $(COCl)_2$ (1.27 g, 9.99 mmol, 874.59 μL, 1.5 eq) and stirred at 0-10° C. for 3 h to give a white mixture. TLC (Petroleum ether:Ethyl acetate=1:1, $SiO_2$) showed that the reaction was completed. The mixture was concentrated to give 4-formylbenzoyl chloride.

To a solution of piperidin-4-ol (672 mg, 6.64 mmol, 4.98e-1 eq) in dioxane (10 mL) was added $NaHCO_3$ aq. (4.32 g, 2 mL), followed by 4-formylbenzoyl chloride (2.25 g crude) in DCM (5 mL) added dropwise at 0° C. The mixture was allowed to stir at 20° C. for 4 h to give a yellow solution. TLC (Ethyl acetate=100%, $SiO_2$) showed that the reaction was completed and quenched with MeOH. The reaction mixture was adjusted to pH 8 with Sat. $NaHCO_3$ and extracted with EtOAc (150 mL×3). The organic layers were dried over $Na_2SO_4$ and concentrated to give a crude product. The crude product was purified by flash column chromatography (eluting with: Petroleum ether/Ethyl acetate=10/1 to 3/5) to give AY-2.

To a solution of AY-2 (100 mg, 428.70 μmol, 1 eq) in DCM (6 mL) were added AP-3 (99.16 mg, 428.70 μmol, 1 eq) and TFA (24.44 mg, 214.35 μmol, 15.87 μL, 0.5 eq), and the mixture stirred at 45° C. for 12 h to give a yellow solution. LCMS showed that the reaction was completed. The reaction mixture was adjusted to pH 8 with Sat. $NaHCO_3$ and extracted with DCM (20 mL×3). The organic layers were dried over $Na_2SO_4$ and concentrated. The residue was purified by preparative TLC (Ethyl acetate: Methanol=20:1) to give a crude product 1 and 2. The crude product 1 and 2 was combined together then purified by preparative HPLC (column: Xtimate C18 150×25 mm×5 μm; mobile phase: [water (0.05% HCl)-ACN]; B %: 4%-34%, 9.5 min) to give AY-3 and the corresponding cis-isomer.

Preparation of Compound 45

To a solution of AY-3 (33 mg, 73.90 μmol, 1 eq, trans-) in $CHCl_3$ (6 mL) was added saturated $NaHCO_3$ (5 mL), followed by a solution of 2-chloroacetyl chloride (41.73 mg, 369.51 μmol, 29.39 μL, 5 eq) in $CHCl_3$ (3 mL) at 0° C. The mixture stirred at 25° C. for 2 h. The mixture stirred at 25° C. for 1 h to give a yellow solution. LCMS showed that some desired product was formed. The reaction mixture was filtered and washed with DCM (10 mL×3). The filtrate was concentrated to give the crude product. The crude product was purified by preparative HPLC (column: Xtimate C18 150×25 mm×5 μm; mobile phase: [water (0.05% HCl)-ACN]; B %: 30%-60%, 6.5 min) to give Compound 45. LC-MS (m/z): 523.1 $[M+H]^+$. $^1H$ NMR (400 MHz, $CDCl_3$) δ ppm 0.07 (s, 1H), 1.43-1.50 (m, 1H), 1.80-2.02 (m, 2H), 2.88 (br s, 4H), 3.13-3.37 (m, 7H), 3.60-4.18 (m, 5H), 5.77 (br s, 1H), 6.40 (br s, 1H), 7.05 (br s, 3H), 7.37-7.46 (m, 6H), 8.37 (br s, 1H).

Procedure AZ: Synthesis of Compound 50

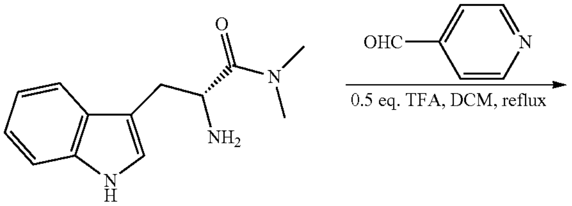

AP-3

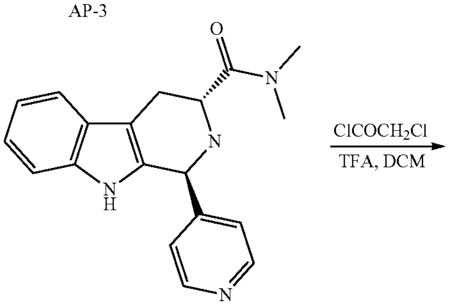

AZ-2

-continued

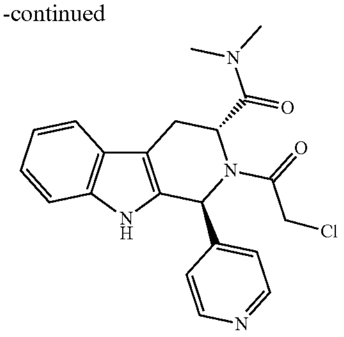

Compound 50

To a solution of AP-3 (200 mg, 864.70 μmol, 1 eq) in DCM (5 mL) was added pyridine-4-carbaldehyde (92.62 mg, 864.70 μmol, 81.24 μL, 1 eq) and TFA (49.30 mg, 432.35 μmol, 32.01 μL, 0.5 eq). The mixture was stirred at 30° C. for 64 h to give a brown suspension. LCMS showed that the reaction was completed. The mixture was adjusted to pH 8 with saturated $NaHCO_3$ and then extracted with DCM (5 mL×3). The organic layers were combined, dried over $Na_2SO_4$, and concentrated to prepare a crude product. The residue was purified by preparative TLC ($SiO_2$, EtOAc: MeOH=10:1) to give AZ-2.

Preparation of Compound 50

To a solution of AZ-2 (34 mg, 106.12 μmol, 1 eq) in $CHCl_3$ (1 mL) were added TEA (53.69 mg, 530.61 μmol, 73.85 μL, 5 eq) and 2-chloroacetyl chloride (59.93 mg, 530.61 μmol, 42.20 μL, 5 eq). The mixture was stirred at 30° C. for 2 h to give a brown solution. LCMS showed that the reaction was completed. A solution of Sat. $NaHCO_3$ (10 mL) was added, and the mixture extracted with DCM (10 mL×3). The organic layers were combined and dried over $Na_2SO_4$, filtered and concentrated to give a crude product. The residue was purified by preparative HPLC (column: YMC-Actus Pro C18 150×30 mm×5 μm; mobile phase: [water (0.1% TFA)-ACN]; B %: 8%-38%, 11 min) to give Compound 50. LC-MS (m/z):397.0 $[M+H]^+$. $^1H$ NMR (400 MHz, METHANOL-$d_4$) δ=8.64 (d, J=6.0 Hz, 2H), 7.98 (brs, 2H), 7.48 (d, J=8.0 Hz, 1H), 7.23 (d, J=7.8 Hz, 1H), 7.12-6.98 (m, 2H), 6.43 (s, 1H), 5.73 (d, J=5.8 Hz, 1H), 4.58-4.41 (m, 1H), 4.38-4.28 (m, 1H), 3.71-3.44 (m, 2H), 3.31 (m, 3H), 2.82 (s, 3H).

Procedure BA: Synthesis of Compound 51

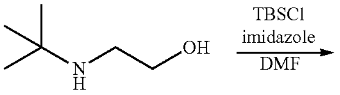

BA-1

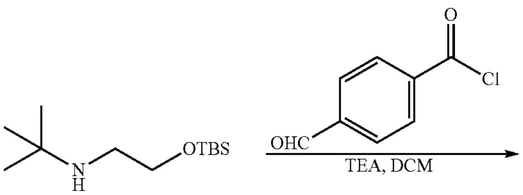

BA-2

-continued

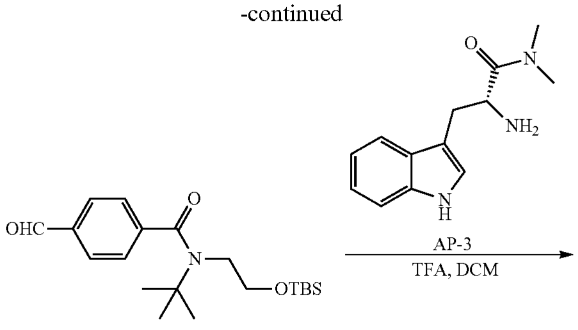

BA-3

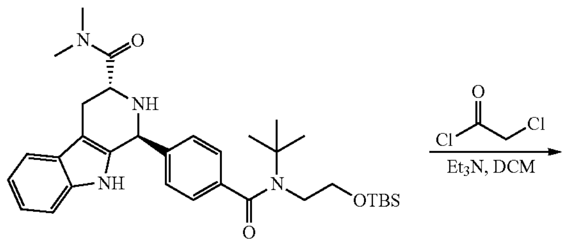

BA-5

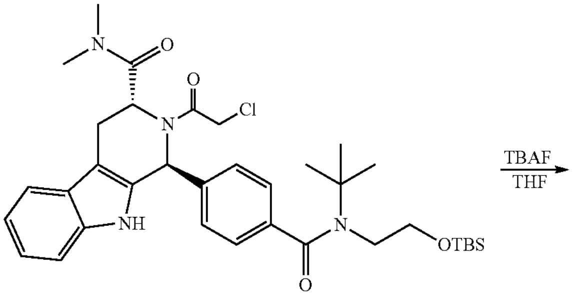

BA-6

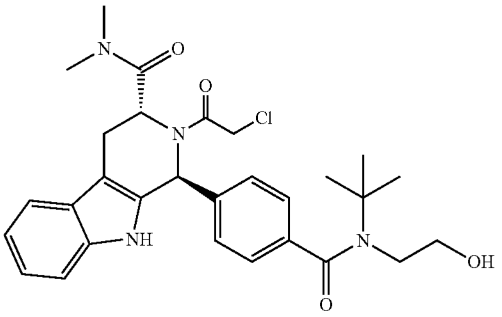

Compound 51

Compound BA-1 (Ig, 8.53 mmol, 1.15 mL, 1 eq) in DMF (10 mL) was mixed with TBSC1 (1.93 g, 12.80 mmol, 1.57 mL, 1.5 eq) and imidazole (1.16 g, 17.07 mmol, 2 eq) at 0° C. The resulting mixture was stirred at 25° C. for 18 h to a muddy mixture. TLC (eluting with: DCM/MeOH=20/1) showed that the reaction was completed. Water (100 mL) was added, and the mixture extracted with EA (30 mL×3). The organic layers were combined, washed with water (30 mL×4), and the organic phase dried by $Na_2SO_4$. The solvent was evaporated to dryness to afford BA-2.

Compound BB-1 (622.71 mg, 4.15 mmol, 1.2 eq) was prepared in DCM (6 mL), oxalyl dichloride (658.08 mg, 5.18 mmol, 453.85 μL, 1.5 eq) and DMF (27.29 mg, 373.30 μmol, 28.72 μL, 1.08e-1 eq) at 25° C. The mixture was stirred at 25° C. for 0.5 h and then stirred at 50° C. for 5 h to afford a colorless mixture. The mixture was evaporated to dryness, the resulting residue suspended in DCM (4 mL) followed by the addition of TEA (699.52 mg, 6.91 mmol, 962.21 μL, 2 eq) and BA-2 (800 mg, 3.46 mmol, 1 eq), and allowed to react at 25° C. for 16 h to afford a brown mixture. TLC (eluting with: PE:EA=5:1) showed that the reaction was completed. $H_2O$ (80 mL) was added to the mixture, which was then extracted with EA (20 mLx3). The organic layers were combined, dried by $Na_2SO_4$, and concentrated to give BA-3.

To a mixture of AP-3 (300 mg, 1.30 mmol, 1 eq) and BA-3 (471.56 mg, 1.30 mmol, 1 eq) in DCM (5 mL) was added TFA (59.16 mg, 518.82 μmol, 38.41 μL, 0.4 eq) at 25° C. The resulting mixture was stirred at 50° C. for 16 h to afford a brown mixture. LC-MS and HPLC showed that AP-3 was not fully consumed. As such, BA-3 (50 mg) was added to the mixture and stirred at 50° C. for 48 h. LC-MS and HPLC showed that the reaction was completed. Saturated $NaHCO_3$ aq. (30 mL) was added, and the mixture extracted with EA (10 mLx3). The organic layers were combined, dried by $Na_2SO_4$, and concentrated to give a crude product. The crude product was purified by preparative TLC (DCM: MeOH=20:1) to afford BA-5. NOE showed that the compound is the trans-isomer.

To the mixture of BA-5 (31.3 mg, 54.26 μmol, 1 eq) and TEA (10.98 mg, 108.52 μmol, 15.10 μL, 2 eq) in DCM (1 mL) was added 2-chloroacetyl chloride (9.19 mg, 81.39 μmol, 6.47 μL, 1.5 eq) at 0° C. and stirred for 1 h to afford a brown mixture. TLC (eluting with EA) showed that the reaction was completed. Water (30 mL) was added and the mixture extracted with DCM (10 mLx3). The combined organic phase was dried by $Na_2SO_4$, and evaporated to dryness to afford BA-6.

Compound BA-6 (35.4 mg, 54.18 μmol, 1 eq) was added to TBAF (1 M, 108.37 μL, 2 eq) in THF (1 mL) and the mixture stirred at 25° C. for 1 h to afford a brown mixture. TLC (eluting with EA) showed that the reaction was completed. The mixture was purified by preparative TLC (EA) to afford Compound 51. LC-MS (m/z): 539.3 $[M+H]^+$. $^1H$ NMR (400 MHz, $CDCl_3$) δ ppm 1.50 (s, 9H), 2.61-3.00 (m, 6H), 3.22-3.65 (m, 4H), 3.78-4.32 (m, 2H), 4.68-5.57 (m, 1H), 6.09-6.81 (m, 1H), 6.92-7.64 (m, 9H), 9.06 (br s, 1H).

A similar scheme was used to synthesize Compound 52: LC-MS (m/z): 575.1 $[M+Na]^+$. $^1H$ NMR (400 MHz, $CDCl_3$) δ ppm 1.52 (s, 9H), 2.87 (br s, 3H), 3.15 (s, 2H), 3.24-3.32 (m, 2H), 3.35 (br d, J=5.52 Hz, 1H), 3.41-3.50 (m, 2H), 4.08-4.21 (m, 1H), 7.02-7.44 (m, 11H), 7.51 (br d, J=9.03 Hz, 1H), 7.97-8.14 (m, 1H).

Procedure BB: Synthesis of Compound 54

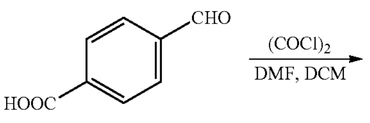

BB-1

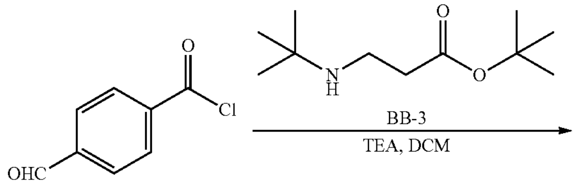

BB-2

-continued

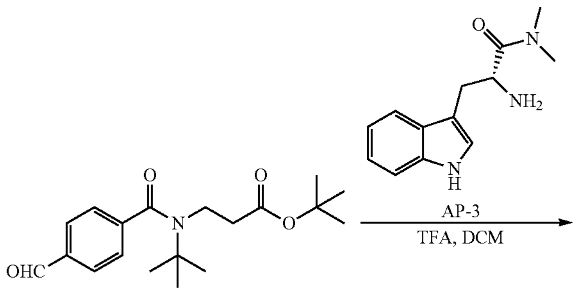

BB-4

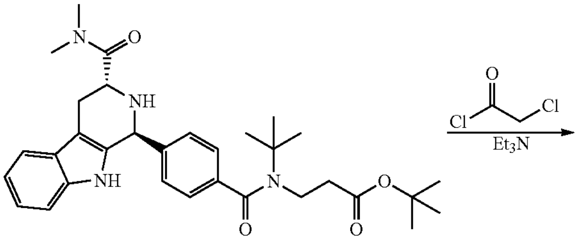

BB-6

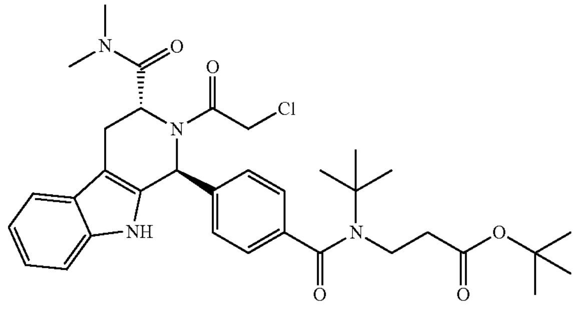

Compound 54

To a mixture of BB-1 (2 g, 13.32 mmol, 1 eq) in DCM were added oxalyl dichloride (2.03 g, 15.99 mmol, 1.40 mL, 1.2 eq) and DMF (23.75 mg, 324.92 μmol, 25.00 μL, 2.44e-2 eq), and the mixture stirred at 25° C. for 0.5 h. The mixture was further stirred at 45° C. for 5 h to afford a brown mixture. The mixture was evaporated to dryness to afford BB-2.

To a mixture of BB-2 (300 mg, 1.78 mmol, 1 eq) in DCM, were added TEA (270.12 mg, 2.67 mmol, 371.55 μL, 1.5 eq) and BB-3 (358.24 mg, 1.78 mmol, 1 eq). The mixture was stirred at 25° C. for 18 h to afford a brown mixture. TLC (PE: EA=1:2) showed that the reaction was completed. Saturated $NaHCO_3$ aqueous 40 mL was added, and the mixture extracted with DCM (15 mLx3). The organic layers were combined, washed with $Na_2CO_3$ (aq.) (15 mLx3), and the organic phase dried by $Na_2SO_4$. The mixture was evaporated to dryness to afford BB-4.

To a mixture of AP-3 (65 mg, 281.03 μmol, 1 eq) and BB-4 (93.70 mg, 281.03 μmol, 1 eq) in DCM (1 mL) was added TFA (12.82 mg, 112.41 μmol, 8.32 μL, 0.4 eq), and the mixture stirred at 25° C. for 18 h to afford a brown mixture. TLC (EA) showed that the reaction was completed. $H_2O$ (20 mL) was added to the mixture, and the aqueous phase extracted with DCM (10 mLx3). The organic layers were combined and dried by $Na_2SO_4$. The mixture was evaporated to dryness. The product was purified by preparative TLC (EA) to afford BB-6.

Preparation of Compound 54

To a mixture of BB-6 (10 mg, 18.29 µmol, 1 eq) and TEA (3.70 mg, 36.58 µmol, 5.09 µL, 2 eq) in DCM (0.5 mL) was added 2-chloroacetyl chloride (3.10 mg, 27.44 µmol, 2.18 µL, 1.5 eq) at 0° C., and the mixture stirred for 4 h to afford a brown mixture. TLC (EA) showed that the reaction was completed. The mixture was purified by preparative TLC (PE: EA=2:1) to afford Compound 54. LC-MS (m/z): 623.1 $[M+H]^+$. $^1H$ NMR (400 MHz, $CDCl_3$) δ ppm 1.24 (br s, 9H), 1.45 (s, 9H), 2.18-2.37 (m, 2H), 2.63-2.99 (m, 5H), 3.06-3.34 (m, 2H), 3.34-3.53 (m, 2H), 3.73-4.15 (m, 2H), 5.11-5.58 (m, 1H), 6.27 (br s, 1H), 6.81-7.56 (m, 11H), 8.32 (s, 1H).

Procedure BC: Synthesis of Compound 55

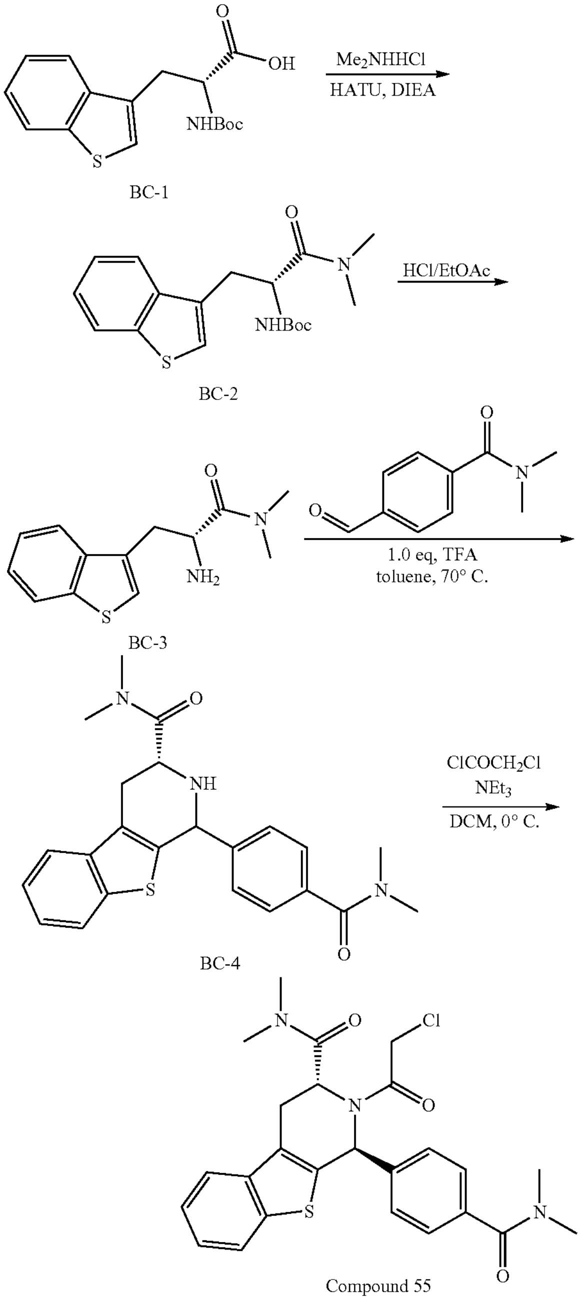

BC-1

BC-2

BC-3

BC-4

Compound 55

-continued

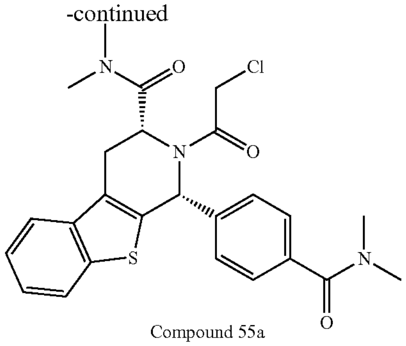

Compound 55a

To a solution of BC-1 (200 mg, 622.30 µmol, 1 eq) and HATU (354.93 mg, 933.45 µmol, 1.5 eq) in DMF (4 mL) was added dropwise DIEA (201.07 mg, 1.56 mmol, 270.98 µL, 2.5 eq) at 0° C., and the mixture stirred at 0° C. for 30 min. N-methyl methanamine (76.12 mg, 933.45 µmol, 85.53 µL, 1.5 eq, HCl salt) was added and the mixture stirred at 0° C. to give a dark red solution. TLC (eluting with: PE/EtOAc=3/1) showed that the reaction was completed. The reaction mixture was partitioned between with water (30 mL) and EtOAc (40 mL), and the aqueous layers extracted with EtOAc (30 mL×2). The organic layers were combined and washed with brine (30 mL), dried over sodium sulfate and then concentrated to give the crude product. The crude product was purified by silica gel chromatography (eluting with: PE/EtOAc=10/1-5/1) to afford BC-2.

Compound BC-2 (200 mg, 573.95 µmol, 1 eq) was dissolved in HCl/EtOAc (5 mL) and the mixture stirred at 20° C. for 4 h to give a yellow solution. TLC (eluting with: PE/EtOAc=0/1) showed that the reaction was completed. The reaction mixture was quenched with Sat. $NaHCO_3$ (15 mL) and extracted with EtOAc (20 mL×3). The organic layers were combined and dried over $Na_2SO_4$ and concentrated to give a crude product. The crude product was purified by flash column chromatography (eluting with: EA/MeOH=10/1-5/1) to afford BC-3.

To a solution of BC-3 (98 mg, 394.62 µmol, 1 eq) and 4-formyl-N, N-dimethyl-benzamide (104.89 mg, 591.92 µmol, 1.5 eq) in toluene (5 mL) was added TFA (45.00 mg, 394.61 µmol, 29.22 µL, 1 eq), and the reaction mixture stirred at 80° C. for 16 h to give a yellow solution. LCMS and TLC (eluting with: EA/MeOH=20/1) showed that the reaction was completed. Following quenching with Sat. $NaHCO_3$ (15 mL), the mixture was extracted with EtOAc (20 mL×3). The organic layers were combined, dried over $Na_2SO_4$, and then concentrated to give a crude product. The crude product was purified by flash column chromatography (eluting with: ethyl acetate/methanol=1:0-5:1) to afford BC-4.

Preparation of Compound 55

To a solution of BC-4 (62.00 mg, 152.14 µmol, 1 eq) and Et3N (30.79 mg, 304.27 µmol, 42.35 µL, 2 eq) in DCM (5 mL) was added dropwise 2-chloroacetyl chloride (34.37 mg, 304.27 µmol, 24.20 µL, 2 eq), and the mixture stirred at 0° C. for 16 h. TLC (eluting with: EA/MeOH=10/1) showed that the reaction was completed. The reaction mixture was quenched with Sat. $NaHCO_3$ (15 mL), and extracted with DCM (20 mL×3). The organic layers were combined, dried over $Na_2SO_4$, and then concentrated to give a crude product. The crude product was purified by preparative HPLC (column: Xtimate C18 150×25 mm×5 μm; mobile phase: [water (0.05% HCl)–ACN]; B %: 30%-60%, 9.5 min) to afford Compound 55 and Compound 55a. LC-MS (m/z): 483.9 [M+H]+. $^1$H NMR (400 MHz, DMSO-d6) δ: 2.71 (s, 3H), 2.81-2.89 (m, 3H), 2.94 (s, 3H), 3.09 (s, 3H), 4.02-4.44 (m, 1H), 4.69 (d, J=13.80 Hz, 1H), 5.61 (s, 1H), 6.58 (s, 1H), 7.28-7.42 (m, 4H), 7.44-7.61 (m, 2H), 7.81 (d, J=8.03 Hz, 1H), 7.87 (d, J=8.03 Hz, 1H).

Procedure BD: Synthesis of Compound 56

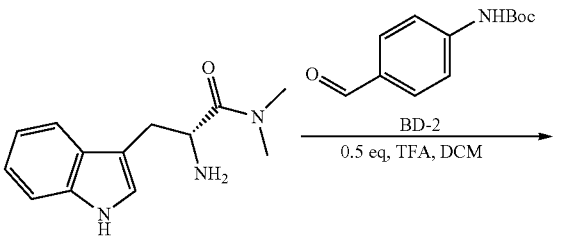

AV-1

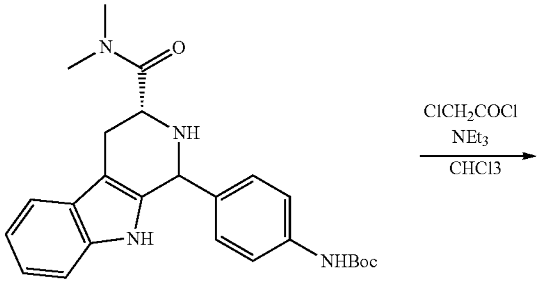

BD-3

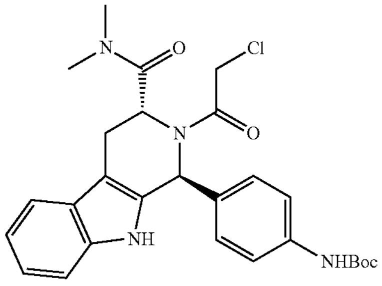

Compound 56

To a solution of AV-1 (0.1 g, 432.35 μmol, 1.1 eq) and BD-2 (86.96 mg, 393.05 μmol, 1 eq) in DCM (4 mL) was added TFA (44.82 mg, 393.05 μmol, 29.10 μL, 1 eq) at 0° C. The reaction mixture was stirred at 20° C. for 8 h to give a yellow solution. TLC (eluting with: EA/MeOH=10/1) showed the reaction was completed. The reaction mixture was partitioned between water (15 mL) and DCM (15 mL), and saturated sodium bicarbonate solution added to adjust the pH to 9. The aqueous layer was extracted with DCM (15 mL×2), and the organic layers combined and concentrated. The crude product was purified by Prep-HPLC (column: Phenomenex Gemini 150×25 mm×10 μm; mobile phase: [water (0.05% HCl)-ACN]; B %: 20%-40%, 9.5 min) to give BD-3. $^1$H NMR (400 MHz, DMSO-d6) δ: 1.46 (s, 9H), 2.69 (s, 3H), 2.80 (s, 3H), 3.73 (d, J=5.27 Hz, 1H), 5.13 (s, 1H), 6.95-7.00 (m, 1H), 7.01-7.09 (m, 3H), 7.26 (d, J=7.78 Hz, 1H), 7.36-7.47 (m, 3H), 9.30 (s, 1H), 10.73 (s, 1H).

To a solution BD-3 (60 mg, 138.08 μmol, 1 eq) and Et3N (27.94 mg, 276.16 μmol, 38.44 μL, 2 eq) in DCM (3 mL)

was added 2-chloroacetyl chloride (23.39 mg, 207.12 μmol, 16.47 μL, 1.5 eq) at 0° C. The reaction mixture was stirred at 20° C. for 16 h to give a yellow solution. TLC (eluting with: EA/MeOH=10/1) showed the reaction was completed. The reaction mixture was partitioned between water (15 mL) and DCM (15 mL), the aqueous layers was extracted with DCM (20 mL×2). The combined organic layers dried over sodium sulfate and concentrated. The product was purified by prep-HPLC (column: Xtimate C18 150×25 mm×5 μm; mobile phase: [water (0.05% HCl)-ACN]; B %: 53%-53%, 9.5 min) to afford Compound 56. LC-MS (m/z): 533.1 [M+Na]+. $^1$H NMR (400 MHz, $CDCl_3$) δ: 1.43 (s, 9H), 2.80 (s, 3H), 2.89 (s, 1H), 3.25 (s, 2H), 3.84 (s, 1H), 4.12 (d, J=7.28 Hz, 1H), 5.36-5.63 (m, 1H), 6.25 (s, 1H), 6.43 (s, 1H), 7.04 (s, 1H), 7.20-7.32 (m, 4H), 7.37-7.49 (m, 1H), 8.01 (s, 1H).

Procedure BE: Synthesis of Compound 58

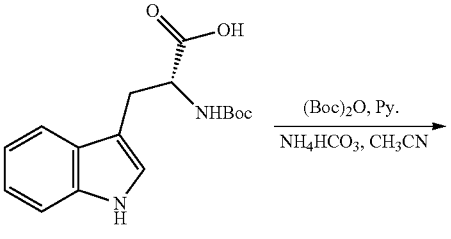

AA-1

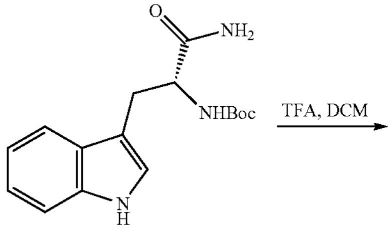

BE-1

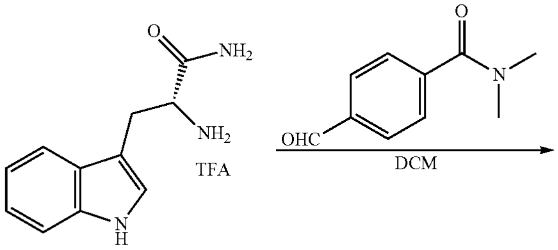

BE-2

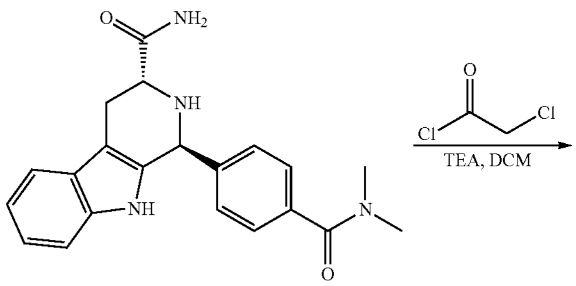

BE-4

-continued

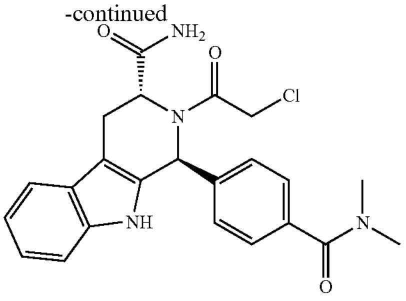

Compound 58

To a stirred solution of AA-1 (3.04 g, 10 mmol, 1 eq), pyridine (490.00 mg, 6.19 mmol, 0.5 mL, 6.19e-1 eq) and $(Boc)_2O$ (2.84 g, 13.00 mmol, 2.99 mL, 1.3 eq) in $CH_3CN$ (15 mL) was added $NH_4HCO_3$ (996.10 mg, 12.60 mmol, 1.04 mL, 1.26 eq). The resulting mixture was stirred at 25° C. for 16 h to afford a brown mixture. TLC (eluting with: DCM/MeOH=5/1) and LC-MS showed the reaction was completed. The mixture was evaporated to dryness and then $H_2O$ (60 mL) added. The solution was extracted with EA (20 mL×3). The combined organic phase was evaporated to dryness to afford BE-2. $^1H$ NMR (400 MHz, $CDCl_3$) δ ppm 1.42 (s, 9H), 3.07-3.38 (m, 2H), 4.48 (br s, 1H), 5.20 (br s, 1H), 5.51 (br s, 1H), 5.84 (br s, 1H), 7.06 (d, J=1.51 Hz, 1H), 7.09-7.16 (m, 1H), 7.16-7.23 (m, 1H), 7.36 (d, J=8.03 Hz, 1H), 7.59-7.75 (m, 1H), 8.31 (br s, 1H).

To a mixture of BE-2 (1.26 g, 4.14 mmol, 1 eq) in DCM (8 mL), TFA (6.16 g, 54.02 mmol, 4 mL, 13.04 eq) was added at 25° C. The resulting mixture was stirred at 25° C. for 16 h to afford a brown mixture. TLC (eluting with: DCM/MeOH=5/1) showed the reaction was completed. The reaction was evaporated to dryness to afford BE-3.

To a mixture of BE-3 (400.0 mg, 1.97 mmol, 1 eq) and 4-formyl-N,N-dimethyl-benzamide (348.75 mg, 1.97 mmol, 1 eq) in DCM (5 mL) was added TFA (89.76 mg, 787.25 μmol, 58.29 μL, 0.4 eq) at 25° C. The resulting mixture was stirred at 50° C. for 18 h to afford a brown mixture. TLC (EA: MeOH=40:1) showed the reaction was completed. 30 mL saturated $NaHCO_3$ (aq.) was added to the reaction mixture, and the resulting mixture extracted with DCM (10 mL×3). The combined organic extracts were dried by $Na_2SO_4$, and the solvent evaporated to dryness to afford the crude product. The product was purified by Prep-HPLC (column: Xtimate C18 150×25 mm×5 μm; mobile phase: [water (0.05% HCl)-ACN]; B %: 2%-32%, 9.5 min) to afford BE-4. $^1H$ NMR (400 MHz, DMSO-d6) δ ppm 2.90 (br s, 3H), 2.93-3.14 (m, 6H), 4.03-4.26 (m, 1H), 4.06-4.17 (m, 1H), 5.99 (br s, 1H), 7.05-7.12 (m, 1H), 7.13-7.20 (m, 1H), 7.27-7.39 (m, 3H), 7.48 (d, J=8.28 Hz, 2H), 7.60 (d, J=8.03 Hz, 1H), 7.70 (br s, 1H), 7.87-8.07 (m, 1H), 9.67 (br s, 1H), 10.37 (br s, 1H), 11.12 (s, 1H).

Preparation of Compound 58

To a mixture of BE-4 (12.2 mg, 30.59 μmol, 1 eq, HCl) and TEA (6.19 mg, 61.17 μmol, 8.51 μL, 2 eq) in DCM (1 mL) was added 2-chloroacetyl chloride (3.80 mg, 33.64 mol, 2.68 μL, 1.1 eq) at 0° C. The resulting mixture was stirred at 0° C. for 2 h to afford a brown mixture. TLC (EA: MeOH=40:1) showed the reaction was completed. The reaction was purified by Prep-TLC (EA: MeOH=40:1) to afford the product. It was purified by Prep-TLC again to afford Compound 58. LC-MS (m/z): 461.0 [M+Na]+.

Procedure BF: Synthesis of Compound 59

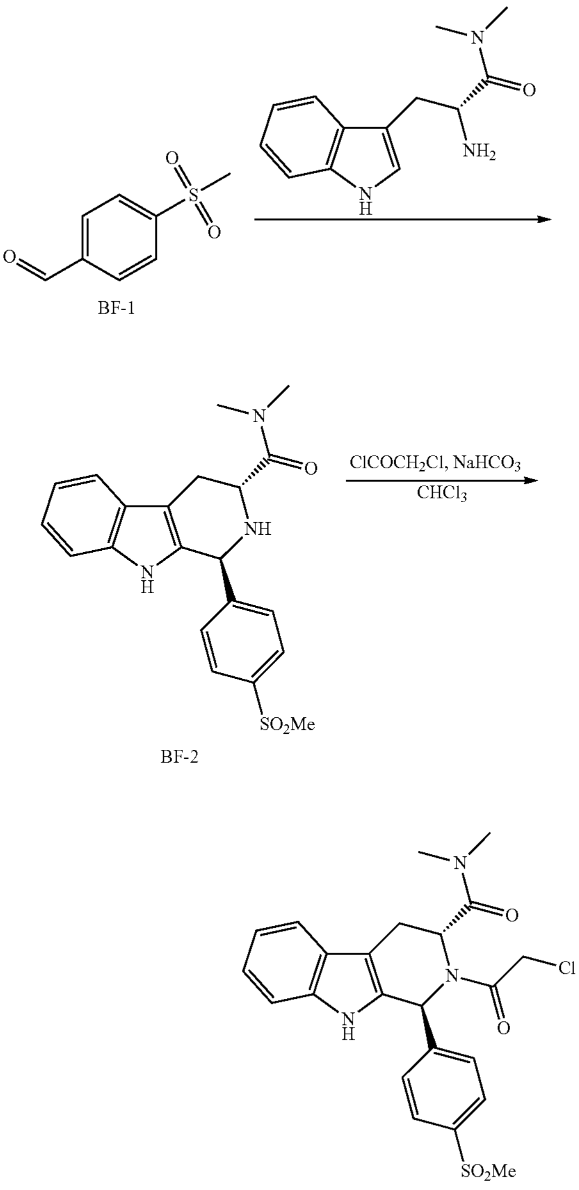

BF-1

BF-2

Compound 59

Preparation of Compound BF-2

To a solution of (2R)-2-amino-3-(1H-indol-3-yl)-N,N-dimethyl-propanamide (200 mg, 864.70 μmol, 1 eq) in DCM (3 mL) were added 4-methylsulfonylbenzaldehyde (159.29 mg, 864.70 μmol, 1 eq) and TFA (49.30 mg, 432.35 μmol, 32.01 μL, 0.5 eq). The mixture was stirred at 25° C. for 12 h to give a yellow solution. LCMS and TLC (eluting with:EtOAc=100%) showed the reaction was completed. The reaction mixture was quenched with Sat. $NaHCO_3$ (5 mL) and extracted with DCM (15 mL×2). The organic layers were dried over $Na_2SO_4$ and concentrated to give the crude product. The product was purified by prep-TLC (eluting with:EtOAc=100%) to give BF-2.

Preparation of Compound 59

To a solution of BF-2 (40 mg, 100.63 μmol, 1 eq) in $CHCl_3$ (2 mL) were added $NaHCO_3$ (84.54 mg, 1.01 mmol, 39.14 μL, 10 eq) and 2-chloroacetyl chloride (34.10 mg, 301.89 μmol, 24.01 μL, 3 eq) at 0° C. The mixture was stirred at 20° C. for 1 h to give a yellow solution. LCMS showed the reaction was completed. The reaction mixture was filtered and washed with DCM (30 mL). The filtrate was concentrated to give the crude product. The product was purified by prep-HPLC (column: Xtimate C18 150×25 mm×5 μm; mobile phase: [water (0.05% HCl)-ACN]; B %: 30%-60%, 9.5 min) to give Compound 59. LC-MS (m/z): 473.9.

Procedure BG: Synthesis of Compound 61

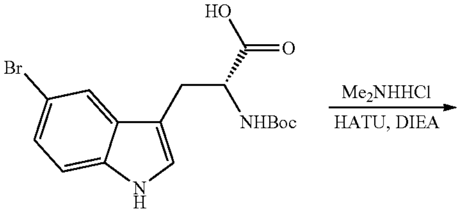

BG-1

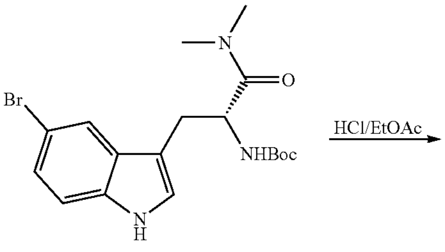

BG-2

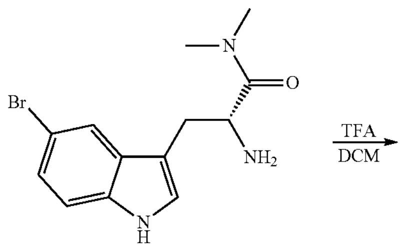

BG-3

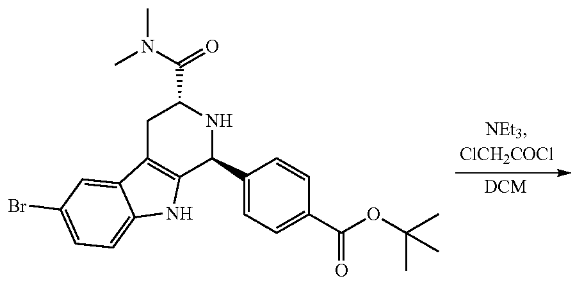

BG-4

-continued

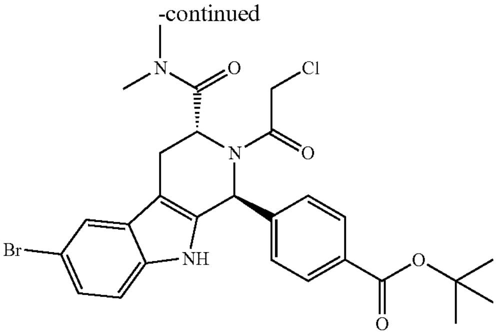

Compound 61

To a stirred mixture of BG-1 (200 mg, 521.87 μmol, 1 eq), HATU (297.65 mg, 782.81 μmol, 1.5 eq) and DIEA (202.34 mg, 1.57 mmol, 272.70 μL, 3 eq) in DMF (2 mL) was added N-methylmethanamine (63.83 mg, 782.81 μmol, 71.72 μL, 1.5 eq, HCl) at 25° C. The resulting mixture was stirred at 25° C. for 18 h to afford a brown mixture. TLC (eluting with: PE/EtOAc=2/1) showed the reaction was completed. $H_2O$ (25 mL) was added and the resulting mixture was extracted with EA (10 mL×3). The combined organic layers were dried by $Na_2SO_4$, and the solvent evaporated to dryness to afford a crude product. The product was purified by a flash column eluting with 20% EA in PE to 50% EA in PE to afford BG-2. $^1$H NMR (400 MHz, $CDCl_3$) δ ppm 1.42 (s, 9H), 2.68 (s, 3H), 2.84 (s, 3H), 3.10 (d, J=6.53 Hz, 2H), 4.87 (q, J=7.03 Hz, 1H), 5.53 (br d, J=8.03 Hz, 1H), 7.07 (s, 1H), 7.16-7.32 (m, 2H), 7.70 (s, 1H), 8.02 (s, 1H), 8.16 (br s, 1H).

The mixture of BG-2 (200 mg, 487.44 μmol, 1 eq) in HCl/EtOAc (4 M, 2.92 mL, 23.96 eq) was stirred at 25° C. for 3 h to afford a brown mixture. LC-MS showed the reaction was completed. The reaction was evaporated to dryness to afford BG-3. LC-MS (m/z): 309.9 [M+H]+.

To the mixture of BG-3 (85.0 mg, 274.03 μmol, 1 eq, free) and tert-butyl 4-formylbenzoate (56.51 mg, 274.03 μmol, 1 eq) in DCM (2 mL) was added TFA (12.50 mg, 109.61 μmol, 8.12 μL, 0.4 eq) at 25° C. The resulting mixture was stirred at 45° C. for 18 h to afford a brown mixture. LC-MS and TLC (PE: EA=1:2) showed the reaction was completed. $H_2O$ (25 mL) was added and the resulting mixture extracted with EA (10 mL×3). The combined organic layers were dried by $Na_2SO_4$, and the solvent evaporated to dryness to afford the crude product. The product was purified by prep-TLC (PE: EA=1:2) to afford BG-4 and the corresponding cis-isomer 61a. BG-4 was the trans-isomer and BG-4a was the cis-isomer according to the comparison of two NMR charts.

BG-4: $^1$H NMR (400 MHz, $CDCl_3$) δ ppm 1.58 (s, 9H), 2.79 (s, 3H), 2.84-3.05 (m, 5H), 3.85 (dd, J=10.04, 4.77 Hz, 1H), 5.32 (s, 1H), 7.17 (d, J=8.53 Hz, 1H), 7.24-7.32 (m, 3H), 7.67 (s, 1H), 7.84 (s, 1H), 7.92 (d, J=8.03 Hz, 2H).

BG-4a: $^1$H NMR (400 MHz, $CDCl_3$) δ ppm 1.60 (s, 9H), 2.89-3.08 (m, 5H), 3.17 (s, 3H), 4.17 (dd, J=9.66, 5.40 Hz, 1H), 5.30 (s, 1H), 7.06-7.14 (m, 1H), 7.20-7.27 (m, 1H), 7.37 (d, J=8.03 Hz, 2H), 7.46-7.58 (m, 1H), 7.64 (s, 1H), 7.93-8.03 (m, 2H).

Preparation of 61

To a mixture of BG-4 (50.0 mg, 100.32 μmol, 1 eq) and TEA (20.30 mg, 200.64 μmol, 27.93 μL, 2 eq) in DCM (1 mL) was added 2-chloroacetyl chloride (17.00 mg, 150.48 μmol, 11.97 μL, 1.5 eq) at 0° C. and the mixture stirred for 2 h to afford a brown mixture. LC-MS and TLC (PE: EA=2:1) showed the reaction was completed. The reaction was purified by prep-TLC (PE: EA=2:1) to afford 61. $^1$H NMR (400 MHz, $CDCl_3$) δ ppm 1.55 (s, 9H), 2.86-3.07 (m, 3H), 3.20-3.55 (m, 5H), 3.75 (br s, 1H), 3.84-4.31 (m, 2H), 5.98-6.29 (m, 1H), 6.47 (br s, 1H), 6.78 (br s, 1H), 7.32-7.65 (m, 3H), 7.93 (br d, J=7.78 Hz, 2H), 9.07 (br s, 1H). LC-MS (m/z): 575.1 [M+H]+.

Procedure BH: Synthesis of Compound 62 and Compound 62a

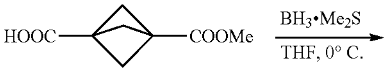

BH-1

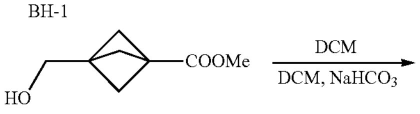

BH-2

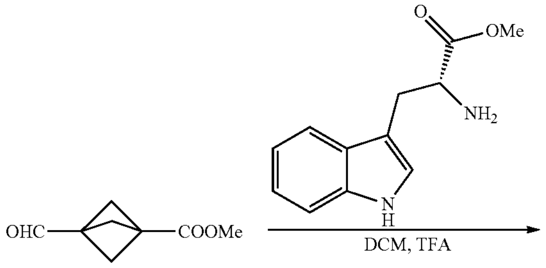

BH-3

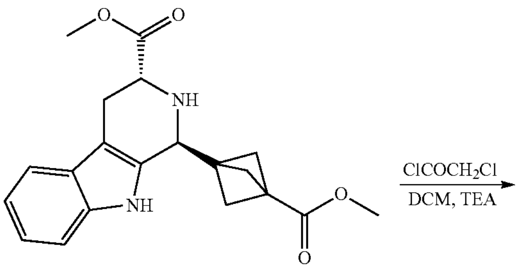

BH-4

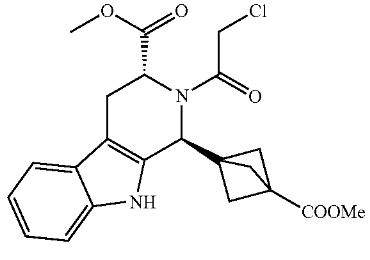

Compound 62

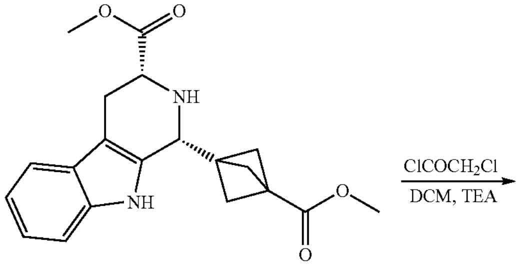

BH-4a

-continued

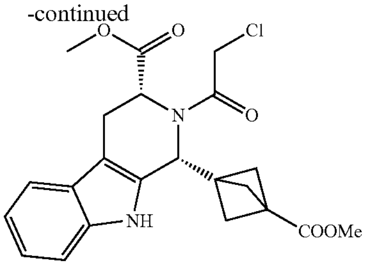

Compound 62a

To a solution of BH-1 (300 mg, 1.76 mmol, 1 eq) in THF (20 mL) was added $BH_3$-$Me_2S$ (10 M, 528.91 μL, 3 eq) at 0° C. The reaction mixture was stirred at 0° C. for 2 h to give a colorless solution. TLC (eluting with: PE/EtOAc=1/1, color developing reagent: $I_2$) showed most of the starting material was consumed. HCl (1 M, 5 mL) was added dropwise until no bubble was produced. The reaction mixture was partitioned between water (20 mL) and EtOAc (20 mL), and the aqueous layer extracted with EtOAc (20 mL×2). The combined organic layers were dried over sodium sulfate and concentrated. The product was purified by silica gel chromatography (PE: EA=10:1-3:1) to give BH-2. $^1$H NMR (400 MHz, $CDCl_3$) δ: 2.00 (s, 6H), 3.64 (s, 2H), 3.68 (s, 3H).

To a solution of BH-2 (248 mg, 1.59 mmol, 1 eq) and $NaHCO_3$ (266.80 mg, 3.18 mmol, 123.52 μL, 2 eq) in DCM (15 mL) was added Dess-Martin periodinane (DMP; 808.20 mg, 1.91 mmol, 589.93 μL, 1.2 eq), and the reaction mixture stirred at 0° C. for 2 h. TLC (eluting with: PE/EtOAc=1/1) showed most of the STM was consumed. The reaction mixture was partitioned between water (20 mL) and EtOAc (20 mL), and the aqueous layer extracted with EtOAc (20 mL×2). The combined organic layers were dried over sodium sulfate and concentrated. The product was purified by silica gel chromatography (PE:EA=10:1-3:1) to afford BH-3. $^1$H NMR (400 MHz, $CDCl_3$) δ: 2.31 (s, 6H), 3.70 (s, 3H), 9.60 (s, 1H).

To a solution of BH-3 (216 mg, 1.40 mmol, 1 eq) and methyl (2R)-2-amino-3-(1H-indol-3-yl)propanoate (366.95 mg, 1.68 mmol, 1.2 eq) in DCM (10 mL) was added TFA (79.88 mg, 700.56 μmol, 51.87 μL, 0.5 eq). The reaction mixture was stirred at 40° C. for 16 h to give a yellow suspension. TLC (eluting with: PE/EtOAc=1/1) showed most of STM was consumed. Saturated sodium bicarbonate was added to adjust pH to 7-8. The reaction mixture was partitioned between water (20 mL) and EtOAc (20 mL). The aqueous layer was extracted with EtOAc (20 mL×2), and the combined organic layers dried over sodium sulfate and concentrated. The product was purified by prep-HPLC (column: Xtimate C18 150×25 mm×5 m; mobile phase: [water (0.05% HCl)-ACN]; B %: 9%-39%, 9.5 min) to give BH-4a and BH-4.

BH-4: $^1$H NMR (400 MHz, DMSO-d6) δ: 2.07-2.29 (m, 6H), 3.05-3.21 (m, 1H), 3.60 (s, 3H), 3.77 (s, 3H), 4.54 (t, J=6.27 Hz, 1H), 4.79-4.90 (m, 1H), 7.01-7.07 (m, 1H), 7.14 (t, J=7.28 Hz, 1H), 7.42 (d, J=8.03 Hz, 1H), 7.50 (d, J=8.03 Hz, 1H), 10.06 (s, 1H), 10.56-10.88 (m, 1H), 10.99-11.10 (m, 1H).

BH-4a: $^1$H NMR (400 MHz, DMSO-d6) δ: 2.14 (dd, J=9.29, 1.25 Hz, 3H), 2.45 (d, J=8.53 Hz, 3H), 3.08-3.20 (m, 1H), 3.22-3.32 (m, 1H), 3.63 (s, 3H), 3.87 (s, 3H), 4.54 (s,

1H), 4.83 (s, 1H), 7.01-7.08 (m, 1H), 7.15 (t, J=7.28 Hz, 1H), 7.49 (t, J=8.91 Hz, 2H), 10.22 (s, 1H), 10.49 (s, 1H), 10.86 (s, 1H).

Preparation of 62

To a solution of BH-4 (49 mg, 125.36 μmol, 1 eq, HCl) and Et3N (25.37 mg, 250.73 μmol, 34.90 μL, 2 eq) in DCM (4 mL) was added dropwise 2-chloroacetyl chloride (21.24 mg, 188.05 μmol, 14.96 μL, 1.5 eq) at 0° C., the reaction mixture was stirred at 0° C. for 16 h to give a yellow solution. TLC (eluting with: PE/EtOAc=1/1) showed most of STM was consumed. The reaction mixture was quenched with Sat. $NaHCO_3$ (15 mL) and extracted with DCM (20 mL×3). The organic layers were dried over $Na_2SO_4$ and concentrated to give the crude product. The product was purified by prep-TLC (Dichloromethane/Methanol=10:1)) to afford 62. LC-MS (m/z): 431.3 [M+H]+. $^1$H NMR (400 MHz, DMSO-d6) δ: 1.66-1.78 (m, 3.3H), 2.02-2.11 (m, 2.7H), 3.41 (s, 2H), 3.46-3.54 (m, 2H), 3.59 (s, 1H), 3.63 (s, 1H), 4.21-4.33 (m, 1H), 4.38 (d, J=13.55 Hz, 0.46H), 4.54 (d, J=13.30 Hz, 0.47H), 4.68 (d, J=13.80 Hz, 0.56H), 5.15 (d, J=8.53 Hz, 1H), 5.34 (s, 0.64H), 6.96-7.02 (m, 1H), 7.07 (q, J=7.19 Hz, 1H), 7.34 (dd, J=13.80, 8.03 Hz, 1H), 7.47 (t, J=7.40 Hz, 1H), 10.94 (s, 0.38H), 11.08 (s, 0.55H).

Preparation of 62a

To a solution of BH-4a (51.68 mg, 145.83 μmol, 1 eq, HCl) and Et3N (29.51 mg, 291.66 μmol, 40.60 μL, 2 eq) in DCM (4 mL) was added dropwise 2-chloroacetyl chloride (24.71 mg, 218.75 μmol, 17.40 μL, 1.5 eq) at 0° C. The reaction mixture was stirred at 0° C. for 16 h to give a yellow solution. LCMS and TLC (eluting with: PE/EtOAc=3/1) showed the reaction was completed. The reaction mixture was quenched with Sat. $NaHCO_3$ (15 mL) and extracted with DCM (20 mL×3). The organic layers were dried over $Na_2SO_4$ and concentrated to give the crude product. The product was purified by prep-TLC (DCM) to afford 62a. LC-MS (m/z): 431.0 [M+H]+. $^1$H NMR (400 MHz, DMSO-d6) δ ppm 1.88-2.02 (m, 6H), 2.85-3.04 (m, 1H), 3.23-3.29 (m, 1H), 3.56 (s, 3H), 3.64 (s, 2H), 3.67 (s, 1H), 4.37 (d, J=13.55 Hz, 0.34H), 4.48 (d, J=13.80 Hz, 0.66H), 4.74 (d, J=13.80 Hz, 0.34H), 4.82 (d, J=13.80 Hz, 0.66H), 4.88 (t, J=7.65 Hz, 0.34H), 5.20 (d, J=5.77 Hz, 0.64H), 5.25 (s, 0.34H), 5.55 (s, 0.66H), 6.96-7.03 (m, 1H), 7.09 (t, J=7.53 Hz, 1H), 7.35-7.40 (m, 1H), 7.44-7.53 (m, 1H), 10.65 (s, 0.66H), 11.02 (s, 0.34H).

Procedure BI: Synthesis of Compound 63

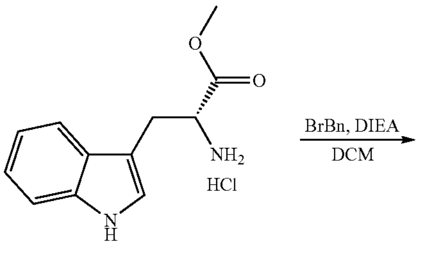

AA-1

-continued

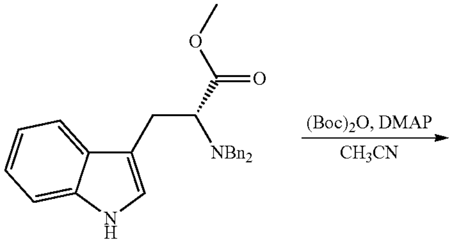

BI-2

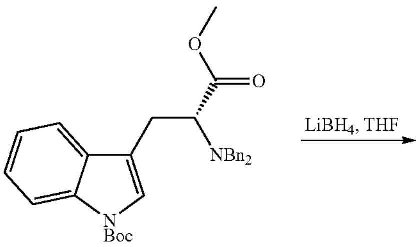

BI-3

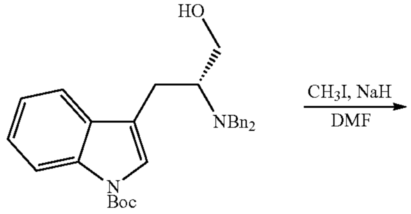

BI-4

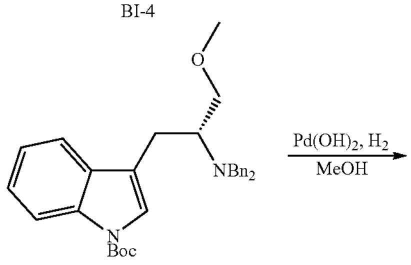

BI-5

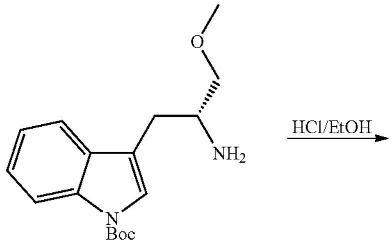

BI-6

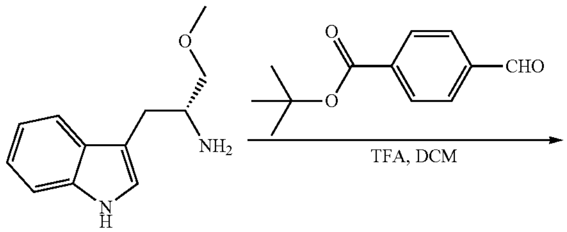

BI-7

-continued

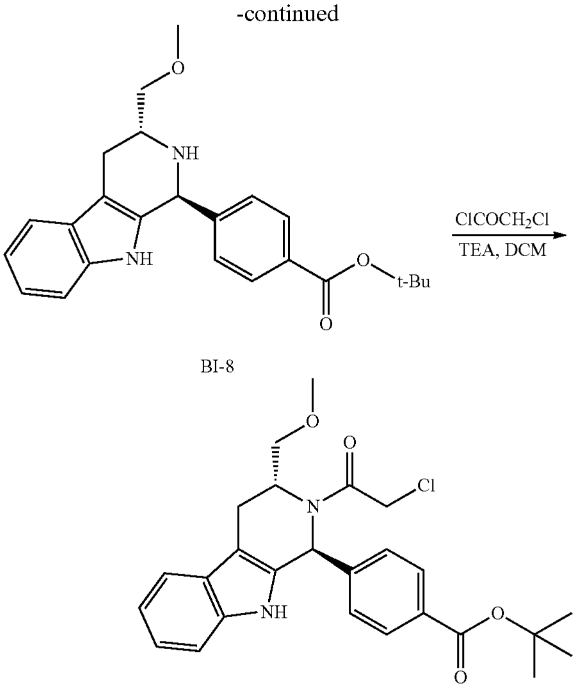

BI-8

Compound 63

To a mixture of AA-1 (5 g, 19.63 mmol, 1 eq, HCl) and DIEA (8.88 g, 68.70 mmol, 11.97 mL, 3.5 eq) in DCM (20 mL), was added dropwise bromomethylbenzene (7.39 g, 43.19 mmol, 5.13 mL, 2.2 eq) at 0° C. The resulting mixture was stirred at 25° C. for 48 h to afford a brown mixture. TLC (eluting with: PE/EtOAc=3/1) showed the reaction was completed. The reaction mixture was quenched with $H_2O$ (50 mL) and extracted with EA (20 mL×3). The combined organic extracts were dried by $Na_2SO_4$, and the solvent evaporated to dryness to afford the crude product. The product was purified by flash column (15% EA in PE to 50% EA in PE) to afford BI-2. $^1$H NMR (400 MHz, $CDCl_3$) δ ppm 3.09 (dd, J=14.31, 5.77 Hz, 1H), 3.38 (dd, J=14.31, 9.29 Hz, 1H), 3.54 (d, J=13.80 Hz, 2H), 3.69 (s, 3H), 3.80 (dd, J=9.16, 5.65 Hz, 1H), 4.01 (d, J=13.80 Hz, 2H), 6.90 (d, J=2.01 Hz, 1H), 6.92-6.98 (m, 1H), 7.07-7.17 (m, 2H), 7.18-7.37 (m, 10H), 7.91 (br s, 1H).

To a mixture of methyl BI-2 (3.9 g, 9.79 mmol, 1 eq) and DMAP (239.13 mg, 1.96 mmol, 0.2 eq) in $CH_3CN$ (45 mL) was added $Boc_2O$ (3.20 g, 14.68 mmol, 3.37 mL, 1.5 eq). The resulting mixture was stirred at 25° C. for 16 h to afford a brown mixture. TLC (PE: EA=6:1) showed the reaction was completed. $H_2O$ (120 mL) was added to the mixture, and the aqueous phase extracted with ethyl acetate (30 mL×3). The combined organic phases was dried with anhydrous $Na_2SO_4$, filtered and concentrated in vacuo to afford BI-3. $^1$H NMR (400 MHz, $CDCl_3$) δ ppm 1.66 (s, 9H), 2.93-3.07 (m, 1H), 3.27 (dd, J=14.43, 8.41 Hz, 1H), 3.33-3.33 (m, 1H), 3.53 (d, J=13.80 Hz, 2H), 3.69-3.83 (m, 4H), 3.99 (d, J=13.55 Hz, 2H), 6.95-7.07 (m, 2H), 7.15-7.36 (m, 12H), 8.02-8.29 (m, 1H).

To a mixture of BI-3 (1.7 g, 3.41 mmol, 1 eq) in THF (15 mL) was added in portions $LiBH_4$ (222.81 mg, 10.23 mmol, 3 eq) at 0° C. The resulting mixture was stirred at 25° C. for 16 h to afford a brown mixture. TLC (PE: EA=6:1) showed BI-3 some remained, and thus the reaction was further stirred at 25° C. for 5 h. Sat. $NaHCO_3$ (50 mL) was added to the mixture and then the mixture extracted with EA (15 mL×3). The combined organic layers were dried by $Na_2SO_4$, and the solvent evaporated to dryness to afford the crude product. The product was purified by a flash column eluting with 5% EA in PE to 10% EA in PE to afford BI-4. $^1$H NMR (400 MHz, $CDCl_3$) δ ppm 1.70 (s, 9H), 2.63 (dd, J=14.18, 9.91 Hz, 1H), 3.01 (br s, 1H), 3.19 (dd, J=14.31, 3.76 Hz, 1H), 3.24-3.33 (m, 1H), 3.46 (dd, J=10.79, 4.52 Hz, 1H), 3.52-3.67 (m, 3H), 4.01 (d, J=13.30 Hz, 2H), 7.11-7.48 (m, 14H), 8.13 (br s, 1H).

To a mixture of BI-4 (2.6 g, 5.52 mmol, 1 eq) in DMF (10 mL) was added NaH (331.46 mg, 8.29 mmol, 60% purity, 1.5 eq) and $CH_3I$ (1.57 g, 11.05 mmol, 687.89 μL, 2 eq) at 0° C. The resulting mixture was stirred for 30 min at 0° C., and then NaH (331.46 mg, 8.29 mmol, 60% purity, 1.5 eq) was added. The resulting mixture was stirred at 25° C. for additional 2 h to afford a brown mixture. LC-MS and TLC (PE: EA=15:1) showed the reaction was completed. $H_2O$ (150 mL) was added to the mixture, and the aqueous phase extracted with ethyl acetate (40 mL×4). The combined organic phases were dried with anhydrous $Na_2SO_4$, filtered and concentrated in vacuum to afford the crude product. The product was purified by a flash column eluting with 5% EA in PE to 10% EA in PE to afford BI-5. $^1$H NMR (400 MHz, $CDCl_3$) δ ppm 1.49 (s, 9H), 2.90 (br dd, J=14.68, 9.16 Hz, 1H), 3.12 (br dd, J=14.68, 5.14 Hz, 1H), 3.30-3.42 (m, 1H), 3.70 (s, 3H), 3.76-3.88 (m, 4H), 4.08-4.21 (m, 1H), 4.29 (dd, J=11.29, 7.03 Hz, 1H), 6.71 (s, 1H), 6.98 (br t, J=7.53 Hz, 1H), 7.03-7.50 (m, 13H).

A mixture of BI-5 (586.2 mg, 1.21 mmol, 1 eq) and $Pd(OH)_2$ (254.80 mg, 362.88 μmol, 20% purity, 0.3 eq) in MeOH (5 mL) under $H_2$ (15 psi) was stirred at 25° C. for 18 h to afford a black mixture. LC-MS showed the reaction was completed. The reaction was filtered and the filtrate evaporated to dryness to afford the crude product. The product was purified by flash column eluting with 10% MeOH in DCM to pure MeOH to afford BI-6. $^1$H NMR (400 MHz, $CDCl_3$) δ ppm 1.46-1.53 (m, 9H), 2.68-2.83 (m, 1H), 2.97 (dd, J=14.31, 5.52 Hz, 1H), 3.39-3.48 (m, 1H), 3.71-3.80 (m, 3H), 3.94 (dd, J=10.42, 7.40 Hz, 1H), 4.06-4.21 (m, 1H), 6.89-6.96 (m, 1H), 7.07-7.15 (m, 1H), 7.23 (td, J=7.65, 1.00 Hz, 1H), 7.28-7.33 (m, 1H), 7.55-7.66 (m, 1H).

BI-6 (300 mg, 985.60 μmol, 1 eq) in HCl/EtOAc (4 M, 4 mL, 16.23 eq) was stirred at 25° C. for 1 h to afford a white mixture. LC-MS showed the reaction was completed. The reaction was evaporated to dryness, and Sat. $NaHCO_3$ (50 mL) aq. was added to the mixture. The aqueous phase was extracted with ethyl acetate (20 mL×3). The combined organic phases were dried with anhydrous $Na_2SO_4$, filtered and concentrated in vacuum to afford BI-7. $^1$H NMR (400 MHz, $CDCl_3$) δ ppm 2.63 (br dd, J=14.18, 8.16 Hz, 1H), 2.86 (br d, J=12.30 Hz, 1H), 3.18 (br d, J=5.27 Hz, 1H), 3.32-3.40 (m, 1H), 3.55-3.66 (m, 1H), 3.69 (s, 3H), 6.75-6.90 (m, 1H), 6.99-7.08 (m, 1H), 7.12-7.28 (m, 2H), 7.52 (d, J=7.78 Hz, 1H).

To a mixture of BI-7 (170.0 mg, 832.24 μmol, 1 eq) and tert-butyl 4-formylbenzoate (171.64 mg, 832.24 μmol, 1 eq) in DCM (2 mL) was added TFA (37.96 mg, 332.90 μmol, 24.65 μL, 0.4 eq) at 25° C. The resulting mixture was stirred at 45° C. for 42 h to afford a brown mixture. LC-MS and TLC (PE: EA=1:2) showed the reaction was completed. Sat. $NaHCO_3$ aq. (50 mL) was added to the mixture, and the aqueous phase extracted with DCM (15 mL×3). The combined organic phase was dried with anhydrous $Na_2SO_4$, filtered and concentrated in vacuum to afford the crude product. The product was purified by perp-TLC (EA: PE=2:1) to afford BI-8 and BI-8a. NOE showed that BI-8a was the cis-isomer. BI-8: $^1H$ NMR (400 MHz, $CDCl_3$) δ ppm 1.58 (s, 9H), 2.47-2.64 (m, 1H), 2.84 (dd, J=15.56, 4.27 Hz, 1H), 2.95-3.11 (m, 1H), 3.35 (s, 3H), 3.52 (dd, J=10.54, 8.53 Hz, 1H), 3.75 (dd, J=10.67, 3.64 Hz, 1H), 5.33 (s, 1H), 7.11-7.18 (m, 1H), 7.19-7.33 (m, 5H), 7.56 (d, J=7.78 Hz, 1H), 7.93 (d, J=8.28 Hz, 2H). BI-8a: $^1H$ NMR (400 MHz, $CDCl_3$) δ ppm 1.59 (s, 9H), 2.55-2.72 (m, 1H), 2.80-2.92 (m, 1H), 3.14 (s, 3H), 3.18-3.30 (m, 1H), 3.61 (dd, J=10.79, 8.28 Hz, 1H), 3.88 (dd, J=10.79, 3.76 Hz, 1H), 5.30 (s, 1H), 7.08-7.19 (m, 1H), 7.22 (d, J=3.76 Hz, 2H), 7.35 (d, J=8.28 Hz, 2H), 7.56 (d, J=7.78 Hz, 1H), 7.97 (d, J=8.28 Hz, 2H).

Preparation of Compound 63

To a mixture of BI-8 (40.0 mg, 101.91 μmol, 1 eq) and TEA (20.63 mg, 203.83 μmol, 28.37 μL, 2 eq) in DCM (1 mL) was added 2-chloroacetyl chloride (17.27 mg, 152.87 μmol, 12.16 μL, 1.5 eq) at 0° C. The resulting mixture was stirred at 0° C. for 2 h to afford a brown mixture. LC-MS and TLC (PE: EA=3:1) showed the reaction was completed. The reaction was purified by perp-TLC (PE: EA=3:1) to afford 63. $^1H$ NMR (400 MHz) δ ppm 1.48 (s, 9H), 2.62-3.84 (m, 7H), 3.98-4.74 (m, 3H), 6.07 (br s, 1H), 6.99-7.41 (m, 6H), 7.45-7.58 (m, 1H), 7.84 (br s, 2H). LC-MS (m/z): 469.1 [M+H]+.

Procedure BJ: Synthesis of Compound 63

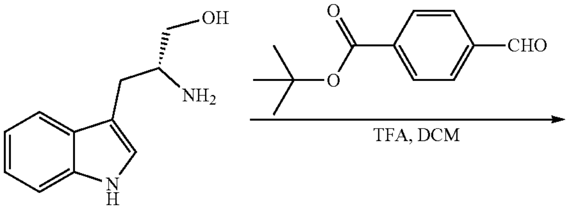

BJ-1

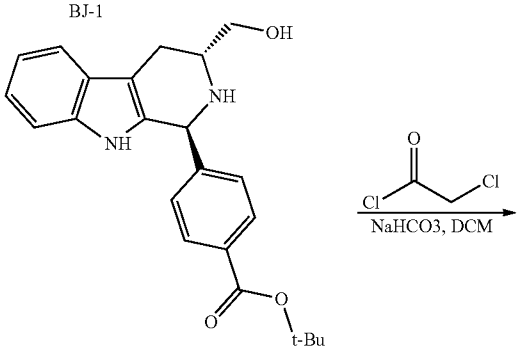

BJ-2

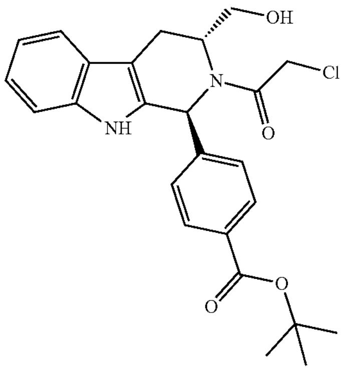

Compound 63

To a solution of BJ-1 (500 mg, 2.63 mmol, 1 eq) in DCM (5 mL) were added tert-butyl 4-formylbenzoate (542.04 mg, 2.63 mmol, 1 eq) and TFA (149.84 mg, 1.31 mmol, 97.30 μL, 0.5 eq). The mixture was heated to 25° C. for 64 h to give a brown solution. LCMS showed the reaction was completed. The mixture was adjusted to pH 8 with saturated $NaHCO_3$, and the mixture extracted with DCM (5 mL×3). The combined organic layers were dried over $Na_2SO_4$ and concentrated to give the crude product. The product was purified by column chromatography ($SiO_2$, Petroleum ether/Ethyl acetate=I/O to 2:3) to give BJ-2. $^1H$ NMR (400 MHz, $CDCl_3$) δ=7.99 (d, J=8.3 Hz, 2H), 7.52 (d, J=7.3 Hz, 1H), 7.47-7.37 (m, 2H), 7.25-7.08 (m, 3H), 5.27 (s, 1H), 4.12 (q, J=7.3 Hz, 1H), 3.93 (dd, J=3.5, 10.8 Hz, 1H), 3.69 (dd, J=8.4, 10.7 Hz, 1H), 3.41-3.32 (m, 1H), 2.88-2.78 (m, 1H), 2.70-2.60 (m, 1H), 1.60 (s, 9H).

Preparation of 63

To a solution of BJ-2 (53 mg, 140.04 μmol, 1 eq) in $CH_2Cl_2$ (2 mL) were added TEA (117.64 mg, 1.16 mmol, 161.82 μL, 8.30 eq) and 2-chloroacetyl chloride (79.08 mg, 700.20 μmol, 55.69 μL, 5 eq) at 0° C. The mixture was stirred at 20° C. for 2 h to give a brown suspension. LCMS showed no desired MS was found. Saturated $NaHCO_3$ aq. (10 mL) and THF (5 mL) were added and the mixture stirred at 25° C. for 24 h to give a brown suspension. LCMS showed the reaction was completed. Brine was added and the mixture extracted with EtOAc (5 mL×3). The combined organic layers were dried over $NaSO_4$, filtered and concentrated to give a residue. The residue was purified by prep-HPLC (column: Xtimate C18 150×25 mm×5 μm; mobile phase: [water (0.1% TFA)-ACN]; B %: 55%-85%, 7.8 min) to give 63. LC-MS (m/z): 477.0 [M+Na]+. $^1H$ NMR (400 MHz, $CDCl_3$) δ=7.94 (br d, J=8.0 Hz, 3H), 7.54 (t, J=6.5 Hz, 2H), 7.19 (d, J=7.5 Hz, 2H), 7.07 (s, 1H), 5.40-5.31 (m, 1H), 4.53 (br s, 1H), 4.43 (s, 1H), 4.28 (s, 1H), 3.61-3.46 (m, 2H), 3.26 (br dd, J=6.5, 16.6 Hz, 1H), 2.92 (s, 1H), 2.08-1.93 (m, 1H), 1.45-1.17 (m, 9H).

Procedure BK: Synthesis of Compound 64

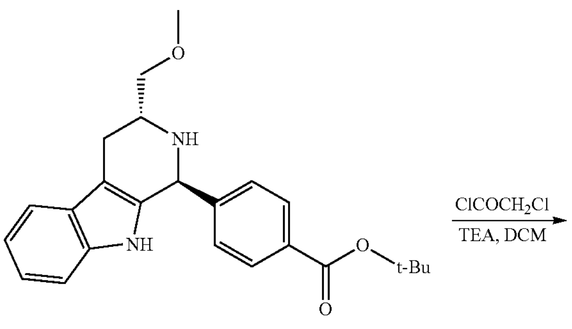

BI-8

-continued

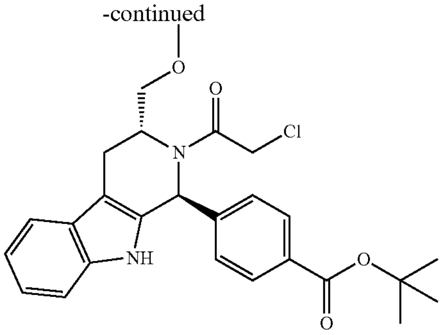

Compound 64

Preparation of 64

To a mixture of BI-8 (15.0 mg, 38.22 μmol, 1 eq) and TEA (7.73 mg, 76.44 μmol, 10.64 μL, 2 eq) in DCM (1 mL) was added 2-chloroacetyl chloride (6.47 mg, 57.33 μmol, 4.56 μL, 1.5 eq) at 0° C. The resulting mixture was stirred at 0° C. for 1 h to afford a brown mixture. TLC (PE: EA=2:1) showed the reaction was completed. The reaction was purified by prep-TLC (PE: EA=2:1) to afford 64. $^1H$ NMR (400 MHz, $CDCl_3$) δ ppm 1.50 (s, 9H), 2.79 (br d, J=16.31 Hz, 1H), 3.05-3.27 (m, 1H), 3.37 (s, 5H), 4.20 (br d, J=12.30 Hz, 1H), 4.37 (br d, J=12.30 Hz, 1H), 4.45 (br d, J=8.03 Hz, 1H), 5.17-5.82 (m, 1H), 7.12 (br s, 2H), 7.17-7.32 (m, 2H), 7.40 (br s, 2H), 7.49 (br d, J=7.78 Hz, 1H), 7.86 (br d, J=8.03 Hz, 2H). LC-MS (m/z): 469.0 [M+H]+.

Procedure BL: Synthesis of Compound 66 and Compound 66a

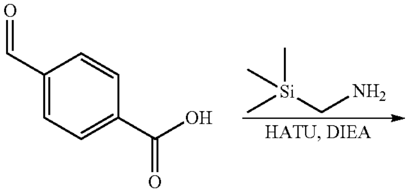

AA-2

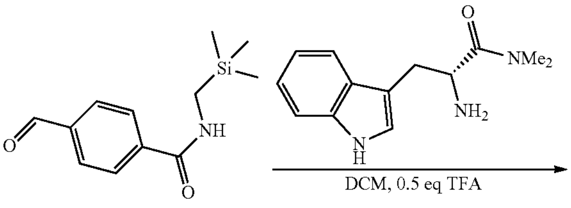

BL-2

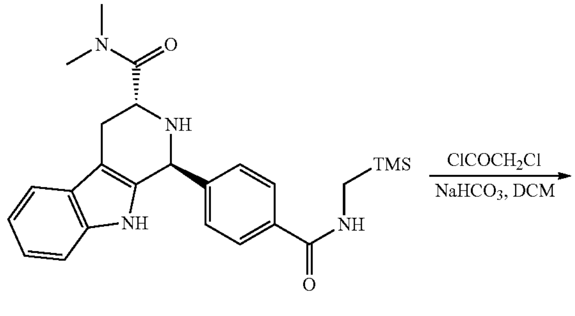

BL-3

-continued

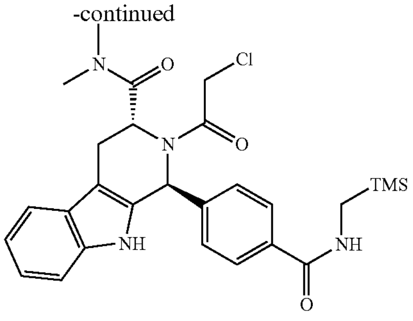

Compound 66

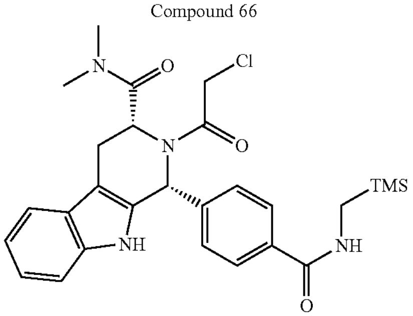

Compound 66a

To a solution of AA-2 (292 mg, 1.94 mmol, 1 eq) in DMF (4 mL) were added DIEA (502.75 mg, 3.89 mmol, 677.56 μL, 2 eq) and HATU (1.11 g, 2.92 mmol, 1.5 eq). Trimethylsilylmethanamine (200.79 mg, 1.94 mmol, 1 eq) was added, and the mixture stirred at 20° C. for 12 h to give a yellow solution. TLC (eluting with: EtOAc=100%, $SiO_2$) showed the reaction was completed. The reaction mixture was diluted with $H_2O$ (40 mL) and extracted with MTBE (25 mL×3). The organic layers were dried over $Na_2SO_4$ and concentrated to give a crude product. The product was purified by flash column (eluting with: Petroleum ether/Ethyl acetate=10/1 to 1:1) to give BL-2. $^1H$ NMR (400 MHz, $CDCl_3$) δ ppm 0.15 (s, 9H), 2.99-3.00 (d, J=5.77 Hz, 2H), 6.00 (br s, 1H), 7.87-7.89 (m, 2H), 7.95-7.97 (m, 2H), 10.08 (s, 1H).

To a solution of BL-2 (100 mg, 424.89 μmol, 1 eq) in DCM (6 mL) were added AP-3 (98.27 mg, 424.89 μmol, 1 eq) and TFA (24.22 mg, 212.45 μmol, 15.73 μL, 0.5 eq). The mixture was stirred at 45° C. for 12 h to give a yellow solution. LCMS showed the reaction was completed. The reaction mixture was adjusted to pH 8 with Sat. $NaHCO_3$ and extracted with DCM (20 mL×3). The organic layers were dried over $Na_2SO_4$ and concentrated. The residue was purified by prep-TLC (Ethyl acetate: Methanol=10:1) to give BL-3 and BL-3a.

BL-3: $^1H$ NMR (400 MHz, $CDCl_3$) δ ppm 0.12 (s, 9H), 1.24-1.26 (m, 1H), 2.80 (s, 3H), 2.92-3.02 (m, 7H), 3.84-3.88 (dd, J=10.04, 5.02 Hz, 1H), 5.93 (br s, 1H), 7.13-7.22 (m, 2H), 7.29-7.33 (m, 3H), 7.55-7.57 (d, J=7.78 Hz, 1H), 7.64-7.66 (d, J=8.28 Hz, 2H), 7.91 (s, 1H).

BL-3a: $^1H$ NMR (400 MHz, $CDCl_3$) δ ppm 0.13-0.15 (s, 9H), 1.25-1.28 (m, 1H), 2.95-2.97 (d, J=5.77 Hz, 2H), 3.00-3.02 (m, 5H), 3.17 (s, 3H), 3.49 (s, 3H), 4.16-4.20 (t, J=7.53 Hz, 1H), 5.30 (s, 1H), 5.97-6.00 (br t, J=5.52 Hz, 1H), 7.11-7.17 (m, 2H), 7.11-7.20 (m, 1H), 7.38-7.40 (d, J=8.03 Hz, 2H), 7.52-7.54 (d, J=7.53 Hz, 1H), 7.69-7.71 (d, J=8.03 Hz, 2H).

Preparation of 66

To a solution of BL-3 (36 mg, 80.24 μmol, 1 eq, trans) in $CHCl_3$ (3 mL) was added $NaHCO_3$ (67.41 mg, 802.44 μmol, 31.21 μL, 10 eq). Then a solution of 2-chloroacetyl chloride (45.32 mg, 401.22 μmol, 31.91 μL, 5 eq) in DCM (0.5 mL) was added at 0° C., and the mixture stirred at 25° for 2 h to give a yellow solution. TLC (eluting with: Petroleum ether: Ethyl acetate=2:1, $SiO_2$) showed the reaction was completed. The reaction mixture was filtered, and the filtrate concentrated to give the crude residue. The residue was purified by prep-TLC (Petroleum ether:Ethyl acetate=2:1) to give 66. LC-MS (m/z): 525.1 [M+H]+. $^1$H NMR (400 MHz, $CDCl_3$) δ ppm 0.06 (m, 1H), 0.07-0.11 (s, 9H), 1.26-1.30 (m, 3H), 2.81-2.94 (m, 7H), 3.12 (br s, 1H), 3.37-3.44 (m, 2H), 4.08-4.13 (m, 1H), 5.89 (br s, 1H), 7.07 (br s, 2H), 7.46 (br s, 3H), 7.68 (br s, 2H), 8.04 (br s, 1H).

Preparation of 66a

To a solution of BL-3a (172 mg, 383.39 μmol, 1 eq, cis in $CHCl_3$ (5 mL) was added $NaHCO_3$ (322.07 mg, 3.83 mmol, 149.11 μL, 10 eq). Then a solution of 2-chloroacetyl chloride (216.51 mg, 1.92 mmol, 152.47 μL, 5 eq) in DCM (0.5 mL) was added at 0° C., and the mixture stirred at 25° for 2 h to give a yellow solution. TLC (eluting with: Petroleum ether: Ethyl acetate=2:1, SiO2) showed the reaction was completed. The solution was filtered and concentrated. The residue was purified by prep-TLC (Petroleum ether:Ethyl acetate=2:1) to give 66a. LC-MS (m/z): 525.0 [M+H]+. $^1$H NMR (400 MHz, $CDCl_3$)$_6$ ppm 0.09-0.13 (m, 9H), 2.41 (s, 3H), 2.86 (s, 3H), 2.94-3.01 (d, J=5.77 Hz, 2H), 3.12-3.18 (dd, J=15.69, 6.15 Hz, 1H), 3.34-3.38 (br, 1H), 4.20-4.33 (m, 2H), 5.44 (br s, 1H), 6.05-6.08 (br, 1H), 6.43 (br, 1H), 7.12-7.18 (m, 2H), 7.28-7.30 (d, J=7.53 Hz, 1H), 7.55-7.57 (br d, J=7.03 Hz, 3H), 7.64-7.66 (m, 2H), 7.81 (s, 1H), 8.27 (s, 1H).

Procedure BM: Synthesis of Compound 67

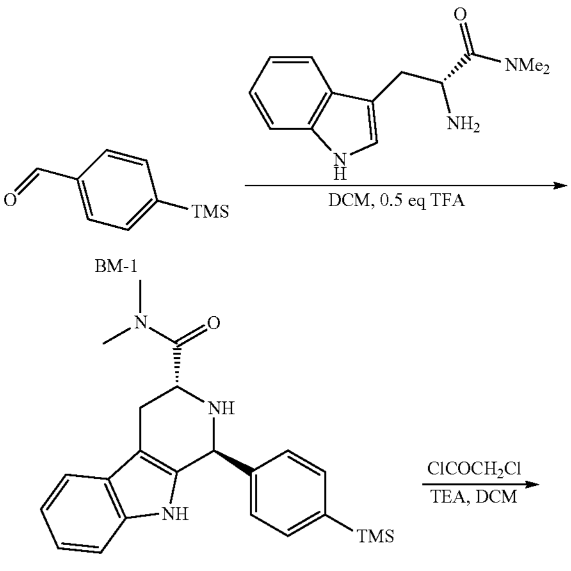

BM-1

BM-2

-continued

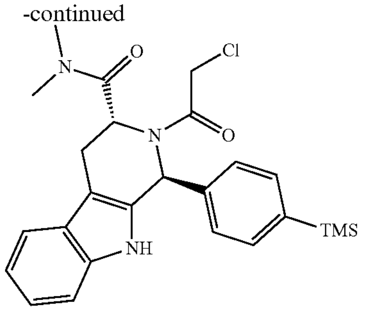

Compound 67

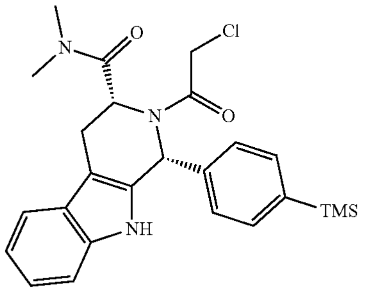

Compound 67a

Preparation of Compound BM-2

To a solution of BM-1 (100 mg, 560.84 μmol, 1 eq) in DCM (5 mL) were added AP-3 (129.72 mg, 560.84 μmol, 1 eq) and TFA (31.97 mg, 280.42 μmol, 20.76 μL, 0.5 eq). The mixture was stirred at 45° C. for 12 h to give a yellow solution. TLC (eluting with: EtOAc/Methanol=10/1, $SiO_2$) showed the reaction was completed. The reaction mixture was adjusted to pH 8 with Sat. $NaHCO_3$ and extracted with DCM (20 mlx3). The organic layers were dried over $Na_2SO_4$ and concentrated to give the crude residue. The residue was purified by prep-TLC (Ethyl acetate: Methanol=20:1) to give BM-2 and BM-2a.

BM-2: $^1$H NMR (400 MHz, $CDCl_3$) δ ppm 0.22-0.27 (m, 9H), 2.80-2.96 (m, 1H), 2.81-2.94 (m, 6H), 2.97-3.06 (m, 2H), 3.92-3.96 (dd, J=9.79, 5.02 Hz, 1H), 5.29 (s, 1H), 5.28-5.31 (m, 1H), 7.13-7.23 (m, 4H), 7.28-7.30 (m, 1H), 7.45-7.47 (d, J=7.78 Hz, 2H), 7.55-7.57 (d, J=7.53 Hz, 1H).

BM-2a: $^1$H NMR (400 MHz, $CDCl_3$) δ ppm 0.25-0.27 (s, 9H), 3.01-3.04 (m, 5H), 3.08-3.17 (s, 3H), 4.19-4.21 (dd, J=9.66, 5.40 Hz, 1H), 5.27 (s, 1H), 7.15-7.16 (quind, J=7.00, 7.00, 7.00, 7.00, 1.13 Hz, 2H), 7.24-7.30 (m, 3H), 7.50-7.55 (m, 3H), 7.55-7.58 (m, 1H).

Preparation of 67

To a solution of BM-2 (29.3 mg, 74.83 μmol, 1 eq, trans) in $CHCl_3$ (3 mL) was added $NaHCO_3$ (62.86 mg, 748.25 μmol, 29.10 μL, 10 eq). Then a solution of 2-chloroacetyl chloride (42.25 mg, 374.13 μmol, 29.76 μL, 5 eq) in DCM (0.5 mL) was added at 0° C., and the mixture stirred at 0° C. for 2 h to give a yellow solution. TLC (eluting with; Petroleum ether:Ethyl acetate=1:1, SiO2) showed the reaction was completed. The reaction mixture was filtered, and the filtrate concentrated to give a crude residue. The residue was purified by prep-TLC (Petroleum ether:Ethyl acetate=1:1) to give 67. LC-MS (m/z): 468.1 [M+H]+. $^1$H NMR (400 MHz, $CDCl_3$) δ ppm 0.07 (s, 1H), 0.23 (s, 9H), 1.25-1.30 (s, 3H), 2.87 (br s, 3H), 3.06 (br s, 2H), 3.35 (br s, 2H), 4.17-4.20 (br d, J=11.04 Hz, 1H), 5.72 (s, 1H), 6.29 (br s, 1H), 7.11 (br s, 2H), 7.20 (br s, 1H), 7.33-7.35 (d, J=7.78 Hz, 2H), 7.47-7.52 (m, 3H), 7.76 (br s, 1H).

Preparation of 67a

To a solution of BM-2a (64 mg, 163.44 μmol, 1 eq, cis) in $CHCl_3$ (4 mL) was added $NaHCO_3$ (137.30 mg, 1.63 mmol, 63.57 μL, 10 eq). Then a solution of 2-chloroacetyl chloride (92.30 mg, 817.20 μmol, 65.00 μL, 5 eq) in DCM (0.5 mL) was added at 0° C., and the mixture stirred at 25° C. for 2 h to give a yellow solution. TLC (eluting with; Petroleum ether:Ethyl acetate=1:1, SiO2) showed the reaction was completed. The reaction mixture was filtered, and the filtrate concentrated to give a crude residue. The residue was purified by prep-TLC (Petroleum ether:Ethyl acetate=1:1) to give 67a. LC-MS (m/z): 468.0 [M+H]+. $^1$H NMR (400 MHz, $CDCl_3$) δ ppm 0.23 (s, 10H), 2.30 (s, 3H), 2.77 (s, 3H), 3.05-3.11 (dd, J=14.81, 6.53 Hz, 1H), 3.42-3.46 (br d, J=15.56 Hz, 1H), 4.30-4.44 (m, 2H), 5.57 (br s, 1H), 6.36 (br s, 1H), 7.13-7.21 (m, 2H), 7.28-7.30 (m, 1H), 7.40-7.41 (d, J=7.78 Hz, 2H), 7.49-7.51 (m, 2H), 7.58-7.60 (d, J=7.78 Hz, 1H), 7.76 (s, 1H).

Procedure BN: Synthesis of Compound 68

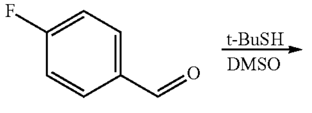

BN-1

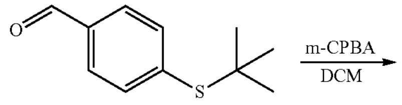

BN-2

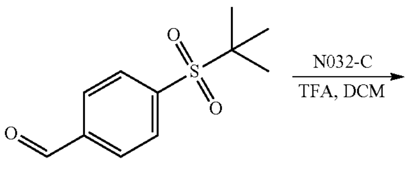

BN-3

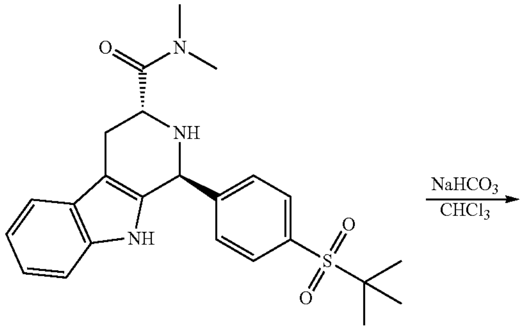

BN-4

-continued

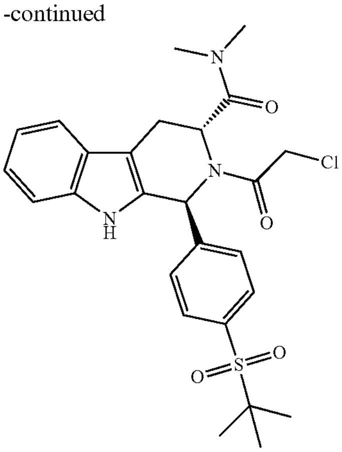

Compound 68

To a solution of BN-1 (3 g, 24.17 mmol, 2.54 mL, 1 eq) in DMSO (12 mL) were added 2-methyl propane-2-thiol (2.40 g, 26.59 mmol, 2.99 mL, 1.1 eq) and $K_2CO_3$ (3.34 g, 24.17 mmol, 1 eq). The mixture was stirred at 100° C. for 3 h to give a yellow solution. TLC (eluting with: PE/EtOAc=10/1, $SiO_2$) showed the reaction was completed. The reaction mixture was quenched with $H_2O$ (120 mL) and extracted with MTBE (60 mL×3). The organic layers were dried over $Na_2SO_4$ and concentrated to give a crude product. The product was purified by a flash column (eluting with: Petroleum ether=100%) to give BN-1. $^1$H NMR (400 MHz, $CDCl_3$) δ ppm 1.34-1.36 (s, 10H), 7.67-7.69 (d, J=8.03 Hz, 2H), 7.81-7.83 (d, J=8.03 Hz, 2H), 10.03 (s, 1H).

To a solution of BN-2 (500 mg, 2.57 mmol, 1 eq) in DCM (10 mL) was added MCPBA (1.15 g, 5.66 mmol, 39.96 μL, 85% purity, 2.2 eq). The mixture stirred at 25° C. for 12 h to give a white solution. TLC (eluting with: PE/EtOAc=3/1, $SiO_2$) showed the reaction was completed. The reaction mixture was quenched with Sat. $NaHCO_3$ (10 ml) and extracted with DCM (10 mL×3). The organic layers were dried over $Na_2SO_4$ and concentrated to give a crude product. The product was purified by a flash column (eluting with: Petroleum ether=100%) to give BN-3. $^1$H NMR (400 MHz, $CDCl_3$) δ ppm 1.37 (s, 9H), 8.07 (s, 4H), 10.15 (s, 1H).

To a solution of BN-3 (320 mg, 1.41 mmol, 1 eq) in DCM (20 mL) were added AP-3 (327.07 mg, 1.41 mmol, 1 eq) and TFA (80.62 mg, 707.05 μmol, 52.35 μL, 0.5 eq). LCMS showed the reaction was completed. The reaction mixture was adjusted to pH 8 with Sat. $NaHCO_3$ and extracted with DCM (30 mL×3). The organic layers were dried over $Na_2SO_4$ and concentrated to give a crude product (604 mg). The product was purified by prep-TLC (Ethyl acetate=100%) to give BN-4 and BN-4a.

BN-4: $^1$H NMR (400 MHz, $CDCl_3$) δ ppm 1.29-1.36 (m, 9H), 2.80 (s, 3H), 2.92-3.04 (m, 5H), 3.79-3.83 (dd, J=9.54, 5.52 Hz, 1H), 5.34 (s, 1H), 7.14-7.24 (m, 2H), 7.33-7.35 (d, J=8.03 Hz, 1H), 7.42-7.44 (d, J=8.28 Hz, 2H), 7.55-7.57 (d, J=7.78 Hz, 1H), 7.75-7.77 (d, J=8.28 Hz, 2H), 8.08 (s, 1H).

BN-4a: $^1$H NMR (400 MHz, $CDCl_3$) δ ppm 1.22-1.28 (m, 2H), 1.34 (s, 9H), 2.78-3.09 (m, 1H), 2.96-3.09 (m, 4H), 3.17 (s, 3H), 3.69-3.74 (q, J=7.11 Hz, 1H), 4.09-4.21 (m, 1H), 5.38 (s, 1H), 7.12-7.21 (dt, J=19.51, 7.18 Hz, 2H), 7.28-7.30 (d, J=7.78 Hz, 1H), 7.52-7.55 (m, 3H), 7.82-7.84 (m, 3H), 7.95-7.96 (m, 1H).

Preparation of 68

To a solution of BN-4 (50 mg, 113.75 μmol, 1 eq, trans) in $CHCl_3$ (8 mL) were added $NaHCO_3$ (95.56 mg, 1.14 mmol, 44.24 μL, 10 eq) and 2-chloroacetyl chloride (38.54 mg, 341.24 μmol, 27.14 μL, 3 eq) at 0° C. The mixture stirred at 25° C. for 2 h to give a yellow solution. LCMS showed the reaction was completed. The reaction mixture was filtered, and the filtrate concentrated to give the crude product. The product was purified by prep-TLC (Petroleum ether:Ethyl acetate=1:1) to give 68. LC-MS (m/z): 516.0 [M+H]+. $^1H$ NMR (400 MHz, $CDCl_3$) δ ppm 1.18-1.30 (m, 9H), 2.84 (s, 3H), 3.11 (br s, 3H), 3.29-3.39 (m, 2H), 3.77-4.09 (m, 2H), 5.28 (br s, 1H), 5.81 (br s, 1H), 6.53-6.66 (m, 1H), 6.90 (br s, 1H), 7.32 (br s, 1H), 7.45-7.55 (m, 2H), 7.71 (br s, 1H), 8.52-8.84 (m, 1H).

Procedure BO: Synthesis of Compound 69

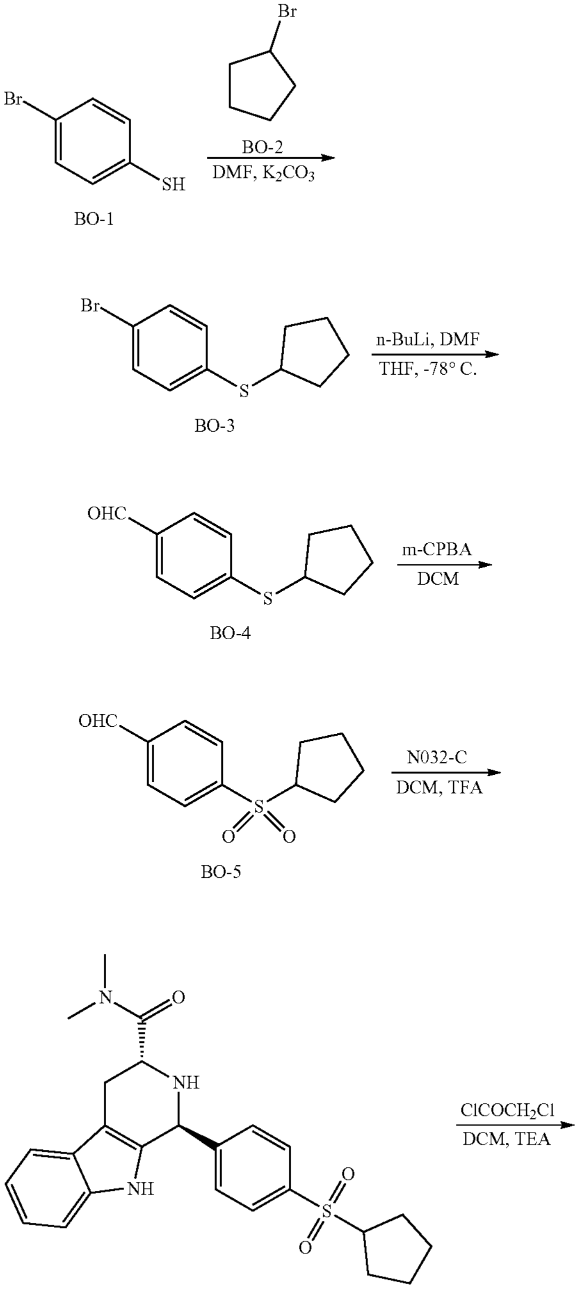

BO-1

BO-3

BO-4

BO-5

BO-6

-continued

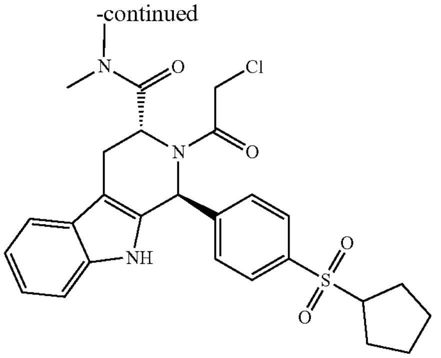

Compound 69

A mixture of BO-1 (1 g, 5.29 mmol, 1 eq), BO-2 (1.02 g, 6.88 mmol, 737.17 μL, 1.3 eq) and $K_2CO_3$ (1.10 g, 7.93 mmol, 1.5 eq) was dissolved in DMF (20 mL), and the reaction mixture stirred at 25° C. for 16 h. TLC (eluting with: PE) showed the reaction was completed. The reaction mixture was partitioned between water (10 mL) and EtOAc (10 mL), and the aqueous layer extracted with EtOAc (20 mL×2). The combined organic layer was dried over sodium sulfate and concentrated. The crude product was purified by silica gel chromatography (PE) to give BO-3. $^1H$ NMR (400 MHz, $CDCl_3$) δ: 1.49-1.60 (m, 4H), 1.65-1.76 (m, 2H), 1.93-2.03 (m, 2H), 3.50 (m, 1H), 7.14 (d, J=8.53 Hz, 2H), 7.32 (d, J=8.28 Hz, 2H).

To a solution of BO-3 (2.44 g, 9.49 mmol, 1 eq) in THF (30 mL) was added dropwise n-BuLi (2.5 M, 4.55 mL, 1.2 eq) at −78° C. The reaction mixture was stirred at −78° C. for 1 h. DMF (1.04 g, 14.23 mmol, 1.09 mL, 1.5 eq) was then added dropwise, and the reaction mixture allowed to rise to 25° C. in 5 h to give a yellow solution. TLC (eluting with: PE/EtOAc=3/1) showed the reaction was completed. MeOH (2 mL) was added to quench the reaction. The reaction mixture was partitioned between water (20 mL) and EtOAc (20 mL), and the aqueous layer extracted with EtOAc (20 mL×2). The crude product was purified by silica gel chromatography (PE) to give BO-4. $^1H$ NMR (400 MHz, $CDCl_3$) δ: 1.61-1.71 (m, 4H), 1.74-1.88 (m, 2H), 2.08-2.25 (m, 2H), 3.68-3.82 (m, 1H), 7.37 (d, J=8.28 Hz, 2H), 7.75 (d, J=8.28 Hz, 2H), 9.91 (s, 1H).

To a solution of BO-4 (1.54 g, 7.46 mmol, 1 eq) in DCM (20 mL), was added MCPBA (2.83 g, 16.42 mmol, 2.2 eq). The reaction mixture was stirred at 0° C. for 2 h to give a colorless solution. LCMS and TLC (eluting with: EA/MeOH=3/1) showed the reaction was completed. $Na_2SO_3$ solution (15 mL) was added to quench the reaction, and the reaction mixture partitioned between water (20 mL) and EtOAc (20 mL). The aqueous layer was extracted with EtOAc (20 mL×2), and the combined organic layers dried over sodium sulfate and concentrated. The product was purified by silica gel chromatography (EtOAc/MeOH=10/1-3/1) to give BO-5. $^1H$ NMR (400 MHz, $CDCl_3$) δ: 1.59-1.67 (m, 2H), 1.74-1.82 (m, 2H), 1.84-1.93 (m, 2H), 2.04-2.12 (m, 2H), 3.45-3.57 (m, 1H), 8.07 (d, J=2.01 Hz, 4H), 10.13 (s, 1H).

To a solution of BO-5 (320.29 mg, 1.38 mmol, 1.1 eq) and AP-3 (300 mg, 1.26 mmol, 1 eq) in DCM (10 mL), was added TFA (71.77 mg, 629.45 μmol, 46.61 μL, 0.5 eq), and the reaction mixture stirred at 45° C. for 16 h to give a suspension. LCMS and TLC (eluting with: EtOAc/MeOH=20/1) showed the reaction was completed. Saturated sodium bicarbonate was added to adjust the pH to 7-8. The aqueous layer was extracted with EtOAc (20 mL×2), and the combined organic layers dried over sodium sulfate and concentrated. The product was purified by Prep-TLC (EtOAc/MeOH=50/1) to give BO-6. $^1$H NMR (400 MHz, DMSO-d6) δ: 1.48-1.64 (m, 4H), 1.68-1.87 (m, 4H), 2.64 (s, 3H), 2.74-2.90 (m, 4H), 3.23 (dd, J=11.92, 5.65 Hz, 1H), 3.63-3.80 (m, 2H), 5.32 (d, J=5.27 Hz, 1H), 6.96-7.03 (m, 1H), 7.04-7.11 (m, 1H), 7.29 (d, J=8.03 Hz, 1H), 7.44-7.50 (m, 3H), 7.84 (d, J=8.28 Hz, 2H), 10.86 (s, 1H).

Preparation of 69

To a solution of BO-6 (132 mg, 292.31 μmol, 1 eq) and Et3N (59.16 mg, 584.61 μmol, 81.37 μL, 2 eq) in DCM (8 mL) was added 2-chloroacetyl chloride (49.52 mg, 438.46 mol, 34.87 μL, 1.5 eq) at 0° C. The reaction mixture was stirred at 0° C. for 16 h to give a yellow solution. TLC (eluting with: EA) showed the reaction was completed. The reaction mixture was quenched with Sat. $NaHCO_3$ (15 mL) and extracted with DCM (20 mL×3). The organic layers were dried over $Na_2SO_4$ and concentrated to give the crude product. The product was purified by Prep-TLC (DCM/MeOH=10/1) to afford 69. LC-MS (m/z): 528.0 [M+H]+. $^1$H NMR (400 MHz, DMSO-d6) δ: 1.48-1.64 (m, 4H), 1.68-1.88 (m, 4H), 2.70 (s, 3H), 3.14 (s, 2H), 3.39 (s, 1H), 3.67-3.77 (m, 1H), 4.67 (d, J=14.31 Hz, 1H), 5.31 (s, 1H), 5.62 (s, 1H), 6.15-6.44 (m, 1H), 6.93-6.99 (m, 1H), 7.00-7.06 (m, 1H), 7.25 (d, J=8.03 Hz, 1H), 7.47 (d, J=7.78 Hz, 1H), 7.65-7.86 (m, 4H), 10.99 (s, 1H).

Procedure BP: Synthesis of Compound 70

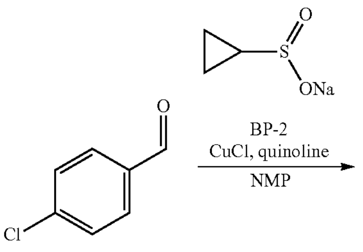

BP-1

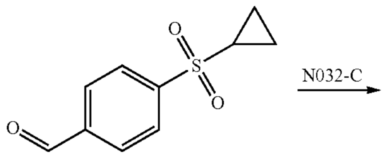

BP-3

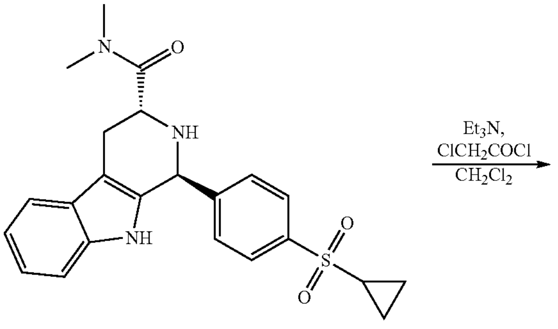

BP-4

-continued

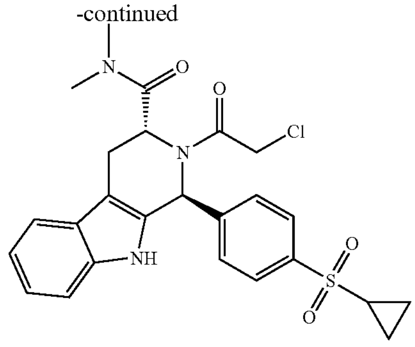

Compound 70

Preparation of Compound BP-3

The mixture of BP-1 (248.22 mg, 2 mmol, 210.36 μL, 1 eq) and BP-2 (281.88 mg, 2.20 mmol, 1.1 eq) in DMSO (15 mL) was stirred at 100° C. for 48 h to afford a brown mixture. TLC (eluting with: PE/EtOAc=3/1) showed the reaction was completed. $H_2O$ (100 mL) was added, and the aqueous phase extracted with ethyl acetate (30 mL×4). The combined organic phase was washed with brine (40 mL), dried with anhydrous $Na_2SO_4$, filtered and then concentrated in vacuum to afford BP-3. $^1$H NMR (400 MHz, DMSO-d6) δ ppm 1.02-1.24 (m, 4H), 2.88-3.01 (m, 1H), 8.07-8.26 (m, 4H), 10.14 (s, 1H).

To a mixture of AP-3 (300 mg, 1.30 mmol, 1 eq) and BP-3 (272.71 mg, 1.30 mmol, 1 eq) in DCM (4 mL) was added TFA (59.16 mg, 518.82 μmol, 38.41 μL, 0.4 eq) at 25° C. The resulting mixture was stirred at 45° C. for 18 h to afford a brown mixture. TLC (eluting with: PE/EtOAc=0/1) showed the reaction was completed. $H_2O$ (60 mL) was added, and the aqueous phase extracted with DCM (20 mL×3). The combined organic phase was dried with anhydrous $Na_2SO_4$, filtered and concentrated in vacuum to afford the crude product. The product was purified by prep-TLC (EA: MeOH=50:1) to afford BP-4 and BP-4a.

BP-4: $^1$H NMR (400 MHz, $CDCl_3$) δ ppm 0.96-1.07 (m, 2H), 1.29-1.37 (m, 2H), 2.35-2.49 (m, 1H), 2.84 (s, 3H), 2.91-3.03 (m, 5H), 3.85 (t, J=7.40 Hz, 1H), 5.35 (s, 1H), 7.13-7.19 (m, 1H), 7.22 (t, J=7.40 Hz, 1H), 7.33 (d, J=8.03 Hz, 1H), 7.44 (d, J=8.28 Hz, 2H), 7.56 (d, J=7.53 Hz, 1H), 7.80 (d, J=8.28 Hz, 2H), 8.00 (s, 1H).

BP-4a: $^1$H NMR (400 MHz, $CDCl_3$) δ ppm 0.95-1.12 (m, 2H), 1.31-1.39 (m, 2H), 2.35-2.52 (m, 1H), 2.92-3.08 (m, 5H), 3.17 (s, 3H), 4.19 (dd, J=9.91, 5.14 Hz, 1H), 5.38 (br s, 1H), 7.09-7.36 (m, 4H), 7.42-7.66 (m, 3H), 7.88 (d, J=8.28 Hz, 2H).

Preparation of 70

To a mixture of BP-4 (140.5 mg, 331.74 μmol, 1 eq) and TEA (67.14 mg, 663.48 μmol, 92.35 μL, 2 eq) in DCM (2 mL) was added 2-chloroacetyl chloride (56.20 mg, 497.61 μmol, 39.58 μL, 1.5 eq) at 0° C. The resulting mixture was stirred at 0° C. for 2 h to afford a brown mixture. TLC (PE: EA=0:1) showed the reaction was completed. The reaction was purified by perp-TLC (EA) to afford 70. $^1$H NMR (400 MHz, $CDCl_3$) δ ppm 0.99 (br d, J=6.53 Hz, 2H), 1.19-1.38 (m, 2H), 2.31-2.47 (m, 1H), 2.92 (br s, 3H), 3.02-4.61 (m, 7H), 5.18-6.17 (m, 1H), 6.34-7.16 (m, 4H), 7.30-8.01 (m, 5H), 8.48-9.26 (m, 1H). LC-MS (m/z): 500.0 [M+H]+.

Procedure BQ: Synthesis of Compound 71 and Compound 71a

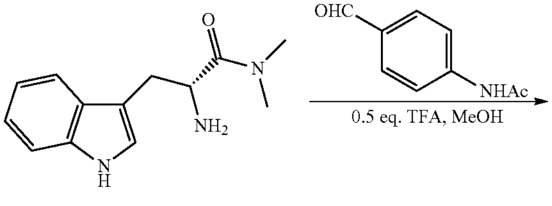

AP-3

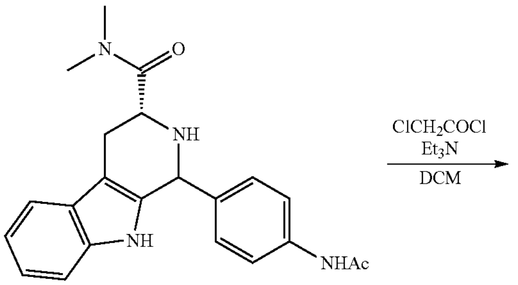

BQ-2

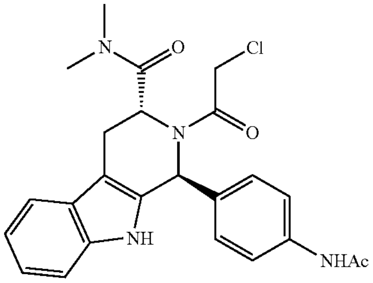

Compound 71

-continued

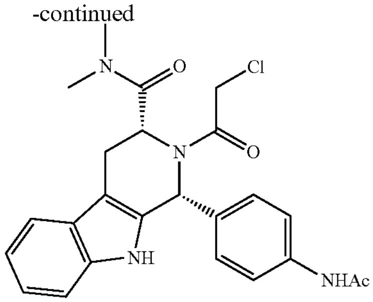

Compound 71a

To a solution of AP-3 (141.75 mg, 612.85 μmol, 1 eq) and N-(4-formylphenyl) acetamide (100 mg, 612.85 μmol, 1 eq) in MeOH (3 mL) was added TFA (34.94 mg, 306.42 μmol, 22.69 μL, 0.5 eq) at 20° C. The reaction was stirred at 80° C. for 16 h to give a yellow solution. TLC (quenched with water, eluting with: EA/MeOH=20/1) showed the reaction was completed. The reaction mixture was distilled (40° C.) to give BQ-2. $^{1}$H NMR (400 MHz, DMSO-d6) δ ppm 2.05 (s, 3H), 2.91 (s, 4H), 3.05 (s, 3H), 3.51 (br dd, J=15.81, 5.02 Hz, 1H), 4.44 (br s, 1H), 5.87 (s, 1H), 7.07 (t, J=7.15 Hz, 1H), 7.11-7.19 (m, 1H), 7.27-7.37 (m, 3H), 7.43 (d, J=8.53 Hz, 1H), 7.69 (d, J=8.53 Hz, 2H), 9.49 (br s, 1H), 10.10-10.27 (m, 2H).

Preparation of 71 and 71a

To a solution of BQ-2 (30 mg, 79.69 μmol, 1 eq) and Et3N (12.10 mg, 119.54 μmol, 16.64 μL, 1.5 eq) in DCM (2 mL) was added 2-chloroacetyl chloride (13.50 mg, 119.54 μmol, 9.51 μL, 1.5 eq) at 0° C., and the mixture stirred at 0° C. for 1 h to give a red solution. LCMS and (eluting with: PE/EA=0/1) showed the reaction was completed. The reaction solution was diluted with DCM (10 mL) and washed with water (10 mL×3). The organic layer was dried over anhydrous $Na_2SO_4$ and concentrated under reduced pressure. The reaction was purified by prep-HPLC (column: Xtimate C18 150×25 mm×5 μm; mobile phase: [water (0.05% HCl)-ACN]; B %: 20%-50%, 9.5 min) to give 71a and 71. LC-MS (m/z): 453.0[M]+. $^{1}$H NMR (400 MHz, $CDCl_3$) δ ppm 2.12 (s, 3H), 2.46-2.76 (m, 1H), 2.78-3.12 (m, 5H), 3.33 (br s, 2H), 4.15 (br d, J=13.80 Hz, 1H), 5.48-6.34 (m, 1H), 6.99-7.23 (m, 3H), 7.28-7.54 (m, 6H), 8.14 (br s, 1H).

Procedure BR: Synthesis of Compound 72 and Compound 73

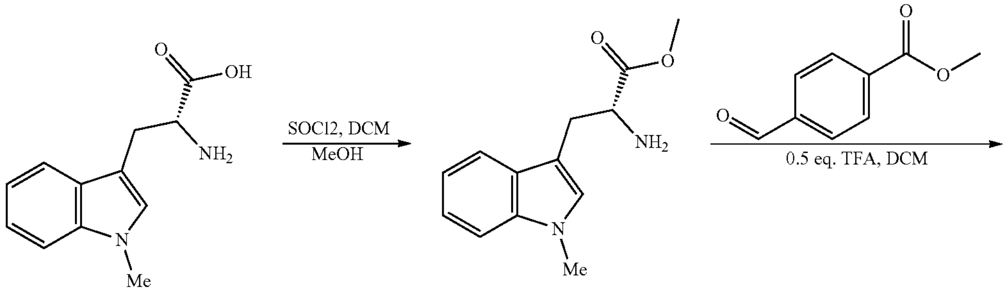

BR-1

BR-2

-continued

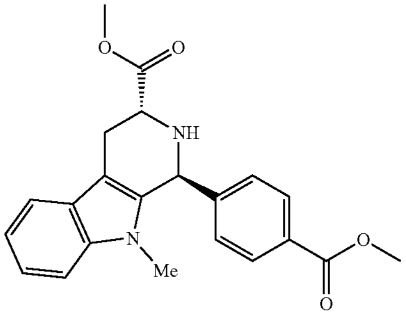

BR-3

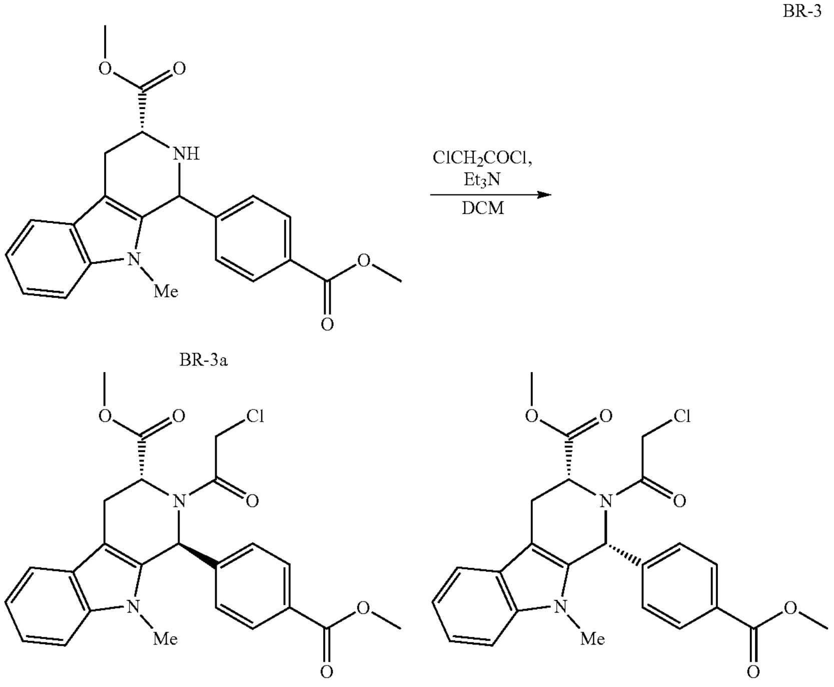

BR-3a

Compound 72

Compound 73

To a solution of BR-1 (200 mg, 916.38 μmol, 1 eq) in MeOH (5 mL) were added $SOCl_2$ (109.02 mg, 916.38 μmol, 66.48 μL, 1 eq) in DCM (1 mL), and the mixture stirred at 30° C. for 16 h to give a brown solution. TLC (quenched with water, eluting with: PE/EA=0/1) showed the reaction was completed. The reaction mixture was evaporated (40° C.) to give BR-2.

To a solution of BR-2 (100 mg, 430.52 μmol, 1 eq) and methyl 4-formylbenzoate (70.67 mg, 430.52 μmol, 1 eq) in DCM (5 mL) was added TFA (24.54 mg, 215.26 μmol, 15.94 μL, 0.5 eq) at 20° C.

The mixture was stirred at 80° C. for 16 h to give a red solution. LCMS and TLC (eluting with: PE/EA=3/1) showed the reaction was completed. The reaction solution was diluted with DCM (10 mL) and washed with water (20 mL×3). The organic layer was dried over anhydrous $Na_2SO_4$ and concentrated under reduced pressure. The mixture was purified by prep-TLC to give BR-3 and BR-3a. $^1H$ NMR (400 MHz, $CDCl_3$) δ ppm 2.99 (dd, J=15.06, 10.29 Hz, 1H), 3.20-3.34 (m, 4H), 3.67-3.81 (m, 4H), 3.91 (s, 3H), 4.05-4.17 (m, 1H), 5.42 (s, 1H), 7.11-7.19 (m, 1H), 7.21-7.25 (m, 2H), 7.27-7.31 (m, 1H), 7.58 (d, J=7.78 Hz, 1H), 7.99 (d, J=8.28 Hz, 2H).

Preparation of 72

To a solution of BR-3 (90 mg, 237.83 μmol, 1 eq) and Et3N (36.10 mg, 356.75 μmol, 49.65 μL, 1.5 eq) in DCM (3 mL) was added 2-chloroacetyl chloride (40.29 mg, 356.75 μmol, 28.37 μL, 1.5 eq) at 30° C. for 1 h to give a yellow solution. TLC (quenched with water, eluting with: PE/EA=3/1) showed the reaction was completed. The reaction was purified by prep-HPLC (column: Xtimate C18 150×25 mm×5 μm; mobile phase: [water (0.05% HCl)-ACN]; B %: 55%-85%, 6.5 min) to give 72. LC-MS (m/z): 455.3[M]+. $^1H$ NMR (400 MHz, $CDCl_3$) δ ppm 3.40-3.70 (m, 7H), 3.88 (br s, 3H), 4.05 (br s, 1H), 5.15 (br s, 1H), 6.27 (s, 1H), 7.10-7.24 (m, 2H), 7.44 (d, J=8.28 Hz, 2H), 7.58 (d, J=7.78 Hz, 1H), 7.93 (br s, 2H).

Preparation of 73

To a solution of BR-3a (60.00 mg, 158.55 μmol, 1 eq) and Et3N (24.07 mg, 237.83 μmol, 33.10 μL, 1.5 eq) in DCM (3 mL) was added 2-chloroacetyl chloride (26.86 mg, 237.83 μmol, 18.92 μL, 1.5 eq) at 30° C., and the mixture stirred for 1 h to give a yellow solution. TLC (quenched with water, eluting with: PE/EA=3/1) showed the reaction was completed. The reaction was purified by prep-TLC to give 73. LC-MS (m/z): 455.4[M]+. $^1$H NMR (400 MHz, $CDCl_3$) δ ppm 2.92 (s, 3H), 3.30 (s, 4H), 3.73 (br d, J=16.06 Hz, 1H), 3.89 (s, 3H), 4.24 (d, J=12.55 Hz, 1H), 4.39 (d, J=12.55 Hz, 1H), 4.96 (br d, J=7.03 Hz, 1H), 7.10 (s, 1H), 7.15-7.23 (m, 1H), 7.28-7.33 (m, 4H), 7.63 (d, J=7.78 Hz, 1H), 7.92 (d, J=8.28 Hz, 2H).

Procedure BS: Synthesis of Compound 74

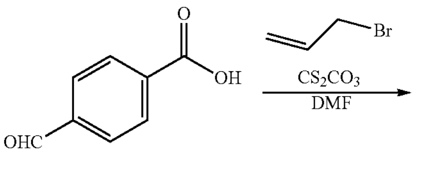

AB-2

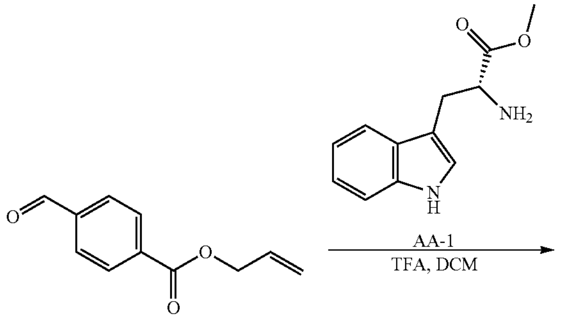

BS-2

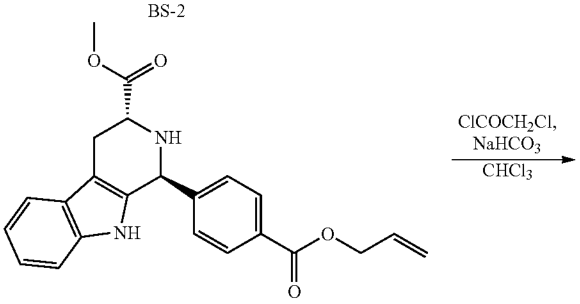

BS-4

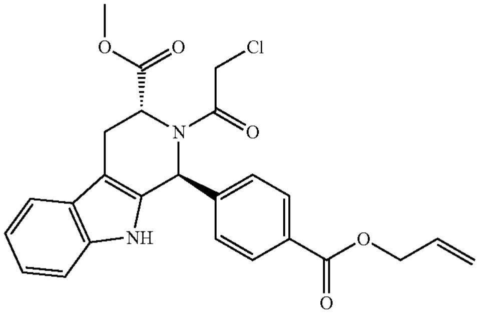

Compound 74

To a solution of AB-2 (500 mg, 3.33 mmol, 1 eq) in DMF (10 mL) were added $Cs_2CO_3$ (3.26 g, 9.99 mmol, 3 eq) and 3-bromoprop-1-ene (805.80 mg, 6.66 mmol, 2 eq). The mixture was stirred and heated to 80° C. for 16 h to give a brown suspension. TLC (PE:EtOAc=2:1) showed the reaction was completed. The mixture was diluted with $H_2O$ (50 mL) and extracted with MTBE (10 mL×3). The organic layers were dried over $Na_2SO_4$, filtered and concentrated. The residue was purified by column chromatography ($SiO_2$, Petroleum ether/Ethyl acetate=I/O to 10/1) to give BS-2. $^1$H NMR (400 MHz, $CDCl_3$) δ=10.11 (s, 1H), 8.23 (d, J=8.3 Hz, 2H), 8.13 (s, 1H), 8.00-7.85 (m, 2H), 6.15-5.93 (m, 1H), 5.53-5.18 (m, 3H), 4.96-4.74 (m, 3H).

To a solution of AA-1 (100 mg, 458.19 μmol, 1 eq) in DCM (5 mL) were added BS-2 (87.14 mg, 458.19 μmol, 1 eq) and TFA (26.12 mg, 229.09 μmol, 16.96 μL, 0.5 eq). The mixture was stirred at 25° C. for 16 h to give a yellow solution. LCMS showed AA-1 was remained. The mixture was heated to 40° C. for 24 h to give a brown solution. TLC (eluting: PE:EtOAc=2:1) showed the reaction was completed. The mixture was adjusted to pH 8 with Sat. $NaHCO_3$ and exacted with DCM (5 mL×3). The combined organic layers were dried over $Na_2SO_4$ and the crude product concentrated. The residue was purified by prep-TLC ($SiO_2$, PE: EtOAc=2:1) to give two products, one of which was BS-4a, and the other of which was BS-4. $^1$H NMR (400 MHz, $CDCl_3$) δ=8.07 (d, J=8.5 Hz, 2H), 7.57-7.46 (m, 3H), 7.44-7.35 (m, 1H), 7.25-7.10 (m, 3H), 6.32-5.81 (m, 1H), 5.46-5.35 (m, 1H), 5.52-5.25 (m, 1H), 5.09-4.70 (m, 2H), 3.99 (dd, J=4.3, 11.0 Hz, 1H), 3.83 (s, 2H), 3.87-3.70 (m, 1H), 3.30-3.19 (m, 1H), 3.11-2.94 (m, 1H).

Preparation of 74

To a solution of BS-4 (43 mg, 110.13 μmol, 1 eq) in DCM (2 mL) were added TEA (111.45 mg, 1.10 mmol, 153.29 μL, 10 eq) and 2-chloroacetyl chloride (62.19 mg, 550.67 μmol, 43.80 μL, 5 eq) at 0° C. The mixture was stirred at 25° C. for 2 h to give a yellow solution. LCMS showed the reaction was completed. The mixture was concentrated to give a crude product. The product was purified by prep-TLC (SiO2, PE: EtOAc=2:1) to give 74. LC-MS (m/z): 489.0 [M+Na]+. $^1$H NMR (400 MHz, $CDCl_3$) δ=8.12-7.93 (m, 1H), 8.17-7.92 (m, 1H), 7.99 (br s, 1H), 7.85-7.66 (m, 1H), 7.58-7.33 (m, 3H), 7.23-7.05 (m, 1H), 7.19-7.05 (m, 1H), 7.25-7.05 (m, 1H), 6.07-5.91 (m, 1H), 5.99 (dt, J=4.8, 11.0 Hz, 1H), 5.37 (br d, J=18.1 Hz, 1H), 5.27 (br d, J=9.0 Hz, 2H), 4.79 (br s, 2H), 4.22-3.77 (m, 2H), 3.67-3.45 (m, 1H), 3.46 (br s, 1H), 3.74-3.16 (m, 3H).

Procedure BT: Synthesis of Compound 75

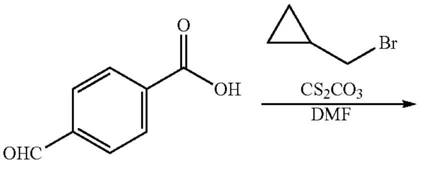

AB-2

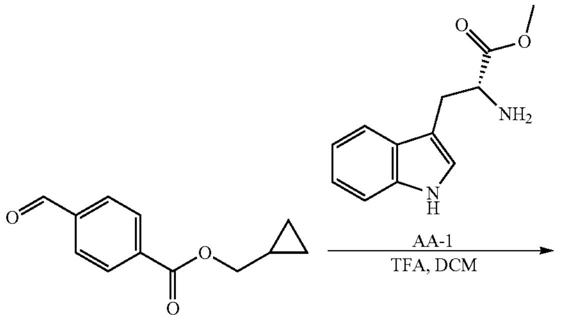

BT-2

-continued

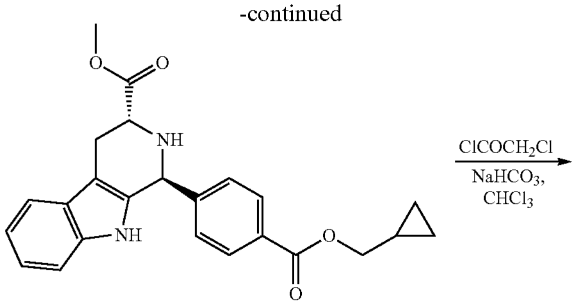

BT-4

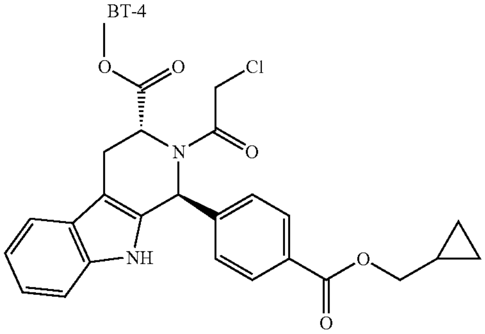

Compound 75

To a solution of AB-2 (500 mg, 3.33 mmol, 1 eq) in DMF (10 mL) were added $Cs_2CO_3$ (3.26 g, 9.99 mmol, 3 eq) and bromomethylcyclopropane (1.12 g, 8.33 mmol, 797.19 μL, 2.5 eq). The mixture was heated to 80° C. for 16 h to give a brown suspension. TLC (PE:EtOAc=2:1) showed the reaction was completed. The mixture was diluted with $H_2O$ (50 mL) and then extracted with MTBE (10 mL×3). The organic layers were dried over $Na_2SO_4$, filtered and concentrated. The product was purified by column chromatography ($SiO_2$, Petroleum ether/Ethyl acetate=1:0) to give BT-2. $^1$H NMR (400 MHz, $CDCl_3$) δ=10.11 (s, 1H), 8.23 (d, J=8.3 Hz, 2H), 7.97 (d, J=7.6 Hz, 2H), 4.22-4.10 (m, 2H), 1.34-1.13 (m, 1H), 0.69-0.53 (m, 2H), 0.45-0.20 (m, 2H).

To a solution of BT-2 (100 mg, 489.67 μmol, 1 eq) in DCM (5 mL) were added methyl (2R)-2-amino-3-(1H-indol-3-yl)propanoate (106.87 mg, 489.67 μmol, 1 eq) and TFA (27.92 mg, 244.83 μmol, 18.13 μL, 0.5 eq). The mixture was stirred at 20° C. for 16 h to give a yellow solution. LCMS showed the reaction was completed. The mixture was adjusted to pH 8 with saturated $NaHCO_3$, and then extracted with DCM (5 mL×3). The combined organic layers was dried over $Na_2SO_4$ and the crude product concentrated. The residue was purified by prep-TLC ($SiO_2$, PE: EtOAc=2:1) to give two products, one of which was BT-4, and the other of which was the cis-isomer. $^1$H NMR (400 MHz, $CDCl_3$) δ=8.04 (d, J=8.0 Hz, 2H), 7.60-7.48 (m, 2H), 7.39 (d, J=8.3 Hz, 2H), 7.21-7.12 (m, 2H), 5.49 (s, 1H), 4.18-4.10 (m, 2H), 4.00-3.91 (m, 1H), 3.73 (s, 3H), 3.33-3.24 (m, 1H), 3.17 (ddd, J=1.3, 6.4, 15.4 Hz, 1H), 2.05 (s, 1H), 0.65-0.59 (m, 2H), 0.40-0.34 (m, 2H).

Preparation of 75

To a solution of BT-4 (15 mg, 37.09 μmol, 1 eq) in $CH_3Cl$ (2 mL) were added TEA (37.53 mg, 370.87 μmol, 51.62 μL, 10 eq) and 2-chloroacetyl chloride (20.94 mg, 185.43 μmol, 14.75 μL, 5 eq) at 0° C. The mixture was stirred at 25° C. for 2 h to give a yellow solution. LCMS showed the reaction was completed. The mixture was concentrated to give the crude product. The product was purified by prep-TLC (SiO2, PE: EtOAc=2:1) to give 75. LC-MS (m/z): 481.1 [M+H]+. $^1$H NMR (400 MHz, $CDCl_3$) δ=8.11-7.86 (m, 2H), 7.73 (br s, 1H), 7.57-7.37 (m, 3H), 7.24-7.10 (m, 3H), 6.11 (br s, 1H), 5.27 (br s, 1H), 4.19-4.09 (m, 2H), 4.09-3.88 (m, 1H), 3.87-3.68 (m, 1H), 3.65 (s, 3H), 1.33-1.15 (m, 1H), 0.59 (br d, J=6.5 Hz, 2H), 0.34 (br d, J=4.0 Hz, 2H).

Procedure BU: Synthesis of Compound 77 and Compound 77a

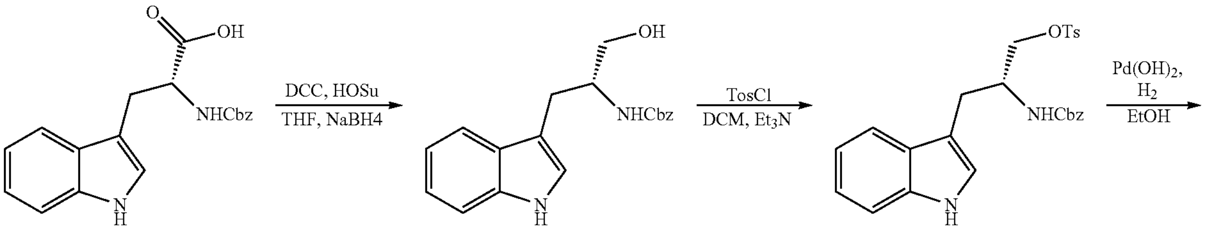

BU-1 BU-2 BU-3

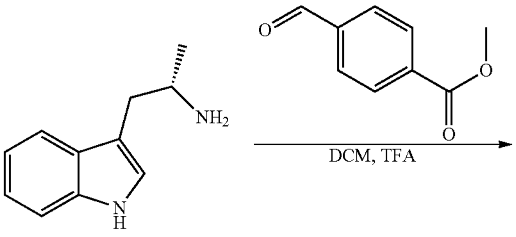

BU-4

-continued

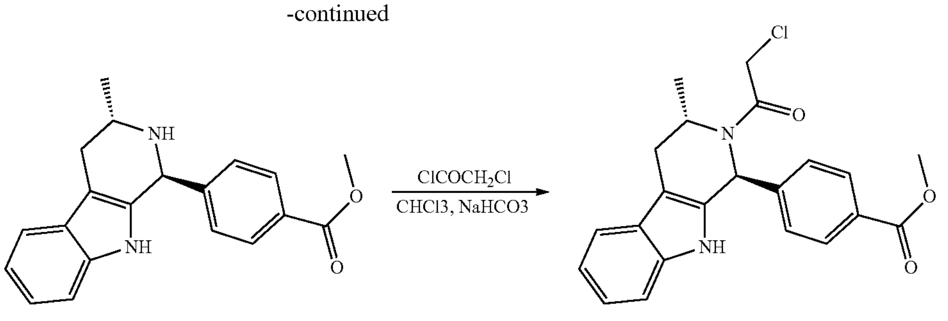

BU-5 Compound 77

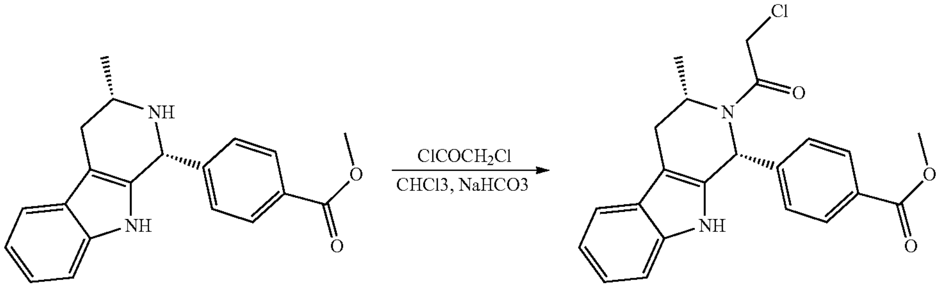

BU-5a Compound 77a

To a solution of BU-1 (5 g, 14.78 mmol, 1 eq) and HOSu (2.04 g, 17.74 mmol, 1.2 eq) in THF (50 mL) was added DCC (3.35 g, 16.26 mmol, 3.29 mL, 1.1 eq) at 0° C. The reaction was stirred at this temperature for about 1 h. The precipitated DCU was filtered and washed with THF (3×10 mL). The combined organic layer was cooled to ice temperature and a solution of sodium $NaBH_4$ (1.12 g, 29.56 mmol, 2 eq) in water (10 mL) was added in one portion, which leads to the vigorous evolution of gas. TLC (eluting with: PE/EtOAc=0/1) showed the reaction was completed. 0.5N HCl (15 mL) was added to quench $NaBH_4$. The reaction mixture was extracted with EtOAc (3×50 mL), and the combined organic layer was washed with 5% $Na_2CO_3$ (3×20 mL), washed with brine (3×20 mL), dried over $Na_2SO_4$, and concentrated in vacuo. The product was purified by silica gel chromatography (PE/EA=10/1-1/1) to give BU-2. $^1H$ NMR (400 MHz, $CDCl_3$) δ: 2.99 (d, J=6.53 Hz, 3H), 3.54-3.70 (m, 2H), 4.03 (s, 1H), 5.08 (s, 2H), 5.26 (d, J=8.03 Hz, 1H), 6.97 (s, 1H), 7.10 (t, J=7.15 Hz, 1H), 7.18 (t, J=7.40 Hz, 2H), 7.32 (d, J=1.76 Hz, 6H), 7.65 (d, J=7.53 Hz, 1H), 8.39 (s, 1H).

To a solution of BU-2 (2 g, 6.17 mmol, 1 eq) and Et3N (1.25 g, 12.33 mmol, 1.72 mL, 2 eq) in DCM (20 mL) was added TosCl (1.41 g, 7.40 mmol, 1.2 eq). The reaction mixture was stirred at 0° C. for 1 h to give a colorless solution. TLC (eluting with: PE/EtOAc=3/1) showed the reaction was completed. The reaction mixture was partitioned between water (20 mL) and EtOAc (20 mL), and the aqueous layer extracted with EtOAc (20 mL×2). The combined organic layers was dried over sodium sulfate and then concentrated. The product was purified by silica gel chromatography (DCM/EtOAc=10/1-5/1) to give BU-3. $^1H$ NMR (400 MHz, $CDCl_3$) δ: 2.42 (s, 3H), 2.94-3.12 (m, 2H), 4.02 (d, J=3.76 Hz, 2H), 4.20 (d, J=4.77 Hz, 1H), 5.02 (d, J=9.03 Hz, 1H), 5.06 (s, 2H), 6.97 (d, J=1.76 Hz, 1H), 7.07-7.14 (m, 1H), 7.19 (t, J=7.53 Hz, 1H), 7.27-7.38 (m, 8H), 7.60 (d, J=7.78 Hz, 1H), 7.74 (d, J=8.28 Hz, 2H), 8.07 (s, 1H).

To a solution of BU-3 (1.06 g, 2.21 mmol, 1 eq) in ethanol (15 mL) was added $Pd(OH)_2$ (93.32 mg, 664.49 μmol, 0.3 eq) at 25° C. under $H_2$ (15 Psi) atmosphere. The reaction mixture was stirred at 25° C. for 2 h. TLC (eluting with: PE/EtOAc=0/1) showed the reaction was completed. The reaction mixture was filtered and the filtrate concentrated. The product was partitioned between EtOAc (15 mL) and saturated sodium bicarbonate (15 mL), and the aqueous layers extracted with EtOAc (15 mL×2). The combined organic layers were dried over sodium sulfate and concentrated. The product was purified by silica gel chromatography (EtOAc/MeOH=1/0-3/1) to give BU-4. $^1H$ NMR (400 MHz, $CDCl_3$) δ: 2.59 (dd, J=14.05, 8.28 Hz, 1H), 2.81 (dd, J=14.18, 4.89 Hz, 1H), 3.14-3.29 (m, 1H), 6.97 (s, 1H), 7.01-7.06 (m, 1H), 7.09-7.15 (m, 1H), 7.29 (d, J=8.03 Hz, 1H), 7.53 (d, J=7.78 Hz, 1H), 8.16 (s, 1H).

To a solution of BU-4 (200 mg, 1.15 mmol, 1 eq) and methyl 4-formylbenzoate (226.11 mg, 1.38 mmol, 1.2 eq) in DCM (10 mL) was added TFA (65.44 mg, 573.91 μmol, 42.49 μL, 0.5 eq) at 40° C. The reaction mixture was stirred at 40° C. to give a yellow solution. TLC (eluting with: PE/EtOAc=1/1) showed the reaction was completed. The reaction mixture was quenched with Sat. $NaHCO_3$ (15 mL) and extracted with DCM (20 mL×3). The combined organic layers were dried over $Na_2SO_4$ and concentrated to give a crude product. The product was purified by silica gel chromatography (PE/EA=10/1-1/1) to afford methyl BU-5a and BU-5.

BU-5: 1H NMR (400 MHz, DMSO-d6) δ: 1.14 (d, J=6.27 Hz, 3H), 2.32-2.42 (m, 1H), 2.82 (dd, J=15.18, 4.14 Hz, 1H), 2.99 (s, 1H), 3.84 (s, 3H), 5.26 (s, 1H), 6.96-7.00 (m, 1H), 7.02-7.08 (m, 1H), 7.27 (d, J=7.78 Hz, 1H), 7.38 (d, J=8.28 Hz, 2H), 7.44 (d, J=7.53 Hz, 1H), 7.92 (d, J=8.28 Hz, 2H), 10.77 (s, 1H).

BU-5a: 1H NMR (400 MHz, DMSO-d6) δ: 1.26 (d, J=6.02 Hz, 3H), 2.38-2.48 (m, 1H), 2.70-2.80 (m, 1H), 3.14 (m, 1H), 3.86 (s, 3H), 5.25 (s, 1H), 6.85-7.03 (m, 2H), 7.18

(d, J=7.53 Hz, 1H), 7.40 (d, J=7.28 Hz, 1H), 7.54 (d, J=8.28 Hz, 2H), 7.96 (d, J=8.28 Hz, 2H), 10.23 (s, 1H).

Preparation of 77

To a solution of BU-5 (22 mg, 68.67 μmol, 1 eq) and Et3N (20.85 mg, 206.00 μmol, 28.67 μL, 3 eq) dissolved in DCM (10 mL) was added 2-chloroacetyl chloride (11.63 mg, 103.00 μmol, 8.19 μL, 1.5 eq) at 0° C. The reaction mixture was stirred at 0° C. for 2 h to give a colorless solution. TLC (eluting with: EA/MeOH=3/1) showed the reaction was completed. The reaction mixture was quenched with Sat. $NaHCO_3$ (15 mL) and extracted with DCM (20 mLx3). The organic layers were dried over $Na_2SO_4$ and concentrated to give a crude product, which was then purified by Prep-TLC (DCM/MeOH=10/1) to afford 77. LC-MS (m/z): 397.0 [M+H]+. $^1$H NMR (400 MHz, DMSO-d6) δ: 1.15 (d, J=6.27 Hz, 3H), 2.92 (d, J=14.31 Hz, 1H), 3.16-3.30 (m, 1H), 3.80 (s, 3H), 4.43 (s, 1H), 4.80 (s, 2H), 5.98 (s, 1H), 6.94-6.99 (m, 1H), 7.00-7.06 (m, 1H), 7.27 (d, J=8.03 Hz, 1H), 7.45 (d, J=7.78 Hz, 1H), 7.54 (d, J=7.78 Hz, 2H), 7.84 (d, J=7.78 Hz, 2H), 11.02 (s, 1H).

Preparation of 77a

To a solution of BU-5a (69 mg, 215.37 μmol, 1 eq) and Et3N (65.38 mg, 646.10 μmol, 89.93 μL, 3 eq) dissolved in DCM (10 mL) was added 2-chloroacetyl chloride (36.49 mg, 323.05 μmol, 25.69 μL, 1.5 eq) at 0° C. The reaction mixture was stirred at 0° C. for 2 h to give a colorless solution. TLC (eluting with: EA/MeOH=3/1) showed the reaction was completed. The reaction mixture was quenched with Sat. $NaHCO_3$ (15 mL) and extracted with DCM (20 mLx3). The organic layers were dried over $Na_2SO_4$ and concentrated to give crude product. The crude product was purified by Prep-TLC (DCM/MeOH=10/1) to afford 77a. LC-MS (m/z): 397.4 [M+H]+. $^1$H NMR (400 MHz, DMSO-d6) δ: 0.91 (d, J=6.78 Hz, 3H), 2.73 (d, J=15.81 Hz, 1H), 3.13-3.19 (m, 1H), 3.84 (s, 3H), 4.55-4.76 (m, 3H), 6.93 (s, 1H), 7.01-7.06 (m, 1H), 7.10-7.17 (m, 1H), 7.38 (d, J=8.03 Hz, 1H), 7.49 (dd, J=7.78, 2.76 Hz, 3H), 7.94 (d, J=8.53 Hz, 2H), 11.16 (s, 1H).

Procedure BV: Synthesis of Compound 78

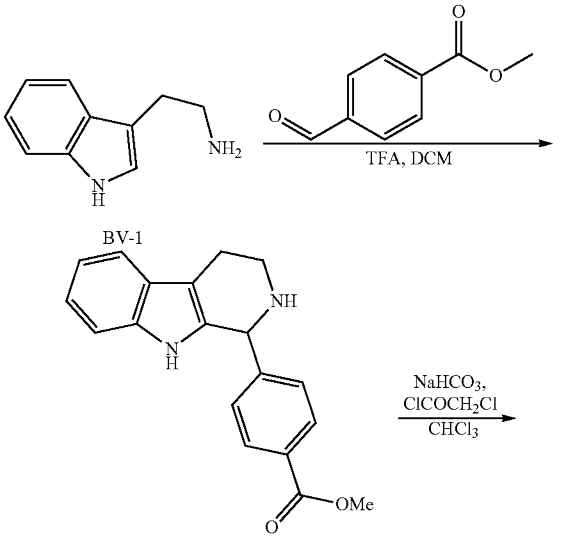

BV-2

-continued

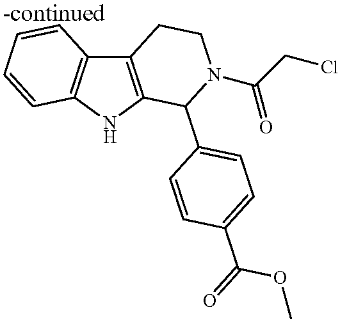

Compound 78

Preparation of Compound BV-2

To a solution of BV-1 (200 mg, 1.25 mmol, 1 eq) in DCM (10 mL) were added methyl 4-formylbenzoate (204.92 mg, 1.25 mmol, 1 eq) and TFA (71.17 mg, 624.16 μmol, 46.21 μL, 0.5 eq). The mixture stirred at 45° C. for 12 h to give a brown solution. TLC (eluting with: PE/EtOAc=1/1, SiO2) showed the reaction was completed. The reaction mixture was adjusted to pH 8 with Sat. $NaHCO_3$ and extracted with DCM (20 mlx3). The organic layers were dried over $Na_2SO_4$ and concentrated to give BV-2. $^1$H NMR (400 MHz, $CDCl_3$)$_6$ ppm 2.82-2.98 (m, 1H), 3.13-3.19 (m, 1H), 3.33-3.39 (dt, J=12.36, 4.74 Hz, 1H), 3.90-3.93 (m, 1H), 3.95-3.99 (m, 1H), 3.97 (s, 2H), 5.23 (s, 1H), 7.11-7.18 (qd, J=7.15, 5.65 Hz, 1H), 7.39-7.41 (d, J=8.03 Hz, 1H), 7.52-7.58 (m, 1H), 7.95-8.02 (m, 3H), 8.20-8.22 (d, J=8.28 Hz, 2H), 10.10 (s, 1H).

Preparation of 78

To a solution of BV-2 (150.00 mg, 489.62 μmol, 1 eq, crude) in $CHCl_3$(10 mL) were added $NaHCO_3$ (411.33 mg, 4.90 mmol, 190.43 μL, 10 eq) and 2-chloroacetyl chloride (165.90 mg, 1.47 mmol, 116.83 μL, 3 eq) at 0° C. The mixture stirred at 25° C. for 2 h to give a yellow solution. TLC (eluting with: PE/EtOAc=1/1, SiO2) showed the reaction was completed. The reaction mixture was filtered and washed with DCM (20 mL). The filtrate was concentrated and the residue purified by prep-TLC (Petroleum ether:Ethyl acetate=1:1) to give 78. LC-MS (m/z): 382.9 [M+H]+. $^1$H NMR (400 MHz, $CDCl_3$) δ ppm 2.94-3.15 (m, 2H), 3.44-3.541 (m, 1H), 3.91-3.94 (s, 3H), 3.94-4.00 (m, 1H), 4.15-4.23 (m, 2H), 6.97 (s, 1H), 7.16-7.23 (m, 2H), 7.33-7.35 (d, J=7.78 Hz, 1H), 7.40-7.42 (d, J=8.28 Hz, 2H), 7.52-7.57 (d, J=7.78 Hz, 1H), 7.85 (s, 1H), 7.96-7.98 (d, J=8.28 Hz, 2H).

Procedure BW: Synthesis of Compound 79

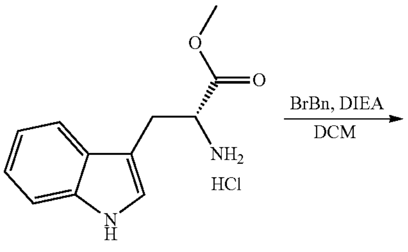

AA-1

-continued

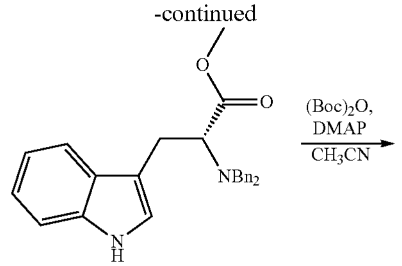

BI-2

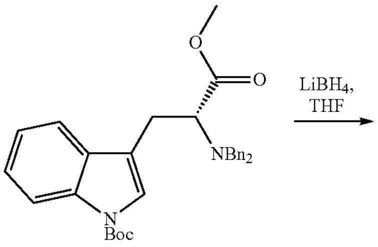

BI-3

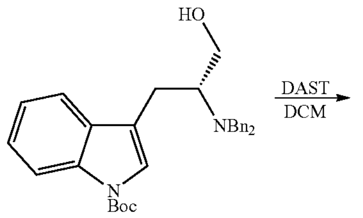

BI-4

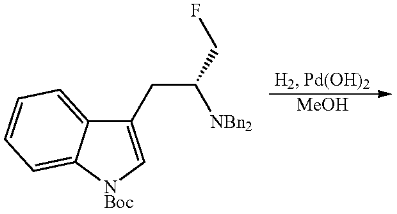

BW-5

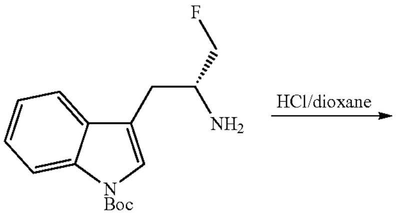

BW-6

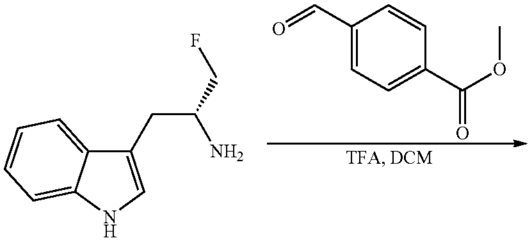

BW-7

-continued

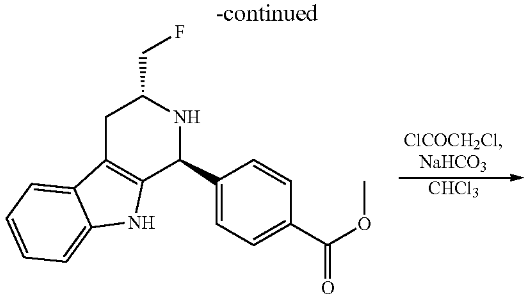

BW-8

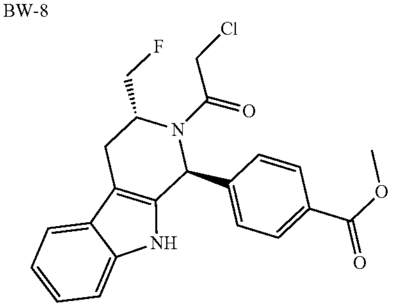

Compound 79

To a solution of AA-1 (10 g, 39.26 mmol, 1 eq, HCl) in DCM (100 mL) were added DIEA (17.76 g, 137.41 mmol, 23.93 mL, 3.5 eq) and BnBr (14.77 g, 86.37 mmol, 10.26 mL, 2.2 eq) at 0° C. The mixture was stirred at 15° C. for 12 h to give a yellow solution. LCMS showed desired mass was found but that AA-1 remained. The mixture was stirred at 15° C. for 14 h, and then stirred at 30° C. for an additional 12 h. LCMS and TLC (eluting with: PE/EtOAc=3/1) showed the reaction was completed. The reaction mixture was quenched with $H_2O$ (100 mL) and extracted with DCM (50 mL×2). The organic layers were dried over $Na_2SO_4$ and concentrated to give the crude product. The crude product was purified by flash column chromatography (eluting with: PE/EtOAc=100% PE to 30%) to give BI-2. $^1$H NMR (400 MHz, $CDCl_3$) δ 7.93 (s, 1H), 7.35-7.27 (m, 7H), 7.26-7.12 (m, 5H), 6.92-6.91 (m, 2H), 4.05-4.02 (m, 2H), 3.84-3.82 (m, 1H), 3.71 (s, 3H), 3.58-3.54 (m, 2H), 3.41-3.37 (m, 1H), 3.13-3.12 (m, 1H).

To a solution of BI-2 (12 g, 30.11 mmol, 1 eq) in CH3CN (100 mL) were added DMAP (367.89 mg, 3.01 mmol, 0.1 eq) and $Boc_2O$ (9.86 g, 45.17 mmol, 10.38 mL, 1.5 eq). The mixture was allowed to stir 15° C. for 12 h to give a yellow solution. LCMS and TLC (eluting with: PE/EtOAc=3/1) showed the reaction was completed. The reaction mixture was quenched with $H_2O$ (100 mL) and extracted with EtOAc (100 mL×2). The organic layers were dried over $Na_2SO_4$ and concentrated to give the crude product. The crude product was purified by flash column chromatography (eluting with: PE/EtOAc=100% PE to 20%) to give BI-3. $^1$H NMR (400 MHz, $CDCl_3$): δ 8.13 (brs, 1H), 7.47-7.25 (m, 12H), 7.06-7.04 (m, 2H), 4.03-4.00 (m, 2H), 3.81-3.77 (m, 4H), 3.57-3.54 (m, 2H), 3.32-3.30 (m, 1H), 3.05-3.02 (m, 1H), 1.68 (s, 9H).

To a solution of BI-3 (10 g, 20.06 mmol, 1 eq) in THF (100 mL) was added $LiBH_4$ (1.31 g, 60.17 mmol, 3 eq) at 0° C. The mixture was allowed to stir at 15° C. for 12 h to give a yellow solution. LCMS showed desired mass was found, and that BI-3-remained. The reaction mixture was quenched with Sat. $NaHCO_3$ (50 mL) and extracted with EtOAc (80 mL×3). The organic layers were dried over $Na_2SO_4$ and concentrated to give the crude product. The crude product was purified by flash column chromatography (eluting with: PE/EtOAc=100% PE to 20%) to give BI-4 and BI-3. $^1$H NMR (400 MHz, $CDCl_3$): δ 8.13 (brs, 1H), 7.41-7.31 (m, 11H), 7.28-7.21 (m, 3H), 4.02-3.99 (m, 2H), 3.63-3.56 (m, 3H), 3.48-3.44 (m, 1H), 3.28-3.21 (m, 2H), 3.16 (brs, 1H), 2.66-2.60 (m, 1H), 1.65 (s, 9H).

To a solution of BI-4 (1.5 g, 3.19 mmol, 1 eq) in DCM (20 mL) was added DAST (1.54 g, 9.56 mmol, 1.26 mL, 3 eq) at −78° C. The mixture was allowed to stir 15° C. for 1 h to give a yellow solution. LCMS showed that the desired mass was found, and BI-4 remained. LCMS and TLC (eluting with: PE/EtOAc=3/1) showed the reaction was completed. The reaction mixture was quenched with Sat. $NaHCO_3$ (50 mL) and extracted with DCM (80 mLx3). The organic layers were dried over $Na_2SO_4$ and concentrated to give the crude product. The crude product was purified by flash column chromatography (eluting with: PE/EtOAc=100% PE to 20%) to give BW-5. $^1$H NMR (400 MHz, $CDCl_3$): δ 8.04 (brs, 1H), 7.35-7.16 (m, 14H), 4.93-4.39 (m, 1H), 3.84-3.60 (m, 4H), 2.92-2.70 (m, 4H), 1.56 (s, 9H).

To a solution of BW-5 (1.2 g, 2.54 mmol, 1 eq) in MeOH (30 mL) was added $Pd(OH)_2$ (100.00 mg, 7.12 μmol, 1% purity) under $N_2$. The suspension was degassed under vacuum and purged with $H_2$ several times. The mixture was stirred under $H_2$ (15 psi) at 15° C. for 1.5 h to give a black suspension. LCMS showed that the desired mass was found, and BW-5 remained. The mixture was stirred at 15° C. for 12 h again. LCMS showed the reaction was completed. The reaction mixture was filtered on celite and washed with MeOH (50 mL). The filtrate was concentrated to give BW-6. The BW-6 was used for the next step without purification.

BW-6 (742 mg, 2.54 mmol, 1 eq) was dissolved in HCl/dioxane (4 M, 30 mL, 47.28 eq). The mixture was stirred at 10° C. for 0.5 h to give a yellow suspension. LCMS showed the reaction was completed. The reaction mixture was concentrated to give a residue, which was then adjusted to pH 8 with Sat. $NaHCO_3$. The water layer was concentrated to give the crude product. The crude product was dissolved in DCM/EtOH (30 mL, 5/1), the mixture filtered and washed with DCM (30 mL). The filtrate was concentrated to give BW-7 which was used in the next step without further purification.

To a solution of BW-7 (100 mg, 520.20 μmol, 1 eq) in DCM (3 mL) were added methyl 4-formylbenzoate (85.40 mg, 520.20 μmol, 1 eq) and TFA (29.66 mg, 260.10 μmol, 19.26 μL, 0.5 eq). The mixture was stirred at 50° C. for 16 h to give a yellow solution. LCMS and TLC (eluting with: PE/EtOAc=1/1) showed the reaction was completed. The reaction mixture was quenched with Sat. $NaHCO_3$ (10 mL) and extracted with DCM (15 mLx3). The organic layers were dried over $Na_2SO_4$ and concentrated to give the crude product. The crude product was purified by prep-TLC (eluting with: PE/EtOAc=1/1) to give two products, BW-8 and the corresponding cis isomer. $^1$H NMR (400 MHz, $CDCl_3$) δ 7.94-7.92 (m, 2H), 7.66 (s, 1H), 7.49-7.47 (m, 1H), 7.24-7.20 (m, 3H), 7.09-7.02 (m, 2H), 5.24 (s, 1H), 4.50-4.35 (m, 2H), 3.76 (s, 3H), 3.41-3.36 (m, 1H), 2.89-2.84 (m, 1H), 2.64-2.58 (m, 1H).

Preparation of 79

To a solution of BW-8 (45 mg, 132.99 μmol, 1 eq) in CHCl3 (3 mL) were added $NaHCO_3$ (111.72 mg, 1.33 mmol, 51.72 μL, 10 eq) and 2-chloroacetyl chloride (45.06 mg, 398.97 μmol, 31.73 μL, 3 eq). The mixture was stirred at 10° C. for 2 h to give a yellow suspension. LCMS and TLC (eluting with: PE/EtOAc=2/1) showed the reaction was completed. The reaction mixture was quenched with $H_2O$ (10 mL) and extracted with DCM (10 mL×2). The organic layers were dried over $Na_2SO_4$ and concentrated to give the crude product. The crude product was purified by prep-TLC (eluting with: PE/EtOAc=2/1) to give 79. LC-MS (m/z): 414.9 [M+H]+. H NMR (400 MHz, $CDCl_3$): δ 7.91-7.89 (m, 2H), 7.61 (brs, 1H), 7.45-7.43 (m, 1H), 7.36-7.34 (m, 2H), 7.16-7.06 (m, 3H), 5.90 (brs, 1H), 4.95 (brs, 1H), 4.53-4.38 (m, 3H), 3.98-3.84 (m, 1H), 3.80 (s, 3H), 3.39-3.30 (m, 1H), 3.01-2.98 (m, 1H).

Procedure BX: Synthesis of Compounds BX and BXa

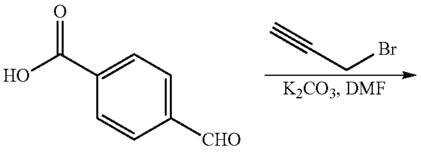

AB-2

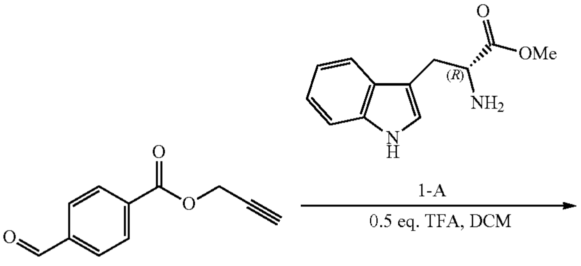

BX-2

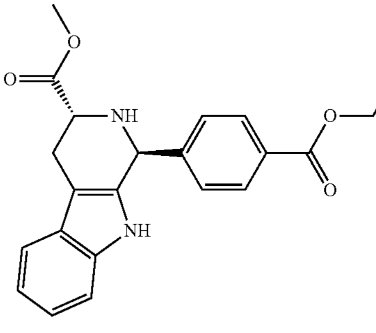

BX-3

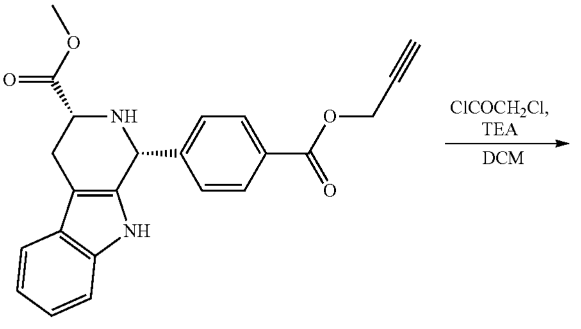

BX-3a

-continued

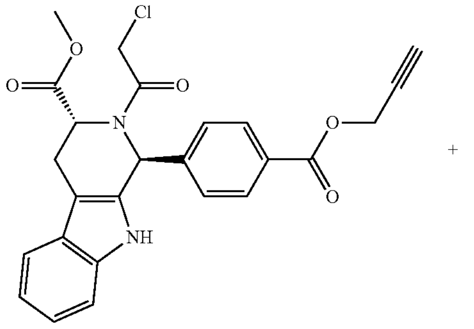

BX

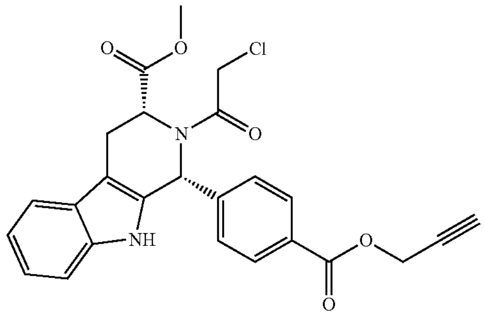

BXa

Preparation of Compound BX-2

AB-2 (1 g, 6.66 mmol, 1 eq) and $K_2CO_3$ (1.01 g, 7.33 mmol, 1.1 eq) in anhydrous DMF (20 mL) was stirred for 30 min at 70° C. The reaction mixture was then cooled to 0° C., and 3-bromoprop-1-yne (871.61 mg, 7.33 mmol, 631.60 μL, 1.1 eq) was added dropwise. The mixture was again stirred at 70° C. for 16 h until it became a black suspension. TLC (eluting with: PE/EtOAc=3/1) showed the reaction was completed. The reaction mixture was partitioned between EtOAc (20 mL) and water (10 mL), and the aqueous layer extracted with EtOAc (20 mL×2). The combined organic layers were washed with brine (20 mL×2), dried over sodium sulfate and concentrated to give the crude product. The product was obtained and then purified by a flash column (PE/EtOAc=7/1-3/1) to give BX-2.

Preparation of Compound BX-3 and BX-3a

To a mixture of methyl (2R)-2-amino-3-(1H-indol-3-yl) propanoate (640.44 mg, 2.93 mmol, 1.1 eq) and BX-2 (502 mg, 2.67 mmol, 1 eq) in DCM (20 mL) was added TFA (304.17 mg, 2.67 mmol, 197.51 μL, 1 eq), and the mixture stirred at 20° C. for 72 h to give a yellow suspension. TLC (eluting with: PE/EtOAc=2/1) showed the reaction was completed. The reaction mixture was partitioned between DCM (10 mL) and water (10 mL). The organic layer was washed with saturated sodium bicarbonate solution (10 mL×2). The aqueous layer was extracted with DCM (10 mL×2). The combined organic layers were washed with brine (20 mL), dried over sodium sulfate and concentrated to give the crude product. The crude product was purified by a flash column (PE/EtOAC=4/1-3/1) to give BX-3 and BX-3a.

BX-3: 1H NMR (400 MHz, $CDCl_3$) δ: 2.51 (t, J=2.38 Hz, 1H), 3.31 (dd, J=15.94, 7.65 Hz, 1H), 3.47 (dd, J=16.19, 5.65 Hz, 1H), 3.75 (s, 3H), 4.14-4.22 (m, 1H), 4.90 (d, J=2.26 Hz, 2H), 5.94 (s, 1H), 7.14-7.31 (m, 1H), 7.23 (td, J=7.47, 1.13 Hz, 1H), 7.27-7.31 (m, 1H), 7.38 (d, J=8.28 Hz, 2H), 7.56 (d, J=7.78 Hz, 1H), 8.00 (d, J=8.28 Hz, 2H), 8.18 (s, 1H).

BX-3a: 1H NMR (400 MHz, $CDCl_3$) δ: 2.54 (t, J=2.51 Hz, 1H), 3.15-3.26 (m, 1H), 3.36 (dd, J=15.69, 3.64 Hz, 2H), 3.78 (s, 3H), 4.07 (dd, J=11.29, 4.52 Hz, 1H), 4.92 (d, J=2.51 Hz, 2H), 5.70 (s, 1H), 7.15-7.26 (m, 3H), 7.45 (d, J=8.28 Hz, 2H), 7.56 (d, J=7.53 Hz, 1H), 7.89 (d, J=8.28 Hz, 2H), 8.00 (s, 1H).

To a solution of BX-3 (225.4 mg, 580.31 μmol, 1 eq) and Et3N (129.19 mg, 1.28 mmol, 177.70 μL, 2.2 eq) in DCM (10 mL) was added 2-chloroacetyl chloride (131.08 mg, 1.16 mmol, 92.31 μL, 2 eq) at 0° C. The reaction mixture was stirred at 0° C. for 4 h to give a yellow solution. TLC (eluting with: PE/EtOAc=3/1) showed the reaction was completed. The reaction mixture was partitioned between DCM (10 mL) and water (10 mL). The organic layer was washed with saturated sodium bicarbonate solution (10 mL×2), and the aqueous layer extracted with DCM (10 mL×2). The combined organic layers were dried over sodium sulfate and concentrated to give the crude product. The crude product was purified by a flash column (PE/EtOAC=5:1-2:1) to give BX. LC-MS (m/z): 486.9 [M+Na]+. $^1$H NMR (400 MHz, $CDCl_3$) δ: 2.43-2.55 (m, 1H), 3.37-3.56 (m, 1H), 3.64 (s, 3H), 3.72 (s, 1H), 3.95-4.19 (m, 2H), 4.88 (s, 2H), 5.26 (s, 1H), 6.06-6.32 (m, 1H), 7.08-7.26 (m, 3H), 7.37-7.59 (m, 3H), 7.84 (s, 1H), 7.90-8.15 (m, 2H).

To a solution of BX-3a (276.20 mg, 711.09 μmol, 1 eq) and Et3N (179.89 mg, 1.78 mmol, 247.44 μL, 2.5 eq) in DCM (10 mL) was added 2-chloroacetyl chloride (160.63 mg, 1.42 mmol, 113.12 μL, 2 eq) at 0° C. The reaction mixture was stirred at 0° C. for 4 h to give a yellow solution. TLC (eluting with: PE/EtOAc=3/1) showed the reaction was completed. The reaction mixture was partitioned between DCM (10 mL) and water (10 mL), and the organic layer washed with saturated sodium bicarbonate solution (10 mL×2). The aqueous layer was extracted with DCM (10 mL×2). The combined organic layers were dried over sodium sulfate and concentrated to give the crude product. The product was purified by a flash column (PE/EtOAC=5:1-3:1) to give BXa. LC-MS (m/z): 486.9 [M+Na]+. $^1$H NMR (400 MHz, $CDCl_3$) δ: 2.52 (t, J=2.38 Hz, 1H), 3.04 (s, 3H), 3.20-3.30 (m, 1H), 3.71 (d, J=15.81 Hz, 1H), 4.19-4.27 (m, 1H), 4.32-4.41 (m, 1H), 4.89 (d, J=2.51 Hz, 2H), 4.97 (d, J=2.26 Hz, 1H), 6.96 (s, 1H), 7.15-7.25 (m, 2H), 7.31 (d, J=8.03 Hz, 1H), 7.36 (d, J=7.53 Hz, 2H), 7.62 (d, J=7.53 Hz, 1H), 7.88 (s, 1H), 7.94 (d, J=7.78 Hz, 2H).

Procedure BY: Synthesis of compound BY and compound BYa
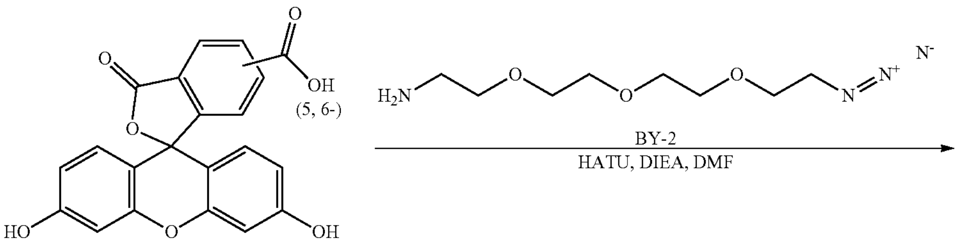
BY-1
300 mg
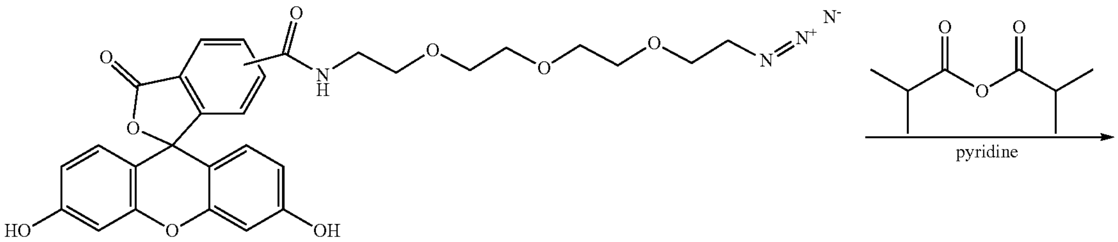
BY-3
552 mg, crude
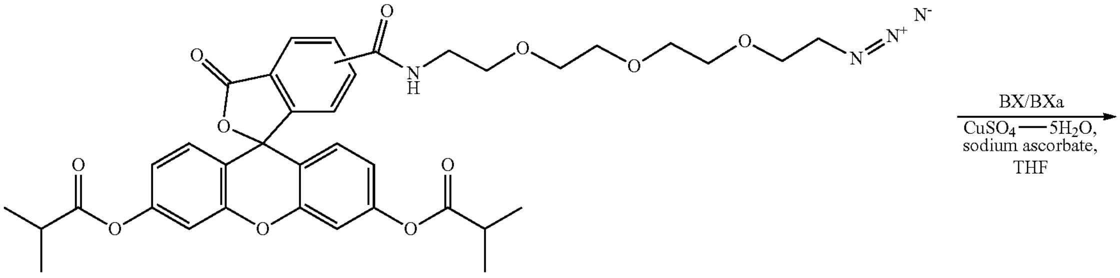
BY-4
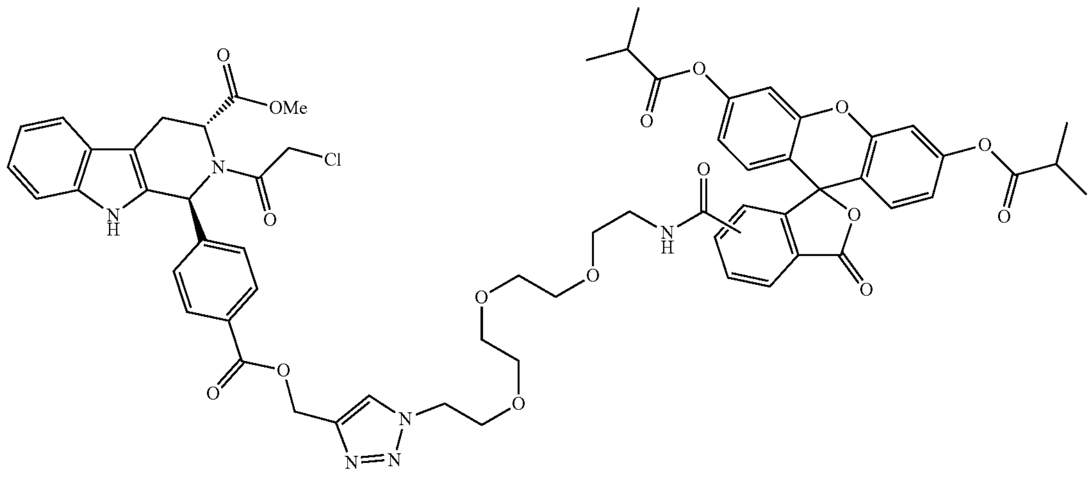
BY -continued

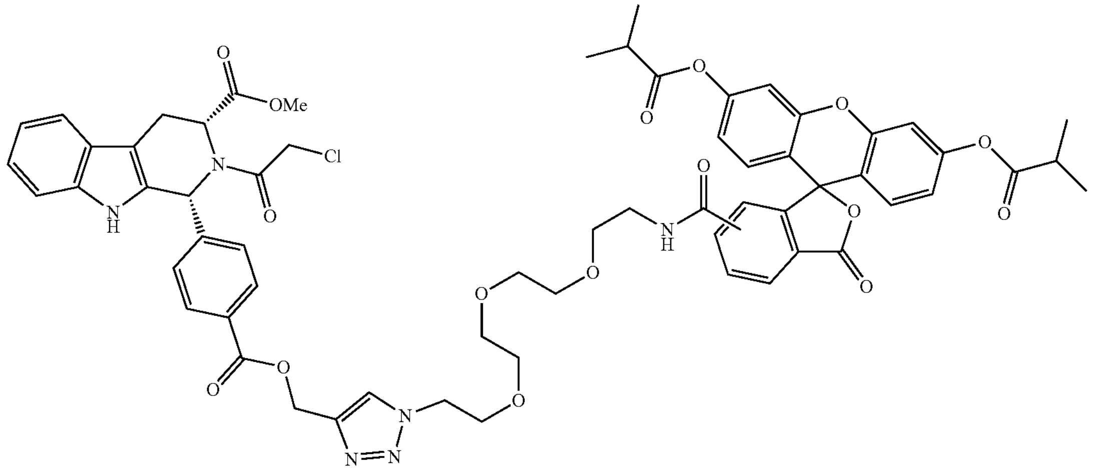

BYa

BY-1 (100 mg, 265.73 μmol, 1 eq) in anhydrous DMF (2 mL) were added HATU (151.56 mg, 398.60 μmol, 1.5 eq) and DIEA (68.69 mg, 531.47 μmol, 92.57 μL, 2 eq). After 0.5 h, BY-2 (63.80 mg, 292.31 μmol, 1.1 eq) was added and the mixture stirred at 20° C. for 12 h to give a red solution. TLC (eluting with: PE/EtOAc=5/1) showed the reaction was completed. The reaction mixture was partitioned between EtOAc (20 mL) and water (10 mL). 1M HCl (5 mL) was added and the aqueous layer extracted with EtOAc (20 mL×2). The combined extracts were dried over sodium sulfate and concentrated to give the crude product. The crude product was purified by a flash column (PE/EtOAc=3: 1-1:2) to give crude BY-3. $^1$H NMR (400 MHz, DMSO-d6) δ: 3.45-3.50 (m, 8H), 3.52-3.61 (m, 8H), 6.53-6.61 (m, 4H), 6.70 (t, J=2.51 Hz, 2H), 8.76 (dd, J=4.39, 0.88 Hz, 2H), 10.18 (s, 2H).

To a solution of BY-3 (250 mg, 433.61 μmol, 1 eq) in pyridine (4 mL) was added 2-methylpropanoyl 2-methylpropanoate (205.78 mg, 1.30 mmol, 215.71 μL, 3 eq) and stirred at 20° C. for 48 h to give a yellow solution. TLC (eluting with: PE/EtOAc=10/1) showed the reaction was completed. The reaction mixture was partitioned between DCM (10 mL) and water (10 mL). The reaction mixture was then partitioned between EtOAc (10 mL) and water (5 mL). 1M HCl (10 mL) was added and the aqueous layer extracted with EtOAC (10 mL×2). The combined organic layers were washed with brine (20 mL), dried over sodium sulfate and concentrated to give the crude product. The product was purified by a flash column (PE:EtOAC=3:1-0:1) to give BY-4. $^1$H NMR (400 MHz, DMSO-d6) δ: 1.24 (d, J=6.78 Hz, 12H), 2.84 (dt, J=13.93, 6.84 Hz, 2H), 3.47 (s, 8H), 3.51-3.61 (m, 8H), 6.91-6.97 (m, 3H), 7.30 (d, J=4.27 Hz, 1.64H), 7.46-7.56 (m, 0.64H), 7.81 (s, 0.36H), 8.14-8.25 (m, 1H), 8.29 (d, J=8.03 Hz, 0.36H), 8.48-8.56 (m, 1.64H), 8.71-8.81 (m, 1H), 8.93 (s, 0.36H).

A mixture of BY-4 (80 mg, 111.62 μmol, 1 eq), -BX (62.27 mg, 133.94 μmol, 1.2 eq), $CuSO_4$-$5H_2O$ (2.79 mg, 11.16 μmol, 0.1 eq) and sodium ascorbate (11.06 mg, 55.81 μmol, 0.5 eq) were dissolved in THF (3 mL) and $H_2O$ (0.5 mL) under $N_2$ atmosphere. The reaction mixture was stirred at 40° C. for 16 h to give a yellow solution. TLC (eluting with EtOAc) showed the reaction was completed. The reaction mixture was partitioned between water (20 mL) and EtOAc (20 mL), and the aqueous layer extracted with EtOAc (20 mL×2). The combined organic layers were dried over sodium sulfate and concentrated. The crude product was purified by prep-HPLC (column: Xtimate C18 150×25 mm×5 μm; mobile phase: [water (0.05% HCl)-ACN]; B %: 60%-90%, 9.5 min) to give BYa (a mixture of 5,6-isomer). LC-MS (m/z): 1181.4 [M+H]+

A mixture of BY-4 (50 mg, 69.76 μmol, 1 eq), BXa (38.92 mg, 83.71 μmol, 1.2 eq), $CuSO_4$-$5H_2O$ (1.74 mg, 6.98 μmol, 0.1 eq) and sodium ascorbate (6.91 mg, 34.88 μmol, 0.5 eq) was dissolved in THF (3 mL) and $H_2O$ (0.5 mL) under $N_2$ atmosphere, and the mixture stirred at 40° C. for 16 h to give a yellow solution. TLC (eluting with: PE/EtOAc=0/1) showed the reaction was completed. The reaction mixture was partitioned between water (20 mL) and EtOAc (20 mL), and the aqueous layer extracted with EtOAc (20 mL×2). The combined organic layers were dried over sodium sulfate and concentrated. The crude product was purified by silica gel chromatography (DCM: MeOH=1:0-20:1), which product was then further purified by prep-HPLC (column: Xtimate C18 150×25 mm×5 μm; mobile phase: [water (0.05% HCl)-ACN]; B %: 65%-95%, 7.8 min) to give BYa (mixture of 5,6-isomer). LC-MS (m/z): 1181.4 [M+H]+.

Procedure BZ: Synthesis of compound BZ

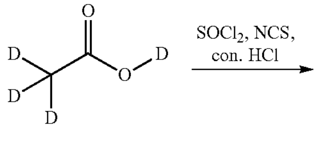

BZ-1

-continued

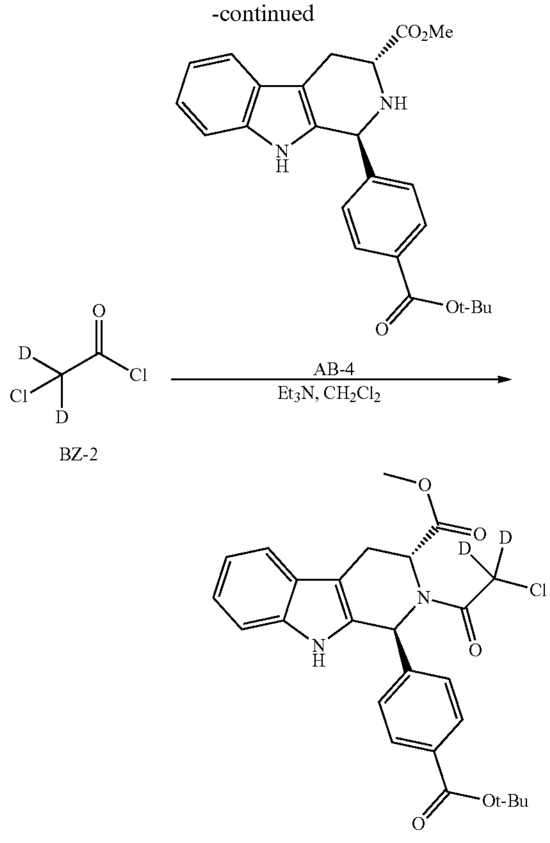

BZ-2

BZ

A solution of BZ-1 (120.0 mg, 2.00 mmol, 1 eq) in $SOCl_2$ (3.28 g, 27.57 mmol, 2 mL, 13.80 eq) was stirred at 70° C. for 1 h, then cooled to 25° C. NCS (533.67 mg, 4.00 mmol, 2 eq) and HCl (12 M, 4.20 μL, 2.52e-2 eq) were added. The resulting mixture was stirred at 80° C. for 1.5 h to afford a brown mixture. The reaction mixture was evaporated to afford BZ-2. The crude product was used in next step without any purification.

To a solution of AB-4 (32 mg, 78.73 μmol, 1 eq) in CHC13 (2 mL) was added $NaHCO_3$ (65 mg, 773.75 μmol, 30.09 μL, 9.83 eq) and BZ-2 (90.50 mg, 787.26 μmol, 10 eq). The resulting mixture was stirred at 25° C. for 10 min to afford a muddy mixture. The mixture was purified by prep-TLC (SiO2, PE: EA=4:1) to afford BZ. LC-MS (m/z): 507.1 [M+Na]+. $^1$H NMR (400 MHz, $CDCl_3$) δ ppm 1.55 (br s, 9H), 3.15-3.77 (m, 5H), 5.15-5.46 (m, 1H), 5.91-6.35 (m, 1H), 7.05-7.24 (m, 3H), 7.33-7.60 (m, 3H), 7.66-8.10 (m, 3H).

Procedure CA: Synthesis of Compound CA

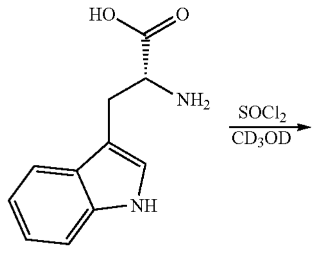

CA-1

-continued

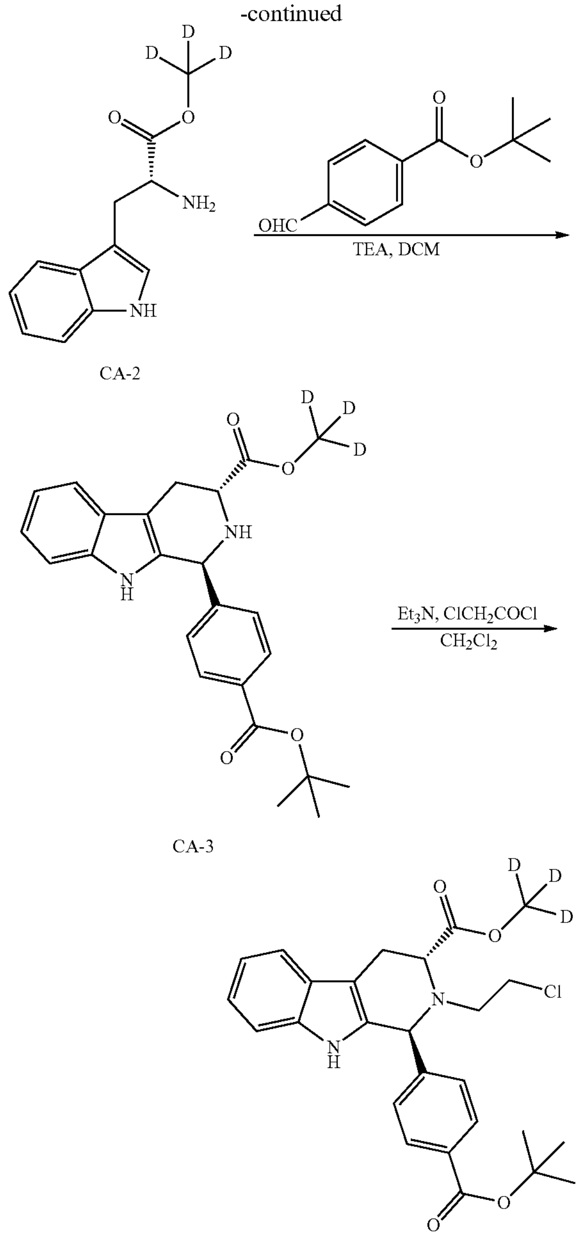

CA-2

CA-3

CA

To the mixture of CA-1 (350 mg, 1.71 mmol, 1 eq) was added $SOCl_2$ (1.15 g, 9.65 mmol, 0.7 mL, 5.63 eq) in $CD_3OD$ (3 mL) at 25° C. The resulting mixture was stirred at 60° C. for 40 min to afford a black mixture. LC-MS showed the reaction was completed. The reaction was evaporated to dryness, and toluene (10 mL) and Et3N (1 mL) was added. The mixture was stirred for 30 min to afford a brown mixture. The mixture was filtered, and the filtrate evaporated to dryness to afford CA-2. 1H NMR (400 MHz, $CDCl_3$) δ ppm 2.99 (dd, J=14.31, 7.53 Hz, 1H), 3.22 (dd, J=14.43, 4.89 Hz, 1H), 3.76 (dd, J=7.65, 4.89 Hz, 1H), 6.93-7.18 (m, 2H), 7.25-7.33 (m, 1H), 7.47-7.66 (m, 1H), 8.06 (br s, 1H).

To a mixture of CA-2 (200.0 mg, 903.87 μmol, 1 eq) and tert-butyl 4-formylbenzoate (186.41 mg, 903.87 μmol, 1 eq) in DCM (2 mL) was added TFA (41.22 mg, 361.55 μmol, 26.77 μL, 0.4 eq) at 25° C. The resulting mixture was stirred at 45° C. for 18 h to afford a brown mixture. LCMS and TLC (PE: EA=3:1) showed the reaction was completed. Sat. $NaHCO_3$ aq. (50 mL) was added to the mixture. The aqueous phase was extracted with DCM (15 mL×3). The combined organic phase was dried with anhydrous $Na_2SO_4$, filtered and concentrated in vacuum to afford the crude product. The crude product was purified by prep-TLC (PE:EA=3:1) to afford CA-3. $^1$H NMR (400 MHz, $CDCl_3$) δ ppm 1.53-1.64 (m, 9H), 3.05-3.19 (m, 1H), 3.23-3.38 (m, 1H), 3.96 (t, J=6.02 Hz, 1H), 5.47 (s, 1H), 7.03-7.29 (m, 2H), 7.35 (d, J=8.28 Hz, 2H), 7.50-7.66 (m, 2H), 7.95 (d, J=8.28 Hz, 2H).

Preparation of Compound CA

To a mixture of CA-3 (50.0 mg, 122.10 μmol, 1 eq) and TEA (24.71 mg, 244.21 μmol, 33.99 μL, 2 eq) in DCM (1 mL) was added 2-chloroacetyl chloride (20.69 mg, 183.15 μmol, 14.57 μL, 1.5 eq) at 0° C. The resulting mixture was stirred at 0° C. for 2 h to afford a brown mixture. LC-MS and TLC (PE: EA=3:1) showed the reaction was completed. The reaction was purified by prep-TLC (PE: EA=3:1) to afford compound CA. $^1$H NMR (400 MHz, $CDCl_3$) δ ppm 1.37-1.56 (m, 9H), 2.92-4.17 (m, 4H), 5.10-5.28 (m, 1H), 5.87-6.27 (m, 1H), 6.95-7.16 (m, 2H), 7.21-7.53 (m, 3H), 7.66-8.41 (m, 3H). LC-MS (m/z):488.1 [M+H]+.

Procedure CB: Synthesis of Compound 80

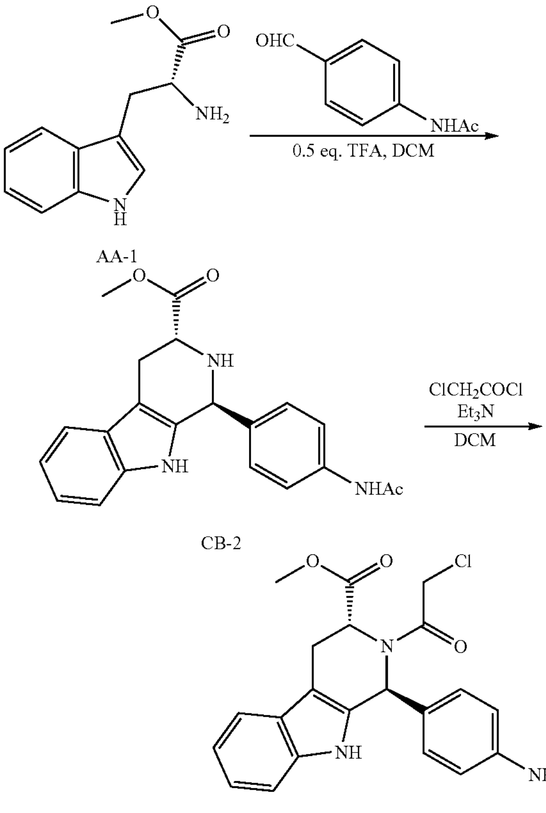

AA-1

CB-2

Compound 80

To a solution of AA-1 (428.01 mg, 1.96 mmol, 1 eq) and N-(4-formylphenyl)acetamide (320 mg, 1.96 mmol, 1 eq) in DCM (15 mL) was added TFA (111.81 mg, 980.55 μmol, 72.60 μL, 0.5 eq) at 30° C. The mixture was stirred at 80° C. for 16 h to give a yellow solution. TLC (quenched with water, eluting with: PE/EA=3/1) showed the reaction was completed. The reaction was purified by prep-HPLC (column: Xtimate C18 150×25 mm×5 μm; mobile phase: [water (0.05% HCl)-ACN]; B %: 5%-35%, 9.5 min) to give CB-2. $^1$H NMR (400 MHz, DMSO-d6) δ ppm 2.05 (s, 2H), 2.10 (s, 1H), 3.19 (br dd, J=15.43, 7.91 Hz, 1H), 3.77 (s, 3H), 4.46 (br s, 1H), 5.93 (br s, 1H), 7.03-7.17 (m, 2H), 7.57 (d, J=8.03 Hz, 1H), 7.64 (br d, J=8.03 Hz, 2H), 7.78-7.87 (m, 2H), 10.21 (br d, J=9.79 Hz, 1H), 10.44 (br s, 1H), 10.81 (br d, J=17.57 Hz, 1H), 11.04 (s, 1H).

Preparation of 80

To a solution of CB-2 (50 mg, 137.59 μmol, 1 eq), Et3N (41.77 mg, 412.76 μmol, 57.45 μL, 3 eq) in DCM (3 mL) at 0° C. was added 2-chloroacetyl chloride (23.31 mg, 206.38 μmol, 16.41 μL, 1.5 eq). The mixture was stirred at 80° C. for 16 h to give a yellow solution. TLC (eluting with: PE/EA=3/1) showed the reaction was completed. The reaction was purified by prep-HPLC (column: Xtimate C18 150×25 mm×5 μm; mobile phase: [water (0.05% HCl)-ACN]; B %: 32%-62%, 9.5 min) to give 80. LC-MS (m/z): 462.0[M+Na]+. $^1$H NMR (400 MHz, $CDCl_3$) δ ppm 2.13 (br s, 3H), 3.63 (s, 3H), 3.78-3.93 (m, 1H), 4.11 (br d, J=12.55 Hz, 1H), 5.28 (br d, J=16.81 Hz, 1H), 6.11 (br s, 1H), 7.07-7.18 (m, 2H), 7.28-7.40 (m, 3H), 7.28-7.40 (m, 3H), 7.52 (br d, J=8.03 Hz, 1H), 8.14 (br s, 1H).

Procedure CC: Synthesis of compound CC

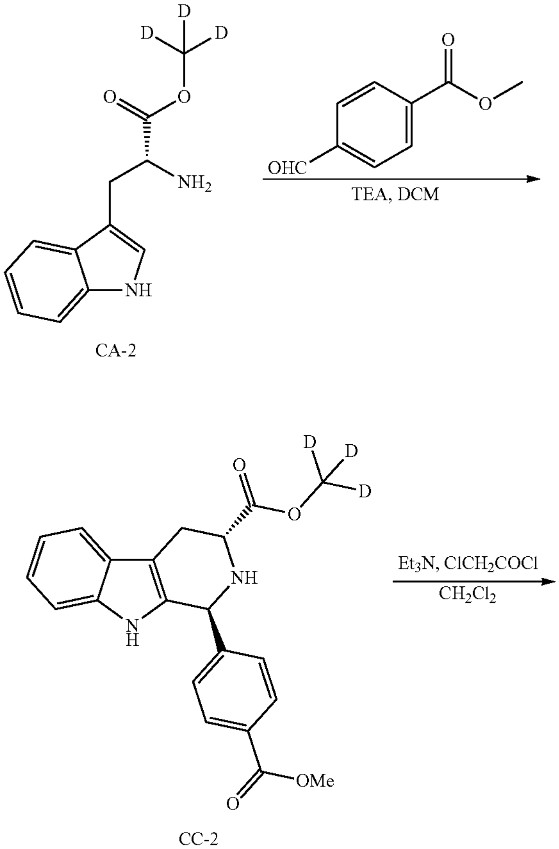

CA-2

CC-2

-continued

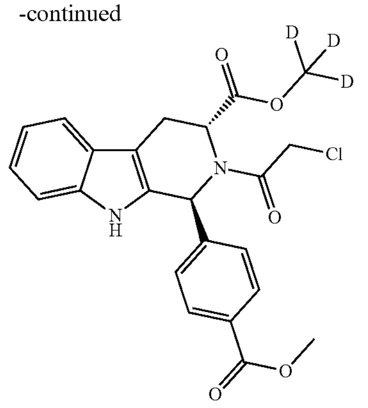

CC

To a mixture of CA-2 (200.0 mg, 903.87 μmol, 1 eq) and methyl 4-formylbenzoate (148.38 mg, 903.87 μmol, 1 eq) in DCM (4 mL) was added TFA (41.22 mg, 361.55 μmol, 26.77 μL, 0.4 eq) at 25° C. The resulting mixture was stirred at 45° C. for 48 h to afford a brown mixture. TLC (eluting with: PE/EtOAc=3/1) showed the reaction was completed. The reaction mixture was quenched by addition Sat. $NaHCO_3$ aq. 50 mL at 25° C., and then extracted with EA 45 mL (15 mL×3). The combined organic layers were washed with sat. $NH_4Cl$ aq.45 mL, dried over $Na_2SO_4$, filtered, and concentrated under reduced pressure to give the crude product, which was then purified by prep-TLC (PE:EA=3:1) to afford CC-2. $^1$H NMR (400 MHz, $CDCl_3$) δ ppm 3.05-3.22 (m, 1H), 3.22-3.38 (m, 1H), 3.23 (br s, 1H), 3.87-4.00 (m, 4H), 5.47 (s, 1H), 7.09-7.21 (m, 1H), 7.23-7.28 (m, 1H), 7.37 (d, J=8.28 Hz, 2H), 7.53-7.68 (m, 2H), 7.99 (d, J=8.28 Hz, 2H).

To a mixture of CC-2 (40.0 mg, 108.87 μmol, 1 eq) and TEA (22.03 mg, 217.74 μmol, 30.31 μL, 2 eq) in DCM (2 mL) was added 2-chloroacetyl chloride (18.44 mg, 163.30 μmol, 12.99 μL, 1.5 eq) at 0° C. The resulting mixture was stirred at 0° C. for 1 h to afford a brown mixture. The reaction was purified by prep-TLC (PE:EA=3:1) to afford CC. $^1$H NMR (400 MHz, $CDCl_3$) δ ppm 3.04-4.20 (m, 7H), 5.01-5.31 (m, 1H), 5.88-6.34 (m, 1H), 6.94-7.22 (m, 3H), 7.24-7.52 (m, 3H), 7.57-8.08 (m, 3H). LC-MS (m/z): 444.9 [M+H]+.

Procedure CD: Synthesis of Compound 81

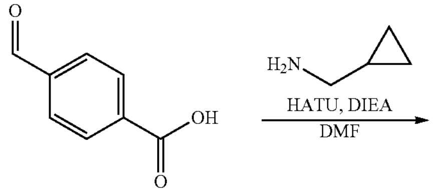

AB-2

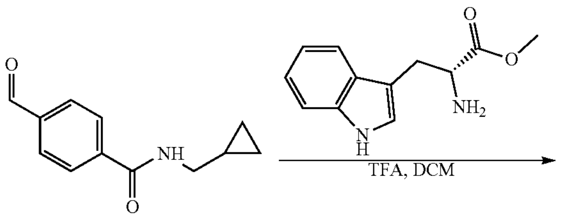

CD-2

-continued

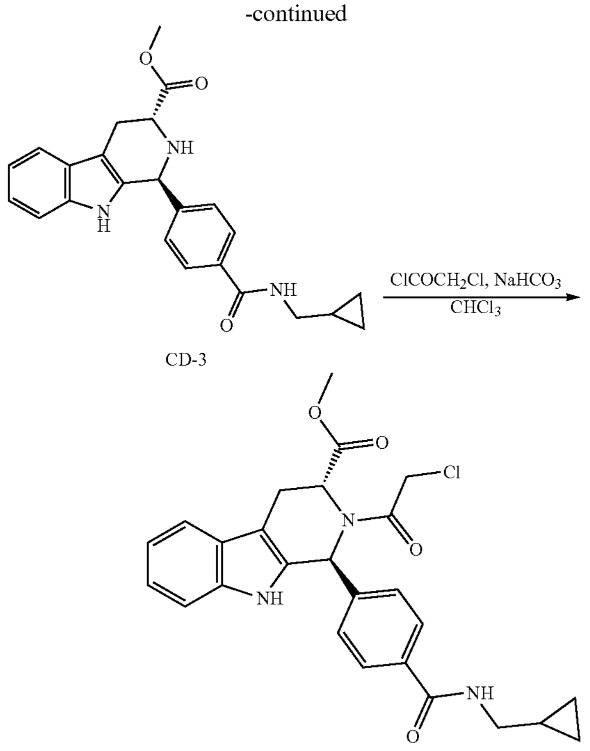

CD-3

Compound 81

Preparation of Compound CD-2

To a solution of AB-2 (1 g, 6.66 mmol, 1 eq) in DMF (10 mL) were added DIEA (1.72 g, 13.32 mmol, 2.32 mL, 2 eq) and HATU (3.80 g, 9.99 mmol, 1.5 eq), followed by cyclopropyl methanamine (568.47 mg, 7.99 mmol, 1.2 eq) at 0° C. The mixture stirred at 20° C. for 2 h to give a yellow solution. TLC (eluting with: Petroleum ether:Ethyl acetate=1:1, $SiO_2$) showed the reaction was completed. The reaction mixture was diluted with $H_2O$ (100 mL) and extracted with MTBE (50 mL×3). The organic layers were dried over $Na_2SO_4$ and concentrated to give a crude product, which was then purified by a flash column (eluting with: Petroleum ether/Ethyl acetate=10/1 to 5/1) to give CD-2. $^1$H NMR (400 MHz, $CDCl_3$) ppm 0.25-0.31 (q, J=4.94 Hz, 2H), 0.54-0.62 (m, 2H), 1.05-1.09 (quint, J=7.64, 7.64, 7.64, 7.64, 4.80, 4.80 Hz, 1H), 1.25 (t, J=7.15 Hz, 1H), 3.32-3.35 (dd, J=7.15, 5.40 Hz, 2H), 4.09-4.14 (q, J=7.03 Hz, 1H), 6.36 (br s, 1H), 7.90-7.97 (m, 4H), 10.05-10.11 (m, 1H).

Preparation of Compound CD-3

To a solution of CD-2 (200 mg, 984.07 μmol, 1 eq) in DCM (10 mL) were added methyl (2R)-2-amino-3-(1H-indol-3-yl)propanoate (214.78 mg, 984.07 μmol, 1 eq) and TFA (56.10 mg, 492.04 μmol, 36.43 μL, 0.5 eq). The mixture stirred at 45° C. for 10 h to give a yellow solution. TLC (eluting with: Petroleum ether:Ethyl acetate=1:2, $SiO_2$) showed the reaction was completed. The reaction mixture was adjusted to pH 8 with Sat. $NaHCO_3$ and extracted with DCM (20 ml×3). The organic layers were dried over $Na_2SO_4$ and concentrated to give a crude product. The residue was purified by prep-TLC (Petroleum ether:Ethyl acetate=1:2) to give CD-3 and the corresponding cis-isomer.

CD-3 (trans-isomer): $^{1}$H NMR (400 MHz, $CDCl_3$) δ ppm 0.25-0.28 (q, J=4.85 Hz, 2H), 0.53-0.57 (m, 2H), 0.99-1.10 (m, 1H), 1.22-1.28 (m, 3H), 2.80 (s, 3H), 3.11-3.26 (m, 2H), 3.28-3.31 (m, 2H), 3.72 (s, 3H), 3.93 (t, J=6.02 Hz, 1H), 4.10-4.15 (q, J=7.28 Hz, 1H), 6.23 (br t, J=4.89 Hz, 1H), 7.13-7.17 (qd, J=7.53, 6.02 Hz, 2H), 7.24 (s, 1H), 7.32-7.34 (d, J=8.28 Hz, 2H), 7.55-7.57 (d, J=7.28 Hz, 1H), 7.69-7.71 (d, J=8.03 Hz, 2H), 7.88 (s, 1H).

CD-3a (cis-isomer): $^{1}$H NMR (400 MHz, $CDCl_3$) δ ppm 0.27-0.30 (q, J=4.85 Hz, 2H), 0.55-0.60 (m, 2H), 1.01-1.12 (m, 1H), 1.25 (q, J=7.03 Hz, 1H), 2.53 (br s, 1H), 2.98-3.28 (m, 2H), 3.29-3.35 (m, 2H), 3.72 (br d, J=7.28 Hz, 1H), 3.83 (s, 3H), 3.99 (dd, J=11.04, 4.02 Hz, 1H), 4.12 (q, J=7.11 Hz, 1H), 6.21 (br s, 1H), 7.14 (tt, J=7.06, 5.36 Hz, 2H), 7.22 (br d, J=7.03 Hz, 1H), 7.42 (s, 1H), 7.48 (d, J=8.28 Hz, 2H), 7.55 (br d, J=6.53 Hz, 1H), 7.78 (d, J=8.03 Hz, 2H).

Preparation of 81

To a solution of CD-3 (50 mg, 123.92 μmol, 1 eq, trans) in CHCl3 (4 mL) were added $NaHCO_3$ (104.10 mg, 1.24 mmol, 48.20 μL, 10 eq) and 2-chloroacetyl chloride (69.98 mg, 619.62 μmol, 49.28 μL, 5 eq). The mixture stirred at 25° C. for 2 h to give a yellow solution. TLC (eluting with: Petroleum ether:Ethyl acetate=1:1, $SiO_2$) showed the reaction was completed. The reaction mixture was quenched with $H_2O$ (10 ml) and then extracted with DCM (20 ml×3). The organic layers were dried over $Na_2SO_4$ and concentrated to give a crude product, which was purified by prep-TLC (Petroleum ether:Ethyl acetate=1:2) to give 81. LC-MS (m/z):502.1 [M+Na]+. $^{1}$H NMR (400 MHz, MeOD) δ ppm 0.27 (br d, J=4.52 Hz, 2H), 0.51 (br d, J=6.78 Hz, 2H), 0.88-0.95 (m, 1H), 1.08 (br s, 1H), 3.22 (br d, J=6.02 Hz, 2H), 3.50 (br d, J=1.51 Hz, 1H), 3.61 (br s, 3H), 3.74 (br d, J=14.56 Hz, 1H), 4.02-4.68 (m, 1H), 4.02-4.30 (m, 1H), 5.09 (br s, 1H), 5.42 (br s, 1H), 6.11 (br s, 1H), 6.38 (br s, 1H), 7.01-7.16 (m, 2H), 7.21-7.33 (m, 2H), 7.47-7.62 (m, 3H), 7.72-7.85 (m, 2H).

Procedure CE: Synthesis of Compound 82

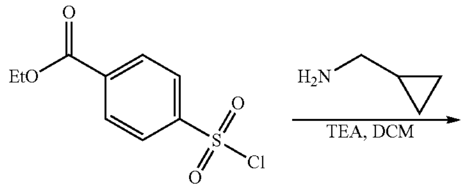

AQ-1

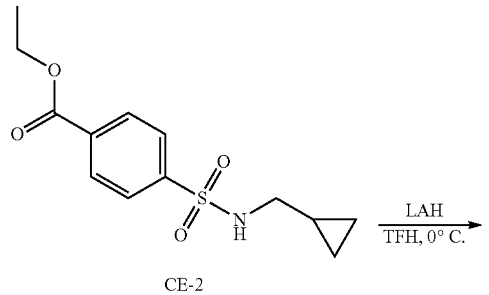

CE-2

-continued

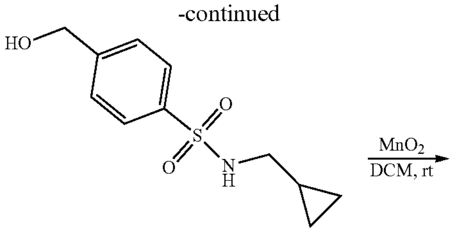

CE-3

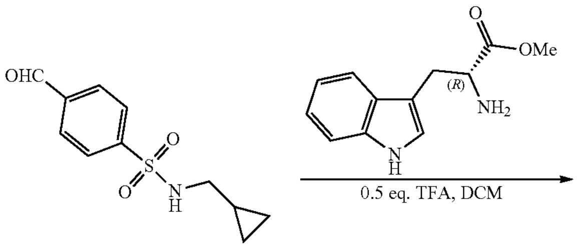

CE-4

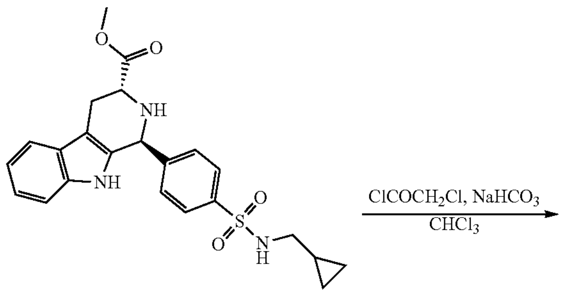

CE-5

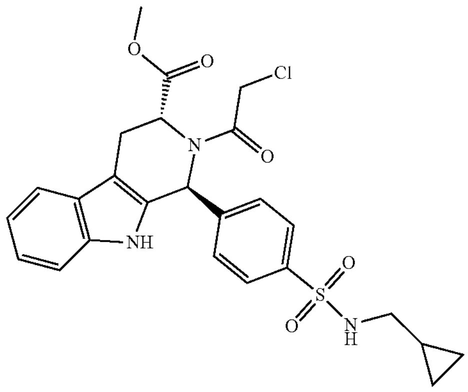

Compound 82

Preparation of Compound CE-2

To a solution of cyclopropylmethanamine (300.29 mg, 4.22 mmol, 1.05 eq) and TEA (1.22 g, 12.06 mmol, 1.68 mL, 3 eq) in DCM (10 mL) was added AQ-1 (1 g, 4.02 mmol, 1 eq). The mixture was stirred at 25° C. for 16 h to give a yellow solution. TLC (PE:EtOAc=3:1) showed the reaction was completed. The reaction mixture was diluted with 1N HCl solution (10 mL) and separated. The organic layer was washed with brine (5 mL), dried over $Na_2SO_4$, filtered, and concentrated under reduced pressure to give the crude product. The product was purified by column chromatography ($SiO_2$, Petroleum ether/Ethyl acetate=I/O to 3:1) to give CE-2. $^{1}$H NMR (400 MHz, $CDCl_3$) δ=8.20-8.16 (m, 2H), 7.97-7.93 (m, 2H), 4.68 (t, J=5.8 Hz, 1H), 4.42 (q, J=7.0 Hz, 2H), 2.87 (dd, J=5.9, 7.2 Hz, 2H), 1.42 (t, J=7.0 Hz, 3H), 0.87 (tquin, J=4.8, 7.6 Hz, 1H), 0.52-0.44 (m, 2H), 0.10 (q, J=5.0 Hz, 2H).

Preparation of Compound CE-3

To a suspension of $LiAlH_4$ (162.03 mg, 4.27 mmol, 2.4 eq) in THF (10 mL) was added dropwise CE-2 (504 mg, 1.78 mmol, 1 eq) in THF (5 mL) at 0° C. The mixture was stirred at 20° C. for 6 h to give a white suspension. TLC (PE:EtOAc=3:1) showed the reaction was completed. The mixture was quenched with $H_2O$ (165 uL) and 165 μL of 15% NaOH solution at 0° C.

The mixture was stirred at 15° C. for 10 minutes before filtration. The filtrate was dried over $Na_2SO_4$ and concentrated under reduced pressure to give CE-3. $^1H$ NMR (400 MHz, $CDCl_3$) δ=7.82 (m, 2H), 7.48 (m, 2H), 4.78 (s, 2H), 3.77-3.71 (m, 1H), 2.81 (m, 2H), 2.43 (br s, 1H), 0.87 (m, 1H), 0.49-0.39 (m, 2H), 0.14-0.05 (m, 2H).

Preparation of Compound CE-4

To a solution of CE-3 (282.3 mg, 1.17 mmol, 1 eq) in DCM (10 mL) was added $MnO_2$ (508.53 mg, 5.85 mmol, 5 eq). The mixture was heated to reflux for 16 h to give a black suspension. TLC (PE:EtOAc=2:1) showed the reaction was completed. LCMS showed no desired MS was found. The reaction mixture was filtered through a pad of celite, and the filtrate concentrated under reduced pressure to give CE-4. $^1H$ NMR (400 MHz, $CDCl_3$) δ=10.11 (s, 1H), 8.08-8.01 (m, 4H), 4.83 (m, 1H), 2.89 (m, 2H), 1.74-1.59 (m, 3H), 0.95-0.81 (m, 1H), 0.51-0.45 (m, 2H), 0.16-0.07 (m, 2H).

Preparation of Compound CE-5

To a solution of CE-4 (87.71 mg, 366.55 μmol, 1 eq) in DCM (5 mL) were added methyl (2R)-2-amino-3-(1H-indol-3-yl)propanoate (80 mg, 366.55 μmol, 1 eq) and TFA (20.90 mg, 183.27 μmol, 13.57 μL, 0.5 eq). The mixture was stirred at 45° C. for 16 h to give a white suspension. TLC (PE:EtOAc=1:1) showed the reaction was completed. The mixture was adjusted to pH 8 with saturated $NaHCO_3$ and then extracted with DCM (10 mL×3). The combined organic layers were dried over $Na_2SO_4$ and concentrated to provide a crude product. The residue was purified by column chromatography ($SiO_2$, Petroleum ether/Ethyl acetate=I/O to 3:1) to give two products, one of which was CE-5 and the other of which was the cis-isomer.

Preparation of 82

To a solution of CE-5 (36.5 mg, 83.04 μmol, 1 eq) in DCM (2 mL) were added TEA (25.21 mg, 249.13 μmol, 34.68 μL, 3 eq) and 2-chloroacetyl chloride (18.76 mg, 166.09 μmol, 13.21 μL, 2 eq) at 0° C. The mixture was stirred at 20° C. for 2 h to give a yellow solution. LCMS showed the reaction was completed. The mixture was concentrated to give a residue, which was purified by prep-TLC (SiO2, PE: EA=1:1) to give 82. LC-MS (m/z): 538.1[M+Na]+. $^1H$ NMR (400 MHz, $CDCl_3$) δ=7.95 (br s, 2H), 7.80 (br s, 1H), 7.59-7.37 (m, 3H), 7.24-7.10 (m, 3H), 6.12 (br s, 1H), 5.38-5.22 (m, 1H), 4.51 (br s, 2H), 4.20-3.92 (m, 2H), 3.91-3.69 (m, 1H), 3.65 (s, 3H), 3.57-3.30 (m, 1H), 2.07 (br s, 6H).

Procedure CF: Synthesis of Compound 83

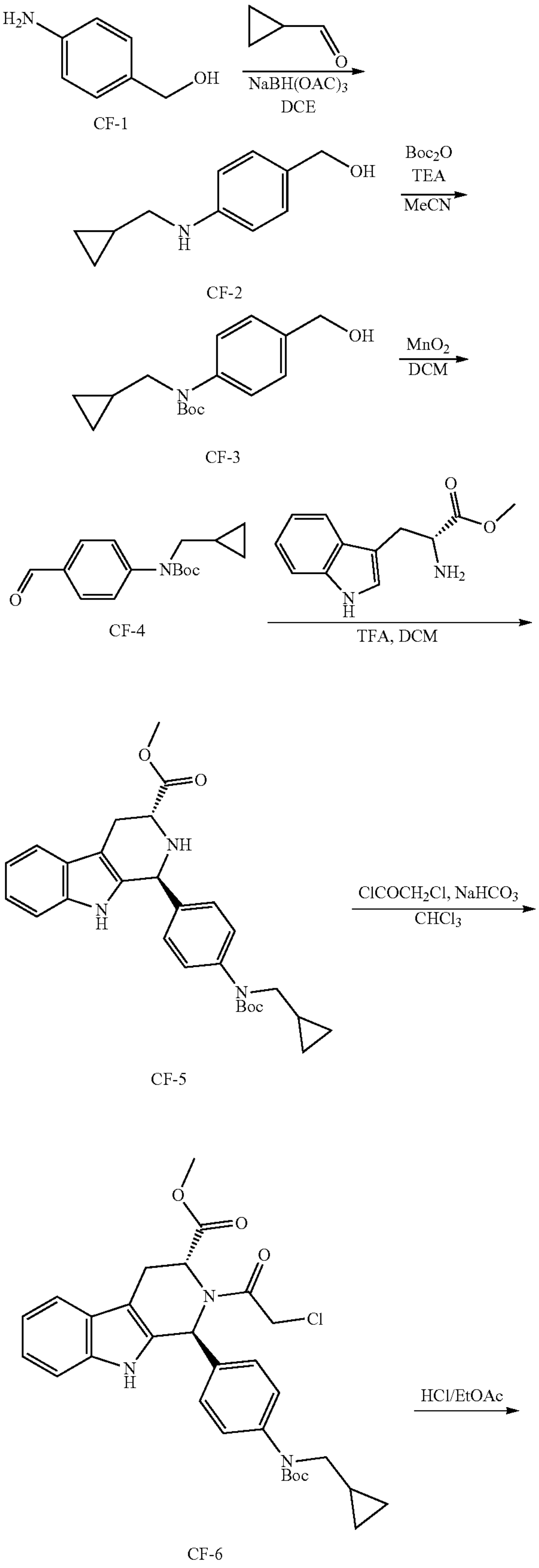

-continued

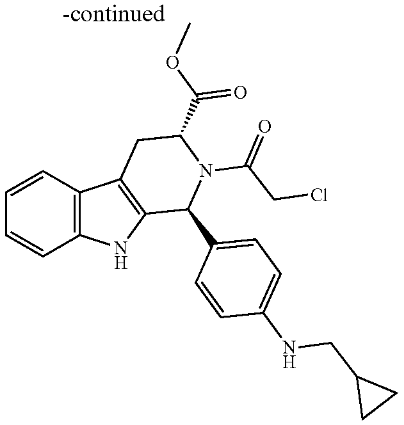

Compound 83

Preparation of Compound CF-2

To a solution of CF-1 (500 mg, 4.06 mmol, 1 eq) in DCE (29 mL) were added cyclopropanecarbaldehyde (284.57 mg, 4.06 mmol, 303.38 μL, 1 eq) and $NaBH(OAc)_3$ (1.29 g, 6.09 mmol, 1.5 eq). The mixture stirred at 25° C. for 2 h to give a yellow solution. LCMS showed the reaction was completed. The reaction mixture was adjusted to pH 8 with Sa. $NaHCO_3$ and extracted with EA (50 ml×3). The organic layers were dried over $Na_2SO_4$ and concentrated to give a crude product. The residue was purified by a flash column (eluting with: Petroleum ether/Ethyl acetate=20/1 to 10:1) to give CF-2. $^1$H NMR (400 MHz, $CDCl_3$) δ 7.19-7.02 (m, 2H), 6.75-6.59 (m, 2H), 4.55 (s, 2H), 2.97-2.92 (m, 2H), 1.28-1.09 (m, 1H), 0.57-0.54 (m, 2H), 0.26-0.23 (m, 2H).

Preparation of Compound CF-3

To a solution of CF-2 (1 g, 5.64 mmol, 1 eq) in MeCN (10 mL) were added $Boc_2O$ (2.46 g, 11.28 mmol, 2.59 mL, 2 eq) and TEA (570.91 mg, 5.64 mmol, 785.30 μL, 1 eq). The mixture stirred at 25° C. for 12 h to give a colorless mixture. LCMS showed the reaction was completed. The mixture was quenched with $H_2O$ (50 ml) and extracted with EA (50 ml×3). The organic layers were dried over $Na_2SO_4$ and concentrated to give a crude product, which was purified by a flash column (eluting with: Petroleum ether/Ethyl acetate=20/1 to 5:1) to give CF-3. $^1$H NMR (400 MHz, $CDCl_3$): δ 7.22-7.20 (m, 2H), 7.11-7.09 (m, 2H), 4.58-4.42 (m, 2H), 3.38-3.33 (m, 2H), 1.58-1.55 (m, 1H), 0.89-0.87 (m, 1H), 0.32-0.28 (m, 2H), 0.01-0.00 (m, 2H).

Preparation of Compound CF-4

To a solution of CF-3 (890 mg, 3.21 mmol, 1 eq) in DCM (25 mL) was added $MnO_2$ (1.39 g, 16.04 mmol, 5 eq). The mixture stirred at 45° C. for 12 h to give a black solution. LCMS showed the reaction was completed and filtered by celite. The organic layers were dried over $Na_2SO_4$ and concentrated to give a crude product. The crude product was purified by a flash column (eluting with: Petroleum ether/Ethyl acetate=1:0 to 5:1) to give CF-4. $^1$H NMR (400 MHz, $CDCl_3$): δ 9.98 (s, 1H), 7.87-7.83 (m, 2H), 7.43-7.26 (m, 2H), 3.59-3.57 (m, 2H), 1.45 (s, 9H), 1.04- 1.00 (m, 1H), 0.47-0.42 (m, 2H), 0.17-0.13 (m, 2H).

Preparation of Compound CF-5

To a solution of CF-4 (100 mg, 363.18 μmol, 1 eq) in DCM (8 mL) were added methyl (2R)-2-amino-3-(1H-indol-3-yl)propanoate (79.27 mg, 363.18 μmol, 1 eq) and TFA (20.71 mg, 181.59 μmol, 13.45 uL, 0.5 eq). The mixture stirred at 45° C. for 12 h to give a yellow solution. LCMS showed the reaction was completed. The reaction mixture was adjusted to pH 8 with Sat. $NaHCO_3$ and extracted with DCM (20 ml×3). The organic layers were dried over $Na_2SO_4$ and concentrated to give a crude product. The residue was purified by prep-TLC (Petroleum ether:Ethyl acetate=2:1) to give CF-5 (trans) and CF-5a (cis isomer). $^1$H NMR (400 MHz, $CDCl_3$): δ 7.61-7.55 (m, 2H), 7.24-7.15 (m, 6H), 5.42 (s, 1H), 4.00-3.98 (m, 1H), 3.74 (s, 3H), 3.48-3.46 (m, 2H), 3.26-3.18 (m, 2H), 1.45 (s, 9H), 1.01-0.99 (m, 1H), 0.44-0.41 (m, 2H), 0.16-0.12 (m, 2H).

Preparation of CF-6. To a solution of CF-5 (50 mg, 105.14 μmol, 1 eq) in $CHCl_3$ (6 mL) was added $NaHCO_3$ (88.32 mg, 1.05 mmol, 40.89 μL, 10 eq), followed by a solution of 2-chloroacetyl chloride (17.81 mg, 157.70 μmol, 12.54 μL, 1.5 eq) in $CHCl_3$ (6 mL) at 0° C. The mixture stirred at 0° C. for 45 min to give a yellow solution. TLC (Petroleum ether:Ethyl acetate=2:1) and LCMS showed the reaction was completed. The reaction mixture was quenched with $H_2O$ (10 ml) and extracted with DCM (20 ml×3). The organic layers were dried over $Na_2SO_4$ and concentrated to give CF-6. The product was used for the next step without further purification.

Preparation of 83

CF-6 (65 mg, 117.74 μmol, 1 eq) was dissolved in HCl/EtOAc (4 M, 10 mL, 339.73 eq), and the mixture stirred at 20° C. for 2 h to give a pink solution. The reaction mixture was adjusted to pH 8 with Sat. $NaHCO_3$ and extracted with DCM (20 ml×3). The organic layers were dried over $Na_2SO_4$ and concentrated to give a crude product. The residue was purified by prep-TLC (Petroleum ether:Ethyl acetate=3:2) to give 83. LC-MS (m/z): 474.1[M+Na]+. $^1$H NMR (400 MHz, MeOD): δ7.24-7.22 (m, 1H), 7.03-6.96 (m, 1H), 6.94-6.85 (m, 2H), 6.80-6.76 (m, 2H), 6.42-6.40 (m, 2H), 5.93 (brs, 1H), 4.28-4.25 (m, 1H), 3.40 (s, 3H), 2.70-2.69 (m, 2H), 0.83-0.80 (m, 1H), 0.29-0.27 (m, 2H), 0.00-0.01 (m, 2H).

Procedure CG: Synthesis of Compound 84

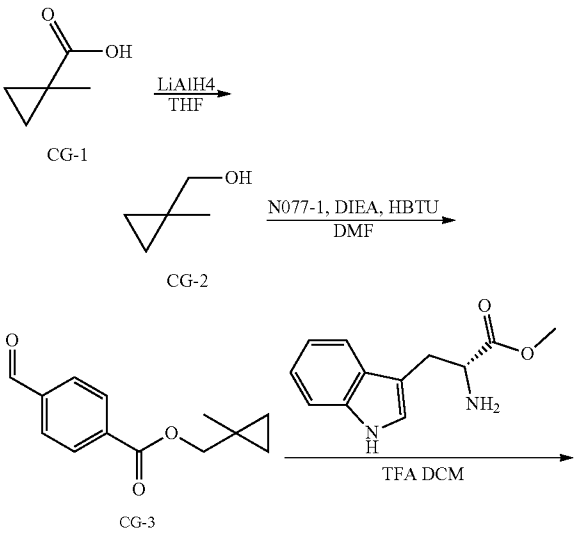

-continued

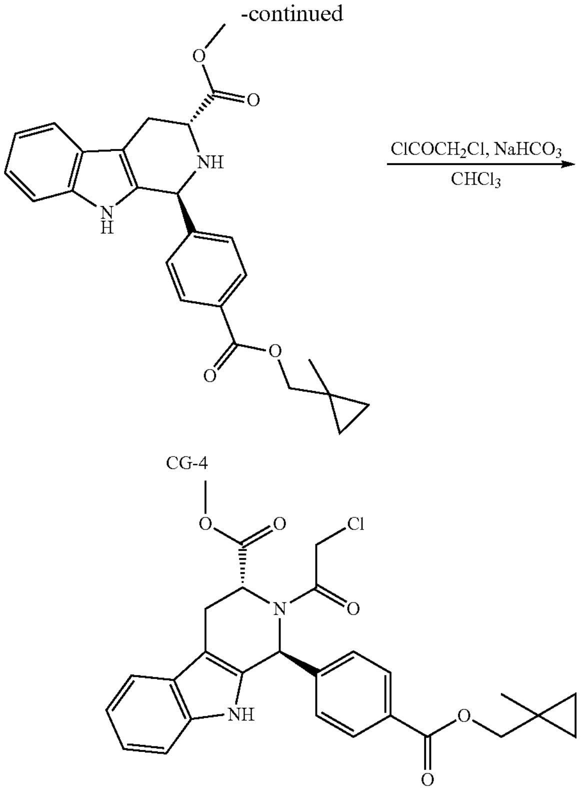

CG-4

Compound 84

Preparation of Compound CG-2

To a solution of CG-1 (200 mg, 2.00 mmol, 1 eq) in THF (10 mL) was added $LiAlH_4$ (151.64 mg, 4.00 mmol, 2 eq) at 0° C. The mixture stirred at 0° C. for 2 h to give a white solution. TLC (eluting with: Petroleum ether:Ethyl acetate=1:1, $SiO_2$) showed the reaction was completed. The reaction mixture were added $H_2O$ (0.15 ml) and NAOH (aq, 15%, 0.15 ml) and $H_2O$ (0.45 ml). The organic layers were filtered with diatom earth and dried over $Na_2SO_4$ and concentrated to give CG-2. The product was used for the next step without further purification. $^1H$ NMR (400 MHz, $CDCl_3$) δ ppm 0.30-0.43 (m, 4H), 1.15 (s, 3H), 1.26 (t, J=7.15 Hz, 1H), 3.39 (s, 2H).

Preparation of Compound CG-3

To a solution of AB-2 ((250 mg, 1.67 mmol, 1 eq) in DMF (12 mL) were added DIEA (645.65 mg, 5.00 mmol, 870.15 µL, 3 eq) and HBTU (1.01 g, 2.66 mmol, 1.6 eq). The mixture stirred at 25° C. for 5 min, followed by addition of CG-2 (157.77 mg, 1.83 mmol, 177.87 µL, 1.1 eq). The mixture stirred at 25° C. for 16 h to give a brown solution. TLC (eluting with; Petroleum ether:Ethyl acetate=2:1, $SiO_2$) showed the reaction was completed. The reaction mixture was diluted with $H_2O$ (150 mL) and extracted with EA (50 mL×3). The organic layers were dried over $Na_2SO_4$ and concentrated to give a crude product, which was purified by a flash column (eluting with: Petroleum ether/Ethyl acetate=50/1 to 5/1) to give CG-3. $^1H$ NMR (400 MHz, $CDCl_3$) δ ppm 0.35-0.54 (m, 4H), 1.16 (s, 3H), 4.09 (s, 2H), 7.89 (d, J=8.28 Hz, 2H), 8.16 (d, J=8.28 Hz, 2H), 10.00-10.08 (m, 1H).

Preparation of Compound CG-4

To a solution of CG-3 (121 mg, 554.42 µmol, 1 eq) in DCM (10 mL) were added methyl (2R)-2-amino-3-(1H-indol-3-yl)propanoate (121.00 mg, 554.42 µmol, 1 eq) and TFA (31.61 mg, 277.21 µmol, 20.52 µL, 0.5 eq). The mixture stirred at 45° C. for 12 h to give a yellow solution. TLC (eluting with: Petroleum ether:Ethyl acetate=2:1, $SiO_2$) showed the reaction was completed. The reaction mixture was adjusted to pH 8 with Sat. $NaHCO_3$ and extracted with DCM (20 ml×3). The organic layers were dried over $Na_2SO_4$ and concentrated to give a crude product, which was purified by prep-TLC (Petroleum ether:Ethyl acetate=2:1) to give CG-4 and CG-4a.

CG-4 (trans isomer): $^1H$ NMR (400 MHz, $CDCl_3$) δ ppm 0.40-0.58 (m, 4H), 1.20 (s, 3H), 3.12-3.33 (m, 2H), 3.70-3.76 (m, 3H), 3.94-4.00 (m, 1H), 4.09-4.15 (m, 2H), 5.49 (s, 1H), 7.16 (qd, J=7.53, 6.02 Hz, 2H), 7.24 (s, 1H), 7.39 (d, J=8.28 Hz, 2H), 7.55-7.63 (m, 2H), 8.03 (d, J=8.28 Hz, 2H).

CG-4a (cis-isomer): $^1H$ NMR (400 MHz, $CDCl_3$) δ ppm 0.40-0.60 (m, 4H), 1.21 (s, 3H), 2.99-3.29 (m, 2H), 3.83 (s, 3H), 3.96-4.04 (m, 1H), 4.13 (s, 2H), 5.33 (s, 1H), 7.10-7.19 (m, 2H), 7.20-7.24 (m, 1H), 7.40 (s, 1H), 7.49 (d, J=8.28 Hz, 2H), 7.53-7.57 (m, 1H), 8.07 (d, J=8.28 Hz, 2H).

Preparation of 84

To a solution of CG-4 (44 mg, 105.14 µmol, 1 eq) in CHCl3 (5 mL) were added $NaHCO_3$ (88.33 mg, 1.05 mmol, 40.89 µL, 10 eq) and 2-chloroacetyl chloride (35.62 mg, 315.42 µmol, 25.09 µL, 3 eq). The mixture stirred at 25° C. for 2 h to give a yellow solution. TLC (eluting with: Petroleum ether:Ethyl acetate=2:1, SiO2) showed the reaction was completed. The reaction mixture was added $H_2O$ (10 ml) and then extracted with DCM (20 ml×3). The organic layers were dried over $Na_2SO_4$ and concentrated to give a crude product, which was purified by prep-TLC (eluting with: Petroleum ether:Ethyl acetate=1:2) to give 84. LC-MS (m/z):517.1 [M+Na]+. $^1H$ NMR (400 MHz, $CDCl_3$) δ ppm 0.27-0.50 (m, 4H), 1.11 (s, 3H), 3.15-3.51 (m, 1H), 3.58 (s, 3H), 3.65 (br s, 1H), 4.01 (br s, 4H), 5.21 (br d, J=12.55 Hz, 1H), 6.00-6.23 (m, 1H), 7.02-7.17 (m, 3H), 7.30-7.52 (m, 3H), 7.60 (br s, 1H), 7.93 (br s, 2H).

Procedure CH: Synthesis of Compound 85

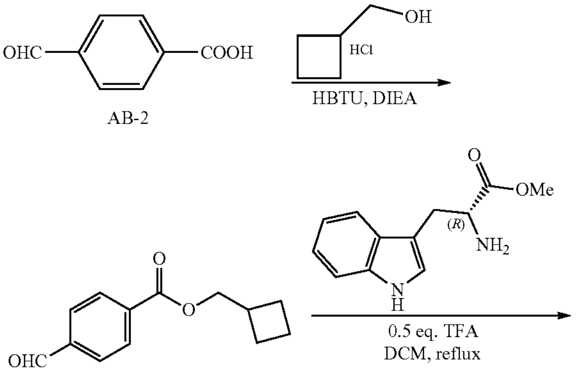

AB-2

CH-2

-continued

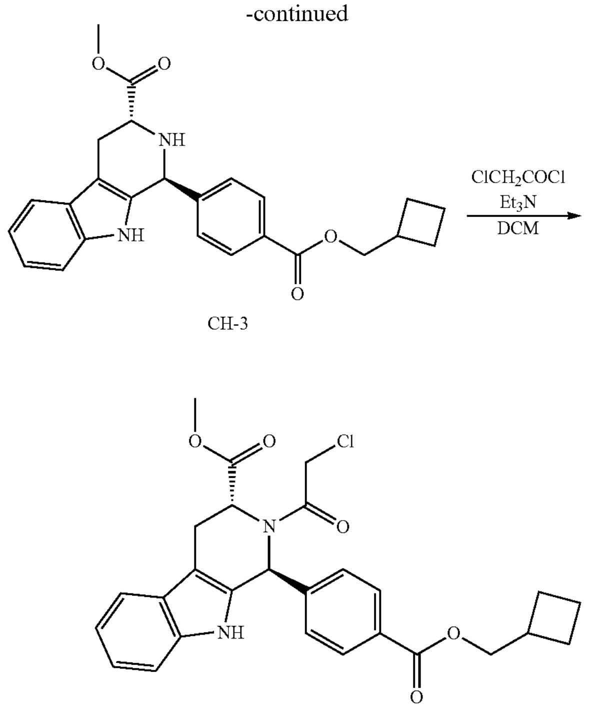

CH-3

Compound 85

Preparation of Compound CH-2

To a suspension of AB-2 (1 g, 6.66 mmol, 1 eq) in DMF (40 mL) were added DIEA (2.58 g, 19.98 mmol, 3.48 mL, 3 eq) and HBTU (4.04 g, 10.66 mmol, 1.6 eq). The reaction mixture was stirred at 25° C. for 5 min, followed by addition of cyclobutylmethanol (631.08 mg, 7.33 mmol, 691.22 μL, 1.1 eq). The reaction mixture was stirred at 25° C. for 16 h to give a red solution. TLC (quenched with water, eluting with: PE/EA=3/1) showed the reaction was completed. The residue was purified by column chromatography ($SiO_2$, 0% to 30% EtOAc in PE) to give CH-2. $^1$H NMR (400 MHz, $CDCl_3$) δ ppm 1.81-2.00 (m, 4H), 2.07-2.19 (m, 2H), 2.76 (dquin, J=14.79, 7.34, 7.34, 7.34, 7.34 Hz, 1H), 4.32 (d, J=6.53 Hz, 2H), 7.92-7.96 (m, 2H), 8.18 (d, J=8.28 Hz, 2H), 10.09 (s, 1H).

Preparation of Compound CH-3

To a solution methyl (2R)-2-amino-3-(1H-indol-3-yl)propanoate (300.01 mg, 1.37 mmol, 1 eq) and CH-2 (300 mg, 1.37 mmol, 1 eq) in DCM (10 mL) was added TFA (78.37 mg, 687.29 μmol, 50.89 μL, 0.5 eq). The mixture was stirred at 80° C. for 16 h. TLC (eluting with: PE/EA=3/1) showed the reaction was completed. The mixture was purified by column chromatography ($SiO_2$, 0 to 40% EA in PE) to give CH-3. $^1$H NMR (400 MHz, $CDCl_3$) δ ppm 1.26 (s, 1H), 1.80-2.00 (m, 5H), 2.05 (s, 1H), 2.07-2.15 (m, 2H), 2.74 (dt, J=14.74, 7.31 Hz, 1H), 3.11-3.19 (m, 1H), 3.24-3.32 (m, 1H), 3.72 (s, 3H), 3.95 (t, J=6.02 Hz, 1H), 4.12 (q, J=7.28 Hz, 1H), 4.28 (d, J=6.53 Hz, 2H), 5.46 (s, 1H), 7.11-7.20 (m, 2H), 7.24 (s, 1H), 7.36 (d, J=8.03 Hz, 2H), 7.56 (d, J=7.28 Hz, 1H), 7.67 (br s, 1H), 7.99 (d, J=8.28 Hz, 2H).

Preparation of 85

To a solution of CH-3 (50 mg, 119.48 μmol, 1 eq) and Et3N (36.27 mg, 358.44 μmol, 49.89 μL, 3 eq) in DCM (5 mL) was added 2-chloroacetyl chloride (20.24 mg, 179.22 μmol, 14.25 μL, 1.5 eq). The reaction was stirred for 0.5 h at 0° C. to give a yellow solution. TLC (quenched with water, eluting with: PE/EA=3/1) showed the reaction was completed. The mixture was purified by prep-TLC to give 85. LC-MS (m/z): 495.4[M+H]+. $^1$H NMR (400 MHz, $CDCl_3$) δ ppm 0.80-1.36 (m, 1H), 1.77-1.98 (m, 4H), 1.99-2.14 (m, 2H), 2.65-2.77 (m, 1H), 3.13-3.55 (m, 1H), 3.64 (s, 3H), 3.68-3.90 (m, 1H), 4.09 (br dd, J=16.31, 9.54 Hz, 2H), 4.25 (br s, 2H), 5.26 (br s, 1H), 6.05-6.31 (m, 1H), 7.07-7.24 (m, 3H), 7.41 (br s, 2H), 7.53 (br d, J=7.78 Hz, 1H), 7.71-7.86 (m, 1H), 7.96 (br s, 2H).

Procedure CI: Synthesis of Compound 86

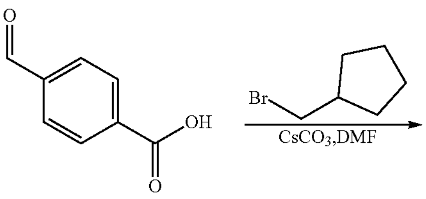

AB-2

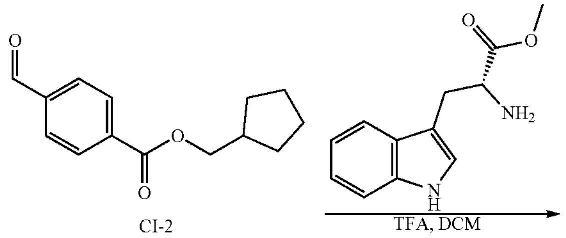

CI-2

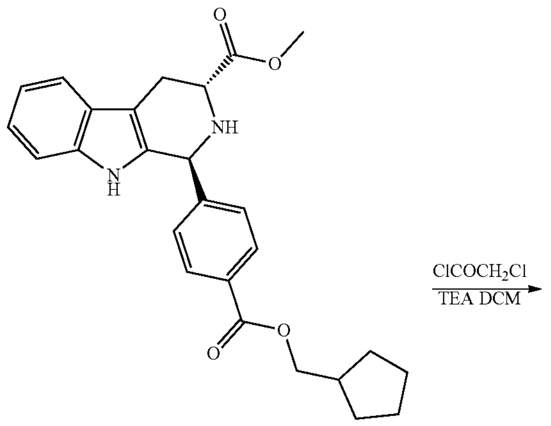

CI-3

-continued

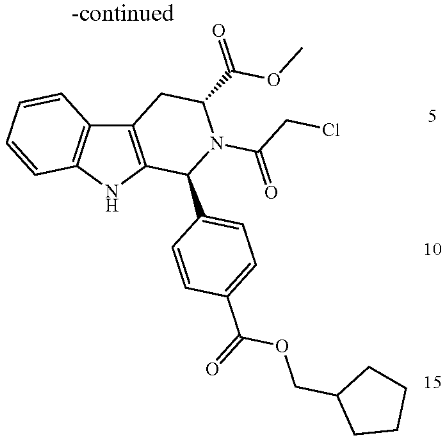

Compound 86

Preparation of Compound CI-2

To a solution of AB-2 (500 mg, 3.33 mmol, 1 eq) in DMF (10 mL) were added $Cs_2CO_3$ (1.09 g, 3.33 mmol, 1 eq) and bromomethylcyclopentane (1.36 g, 8.33 mmol, 2.5 eq). The mixture was stirred heated to 80° C. for 16 h to give a brown suspension. TLC (eluting with: PE/EtOAc=5/1) showed the reaction was completed. The reaction mixture was quenched with $H_2O$ (50 mL) and extracted with MBTE (30 mL×3). The organic layers were dried over $Na_2SO_4$ and concentrated to give the crude product, which was purified by a flash column ($SiO_2$, Petroleum ether/Ethyl acetate=I/O to 1:1) to give CI-2. $^1H$ NMR (400 MHz, $CDCl_3$) δ=10.22-10.01 (m, 1H), 8.20 (d, J=8.3 Hz, 2H), 7.95 (d, J=8.0 Hz, 2H), 4.25 (d, J=7.0 Hz, 2H), 2.36 (spt, J=7.6 Hz, 1H), 2.05-1.76 (m, 2H), 1.67-1.25 (m, 6H).

Preparation of Compound CI-3

To a solution of CI-2 (100 mg, 430.53 µmol, 1 eq) in DCM (5 mL) were added methyl 1-A (93.96 mg, 430.53 µmol, 1 eq) and TFA (24.54 mg, 215.26 µmol, 15.94 µL, 0.5 eq). The mixture was stirred at 25° C. for 16 h. TLC (eluting with: PE/EtOAc=2/1) showed the reaction was completed. The reaction solution was diluted with DCM (40 mL), then washed with sat. aqu. $NaHCO_3$ (40 mL). The organic layer was dried over anhydrous $Na_2SO_4$, filtered, and concentrated under reduced pressure to give the crude product, which was then purified by a flash column ($SiO_2$, Petroleum ether/Ethyl acetate=I/O to 1:1) to give CI-3. $^1H$ NMR (400 MHz, $CDCl_3$) δ=8.01 (d, J=8.3 Hz, 2H), 7.62-7.48 (m, 2H), 7.39 (d, J=8.3 Hz, 2H), 7.21-7.09 (m, 2H), 5.49 (s, 1H), 4.21 (d, J=7.0 Hz, 2H), 3.96 (s, 1H), 3.73 (s, 3H), 3.33-3.12 (m, 2H), 2.34 (quin, J=7.4 Hz, 1H), 1.82 (br d, J=8.0 Hz, 2H), 1.63 (br dd, J=7.2, 13.7 Hz, 4H), 1.42-1.23 (m, 1H).

Preparation of 86

To a solution of CI-3 (73 mg, 168.78 µmol, 1 eq) in DCM (5 mL) were added TEA (170.79 mg, 1.69 mmol, 234.93 µL, 10 eq) and 2-chloroacetyl chloride (57.19 mg, 506.35 µmol, 40.27 µL, 3 eq). The mixture was stirred at 0° C. to 25° C. for 2 h to give a brown suspension. LCMS and TLC (eluting with: PE/EtOAc=2/1) showed the reaction was completed. The crude product by purified by a flash column ($SiO_2$, Petroleum ether/Ethyl acetate=I/O to 1:1) to give 86. LC-MS (m/z): 509.1 [M+H]+. $^1H$ NMR (400 MHz, METHANOL-d4) δ=8.25-7.79 (m, 2H), 7.70-7.41 (m, 3H), 7.35-6.95 (m, 3H), 6.48-6.03 (m, 1H), 5.54-5.02 (m, 1H), 4.67-4.35 (m, 1H), 4.33-4.00 (m, 1H), 4.35-3.97 (m, 2H), 3.80-3.41 (m, 5H), 2.45-2.20 (m, 1H), 1.83 (br d, J=6.3 Hz, 2H), 1.74-1.49 (m, 1H), 1.76-1.48 (m, 3H), 1.48-1.21 (m, 2H).

Procedure CJ: Synthesis of Compound 87

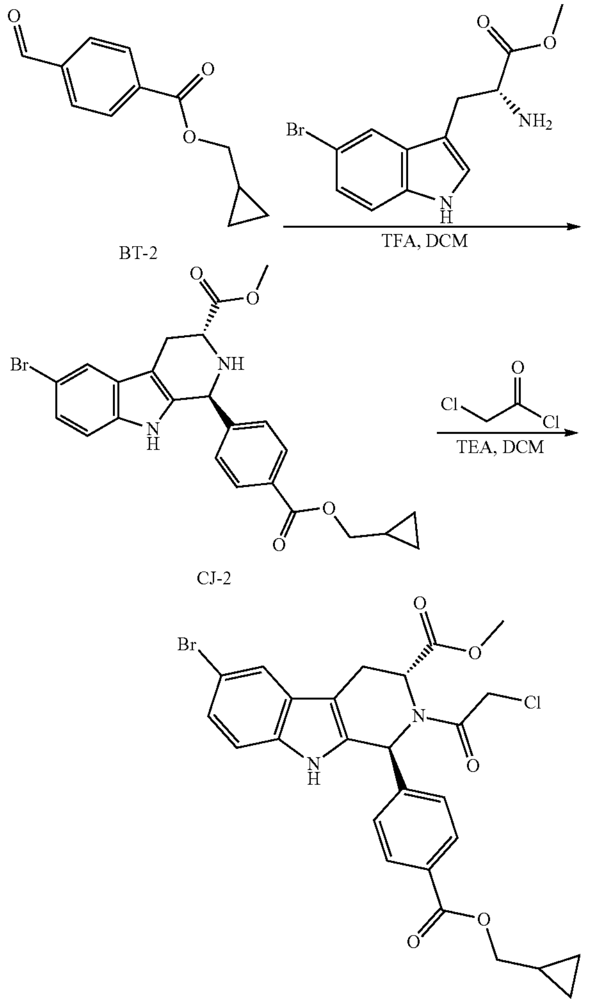

BT-2

CJ-2

Compound 87

To a solution of BT-2 (54.98 mg, 269.23 µmol, 1 eq) and methyl (2R)-2-amino-3-(5-bromo-1H-indol-3-yl) propanoate (80 mg, 269.23 µmol, 1 eq) in DCM (5 mL) was added TFA (15.35 mg, 134.61 µmol, 9.97 µL, 0.5 eq). The mixture was heated to 40° C. for 16 h to give a brown solution. LCMS showed the reaction was completed. The mixture was adjusted to pH 8 with Sat. $NaHCO_3$, and extracted with DCM (10 mL×3). The combined organic layers were dried over $Na_2SO_4$ and concentrated to provide the crude product. The residue was purified by prep-TLC ($SiO_2$, PE: EtOAc=2: 1) to give two products, one of which was CJ-2 and other of which was the cis-isomer. $^1H$ NMR (400 MHz, $CDCl_3$) δ=8.07-8.01 (m, J=8.3 Hz, 2H), 7.68 (d, J=1.8 Hz, 1H), 7.62 (s, 1H), 7.42-7.35 (m, J=8.3 Hz, 2H), 7.25 (dd, J=2.0, 8.5 Hz, 1H), 7.11 (m, 1H), 5.48 (s, 1H), 4.16 (m, 2H), 4.00-3.93 (m, 1H), 3.73 (s, 3H), 3.24 (ddd, J=1.1, 5.5, 15.4 Hz, 1H), 3.13 (ddd, J=1.4, 6.0, 15.4 Hz, 1H), 2.05 (s, 1H), 1.26-1.21 (m, 1H), 0.64-0.58 (m, 2H), 0.40-0.33 (m, 2H).

Preparation of 87

To a solution of CJ-2 (25 mg, 51.72 μmol, 1 eq) and TEA (15.70 mg, 155.17 μmol, 21.60 μL, 3 eq) in $CH_2Cl_2$ (2 mL) was added 2-chloroacetyl chloride (11.68 mg, 103.44 μmol, 8.23 μL, 2 eq) at 0° C. The mixture was stirred at 20° C. for 2 h to give a brown solution. LCMS showed the reaction was completed. The mixture was concentrated to give a residue. The residue was purified by prep-TLC (SiO2, PE: EtOAc=2: 1) to give 87. LC-MS (m/z): 582.9[M+Na]+. $^1$H NMR (400 MHz, $CDCl_3$) δ=8.13-7.88 (m, 3H), 7.66 (s, 1H), 7.53-7.33 (m, 2H), 7.23 (m, 1H), 7.07 (br d, J=8.3 Hz, 1H), 6.30-6.04 (m, 1H), 5.45-5.18 (m, 1H), 4.98-4.69 (m, 1H), 4.19-3.97 (m, 4H), 3.66-3.4(m, 4H), 1.26 (br s, 1H), 0.59 (m, 2H), 0.33 (m, 2H).

Procedure CK: Synthesis of Compound 88

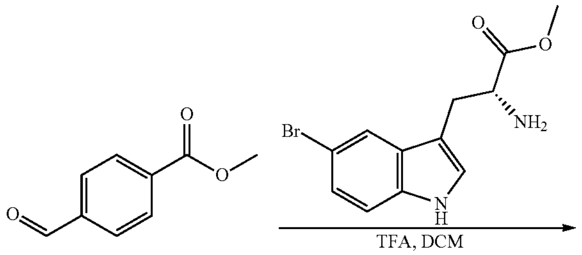

AA-2

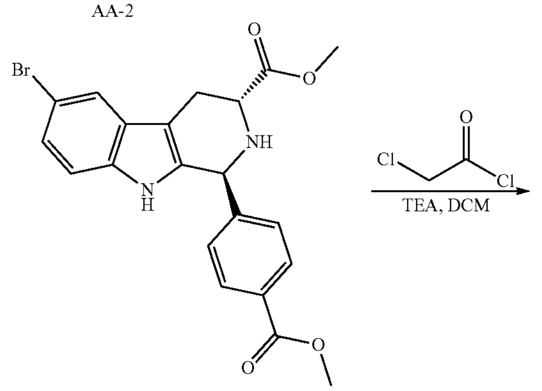

CK-2

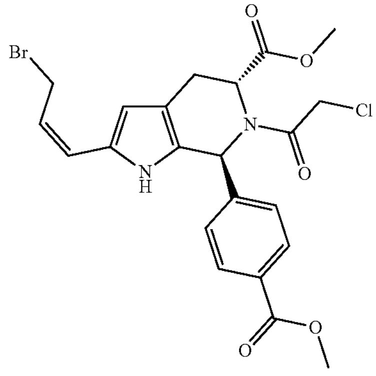

Compound 88

To a solution of AA-2 (44.20 mg, 269.23 μmol, 1 eq) and methyl (2R)-2-amino-3-(5-bromo-1H-indol-3-yl) propanoate (80 mg, 269.23 μmol, 1 eq) in DCM (5 mL) was added TFA (15.35 mg, 134.61 μmol, 9.97 μL, 0.5 eq). The mixture was heated to 40° C. for 16 h to give a brown solution. LCMS showed the reaction was completed. The mixture was adjusted to pH 8 with Sat. $NaHCO_3$, and extracted with DCM (10 mL×3). The combined organic layers were dried over $Na_2SO_4$ and concentrated to provide the crude product. The residue was purified by prep-TLC ($SiO_2$, PE:EtOAc=2:1) to give two products, one of which was CK-2, and the other of which was the cis-isomer. $^1$H NMR (400 MHz, $CDCl_3$) δ=8.04-7.99 (m, J=8.3 Hz, 2H), 7.69 (m, 1H), 7.60 (s, 1H), 7.40-7.36 (m, J=8.3 Hz, 2H), 7.25 (dd, J=2.0, 8.8 Hz, 1H), 7.12 (d, J=8.5 Hz, 1H), 5.48 (s, 1H), 3.99-3.91 (m, 4H), 3.73 (s, 3H), 3.24 (ddd, J=1.3, 5.5, 15.3 Hz, 1H), 3.14 (ddd, J=1.4, 6.0, 15.4 Hz, 1H).

Preparation of 88

To a solution of CK-2 (28 mg, 63.16 μmol, 1 eq) in $CH_2Cl_2$ (2 mL) were added TEA (19.17 mg, 189.49 μmol, 26.38 μL, 3 eq) and 2-chloroacetyl chloride (14.27 mg, 126.33 μmol, 10.05 μL, 2 eq) at 0° C. The mixture was stirred at 20° C. for 2 h to give a yellow solution. LCMS showed the reaction was completed. The mixture was concentrated to a residue, which was then purified by prep-TLC ($SiO_2$, PE: EtOAc=2:1) to give 88. LC-MS (m/z): 549.2[M+Na]+. $^1$H NMR (400 MHz, $CDCl_3$) δ=8.13-7.88 (m, 3H), 7.66 (s, 1H), 7.53-7.33 (m, 2H), 7.23 (m, 1H), 7.07 (m, 1H), 6.30-6.04 (m, 1H), 5.45-5.18 (m, 1H), 4.98-4.69 (m, 1H), 4.19-3.75 (m, 5H), 3.66-3.4 (m, 3H).

Procedure CL: Synthesis of Compound 89

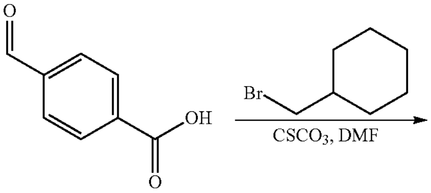

AB-2

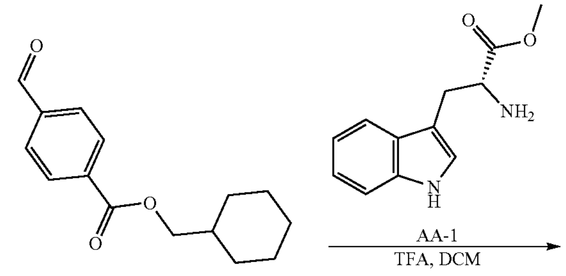

CL-2

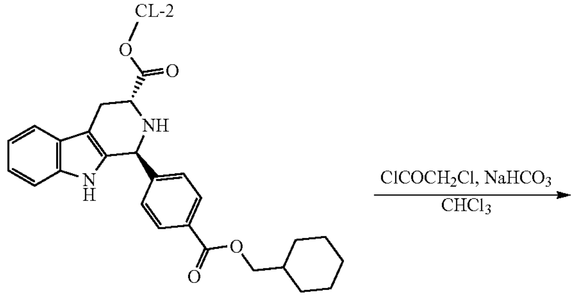

CL-3

-continued

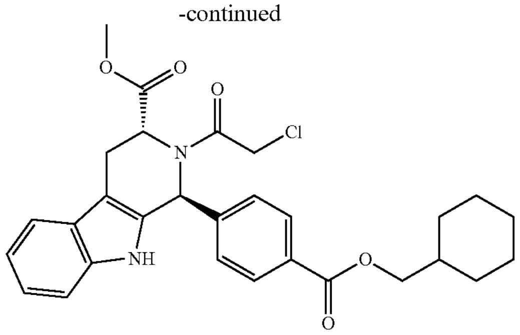

Compound 89

Preparation of Compound CL-2

To a solution of AB-2 (500 mg, 3.33 mmol, 1 eq) in DMF (20 mL) were added $CS_2CO_3$ (1.09 g, 3.33 mmol, 1 eq) and bromomethylcyclohexane (1.47 g, 8.33 mmol, 1.16 mL, 2.5 eq). The mixture was stirred with heating to 80° C. for 16 h to give a brown suspension. LCMS showed the desired product was found, but that AB-2 remained. Stirring was continued at 80° C. for another 16 h. LCMS and TLC (eluting with: PE/EtOAc=5/1) showed the reaction was completed. The reaction mixture was quenched with $H_2O$ (50 mL), extracted with MBTE (30 mL×3), the organic layers dried over $Na_2SO_4$, and then concentrated to give the crude product. The product was purified by a flash column ($SiO_2$, Petroleum ether/Ethyl acetate=l/0 to 1:1) to give CL-2. $^1$H NMR (400 MHz, $CDCl_3$) δ=10.10 (s, 1H), 10.28-9.84 (m, 1H), 10.59-9.77 (m, 1H), 8.27-7.91 (m, 4H), 4.17 (br d, J=6.3 Hz, 2H), 1.98-0.96 (m, 11H).

Preparation of Compound CL-3

To a solution of CL-2 (151.6 mg, 615.51 μmol, 1 eq) in DCM (5 mL) were added TFA (35.09 mg, 307.75 μmol, 22.79 μL, 0.5 eq) and AA-1. The mixture was stirred at 25° C. for 16 h to give a brown suspension. TLC (eluting with: PE/EtOAc=2/1) showed the reaction was completed. The reaction solution was diluted with DCM (40 mL), and then washed with sat. aqu. $NaHCO_3$ (40 mL). The organic layer was dried over anhydrous $Na_2SO_4$, filtered, and concentrated under reduced pressure to give the crude product, which was purified by prep-TLC ($SiO_2$, PE:EtOAc=2:1) to give CL-3. H NMR (400 MHz, $CDCl_3$)=8.01 (d, J=8.3 Hz, 1H), 7.63-7.48 (m, 1H), 7.38 (d, J=8.3 Hz, 1H), 7.26 (s, 5H), 5.72-5.19 (m, 1H, 4.24-3.80 (m, 2H), 3.72 (s, 2H), 3.36-3.06 (m, 1H), 2.05 (s, 1H), 1.93-1.58 (m, 4H), 1.51-1.17 (m, 4H), 1.12-0.84 (m, 2H).

Preparation of 89

To a solution of CL-3 (174.00 mg, 389.67 μmol, 1 eq) in DCM (10 mL) were added TEA (394.30 mg, 3.90 mmol, 542.37 μL, 10 eq) and 2-chloroacetyl chloride (44.01 mg, 389.67 μmol, 30.99 μL, 1 eq). The mixture was stirred at 25° C. for 2 h. LCMS and TLC (eluting with: PE/EtOAc=2/1) showed the reaction was completed. The reaction solution was diluted with DCM (40 mL), and then washed with sat. aqu. $NaHCO_3$ (40 mL). The organic layer was dried over anhydrous $Na_2SO_4$, filtered, and concentrated under reduced pressure to give crude product. The residue was purified by prep-TLC (SiO2, PE:EtOAc=2:1) to give 89. LC-MS (m/z): 523.1[M+H]+. $^1$H NMR (400 MHz, $CDCl_3$) δ=7.99-7.65 (m, 2H), 7.50-7.24 (m, 2H), 7.15-7.00 (m, 1H), 6.24-5.94 (m, 1H), 5.19 (br s, 1H), 4.16-3.70 (m, 3H), 3.66-3.53 (m, 3H), 1.85-1.49 (m, 6H), 1.29-0.82 (m, 5H).

Procedure CM: Synthesis of Compound 90

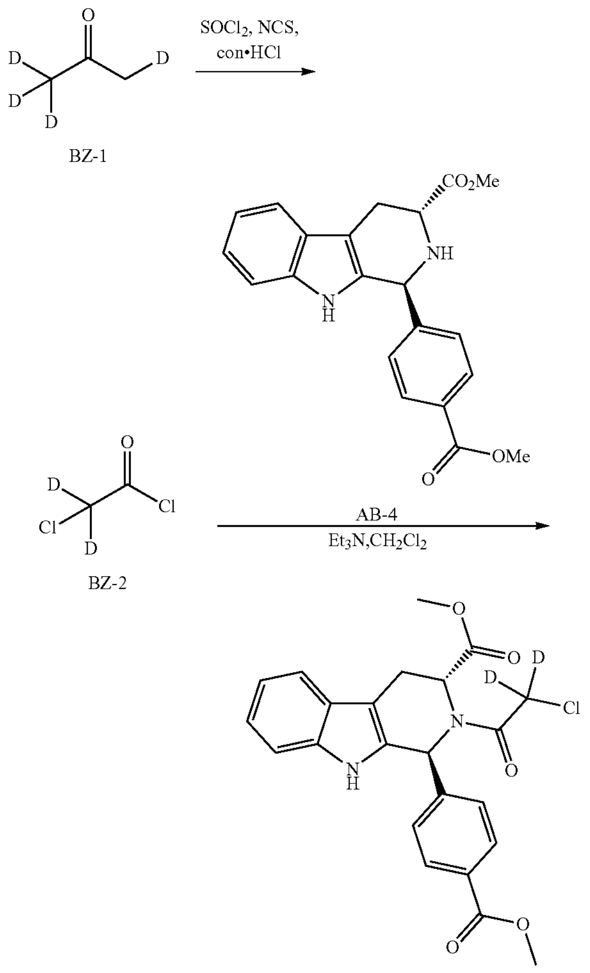

BZ-1

BZ-2

Compound 90

Preparation of Compound BZ-2

A solution of BZ-1 (160 mg, 2.50 mmol, 1 eq) in $SOCl_2$ (4.10 g, 34.46 mmol, 2.50 mL, 13.8 eq) was stirred at 70° C. for 1 h, then cooled to 25° C. NCS (666.87 mg, 4.99 mmol, 2 eq) and HCl (12 M, 5.24 μL, 2.52e-2 eq) were added, and the resulting mixture stirred at 80° C. for 1.5 h to afford a brown mixture. The reaction mixture was evaporated to afford BZ-2. The product was used in the next step without any purification.

Preparation of Compound 90

To a solution of BZ-2 (50 mg, 137.21 μmol, 1 eq) and Et3N (27.77 mg, 274.43 μmol, 38.20 μL, 2 eq) in DCM (3 mL) was added AB-4 (157.73 mg, 1.37 mmol, 10 eq). The reaction mixture was stirred at 0° C. for 16 h to give a brown solution, followed by stirring at 25° C. for 10 min to afford a muddy mixture. The crude product was purified by Prep- TLC (DCM/EA=10/1) to give 90. LC-MS (m/z): 443.4 [M+H]+. $^1$H NMR (400 MHz, DMSO-d6) δ: 3.51-3.57 (m, 3H), 3.81 (s, 3H), 4.90 (s, 1H), 4.71 (s, 1H), 5.41 (s, 1H), 5.99-6.46 (m, 1H), 6.94-7.10 (m, 2H), 7.19-7.34 (m, 1H), 7.49 (d, J=7.78 Hz, 1H), 7.53-7.72 (m, 2H), 7.81-8.00 (m, 2H), 10.91-11.19 (m, 1H).

Procedure CN: Synthesis of Compound 91

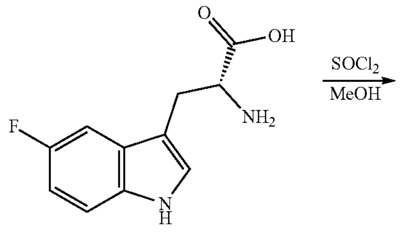

CN-1

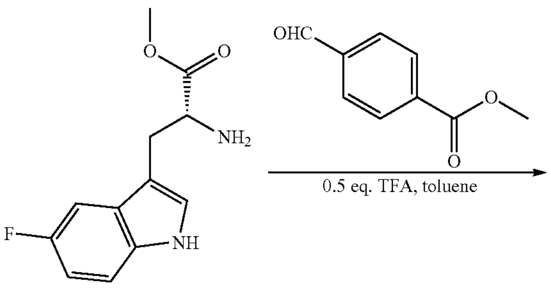

CN-2

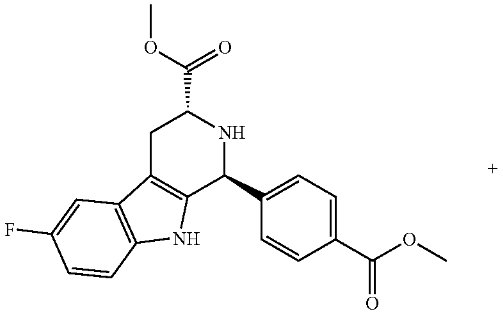

CN-3

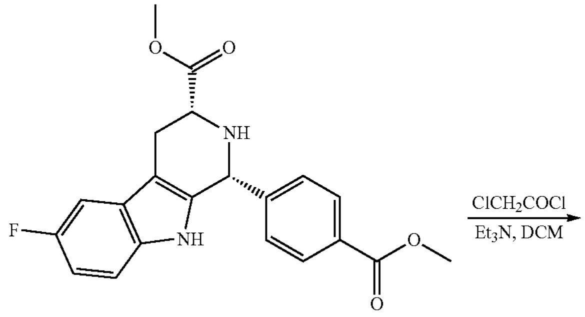

CN-3a

-continued

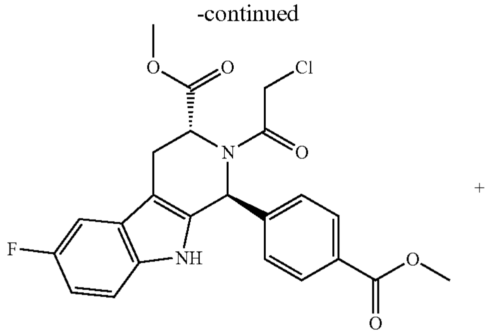

Compound 91

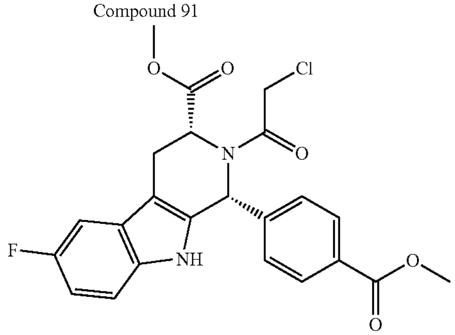

Compound 91a

Preparation of Compound CN-2

To a solution of CN-1 (100 mg, 450.01 μmol, 1 eq) in MeOH (5 mL) was added $SOCl_2$ (267.69 mg, 2.25 mmol, 163.23 μL, 5 eq) at 45° C. The reaction was stirred at 45° C. for 16 h to give a yellow solution. TLC (quenched with water, eluting with: 'PE/EA=0/1) showed the reaction was completed. The mixture was concentrated and diluted with EA (10 mL) and washed with $NaHCO_3$ solution (10 mL×3). The organic layer was dried over anhydrous $Na_2SO_4$ and concentrated under reduced pressure to give CN-2.

Preparation of Compounds CN-3 and CN-3a

To a solution of CN-2 (50 mg, 211.65 μmol, 1 eq) and methyl 4-formylbenzoate (38.22 mg, 232.81 μmol, 1.1 eq) in toluene (5 mL) was added TFA (12.07 mg, 105.82 μmol, 7.84 μL, 0.5 eq) at 25° C. The reaction was stirred at 80° C. for 16 h to give a yellow solution. LCMS showed the reaction was completed. The mixture was purified by prep-HPLC (column: Xtimate C18 150×25 mm×5 μm; mobile phase: [water (0.05% HCl)-ACN]; B %: 15-45 (8 min) %-45%, 9.5 min) to give CN-3 and CN-3a.

Preparation of 91a

To a solution of CN-3a (10 mg, 26.15 μmol, 1 eq) and Et3N (7.94 mg, 78.46 μmol, 10.92 μL, 3 eq) in DCM (1 mL) was added 2-chloroacetyl chloride (4.43 mg, 39.23 μmol, 3.12 μL, 1.5 eq). The mixture was stirred at 0° C. for 1 h to give a yellow solution. TLC (quenched with water, eluting with: PE/EA=3/1) showed the reaction was completed. The mixture was purified by prep-TLC to give 91a. LC-MS (m/z): 459.4[M+H]+

Preparation of 91

To a solution of CN-3 (10 mg, 26.15 μmol, 1 eq) and Et3N (7.94 mg, 78.46 μmol, 10.92 μL, 3 eq) in DCM (1 mL) was added 2-chloroacetyl chloride (4.43 mg, 39.23 μmol, 3.12 μL, 1.5 eq). The mixture was stirred at 0° C. for 1 h to give a yellow solution. TLC (quenched with water, eluting with: PE/EA=3/1) showed the reaction was completed. The mixture was purified by prep-TLC to give 91. LC-MS (m/z): 459.4[M+H]+.

Procedure CO: Synthesis of Compound 93

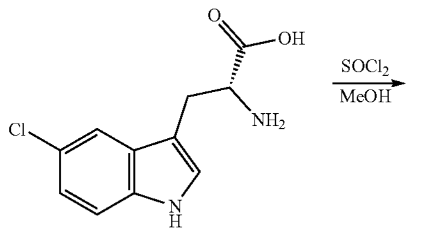

CO-1

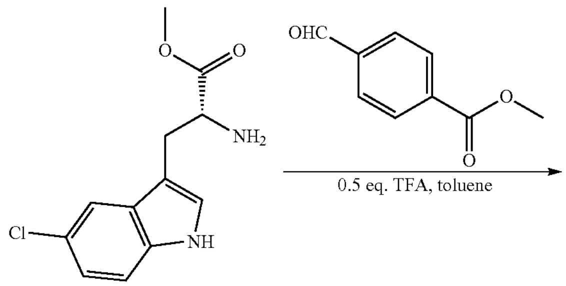

CO-2

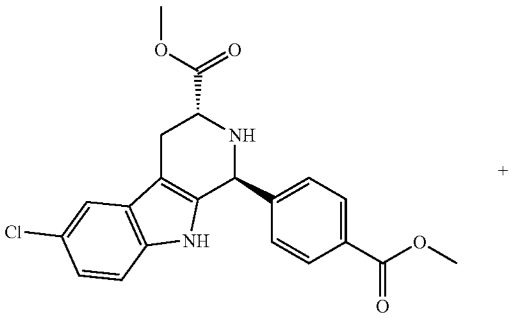

CO-3

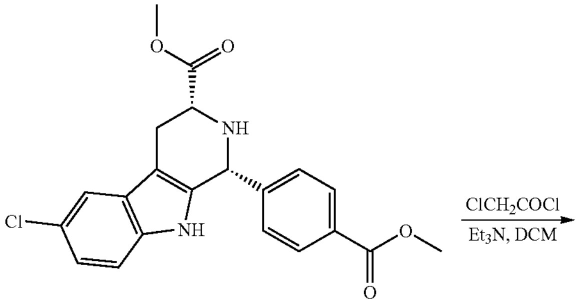

CO-3a

-continued

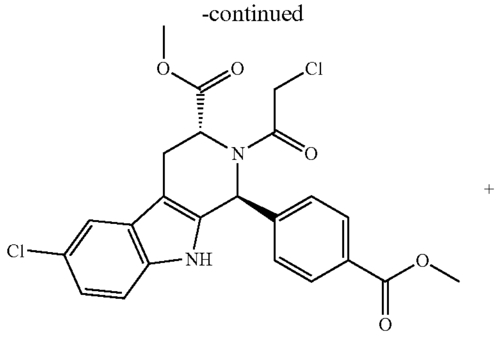

Compound 93

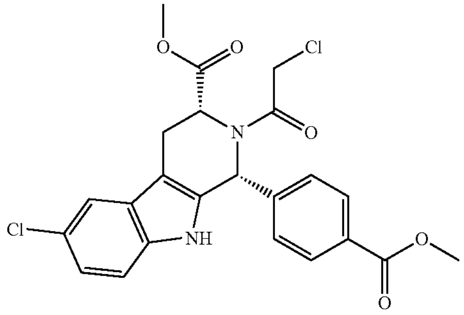

Compound 93a

Preparation of Compound CO-2

To a solution of CO-1 (100 mg, 418.99 μmol, 1 eq) in MeOH (5 mL) was added $SOCl_2$ (249.24 mg, 2.09 mmol, 151.97 μL, 5 eq). The reaction was stirred at 45° C. for 16 h to give a yellow solution. TLC (quenched with water, eluting with: PE/EA=0/1) showed the reaction was completed. The mixture was concentrated and then diluted with EA (10 mL) and washed with $NaHCO_3$ solution (10 mL×3). The organic layers were dried over anhydrous $Na_2SO_4$ and concentrated under reduced pressure to give CO-2.

Preparation of Compounds CO-3 and CO-3a

To a solution of CO-2 (90 mg, 356.16 μmol, 1 eq) and methyl 4-formylbenzoate (64.31 mg, 391.78 μmol, 1.1 eq) in toluene (5 mL) was added TFA (20.31 mg, 178.08 μmol, 13.19 μL, 0.5 eq) at 25° C. The reaction was stirred at 80° C. for 16 h to give a yellow solution. LCMS showed the reaction was completed. The reaction was purified by prep-HPLC (column: Xtimate C18 150×25 mm×5 μm; mobile phase: [water (0.05% HCl)-ACN]; B %: 17%-47%, 9.5 min) to give CO-3 and CO-3a.

Preparation of 93a

To a solution of CO-3a (20 mg, 50.15 μmol, 1 eq) and Et3N (15.22 mg, 150.44 μmol, 20.94 μL, 3 eq) in DCM (5 mL) was added 2-chloroacetyl chloride (8.50 mg, 75.22 μmol, 5.98 μL, 1.5 eq). The mixture was stirred at 0° C. for 1 h to give a yellow solution. TLC (quenched with water, eluting with: PE/EA=3/1) showed the reaction was completed. The mixture was purified by prep-TLC to give 93a. LC-MS (m/z): 475.4[M+H]+

Preparation of 93

To a solution of CO-3 (20 mg, 50.15 μmol, 1 eq) and Et3N (15.22 mg, 150.44 μmol, 20.94 μL, 3 eq) in DCM (5 mL) was added 2-chloroacetyl chloride (8.50 mg, 75.22 μmol, 5.98 μL, 1.5 eq). The mixture was stirred at 0° C. for 1 h to give a yellow solution. TLC (quenched with water, eluting with: PE/EA=3/1) showed the reaction was completed. The mixture was purified by prep-TLC to give 93. LC-MS (m/z): 475.4[M+H]+.

Procedure CP: Synthesis of Compound 95

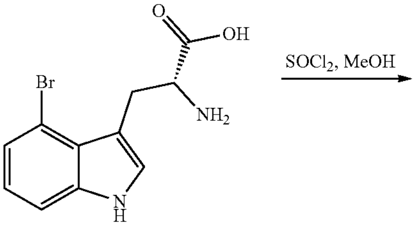

CO-1

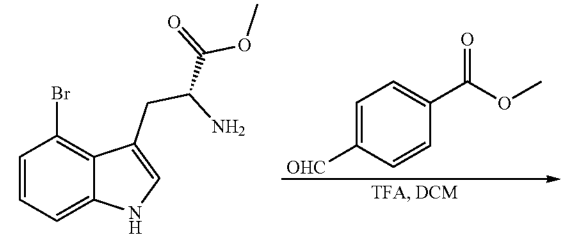

CO-2

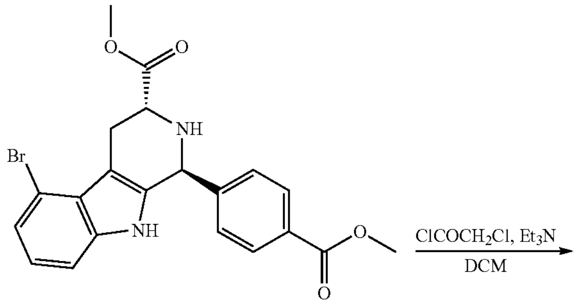

CO-3

-continued

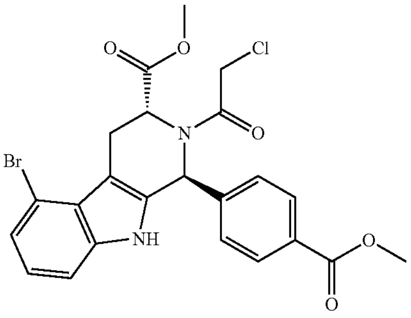

Compound 95

Preparation of Compound CO-2

To a solution of CO-1 (100.00 mg, 353.21 μmol, 1 eq) in MeOH (5 mL) was added $SOCl_2$ (210.10 mg, 1.77 mmol, 128.11 μL, 5 eq). The mixture was stirred at 45° C. for 1 h to give a yellow solution. LCMS showed the reaction was completed. The reaction solution was concentrated, diluted with DCM (5 mL), and washed with $NaHCO_3$ solution (5 mL×3). The organic layer was dried over anhydrous $Na_2SO_4$ and concentrated under reduced pressure to give CO-2.

Preparation of Compound CO-3

To a solution of CO-2 (75.00 mg, 252.40 μmol, 1 eq) and methyl 4-formylbenzoate (41.43 mg, 252.40 μmol, 1 eq) in toluene (5 mL) was added TFA (14.39 mg, 126.20 μmol, 9.34 μL, 0.5 eq) at 20° C. The mixture was stirred at 80° C. for 16 h to give a yellow solution. TLC (eluting with: PE/EA=3/1) showed the reaction was completed. The reaction was purified by prep-TLC to give CO-3. $^1H$ NMR (400 MHz, $CDCl_3$) δ ppm 3.48-3.56 (m, 1H), 3.61-3.68 (m, 1H), 3.74 (s, 3H), 3.91 (s, 4H), 5.45 (s, 1H), 6.94-7.01 (m, 1H), 7.17 (d, J=8.13 Hz, 1H), 7.38 (d, J=8.25 Hz, 2H), 7.63 (s, 1H), 8.01 (d, J=8.25 Hz, 2H).

Preparation of 95

To a solution of CO-3 (30 mg, 67.68 μmol, 1 eq) and Et3N (20.54 mg, 203.03 μmol, 28.26 μL, 3 eq) in DCM (5 mL) was added 2-chloroacetyl chloride (11.47 mg, 101.51 μmol, 8.07 μL, 1.5 eq). The mixture was stirred at 0° C. for 1 h to give a yellow solution. TLC (quenched with water, eluting with: PE/EA=2/1) showed the reaction was completed. The reaction was purified by prep-TLC to give 95. LC-MS (m/z): 521.4[M+H]+. $^1H$ NMR (400 MHz, DMSO-d6) δ ppm 3.54 (br s, 3H), 3.80 (br s, 3H), 4.14 (br d, J=15.51 Hz, 1H), 4.43 (br d, J=14.13 Hz, 1H), 4.71 (d, J=14.26 Hz, 1H), 5.40 (br s, 1H), 6.04 (br s, 1H), 6.88-7.02 (m, 1H), 7.09-7.37 (m, 2H), 7.57 (br d, J=7.50 Hz, 2H), 7.84 (br d, J=7.88 Hz, 2H), 11.39-11.66 (m, 1H).

Procedure CQ: Synthesis of Compound 96

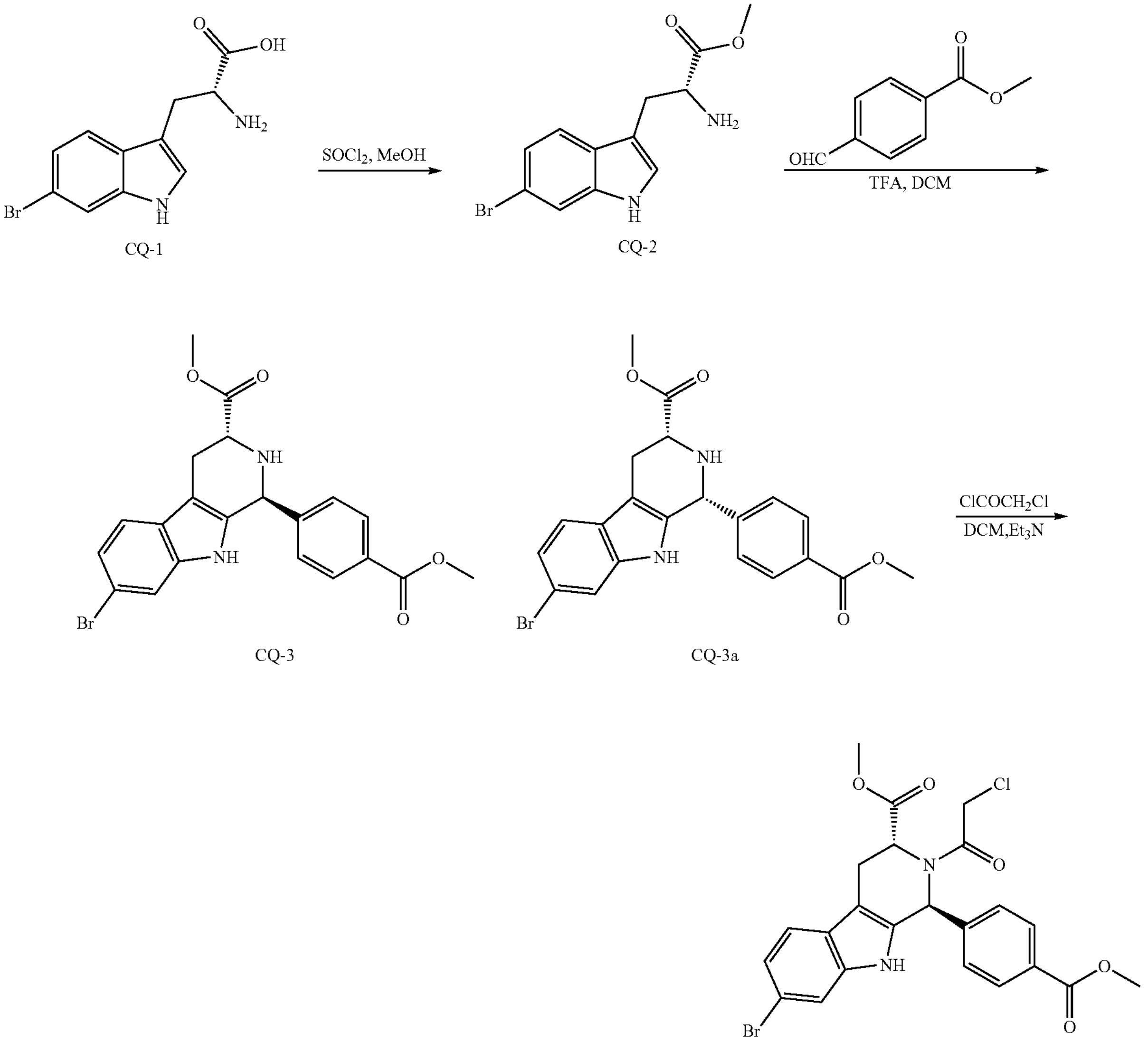

CQ-1 CQ-2 CQ-3 CQ-3a

Compound 96

Preparation of CQ-2. To a solution of CQ-1 (100 mg, 353.21 μmol, 1 eq) in MeOH (5 mL) was added $SOCl_2$ (210.10 mg, 1.77 mmol, 128.11 μL, 5 eq). The mixture was stirred at 45° C. for 16 h to give a blue solution. TLC (eluting with: PE/EA=0/1) showed the reaction was completed. The mixture was purified by prep-TLC to give CQ-2.

Preparation of CQ-3. To a solution of CQ-2 (60 mg, 201.92 μmol, 1 eq) and methyl 4-formylbenzoate (33.15 mg, 201.92 μmol, 1 eq) in toluene (5 mL) was added TFA (11.51 mg, 100.96 μmol, 7.47 μL, 0.5 eq) at 20° C. The mixture was stirred at 80° C. for 16 h to give a yellow solution. TLC (eluting with: PE/EA=3/1) showed the reaction was completed. The mixture was purified by prep-TLC to give CQ-3 and CQ-3a. $^1$H NMR (400 MHz, $CDCl_3$) δ ppm 2.51 (br s, 1H), 2.94-3.03 (m, 1H), 3.16-3.24 (m, 1H), 3.81 (s, 3H), 3.91 (s, 3H), 3.96 (dd, J=11.04, 4.27 Hz, 1H), 5.26 (s, 1H), 7.22 (dd, J=8.53, 1.76 Hz, 1H), 7.34 (d, J=1.51 Hz, 1H), 7.38 (d, J=8.28 Hz, 1H), 7.44 (d, J=8.28 Hz, 2H), 7.58 (s, 1H), 8.00 (d, J=8.28 Hz, 2H).

Preparation of 96

To a solution of CQ-3 (30 mg, 67.68 μmol, 1 eq) and Et3N (20.54 mg, 203.03 μmol, 28.26 μL, 3 eq) in DCM (5 mL) was added 2-chloroacetyl chloride (11.47 mg, 101.51 μmol, 8.07 μL, 1.5 eq). The mixture was stirred at 0° C. for 1 h to give a yellow solution. LCMS showed the reaction was completed. The mixture was purified by prep-TLC to give 96. LC-MS (m/z): 521.3[M+H]+. $^1$H NMR (400 MHz, $CDCl_3$) δ ppm 3.33 (d, J=5.52 Hz, 1H), 3.49 (s, 1H), 3.65 (s, 4H), 3.88 (br s, 3H), 3.99-4.17 (m, 2H), 5.26 (br s, 1H), 6.02-6.28 (m, 1H), 7.19-7.24 (m, 1H), 7.38 (br d, J=8.53 Hz, 3H), 7.76-8.16 (m, 3H).

Procedure CR: Synthesis of Compound 97

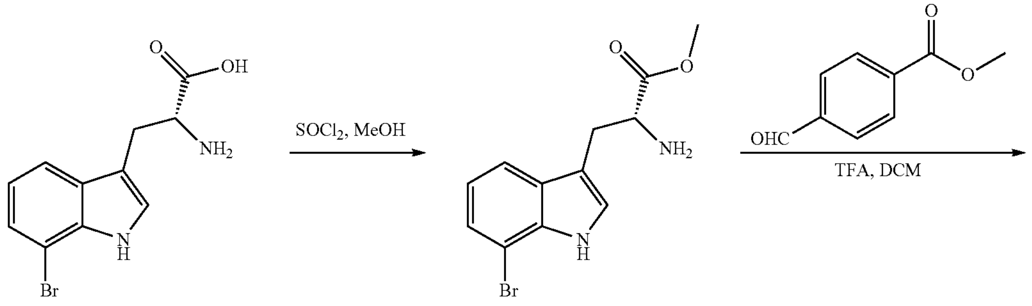

CR-1 CR-2

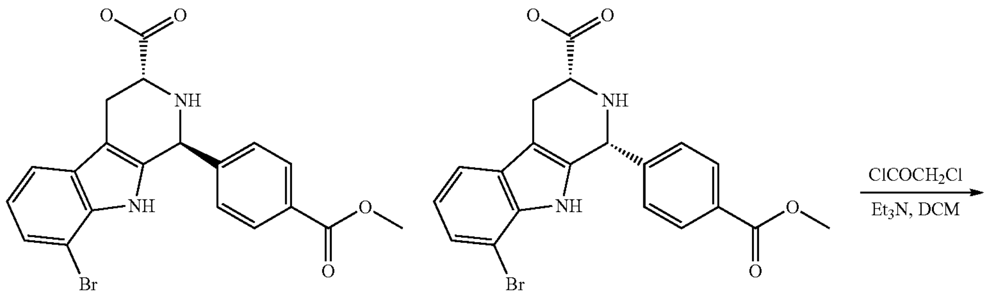

CR-3 CR-3a

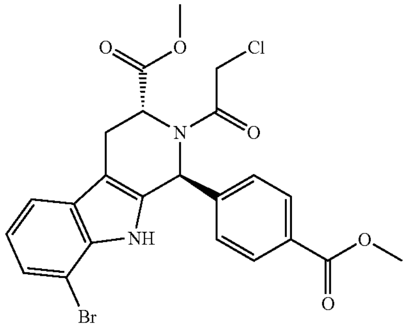

Compound 97

Preparation of Compound CR-2

To a solution of CR-1 (150 mg, 529.81 μmol, 1 eq) in MeOH (5 mL) was added $SOCl_2$ (315.16 mg, 2.65 mmol, 192.17 μL, 5 eq) at 15° C. The mixture was stirred at 45° C. for 3 h. LCMS showed the reaction was completed. The solution was concentrated, diluted with DCM (5 mL), and then washed with brine (5 mL×3). The organic layer was dried over anhydrous $Na_2SO_4$ and concentrated under reduced pressure to give CR-2.

Preparation of Compound CR-3

To a solution of CR-2 (120 mg, 403.84 μmol, 1 eq) and methyl 4-formylbenzoate (66.29 mg, 403.84 μmol, 1 eq) in toluene (5 mL) was added TFA (23.02 mg, 201.92 μmol, 14.95 μL, 0.5 eq) at 10° C. The mixture was stirred at 80° C. for 16 h to give a yellow solution. TLC (eluting with: PE/EA=3/1) showed the reaction was completed. The mixture was purified by prep-TLC to give CR-3a and CR-3. $^1$H NMR (400 MHz, $CDCl_3$) δ ppm 2.97-3.07 (m, 1H), 3.18-3.25 (m, 1H), 3.82 (s, 3H), 3.93 (s, 3H), 3.97 (dd, J=10.92, 4.14 Hz, 1H), 5.33 (s, 1H), 7.01 (t, J=7.78 Hz, 1H), 7.31 (d, J=7.53 Hz, 1H), 7.46-7.52 (m, 4H), 8.07 (d, J=8.28 Hz, 2H).

Preparation of 97

To a solution of CR-3 (19 mg, 42.86 μmol, 1 eq) and Et3N (13.01 mg, 128.58 μmol, 17.90 μL, 3 eq) in DCM (5 mL) was added 2-chloroacetyl chloride (7.26 mg, 64.29 μmol, 5.11 μL, 1.5 eq). The mixture was stirred at 0° C. for 1 h to give a yellow solution. TLC (quenched with water, eluting with: PE/EA=3/1) showed the reaction was completed. The mixture was purified by prep-TLC to give 97. LC-MS (m/z): 521.3[M+H]+. $^1$H NMR (400 MHz, $CDCl_3$) δ ppm 3.21-3.57 (m, 1H), 3.65 (s, 3H), 3.89 (br s, 3H), 3.98-4.15 (m, 1H), 5.23 (br s, 1H), 6.15 (br s, 1H), 7.01 (t, J=7.78 Hz, 1H), 7.31 (br d, J=7.53 Hz, 1H), 7.47 (br d, J=8.03 Hz, 3H), 8.00 (br s, 2H).

Procedure CS: Synthesis of Compound 98 and Compound 98a

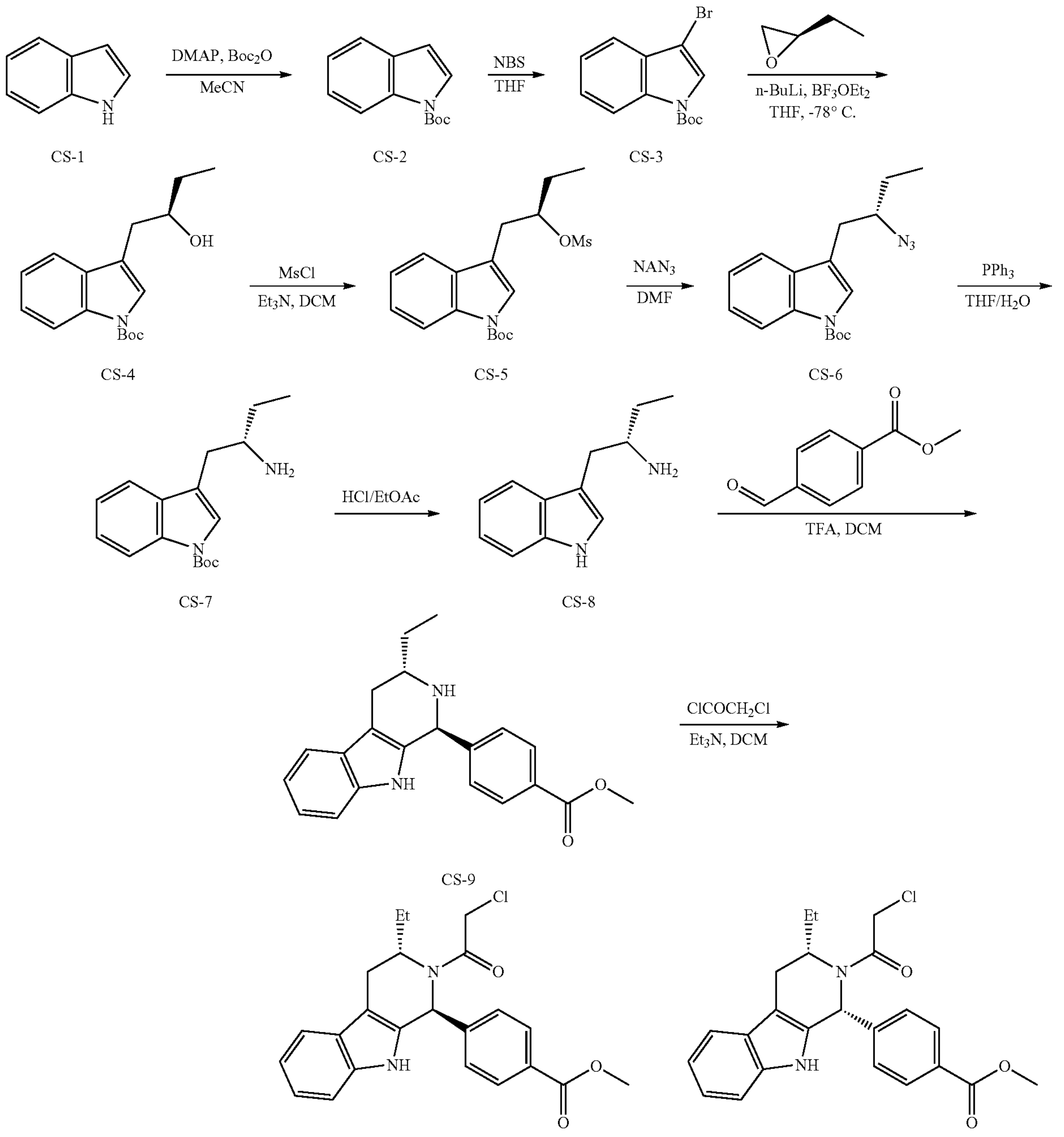

CS-1 CS-2 CS-3 CS-4 CS-5 CS-6 CS-7 CS-8 CS-9

Compound 98 Compound 99

Preparation of Compound CS-2

To a solution of CS-1 (5 g, 42.68 mmol, 1 eq) and DMAP (521.43 mg, 4.27 mmol, 0.1 eq) in MeCN (60 mL) was added slowly a solution of $Boc_2O$ (13.97 g, 64.02 mmol, 14.71 mL, 1.5 eq) in MeCN (5 mL). The mixture was stirred at 20° C. for 18 h under $N_2$ atmosphere to give a yellow solution. TLC (quenched with water, eluting with: PE/EA=4/1) showed the reaction was completed. The reaction was concentrated, and then diluted with EA (10 mL), and washed with 1M HCl, $NaHCO_3$ solution, brine (10 mL×3). The organic layer was dried over anhydrous $Na_2SO_4$ and concentrated under reduced pressure to give CS-2. $^1H$ NMR (400 MHz, $CDCl_3$) δ ppm 1.70 (s, 9H), 6.59 (d, J=3.76 Hz, 1H), 7.23-7.28 (m, 1H), 7.31-7.37 (m, 1H), 7.55-7.66 (m, 2H), 8.20 (br d, J=7.78 Hz, 1H).

Preparation of CS-3. To a solution of CS-2 (11 g, 50.63 mmol, 1 eq) in THF (400 mL) was added all at once NBS (9.91 g, 55.69 mmol, 1.1 eq) at 20° C. The reaction was stirred at 20° C. for 18 h to give a yellow solution. TLC (eluting with: PE/EA=0/1) showed the reaction was completed. The reaction was purified by flash chromatography ($SiO_2$, 100% PE) to give CS-3. $^1H$ NMR (400 MHz, $CDCl_3$)

δ ppm 1.68 (s, 11H), 7.30-7.42 (m, 2H), 7.54 (d, J=7.78 Hz, 1H), 7.66 (s, 1H), 8.16 (br d, J=7.28 Hz, 1H).

Preparation of CS-4. To a solution of CS-3 (2 g, 6.75 mmol, 1 eq) in THF (20 mL) was added dropwise n-BuLi (2.5 M, 2.97 mL, 1.1 eq) at −78° C. The mixture was stirred at −78° C. for 0.5 h. (2R)-2-ethyloxirane (584.06 mg, 8.10 mmol, 1.2 eq) in THF (5 mL) was added dropwise, followed by dropwise addition of $BF_3$.Et20 (766.41 mg, 5.40 mmol, 666.44 μL, 0.8 eq). The mixture was stirred at −78° C. for 1 h. LCMS and TLC (eluting with: PE/EtOAc=1/1) showed the reaction was completed. The reaction mixture was quenched with Sat. $NH_4Cl$ (40 mL) and extracted with EtOAc (40 mL×2). The organic layers were dried over $Na_2SO_4$ and concentrated to give the crude product, which was then purified by a flash column (eluting with: PE/EtOAc=100% PE to 40%) to give CS-4.

Preparation of CS-5. To a solution of CS-4 (100 mg, 345.58 μmol, 1 eq) in DCM (5 mL) were added Et3N (69.94 mg, 691.16 μmol, 96.20 μL, 2 eq), DMAP (4.22 mg, 34.56 μmol, 0.1 eq) and MsCl (79.17 mg, 691.16 μmol, 53.50 μL, 2 eq) at 0° C. The mixture was allowed to stir at 15° C. for 1 h to give a yellow solution. LCMS showed the reaction was completed. The reaction mixture was quenched with $H_2O$ (10 mL) and extracted with DCM (10 mL×3). The organic layers were dried over $Na_2SO_4$ and concentrated to give CS-5. The product was used for the next step without further purification.

Preparation of CS-6. To a solution of CS-5 (130 mg, 353.78 μmol, 1 eq) in DMF (3 mL) was added $NaN_3$ (92.00 mg, 1.42 mmol, 4 eq). The mixture was stirred at 15° C. for 12 h to give a yellow solution. LCMS showed the reaction was completed. The reaction mixture was quenched with $H_2O$ (40 mL) and extracted with MBTE (20 mL×2). The organic layers were dried over $Na_2SO_4$ and concentrated to give the residue. This product was used for next step without further purification.

Preparation of CS-7. To a solution of CS-6 (110 mg, 349.89 μmol, 1 eq) in $H_2O$ (2 mL)/THF (2 mL) was added $PPh_3$ (275.32 mg, 1.05 mmol, 3 eq). The mixture was stirred at 60° C. for 1 h to give a yellow solution. LCMS showed the reaction was completed. The reaction mixture was used the next step without further purification.

Preparation of CS-8. HCl (2 M, 6 mL, 15.18 eq) was added CS-7 (228 mg, 790.61 μmol, 1 eq) from a mixture of CS-7 and the corresponding (R)-isomer. The mixture was stirred at 15° C. for 1.5 h to give a yellow solution. LCMS showed the reaction was completed. The reaction mixture was extracted with MBTE (15 mL×3), and the pH of the water layer adjusted to pH 8 with Sat. $NaHCO_3$. The mixture was concentrated to give the crude product. The crude product was dissolved in DCM/EtOH (10/1, 30 mL), the mixture filtered and washed with DCM (20 mL). The filtrate was concentrated to give CS-8.

Preparation of CS-9. To a solution of CS-8 (80 mg, 424.93 μmol, 1 eq) in DCM (3 mL) were added methyl 4-formylbenzoate (69.76 mg, 424.93 μmol, 1 eq) and TFA (24.23 mg, 212.46 μmol, 15.73 μL, 0.5 eq). The mixture was stirred at 45° C. for 60 h to give yellow solution. LCMS and TLC (eluting with: PE/EtOAc=1/1) showed the reaction was completed. The reaction mixture was quenched with Sat. $NaHCO_3$ (5 mL) and extracted with DCM (15 mL×2). The organic layers were dried over $Na_2SO_4$ and concentrated to give the crude product. The crude product was purified by prep-TLC (eluting with: PE/EtOAc=1/1) to give CS-9 (trans) and CS-9a (cis).

CS-9 (trans): $^1$H NMR (400 MHz, $CDCl_3$) δ 7.96-7.91 (m, 2H), 7.89 (brs, 1H), 7.50-7.48 (m, 1H), 7.26-7.21 (m, 3H), 7.12-7.07 (m, 2H), 5.23 (s, 1H), 3.86 (s, 3H), 2.94-2.85 (m, 2H), 2.50-2.44 (m, 1H), 1.49-1.46 (m, 2H), 0.89 (t, J=7.2 Hz, 3H).

CS-9a (cis): $^1$H NMR (400 MHz, $CDCl_3$) δ 7.96-7.94 (m, 2H), 7.46-7.39 (m, 4H), 7.06-7.03 (m, 3H), 5.20 (s, 1H), 3.82 (s, 3H), 3.01-3.00 (m, 1H), 2.88-2.83 (m, 1H), 2.53-2.49 (m, 1H), 1.63-1.59 (m, 2H), 1.01 (t, J=7.6 Hz, 3H).

Preparation of 98

To a solution of CS-9 (trans) (28 mg, 83.73 μmol, 1 eq) in $CHCl_3$ (3 mL) were added $NaHCO_3$ (70.34 mg, 837.29 μmol, 32.56 μL, 10 eq) and 2-chloroacetyl chloride (28.37 mg, 251.19 μmol, 19.98 μL, 3 eq) at 0° C. The mixture was allowed to stir at 15° C. for 12 h to give a yellow suspension. LCMS and TLC (eluting with: PE/EtOAc=2/1) showed the reaction was completed. The reaction mixture was quenched with $H_2O$ (10 mL) and extracted with DCM (15 mL×2). The organic layers were dried over $Na_2SO_4$ and concentrated to give the crude product. The product was purified by prep-TLC (eluting with: PE/EtOAc=2/1) to give 98. LC-MS (m/z): 411.0 [M+H]+. $^1$H NMR (400 MHz, $CDCl_3$): δ 7.87-7.85 (m, 2H), 7.69 (brs, 1H), 7.46-7.44 (m, 1H), 7.32-7.30 (m, 2H), 7.07-7.04 (m, 3H), 5.82 (s, 1H), 4.38-3.91 (m, 3H), 3.84 (s, 3H), 3.24-3.22 (m, 1H), 3.06-3.02 (m, 1H), 1.60-1.58 (m, 2H), 0.90 (t, J=7.2 Hz, 3H).

Preparation of 98a

To a solution of CS-9a (cis) (40.00 mg, 119.61 μmol, 1 eq) in $CHCl_3$ (3 mL) were added $NaHCO_3$ (100.48 mg, 1.20 mmol, 46.52 μL, 10 eq) and 2-chloroacetyl chloride (40.53 mg, 358.84 μmol, 28.54 μL, 3 eq) at 0° C. The mixture was allowed to stir at 15° C. for 12 h. LCMS and TLC (eluting with: PE/EtOAc=2/1) showed the reaction was completed. The reaction mixture was quenched with $H_2O$ (10 mL) and extracted with DCM (15 mL×2). The organic layers were dried over $Na_2SO_4$ and concentrated to give the crude product, which was processed by prep-TLC (eluting with: PE/EtOAc=2/1) to give 99. LC-MS (m/z): 622.1 [M+H]+. $^1$H NMR (400 MHz, $CDCl_3$): δ 7.99 (brs, 1H), 7.86-7.84 (m, 2H), 7.49-7.46 (m, 3H), 7.31-7.29 (m, 1H), 7.17-7.10 (m, 2H), 6.97 (s, 1H), 4.24-4.12 (m, 3H), 3.86 (s, 3H), 3.15-3.10 (m, 1H), 2.95-2.87 (m, 1H), 1.46-1.41 (m, 2H), 0.51 (t, J=7.2 Hz, 3H).

Procedure CT: Synthesis of Compound 100

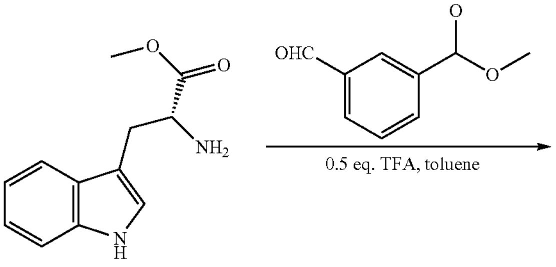

AA-1

-continued

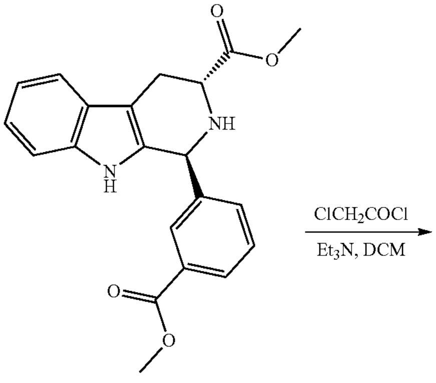

CT-2

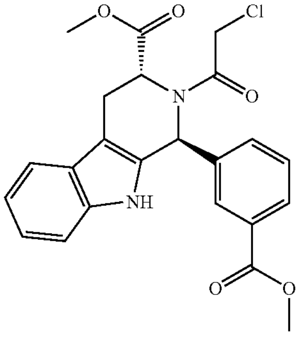

Compound 100

Preparation of Compound CT-2

To a solution of AA-1 (500 mg, 2.29 mmol, 1 eq) and methyl 3-formylbenzoate (376.08 mg, 2.29 mmol, 1 eq) in toluene (15 mL) was added TFA (130.61 mg, 1.15 mmol, 84.81 μL, 0.5 eq) at 20° C. The reaction was stirred at 80° C. for 16 h to give a yellow solution. TLC (quenched with water, eluting with: PE/EA=3/1) showed the reaction was completed. The mixture was purified by flash chromatography ($SiO_2$, PE/EA=3/1) to give CT-2. $^1H$ NMR (400 MHz, $CDCl_3$) δ ppm 3.14-3.22 (m, 1H), 3.26-3.34 (m, 1H), 3.72 (s, 3H), 3.89 (s, 3H), 4.00 (t, J=5.77 Hz, 1H), 5.49 (s, 1H), 7.15 (quind, J=7.15, 7.15, 7.15, 7.15, 1.25 Hz, 2H), 7.23 (s, 1H), 7.38-7.44 (m, 1H), 7.46-7.51 (m, 1H), 7.53-7.59 (m, 2H), 7.97-8.04 (m, 2H).

Preparation of 100

To a solution of CT-2 (50 mg, 137.21 μmol, 1 eq) and Et3N (41.65 mg, 411.64 μmol, 57.30 μL, 3 eq) in DCM (5 mL) was added 2-chloroacetyl chloride (23.25 mg, 205.82 μmol, 16.37 μL, 1.5 eq) at 0° C. The reaction was stirred at 0° C. for 1 h to give a yellow solution. TLC (eluting with: PE/EA=3/1) showed the reaction was completed. The reaction was purified by prep-TLC to give 100. LC-MS (m/z): 441.4[M+H]+. $^1H$ NMR (400 MHz, $CDCl_3$) δ ppm 3.64 (s, 3H), 3.90 (br s, 3H), 4.09 (br d, J=19.83 Hz, 2H), 5.19-5.48 (m, 1H), 6.13 (br s, 1H), 7.08-7.19 (m, 2H), 7.35 (br s, 1H), 7.54 (br d, J=7.78 Hz, 2H), 7.68-7.92 (m, 2H), 8.06 (br s, 1H).

Procedure CU: Synthesis of Compound 101

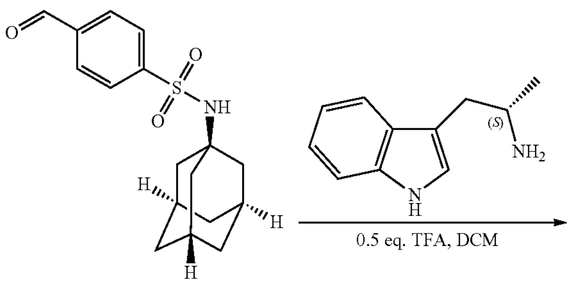

AQ-4

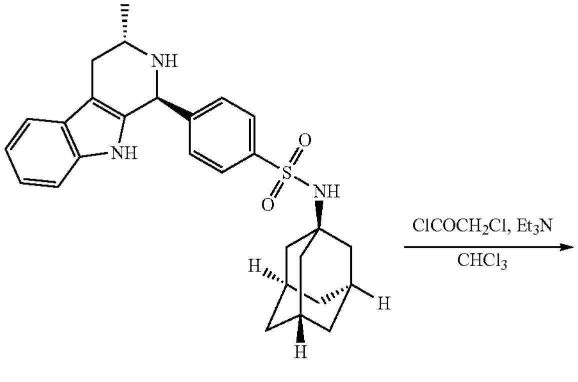

CU-2

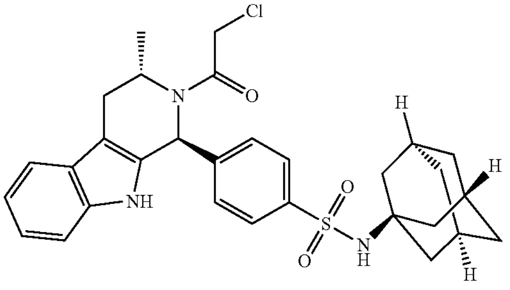

Compound 101

Preparation of Compound CU-2

To a solution of AQ-4 (155.82 mg, 487.83 μmol, 1 eq) and (2S)-1-(1H-indol-3-yl) propan-2-amine (85 mg, 487.83 μmol, 1 eq) in DCM (5 mL) was added TFA (27.81 mg, 243.91 μmol, 18.06 μL, 0.5 eq). The mixture was heated at 45° C. for 16 h to give a brown suspension. TLC (PE:EA=3:2) and LCMS showed—starting material remained. Thus, the reaction mixture was heated at 45° C. for an additional 64 h, which resulted in a brown suspension. TLC (PE:EA=1:1) showed the reaction was completed. The mixture was diluted with Sat. $NaHCO_3$ (10 mL) and extracted with DCM (5 mL×3). The combined organic layers were dried over $Na_2SO_4$, filtered and concentrated. The residue was purified by prep-TLC ($SiO_2$, PE: EA=1:1) to give CU-2 and its cis-isomer. $^1H$ NMR (400 MHz, $CDCl_3$) δ=7.82 (m, 2H), 7.70-7.50 (m, 2H), 7.45-7.28 (m, 3H), 7.24-7.07 (m, 3H), 5.30 (d, J=5.3 Hz, 1H), 4.42 (m, 1H), 3.57 (t, J=8.2 Hz, 1H), 3.37-3.12 (m, 2H), 2.96 (m, 1H), 1.84-1.74 (m, 5H), 1.62-1.52 (m, 10H), 1.25 (br s, 3H).

Preparation of 101

To a solution of CU-2 (10 mg, 21.02 μmol, 1 eq) in DCM (1 mL) were added TEA (8.51 mg, 84.10 μmol, 11.71 μL, 4 eq) and 2-chloroacetyl chloride (4.75 mg, 42.05 μmol, 3.34 μL, 2 eq) at 0° C. The mixture was stirred at 20° C. for 2 h to give a yellow solution. LCMS showed the reaction was completed. The mixture was concentrated to give a residue, which was processed by prep-HPLC (column: Xtimate C18 150×25 mm×5 μm; mobile phase: [water (0.05% HCl)-ACN]; B %: 65%-95%, 6.5 min) to give 101. LC-MS (m/z): 574.1[M+Na]+. $^1$H NMR (400 MHz, DMSO-d6) δ=11.02 (br d, J=1.6 Hz, 1H), 7.70 (br d, J=6.5 Hz, 2H), 7.56 (br d, J=7.4 Hz, 2H), 7.46 (d, J=7.8 Hz, 1H), 7.42 (s, 1H), 7.06-6.94 (m, 2H), 6.00 (br s, 1H), 4.86-4.65 (m, 2H), 3.03-2.81 (m, 1H), 1.87 (br s, 3H), 1.67-1.62 (m, 6H), 1.24 (br s, 6H), 1.15 (d, J=6.4 Hz, 3H).

Procedure CV: Synthesis of Compound 102

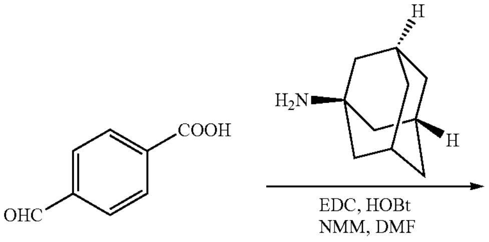

AB-2

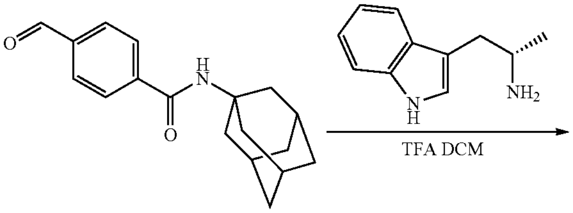

CV-2

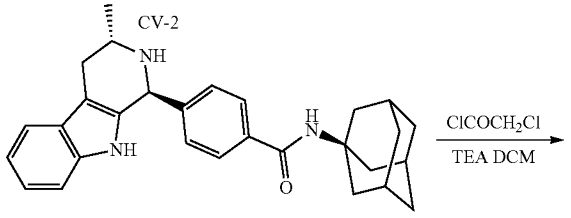

CV-3

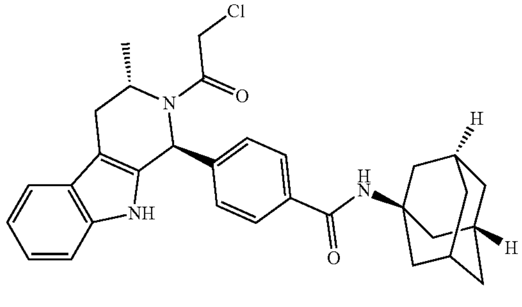

Compound 102

Preparation of Compound CV-2

To a solution of AB-2 (500 mg, 3.33 mmol, 1 eq), EDCI (702.29 mg, 3.66 mmol, 1.1 eq), NMM (842.16 mg, 8.33 mmol, 915.39 μL, 2.5 eq), HOBt (450.02 mg, 3.33 mmol, 1 eq) in DMF (10 mL) was added adamantan-1-amine (503.72 mg, 3.33 mmol, 1 eq) at 0° C. The mixture was stirred at 20° C. for 16 h to give a yellow suspension. TLC (PE:EA=2:1) showed the reaction was completed. The reaction solution was diluted with MTBE (20 mL), washed with 1N HCl (15 mL), washed with Sat. $NaHCO_3$ (20 mL) and brine (20 mL), and then extracted with MTBE (10 mL×5). The combined organic layers were dried over anhydrous $Na_2SO_4$, filtered, and concentrated under reduced pressure. The residue was processed by column chromatography ($SiO_2$, Petroleum ether/Ethyl acetate=I/O to 5:1) to give CV-2. $^1$H NMR (400 MHz, $CDCl_3$) δ=10.08 (s, 1H), 7.97-7.84 (m, 4H), 5.83 (br s, 1H), 2.15 (s, 9H), 1.74 (br s, 6H), 1.58 (s, 1H).

Preparation of Compound CV-3

To a solution of CV-2 (120 mg, 423.48 μmol, 1 eq) and (2S)-1-(1H-indol-3-yl) propan-2-amine (73.79 mg, 423.48 μmol, 1 eq) in toluene (3 mL) was stirred at 105° C. for 30 min. AcOH (378.00 mg, 6.29 mmol, 360.00 μL, 14.86 eq) was added to the mixture and stirred at 105° C. for 15.5 h to give a brown suspension. TLC (PE:EA=2:1) showed the reaction was completed. The mixture was diluted with Sat. $NaHCO_3$ (20 mL) and extracted with EA (10 mL×3). The combined organic layers were dried over $Na_2SO_4$, filtered and concentrated. The residue was purified by prep-TLC (SiO2, PE: EA=2:3) to give CV-3. $^1$H NMR (400 MHz, $CDCl_3$) δ=7.72 (br s, 1H), 7.65 (d, J=7.7 Hz, 2H), 7.56 (d, J=7.6 Hz, 1H), 7.31-7.28 (m, 2H), 7.16 (m, 3H), 5.76 (s, 1H), 5.29 (m, 2H), 4.13 (m, 1H), 3.28-3.20 (m, 1H), 2.97 (m, 1H), 2.54 (m, 1H), 2.12 (s, 8H), 1.73 (m, 8H), 1.24 (m, 3H).

Preparation of 102

To a solution of CV-3 (16 mg, 36.40 μmol, 1 eq) in DCM (2 mL) were added TEA (11.05 mg, 109.19 μmol, 15.20 μL, 3 eq) and 2-chloroacetyl chloride (12.33 mg, 109.19 μmol, 8.68 μL, 3 eq) at 0° C. The mixture was stirred at 15° C. for 2 h to give a yellow solution. LCMS showed the reaction was completed. The reaction mixture was concentrated, the residue purified by prep-TLC (SiO2, PE: EA=1:1) to give 102. LC-MS (m/z): 557.6[M+MeCN+H]+. $^1$H NMR (400 MHz, $CDCl_3$) δ=7.99 (s, 1H), 7.62-7.48 (m, 3H), 7.32 (m, 2H), 7.24-7.07 (m, 3H), 5.92 (br s, 1H), 5.69 (s, 1H), 4.82 (br s, 1H), 4.25 (br s, 1H), 4.10-3.98 (m, 1H), 3.39 (m, 1H), 2.97 (m, 1H), 2.14-2.06 (m, 9H), 1.71 (br s, 6H), 1.35 (m, 3H).

Procedure CW: Synthesis of Compound 103

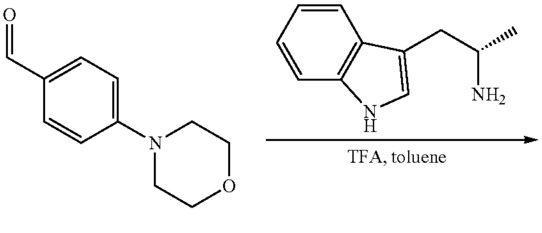

CW-1

-continued

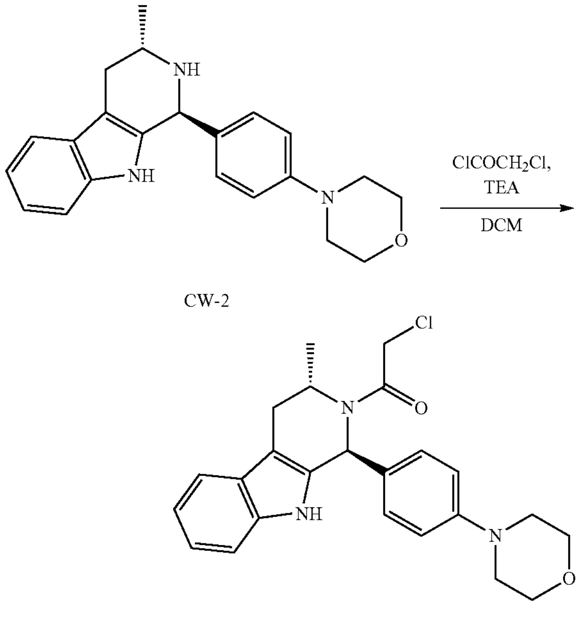

CW-2

Compound 103

Preparation of Compound CW-2

To a solution of CW-1 (200 mg, 1.05 mmol, 1 eq) and (2S)-1-(1H-indol-3-yl)propan-2-amine (182.24 mg, 1.05 mmol, 1 eq) in toluene (5 mL) was heated at 105° C. for 30 min. AcOH (525.00 mg, 8.74 mmol, 0.5 mL, 8.36 eq) was added to the mixture and stirred at 105° C. for 20 h to give a brown suspension. TLC (EA:MeOH=20:1) showed the reaction was completed. The mixture was quenched with Sat. $NaHCO_3$ (20 mL) and extracted with EA (10 mL×3). The combined organic layers were dried over $Na_2SO_4$, filtered and concentrated. The residue was purified by prep-TLC (SiO2, EA:MeOH=20:1) to give CW-2. $^1$H NMR (400 MHz, $CDCl_3$) δ=7.68 (br s, 1H), 7.55 (m, 1H), 7.22-7.08 (m, 4H), 6.85 (m, 2H), 5.18 (s, 1H), 4.13 (m, 1H), 3.86 (m, 4H), 3.39-3.24 (m, 1H), 3.20-3.10 (m, 4H), 2.97 (m, 1H), 2.55 (m, 1H), 1.27 (m, 3H).

Preparation of 103

To a solution of CW-2 (90 mg, 259.03 μmol, 1 eq) and TEA (52.42 mg, 518.06 μmol, 72.11 μL, 2 eq) in DCM (5 mL) was added 2-chloroacetyl chloride (87.77 mg, 777.08 μmol, 61.81 μL, 3 eq) at 0° C. The mixture was stirred at 20° C. for 2 h to give a brown suspension. TLC (PE:EA=1:2) showed the reaction was completed. The mixture was concentrated, and the residue subject to purification by prep-TLC (SiO2, PE: EA=1:2) to give 103. LC-MS (m/z): 424.2[M+H]+. $^1$H NMR (400 MHz, $CDCl_3$) δ=7.69 (s, 1H), 7.52 (d, J=7.3 Hz, 1H), 7.26-7.19 (m, 3H), 7.18-7.10 (m, 2H), 6.81 (m, 2H), 5.90 (s, 1H), 5.05-4.77 (m, 1H), 4.26-4.02 (m, 1H), 4.02-3.88 (m, 1H), 3.82 (m, 4H), 3.42-3.23 (m, 1H), 3.11 (m, 4H), 3.01-2.87 (m, 1H), 1.32 (m, 3H).

Procedure CX: Synthesis of Compounds 104 and Compound 105

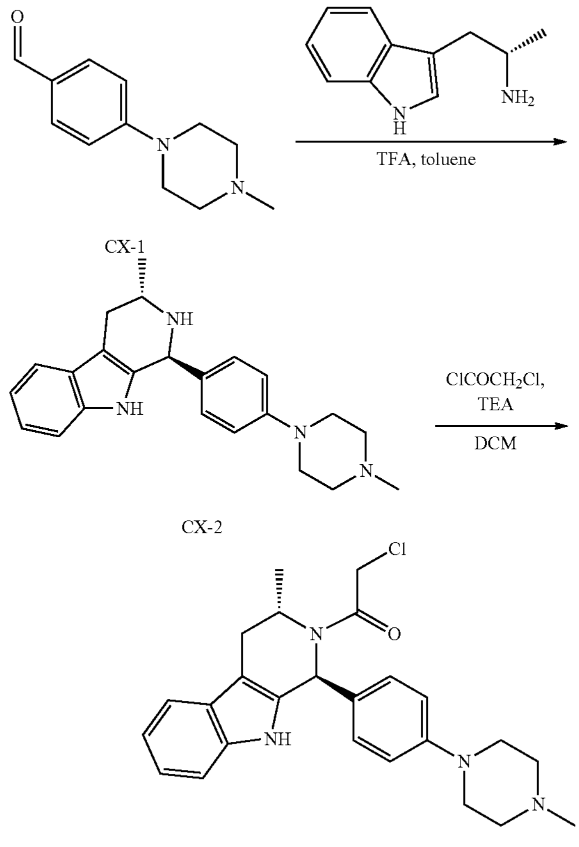

CX-1

CX-2

Compound 104

Preparation of Compound CX-2

To a solution of (2S)-1-(1H-indol-3-yl) propan-2-amine (100 mg, 573.92 μmol, 1 eq) in toluene (5 mL) was added CX-1 (117.23 mg, 573.92 μmol, 1 eq), and the mixture heated at 105° C. for 30 min. AcOH (525.00 mg, 8.74 mmol, 0.5 mL, 15.23 eq) was added, and the mixture heated to 105° C. for 16 h to give a yellow solution. LCMS showed the reaction was completed. The mixture was diluted with Sat. $NaHCO_3$ (20 mL) and extracted with DCM (10 m×5). The combined organic layers were dried over $Na_2SO_4$, filtered and concentrated to give CX-2.

Preparation of 104

To a solution of CX-2 (176 mg, 488.22 μmol, 1 eq) in DCM (10 mL) were added TEA (148.21 mg, 1.46 mmol, 203.86 μL, 3 eq) and 2-chloroacetyl chloride (110.28 mg, 976.44 μmol, 77.66 μL, 2 eq) at 0° C. The mixture was stirred at 20° C. for 1 h to give a brown suspension. LCMS showed the reaction was completed. The mixture was concentrated to give a residue, which was then subject to purification by prep-HPLC (column: Boston Green ODS 150×30 5 u; mobile phase: [water (0.1% TFA)-ACN]; B %: 28%-48%, 10 min) to give 2 products, one of which was 104, and the other of which was 105.

Compound 104

LC-MS (m/z): 437.5[M+H]+. 1H NMR (400 MHz, DMSO-d6) δ=7.43 (m, 1H), 7.27 (m, 3H), 7.08-6.85 (m,

5H), 5.93 (br s, 1H), 4.86-4.58 (m, 2H), 4.03-3.91 (m, 1H), 3.27-3.01 (m, 1H), 2.95-2.85 (m, 1H), 2.82-2.82 (m, 1H), 2.76 (br s, 4H), 2.73-2.58 (m, 2H), 1.12 (m, 3H).

Compound 105

LC-MS (m/z): 437.5[M+H]+. 1H NMR (400 MHz, DMSO-d6) δ=7.47 (m, 1H), 7.34 (m, 1H), 7.22 (m, 2H), 7.10 (m, 1H), 7.05-6.88 (m, 3H), 4.61 (m, 1H), 3.80 (br s, 2H), 3.20-3.06 (m, 4H), 2.85 (s, 3H), 2.73 (m, 2H), 2.55-2.52 (m, 2H), 0.98 (m, 3H).

Procedure CY: Synthesis of Compound 106 and Compound 107

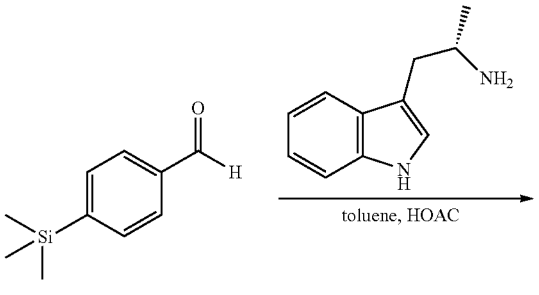

BM-1

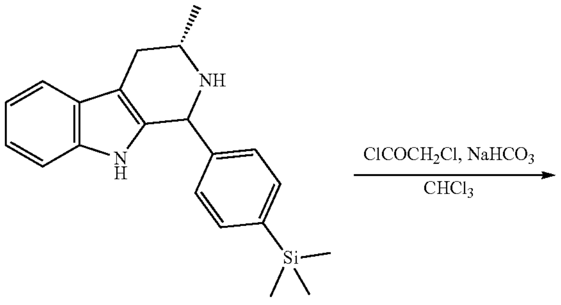

CY-2

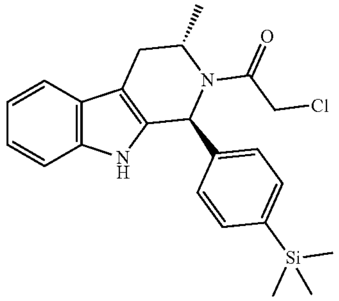

Compound 106

-continued

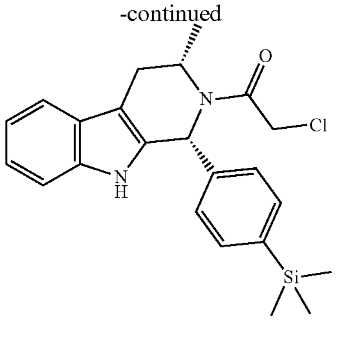

Compound 107

Preparation of Compound CY-2

To a solution of BM-1 (100 mg, 560.84 μmol, 1 eq) in toluene (5 mL) were added (2S)-1-(1H-indol-3-yl)propan-2-amine (195.45 mg, 1.12 mmol, 2 eq) and HOAC (33.68 mg, 560.84 μmol, 32.08 μL, 1 eq). The mixture was stirred at 105° C. for 12 h to give a yellow solution. TLC (eluting with: Petroleum ether:Ethyl acetate=2:1, SiO2) showed presence of some desired product. The pH 8 was adjusted to with Sat. $NaHCO_3$ and extracted with DCM (50 mL×3). The organic layers were dried over $Na_2SO_4$ and concentrated to give a crude product. The residue was purified by prep-TLC (Petroleum ether:Ethyl acetate=2:1) to give CY-2.

Preparation of 106

To a solution of CY-2 (105 mg, 313.87 μmol, 1 eq) in DMF (12 mL) were added DIEA (645.65 mg, 5.00 mmol, 870.15 μL, 3 eq) and HBTU (1.01 g, 2.66 mmol, 1.6 eq) in $CHCl_3$ (5 mL), and $NaHCO_3$ (263.69 mg, 3.14 mmol, 122.08 μL, 10 eq). To this mixture was added a solution of 2-chloroacetyl chloride (106.35 mg, 941.62 μmol, 74.89 μL, 3 eq) in DCM (0.5 mL), and the mixture stirred at 0° C. for 2 h to give a yellow solution. LCMS showed the reaction was completed. The reaction was quenched with $H_2O$ (10 mL) and extracted with DCM (50 mL×3). The organic layers were dried over $Na_2SO_4$ and concentrated to give a crude product, which was purified by prep-TLC (Petroleum ether: Ethyl acetate=3:1) to give 106 and 107.

Compound 106

LC-MS (m/z):411.0 [M+H]+. 1H NMR (400 MHz, $CDCl_3$) δ ppm 0.21 (s, 9H), 0.88 (br d, J=11.29 Hz, 2H), 1.32 (br d, J=6.53 Hz, 3H), 2.96 (br d, J=15.81 Hz, 1H), 3.34 (br s, 1H), 4.13 (s, 2H), 4.93 (s, 1H), 5.93 (br s, 1H), 7.09-7.18 (m, 2H), 7.25 (br s, 1H), 7.31 (br d, J=8.03 Hz, 2H), 7.43 (br d, J=7.53 Hz, 2H), 7.52 (br d, J=7.53 Hz, 1H), 7.64 (br s, 1H).

Compound 107

LC-MS (m/z):411.0 [M+H]+. 1H NMR (400 MHz, DMSO) δ ppm 0.00 (s, 9H), 0.77 (d, J=7.03 Hz, 3H), 2.43-2.55 (m, 1H), 2.84-2.95 (m, 1H), 4.33-4.46 (m, 3H), 6.61 (br s, 1H), 6.76-6.82 (m, 1H), 6.88 (t, J=7.03 Hz, 1H), 7.11 (dd, J=8.03, 3.51 Hz, 3H), 7.26 (br d, J=5.52 Hz, 3H).

Procedure CZ: Synthesis of Compound 108

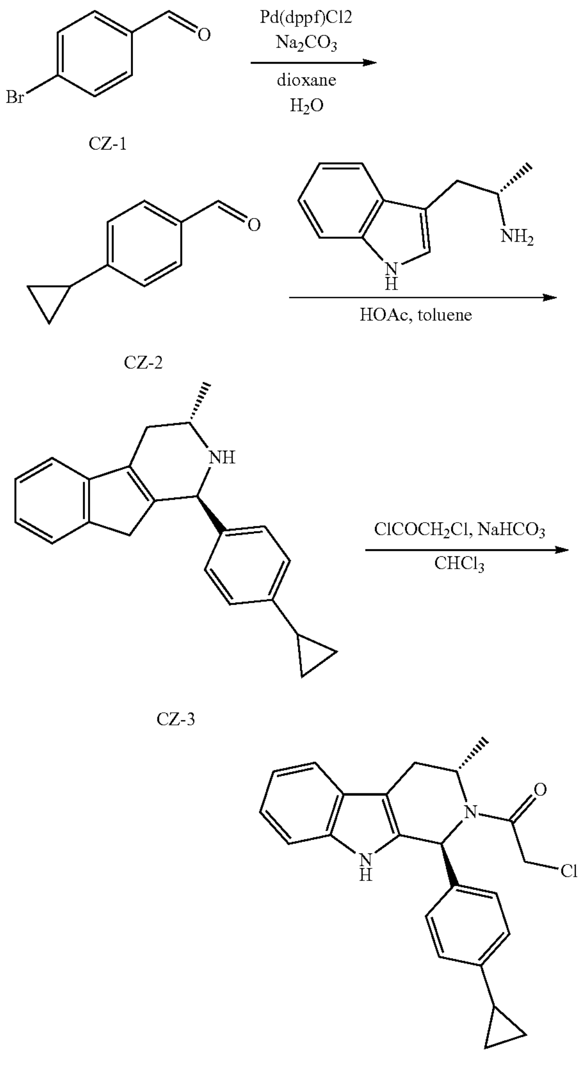

CZ-1

CZ-2

CZ-3

Compound 108

Preparation of Compound CZ-2

To a solution of CZ-1 (500 mg, 2.70 mmol, 1 eq) in in dioxane (10 mL)/$H_2O$ (2 mL) were added cyclopropylboronic acid (348.20 mg, 4.05 mmol, 1.5 eq), $Na_2CO_3$ (859.29 mg, 8.11 mmol, 3 eq) and Pd(dppf)$Cl_2$ (197.74 mg, 270.24 μmol, 0.1 eq) under $N_2$. The mixture stirred at 110° C. for 12 h under $N_2$ to give a black solution. HPLC showed the reaction was completed. The reaction mixture was concentrated to give the crude product, which was then purified by a flash column (eluting with; Petroleum ether:Ethyl acetate=100% to 10%) to give CZ-2. $^1$H NMR (400 MHz, $CDCl_3$) δ ppm 0.79-0.86 (m, 2H), 1.08-1.15 (m, 2H), 1.94-2.02 (m, 1H), 7.21 (d, J=8.28 Hz, 2H), 7.74-7.82 (m, 2H), 9.96 (s, 1H).

Preparation of CZ-3. To a solution of CZ-2 ((100 mg, 684.06 μmol, 1 eq) in toluene (4 mL) was added (2S)-1-(1H-indol-3-yl)propan-2-amine (143.03 mg, 820.87 μmol, 1.2 eq). The mixture stirred at 15° C. for 30 min. HOAc (420.00 mg, 6.99 mmol, 0.4 mL, 10.22 eq) was then added, and the mixture stirred at 105° C. for 12 h to give a yellow solution. LCMS showed the reaction was completed. The reaction mixture was adjusted to pH 8 with Sat. $NaHCO_3$ and extracted with EA (30 ml×3). The organic layers were dried over $Na_2SO_4$ and concentrated to give a crude product, which was then purified by prep-TLC (Petroleum ether: Ethyl acetate=1:2) to give CZ-3 and CZ-3a. $^1$H NMR (400 MHz, $CDCl_3$) δ ppm 0.57-0.63 (m, 2H), 0.89 (dd, J=8.53, 1.76 Hz, 2H), 1.18 (s, 3H), 1.80 (td, J=8.78, 4.27 Hz, 1H), 2.48 (br dd, J=15.56, 8.28 Hz, 1H), 2.87-2.94 (m, 1H), 3.25 (br s, 1H), 5.18 (s, 1H), 6.94 (d, J=8.03 Hz, 2H), 7.02-7.11 (m, 4H), 7.47 (d, J=7.28 Hz, 1H), 7.53 (br s, 1H).

Preparation of Compound 108

To a solution of CZ-3 (23 mg, 76.06 μmol, 1 eq) in CHCl3 (3 mL) were added $NaHCO_3$ (63.89 mg, 760.55 μmol, 29.58 μL, 10 eq) and 2-chloroacetyl chloride (25.77 mg, 228.17 μmol, 18.15 μL, 3 eq) at 0° C. The mixture stirred at 0° C. for 2 h to give a yellow solution. LCMS showed the reaction was completed. The reaction mixture was quenched with $H_2O$ (10 ml) and extracted with DCM (20 ml×3). The organic layers were dried over $Na_2SO_4$ and concentrated to give a crude product. The residue was purified by prep-TLC (Petroleum ether:Ethyl acetate=2:1) to give 108. LC-MS (m/z):400.9 [M+Na]+. $^1$H NMR (400 MHz,MeOD) δ ppm 0.62 (br d, J=4.63 Hz, 2H), 0.91 (br d, J=6.88 Hz, 2H), 1.23-1.35 (m, 3H), 1.78-1.94 (m, 1H), 2.98 (dd, J=15.51, 2.00 Hz, 1H), 3.40-3.54 (m, 1H), 3.78-4.75 (m, 2H), 5.99 (br s, 1H), 6.95-7.10 (m, 4H), 7.21-7.32 (m, 3H), 7.45 (d, J=7.75 Hz, 1H).

Procedure DA: Synthesis of Compound 109

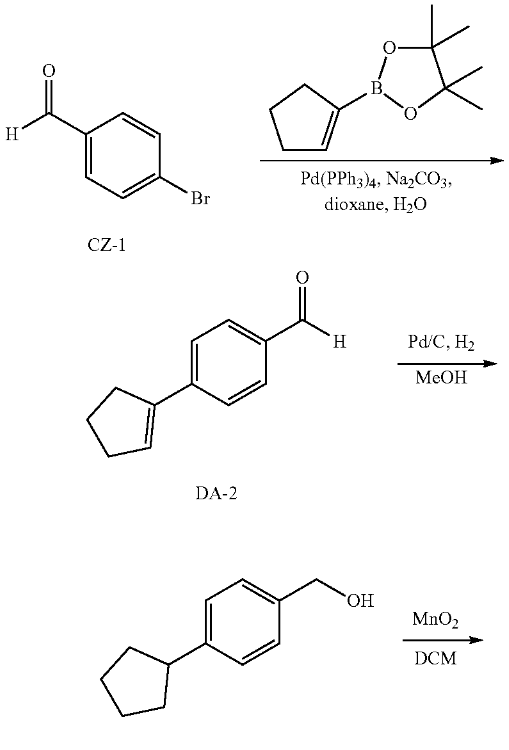

CZ-1

DA-2

DA-3

-continued

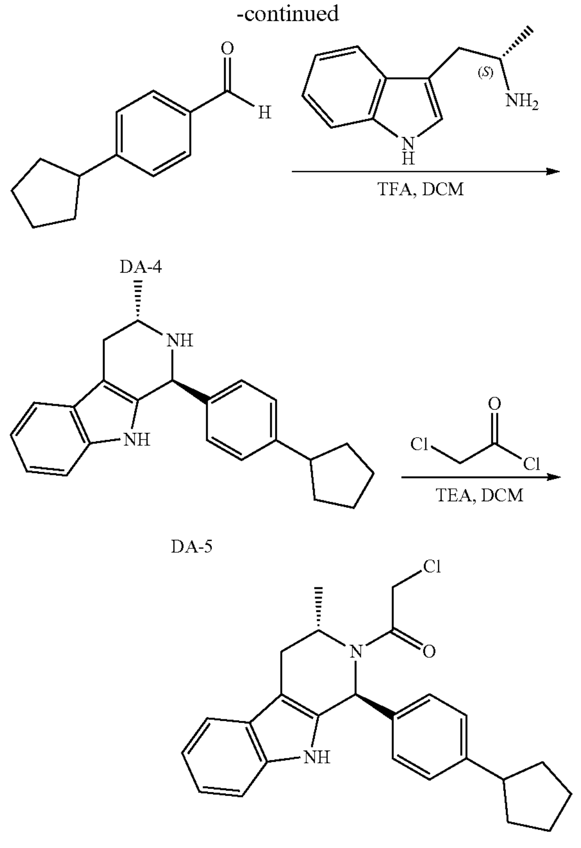

DA-4

DA-5

Compound 109

Preparation of Compound DA-2

To a solution of CZ-1 (223.78 mg, 1.21 mmol, 1 eq) and 2-(cyclopenten-1-yl)-4,4,5,5-tetramethyl-1,3,2-dioxaborolane (320 mg, 1.65 mmol, 1.36 eq) in dioxane (10 mL) and $H_2O$ (2 mL) were added $Na_2CO_3$ (384.58 mg, 3.63 mmol, 3 eq) and Pd(PPh3)$_4$ (69.88 mg, 60.47 μmol, 0.05 eq). The mixture was heated to 90° C. for 16 h to give a black suspension. TLC (PE:EA=10:1) showed the CZ-1 was remained. The reaction mixture was further heated at 90° C. for an additional 6 h to give a black suspension. TLC (PE:EA=10:1) showed the reaction was completed. The mixture was diluted with $H_2O$ (20 mL) and extracted with EA (10 mL×5). The combined organic layers were dried over $Na_2SO_4$, filtered and concentrated. The residue was purified by column chromatography ($SiO_2$, Petroleum ether/Ethyl acetate=I/O to 10:1) to give DA-2. $^1$H NMR (400 MHz, $CDCl_3$) δ=10.02-9.96 (m, 1H), 7.83 (d, J=8.3 Hz, 2H), 7.58 (d, J=8.3 Hz, 2H), 6.41 (m, 1H), 2.79-2.72 (m, 2H), 2.59 (m, 7.5 Hz, 2H), 2.06 (m, 2H).

Preparation of DA-3. To a solution of DA-2 (237 mg, 1.38 mmol, 1 eq) in MeOH (5 mL) was added Pd/C (46 mg, 10% purity) (50% wet, 10% Pd). The reaction suspension was degassed under vacuum and purged with $H_2$ several times. The mixture was stirred under $H_2$ (15 psi) at 10° C. for 3 h to give a black suspension. TLC (PE:EA=5:1) and HPLC showed the reaction was completed. LCMS showed no desired MS was found. The reaction mixture was filtered on celite, and the filtrate concentrated to give DA-3. H NMR (400 MHz, $CDCl_3$) δ=7.27-7.12 (m, 4H), 4.58 (br s, 2H), 3.01-2.83 (m, 1H), 1.99 (br s, 2H), 1.74 (br s, 2H), 1.69-1.57 (m, 2H), 1.57-1.33 (m, 4H).

Preparation of DA-4. To a suspension of $MnO_2$ (545.04 mg, 6.27 mmol, 5 eq) in DCM (10 mL) was added DA-3 (221 mg, 1.25 mmol, 1 eq). The mixture was heated at 45° C. for 16 h to give a black suspension. TLC (PE:EA=5:1) showed the reaction was completed. The reaction mixture was filtered on celite, and the filtrate concentrated to give DA-4. $^1$H NMR (400 MHz, $CDCl_3$) δ=9.98 (s, 1H), 7.83-7.78 (m, 2H), 7.40 (d, J=8.3 Hz, 2H), 3.13-2.96 (m, 1H), 2.17-2.03 (m, 2H), 1.87-1.80 (m, 2H), 1.77-1.69 (m, 2H), 1.66-1.59 (m, 2H).

Preparation of DA-5. A solution of DA-4 (50 mg, 286.96 μmol, 1 eq) and (2S)-1-(1H-indol-3-yl)propan-2-amine (50.00 mg, 286.96 μmol, 1 eq) was prepared in toluene (2 mL) under $N_2$. The mixture was heated at 105° C. for 30 min followed by addition of AcOH (210.00 mg, 3.50 mmol, 200.00 μL, 12.19 eq). The mixture was heated at 105° C. for 2 h to give a brown suspension. LCMS and TLC (PE:EA=3:2) showed the reaction was completed. The mixture was diluted with Sat. $NaHCO_3$ and exacted with EA (5 mL×3). The combined organic layers were dried over $Na_2SO_4$, filtered and concentrated. The residue was purified by prep-TLC ($SiO_2$, PE: EA=3:2) to give DA-5 and its cis-isomer. $^1$H NMR (400 MHz, $CDCl_3$) δ=7.56 (br s, 1H), 7.47 (d, J=7.3 Hz, 1H), 7.15-7.03 (m, 6H), 5.22 (m, 1H), 3.34-3.22 (m, 1H), 2.95-2.85 (m, 2H), 2.49 (m, 1H), 2.02-1.86 (m, 2H), 1.75-1.46 (m, 8H), 1.28-1.09 (m, 3H).

Preparation of 109

To a solution of DA-5 (17 mg, 51.44 μmol, 1 eq) and TEA (15.62 mg, 154.33 μmol, 21.48 μL, 3 eq) in DCM (2 mL) was added 2-chloroacetyl chloride (17.43 mg, 154.33 μmol, 12.27 μL, 3 eq) at 0° C. The mixture was stirred at 20° C. for 2 h to give a brown solution. LCMS showed the reaction was completed. The mixture was concentrated, and the resulting residue purified by prep-TLC ($SiO_2$, PE:EA=2:1) to give 109. LC-MS (m/z):407.5 [M+H]+. $^1$H NMR (400 MHz, $CDCl_3$) δ=7.66 (s, 1H), 7.52 (d, J=7.4 Hz, 1H), 7.24 (d, J=8.5 Hz, 3H), 7.19-7.09 (m, 4H), 5.93 (s, 1H), 4.15 (m, 2H), 3.43-3.24 (m, 1H), 2.98-2.88 (m, 2H), 2.06-1.97 (m, 2H), 1.80-1.72 (m, 2H), 1.71-1.62 (m, 2H), 1.55-1.46 (m, 2H), 1.32 (m, 3H).

Procedure DB: Synthesis of Compound 110

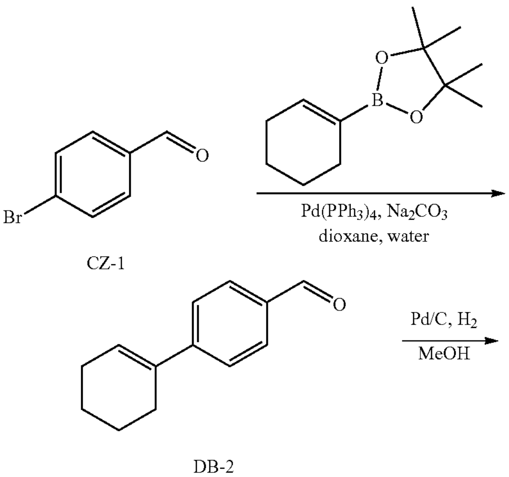

CZ-1

DB-2

-continued

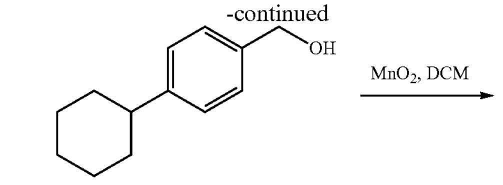

DB-3

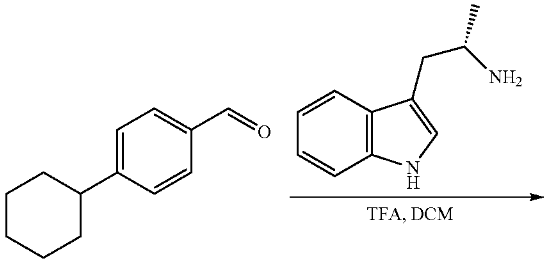

DB-4

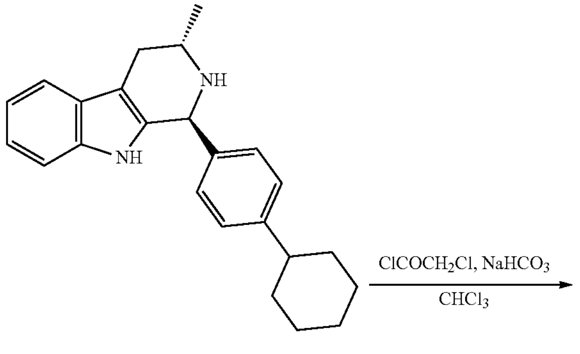

DB-5

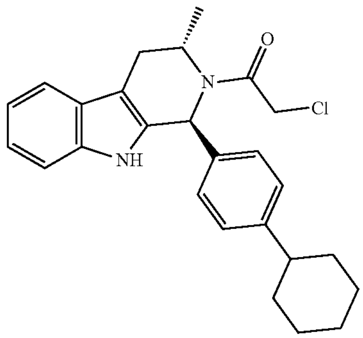

Compound 110

Preparation of DB-2. To a solution of CZ-1 (1 g, 5.40 mmol, 1 eq) and 2-(cyclohexen-1-yl)-4,4,5,5-tetramethyl-1,3,2-dioxaborolane (1.53 g, 7.35 mmol, 1.58 mL, 1.36 eq) in dioxane (50 mL) and $H_2O$ (10 mL) were added $Na_2CO_3$ (1.72 g, 16.21 mmol, 3 eq) and palladium; triphenylphosphane (312.28 mg, 270.24 μmol, 0.05 eq). The mixture was stirred at 90° C. for 12 h to give a yellow suspension. TLC (eluting with: Petroleum ether:Ethyl acetate=10:1, SiO2) showed the reaction was completed. $H_2O$ (100 ml) was added to the reaction mixture and extracted with EA (50 mL×3). The organic layers were dried over $Na_2SO_4$ and concentrated to give a crude product. The residue was purified by a flash column (eluting with: Petroleum ether/Ethyl acetate=20/1 to 10/1) to give DB-2. $^1$H NMR (400 MHz, $CDCl_3$) δ ppm 1.58-1.78 (m, 5H), 2.15-2.40 (m, 5H), 6.22-6.27 (m, 1H), 7.46 (d, J=8.38 Hz, 2H), 7.72-7.78 (m, 2H), 9.91 (s, 1H).

Preparation of DB-3. To a solution of DB-2 (246 mg, 1.32 mmol, 1 eq) in MeOH (10 mL) was added Pd/C (50 mg, 10% purity) and stirred at 25° C. for 1 h under $H_2$ to give a black solution. TLC (eluting with; Petroleum ether:Ethyl acetate=10:1, $SiO_2$) showed the reaction was completed. The reaction mixture was filtered by celite, and the organic layers concentrated to give a crude product. The product was purified by a flash column (eluting with: Petroleum ether/Ethyl acetate=20/1 to 10/1) to give DB-3. $^1$H NMR (400 MHz, $CDCl_3$) δ ppm 1.12-1.41 (m, 6H), 1.64-1.83 (m, 5H), 2.39-2.47 (m, 1H), 4.59 (d, J=6.02 Hz, 2H), 7.12-7.17 (m, 2H), 7.21-7.25 (m, 2H).

Preparation of DB-4. To a solution of DB-3 (136 mg, 714.73 μmol, 1 eq) in DCM (8 mL) was added $MnO_2$ (310.68 mg, 3.57 mmol, 5 eq), and the mixture stirred at 45° C. for 12 h to give a black solution. TLC (eluting with: Petroleum ether:Ethyl acetate=10:1, SiO2) showed the reaction was completed. The reaction mixture was filtered by celite, and the organic layers dried over $Na_2SO_4$ and concentrated to give DB-4. It was used for the next step without further purification. $^1$H NMR (400 MHz, $CDCl_3$) δ ppm 1.17-1.43 (m, 5H), 1.66-1.85 (m, 5H), 2.46-2.57 (m, 1H), 7.29 (d, J=8.28 Hz, 2H), 7.73 (d, J=8.28 Hz, 2H), 9.89 (s, 1H).

Preparation of DB-5. To a solution of DB-4 (125 mg, 663.96 μmol, 1 eq) in toluene (8 mL) were added (2S)-1-(1H-indol-3-yl)propan-2-amine (138.83 mg, 796.75 μmol, 1.2 eq) and HOAc (840.00 mg, 13.99 mmol, 0.8 mL, 21.07 eq). The mixture stirred at 105° C. for 12 h to give brown solution. LCMS showed the reaction was completed. The reaction mixture was adjusted to pH 8 with Sat. $NaHCO_3$ and extracted with EA (50 ml×3). The organic layers were dried over $Na_2SO_4$ and concentrated to give a crude product, which was the purified by prep-HPLC (column: Xtimate C18 150×25 mm×5 μm; mobile phase: water (0.05% HCl)-ACN]; B %: 35%-55%, 6.5 min) to give DB-5. $^1$H NMR (400 MHz,MeOD) δ ppm 1.23-1.50 (m, 5H), 1.52 (d, J=6.53 Hz, 3H), 1.73-1.92 (m, 5H), 2.59 (br s, 1H), 2.93 (dd, J=15.81, 8.28 Hz, 1H), 3.14-3.29 (m, 1H), 3.50 (s, 1H), 3.82-3.92 (m, 1H), 5.89 (s, 1H), 7.08-7.14 (m, 1H), 7.18 (t, J=7.03 Hz, 1H), 7.26-7.33 (m, 3H), 7.34-7.39 (m, 2H), 7.57 (d, J=7.78 Hz, 1H).

Preparation of 110

To a solution of DB-5 (24.7 mg, 71.70 μmol, 1 eq) in CHCl3 (3 mL) were added $NaHCO_3$ (60.23 mg, 717.00 μmol, 27.89 μL, 10 eq) and 2-chloroacetyl chloride (24.29 mg, 215.10 μmol, 17.11 μL, 3 eq) at 0° C. The mixture stirred at 0° C. for 2 h to give a yellow solution. LCMS showed the reaction was completed. The reaction mixture was quenched with $H_2O$ (10 ml) and extracted with DCM (20 ml×3). The organic layers were dried over $Na_2SO_4$ and concentrated to give a crude product. The crude product was purified by prep-TLC (Petroleum ether:Ethyl acetate=2:1) to give 110. LC-MS (m/z):443.0 [M+Na]+. $^1$H NMR (400 MHz, $CDCl_3$) δ ppm 1.17-1.32 (m, 8H), 1.60-1.78 (m, 5H), 2.36 (br s, 1H), 2.84-3.29 (m, 2H), 3.82-4.16 (m, 2H), 4.85 (br s, 1H), 5.86 (s, 1H), 7.01-7.10 (m, 4H), 7.13-7.18 (m, 3H), 7.44 (d, J=7.38 Hz, 1H), 7.56 (s, 1H), 2H), 2.06-1.97 (m, 2H), 1.80-1.72 (m, 2H), 1.71-1.62 (m, 2H), 1.55-1.46 (m, 2H), 1.32 (m, 3H).

Procedure DC: Synthesis of Compound 112

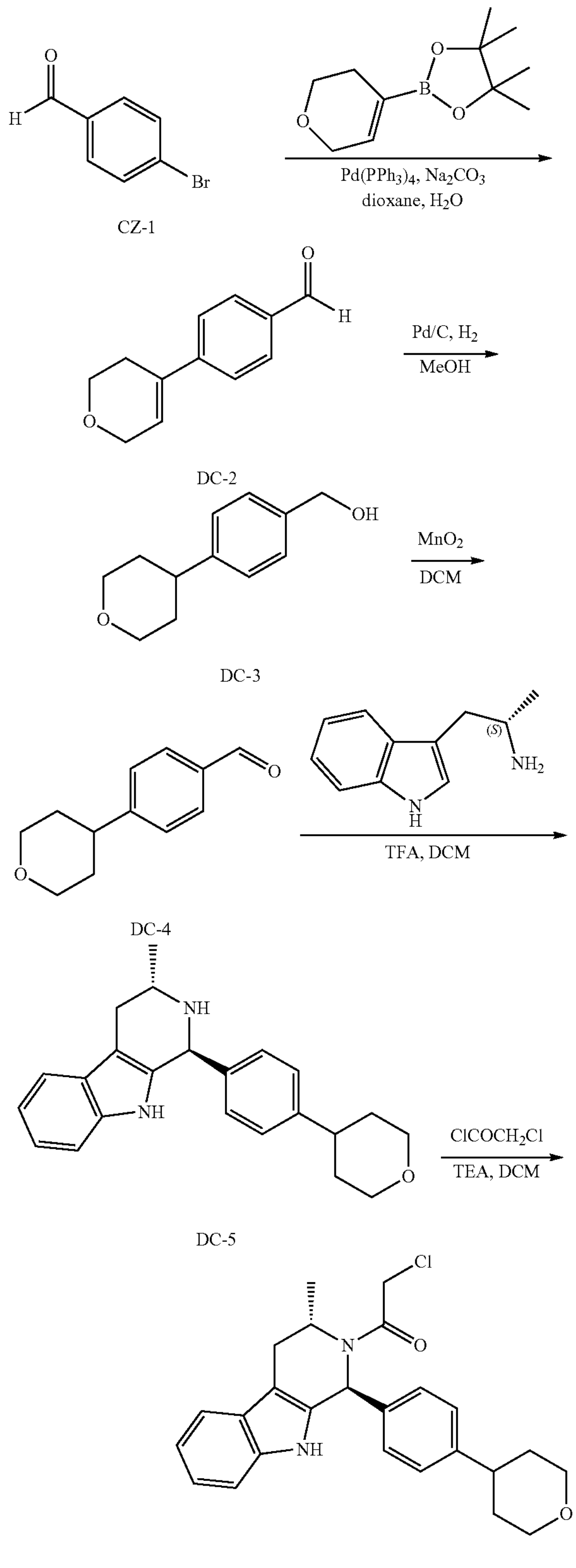

Compound 112

Preparation of DC-2. To a solution of CZ-1 (323.02 mg, 1.75 mmol, 1 eq) in dioxane (10 mL) were added 2-(3,6-dihydro-2H-pyran-4-yl)-4,4,5,5-tetramethyl-1,3,2-dioxaborolane (500 mg, 2.38 mmol, 1.36 eq), $H_2O$ (2 mL), $Na_2CO3$ (555.14 mg, 5.24 mmol, 3 eq) and palladium; triphenylphosphane (100.87 mg, 87.29 μmol, 0.05 eq). The mixture was heated at 90° C. for 40 h to give a black suspension. TLC (PE:EA=10:1) and HPLC showed the reaction was completed. The mixture was diluted with $H_2O$ (20 mL) and extracted with EA (10 mL×5). The combined organic layers were dried over $Na_2SO_4$, filtered and concentrated. The residue was purified by column chromatography ($SiO_2$, Petroleum ether/Ethyl acetate=I/O to 10:1) to give DC-2. $^1H$ NMR (400 MHz, $CDCl_3$) δ=10.01 (s, 1H), 7.87 (m, 2H), 7.56 (m, 2H), 6.32 (m, 1H), 4.37 (m, 2H), 3.96 (m, 2H), 2.67-2.49 (m, 2H), Preparation of DC-3. To a solution of DC-2 (280 mg, 1.49 mmol, 1 eq) in MeOH (5 mL) was added Pd/C (28 mg, 10% purity) (50% wet, 10% Pd). The reaction suspension was degassed under vacuum, purged with $H_2$ several times, and then stirred under $H_2$ (15 psi) at 10° C. for 3 h to give a black suspension. TLC (PE:EA=5:1) showed the reaction was completed. The reaction mixture was filtered on celite, and the filtrate concentrated to give DC-3. $^1H$ NMR (400 MHz, $CDCl_3$) δ=7.34 (d, J=8.0 Hz, 2H), 7.26-7.22 (m, 2H), 4.68 (m, 2H), 4.12-4.06 (m, 2H), 3.58-3.49 (m, 2H), 2.81-2.73 (m, 1H), 1.88-1.74 (m, 4H).

Preparation of DC-4. To a solution of DC-3 (114 mg, 592.97 μmol, 1 eq) in DCM (4 mL) was added $MnO_2$ (257.75 mg, 2.96 mmol, 5 eq). The mixture was heated at 40° C. for 16 h to give a black suspension. TLC (PE:EA=2:1) showed the reaction was completed. The reaction mixture was filtered on celite, and the filtrate concentrated to give DC-4. $^1H$ NMR (400 MHz, $CDCl_3$) δ=9.99 (s, 1H), 7.88-7.81 (m, 2H), 7.43-7.37 (m, 2H), 5.31 (s, 1H), 4.11 (m, 2H), 3.55 (dt, J=2.6, 11.5 Hz, 2H), 2.93-2.79 (m, 1H), 1.91-1.73 (m, 4H).

Preparation of DC-5. To a solution of DC-4 (110 mg, 578.22 μmol, 1 eq) in toluene (3 mL) was added (2S)-1-(1H-indol-3-yl)propan-2-amine (100.75 mg, 578.22 μmol, 1 eq) under $N_2$. The mixture was heated at 105° C. for 30 min, and AcOH added (315.00 mg, 5.25 mmol, 300.00 μL, 9.07 eq). The mixture was heated at 105° C. for 15.5 h to give a brown suspension. LCMS and TLC (PE:EA=0:1) showed the reaction was completed. The mixture was diluted with Sat. $NaHCO_3$ and extracted with EA (5 mL×3). The combined organic layers were dried over $Na_2SO_4$, filtered and concentrated. The residue was purified by prep-TLC ($SiO_2$, PE: EA=0:1) to give 2 products, one of which was DC-5 and other of which was the trans-isomer. $^1H$ NMR (400 MHz, $CDCl_3$) δ=7.71-7.59 (m, 1H), 7.55 (m, 1H), 7.25-7.11 (m, 6H), 5.31-5.22 (m, 1H), 4.10-4.04 (m, 2H), 3.52 (m, 2H), 3.35-3.27 (m, 1H), 2.96 (m, 1H), 2.79-2.70 (m, 1H), 2.54 (m, 1H), 1.87-1.61 (m, 6H), 1.24 (d, J=6.3 Hz, 3H).

Preparation of 112

To a solution of DC-5 (40 mg, 115.45 μmol, 1 eq) in DCM (2 mL) were added TEA (35.05 mg, 346.36 μmol, 48.21 μL, 3 eq) and 2-chloroacetyl chloride (39.12 mg, 346.36 mol, 27.55 μL, 3 eq) at 0° C. The mixture was stirred at 20° C. for 2 h to give a brown suspension. LCMS showed the reaction was completed. The mixture was concentrated, and the residue purified by prep-TLC ($SiO_2$, PE: EA=1:2) to give 112. LC-MS (m/z):423.1 [M+H]+. $^1H$ NMR (400 MHz, $CDCl_3$) δ=7.72 (br s, 1H), 7.52 (m, 1H), 7.28 (s, 1H), 7.27-7.24 (m, 2H), 7.18-7.10 (m, 4H), 5.94 (s, 1H), 5.03-

4.76 (m, 1H), 4.25-3.97 (m, 4H), 3.49 (m, 2H), 3.41-3.19 (m, 1H), 2.96 (m, 1H), 2.77-2.63 (m, 1H), 1.82-1.68 (m, 4H), 1.32 (m, 3H).

Procedure DD: Synthesis of Compound 113

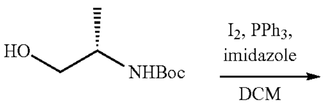

DD-7

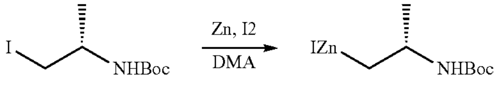

DD-8 DD-9

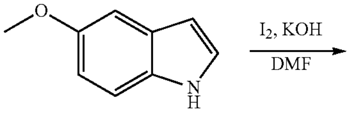

DD-1

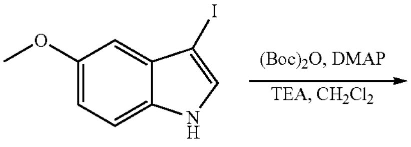

DD-2

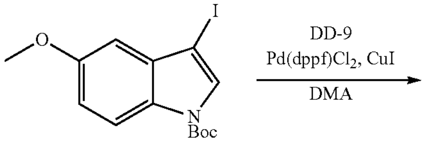

DD-3

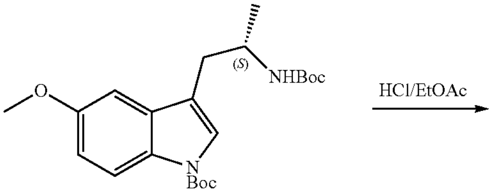

DD-4

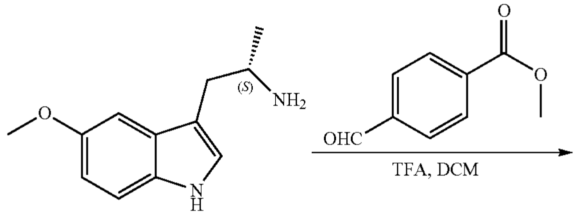

DD-5

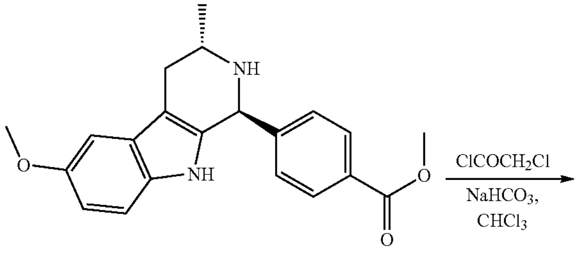

DD-6

-continued

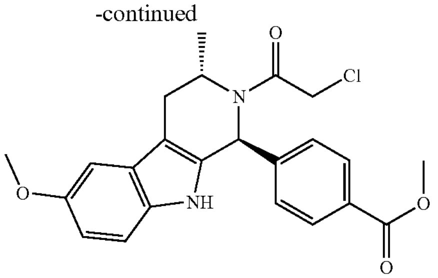

Compound 113

Preparation of DD-8. To a solution of $PPh_3$ (65.86 g, 251.11 mmol, 2.2 eq) in DCM (500 mL) was added 12 (63.73 g, 251.11 mmol, 50.58 mL, 2.2 eq) at 0° C. The mixture was stirred at 0° C. for 15 min, then imidazole (19.43 g, 285.35 mmol, 2.5 eq) in DCM (50 mL) was added dropwise at 0° C. The mixture was stirred at 0° C. for 15 min. DD-7 (20 g, 114.14 mmol, 1 eq) in DCM (50 mL) was added dropwise at 0° C., and the mixture allowed to stir at 10° C. for 12 h to give a yellow suspension. TLC (eluting with: PE/EtOAc=5/1) showed the reaction was completed. The reaction mixture was diluted with PE (500 mL), filtered, and the filtrate concentrated to give the crude product. The product was purified by a flash column (eluting with: PE/EtOAc=100% to 20%) to give impure DD-8. The resulting DD-8 was triturated with hexane (70 mL) to give DD-8. $^1$H NMR (400 MHz, $CDCl_3$) δ 4.54 (brs, 1H), 3.54 (brs, 1H), 3.42 (brs, 1H), 3.33-3.29 (m, 1H), 1.46 (s, 9H), 1.22-1.21 (d, J=6.4 Hz, 1H).

Preparation of DD-9. Zinc (10 g) was treated with 1N HCl aqueous (30 mL) with stirring for 10 min, filtered and washed with water (30 mL), EtOH (30 mL) and toluene (30 mL) in sequence and then dried in vacuum to afford the zinc powder for next step.

A mixture of activated Zn (1.83 g, 28.06 mmol, 4 eq) and $I_2$ (89.02 mg, 350.73 μmol, 70.65 μL, 0.05 eq) in DMA (20 mL) was stirred at 10° C. for 5 min, followed by dropwise addition of tert-butyl N-[(1S)-2-iodo-1-methyl-ethyl]carbamate DD-9 (2 g, 7.01 mmol, 1 eq) in DMA (10 mL). The reaction mixture was stirred at 10° C. for 25 min to give a black suspension. The reaction mixture (0.233 moL/L) was used for the next step without further purification.

Preparation of DD-2. To a solution of 5-methoxy-1H-indole-(5 g, 33.97 mmol, 1 eq) in DMF were added KOH (4.77 g, 84.93 mmol, 2.5 eq) and $I_2$ (8.62 g, 33.97 mmol, 6.84 mL, 1 eq) in DMF (40 mL) at 15° C. The mixture was stirred at 15° C. for 2 h to give a brown solution. TLC (PE:EA=4:1) showed the reaction was completed. The reaction was poured into ice and water (400 mL) containing ammonia (0.5%) and sodium sulfite (0.1% aqueous solution), and then extracted with MTBE (50 mL×4). The combined organic layers were dried over $Na_2SO_4$, filtered and concentrated to give DD-2. $^1$H NMR (400 MHz, $CDCl_3$) δ=8.54 (br s, 1H), 7.20-7.12 (m, 2H), 6.85-6.75 (m, 2H), 3.81 (s, 3H).

Preparation of DD-3. To a solution of DD-2 (9.28 g, 33.98 mmol, 1 eq) in DCM (40 mL) were added $(Boc)_2O$ (8.90 g, 40.78 mmol, 9.37 mL, 1.2 eq), DMAP (415.18 mg, 3.40 mmol, 0.1 eq) and TEA (5.16 g, 50.98 mmol, 7.10 mL, 1.5 eq) at 0° C. The mixture was stirred at 15° C. for 16 h to give a black suspension. TLC (PE:EA=5:1) showed the reaction was completed. The mixture was quenched with $H_2O$ (40 mL) and extracted with DCM (20 mL×3). The mixture was dried over $Na_2SO_4$, filtered and concentrated. The residue was purified by column chromatography ($SiO_2$, Petroleum ether/Ethyl acetate=I/O to 5:1) to give DD-3. $^1H$ NMR (400 MHz, $CDCl_3$) δ=8.01 (m, 1H), 7.71 (s, 1H), 6.98 (m, 1H), 6.85 (m, 1H), 3.90 (s, 3H), 1.67 (s, 9H).

Preparation of DD-4. To a solution of DD-3 (1.5 g, 4.02 mmol, 1 eq) in DMA (5 mL) were added CuI (76.55 mg, 401.95 μmol, 0.1 eq), DD-9 (2.40 g, 6.83 mmol, 1.7 eq) and $Pd(dppf)Cl_2$ (294.11 mg, 401.95 μmol, 0.1 eq). The mixture was stirred at 90° C. for 2 h to give a black suspension. LCMS and TLC (eluting with: PE/EtOAc=3/1) showed the reaction was completed. The reaction mixture was quenched with $H_2O$ (50 mL) and extracted with MBTE (40 mL×3). The organic layers were dried over $Na_2SO_4$ and concentrated to give the crude product. The product was purified by a flash column (eluting with: PE/EtOAc=100% PE to 20%) to give DD-4.

Preparation of DD-5. DD-4 (300 mg, 741.66 μmol, 1 eq) was dissolved in HCl/MeOH (4 M, 10 mL, 53.93 eq), and stirred at 10° C. for 12 h to give a yellow solution. LCMS showed the reaction was completed. The reaction mixture was concentrated to give the crude product. The product was dissolved in $H_2O$ (20 mL) and extracted with MBTE (20 mL×2). The water layer was adjusted to pH 8 with Sat. $NaHCO_3$ and concentrated to give the crude product. The product was dissolved in DCM/EtOH (30 mL, 5/1), filtered, and washed with DCM (20 mL). The filtrate was concentrated to give DD-5. $^1H$ NMR (400 MHz, $CDCl_3$) δ 7.95 (brs, 1H), 7.17 (s, 1H), 6.98-6.93 (m, 2H), 6.80-6.78 (m, 1H), 3.65 (s, 3H), 3.24-3.20 (m, 1H), 2.79-2.74 (m, 1H), 2.59-2.53 (m, 1H), 1.11-1.09 (d, J=6.4 Hz, 3H).

Preparation of DD-6. To a solution of DD-5 (80 mg, 391.64 μmol, 1 eq) in DCM (3 mL) were added methyl 4-formylbenzoate (64.29 mg, 391.64 μmol, 1 eq) and TFA (44.66 mg, 391.64 μmol, 29.00 μL, 1 eq). The mixture was stirred at 50° C. for 12 h to give a yellow solution. LCMS and TLC (eluting with: PE/EtOAc=1/2) showed the reaction was completed. The reaction mixture was quenched with Sat. $NaHCO_3$ (10 mL) and extracted with DCM (20 mL×3). The organic layers were dried over $Na_2SO_4$ and concentrated to give the crude product. The product was purified by prep-TLC (eluting with: PE/EtOAc=1/2) to give DD-6 (trans) and DD-6a (cis).

Preparation of 113

To a solution of DD-6 (18 mg, 51.37 μmol, 1 eq) in $CHCl_3$ (3 mL) were added $NaHCO_3$(43.15 mg, 513.68 μmol, 19.98 μL, 10 eq) and 2-chloroacetyl chloride (17.41 mg, 154.11 μmol, 12.26 μL, 3 eq). The mixture was stirred at 10° C. for 2 h to give a yellow solution. LCMS and TLC (eluting with: PE/EtOAc=2/1) showed the reaction was completed. The reaction mixture was quenched with $H_2O$ (10 mL) and extracted with DCM (10 mL). The organic layers were dried over $Na_2SO_4$ and concentrated to give the crude product. The product was purified by prep-TLC (eluting with: PE/EtOAc=2/1) to give 113. LC-MS (m/z): 448.9 [M+H]+. $^1H$ NMR (400 MHz, $CDCl_3$): δ 7.87-7.85 (m, 2H), 7.69 (brs, 1H), 7.46-7.44 (m, 1H), 7.32-7.30 (m, 2H), 7.07-7.04 (m, 3H), 5.82 (s, 1H), 4.38-3.91 (m, 3H), 3.84 (s, 3H), 3.24-3.22 (m, 1H), 3.06-3.02 (m, 1H), 1.60-1.58 (m, 2H), 0.90 (t, J=7.2 Hz, 3H).

Procedure DE: Synthesis of Compound 114

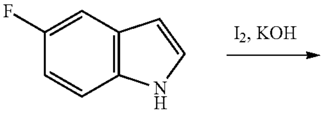

DE-1

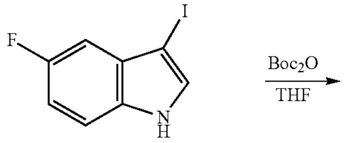

DE-2

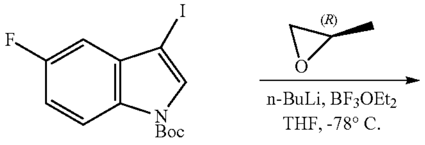

DE-3

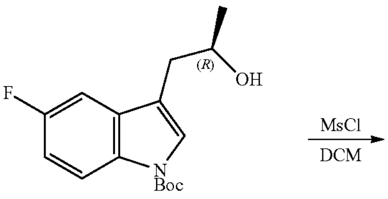

DE-4

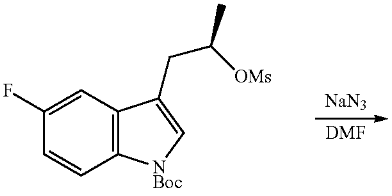

DE-5

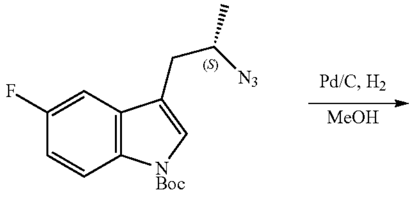

DE-6

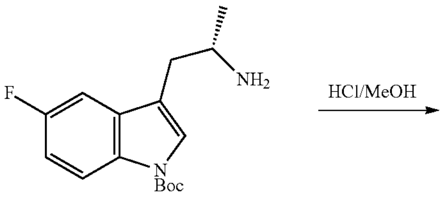

DE-7

-continued

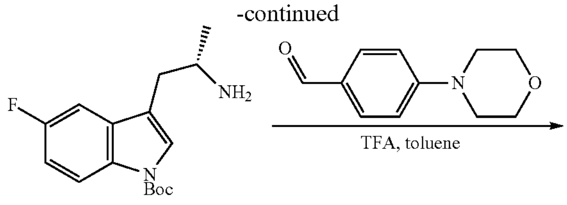

DE-8

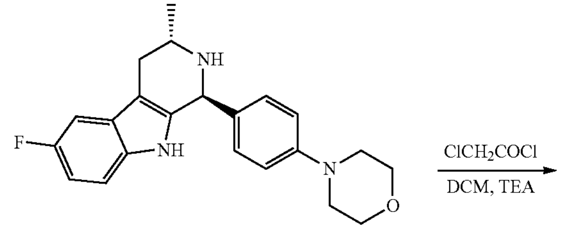

DE-9

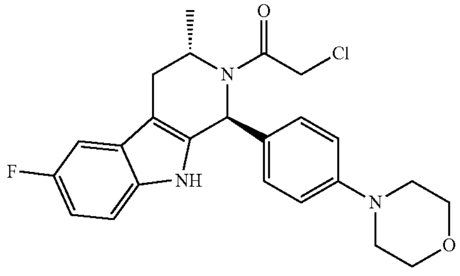

Compound 114

Preparation of Compound DE-2

To a solution of DE-1 (10 g, 74.00 mmol, 1 eq) in DMF (100 mL) were added KOH (10.38 g, 185.00 mmol, 2.5 eq), followed by 12 (18.78 g, 74.00 mmol, 14.91 mL, 1 eq) in DMF (100 mL) added dropwise. The mixture was stirred at 5° C. for 2 h to give a yellow solution. TLC (eluting with: PE/EtOAc=5/1) showed the reaction was completed. The reaction mixture was quenched with $H_2O$ (600 mL) and extracted with MBTE (200 mL×3). The organic layers were dried over $Na_2SO_4$ and concentrated to give the crude product, which was used for the next step without further purification.

Preparation of DE-3. To a solution of DE-2 (19.32 g, 74.01 mmol, 1 eq) in $CH_3CN$ (200 mL) were added $Boc_2O$ (16.15 g, 74.01 mmol, 17.00 mL, 1 eq) and DMAP (452.10 mg, 3.70 mmol, 0.05 eq). The mixture was stirred at 5° C. for 12 h to give a yellow solution. LCMS showed the reaction was completed. The reaction mixture was quenched with $H_2O$ (800 mL) and filtered. The product was collected, dried over $Na_2SO_4$ and concentrated to give DE-3. The product was used for the next step without further purification. $^1$H NMR (400 MHz, $CDCl_3$) δ=8.12 (br s, 1H), 7.84 (s, 1H), 7.13-7.09 (m, 2H), 1.69 (s, 9H).

Preparation of DE-4. To a solution of DE-3 (9.3 g, 25.75 mmol, 1 eq) in THF (60 mL) was added dropwise n-butyllithium (2.5 M, 11.33 mL, 1.1 eq) at −70° C. The mixture was stirred at −70° C. for 10 min. A solution of (2R)-2-methyloxirane (1.79 g, 30.90 mmol, 2.16 mL, 1.2 eq) in THF (5 mL) was added dropwise, followed by dropwise addition of $BF_3.Et_2O$ (2.92 g, 20.60 mmol, 2.54 mL, 0.8 eq). The mixture was stirred at −70° C. for 2 h 50 min to give a yellow suspension. TLC (PE:EA=3:1) showed the reaction was completed, but the DE-3 was not completely consumed. The mixture was quenched with Sat. $NH_4Cl$ (40 mL) and extracted with EA (20 mL×3). The combined organic layers were dried over $Na_2SO_4$, filtered and concentrated. The residue was purified by column chromatography ($SiO_2$, Petroleum ether/Ethyl acetate=1/01 to 5:1) to give DE-4. $^1$H NMR (400 MHz, $CDCl_3$) δ=8.08 (br s, 1H), 7.51 (s, 1H), 7.20 (m, 1H), 7.04 (m, 1H), 4.17-4.11 (m, 1H), 2.86-2.70 (m, 2H), 1.67 (s, 9H), 1.31-1.29 (m, 3H).

Preparation of DE-5. To a solution of DE-4 (3 g, 10.23 mmol, 1 eq) in DCM (50 mL) were added TEA (2.07 g, 20.45 mmol, 2.85 mL, 2 eq), DMAP (124.94 mg, 1.02 mmol, 0.1 eq) and MsCl (2.34 g, 20.45 mmol, 1.58 mL, 2 eq) at 0° C. The mixture was stirred at 10° C. for 1 h to give a yellow suspension. LCMS showed the reaction was completed. The reaction mixture was quenched with $H_2O$ (20 mL) and extracted with DCM (20 mL×3). The organic layers were dried over $Na_2SO_4$ and concentrated to give DE-5.

Preparation of DE-6. To a solution of DE-5 (4.23 g, 11.38 mmol, 1 eq) in DMF (40 mL) was added $NaN_3$ (1.48 g, 22.76 mmol, 2 eq). The mixture was heated at 50° C. for 16 h to give a yellow suspension. LCMS showed the reaction was completed. The reaction mixture was quenched with Sat. $NaHCO_3$ (20 mL) and diluted with $H_2O$ (100 mL). The mixture was extracted with MBTE (40 mL×3).

The combined organic layers were dried over $Na_2SO_4$ and concentrated. The residue was purified by column chromatography ($SiO_2$, Petroleum ether/Ethyl acetate=I/O to 10:1) to give DE-6. $^1$H NMR (400 MHz, $CDCl_3$) δ=8.14-7.96 (m, 1H), 7.50 (s, 1H), 7.28-7.25 (m, 1H), 7.18 (m, 1H), 3.90-3.76 (m, 1H), 2.90-2.74 (m, 2H), 1.71-1.66 (m, 9H), 1.38-1.33 (m, 3H).

Preparation of DE-7. To a solution of DE-6 (2.9 g, 9.11 mmol, 1 eq) in MeOH (30 mL) was added Pd/C (290 mg, 10% purity). The mixture was stirred under $H_2$ at 10° C. for 16 h to give a black suspension. TLC (EA:MeOH=5:1) showed the reaction was completed. The mixture was filtered and concentrated to give DE-7. $^1$H NMR (400 MHz, $CDCl_3$) δ=8.13-7.98 (m, 1H), 7.47 (s, 1H), 7.19 (m, 8.8 Hz, 1H), 7.03 (m, 1H), 3.48 (s, 1H), 3.33-3.16 (m, 1H), 2.78-2.71 (m, 1H), 2.57 (m, 1H), 1.66 (s, 9H), 1.18 (m, 3H).

Preparation of Compound DE-8

DE-7 (2.36 g, 8.07 mmol, 1 eq) was dissolved in HCl/MeOH (4 M, 1.00 eq) at 0° C. The mixture was stirred at 10° C. for 16 h to give a brown solution. LCMS showed DE-7 was not completely consumed. The mixture was further stirred at 10° C. for 24 h to give a brown solution. LCMS showed the reaction was completed. The residue was quenched with MTBE (30 mL), extracted with $H_2O$ (30 mL×3). The combine water layers were concentrated, and adjusted to pH 8 with Sat. $NaHCO_3$ (50 mL), and then concentrated to give a residue. The residue was washed with DCM (50 mL) and MeOH (5 mL), filtered and then concentrated to give DE-8. $^1$H NMR (400 MHz, $CDCl_3$) δ=8.59 (br s, 1H), 7.24 (m, 2H), 7.06 (s, 1H), 3.33-3.20 (m, 1H), 2.95-2.76 (m, 1H), 2.61 (m, 1H), 1.20-1.13 (m, 3H).

Preparation of DE-9. To a solution of DE-8 (100 mg, 520.20 μmol, 1 eq) in toluene (3 mL) was added 4-morpholinobenzaldehyde (99.48 mg, 520.20 μmol, 1 eq). The mixture was heated to 105° C. for 30 min, and followed with addition of AcOH (315.00 mg, 5.25 mmol, 0.3 mL, 10.08 eq). The mixture was heated to 105° C. for 15.5 h to give a brown suspension. TLC (EA:MeOH=10:1) showed the reaction was completed. The mixture was quenched with Sat.

$NaHCO_3$ (20 mL), and extracted with EtOAc (10 mL×3). The combined organic layers were dried over $Na_2SO_4$, filtered and concentrated. The residue was purified by prep-TLC ($SiO_2$, EA: MeOH=10:1) to give DE-9. $^1H$ NMR (400 MHz, $CDCl_3$) δ=7.93-7.65 (m, 1H), 7.20-7.09 (m, 4H), 6.95-6.76 (m, 3H), 5.21 (br s, 1H), 3.85 (t, J=4.8 Hz, 4H), 3.41-3.26 (m, 1H), 3.20-3.07 (m, 4H), 3.01-2.74 (m, 1H), 2.62-2.46 (m, 1H), 1.27-1.23 (m, 3H).

Preparation of 114

To a solution of DE-9 (20 mg, 54.73 μmol, 1 eq) and TEA (16.61 mg, 164.18 μmol, 22.85 μL, 3 eq) in DCM (1 mL) was added 2-chloroacetyl chloride (18.54 mg, 164.18 μmol, 13.06 μL, 3 eq) at 0° C. The mixture was stirred at 10° C. for 2 h to give a brown solution. LCMS showed the reaction was completed. The mixture was concentrated, and the residue purified by prep-TLC ($SiO_2$, PE: EA=1:1) to give 114. LC-MS (m/z):442.1 [M+H]+. $^1H$ NMR (400 MHz, $CDCl_3$) δ=7.64 (s, 1H), 7.22 (d, J=8.5 Hz, 2H), 7.18-7.11 (m, 2H), 6.91-6.79 (m, 3H), 5.88 (s, 1H), 5.06-4.78 (m, 1H), 4.20-4.08 (m, 1H), 4.23-4.06 (m, 1H), 3.82 (m, 4H), 3.36-3.22 (m, 1H) 3.12 (m, 4H), 2.87 (m, 1H), 1.31 (m, 3H).

Procedure DF: Synthesis of Compound 115

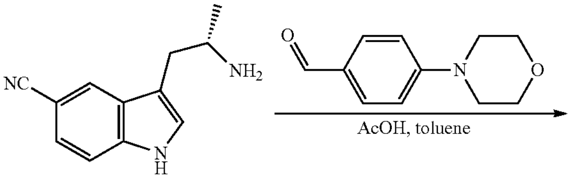

DF-1

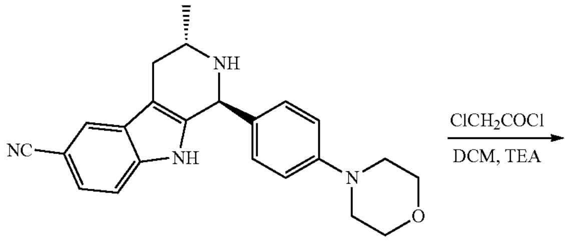

DF-2

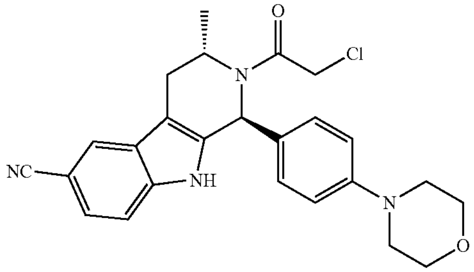

Compound 115

Preparation of DF-2. A solution of DF-1 (250 mg, 1.25 mmol, 1 eq) and 4-morpholinobenzaldehyde (239.93 mg, 1.25 mmol, 1 eq) in toluene (5 mL) was stirred at 105° C. for 30 min. AcOH (525.00 mg, 8.74 mmol, 0.5 mL, 6.97 eq) was added and the mixture stirred at 105° C. for 15.5 h to give a brown solution. LCMS and TLC (EA:MeOH=10:1) showed the reaction was completed. The mixture was diluted with Sat. $NaHCO_3$ (20 mL) and extracted with EA (10 mL×3). The combined organic layers were dried over $Na_2SO_4$, filtered and concentrated. The residue was purified by prep-TLC ($SiO_2$, EA: MeOH=10:1) to give DF-2. $^1H$ NMR (400 MHz, $CDCl_3$) δ=7.88 (s, 1H), 7.43-7.37 (m, 1H), 7.31 (s, 1H), 7 7.10 (m, 2H), 6.86 (m, 2H), 5.22 (br s, 1H), 3.91-3.80 (m, 4H), 3.38-3.25 (m, 1H), 3.21-3.08 (m, 4H), 2.95 (m, 1H), 2.54 (br s, 1H), 1.27-1.24 (m, 3H).

Preparation of 115

To a solution of DF-2 (17 mg, 45.64 μmol, 1 eq) in DCM (1 mL) were added TEA (13.86 mg, 136.93 μmol, 19.06 μL, 3 eq) and 2-chloroacetyl chloride (15.46 mg, 136.93 μmol, 10.89 μL, 3 eq) at 0° C. The mixture was stirred at 10° C. for 2 h to give a brown solution. TLC (PE:EA=0:1) showed the reaction was completed. The mixture was concentrated, and the resulting residue purified by prep-TLC ($SiO_2$, PE: EA=0:1) to give 115. LC-MS (m/z): 449.1[M+H]+. $^1H$ NMR (400 MHz, $CDCl_3$) δ=7.99 (s, 1H), 7.86 (s, 1H), 7.39 (m, 1H), 7.29 (s, 1H), 7.21 (m, 2H), 6.83 (m, 2H), 5.90 (s, 1H), 5.03-4.78 (m, 1H), 4.13 (m, 1H), 4.06-3.89 (m, 1H), 3.82 (m, 4H), 3.34 (m, 1H), 3.12 (m, 4H), 3.01-2.87 (m, 1H), 1.31 (d, J=6.6 Hz, 3H).

Procedure DG: Synthesis of Compound 116

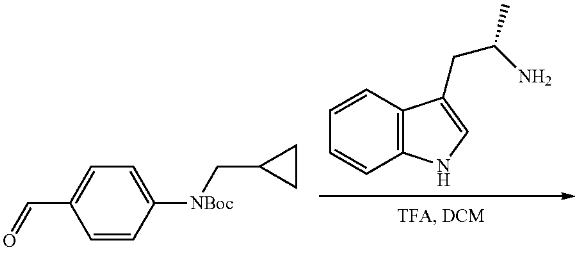

CF-4

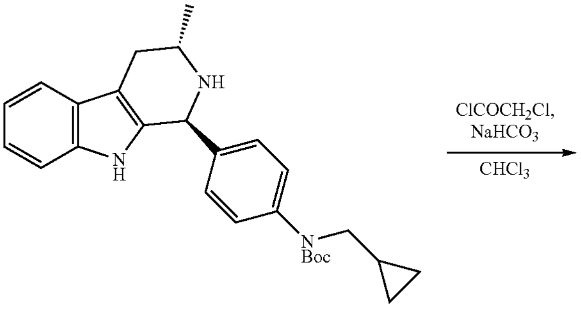

DG-2

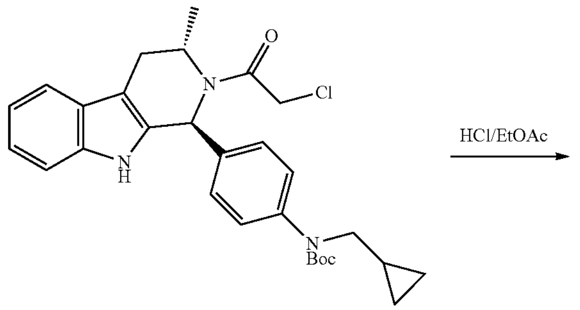

DG-3

-continued

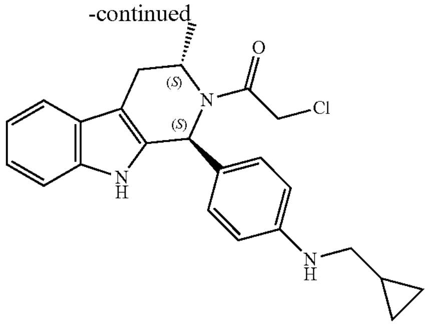

Compound 116

Preparation of DG-2. To a solution of CF-4 (300 mg, 1.09 mmol, 1 eq) in toluene (15 mL) was added (2S)-1-(1H-indol-3-yl)propan-2-amine (227.81 mg, 1.31 mmol, 1.2 eq). The mixture stirred at 15° C. for 30 min, followed by addition of HOAc (32.71 mg, 544.78 μmol, 31.16 μL, 0.5 eq). The mixture stirred at 105° C. for 12 h to give a yellow solution. LCMS showed the reaction was completed. The reaction mixture was adjusted to pH 8 with Sat. $NaHCO_3$ and extracted with EA (20 ml×3). The organic layers were dried over $Na_2SO_4$ and concentrated to give a crude product. The product was purified by prep-TLC (Ethyl acetate=100%) to give DG-2. $^1$H NMR (400 MHz, $CDCl_3$) δ ppm-0.02-0.04 (m, 2H), 0.27-0.33 (m, 2H), 0.81-0.93 (m, 1H), 1.11 (br d, J=6.27 Hz, 3H), 1.31 (s, 9H), 2.40 (br dd, J=14.93, 8.91 Hz, 1H), 2.83 (br d, J=11.29 Hz, 1H), 3.18 (br s, 1H), 3.33 (d, J=7.03 Hz, 2H), 5.10 (s, 1H), 6.96-7.07 (m, 7H), 7.15 (s, 1H), 7.41 (d, J=7.53 Hz, 1H), 7.57 (br s, 1H).

Preparation of DG-3. To a solution of DG-2 (23 mg, 53.29 μmol, 1 eq) in $CHCl_3$ (3 mL) was added $NaHCO_3$ (44.77 mg, 532.94 μmol, 20.73 μL, 10 eq). A solution of 2-chloroacetyl chloride (9.03 mg, 79.94 μmol, 6.36 μL, 1.5 eq) in CHCl3 (1 mL) was added at 0° C., and the mixture stirred at 0° C. for 1 h to give a yellow solution. LCMS showed the reaction was completed. The reaction mixture was quenched with $H_2O$ (5 ml) and extracted with DCM (20 ml×3). The organic layers were dried over $Na_2SO_4$ and concentrated to give a crude product. The product was purified by prep-TLC (Petroleum ether:Ethyl acetate=2:1) to give DG-3.

Preparation of 116

DG-3 (13.8 mg, 27.16 μmol, 1 eq) was dissolved in HCl/EtOAc (4 M, 2 ML mL, 294.52 eq), and the mixture stirred at 20° C. for 1 h to give a pink solution. LCMS showed the reaction was completed. The reaction mixture was adjusted to pH 8 with Sat. $NaHCO_3$ and extracted with EA (20 ml×3). The organic layers were dried over $Na_2SO_4$ and concentrated to give a crude product. The product was purified by prep-TLC (Petroleum ether:Ethyl acetate=1:1) to give 116. LC-MS (m/z):408.2 [M+H]+.

Procedure DH: Synthesis of Compound 117

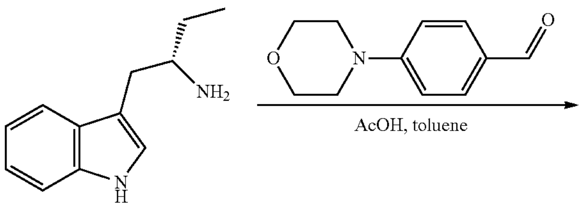

CS-8

-continued

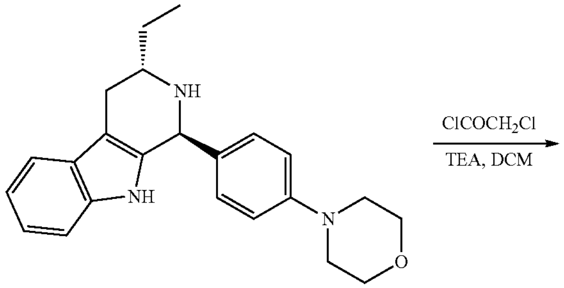

DH-2

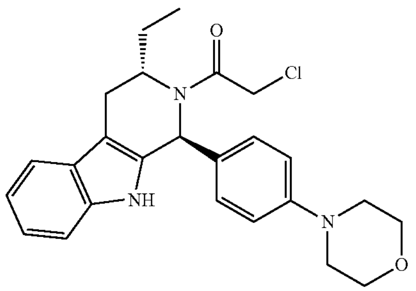

Compound 117

Preparation of DH-2. To a solution of CS-8 (100 mg, 531.16 μmol, 1 eq) in toluene (3 mL) was added 4-morpholinobenzaldehyde (101.57 mg, 531.16 μmol, 1 eq), and the mixture heated to 105° C. for 30 min. AcOH (31.90 mg, 531.16 μmol, 30.38 μL, 1 eq) was added and stirred at 105° C. for 15.5 h to give a brown suspension. TLC (EA: MeOH=20:1) showed the reaction was completed. The mixture was diluted with Sat. $NaHCO_3$ 20 mL and extracted with EA (10 mL×3). The combined organic layers were dried over $Na_2SO_4$, filtered and concentrated. The residue was purified by prep-TLC ($SiO_2$, EA: MeOH=20:1) to give DH-2. $^1$H NMR (400 MHz, $CDCl_3$) δ=7.59 (br s, 1H), 7.48 (m, 1H), 7.12-7.03 (m, 4H), 6.77 (m, 2H), 5.10 (s, 1H), 3.78 (m, 4H), 3.12-3.03 (m, 4H), 3.02-2.87 (m, 2H), 2.47 (m, 1H), 1.55-1.46 (m, 2H), 0.89 (m, 3H).

Preparation of 117

To a solution of DH-2 (50 mg, 138.32 μmol, 1 eq) in DCM (3 mL) were added TEA (41.99 mg, 414.96 μmol, 57.76 μL, 3 eq) and 2-chloroacetyl chloride (46.87 mg, 414.96 μmol, 33.00 μL, 3 eq) at 0° C. The mixture was stirred at 10° C. for 2 h to give a brown solution. TLC (PE:EA=1:1) showed the reaction was completed. The mixture was concentrated, and the resulting residue purified by prep-TLC ($SiO_2$, PE: EA=1:1) to give 117. LC-MS (m/z):438 [M+H]+. $^1$H NMR (400 MHz, $CDCl_3$) δ=7.63 (br s, 1H), 7.52 (m, 1H), 7.25-7.20 (m, 3H), 7.17-7.09 (m, 2H), 6.81 (m, 2H), 5.86 (br s, 1H), 4.66-4.38 (m, 1H), 4.21-4.09 (m, 1H), 3.82 (t, J=4.8 Hz, 4H), 3.30-3.06 (m, 6H), 1.8-1.46 (m, 2H), 0.94 (m, 3H).

Procedure DI: Synthesis of Compound 118

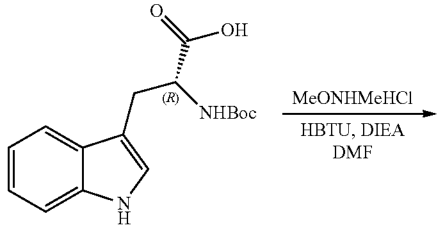

DI-1

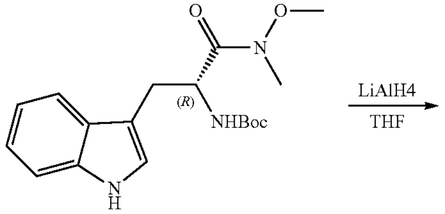

DI-2

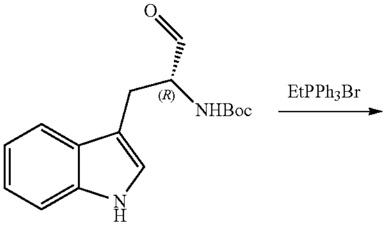

DI-3

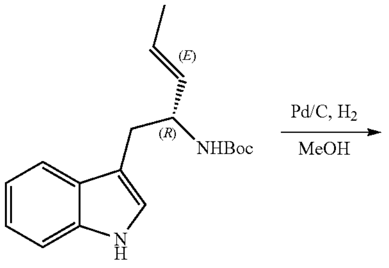

DI-4

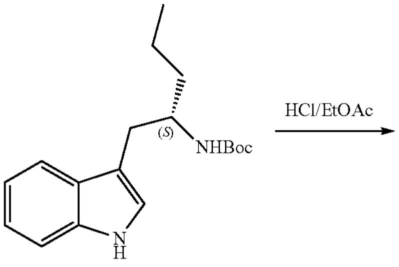

DI-5

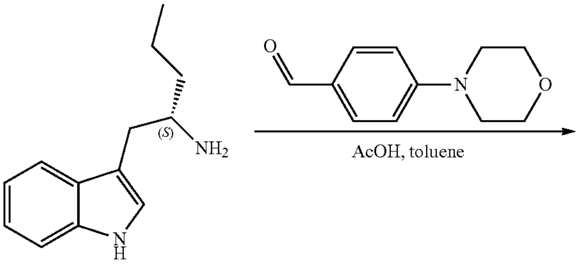

DI-6

-continued

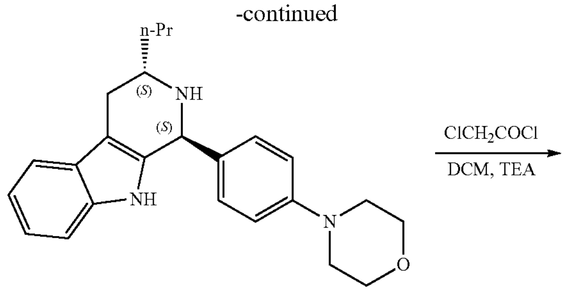

DI-7

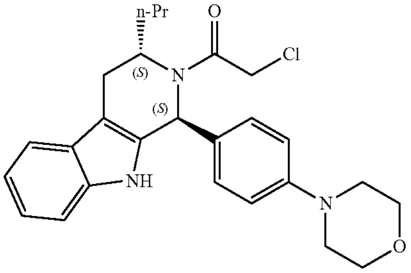

Compound 118

Preparation of Compound DI-2

To a solution of DI-1 (10 g, 32.86 mmol, 1 eq) in DMF (150 mL) were added DIEA (12.74 g, 98.57 mmol, 17.17 mL, 3 eq) and HBTU (19.94 g, 52.57 mmol, 1.6 eq). The reaction mixture was stirred at 10° C. for 5 min, followed by addition of $C_2H7NO.HCl$ (6.41 g, 65.72 mmol, 2 eq, HCl). The reaction mixture was stirred at 10° C. for 16 h to give a yellow solution. LCMS showed the reaction was completed. The residue was purified by column chromatography ($SiO_2$, 0% to 50% EtOAc in PE) to give DI-2. $^1H$ NMR (400 MHz, $CDCl_3$) δ ppm 1.40 (s, 9H), 2.80 (s, 1H), 3.14 (br s, 3H), 3.19-3.27 (m, 2H), 3.64 (br s, 3H), 4.96-5.30 (m, 2H), 7.04 (s, 1H), 7.08-7.14 (m, 1H), 7.14-7.20 (m, 1H), 7.33 (br d, J=8.03 Hz, 1H), 7.59 (br d, J=7.53 Hz, 1H), 8.11 (br s, 1H).

Preparation of DI-3. To a solution of DI-2 (9 g, 25.91 mmol, 1 eq) in THF (20 mL) was added $LiAlH_4$ (1.47 g, 38.86 mmol, 1.5 eq) slowly at 0° C. for 0.5 h to give a yellow solution. TLC (eluting with: PE/EA=1/1) showed the reaction was completed. The residue was purified by column chromatography ($SiO_2$, 0% to 40% EtOAc in PE) to give DI-3. $^1H$ NMR (400 MHz, $CDCl_3$) δ ppm 1.42-1.47 (m, 9H), 3.19-3.37 (m, 2H), 4.51 (br d, J=6.27 Hz, 1H), 5.18 (br d, J=4.52 Hz, 1H), 7.01 (s, 1H), 7.11-7.17 (m, 1H), 7.21 (t, J=7.15 Hz, 1H), 7.36 (d, J=8.03 Hz, 1H), 7.60 (br d, J=7.78 Hz, 1H), 8.29 (br s, 1H), 9.63 (s, 1H).

Preparation of DI-4. To a solution of ethyl(triphenyl) phosphonium bromide (4.02 g, 10.82 mmol, 1.2 eq) was added dropwise LiHMDS (1 M, 13.53 mL, 1.5 eq) in THF (10 mL). The mixture was stirred at 0° C. for 40 min. The mixture was cooled at −78° C., and DI-3 (2.6 g, 9.02 mmol, 1 eq) in toluene (10 mL) added for 1 h to give a yellow solution. TLC (quenched with water, eluting with: PE/EA=3/1) showed the reaction was completed. The mixture was purified by column chromatography ($SiO_2$, 0% to 50% EtOAc in PE) to give DI-4. $^1H$ NMR (400 MHz, $CDCl_3$) δ ppm 1.42 (s, 9H), 1.58 (dd, J=6.90, 1.63 Hz, 3H), 1.64 (d, J=6.27 Hz, 1H), 2.91-3.01 (m, 2H), 4.39-4.60 (m, 1H), 4.74 (br s, 1H), 5.30 (ddd, J=10.60, 8.85, 1.63 Hz, 1H), 5.45-5.57 (m, 1H), 7.02 (d, J=2.01 Hz, 1H), 7.08-7.14 (m, 1H), 7.15-7.22 (m, 1H), 7.35 (d, J=8.03 Hz, 1H), 7.65 (d, J=7.78 Hz, 1H), 8.07 (br s, 1H).

Preparation of DI-5. A solution of DI-4 (300 mg, 998.69 μmol, 1 eq) and Pd/C (50 mg, 50% purity) in MeOH (10 mL) was stirred under $H_2$ at 10° C. for 2 h to give a yellow solution. TLC (quenched with water, eluting with: PE/EA=5/1) showed the reaction was completed. The mixture was purified by prep-TLC (PE/EA=3/1) to give DI-5. $^1$H NMR (400 MHz, $CDCl_3$) δ ppm 0.88 (t, J=6.94 Hz, 3H), 1.28-1.38 (m, 4H), 1.42 (br s, 9H), 2.93 (br d, J=4.88 Hz, 2H), 3.93 (br s, 1H), 4.38 (br d, J=7.13 Hz, 1H), 7.02 (br s, 1H), 7.09-7.15 (m, 1H), 7.19 (t, J=7.13 Hz, 1H), 7.36 (d, J=8.00 Hz, 1H), 7.63 (br d, J=7.75 Hz, 1H), 8.06 (br s, 1H).

Preparation of DI-6. DI-5 (250 mg, 826.69 μmol, 1 eq) was dissolved in HCl/MeOH (4 M, 10 mL, 48.39 eq) and stirred at 10° C. for 12 h to give a yellow solution. LCMS showed the reaction was completed. The reaction mixture was concentrated to give the crude product. The crude product was adjusted to pH 8 with Sat. $NaHCO_3$ and concentrated to give a residue. The residue was washed with DCM/EtOH (10/1, 20 mL) to give DI-6, which was used for the next step without further purification. $^1$H NMR (400 MHz, $CDCl_3$) δ=8.01 (m, 1H), 7.71 (s, 1H), 6.98 (m, 1H), 6.85 (m, 1H), 3.90 (s, 3H), 1.67 (s, 9H).

Preparation of DI-7. To a solution of DI-6 (150 mg, 741.49 μmol, 1 eq) in DCM (10 mL) were added 4-morpholinobenzaldehyde (141.79 mg, 741.49 μmol, 1 eq) and TFA (126.82 mg, 1.11 mmol, 82.35 μL, 1.5 eq). The mixture was stirred at 50° C. for 12 h to give a green solution. LCMS showed the reaction was completed. The reaction mixture was quenched with Sat. $NaHCO_3$ (10 mL) and extracted with DCM (20 mL×2). The organic layers were dried over $Na_2SO_4$ and concentrated to give the crude product. The product was purified by a flash column (eluting with: PE/EtOAc=100% PE to 50%) to give DI-7. $^1$H NMR (400 MHz, $CDCl_3$) δ 7.66-7.42 (m, 3H), 7.10-7.02 (m, 4H), 6.78-6.76 (m, 2H), 5.09 (s, 1H), 3.79-3.76 (m, 4H), 3.10-2.85 (m, 6H), 2.46-2.44 (m, 1H), 1.46-1.41 (m, 2H), 1.34-1.28 (m, 2H), 0.82-0.76 (m, 3H).

Preparation of 118

To a solution of DI-7 (70 mg, 186.42 μmol, 1 eq) in DCM (5 mL) were added $NaHCO_3$ (156.60 mg, 1.86 mmol, 72.50 μL, 10 eq) and 2-chloroacetyl chloride (63.16 mg, 559.25 μmol, 44.48 μL, 3 eq). The mixture was stirred at 10° C. for 2 h to give a blue suspension. LCMS showed the reaction was completed. The reaction mixture was quenched with $H_2O$ (10 mL) and extracted with DCM (10 mL×3). The organic layers were dried over $Na_2SO_4$ and concentrated to give the crude product. The product was purified by a flash column (eluting with: PE/EtOAc=100% to 30%) to give 118. LC-MS (m/z): 474.0 [M+Na]+. $^1$H NMR (400 MHz, MeOD): δ 7.45-7.43 (m, 1H), 7.28-7.24 (m, 3H), 7.05-7.01 (m, 2H), 6.99-6.90 (m, 2H), 6.01 (brs, 1H), 4.36-4.05 (m, 3H), 3.79-3.72 (m, 4H), 3.12-2.94 (m, 6H), 1.34-1.29 (m, 4H), 0.85-0.84 (m, 3H).

Procedure DJ: Synthesis of Compound 120

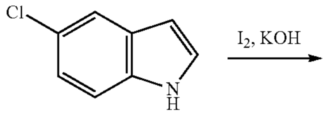

DJ-1

-continued

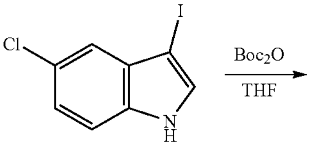

DJ-2

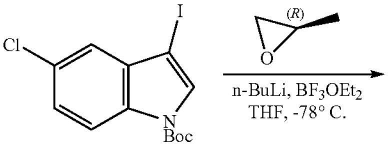

DJ-3

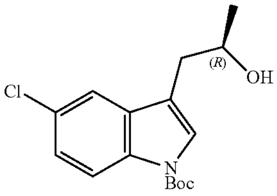

DJ-4

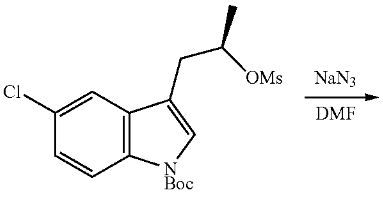

DJ-5

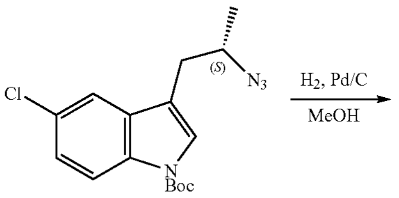

DJ-6

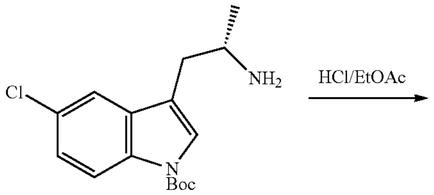

DJ-7

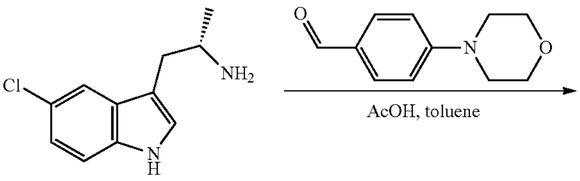

DJ-8

-continued

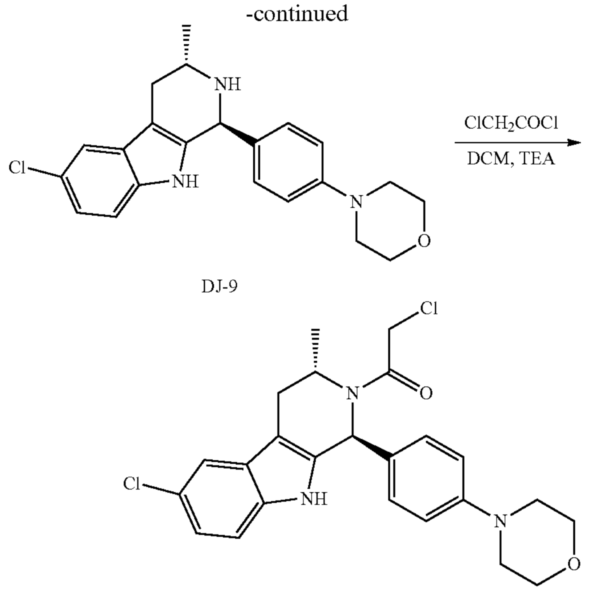

DJ-9

Compound 120

Preparation of DJ-2. To a solution of DJ-1 (1 g, 6.60 mmol, 1 eq) in DMF (10 mL) was added KOH (925.27 mg, 16.49 mmol, 2.5 eq) followed by dropwise addition of $I_2$ (1.67 g, 6.60 mmol, 1.33 mL, 1 eq) in DMF (10 mL). The mixture was stirred at 10° C. for 2 h to give a red-brown solution. LCMS showed the reaction was completed. The reaction mixture was quenched with $H_2O$ (60 mL) and extracted with MBTE (20 mL×3). The organic layers were dried over $Na_2SO_4$ and concentrated to give the crude product, which was used for next step without further purification.

Preparation of DJ-3. To a solution of DJ-2 (1.83 g, 6.59 mmol, 1 eq) in $CH_3CN$ (20 mL) were added $Boc_2O$ (2.16 g, 9.89 mmol, 2.27 mL, 1.5 eq) and DMAP (80.57 mg, 659.49 μmol, 0.1 eq). The mixture was stirred at 10° C. for 12 h to give a yellow suspension. LCMS and TLC (eluting with: PE/EtOAc=5/1) showed the reaction was completed. The reaction mixture was quenched with $H_2O$ (50 mL) and extracted with EtOAc (50 mL×3). The organic layers were dried over $Na_2SO_4$ and concentrated to give the crude product. The product was purified by a flash column (eluting with: PE/EtOAc=100% to 20%) to give DJ-3. $^1H$ NMR (400 MHz, $CDCl_3$): δ 8.08-8.06 (m, 1H), 7.74 (s, 1H), 7.35-7.33 (m, 1H), 7.32-7.31 (m, 1H), 1.67 (m, 9H).

Preparation of DJ-4. To a solution of DJ-3 (8 g, 21.19 mmol, 1 eq) in THF (80 mL) was added dropwise n-BuLi (2.5 M, 9.32 mL, 1.1 eq) at −78° C., and the mixture stirred at −78° C. for 0.5 h. (2R)-2-methyloxirane (1.48 g, 25.42 mmol, 1.78 mL, 1.2 eq) in THF (10 mL) was added dropwise at −78° C., followed by dropwise addition BF3.$Et_2O$ (2.41 g, 16.95 mmol, 2.09 mL, 0.8 eq). The mixture was stirred at −78° C. for 1 h to give a yellow solution. LCMS and TLC (eluting with: PE/EtOAc=3/1) showed the reaction was completed. The reaction mixture was quenched with Sat. $NH_4Cl$ (50 mL) and extracted with EtOAc (50 mL×3). The organic layers were dried over $Na_2SO_4$ and concentrated to give the crude product. The product was purified by a flash column (eluting with: PE/EtOAc=100% to 30%) to give DJ-4.

Preparation of DJ-5. To a solution of DJ-4 (3.8 g, 12.27 mmol, 1 eq) in DCM (40 mL) were added $Et_3N$ (3.10 g, 30.67 mmol, 4.27 mL, 2.5 eq) and MsCl (1.55 g, 13.49 mmol, 1.04 mL, 1.1 eq). The mixture was stirred at 5° C. for 1 hr to give a yellow solution. TLC showed no new spots, and that DJ-4 remained. An additional 1.55 g of MsCl was added, and the mixture stirred at 5° C. for 1 h. LCMS showed the reaction was completed. The reaction mixture was quenched with $H_2O$ (100 mL) and extracted with DCM (100 mL×2). The organic layers were dried over $Na_2SO_4$ and concentrated to give DJ-5, which was used without further purification.

Preparation of DJ-6. To a solution of DJ-5 (4.76 g, 12.27 mmol, 1 eq) in DMF (50 mL) was added $NaN_3$ (1.20 g, 18.41 mmol, 1.5 eq). The mixture was stirred at 60° C. for 12 h to give a yellow solution. LCMS showed the reaction was completed. The reaction mixture was quenched with $H_2O$ (200 mL) and extracted with MBTE (50 mL×3). The organic layers were dried over $Na_2SO_4$ and concentrated to give the crude product, which was used for the next step without further purification.

Preparation of DJ-7. To a solution of DJ-6 (4.11 g, 12.28 mmol, 1 eq) in THF (40 mL)/$H_2O$ (10 mL) was added $PPh_3$ (4.83 g, 18.41 mmol, 1.5 eq). The mixture was stirred at 60° C. for 12 h to give a yellow solution. LCMS and TLC (eluting with: 100% EtOAc) showed the reaction was completed. The reaction mixture was quenched with $H_2O$ (20 mL) and extracted with EtOAc (50 mL×3). The organic layers were dried over $Na_2SO_4$ and concentrated to give the crude product. The product was purified by a flash column (eluting with: PE/EtOAc=100% to 100% EtOAc) to give DJ-7. $^1H$ NMR (400 MHz, $CDCl_3$): δ 7.98 (brs, 1H), 7.48-7.37 (m, 2H), 7.21-7.18 (m, 1H), 3.70-3.67 (m, 1H), 3.26-3.19 (m, 1H), 2.74-2.65 (m, 1H), 2.52-2.49 (m, 1H), 1.59 (m, 9H), 1.11-1.10 (m, 3H).

Preparation of DJ-8. DJ-7 (2 g, 6.48 mmol, 1 eq) was dissolved in HCl/MeOH (4 M, 30 mL, 18.53 eq) and stirred at 10° C. for 12 h to give a yellow solution. LCMS showed the reaction was completed. The reaction mixture was concentrated to give the crude product. The product was dissolved in $H_2O$ (20 mL) and extracted with MBTE (20 mL×2). The water layer was adjusted to pH 8 with $NaHCO_3$ and the mixture concentrated to give the crude product. The product was dissolved in DCM/EtOH (10/1, 30 mL), filtered and washed with DCM (30 mL). The filtrate was concentrated to give DJ-8. $^1H$ NMR (400 MHz, $CDCl_3$): δ 8.12 (brs, 1H), 7.50-7.49 (m, 2H), 7.22-7.19 (m, 1H), 7.08-7.00 (m, 2H), 3.24-3.16 (m, 1H), 2.78-2.74 (m, 1H), 2.57-2.52 (m, 1H), 1.16-1.10 (m, 3H).

Preparation of DJ-9. To a solution of DJ-8 (200 mg, 958.37 μmol, 1 eq) in DCM (20 mL) were added 4-morpholinobenzaldehyde (183.27 mg, 958.37 μmol, 1 eq) and TFA (163.91 mg, 1.44 mmol, 106.44 μL, 1.5 eq). The mixture was stirred at 50° C. for 24 h to give a yellow solution. LCMS and TLC (eluting with: EtOAc=100%) showed the reaction was completed. The reaction mixture was quenched with Sat. $HCO_3$ (30 mL) and extracted with DCM (20 mL×3). The organic layers were dried over $Na_2SO_4$ and concentrated to give the crude product. The product was purified by a flash column (eluting with: PE/EtOAc=100% PE to 50%) to give DJ-9.

Preparation of 120

To a solution of DJ-9 (70 mg, 183.30 μmol, 1 eq) in DCM (5 mL) were added $NaHCO_3$ (153.98 mg, 1.83 mmol, 71.29 μL, 10 eq) and 2-chloroacetyl chloride (62.11 mg, 549.89 μmol, 43.74 μL, 3 eq). The mixture was stirred at 10° C. for 12 h to give a yellow suspension. LCMS and TLC (eluting with: PE/EtOAc=1/1) showed the reaction was completed. The reaction mixture was quenched with $H_2O$ (10 mL) and extracted with DCM (15 mL×2). The organic layers were dried over $Na_2SO_4$ and concentrated to give the crude product. The product was purified by prep-TLC (eluting with: PE/EtOAc=1/1) to give 120. LC-MS (m/z): 457.8 [M+H]+. $^1$H NMR (400 MHz, MeOD): δ 7.48 (s, 1H), 7.31-7.29 (m, 3H), 7.14-7.09 (m, 1H), 6.93-6.91 (m, 2H), 4.69 (brs, 1H), 4.50-4.44 (m, 2H), 3.85-3.81 (m, 4H), 3.19-3.13 (m, 5H), 2.83-2.79 (m, 1H), 1.17-1.13 (m, 3H).

Procedure DK: Synthesis of Compound 121

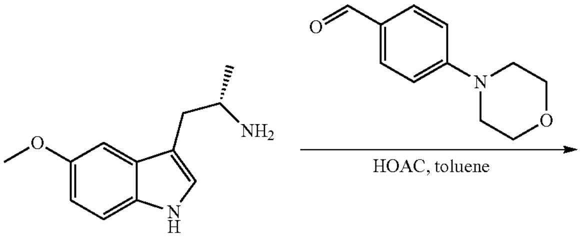

DD-5

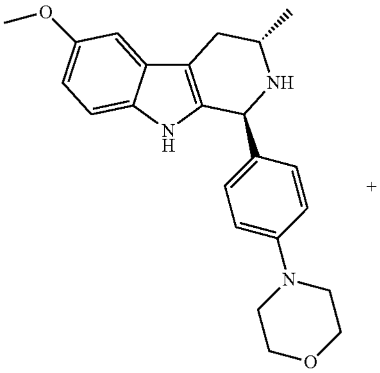

DK-2

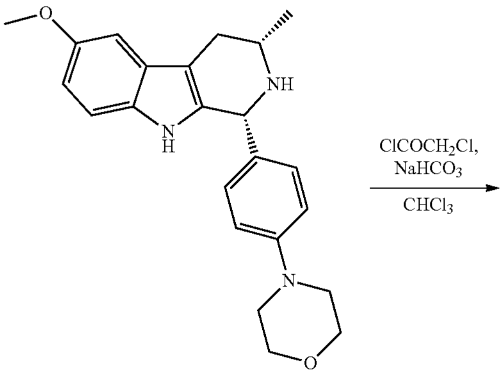

DK-2a

-continued

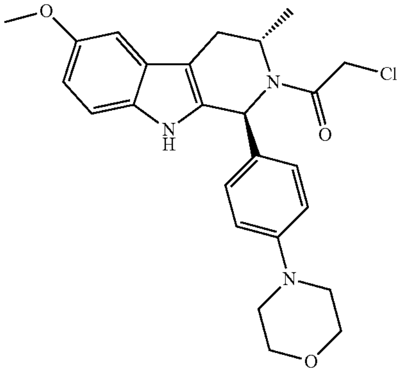

Compound 121

Preparation of DK-2. To a solution of DD-5 (110 mg, 538.51 μmol, 1 eq) in toluene (5 mL) was added 4-morpholinobenzaldehyde (102.98 mg, 538.51 μmol, 1 eq). The mixture was stirred at 15° C. for 30 min, followed by addition of HOAC (32.34 mg, 538.51 μmol, 30.80 μL, 1 eq). The mixture stirred at 105° C. for 12 h to give a yellow solution. LCMS showed the some desired product was found. The reaction mixture was adjusted to pH 8 with Sat. $NaHCO_3$ and extracted with DCM (20 ml×3). The organic layers were dried over $Na_2SO_4$ and concentrated to give a crude product The residue was purified by prep-TLC (Ethyl acetate: Methanol=10:1) to give DK-2 and DK-2a. $^1$H NMR (400 MHz, $CDCl_3$) δ ppm 1.27 (d, J=6.27 Hz, 3H), 2.48 (br s, 1H), 2.77 (br d, J=12.55 Hz, 1H), 3.07-3.11 (m, 4H), 3.21 (br s, 1H), 3.76-3.82 (m, 7H), 5.08 (br s, 1H), 6.71 (dd, J=8.78, 2.51 Hz, 1H), 6.82 (d, J=8.78 Hz, 2H), 6.90 (d, J=2.26 Hz, 1H), 7.02 (d, J=8.78 Hz, 1H), 7.16-7.18 (m, 1H), 7.21 (br s, 1H).

Preparation of 121

To a solution of DK-2 (61 mg, 161.60 μmol, 1 eq) in CHCl3 (3 mL) were added $NaHCO_3$ (135.75 mg, 1.62 mmol, 62.85 μL, 10 eq) and 2-chloroacetyl chloride (54.75 mg, 484.80 μmol, 38.56 μL, 3 eq). The mixture stirred at 0° C. for 2 h to give a blue solution. LCMS showed the reaction was completed. The reaction mixture was quenched with $H_2O$ (10 ml) and extracted with DCM (30 ml×3). The organic layers were dried over $Na_2SO_4$ and concentrated to give a crude product. The product was purified by HPLC (column: Xtimate C18 150×25 mm×5 μm; mobile phase: [water (0.05% HCl)-ACN]; B %: 30%-60%, 9.5 min) to give 121. LC-MS (m/z):476.0 [M+Na]. $^1$H NMR (400 MHz, $CDCl_3$) δ ppm 1.33 (d, J=6.27 Hz, 3H), 2.91 (br d, J=16.56 Hz, 1H), 3.13 (br s, 3H), 3.52 (d, J=5.02 Hz, 5H), 3.84 (t, J=4.64 Hz, 4H), 3.87 (s, 3H), 5.88 (s, 1H), 6.79-6.85 (m, 3H), 6.97 (s, 1H), 7.15 (d, J=8.78 Hz, 1H), 7.23 (d, J=8.78 Hz, 2H), 7.49 (s, 1H).

Procedure DL: Synthesis of Compound 232
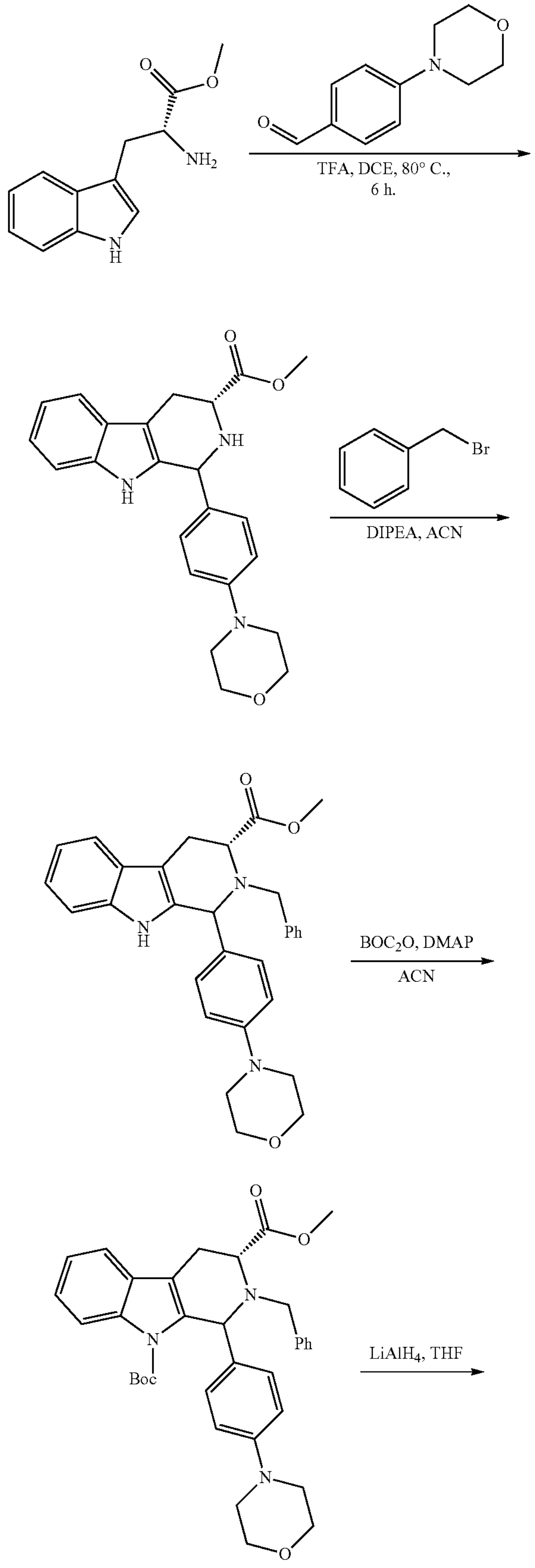
-continued
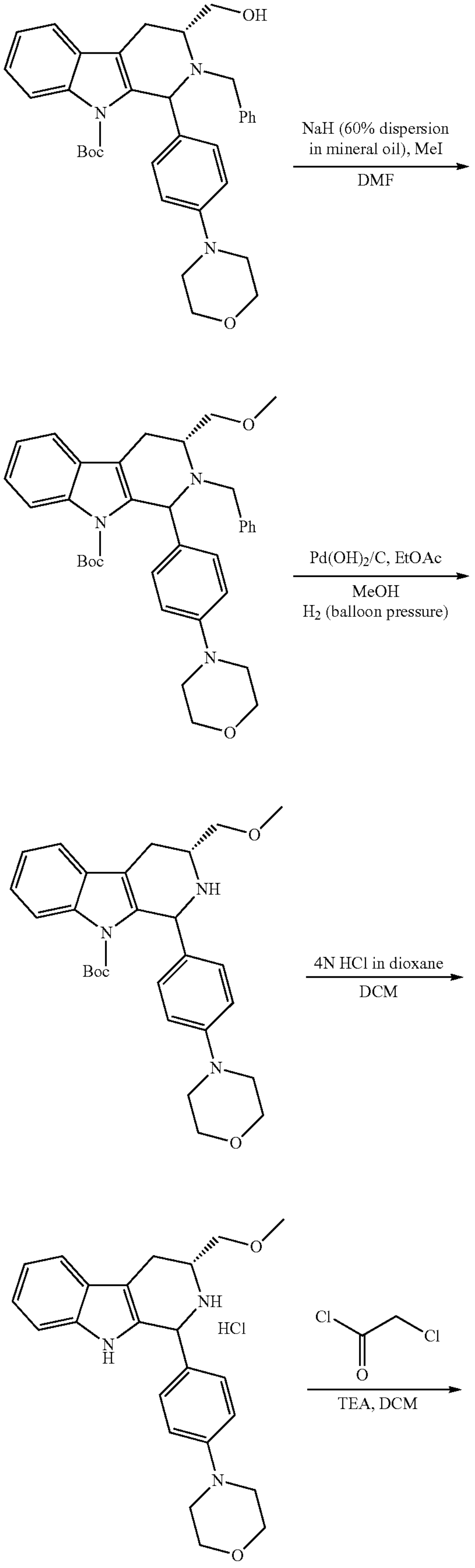

-continued

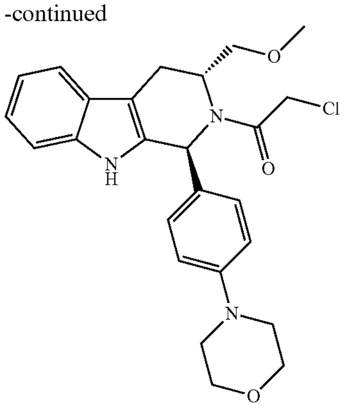

Compound 232

(methyl-(3R)-1-(4-morpholinophenyl)-2,3,4,9-tetrahydro-1H-pyrido[3,4-b]indole-3-carboxylate): To a solution of methyl D-tryptophanate (1.0 g, 4.58 mmol, 1 eq) and 4-morpholinobenzaldehyde (0.96 g, 5.04 mmol, 1 eq) in DCE (10 mL) was added slowly TFA (0.7 mL, 9.16 mmol, 2 eq) at 0° C. The reaction mixture was stirred at 80° C. for 16 h and TLC (70% EtOAc in hexane) showed disappearance of the starting material. The reaction was cooled to room temperature and was concentrated under reduced pressure, and the crude product diluted with EtOAc (50 mL), washed with saturated $NaHCO_3$ solution (2×20 mL) and brine solution (2×10 mL). The organic layer was dried over anhydrous $Na_2SO_4$, filtered and concentrated under reduced pressure. The crude product was purified by flash chromatography using 0-60% EtOAc in hexane as eluent to give methyl (3R)-1-(4-morpholinophenyl)-2,3,4,9-tetrahydro-1H-pyrido[3,4-b]indole-3-carboxylate. LC-MS (m/z)=392.3 $[M+H]^+$. $^1H$ NMR (400 MHz, $CDCl_3$) δ ppm 3.02-3.09 (m, 1H), 3.09-3.17 (m, 4H), 3.33-3.36 (m, 2H), 3.71 (s, 2H), 3.83-3.85 (m, 5H), 3.97-3.98 (m, 1H), 5.17 (s, 1H), 6.86-6.92 (m, 2H), 7.13-7.16 (m, 5H), 7.51-7.53 (m, 2H).

Methyl-(3R)-2-benzyl-1-(4-morpholinophenyl)-2,3,4,9-tetrahydro-1H-pyrido[3,4-b]indole-3-carboxylate: To a solution of methyl (3R)-1-(4-morpholinophenyl)-2,3,4,9-tetrahydro-1H-pyrido[3,4-b]indole-3-carboxylate (1.6 g, 4.09 mmol, 1 eq) in acetonitrile (16 mL) was added DIPEA (1.0 g, 8.06 mmol, 2 eq) and benzyl bromide (0.9 g, 5.31 mmol, 1.3 eq) at room temperature. The reaction was stirred at 80° C. for 6 h. TLC (20% EtOAc in hexane) showed the reaction was completed. The reaction was cooled to room temperature and was concentrated under reduced pressure to get the crude product. The crude was purified by flash chromatography using 0-30% EtOAc in hexane as an eluent to give methyl (3R)-2-benzyl-1-(4-morpholinophenyl)-2,3,4,9-tetrahydro-1H-pyrido[3,4-b]indole-3-carboxylate. LC-MS (m/z)=482.3 $[M+H]^+$. $^1H$ NMR (400 MHz, $CDCl_3$) δ ppm 3.14-3.30 (m, 6H), 3.33-3.35 (m, 1H), 3.61 (s, 3H), 3.83-3.86 (m, 5H), 3.92 (bs, 1H), 5.38 (s, 1H), 6.87-7.02 (m, 2H), 7.05-7.06 (m, 2H), 7.08-7.11 (m, 2H), 7.18-7.28 (m, 5H), 7.32-7.34 (m, 2H), 7.49 (d, J=7.6 Hz, 1H).

9-(tert-butyl)-3-methyl-(3R)-2-benzyl-1-(4-morpholinophenyl)-1,2,3,4-tetrahydro-9H-pyrido[3,4-b]indole-3,9-dicarboxylate: To a solution of methyl (3R)-2-benzyl-1-(4-morpholinophenyl)-2,3,4,9-tetrahydro-1H-pyrido[3,4-b]indole-3-carboxylate (2.0 g, 4.15 mmol, 1 eq) in acetonitrile (20 mL) was added DMAP (50 mg, 0.41 mmol, 0.1 eq) and $BOC_2O$ (1.17 g, 5.40 mmol, 1.3 eq) at room temperature. The reaction was stirred at room temperature for 16 h. TLC (20% EtOAc in hexane) showed the reaction was completed. The reaction was cooled to room temperature and was concentrated under reduced pressure to get the crude product. The crude was purified by flash chromatography using 0-15% EtOAc in hexane as an eluent to give 9-(tert-butyl) 3-methyl (3R)-2-benzyl-1-(4-morpholinophenyl)-1,2,3,4-tetrahydro-9H-pyrido[3,4-b]indole-3,9-dicarboxylate. LC-MS (m/z)=582.3 $[M+H]^+$. $^1H$ NMR (400 MHz, $CDCl_3$) δ ppm 1.05 (s, 9H), 2.89-3.06 (m, 5H), 3.12-3.19 (m, 1H), 3.54-3.57 (m, 1H), 3.81 (s, 3H), 3.85-3.86 (m, 4H), 3.88-3.89 (m, 1H), 3.93-3.96 (m, 1H), 5.30 (d, J=4.4 Hz, 1H), 6.72 (d, J=8.0 Hz, 2H), 6.88 (d, J=8.0 Hz, 2H), 7.36-7.38 (m, 5H), 7.50-7.56 (m, 3H), 8.31 (d, J=8.0 Hz, 1H).

tert-butyl-(3R)-2-benzyl-3-(hydroxymethyl)-1-(4-morpholinophenyl)-1,2,3,4-tetrahydro-9H-pyrido[3,4-b]indole-9-carboxylate: To a solution of 9-(tert-butyl) 3-methyl (3R)-2-benzyl-1-(4-morpholinophenyl)-1,2,3,4-tetrahydro-9H-pyrido[3,4-b]indole-3,9-dicarboxylate (1.2 g, 2.06 mmol, 1 eq) in THF (12 mL) was added $LiAlH_4$ 1M solution in THF (2.47 mL, 2.47 mmol, 1.2 eq) at −40° C. and stirred for 4 h at the same temperature. After this time reaction mixture was allowed to stir at 0° C. for 5 h. TLC (30% EtOAc in hexane) showed the reaction was completed. The reaction mixture was quenched with brine solution (1.0 mL) at 0° C. and the obtained solid portion was removed by filtration. Filtrate was evaporated under reduced pressure to get the crude product. The crude was purified by flash chromatography using 0-30% EtOAc in hexane as an eluent to give tert-butyl (3R)-2-benzyl-3-(hydroxymethyl)-1-(4-morpholinophenyl)-1,2,3,4-tetrahydro-9H-pyrido[3,4-b]indole-9-carboxylate. LC-MS (m/z)=554.3 $[M+H]^+$. $^1H$ NMR (400 MHz, $CDCl_3$) δ ppm 1.03 (s, 9H), 2.58-2.69 (m, 2H), 2.78 (bs, 1H), 3.05-3.06 (m, 4H), 3.32-3.37 (m, 1H), 3.40-3.43 (m, 1H), 3.63 (bs, 1H), 3.80-3.84 (m, 4H), 3.98-4.01 (m, 1H), 4.24-4.25 (m, 1H), 5.37 (s, 1H), 6.69-6.78 (m, 4H), 7.30-7.34 (m, 4H), 7.36-7.40 (m, 3H), 7.50 (d, J=7.2 Hz, 1H), 8.34 (d, J=8.0 Hz, 1H).

tert-butyl-(3R)-2-benzyl-3-(methoxymethyl)-1-(4-morpholinophenyl)-1,2,3,4-tetrahydro-9H-pyrido[3,4-b]indole-9-carboxylate: To a solution of tert-butyl (3R)-2-benzyl-3-(hydroxymethyl)-1-(4-morpholinophenyl)-1,2,3,4-tetrahydro-9H-pyrido[3,4-b]indole-9-carboxylate (0.74 g, 1.33 mmol, 1 eq) in DMF (7.0 mL) was added NaH 60% dispersion in mineral oil (0.21 g, 5.35 mmol, 4.0 eq) at 0° C. and stirred for 30 min at the same temperature. Then methyl iodide (0.94 g, 6.65 mmol, 5.0 eq) was added to the above reaction mixture at 0° C. Finally, this reaction mixture was stirred at room temperature for 16 h. TLC (40% EtOAc in hexane) showed the reaction was completed. The reaction mixture was quenched with ice cold water (5.0 mL) at 0° C. Then the product was extracted with ethyl acetate (35 mL) and washed brine solution (10 mL), dried over $Na_2SO_4$, filtered and concentrated under reduced pressure to give the crude product. Obtained crude product was purified by flash column chromatography using 0-40% EtOAc in hexane as an eluent to give the tert-butyl (3R)-2-benzyl-3-(methoxymethyl)-1-(4-morpholinophenyl)-1,2,3,4-tetrahydro-9H-pyrido[3,4-b]indole-9-carboxylate. LC-MS (m/z)=568.3 $[M+H]^+$. $^1H$ NMR (400 MHz, $CDCl_3$) δ ppm 1.02 (s, 9H), 3.27-3.29 (m, 4H), 3.39-3.48 (m, 4H), 3.51 (bs, 1H), 3.58-3.67 (m, 3H), 3.68-3.71 (m, 1H), 3.81 (bs, 4H), 3.96-4.02 (m, 1H), 5.22 (s, 1H), 6.71-6.75 (m, 2H), 6.83-6.85 (m, 2H), 7.32-7.34 (m, 5H), 7.47-7.51 (m, 2H), 7.53-7.59 (m, 1H), 8.31 (d, J=8.0 Hz, 1H).

tert-butyl-(3R)-3-(methoxymethyl)-1-(4-morpholinophenyl)-1,2,3,4-tetrahydro-9H-pyrido[3,4-b]indol-9-carboxylate: To a stirred solution of tert-butyl (3R)-2-benzyl-3-

(methoxymethyl)-1-(4-morpholinophenyl)-1,2,3,4-tetrahydro-9H-pyrido[3,4-b]indole-9-carboxylate (0.425 g, 0.75 mmol, 1 eq) in ethyl acetate (5 mL) and methanol (5 mL) was added palladium hydroxide on carbon (10 mg) under $N_2$ atmosphere. The reaction mixture was stirred under hydrogen atmosphere (balloon pressure) at room temperature for 5 h. TLC (30% EtOAc in hexane) showed the reaction was completed, then the mixture was degasified with nitrogen and filtered through celite bed and the filtrate was concentrated under reduced pressure. Obtained crude product was purified by flash column chromatography using 0-30% EtOAc in hexane as an eluent to give tert-butyl (3R)-3-(methoxymethyl)-1-(4-morpholinophenyl)-1,2,3,4-tetrahydro-9H-pyrido[3,4-b]indole-9-carboxylate. LC-MS (m/z): 478.3 $[M+H]^+$. $^1H$ NMR (400 MHz, $CDCl_3$) δ ppm 1.33 (s, 9H), 2.57-2.60 (m, 1H), 2.69-2.74 (m, 1H), 3.03-3.06 (m, 2H), 3.08-3.11 (m, 4H), 3.29 (s, 3H), 3.40-3.45 (m, 2H), 3.82-3.84 (m, 4H), 5.68 (s, 1H), 6.78 (d, J=8.4 Hz, 2H), 6.97 (d, J=8.8 Hz, 2H), 7.28-7.32 (m, 2H), 7.46 (d, J=7.6 Hz, 1H), 8.22 (d, J=8.4 Hz, 1H). 4-(4-((3R)-3-(methoxymethyl)-2,3,4,9-tetrahydro-1H-pyrido[3,4-b]indol-1-yl)phenyl)morpholine hydrogen chloride: To a solution of tert-butyl (3R)-3-(methoxymethyl)-1-(4-morpholinophenyl)-1,2,3,4-tetrahydro-9H-pyrido[3,4-b]indole-9-carboxylate (0.125 g, 0.26 mmol, 1 eq) in DCM (2.0 mL) was added 4N HCl in 1,4-dioxane (1.0 mL) at room temperature. The reaction mixture was stirred at room temperature for 16 h. LCMS and TLC (70% EtOAc in hexane) showed the reaction was completed. After this time, reaction mixture was concentrated to give 4-(4-((3R)-3-(methoxymethyl)-2,3,4,9-tetrahydro-1H-pyrido[3,4-b]indol-1-yl)phenyl)morpholine hydrogen chloride. LC-MS (m/z): 378.2 $[M+H]^+$. $^1H$ NMR (400 MHz, DMSO-$d_6$): δ 2.87-2.93 (m, 1H), 3.09-3.11 (m, 4H), 3.30 (s, 3H), 3.52-3.54 (m, 3H), 3.64-3.70 (m, 5H), 5.72 (s, 1H), 6.95-7.02 (m, 3H), 7.08-7.19 (m, 3H), 7.28 (d, J=8.0 Hz, 1H), 7.51-7.54 (m, 1H), 9.09 (bs, 1H), 10.00 (bs, 1H), 10.94 (s, 1H).

2-chloro-1-((1 S,3R)-3-(methoxymethyl)-1-(4-morpholinophenyl)-1,3,4,9-tetrahydro-2H-pyrido[3,4-b]indol-2-yl)ethan-1-one: To a solution of 4-(4-((3R)-3-(methoxymethyl)-2,3,4,9-tetrahydro-1H-pyrido[3,4-b]indol-1-yl)phenyl)morpholine hydrogen chloride (0.11 g, 0.46 mmol, 1 eq) in DCM (2.5 mL) was added triethyl amine (0.078 g, 0.78 mmol, 3.0 eq) at 0° C., followed by 2-chloroacetyl chloride (0.036 g, 0.31 mmol, 1.2 eq). The mixture was stirred at 0° C. for 1.5 h under $N_2$ atmosphere. TLC (70% EtOAc in hexane) showed the reaction was completed. Then the reaction was diluted with saturated aqueous solution of $NaHCO_3$ (5 mL) and was extracted with DCM (15 mL). The organic layer was dried over anhydrous $Na_2SO_4$, filtered and concentrated under reduced pressure to get the crude. The crude product was purified by preparative TLC using 60% EtOAc in n-Hexane as mobile phase to give 2-chloro-1-((1 S,3R)-3-(methoxymethyl)-1-(4-morpholinophenyl)-1,3,4,9-tetrahydro-2H-pyrido[3,4-b]indol-2-yl)ethan-1-one. (Trans isomer confirmed by nOe experiment). LC-MS (m/z)=454.4 $[M+H]^+$. $^1H$ NMR (400 MHz, $CDCl_3$): δ 3.06-3.10 (m, 5H), 3.26 (s, 3H), 3.37-3.48 (m, 3H), 3.80 (t, J=4.6 Hz, 4H), 4.02 (bs, 1H), 4.50 (bs, 1H), 4.79 (bs, 1H), 5.81 (s, 1H), 6.79 (d, J=8.4 Hz, 2H), 7.08-7.14 (m, 2H), 7.21-7.23 (m, 3H), 7.50 (d, J=7.2 Hz, 1H), 7.55 (s, 1H).

Procedure DM: Synthesis of Compound 158 and 159

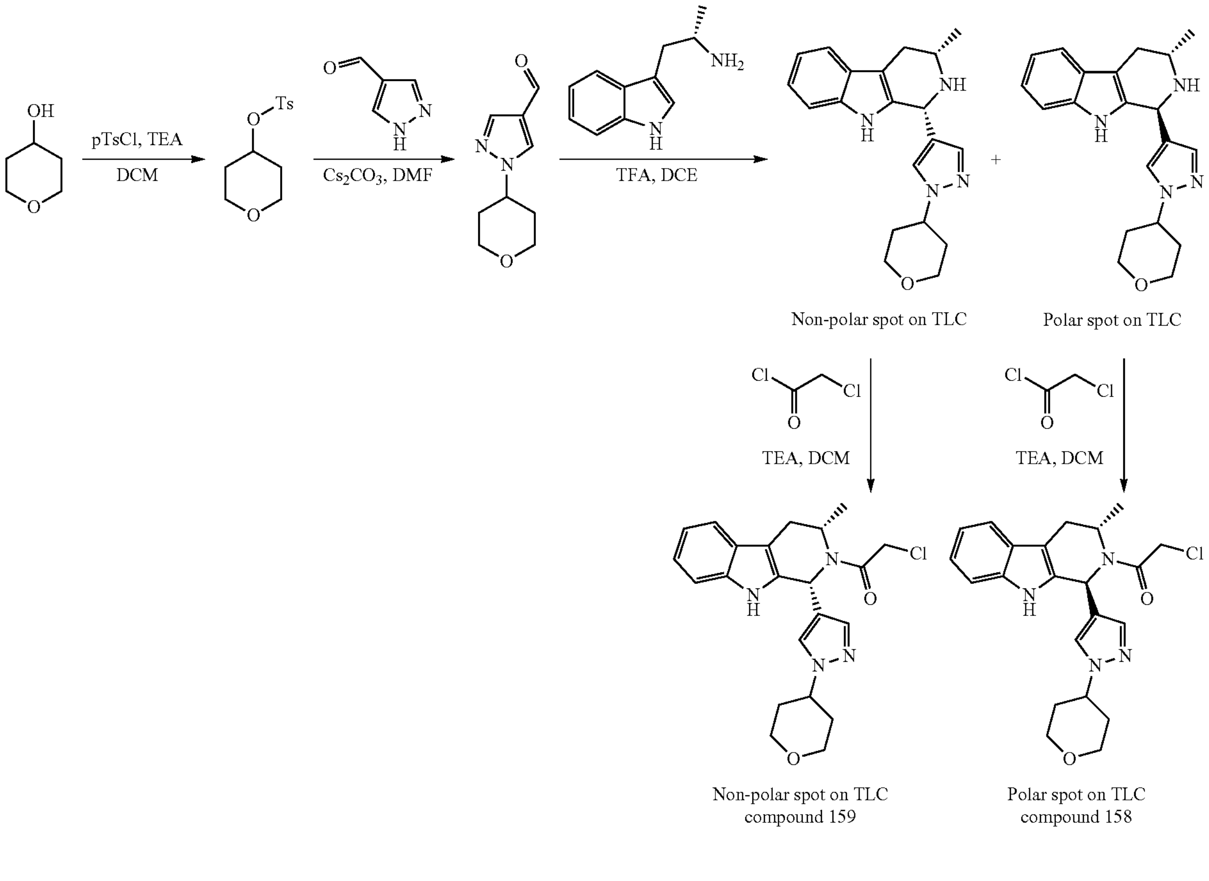

Non-polar spot on TLC
compound 159

Polar spot on TLC
compound 158

Tetrahydro-2H-pyran-4-yl 4-methylbenzenesulfonate: To a solution of tetrahydro-2H-pyran-4-ol (0.5 g, 4.90 mmol, 1 eq) in DCM (10 mL) was added triethyl amine (0.74 g, 7.35 mmol, 1.5 eq) followed by 4-methylbenzenesulfonyl chloride (1.0 g, 5.39 mmol, 1.1 eq) at 0° C. The reaction mixture was stirred at room temperature for 16 h. TLC (40% EtOAc in hexane) showed the reaction was completed. Then the reaction mixture was diluted with DCM (30 mL) and saturated aqueous solution of $NaHCO_3$ (10 mL). Organic layer was separated, washed with brine solution (5 mL), dried over anhydrous $Na_2SO_4$, filtered and concentrated under reduced pressure to get the crude product. Obtained crude product was purified by flash column chromatography using 0-30% EtOAc in hexane as an eluent to give tetrahydro-2H-pyran-4-yl 4-methylbenzenesulfonate. $^1H$ NMR (400 MHz, $CDCl_3$) δ ppm 1.70-1.79 (m, 2H), 1.83-1.87 (m, 2H), 2.60 (s, 3H), 3.43-3.49 (m, 2H), 3.83-3.89 (m, 2H), 4.66-4.72 (m, 1H), 7.33 (d, J=8.0 Hz, 2H), 7.80 (d, J=8.4 Hz, 2H).

1-(tetrahydro-2H-pyran-4-yl)-1H-pyrazole-4-carbaldehyde: To a solution of tetrahydro-2H-pyran-4-yl 4-methylbenzenesulfonate (0.6 g, 2.34 mmol, 1 eq) and 1H-pyrazole-4-carbaldehyde (0.225 g, 2.34 mmol, 1 eq) in DMF (10 mL) was added $Cs_2CO_3$ (0.83 g, 2.57 mmol, 1.1 eq) at room temperature. The reaction mixture was stirred at 90° C. for 16 h. TLC (70% EtOAc in hexane) showed the reaction was completed. The reaction was cooled to room temperature and was diluted with EtOAc (50 mL) and water (25 mL). Organic layer was separated, washed with water (3×25 mL), brine solution (10 mL), dried over anhydrous $Na_2SO_4$, filtered and concentrated under reduced pressure to get the crude product.

Obtained crude product was purified by flash column chromatography using 0-50% EtOAc in hexane as an eluent to give 1-(tetrahydro-2H-pyran-4-yl)-1H-pyrazole-4-carbaldehyde. LC-MS (m/z)=181 $[M+H]^+$. $^1H$ NMR (400 MHz, $CDCl_3$) δ ppm 2.03-2.15 (m, 4H), 3.54 (t, J=11.6 Hz, 2H), 4.10-4.13 (m, 2H), 4.35-4.41 (m, 1H), 7.98 (s, 2H), 9.86 (s, 1H).

(3S)-3-methyl-1-(1-(tetrahydro-2H-pyran-4-yl)-1H-pyrazol-4-yl)-2,3,4,9-tetrahydro-1H-pyrido[3,4-b]indole: To a solution of (S)-1-(1H-indol-3-yl)propan-2-amine (0.24 g, 1.38 mmol, 1 eq) and 1-(tetrahydro-2H-pyran-4-yl)-1H-pyrazole-4-carbaldehyde (0.26 g, 1.45 mmol, 1.05 eq) in DCE (5.0 mL) was added slowly TFA (0.3 g, 2.76 mmol, 2 eq) at 0° C. The reaction mixture was stirred at 80° C. for 16 h. TLC 70% (EtOAc in hexane) showed the reaction was completed. The reaction was cooled to room temperature and was concentrated under reduced pressure, and then obtained crude was diluted with EtOAc (30 mL) and saturated aqueous solution of $NaHCO_3$ (15 mL). Organic layer was separated, washed with brine solution (10 mL), dried over anhydrous $Na_2SO_4$, filtered and concentrated under reduced pressure to get the crude product. Obtained crude product was purified by flash chromatography using 0-60% EtOAc in hexane as an eluent to give methyl (3R)-1-(4-morpholinophenyl)-2,3,4,9-tetrahydro-1H-pyrido[3,4-b]indole-3-carboxylate. Note: Non-polar & polar spots were collected separately and taken forward separately for next step. LC-MS (m/z)=337.2 $[M+H]^+$ For non-polar spot: $^1H$ NMR (400 MHz, $CDCl_3$) δ ppm 1.25-1.26 (m, 3H), 1.98-2.08 (m, 4H), 2.47-2.55 (m, 1H), 2.84-2.91 (m, 1H), 3.23-3.26 (m, 1H), 3.46-3.54 (m, 2H), 4.02-4.14 (m, 2H), 4.21-4.33 (m, 1H), 5.26 (s, 1H), 7.08-7.18 (m, 2H), 7.42 (s, 1H), 7.43-7.52 (m, 2H), 7.65 (s, 1H), 7.71 (s, 1H). NH proton was not observed in the $^1H$ NMR. nOe experiment: concluded as cis isomer.

For polar spot: $^1H$ NMR (400 MHz, $CDCl_3$) δ ppm 1.26 (d, J=6.0 Hz, 3H), 1.95-2.04 (m, 4H), 2.45-2.51 (m, 1H), 2.84-2.90 (m, 1H), 3.25 (bs, 1H), 3.49 (t, J=10.6 Hz, 2H), 4.06 (d, J=10.8 Hz, 2H), 4.21-4.29 (m, 1H), 5.27 (s, 1H), 7.09-7.16 (m, 2H), 7.25-7.28 (m, 2H), 7.42 (s, 1H), 7.51 (d, J=7.6 Hz, 1H), 7.72 (s, 1H). NH proton was not observed in the $^1H$ NMR. nOe experiment:—Concluded as trans Isomer.

Preparation of Compound 159

2-chloro-1-((3S)-3-methyl-1-(1-(tetrahydro-2H-pyran-4-yl)-1H-pyrazol-4-yl)-1,3,4,9-tetrahydro-2H-pyrido[3,4-b]indol-2-yl)ethan-1-one: To a solution of (3S)-3-methyl-1-(1-(tetrahydro-2H-pyran-4-yl)-1H-pyrazol-4-yl)-2,3,4,9-tetrahydro-1H-pyrido[3,4-b]indole (0.18 g, 0.53 mmol, 1 eq) in DCM (5 mL) was added triethyl amine (0.133 g, 1.32 mmol, 2.5 eq) at 0° C., followed by 2-chloroacetyl chloride (0.079 g, 0.69 mmol, 1.3 eq). The mixture was stirred at 0° C. for 1.0 h under $N_2$ atmosphere. TLC (50% EtOAc in hexane) showed the reaction was completed. Then the reaction was diluted with saturated aqueous solution of $NaHCO_3$ (5 mL) and was extracted with DCM (15 mL). The organic layer was dried over anhydrous $Na_2SO_4$, filtered and concentrated under reduced pressure to get the crude. The crude product was purified by preparative TLC using 70% EtOAc in n-Hexane as mobile phase to give 2-chloro-1-((3S)-3-methyl-1-(1-(tetrahydro-2H-pyran-4-yl)-tetrahydro-2H-pyrido[3,4-b]indol-2-yl)ethan-1-one. LC-MS (m/z)=413.3 $[M+H]^+$. $^1H$ NMR (400 MHz, $CDCl_3$): δ 1.25 (d, J=6.0 Hz, 3H), 2.02-2.09 (m, 4H), 2.83-2.87 (m, 1H), 3.14-3.17 (m, 1H), 3.50-3.52 (m, 2H), 4.06-4.08 (m, 2H), 4.20-4.24 (m, 3H), 4.55 (bs, 1H), 6.63 (s, 1H), 7.15-7.16 (m, 2H), 7.33-7.36 (m, 2H), 7.52 (d, J=7.2 Hz, 1H), 7.63 (s, 1H), 7.93 (s, 1H).

Preparation of Compound 158

2-chloro-1-((3S)-3-methyl-1-(1-(tetrahydro-2H-pyran-4-yl)-1H-pyrazol-4-yl)-1,3,4,9-tetrahydro-2H-pyrido[3,4-b]indol-2-yl)ethan-1-one: To a solution of (3S)-3-methyl-1-(1-(tetrahydro-2H-pyran-4-yl)-1H-pyrazol-4-yl)-2,3,4,9-tetrahydro-1H-pyrido[3,4-b]indole (0.17 g, 0.50 mmol, 1 eq) in DCM (5 mL) was added triethyl amine (0.126 g, 1.25 mmol, 2.5 eq) at 0° C., followed by 2-chloroacetyl chloride (0.074 g, 0.65 mmol, 1.3 eq). The mixture was stirred at 0° C. for 1.0 h under $N_2$ atmosphere. TLC (50% EtOAc in hexane) showed the reaction was completed. Then the reaction was diluted with saturated aqueous solution of $NaHCO_3$ (5 mL) and was extracted with DCM (15 mL). The organic layer was dried over anhydrous $Na_2SO_4$, filtered and concentrated under reduced pressure to get the crude. The crude product was purified by preparative TLC using 70% EtOAc in n-Hexane as mobile phase to give 2-chloro-1-((3S)-3-methyl-1-(1-(tetrahydro-2H-pyran-4-yl)-tetrahydro-2H-pyrido[3,4-b]indol-2-yl)ethan-1-one. LC-MS (m/z)=413.3 $[M+H]^+$. $^1H$ NMR (400 MHz, $CDCl_3$): δ 1.29 (s, 3H), 1.99 (m, 4H), 2.93-2.96 (m, 1H), 3.10-3.20 (m, 1H), 3.40-3.52 (m, 2H), 4.02-4.05 (m, 2H), 4.14-4.24 (m, 3H), 4.51 (bs, 1H), 6.18 (s, 1H), 7.14-7.19 (m, 3H), 7.31-7.33 (m, 1H), 7.38 (s, 1H), 7.53 (d, J=6.4 Hz, 1H), 7.90 (s, 1H).

Procedure DN: Synthesis of Compound 211

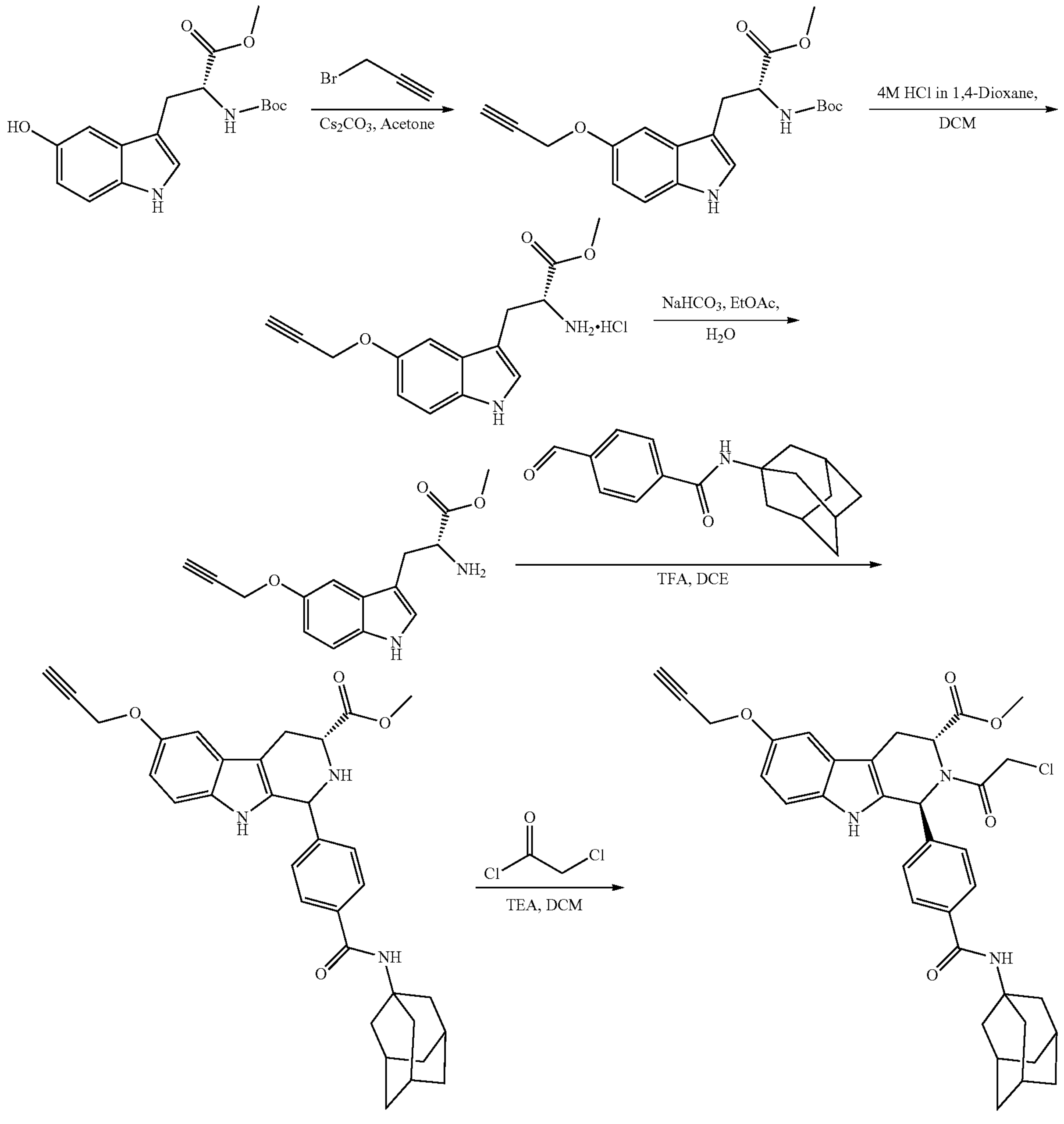

Polar spot from cyclization reaction was isolated and taken forward

211

Methyl (R)-2-((tert-butoxycarbonyl)amino)-3-(5-(prop-2-yn-1-yloxy)-1H-indol-3-yl)propanoate: To a solution of methyl (R)-2-((tert-butoxycarbonyl)amino)-3-(5-hydroxy-1H-indol-3-yl)propanoate (0.31 g, 0.93 mmol, 1 eq) in acetone (10 mL) was added cesium carbonate (0.33 g, 1.02 mmol, 1.1 eq) followed by 3-bromoprop-1-yne (0.08 mL, 1.02 mmol, 1.1 eq) at 0° C. The reaction mixture was stirred at room temperature for 5 h. After consumption of the starting material (TLC, 40% EtOAc in hexane), solid portion was removed by filtration through celite bed; filtrate was concentrated under reduced pressure and the crude product was purified by flash column chromatography on silica gel using EtOAc/hexane as the eluent to produce methyl (R)-2-((tert-butoxycarbonyl)amino)-3-(5-(prop-2-yn-1-yloxy)-1H-indol-3-yl)propanoate. LC-MS (m/z)=273.1 [M+H]+–100. $^{1}$H NMR (400 MHz, DMSO-$d_6$) δ ppm 1.29 (s, 9H), 2.89-3.04 (m, 2H), 3.48 (s, 1H), 3.58 (s, 3H), 4.16 (bs, 1H), 4.72 (s, 2H), 6.74 (d, J=8.8 Hz, 1H), 7.08 (d, J=16 Hz, 2H), 7.21 (d, J=8.0 Hz, 2H), 10.71 (s, 1H).

Methyl (R)-2-amino-3-(5-(prop-2-yn-1-yloxy)-1H-indol-3-yl)propanoate hydrochloride: To a solution of methyl (R)-2-((tert-butoxycarbonyl)amino)-3-(5-(prop-2-yn-1-yloxy)-1H-indol-3-yl)propanoate (0.3 g, 0.81 mmol, 1 eq) in DCM (10 mL) was added 4N HCl in 1,4-dioxane (4.0 mL)

at 0° C. The reaction mixture was stirred at room temperature for 1 h. LCMS and TLC (5% MeOH in DCM) showed the reaction was completed. After this time, reaction mixture was concentrated to give methyl (R)-2-amino-3-(5-(prop-2-yn-1-yloxy)-1H-indol-3-yl)propanoate hydrochloride. $^1$H NMR (400 MHz, DMSO-$d_6$) δ ppm 3.21 (d, J=6.0 Hz, 2H), 3.45 (s, 1H), 3.66 (s, 3H), 4.23 (bs, 1H), 4.74 (d, J=2.0 Hz, 2H), 6.78 (d, J=8.8 Hz, 1H), 7.10 (s, 1H), 7.18-7.19 (m, 1H), 7.26 (d, J=8.8 Hz, 1H), 8.46 (bs, 3H), 10.95 (s, 1H).

Methyl (R)-2-amino-3-(5-(prop-2-yn-1-yloxy)-1H-indol-3-yl)propanoate: To a solution of methyl (R)-2-amino-3-(5-(prop-2-yn-1-yloxy)-1H-indol-3-yl)propanoate hydrochloride (0.17 g, 0.55 mmol, 1 eq) in EtOAc (30 mL) and water (5 mL) was added $NaHCO_3$ (0.23 g, 2.75 mmol, 5 eq) at room temperature and stirred this reaction mass for 30 min. Then the organic layer was separated, dried over anhydrous MgSO4, filtered and concentrated under reduced pressure to get the methyl (R)-2-amino-3-(5-(prop-2-yn-1-yloxy)-1H-indol-3-yl)propanoate. LC-MS (m/z)=273.1 $[M+H]^+$. $^1$H NMR (400 MHz, $CDCl_3$) δ ppm 2.51 (s, 1H), 3.00-3.06 (m, 1H), 3.22-3.27 (m, 1H), 3.71 (s, 3H), 3.82-3.86 (m, 1H), 4.73 (d, J=2.0 Hz, 2H), 6.92 (d, J=8.8 Hz, 1H), 7.07 (s, 1H), 7.16 (s, 1H), 7.27 (s, 1H), 8.00 (bs, 1H). $NH_2$ protons were not observed in $^1$H NMR.

Methyl-(1 S,3R)-1-(4-(((3R,5R,7R)-adamantan-1-yl)carbamoyl)phenyl)-6-(prop-2-yn-1-yloxy)-2,3,4,9-tetrahydro-1H-pyrido[3,4-b]indole-3-carboxylate: To a solution of methyl (R)-2-amino-3-(5-(prop-2-yn-1-yloxy)-1H-indol-3-yl)propanoate (130 mg, 0.47 mmol, 1 eq) and N-((3s,5s,7s)-adamantan-1-yl)-4-formylbenzamide (149 mg, 0.52 mmol, 1.1 eq) in DCE (3.0 mL) was added slowly TFA (107 mg, 0.94 mmol, 2 eq) at 0° C. The reaction mixture was stirred at 80° C. for 5 h. TLC 5% MeOH in DCM) showed the reaction was completed. The reaction was cooled to room temperature and was concentrated under reduced pressure, and then obtained crude was diluted with EtOAc (25 mL), washed with saturated $NaHCO_3$ solution (2×7 mL) and brine solution (10 mL). The organic layer was dried over anhydrous $Na_2SO_4$, filtered and concentrated under reduced pressure to get the crude product. The crude was purified by flash chromatography using 0-5% MeOH in DCM as an eluent to give methyl (1S,3R)-1-(4-(((3R,5R,7R)-adamantan-1-yl)carbamoyl)phenyl)-6-(prop-2-yn-1-yloxy)-2,3,4,9-tetrahydro-1H-pyrido[3,4-b]indole-3-carboxylate [Polar spot on TLC-Trans isomer]) and non-polar spot on TLC i.e., Cis isomer was also separately isolated. LC-MS (m/z)=538.3 $[M+H]^+$. $^1$H NMR (400 MHz, $CDCl_3$) δ ppm 1.71 (s, 6H), 2.10 (s, 9H), 2.52 (s, 1H), 3.09-3.14 (m, 1H), 3.48-3.53 (m, 1H), 3.72 (s, 3H), 3.95 (bs, 1H), 4.92 (s, 2H), 5.43 (s, 1H), 5.74 (s, 1H), 6.88 (d, J=8.4 Hz, 1H), 7.09-7.16 (m, 2H), 7.34 (d, J=8.0 Hz, 2H), 7.51 (bs, 1H), 7.66 (d, J=7.6 Hz, 2H). NH proton was not observed in $^1$H NMR.

Preparation of Compound 211

Methyl-(1S,3R)-1-(4-(((3R,5R,7R)-adamantan-1-yl)carbamoyl)phenyl)-2-(2-chloroacetyl)-6-(prop-2-yn-1-yloxy)-2,3,4,9-tetrahydro-1H-pyrido[3,4-b]indole-3-carboxylate: To a solution of methyl (1S,3R)-1-(4-(((3R,5R,7R)-adamantan-1-yl)carbamoyl)phenyl)-6-(prop-2-yn-1-yloxy)-2,3,4,9-tetrahydro-1H-pyrido[3,4-b]indole-3-carboxylate (90 mg, 0.16 mmol, 1 eq) in DCM (2.0 mL) was added triethyl amine (44 mg, 0.4 mmol, 2.5 eq) at 0° C., followed by 2-chloroacetyl chloride (24 mg, 0.21 mmol, 1.3 eq). The mixture was stirred at 0° C. for 1.0 h under $N_2$ atmosphere. TLC (45% EtOAc in hexane) showed the reaction was completed. Then the reaction was diluted with saturated aqueous solution of $NaHCO_3$ (5 mL) and was extracted with DCM (20 mL). The organic layer was dried over anhydrous $Na_2SO_4$, filtered and concentrated under reduced pressure. The crude product was initially purified by preparative TLC using EtOAc in Hexane as mobile phase to give compound 211. LC-MS (m/z)=614.4 $[M+H]^+$. $^1$H NMR (400 MHz, DMSO-$d_6$) recorded at 70° C. δ ppm 1.64 (s, 6H), 2.03 (s, 9H), 3.19-3.28 (m, 2H), 3.40-3.44 (m, 1H), 3.52 (s, 3H), 4.20-4.25 (m, 1H), 4.54 (d, J=14 Hz, 1H), 4.70 (s, 2H), 5.20 (bs, 1H), 6.12 (bs, 1H), 6.72 (d, J=9.2 Hz, 1H), 7.04 (s, 1H), 7.13-7.15 (m, 2H), 7.44 (d, J=8.0 Hz, 2H), 7.63 (d, J=6.8 Hz, 2H), 10.61 (s, 1H).

Procedure DO: Synthesis of Compound 152

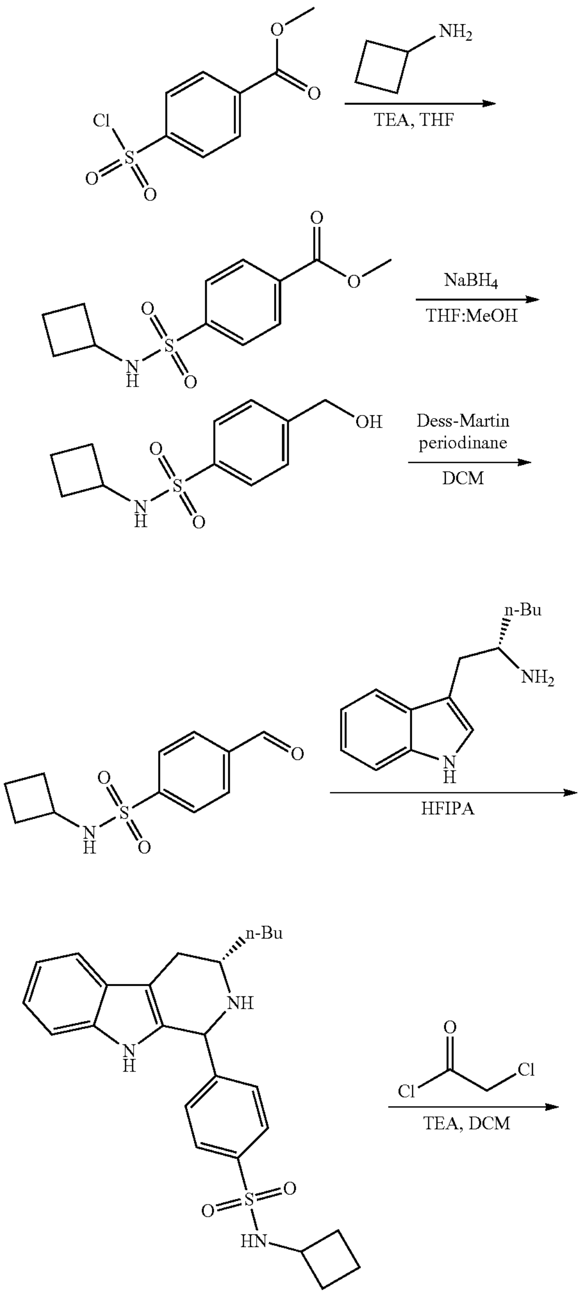

Trans Isomer was taken forward for chloro acetamide preparation

-continued

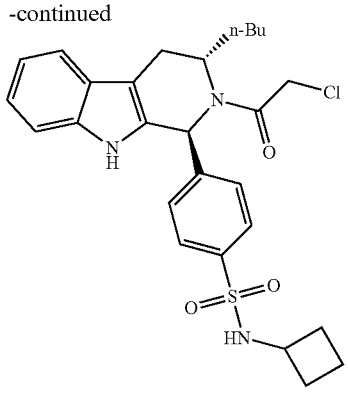

Methyl 4-(N-cyclobutylsulfamoyl)-benzoate: To a stirred solution of cyclobutanamine (0.303 g, 4.26 mmol, 1.0 eq) in THF (15 mL) was added triethyl amine (1.78 mL, 12.78 mmol, 3.0 eq) followed by methyl 4-(chlorosulfonyl)benzoate (1.0 g, 4.26 mmol, 1.0 eq) at 0° C. The reaction was stirred at room temperature for 2 h. TLC (50% EtOAc in n-Hexane) showed the reaction was completed. After the consumption of starting material, solvent was evaporated under reduced pressure, to get the crude. The crude product was purified by silica gel chromatography (eluting with: Hexane/EtOAc=50:50) to give methyl 4-(N-cyclobutylsulfamoyl)benzoate. LC-MS (m/z)=268.1 $[M+H]^+$. $^1H$ NMR (400 MHz, $CDCl_3$) δ: 1.56-1.67 (m, 2H), 1.71-1.78 (m, 2H), 2.13-2.15 (m, 2H), 3.96 (s, 3H), 3.80-3.88 (m, 1H), 4.65 (d, J=4.0 Hz, 1H), 7.92 (d, J=8.0 Hz, 2H), 8.16 (d, J=7.6 Hz, 2H).

N-cyclobutyl-4-(hydroxymethyl)benzenesulfonamide: To a solution of methyl 4-(N-cyclobutylsulfamoyl)benzoate (1.0 mg, 3.713 mmol, 1.0 eq) in mixture of THF (15 mL) and methanol (15 mL) at 0° C., NaBH4 (1.4 g, 37.13 mmol, 10.0 eq) was added. Then reaction mixture was refluxed for 16 h. Reaction mixture was cooled to room temperature. TLC (40% EtOAc in n-Hexane) showed the reaction was completed. Solvent was evaporated under reduced pressure. Obtained crude was quenched with saturated ammonium chloride and extracted with ethyl acetate (2×25 mL). Combined organic layer was washed with water (10 mL), dried over anhydrous $Na_2SO_4$ and concentrated to give the crude product. The crude product was purified by silica gel chromatography by (eluting with: 40% EtOAc in n-Hexane) to give N-cyclobutyl-4-(hydroxymethyl)benzenesulfonamide. LC-MS (m/z)=241.9 $[M+H]^+$. $^1H$ NMR (400 MHz, DMSO-d6) δ: 1.49-1.61 (m, 2H), 1.8073-1.80 (m, 2H), 2.12-2.20 (m, 2H), 3.75-3.85 (m, 1H), 4.59 (d, J=8.0 Hz, 1H), 4.79 (s, 2H), 7.49 (d, J=8.0 Hz, 2H), 7.83 (d, J=8.4 Hz, 2H).

N-cyclobutyl-4-formylbenzenesulfonamide: To a solution of N-cyclobutyl-4-(hydroxymethyl)benzenesulfonamide (500 mg, 2.072 mmol, 1 eq) in DCM (15 mL) was added Dess martin periodinane (1.318 g, 3.108 mmol, 1.5 eq) at 0° C. The reaction mixture was stirred at rt for 2 h. TLC (40% EtOAc in n-Hexane) showed the reaction was completed. Then the reaction mixture was quenched with saturated sodium bicarbonate solution and extracted with DCM (2×25 mL). Combined organic layer was washed with (10 mL) water and brine solution and dried over $Na_2SO_4$ and concentrated to give crude product. The crude product was purified by flash column chromatography using ethyl acetate in Hexane as an eluent. Product fractions were collected and concentrated under reduced pressure to give N-cyclobutyl-4-formylbenzenesulfonamide. LC-MS (m/z): 238.1 $[M-H]^-$. $^1H$ NMR (400 MHz, CDCl3) δ: 1.56-1.68 (m, 2H), 1.73-1.83 (m, 2H), 2.04-2.17 (m, 2H), 3.80-3.90 (m, 1H), 7.25 (s, 1H), 8.02 (s, 4H), 10.10 (s, 1H).

4-((3S)-3-butyl-2,3,4,9-tetrahydro-1H-pyrido[3,4-b]indol-1-yl)-N-cyclobutylbenzenesulfonamide: In a sealed tube, To a solution of compound (S)-1-(1H-indol-3-yl)hexan-2-amine (0.150 g, 0.693 mmol, 1.0 eq) in HFIPA (1.0 mL), compound N-cyclobutyl-4-formylbenzenesulfonamide (0.199 g, 0.831 mmol, 1.2 eq) was added. Then the reaction mixture was sealed and heated at 80° C. for 12 h. Reaction mixture was cooled to room temperature and diluted with DCM and was evaporated under reduced pressure to get the crude product. The crude product was purified by preparative TLC using 45% EtOAc in n-Hexane as mobile phase to give product as cis and trans isomer of 4-((3S)-3-butyl-2,3,4,9-tetrahydro-1H-pyrido[3,4-b]indol-1-yl)-N-cyclobutylbenzenesulfonamide where trans isomer was characterized by nOe experiment and was collected separately and taken for the next step.

Trans (Polar spot in TLC): 60 mg; Cis (Non polar in TLC). Only polar spot was taken forward for the next step. LC-MS (m/z): 437.9 $[M+H]^+$. $^1H$ NMR (400 MHz, $CDCl_3$) δ ppm: 0.86-0.96 (m, 3H), 1.25-1.40 (m, 4H), 1.42-1.62 (m, 4H), 1.73-1.80 (m, 2H), 2.01-2.13 (m, 2H), 2.47-2.59 (m, 1H), 2.92-2.95 (m, 2H), 3.13 (s, 1H), 3.79-3.81 (m, 1H), 4.61 (t, J=12.0 Hz, 1H), 7.13-7.23 (m, 3H), 7.29-7.31 (m, 1H), 7.38 (d, J=7.2 Hz, 1H), 7.55 (t, J=8.0 Hz, 2H), 7.68 (s, 1H), 7.78 (d, J=7.6 Hz, 1H), 7.84 (d, J=7.6 Hz, 1H). nOe experiment:—Concluded as Trans Isomer.

Preparation of Compound 152

4-((1S,3S)-3-butyl-2-(2-chloroacetyl)-2,3,4,9-tetrahydro-1H-pyrido[3,4-b]indol-1-yl)-N-cyclobutylbenzenesulfonamide: To a solution of 4-((3S)-3-butyl-2,3,4,9-tetrahydro-1H-pyrido[3,4-b]indol-1-yl)-N-cyclobutylbenzenesulfonamide (polar isomer (trans) was used as a starting material) (60 mg, 0.137 mmol, 1 eq) in DCM (5 mL), was added triethyl amine (0.05 mL, 0.411 mmol, 3.0 eq) at 0° C., followed by 2-chloroacetyl chloride (0.015 mL, 0.191 mmol, 1.4 eq). The mixture was stirred at 0° C. for 20 minutes under $N_2$ atmosphere. TLC (40% EtOAc in hexane) showed the reaction was completed. Then the reaction was diluted with saturated aqueous solution of $NaHCO_3$ (5 mL) and was extracted with DCM (15 mL). The organic layer was dried over anhydrous $Na_2SO_4$, filtered and concentrated under reduced pressure to get the crude. The crude product was purified by preparative TLC using 45% EtOAc in n-Hexane as mobile phase to give compound 152. LC-MS (m/z): 514.2 [M+H]+. $^1H$ NMR (400 MHz, $CDCl_3$) δ ppm 0.77 (d, J=6.0 Hz, 3H), 1.21 (s, 4H), 1.42 (m, 2H), 1.67 (t, 2H), 1.82 (d, 2H), 3.05 (s, 1H), 3.51-3.53 (m, 1H), 4.46 (s, 2H), 4.66 (s, 1H), 5.95 (bs, 1H), 6.93-7.01 (m, 2H), 7.24 (d, J=7.6 Hz, 1H), 7.46 (d, J=8.0 Hz, 1H), 7.53 (d, J=6.4 Hz, 2H), 7.62 (s, 2H), 7.85 (d, J=6.4 Hz, 1H), 10.89 (s, 1H).

Procedure DP: Synthesis of Compound 220

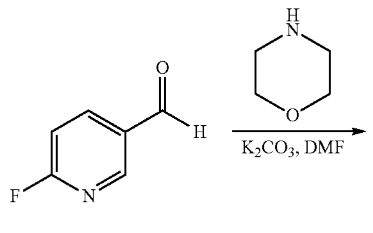

-continued

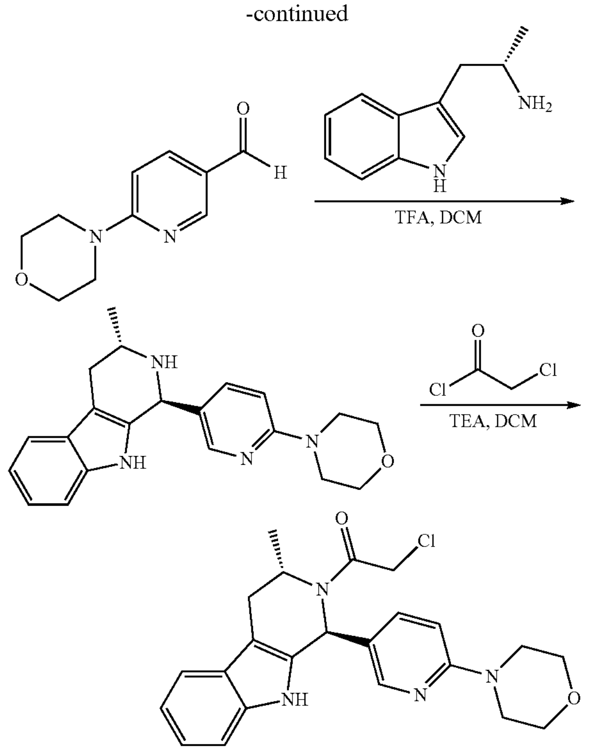

220

6-morpholinonicotinaldehyde: To a solution of 6-fluoronicotinaldehyde (0.5 g, 4 mmol, 1 eq) in DMF (15 mL) was added slowly $K_2CO_3$ (0.82 g, 6 mmol, 1.5 eq) and morpholine (0.4 mL, 4.8 mmol, 1.2 eq) at 0° C. The mixture was stirred at 110° C. for 16 h under $N_2$ atmosphere. TLC (50% EtOAc in hexane) showed the reaction was completed. The reaction was cooled to room temperature and was concentrated under reduced pressure, and then the crude was diluted with EtOAc (150 mL), washed with water (2×15 mL). The organic layer was dried over anhydrous $Na_2SO_4$, concentrated under reduced pressure to crude product, The crude was purified by flash chromatography using 20-25% EtOAc in hexane as an eluent to give 6-morpholinonicotinaldehyde. $^1H$ NMR (400 MHz, $CDCl_3$) δ ppm 3.66 (s, 8H), 6.92 (d, J=9.2 Hz, 1H), 7.87-7.89 (m, 2H), 9.73 (s, 1H).

4-(5-((1S,3S)-3-methyl-2,3,4,9-tetrahydro-1H-pyrido[3,4-b]indol-1-yl)pyridin-2-yl)morpholine: To a solution of (S)-1-(1-(1H-indol-3-yl)propan-2-amine (0.15 g, 0.860 mmol, 1 eq) in DCM (15.0 mL) was added 6-morpholinonicotinaldehyde (0.19 g, 1.032 mmol, 1.2 eq) and TFA (0.14 mL, 1.72 mmol, 2 eq). The mixture was stirred at room temperature for 16 h. TLC (5% MeOH in DCM) showed the reaction was completed. The reaction mixture was cooled to room temperature and diluted with ethyl acetate (100 mL) and washed with saturated NaaHCO3 solution (10 mL) and water (2×5 m). The organic layers were dried over $Na_2SO_4$ and concentrated to give the crude product. The crude product was purified by flash column chromatography using 3% MeOH in DCM as an eluent to give the product 4-(5-((1S,3S)-3-methyl-2,3,4,9-tetrahydro-1H-pyrido[3,4-b]indol-1-yl)pyridin-2-yl)morpholine. LC-MS (m/z)=349 $[M+H]^+$. $^1H$ NMR (400 MHz, DMSO-d6) δ 1.11-1.20 (m, 3H), 2.30-2.48 (m, 2H), 2.65-2.69 (m, 1H), 3.02-3.07 (m, 1H), 3.37-3.39 (m, 4H), 3.60-3.66 (m, 4H), 4.99 (s, 1H), 6.76 (d, J=8.8 Hz, 1H), 6.88-6.96 (m, 2H), 7.14 (d, J=8.0 Hz, 1H), 7.35-7.39 (m, 2H), 8.08 (s, 1H).

Preparation of Compound 220

2-chloro-1-((1S,3S)-3-methyl-1-(4-morpholinophenyl)-1,3,4,9-tetrahydro-2H-pyrido[3,4-b]indol-2-yl)-ethan-1-one: To a solution of 4-(5-((1S,3S)-3-methyl-2,3,4,9-tetrahydro-1H-pyrido[3,4-b]indol-1-yl)pyridin-2-yl)morpholine (0.085 g, 0.24 mmol, 1 eq) in CH2C12 (10.0 mL) was added TEA (0.1 mL, 0.73 mmol, 3.0 eq) at 0° C., stirred for 15 mins and then and 2-chloroacetyl chloride (0.03 mL, 0.36 mmol, 1.5 eq) was added at 0° C. The mixture was allowed to stir at room temperature for 1 hr. LCMS and TLC (40% EtOAc in hexane) showed the reaction was completed. The reaction mixture was diluted with saturated $NaHCO_3$solution (10 mL) and was extracted with DCM (2×50 mL). The organic layers were dried over $Na_2SO_4$ and concentrated to give the crude product. The crude product was purified by flash column chromatography using 30% EtOAc in hexane as an eluent to give 2-chloro-1-((1S,3S)-3-methyl-1-(4-morpholinophenyl)-1,3,4,9-tetrahydro-2H-pyrido[3,4-b]indol-2-yl)ethan-1-one. Trans geometry was confirmed by COSY and NOESY. LC-MS (m/z): 425 $[M+H]^+$. $^1H$ NMR (400 MHz, DMSO): δ 1.03-1.05 (m, 3H), 2.72-2.76 (m, 1H), 3.05-3.10 (m, 1H), 3.37-3.40 (m, 4H), 3.64-3.66 (m, 4H), 4.57 (s, 3H), 6.65 (bs, 1H), 6.76 (d, J=9.2 Hz, 1H), 6.97-7.00 (m, 1H), 7.05-7.09 (m, 1H), 7.30 (d, J=8.4 Hz, 1H), 7.42-7.46 (m, 2H), 8.08 (s, 1H).

A similar synthetic scheme was used to synthesize Compound 123, Compound 124, Compound 202, Compound 212 and Compound 174.

Compound 123

LC-MS (m/z): 417.9 $[M+H]^+$. $^1H$ NMR (400 MHz, DMSO-$d_6$): δ 0.94-0.95 (m, 3H), 2.70-2.74 (m, 1H), 3.11-3.14 (m, 1H), 4.63 (bs, 3H), 6.86 (bs, 1H), 7.00-7.10 (m, 2H), 7.31-7.35 (m, 3H), 7.48-7.50 (m, 3H), 7.76 (d, J=7.6 Hz, 2H), 11.05 (s, 1H).

Compound 124

LC-MS (m/z): 424.9 $[M+H]^+$. H NMR (400 MHz, DMSO-$d_6$): δ 1.02-1.04 (m, 3H), 1.11-1.13 (m, 3H), 2.85-2.89 (m, 2H), 3.16-3.20 (m, 2H), 3.31-3.38 (m, 6H), 3.62-3.65 (m, 8H), 4.34 (bs, 1H), 4.58 (s, 3H), 4.64-4.71 (m, 2H), 5.84 (bs, 1H), 6.65-6.76 (m, 2H), 6.78-6.92 (m, 1H), 7.00-7.09 (m, 3H), 7.10-7.19 (m, 1H), 7.20-7.22 (m, 1H), 7.24-7.29 (m, 1H), 7.31-7.46 (m, 3H), 8.07 (s, 1H), 8.14 (s, 1H), 10.86 (s, 1H), 10.95 (s, 1H).

Compound 202

LC-MS (m/z): 424.9 $[M+H]^+$. $^1H$ NMR (400 MHz, DMSO-$d_6$): δ 1.11-1.13 (m, 3H), 2.85-2.89 (m, 1H), 3.16-3.20 (m, 1H), 3.29 (s, 4H), 3.62 (s, 4H), 4.33 (bs, 1H), 4.64-4.71 (m, 2H), 5.84 (bs, 1H), 6.66 (d, J=8 Hz, 1H), 6.92-7.02 (m, 2H), 7.23 (d, J=8 Hz, 1H), 7.41-7.43 (m, 2H), 8.14 (s, 1H), 10.86 (s, 1H).

Compound 212

LC-MS (m/z): 452.3 $[M+H]^+$. $^1H$ NMR (400 MHz, DMSO-$d_6$): δ 1.21-1.25 (m, 6H), 1.29-1.31 (m, 3H), 2.36 (bs, 2H), 2.90-2.94 (m, 1H), 3.28-3.38 (m, 3H), 3.74 (bs,

2H), 3.95 (bs, 1H), 4.12 (bs, 1H), 4.90 (bs, 1H), 5.87 (s, 1H), 6.81 (bs, 2H), 7.08-7.15 (m, 2H), 7.19-7.25 (m, 3H), 7.50 (d, J=7.6 Hz, 1H), 7.60 (s, 1H).

Compound 174

LC-MS (m/z): 451.5 $[M+H]^+$. $^1H$ NMR (400 MHz, DMSO-$d_6$): δ 0.35-0.46 (m, 4H), 1.21-1.23 (m, 3H), 2.04-2.06 (m, 1H), 2.93-2.97 (m, 1H), 3.35-3.38 (m, 1H), 4.52 (bs, 1H), 5.19 (bs, 1H), 6.17 (s, 1H), 6.95-7.04 (m, 2H), 7.25-7.27 (m, 1H), 7.45-7.50 (m, 4H), 7.83 (s, 1H), 10.73 (s, 1H).

Procedure DQ: Synthesis of Compound 209
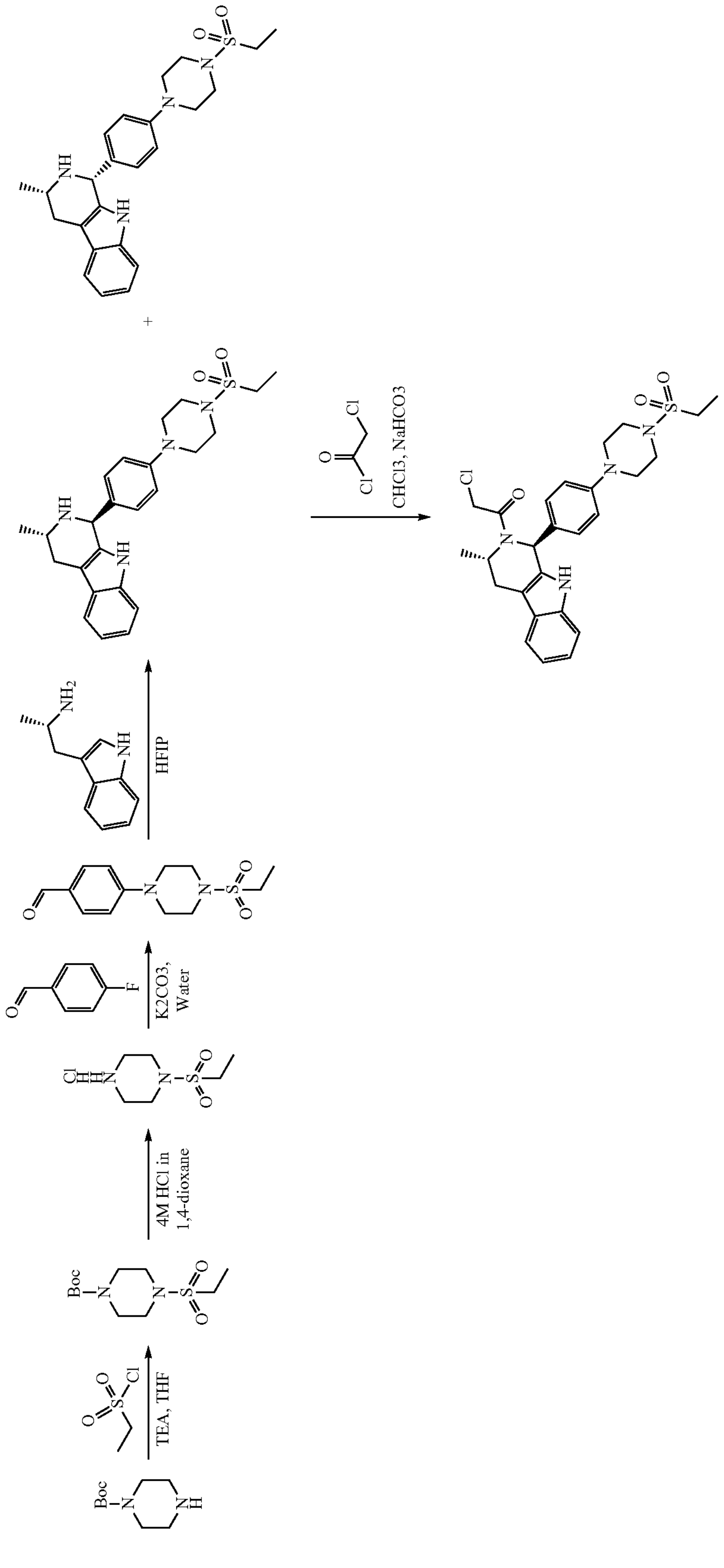
209 tert-butyl 4-(ethylsulfonyl)piperazine-1-carboxylate: Commercial 1-Boc-piperazine (3.0 g, 16.11 mmol, 1 eq) was dissolved in methylene chloride (30 mL), then to the reaction mixture, which was stirred at −40° C., were added triethylamine (5.61 mL, 40.26 mmol, 2.5 eq) and ethane sulfonyl chloride (1.83 mL, 19.33 mmol, 1.2 eq). The whole mixture was warmed up gradually and stirred for 14 hours. The whole mixture was poured into water and extracted with ethyl acetate. The organic layer of the extract was washed with dilute hydrochloric acid and saturated saline successively, then dried with sodium sulfate. The solvent was removed under reduced pressure and the residue was purified with silica-gel column chromatography to provide tert-butyl 4-(ethylsulfonyl)piperazine-1-carboxylate. $^1$H NMR (400 MHz, CDC13): 1.34-1.38 (m, 3H), 1.45 (s, 9H), 2.91-2.97 (m, 2H), 3.23-3.25 (m, 4H), 3.49-3.51 (m, 4H). 1-(ethylsulfonyl)piperazine hydrochloride: tert-butyl 4-(ethylsulfonyl)piperazine-1-carboxylate (3.82 g, 13.72 mmol, 1 eq) was dissolved in the methylene chloride (30 mL), then to the redaction mixture, which was stirred at room temperature, was added 4N hydrochloric acid (dioxane solvent) (15 mL). The whole mixture was stirred at room temperature for 12 hours, then the resulting product filtered to give 4-(4-(ethylsulfonyl)piperazin-1-yl)benzaldehyde. $^1$H-NMR (DMSO-$d_6$) δ: 1.19 (t, J=7.2 Hz, 3H), 3.13-3.15 (m, 6H), 3.39 (bs, 4H), 9.1 (bs, 2H).

4-(4-(ethylsulfonyl)piperazin-1-yl)benzaldehyde: To a solution of 6-fluoronicotinaldehyde (0.35 g, 2.8 mmol, 1 equiv) in water (15 mL) was added slowly K2CO3 (0.97 g, 7.05 mmol, 2 eq) and 1-(ethylsulfonyl)piperazine hydrochloride (0.66 g, 3.10 mmol) at 0° C. The mixture was stirred at 100° C. for 12 h under $N_2$ atmosphere. TLC (40% EtOAc in hexane) showed the reaction was completed. The reaction was cooled to room temperature and was concentrated under reduced pressure, and then the crude was diluted with EtOAc (150 mL), washed with water (2×15 mL). The organic layer was dried over anhydrous $Na_2SO_4$, concentrated under reduced pressure to crude product, The crude was purified by flash chromatography using 30% EtOAc in hexane as an eluent to give 4-(4-(ethylsulfonyl)piperazin-1-yl)benzaldehyde. $^1$H NMR (400 MHz, DMSO-d6) δ ppm 1.15-1.34 (m, 3H), 3.05-3.11 (m, 2H), 3.26-3.30 (m, 4H), 3.46-3.48 (m, 4H), 9.73 (s, 1H), 7.07 (d, J=8.8 Hz, 2H), 7.69 (d, J=9.6 Hz, 2H), 9.72 (s, 1H).

(3S)-1-(4-(4-(ethylsulfonyl)piperazin-1-yl)phenyl)-3-methyl-2,3,4,9-tetrahydro-1H-pyrido[3,4-b]indole (cis- and trans-): To a solution of (S)-1-(1H-indol-3-yl)propan-2-amine (0.090 g, 0.51 mmol, 1 eq) in HFIP (2.0 mL) was added 4-(4-(ethylsulfonyl)piperazin-1-yl)benzaldehyde (0.145 g, 0.51 mmol, 1 eq). The mixture was stirred at 80° C. for 12 h. TLC (5% MeOH in DCM) showed the reaction was completed. The reaction mixture was cooled to room temperature and diluted with ethyl acetate (10 mL) and washed with saturated NaaHCO3 solution (5 mL) and water (5 mL). The organic layers were dried over $Na_2SO_4$ and concentrated to give the crude product. The crude product was purified by flash column chromatography using 2-3% MeOH in DCM as an eluent to give the (1S,3S)-1-(4-(4-(ethylsulfonyl)piperazin-1-yl)phenyl)-3-methyl-2,3,4,9-tetrahydro-1H-pyrido[3,4-b]indole (trans, polar by TLC) and (1R,3S)-1-(4-(4-(ethylsulfonyl)piperazin-1-yl)phenyl)-3-methyl-2,3,4,9-tetrahydro-1H-pyrido[3,4-b]indole (Cis, non-polar by TLC).

Analytical data of trans compound: LC-MS (m/z)=439.3 $[M+H]^+$. $^1$H NMR (400 MHz, $CDCl_3$) δ 1.11-1.10 (m, 3H), 1.19-1.22 (m, 3H), 2.58 (s, 1H), 2.76-2.79 (m, 1H), 3.04-3.08 (m, 3H), 3.10-3.14 (m, 3H), 3.15-3.27 (m, 5H), 5.09 (bs, 1H), 6.88-6.99 (m, 3H), 7.01-7.06 (m, 2H), 7.21 (d, J=8 Hz, 1H), 7.38 (d, J=8.0 Hz, 1H), 10.60 (s, 1H).

Analytical data of cis compound: LC-MS (m/z)=439.3 $[M+H]^+$. $^1$H NMR (400 MHz, $CDCl_3$) δ 1.20-1.23 (m, 6H), 2.48-2.47 (m, 1H), 2.67-2.71 (m, 1H), 2.67-2.71 (m, 1H), 3.05-3.11 (m, 4H), 3.17-3.18 (m, 4H), 3.23-3.28 (m, 3H), 5.02 (bs, 1H), 6.87-6.95 (m, 4H), 7.15-7.20 (m, 3H), 7.34 (d, J=7.2 Hz, 1H), 10.11 (s, 1H).

Preparation of Compound 209

2-chloro-1-((1 S,3S)-1-(4-(4-(ethylsulfonyl)piperazin-1-yl)phenyl)-3-methyl-1,3,4,9-tetrahydro-2H-pyrido[3,4-b]indol-2-yl)ethan-1-one: (1S,3S)-1-(4-(4-(ethylsulfonyl)piperazin-1-yl)phenyl)-3-methyl-2,3,4,9-tetrahydro-1H-pyrido[3,4-b]indole (0.09 g, 0.20 mmol, 1 eq) in $CHCl_3$ (15.0 mL) was added $NaHCO_3$ (0.03 g, 0.41 mmol, 2.0 eq) at 0° C., stirred for 15 mins and then and 2-chloroacetyl chloride (0.02 mL, 0.24 mmol, 1.2 eq) was added at 0° C. The mixture was allowed to stir at room temperature for 2 hr. LCMS and TLC (5% MeOH in DCM) showed the reaction was completed. The reaction mixture was diluted with saturated $NaHCO_3$solution (10 mL) and was extracted with DCM (2×50 mL). The organic layers were dried over $Na_2SO_4$ and concentrated to give the crude product. The crude product was purified by flash column chromatography using 3% MeOH in DCM as an eluent to give 2-chloro-1-((1S,3S)-1-(4-(4-(ethylsulfonyl)piperazin-1-yl)phenyl)-3-methyl-1,3,4,9-tetrahydro-2H-pyrido[3,4-b]indol-2-yl)ethan-1-one. LC-MS (m/z): 515.4 $[M+H]^+$. $^1$H NMR (400 MHz, DMSO-d6): δ 1.11-1.09 (m, 3H), 1.20-1.21 (m, 3H), 2.88-3.02 (m, 1H), 3.09-3.11 (m, 3H), 3.18-3.22 (m, 4H), 3.23-3.24 (m, 4H), 3.28-3.38 (m, 2H), 4.62 (bs, 1H), 4.76 (bs, 1H), 5.89 (bs, 1H), 6.83-6.85 (m, 2H), 6.91-7.01 (m, 2H), 7.21-7.24 (m, 3H), 7.40 (d, J=8.0 Hz, 1H), 10.89 (s, 1H).

Procedure DR: Synthesis of Compound 171

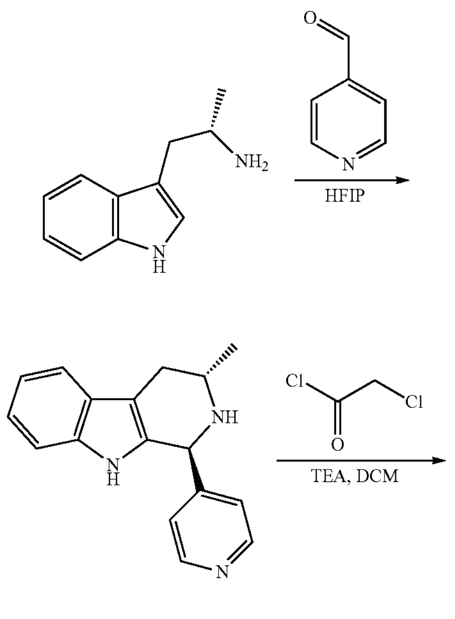

-continued

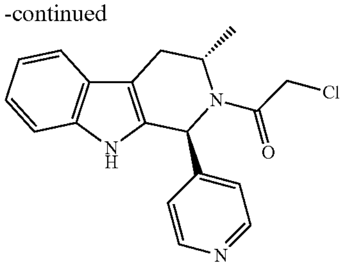

171

(3S)-3-methyl-1-(pyridin-4-yl)-2,3,4,9-tetrahydro-1H-pyrido[3,4-b]indole: To a solution of (S)-1-(1H-indol-3-yl) propan-2-amine (0.25 g, 0.94 mmol, 1 eq) in HFIP (3 mL) was added isonicotinaldehyde (0.1 mL, 1.03 mmol, 1.1 eq). The reaction mixture was stirred at 80° C. for 16 h. TLC (5% MeOH in DCM) showed the reaction was completed. The reaction was cooled to room temperature and was concentrated under reduced pressure. The crude was purified by flash chromatography using 2-3% MeOH in DCM as an eluent to give (3S)-3-methyl-1-(pyridin-4-yl)-2,3,4,9-tetrahydro-1H-pyrido[3,4-b]indole. LC-MS (m/z)=264.2 $[M+H]^+$. $^1H$ NMR (400 MHz, DMSO-d6) δ ppm 1.11 (s, 3H), 2.74 (d, J=14.8 Hz, 2H), 2.87 (s, 1H), 5.08 (s, 1H), 7.02-6.94 (m, 2H), 7.22 (s, 3H), 7.39 (s, 1H), 8.47 (s, 2H), 10.76 (s, 1H).

Preparation of Compound 171

2-chloro-1-((3S)-3-methyl-1-(pyridin-4-yl)-1,3,4,9-tetrahydro-2H-pyrido[3,4-b]indol-2-yl)ethan-1-one: To a solution of (3S)-3-methyl-1-(pyridin-4-yl)-2,3,4,9-tetrahydro-1H-pyrido[3,4-b]indole (0.1 g, 0.38 mmol, 1 eq) in DCM (5.0 mL) was added triethyl amine (0.1 mL, 0.95 mmol, 2.5 eq) at 0° C., stirred for 15 mins and then 2-chloroacetyl chloride (0.04 mL, 0.49 mmol, 1.3 eq) was added at 0° C. The mixture was stirred at room temperature for 2 h under $N_2$ atmosphere. TLC (5% MeOH in DCM) showed the reaction was completed. The reaction was cooled to room temperature and was diluted with ice cold water (5 mL) and was extracted with ethyl acetate (25 mL). The organic layer was dried over anhydrous $Na_2SO_4$, concentrated under reduced pressure to get the crude. The crude product was purified by preparative TLC using 2-4% MeOH in DCM as an eluent to get the product. Compound was further purified by Prep HPLC (Analytical condition: Column: Kinetex C18 (100 mm×4.6 mm×2.6 μm), mobile phase (A): 0.1% TFA in water, mobile phase (B): ACN, Flow rate: 0.75 mL/min, to give 2-chloro-1-((3S)-3-methyl-1-(pyridin-4-yl)-1,3,4,9-tetrahydro-2H-pyrido[3,4-b]indol-2-yl)ethan-1-one. LC-MS (m/z)=340.3$[M+H]^+$. $^1H$ NMR (400 MHz, DMSO-d6): δ 1.11 (d, J=6.0 Hz, 3H), 2.91-2.87 (m, 1H), 3.20-3.18 (m, 1H), 4.45 (s, 1H), 4.76 (s, 2H), 5.88 (s, 1H), 6.94 (t, J=7.6 Hz, 1H), 7.02 (t, J=6.8 Hz, 1H), 7.26 (d, J=7.6 Hz, 1H), 7.38 (s, 2H), 7.43 (d, J=7.6 Hz, 1H), 8.40 (s, 2H), 10.99 (s, 1H).

Procedure DS: Synthesis of Compound 127

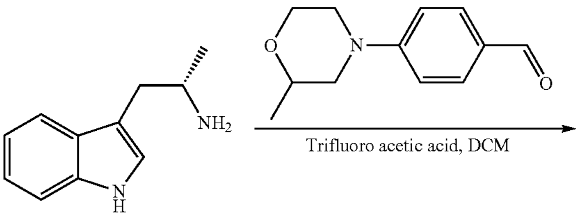

-continued

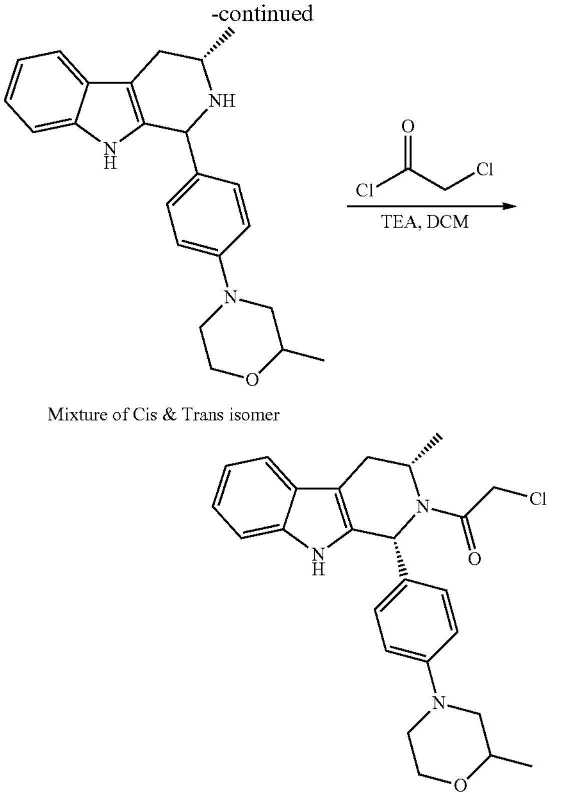

127

2-methyl-4-(4-((3S)-3-methyl-2,3,4,9-tetrahydro-1H-pyrido[3,4-b]indol-1-yl)phenyl)morpholine: To a stirred mixture of (S)-1-(1H-indol-3-yl)propan-2-amine (0.15 g, 0.860 mmol, 1 eq) and 4-(2-methylmorpholino)benzaldehyde (0.19 g, 0.946 mmol, 1.1 eq) in dichloromethane (5 mL) was added slowly trifluoro acetic acid (0.13 mL, 1.721 mmol, 2.0 eq) at 0° C. The mixture was allowed to warm to room temperature and stirred for 16 h under $N_2$ atmosphere. The progress of the reaction was monitored by TLC (5% Methanol in dichloromethane). The reaction mixture was diluted with dichloromethane (50 mL) and washed with saturated sodium bicarbonate (50 mL), brine (20 mL), dried over anhydrous $Na_2SO_4$, concentrated under reduced pressure to crude product, which was purified by flash column chromatography using 5% of methanol in dichloromethane as eluent to obtain 2-methyl-4-(4-((3S)-3-methyl-2,3,4,9-tetrahydro-1H-pyrido[3,4-b]indol-1-yl)phenyl)morpholine. LC-MS (m/z)=362.1 $[M+H]^+$ Preparation of Compound 127

2-chloro-1-((1R,3S)-3-methyl-1-(4-(2-methylmorpholino)phenyl)-1,3,4,9-tetrahydro-2H-pyrido[3,4-b]indol-2-yl)ethan-1-one: To a solution of 2-methyl-4-(4-((3S)-3-methyl-2,3,4,9-tetrahydro-1H-pyrido[3,4-b]indol-1-yl)phenyl)morpholine (0.08 g, 0.221 mmol, 1 eq) in dichloromethane (5 mL) was added triethylamine (0.093 mL, 0.664 mmol, 3 eq) at room temperature, the reaction mixture was allowed to cool to 0° C. and 2-chloroacetyl chloride (0.023 mL, 0.287 mml, 1.3 eq). The resulting mixture slowly allowed to warm to room temperature and stirred for 16 h. The progress of the reaction was monitored by TLC, after completion of reaction; the mixture was diluted with DCM (50 mL), washed with water (20 mL), brine (20 mL), dried over anhydrous $Na_2SO4$, filtered and concentrated to get the crude. The crude was purified by preparative TLC using 30% EtOAc in hexane as an eluent to give 2-chloro-1-((3S)-3-methyl-1-(4-(2-methylmorpholino)phenyl)-1,3,4,9-tetrahydro-2H-pyrido[3,4-b]indol-2-yl)ethan-1-one. LC-MS (m/z)=438.4 $[M+H]^+$; $^1H$ NMR (400 MHz, DMSO-d6) δ ppm 0.82-0.83 (m, 1H), 0.97 (d, J=6.8 Hz, 2H), 1.11 (d, J=5.2 Hz, 2H), 1.22 (bs, 1H), 2.23-2.26 (m, 1H), 2.57-2.60 (m, 1H), 2.68-2.72 (m, 1H), 3.07 (m, 1H), 3.43 (d, J=11.2 Hz, 1H), 3.51-3.60 (m, 3H), 3.87 (d, J=12.0 Hz, 1H), 4.57 (m, 3H), 6.76 (s, 1H), 6.85 (d, J=8.0 Hz, 2H), 6.98 (t, J=7.6 Hz, 1H), 7.07 (t, J=7.2 Hz, 1H), 7.15 (d, J=8.4 Hz, 2H), 7.30 (d, J=8.0 Hz, 1H), 7.44 (d, J=7.6 Hz, 1H), 10.97 (s, 1H).

give a yellow solution. The progress of the reaction was monitored by TLC. After completion of reaction, the reaction was diluted with ethyl acetate (500 mL), washed with saturated sodium bicarbonate solution (2×200 mL), water (200 mL), brine (100 mL), dried over anhydrous sodium sulphate, filtered and concentrated to give a crude product. The crude was purified by flash column chromatography using 10% methanol in dichloromethane as eluent to get mixture of isomers, later it was separated by using chiral HPLC method [Analytical conditions: Column: ChiralPak IA (100 mm×4.6 mm×3 μm), mobile phase: n-hexane: ethanol with 0.1% DEA (90:10), flow rate: 1.0 mL/min] to get 4-(4-((1R,3S)-3-methyl-2,3,4,9-tetrahydro-1H-pyrido[3,4-b]indol-1-yl)phenyl)morpholine (nonpolar spot by TLC Procedure DT: Alternative Synthesis of Compound 125 and Compound 103

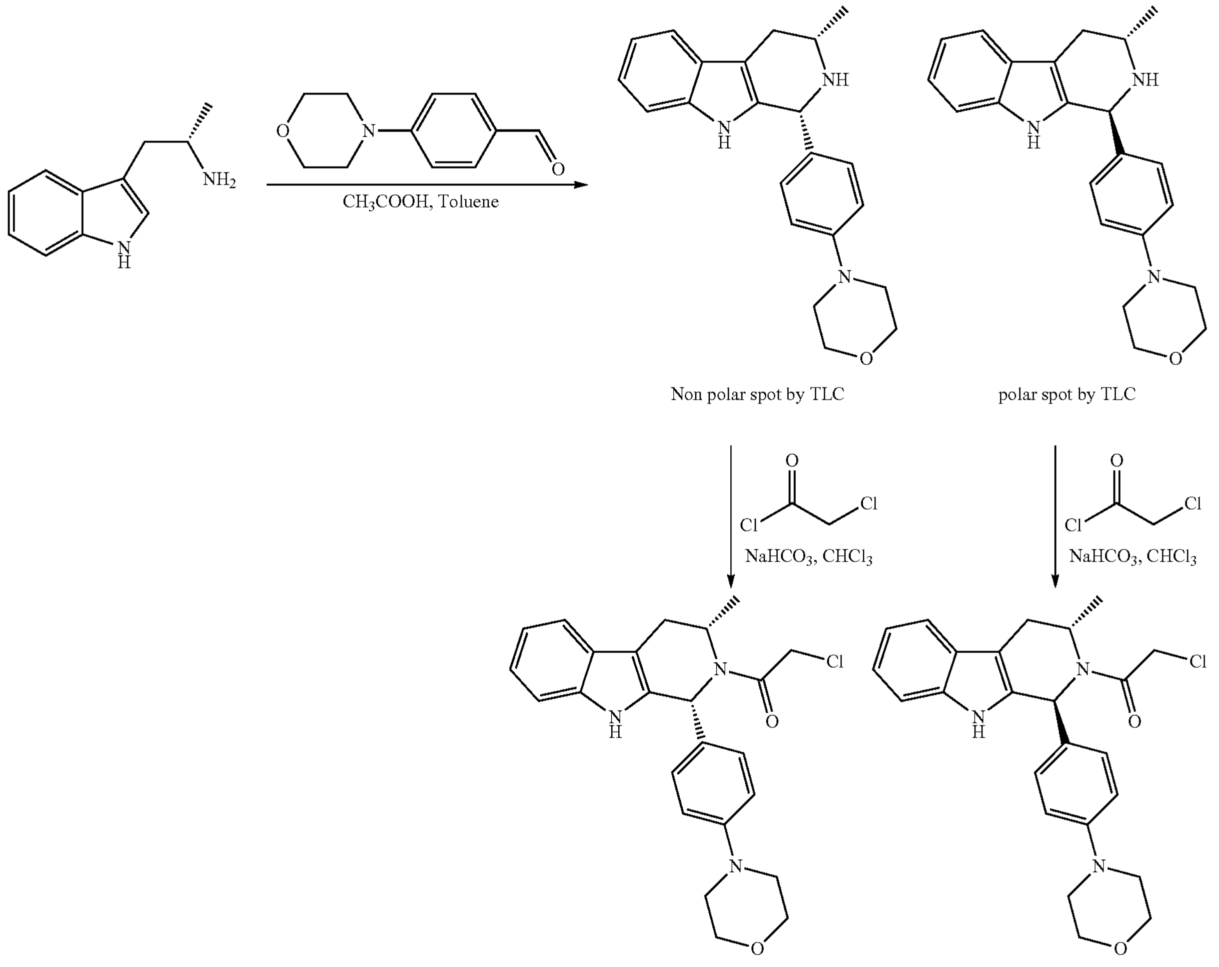

125

103

4-(4-((1R,3S)-3-methyl-2,3,4,9-tetrahydro-1H-pyrido[3,4-b]indol-1-yl)phenyl)morpholine & 4-(4-((1S,3S)-3-methyl-2,3,4,9-tetrahydro-1H-pyrido[3,4-b]indol-1-yl)phenyl)morpholine: To a stirred mixture of (S)-1-(1H-indol-3-yl)propan-2-amine (0.7 g, 4.017 μmol, 1 eq) in toluene (25 mL) was added 4-morpholinobenzaldehyde (0.77 g, 4.017 μmol, 1 eq). The mixture was allowed to cool to 0° C. and acetic acid (0.23 mL, 4.017 μmol, 1 eq) was added. The resulting mixture was gradually allowed to warm to room temperature, then heated to 120° C. and stirred for 12 h to compared to corresponding to other isomer) and 4-(4-((1S,3S)-3-methyl-2,3,4,9-tetrahydro-1H-pyrido[3,4-b]indol-1-yl)phenyl)morpholine (polar spot by TLC compared to corresponding to other isomer).

Analytical data of nonpolar spot: LC-MS (m/z)=348.1 $[M+H]^+$; $^1H$ NMR (400 MHz, $CDCl_3$) δ ppm 1.33 (d, J=6.00 Hz, 3H), 2.54-2.60 (m, 1H), 2.85-2.89 (m, 1H), 3.15 (bs, 4H), 3.28 (br s, 1H), 3.85 (bs, 4H), 5.16 (s, 1H), 6.88 (d, J=8.4 Hz, 2H), 7.07-7.20 (m, 3H), 7.28 (m, 2H), 7.39 (s, 1H), 7.50 (d, J=6.8 Hz, 1H). Structure elucidation was done by noe and cosy experiments.

Analytical data of polar spot: LC-MS (m/z)=348.2 $[M+H]^+$; $^1H$ NMR (400 MHz, $CDCl_3$) δ ppm 1.24 (d, J=5.2 Hz, 3H), 2.51-2.56 (m, 1H), 2.96 (d, J=12.8 Hz, 1H), 3.13 (bs, 4H), 3.32 (bs, 1H), 3.83 (bs, 4H), 5.18 (s, 1H), 6.83 (d, J=7.6 Hz, 2H), 7.12 (m, 4H), 7.25 (m, 1H), 7.53 (d, J=7.2 Hz, 1H), 7.66 (s, 1H). Structure elucidation by noe and cosy experiment.

Preparation of Compounds 125 and 103

2-chloro-1-((1R,3S)-3-methyl-1-(4-morpholinophenyl)-1,3,4,9-tetrahydro-2H-pyrido[3,4-b]indol-2-yl)ethan-1-one (125) & 2-chloro-1-((1S,3S)-3-methyl-1-(4-morpholinophenyl)-1,3,4,9-tetrahydro-2H-pyrido[3,4-b]indol-2-yl)ethan-1-one (103): To a stirred mixture of 4-(4-((1R,3S)-3-methyl-2,3,4,9-tetrahydro-1H-pyrido[3,4-b]indol-1-yl)phenyl) morpholine (0.2 g, 575 mmol, 1 eq) and sodium bicarbonate (0.096 g, 1.151 mmol, 2 eq) in chloroform (10 mL), was added 2-chloroacetyl chloride (0.08 mL, 1.036 mmol, 1.8 eq) at 0° C. under nitrogen atmosphere. The resulting mixture was allowed to warm to room temperature and stirred for 4 h. The progress of the reaction was monitored by TLC (30% ethyl acetate in dichloromethane). After completion of reaction, the mixture was diluted with dichloromethane (100 mL), washed with water (2×50 mL), dried over anhydrous sodium sulfate, filtered and concentrated under reduced pressure to get crude product. The crude product was purified flash column chromatography using 20% ethyl acetate in dichloromethane as eluent to obtain 2-chloro-1-((1R,3S)-3-methyl-1-(4-morpholinophenyl)-1,3,4,9-tetrahydro-2H-pyrido[3,4-b]indol-2-yl)ethan-1-one (125). LC-MS (m/z)=424.3 $[M+H]^+$; $^1H$ NMR (400 MHz, DMSO-d6) δ ppm 0.96 (d, J=6.4 Hz, 3H), 2.70 (d, J=16.0 Hz, 1H), 3.05 (bs, 5H), 3.69 (bs, 4H), 4.58 (m, 3H), 6.76 (s, 1H), 6.86 (d, J=8.0 Hz, 2H), 6.98 (t, J=7.6 Hz, 1H), 7.07 (t, J=7.2 Hz, 1H), 7.16 (d, J=8.4 Hz, 2H), 7.30 (d, J=8.0 Hz, 1H), 7.44 (d, J=7.6 Hz, 1H), 11.00 (s, 1H).

Procedure similar to above provided 2-chloro-1-((1S,3S)-3-methyl-1-(4-morpholinophenyl)-1,3,4,9-tetrahydro-2H-pyrido[3,4-b]indol-2-yl)ethan-1-one (103): LC-MS (m/z)=424.3 $[M+H]^+$; $^1H$ NMR (400 MHz, DMSO-d6) δ ppm 1.10 (d, J=6.4 Hz, 3H), 2.86 (d, J=15.2 Hz, 1H), 3.00 (s, 4H), 3.10 (bs, 1H), 3.66 (s, 4H), 4.31 (bs, 1H), 4.62 (bs, 1H), 4.76 (bs, 1H), 5.90 (bs, 1H), 6.82 (m, 2H), 6.92 (t, J=7.2 Hz, 1H), 6.99 (t, J=7.2 Hz, 1H), 7.20-7.24 (m, 3H), 7.40 (d, J=8.0 Hz, 1H), 10.88 (s, 1H).

Procedure DU: Synthesis of Compound 127 and Compound 215

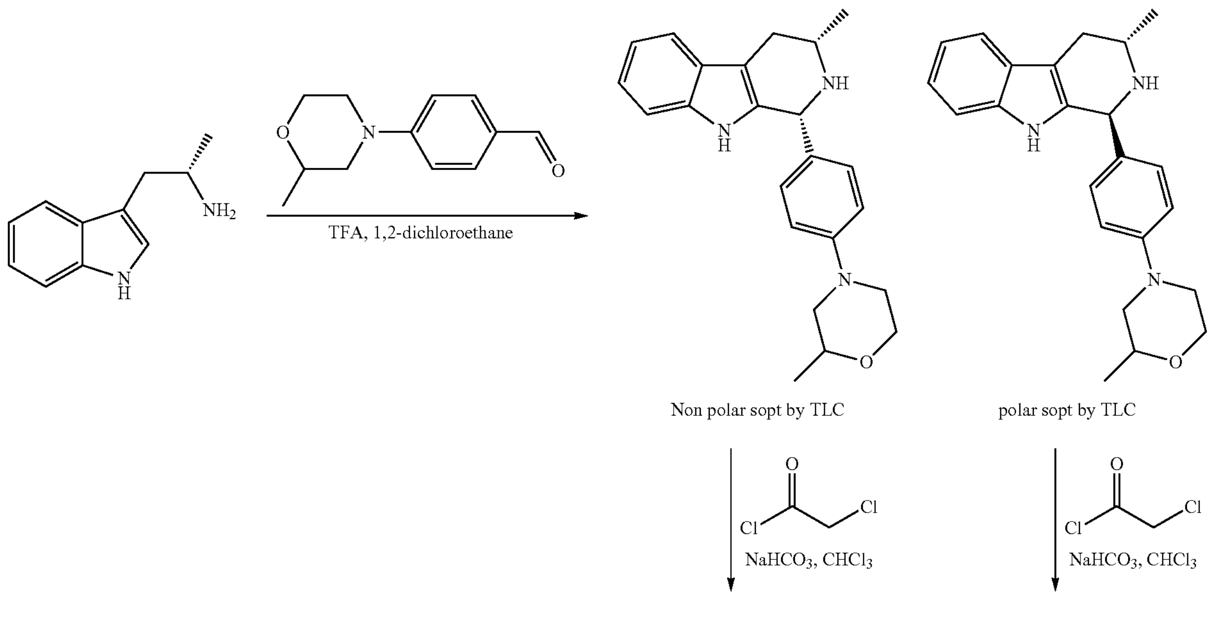

-continued

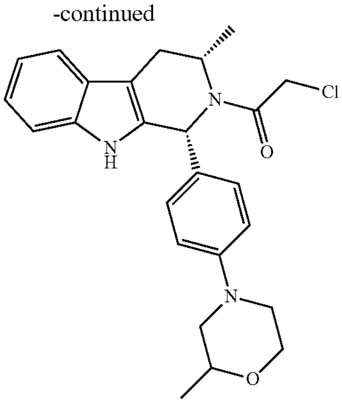

Non polar sopt by TLC
127

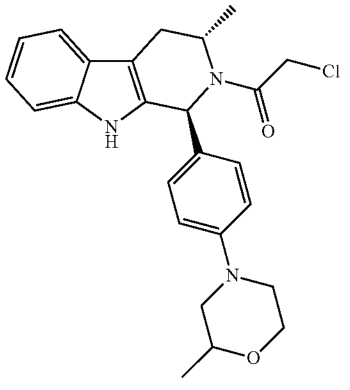

polar sopt by TLC
215 methyl-4-(4-((1R,3S)-3-methyl-2,3,4,9-tetrahydro-1H-pyrido[3,4-b]indol-1-yl)phenyl)morpholine & 2-methyl-4-(4-((1S,3S)-3-methyl-2,3,4,9-tetrahydro-1H-pyrido[3,4-b]indol-1-yl)phenyl)morpholine: In a seal tube, to a stirred mixture of (S)-1-(1H-indol-3-yl)propan-2-amine (0.2 g, 1.147 mmol, 1 eq) and 4-(2-methylmorpholino)benzaldehyde (0.23 g, 1.147 mmol, 1.0 eq) in 1,2 dichloro ethane (10 mL) was added trifluoro acetic acid (0.17 mL, 2.295 mmol, 2 eq) at 0° C. under $N_2$ atmosphere. The seal tube was closed and the mixture was heated to 80° C. for 12 h. The progress of the reaction was monitored by TLC (5% methanol in dichloromethane). After completion of reaction, the reaction was allowed to cool to room temperature and poured on to saturated sodium bicarbonate solution (50 mL). The mixture was extracted with ethyl acetate (2×50 mL). The combined organics were washed with water (2×50 mL), brine (20 mL), dried over anhydrous sodium sulfate, filtered and concentrated under reduced pressure. The crude was purified by flash column chromatography using 6% methanol in dichloromethane as eluent to obtain pure 2 isomers, 2-methyl-4-(4-((1R,3S)-3-methyl-2,3,4,9-tetrahydro-1H-pyrido[3,4-b]indol-1-yl)phenyl)morpholine (nonpolar spot by TLC compared to corresponding to other isomer) and 2-methyl-4-(4-((1S,3S)-3-methyl-2,3,4,9-tetrahydro-1H-pyrido[3,4-b]indol-1-yl)phenyl)morpholine (polar spot by TLC compared to corresponding to other isomer). Analytical data of nonpolar spot: LC-MS (m/z)=362.1 $[M+H]^+$; Analytical data of polar spot: LC-MS (m/z)=362.3 $[M+H]^+$.

Preparation of Compounds 127 and 215

2-chloro-1-((1R,3S)-3-methyl-1-(4-(2-methylmorpholino)phenyl)-1,3,4,9-tetrahydro-2H-pyrido[3,4-b]indol-2-yl)ethan-1-one: To a stirred mixture of 2-methyl-4-(4-((1R,3S)-3-methyl-2,3,4,9-tetrahydro-1H-pyrido[3,4-b]indol-1-yl)phenyl)morpholine (0.15 g, 0.465 mmol, 1 eq) and sodium bicarbonate (0.078 g, 0.93 mmol, 2 eq) in chloroform (10 mL), was added 2-chloroacetyl chloride (0.055 mL, 0.697 mmol, 1.5 eq) at 0° C. under nitrogen atmosphere. The resulting mixture was allowed to warm to room temperature and stirred for 3 h. The progress of the reaction was monitored by TLC (30% ethyl acetate in hexane). After completion of reaction, the mixture was diluted with dichloromethane (100 mL), washed with water (2×50 mL), dried over anhydrous sodium sulfate, filtered and concentrated under reduced pressure to get crude product. The crude product was purified flash column chromatography using 28% ethyl acetate in hexane as eluent to obtain title compound 2-chloro-1-((1R,3S)-3-methyl-1-(4-(2-methylmorpholino)phenyl)-1,3,4,9-tetrahydro-2H-pyrido[3,4-b]indol-2-yl)ethan-1-one (127). LC-MS (m/z)=438.1 $[M+H]^+$; $^1H$ NMR (400 MHz, $CDCl_3$): δ ppm 1.20-1.25 (m, 6H), 2.49 (t, J=10.8 Hz, 1H), 2.85 (d, J=15.2 Hz, 2H), 3.16-3.21 (m, 1H), 3.39-3.47 (m, 2H), 3.80 (bs, 2H), 4.00 (d, J=9.2 Hz, 1H), 4.21 (s, 2H), 4.60 (bs, 1H), 6.80 (bs, 3H), 7.13-7.23 (m, 2H), 7.31-7.37 (m, 3H), 7.53 (d, J=7.2 Hz, 1H), 7.81 (s, 1H). Chiral HPLC purity 41.83: 55.88.

A similar synthetic scheme was used to synthesize compound 215. LC-MS (m/z): 438.3 $[M+H]^+$. $^1H$ NMR (400 MHz, DMSO-$d_6$): δ 1.21 (d, J=6.0 Hz, 3H), 1.30 (d, J=6.0 Hz, 3H), 2.44 (t, J=11.2 Hz, 1H), 2.78-2.81 (m, 1H), 2.92 (d, J=15.2 Hz, 1H), 3.28-3.42 (m, 3H), 3.70-3.76 (m, 2H), 3.95-3.98 (m, 2H), 4.12 (m, 1H), 4.91 (bs, 1H), 5.87 (s, 1H), 6.80 (d, J=7.6 Hz, 2H), 7.08-7.13 (m, 2H), 7.15-7.25 (m, 3H), 7.50 (d, J=7.6 Hz, 1H), 7.58 (s, 1H).

Procedure DV: Synthesis of Compound 172

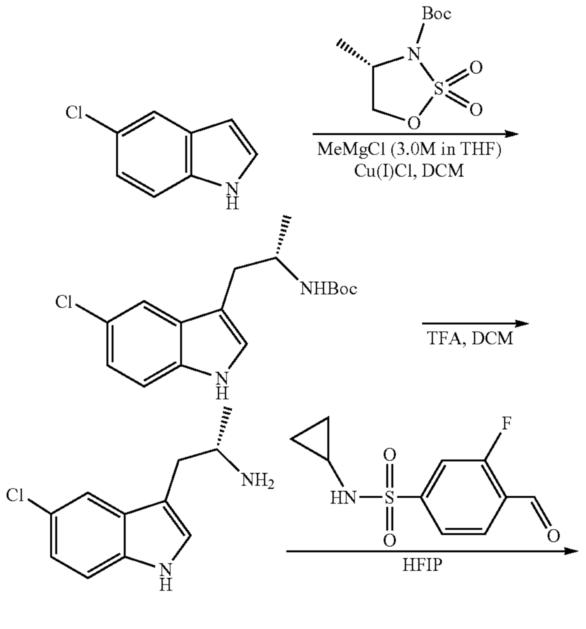

-continued

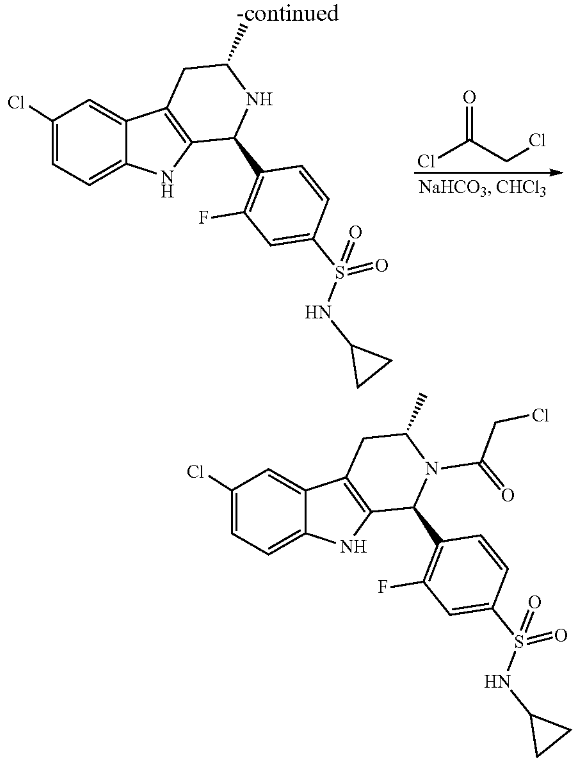

compound 172 tert-butyl (S)-(1-(5-chloro-1H-indol-3-yl)propan-2-yl) carbamate: The 5-chloro-1H-indole (0.3 g, 1.979 mmol, 1 eq) and cuprous chloride (0.25 g, 2.572 mmol, 1.3 eq) were taken in round bottom flask and was purged with argon, then dichloromethane (10 mL) was added and the reaction mixture was cooled to 0° C. Then, MeMgCl (3M in THF) (0.85 mL, 2.572 mmol, 1.3 eq) was added drop wise over a period of 5 min. The reaction mixture was stirred for 1 h at 0° C. After 1 h, a solution of tert-butyl (S)-4-methyl-1,2,3-oxathiazolidine-3-carboxylate 2,2-dioxide (0.33 g, 1.385 mmol, 0.7 eq) in dichloromethane (3 mL) was added at −20° C. drop wise. The resulting mixture was stirred for 6 h at −20° C. After 6 h, the reaction was quenched with 10% citric acid solution at −20° C. and the mixture was allowed to warm to room temperature, filtered the mixture through celite pad, washed the celite pad with dichloromethane, The organic layer was separated and the aqueous layer was extracted with dichloromethane (2×20 mL). The combined organics were washed with brine (20 mL), dried over anhydrous sodium sulfate, filtered and concentrated to give the crude product, which was purified by flash column chromatography using 20% ethyl acetate in hexane as an eluent to obtain tert-butyl (S)-(1-(5-chloro-1H-indol-3-yl)propan-2-yl)carbamate. LC-MS (m/z)=253.1 [$(M+H)^+$- t-butyl group]. $^1$H NMR (400 MHz, DMSO-d6) δ ppm 0.98 (d, J=6.0 Hz, 3H), 1.32 (s, 9H), 2.62-2.65 (m, 1H), 2.73-2.78 (m, 1H), 3.62-3.69 (m, 1H), 6.72 (d, J=7.6 Hz, 1H), 7.01 (d, J=8.4 Hz, 1H), 7.15 (s, 1H), 7.30 (d, J=8.4 Hz, 1H), 7.54 (s, 1H), 10.97 (s, 1H).

(S)-1-(5-chloro-1H-indol-3-yl)propan-2-amine: To a solution of tert-butyl (S)-(1-(5-chloro-1H-indol-3-yl)propan-2-yl)carbamate (0.2 g, 0.647 mmol, 1 eq) in dichloromethane (2.0 mL) was added trifluoroacetic acid (0.5 mL) at 0° C. The mixture was allowed to stir at room temperature for 3 h. The progress of the reaction was monitored by TLC, after completion of reaction; the reaction mixture was concentrated under reduced pressure. The obtained crude was dissolved with ice cold water (5 mL) and was basified by 5% sodium hydroxide solution (pH adjusted to 9). The compound was extracted with dichloromethane (3×20 mL). The combined organics were washed with brine (10 mL), dried over anhydrous sodium sulfate, filtered and concentrated to obtain (S)-1-(5-chloro-1H-indol-3-yl)propan-2-amine. LC-MS (m/z)=209.1 $[M+H]^+$; $^1$H NMR (400 MHz, DMSO-d6) δ ppm 0.93 (d, J=5.6 Hz, 3H), 2.58 (d, J=6.0 Hz, 2H), 2.99-3.035 (m, 1H), 7.01 (d, J=8.0 Hz, 1H), 7.18 (s, 1H), 7.31 (d, J=8.4 Hz, 1H), 7.53 (s, 1H), 10.99 (s, 1H), (Note: $NH_2$ peaks were not detected in NMR). 4-((1S,3S)-6-chloro-3-methyl-2,3,4,9-tetrahydro-1H-pyrido[3,4-b]indol-1-yl)-N-cyclopropyl-3-fluorobenzenesulfonamide: In a seal tube, (S)-1-(5-chloro-1H-indol-3-yl)propan-2-amine (0.15 g, 0.718 mmol, 1 eq), N-cyclopropyl-3-fluoro-4-formylbenzenesulfonamide (0.17 g, 0.178 mmol, 1.0 eq) and hexafluoro-2-propanol (HFIP) (2.0 mL) were taken. The seal tube closed and the mixture was heated to 80° C. and stirred for 16 h. The progress of the reaction was monitored by TLC (5% methanol in dichloromethane), the reaction was cooled to room temperature, concentrated under reduced pressure to obtain crude, which was purified by flash column chromatography using 4% methanol in dichloromethane as an eluent to obtain 4-((1S,3S)-6-chloro-3-methyl-2,3,4,9-tetrahydro-1H-pyrido[3,4-b]indol-1-yl)-N-cyclopropyl-3-fluorobenzenesulfonamide. The isolated product was treated with metal scavenger quadrasil TA (compound was dissolved with THF (10 mL) and quadrasil TA (3 g) was added, the mixture was stirred for 1 h, filtered. This is repeated one more time and concentrated). LC-MS (m/z)=432.2 $[M+H]^+$.

Preparation of Compound 172

4-((1S,3S)-6-chloro-2-(2-chloroacetyl)-3-methyl-2,3,4,9-tetrahydro-1H-pyrido[3,4-b]indol-1-yl)-N-cyclopropyl-3-fluorobenzenesulfonamide: To a stirred solution of 4-((1S,3S)-6-chloro-3-methyl-2,3,4,9-tetrahydro-1H-pyrido[3,4-b]indol-1-yl)-N-cyclopropyl-3-fluorobenzenesulfonamide (0.035 g, 0.080 mmol, 1 eq) and sodium bicarbonate (0.02 g, 0.242 mmol, 3.0 eq) in chloroform was added 2-chloroacetyl chloride (0.011 mL, 0.145 mmol, 1.8 eq) at 0° C. The mixture was gradually allowed to warm to room temperature and stirred for 2.5 h. The progress of the reaction was monitored by TLC (40% ethyl acetate in hexane). After completion of reaction, the reaction mixture was diluted with dichloromethane (30 mL), washed with water (2×20 mL), dried over anhydrous sodium sulfate, filtered and concentrated under reduced pressure to obtain crude product. which was purified by flash column chromatography using 40% ethyl acetate in hexane as an eluent to obtain 4-((1S,3S)-6-chloro-2-(2-chloroacetyl)-3-methyl-2,3,4,9-tetrahydro-1H-pyrido[3,4-b]indol-1-yl)-N-cyclopropyl-3-fluorobenzenesulfonamide. LC-MS (m/z): 510.2 $[M+H]^+$; $^1$H NMR (400 MHz, DMSO-d6): δ 0.34 (d, J=3.2 Hz, 2H), 0.44 (d, J=4.4 Hz, 2H), 1.13 (d, J=6.4 Hz, 3H), 2.02 (m, 1H), 2.92 (d, J=15.2 Hz, 1H), 3.23 (m, 1H), 4.43 (d, J=12.4 Hz, 1H), 4.69-4.76 (m, 2H), 6.14 (s, 1H), 7.02 (dd, J=1.6 Hz, 8.8 Hz, 1H), 7.25 (d, J=8.8 Hz, 1H), 7.39-7.45 (m, 2H), 7.50-7.54 (m, 2H), 7.97 (d, J=2.8 Hz, 1H), 11.04 (s, 1H).

Procedure DX: Synthesis of Compound 151

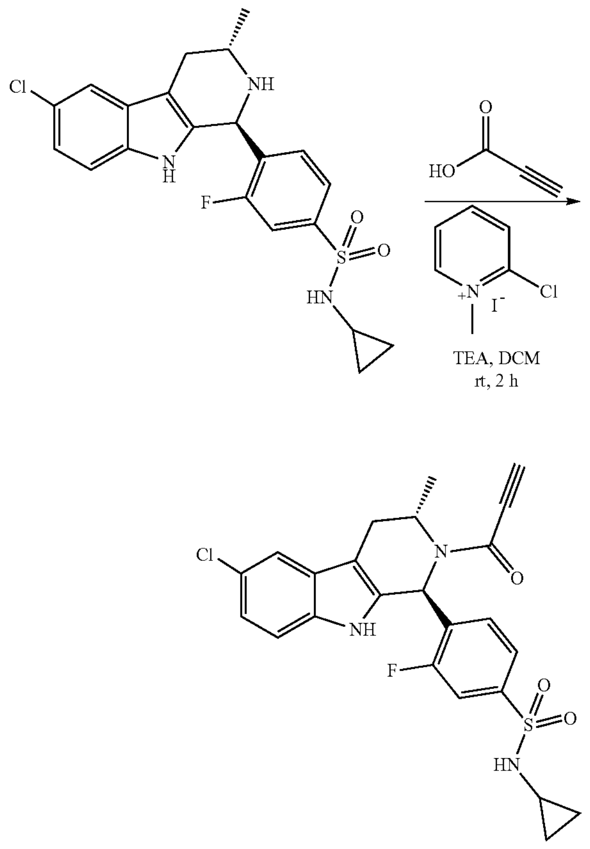

Compound 151

4-((1S,3S)-6-chloro-3-methyl-2-propioloyl-2,3,4,9-tetrahydro-1H-pyrido[3,4-b]indol-1-yl)-N-cyclopropyl-3-fluorobenzenesulfonamide: To a stirred mixture of 4-((1S,3S)-6-chloro-3-methyl-2,3,4,9-tetrahydro-1H-pyrido[3,4-b]indol-1-yl)-N-cyclopropyl-3-fluorobenzenesulfonamide (0.04 g, 0.092 mmol, 1 eq), in dichloromethane (3 mL) was added triethylamine (0.03 mL, 0.221 mmol, 2.4 eq), propiolic acid (0.005 mL, 0.092 mmol, 1 eq) and followed by the addition of 2-Chloro-1-methylpyridinium iodide (0.028 g, 0.11 mmol, 1.2 eq) at room temperature. The mixture was stirred for 10 min. The progress of the reaction was monitored by TLC (40% ethyl acetate in hexane). After completion of reaction, the mixture was diluted with dichloromethane (20 mL), washed with water (20 mL), brine (10 mL), dried over anhydrous sodium sulfate, filtered and concentrated under reduced pressure to obtain crude product. which was purified by preparative TLC using 40% ethyl acetate in hexane as an eluent to obtain 4-((1S,3S)-6-chloro-3-methyl-2-propioloyl-2,3,4,9-tetrahydro-1H-pyrido[3,4-b]indol-1-yl)-N-cyclopropyl-3-fluorobenzenesulfonamide. LC-MS (m/z): 486.0 $[M+H]^+$; $^1H$ NMR (400 MHz, DMSO-d6, at 70° C.): δ 0.36 (bs, 2H), 0.46 (m, 2H), 1.22 (d, J=6.8 Hz, 3H), 2.10 (s, 1H), 2.97 (d, J=16.0 Hz, 1H), 3.31 (bs, 1H), 4.51 (bs, 1H), 5.19 (bs, 1H), 6.18 (s, 1H), 7.04 (d, J=8.4 Hz, 1H), 7.27 (s, 1H), 7.46-7.52 (m, 4H), 7.81 (s, 1H), 10.94 (s, 1H).

Procedure DY: Synthesis of Compound 168

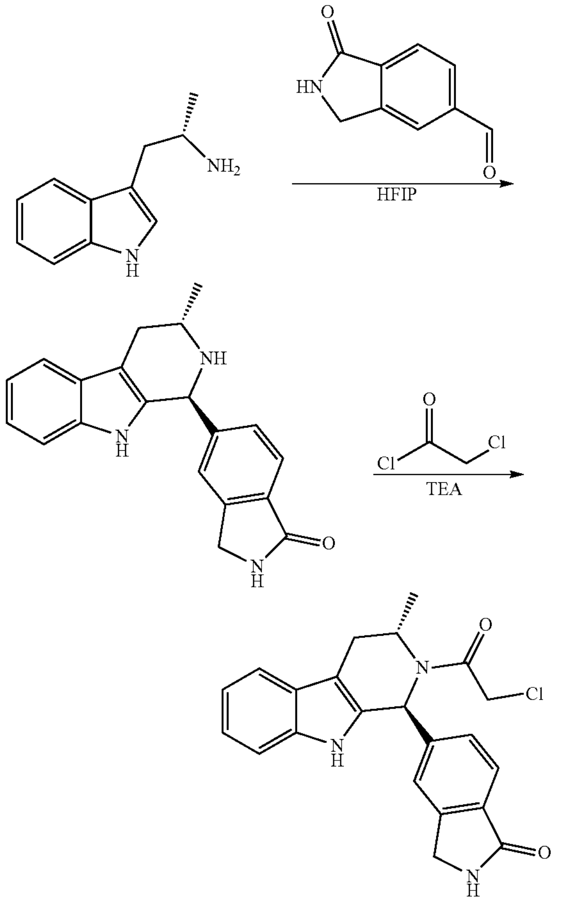

Compound 168

5-((1S,3S)-3-methyl-2,3,4,9-tetrahydro-1H-pyrido[3,4-b]indol-1-yl)isoindolin-1-one: In a seal tube, (S)-1-(1H-indol-3-yl)propan-2-amine (0.3 g, 1.721 mmol, 1 eq), 1-oxoisoindoline-5-carbaldehyde (0.27 g, 1.721 mmol, 1.0 eq) and hexafluoro-2-propanol (HFIP) (1.0 mL) were taken and the seal tube was closed. The mixture was heated to 80° C. and stirred for 16 h. The progress of the reaction was monitored by TLC (10% methanol in dichloromethane), the reaction was cooled to room temperature, concentrated under reduced pressure to obtain crude, which was purified by flash column chromatography using 15% methanol in dichloromethane as an eluent to obtain 5-((1S,3S)-3-methyl-2,3,4,9-tetrahydro-1H-pyrido[3,4-b]indol-1-yl)isoindolin-1-one. LC-MS (m/z)=318.2 [M+H]+.

Preparation of Compound 168

5-((1S,3S)-2-(2-chloroacetyl)-3-methyl-2,3,4,9-tetrahydro-1H-pyrido[3,4-b]indol-1-yl)isoindolin-1-one: To a stirred solution of 5-((1S,3S)-3-methyl-2,3,4,9-tetrahydro-1H-pyrido[3,4-b]indol-1-yl)isoindolin-1-one (0.04 g, 0.126 mmol, 1.0 eq) and triethylamine (0.053 g, 0.378 mmol, 3.0 eq) in chloroform was added 2-chloroacetyl chloride (0.02 mL, 0.252 mmol, 2.0 eq) at 0° C. The mixture was gradually allowed to warm to room temperature and stirred for 4 h. The progress of the reaction was monitored by TLC (10% methanol in dichloromethane). After completion of reaction, the reaction mixture was diluted with dichloromethane (30 mL), washed with water (2×20 mL), dried over anhydrous sodium sulfate, filtered and concentrated under reduced pressure to obtain crude product. This was purified by flash column chromatography using 6% methanol in dichloromethane as an eluent. The isolated product was re-purified by preparative HPLC [Analytical Conditions: column: Inertsil ODS 3V (150 mm×4.6 mm×5 μM), mobile phase (A): 0.1% ammonia in water, mobile phase (B): acetonitrile, flow rate: 1.0 mL/min. Composition of B: 0/20,3/20,7/80,17/80, 18/20,20/20] to obtain 5-((1S,3S)-2-(2-chloroacetyl)-3-methyl-2,3,4,9-tetrahydro-1H-pyrido[3,4-b]indol-1-yl) isoindolin-1-one. LC-MS (m/z): 394.3 $[M+H]^+$; $^1H$ NMR (400 MHz, DMSO-d6): δ 1.13 (d, J=6.4 Hz, 3H), 2.90 (d, J=14.8 Hz, 1H), 3.32 (m, 1H), 4.22-4.32 (m, 2H), 4.42 (bs, 1H), 4.79 (bs, 2H), 6.01 (bs, 1H), 6.91-7.02 (m, 2H), 7.23 (d, J=8.0 Hz, 1H), 7.42 (d, J=7.6 Hz, 1H), 7.53 (bs, 3H), 8.43 (s, 1H), 10.94 (s, 1H).

Procedure DZ: Synthesis of Compound 166

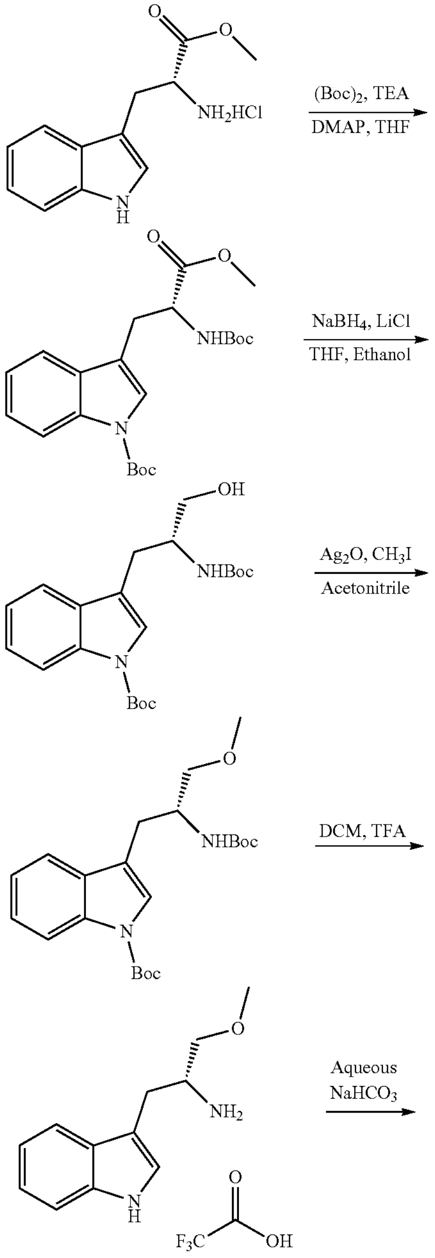

-continued

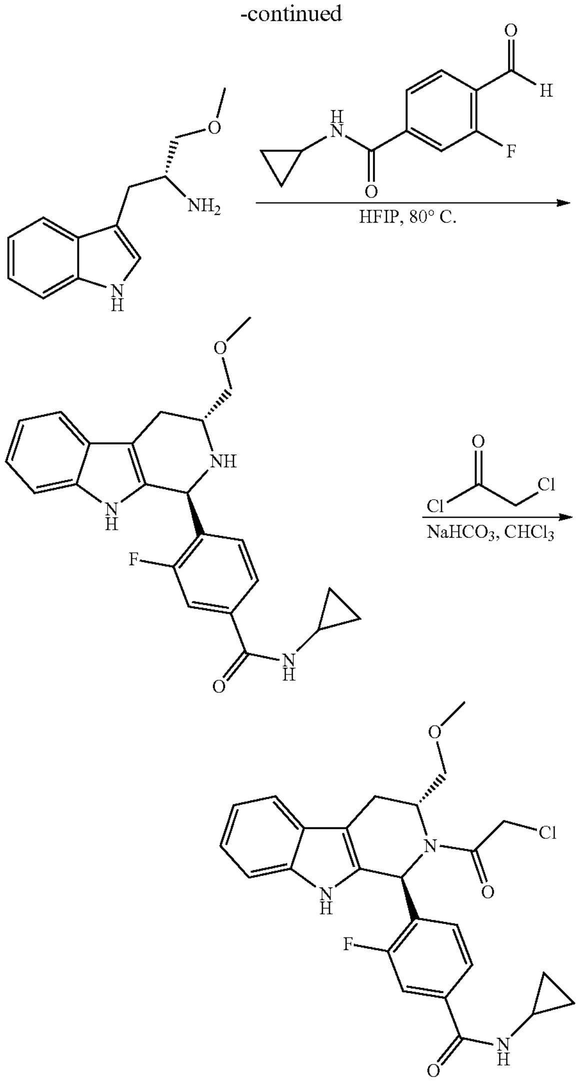

Compound 166 tert-butyl (R)-3-(2-((tert-butoxycarbonyl)amino)-3-methoxy-3-oxopropyl)-1H-indole-1-carboxylate: To a solution of methyl D-tryptophanate hydrochloride (5.0 g, 19.63 mmol, 1 eq) in tetrahydrofuran was added triethylamine (2.75 mL, 19.63 mmol, 1 eq) and 4-dimethylaminopyridine (3.59 g, 29.44 mmol, 1.5 eq) at room temperature. The mixture was allowed to cool to 0° C. and di-tert-butyl dicarbonate (11.27 mL, 49.075 mmol, 2.5 eq) was added at 0° C. slowly. The resulting mixture was allowed to warm to room temperature and stirred for 16 h. The progress of the reaction was monitored by TLC (30% ethyl acetate in hexane). After completion of reaction, the mixture was diluted with water (20 mL), extracted with ethyl acetate (2×150 mL). The combined organic layer were washed with water (40 mL), brine (20 mL), dried over anhydrous sodium sulfate, filtered and concentrated under reduced pressure. The crude product was purified by flash column chromatography using 20% ethyl acetate in hexane as an eluent to obtain tert-butyl (R)-3-(2-((tert-butoxycarbonyl)amino)-3-methoxy-3-oxopropyl)-1H-indole-1-carboxylate. $^1H$ NMR (400 MHz, DMSO-d6) δ ppm 1.36 (s, 9H), 1.60 (s, 9H), 2.93-2.99 (m, 1H), 3.06-3.08 (m, 1H), 3.61 (s, 3H), 4.25 (bs, 1H), 7.23-7.35 (m, 3H), 7.49-7.54 (m, 2H), 8.00-8.02 (m, 1H).

tert-butyl (R)-3-(2-((tert-butoxycarbonyl)amino)-3-hydroxypropyl)-1H-indole-1-carboxylate: To a stirred solution of tert-butyl (R)-3-(2-((tert-butoxycarbonyl)amino)-3-methoxy-3-oxopropyl)-1H-indole-1-carboxylate (0.2 g, 0.477 mmol 1 eq) in tetrahydrofuran (5 mL) was added lithium chloride (0.05 g, 1.19 mmol, 2.5 eq) at room temperature. The mixture was allowed to cool to 0° C. and sodium borohydride (0.045 g, 1.19 mmol, 2.5 eq). The resulting mixture was allowed to warm to room temperature and stirred for 10 min, and then ethanol (5 mL) was added and stirred for 14 h. The progress of the reaction was monitored by TLC (30% ethyl acetate in hexane). After completion of reaction, the reaction mixture was quenched with saturated aqueous ammonium chloride and extracted with ethyl acetate (2×10 mL). The combined organic layers were washed with water (5 mL), brine (2 mL), dried over anhydrous sodium sulfate, filtered and concentrated under reduced pressure to obtain crude. The crude was purified by flash column chromatography using 25% ethyl acetate in hexane as an eluent to obtain tert-butyl (R)-3-(2-((tert-butoxycarbonyl)amino)-3-hydroxypropyl)-1H-indole-1-carboxylate. LC-MS (m/z)=391.3 $[M+H]^+$; $^1H$ NMR (400 MHz, $CDCl_3$) δ ppm 1.42 (s, 9H), 1.66 (s, 10H), 2.93-2.95 (m, 2H), 3.61-3.64 (m, 1H), 3.69-3.71 (m, 1H), 3.98 (s, 1H), 4.82 (s, 1H), 7.22-7.25 (m, 1H), 7.29-7.33 (m, 1H), 7.43 (s, 1H), 7.60-7.61 (m, 1H), 8.12 (s, 1H).

tert-butyl (R)-3-(2-((tert-butoxycarbonyl)amino)-3-methoxypropyl)-1H-indole-1-carboxylate: To a solution of tert-butyl (R)-3-(2-((tert-butoxycarbonyl)amino)-3-hydroxypropyl)-1H-indole-1-carboxylate (0.14 g, 0.358 mmol, 1 eq) in acetonitrile was added silver (X) oxide (0.415 g, 1.79 mmol, 5 eq) and followed by the addition of methyl iodide (0.115 mL, 1.79 mmol, 5 eq) at room temperature. The reaction mixture stirred at room temperature for 72 h. The progress of the reaction was monitored by TLC (30% ethyl acetate in hexane). After completion of reaction, the mixture was filtered through celilte pad, washed with ethyl acetate (50 mL). The filtrate was concentrated under reduced pressure to obtain crude product. The crude was purified by flash column chromatography using 20% ethyl acetate in hexane as an eluent to obtain title product tert-butyl (R)-3-(2-((tert-butoxycarbonyl)amino)-3-methoxypropyl)-1H-indole-1-carboxylate. LC-MS (m/z)=405.3 $[M+H]^+$; $^1H$ NMR (400 MHz, $CDCl_3$) δ ppm 1.43 (s, 9H), 1.65 (s, 9H), 2.90-2.95 (m, 2H), 3.28-3.33 (m, 5H), 4.00 (s, 1H), 4.92 (s, 1H), 7.21-7.23 (m, 1H), 7.28-7.32 (m, 1H), 7.42 (s, 1H), 7.63-7.65 (m, 1H), 8.10 (s, 1H).

(R)-1-(1H-indol-3-yl)-3-methoxypropan-2-amine 2,2,2-trifluoroacetic acid: To stirred solution of tert-butyl (R)-3-(2-((tert-butoxycarbonyl)amino)-3-methoxypropyl)-1H-indole-1-carboxylate (0.065 g, 0.16 mmol, 1 eq) in dichloromethane was added 2,2,2-trifluoroacetic acid (1 mL) at 0° C. The reaction mixture was allowed to warm to room temperature and stirred for 12 h. The progress of the reaction was monitored by TLC (30% ethyl acetate in hexane). After completion of reaction, the mixture was concentrated under reduced pressure to obtain (R)-1-(1H-indol-3-yl)-3-methoxypropan-2-amine 2,2,2-trifluoroacetic acid, which was taken as such to next step without purification. LC-MS (m/z)=205.1 $[M+H]^+$. $^1H$ NMR (400 MHz, DMSO-$d_6$) δ ppm 2.92-2.95 (m, 2H), 3.26 (s, 3H), 3.31-3.35 (m, 1H), 3.42-3.52 (m, 2H), 6.98-7.01 (m, 1H), 7.07-7.10 (m, 1H), 7.21 (s, 1H), 7.35 (d, J=8.0 Hz, 1H), 7.53 (d, J=8.0 Hz, 1H), 7.83 (bs, 3H), 10.99 (s, 1H).

(R)-1-(1H-indol-3-yl)-3-methoxypropan-2-amine: To a stirred mixture of (R)-1-(1H-indol-3-yl)-3-methoxypropan-2-amine 2,2,2-trifluoroacetic acid was portioned between sodium bicarbonate solution and dichloromethane and stirred for 10 min. The organic layer was separated and the aqueous layer was extracted with dichloromethane (2×50 mL), the combined organics were washed with brine (50 mL), dried over anhydrous sodium sulfate, filtered and concentrated under reduced pressure to obtain crude. The crude was purified by flash column chromatography using 8% methanol in dichloromethane as an eluent to obtain (R)-1-(1H-indol-3-yl)-3-methoxypropan-2-amine. LC-MS (m/z)=205.2 $[M+H]^+$; $^1H$ NMR (400 MHz, DMSO-$d_6$) δ ppm 1.87 (bs, 2H), 2.48-2.60 (m, 2H), 2.73-2.77 (dd, J=4.8 Hz, 14.4 Hz, 1H), 3.11-3.14 (m, 2H), 3.22 (s, 3H), 6.94 (t, J=7.6 Hz, 1H), 7.03 (t, J=7.2 Hz, 1H), 7.11 (s, 1H), 7.30 (d, J=8.4 Hz, 1H), 7.49 (d, J=7.6 Hz, 1H), 10.80 (s, 1H).

N-cyclopropyl-3-fluoro-4-((1S,3R)-3-(methoxymethyl)-2,3,4,9-tetrahydro-1H-pyrido[3,4-b]indol-1-yl)benzamide: In a seal tube, (R)-1-(1H-indol-3-yl)-3-methoxypropan-2-amine (0.22 g, 1.077 mmol, 1 eq), N-cyclopropyl-3-fluoro-4-formylbenzamide (0.26 g, 1.077 mmol, 1.0 equiv) and hexafluoro-2-propanol (HFIP) (1.0 mL) were taken and the seal tube was closed. The mixture was heated to 80° C. and stirred for 16 h. The progress of the reaction was monitored by TLC (5% methanol in dichloromethane), the reaction was cooled to room temperature, concentrated under reduced pressure to obtain crude, which was purified by flash column chromatography using 3% methanol in dichloromethane as an eluent to obtain N-cyclopropyl-3-fluoro-4-((1S,3R)-3-(methoxymethyl)-2,3,4,9-tetrahydro-1H-pyrido[3,4-b]indol-1-yl)benzamide. LC-MS (m/z)=428.2 $[M+H]^+$. H NMR (400 MHz, $CDCl_3$): δ 0.64 (s, 4H), 2.26 (bs, 1H), 2.57-2.63 (m, 1H), 2.85-2.88 (m, 1H), 3.29 (bs, 1H), 3.34 (s, 3H), 3.42-3.54 (m, 2H), 4.87 (s, 1H), 5.68 (s, 1H), 7.12-7.21 (m, 3H), 7.25-7.31 (m, 1H), 7.54 (d, J=7.2 Hz, 2H), 7.67 (d, J=9.2 Hz, 1H), 7.57 (s, 1H).

Preparation of Compound 166

4-((1S,3R)-2-(2-chloroacetyl)-3-(methoxymethyl)-2,3,4,9-tetrahydro-1H-pyrido[3,4-b]indol-1-yl)-N-cyclopropyl-3-fluorobenzamide: To a stirred solution of N-cyclopropyl-3-fluoro-4-((1 S, 3R)-3-(methoxymethyl)-2,3,4,9-tetrahydro-1H-pyrido[3,4-b]indol-1-yl)benzamide (0.075 g, 0.174 mmol, 1.0 eq) and sodium bicarbonate (0.044 g, 0.523 mmol, 3.0 eq) in chloroform was added 2-chloroacetyl chloride (0.02 mL, 0.261 mmol, 1.5 eq) at 0° C. The mixture was gradually allowed to warm to room temperature and stirred for 2 h. The progress of the reaction was monitored by TLC (30% ethyl acetate in hexane). After completion of reaction, the reaction mixture was diluted with dichloromethane (30 mL), washed with water (2×20 mL), dried over anhydrous sodium sulfate, filtered and concentrated under reduced pressure to obtain crude product. This was purified by flash column chromatography using 20% ethyl acetate in dichloromethane as an eluent to obtain 4-((1S,3R)-2-(2-chloroacetyl)-3-(methoxymethyl)-2,3,4,9-tetrahydro-1H-pyrido[3,4-b]indol-1-yl)-N-cyclopropyl-3-fluorobenzamide. LC-MS (m/z): 506.1 [M+H]+; 1H NMR (400 MHz, DMSO-d6): δ 0.34 (bs, 2H), 0.45 (bs, 2H), 2.02 (s, 1H), 3.00-3.03 (m, 1H), 3.18 (s, 3H), 3.22-3.32 (m, 3H), 4.36 (d, J=13.2 Hz, 1H), 4.73 (d, J=12.8 Hz, 2H), 6.12 (s, 1H), 6.94-7.04 (m, 2H), 7.23 (d, J=7.6 Hz, 1H), 7.43-7.52 (m, 4H), 7.96 (s, 1H), 10.80 (s, 1H).

Procedure EA: Synthesis of Compound 234 and Compound 128

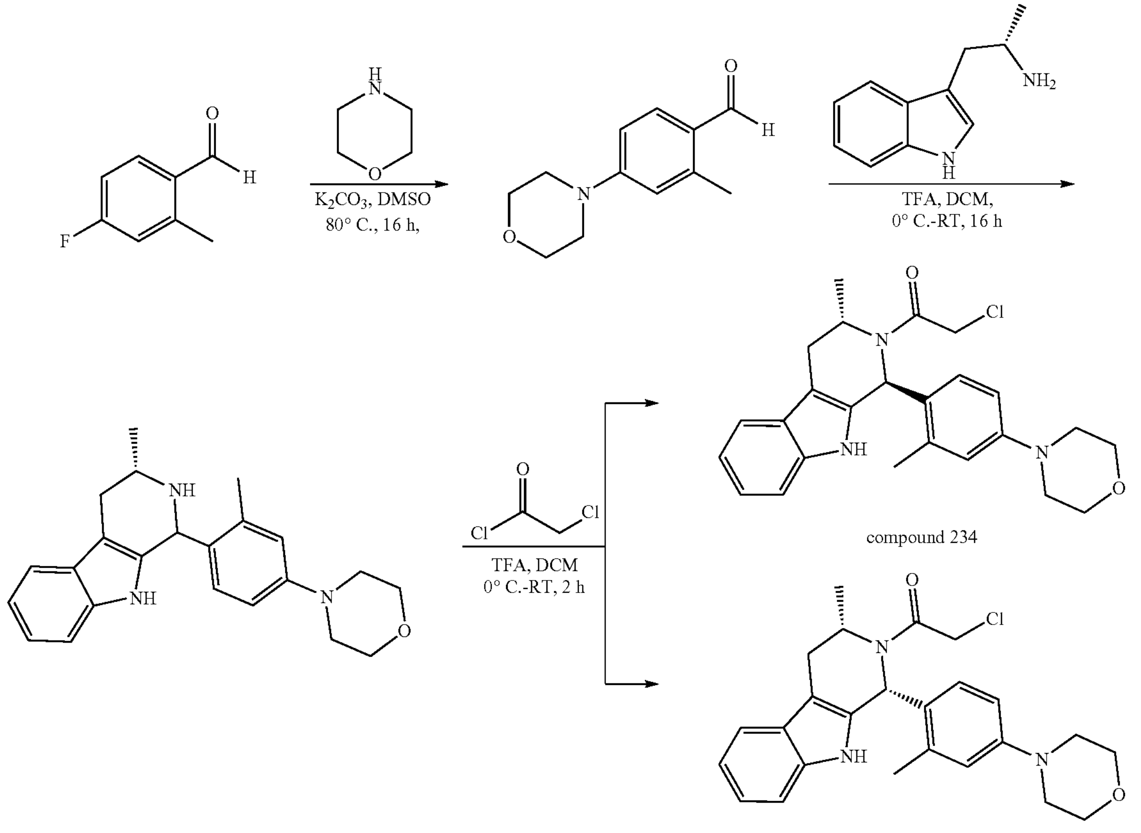

compound 234 compound 128

2-methyl-4-morpholinobenzaldehyde(3): To a solution of 4-fluoro-2-methylbenzaldehyde (0.5 g, 3.61 mmol, 1.0 eq) in DMSO (10 mL) was added slowly $K_2CO_3$ (1.5 g, 10.85 mmol, 3.0 eq) and morpholine (0.94 g, 10.85 mmol, 1.0 eq) at 0° C. The mixture was stirred at 80° C. for 16 h under $N_2$ atmosphere. TLC (30% EtOAc in hexane) showed the reaction was completed. The reaction was cooled to room temperature and was concentrated under reduced pressure, and then the crude was diluted with EtOAc (150 mL), washed with water (2×50 mL). The organic layer was dried over anhydrous $Na_2SO_4$, concentrated under reduced pressure to crude product. The crude was purified by flash chromatography using 20% EtOAc in hexane as an eluent to give 2-methyl-4-morpholinobenzaldehyde. LC-MS (m/z)=206.0 $[M+H]^+$. $^1H$ NMR (400 MHz, $CDCl_3$) δ ppm 2.62 (s, 3H), 3.32-3.34 (m, 4H), 3.83-3.85 (m, 4H), 6.64 (s, 1H), 6.79 (d, J=8.8 Hz, 1H), 7.73 (d, J=8.8 Hz, 1H), 10.03 (s, 1H).

4-(3-methyl-4-((3S)-3-methyl-2,3,4,9-tetrahydro-1H-pyrido[3,4-b]indol-1-yl)phenyl)morpholine(5): To a solution of (S)-1-(1H-indol-3-yl)propan-2-amine (0.230 g, 1.31 mmol, 1.0 eq) in DCE (10.0 mL) was added 2-methyl-4-morpholinobenzaldehyde (0.298 g, 1.45 mmol, 1.1 eq) and TFA (0.30 g, 2.63 mmol, 2.0 eq). The mixture was stirred at 50° C. for 16 h. TLC (5% MeOH in DCM) showed the reaction was completed. The reaction mixture was cooled to room temperature and diluted with ethyl acetate (80 mL) and washed with saturated $NaHCO_3$ solution (10 mL) and water (2×15 mL). The organic layers were dried over $Na_2SO_4$ and concentrated to give the crude product. The crude product was purified by flash column chromatography using 70-80% EtOAc in hexane as an eluent to give the product 4-(3-methyl-4-((3S)-3-methyl-2,3,4,9-tetrahydro-1H-pyrido[3,4-b]indol-1-yl)phenyl)morpholine. LC-MS (m/z)=438.0 $[M+H]^+$

Preparation of Compound 234 and 128

2-chloro-1-((1S,3S)-3-methyl-1-(2-methyl-4-morpholinophenyl)-1,3,4,9-tetrahydro-2H-pyrido[3,4-b]indol-2-yl)ethan-1-one (234) and 2-chloro-1-((1R,3S)-3-methyl-1-(2-methyl-4-morpholinophenyl)-1,3,4,9-tetrahydro-2H-pyrido[3,4-b]indol-2-yl)ethan-1-one (128): To a solution of 4-(3-methyl-4-((3S)-3-methyl-2,3,4,9-tetrahydro-1H-pyrido[3,4-b]indol-1-yl)phenyl)morpholine (0.100 g, 0.276 mmol, 1.0 eq) in DCM (8.0 mL) was added TEA (0.03 mL, 0.55 mmol, 2.0 eq) at 0° C., stirred for 15 mins and then and 2-chloroacetyl chloride (0.046 g, 0.41 mmol, 1.5 eq) was added at 0° C. The mixture was allowed to stir at room temperature for 1 hr. LCMS and TLC (20% EtOAc in hexane) showed the reaction was completed. The reaction mixture was diluted with saturated $NaHCO_3$ solution (10 mL) and was extracted with DCM (2×50 mL). The organic layers were dried over $Na_2SO_4$ and concentrated to give the crude product. The crude product was purified by flash column chromatography followed by preparative TLC with 30% EtOAc in hexane as eluent to give cis and trans isomers of 2-chloro-1-((3S)-3-methyl-1-(2-methyl-4-morpholinophenyl)-1,3,4,9-tetrahydro-2H-pyrido[3,4-b]indol-2-yl)ethan-1-one.

Compound 234

LC-MS(ES) (m/z): 438.3 [M+H]. $^1$H NMR (400 MHz, DMSO): δ 1.08-1.09 (m, 3H), 2.39 (s, 3H), 2.64-2.75 (m, 1H), 3.05 (m, 5H), 3.68 (S, 4H), 4.56-4.59 (m, 3H), 4.64 (bs, 1H), 6.03-6.03 (m, 3H), 6.78 (s, 1H), 7.96-7.03 (m, 2H), 7.26-7.28 (m, 1H), 7.41-7.43 (m, 1H), 10.59 (s, 1H).

Compound 128

LC-MS(ES) (m/z): 438.3 [M+H]$^+$. $^1$H NMR (400 MHz, DMSO): δ 1.13-1.15 (m, 3H), 2.64 (s, 3H), 2.84-2.88 (m, 1H), 3.09 (m, 5H), 3.65 (s, 4H), 4.64 (bs, 1H), 5.55-5.58 (m, 2H), 4.73 (s, 3H), 5.96 (s, 1H), 6.54 (m, 2H), 6.66 (s, 1H), 6.83-6.85 (m, 1H), 6.99 (m, 2H), 7.20-7.22 (m, 1H), 7.40-7.42 (m, 1H), 10.59 (s, 1H).

Procedure EC: Synthesis of Compound 214

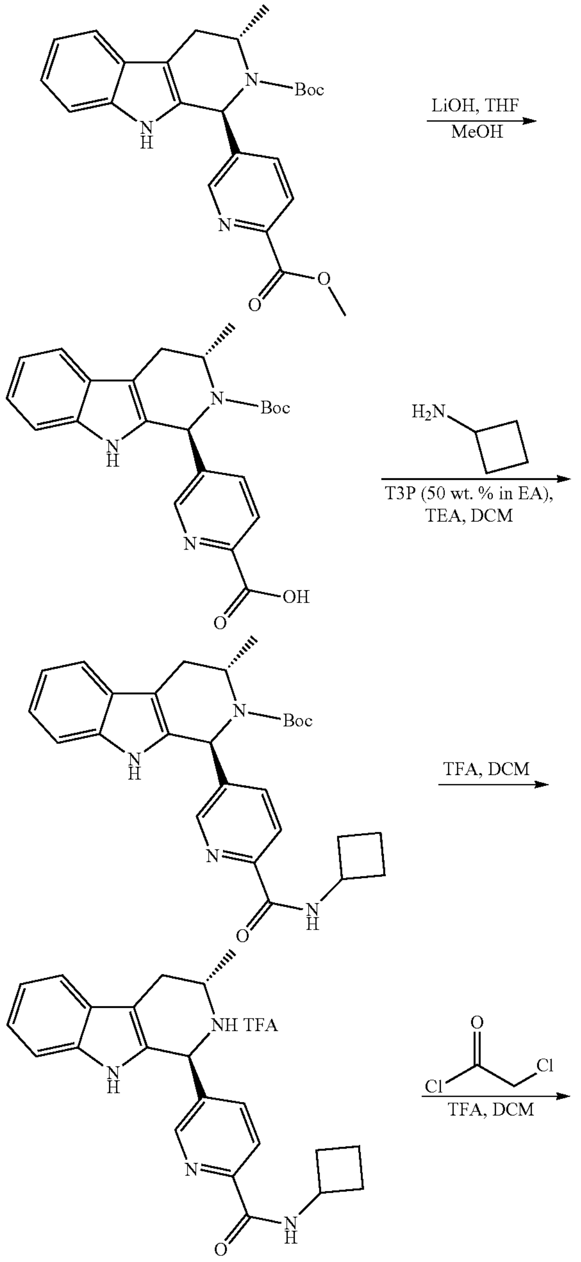

-continued

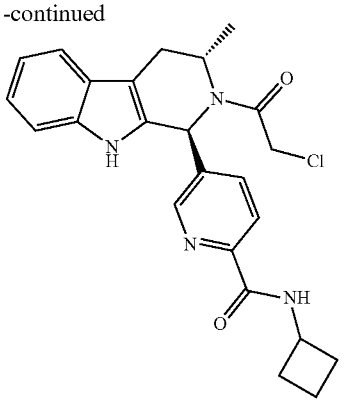

Compound 214

5-((1S,3S)-2-(tert-butoxycarbonyl)-3-methyl-2,3,4,9-tetrahydro-1H-pyrido[3,4-b]indol-1-yl)picolinic acid: To a solution of compound tert-butyl (1S,3S)-1-(6-(methoxycarbonyl)pyridin-3-yl)-3-methyl-1,3,4,9-tetrahydro-2H-pyrido [3,4-b]indole-2-carboxylate (0.090 g, 0.21 mmol, 1 eq) in a mixture of THF: MeOH: $H_2O$ (9 mL: 1 mL) were added Lithium hydroxide (0.044 g, 1.06 mmol, 5 eq) and allowed to stirrer at room temperature for 16 h. TLC (5% MeOH in DCM) showed the reaction was completed. The reaction mixture was concentrated under reduced pressure, and the crude was acidified with 5% citric acid solution (pH=9). Reaction mixture was diluted with EtOAc (50 mL) and the organic layer was separated and dried over anhydrous $Na_2SO_4$, concentrated under reduced pressure to give crude product 5-((1S,3S)-2-(tert-butoxycarbonyl)-3-methyl-2,3,4,9-tetrahydro-1H-pyrido[3,4-b]indol-1-yl)picolinic acid. LC-MS (m/z):408.0 [M+H]$^+$ tert-butyl-(1S,3S)-1-(6-(cyclobutylcarbamoyl)pyridin-3-yl)-3-methyl-1,3,4,9-tetrahydro-2H-pyrido[3,4-b]indole-2-carboxylate: To a solution of compound 5-((1S,3S)-2-(tert-butoxycarbonyl)-3-methyl-2,3,4,9-tetrahydro-1H-pyrido[3,4-b]indol-1-yl)picolinic acid (0.065 g, 0.159 mmol, 1 eq) in DCM (10 mL) was added triethylamine (0.03 mL, 0.47 mmol, 3 eq) and cyclobutanamine (0.01 g, 0.19 mmol, 1.2 eq) at 0° C. and the mixture was stirred for 15 min. To the above reaction mixture T3P (50% wt in EtOAc) (0.19 mL, 0.31 mmol, 2 eq) was added at the same temperature and stirred for 16 h. TLC (70% EtOAc in hexane) showed the reaction was completed. The reaction mixture was concentrated under reduced pressure, and the crude was diluted with EtOAc (50 mL), washed with water (2×50 mL). The organic layer was dried over anhydrous $Na_2SO_4$, concentrated under reduced pressure to give crude product tert-butyl (1S,3S)-1-(6-(cyclobutylcarbamoyl)pyridin-3-yl)-3-methyl-1,3,4,9-tetrahydro-2H-pyrido[3,4-b]indole-2-carboxylate. LC-MS (m/z): 461.0 [M+H]$^+$ N-cyclobutyl-5-((1R,3S)-3-methyl-2-(2,2,2-trifluoroacetyl)-2,3,4,9-tetrahydro-1H-214-indeno[2,1-c]pyridin-1-yl)picolinamide: To a solution of compound tert-butyl (1S,3S)-1-(6-(cyclobutylcarbamoyl)pyridin-3-yl)-3-methyl-1,3,4,9-tetrahydro-2H-pyrido[3,4-b]indole-2-carboxylate (0.40 g, 0.08 mmol, 1 eq) in DCM (10 mL) was added Trifluoroacetic acid (0.01 g, 0.09 mmol, 1.1 eq) at 0° C. and the mixture was stirred for 2 h. TLC (50% EtOAc in hexane) showed the reaction was completed. The reaction mixture was concentrated under reduced pressure to give crude product N-cyclobutyl-5-((1R,3S)-3-methyl-2-(2,2,2-trifluoroacetyl)-2,3,4,9-tetrahydro-1H-214-indeno[2,1-c]pyridin-1-yl)picolinamide. LC-MS (m/z): 361.0 $[M+H]^+$ Preparation of Compound 214

5-((1S,3S)-2-(2-chloroacetyl)-3-methyl-2,3,4,9-tetrahydro-1H-pyrido[3,4-b]indol-1-yl)-N-cyclobutylpicolinamide: To a solution of N-cyclobutyl-5-((1R,3S)-3-methyl-2-(2,2,2-trifluoroacetyl)-2,3,4,9-tetrahydro-1H-214-indeno [2,1-c]pyridin-1-yl)picolinamide (0.05 g, 0.11 mmol, 1 eq) in DCM (8.0 mL) was added TEA (0.01 mL, 0.22 mmol, 2.0 eq) at 0° C., stirred for 15 mins and then and 2-chloroacetyl chloride (0.019 g, 0.17 mmol, 1.5 eq) was added at 0° C. The mixture was allowed to stir at room temperature for 1 hr. LCMS and TLC (50% EtOAc in hexane) showed the reaction was completed. The reaction mixture was diluted with saturated $NaHCO_3$ solution (10 mL) and was extracted with DCM (2×50 mL). The organic layers were dried over $Na_2SO_4$ and concentrated to give the crude product. The crude product was purified by flash column chromatography using 50% c as an eluent to give 5-((1 S,3S)-2-(2-chloroacetyl)-3-methyl-2,3,4,9-tetrahydro-1H-pyrido[3,4-b]indol-1-yl)-N-cyclobutylpicolinamide. LC-MS (m/z): 437.2 $[M+H]^+$. $^1H$ NMR ($CDCl_3$) δ 1.16 (d, J=6 Hz, 3H), 1.61 (s, 2H), 1.96-2.11 (m, 5H), 2.65-2.93 (m, 2H), 4.36-4.38 (m, 2H), 4.75 (m, 2H), 5.99 (s, 1H), 7.02-7.95 (m, 2H), 7.46 (d, J=7.2 Hz, 1H), 7.82 (s, 2H), 8.64 (s, 1H), 8.75 (d, J=8.4 Hz, 1H), 10.95 (s, 1H).

Procedure ED: Synthesis of Compound 213

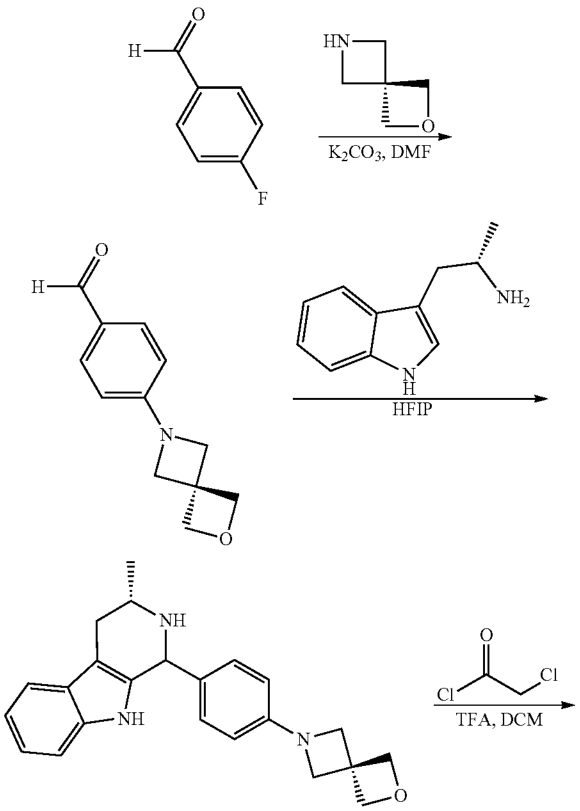

Cis and trans isomers

-continued

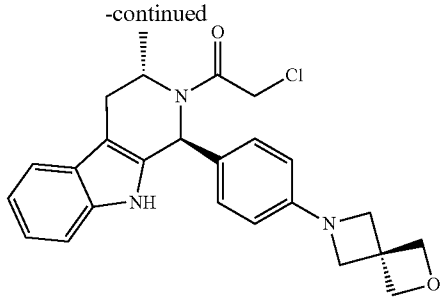

compound 213

4-(2-oxa-6-azaspiro[3.3]heptan-6-yl)benzaldehyde: To a solution of 4-fluorobenzaldehyde (0.5 g, 4.02 mmol, 1.0 eq) in DMF (10 mL) was added slowly $K_2CO_3$ (1.1 g, 8.05 mmol, 2.0 eq) and 2-oxa-6-azaspiro[3.3]heptane (0.47 g, 4.83 mmol, 1.2 eq) at 0° C. The mixture was stirred at 80° C. for 16 h under $N_2$ atmosphere. TLC (50% EtOAc in hexane) showed the reaction was completed. The reaction was cooled to room temperature and was concentrated under reduced pressure, and then the crude was diluted with EtOAc (150 mL), washed with water (2×50 mL). The organic layer was dried over anhydrous $Na_2SO_4$, concentrated under reduced pressure to crude product. The crude was purified by flash chromatography using 20% EtOAc in hexane as an eluent to give 4-(2-oxa-6-azaspiro[3.3]heptan-6-yl)benzaldehyde. LC-MS (m/z)=204.0 $[M+H]^+$. $^1H$ NMR (400 MHz, DMSO-$d_6$) δ 4.13 (s, 4H), 4.70 (s, 4H), 6.47 (d, J=8 Hz, 2H), 7.66 (d, J=8 Hz, 2H), 9.64 (s, 1H).

6-(4-((3S)-3-methyl-2,3,4,9-tetrahydro-1H-pyrido[3,4-b] indol-1-yl)phenyl)-2-oxa-6-azaspiro[3.3]heptane: To a solution of 4-(2-oxa-6-azaspiro[3.3]heptan-6-yl)benzaldehyde (0.116 g, 0.63 mmol, 1.2 eq) in HFIP (5 mL) was added (S)-1-(1H-indol-3-yl)propan-2-amine (0.1 g, 0.57 mmol, 1.0 eq) and stirred for 16 hours at 80° C. LCMS and TLC (5% MeOH in DCM) showed the reaction was completed. The organic solvents were removed under reduced pressure to crude product. The crude product was purified by flash column chromatography using 10-15% MeOH in DCM as an eluent to give 6-(4-((3S)-3-methyl-2,3,4,9-tetrahydro-1H-pyrido[3,4-b]indol-1-yl)phenyl)-2-oxa-6-azaspiro[3.3] heptane. LC-MS(ES) (m/z): 360.0 $[M+H]^+$, Preparation of Compound 213

1-((1S,3S)-1-(4-(2-oxa-6-azaspiro[3.3]heptan-6-yl)phenyl)-3-methyl-1,3,4,9-tetrahydro-2H-pyrido[3,4-b]indol-2-yl)-2-chloroethan-1-one: To a solution of 6-(4-((3S)-3-methyl-2,3,4,9-tetrahydro-1H-pyrido[3,4-b]indol-1-yl) phenyl)-2-oxa-6-azaspiro[3.3]heptane (0.100 g, 0.27 mmol, 1.0. eq) in DCM (8.0 mL) was added TEA (0.037 mL, 0.55 mmol, 2.0 eq) at 0° C., stirred for 15 mins and then and 2-chloroacetyl chloride (0.047 g, 0.41 mmol, 1.5 eq) was added at 0° C. The mixture was allowed to stir at room temperature for 1 hr. LCMS and TLC (50% EtOAc in hexane) showed the reaction was completed. The reaction mixture was diluted with saturated $NaHCO_3$ solution (10 mL) and was extracted with DCM (2×50 mL). The organic layers were dried over $Na_2SO_4$ and concentrated to give the crude product. The crude product was purified by flash column chromatography to give 1-((1S,3S)-1-(4-(2-oxa-6-azaspiro[3.3]heptan-6-yl)phenyl)-3-methyl-1,3,4,9-tetrahydro-2H-pyrido[3,4-b]indol-2-yl)-2-chloroethan-1-one. LC-MS(ES) (m/z): 436.0 $[M+H]^+$. $^1H$ NMR (400 MHz, DMSO-$d_6$) 1.08-1.10 (m, 3H), 2.83-2.86 (m, 2H), 3.95-4.07 (m, 7H), 4.63-4.72 (m, 5H), 6.31 (s, 2H), 5.87 (s, 1H), 6.92-6.98 (m, 2H), 7.14-7.23 (m, 3H), 7.38-7.40 (m, 2H), 10.86 (s, 1H).

Procedure EE: Synthesis of Compound 173
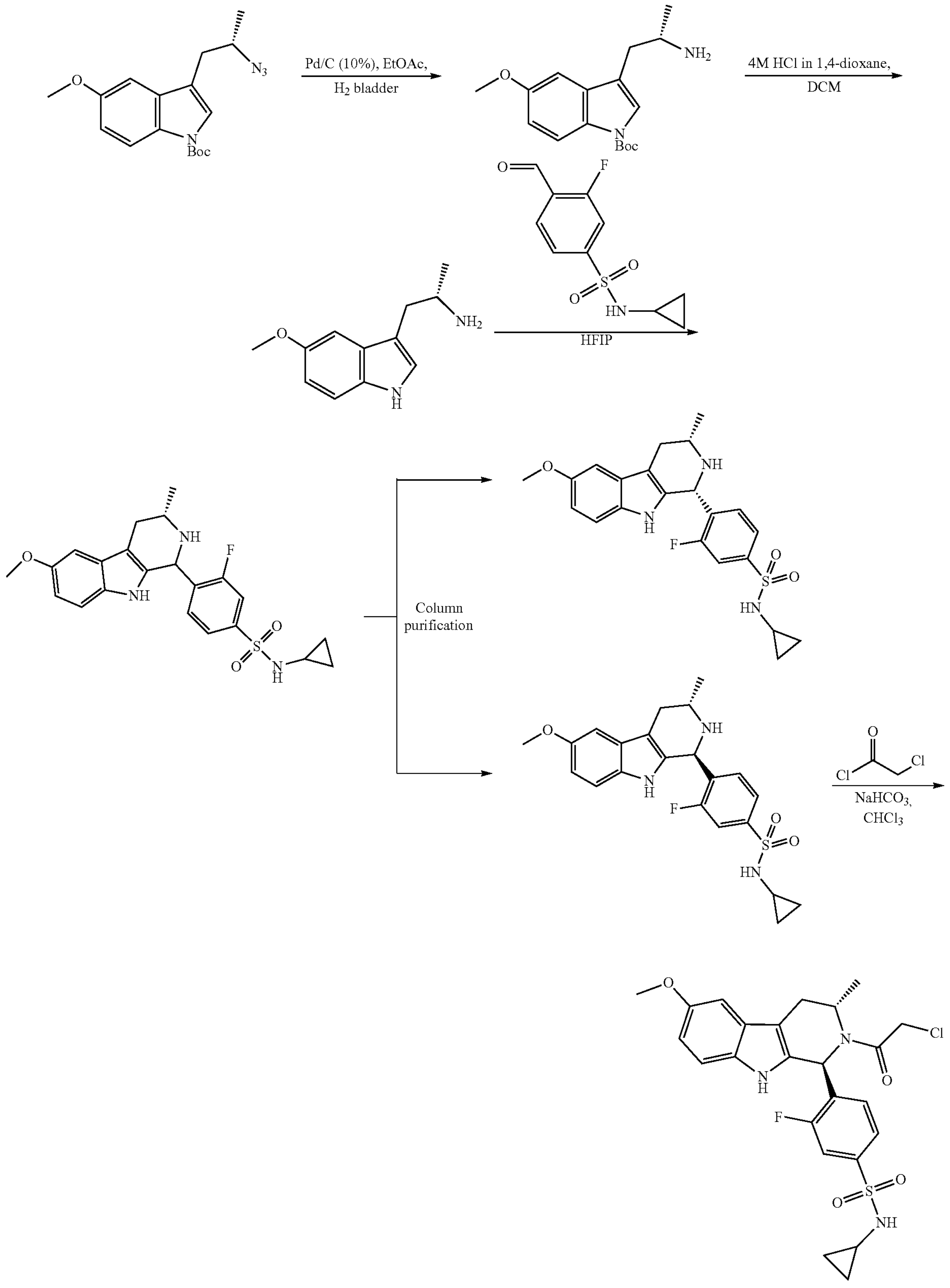
compound 173

N-cyclopropyl-3-fluoro-4-((3S)-6-methoxy-3-methyl-2,3,4,9-tetrahydro-1H-pyrido[3,4-b]indol-1-yl)benzenesulfonamide: To a solution of N-cyclopropyl-3-fluoro-4-formylbenzenesulfonamide (0.142 g, 0.58 mmol, 1.0 eq) in HFIP (5 mL) was added (S)-1-(5-methoxy-1H-indol-3-yl)propan-2-amine (0.120 g, 0.58 mmol, 1.0 eq) and stirred for 16 hours at 80° C. LCMS and TLC (5% MeOH in DCM) showed the reaction was completed. The organic solvents were removed under reduced pressure to crude product.

The crude product was purified by flash column chromatography using 0-5% MeOH in DCM as an eluent to give N-cyclopropyl-3-fluoro-4-((3S)-6-methoxy-3-methyl-2,3,4,9-tetrahydro-1H-pyrido[3,4-b]indol-1-yl)benzenesulfonamideheptane. LC-MS(ES) (m/z): 430.0 [M+H]$^+$.

Preparation of Compound 173

4-((3S)-2-(2-chloroacetyl)-6-methoxy-3-methyl-2,3,4,9-tetrahydro-1H-pyrido[3,4-b]indol-1-yl)-N-cyclopropyl-3-fluorobenzenesulfonamide: To a solution of N-cyclopropyl-3-fluoro-4-((3S)-6-methoxy-3-methyl-2,3,4,9-tetrahydro-1H-pyrido[3,4-b]indol-1-yl)benzenesulfonamide (0.030 g, 0.139 mmol, 1.0 eq) in DCM (8.0 mL) was added $NaHCO_3$ (0.023 mL, 0.27 mmol, 2.0 eq) at 0° C., stirred for 15 mins and then and 2-chloroacetyl chloride (0.018 g, 0.16 mmol, 1.2 eq) was added at 0° C. The mixture was allowed to stir at room temperature for 1 hr. LCMS and TLC (5% MeOH in DCM) showed the reaction was completed. The reaction mixture was diluted with DCM and extracted with DCM (2×50 mL). The organic layers were dried over $Na_2SO_4$ and concentrated to give the crude product. The crude product was purified by flash column chromatography using 50% c as an eluent and Compound was further purified by Prep HPLC (Analytical condition: Column: Kinetex C18 (100 mm×4.6 mm×2.6 m), mobile phase (A): 0.1% TFA in water, mobile phase (B): ACN, Flow rate: 0.75 mL/min to give 4-((3S)-2-(2-chloroacetyl)-6-methoxy-3-methyl-2,3,4,9-tetrahydro-1H-pyrido[3,4-b]indol-1-yl)-N-cyclopropyl-3-fluorobenzenesulfonamide. LC-MS (m/z): 506.0 [M+H]$^+$. $^1$H NMR (400 MHz, DMSO-$d_6$): δ 0.6-0.65 (m, 4H). 1.32-1.33 (m, 3H), 2.20 (d, J=4.8 Hz, 1H), 2.94 (d, J=16 Hz, 1H), 3.35 (d, J=10.8 Hz, 1H), 3.84 (s, 3H), 4.11 (bs, 1H), 4.31 (bs, 1H), 4.77 (s, 1H), 4.86 (s, 1H), 6.23 (s, 1H), 6.83- 6.85 (m, 1H), 6.93 (s, 1H), 7.19-7.25 (m, 1H), 7.37-7.37 (m, 1H), 7.51-7.63 (m, 2H), 7.83 (s, 1H).

Procedure EF: Synthesis of Compound 165

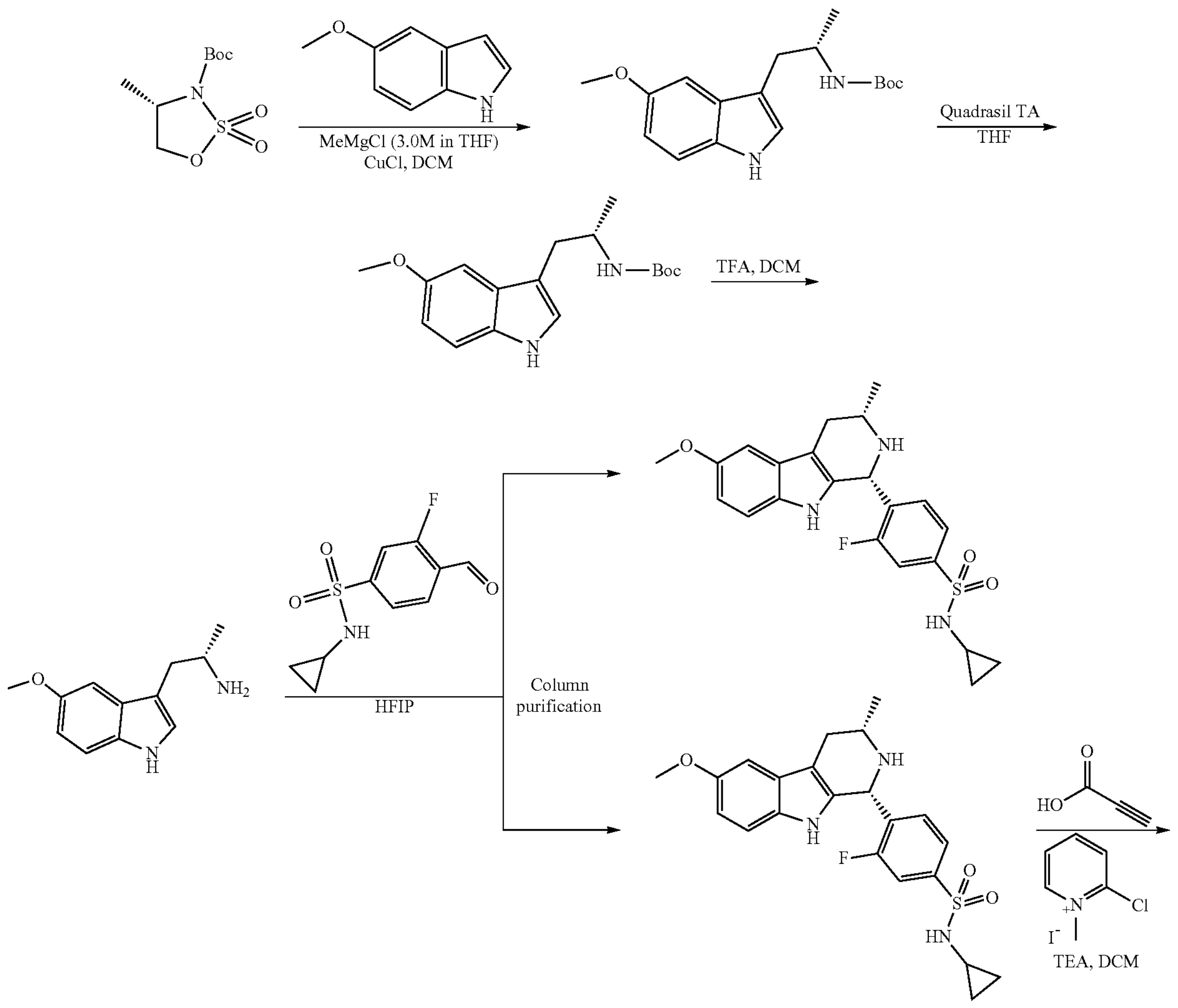

-continued

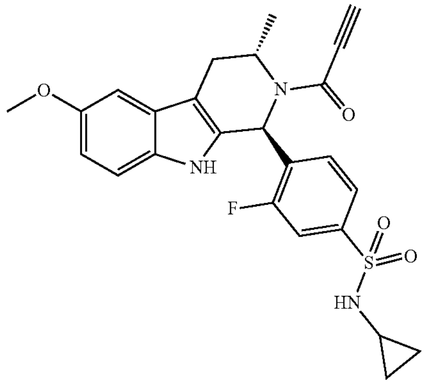

Compound 165 tert-butyl (S)-(1-(5-methoxy-1H-indol-3-yl)propan-2-yl) carbamate: To a mixture of 5-methoxy-1H-indole (0.3 g, 2.03 mmol, 1 eq) and cuprous chloride (0.26 g, 2.65 mmol, 1.3 eq) in round bottom flask was purged with vacuum and then DCM (10 mL) was added and the reaction mixture was cooled to 0° C. and MeMgCl (0.8 mL, 2.65 mmol, 1.3 eq) was added dropwise. The reaction mixture was maintained at 0° C. for 1 h. Then (S)-3,4-dimethyl-1,2,3-oxathiazolidine 2,2-dioxide (0.338 g, 1.42 mmol, 0.7 eq) in DCM (3 mL) was added at −20° C. dropwise and the reaction was stirred at −20° C. for 5 h. TLC (40% EtOAc in hexane) showed the formation of new spot. The reaction mixture was concentrated under reduced pressure to get the crude which was dissolved in EtOAc (100 mL) and was quenched with 10% citric acid at 0° C. and the reaction mixture was filtered through celite bed. The bed was washed with DCM (50 mL) and filtrate was washed with water (2×10 mL) and brine solution (10 mL). The organic layers were dried over $Na_2SO_4$ and concentrated to give the crude product. The crude product was purified by flash column chromatography using 20% EtOAc in hexane as an eluent to give tert-butyl (S)-(1-(5-methoxy-1H-indol-3-yl)propan-2-yl)carbamate. LC-MS (m/z)=249.2 $[M+H]^+$—after cleavage of t-butyl group. $^1H$ NMR (400 MHz, DMSO-d6) δ ppm 1.00 (d, J=6.0 Hz, 3H), 1.33 (s, 9H), 2.60-2.64 (m, 1H), 2.77-2.79 (m, 1H), 3.47-3.69 (m, 1H), 3.73 (s, 3H), 3.66-6.71 (m, 2H), 7.03 (s, 2H), 7.19 (d, J=8.0 Hz, 1H), 10.59 (s, 1H).

tert-butyl (S)-(1-(5-methoxy-1H-indol-3-yl)propan-2-yl) carbamate: To a solution of tert-butyl (S)-(1-(5-methoxy-1H-indol-3-yl)propan-2-yl)carbamate (0.22 g, 0.72 mmol, 1 eq) in THF (20.0 mL) was added Quadrasil TA (2.0 g, 2.0 eq). The mixture was stirred at room temperature for 1 h. The reaction mixture was filtered through sintered funnel and to the filtrate was again added Quadrasil TA (2.0 g, 2.0 eq) and reaction was stirred at room temperature for 1 h. The reaction mixture was filtered through sintered funnel and to the filtrate was concentrated under reduced pressure to give tert-butyl (S)-(1-(5-methoxy-1H-indol-3-yl)propan-2-yl) carbamate. LC-MS (m/z)=249.0 $[M+H]^+$ (S)-1-(5-methoxy-1H-indol-3-yl)propan-2-amine: To a solution of tert-butyl (S)-(1-(5-methoxy-1H-indol-3-yl)propan-2-yl)carbamate (0.2 g, 0.65 mmol, 1 eq) in DCM (10.0 mL) was added trifluoro acetic acid (0.06 mL) at 0° C. The mixture was allowed to stir at room temperature for 3 h. TLC (5% MeOH in DCM) showed the reaction was completed. The reaction mixture was concentrated under reduced pressure to get the crude. It was diluted with ice cold water (5 mL) and was basified by 5% NaOH solution (pH adjusted to 9) and was extracted with EtOAc (100 mL). The organic layers were dried over $Na_2SO_4$ and concentrated under reduced pressure to get (S)-1-(5-methoxy-1H-indol-3-yl) propan-2-amine. LC-MS (m/z)=205.2 $[M+H]^-$ N-cyclopropyl-3-fluoro-4-((1S,3S)-6-methoxy-3-methyl-2,3,4,9-tetrahydro-1H-pyrido[3,4-b]indol-1-yl)benzenesulfonamide: To a solution of (S)-1-(5-methoxy-1H-indol-3-yl)propan-2-amine (0.160 g, 0.78 mmol, 1 eq) in HFIP (2.0 mL) was added N-cyclopropyl-3-fluoro-4-formylbenzenesulfonamide (0.190 g, 0.78 mmol, 1 eq). The mixture was stirred at 80° C. for 16 h in a sealed tube. TLC (50% EtOAc in hexane) showed the reaction was completed. The reaction mixture was cooled to room temperature and concentrated under reduced pressure to give the crude product. The crude product was purified by flash column chromatography using 30-35% EtOAc in hexane as eluent to give N-cyclopropyl-3-fluoro-4-((1S,3S)-6-methoxy-3-methyl-2,3,4,9-tetrahydro-1H-pyrido[3,4-b]indol-1-yl)benzenesulfonamide (polar spot on TLC). LC-MS (m/z)=430.1$[M+H]^+$

Preparation of Compound 165

N-cyclopropyl-3-fluoro-4-((1S,3S)-6-methoxy-3-methyl-2-propioloyl-2,3,4,9-tetrahydro-1H-pyrido[3,4-b]indol-1-yl)benzenesulfonamide: To a solution of N-cyclopropyl-3-fluoro-4-((1S,3S)-6-methoxy-3-methyl-2,3,4,9-tetrahydro-1H-pyrido[3,4-b]indol-1-yl)benzenesulfonamide (0.06 g, 0.13 mmol, 1.0 eq) in DCM (10.0 mL) was added triethyl amine (0.052 mL, 0.33 mmol, 2.4 eq) at room temperature, stirred for 5 mins and then added propiolic acid (0.009 mL, 0.13 mmol, 1.0 eq) and 2-chloro-1-methyl pyridinium iodide (0.042 g, 0.16 mmol, 1.2 eq). The mixture was allowed to stir at room temperature for 30 mins. TLC (40% EtOAc in hexane) showed the reaction was completed. The reaction mixture was diluted with DCM (100 mL) and was washed with water (2×10 mL). The organic layers were dried over $Na_2SO_4$ and concentrated to give the crude product. The crude product was purified by flash column chromatography using 20-25% EtOAc in hexane as an eluent and compound was further purified by Prep HPLC (Analytical condition: Column: Kinetex C18 (100 mm×4.6 mm×2.6 μm), mobile phase (A): 0.1% TFA in water, mobile phase (B): ACN, Flow rate: 0.75 mL/min to give N-cyclopropyl-3-fluoro-4-((1S,3S)-6-methoxy-3-methyl-2-propioloyl-2,3,4,9-tetrahydro-1H-pyrido[3,4-b]indol-1-yl)benzenesulfonamide. LC-MS (m/z): 482.1 [M+H]+. $^1H$ NMR (400 MHz, DMSO-$d_6$): δ 0.34-0.44 (m, 3H), 1.21 (s, 4H), 2.01 (bs, 2H), 2.90-2.94 (m, 1H), 3.72 (s, 3H), 4.64 (s, 1H), 5.10 (s, 1H), 6.12 (s, 1H), 6.65-6.67 (m, 1H), 6.96 (s, 1H), 7.11-7.13 (m, 1H), 7.45-7.83 (m, 3H), 7.97 (s, 1H), 10.68 (s, 1H).

Procedure EG: Synthesis of Compound 150

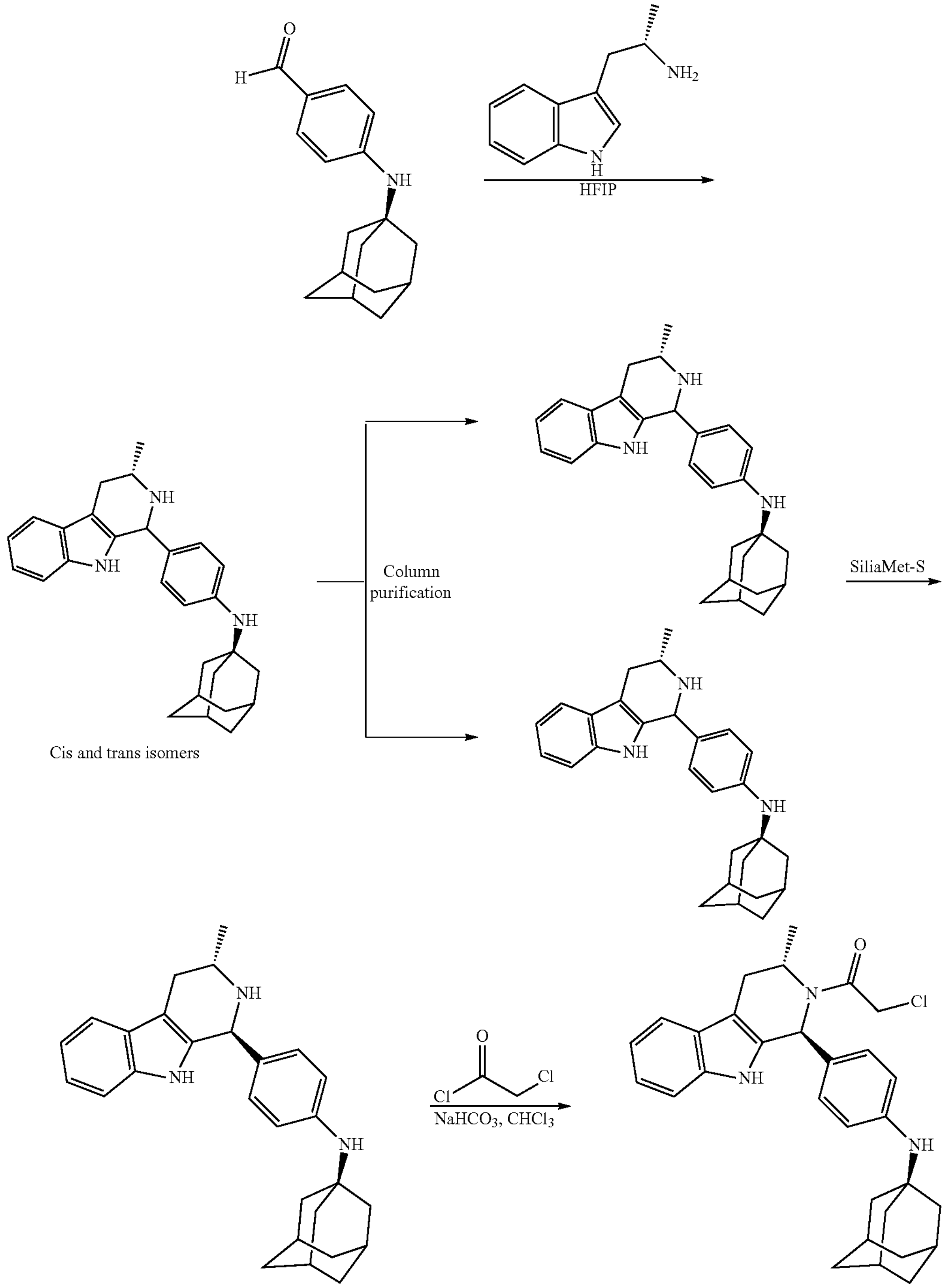

150

(3R,5R,7R)—N-(4-((1 S,3S)-3-methyl-2,3,4,9-tetrahydro-1H-pyrido[3,4-b]indol-1-yl)phenyl)adamantan-1-amine: To a solution of (S)-1-(1H-indol-3-yl)propan-2-amine (0.19 g, 1.09 mmol, 1 eq) in HFIP (2.0 mL) was added 4-(((3s,5s,7s)-adamantan-1-yl)amino)benzaldehyde (0.278 g, 1.09 mmol, 1 eq). The mixture was stirred at 80° C. for 16 h in a sealed tube. TLC (50% EtOAc in hexane) showed the reaction was completed. The reaction mixture was cooled to room temperature and concentrated under reduced pressure to give the crude product. The crude product was purified by flash column chromatography using 30-35% EtOAc in hexane as an eluent to give the cis isomer and trans isomer. The trans isomer was taken for treatment with SiliaMet-S scavenger to give (3R,5R,7R)—N-(4-((1S,3S)-3-methyl-2,3,4,9-tetrahydro-1H-pyrido[3,4-b]indol-1-yl) phenyl)adamantan-1-amine (trans) which was taken to the next step. LC-MS (m/z)=412.0 [M+H]$^+$ Preparation of Compound 150

1-((1 S,3S)-1-(4-(((3R,5R,7R)-adamantan-1-yl)amino) phenyl)-3-methyl-1,3,4,9-tetrahydro-2H-pyrido[3,4-b]indol-2-yl)-2-chloroethan-1-one: To a solution of (3R,5R,7R)—N-(4-((1S,3S)-3-methyl-2,3,4,9-tetrahydro-1H-pyrido[3,4-b]indol-1-yl)phenyl)adamantan-1-amine (0.06 g, 0.14 mmol, 1 eq) in $CHCl_3$ (8.0 mL) was added $NaHCO_3$ (0.024 g, 0.29 mmol, 2.0 eq) at 0° C., stirred for 15 mins and then and 2-chloroacetyl chloride (0.02 mL, 0.29 mmol, 2.0 eq) was added at 0° C. The mixture was allowed to stir at room temperature for 1 h. TLC (40% EtOAc in hexane) showed the reaction was completed. The reaction mixture was concentrated under reduced pressure to give the crude product. The crude product was purified by flash column chromatography using 20-25% EtOAc in hexane as an eluent and compound was further purified by Prep HPLC (Analytical condition: Column: Kinetex C18 (100 mm×4.6 mm×2.6 μm), mobile phase (A): 0.1% TFA in water, mobile phase (B): ACN, Flow rate: 0.75 mL/min to give 1-((1S,3S)-1-(4-(((3R,5R,7R)-adamantan-1-yl)amino)phenyl)-3-methyl-1,3,4,9-tetrahydro-2H-pyrido[3,4-b]indol-2-yl)-2-chloroethan-1-one. LC-MS (m/z): 488.2 [M+H]$^+$. $^1$H NMR (400 MHz, DMSO-$d_6$): δ 1.09-1.11 (m, 3H), 1.58 (s, 6H), 1.79 (s, 6H), 2.07 (s, 3H), 2.83-2.86 (m, 1H), 3.08-3.32 (m, 1H), 4.57 (bs, 1H), 4.75-4.86 (m, 2H), 5.85 (s, 1H), 6.64 (s, 2H), 6.91-7.00 (m, 5H), 7.24-7.26 (m, 1H), 7.39-7.41 (m, 1H), 10.87 (s, 1H).

Procedure EH: Synthesis of Compound 129 and Compound 233

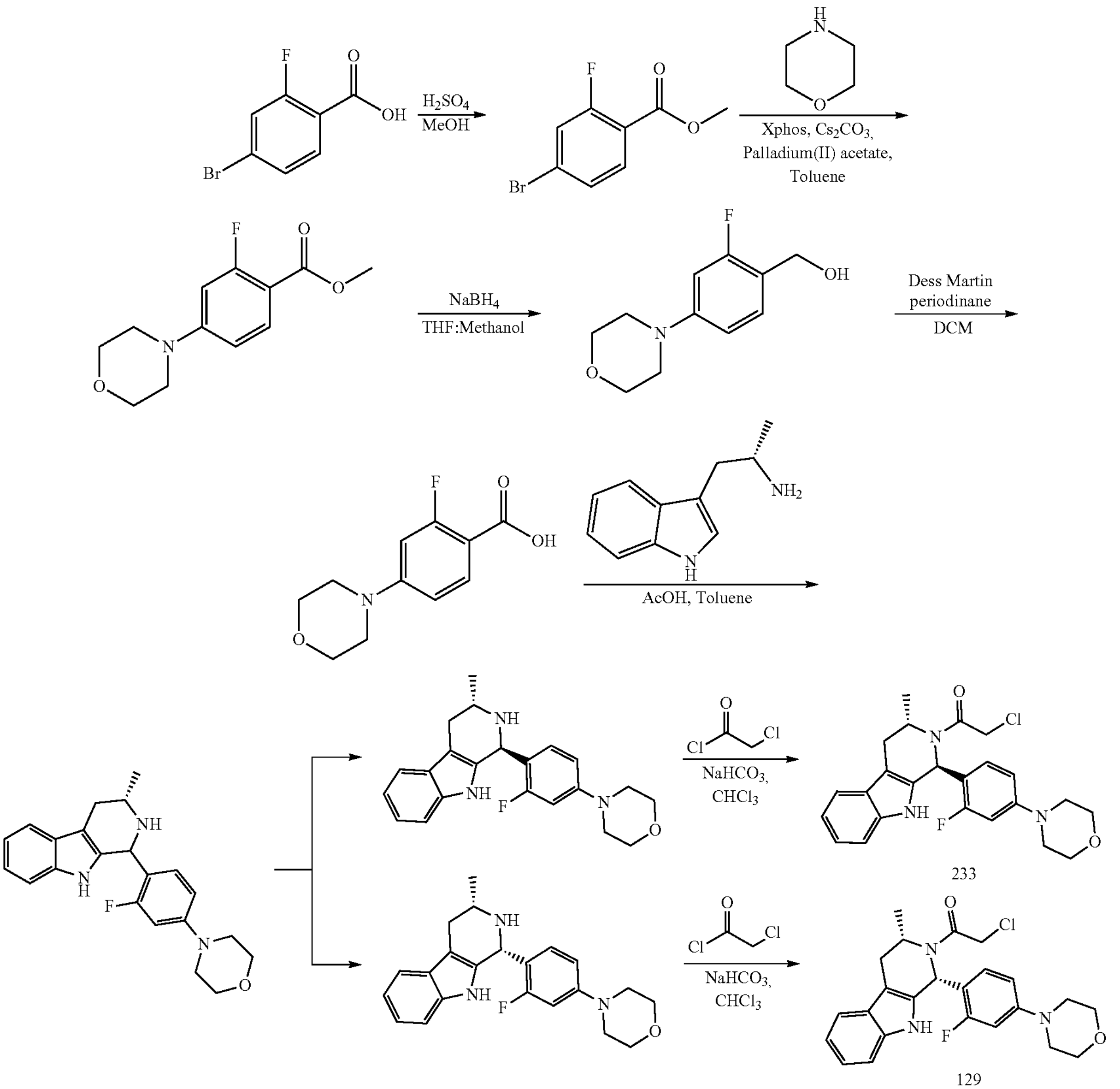

233

129 methyl 4-bromo-2-fluorobenzoate: To a solution of 4-bromo-2-fluorobenzoic acid (4.0 g, 18.26 mmol, 1 eq) in MeOH (30 mL) was added slowly sulphuric acid (0.5 mL) at 0° C. The mixture was stirred at 60° C. for 16 h under $N_2$ atmosphere. TLC (30% EtOAc in hexane) showed the reaction was completed. The reaction was cooled to room temperature and was concentrated under reduced pressure, and then the crude was diluted with EtOAc (150 mL), washed with saturated $NaHCO_3$ solution (2×20 mL) and water (2×10 mL). The organic layer was dried over anhydrous $Na_2SO_4$, concentrated under reduced pressure to give methyl 4-bromo-2-fluorobenzoate. $^1H$ NMR (400 MHz, $CDCl_3$) δ ppm 3.92 (s, 3H), 7.25-7.36 (m, 2H), 7.81 (t, J=7.8 Hz, 1H).

methyl 2-fluoro-4-morpholinobenzoate: To a solution of morpholine (1.3 g, 14.92 mmol, 1 eq) and methyl 4-bromo-2-fluorobenzoate (3.82 g, 16.41 mmol, 1.1 eq) in toluene (25.0 mL) was added cesium carbonate (7.3 g, 22.38 mmol, 1.5 eq) at room temperature, purged under argon for 25 mins and then X-Phos (0.35 g, 0.75 mmol, 0.05 eq) and palladium acetate (0.17 g, 0.75 mmol, 0.05 eq) was added. The reaction was stirred at 110° C. for 16 h in a sealed tube. TLC (20% EtOAc in hexane) showed the reaction was completed. The reaction was cooled to room temperature, filtered through celite bed and the bed was washed with EtOAc (150 mL). Combined organic layer was dried over anhy. Na2SO4, filtered and concentrated to get the crude. The crude was purified by flash chromatography using 20-25% EtOAc in hexane as an eluent to give methyl 2-fluoro-4-morpholinobenzoate. LC-MS (m/z)=240.1 $[M+H]^+$. $^1H$ NMR (400 MHz, DMSO-d6) δ ppm 3.22-3.23 (m, 4H), 3.68 (s, 4H), 3.74 (s, 3H), 6.77 (t, J=13.0 Hz, 2H), 7.69 (t, J=8.8 Hz, 1H).

(2-fluoro-4-morpholinophenyl)methanol: To a solution of methyl 2-fluoro-4-morpholinobenzoate (2.08 g, 8.67 mmol, 1 eq) in THF (16 mL) and MeOH (2.0 mL) was added sodium borohydride (2.62 g, 69.33 mmol, 8.0 eq) at 0° C. and the reaction was stirred at 65° C. for 16 h. TLC (30% EtOAc in hexane) showed the reaction was completed. The reaction mixture was concentrated under reduced pressure to get the crude which was dissolved in EtOAc (200 mL) and was washed with water (2×25 mL). The organic layers were dried over $Na_2SO_4$ and concentrated to give the crude product. The crude product was purified by flash column chromatography using 20-25% EtOAc in hexane as an eluent to give (2-fluoro-4-morpholinophenyl)methanol. LC-MS (m/z)=212.1 [M+H]+. $^1H$ NMR (400 MHz, DMSO-d6) δ ppm 3.07 (s, 4H), 3.68 (s, 4H), 4.38 (s, 2H), 5.00 (s, 1H), 6.65-6.71 (m, 2H), 7.22 (t, J=8.6 Hz, 1H).

2-fluoro-4-morpholinobenzaldehyde: To a solution of (2-fluoro-4-morpholinophenyl)methanol (1.4 g, 6.63 mmol, 1 eq) in DCM (50.0 mL) was added Desmartin periodinane (4.22 g, 9.94 mmol, 1.5 eq) at 0° C. The mixture was allowed to stir at room temperature for 2 hr. TLC (20% EtOAc in hexane) showed the reaction was completed. The reaction mixture was quenched with saturated $NaHCO_3$solution (20 mL) at 0° C. and extracted with DCM (2×100 mL). The organic layers were dried over $Na_2SO_4$ and concentrated to give 2-fluoro-4-morpholinobenzaldehyde. Used for next step without further purification. LC-MS (m/z)=210.1 $[M+H]^+$ 4-(3-fluoro-4-((3S)-3-methyl-2,3,4,9-tetrahydro-1H-pyrido[3,4-b]indol-1-yl)phenyl)morpholine: To a solution of (S)-1-(1H-indol-3-yl)propan-2-amine (0.6 g, 3.44 mmol, 1 eq) in toluene (10.0 mL) was added 2-fluoro-4-morpholinobenzaldehyde (0.72 g, 3.44 mmol, 1 eq) and AcOH (0.2 mL, 3.44 mmol, 1.0 eq). The mixture was stirred at 120° C. for 16 h. TLC (10% MeOH in DCM) showed the reaction was completed. The reaction mixture was cooled to room temperature and diluted with ethyl acetate (200 mL) and washed with saturated NaaHCO3 solution (20 mL) and water (2×15 mL). The organic layers were dried over $Na_2SO_4$ and concentrated to give the crude product. The crude product was purified by flash column chromatography using 20-25% EtOAc in hexane as an eluent to give the diastereomeric product which was further separated by Chiral Prep HPLC (Analytical condition: Column: CHIRALPAK IC (100 mm×4.6 mm×3 μM), mobile phase: n-hexane: IPA with 0.1% DEA (50:50), Flow rate: 1.0 mL/min) to give 4-(3-fluoro-4-((1S,3S)-3-methyl-2,3,4,9-tetrahydro-1H-pyrido[3,4-b]indol-1-yl)phenyl)morpholine (trans, polar by TLC) and 4-(3-fluoro-4-((1R,3S)-3-methyl-2,3,4,9-tetrahydro-1H-pyrido[3,4-b]indol-1-yl)phenyl)morpholine (cis, non-polar by TLC).

Analytical data of trans compound (trans geometry was confirmed by COSY and NOESY): LC-MS (m/z)=366.2 $[M+H]^+$. $^1H$ NMR (400 MHz, $CDCl_3$) δ 1.21-1.28 (m, 3H), 2.49-2.55 (m, 1H), 2.92 (dd, J=4.0 Hz, 15.2 Hz, 1H), 3.13 (t, J=4.8 Hz, 4H), 3.22-3.27 (m, 1H), 3.82 (t, J=4.8 Hz, 4H), 3.99-4.05 (m, 1H), 5.58 (s, 1H), 6.48 (dd, J=2.0 Hz, 8.8 Hz, 1H), 6.64 (dd, J=2.0 Hz, 13.0 Hz, 1H), 6.75 (t, J=8.6 Hz, 1H), 7.09-7.18 (m, 2H), 7.27 (s, 1H), 7.53 (d, J=7.6 Hz, 1H), 7.67 (s, 1H).

Analytical data of cis compound (cis geometry is confirmed by COSY and NOESY): LC-MS (m/z)=366.2$[M+H]^+$. $^1H$ NMR (400 MHz, $CDCl_3$) δ 1.35 (d, J=6.0 Hz, 3H), 2.53-2.59 (m, 1H), 2.86 (dd, J=2.0 Hz, 17.2 Hz, 1H), 3.15 (t, J=5.0 Hz, 4H), 3.27-3.32 (m, 1H), 3.84 (t, J=5.0 Hz, 4H), 3.99-4.05 (m, 1H), 5.53 (s, 1H), 6.60-6.91 (m, 2H), 7.09-7.22 (m, 4H), 7.49-7.51 (m, 2H).

2-chloro-1-((1 S,3S)-1-(2-fluoro-4-morpholinophenyl)-3-methyl-1,3,4,9-tetrahydro-2H-pyrido[3,4-b]indol-2-yl)ethan-1-one: To a solution of 4-(3-fluoro-4-((1S,3S)-3-methyl-2,3,4,9-tetrahydro-1H-pyrido[3,4-b]indol-1-yl)phenyl)morpholine (trans) (0.13 g, 0.35 mmol, 1 eq) in $CHCl_3$ (8.0 mL) was added $NaHCO_3$ (0.06 g, 0.70 mmol, 2.0 eq) at 0° C., stirred for 15 mins and then and 2-chloroacetyl chloride (0.04 mL, 0.53 mmol, 1.5 eq) was added at 0° C. The mixture was allowed to stir at room temperature for 2 hr. LCMS and TLC (50% EtOAc in hexane) showed the reaction was completed. The reaction mixture was diluted with saturated $NaHCO_3$solution (10 mL) and was extracted with DCM (2×50 mL). The organic layers were dried over $Na_2SO_4$ and concentrated to give the crude product. The crude product was purified by flash column chromatography using 40-50% EtOAc in hexane as an eluent to give 2-chloro-1-((1S,3S)-1-(2-fluoro-4-morpholinophenyl)-3-methyl-1,3,4,9-tetrahydro-2H-pyrido[3,4-b]indol-2-yl)ethan-1-one. LC-MS (m/z): 442.3 $[M+H]^+$. $^1H$ NMR (400 MHz, $CDCl_3$): δ 1.29 (d, J=6.0 Hz, 3H), 2.92 (d, J=14.8 Hz, 1H), 3.08 (d, J=2.4 Hz, 4H), 3.27 (bs, 1H), 3.79 (t, J=4.4 Hz, 4H), 3.98-4.13 (m, 1H), 4.22 (bs, 1H), 4.90 (bs, 1H), 6.24 (s, 1H), 6.52-6.57 (m, 2H), 7.02-7.17 (m, 3H), 7.25-7.29 (m, 1H), 7.49 (d, J=7.6 Hz, 1H), 7.94 (s, 1H).

2-chloro-1-((1R,3S)-1-(2-fluoro-4-morpholinophenyl)-3-methyl-1,3,4,9-tetrahydro-2H-pyrido[3,4-b]indol-2-yl)ethan-1-one: To a solution of 4-(3-fluoro-4-((1R,3S)-3-methyl-2,3,4,9-tetrahydro-1H-pyrido[3,4-b]indol-1-yl)phenyl)morpholine (cis) (0.17 g, 0.46 mmol, 1 eq) in $CHCl_3$ (10.0 mL) was added $NaHCO_3$ (0.077 g, 0.92 mmol, 2.0 eq) at 0° C., stirred for 15 mins and then and 2-chloroacetyl chloride (0.05 mL, 0.69 mmol, 1.5 eq) was added at 0° C. The mixture was allowed to stir at room temperature for 2 hr. LCMS and TLC (50% EtOAc in hexane) showed the reaction was completed. The reaction mixture was diluted with DCM (100 mL) and was washed with saturated $NaHCO_3$solution (10 mL) and water (2×10 mL). The organic layers were dried over $Na_2SO_4$ and concentrated to give the crude product. The crude product was purified by flash column chromatography using 40-50% EtOAc in hexane as an eluent to give 2-chloro-1-((1R,3S)-1-(2-fluoro-4-morpholinophenyl)-3-methyl-1,3,4,9-tetrahydro-2H-pyrido[3,4-b]indol-2-yl)ethan-1-one. LC-MS (m/z): 422.3 $[M+H]^+$. $^1H$ NMR (400 MHz, DMSO-d6): δ 1.09 (d, J=6.4 Hz, 3H), 2.72 (d, J=15.2 Hz, 1H), 3.04-3.09 (m, 5H), 3.68 (t, J=4.4 Hz, 4H), 4.56 (bs, 3H), 6.65-6.74 (m, 3H), 6.90-6.99 (m, 2H), 7.05 (t, J=7.6 Hz, 1H), 7.29 (d, J=8.0 Hz, 1H), 7.43 (d, J=8.0 Hz, 1H), 10.78 (s, 1H).

A similar synthetic scheme was used to synthesize 129 and 233.

Compound 129

LC-MS (m/z): 442.3 $[M+H]^+$. $^1H$ NMR (400 MHz, DMSO-$d_6$): δ 1.35 (d, J=6.0 Hz, 3H), 2.85 (d, J=15.2 Hz, 1H), 3.16 (s, 5H), 3.82 (d, J=4.4 Hz, 4H), 4.14 (bs, 1H), 4.20-4.23 (m, 1H), 4.80 (bs, 1H), 6.57-6.65 (m, 3H), 7.10-7.19 (m, 3H), 7.25-7.30 (m, 1H), 7.50 (d, J=6.8 Hz, 1H), 7.86 (s, 1H).

Compound 233

LC-MS (m/z): 442.3 $[M+H]^+$. $^1H$ NMR (400 MHz, DMSO-$d_6$): δ 1.29 (d, J=6.4 Hz, 3H), 2.92 (d, J=15.2 Hz, 1H), 3.08 (d, J=2.8 Hz, 4H), 3.25 (bs, 1H), 3.79 (t, J=4.6 Hz, 4H), 3.98 (bs, 1H), 4.21 (bs, 1H), 4.91 (bs, 1H), 6.24 (s, 1H), 6.52-6.57 (m, 2H), 7.02-7.16 (m, 3H), 7.25-7.29 (m, 1H), 7.50 (d, J=8.4 Hz, 1H), 7.89 (s, 1H).

Procedure EI: Synthesis of Compound 163

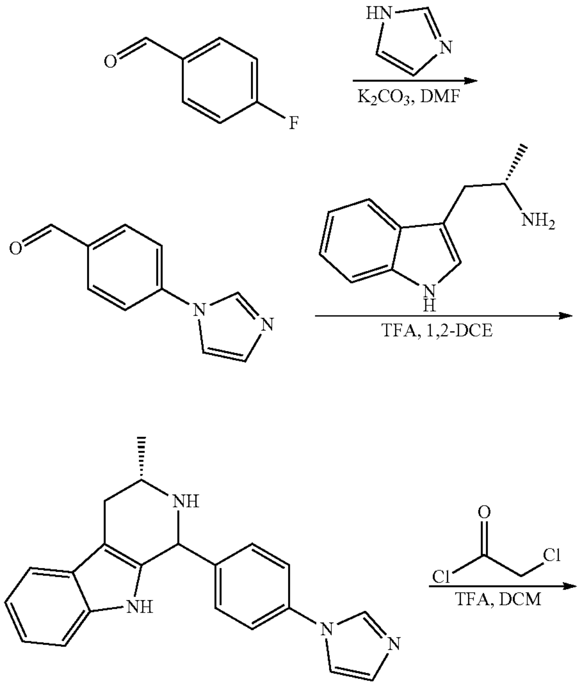

-continued

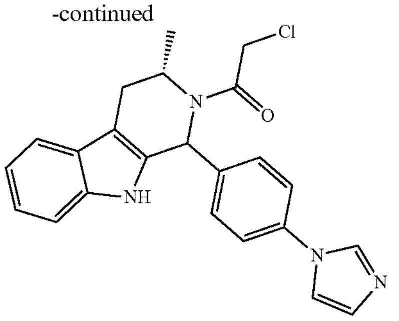

163

4-(1H-imidazol-1-yl)benzaldehyde: To a solution of 4-fluorobenzaldehyde (1.0 g, 8.05 mmol, 1 eq) in DMF (10.0 mL) was added $K_2CO_3$ (1.66 g, 12.07 mmol, 1.5 eq) and then 1H-imidazole (0.66 g, 9.66 mmol, 1.2 eq) was added. The mixture was stirred at 120° C. for 5 h under $N_2$ atmosphere. TLC (50% EtOAc in hexane) showed the reaction was completed. The reaction was cooled to room temperature and was diluted with EtOAc (150 mL), washed with water (2×20 mL). The organic layer was dried over anhydrous $Na_2SO_4$, concentrated under reduced pressure to get the crude. The crude product was purified by flash column chromatography using 50-60% EtOAc in hexane as an eluent to give 4-(1H-imidazol-1-yl)benzaldehyde. LC-MS (m/z)=173.1$[M+H]^+$. $^1H$ NMR (400 MHz, DMSO-d6) δ ppm 7.14 (s, 1H), 7.90 (d, J=9.6 Hz, 3H), 8.02 (d, J=8.0 Hz, 2H), 8.43 (s, 1H), 10.00 (s, 1H).

(3S)-1-(4-(1H-imidazol-1-yl)phenyl)-3-methyl-2,3,4,9-tetrahydro-1H-pyrido[3,4-b]indole: To a solution of (S)-1-(1H-indol-3-yl)propan-2-amine (0.15 g, 0.86 mmol, 1 eq) in 1,2-DCE (10.0 mL) was added 4-(1H-imidazol-1-yl)benzaldehyde (0.16 g, 0.95 mmol, 1.1 eq) and then trifluoroacetic acid (0.13 mL, 1.72 mmol, 2.0 eq) was added at 0° C. The mixture was stirred at 80° C. for 6 h under $N_2$ atmosphere. TLC (5% MeOH in DCM) showed the reaction was completed. The reaction was cooled to room temperature and was diluted with DCM (100 mL) and was washed with water (2×10 mL). The organic layer was dried over anhydrous $Na_2SO_4$, concentrated under reduced pressure to get the crude. The crude product was purified by flash column chromatography using 5-10% MeOH in DCM as an eluent to give (3S)-1-(4-(1H-imidazol-1-yl)phenyl)-3-methyl-2,3,4,9-tetrahydro-1H-pyrido[3,4-b]indole. LC-MS (m/z)=329.2$[M+H]^+$ Preparation of Compound 163

1-((3S)-1-(4-(1H-imidazol-1-yl)phenyl)-3-methyl-1,3,4,9-tetrahydro-2H-pyrido[3,4-b]indol-2-yl)-2-chloroethan-1-one: To a solution of (3S)-1-(4-(1H-imidazol-1-yl)phenyl)-3-methyl-2,3,4,9-tetrahydro-1H-pyrido[3,4-b]indole (0.26 g, 0.79 mmol, 1 eq) in DCM (10.0 mL) was added triethyl amine (0.33 mL, 2.37 mmol, 3.0 eq) at 0° C., stirred for 15 mins and then 2-chloroacetyl chloride (0.075 mL, 0.95 mmol, 1.2 eq) was added at 0° C. The mixture was stirred at room temperature for 2 h under $N_2$ atmosphere. TLC (10% MeOH in DCM) showed the reaction was completed. The reaction was cooled to room temperature and was diluted with ice cold water (10 mL) and was extracted with DCM (100 mL). The organic layer was dried over anhydrous $Na_2SO_4$, concentrated under reduced pressure to get the crude. The crude product was purified by flash column chromatography using 5-7% MeOH in DCM as an eluent to get the product. Compound was further purified by Prep HPLC (Analytical condition: Column: Inertsil ODS 3V (250 mm×4.6 mm×5 μM), mobile phase (A): 0.1% Ammonia in water, mobile phase (B): ACN, Flow rate: 1.0 mL/min, Isocractic: (A:B):(50:50)) to give 1-((3S)-1-(4-(1H-imidazol-1-yl)phenyl)-3-methyl-1,3,4,9-tetrahydro-2H-pyrido[3, 4-b]indol-2-yl)-2-chloroethan-1-one. (Cis and trans isomers were not separated). LC-MS (m/z)=405.1[M+H]$^+$. $^1$H NMR (400 MHz, $CDCl_3$): δ 1.20-1.25 (m, 3H), 2.88 (d, J=14.8 Hz, 1H), 3.21 (bs, 1H), 4.25 (s, 2H), 4.65 (bs, 1H), 6.94 (bs, 2H), 7.20-7.25 (m, 3H), 7.32-7.36 (m, 3H), 7.54-7.61 (m, 3H), 7.79 (bs, 1H), 8.03 (bs, 1H).

stirred for 10 mins and then EDC.HCl (1.53 g, 7.96 mmol, 1.5 eq) and HOBt (0.86 g, 6.37 mmol, 1.2 eq) was added. The mixture was stirred for 5 mins and then pyridin-2-amine (0.5 g, 5.31 mmol, 1.0 eq) was added and the reaction was stirred at room temperature for 16 h under $N_2$ atmosphere. TLC (40% EtOAc in hexane) showed the reaction was completed. The reaction was diluted with ice and extracted with ethyl acetate (150 mL). The organic layer was washed with saturated $NaHCO_3$solution (2×10 mL) and water (2×10 mL). Combined organic layer was dried over anhydrous $Na_2SO_4$, concentrated under reduced pressure to get the crude. The crude product was purified by flash column Procedure EJ: Synthesis of Compound 160 and Compound 219

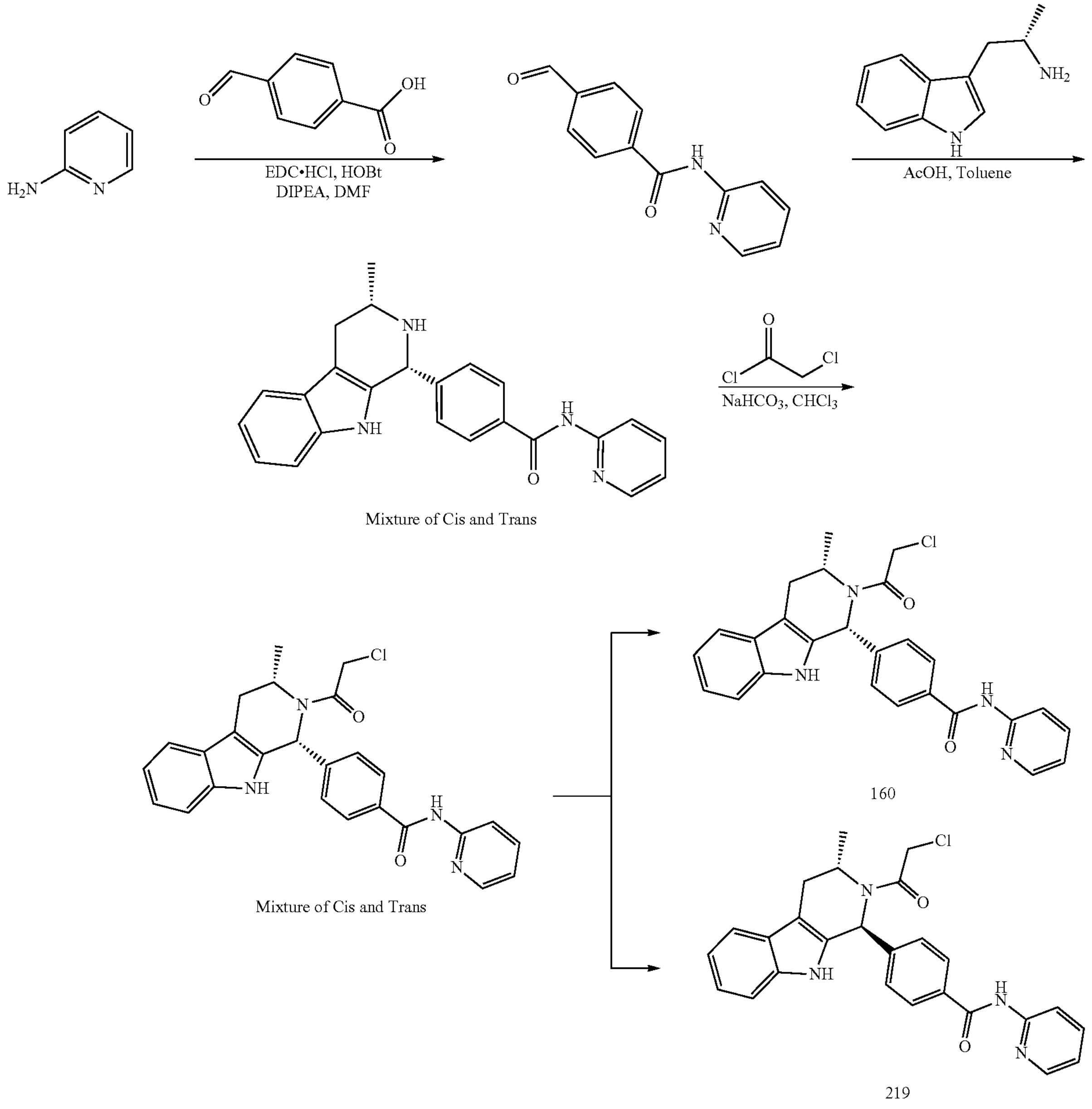

4-formyl-N-(pyridin-2-yl)benzamide: To a solution of 4-formylbenzoic acid (0.96 g, 6.37 mmol, 1.2 eq) in DMF (10.0 mL) was added DIPEA (1.85 mL, 10.62 mmol, 2.0 eq), chromatography using 25-30% EtOAc in hexane as an eluent to give 4-formyl-N-(pyridin-2-yl)benzamide. LC-MS (m/z)=227.1[M+H]+. $^1$H NMR (400 MHz, DMSO-d6) δ ppm 7.17 (t, J=5.4 Hz, 1H), 7.84 (t, J=7.4 Hz, 1H), 8.00 (d, J=7.2 Hz, 2H), 8.16-8.17 (m, 3H), 8.39 (d, J=2.8 Hz, 1H), 10.09 (s, 1H), 11.01 (s, 1H).

4-((3S)-3-methyl-2,3,4,9-tetrahydro-1H-pyrido[3,4-b]indol-1-yl)-N-(pyridin-2-yl)benzamide: To a solution of (S)-1-(1H-indol-3-yl)propan-2-amine (0.25 g, 1.43 mmol, 1.0 eq) in toluene (10.0 mL) was added 4-formyl-N-(pyridin-2-yl)benzamide (0.32 g, 1.43 mmol, 1.0 eq) and then acetic acid (0.08 mL, 1.43 mmol, 1.0 eq) was added at room temperature. The mixture was stirred at 120° C. for 16 h under $N_2$ atmosphere. TLC (70% EtOAc in hexane) showed the reaction was completed. The reaction was cooled to room temperature and was concentrated under reduced pressure to obtain the crude which was diluted with EtOAc (100 mL) and was washed with saturated $NaHCO_3$solution (2×10 mL) and water (2×10 mL). The organic layer was dried over anhydrous $Na_2SO_4$, concentrated under reduced pressure to get the crude. The crude product was purified by flash column chromatography using 60-70% EtOAc in hexane as an eluent to give 4-((3S)-3-methyl-2,3,4,9-tetrahydro-1H-pyrido[3,4-b]indol-1-yl)-N-(pyridin-2-yl)benzamide. LC-MS (m/z)=383.2 $[M+H]^+$ 4-((3S)-2-(2-chloroacetyl)-3-methyl-2,3,4,9-tetrahydro-1H-pyrido[3,4-b]indol-1-yl)-N-(pyridin-2-yl)benzamide: To a solution of 4-((3S)-3-methyl-2,3,4,9-tetrahydro-1H-pyrido[3,4-b]indol-1-yl)-N-(pyridin-2-yl)benzamide (0.33 g, 0.86 mmol, 1 eq) in CHC13 (10.0 mL) was added $NaHCO_3$(0.144 g, 1.72 mmol, 2.0 eq) at 0° C., stirred for 15 mins and then 2-chloroacetyl chloride (0.1 mL, 1.29 mmol, 1.5 eq) was added at 0° C. The mixture was stirred at room temperature for 2 h under $N_2$ atmosphere. TLC (50% EtOAc in hexane) showed the reaction was completed. The reaction was quenched with ice and was extracted with DCM (100 mL). The organic layer was washed with saturated $NaHCO_3$solution (10 mL) and water (10 mL), separated the layers, dried the organic layer over anhydrous $Na_2SO_4$, concentrated under reduced pressure to get the crude. The crude product was purified by flash column chromatography using 25-30% EtOAc in hexane as an eluent to afford 4-((1R,3S)-2-(2-chloroacetyl)-3-methyl-2,3,4,9-tetrahydro-1H-pyrido[3,4-b]indol-1-yl)-N-(pyridin-2-yl)benzamide (peak 1, assigned as cis, non-polar on TLC when compared to the other corresponding isomer).

Compound 160 (cis): LC-MS (m/z)=459.1$[M+H]^+$. $^1H$ NMR (400 MHz, $CDCl_3$): δ 1.14 (d, J=6.8 Hz, 3H), 2.86 (d, J=16.0 Hz, 1H), 3.23 (dd, J=5.6 Hz, 15.6 Hz, 1H), 4.26 (s, 2H), 4.62 (bs, 1H), 6.96 (s, 1H), 7.10 (t, J=6.0 Hz, 1H), 7.17 (t, J=7.2 Hz, 1H), 7.23 (s, 1H), 7.40 (d, J=7.6 Hz, 1H), 7.54-7.60 (m, 3H), 7.78-7.86 (m, 3H), 8.15 (s, 1H), 8.30 (d, J=4.0 Hz, 1H), 8.41 (d, J=8.0 Hz, 1H), 8.87 (bs, 1H).

Compound 219 (trans): Peak 2 (polar spot on TLC) was further purified by Prep HPLC (Analytical condition: Column: Inertsil ODS 3V (250 mm×4.6 mm×5 μM), mobile phase (A): 100% water, mobile phase (B): ACN, Flow rate: 1.0 mL/min, Composition of B: 0/10, 12/70, 25/90, 27/10, 30/10) to give 4-((1S,3S)-2-(2-chloroacetyl)-3-methyl-2,3,4,9-tetrahydro-1H-pyrido[3,4-b]indol-1-yl)-N-(pyridin-2-yl)benzamide (peak 2, assigned as trans, polar spot on TLC when compared to the other corresponding isomer). LC-MS (m/z)=459.3 $[M+H]^+$. $^1H$ NMR (400 MHz, $CDCl_3$): δ 1.34 (d, J=6.4 Hz, 3H), 2.97 (d, J=15.6 Hz, 1H), 3.39 (bs, 1H), 4.09 (bs, 1H), 4.24 (bs, 1H), 4.82 (bs, 1H), 5.95 (s, 1H), 7.04-7.07 (m, 1H), 7.09-7.16 (m, 2H), 7.23 (s, 1H), 7.39 (d, J=8.0 Hz, 2H), 7.52 (d, J=7.2 Hz, 1H), 7.71-7.76 (m, 3H), 7.96 (s, 1H), 8.28 (d, J=3.6 Hz, 1H), 8.34 (d, J=8.4 Hz, 1H), 8.49 (s, 1H).

Procedure EK: Synthesis of Compound 210

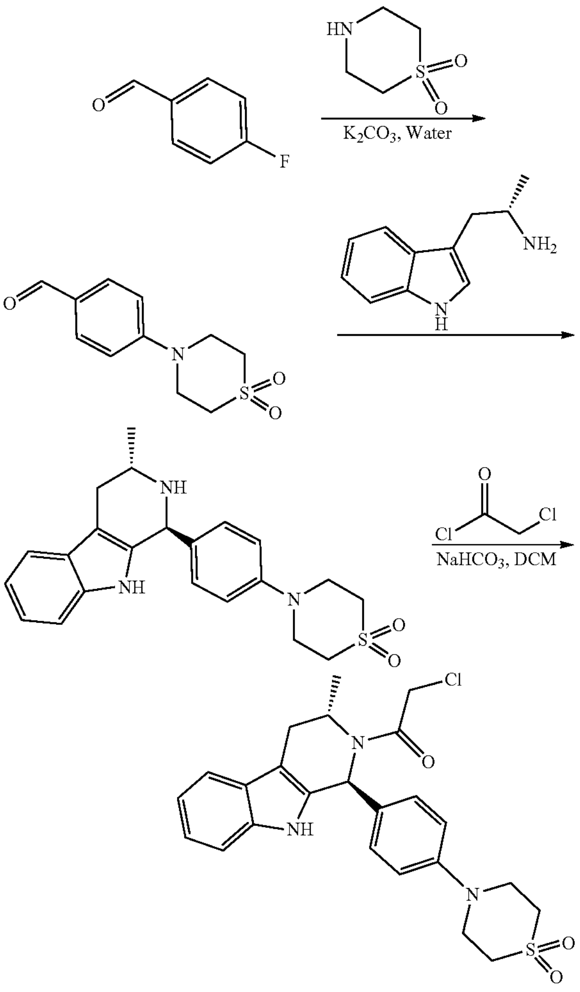

210

4-(1,1-dioxidothiomorpholino)benzaldehyde: To a solution of 4-fluorobenzaldehyde (0.4 g, 3.22 mmol, 1.0 eq.) and thiomorpholine 1,1-dioxide (0.65 g, 4.83 mmol, 1.5 eq.) in water (20.0 mL) was added $K_2CO_3$ (0.67 g, 4.83 mmol, 1.5 eq.). The mixture was stirred at 100° C. for 16 h under $N_2$ atmosphere. TLC (30% EtOAc in hexane) showed the reaction was completed. The reaction was cooled to room temperature and was extracted with EtOAc (2×100 mL). The organic layer was dried over anhydrous $Na_2SO_4$, concentrated under reduced pressure to get the crude. The crude product was purified by flash column chromatography using 25-30% EtOAc in hexane as an eluent to give 4-(1,1-dioxidothiomorpholino)benzaldehyde. LC-MS (m/z)=240.1 $[M+H]^+$. $^1H$ NMR (400 MHz, DMSO-d6) δ ppm 3.12 (s, 4H), 3.95 (s, 4H), 7.14 (d, J=8.8 Hz, 2H), 7.74 (d, J=8.8 Hz, 2H), 9.74 (s, 1H).

4-(4-((1 S,3S)-3-methyl-2,3,4,9-tetrahydro-1H-pyrido[3,4-b]indol-1-yl)phenyl)thiomorpholine 1,1-dioxide: To a solution of (S)-1-(1H-indol-3-yl)propan-2-amine (0.07 g, 0.4 mmol, 1.0 eq.) in HFIP (3.0 mL) was added 4-(1,1-dioxidothiomorpholino)benzaldehyde (0.096 g, 0.40 mmol, 1.0 eq.). The mixture was stirred at 80° C. for 16 h in a sealed tube. TLC (5% MeOH in DCM) showed the reaction was completed. The reaction was cooled to room temperature and was concentrated under reduced pressure to get the crude. The crude product was purified by flash column chromatography using 2-3% MeOH in DCM as an eluent to give 4-(4-((1S,3S)-3-methyl-2,3,4,9-tetrahydro-1H-pyrido[3,4-b]indol-1-yl)phenyl)thiomorpholine 1,1-dioxide. LC-MS (m/z)=396.0[M+H]$^+$ Preparation of Compound 210

2-chloro-1-((1 S,3S)-1-(4-(1,1-dioxidothiomorpholino)phenyl)-3-methyl-1,3,4,9-tetrahydro-2H-pyrido[3,4-b]indol-2-yl)ethan-1-one: To a solution of 4-(4-((1S,3S)-3-methyl-2,3,4,9-tetrahydro-1H-pyrido[3,4-b]indol-1-yl)phenyl)thiomorpholine 1,1-dioxide (0.05 g, 0.13 mmol, 1 eq.) in chloroform (8.0 mL) was added sodium bicarbonate (0.021 g, 0.26 mmol, 2.0 eq.) at 0° C., stirred for 15 mins and then 2-chloroacetyl chloride (0.02 mL, 0.13 mmol, 1.5 eq.) was added at 0° C. The mixture was stirred at room temperature for 1 h under $N_2$ atmosphere. TLC (5% MeOH in DCM) showed the reaction was completed. The reaction was diluted with DCM (80 mL) and was washed with water (2×10 mL). The organic layer was dried over anhydrous $Na_2SO_4$, concentrated under reduced pressure to get the crude. The crude product was purified by flash column chromatography using 2-3% MeOH in DCM as an eluent to get the product which was further purified by prep TLC using 2% MeOH in DCM as an eluent (eluted thrice) to give 2-chloro-1-((1S,3S)-1-(4-(1,1-dioxidothiomorpholino)phenyl)-3-methyl-1,3,4,9-tetrahydro-2H-pyrido[3,4-b]indol-2-yl)ethan-1-one. LC-MS (m/z)=472.2 [M+H]$^+$. $^1$H NMR (400 MHz, DMSO-d6): δ 1.10 (d, J=6.4 Hz, 3H), 2.86 (d, J=15.6 Hz, 1H), 3.04-3.14 (m, 5H), 3.66 (s, 4H), 4.30 (bs, 1H), 4.62 (bs, 1H), 4.77 (bs, 1H), 5.91 (bs, 1H), 6.88-6.95 (m, 3H), 7.00 (t, J=7.2 Hz, 1H), 7.23-7.25 (m, 3H), 7.40 (d, J=7.6 Hz, 1H), 10.92 (s, 1H).

Procedure EL: Alternative Synthesis of Compound 104

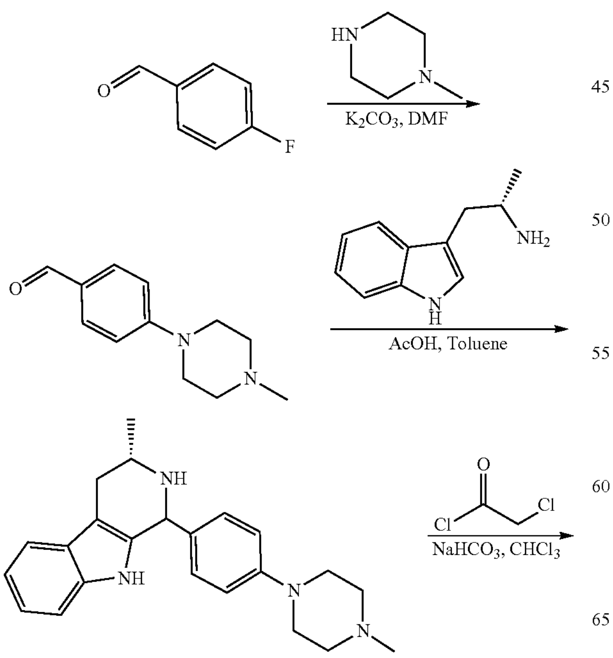

-continued

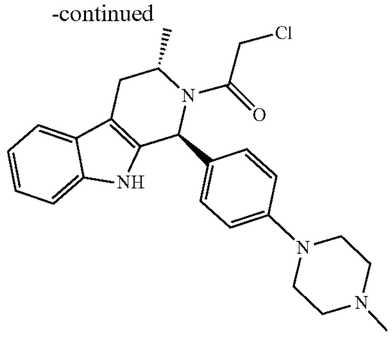

104

4-(4-methylpiperazin-1-yl)benzaldehyde: To a solution of 4-fluorobenzaldehyde (0.5 g, 4.03 mmol, 1.0 eq.) and 1-methylpiperazine (0.6 g, 6.04 mmol, 1.5 eq.) in DMF (20.0 mL) was added $K_2CO_3$ (0.83 g, 6.04 mmol, 1.5 eq.). The mixture was stirred at 130° C. for 16 h under $N_2$ atmosphere. TLC (5% MeOH in DCM) showed the reaction was completed. The reaction was quenched with ice and was extracted with EtOAc (2×100 mL). The organic layer was dried over anhydrous $Na_2SO_4$, concentrated under reduced pressure to get the crude. The crude product was purified by flash column chromatography using 3-4% MeOH in DCM as an eluent to give 4-(4-methylpiperazin-1-yl)benzaldehyde. LC-MS (m/z)=205.2[M+H]$^+$. $^1$H NMR (400 MHz, DMSO-d6) δ ppm 2.19 (s, 3H), 2.40 (t, J=5.2 Hz, 4H), 3.35 (t, J=5.0 Hz, 4H), 7.02 (d, J=8.8 Hz, 2H), 7.68 (d, J=8.8 Hz, 2H), 9.69 (s, 1H).

(3S)-3-methyl-1-(4-(4-methylpiperazin-1-yl)phenyl)-2,3,4,9-tetrahydro-1H-pyrido[3,4-b]indole: To a solution of (S)-1-(1H-indol-3-yl)propan-2-amine (0.2 g, 1.15 mmol, 1.0 eq.) and 4-(4-methylpiperazin-1-yl)benzaldehyde (0.23 g, 1.15 mmol, 1.0 eq.) in toluene (10.0 mL) was added acetic acid (0.066 mL, 1.15 mmol, 1.0 eq.) at 0° C. The mixture was stirred at 120° C. for 16 h. TLC (10% MeOH in DCM) showed the reaction was completed. The reaction was cooled to room temperature and was concentrated under reduced pressure to get the crude. The crude product was purified by flash column chromatography using 5-8% MeOH in DCM as an eluent to give (3S)-3-methyl-1-(4-(4-methylpiperazin-1-yl)phenyl)-2,3,4,9-tetrahydro-1H-pyrido[3,4-b]indole. LC-MS (m/z)=361.3[M+H]$^+$ Preparation of Compound 104

2-chloro-1-((1 S,3S)-3-methyl-1-(4-(4-methylpiperazin-1-yl)phenyl)-1,3,4,9-tetrahydro-2H-pyrido[3,4-b]indol-2-yl)ethan-1-one: To a solution of (3S)-3-methyl-1-(4-(4-methylpiperazin-1-yl)phenyl)-2,3,4,9-tetrahydro-1H-pyrido[3,4-b]indole (0.25 g, 0.69 mmol, 1 eq.) in chloroform (10.0 mL) was added sodium bicarbonate (0.12 g, 1.38 mmol, 2.0 eq.) at 0° C., stirred for 15 mins and then 2-chloroacetyl chloride (0.08 mL, 1.04 mmol, 1.5 eq.) was added at 0° C. The mixture was stirred at room temperature for 1.5 h under $N_2$ atmosphere. TLC (5% MeOH in DCM) showed the reaction was completed. The reaction was concentrated under reduced pressure to get the crude. The crude product was purified by flash column chromatography using 3-7% MeOH in DCM as an eluent to get the product which was further purified by Prep HPLC (Analytical condition: Column: KINETEX C18 (100 mm×4.6 mm×2.6 m), mobile phase (A): 0.1% TFA in water, mobile phase (B): ACN, Flow rate: 0.75 mL/min, Composition of B: 0/20, 5/90, 6/90, 8/20, 10/20) to give 2-chloro-1-((1S,3S)-3-methyl-1-(4-(4-methylpiperazin-1-yl)phenyl)-1,3,4,9-tetrahydro-2H-pyrido[3,4-b]indol-2-yl)ethan-1-one. LC-MS (m/z)=437.36 $[M+H]^+$. $^1H$ NMR (400 MHz, DMSO-d6): δ 1.10 (d, J=6.4 Hz, 3H), 2.15 (s, 2H), 2.37 (s, 4H), 2.84-2.87 (m, 1H), 3.02 (s, 4H), 3.08-3.13 (m, 3H), 4.60-4.77 (m, 2H), 5.89 (s, 1H), 6.80 (s, 2H), 6.91-7.01 (m, 2H), 7.17-7.26 (m, 3H), 7.40 (d, J=8.0 Hz, 1H), 10.88 (s, 1H).
Procedure EM: Synthesis of Compound 169 and Compound 167
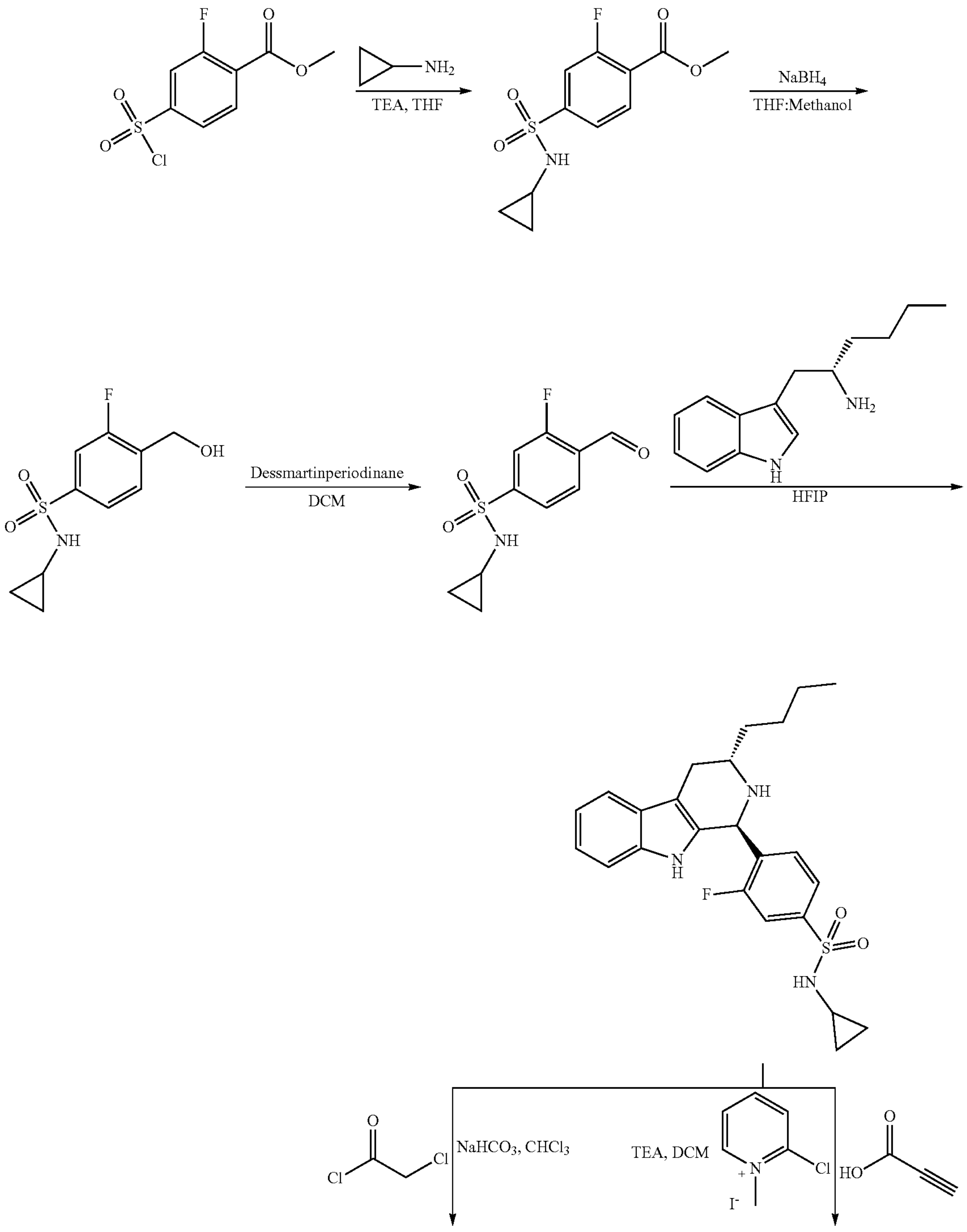

-continued

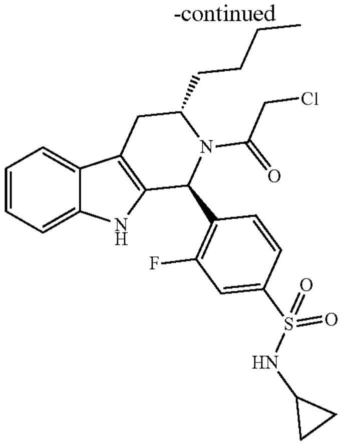

169

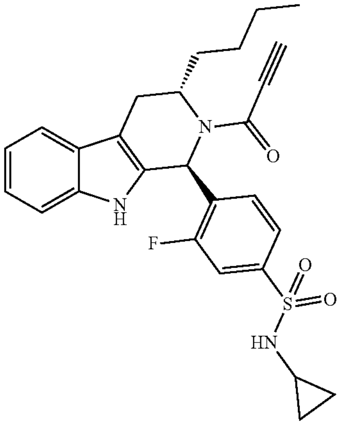

167

Methyl 4-(N-cyclopropylsulfamoyl)-2-fluorobenzoate: To a solution of methyl 4-(chlorosulfonyl)-2-fluorobenzoate (1.0 g, 3.96 mmol, 1 eq) and cyclopropanamine (0.27 mL, 3.96 mmol, 1 eq) in THF (25.0 mL) was added triethyl amine (1.67 mL, 11.88 mmol, 3.0 eq.) at 0° C. The mixture was stirred at room temperature for 12 h under $N_2$ atmosphere. TLC (30% EtOAc in hexane) showed the reaction was completed. The reaction was diluted with EtOAc (150 mL), washed with water (2×10 mL). The organic layer was dried over anhydrous $Na_2SO_4$, concentrated under reduced pressure to get the crude. The crude was purified by flash chromatography using 30-35% EtOAc in hexane as an eluent to give methyl 4-(N-cyclopropylsulfamoyl)-2-fluorobenzoate. LC-MS (m/z)=274.2 $[M+H]^+$. $^1H$ NMR (400 MHz, $CDCl_3$) δ ppm 0.36 (s, 2H), 0.48-0.51 (m, 2H), 2.15-2.17 (m, 1H), 3.87 (s, 2H), 7.66-7.73 (m, 2H), 8.10 (t, J=7.6 Hz, 1H), 8.20 (s, 1H).

N-cyclopropyl-3-fluoro-4-(hydroxymethyl)benzenesulfonamide: To a solution of methyl 4-(N-cyclopropylsulfamoyl)-2-fluorobenzoate (1.01 g, 3.69 mmol, 1 eq) in THF (10 mL) and MeOH (10.0 mL) was added sodium borohydride (1.37 g, 36.96 mmol, 10.0 eq) at 0° C. and the reaction was stirred at 80° C. for 12 h. TLC (50% EtOAc in hexane) showed the reaction was completed. The reaction mixture was concentrated under reduced pressure to get the crude which was dissolved in EtOAc (100 mL) and was washed with water (2×10 mL). The organic layers were dried over $Na_2SO_4$ and concentrated to give the crude product. The crude product was purified by flash column chromatography using 30-40% EtOAc in hexane as an eluent to give N-cyclopropyl-3-fluoro-4-(hydroxymethyl)benzenesulfonamide. LC-MS (m/z)=244.1 $[M+H]^-$. $^1H$ NMR (400 MHz, DMSO-d6) δ ppm 0.35 (s, 2H), 0.46 (d, J=5.2 Hz, 2H), 2.09 (s, 1H), 4.06 (d, J=4.8 Hz, 2H), 5.49 (t, J=5.0 Hz, 1H), 7.49 (d, J=9.6 Hz, 1H), 7.62-7.71 (m, 2H), 7.97 (s, 1H).

N-cyclopropyl-3-fluoro-4-formylbenzenesulfonamide: To a solution of N-cyclopropyl-3-fluoro-4-(hydroxymethyl) benzenesulfonamide (0.7 g, 2.85 mmol, 1 eq) in DCM (25.0 mL) was added Desmartin periodinane (1.8 g, 4.28 mmol, 1.5 eq) at 0° C. The mixture was allowed to stir at room temperature for 2 h. TLC (50% EtOAc in hexane) showed the reaction was completed. The reaction mixture was quenched with saturated $NaHCO_3$ solution at 0° C. and extracted with DCM (100 mL). The organic layers were dried over $Na_2SO_4$ and concentrated to get the crude. The crude product was purified by flash column chromatography using 30-35% EtOAc in hexane as an eluent to give N-cyclopropyl-3-fluoro-4-formylbenzenesulfonamide. LC-MS (m/z)=242.1 $[M+H]^-$. $^1H$ NMR (400 MHz, DMSO-d6) δ ppm 0.37 (s, 2H), 0.50 (d, J=6.0 Hz, 2H), 2.17 (s, 1H), 7.72-7.78 (m, 2H), 8.05 (t, J=7.2 Hz, 1H), 8.24 (s, 1H). 10.23 (s, 1H).

4-((1S,3S)-3-butyl-2,3,4,9-tetrahydro-1H-pyrido[3,4-b]indol-1-yl)-N-cyclopropyl-3-fluorobenzenesulfonamide: To a solution of (S)-1-(1H-indol-3-yl)hexan-2-amine (0.16 g, 0.74 mmol, 1 eq) in HFIP (2.0 mL) was added N-cyclopropyl-3-fluoro-4-formylbenzenesulfonamide (0.22 g, 0.89 mmol, 1.2 eq). The mixture was stirred at 80° C. for 16 h. TLC (30% EtOAc in hexane) showed the reaction was completed. The reaction mixture was cooled to room temperature and concentrated under reduced pressure to give the crude product. The crude product was purified by flash column chromatography using 20-25% EtOAc in hexane as an eluent to give 4-((1S,3S)-3-butyl-2,3,4,9-tetrahydro-1H-pyrido[3,4-b]indol-1-yl)-N-cyclopropyl-3-fluorobenzenesulfonamide. LC-MS (m/z)=442.2$[M+H]^+$. $^1H$ NMR (400 MHz, DMSO-d6) δ 0.35 (s, 2H), 0.47 (d, J=5.6 Hz, 2H), 0.78 (t, J=6.8 Hz, 3H), 1.13-1.17 (m, 2H), 1.25-1.26 (m, 2H), 1.40-1.41 (m, 2H), 2.08 (bs, 1H), 2.30 (t, J=11.8 Hz, 2H), 2.64-2.82 (m, 2H), 5.47 (s, 1H), 6.89-7.04 (m, 3H), 7.22 (d, J=7.2 Hz, 1H), 7.42-7.49 (m, 2H), 7.58 (d, J=9.2 Hz, 1H), 8.00 (s, 1H), 10.64 (s, 1H).

Preparation of Compound 169

4-((1S,3S)-3-butyl-2-(2-chloroacetyl)-2,3,4,9-tetrahydro-1H-pyrido[3,4-b]indol-1-yl)-N-cyclopropyl-3-fluorobenzenesulfonamide: To a solution of 4-((1S,3S)-3-butyl-2,3,4,9-tetrahydro-1H-pyrido[3,4-b]indol-1-yl)-N-cyclopropyl-3-fluorobenzenesulfonamide (0.06 g, 0.14 mmol, 1 eq) in $CHCl_3$ (10.0 mL) was added $NaHCO_3$ (0.023 g, 0.28 mmol, 2.0 eq) at 0° C., stirred for 15 mins and then and 2-chloroacetyl chloride (0.02 mL, 0.20 mmol, 1.5 eq) was added at 0° C. The mixture was allowed to stir at room temperature for 1.5 hr. TLC (40% EtOAc in hexane) showed the reaction was completed. The reaction mixture was concentrated under reduced pressure to give the crude product. The crude product was purified by flash column chromatography using 20-25% EtOAc in hexane as an eluent to give 4-((1S,3S)-3-butyl-2-(2-chloroacetyl)-2,3,4,9-tetrahydro-1H-pyrido[3,4-b]indol--yl)-N-cyclopropyl-3-fluorobenzenesulfonamide. LC-MS (m/z): 518.2 $[M+H]^+$. $^1H$ NMR (400 MHz, DMSO-d6): δ 0.34-0.44 (m, 4H), 0.76 (s, 3H), 1.21 (s, 4H), 1.44 (s, 2H), 2.02 (s, 1H), 3.03 (d, J=15.2 Hz, 1H), 3.10-3.20 (m, 1H), 4.39-4.49 (m, 2H), 6.68 (d, J=13.6 Hz, 1H), 6.10 (s, 1H), 6.94-7.03 (m, 2H), 7.23 (d, J=7.6 Hz, 1H), 7.37-7.52 (m, 4H), 7.97 (s, 1H), 10.80 (s, 1H).

Preparation of Compound 167

4-((1S,3S)-3-butyl-2-propioloyl-2,3,4,9-tetrahydro-1H-pyrido[3,4-b]indol-1-yl)-N-cyclopropyl-3-fluorobenzene-sulfonamide: To a solution of 4-((1S,3S)-3-butyl-2,3,4,9-tetrahydro-1H-pyrido[3,4-b]indol-1-yl)-N-cyclopropyl-3-fluorobenzenesulfonamide (0.06 g, 0.14 mmol, 1 eq) in DCM (8.0 mL) was added triethyl amine (0.05 mL, 0.34 mmol, 2.4 eq) at room temperature, stirred for 5 mins and then added propiolic acid (0.01 mL, 0.14 mmol, 1.0 eq) and 2-chloro-1-methyl pyridinium iodide (0.043 g, 0.17 mmol, 1.2 eq). The mixture was allowed to stir at room temperature for 16 hr. TLC (50% EtOAc in hexane) showed the reaction was completed. The reaction mixture was diluted with water (10 mL) and was extracted with DCM (100 mL). Organic layer was washed with brine solution (10 mL). The organic layers were dried over $Na_2SO_4$ and concentrated to give the crude product. The crude product was purified by Prep HPLC (Analytical condition: Column: Inertsil ODS 3V (150 mm×4.6 mm×5 PM), mobile phase (A): 0.1% ammonia in water, mobile phase (B): ACN, Flow rate: 1.0 mL/min, Composition of B: 0/20, 3/20, 7/80, 17/80, 18/20, 20/20) to give 4-((1S,3S)-3-butyl-2-propioloyl-2,3,4,9-tetrahydro-1H-pyrido[3,4-b]indol-1-yl)-N-cyclopropyl-3-fluorobenzenesulfonamide. LC-MS (m/z): 494.4 $[M+H]^+$. $^1H$ NMR (400 MHz, DMSO-d6): δ 0.35-0.46 (m, 4H), 0.80 (s, 3H), 1.23 (bs, 4H), 1.51 (bs, 2H), 2.09 (s, 1H), 3.03-3.10 (m, 2H), 4.51 (s, 1H), 4.96 (s, 1H), 6.12 (s, 1H), 6.97-7.03 (m, 2H), 7.25-7.30 (m, 1H), 7.47 (d, J=7.6 Hz, 4H), 7.83 (s, 1H), 10.71 (s, 1H).

Procedure EN: Synthesis of Compound 164 and Compound 153

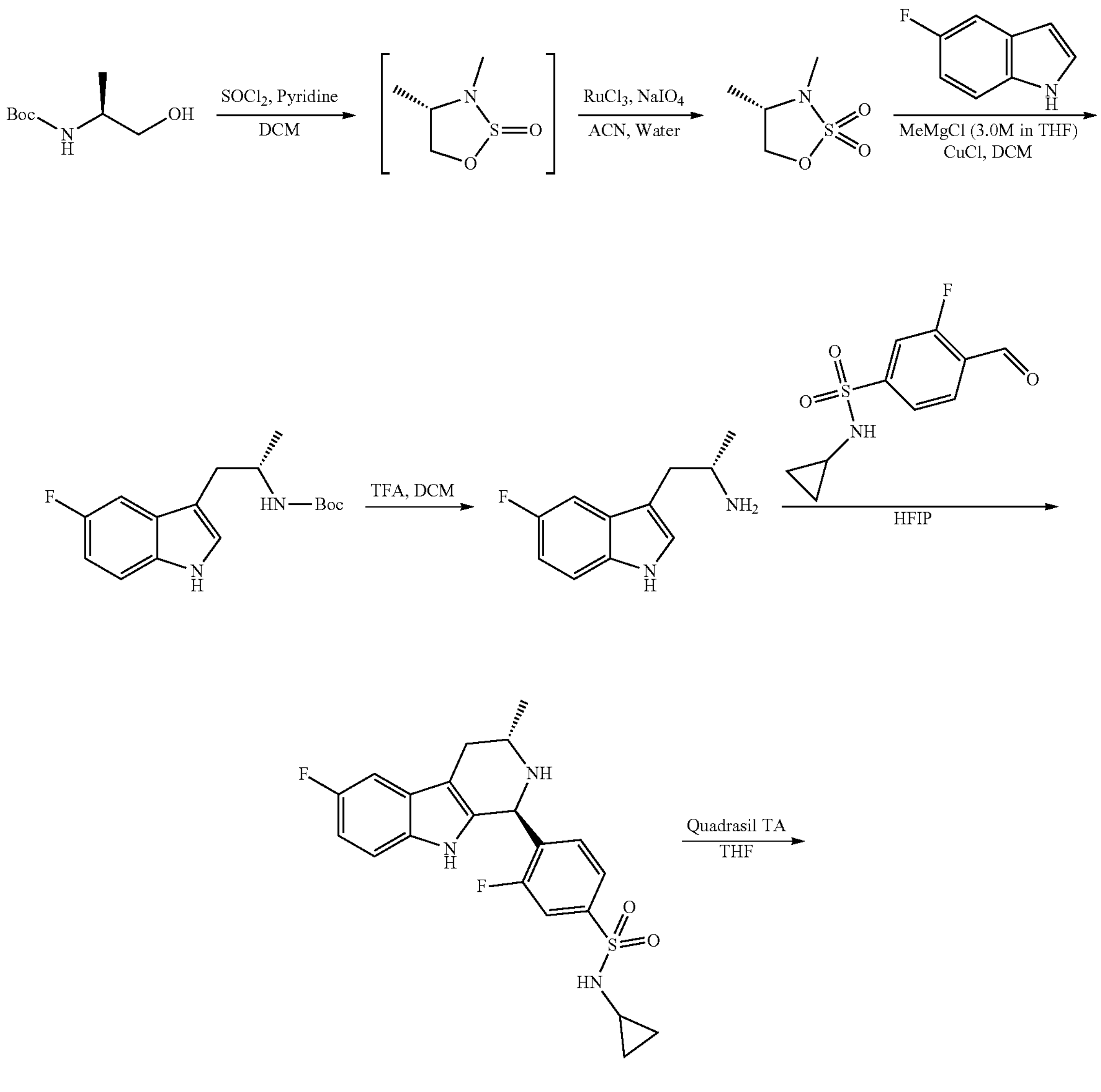

-continued

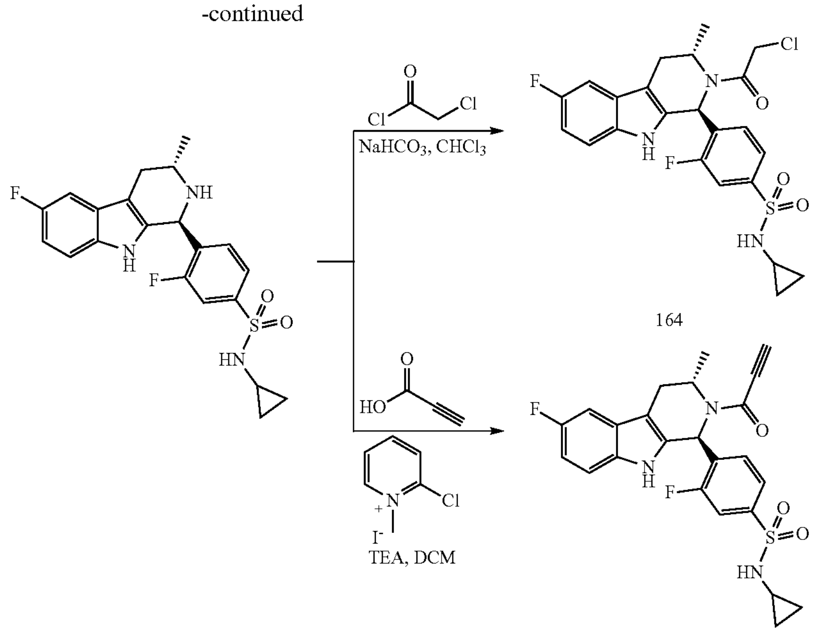

164

153

(S)-3,4-dimethyl-1,2,3-oxathiazolidine 2,2-dioxide: To a solution of thionyl chloride (2.07 mL, 28.53 mmol, 2.5 eq) in DCM (20.0 mL) at −40° C. was added tert-butyl (S)-(1-hydroxypropan-2-yl)carbamate (2.0 g, 11.41 mmol, 1 eq) in DCM (5.0 mL) and pyridine (4.8 mL, 59.33 mmol, 5.2 eq.). The mixture was stirred at −40° C. for 2 h under $N_2$ atmosphere. TLC (40% EtOAc in hexane) showed the reaction was completed. The reaction was diluted with DCM: EtOAc (1:1) and the precipitate was filtered. The filtrate was washed with brine (50 mL). The organic layer was dried over anhydrous $Na_2SO_4$, concentrated under reduced pressure to get (4S)-3,4-dimethyl-1,2,3-oxathiazolidine 2-oxide. (4S)-3,4-dimethyl-1,2,3-oxathiazolidine 2-oxide (4.0 g, 18.08 mmol, 1.0 eq) was dissolved in ACN (10 mL) and ruthenium chloride (0.02 g, 0.09 mmol, 0.005 eq) and sodium metaperiodate (4.25 g, 19.88 mmol, 1.1 eq) was added at 0° C. and then water (10 mL) was added. The mixture was stirred at room temperature for 2 h. TLC (40% EtOAc in hexane) showed the reaction was completed. The reaction mixture was filtered through celite bed and the bed was washed with EtOAc (100 mL). The filtrate was washed with $NaHCO_3$solution (2×10 mL), water (20 mL) and brine solution (20 mL). The organic layer was dried over anhydrous $Na_2SO_4$, concentrated under reduced pressure to get the crude. The crude was purified by flash chromatography using 30-40% EtOAc in hexane as an eluent to give (S)-3,4-dimethyl-1,2,3-oxathiazolidine 2,2-dioxide. $^1H$ NMR (400 MHz, $CDCl_3$) δ ppm 1.49-1.57 (m, 12H), 4.17-4.20 (m, 1H), 4.40-4.42 (m, 1H), 4.64-4.68 (m, 1H).

tert-butyl (S)-(1-(5-fluoro-1H-indol-3-yl)propan-2-yl) carbamate: To a mixture of 5-fluoro-1H-indole (0.25 g, 1.85 mmol, 1 eq) and cuprous chloride (0.24 g, 2.40 mmol, 1.3 eq) in round bottom flask was purged with vacuum and then DCM (10 mL) was added and the reaction mixture was cooled to 0° C. and MeMgCl (0.8 mL, 2.40 mmol, 1.3 eq) was added dropwise. The reaction mixture was maintained at 0° C. for 1 h. Then (S)-3,4-dimethyl-1,2,3-oxathiazolidine 2,2-dioxide (0.31 g, 1.29 mmol, 0.7 eq) in DCM (3 mL) was added at −20° C. dropwise and the reaction was stirred at −20° C. for 5 h. TLC (20% EtOAc in hexane) showed the formation of new spot. The reaction mixture was concentrated under reduced pressure to get the crude which was dissolved in EtOAc (100 mL) and was quenched with 10% citric acid at 0° C. and the reaction mixture was filtered through celite bed. The bed was washed with DCM (50 mL) and filtrate was washed with water (2×10 mL) and brine solution (10 mL). The organic layers were dried over $Na_2SO_4$ and concentrated to give the crude product. The crude product was purified by flash column chromatography using 20% EtOAc in hexane as an eluent to give tert-butyl (S)-(1-(5-fluoro-1H-indol-3-yl)propan-2-yl)carbamate. LC-MS (m/z)=237.1 $[M+H]^+$- after cleavage of t-butyl group. $^1H$ NMR (400 MHz, DMSO-d6) δ ppm 0.98 (d, J=6.0 Hz, 3H), 1.32 (s, 9H), 2.58-2.76 (m, 2H), 3.63-3.66 (m, 1H), 6.72 (d, J=7.2 Hz, 1H), 6.86 (t, J=9.0 Hz, 1H), 7.15 (s, 1H), 7.26-7.27 (m, 2H), 10.87 (s, 1H).

(S)-1-(5-fluoro-1H-indol-3-yl)propan-2-amine: To a solution of tert-butyl (S)-(1-(5-fluoro-1H-indol-3-yl)propan-2-yl)carbamate (0.2 g, 0.68 mmol, 1 eq) in DCM (10.0 mL) was added trifluoro acetic acid (0.5 mL)) at 0° C. The mixture was allowed to stir at room temperature for 3 h. TLC (40% EtOAc in hexane) showed the reaction was completed. The reaction mixture was concentrated under reduced pressure to get the crude. It was diluted with ice cold water (5 mL) and was basified by 5% NaOH solution (pH adjusted to 9) and was extracted with EtOAc (100 mL). The organic layers were dried over $Na_2SO_4$ and concentrated under reduced pressure to get (S)-1-(5-fluoro-1H-indol-3-yl)propan-2-amine. LC-MS (m/z)=193.1 $[M+H]^-$ N-cyclopropyl-3-fluoro-4-((1S,3S)-6-fluoro-3-methyl-2,3,4,9-tetrahydro-1H-pyrido[3,4-b]indol-1-yl)benzenesulfonamide: To a solution of (S)-1-(5-fluoro-1H-indol-3-yl)propan-2-amine (0.14 g, 0.72 mmol, 1 eq) in HFIP (2.0 mL) was added N-cyclopropyl-3-fluoro-4-formylbenzenesulfonamide (0.21 g, 0.87 mmol, 1.2 eq). The mixture was stirred at 80° C. for 16 h in a sealed tube. TLC (50% EtOAc in hexane) showed the reaction was completed. The reaction mixture was cooled to room temperature and concentrated under reduced pressure to give the crude product. The crude product was purified by flash column chromatography using 30-35% EtOAc in hexane as an eluent to give N-cyclopropyl-3-fluoro-4-((1S,3S)-6-fluoro-3-methyl-2,3,4,9-tetrahydro-1H-pyrido[3,4-b]indol-1-yl)benzenesulfonamide. LC-MS (m/z)=418.1[M+H]$^+$ Procedure for the scavenger treatment of N-cyclopropyl-3-fluoro-4-((1S,3S)-6-fluoro-3-methyl-2,3,4,9-tetrahydro-1H-pyrido[3,4-b]indol-1-yl)benzenesulfonamide: To a solution of N-cyclopropyl-3-fluoro-4-((1 S,3S)-6-fluoro-3-methyl-2,3,4,9-tetrahydro-1H-pyrido[3,4-b]indol-1-yl) benzenesulfonamide (0.06 g, 0.14 mmol, 1 eq) in THF (50.0 mL) was added Quadrasil TA (2.0 g, 2.0 eq). The mixture was stirred at room temperature for 1 h. The reaction mixture was filtered through sintered funnel and to the filtrate was again added Quadrasil TA (2.0 g, 2.0 eq) and reaction was stirred at room temperature for 1 h. The reaction mixture was filtered through sintered funnel and to the filtrate was concentrated under reduced pressure to give N-cyclopropyl-3-fluoro-4-((1S,3S)-6-fluoro-3-methyl-2,3,4,9-tetrahydro-1H-pyrido[3,4-b]indol-1-yl)benzenesulfonamide. LC-MS (m/z)=418.1[M+H]$^+$

Preparation of Compound 164

4-((1S,3S)-2-(2-chloroacetyl)-6-fluoro-3-methyl-2,3,4,9-tetrahydro-1H-pyrido[3,4-b]indol-1-yl)-N-cyclopropyl-3-fluorobenzenesulfonamide: To a solution of N-cyclopropyl-3-fluoro-4-((1 S,3S)-6-fluoro-3-methyl-2,3,4,9-tetrahydro-1H-pyrido[3,4-b]indol-1-yl)benzenesulfonamide (0.05 g, 0.12 mmol, 1 eq) in $CHCl_3$ (8.0 mL) was added $NaHCO_3$ (0.02 g, 0.24 mmol, 2.0 eq) at 0° C., stirred for 15 mins and then and 2-chloroacetyl chloride (0.014 mL, 0.18 mmol, 1.5 eq) was added at 0° C. The mixture was allowed to stir at room temperature for 1 h. TLC (40% EtOAc in hexane) showed the reaction was completed. The reaction mixture was concentrated under reduced pressure to give the crude product. The crude product was purified by flash column chromatography using 20-25% EtOAc in hexane as an eluent to give 4-((1S,3S)-2-(2-chloroacetyl)-6-fluoro-3-methyl-2,3,4,9-tetrahydro-1H-pyrido[3,4-b]indol-1-yl)-N-cyclopropyl-3-fluorobenzenesulfonamide. LC-MS (m/z): 494.0 [M+H]$^+$. $^1$H NMR (400 MHz, DMSO-d6): δ 0.35-0.46 (m, 4H), 1.18 (d, J=5.6 Hz, 3H), 2.00-2.10 (m, 1H), 2.89 (d, J=15.6 Hz, 1H), 3.20-3.30 (m, 1H), 4.44-4.46 (m, 1H), 4.70-4.76 (m, 2H), 6.15 (s, 1H), 6.87 (t, J=8.2 Hz, 1H), 7.25-7.27 (m, 2H), 7.40-7.45 (m, 2H), 7.52 (d, J=9.2 Hz, 1H), 7.98 (s, 1H), 10.94 (s, 1H).

Preparation of Compound 153

N-cyclopropyl-3-fluoro-4-((1S,3S)-6-fluoro-3-methyl-2-propioloyl-2,3,4,9-tetrahydro-1H-pyrido[3,4-b]indol-1-yl) benzenesulfonamide: To a solution of N-cyclopropyl-3-fluoro-4-((1 S,3S)-6-fluoro-3-methyl-2,3,4,9-tetrahydro-1H-pyrido[3,4-b]indol-1-yl)benzenesulfonamide (0.08 g, 0.19 mmol, 1.0 eq) in DCM (10.0 mL) was added triethyl amine (0.064 mL, 0.46 mmol, 2.4 eq) at room temperature, stirred for 5 mins and then added propiolic acid (0.012 mL, 0.19 mmol, 1.0 eq) and 2-chloro-1-methyl pyridinium iodide (0.06 g, 0.23 mmol, 1.2 eq). The mixture was allowed to stir at room temperature for 30 mins. TLC (40% EtOAc in hexane) showed the reaction was completed. The reaction mixture was diluted with DCM (100 mL) and was washed with water (2×10 mL. The organic layers were dried over $Na_2SO_4$ and concentrated to give the crude product. The crude product was purified by flash column chromatography using 20-25% EtOAc in hexane as an eluent to give N-cyclopropyl-3-fluoro-4-((1S,3S)-6-fluoro-3-methyl-2-propioloyl-2,3,4,9-tetrahydro-1H-pyrido[3,4-b]indol-1-yl)benzenesulfonamide. LC-MS (m/z): 469.8[M+H]$^+$. $^1$H NMR (400 MHz, DMSO-d6): δ 0.35 (s, 2H), 0.45-0.46 (m, 2H), 1.20 (d, J=6.8 Hz, 3H), 2.02 (bs, 1H), 2.94 (d, J=15.2 Hz, 1H), 3.45 (s, 1H), 4.66 (s, 1H), 5.17 (t, J=6.0 Hz, 1H), 6.16 (s, 1H), 6.88 (t, J=9.2 Hz, 1H), 7.22-7.27 (m, 2H), 7.46 (s, 1H), 7.51 (d, J=9.6 Hz, 1H), 7.56-7.60 (m, 1H), 7.99 (s, 1H), 10.98 (s, 1H).

Procedure EO: Synthesis of Compound EO

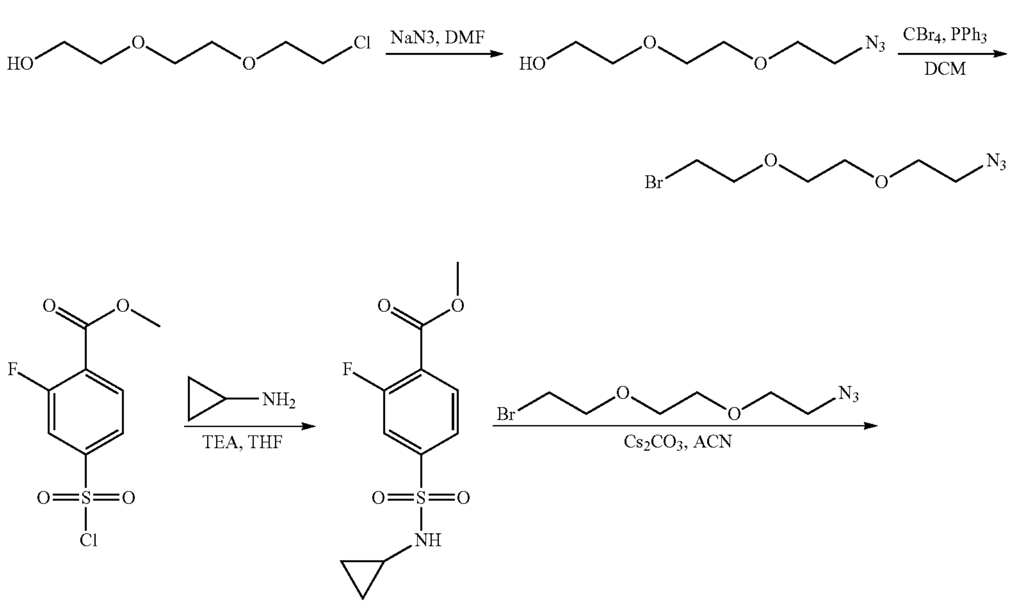

-continued
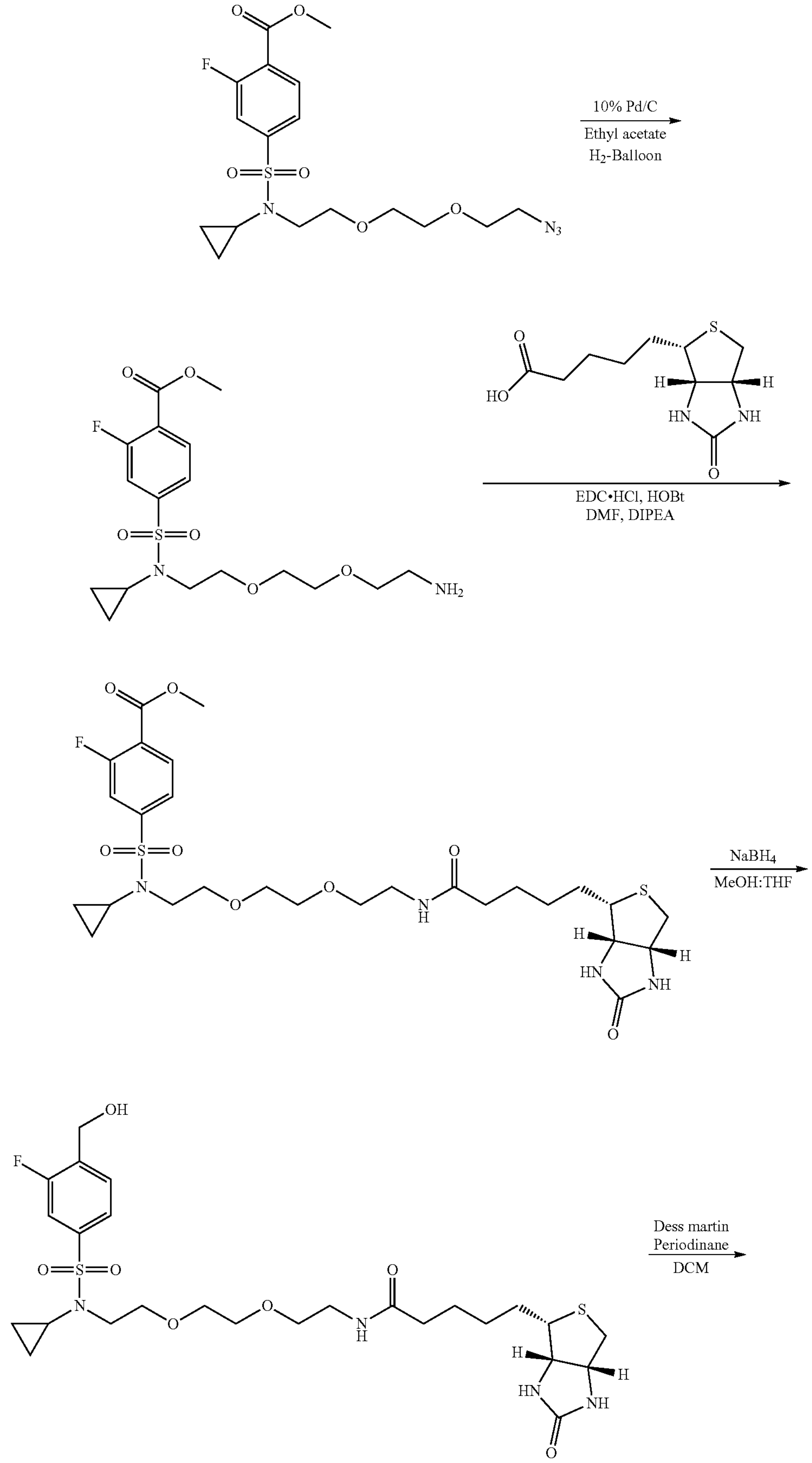

-continued

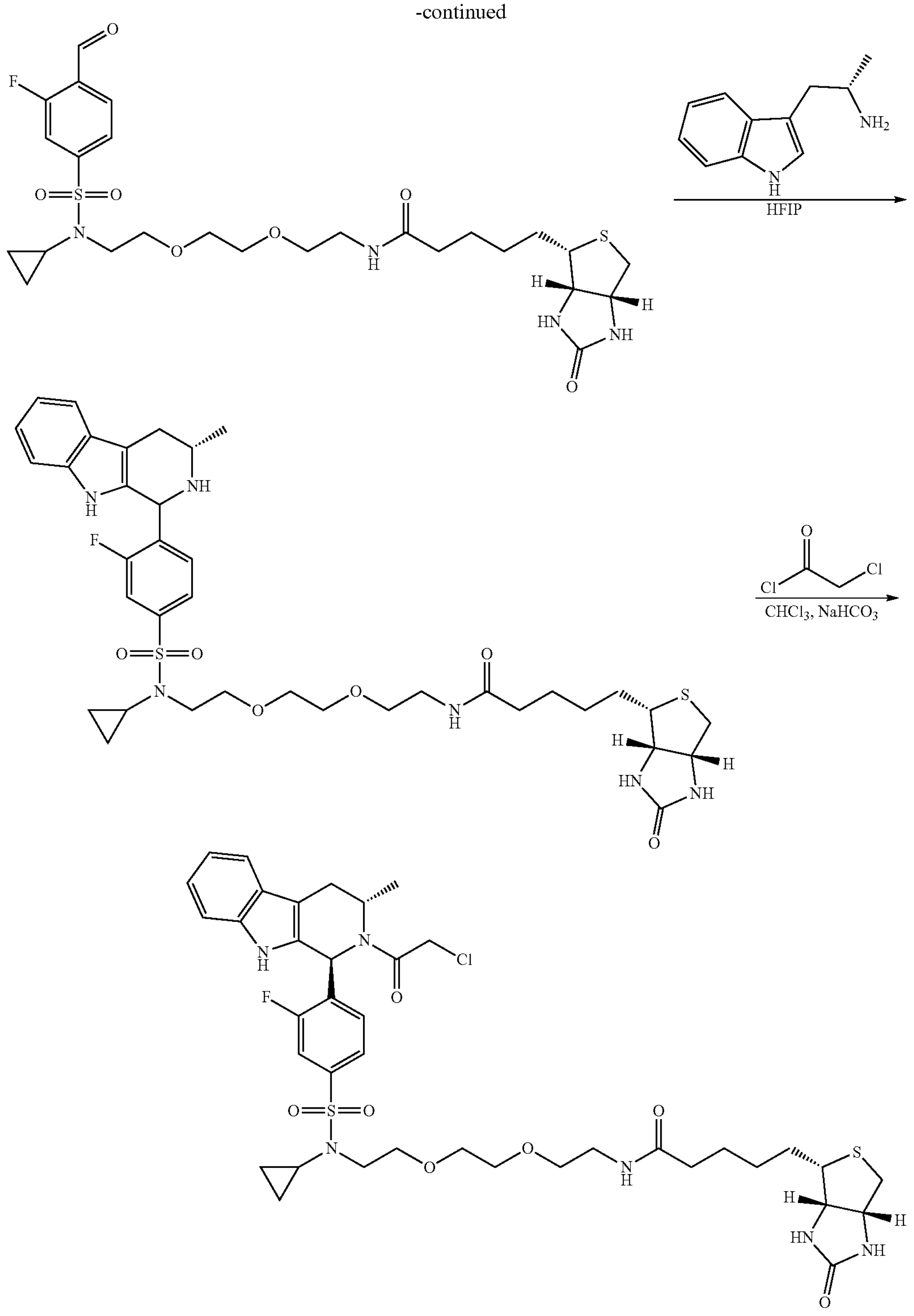

EO 2-(2-(2-azidoethoxy)ethoxy)ethan-1-ol: To a solution of 2-(2-(2-chloroethoxy)ethoxy)ethan-1-ol (5.0 g, 29.72 mmol, 1 eq.) in DMF (15 mL) at 0° C. sodium azide (2.9 g, 44.58 mmol, 1.5 eq) was added. Then reaction mixture was heated at 100° C. for 16 h. Reaction mixture cool to room temperature and diluted with water and extracted with ethyl acetate (2×100 mL). Combined organic layer washed with ice water (50 mL), brine (25 mL), dried over anhydrous $Na_2SO_4$, filtered and concentrated under reduced pressure to get the crude product. 2-(2-(2-azidoethoxy)ethoxy)ethan-1-ol. $^1$H NMR (400 MHz, CDCl3) δ ppm: 3.40 (t, J=4.8 Hz, 2H), 3.61 (t, J=4.4 Hz, 2H), 3.68-3.69 (m, 6H), 3.74 (t, J=4.4 Hz, 2H). 1-azido-2-(2-(2-bromoethoxy)ethoxy)ethane: To a solution of 2-(2-(2-azidoethoxy)ethoxy)ethan-1-ol (2.2 g, 12.55 mmol, 1 eq) in DCM (40 mL) at 0° C. Triphenylphosphine (3.95 g, 15.06 mmol, 1.2 eq) and Carbon tetra bromide (4.99 g, 15.06 mmol, 1.2 eq) were added, Then reaction mixture stirred at room temperature for 16 h. Then the reaction was diluted with water (15 mL) and was extracted with DCM (2×15 mL). The organic layer was dried over anhydrous $Na_2SO_4$, filtered and concentrated under reduced pressure to get the crude. The crude was purified by flash chromatography using 15-25% EtOAc in hexane as an eluent to give 1-azido-2-(2-(2-bromoethoxy)ethoxy)ethane. LC-MS (m/z)=Desired mass not ionized. $^1$H NMR (400 MHz, $CDCl_3$): δ 3.38-3.39 (m, 2H), 3.46-3.49 (m, 2H), 3.68 (s, 6H), 3.81-3.84 (m, 2H).

Methyl 4-(N-cyclopropylsulfamoyl)-2-fluorobenzoate: To a solution of methyl 4-(chlorosulfonyl)-2-fluorobenzoate (0.750 g, 2.96 mmol, 1 eq) and cyclopropanamine (0.169 g, 2.96 mmol, 1 eq) in THF (20.0 mL) was added triethyl amine (1.25 mL, 8.90 mmol, 3.0 eq.) at 0° C. The mixture was stirred at room temperature for 2 h under $N_2$ atmosphere. TLC (40% EtOAc in hexane) showed the reaction was completed. The reaction was diluted with EtOAc (150 mL), washed with water (2×10 mL). The organic layer was dried over anhydrous $Na_2SO_4$, concentrated under reduced pressure to get the crude. The crude was purified by flash chromatography using 15-25% EtOAc in hexane as an eluent to give methyl 4-(N-cyclopropylsulfamoyl)-2-fluorobenzoate. LC-MS (m/z)=272.1 [M−H]-. $^1$H NMR (400 MHz, $CDCl_3$) δ: ppm 0.64-0.68 (m, 4H), 3.27-3.32 (m, 1H), 3.97 (s, 3H), 4.91 (s, 1H), 7.67-7.74 (m, 2H), 8.07-8.11 (m, 1H).

Methyl 4-(N-(2-(2-(2-azidoethoxy)ethoxy)ethyl)-N-cyclopropylsulfamoyl)-2-fluorobenzoate: To a solution of methyl 4-(N-cyclopropylsulfamoyl)-2-fluorobenzoate (0.440 g, 1.61 mmol, 1 eq) in Acetonitrile (20 mL) at 0° C. Cs2CO3 (0.628 g, 1.93 mmol, 1.2 eq) followed by 1-azido-2-(2-(2-bromoethoxy)ethoxy)ethane (0.460 g, 1.93 mmol, 1.2 eq) added. Then reaction mixture heated at 80° C. for 4 h. Reaction mixture cool to rt, evaporated under reduced pressure to get crude product. The crude was purified by flash chromatography using 15-20% EtOAc in hexane as an eluent to give methyl 4-(N-(2-(2-(2-azidoethoxy)ethoxy)ethyl)-N-cyclopropylsulfamoyl)-2-fluorobenzoate. LC-MS (m/z)=431.2 [M+H]$^+$. $^1$H NMR (400 MHz, $CDCl_3$) δ ppm: 0.73-0.74 (m, 2H), 0.91 (s, 2H), 2.17 (s, 1H), 3.37-3.44 (m, 4H), 3.58 (s, 4H), 3.64-3.66 (m, 4H), 3.96 (s, 3H), 7.64-7.71 (m, 2H), 8.05-8.09 (m, 1H).

Methyl 4-(N-(2-(2-(2-aminoethoxy)ethoxy)ethyl)-N-cyclopropylsulfamoyl)-2-fluorobenzoate: To a solution of methyl 4-(N-(2-(2-(2-azidoethoxy)ethoxy)ethyl)-N-cyclopropylsulfamoyl)-2-fluorobenzoate (0.520 g, 1.19 mmol, 1 equiv) in ethyl acetate (25 mL) 10% Pd/C was added. The reaction mixture was stirred under H2-Balloon at rt for 5 h. Then reaction mixture filtered through celite bed. Celited bed thoroughly washed with ethylacetate. Organic layer concentrated under reduced pressure to get crude methyl 4-(N-(2-(2-(2-aminoethoxy)ethoxy)ethyl)-N-cyclopropylsulfamoyl)-2-fluorobenzoate. LC-MS (m/z)=401.5 [M+H]$^+$ Methyl-4-(N-cyclopropyl-N-(2-(2-(2-(5-((3aS,4S,6aR)-2-oxohexahydro-1H-thieno[3,4-d]imidazol-4-yl)pentanamido)ethoxy)ethoxy)ethyl)sulfamoyl)-2-fluorobenzoate: To a solution of 5-((3aS,4S,6aR)-2-oxohexahydro-1H-thieno[3,4-d]imidazol-4-yl)pentanoic acid (0.298 g, 1.22 mmol, 1.2 eq) in DMF (20.0 mL) was added DIPEA (0.575 mL, 3.33 mmol, 3.0 eq), and methyl 4-(N-(2-(2-(2-aminoethoxy)ethoxy)ethyl)-N-cyclopropylsulfamoyl)-2-fluorobenzoate (0.450 g, 1.11 mmol, 1 equiv) and stirred for 5 mins and then EDC.HCl (0.318 g, 1.66 mmol, 1.5 eq) and HOBt (0.225 g, 1.66 mmol, 1.5 eq) was added. Then reaction was stirred at room temperature for 12 h under $N_2$ atmosphere. TLC (10% methanol in DCM) showed the reaction was completed. The reaction was diluted with ice and extracted with ethyl acetate (150 mL). The organic layer was washed with saturated $NaHCO_3$solution (2×10 mL) and water (2×15 mL). Combined organic layer was dried over anhydrous $Na_2SO_4$, concentrated under reduced pressure to get the crude. The crude product was purified by flash column chromatography using 6-7% methanol in DCM as an eluent to give methyl 4-(N-cyclopropyl-N-(2-(2-(2-(5-((3aS,4S,6aR)-2-oxohexahydro-1H-thieno[3,4-d]imidazol-4-yl)pentanamido)ethoxy)ethoxy)ethyl)sulfamoyl)-2-fluorobenzoate. LC-MS (m/z)=631.3 [M+H]$^+$ N-(2-(2-(2-((N-cyclopropyl-3-fluoro-4-(hydroxymethyl)phenyl)sulfonamido)ethoxy)ethoxy)ethyl)-5-((3aS,4S,6aR)-2-oxohexahydro-1H-thieno[3,4-d]imidazol-4-yl)pentanamide: To a solution of methyl 4-(N-cyclopropyl-N-(2-(2-(2-(5-((3aS,4S,6aR)-2-oxohexahydro-1H-thieno[3,4-d]imidazol-4-yl)pentanamido)ethoxy)ethoxy)ethyl)sulfamoyl)-2-fluorobenzoate (0.500 g, 0.792 mmol, 1 eq) in THF (12 mL) and MeOH (12.0 mL) was added sodium borohydride (0.299 g, 7.92 mmol, 10.0 eq) at 0° C. and the reaction was stirred at 80° C. for 14 h. The reaction mixture was concentrated under reduced pressure to get the crude which was dissolved in EtOAc (100 mL) and was washed with water (2×10 mL). The organic layers were dried over $Na_2SO_4$ and concentrated to give the crude product. The crude product was purified by flash column chromatography using 8-9% methanol in DCM as an eluent to give N-(2-(2-(2-((N-cyclopropyl-3-fluoro-4-(hydroxymethyl)phenyl)sulfonamido)ethoxy)ethoxy)ethyl)-5-((3aS,4S,6aR)-2-oxohexahydro-1H-thieno[3,4-d]imidazol-4-yl)pentanamide. LC-MS (m/z)=603.3 [M+H]$^+$ 1H NMR (400 MHz, DMSO-d6) δ ppm 0.35 (s, 2H), 0.46 (d, J=5.2 Hz, 2H), 2.09 (s, 1H), 4.06 (d, J=4.8 Hz, 2H), 5.49 (t, J=5.0 Hz, 1H), 7.49 (d, J=9.6 Hz, 1H), 7.62-7.71 (m, 2H), 7.97 (s, 1H).

N-(2-(2-(2-((N-cyclopropyl-3-fluoro-4-formylphenyl)sulfonamido)ethoxy)ethoxy)ethyl)-5-((3aS,4S,6aR)-2-oxohexahydro-1H-thieno[3,4-d]imidazol-4-yl)pentanamide: To a solution of N-(2-(2-(2-((N-cyclopropyl-3-fluoro-4-(hydroxymethyl)phenyl)sulfonamido)ethoxy)ethoxy)ethyl)-5-((3aS,4S,6aR)-2-oxohexahydro-1H-thieno[3,4-d]imidazol-4-yl)pentanamide (0.180 g, 0.298 mmol, 1 eq) in DCM (8.0 mL) was added Desmartin periodinane (0.126 g, 0.298 mmol, 1.0 eq) at 0° C. The mixture was allowed to stir at room temperature for 5 h. The reaction mixture was quenched with saturated $NaHCO_3$ solution at 0° C. and extracted with DCM (100 mL). The organic layers were dried over $Na_2SO_4$ and concentrated to get the crude. The crude product was purified by flash column chromatography using 6-7% methanol in DCM as an eluent to give N-(2-(2-(2-((N-cyclopropyl-3-fluoro-4-formylphenyl)sulfonamido)ethoxy)ethoxy)ethyl)-5-((3 aS,4S,6aR)-2-oxohexahydro-1H-thieno[3,4-d]imidazol-4-yl)pentanamide. LC-MS (m/z)=601.3 [M+H]$^+$ N-(2-(2-(2-((N-cyclopropyl-3-fluoro-4-((S)-3-methyl-2,3,4,9-tetrahydro-1H-pyrido[3,4-b]indol-1-yl)phenyl)sulfonamido)ethoxy)ethoxy)ethyl)-5-((3aS,4S,6aR)-2-oxohexahydro-1H-thieno[3,4-d]imidazol-4-yl)pentanamide: In a sealed tube to a solution of (S)-1-(1H-indol-3-yl)propan-2-amine (0.026 g, 0.149 mmol, 1 eq) in HFIP (2.0 mL) was added N-(2-(2-(2-((N-cyclopropyl-3-fluoro-4-formylphenyl)sulfonamido)ethoxy)ethoxy)ethyl)-5-((3aS,4S,6aR)-2-oxohexahydro-1H-thieno[3,4-d]imidazol-4-yl)pentanamide (0.090 g, 0.149 mmol, 1.0 eq). The mixture was stirred at 80° C. for 16 h. TLC (30% EtOAc in hexane) showed the reaction was completed. The reaction mixture was cooled to room temperature and concentrated under reduced pressure to give the crude product. The crude product was purified by flash column chromatography using 6-7% methanol in DCM as an eluent to give N-(2-(2-(2-((N-cyclopropyl-3-fluoro-4-((S)-3-methyl-2,3,4,9-tetrahydro-1H-pyrido[3,4-b]indol-1-yl)phenyl)sulfonamido)ethoxy)ethoxy)ethyl)-5-((3aS,4S,6aR)-2-oxohexahydro-1H-thieno[3,4-d]imidazol-4-yl)pentanamide. LC-MS (m/z)=757.3 $[M+H]^+$ Preparation of Compound EO N-(2-(2-(2-((4-((S)-2-(2-chloroacetyl)-3-methyl-2,3,4,9-tetrahydro-1H-pyrido[3,4-b]indol-1-yl)-N-cyclopropyl-3-fluorophenyl)sulfonamido)ethoxy)ethoxy)ethyl)-5-((3aS,4S,6aR)-2-oxohexahydro-1H-thieno[3,4-d]imidazol-4-yl)pentanamide: To a solution of N-(2-(2-(2-((N-cyclopropyl-3-fluoro-4-((S)-3-methyl-2,3,4,9-tetrahydro-1H-pyrido[3,4-b]indol-1-yl)phenyl)sulfonamido)ethoxy)ethoxy)ethyl)-5-((3aS,4S,6aR)-2-oxohexahydro-1H-thieno[3,4-d]imidazol-4-yl)pentanamide (0.040 g, 0.052 mmol, 1 eq) in $CHCl_3$ (5.0 mL) was added $NaHCO_3$ (0.009 g, 0.28 mmol, 2.0 eq) at 0° C., stirred for 15 mins and then and 2-chloroacetyl chloride (0.006 mL, 0.07 mmol, 1.5 eq) was added at 0° C. The mixture was allowed to stir at room temperature for 6 hr. The reaction mixture was concentrated under reduced pressure to give the crude product and taken for Preparative HPLC Purification (Column: intersil ODS 3V (150 mm×4.6 mm×5 μm); Mobile phase A: 0.1% Ammonia in water; Mobile phase B: Acetonitrile). LC-MS (m/z): 832.7 $[M+H]^+$ A similar synthetic scheme was used to synthesize Compound 170: LC-MS (m/z): 490.3 $[M+H]^+$. $^1H$ NMR (400 MHz, DMSO-$d_6$): δ 0.64-0.69 (m, 4H), 1.14-1.15 (m, 3H), 1.77 (s, 1H), 2.62 (s, 3H), 2.88-2.92 (m, 1H), 3.31 (s, 1H), 4.46 (s, 1H), 4.70-4.76 (m, 2H), 6.16 (s, 1H), 6.94-6.97 (m, 1H), 7.00-7.04 (m, 1H), 7.24-7.26 (m, 1H), 7.45-7.47 (m, 3H), 7.53-7.56 (m, 1H), 10.84 (s, 1H).

Procedure EQ: Synthesis of Compound 162

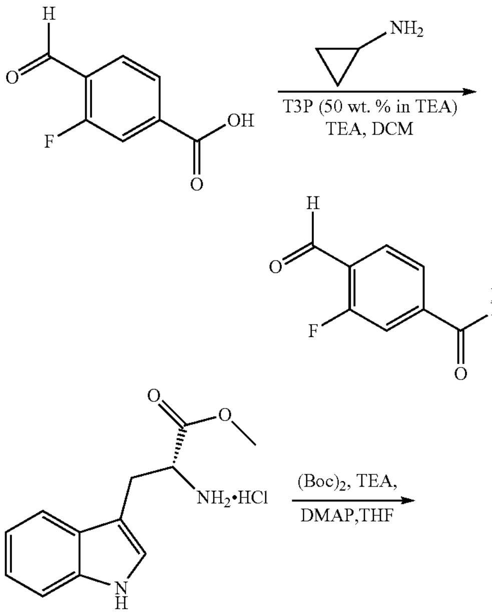

-continued

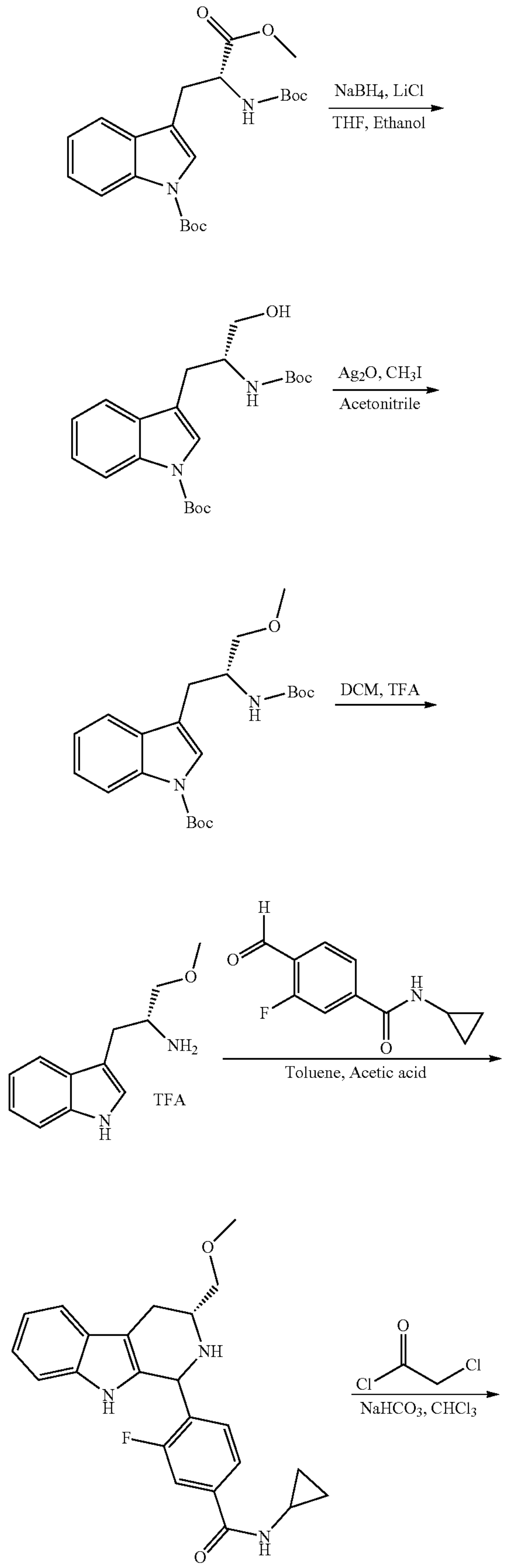

-continued

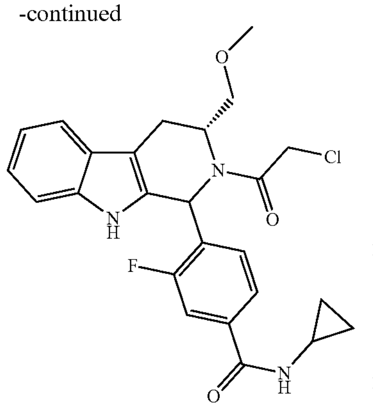

162

N-cyclopropyl-3-fluoro-4-formylbenzamide: To a stirred solution of 3-fluoro-4-formylbenzoic acid (0.750 g, 4.46 mmol, 1.0 eq.) in DCM (20 mL) was added triethyl amine (1.84 mL, 13.15 mmol, 3 eq.) and T3P (50% wt. in ethyl acetate) (4.2 mL, 6.68 mmol, 1.5 eq.) was added drop wise at 0° C. The reaction was stirred at room temperature for 10 minutes then cyclopropanamine (0.254 g, 4.46 mmol, 1 eq) was added then reaction mixture was allowed to stir at rt for 14 h. After consumption of the starting material the reaction mixture was diluted with water (6 mL) and extracted with DCM (2×10 mL mL), and Combined organic layer was washed with saturated sodium bicarbonate solution (12 mL) and brine (10 mL). dried over anhydrous sodium sulfate, filtered and concentrated to get the crude. Crude was purified by flash column chromatography using 15-20% ethyl acetate in hexane as an eluent to get the product N-cyclopropyl-3-fluoro-4-formylbenzamide. LC-MS (m/z)=208.1 [M+H]+. $^1$H NMR (400 MHz, $CDCl_3$) δ ppm: 0.65 (s, 2H), 0.90-0.92 (m, 2H), 2.91-2.92 (m, 1H), 6.27 (s, 1H), 7.54-7.62 (m, 2H), 7.90-7.93 (m, 1H), 10.38 (s, 1H).

tert-butyl (R)-3-(2-((tert-butoxycarbonyl)amino)-3-methoxy-3-oxopropyl)-1H-indole-1-carboxylate: To a solution of methyl D-tryptophanate hydrochloride (5.0 g, 19.63 mmol, 1 eq) in THF at 0° C., TEA (2.75 mL, 19.63 mmol, 1 eq), $Boc_2O$ (1 eq) and DMAP (3.59 g, 29.44 mmol, 1.5 eq) were added. Then reaction mixture was allowed to stir at rt for 14 h. Reaction mixture was diluted with water (20 mL), extracted with ethyl acetate (2×150 mL). Combined organic layer washed with brine (20 mL), water (40 mL), dried over anhydrous sodium sulphate. Organic layer filtered and concentrated under reduced pressure. Crude was purified by flash column chromatography using 15-20% of ethyl acetate in hexane as an eluent to get the product tert-butyl (R)-3-(2-((tert-butoxycarbonyl)amino)-3-methoxy-3-oxopropyl)-1H-indole-1-carboxylate. $^1$H NMR (400 MHz, DMSO-d6) δ ppm: 1.36 (s, 9H). 1.60 (s, 9H), 2.93-2.99 (m, 1H), 3.06-3.08 (m, 1H), 3.61 (s, 3H), 4.25 (bs, 1H), 7.23-7.35 (m, 3H), 7.49-7.54 (m, 2H), 8.00-8.02 (m, 1H).

tert-butyl (R)-3-(2-((tert-butoxycarbonyl)amino)-3-hydroxypropyl)-1H-indole-1-carboxylate: To a solution of tert-butyl (R)-3-(2-((tert-butoxycarbonyl)amino)-3-methoxy-3-oxopropyl)-1H-indole-1-carboxylate (0.200 g, 0.477 mmol 1 eq) in THF (5 mL) at 0° C. LiCl (0.050 g, 1.19 mmol, 2.5 eq) was added followed by addition of sodium borohydride (0.045 g, 2.5 eq, 1.19 mmol).Then reaction mixture was stirred at rt for 10 minutes then ethanol (5 mL) was added and stirred for 14 h. Then reaction mixture was quenched with aqueous ammonium chloride and extracted with ethyl acetate (2×10 mL). Combined organic layer washed with brine (2 mL), water (5 mL),dried over anhydrous sodium sulphate. Organic layer filtered and concentrated under reduced pressure. Crude was purified by flash column chromatography using 20-25% ethyl acetate in hexane as an eluent to get the product tert-butyl (R)-3-(2-((tert-butoxycarbonyl)amino)-3-hydroxypropyl)-1H-indole-1-carboxylate. LC-MS (m/z)=391.3 [M+H]+. $^1$H NMR (400 MHz, CDCl3) δ ppm: 1.42 (s, 9H), 1.66 (s, 10H), 2.93-2.95 (m, 2H), 3.61-3.64 (m, 1H), 3.69-3.71 (m, 1H), 3.98 (s, 1H), 4.82 (s, 1H), 7.22-7.25 (m, 1H), 7.29-7.33 (m, 1H), 7.43 (s, 1H), 7.60-7.61 (m, 1H), 8.12 (s, 1H).

tert-butyl (R)-3-(2-((tert-butoxycarbonyl)amino)-3-methoxypropyl)-1H-indole-1-carboxylate: To a solution of tert-butyl (R)-3-(2-((tert-butoxycarbonyl)amino)-3-hydroxypropyl)-1H-indole-1-carboxylate (0.140 g, 0.358 mmol, 1 equiv) in Acetonitrile at rt $Ag_2O$ (0.415 g, 1.79 mmol, 5 eq) was added followed by methyl iodide (0.115 mL, 1.79 mmol, 5 eq).The reaction mixture stirred at rt for 72 h. Reaction mixture was filtered through celilte, washed with ethyl acetate (50 mL).Filtrated was concentrated under reduced pressure to get crude Product. Crude was purified by flash column chromatography using 15-20% ethyl acetate in hexane as an eluent to get the product tert-butyl (R)-3-(2-((tert-butoxycarbonyl)amino)-3-methoxypropyl)-1H-indole-1-carboxylate. LC-MS (m/z)=405.3 [M+H]+. 1H NMR (400 MHz, CDCl3) δ ppm: 1.43 (s, 9H), 1.65 (s, 9H), 2.90-2.95 (m, 2H), 3.28-3.33 (m, 5H), 4.00 (s, 1H), 4.92 (s, 1H), 7.21-7.23 (m, 1H), 7.28-7.32 (m, 1H), 7.42 (s, 1H), 7.63-7.65 (m, 1H), 8.10 (s, 1H), (R)-1-(1H-indol-3-yl)-3-methoxypropan-2-amine 2,2,2-trifluoroacetaldehyde: To a solution of tert-butyl (R)-3-(2-((tert-butoxycarbonyl)amino)-3-methoxypropyl)-1H-indole-1-carboxylate (0.065 g, 0.160 mmol, 1 eq) in DCM at 0° C. TFA (1 mL) was added. Then reaction mixture stirred at rt for 12 h. Solvent was evaporated under reduced pressure. Obtained crude dried and taken for next step. LC-MS (m/z)=205.1 [M+H]+. 1H NMR (400 MHz, DMSO-d6) δ ppm: 2.92-2.95 (m, 2H), 3.26 (s, 3H), 3.31-3.35 (m, 1H), 3.42-3.52 (m, 2H), 6.98-7.01 (m, 1H), 7.07-7.10 (m, 1H), 7.21 (s, 1H), 7.35 (d, J=8.0 Hz, 1H), 7.53 (d, J=8.0 Hz, 1H), 7.83 (bs, 3H), 10.99 (s, 1H).

N-cyclopropyl-3-fluoro-4-((3R)-3-(methoxymethyl)-2,3,4,9-tetrahydro-1H-pyrido[3,4-b]indol-1-yl)benzamide: To a solution of (R)-1-(1H-indol-3-yl)-3-methoxypropan-2-amine2,2,2-trifluoroacetaldehyde (45 mg, 0.143 mmol, 1 eq) in toluene (5 mL) was added N-cyclopropyl-3-fluoro-4-formylbenzamide (0.029 g, 0.143 mmol, 1 eq). Then AcOH (0.008 mL, 0.143 mmol, 1 eq) was added. The mixture stirred at 120° C. for 8 hr to give a yellow solution. The reaction mixture was basified to pH=8 with Sat $NaHCO_3$and extracted with ethyl acetate (2×10 mL The organic layers were dried over $Na_2SO4$ and concentrated to give a crude product. Crude was purified by flash column chromatography using 3-4% Methanol in DCM as eluent to get the product N-cyclopropyl-3-fluoro-4-((3R)-3-(methoxymethyl)-2,3,4,9-tetrahydro-1H-pyrido[3,4-b]indol-1-yl)benzamide. LC-MS (m/z)=394.2 [M+H]+.

Preparation of Compound 162

4-((3R)-2-(2-chloroacetyl)-3-(methoxymethyl)-2,3,4,9-tetrahydro-1H-pyrido[3,4-b]indol-1-yl)-N-cyclopropyl-3-fluorobenzamide: To a solution of N-cyclopropyl-3-fluoro-4-((3R)-3-(methoxymethyl)-2,3,4,9-tetrahydro-1H-pyrido[3,4-b]indol-1-yl)benzamide (mixture of cis and trans) (0.035 g, 0.08 mmol, 1 eq) in $CHCl_3$ (5 mL) $NaHCO_3$(0.014 g, 1.18 mmol, 2 eq) was added. After stirring 5 minutes was added 2-chloroacetyl chloride (0.010 mL, 0.133 mmol, 1.5 eq) drop wise at 0° C. The reaction mixture was stirred at rt for 3.5 hr to give a light yellow suspension. The reaction mixture was diluted with water (5 mL) and extracted with DCM (2×15 mL). The organic layers were dried over $Na_2SO4$ and concentrated to give crude product. Crude was purified by flash column chromatography using 40-50% ethyl acetate in hexane as an eluent to get the product 4-((3R)-2-(2-chloroacetyl)-3-(methoxymethyl)-2,3,4,9-tetrahydro-1H-pyrido[3,4-b]indol-1-yl)-N-cyclopropyl-3-fluorobenzamide (1:4 mixture of diastereomer). LC-MS (m/z)=470.3 [M+H]+. 1H NMR (400 MHz, DMSO-d6) δ ppm: 0.54 (s, 2H), 0.65-0.68 (m, 2H), 2.81-2.82 (m, 1H), 2.88-2.92 (m, 1H), 3.01 (s, 4H), 3.17-3.24 (m, 2H), 4.04-4.46 (m, 1H), 4.59 (bs, 1H), 4.71-4.75 (m, 1H), 6.09 (s, 0.2H), 6.73 (s, 0.8H), 6.92-7.10 (m, 3H), 7.12-7.27 (m, 1H), 7.42-7.49 (m, 1H), 7.50-7.56 (m, 1H), 7.63-7.65 (m, 1H), 8.38-8.49 (m, 1H), 10.67-10.74 (s, 1H).

Methyl-4-(N-cyclopropylsulfamoyl)-2-fluorobenzoate: To a stirred solution of cyclopropanamine (0.169 g, 2.96 mmol, 1 eq) in THF (15 mL) was added triethyl amine (1.25 mL, 8.94 mmol, 3 eq.) followed by methyl 4-(chlorosulfonyl)-2-fluorobenzoate (0.750 g, 2.96 mmol, 1 eq.) at 0° C. The reaction was stirred at room temperature for 2 h. After consumption of the starting material (50% EA in Hexane), solvent was evaporated under reduced pressure, to get the crude. The crude product was purified by silica gel chromatography (eluting with: Hexane/EtOAc=50:50) to give methyl 4-(N-cyclopropylsulfamoyl)-2-fluorobenzoate. LC-MS (m/z)=272.1 [M−H]-. $^1$H NMR (400 MHz, $CDCl_3$) δ: 0.63 (s, 4H), 2.30 (s, 1H), 3.74 (s, 3H), 4.96 (s, 1H), 7.67-7.74 (m, 2H), 8.07-8.11 (m, 1H).

N-cyclopropyl-3-fluoro-4-(hydroxymethyl)benzenesulfonamide: To a solution of methyl 4-(N-cyclopropylsulfamoyl)-2-fluorobenzoate (710 mg, 2.58 mmol, 1 eq) in mixture of THF (15 mL) and methanol (15 mL) at 0° C. $NaBH_4$ (0.982 g, 25.8 mmol, 10 eq) was added. Then reaction Procedure ER: Synthesis of Compound 161 and Compound 217

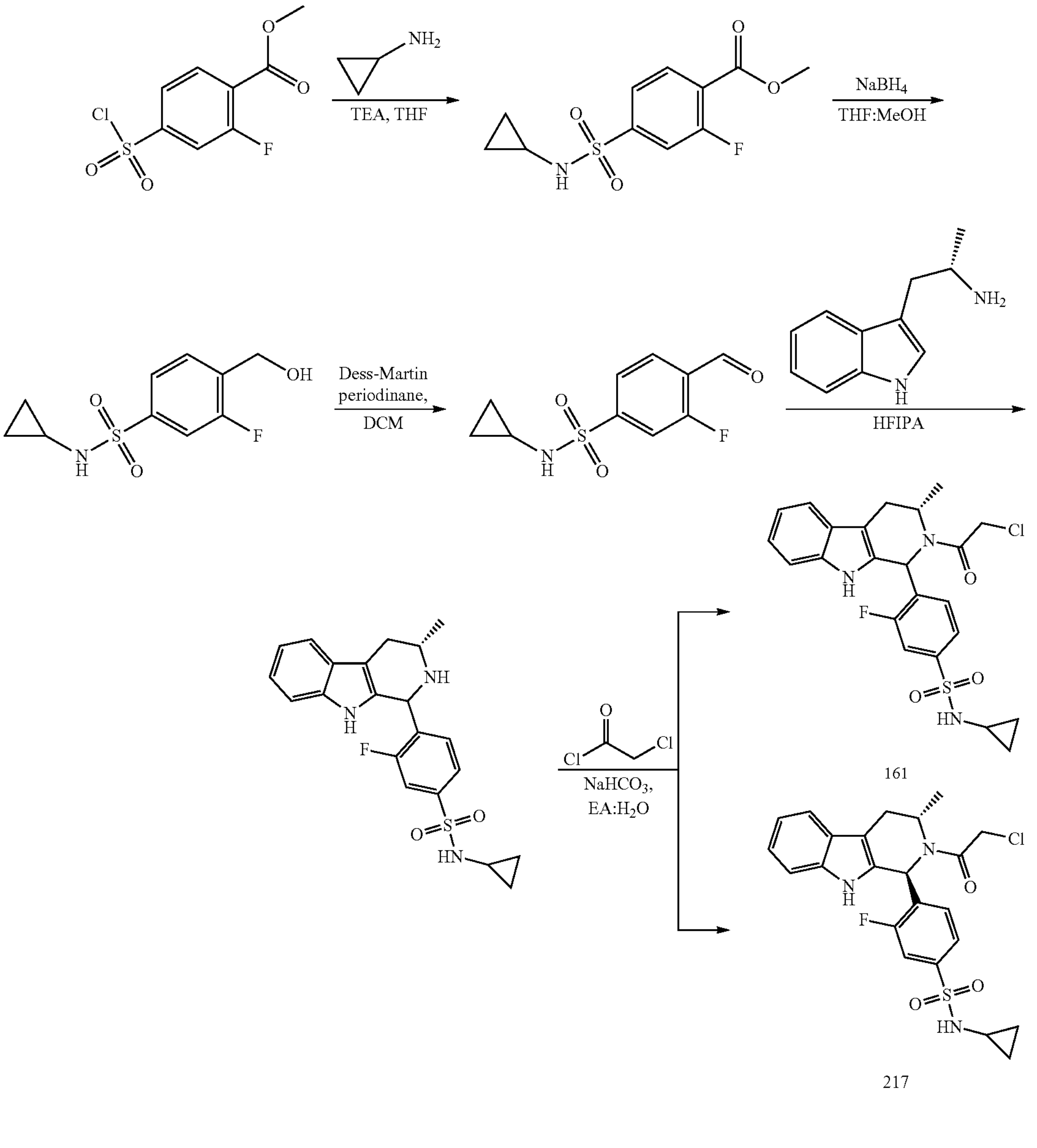

161

217 mixture reflux for 18 h. Reaction mixture cool to room temperature, solvent was evaporated under reduced pressure. Obtained crude quenched with saturated ammonium chloride and extracted with ethyl acetate (2×25 mL).Combined organic layer washed with water (10 mL).The organic layers were dried over $Na_2SO_4$ and concentrated to give crude product. The crude product was purified by silica gel chromatography (eluting with: Hexane/EtOAc=50:50) to give N-cyclopropyl-3-fluoro-4-(hydroxymethyl)benzenesulfonamide. LC-MS (m/z)=246.1 $[M+H]^+$. $^1$H NMR (400 MHz, DMSO-d6) δ: 0.36-0.41 (m, 2H), 0.42-0.47 (m, 2H), 2.09-2.11 (m, 1H), 4.60 (d, J=5.2 Hz, 2H), 5.47 (t, J=5.6 Hz, 1H), 7.49 (d, J=9.6 Hz, 1H), 7.64-7.68 (m, 1H), 7.70-7.72 (m, 1H), 7.97 (s, 1H).

N-cyclopropyl-3-fluoro-4-formylbenzenesulfonamide: To a solution of N-cyclopropyl-3-fluoro-4-(hydroxymethyl) benzenesulfonamide (410 mg, 1.67 mmol, 1 eq) in DCM (15 mL) was added Dess martin periodinane (1.06 g, 2.50 mmol, 1.5 eq) at 0° C. The reaction mixture was stirred at rt for 2 hr. Then reaction mixture was quenched with saturated sodium bi carbonate and extracted with DCM (2×25 mL). The organic layers were dried over $Na_2SO_4$ and concentrated to give crude product. This was purified by flash column chromatography using ethyl acetate in Hexane as eluent. Product fractions collected and concentrated under reduced pressure to give N-cyclopropyl-3-fluoro-4-formylbenzenesulfonamide. LC-MS (m/z): 242.1 [M−H]-. $^1$H NMR (400 MHz, CDCl3) δ: 0.65-0.67 (m, 4H), 2.32 (bs, 1H), 4.97 (s, 1H), 7.74-7.81 (m, 2H), 8.02-8.06 (m, 1H), 10.42 (s, 1H).

N-cyclopropyl-3-fluoro-4-((3S)-3-methyl-2,3,4,9-tetrahydro-1H-pyrido[3,4-b]indol-1-yl)benzenesulfonamide: In a sealed tube to a solution of compound (S)-1-(1H-indol-3-yl)propan-2-amine (0.180 g, 1.03 mmol, 1 eq) in HFIPA (2 mL) compound N-cyclopropyl-3-fluoro-4-formylbenzenesulfonamide (0.251 g, 1.03 mmol, 1 eq) was added. Then reaction mixture was sealed and heated at 80° C. for 12 h. Reaction mixture was evaporated under reduced pressure to get the crude product. This was purified by flash column chromatography using ethyl acetate in Hexane as eluent. Product fractions (mixture of cis and trans) collected and concentrated under reduced pressure to give mixture of cis and trans of N-cyclopropyl-3-fluoro-4-((3S)-3-methyl-2,3,4,9-tetrahydro-1H-pyrido[3,4-b]indol-1-yl)benzenesulfonamide. LC-MS (m/z): 400.2 $[M+H]^+$ Preparation of Compound 161 and 217

4-((1R,3S)-2-(2-chloroacetyl)-3-methyl-2,3,4,9-tetrahydro-1H-pyrido[3,4-b]indol-1-yl)-N-cyclopropyl-3-fluorobenzenesulfonamide (161) and 4-((1 S,3S)-2-(2-chloroacetyl)-3-methyl-2,3,4,9-tetrahydro-1H-pyrido[3,4-b]indol-1-yl)-N-cyclopropyl-3-fluorobenzenesulfonamide (217): To a solution of N-cyclopropyl-3-fluoro-4-((3S)-3-methyl-2,3,4,9-tetrahydro-1H-pyrido[3,4-b]indol-1-yl)benzenesulfonamide (mixture of cis and trans) (320 mg, 0.801 mmol, 1 eq) in ethyl acetate (5 mL) aqueous $NaHCO_3$(0.134 mg, 1.60 mmol, 2 eq) in water (5 mL) was added. After stirring 5 minutes was added 2-chloroacetyl chloride (0.095 mL, 1.201 mmol, 1.5 eq) dropwise at 0° C. The reaction mixture was stirred at rt for 3 hr to give a light yellow suspension. The reaction mixture was diluted with water (5 mL) and extracted with ethyl acetate (2×20 mL). The organic layers were dried over $Na_2SO_4$ and concentrated to give crude product which was purified by flash column chromatography using ethyl acetate in hexane as eluent. Product fractions collected and concentrated under reduced pressure to give isomer 1 (no-Polar on TLC compared to other isomer) 4-((1R,3S)-2-(2-chloroacetyl)-3-methyl-2,3,4,9-tetrahydro-1H-pyrido[3,4-b]indol-1-yl)-N-cyclopropyl-3-fluorobenzenesulfonamide and isomer 2 (polar on TLC compared to other isomer) 4-((1S,3S)-2-(2-chloroacetyl)-3-methyl-2,3,4,9-tetrahydro-1H-pyrido[3,4-b]indol-1-yl)-N-cyclopropyl-3-fluorobenzenesulfonamide.

Isomer-1 (161): LC-MS (m/z): 476.0 [M+H]+. $^1$H NMR (400 MHz, DMSO-d6) δ: 0.36 (s, 2H), 0.47-0.48 (m, 2H), 1.11 (s, 3H), 2.11 (s, 1H), 2.75-2.79 (m, 1H), 3.07-3.11 (m, 1H), 4.60 (bs, 3H), 6.83 (s, 1H), 6.99-7.01 (m, 1H), 7.05-7.07 (m, 1H), 7.30-7.34 (m, 2H), 7.46 (d, J=7.2 Hz, 1H), 7.54-7.59 (m, 2H), 8.03 (s, 1H), 10.82 (s, 1H).

Isomer-2 (217): LC-MS (m/z): 476.0 [M+H]+. $^1$H NMR (400 MHz, DMSO-d6) δ: 0.34 (s, 2H), 0.44 (s, 2H), 1.14 (s, 3H), 2.02 (s, 1H), 3.17-3.18 (m, 1H), 3.23-3.28 (m, 1H), 4.43 (s, 1H), 4.68-4.74 (m, 2H), 6.14 (s, 1H), 6.95-7.01 (m, 2H), 7.23 (s, 1H), 7.49-7.50 (m, 4H), 7.94 (s, 1H), 10.81 (s, 1H).

Procedure ES: Synthesis of Compound 130 and Compound 28

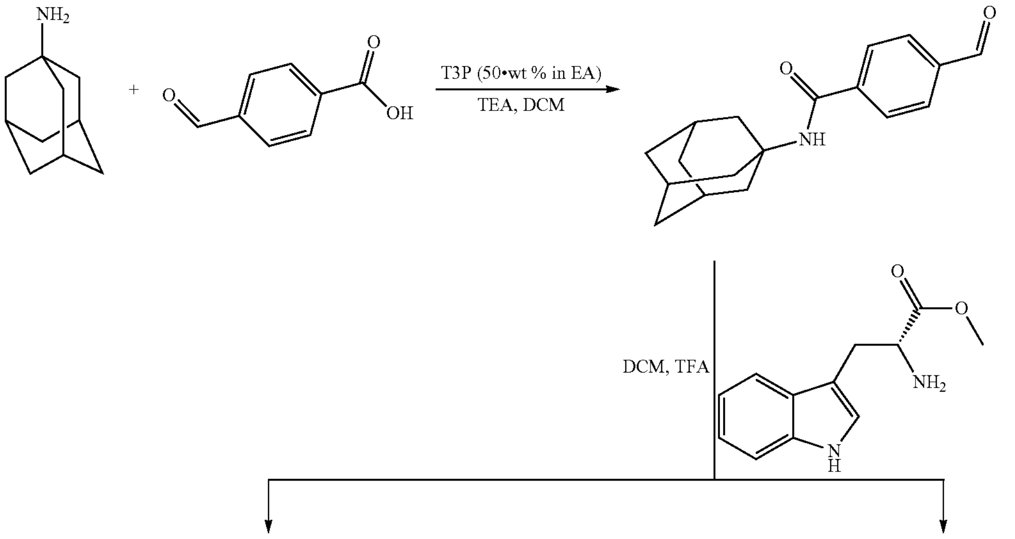

-continued

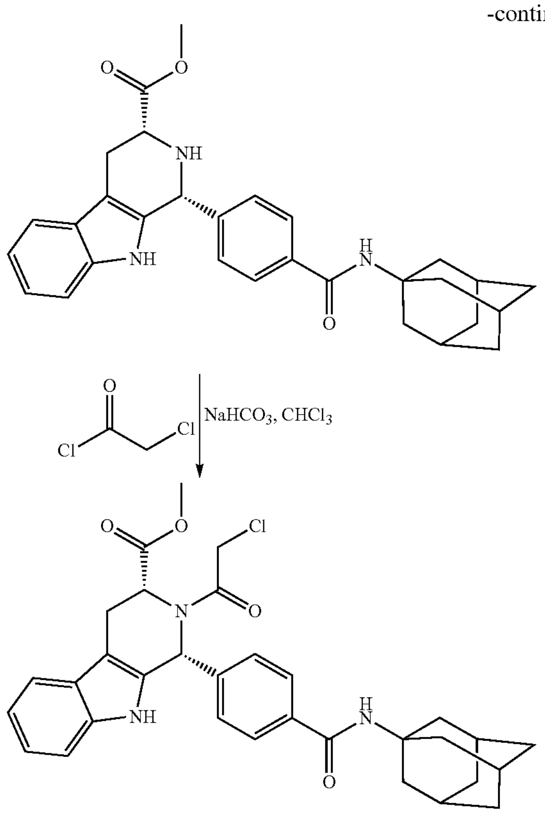

130

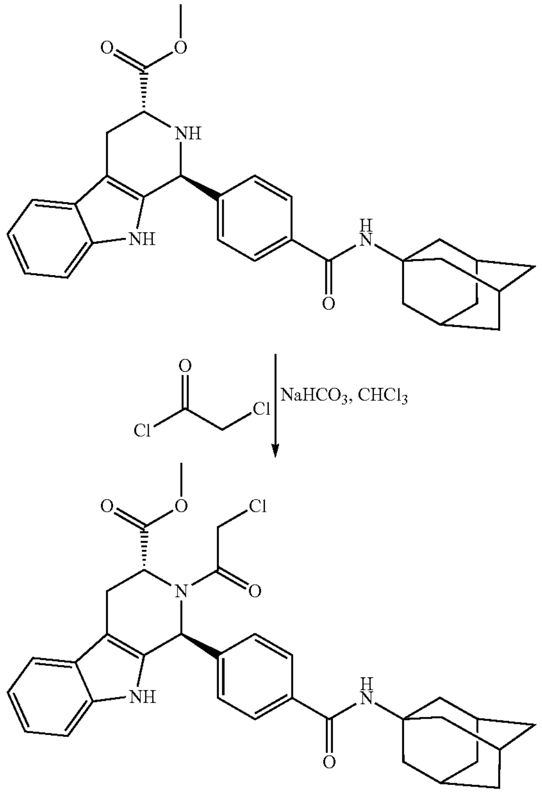

28

N-((3s,5s,7s)-adamantan-1-yl)-4-formylbenzamide: To a stirred solution of 4-formylbenzoic acid (1.04 g, 6.34 mmol, 1.2 eq) in DCM (25 mL) was added triethyl amine (2.23 mL, 15.86 mmol, 3 eq.) followed by $T_3P$ (50% wt. in ethyl acetate) (5.04 mL, 7.93 mmol, 1.5 eq.) at 0° C. The reaction was stirred at room temperature for 15 minutes then (3s,5s,7s)-adamantan-1-amine (0.8 g, 5.28 mmol, 1.0 eq) was added. Then reaction mixture was allowed to stir at room temperature for 14 h. After consumption of the starting material (40% EA in Hexane), the reaction mixture was diluted with water (10 mL) and extracted with DCM (2×25 mL), and Combined organic layer was washed with saturated sodium bicarbonate solution (15 mL) and water (10 mL). dried over anhydrous sodium sulfate, filtered and concentrated to get the crude. Crude was purified by flash column chromatography using ethyl acetate in Hexane as an eluent to get the product N-((3s,5s,7s)-adamantan-1-yl)-4-formylbenzamide. The crude product was purified by silica gel chromatography (eluting with: Hexane/EtOAc=60:40) to give N-(3s,5s,7s)-adamantan-1-yl)-4-formylbenzamide. LC-MS (m/z)=284.2 $[M+H]^+$. $^1H$ NMR (400 MHz, $CDCl_3$) δ: 1.64 (s, 6H), 2.05 (s, 9H), 7.82 (s, 1H), 7.93 (s, 4H), 10.05 (s, 1H).

methyl (1R,3R)-1-(4-(((3S,5S,7S)-adamantan-1-yl)carbamoyl)phenyl)-2,3,4,9-tetrahydro-1H-pyrido[3,4-b]indole-3-carboxylate and methyl (1S,3R)-1-(4-(((3R,5R,7R)-adamantan-1-yl)carbamoyl)phenyl)-2,3,4,9-tetrahydro-1H-pyrido[3,4-b]indole-3-carboxylate: To a solution of N-((3s,5s,7s)-adamantan-1-yl)-4-formylbenzamide (900 mg, 3.176 mmol, 1 eq) and methyl D-tryptophanate (0.831 mg, 3.811 mmol, 1.2 eq) in DCM (25 mL) was added TFA (0.243 mL, 3.17 mmol, 1 eq). The reaction mixture was stirred at 20° C. to for 20 hr to give a dark red solution. The reaction mixture was quenched with sat. $NaHCO_3$ (15 mL) and extracted with DCM (2×25 mL). The organic layers were dried over $Na_2SO_4$ and concentrated to give crude product. This was purified by using following chiral HPLC method (Column: CHIRALPAK IA (100 mm×4.6 mm×3 μm); Mobile Phase: n-Hexane IPA with 0.1% DEA; Flow rate: 1.0 mL/min). Product fractions collected and concentrated under reduced pressure to give methyl (1R,3R)-1-(4-(((3S,5S,7S)-adamantan-1-yl)carbamoyl)phenyl)-2,3,4,9-tetrahydro-1H-pyrido[3,4-b]indole-3-carboxylate (Xn TLC non Polar compared to other isomer) and methyl (1S,3R)-1-(4-(((3R,5R,7R)-adamantan-1-yl)carbamoyl)phenyl)-2,3,4,9-tetrahydro-1H-pyrido[3,4-b]indole-3-carboxylate (Xn TLC Polar compared to other isomer).

Isomer-1 (cis-isomer): (non-polar spot compared to trans-isomer): LC-MS (m/z)=484.3 $[M+H]^+$. $^1H$ NMR (400 MHz, $CDCl_3$) δ: 1.71 (s, 6H), 2.11 (s, 9H), 2.94-3.02 (m, 1H), 3.20-3.23 (m, 1H), 3.80 (s, 3H), 3.94-3.96 (m, 1H), 5.24 (s, 1H), 5.82 (s, 1H), 6.91-7.16 (m, 3H), 7.38 (d, J=7.6 Hz, 2H), 7.51-7.52 (m, 1H), 7.63 (d, J=7.2 Hz, 2H), 7.73 (s, 1H).

Isomer-2 (trans-isomer) (polar spot compared to cis-isomer): LC-MS (m/z)=484.3 $[M+H]^+$. $^1H$ NMR (400 MHz, $CDCl_3$) δ: 1.70 (s, 6H), 2.10 (s, 9H), 3.08-3.12 (m, 1H), 3.23-3.26 (m, 1H), 3.70 (s, 3H), 4.10-4.12 (m, 1H), 5.39 (s, 1H), 5.75 (s, 1H), 7.11-7.28 (m, 5H), 7.53-7.78 (m, 3H), 7.97 (s, 1H).

Preparation of Compound 130

Methyl-(1R,3R)-1-(4-(((3S,5S,7S)-adamantan-1-yl)carbamoyl)phenyl)-2-(2-chloroacetyl)-2,3,4,9-tetrahydro-1H-pyrido[3,4-b]indole-3-carboxylate: To a solution of methyl (1R,3R)-1-(4-(((3S,5S,7S)-adamantan-1-yl)carbamoyl)phenyl)-2,3,4,9-tetrahydro-1H-pyrido[3,4-b]indole-3-carboxylate (200 mg, 0.413 mmol, 1 eq) and $NaHCO_3$(52 mg, 0.620 mmol, 1.5 eq) in CHCl3 (10 mL) was added 2-chloroacetyl chloride (0.039 mL, 0.496 mmol, 1.2 eq) drop wise at 0° C. The reaction mixture was stirred at rt for 3.5 hr to give a light yellow suspension. The reaction mixture was diluted with water (5 mL) and extracted with DCM (2×25 mL). The organic layers were dried over $Na_2SO_4$ and concentrated to give crude product. Which was purified by flash column chromatography using ethyl acetate in Hexane as eluent. Product fractions collected and concentrated under reduced pressure to give methyl (1R,3R)-1-(4-(((3S,5S,7S)-adamantan-1-yl)carbamoyl)phenyl)-2-(2-chloroacetyl)-2,3,4,9-tetrahydro-1H-pyrido[3,4-b]indole-3-carboxylate. LC-MS (m/z): 560.2 $[M+H]^+$. $^1H$ NMR (400 MHz, CDCl3) δ: 1.70 (s, 6H), 2.07-2.16 (m, 9H), 3.04 (s, 3H), 3.19-3.24 (m, 1H), 3.66-3.77 (m, 1H), 4.18-4.22 (m, 1H), 4.33-4.36 (m, 1H), 4.93 (bs, 1H), 5.82 (s, 1H), 6.82 (s, 1H), 7.18-7.25 (m, 4H), 7.32 (d, J=8.0 Hz, 1H), 7.50 (d, J=7.2 Hz, 2H), 7.60-7.66 (m, 1H), 8.63 (s, 1H).

Preparation of Compound 28

Methyl-(1S,3R)-1-(4-(((3R,5R,7R)-adamantan-1-yl)carbamoyl)phenyl)-2-(2-chloroacetyl)-2,3,4,9-tetrahydro-1H-pyrido[3,4-b]indole-3-carboxylate: To a solution of methyl (1S,3R)-1-(4-(((3R,5R,7R)-adamantan-1-yl)carbamoyl)phenyl)-2,3,4,9-tetrahydro-1H-pyrido[3,4-b]indole-3-carboxylate (80 mg, 0.165 mmol, 1 eq) and $NaHCO_3$(27 mg, 0.330 mmol, 2 eq) in CHCl3 (5 mL) was added 2-chloroacetyl chloride (0.019 mL, 0.248 mmol, 1.5 eq) drop wise at 0° C. The reaction mixture was stirred at rt for 3.5 hr to give a light yellow suspension. The reaction mixture was diluted with water (5 mL) and extracted with DCM (2×25 mL). The organic layers were dried over $Na_2SO_4$ and concentrated to give crude product which was purified by flash column chromatography using ethyl acetate in hexane as eluent. Product fractions collected and concentrated under reduced pressure to give methyl (3R)-1-(4-(((3S,5S,7S)-adamantan-1-yl)carbamoyl)phenyl)-2-(2-chloroacetyl)-2,3,4,9-tetrahydro-1H-pyrido[3,4-b]indole-3-carboxylate. LC-MS (m/z): 560.2 $[M+H]^+$. $^1H$ NMR (400 MHz, DMSO-d6, VT at 80° C.) δ: 1.63 (s, 6H), 2.02 (s, 9H), 3.28-3.31 (m, 1H), 3.46-3.51 (m, 4H), 4.23 (bs, 1H), 4.56-4.60 (m, 1H), 5.23 (bs, 1H), 6.14 (bs, 1H), 6.93-7.03 (m, 2H), 7.22-7.24 (m, 2H), 7.43-7.46 (m, 3H), 7.63 (d, J=7.2 Hz, 2H), 10.74 (s, 1H).

Procedure ET: Synthesis of Compound 175

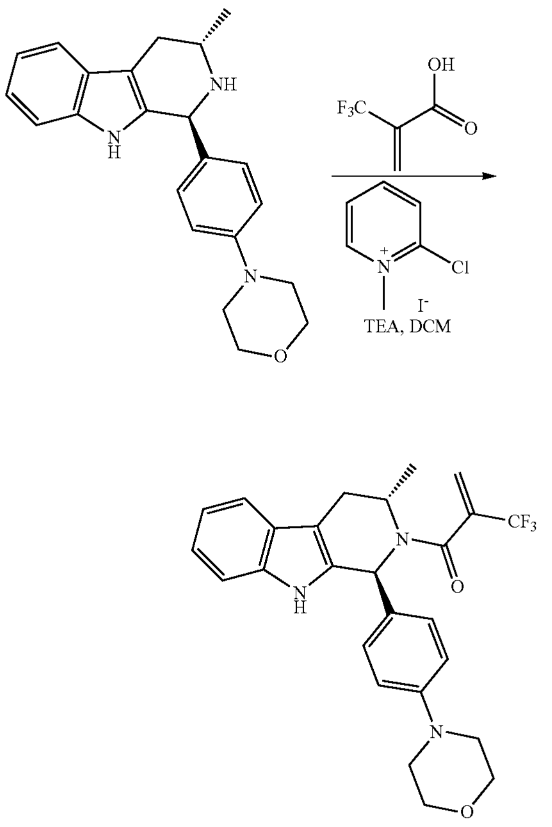

175

1-((1S,33 S)-3-methyl-1-(4-morpholinophenyl)-1,3,4,9-tetrahydro-2H-pyrido[3,4-b]indol-2-yl)-2-(trifluoromethyl)prop-2-en-1-one: To a solution of 4-(4-((1S,3S)-3-methyl-2,3,4,9-tetrahydro-1H-pyrido[3,4-b]indol-1-yl)phenyl)morpholine (0.200 g, 0.575 mmol, 1 eq.) and 2-(trifluoromethyl)acrylic acid (0.080 g, 0.575 mmol, 1 eq) in DCM (8 mL) was added triethylamine (0.194 mL, 1.38 mmol, 2.4 eq) followed by 2-Chloro-1-methyl-pyridinium iodide (0.176 g, 0.690 mmol, 1.2 eq) at room temperature. The reaction mixture was stirred at room temperature for 16 h. After consumption of the starting material (TLC, 80% ethyl acetate in Hexane), the reaction was diluted with saturated aqueous solution of $NaHCO_3$ (5 mL) and was extracted with DCM (25 mL). The organic layer was dried over anhydrous $Na_2SO_4$, filtered and concentrated under reduced pressure to get the crude product. Obtained crude product was purified by flash column chromatography on silica gel using 26-30% ethyl acetate in hexane as the eluent to get 1-((1S,3S)-3-methyl-1-(4-morpholinophenyl)-1,3,4,9-tetrahydro-2H-pyrido[3,4-b]indol-2-yl)-2-(trifluoromethyl)prop-2-en-1-one. LC-MS (m/z)=470.4 $[M+H]^+$. $^1H$ NMR (400 MHz, DMSO-$d_6$) δ ppm: 1.14-1.15 (m, 3H), 2.82-2.86 (m, 1H), 3.00 (s, 4H), 3.18-3.22 (m, 1H), 3.66 (s, 4H), 4.63 (s, 1H), 5.89 (s, 1H), 6.12 (s, 1H), 6.26 (s, 1H), 6.80 (d, J=8.4 Hz, 2H), 6.93 (d, J=7.2 Hz, 1H), 7.00 (t, J=7.2 Hz, 1H), 7.18 (d, J=8.4 Hz, 2H), 7.23 (d, J=8.4 Hz, 1H), 7.40-7.41 (m, 1H), 10.75 (s, 1H).

Procedure EV: Synthesis of Compound 133 and Compound 218

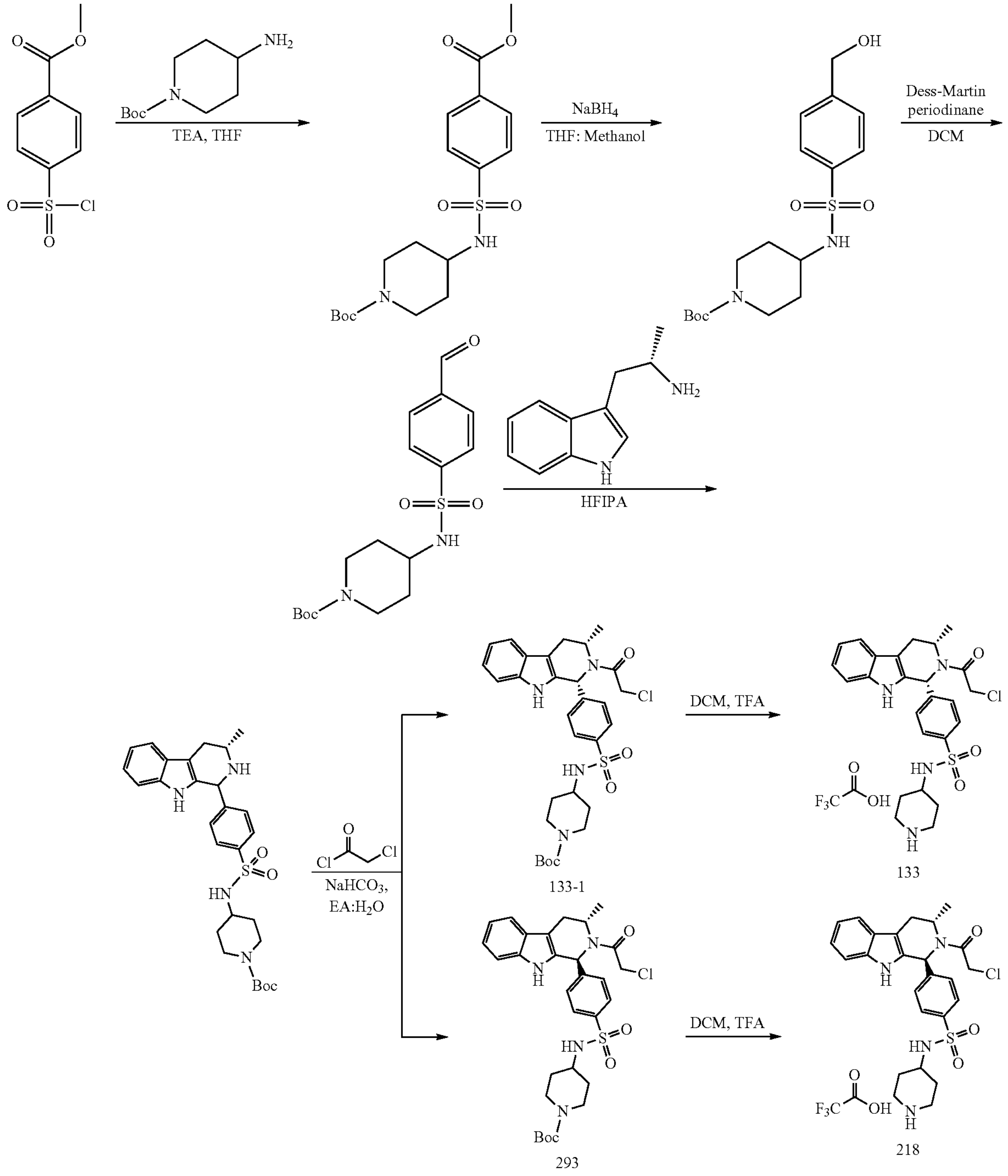

133-1

133

293

218 tert-butyl 4-((4-(methoxycarbonyl)phenyl)sulfonamido)piperidine-1-carboxylate: To a stirred solution of methyl 4-(chlorosulfonyl)benzoate (2.0 g, 8.547 mmol, 1 eq) and triethylamine (3.5 mL, 25.64 mmol, 3.0 eq.) in tetrahydrofuron was added tert-butyl 4-aminopiperidine-1-carboxylate (2.0 g, 10.25 mmol, 1.2 eq) at 0° C. The mixture was allowed to warm to room temperature and stirred 18 h. The progress of the reaction was monitored by TLC (50% ethyl acetate in hexane). After completion of reaction, the reaction was diluted with ethyl acetate (200 mL), washed with water (2×50 mL), brine (50 mL), dried over anhydrous sodium sulfate, filtered and concentrated under reduced pressure to obtain crude. The crude was purified by flash chromatography using 30% ethyl acetate in hexane as an eluent to obtain tert-butyl 4-((4-(methoxycarbonyl)phenyl)sulfonamido)piperidine-1-carboxylate. LC-MS (m/z)=299.2 ($[M+H]^+$- Boc group).

tert-butyl 4-((4-(hydroxymethyl)phenyl)sulfonamido)piperidine-1-carboxylate: To a stirred solution of tert-butyl 4-((4-(methoxycarbonyl)phenyl)sulfonamido)piperidine-1-carboxylate (0.8 g, 2.009 mmol, 1 eq) in a mixture of tetrahydrofuron (20 mL) and methanol (20.0 mL) was added sodium borohydride (0.6 g, 16.076 mmol, 8.0 eq) at 0° C. The resulting mixture was gradually allowed to warm to room temperature and the reaction was heated to 80° C. for 18 h. The progress of the reaction was monitored by TLC (80% ethyl acetate in hexane). After completion of reaction, the reaction mixture was concentrated under reduced pressure. The obtained residue was dissolved water (100 mL) and ethyl acetate (100 mL). The organic layer was separated and the aqueous layer was extracted with ethyl acetate (2×100 mL), The combined organics were washed with brine (50 mL), dried over anhydrous sodium sulfate, filtered and concentrated under reduced pressure to obtain crude. The crude product was purified by flash column chromatography using 70% ethyl acetate in hexane as an eluent to obtain tert-butyl 4-((4-(hydroxymethyl)phenyl)sulfonamido)piperidine-1-carboxylate. LC-MS (m/z)=271.1 ([M+H]$^+$- Boc group); $^1$H NMR (400 MHz, DMSO-d6) δ ppm 1.12-1.19 (m, 2H), 1.32 (s, 9H), 1.48 (d, J=10.8 Hz, 2H), 2.72 (bs, 2H), 3.11 (bs, 1H), 3.66 (d, J=12.8 Hz, 2H), 4.55 (d, J=5.2 Hz, 2H), 5.36 (t, J=5.2 Hz, 1H), 7.48 (d, J=7.6 Hz, 2H), 7.68 (d, J=6.8 Hz, 1H), 7.74 (d, J=8.0 Hz, 2H).

N-cyclopropyl-3-fluoro-4-formylbenzenesulfonamide: To a stirred solution of tert-butyl 4-((4-formylphenyl)sulfonamido)piperidine-1-carboxylate (0.5 g, 1.35 mmol, 1 eq) in dichloromethane (20.0 mL) was added Desmartin periodinane (0.85 g, 2.02 mmol, 1.5 eq) at 0° C. The mixture was allowed to warm to room temperature and stirred for 2 h. The progress of the reaction was monitored by TLC (70% ethyl acetate in hexane). After completion of reaction, the reaction mixture was cooled to 0° C. and quenched with saturated sodium bicarbonate solution and the aqueous layer was extracted with dichloromethane (2×50 mL). The organic layers were dried over anhydrous sodium sulfate, filtered and concentrated under reduced pressure to obtain crude. The crude product was purified by flash column chromatography using 70% ethyl acetate in hexane as an eluent to obtain tert-butyl 4-((4-formylphenyl)sulfonamido)piperidine-1-carboxylate. LC-MS (m/z)=313.1 [(M+H)$^+$- (t-butyl group)]; $^1$H NMR (400 MHz, DMSO-d6) δ ppm 1.13-1.20 (m, 2H), 1.32 (s, 9H), 1.51 (d, J=12.0 Hz, 2H), 2.73 (bs, 2H), 3.20-3.23 (m, 1H), 3.68 (d, J=12.4 Hz, 2H), 7.99-8.00 (m, 3H), 8.07 (t, J=7.6 Hz, 2H), 10.07 (s, 1H).

tert-butyl-4-((4-((3S)-3-methyl-2,3,4,9-tetrahydro-1H-pyrido[3,4-b]indol-1-yl)phenyl)sulfonamido)piperidine-1-carboxylate: In a sealed tube, (S)-1-(1H-indol-3-yl)propan-2-amine (0.2 g, 0.543 mmol, 1 eq), tert-butyl 4-((4-formylphenyl)sulfonamido)piperidine-1-carboxylate (0.11 g, 0.651 mmol, 1.0 equiv) and hexafluoro-2-propanol (HFIP) (2.0 mL). The seal tube closed and the mixture was heated to 50° C. and stirred for 16 h. The progress of the reaction was monitored by TLC (10% methanol in dichloromethane), the reaction was cooled to room temperature, concentrated under reduced pressure to obtain crude, which was purified by flash column chromatography using 6% methanol in dichloromethane as an eluent to obtain tert-butyl 4-((4-((3S)-3-methyl-2,3,4,9-tetrahydro-1H-pyrido[3,4-b]indol-1-yl)phenyl)sulfonamido)piperidine-1-carboxylate. LC-MS (m/z)=525.3 [M+H]$^+$.

tert-butyl-4-((4-((1R,3S)-2-(2-chloroacetyl)-3-methyl-2,3,4,9-tetrahydro-1H-pyrido[3,4-b]indol-1-yl)phenyl)sulfonamido)piperidine-1-carboxylate and tert-butyl-4-((4-((1S,3S)-2-(2-chloroacetyl)-3-methyl-2,3,4,9-tetrahydro-1H-pyrido[3,4-b]indol-1-yl)phenyl)sulfonamido)piperidine-1-carboxylate: To a stirred solution of tert-butyl 4-((4-((3S)-3-methyl-2,3,4,9-tetrahydro-1H-pyrido[3,4-b]indol-1-yl) phenyl)sulfonamido)piperidine-1-carboxylate (0.310 g, 0.590 mmol, 1 eq) in ethyl acetate (4 mL) at 0° C. sodium bi carbonate (0.099 g, 1.18 mmol, 2 eq) in water (4 mL) added. After stirring for 5 minutes was added 2-chloroacetyl chloride (0.070 mL, 0.886 mmol, 1.5 eq). The mixture was allowed to warm to room temperature and stirred for 2.5 h. The progress of the reaction was monitored by TLC (60% ethyl acetate in hexane). After completion of reaction, the reaction mixture was cooled to 0° C. and quenched with water (5 mL) and the aqueous layer was extracted with ethyl acetate (2×50 mL). The organic layers were dried over anhydrous sodium sulfate, filtered and concentrated under reduced pressure to obtain crude. The crude product was purified by flash column chromatography using 40-45% ethyl acetate in hexane as an eluent to obtain tert-butyl 4-((4-((1R,3S)-2-(2-chloroacetyl)-3-methyl-2,3,4,9-tetrahydro-1H-pyrido[3,4-b]indol-1-yl)phenyl)sulfonamido)piperidine-1-carboxylate and at 50-55% tert-butyl-4-((4-((1 S,3S)-2-(2-chloroacetyl)-3-methyl-2,3,4,9-tetrahydro-1H-pyrido[3,4-b]indol-1-yl)phenyl)sulfonamido)piperidine-1-carboxylate.

Analysis of compound 133-1: LC-MS (m/z)=601.4 [(M+H)$^+$. $^1$H NMR (400 MHz, DMSO-d6) δ ppm 0.85-0.86 (m, 3H), 1.14-1.17 (m, 2H), 1.33-1.46 (m, 11H), 2.65-2.72 (m, 3H), 3.11 (bs, 2H), 3.63 (bs, 2H), 4.61-4.69 (m, 3H), 6.91 (bs, 1H), 7.01-7.03 (m, 1H), 7.36 (d, J=7.6 Hz, 1H), 7.46-7.50 (m, 3H), 11.12 (s, 1H).

Analysis of compound 293: LC-MS (m/z)=601.4 [(M+H)$^+$. $^1$H NMR (400 MHz, DMSO-d6) δ ppm: 1.12-1.13 (m, 5H), 1.32 (s, 9H), 1.44 (bs, 2H), 2.65-2.69 (m, 2H), 2.88-2.91 (m, 1H), 3.09 (bs, 1H), 3.20 (s, 1H), 3.62-3.64 (m, 2H), 4.41 (s, 1H), 4.77 (bs, 2H), 5.97 (bs, 1H), 6.93-7.03 (m, 2H), 7.24 (d, J=8.0 Hz, 1H), 7.43 (d, J=8.0 Hz, 1H), 7.54-7.65 (m, 5H), 10.93 (s, 1H).

Preparation of Compound 133

4-((1R,3S)-2-(2-chloroacetyl)-3-methyl-2,3,4,9-tetrahydro-1H-pyrido[3,4-b]indol-1-yl)-N-(piperidin-4-yl)benzenesulfonamide2,2,2-trifluoroacetic acid: To a solution of tert-butyl 4-((4-((1R,3S)-2-(2-chloroacetyl)-3-methyl-2,3,4,9-tetrahydro-1H-pyrido[3,4-b]indol-1-yl)phenyl)sulfonamido)piperidine-1-carboxylate (0.080 g, 0.133 mmol, 1 eq) in DCM at 0° C. was added TFA (1 mL). Then reaction mixture was stirred at 0° C. fo rl.5 h and at room temperature 1 h. Solvent was evaporated under reduced pressure. Obtained crude dissolved in acetonitrile (1 mL) and water (1 mL) mixture and kept under lyophilization for 14 h. LC-MS (m/z)=501.1 [(M+H)$^+$. $^1$H NMR (400 MHz, DMSO-d6) δ ppm 0.87 (d, J=6.4 Hz, 3H), 1.45-1.47 (m, 2H), 1.65 (bs, 2H), 2.65-2.72 (m, 1H), 2.84-2.86 (m, 2H), 3.11 (s, 2H), 3.28 (bs, 1H), 3.93 (bs, 1H), 4.64-4.69 (m, 3H), 6.89 (s, 1H), 7.01-7.03 (m, 1H), 7.09-7.13 (m, 1H), 7.36 (d, J=8.0 Hz, 1H), 7.48-7.52 (m, 3H), 7.75-7.78 (m, 2H), 7.95 (d, J=7.2 Hz, 1H), 8.15 (bs, 1H), 8.40 (bs, 1H), 11.10 (s, 1H).

Preparation of Compound 218

4-((1S,3S)-2-(2-chloroacetyl)-3-methyl-2,3,4,9-tetrahydro-1H-pyrido[3,4-b]indol-1-yl)-N-(piperidin-4-yl)benzenesulfonamide: To a solution of tert-butyl 4-((4-((1 S,3S)-2-(2-chloroacetyl)-3-methyl-2,3,4,9-tetrahydro-1H-pyrido [3,4-b]indol-1-yl)phenyl)sulfonamido)piperidine-1-carboxylate (0.080 g, 0.133 mmol, 1 eq) in DCM (5 mL) at 0° C. was added TFA (1 mL). Then reaction mixture was stirred at 0° C. for 1.5 h and at room temperature 1 h. Solvent was evaporated under reduced pressure. Obtained crude purified by following preparative HPLC (Column: X-Bridge C18 (100 mm×4.6 mm×3.5 μM); Mobile phase (A): 0.1%

TEA in water; Mobile phase (B): Acetonitrile). LC-MS (m/z)=501.2 [(M+H)+]. $^1$H NMR (400 MHz, DMSO-d6) VT at 60° C.: δ ppm 0.14 (s, 3H), 1.50 (s, 2H), 1.70 (s, 2H), 2.87-2.97 (m, 7H), 4.29 (s, 1H), 4.62 (s, 1H), 4.79 (s, 1H), 6.02 (s, 1H), 6.95-7.00 (m, 2H), 7.25 (s, 1H), 7.43 (s, 1H), 7.50-7.54 (m, 2H), 7.68-7.81 (m, 3H), 8.15 (s, 1H), 8.36 (s, 1H), 10.85 (bs, 1H).

Procedure EW: Synthesis of Compound 134

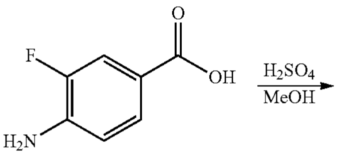

EW-1

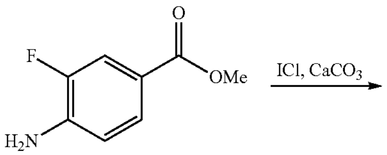

EW-2

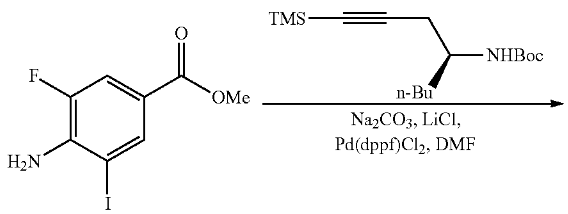

EW-3

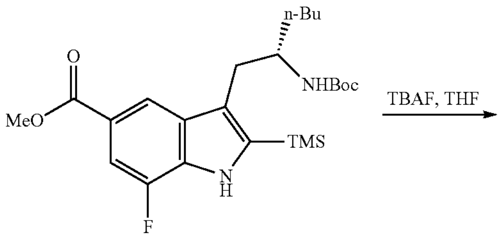

EW-4

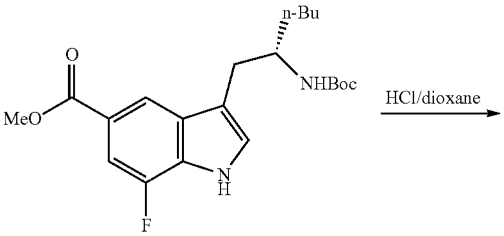

EW-5

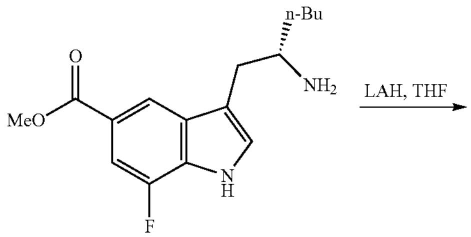

EW-6

-continued

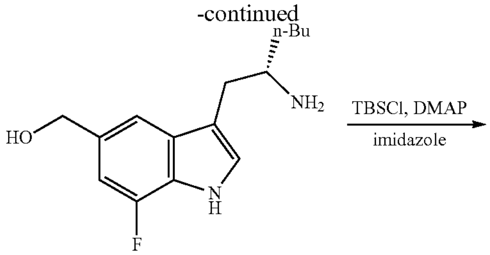

EW-6a

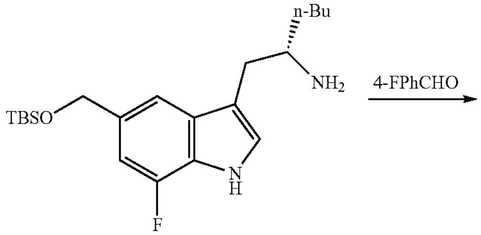

EW-7a

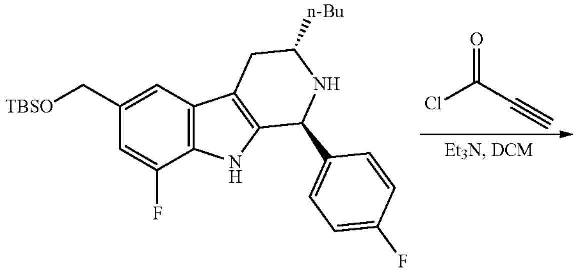

EW-8a

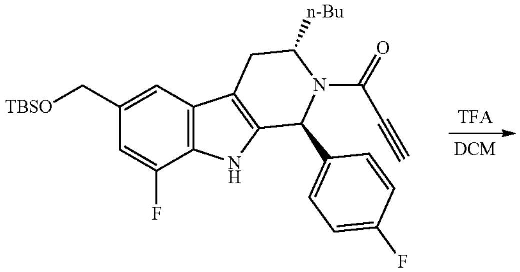

EW-9

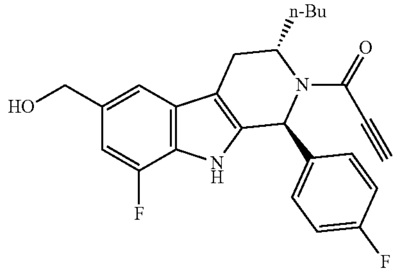

Compound 134

To solution of EW-1 (44 g, 283.64 mmol, 1 eq) in MeOH (600 mL) was added $H_2SO_4$ (55.20 g, 551.56 mmol, 30 mL, 98% purity, 1.94 eq). The mixture was stirred at 80° C. for 12 hr to give a brown solution. Remove most solvent. To aqueous solution of $NaHCO_3$ (300 mL) was added the reaction solution and adjusted pH=8. The suspension was dissolved in EtOAc (200 mL), extracted with EtOAc (80 mL×2). The organic layers were combined and dried over sodium sulfate, filtered and concentrated to give the crude product. The crude product was triturated with MTBE/PE (45 mL/120 mL) and filtered to give EW-2. $^1$H NMR (400 MHz, $CDCl_3$) δ ppm 7.64-7.69 (m, 2H), 6.72-6.79 (m, 1H), 4.08-4.19 (m, 2H), 3.87 (s, 3H).

To a solution of EW-2 (14.74 g, 86.96 mmol, 1 eq) in EtOH (150 mL) and $H_2O$ (100 mL) were added $CaCO_3$ (15.67 g, 156.53 mmol, 1.8 eq) and IC1 (21.18 g, 130.44 mmol, 6.66 mL, 1.5 eq). The mixture was stirred at 25° C. for 36 hr to give a brown suspension. TLC showed the desired spot found. The reaction was diluted with saturated $NaHCO_3$ (200 mL) and extracted with EtOAc (150 mL×3). The combine organic layers were washed with brine (100 mL) and dried over sodium sulfate, filtered and concentrated to give the crude product. The crude product was purified by flash column ($SiO_2$, EtOAc in PE from 0 to 30%) to give EW-3. $^1$H NMR (400 MHz, $CDCl_3$) δ ppm 8.15 (s, 1H), 7.62-7.68 (m, 1H), 4.59 (br s, 2H), 3.88 (s, 3H).

To a solution of tert-butyl (S)-(1-(trimethylsilyl)oct-1-yn-4-yl)carbamate (1.9 g, 6.39 mmol, 1.1 eq) and EW-3 (1.71 g, 5.81 mmol, 1 eq) in DMF (15 mL) were added $Na_2CO_3$ (1.23 g, 11.61 mmol, 2 eq), LiCl (246.13 mg, 5.81 mmol, 118.90 μL, 1 eq) and Pd(dppf)$Cl_2$ (424.81 mg, 580.58 μmol, 0.1 eq) under $N_2$. The mixture was stirred at 100° C. under $N_2$ for 12 hr to give a brown solution. TLC showed the reaction was completed. The reaction was diluted with EtOAc/brine (80/20 mL) and filtered through celite. The filtrate was washed with brine (60 mL×3) and dried over sodium sulfate, filtered and concentrated to give the crude product. The crude product was purified by flash column ($SiO_2$, EtOAc in PE from 0 to 9%) to give EW-4. $^1$H NMR (400 MHz, $CDCl_3$) δ ppm 8.22 (br s, 2H), 7.57 (br d, J=11.80 Hz, 1H), 4.36 (br d, J=7.78 Hz, 1H), 3.84-3.96 (m, 4H), 2.86-3.04 (m, 2H), 1.25 (s, 15H), 0.86 (t, J=6.90 Hz, 3H), 0.44 (s, 9H).

To a solution of EW-4 (2.3 g, 4.95 mmol, 1 eq) in THF (20 mL) was added TBAF (1 M, 20 mE, 4.04 eq). The mixture was stirred at 30° C. for 12 h to give a brown solution. TLC (PE/EtOAc=3:1) showed new spot found. The reaction was diluted with $H_2O$ (70 mL) and extracted with EtOAc (60 mL×3). The combined organic layers were washed with brine (60 mL) and dried over sodium sulfate, filtered and concentrated to give the crude product. The crude product was purified by flash column ($SiO_2$, EtOAc in PE from 0 to 25%) to give EW-5. $^1$H NMR (400 MHz, $CDCl_3$) δ ppm 8.43 (br s, 1H), 8.17 (s, 1H), 7.61 (d, J=11.76 Hz, 1H), 7.15 (br s, 1H), 4.36 (br d, J=8.25 Hz, 1H), 3.94 (s, 4H), 2.83-3.03 (m, 2H), 1.23-1.45 (m, 15H), 0.86-0.92 (m, 3H).

EW-5 (1.21 g, 3.08 mmol, 1 eq) was dissolved in HCl/dioxane (4 M, 30 mL, 38.92 eq). The reaction was stirred at 10° C. for 12 h to give a yellow solution. TLC (PE/EtOAc=3:1) showed the reaction was completed. The reaction was concentrated to give the crude product. The crude product was dissolved in $H_2O$ (3 mL) and adjusted to pH=8 with saturated $NaHCO_3$, concentrated to give the residue. The residue was washed with DCM/EtOH (150 mL/15 mL) and filtered to give EW-6, which was used in the next step without further purification. $^1$H NMR (400 MHz, $CDCl_3$) δ ppm 8.87 (br s, 1H), 8.18 (s, 1H), 7.59 (dd, J=11.80, 1.00 Hz, 1H), 7.13 (s, 1H), 3.94 (s, 3H), 3.72 (s, 2H), 3.07-3.16 (m, 1H), 2.97 (dd, J=14.31, 4.27 Hz, 1H), 2.64 (dd, J=14.31, 8.78 Hz, 1H), 1.33-1.49 (m, 6H), 0.93 (t, J=7.03 Hz, 3H).

To a solution of EW-6 (500 mg, 1.71 mmol, 1 eq) in THF (10 mL) was added $LiAlH_4$ (389.48 mg, 10.26 mmol, 6 eq) at 0° C. The mixture was stirred at 0° C. for 2 hr to give a yellow solution. LCMS showed the reaction was completed. The reaction mixture was quenched with $H_2O$ (0.39 mL), NaOH (15%, 0.39 mL) and $H_2O$ (1.17 mL). The mixture was diluted with THF (50 mL) and filtered on celite. The filtrate was dried over $Na_2SO_4$ and concentrated to give EW-6a, which was used in the next step without further purification. $^1$H NMR (400 MHz, $CDCl_3$) δ=8.47 (brs, 1H), 7.37 (s, 1H), 7.09 (s, 1H), 6.99-6.96 (m, 1H), 4.78 (s, 2H), 3.21-3.08 (m, 1H), 2.97-2.92 (m, 1H), 2.63-2.57 (m, 1H), 1.56-1.54 (m, 6H), 0.96-0.90 (d, J=6.8 Hz, 3H).

To a solution of EW-6a (400 mg, 1.51 mmol, 1 eq) in DMF (10 mL) were added TBSCl (273.69 mg, 1.82 mmol, 222.51 μL, 1.2 eq), DMAP (18.49 mg, 151.32 μmol, 0.1 eq), imidazole (309.05 mg, 4.54 mmol, 3 eq). The mixture was stirred at 10° C. for 2 hr to give a yellow solution. LCMS and TLC (eluting with: EtOAc/MeOH=5/1) showed the reaction was completed. The reaction mixture was concentrated to give the crude product. The crude product was purified by flash column (eluting with: ETOAc/MeOH=100% EtOAc to 20%) to give EW-7a. $^1$H NMR (400 MHz, $CDCl_3$) δ=8.54 (brs, 1H), 7.10 (s, 1H), 7.07 (s, 1H), 6.77-6.74 (m, 1H), 4.66 (s, 2H), 3.25-3.22 (m, 1H), 3.02-2.92 (m, 2H), 1.69-1.14 (m, 6H), 0.83 (s, 9H), 0.81-0.77 (m, 3H), 0.00 (s, 6H).

To a solution of EW-7a (190 mg, 501.85 μmol, 1 eq) in toluene (10 mL) was added 4-fluorobenzaldehyde (62.29 mg, 501.85 μmol, 52.78 μL, 1 eq) and 4A molecular sieves (4 g). The mixture was stirred at 120° C. for 12 hr to give a yellow suspension. The mixture was filtered. The filtrate was added TFA (57.22 mg, 501.85 μmol, 37.16 μL, 1 eq). The mixture was stirred at 120° C. for 30 hr to give a yellow solution. LCMS and TLC (eluting with: PE/EtOAc=5/1) showed the reaction was completed. The reaction mixture was basified to pH=8 with $Et_3N$. The mixture was concentrated to give the crude product. The crude product was purified by prep-TLC (eluting with: PE/EtOAc=1/1) to give EW-8a and [(3S)-3-butyl-8-fluoro-1-(4-fluorophenyl)-2,3,4,9-tetrahydro-1H-pyrido[3,4-b]indol-6-yl]methanol. $^1$H NMR (400 MHz, $CDCl_3$) δ=7.66 (brs, 1H), 7.14-7.05 (m, 3H), 6.91-6.88 (m, 2H), 6.79-6.76 (m, 1H), 5.10 (s, 1H), 4.68 (s, 2H), 2.95-2.81 (m, 2H), 2.40-2.38 (m, 1H), 1.42-1.14 (m, 6H), 0.83 (s, 9H), 0.77-0.73 (m, 3H), 0.00 (s, 6H).

To a solution of EW-8a (60 mg, 123.79 μmol, 1 eq) in DCM (5 mL) were added $Et_3N$ (62.63 mg, 618.95 μmol, 86.15 μL, 5 eq) and prop-2-ynoyl chloride (32.86 mg, 371.37 μmol, 3 eq) at 0° C. The mixture was allowed to stir at 10° C. for 12 hr to give a yellow solution. LCMS and TLC (eluting with: PE/EtOAc=3/1) showed the reaction was completed. The reaction mixture was quenched with $H_2O$ (15 mL) and extracted with DCM (15 mL*3). The organic layers were dried over $Na_2SO_4$ and concentrated to give the crude product. The crude product was purified by prep-TLC (eluting with: PE/EtOAc=3/1) to give EW-9.

Preparation of Compound 134

To a solution of EW-9 (16 mg, 29.81 μmol, 1 eq) in DCM (5 mL) was added TFA (154.00 mg, 1.35 mmol, 0.1 mL, 45.31 eq). The mixture was stirred at 10° C. for 1 hr to give a yellow solution. LCMS and TLC (eluting with: PE/EtOAc=1/1) showed the reaction was completed. The reaction was concentrated to give the residue. The residue was dissolved in MeOH (10 mL). The mixture was stirred at 40° C. for 1 hr. LCMS showed the reaction was completed. The reaction mixture was concentrated to give the crude product. The crude product was purified by prep-TLC (eluting with: PE/EtOAc=1/1) to give Compound 134. LC-MS (m/z): 423.1 $[M+H]^+$. $^1$H NMR (400 MHz, $CDCl_3$) δ=7.67 (brs, 1H), 7.45-7.20 (m, 3H), 6.93-6.84 (m, 3H), 5.81 (s, 1H), 4.0 (brs, 2H), 4.70-4.68 (m, 2H), 3.83-2.97 (m, 4H), 1.32-1.18 (m, 6H), 0.81-0.79 (m, 3H).

Procedure EX: Synthesis of Compound 145

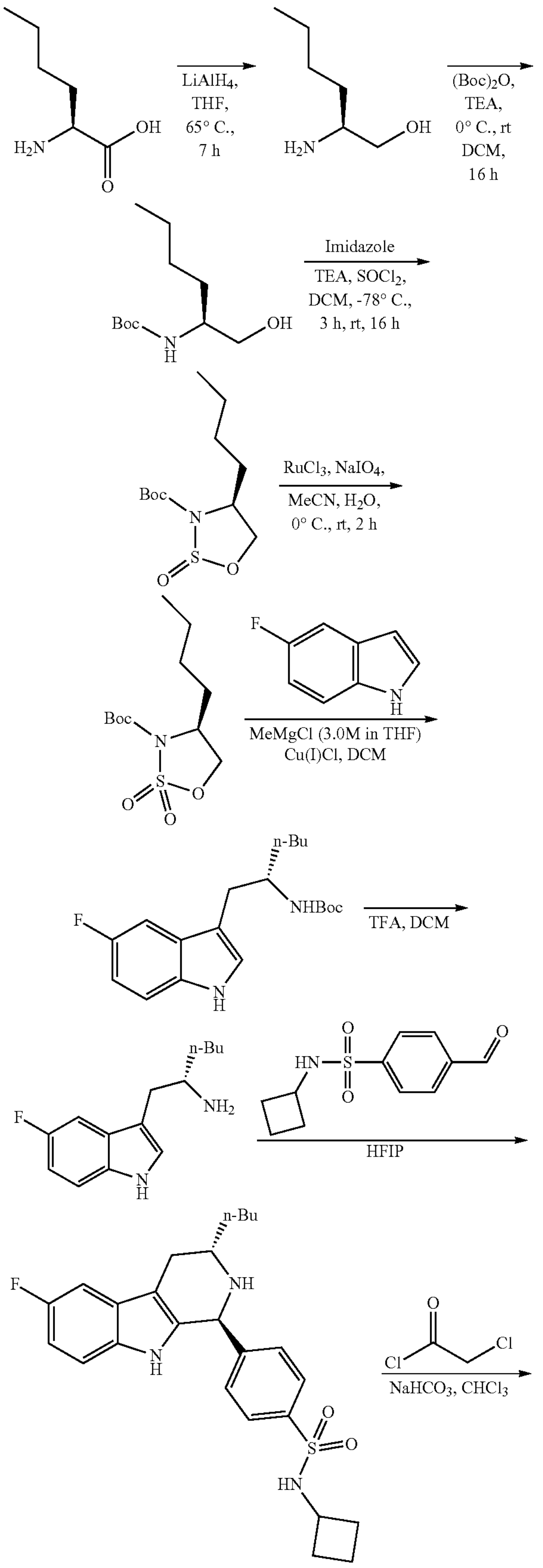

-continued

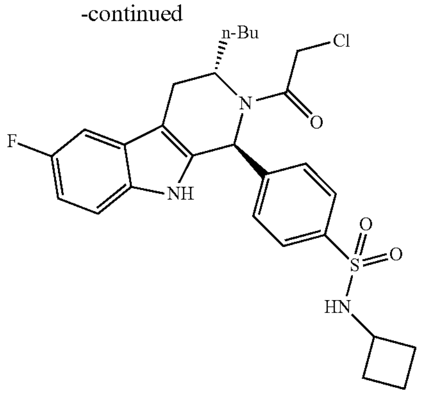

compound 145

(S)-2-aminohexan-1-ol: To a solution of (S)-2-amino-hexanoic acid (5 g, 38.14 mmol, 1 eq) in THF (140.0 mL) at −0° C. was added 1 M LAH solution in THF (76.28 mL, 76.28 mmol, 2 eq). Reaction mixture was warmed to room temperature, then the mixture was stirred at 65° C. for 7 h under $N_2$ atmosphere. TLC (10% MeOH in DCM) showed the reaction was completed. Reaction mixture was cooled to room temperature, The reaction was diluted with Diethyl ether (50 mL), after fisher-workup, reaction mixture was filtered through sintered funnel, using di ethyl ether, filtrate was concentrated under reduced pressure to get the product, without further purification crude product was forward to next step. $^1H$ NMR (400 MHz, $CDCl_3$) δ ppm 0.83-0.91 (m, 3H), 1.2-1.42 (m, 6H), 2.82-2.83 (m, 1H), 3.24-3.29 (m, 1H), 3.57-3.61 (m, 1H).

tert-butyl (S)-(1-hydroxyhexan-2-yl)carbamate: To a solution of (S)-2-aminohexan-1-ol (4.2 g, 35.83 mmol, 1 equiv.) in DCM (40 mL) was added TEA (10 mL, 71.67 mmol, 2 equiv) at 0° C. drop wise, it was stirred for 5 mins, then di-tert-butyl dicarbonate (9.86 mL, 43.00 mmol, 1.2 equiv). After stirring at room temperature for 18 h, washed with water (75 mL) and brine (75 mL), dried over $Na_2SO_4$, and concentrated in vacuo. The residue was subjected to combiflash silica gel chromatography equipped MeOH in DCM as an eluent to give the product. $^1H$ NMR (400 MHz, $CDCl_3$) δ ppm 0.89 (s, 3H), 1.32-1.43 (m, 6H), 1.44 (s, 9H), 3.50-3.54 (m, 1H), 3.61-3.67 (m, 2H), 4.59 (bs, 1H).

tert-butyl (4S)-4-butyl-1,2,3-oxathiazolidine-3-carboxylate 2-oxide: To a solution of 1H-imidazole (5.1 g, 75.57 mmol, 4 equiv) and triethylamine (7.9 mL, 56.68 mmol, 3 equiv) in anhydrous dichloromethane (30 mL) at −78° C. was added thionyl chloride (1.5 mL, 20.78 mmol, 1.1 equiv) dropwise. The reaction mixture was stirred for 5 mins while cooling −78° C. and tert-butyl (S)-(1-hydroxyhexan-2-yl) carbamate (4.1 g, 18.89 mmol, 1 equiv) in anhydrous dichloromethane (30 mL) was added dropwise over 30 mins. The reaction mixture was stirred at −78° C. for 3 hours. The reaction mixture was stirred while warming to room temperature overnight. Water was added (100 mL) and phase separated. The aqueous phase was further extracted into dichloromethane (150 mL), The combined organics were washed with water (100 mL), dried over with anhydrous $Na_2SO4$, filtered and concentrated under reduced pressure to get the crude material of tert-butyl (4S)-4-butyl-1,2,3-oxathiazolidine-3-carboxylate 2-oxide, without further purification crude product was forward to next step.

tert-butyl (S)-4-butyl-1,2,3-oxathiazolidine-3-carboxylate 2,2-dioxide: Ruthenium(III)chloride hydrate (0.002 g, 0.013 mmol, 0.007 equiv), was added to a stirred solution of tert-butyl (4S)-4-butyl-1,2,3-oxathiazolidine-3-carboxylate 2-oxide (5 g, 19.01 mmol, 1 equiv), in acetonitrile (50 mL) and water (50 mL) at 0° C., followed by portion wise addition of sodium periodate (4.4 g, 20.91 mmol, 1.1 equiv). The biphasic mixture was stirred at 20° C. for 2 hours. Water (250 mL) was added and the mixture was extracted into ethyl acetate (2×150 mL). The combined organics were washed with water (150 mL), brine (150 mL), dried over with $Na_2SO4$,filtered and concentrated under reduced pressure to get the crude product, crude product was purified by column chromatography using 10% ethylacetate in Hexane as an eluent to give the tert-butyl (S)-4-butyl-1,2,3-oxathiazolidine-3-carboxylate 2,2-dioxide. $^1H$ NMR (400 MHz, $CDCl_3$) δ ppm 0.90-1.25 (m, 3H), 1.31-1.38 (m, 6H), 1.48 (s, 9H), 1.75-1.95 (m, 2H), 4.27-4.32 (m, 2H), 4.61-4.65 (m, 1H).

tert-butyl (S)-(1-(5-fluoro-1H-indol-3-yl)hexan-2-yl)carbamate: The 5-fluoro-1H-indole (2.0 g, 14.809 mmol, 1 eq) and cuprous chloride (1.9 g, 19.252 mmol, 1.3 eq) were taken in round bottom flask and was purged with argon, then dichloromethane (25 mL) was added and the reaction mixture was cooled to 0° C. Then, MeMgCl (3M in THF) (6.43 mL, 19.252 mmol, 1.3 eq) was added drop wise over a period of 10 min. The reaction mixture was stirred for 1 h at 0° C. After 1 h, a solution of tert-butyl (S)-4-butyl-1,2,3-oxathiazolidine-3-carboxylate 2,2-dioxide (2.9 g, 10.366 mmol, 0.7 eq) in dichloromethane (20 mL) was added at −20° C. drop wise. The resulting mixture was stirred for 6 h at −20° C. After 6 h, the reaction was quenched with 10% citric acid solution at −20° C. and the mixture was allowed to warm to room temperature, filtered the mixture through celite pad, washed the celite pad with dichloromethane. The organic layer was separated and the aqueous layer was extracted with dichloromethane (2×50 mL). The combined organics were washed with brine (20 mL), dried over anhydrous sodium sulfate, filtered and concentrated to give the crude product, which was purified by flash column chromatography using 15% ethyl acetate in hexane as an eluent to obtain tert-butyl (S)-(1-(5-fluoro-1H-indol-3-yl)hexan-2-yl)carbamate.

The isolated product was treated with metal scavenger quadrasil AP (compound was dissolved with THF (30 mL) and quadrasil TA (10 g) was added, the mixture was stirred for 1 h, filtered. This is repeated one more time and concentrated). LC-MS (m/z)=333.2 $[M-H]^+$.

(S)-1-(5-fluoro-1H-indol-3-yl)hexan-2-amine: To a solution of tert-butyl (S)-(1-(5-fluoro-1H-indol-3-yl)hexan-2-yl) carbamate (2.8 g, 8.372 mmol, 1 eq) in dichloromethane (10 mL) was added trifluoroacetic acid (5 mL) at 0° C. The mixture was allowed to stir at room temperature for 3 h. The progress of the reaction was monitored by TLC, after completion of reaction; the reaction mixture was concentrated under reduced pressure. The obtained crude was dissolved with ice cold water (5 mL) and was basified by 5% sodium hydroxide solution (pH adjusted to 12). The compound was extracted with dichloromethane (3×100 mL). The combined organics were washed with brine (50 mL), dried over anhydrous sodium sulfate, filtered and concentrated. The obtained crude was triturated with n-pentane, decanted the n-pentane and dried under vacuum to obtain (S)-1-(5-fluoro-1H-indol-3-yl)hexan-2-amine. LC-MS (m/z)=235.0 $[M+H]^+$.

4-((1S,3S)-3-butyl-6-fluoro-2,3,4,9-tetrahydro-1H-pyrido[3,4-b]indol-1-yl)-N-cyclobutylbenzenesulfonamide: In seal tube, (S)-1-(5-fluoro-1H-indol-3-yl)hexan-2-amine (0.5 g, 2.133 mmol, 1 eq), N-cyclobutyl-4-formylbenzenesulfonamide (0.51 g, 2.133 mmol, 1.0 eq) and hexafluoro-2-propanol (HFIP) (8 mL) were taken. The seal tube was closed and the mixture was heated to 90° C. and stirred for 16 h. The progress of the reaction was monitored by TLC (5% methanol in dichloromethane), the reaction was cooled to room temperature, concentrated under reduced pressure to obtain crude, which was purified by flash column chromatography using 2% methanol in dichloromethane as an eluent to obtain 4-((1 S,3S)-3-butyl-6-fluoro-2,3,4,9-tetrahydro-1H-pyrido[3,4-b]indol-1-yl)-N-cyclobutylbenzenesulfonamide. LC-MS (m/z)=456.0 $[M+H]^+$.

Preparation of Compound 145

4-((1S,3S)-3-butyl-2-(2-chloroacetyl)-6-fluoro-2,3,4,9-tetrahydro-1H-pyrido[3,4-b]indol-1-yl)-N- cyclobutylbenzenesulfonamide: To a stirred solution of 4-((1S,3S)-3-butyl-6-fluoro-2,3,4,9-tetrahydro-1H-pyrido[3,4-b]indol-1-yl)-N-cyclobutylbenzenesulfonamide (0.15 g, 0.329 mmol, 1 eq) and sodium bicarbonate (0.08 g, 0.987 mmol, 3.0 eq) in chloroform was added 2-chloroacetyl chloride (0.05 mL, 0.658 mmol, 2.0 eq) at 0° C. The mixture was gradually allowed to warm to room temperature and stirred for 2.5 h. The progress of the reaction was monitored by TLC (50% ethyl acetate in hexane). After completion of reaction, the reaction mixture was diluted with dichloromethane (50 mL), washed with water (2×30 mL), dried over anhydrous sodium sulfate, filtered and concentrated under reduced pressure to obtain crude product. which was purified by flash column chromatography using 40% ethyl acetate in hexane as an eluent to obtain 4-((1S,3S)-3-butyl-2-(2-chloroacetyl)-6-fluoro-2,3,4,9-tetrahydro-1H-pyrido[3,4-b]indol-1-yl)-N-cyclobutylbenzenesulfonamide. LC-MS (m/z)=529.9 $[M-H]^+$; $^1H$ NMR (400 MHz, DMSO-d6) δ 0.76 (t, J=6.0 Hz, 3H), 1.26 (m, 4H), 1.38-1.44 (m, 3H), 1.67 (bs, 2H), 1.82-1.83 (m, 2H), 3.00-3.16 (m, 2H), 3.46-3.55 (m, 2H), 4.45 (m, 2H), 4.65 (m, 1H), 5.92 (bs, 1H), 6.84 (m, 1H), 7.22-7.27 (m, 2H), 7.51-7.53 (m, 2H), 7.62 (bs, 2H), 7.85 (d, J=8.0 Hz, 1H), 11.00 (s, 1H).

Procedure EY: Synthesis of Compound 143

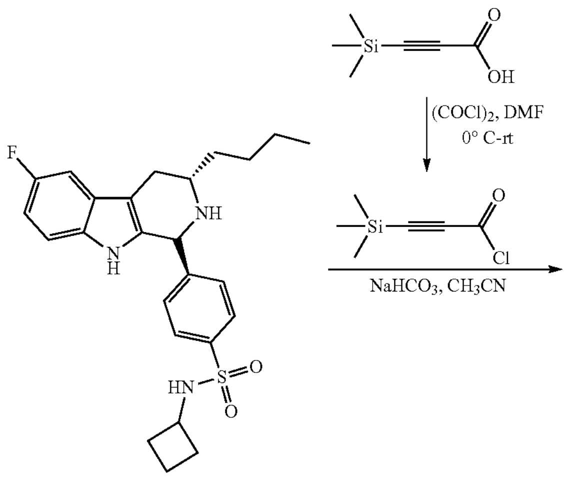

-continued

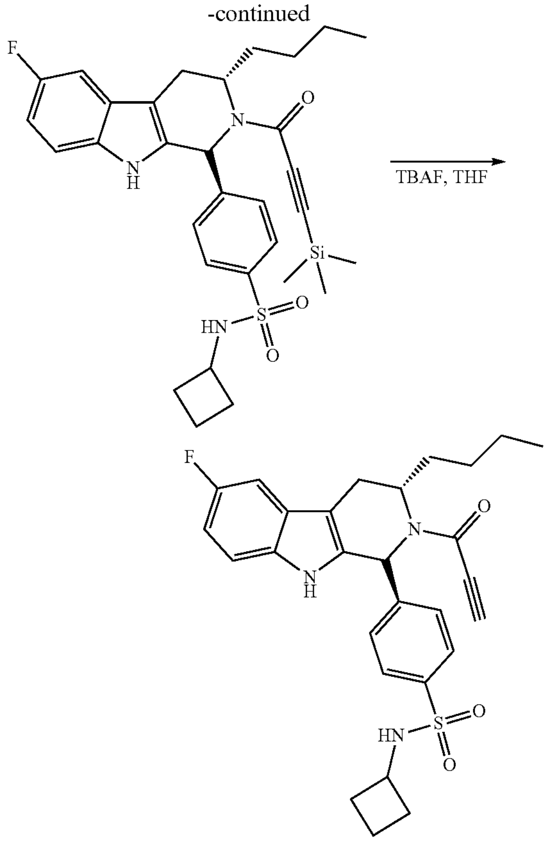

compound 143

3-(trimethylsilyl)propioloyl chloride: To a stirred solution of 3-(trimethylsilyl)propiolic acid (0.080 g, 0.562 mmol, 1 eq) in DMF (0.002 mL, 0.022 mmol, 0.04 eq) was added oxalyl chloride (0.053 mL, 0618 mmol, 1.1 eq) at 0° C. The mixture was allowed to warm room temperature and stirred 30 minutes. Then, the reaction mixture was concentrated under reduced pressure to obtain 3-(trimethylsilyl)propioloyl chloride. The crude was taken as such to next step.

4-((1R,3S)-3-butyl-6-fluoro-2-(3-(trimethylsilyl)propioloyl)-2,3,4,9-tetrahydro-1H-pyrido[3,4-b]indol-1-yl)-N-cyclobutylbenzenesulfonamide: To a stirred solution of 4-((1R,3S)-3-butyl-6-fluoro-2,3,4,9-tetrahydro-1H-pyrido[3,4-b]indol-1-yl)-N-cyclobutylbenzenesulfonamide (0.150 g, 0.329 mmol, 1.0 eq) in acetonitrile (10 mL) was added sodium bicarbonate (0.276 g, 3.29 mmol, 10.0 eq) at 0° C. After stirring for 5 minutes, a solution of 3-(trimethylsilyl) propioloyl chloride (0.079 g, 0.493 mmol, 1.5 eq) in acetonitrile was added. The resulting mixture was gradually allowed to warm to room temperature and stirred for 1 h. The progress of the reaction was monitored by TLC (50% ethyl acetate in hexane). After completion of reaction, the reaction mixture was filtered through celite pad, washed the celite pad with acetonitrile. The filtrate was concentrated under reduced pressure to obtain 4-((1R,3S)-3-butyl-6-fluoro-2-(3-(trimethylsilyl)propioloyl)-2,3,4,9-tetrahydro-1H-pyrido[3,4-b]indol-1-yl)-N-cyclobutylbenzenesulfonamide. The isolated crude product was taken as such to next step without further purification. LC-MS (m/z)=579.8 ([M+H]$^+$.

Preparation of Compound 143

4-((1S,3S)-3-butyl-6-fluoro-2-propioloyl-2,3,4,9-tetrahydro-1H-pyrido[3,4-b]indol-1-yl)-N-cyclobutylbenzenesulfonamide: To a stirred solution of 4-((1R,3S)-3-butyl-6-fluoro-2-(3-(trimethylsilyl)propioloyl)-2,3,4,9-tetrahydro-1H-pyrido[3,4-b]indol-1-yl)-N-cyclobutylbenzenesulfonamide (0.220 g, 0.379 mmol, 1 eq) in THF (8.0 mL) was added tetra butyl ammonium fluoride (1M in THF) (0.758 mL, 0.758 mmol, 2 eq) at 0° C. The mixture was allowed to warm room temperature and stirred for 30 minutes. The progress of the reaction was monitored by TLC (5% methanol in DCM). After completion of reaction, the reaction mixture was concentrated under reduced pressure, the obtained crude was diluted with water (5 mL) and extracted with ethyl acetate (2×5 mL). The organic layers were dried over anhydrous sodium sulfate, filtered and concentrated under reduced pressure. The crude product was purified by preparative TLC using 2% methanol in DCM as an eluent to obtain 4-((1S,3S)-3-butyl-6-fluoro-2-propioloyl-2,3,4,9-tetrahydro-1H-pyrido[3,4-b]indol-1-yl)-N-cyclobutylbenzenesulfonamide. LC-MS (m/z)=508.3 [M+H]$^+$. H NMR (400 MHz, DMSO-d6) δ ppm 0.71-0.84 (m, 3H), 1.03-1.33 (m, 4H), 1.37-1.45 (m, 3H), 1.65-1.97 (m, 4H), 2.82-2.85 (m, 0.5H), 2.920-2.94 (m, 0.5H), 3.03-3.07 (m, 1H), 3.37-3.42 (m, 1H), 3.50-3.52 (m, 0.7H), 3.99 (s, 0.3H), 4.54-4.63 (m, 1H), 4.92-4.93 (m, 1H), 5.92 (s, 0.5H), 6.58 (s, 0.5H), 6.82-6.91 (m, 1H), 7.20-7.49 (m, 2H), 7.50 (d, J=8.4 Hz, 2H), 7.62 (d, J=8.4 Hz, 2H), 7.74-7.94 (m, 1H), 10.99 (s, 0.7H), 11.22 (s, 0.3H).

Procedure EZ: Synthesis of Compound 144

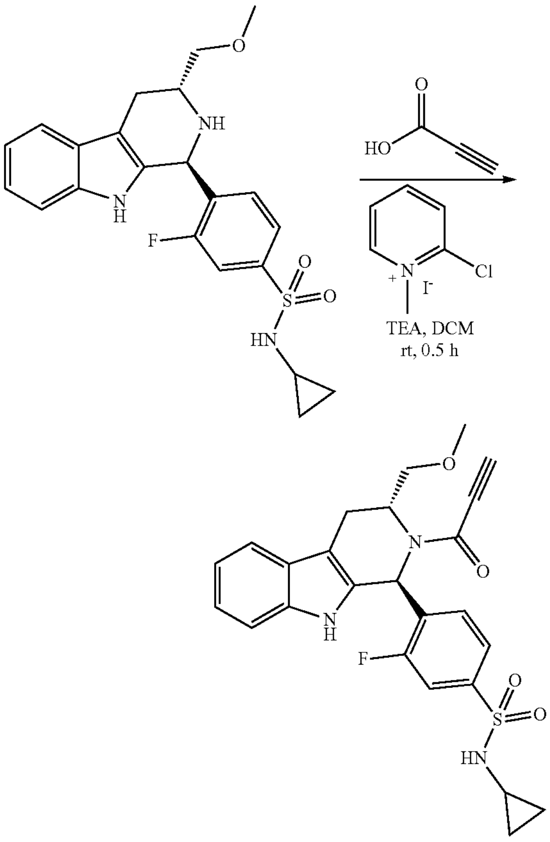

compound 144

N-cyclopropyl-3-fluoro-4-((1S,3R)-3-(methoxymethyl)-2-propioloyl-2,3,4,9-tetrahydro-1H-pyrido[3,4-b]indol-1-yl)benzenesulfonamide: To a stirred mixture of N-cyclopropyl-3-fluoro-4-((1S,3R)-3-(methoxymethyl)-2,3,4,9-tetrahydro-1H-pyrido[3,4-b]indol-1-yl)benzenesulfonamide (0.17 g, 0.395 mmol, 1 eq), in dichloromethane (5 mL) was added triethylamine (0.13 mL, 0.949 mmol, 2.4 eq), propiolic acid (0.024 mL, 0.395 mmol, 1 eq) and followed by the addition of 2-Chloro-1-methylpyridinium iodide (0.12 g, 0.474 mmol, 1.2 eq) at room temperature. The mixture was stirred for 30 min. The progress of the reaction was monitored by TLC (30% ethyl acetate in dichloromethane). After completion of reaction, the mixture was diluted with dichloromethane (50 mL), washed with water (20 mL), brine (10 mL), dried over anhydrous sodium sulfate, filtered and concentrated under reduced pressure to obtain crude product. which was purified by flash column chromatography using 30% ethyl acetate in dichloromethane as an eluent to obtain N-cyclopropyl-3-fluoro-4-((1S,3R)-3-(methoxymethyl)-2-propioloyl-2,3,4,9-tetrahydro-1H-pyrido[3,4-b]indol-1-yl)benzenesulfonamide. LC-MS (m/z)=482.1 $[M+H]^+$; $^1H$ NMR (400 MHz, DMSO-d6, at 70° C.) δ 0.37-0.46 (m, 4H), 2.11 (s, 1H), 3.10 (m, 2H), 3.23 (s, 3H), 3.32 (s, 2H), 4.43 (s, 1H), 5.14 (s, 1H), 6.12 (s, 1H), 6.98-7.04 (m, 2H), 7.21 (s, 1H), 7.47 (bs, 4H), 7.78 (s, 1H), 10.85 (s, 1H).

Procedure FA: Synthesis of Compound 147

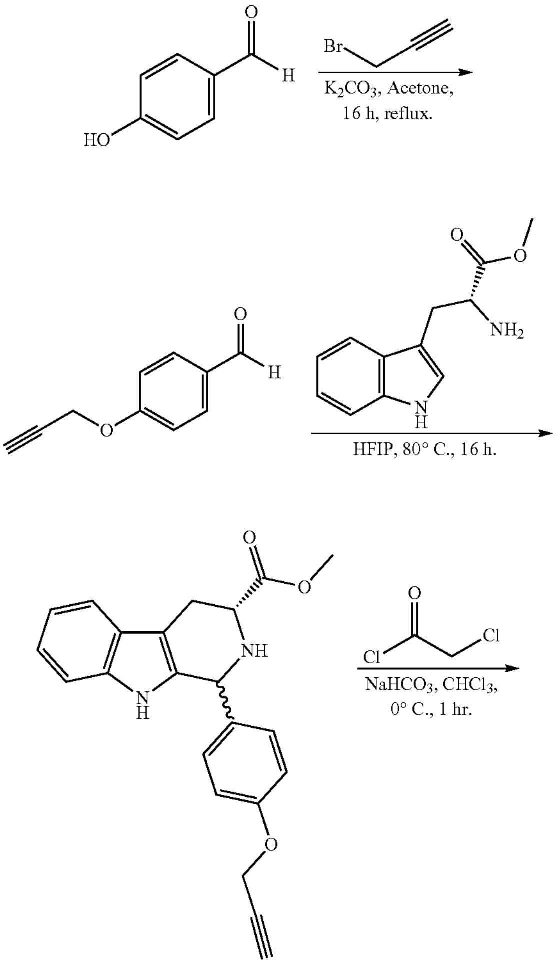

Trans isomer was taken forward

-continued

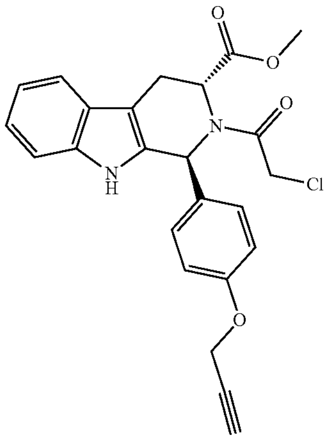

compound 147

4-(prop-2-yn-1-yloxy) benzaldehyde: To a solution of 4-hydroxybenzaldehyde (2.0 g, 16.37 mmol, 1.0 eq) in Acetone (10 mL) was added $K_2CO_3$ (3.39 g, 24.56 mmol, 1.5 eq) and 3-bromoprop-1-yne (5.84 g, 49.13 mmol, 1.0 eq) at room temperature and the reaction mixture was refluxed at 50° C. for 16 h under $N_2$ atmosphere. After this time, TLC (40% EtOAc in hexane) showed the reaction was completed. The reaction was cooled to room temperature and was concentrated under reduced pressure to crude product. The crude was purified by flash chromatography using 20% EtOAc in hexane as an eluent to give 4-(prop-2-yn-1-yloxy) benzaldehyde. LC-MS (m/z)=161.0 $[M+H]^+$; $^1H$ NMR (400 MHz, $CDCl_3$) δ ppm 4.78-4.79 (m, 3H), 7.06 (d, J=8.8 Hz, 2H), 7.87 (d, J=8.4 Hz, 2H), 9.91 (s, 1H).

methyl (1S,3R)-1-(4-(prop-2-yn-1-yloxy)phenyl)-2,3,4,9-tetrahydro-1H-pyrido[3,4-b]indole-3-carboxylate: To a solution of 4-(prop-2-yn-1-yloxy) benzaldehyde (0.61 g, 3.85 mmol, 1.2 eq) in HFIP (5.0 mL) was added methyl D-tryptophanate (0.70 g, 1.0 mmol, 1.2 eq) and stirred for 16 hours at 80° C. LCMS and TLC (50% EtOAc in hexane) showed the reaction was completed. The organic solvents were removed under reduced pressure to crude product. The crude product was purified by flash column chromatography using 40% EtOAc in Hexane as eluent to give methyl (1S,3R)-1-(4-(prop-2-yn-1-yloxy)phenyl)-2,3,4,9-tetrahydro-1H-pyrido[3,4-b]indole-3-carboxylate. LC-MS (m/z)=410.0 $[M+H]^+$.

Preparation of Compound 147 methyl (1S,3R)-2-(2-chloroacetyl)-1-(4-(prop-2-yn-1-yloxy)phenyl)-2,3,4,9-tetrahydro-1H-pyrido[3,4-b]indole-3-carboxylate: To a solution of methyl (1S,3R)-1-(4-(prop-2-yn-1-yloxy)phenyl)-2,3,4,9-tetrahydro-1H-pyrido[3,4-b]indole-3-carboxylate (0.15 g, 0.41 mmol, 1.0. eq) in Chloroform (10.0 mL) was added $NaHCO_3$ (0.116 g, 1.38 mmol, 2.0 eq.) at 0° C. and stirred for 15 mins and then and 2-chloroacetyl chloride (0.056 g, 0.49 mmol, 1.2 eq.) was added at 0° C. The mixture was allowed to stir at that temperature for 1 hr. LCMS and TLC (50% EtOAc in hexane) showed the reaction was completed. The reaction mixture was diluted with DCM (50 mL). The organic layers were separated, dried over $Na_2SO_4$ and concentrated under reduced pressure to give the crude product. The crude product was purified by flash column chromatography using 10-20% EtOAc in Hexane as an eluent to give methyl (1S,3R)-2-(2-chloroacetyl)-1-(4-(prop-2-yn-1-yloxy)phenyl)-2,3,4,9-tetrahydro-1H-pyrido[3,4-b]indole-3-carboxylate. LC-MS(m/z)=437.1 $[M+H]^+$; $^1H$ NMR (400 MHz, DMSO-$d_6$) 3.13-3.22 (m, 1H), 3.27-3.37 (m, 2H), 3.51 (s, 3H), 4.19-4.22 (m, 1H), 4.56-4.59 (m, 1H), 4.71 (s, 2H), 5.10 (bs, 1H), 6.10 (s, 1H), 6.91-7.04 (m, 4H), 7.23-7.25 (m, 1H), 7.34-7.35 (m, 2H), 7.43-7.45 (m, 1H), 10.77 (s, 1H).

-continued

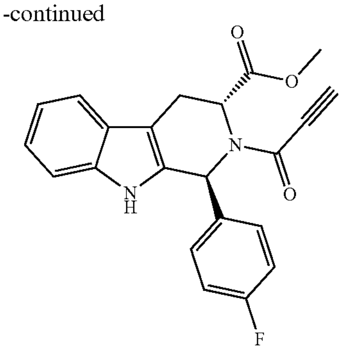

compound 146

Procedure FB: Synthesis of Compound 146

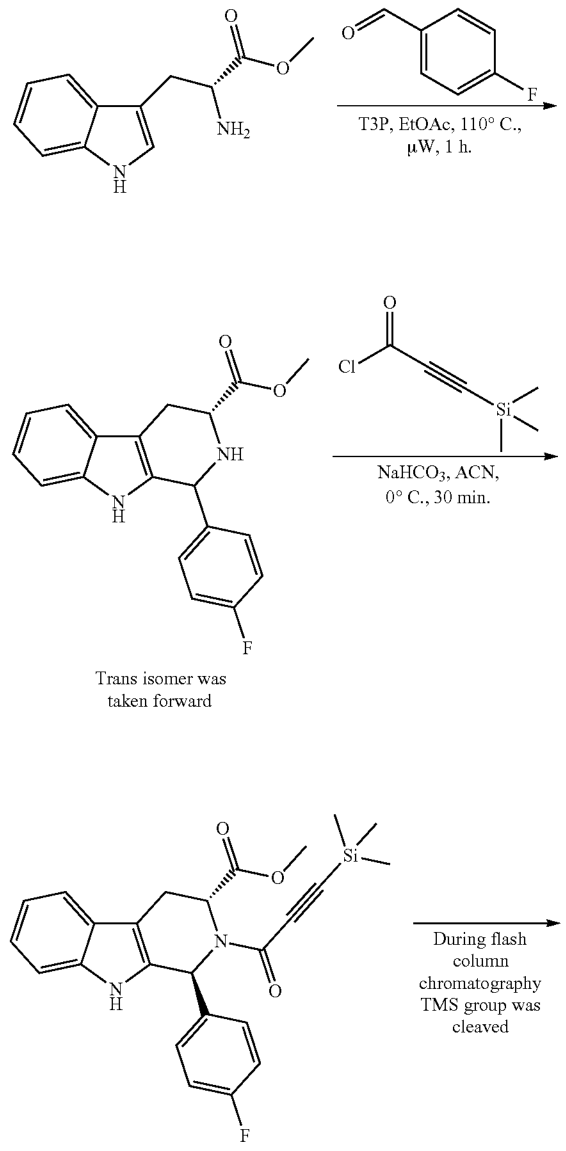

methyl (1S,3R)-1-(4-fluorophenyl)-2,3,4,9-tetrahydro-1H-pyrido[3,4-b]indole-3-carboxylate: To a stirred solution of methyl D-tryptophanate (0.6 g, 2.749 mmol, 1.0 eq) in ethylacetate (5 mL) was added 4-fluorobenzaldehyde (0.3 mL, 2.749 mmol, 1.0 eq) at room temperature. The mixture was cooled to 0° C. and T3P (4.37 mL, 6.8725 mmol, 2.5 eq) was added and heated to 110° C. for 1 h under microwave condition. The progress of the reaction was monitored by TLC (40% ethyl acetate in hexane). After completion of reaction, the reaction was diluted with ethyl acetate (50 mL), washed with water (2×10 mL), brine (10 mL), dried over anhydrous sodium sulfate, filtered and concentrated under reduced pressure to obtain crude. The crude was purified by flash chromatography using 30% ethyl acetate in hexane as an eluent to obtain methyl (1S,3R)-1-(4-fluorophenyl)-2,3,4,9-tetrahydro-1H-pyrido[3,4-b]indole-3-carboxylate.

LC-MS (m/z)=324.9 $[M+H]^+$; $^1H$ NMR (400 MHz, CDCl3) δ ppm 3.13-3.18 (m, 1H), 3.26-3.34 (m, 1H), 3.48 (s, 1H), 3.53 (s, 3H), 3.89-3.98 (m, 1H), 5.44 (s, 1H), 7.02 (t, J=8 Hz, 2H), 7.15 (t, J=8.4 Hz, 2H), 7.24-7.40 (m, 2H), 7.54-7.56 (m, 2H).

Preparation of Compound 146 methyl (1S,3R)-1-(4-fluorophenyl)-2-propioloyl-2,3,4,9-tetrahydro-1H-pyrido[3,4-b]indole-3-carboxylate: To 3-(trimethylsilyl)propiolic acid (0.197 g, 1.38 mmol, 1.0 eq), DMF (0.004 g, 0.05 mmol, 0.04 eq) and oxalyl chloride (0.13 mL, 1.52 mmol, 1.1 eq) was added and stirred for 30 mins. After this time reaction mixture was concentrated under reduced pressure to get the crude 3-(trimethylsilyl) propioloyl chloride and this crude was diluted with ACN (1 mL) and added to a reaction mixture containing a stirred solution of methyl (1S,3R)-1-(4-fluorophenyl)-2,3,4,9-tetrahydro-1H-pyrido[3,4-b]indole-3-carboxylate (0.3 g, 0.925 mmol, 1.0 eq) and $NaHCO_3$ (0.583 g, 0.925 mmol, 7.5 eq) in ACN (5 mL) at 0° C. and stirred for 15 mins. LCMS and TLC (50% EtOAc in hexane) showed the reaction was completed. The reaction was filtered and concentrated under reduced pressure to give the crude product. The crude product was purified by flash column chromatography using 20-22% EtOAc in Hexane as an eluent to give methyl (1S,3R)-1-(4-fluorophenyl)-2-propioloyl-2,3,4,9-tetrahydro-1H-pyrido[3,4-b]indole-3-carboxylate. LC-MS (m/z)=377.12 $[M+H]^+$; $^1H$ NMR (400 MHz, CDCl3) δ ppm 3.15-3.24 (m, 1H), 3.44-3.51 (m, 1H), 3.53 (s, 3H), 4.66-4.72 (m, 1H), 6.02 (s, 1H), 6.59 (s, 1H), 6.93-7.09 (m, 3H), 7.19-7.39 (m, 2H), 7.40-7.44 (m, 3H), 10.78 (s, 1H).

Procedure FC: Synthesis of Compound 149 and Compound 148

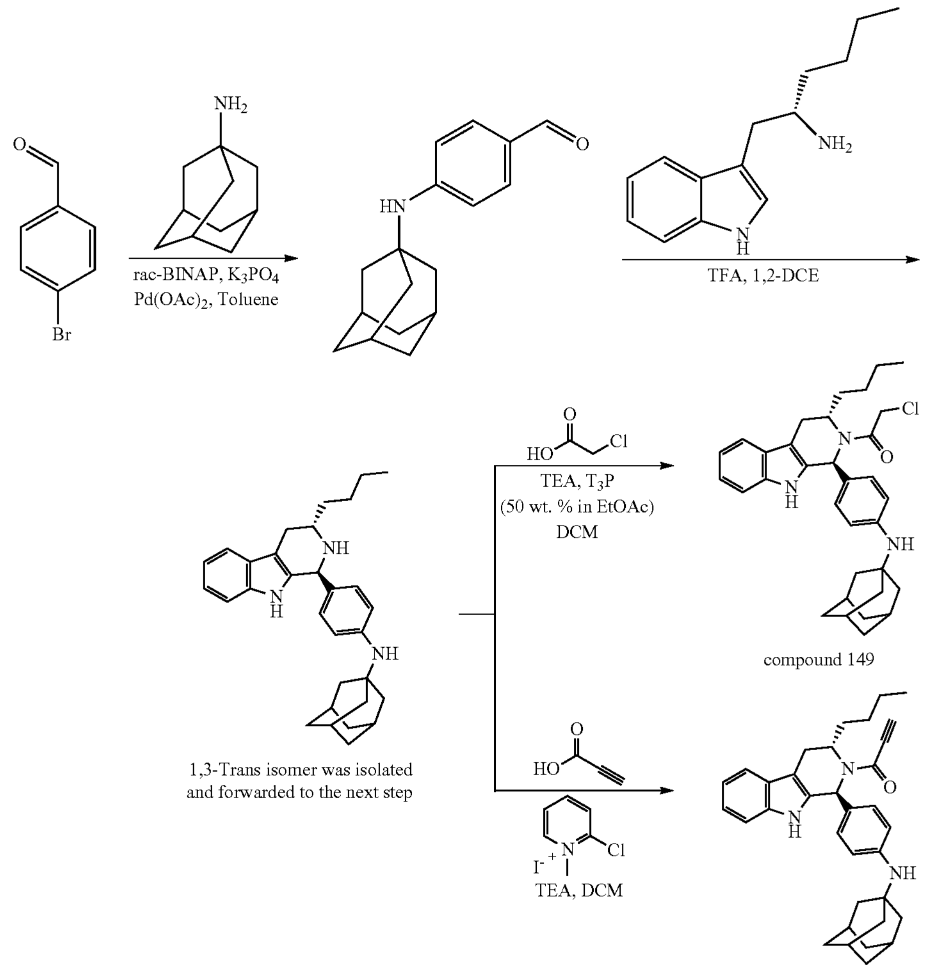

compound 149 compound 148

4-(((3s,5s,7s)-adamantan-1-yl)amino)benzaldehyde: To a stirred solution of 4-bromobenzaldehyde (4.1 g, 22.16 mmol, 1 eq) and (3s,5s,7s)-adamantan-1-amine (5 g, 33.24 mmol, 1.5 eq) in toluene was added rac-BINAP (0.69 g, 1.10 mmol, 0.05 eq), potassium phosphate tribasic (9.39 g, 13.29 mmol, 2 eq) at room temperature. The reaction mixture was purged under argon for 15 mins and then palladium acetate (0.15 g, 0.66 mmol, 0.03 eq) was added and the reaction was stirred at 110° C. for 16 h. The progress of the reaction was monitored by TLC (10% ethyl acetate in hexane). After completion of reaction, the reaction mixture was filtered through celite bed and the bed was washed with ethyl acetate (50 mL).The filtrate was concentrated under reduced pressure to obtain crude. The crude was purified by flash chromatography using 8-9% ethyl acetate in hexane as an eluent to obtain 4-(((3s,5s,7s)-adamantan-1-yl)amino)benzaldehyde. LC-MS (m/z)=256.0 ($[M+H]^+$. $^1H$ NMR (400 MHz, DMSO-d6) δ ppm 1.62-1.70 (m, 6H), 1.94 (s, 6H), 2.07 (bs, 3H), 6.38 (s, 1H), 6.81 (d, J=8.4 Hz, 2H), 7.51 (d, J=8.4 Hz, 2H), 9.55 (s, 1H).

(3R,5R,7R)—N-(4-((1S,3S)-3-butyl-2,3,4,9-tetrahydro-1H-pyrido[3,4-b]indol-1-yl)phenyl)adamantan-1-amine: In a sealed tube, (S)-1-(1H-indol-3-yl)hexan-2-amine (0.4 g, 1.85 mmol, 1 eq), 4-(((3s,5s,7s)-adamantan-1-yl)amino)benzaldehyde (0.52 g, 2.03 mmol, 1.1 eq) and DCM (5.0 mL) was taken and to that trifluoro acetic acid (0.28 mL, 3.70 mmol, 2 eq) was added at 0° C. The reaction mixture was heated to 80° C. and stirred for 6 h. The progress of the reaction was monitored by TLC (70% ethyl acetate in hexane). The reaction was cooled to room temperature, concentrated under reduced pressure to obtain crude, which was dissolved in ethyl acetate (100 mL) and was washed with sodium bicarbonate solution (20 mL) and water (2×10 mL). Combined organic layer was dried over anhydrous sodium sulfate, filtered and concentrated under reduced pressure to obtain the crude which was purified by flash column chromatography using 30-35% ethyl acetate in hexane to obtain the desired product. Scavenger treatment was performed by dissolving the product in THF (15 mL) and adding quadrasil TA (0.003 g, 1.0 eq). The mixture was stirred at room temperature for 1 h and then filtered through sintered funnel. The filtrate was concentrated under reduced pressure to obtain tert-butyl (3R,5R,7R)—N-(4-((1S,3S)-3-butyl-2,3,4,9-tetrahydro-1H-pyrido[3,4-b]indol-1-yl)phenyl)adamantan-1-amine. LC-MS (m/z)=454.0 $[M+H]^+$.

Preparation of Compound 149

1-((1S,3S)-1-(4-(((3R,5R,7R)-adamantan-1-yl)amino)phenyl)-3-butyl-1,3,4,9-tetrahydro-2H-pyrido[3,4-b]indol- 2-yl)-2-chloroethan-1-one: To a solution of 2-chloroacetic acid (0.021 g, 0.22 mmol, 1 eq) in DCM at 0° C. was added TEA (0.12 mL, 0.88 mmol, 4 eq), stirred for 15 mins and then T3P (50 wt. % in EtOAc) (0.26 mL, 0.44 mmol, 2 eq) was added and stirred for another 5 mins. Then (3R,5R,7R)—N-(4-((1S,3S)-3-butyl-2,3,4,9-tetrahydro-1H-pyrido[3,4-b]indol-1-yl)phenyl)adamantan-1-amine (0.1 g, 0.27 mmol, 1 eq) was added to the reaction mixture and then reaction mixture was stirred at room temperature for 3 h. The progress of the reaction was monitored by TLC (30% ethyl acetate in hexane). The reaction mixture was diluted with DCM (100 mL) and was washed with sodium bicarbonate solution (10 mL) and water (10 mL). Combined organic layer was dried over anhydrous sodium sulfate, filtered and concentrated under reduced pressure to obtain the crude which was purified by flash column chromatography using 20-25% ethyl acetate in hexane to obtain 1-((1S,3S)-1-(4-(((3R,5R,7R)-adamantan-1-yl)amino)phenyl)-3-butyl-1,3,4,9-tetrahydro-2H-pyrido[3,4-b]indol-2-yl)-2-chloroethan-1-one. LC-MS (m/z)=430.4 $[(M+H)^+$. $^1H$ NMR (400 MHz, DMSO-d6) δ ppm 0.75-0.77 (m, 3H), 1.16-1.22 (m, 4H), 1.38 (bs, 2H), 1.59 (s, 6H), 1.79 (s, 6H), 2.00 (s, 3H), 2.96 (s, 2H), 4.42 (bs, 1H), 4.52 (bs, 1H), 4.87 (bs, 1H), 5.86 (bs, 1H), 6.65 (bs, 2H), 6.92-7.00 (m, 5H), 7.24 (d, J=8.0 Hz, 1H), 7.42 (d, J=7.6 Hz, 1H), 10.84 (s, 1H).

Preparation of Compound 148

1-((1 S,3S)-1-(4-(((3R,5R,7R)-adamantan-1-yl)amino)phenyl)-3-butyl-1,3,4,9-tetrahydro-2H-pyrido[3,4-b]indol-2-yl)prop-2-yn-1-one: To a solution of (3R,5R,7R)—N-(4-((1S,3S)-3-butyl-2,3,4,9-tetrahydro-1H-pyrido[3,4-b]indol-1-yl)phenyl)adamantan-1-amine (0.07 g, 0.15 mmol, 1 eq) in DCM at room temperature was added TEA (0.05 mL, 0.36 mmol, 2.4 eq), stirred for 5 mins and then propiolic acid (0.01 mL, 0.15 mmol, 1 eq) and 2-chloro-1-methyl-pyridinium iodide (0.046 g, 0.18 mmol, 1.2 eq) was added to the reaction mixture and then reaction mixture was stirred at room temperature for 30 mins. The progress of the reaction was monitored by TLC (30% ethyl acetate in hexane). The reaction mixture was diluted with DCM (100 mL) and was washed with water (10 mL). Combined organic layer was dried over anhydrous sodium sulfate, filtered and concentrated under reduced pressure to obtain the crude which was purified by flash column chromatography using 20-25% ethyl acetate in hexane to obtain 1-((1 S,3S)-1-(4-(((3R,5R,7R)-adamatantan-1-yl)amino)phenyl)-3-butyl-1,3,4,9-tetrahydro-2H-pyrido[3,4-b]indol-2-yl)prop-2-yn-1-one. LC-MS (m/z)=506.3 $[(M+H)^+$. $^1H$ NMR (400 MHz, DMSO-d6) VT at 65° C.: δ ppm 0.76 (s, 3H), 1.00-1.25 (m, 6H), 1.61 (s, 6H), 1.81 (s, 6H), 2.02 (s, 3H), 4.40 (s, 2H), 4.71 (s, 2H), 5.85 (s, 1H), 6.52 (s, 1H), 6.62 (s, 1H), 6.74 (s, 1H), 6.90-7.10 (m, 4H), 7.27 (s, 1H), 7.43 (d, J=7.6 Hz, 1H), 10.67 (s, 1H).

The compounds provided in Table 1, as well as those tested in the biological assays shown in the tables below, can be or were, synthesized according to the procedures described above using the appropriate reagents and starting materials. Data for select compounds is provided below in Table 1a.

TABLE 1a

| Compound No. | MS $[M + H]^+$ |
|---|---|
| K601 | 441.1 |
| 1 | 505.0 $[M + Na]^+$ |
| 2 | 483.1 |
| 4 | 426.9 $[M + Na]^+$ |
| 5 | 412.9 |
| 6 | 575.1 |
| 7 | 462.0 $[M + Na]^+$ |
| 8 | 475.9 $[M + Na]^+$ |
| 9 | 504.1 $[M + Na]^+$ |
| 10 | 540.0 |
| 11 | 470.1 |
| 12 | 441.0 |
| 13 | 482.7 |
| 14 | 612.1 $[M + Na]^+$ |
| 15 | 469.0 |
| 16 | 591.1 $[M + Na]^+$ |
| 19 | 525.0 |
| 20 | 533.1 $[M + Na]^+$ |
| 21 | 496.0 |
| 22 | 475.9 |
| 23 | 490.1 |
| 24 | 618.0 $[M + Na]^+$ |
| 25 | 509.0 |
| 26 | 496.0 |
| 27 | 539.1 |
| 28 | 560.1 |
| 29 | 532.1 |
| 30 | 622.1 |
| 31 | 495.0 |
| 32 | 510.0 |
| 35 | 568.0 $[M + Na]^+$ |
| 37 | 517.9 |
| 38 | 467.0 |
| 39 | 523.0 |
| 41 | 482.0 $[M + Na]^+$ |
| 42 | 403.0 $[M + H\text{-}Boc]^+$ |
| 45 | 523.1 |
| 49 | 559.0 |
| 50 | 397.0 |
| 51 | 539.3 |
| 52 | 575.1 $[M + Na]^+$ |
| 54 | 623.1 |
| 56 | 533.1 $[M + Na]^+$ |
| 58 | 461.0 $[M + Na]^+$ |
| 59 | 473.9 |
| 61 | 576.1 |
| 63a | 477.0 $[M + Na]^+$ |
| 63 | 469.1 |
| 66 | 525.1 |
| 67 | 468.1 |
| 68 | 516.0 |
| 69 | 528.0 |
| 70 | 500.0 |
| 71 | 453.0 |
| 72 | 455.3 |
| 74 | 489.0 $[M + Na]^+$ |
| 75 | 481.1 |
| 76 | 525.1 |
| 77 | 397.0 |
| 79 | 414.9 |
| 80 | 462.0 $[M + Na]^+$ |
| 81 | 502.1 $[M + Na]^+$ |
| 82 | 538.1 $[M + Na]^+$ |
| 83 | 474.1 $[M + Na]^+$ |
| 84 | 517.1 $[M + Na]^+$ |
| 85 | 495.4 |
| 86 | 509.1 |
| 87 | 582.9 $[M + Na]^+$ |
| 88 | 542.9 $[M + Na]^+$ |
| 89 | 523.1 |
| 90 | 443.4 |
| 91 | 459.4 |
| 93 | 475.4 |
| 95 | 521.4 |
| 96 | 521.3 |
| 97 | 521.3 |
| 98 | 411.0 |
| 100 | 441.4 |
| 101 | 574.1 $[M + Na]^+$ |
| 102 | 557.6 $[M + MeCN + H]^+$ |

TABLE 1a-continued

| Compound No. | MS $[M + H]^+$ |
|---|---|
| 103 | 424.2 |
| 104 | 437.5 |
| 106 | 411.0 $[M + H]^+$ |
| 108 | 400.9 $[M + Na]^+$ |
| 109 | 407.5 $[M + H]^+$ |
| 110 | 443.0 $[M + Na]^+$ |
| 112 | 423.1 |
| 113 | 448.9 $[M + Na]^+$ |
| 114 | 442.1 |
| 115 | 449.1 $[M + H]^+$ |
| 116 | 408.2 |
| 117 | 438 |
| 118 | 474.0 $[M + Na]^+$ |
| 119 | 474.0 $[M + Na]^+$ |
| 120 | 457.8 |
| 121 | 476.0 $[M + Na]^+$ |
| 122 | 454.1 |
| 123 | 417.9 |
| 124 | 424.9 |
| 125 | 424.3 |
| 127 | 438.1 |
| 128 | 438.3 |
| 129 | 442.3 |
| 130 | 560.2 |
| 132 | 438.1 |
| 133 | 501.1 |
| 134 | 423.1 |
| 143 | 508 |
| 144 | 482 |
| 144 | 482 |
| 145 | 533 |
| 146 | 377 |
| 147 | 438 |
| 148 | 506 |
| 149 | 531 |
| 150 | 488.2 |
| 151 | 486 |
| 152 | 514.2 |
| 153 | 469.8 |
| 154 | 365.0 |
| 155 | 405.1 |
| 156 | 411.0 |
| 157 | 425 |
| 158 | 413.3 |
| 159 | 413.3 |
| 160 | 459.1 |
| 161 | 476 |
| 162 | 470.3 |
| 163 | 405.1 |
| 164 | 494 |
| 165 | 482.1 |
| 166 | 506.1 |
| 167 | 494.4 |
| 168 | 394.3 |
| 169 | 518.2 |
| 170 | 490.3 |
| 171 | 340.3 |
| 172 | 510.2 |
| 173 | 506 |
| 174 | 451.5 |
| 175 | 470.4 |
| 176 | 403.0 |
| 177 | 387.1 |
| 179 | 377.0 |
| 180 | 389.1 |
| 182 | 323.1 |
| 184 | 445.0 |
| 186 | 395.0 |
| 189 | 708.3 |
| 192 | 399.0 |
| 193 | 344.8 |
| 194 | 339.9 |
| 195 | 392.9 |
| 196 | 348.9 |
| 197 | 369.0 |
| 198 | 350.9 |
| 199 | 350.9 |
| 200 | 351.1 |

TABLE 1a-continued

| Compound No. | MS $[M + H]^+$ |
|---|---|
| 201 | 351 |
| 202 | 318.9 |
| 205 | 375.0 |
| 206 | 332.9 |
| 207 | 542.2 |
| 209 | 515.4 |
| 210 | 472.2 |
| 211 | 614.4 |
| 212 | 452.3 |
| 213 | 436 |
| 214 | 437.2 |
| 215 | 438.1 |
| 216 | 442.1 |
| 217 | 476 |
| 218 | 501.2 |
| 219 | 459.3 |
| 220 | 424.9 |
| 221 | 356.9 |
| 222 | 465.0 |
| 223 | 582.1 $[M + Na]^+$ |
| 224 | 436.0 $[M + Na]^+$ |
| 225 | 430.1 |
| 226 | 347.0 |
| 227 | 430.0 $[M + Na]^+$ |
| 228 | 416.1 |
| 229 | 416.1 |
| 230 | 470.1 |
| 231 | 399.9 |
| 232 | 454.4 |
| 233 | 442.3 |
| 234 | 438.3 |
| 235 | 482.1 |
| 236 | 411.0 |
| 237 | 461.0 $[M + Na]^+$ |
| 238 | 401.9 |
| 239 | 393.8 |
| 240 | 466 |
| 259 | 411.0 |
| 263 | 517.0 |
| 264 | 525.1 |
| 265 | 398.9 |
| 272 | 431.0 |
| 273 | 476.1 |
| 274 | 419.0 |
| CC | 444.9 |
| BX | 486.9 [M + Na]+ |
| CA | 488.1 |
| BZ | 507.1 [M + Na]+ |

BIOLOGICAL EXAMPLES

Example 1: Whole Blood Stability Assays

Fresh blood samples were collected from male human donor and male CD-1 mouse with EDTA-$K_2$ as anti-coagulant. Blood was collected on the day of experiment and stored on wet ice at 4° C., and then equilibrated to room temperature before use.

Compounds were dissolved in DMSO at 10 mM concentration. Propantheline bromide, used as a positive control, was prepared in water at 10 mM concentration.

One mM intermediate solution of test compounds were prepared by diluting 10 μL of the stock solution (10 mM) with 90 μL DMSO. One mM intermediate solution of positive control compound was prepared by diluting 10 μL of the stock solution (10 mM) with 90 μL water. 100 μM working solutions were prepared by diluting 10 μL of the intermediate solutions (test compounds and positive control) with 90 μL 45% MeOH/$H_2O$.

An aliquot of 98 μL of blank blood was spiked with 2 μL of working solution (100 μM) to achieve 2 μM of final concentration for test compounds and positive control. The solution samples were incubated for 0, 30, and 60 minutes at 37° C. in a water bath. The samples were labeled as T0, T30 and T60, for 0, 30, 60 minute incubation time, respectively.

At the end of the incubation, 100 μL of water was added into the sample wells and mixed well, then 800 μL of 100% acetonitrile containing internal standards (200 ng/mL tolbutamide and 20 ng/mL buspirone) added into each sample container. The sample containers were mixed at 800 rpm for 10 minutes and centrifuged at 4000 rpm for 20 minutes. A 100 μL aliquot of supernatant from each container was transferred to sample plates and mixed with 200 μL water. All samples were shaken on the plate shaker at 800 rpm for about 10 minutes before LC-MS analysis.

The Ace 5 Phenyl 50×2.1 mm column was used for the HPLC analysis. The mobile phases were 0.1% formic acid in water (mobile phase A); and 0.1% formic acid in acetonitrile (mobile phase B). The injection volume was 10 μL. Mass spectrometer was calibrated and tuned for each test compound.

The % remaining of test compound in blood was calculated using following equation:

% Remaining=100×(PAR at a specified incubation time/PAR at T0)

where PAR is the Peak Area Ratio of analyte versus internal standard (VS).

Stability in whole blood for K601 (RSL3), K601 (RSL3) metabolites (compounds 3, 4, and 5) and additional compound examples are shown in Table 24.

Example 2: Pharmacokinetic (PK) Studies in Balb/C Nude Mice Via Intraperitoneal Injection Test compounds were dissolved either in 20% (w/w) sulfobutylether-β-cyclodextrin (SBECD) pH 3-7 aqueous solution, or 5% DMSO/(30-50%) PEG400/(65-45%) water. Test compound dosing solutions were administered intraperitoneally to Balb/c nude male mice. Blood samples were collected at various time points with EDTA-$K_2$ as anticoagulant on ice, and centrifuged to obtain plasma samples. The plasma samples were stored at −20° C. until analysis.

Into 10 μL of test compound plasma samples were added 2 μL DMSO then 200 μL of 5 ng/mL internal standard (VTSD) (Terfenadine) in MeOH/acetonitrile. The mixture was vortexed for 1 minute and centrifuged at 4000 rpm for 15 minutes. Calibration standards were prepared by spiking known amount of test compounds into blank plasma samples. The supernatant solution was diluted 5 times with Acetonitrile/$H_2O$ (with 0.1% formic acid, 1:1, v/v), and this is the solution for LC-MS/MS analysis. The limit of quantification (LOQ) was 1 ng/mL.

Typical HPLC mobile phases were mobile phase of 5 mM $NH_4OAc$ (with 0.05% formic acid); and mobile phase B of acetonitrile (with 0.1% formic acid). The HPLC column was Kinetex C18 (30 mm×3.00 mm). Mass spectrometer was tuned for each compound in the Multiple Reaction Monitoring (MRM) scanning mode and in the electrospray ionization mode. The lower limit of quantification was 1-10 ng.

A typical HPLC gradient table is described below:

TABLE 2

| Time (min) | Flow Rate (mL/min) | A (%) | B (%) |
|---|---|---|---|
| 0.40 | 0.7 | 80.0 | 20.0 |
| 1.50 | 0.7 | 5.00 | 95.0 |
| 2.20 | 0.7 | 5.00 | 95.0 |
| 2.21 | 0.7 | 80.0 | 20.0 |
| 3.00 | 0.7 | 80.0 | 20.0 |

A. PK profiles of K601 (RSL3, or (1S,3R)-RSL3)) and its Metabolites in Balb/C Nude Mice via Intraperitoneal Injection The PK profiles of K601 (RSL3) and its metabolites are shown below. In this study, K601 (RSL3) was formulated in 5% DMSO/30% PEG 400/65% water at 1.5 mg/mL. The volume of injection via intraperitoneal route was 10 mL/kg for a dose of 15 mg/kg. K601 (RSL3) and its metabolites (hydrolyzed products in vivo) were analyzed by LC-MS with the method described above. The limit of quantification (LOQ) was 1 ng/mL.

It can be observed that RSL3 rapidly hydrolyzes in vivo and is nearly undetectable at 30 minutes after injection. Correspondingly, all three hydrolyzed products of K601 (RSL3), denoted as compound 4, compound 5, and compound 3, respectively, were detected in vivo at 30 minutes, 1 hour and 2 hours. The PK parameters are summarized in the table below. Compound 4, compound 5, and compound 3 are inactive (see Table 24).

The PK profile of K601 (RSL3) indicated that K601 (RSL3) does not have the pharmaceutical property for systemic administration.

TABLE 3a

PK Profile of K601 (RSL3).
PK Profile of K601 (RSL3), IP 15 mg/kg, Balb/C Nude Mice

| | Calculated Concentration (ng/mL) | | | | |
|---|---|---|---|---|---|
| Time (h) | Mouse #1 | Mouse #2 | Mouse #3 | Mean | SD |
| 0.5 | 1.18 | BLOQ | 1.17 | 0.783 | NA |
| 1 | BLOQ | BLOQ | BLOQ | NA | NA |
| 2 | BLOQ | BLOQ | BLOQ | NA | NA |
| 4 | BLOQ | 1.63 | BLOQ | 0.543 | NA |

BLOQ = Below limit of quantification (which was 1 ng/mL)

TABLE 3b

PK Profile of Compound 4.
PK Profile of Compound 4, IP 15 mg/kg, Balb/C Nude Mice

| | Calculated Concentration (ng/mL) | | | | |
|---|---|---|---|---|---|
| Time (h) | Mouse #1 | Mouse #2 | Mouse #3 | Mean | SD |
| 0.5 | 739 | 476 | 487 | 567 | 149 |
| 1 | 160 | 85.6 | 96.6 | 114 | 40 |
| 2 | 28.0 | 15.4 | 9.53 | 17.6 | 9.4 |
| 4 | BLOQ | 1.04 | BLOQ | 0.35 | NA |

BLOQ = Below limit of quantification (which was 1 ng/mL)

TABLE 3c

| PK Profile of Compound 5. PK Profile of Compound 5, IP 15 mg/kg, Balb/C Nude Mice | | | | | |
|---|---|---|---|---|---|
| | Calculated Concentration (ng/mL) | | | | |
| Time (h) | Mouse #1 | Mouse #2 | Mouse #3 | Mean | SD |
| 0.5 | 43.5 | 22.5 | 45.5 | 37.2 | 12.7 |
| 1 | 45.1 | 23.0 | 34.9 | 34.3 | 11.1 |
| 2 | 24.1 | 9.91 | 12.8 | 15.6 | 7.5 |
| 4 | 2.61 | BLOQ | 1.44 | 1.35 | NA |

BLOQ = Below limit of quantification (which was 1 ng/mL)

TABLE 3d

| PK Profile of Compound 3. PK Profile of Compound 3, IP 15 mg/kg, Balb/C Nude Mice | | | | | |
|---|---|---|---|---|---|
| | Calculated Concentration (ng/mL) | | | | |
| Time (h) | Mouse #1 | Mouse #2 | Mouse #3 | Mean | SD |
| 0.5 | 932 | 640 | 647 | 740 | 167 |
| 1 | 226 | 121 | 140 | 162 | 56 |
| 2 | 32.9 | 21.2 | 12.8 | 22.3 | 10.1 |
| 4 | BLOQ | BLOQ | 5.13 | 1.71 | NA |

BLOQ = Below limit of quantification (which was 1 ng/mL)

Summary of PK Parameters of K601 and its Metabolites in Mouse Plasma after Intraperitoneal (VP) Injection at 15 mg/kg are given below.

TABLE 3e

| Compound ID | $t_{1/2}$ (hr) | $t_{max}$ (hr) | $C_{max}$ (ng/mL) | $AUC_{last}$ (hr * ng/mL) | $AUC_{Inf}$ (hr * ng/mL) | AUC Extr (%) | $MRT_{Inf}$ (hr) |
|---|---|---|---|---|---|---|---|
| K601 | NC | 1.67 | 1.33 | 1.28 | NC | NC | NC |
| 4 | 0.358 | 0.500 | 567 | 384 | 389 | 1.30 | 0.696 |
| 5 | 0.846 | 0.833 | 37.9 | 65.8 | 72.7 | 12.7 | 1.53 |
| 3 | 0.494 | 0.500 | 740 | 516 | 523 | 1.20 | 0.735 |

* NC = not calculatable.

B. PK profiles of Compound 1 in Balb/C Nude Mice via Intraperitoneal Injection

The PK profiles of compound 1 are shown below. In this study, the compound was formulated in 20% (w/w) sulfobutylether-β-cyclodextrin (SBECD), pH 5 aqueous solution at 1.5 mg/mL. The volume of injection via intraperitoneal route was 10 mL/kg for a dose of 15 mg/kg. The concentration of test compounds in plasma were analyzed by LC-MS with the method described above. The limit of quantification was 1 ng/mL.

Surprisingly, at the same dose of 15 mg/kg in mouse via IP administration, compound 1 showed higher exposure such as the maximal concentration (Cmax), and the Area-under-the-curve (AUC) than K601 (RSL3) with a modification at the 1S position. The mean AUC for compound 1 is 123 ng/mL*hour and the mean Cmax is 126 ng/mL. In comparison the mean AUC for K601 (RSL) is 1.28 ng/mL*hour, and the mean Cmax is 1.33 ng/mL.

TABLE 4a

| PK Profile of Compound 1. PK Profile of Compound 1, IP 15 mg/kg, Balb/C Nude Mice | | | | | |
|---|---|---|---|---|---|
| | Calculated Concentration (ng/mL) | | | | |
| Time (h) | Mouse #1 | Mouse #2 | Mouse #3 | Mean | SD |
| 0.5 | 146 | 111 | 120 | 126 | 18 |
| 1 | 56.1 | 37.1 | 34.7 | 42.6 | 11.7 |
| 2 | 20.0 | 9.41 | 15.4 | 14.9 | 5.3 |
| 4 | 5.56 | 5.23 | 6.44 | 5.74 | 0.63 |

PK Parameters of K601 and compound 1 in Mouse Plasma after Intraperitoneal (IP) Injection at 15 mg/kg TABLE 4b

| Compound ID | $t_{1/2}$ (hr) | $t_{max}$ (hr) | $C_{max}$ (ng/mL) | $AUC_{last}$ (hr * ng/mL) | $AUC_{Inf}$ (hr * ng/mL) | AUC Extr (%) | $MRT_{Inf}$ (hr) |
|---|---|---|---|---|---|---|---|
| K601 | NC | 1.67 | 1.33 | 1.28 | NC | NC | NC |
| 1 | 1.12 | 0.500 | 126 | 123 | 132 | 7.26 | 1.40 |

C. PK profile of Compound BX also known as (1S,3R)-RSL3-alkyne in Balb/C Nude Mice via Intraperitoneal Injection The PK profile of compound BX is shown below. This compound is disclosed in Yang et al., 2013, Cell 156, 317-331. It was formulated in 5% DMSO/50% PEG400/45% Water pH adjusted to 4 with HCl as an aqueous solution at 1.0 mg/mL. The volume of injection via intraperitoneal route was 15 mL/kg for a dose of 15 mg/kg. The concentration of test compounds in plasma were analyzed by LC-MS with the method described above. The limit of quantification was 1 ng/mL. No compound BX was detected in the plasma. The limit of quantification was 1 ng/mL.

TABLE 5

PK Profile of Compound BX, IP 15 mg/kg, Balb/C Nude Mice

| | Calculated Concentration (ng/mL) | | | | |
|---|---|---|---|---|---|
| Time (h) | Mouse #10 | Mouse #11 | Mouse #12 | Mean | SD |
| 0.5 | BLOQ | BLOQ | BLOQ | NA | NA |
| 1 | BLOQ | BLOQ | BLOQ | NA | NA |
| 2 | BLOQ | BLOQ | BLOQ | NA | NA |
| 4 | BLOQ | BLOQ | BLOQ | NA | NA |

BLOQ = Below limit of quantification (which was 1 ng/mL)

D. PK profile of Compound 24, Compound 28 and Compound 67 in Balb/C Nude Mice via Intraperitoneal Injection The PK profiles of compounds 24, 28 and 67 are shown below. Compounds 24 and 28 were formulated in 20% (w/w) sulfobutylether-β-cyclodextrin (SBECD) with pH 3 and pH 4, respectively, as an aqueous solution at 1.0 mg/mL. Compound 67 was in 5% DMSO/50% PEG 400/45% water pH 4 (adjusted with 12 N HCl) aqueous solution at 1.0 mg/mL. The injection volume via intraperitoneal route was 10 mL/kg for a dose of 15 mg/kg. The concentration of test compounds in plasma were analyzed by LC-MS with the method described above. The limit of quantification was 1 ng/mL. At the same dose of 15 mg/kg in mouse via IP administration, compounds 24 and 28 showed higher exposure such as the maximal concentration (Cmax), and the Area-under-the-curve (AUC) than K601 (RSL3) with a modification at the 1S-position. Compound 67 showed higher exposure such as the maximal concentration (Cmax), and the Area-under-the-curve (AUC) than K601 (RSL3) with modifications at the 1S-position and the 3R-position.

TABLE 6

PK Profile of Compound 24
PK Profile of Compound 24, IP 15 mg/kg, Balb/C Nude Mice

| | Calculated Concentration (ng/mL) | | | | |
|---|---|---|---|---|---|
| Time (h) | Mouse #1 | Mouse #2 | Mouse #3 | Mean | SD |
| 0.5 | 332 | 557 | 504 | 464 | 118 |
| 1 | 355 | 305 | 290 | 317 | 34.0 |
| 2 | 50.5 | 39.8 | 43.3 | 44.5 | 5.46 |
| 4 | 3.41 | 5.46 | 4.81 | 4.56 | 1.05 |

TABLE 7

PK Profile of Compound 28
PK Profile of Compound 28, IP 15 mg/kg, Balb/C Nude Mice

| | Calculated Concentration (ng/mL) | | | | |
|---|---|---|---|---|---|
| Time (h) | Mouse #4 | Mouse #5 | Mouse #6 | Mean | SD |
| 0.5 | 743 | 652 | 865 | 753 | 118 |
| 1 | 307 | 234 | 451 | 331 | 34.0 |
| 2 | 54.8 | 42.9 | 80 | 59.2 | 5.46 |
| 4 | 12.5 | 9.66 | 11.7 | 11.3 | 1.05 |

TABLE 8

PK Profile of Compound 67
PK Profile of Compound 67, IP 15 mg/kg, Balb/C Nude Mice

| | Calculated Concentration (ng/mL) | | | | |
|---|---|---|---|---|---|
| Time (h) | Mouse #7 | Mouse #8 | Mouse #9 | Mean | SD |
| 0.5 | 90.6 | 150 | 94.4 | 112 | 33 |
| 1 | 38.7 | 43.7 | 72.8 | 51.7 | 18.4 |
| 2 | 10.9 | 21.6 | 28.0 | 20.2 | 8.6 |
| 4 | 16.6 | 12.9 | 13.6 | 14.4 | 2.0 |

Example 3: Pharmacokinetic (PK) Studies Via Intravenous Infusion

Test compounds were dissolved either in 20% (w/w) sulfobutylether-β-cyclodextrin (SBECD) pH 3-7 aqueous solution, or 5% DMSO/(30-50%)PEG400/(65-45%) water. Test compound dosing solutions were administered via intravenous infusion to Sprague-Dawley male rat. Blood samples were collected at various time points with EDTA-$K_2$ as anti-coagulant on ice, and centrifuged to obtain plasma samples. The plasma samples were stored at −20° C. until analysis.

Into 50 μL of test compound plasma samples were added 5 μL DMSO then 200 μL of 25 ng/mL internal standard (ITSD) (Verapamil) in MeOH/acetonitrile (1:1, v/v). The mixture was vortexed for 1 minute and centrifuged at 4000 rpm for 15 minutes. Calibration standards were prepared by spiking known amount of test compounds into blank plasma samples. The supernatant solution was diluted 5 times with $H_2O$ (with 0.1% formic acid, 1:1, v/v), and this is the solution for LC-MS/MS analysis. The limit of quantification (LOQ) was 1 ng/mL.

Typical HPLC mobile phases were mobile phase A of water with 0.1% formic acid; and mobile phase B of acetonitrile (with 0.1% formic acid). The HPLC column was Kinetex C18 (30 mm×3.00 mm). Mass spectrometer was tuned for each compound in the Multiple reaction monitoring (MRM) scanning mode and in the electrospray ionization mode. The lower limit of quantification was 1-10 ng. A typical HPLC gradient table is described below:

TABLE 9

| Time (min) | Flow Rate (mL/min) | A (%) | B (%) |
|---|---|---|---|
| 0.40 | 0.7 | 80.0 | 20.0 |
| 1.50 | 0.7 | 5.00 | 95.0 |
| 2.20 | 0.7 | 5.00 | 95.0 |
| 2.21 | 0.7 | 80.0 | 20.0 |
| 3.00 | 0.7 | 80.0 | 20.0 |

A. PK profiles of Compound 24 and Compound 28 in Sprague-Dawley Rat via Intravenous Infusion The PK profiles of compound 24 and compound 28 are shown below. In this study, both compounds were formulated in 20% (w/w) sulfobutylether-β-cyclodextrin (SBECD) pH 4 aqueous solution at 1.0 mg/mL. The volume of injection via intravenous infusion route was adjusted for a dose of 2, 4 and 8 mg/kg. The concentration of test compounds in plasma were analyzed by LC-MS with the method described above. The limit of quantification was 1 ng/mL.

TABLE 9a

PK Profiles of Compound 24
PK Profiles of Compound 24, 1 hour-IV infusion, 2, 4, and 8 mg/kg, Sprague-Dawley Rat

| | IV infusion (1-hr) | | |
|---|---|---|---|
| | 2 mg/kg | 4 mg/kg | 8 mg/kg |
| | Plasma Concentration (ng/mL) | | |
| Time (hr) | Rat #1 | Rat #2 | Rat #3 |
| 1.0167 | 51.7 | 159 | 259 |
| 1.0833 | 14.1 | 36.4 | 97.5 |
| 1.25 | 4.95 | 13.8 | 34.0 |
| 1.5 | 2.18 | 5.07 | 17.3 |
| 2 | BLOQ | 2.62 | 6.52 |
| 3 | BLOQ | BLOQ | 2.92 |
| 5 | BLOQ | BLOQ | BLOQ |

BLOQ = Below limit of quantification (which was 1 ng/mL)

TABLE 9b

PK Profiles of Compound 28
PK Profiles of Compound 28, 1 hour-IV infusion, 2, 4, and 8 mg/kg, Sprague-Dawley Rat

| | IV infusion (1-hr) | | |
|---|---|---|---|
| | 2 mg/kg | 4 mg/kg | 8 mg/kg |
| | Plasma Concentration (ng/mL) | | |
| Time (h) | Rat #4 | Rat #5 | Rat #6 |
| 1.0167 | 32.7 | 57.8 | 233 |
| 1.0833 | 18.0 | 26.9 | 85.2 |

TABLE 9b-continued

PK Profiles of Compound 28
PK Profiles of Compound 28, 1 hour-IV infusion, 2, 4, and 8 mg/kg, Sprague-Dawley Rat

| | IV infusion (1-hr) | | |
|---|---|---|---|
| | 2 mg/kg | 4 mg/kg | 8 mg/kg |
| | Plasma Concentration (ng/mL) | | |
| Time (h) | Rat #4 | Rat #5 | Rat #6 |
| 1.25 | 11.0 | 26.6 | 42.7 |
| 1.5 | 6.80 | 19.8 | 28.7 |
| 2 | 5.54 | 15.7 | 17.6 |
| 3 | 3.86 | 9.99 | 12.7 |
| 5 | 1.88 | 4.00 | 6.92 |

B. PK profiles of Compounds 148, 149, 150, 156 and 169 in Balb/C Nude Mice via Intravenous Infusion The PK profiles of compounds 148, 149, 150, 156 and 169 are shown below. Compound 156 was formulated in 30% Kolliphor EL (Cremophor EL) in water and compounds 148, 149, 150 and 169 were formulated in 30% Kolliphore EL with 1% poloxamar 407 in water. All compounds were dosed at 5 mg/kg. Blood samples were collected at various time points and analyzed using the method described above.

TABLE 10a

PK profile of Compound 156
IV Plasma Concentration (ng/mL),
BID q12, post $2^{nd}$ dose

| Time (h) | 5 mg/kg |
|---|---|
| 0.0833 | 18500 |
| 0.25 | 4640 |
| 0.5 | 984 |
| 1 | 302 |
| 2 | 105 |
| 4 | 45.9 |
| 8 | 24.4 |

TABLE 10b

PK profile of Compound 156

| $t_{1/2}$ (hr) | $C_0$ (ng/mL) | $AUC_{last}$ (hr * ng/mL) | $AUC_{Inf}$ (hr * ng/mL) | $V_z$ (L/kg) | $V_{ss}$ (L/kg) | CL (mL/min/kg) | $MRT_{Inf}$ (hr) |
|---|---|---|---|---|---|---|---|
| 3.00 | 38200 | 5809 | 5918 | 3.72 | 0.480 | 14.5 | 0.553 |

TABLE 11a

PK profile of Compound 148

| $t_{1/2}$ (h) | $C_0$ (ng/mL) | $C_{max}$ (ng/mL) | $AUC_{0-t}$ (ng · h/mL) | $AUC_{0-\infty}$ (ng · h/mL) | CL (mL/min/kg) | $V_d$ (L/kg) | $V_{ss}$ (L/kg) |
|---|---|---|---|---|---|---|---|
| 5.76 | 40558 | 33024 | 17225 | 17411 | 4.79 | 2.39 | 0.47 |

Time points considered for $t_{1/2}$ calculation: 4-24 h

TABLE 11b

| PK profile of Compound 149 | | | | | | | |
|---|---|---|---|---|---|---|---|
| $t_{1/2}$ (h) | $C_0$ (ng/mL) | $C_{max}$ (ng/mL) | $AUC_{0-t}$ (ng · h/mL) | $AUC_{0-\infty}$ (ng · h/mL) | CL (mL/min/kg) | $V_d$ (L/kg) | $V_{ss}$ (L/kg) |
| 2.12 | 29386 | 21978 | 6536 | 6549 | 13.0 | 2.34 | 0.53 |

Time points considered for $t_{1/2}$ calculation: 2-8 h

TABLE 11c

| PK profile of Compound 150 | | | | | | | |
|---|---|---|---|---|---|---|---|
| $t_{1/2}$ (h) | $C_0$ (ng/mL) | $C_{max}$ (ng/mL) | $AUC_{0-t}$ (ng · h/mL) | $AUC_{0-\infty}$ (ng · h/mL) | CL (mL/min/kg) | $V_d$ (L/kg) | $V_{ss}$ (L/kg) |
| 0.33 | 3401 | 2264 | 735 | 740 | 113 | 3.25 | 1.64 |

Time points considered for $t_{1/2}$ calculation: 0.25-2 h

TABLE 11d

| PK profile of Compound 169 | | | | | | | |
|---|---|---|---|---|---|---|---|
| $t_{1/2}$ (h) | $C_0$ (ng/mL) | $C_{max}$ (ng/mL) | $AUC_{0-t}$ (ng · h/mL) | $AUC_{0-\infty}$ (ng · h/mL) | CL (mL/min/kg) | $V_d$ (L/kg) | $V_{ss}$ (L/kg) |
| 0.25 | 5384 | 2218 | 760 | 762 | 109 | 2.39 | 0.98 |

Time points considered for $t_{1/2}$ calculation: 0.25-2 h (1 h excluded)

Example 4: Inducer Compound Effect on Growth of Cancer and Normal Epithelial Cells Cell viability assay was performed to assess the potency of the compounds in human cancer cell lines KP4 (pancreatic ductal adenocarcinoma), MiaPaCa-2 (pancreatic carcinoma), AsPC-1 (pancreatic adenocarcinoma, ascites), 143B (osteosarcoma), and SJSA-1 (osteosarcoma). Selected compounds were also assayed in a human breast epithelial cell line MCF-10A, a nontumorigenic cell line as a control to assess differential activity. Cells at a density of 500-5,000 cells/well were seeded in 96-well plates and incubated at 37° C. overnight. A series of 9 different concentrations of compound stocks (500×) were created by 3-fold serial dilution in DMSO. These compounds were further diluted in culture media and then added to cells so that the final DMSO concentration was equal to 0.25% or less. After 96 hours of incubation, 50 μL of CellTiter Glo reagent (Promega) was added to each well and luminescence was measured after 10 minutes using EnVision (PerkinElmer). Compounds titrated from top concentration of up to 30 μM. The select compounds were tested initially from 30 μM as the top concentration in duplicates (range of 4.6 nM-30 μM). The top concentration was then adjusted to higher (from up to 1000 μM) or lower for compounds that showed potency out of the initial range. Luminescence from cells treated with DMSO alone was set as Max and % of inhibition was calculated as follows: Inhibition %=(Max-Sample value)/Max*100. Data was analyzed using XL-fit software (ID Business Solutions Ltd.). $IC_{50}$, relative $IC_{50}$, or % of top inhibition was calculated.

A group of selected analogs were further profiled in cell viability assays described above in multiple additional cancer cell lines, including lung cancer, melanoma, hepatocarcinoma, pancreatic cancer, leukemia, lymphoma, ovarian cancer, breast cancer, colon cancer, and sarcoma cell lines. Initial cell seeding numbers were adjusted for each cell line. Typically, 500-5000 cells/well for adherent cells and 5000-10000/well for suspension cells were seeded in 96-well plates.

The results of the assay in lung cancer cell lines H1299 and H2228 are given in Table 12.

TABLE 12

| | $IC_{50}$ μM | |
|---|---|---|
| Compound ID | H1299 | H2228 |
| K601 | 0.035 | 0.075 |
| 24 | 0.003 | 0.018 |
| 28 | 0.005 | 0.019 |
| 29 | 0.005 | 0.032 |
| 83 | 0.041 | 0.112 |
| 92 | 0.013 | 0.050 |
| 94 | 0.005 | 0.019 |
| 98 | 0.006 | 0.017 |
| 101 | 0.038 | 0.163 |
| 102 | 0.003 | 0.009 |
| 103 | 0.021 | 0.034 |
| 106 | 0.007 | 0.055 |
| 109 | 0.032 | 0.057 |
| 112 | 0.038 | 0.066 |
| 113 | 0.079 | 0.145 |
| 110 | 0.030 | 0.051 |

The results of the assay in the melanoma cell line MDA-MB-435S are given in Table 13.

TABLE 13

| Compound ID | $IC_{50}$ μM |
|---|---|
| K601 | 0.037 |
| 24 | 0.004 |
| 28 | 0.004 |
| 29 | 0.006 |
| 83 | 0.047 |
| 92 | 0.017 |

TABLE 13-continued

| Compound ID | $IC_{50}$ μM |
|---|---|
| 94 | 0.009 |
| 98 | 0.007 |
| 101 | 0.036 |
| 102 | 0.004 |
| 103 | 0.038 |
| 106 | 0.017 |
| 109 | 0.017 |
| 112 | 0.030 |
| 113 | 0.048 |
| 110 | 0.014 |

The results of the assay in the hepatocellular carcinoma Huh7 are given in Table 14

TABLE 14

| Compound ID | $IC_{50}$ μM |
|---|---|
| K601 | 0.242 |
| 24 | 0.022 |
| 28 | 0.026 |
| 29 | 0.013 |
| 83 | 0.120 |
| 92 | 0.073 |
| 94 | 0.026 |
| 98 | 0.027 |
| 101 | 0.072 |
| 102 | 0.011 |
| 103 | 0.084 |
| 106 | 0.028 |
| 109 | 0.043 |
| 112 | 0.081 |
| 113 | 0.157 |
| 110 | 0.035 |

The results of the assay in the pancreatic cell lines are given in Table 15a for PANC1, Table 15b for MiaPaCa-2, and Table 15c for AsPC-1.

TABLE 15a

| PANC1 | |
|---|---|
| Compound ID | $IC_{50}$ μM |
| K601 | 0.116 |
| 24 | 0.019 |
| 28 | 0.038 |
| 29 | 0.027 |
| 83 | >1 |
| 92 | 0.078 |
| 94 | 0.047 |
| 98 | 0.043 |
| 101 | 0.169 |
| 102 | 0.030 |
| 103 | 0.161 |
| 106 | 0.055 |
| 109 | 0.069 |
| 112 | 0.081 |
| 113 | 0.214 |
| 110 | 0.072 |

TABLE 15b

| MiaPaCa-2 | |
|---|---|
| Compound ID | $IC_{50}$ μM |
| K601 | 0.015 |
| 1 | 0.005 |
| 2 | 0.060 |
| 6 | 0.055 |

TABLE 15b-continued

| MiaPaCa-2 | |
|---|---|
| Compound ID | $IC_{50}$ μM |
| 9 | 0.012 |
| 11 | 0.091 |
| 7 | 0.119 |
| 12 | 0.069 |
| 13 | 0.131 |
| 23 | 0.036 |
| 23a | 3.152 |
| 265 | 0.246 |
| 15 | 1.322 |
| 16 | 0.024 |
| 19 | 0.063 |
| 20 | 0.037 |
| 21a | 1.015 |
| 24 | 0.002 |
| 25 | 0.858 |
| 263 | 5.568 |
| 10 | 1.591 |
| 21 | 0.064 |
| 8 | 0.077 |
| 22 | 0.039 |
| 14 | 0.144 |
| 26 | 0.052 |
| 28 | 0.002 |
| 35 | 0.117 |
| 27 | 0.466 |
| 27a | 3.000 |
| 37 | 0.279 |
| 29 | 0.033 |
| 38 | 3.634 |
| 41 | 0.040 |
| 54 | 0.217 |
| 56 | 0.759 |
| 52 | 0.243 |
| 59 | 0.591 |
| 66 | 0.159 |
| 66a | 1.157 |
| 67 | 0.805 |
| 67a | 1.360 |

TABLE 15c

| AsPC-1 | |
|---|---|
| Compound ID | $IC_{50}$ μM |
| K601 | 0.105 |
| 75 | 0.028 |
| CA | 0.023 |
| BZ | 0.030 |
| 74 | 0.107 |
| 77 | 0.074 |
| CC | 0.118 |
| 87 | 0.022 |
| 88 | 0.030 |
| 82 | 0.061 |
| 81 | 0.073 |
| 76 | 0.035 |
| 85 | 0.029 |
| 86 | 0.021 |
| 90 | 0.132 |
| 24 | 0.019 |
| 28 | 0.019 |
| 29 | 0.023 |

The results of the assay in the leukemia cell lines are given in Table 16a for MV-4-1 and Table 16b for HL-60 and Kasumi-1.

TABLE 16a

| MV-4-1 | |
|---|---|
| Compound ID | $IC_{50}$ μM |
| K601 | 0.258 |
| 24 | 0.021 |
| 28 | 0.032 |
| 29 | 0.048 |
| 83 | 0.524 |
| 92 | 0.129 |
| 94 | 0.083 |
| 98 | 0.065 |
| 101 | 0.174 |
| 102 | 0.023 |
| 103 | 0.230 |
| 106 | 0.170 |
| 109 | 0.168 |
| 112 | 0.270 |
| 113 | 0.532 |
| 110 | 0.164 |

TABLE 16b

| HL-60 and Kasumi-1 | | |
|---|---|---|
| | $IC_{50}$ μM | |
| Compound ID | HL-60 | Kasumi-1 |
| K601 | 0.104 | 0.203 |
| 24 | 0.016 | 0.088 |
| 28 | 0.009 | 0.034 |
| 29 | 0.031 | 0.028 |
| 114 | 0.120 | 0.145 |

The results of the assay in the lymphoma cell lines REC-1 and Raji are given in Table 17.

TABLE 17

| | $IC_{50}$ μM | |
|---|---|---|
| Compound ID | REC-1 | Raji |
| K601 | 0.227 | 0.092 |
| 24 | 0.033 | 0.009 |
| 28 | 0.039 | 0.014 |
| 29 | 0.027 | 0.009 |
| 83 | 0.516 | 0.151 |
| 92 | 0.070 | 0.028 |
| 94 | 0.029 | 0.009 |
| 98 | 0.061 | 0.020 |
| 101 | 0.191 | 0.075 |
| 102 | 0.031 | 0.010 |
| 103 | 0.186 | 0.074 |
| 106 | 0.156 | 0.031 |
| 109 | 0.106 | 0.038 |
| 112 | 0.140 | 0.046 |
| 113 | 0.222 | 0.081 |
| 110 | 0.096 | 0.033 |

The results of the assay in the ovarian cancer cell line SK-OV-3 are given in Table 18.

TABLE 18

| Compound ID | $IC_{50}$ μM |
|---|---|
| K601 | 0.142 |
| 24 | 0.017 |
| 28 | 0.021 |
| 29 | 0.012 |
| 83 | 0.230 |
| 92 | 0.047 |

TABLE 18-continued

| Compound ID | $IC_{50}$ μM |
|---|---|
| 94 | 0.018 |
| 98 | 0.030 |
| 101 | 0.114 |
| 102 | 0.013 |
| 103 | 0.113 |
| 106 | 0.087 |
| 109 | 0.063 |
| 112 | 0.102 |
| 113 | 0.146 |
| 110 | 0.053 |

The results of the assay in the breast cancer cell line HCC1954 are given in Table 19.

TABLE 19

| Compound ID | $IC_{50}$ μM |
|---|---|
| K601 | 0.180 |
| 24 | 0.039 |
| 28 | 0.040 |
| 29 | 0.038 |
| 83 | 0.333 |
| 92 | 0.096 |
| 94 | 0.068 |
| 98 | 0.063 |
| 101 | 0.613 |
| 102 | 0.038 |
| 103 | 0.137 |
| 106 | 0.120 |
| 109 | 0.108 |
| 112 | 0.101 |
| 113 | 0.200 |
| 110 | 0.101 |

The results of the assay in the colon cancer cell lines HT29 and SW480 are given in Table 20.

TABLE 20

| | $IC_{50}$ μM | |
|---|---|---|
| Compound ID | HT29 | SW480 |
| K601 | 0.832 | 0.619 |
| 24 | 0.087 | 0.167 |
| 28 | 0.071 | 0.379 |
| 29 | 0.049 | 2.0 |
| 83 | 0.338 | 10.5 |
| 92 | 0.228 | 0.533 |
| 94 | 0.110 | ND |
| 98 | 0.094 | ND |
| 101 | 0.403 | ND |
| 102 | 0.048 | ND |
| 103 | 0.448 | ND |
| 106 | 0.189 | ND |
| 109 | 0.174 | ND |
| 112 | 0.198 | ND |
| 113 | 0.494 | ND |
| 110 | 0.112 | ND |

ND: not determined.

The results of the assay in sarcoma cell lines are given in Table 21a for HT-1080 luc2 (fibrosarcoma expressing a luciferase gene), Table 21b for 143B (osteosarcoma), and Table 21c for SJSA-1 (osteosarcoma).

TABLE 21a

| HT-1080 luc2 | |
|---|---|
| Compound ID | $IC_{50}$ μM |
| K601 | 0.027 |
| 24 | 0.015 |
| 28 | 0.006 |
| 29 | 0.005 |
| 83 | 0.038 |
| 92 | 0.012 |
| 94 | 0.008 |
| 98 | 0.009 |
| 101 | 0.039 |
| 102 | 0.004 |
| 103 | 0.028 |
| 106 | 0.011 |
| 109 | 0.019 |
| 112 | 0.024 |
| 113 | 0.069 |
| 110 | 0.017 |

TABLE 21b

| 143B | |
|---|---|
| Compound ID | $IC_{50}$ μM |
| K601 | 0.032 |
| 1 | 0.009 |
| 2 | 0.153 |
| 6 | 0.087 |
| 9 | 0.032 |
| 11 | 0.135 |
| 7 | 0.273 |
| 12 | 0.081 |
| 13 | 0.109 |
| 23 | 0.034 |
| 19 | 0.101 |
| 20 | 0.075 |
| 24 | 0.004 |
| 16 | 0.104 |
| 10 | 4.411 |
| 21 | 0.090 |
| 8 | 0.143 |
| 22 | 0.074 |

TABLE 21c

| SJSA-1 | |
|---|---|
| Compound ID | $IC_{50}$ μM |
| K601 | 0.067 |
| 1 | 0.018 |
| 2 | 0.236 |
| 6 | 0.146 |
| 9 | 0.069 |
| 11 | 0.327 |
| 7 | 0.687 |
| 12 | 0.149 |
| 13 | 0.157 |
| 23 | 0.090 |
| 19 | 0.215 |
| 20 | 0.149 |
| 24 | 0.013 |
| 16 | 0.200 |
| 10 | 15.3 |
| 21 | 0.170 |
| 8 | 0.250 |
| 22 | 0.202 |
| 26 | 0.339 |
| 28 | 0.019 |
| 35 | 0.313 |
| 27 | 1.41 |
| 37 | 0.630 |

TABLE 21c-continued

| SJSA-1 | |
|---|---|
| Compound ID | $IC_{50}$ μM |
| 29 | 0.014 |
| 114 | 0.115 |
| 118 | 0.028 |

The results of the assay in the non-tumorigenic breast epithelial cell line MCF-10A are given in Table 22. Paclitaxel was used as the positive control for cytotoxicity.

TABLE 22

| Compound ID | $IC_{50}$ μM |
|---|---|
| paclitaxel | 0.001 |
| K601 | 2.95 |
| 1 | 0.85 |
| 6 | 3.76 |
| 9 | 2.27 |
| 12 | 1.42 |
| 13 | 3.05 |
| 23 | 2.39 |
| 19 | 0.43 |
| 20 | 0.82 |
| 24 | 0.41 |
| 16 | 1.95 |
| 10 | >30 |
| 21 | 1.58 |
| 22 | 3.30 |
| 26 | 3.97 |
| 28 | 0.36 |
| 35 | 4.15 |
| 27 | 9.41 |
| 29 | 0.41 |
| 37 | 5.46 |
| 38 | 19.59 |
| 41 | 0.04 |
| 54 | 0.56 |
| 56 | 1.51 |
| 52 | 0.18 |
| 59 | 8.78 |
| 75 | 1.29 |
| CA | 0.47 |
| BZ | 0.59 |
| 74 | 6.56 |
| 77 | 0.89 |
| CC | 1.68 |
| 87 | 0.46 |
| 88 | 0.46 |
| 82 | 3.74 |
| 81 | 2.66 |
| 76 | 1.11 |
| 85 | 0.50 |
| 86 | 0.33 |
| 90 | 1.48 |
| 84 | 0.48 |
| 89 | 0.42 |
| 92 | 1.14 |
| 94 | 0.46 |
| 83 | 3.79 |
| 109 | 1.14 |
| 101 | 1.07 |
| 98 | 0.92 |
| 102 | 0.22 |
| 103 | 1.37 |

In the non-tumorigenic breast epithelial cell line MCF-10A, the majority of compounds tested, except for compound 41 which showed an $IC_{50}$>0.1 μM (0.040 μM), showed an $IC_{50}$>1 μM. The results indicate that the compounds do not inhibit non-tumor cells efficiently, thus providing therapeutic window selectively targeting tumors. The differential sensitivity (defined as $IC_{50}$ of MCF-10A/$IC_{50}$ of a sensitive tumor cell line) often exceeds 100 fold and up to over 1000 fold. Examples of compounds demonstrating >100 fold differential sensitivity is shown in Table 23.

TABLE 23

| Compound ID |
|---|
| K601 |
| 1 |
| 6 |
| 9 |
| 12 |
| 13 |
| 23 |
| 24 |
| 16 |
| 21 |
| 22 |
| 26 |
| 28 |
| 35 |
| 37 |
| 29 |

Example 5: Inducer Compound Effect on Growth of A549 and KP4 Cells

Cell viability assay was performed to assess the potency of the compounds in cancer cell line KP4 (pancreatic ductal adenocarcinoma). Cells at a density of 1,000-10,000 cells/well were seeded in 96-well plates and incubated at 37° C. overnight. A series of 9 different concentrations of compound stocks (500×) were created by 3-fold serial dilution in DMSO. These compounds were further diluted in culture media and then added to cells so that the final DMSO concentration was equal to 0.25% or less. After 96 hours of incubation, 50 μL of CellTiter Glo reagent (Promega) was added to each well and luminescence was measured after 10 minutes using EnVision (PerkinElmer). All compounds were tested initially from 30 μM as the top concentration in duplicates (range of 4.6 nM-30 μM). The top concentration was then adjusted to higher (from up to 1000 μM) or lower (from as low as 0.1 μM) for compounds that showed potency out of the initial range. Luminescence from cells treated with DMSO alone was set as Max and % of inhibition was calculated as follows: Inhibition %=(Max-Sample value)/Max*100. Data was analyzed using XL-fit software (ID Business Solutions Ltd.). $IC_{50}$, relative $IC_{50}$, or % of top inhibition was calculated.

The results of the assay on stability in blood and $IC_{50}$ values for pancreatic cancer cell line KP4 are given below in Table 24. "A" indicates an $IC_{50}$<0.01 μM or $IC_{50}$ ratio (compound to K601 or RSL-3)<5; "B" indicates an $IC_{50}$ of >0.01 μM and <0.1 μM, or $IC_{50}$ ratio (compound to K601 or RSL-3)>5 and <50; "C" indicates an $IC_{50}$>0.1 μM and <0.5 μM, or $IC_{50}$ ratio (compound to K601 or RSL-3)>50 and <250; "D" indicates an $IC_{50}$>0.5 μM and <1 μM, or $IC_{50}$ ratio (compound to K601 or RSL-3)>250 and <500; "E" indicates $IC_{50}$ value of >1 μM, or $IC_{50}$ ratio (compound to K601 or RSL-3)>500. For compounds 1-122, except for the compounds listed below, the $IC_{50}$ for A549 is greater than 1 μM. For compounds 41, 52, 54, 61a, 93, and 120, $IC_{50}$ for A549 is 0027-0.04 μM, 0.28-0.36 μM, 0.79 PM, 0.21 μM, 0.25 μM, and 0.81 μM, respectively. Additional data for select compounds tested is shown in Table 25.

TABLE 24

| | | Whole Blood Stability % Remaining at 37° C. | | | $IC_{50}$ |
|---|---|---|---|---|---|
| Structure | Compound No. | Time (min) | Mouse | Human | μM KP4 |
| 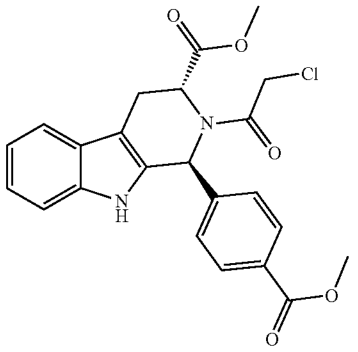 [SMILES: COC(=O)c1ccc([C@H]2c3[nH]c4ccccc4c3C[C@H](C(=O)OC)N2C(=O)CCl)cc1] | K601 (RSL3) | 60<br>30<br>0 | 0.2<br>0.2<br>100.0 | 42.5<br>60.8<br>100.0 | A |
| 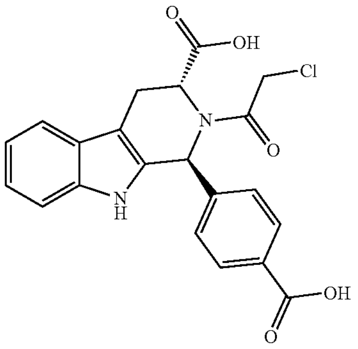 [SMILES: O=C(O)c1ccc([C@H]2c3[nH]c4ccccc4c3C[C@H](C(=O)O)N2C(=O)CCl)cc1] | 5 | 60<br>30<br>0 | 67.9<br>86.3<br>100.0 | 82.0<br>106.3<br>100.0 | E |

TABLE 24-continued
| Structure | Compound No. | Whole Blood Stability % Remaining at 37° C. Time (min) | Mouse | Human | $IC_{50}$ μM KP4 |
|---|---|---|---|---|---|
| 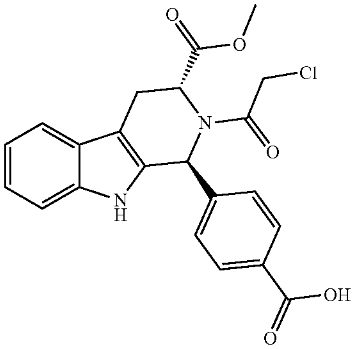 [SMILES: COC(=O)[C@H]1Cc2c([nH]c3ccccc23)[C@H](c2ccc(C(=O)O)cc2)N1C(=O)CCl] | 4 | 60<br>30<br>0 | 63.9<br>76.6<br>100.0 | 57.9<br>59.3<br>100.0 | E |
| 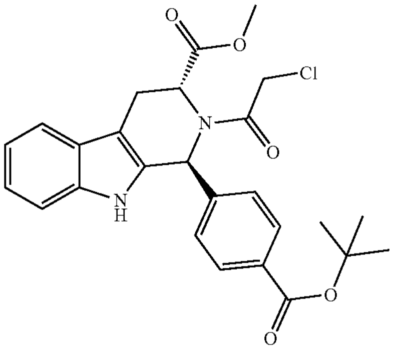 [SMILES: COC(=O)[C@H]1Cc2c([nH]c3ccccc23)[C@H](c2ccc(C(=O)OC(C)(C)C)cc2)N1C(=O)CCl] | 1 | 60<br>30<br>0 | 46.6<br>59.6<br>100.0 | 43.0<br>60.5<br>100.0 | A |
| 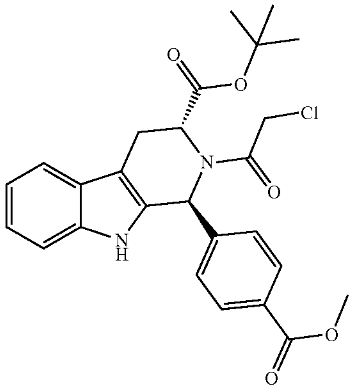 [SMILES: COC(=O)c1ccc([C@H]2c3[nH]c4ccccc4c3C[C@H](C(=O)OC(C)(C)C)N2C(=O)CCl)cc1] | 2 | 60<br>30<br>0 | 0.1<br>0.1<br>100.0 | 39.4<br>58.5<br>100.0 | B |
| 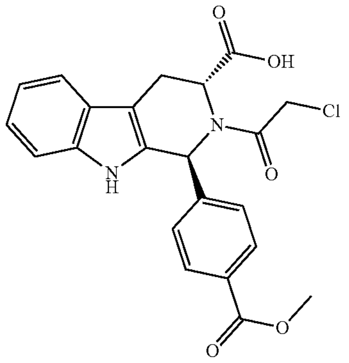 [SMILES: COC(=O)c1ccc([C@H]2c3[nH]c4ccccc4c3C[C@H](C(=O)O)N2C(=O)CCl)cc1] | 3 | 60<br>30<br>0 | 23.6<br>51.3<br>100 | 29.4<br>43.0<br>100 | E |

TABLE 24-continued
| Structure | Compound No. | Whole Blood Stability % Remaining at 37° C. Time (min) | Mouse | Human | $IC_{50}$ μM KP4 |
|---|---|---|---|---|---|
| 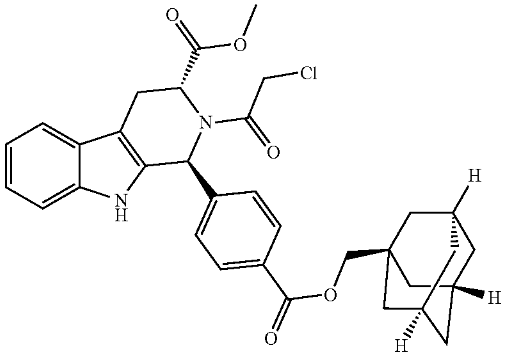 [SMILES: COC(=O)[C@H]1Cc2c([nH]c3ccccc23)[C@H](c2ccc(C(=O)OC[C@]34C[C@H]5C[C@H](C[C@H](C5)C3)C4)cc2)N1C(=O)CCl] | 6 | 60<br>30<br>0 | 4.7<br>12.4<br>100.0 | 33.0<br>54.8<br>100.0 | B |
| 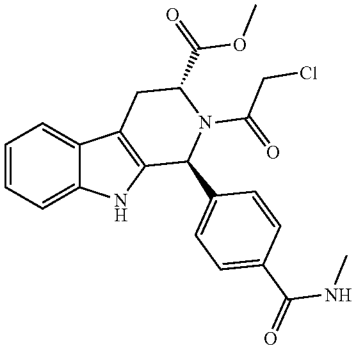 [SMILES: CNC(=O)c1ccc([C@H]2c3[nH]c4ccccc4c3C[C@H](C(=O)OC)N2C(=O)CCl)cc1] | 7 | 60<br>30<br>0 | 48.6<br>68.2<br>100.0 | 44.5<br>60.1<br>100.0 | B |
| 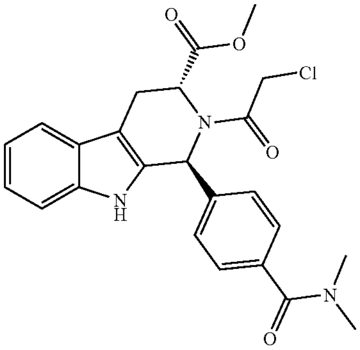 [SMILES: COC(=O)[C@H]1Cc2c([nH]c3ccccc23)[C@H](c2ccc(C(=O)N(C)C)cc2)N1C(=O)CCl] | 8 | 60<br>30<br>0 | 30.5<br>53.0<br>100.0 | 26.5<br>52.0<br>100.0 | A |
| 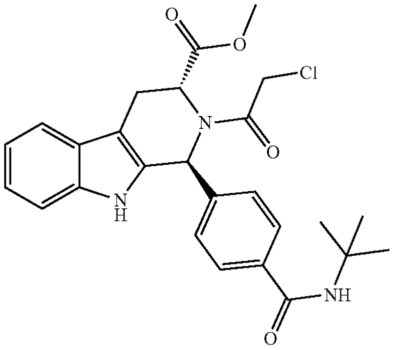 [SMILES: COC(=O)[C@H]1Cc2c([nH]c3ccccc23)[C@H](c2ccc(C(=O)NC(C)(C)C)cc2)N1C(=O)CCl] | 9 | 60<br>30<br>0 | 40.6<br>61.9<br>100.0 | 47.0<br>53.8<br>100.0 | A |

TABLE 24-continued
| Structure | Compound No. | Whole Blood Stability % Remaining at 37° C. Time (min) | Mouse | Human | $IC_{50}$ μM KP4 |
|---|---|---|---|---|---|
| 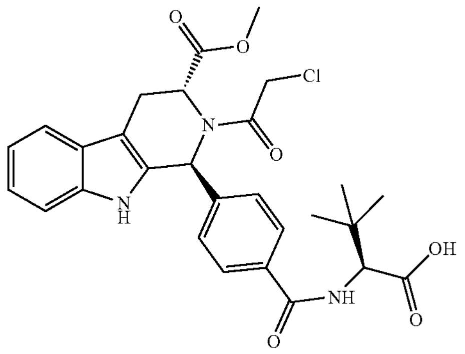 [SMILES: COC(=O)[C@H]1Cc2c([nH]c3ccccc23)[C@H](c2ccc(C(=O)N[C@H](C(=O)O)C(C)(C)C)cc2)N1C(=O)CCl] | 10 | 60<br>30<br>0 | 65.0<br>82.2<br>100.0 | 54.3<br>84.0<br>100.0 | D |
| 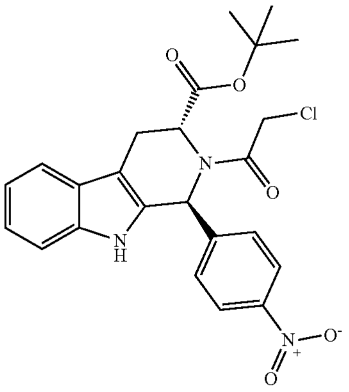 | 11 | 60<br>30<br>0 | 38.6<br>56.9<br>100.0 | 59.9<br>67.1<br>100.0 | B |
| 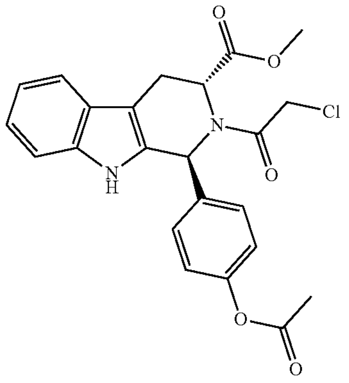 [SMILES: COC(=O)[C@H]1Cc2c([nH]c3ccccc23)[C@H](c2ccc(OC(C)=O)cc2)N1C(=O)CCl] | 12 | 60<br>30<br>67.1 | 0.0<br>0.0<br>100.0 | 0.1<br>0.0<br>100.0 | B |
| 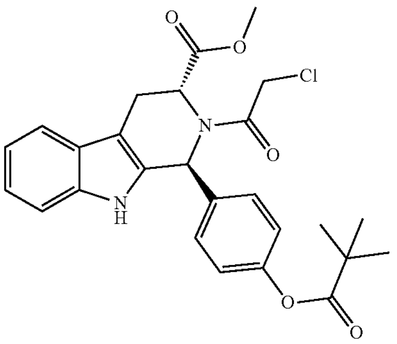 [SMILES: COC(=O)[C@H]1Cc2c([nH]c3ccccc23)[C@H](c2ccc(OC(=O)C(C)(C)C)cc2)N1C(=O)CCl] | 13 | 60<br>30<br>0 | 0.0<br>0.0<br>100.0 | 29.2<br>34.9<br>100.0 | C |

TABLE 24-continued
| Structure | Compound No. | Whole Blood Stability % Remaining at 37° C. Time (min) | Mouse | Human | $IC_{50}$ μM KP4 |
|---|---|---|---|---|---|
| 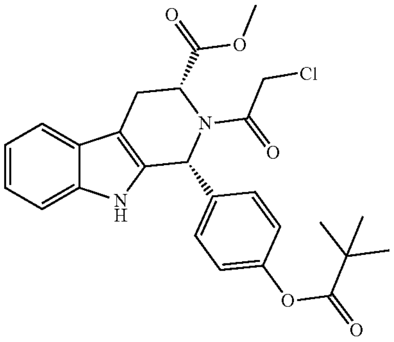 [SMILES: COC(=O)[C@H]1Cc2c([nH]c3ccccc23)[C@@H](c2ccc(OC(=O)C(C)(C)C)cc2)N1C(=O)CCl] | 13a | 60<br>30<br>0 | 0.0<br>0.0<br>100.0 | 59.9<br>56.6<br>100.0 | D |
| 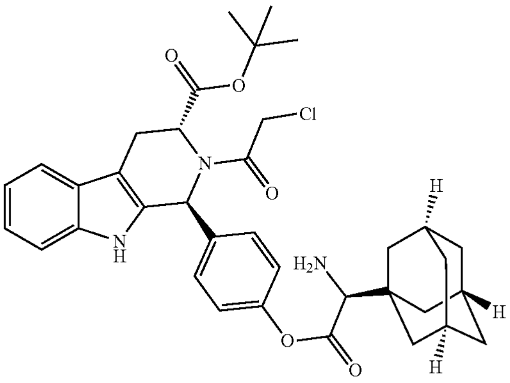 [SMILES: CC(C)(C)OC(=O)[C@H]1Cc2c([nH]c3ccccc23)[C@H](c2ccc(OC(=O)[C@@H](N)C34C[C@H]5C[C@@H](C3)C[C@@H](C4)C5)cc2)N1C(=O)CCl] | 14 | 60<br>30<br>0 | 0.7<br>2.8<br>100.0 | 0.0<br>0.0<br>100.0 | B |
| 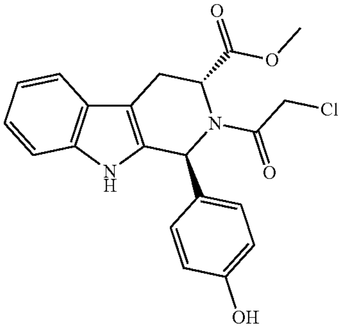 [SMILES: COC(=O)[C@H]1Cc2c([nH]c3ccccc23)[C@H](c2ccc(O)cc2)N1C(=O)CCl] | 265 | 60<br>30<br>0 | 61.6<br>75.5<br>100.0 | 45.2<br>61.6<br>100.0 | C |
| 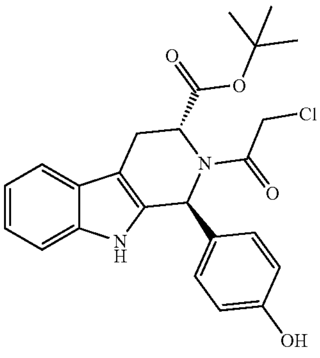 [SMILES: CC(C)(C)OC(=O)[C@H]1Cc2c([nH]c3ccccc23)[C@H](c2ccc(O)cc2)N1C(=O)CCl] | 294 | N/A | N/A | N/A | N/A |

TABLE 24-continued
| Structure | Compound No. | Whole Blood Stability % Remaining at 37° C. Time (min) | Mouse | Human | $IC_{50}$ μM KP4 |
|---|---|---|---|---|---|
| 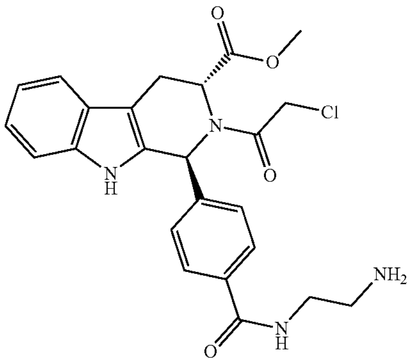 [SMILES: COC(=O)[C@H]1Cc2c([nH]c3ccccc23)[C@H](c2ccc(C(=O)NCCN)cc2)N1C(=O)CCl] | 15 | 60<br>30<br>0 | 50.2<br>83.0<br>100.0 | 66.8<br>72.7<br>100.0 | C |
| 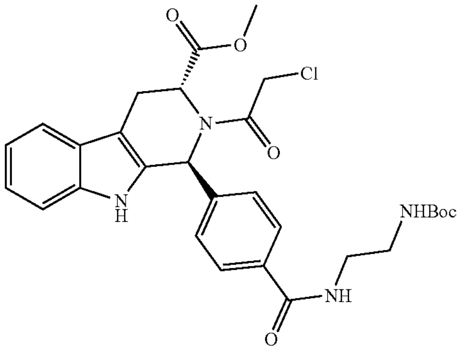 [SMILES: COC(=O)[C@H]1Cc2c([nH]c3ccccc23)[C@H](c2ccc(C(=O)NCCNC(=O)OC(C)(C)C)cc2)N1C(=O)CCl] | 16 | 60<br>30<br>0 | 63.3<br>84.1<br>100.0 | 36.9<br>54.3<br>100.0 | A |
| 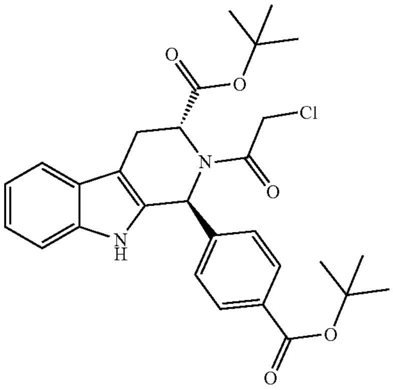 [SMILES: CC(C)(C)OC(=O)c1ccc([C@H]2c3[nH]c4ccccc4c3C[C@H](C(=O)OC(C)(C)C)N2C(=O)CCl)cc1] | 19 | 60<br>30<br>0 | 21.2<br>44.5<br>100.0 | 35.6<br>44.4<br>100.0 | A |
| 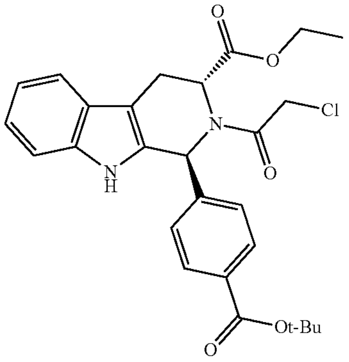 [SMILES: CCOC(=O)[C@H]1Cc2c([nH]c3ccccc23)[C@H](c2ccc(C(=O)OC(C)(C)C)cc2)N1C(=O)CCl] | 20 | 60<br>30<br>0 | 19.1<br>39.9<br>100.0 | 41.6<br>50.7<br>100.0 | A |

TABLE 24-continued
| Structure | Compound No. | Whole Blood Stability % Remaining at 37° C. Time (min) | Mouse | Human | $IC_{50}$ μM KP4 |
|---|---|---|---|---|---|
| 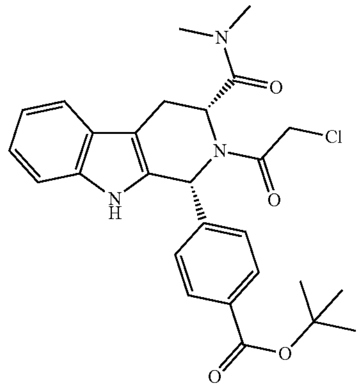 [SMILES: CN(C)C(=O)[C@H]1Cc2c([nH]c3ccccc23)[C@@H](c2ccc(C(=O)OC(C)(C)C)cc2)N1C(=O)CCl] | 21a | N/A | N/A | N/A | C |
| 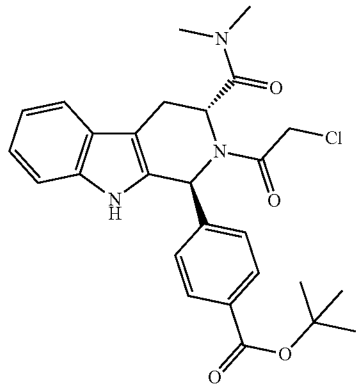 [SMILES: CN(C)C(=O)[C@H]1Cc2c([nH]c3ccccc23)[C@H](c2ccc(C(=O)OC(C)(C)C)cc2)N1C(=O)CCl] | 21 | 60<br>30<br>0 | 3.2<br>14.0<br>100.0 | 24.3<br>49.7<br>100.0 | B |
| 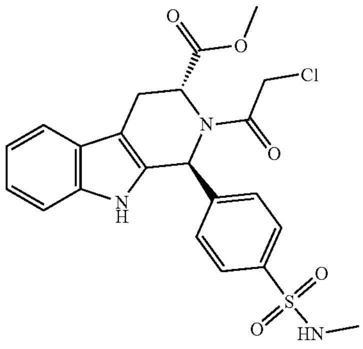 [SMILES: CNS(=O)(=O)c1ccc([C@H]2c3[nH]c4ccccc4c3C[C@H](C(=O)OC)N2C(=O)CCl)cc1] | 22 | 60<br>30<br>0 | 27.6<br>47.4<br>100.0 | 24.9<br>58.8<br>100.0 | A |
| 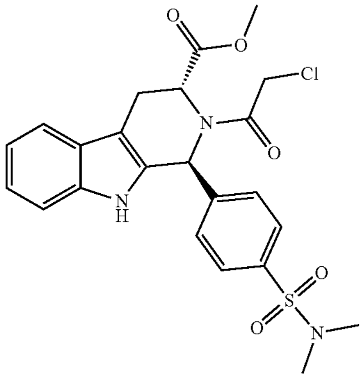 [SMILES: COC(=O)[C@H]1Cc2c([nH]c3ccccc23)[C@H](c2ccc(S(=O)(=O)N(C)C)cc2)N1C(=O)CCl] | 23 | 60<br>30<br>0 | 34.4<br>55.5<br>100.0 | 30.8<br>48.9<br>100.0 | A |

TABLE 24-continued
| Structure | Compound No. | Whole Blood Stability % Remaining at 37° C. Time (min) | Mouse | Human | $IC_{50}$ μM KP4 |
|---|---|---|---|---|---|
| 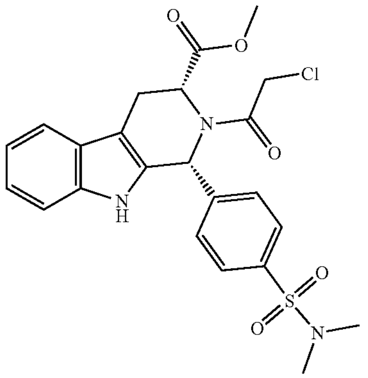 [SMILES: COC(=O)[C@H]1Cc2c([nH]c3ccccc23)[C@@H](c2ccc(S(=O)(=O)N(C)C)cc2)N1C(=O)CCl] | 23a | 60<br>30<br>0 | 78.6<br>83.8<br>100.0 | 72.7<br>83.2<br>100.0 | E |
| 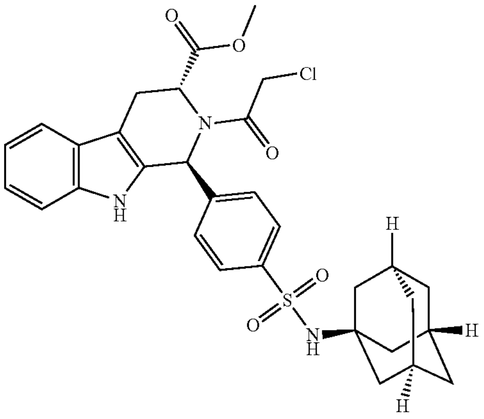 [SMILES: COC(=O)[C@H]1Cc2c([nH]c3ccccc23)[C@H](c2ccc(S(=O)(=O)N[C@]34C[C@H]5C[C@H](C[C@H](C5)C3)C4)cc2)N1C(=O)CCl] | 24 | 60<br>30<br>0 | 37.0<br>62.0<br>100.0 | 50.2<br>61.7<br>100.0 | A |
| 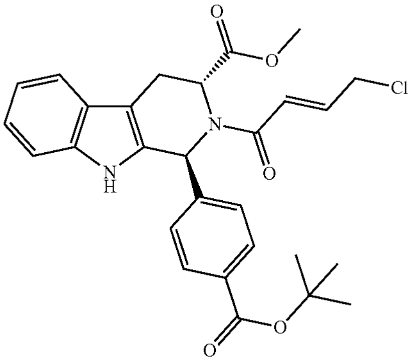 [SMILES: COC(=O)[C@H]1Cc2c([nH]c3ccccc23)[C@H](c2ccc(C(=O)OC(C)(C)C)cc2)N1C(=O)/C=C/CCl] | 25 | 60<br>30<br>0 | 24.4<br>46.2<br>100.0 | 51.9<br>55.0<br>100.0 | C |
| 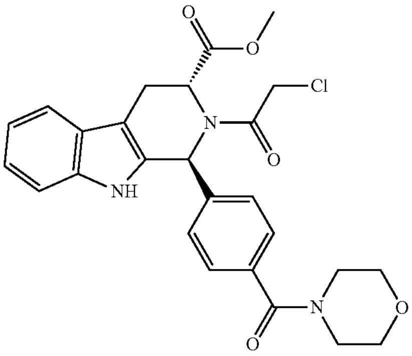 [SMILES: COC(=O)[C@H]1Cc2c([nH]c3ccccc23)[C@H](c2ccc(C(=O)N3CCOCC3)cc2)N1C(=O)CCl] | 26 | 60<br>30<br>0 | 55.7<br>67.7<br>100.0 | 22.9<br>47.1<br>100.0 | B |

TABLE 24-continued
| Structure | Compound No. | Whole Blood Stability % Remaining at 37° C. Time (min) | Mouse | Human | $IC_{50}$ μM KP4 |
|---|---|---|---|---|---|
| 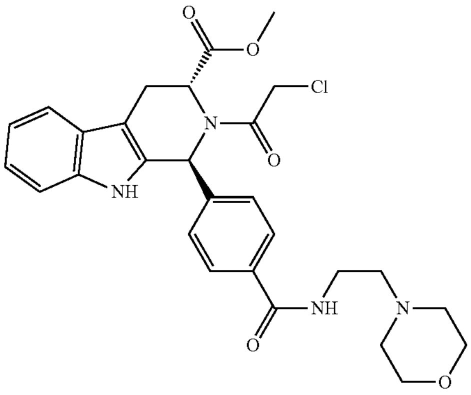 [SMILES: COC(=O)[C@H]1Cc2c([nH]c3ccccc23)[C@H](c2ccc(C(=O)NCCN3CCOCC3)cc2)N1C(=O)CCl] | 27 | 60<br>30<br>0 | 73.2<br>78.2<br>100.0 | 48.3<br>63.9<br>100.0 | B |
| 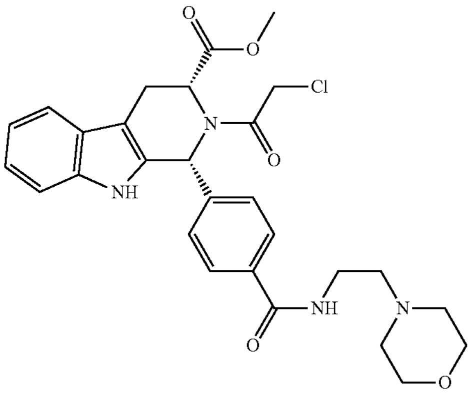 [SMILES: COC(=O)[C@H]1Cc2c([nH]c3ccccc23)[C@@H](c2ccc(C(=O)NCCN3CCOCC3)cc2)N1C(=O)CCl] | 27a | 60<br>30<br>0 | 81.1<br>92.5<br>100.0 | 40.9<br>54.1<br>100.0 | C |
| 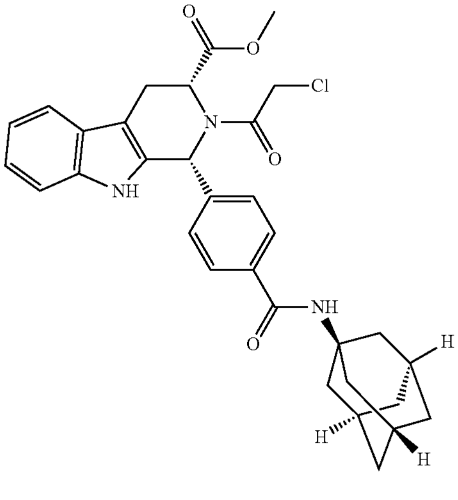 [SMILES: COC(=O)[C@H]1Cc2c([nH]c3ccccc23)[C@@H](c2ccc(C(=O)N[C@]34C[C@H]5C[C@H](C[C@H](C5)C3)C4)cc2)N1C(=O)CCl] | 28 | 60<br>30<br>0 | 68.9<br>78.3<br>100.0 | 51.6<br>73.4<br>100.0 | A |

TABLE 24-continued
| Structure | Compound No. | Whole Blood Stability % Remaining at 37° C. Time (min) | Mouse | Human | $IC_{50}$ μM KP4 |
|---|---|---|---|---|---|
| 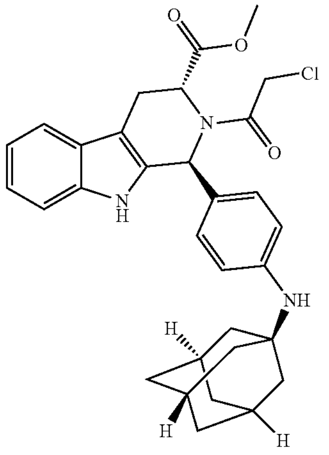 [SMILES: COC(=O)[C@H]1Cc2c([nH]c3ccccc23)[C@H](c2ccc(N[C@]34CC5C[C@H](C[C@H](C5)C3)C4)cc2)N1C(=O)CCl] | 29 | 60<br>30<br>0 | 51.1<br>61.9<br>100.0 | 49.2<br>67.3<br>100.0 | A |
| 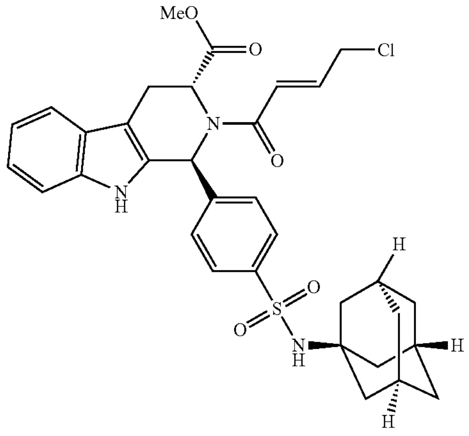 [SMILES: COC(=O)[C@H]1Cc2c([nH]c3ccccc23)[C@H](c2ccc(S(=O)(=O)N[C@]34C[C@H]5C[C@H](C[C@H](C5)C3)C4)cc2)N1C(=O)/C=C/CCl] | 30 | 60<br>30<br>0 | 75.9<br>85.3<br>100.0 | 38.1<br>62.1<br>100.0 | D |
| 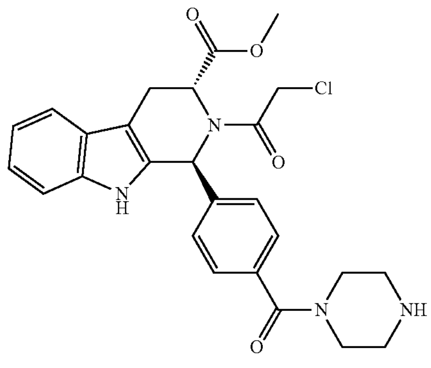 [SMILES: COC(=O)[C@H]1Cc2c([nH]c3ccccc23)[C@H](c2ccc(C(=O)N3CCNCC3)cc2)N1C(=O)CCl] | 31 | 60<br>30<br>0 | 75.5<br>90.0<br>100.0 | 32.6<br>49.4<br>100.0 | C |

TABLE 24-continued
| Structure | Compound No. | Whole Blood Stability % Remaining at 37° C. Time (min) | Mouse | Human | $IC_{50}$ μM KP4 |
|---|---|---|---|---|---|
| 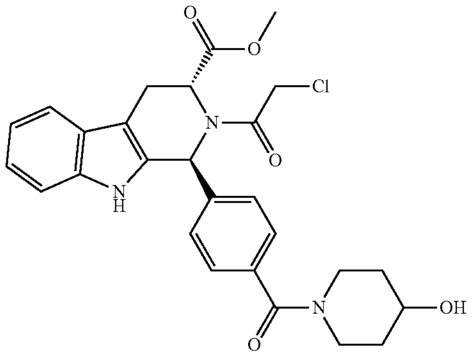 [SMILES: COC(=O)[C@H]1Cc2c([nH]c3ccccc23)[C@H](c2ccc(C(=O)N3CCC(O)CC3)cc2)N1C(=O)CCl] | 32 | 60<br>30<br>0 | 0.0<br>0.0<br>100.0 | 0.1<br>0.1<br>100.0 | E |
| 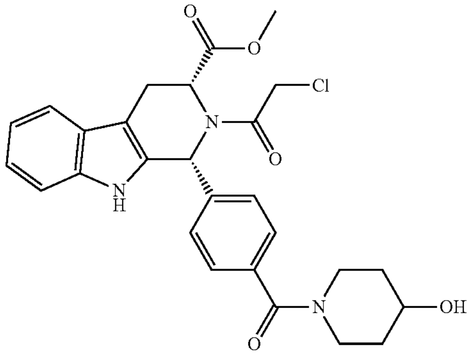 [SMILES: COC(=O)[C@H]1Cc2c([nH]c3ccccc23)[C@@H](c2ccc(C(=O)N3CCC(O)CC3)cc2)N1C(=O)CCl] | 32a | 60<br>30<br>0 | 0.0<br>0.0<br>100.0 | 0.9<br>1.9<br>100.0 | E |
| 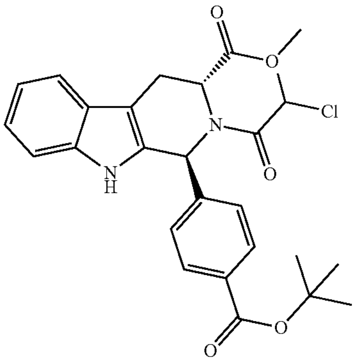 [SMILES: COC(=O)[C@H]1Cc2c([nH]c3ccccc23)[C@H](c2ccc(C(=O)OC(C)(C)C)cc2)N1C(=O)C(C)Cl] | 33 | 60<br>30<br>0 | 69.3<br>78.9<br>100.0 | 103.8<br>104.7<br>100.0 | E |
| 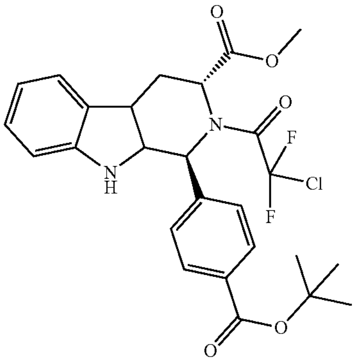 [SMILES: COC(=O)[C@H]1CC2c3ccccc3NC2[C@H](c2ccc(C(=O)OC(C)(C)C)cc2)N1C(=O)C(F)(F)Cl] | 34 | 60<br>30<br>0 | 80.6<br>75.6<br>100.0 | 113.4<br>104.9<br>100.0 | E |

TABLE 24-continued
| Structure | Compound No. | Whole Blood Stability % Remaining at 37° C. Time (min) | Mouse | Human | $IC_{50}$ μM KP4 |
|---|---|---|---|---|---|
| 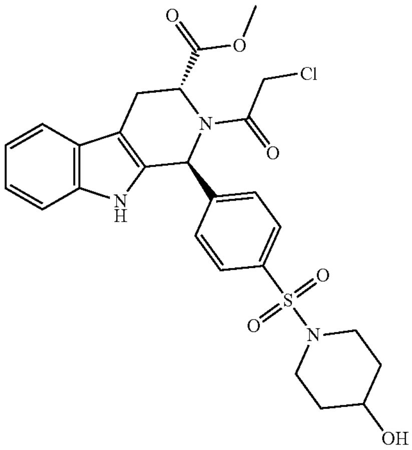 [SMILES: COC(=O)[C@H]1Cc2c([nH]c3ccccc23)[C@H](c2ccc(S(=O)(=O)N3CCC(O)CC3)cc2)N1C(=O)CCl] | 35 | 60<br>30<br>0 | 14.8<br>32.9<br>100.0 | 20.5<br>39.3<br>100.0 | B |
| 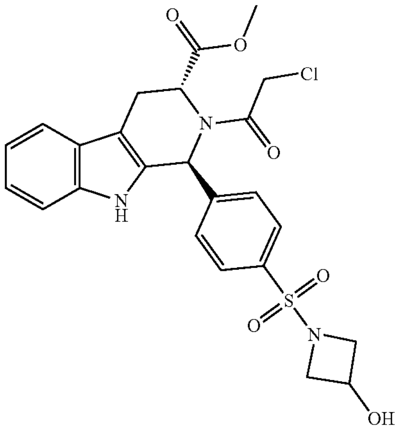 [SMILES: COC(=O)[C@H]1Cc2c([nH]c3ccccc23)[C@H](c2ccc(S(=O)(=O)N3CC(O)C3)cc2)N1C(=O)CCl] | 37 | 60<br>30<br>0 | 9.8<br>25.4<br>100.0 | 17.9<br>37.8<br>100.0 | B |
| 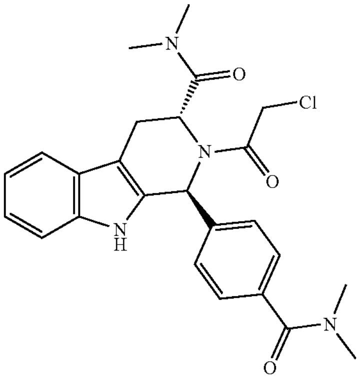 [SMILES: CN(C)C(=O)c1ccc([C@H]2c3[nH]c4ccccc4c3C[C@H](C(=O)N(C)C)N2C(=O)CCl)cc1] | 38 | 60<br>30<br>0 | 62.0<br>72.9<br>100.0 | 28.5<br>46.2<br>100.0 | D |

TABLE 24-continued
| Structure | Compound No. | Whole Blood Stability % Remaining at 37° C. Time (min) | Mouse | Human | $IC_{50}$ μM KP4 |
|---|---|---|---|---|---|
| 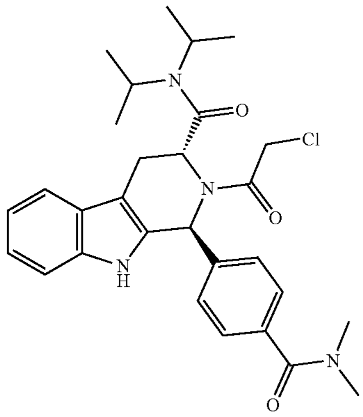 [SMILES: CC(C)N(C(=O)[C@H]1Cc2c([nH]c3ccccc23)[C@H](c2ccc(C(=O)N(C)C)cc2)N1C(=O)CCl)C(C)C] | 39 | 60<br>30<br>0 | 60.4<br>73.2<br>100.0 | 50.4<br>64.5<br>100.0 | C |
| 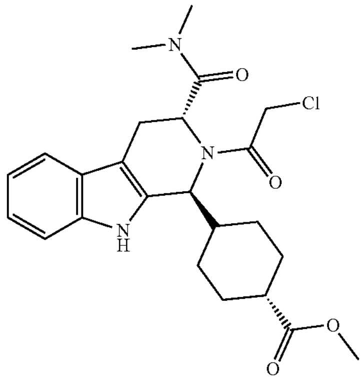 | 41 | 60<br>30<br>0 | 0.0<br>0.0<br>100.0 | 100.0<br>82.4<br>100.0 | B |
| 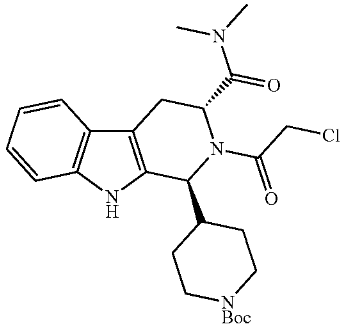 [SMILES: CN(C)C(=O)[C@H]1Cc2c([nH]c3ccccc23)[C@H](C2CCN(C(=O)OC(C)(C)C)CC2)N1C(=O)CCl] | 42 | 60<br>30<br>0 | 62.0<br>72.9<br>100.0 | 28.5<br>46.2<br>100.0 | E |
| 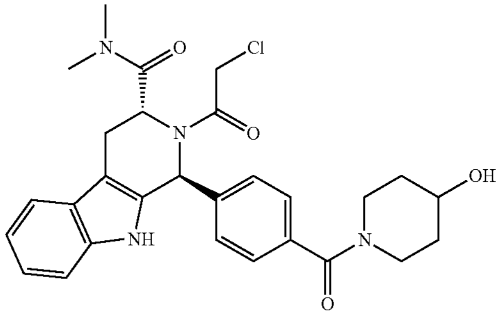 [SMILES: CN(C)C(=O)[C@H]1Cc2c([nH]c3ccccc23)[C@H](c2ccc(C(=O)N3CCC(O)CC3)cc2)N1C(=O)CCl] | 45 | 60<br>30<br>0 | 81.5<br>91.2<br>100.0 | 56.4<br>71.4<br>100.0 | E |

TABLE 24-continued
| Structure | Compound No. | Whole Blood Stability % Remaining at 37° C. Time (min) | Mouse | Human | $IC_{50}$ µM KP4 |
|---|---|---|---|---|---|
| 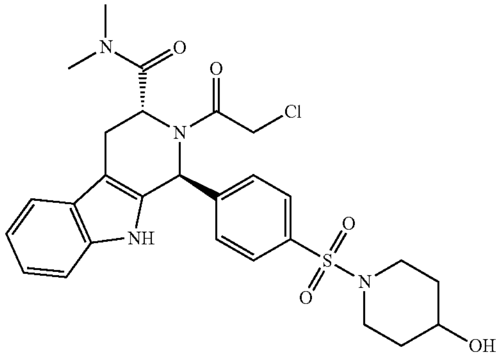 [SMILES: CN(C)C(=O)[C@H]1Cc2c([nH]c3ccccc23)[C@H](c2ccc(S(=O)(=O)N3CCC(O)CC3)cc2)N1C(=O)CCl] | 49 | 60<br>30<br>0 | 52.5<br>82.5<br>100.0 | 13.7<br>43.0<br>100.0 | E |
| 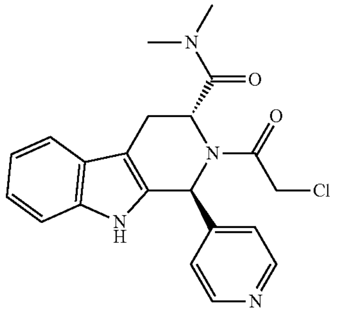 [SMILES: CN(C)C(=O)[C@H]1Cc2c([nH]c3ccccc23)[C@H](c2ccncc2)N1C(=O)CCl] | 50 | N/A | N/A | N/A | C |
| 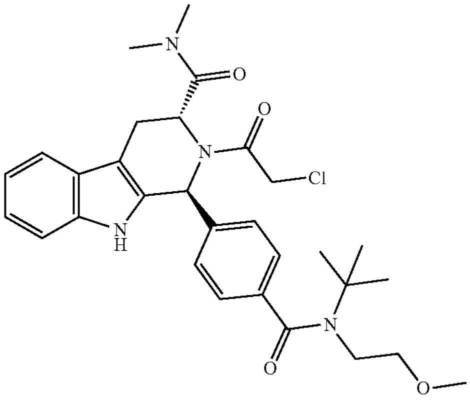 [SMILES: COCCN(C(=O)c1ccc([C@H]2c3[nH]c4ccccc4c3C[C@H](C(=O)N(C)C)N2C(=O)CCl)cc1)C(C)(C)C] | 52 | 60<br>30<br>0 | 52.0<br>79.9<br>100.0 | 59.4<br>51.8<br>100.0 | B |

TABLE 24-continued
| Structure | Compound No. | Whole Blood Stability % Remaining at 37° C. Time (min) | Mouse | Human | $IC_{50}$ μM KP4 |
|---|---|---|---|---|---|
| 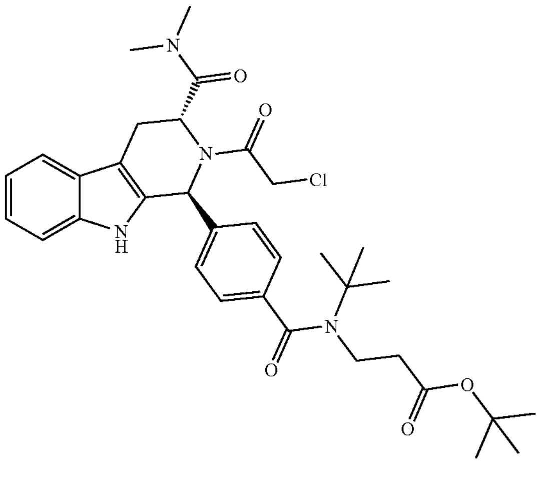 [SMILES: CN(C)C(=O)[C@H]1Cc2c([nH]c3ccccc23)[C@H](c2ccc(C(=O)N(CCC(=O)OC(C)(C)C)C(C)(C)C)cc2)N1C(=O)CCl] | 54 | 60<br>30<br>0 | 13.8<br>42.9<br>100.0 | 40.4<br>44.9<br>100.0 | B |
| 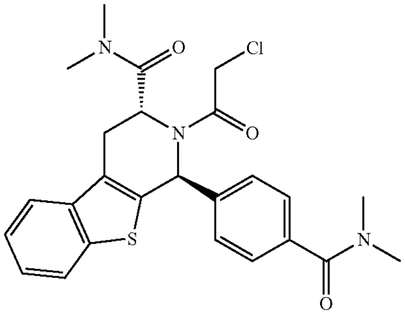 [SMILES: CN(C)C(=O)c1ccc([C@H]2c3sc4ccccc4c3C[C@H](C(=O)N(C)C)N2C(=O)CCl)cc1] | 55 | 60<br>30<br>0 | 24.6<br>51.4<br>100.0 | 20.6<br>50.6<br>100.0 | C |
| 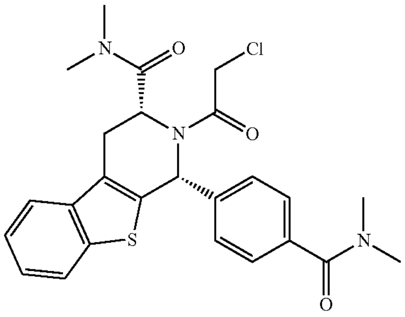 [SMILES: CN(C)C(=O)c1ccc([C@@H]2c3sc4ccccc4c3C[C@H](C(=O)N(C)C)N2C(=O)CCl)cc1] | 55a | 60<br>30<br>0 | 60.4<br>82.3<br>100.0 | 16.7<br>42.6<br>100.0 | D |
| 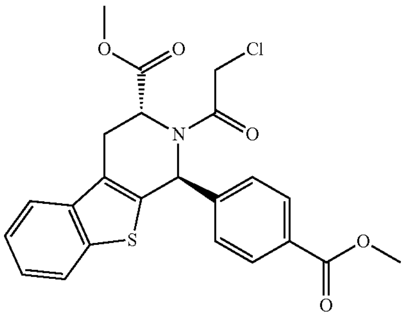 [SMILES: COC(=O)c1ccc([C@H]2c3sc4ccccc4c3C[C@H](C(=O)OC)N2C(=O)CCl)cc1] | 55c | 60<br>30<br>0 | 0.0<br>0.0<br>100.0 | 27.5<br>46.0<br>100.0 | B |

TABLE 24-continued
| Structure | Compound No. | Whole Blood Stability % Remaining at 37° C. Time (min) | Mouse | Human | $IC_{50}$ μM KP4 |
|---|---|---|---|---|---|
| 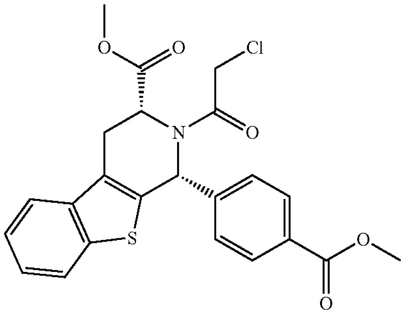 [SMILES: COC(=O)c1ccc([C@@H]2c3sc4ccccc4c3C[C@H](C(=O)OC)N2C(=O)CCl)cc1] | 55d | 60<br>30<br>0 | 0.0<br>0.0<br>100.0 | 41.2<br>60.8<br>100.0 | C |
| 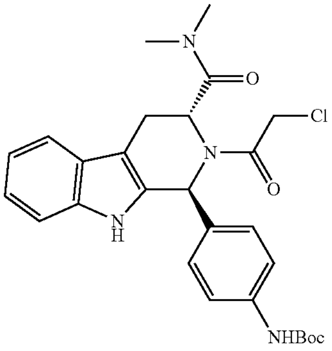 [SMILES: CN(C)C(=O)[C@H]1Cc2c([nH]c3ccccc23)[C@H](c2ccc(NC(=O)OC(C)(C)C)cc2)N1C(=O)CCl] | 56 | 60<br>30<br>0 | 38.9<br>84.1<br>100.0 | 60.7<br>59.3<br>100.0 | B |
| 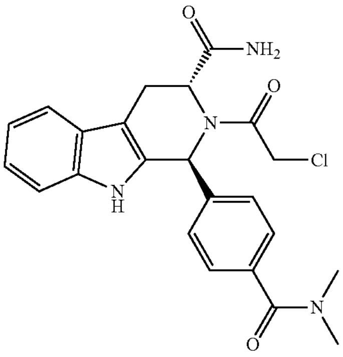 [SMILES: CN(C)C(=O)c1ccc([C@H]2c3[nH]c4ccccc4c3C[C@H](C(N)=O)N2C(=O)CCl)cc1] | 58 | 60<br>30<br>0 | 67.0<br>89.9<br>100.0 | 40.5<br>64.4<br>100.0 | E |
| 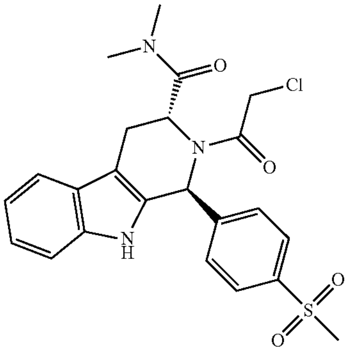 [SMILES: CN(C)C(=O)[C@H]1Cc2c([nH]c3ccccc23)[C@H](c2ccc(S(C)(=O)=O)cc2)N1C(=O)CCl] | 59 | 60<br>30<br>0 | 65.6<br>97.9<br>100.0 | 51.5<br>48.9<br>100.0 | C |

TABLE 24-continued
| Structure | Compound No. | Whole Blood Stability % Remaining at 37° C. Time (min) | Mouse | Human | $IC_{50}$ μM KP4 |
|---|---|---|---|---|---|
| 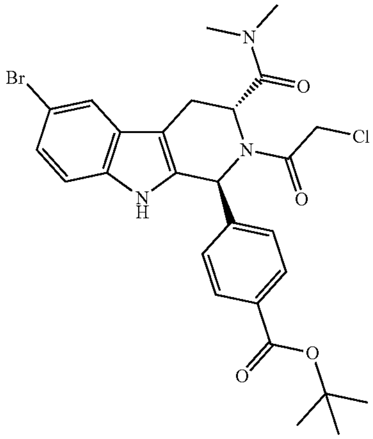 [SMILES: CN(C)C(=O)[C@H]1Cc2c([nH]c3ccc(Br)cc23)[C@H](c2ccc(C(=O)OC(C)(C)C)cc2)N1C(=O)CCl] | 61 | 60<br>30<br>0 | 6.8<br>20.5<br>100.0 | 34.0<br>49.2<br>100.0 | A |
| 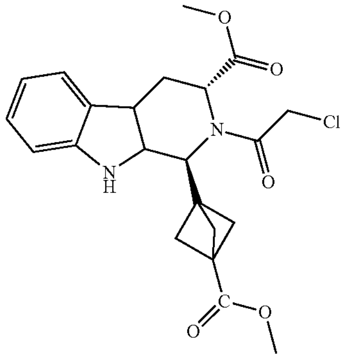 [SMILES: COC(=O)[C@H]1CC2c3ccccc3NC2[C@H](C23CC(C(=O)OC)(C2)C3)N1C(=O)CCl] | 62 | 60<br>30<br>0 | 0.0<br>0.0<br>100.0 | 43.5<br>82.4<br>100.0 | B |
| 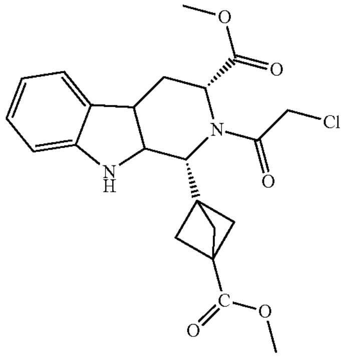 [SMILES: COC(=O)[C@H]1CC2c3ccccc3NC2[C@@H](C23CC(C(=O)OC)(C2)C3)N1C(=O)CCl] | 62a | 60<br>30<br>0 | 0.0<br>0.0<br>100.0 | 66.5<br>116.4<br>100.0 | C |

TABLE 24-continued
| Structure | Compound No. | Whole Blood Stability % Remaining at 37° C. Time (min) | Mouse | Human | $IC_{50}$ μM KP4 |
|---|---|---|---|---|---|
| 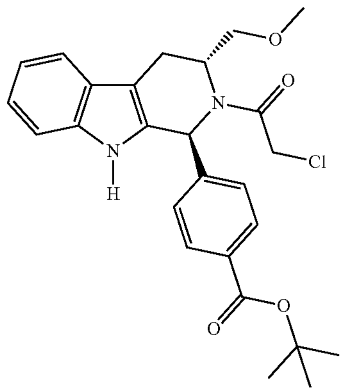 [SMILES: COC[C@H]1Cc2c([nH]c3ccccc23)[C@H](c2ccc(C(=O)OC(C)(C)C)cc2)N1C(=O)CCl] | 63 | 60<br>30<br>0 | 108.4<br>97.0<br>100.0 | 70.7<br>113.1<br>100.0 | B |
| 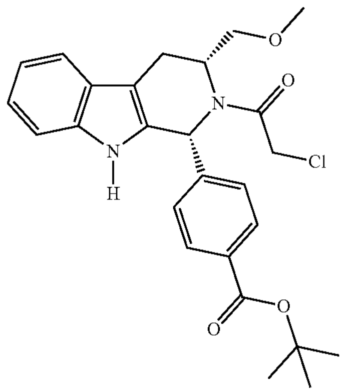 [SMILES: COC[C@H]1Cc2c([nH]c3ccccc23)[C@@H](c2ccc(C(=O)OC(C)(C)C)cc2)N1C(=O)CCl] | 64 | 60<br>30<br>0 | 0.0<br>0.0<br>100.0 | 14.7<br>44.3<br>100.0 | C |
| 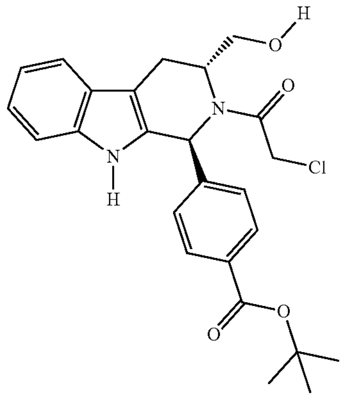 [SMILES: CC(C)(C)OC(=O)c1ccc([C@H]2c3[nH]c4ccccc4c3C[C@H](CO)N2C(=O)CCl)cc1] | 63a | 60<br>30<br>0 | 0.0<br>4.5<br>100.0 | 13.2<br>35.0<br>100.0 | E |

TABLE 24-continued
| Structure | Compound No. | Whole Blood Stability % Remaining at 37° C. Time (min) | Mouse | Human | $IC_{50}$ μM KP4 |
|---|---|---|---|---|---|
| 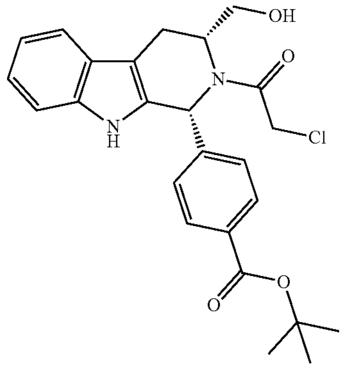 [SMILES: CC(C)(C)OC(=O)c1ccc([C@@H]2c3[nH]c4ccccc4c3C[C@H](CO)N2C(=O)CCl)cc1] | 64a | 60<br>30<br>0 | 3.2<br>8.3<br>100.0 | 15.5<br>38.0<br>100.0 | E |
| 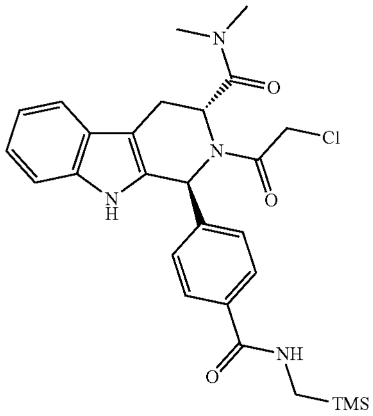 [SMILES: CN(C)C(=O)[C@H]1Cc2c([nH]c3ccccc23)[C@H](c2ccc(C(=O)NC[Si](C)(C)C)cc2)N1C(=O)CCl] | 66 | 60<br>30<br>0 | 26.8<br>69.8<br>100.0 | 45.8<br>79.1<br>100.0 | B |
| 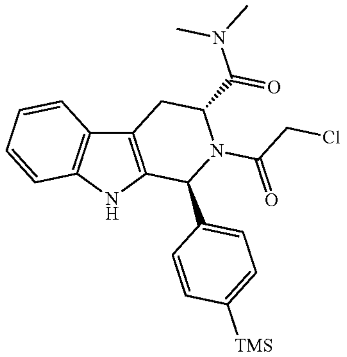 [SMILES: CN(C)C(=O)[C@H]1Cc2c([nH]c3ccccc23)[C@H](c2ccc([Si](C)(C)C)cc2)N1C(=O)CCl] | 67 | 60<br>30<br>0 | 13.3<br>38.7<br>100.0 | 37.3<br>56.8<br>100.0 | B |
| 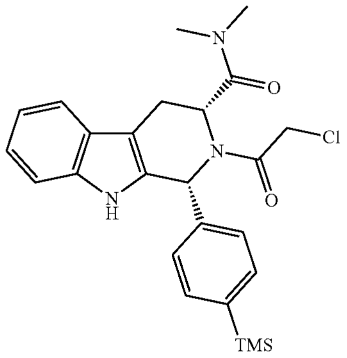 [SMILES: CN(C)C(=O)[C@H]1Cc2c([nH]c3ccccc23)[C@@H](c2ccc([Si](C)(C)C)cc2)N1C(=O)CCl] | 67a | 60<br>30<br>0 | 18.2<br>52.4<br>100.0 | 15.5<br>35.5<br>100.0 | E |

TABLE 24-continued
| Structure | Compound No. | Whole Blood Stability % Remaining at 37° C. Time (min) | Mouse | Human | $IC_{50}$ μM KP4 |
|---|---|---|---|---|---|
| 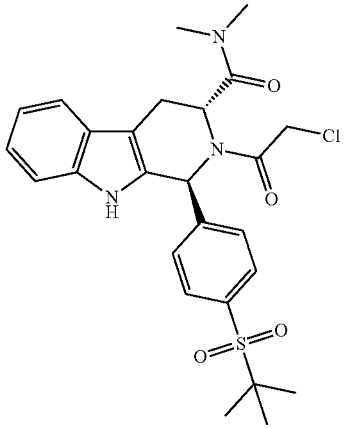 [SMILES: CN(C)C(=O)[C@H]1Cc2c([nH]c3ccccc23)[C@H](c2ccc(S(=O)(=O)C(C)(C)C)cc2)N1C(=O)CCl] | 68 | 60 | 36.9 | 20.6 | B |
| | | 30 | 65.0 | 36.8 | |
| | | 0 | 100.0 | 100.0 | |
| 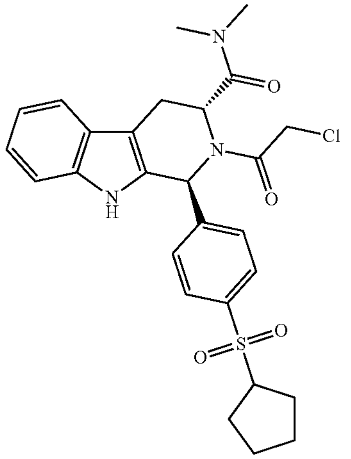 [SMILES: CN(C)C(=O)[C@H]1Cc2c([nH]c3ccccc23)[C@H](c2ccc(S(=O)(=O)C3CCCC3)cc2)N1C(=O)CCl] | 69 | 60 | 29.3 | 18.3 | B |
| | | 30 | 63.8 | 48.4 | |
| | | 0 | 100.0 | 100.0 | |
| 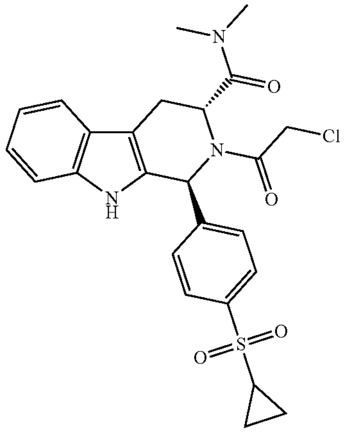 [SMILES: CN(C)C(=O)[C@H]1Cc2c([nH]c3ccccc23)[C@H](c2ccc(S(=O)(=O)C3CC3)cc2)N1C(=O)CCl] | 70 | 60 | 36.6 | 23.8 | C |
| | | 30 | 63.3 | 46.0 | |
| | | 0 | 100.0 | 100.0 | |

TABLE 24-continued
| Structure | Compound No. | Whole Blood Stability % Remaining at 37° C. Time (min) | Mouse | Human | $IC_{50}$ μM KP4 |
|---|---|---|---|---|---|
| 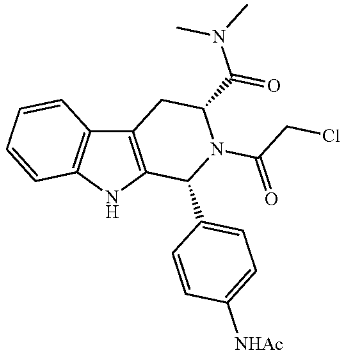 [SMILES: CC(=O)Nc1ccc([C@@H]2c3[nH]c4ccccc4c3C[C@H](C(=O)N(C)C)N2C(=O)CCl)cc1] | 71a | 60<br>30<br>0 | 43.8<br>76.5<br>100.0 | 25.7<br>54.9<br>100.0 | E |
| 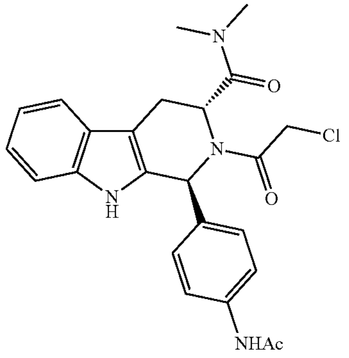 [SMILES: CC(=O)Nc1ccc([C@H]2c3[nH]c4ccccc4c3C[C@H](C(=O)N(C)C)N2C(=O)CCl)cc1] | 71 | 60<br>30<br>0 | 75.5<br>90.4<br>100.0 | 59.3<br>80.4<br>100.0 | E |
| 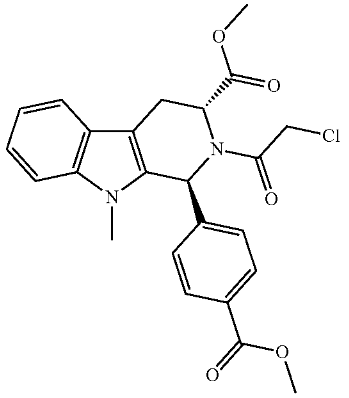 [SMILES: COC(=O)c1ccc([C@H]2c3c(c4ccccc4n3C)C[C@H](C(=O)OC)N2C(=O)CCl)cc1] | 72 | 60<br>30<br>0 | 0.2<br>0.0<br>100.0 | 7.0<br>28.0<br>100.0 | B |
| 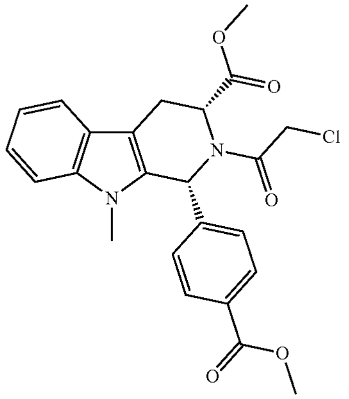 [SMILES: COC(=O)c1ccc([C@@H]2c3c(c4ccccc4n3C)C[C@H](C(=O)OC)N2C(=O)CCl)cc1] | 73 | 60<br>30<br>0 | 1.1<br>48.5<br>100.0 | 36.1<br>55.1<br>100.0 | D |

TABLE 24-continued
| Structure | Compound No. | Whole Blood Stability % Remaining at 37° C. Time (min) | Mouse | Human | $IC_{50}$ μM KP4 |
|---|---|---|---|---|---|
| 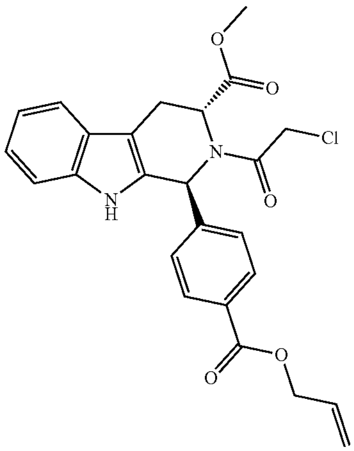 [SMILES: C=CCOC(=O)c1ccc([C@H]2c3[nH]c4ccccc4c3C[C@H](C(=O)OC)N2C(=O)CCl)cc1] | 74 | 60<br>30<br>0 | 0.0<br>0.0<br>100.0 | 29.0<br>58.2<br>100.0 | A |
| 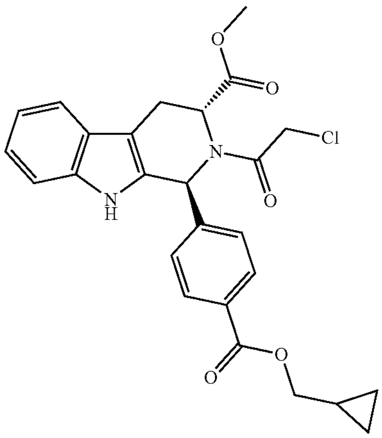 [SMILES: COC(=O)[C@H]1Cc2c([nH]c3ccccc23)[C@H](c2ccc(C(=O)OCC3CC3)cc2)N1C(=O)CCl] | 75 | 60<br>30<br>0 | 0.9<br>1.8<br>100.0 | 41.5<br>68.1<br>100.0 | A |
| 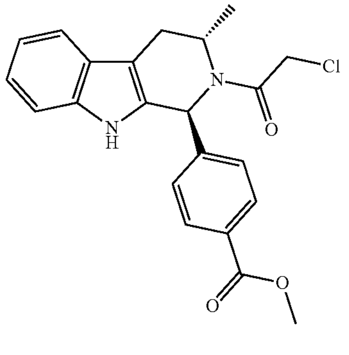 [SMILES: COC(=O)c1ccc([C@H]2c3[nH]c4ccccc4c3C[C@H](C)N2C(=O)CCl)cc1] | 77 | 60<br>30<br>0 | 0.0<br>0.5<br>100.0 | 27.5<br>54.1<br>100.0 | A |

TABLE 24-continued
| Structure | Compound No. | Whole Blood Stability % Remaining at 37° C. Time (min) | Mouse | Human | $IC_{50}$ μM KP4 |
|---|---|---|---|---|---|
| 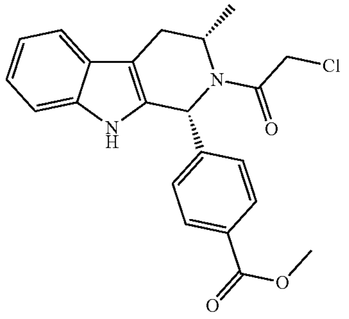 [SMILES: COC(=O)c1ccc([C@@H]2c3[nH]c4ccccc4c3C[C@H](C)N2C(=O)CCl)cc1] | 77a | 60<br>30<br>0 | 0.0<br>0.0<br>100.0 | 14.8<br>47.5<br>100.0 | D |
| 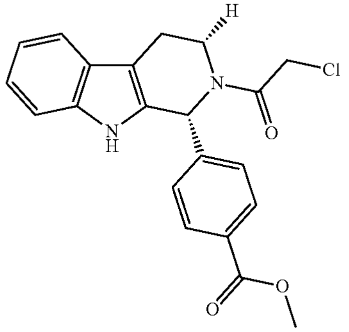 | 78 (1S,1R mixture) | 60<br>30<br>0 | 0.0<br>0.0<br>100.0 | 15.5<br>39.1<br>100.0 | C |
| 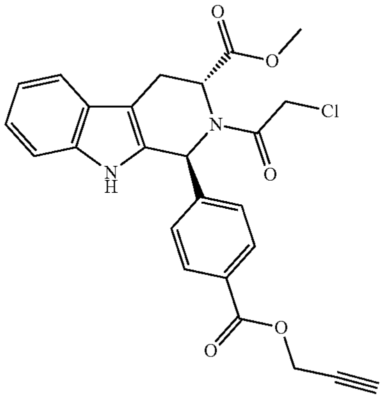 [SMILES: C#CCOC(=O)c1ccc([C@H]2c3[nH]c4ccccc4c3C[C@H](C(=O)OC)N2C(=O)CCl)cc1] | BX | 60<br>30<br>0 | 0.0<br>0.0<br>100.0 | 51.1<br>70.1<br>100.0 | A |
| 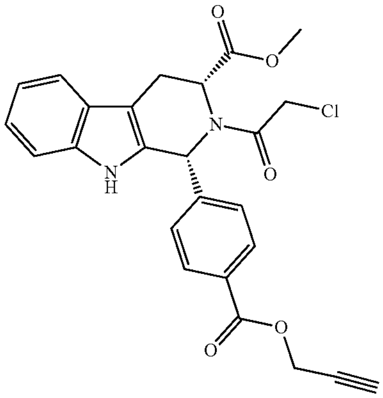 [SMILES: C#CCOC(=O)c1ccc([C@@H]2c3[nH]c4ccccc4c3C[C@H](C(=O)OC)N2C(=O)CCl)cc1] | BXa | 60<br>30<br>0 | 0.0<br>0.0<br>100.0 | 46.8<br>95.7<br>100.0 | B |

TABLE 24-continued
| Structure | Compound No. | Whole Blood Stability % Remaining at 37° C. Time (min) | Mouse | Human | IC50 μM KP4 |
|---|---|---|---|---|---|
| 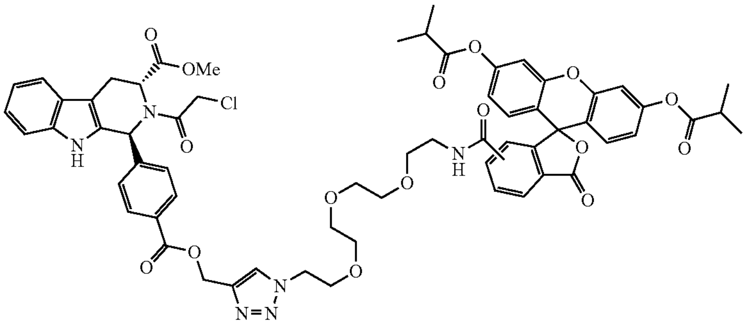 | BY | N/A | N/A | N/A | B |
| 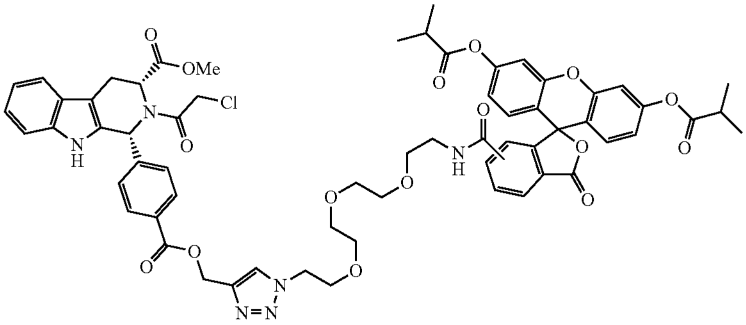 | BYa | N/A | N/A | N/A | E |
| 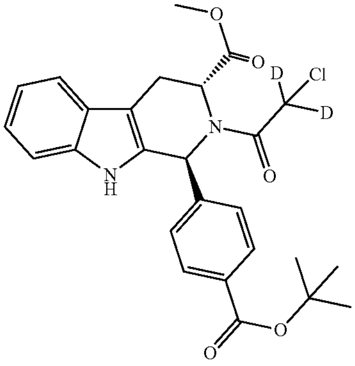 [SMILES: [2H]C([2H])(Cl)C(=O)N1[C@@H](c2ccc(C(=O)OC(C)(C)C)cc2)c2[nH]c3ccccc3c2C[C@@H]1C(=O)OC] | BZ | 60<br>30<br>0 | 30.7<br>65.4<br>100.0 | 40.8<br>73.5<br>100.0 | A |
| 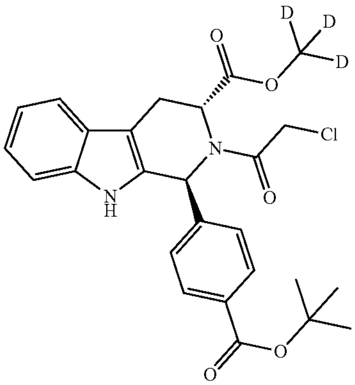 [SMILES: [2H]C([2H])([2H])OC(=O)[C@H]1Cc2c([nH]c3ccccc23)[C@H](c2ccc(C(=O)OC(C)(C)C)cc2)N1C(=O)CCl] | CA | 60<br>30<br>0 | 33.2<br>80.8<br>100.0 | 48.9<br>86.9<br>100.0 | A |

TABLE 24-continued
| Structure | Compound No. | Whole Blood Stability % Remaining at 37° C. Time (min) | Mouse | Human | IC$_{50}$ μM KP4 |
|---|---|---|---|---|---|
| 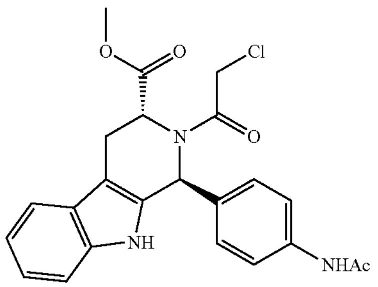 [SMILES: COC(=O)[C@H]1Cc2c([nH]c3ccccc23)[C@H](c2ccc(NC(C)=O)cc2)N1C(=O)CCl] | 80 | 60<br>30<br>0 | 58.6<br>72.3<br>100.0 | 49.6<br>60.9<br>100.0 | B |
| 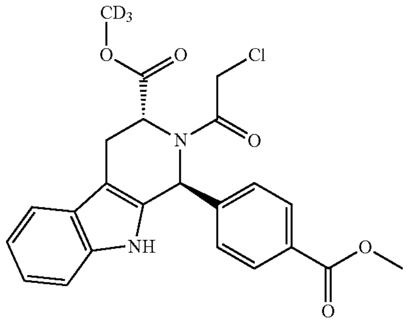 [SMILES: [2H]C([2H])([2H])OC(=O)[C@H]1Cc2c([nH]c3ccccc23)[C@H](c2ccc(C(=O)OC)cc2)N1C(=O)CCl] | CC | 60<br>30<br>0 | 0.0<br>0.0<br>100.0 | 33.5<br>63.8<br>100.0 | A |
| 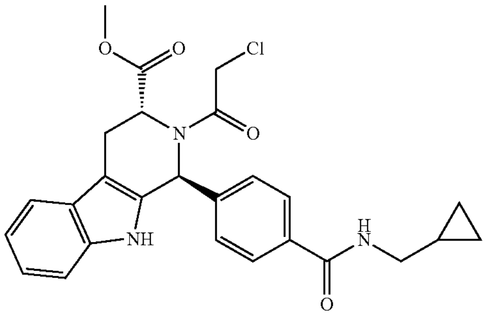 [SMILES: COC(=O)[C@H]1Cc2c([nH]c3ccccc23)[C@H](c2ccc(C(=O)NCC3CC3)cc2)N1C(=O)CCl] | 81 | 60<br>30<br>0 | 39.8<br>64.2<br>100.0 | 40.6<br>48.0<br>100.0 | A |
| 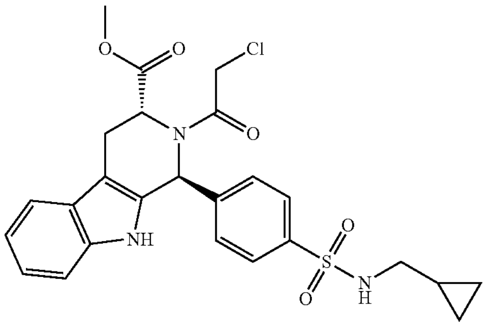 [SMILES: COC(=O)[C@H]1Cc2c([nH]c3ccccc23)[C@H](c2ccc(S(=O)(=O)NCC3CC3)cc2)N1C(=O)CCl] | 82 | 60<br>30<br>0 | 21.7<br>43.1<br>100.0 | 34.5<br>47.6<br>100.0 | A |

TABLE 24-continued
| Structure | Compound No. | Whole Blood Stability % Remaining at 37° C. Time (min) | Mouse | Human | $IC_{50}$ μM KP4 |
|---|---|---|---|---|---|
| 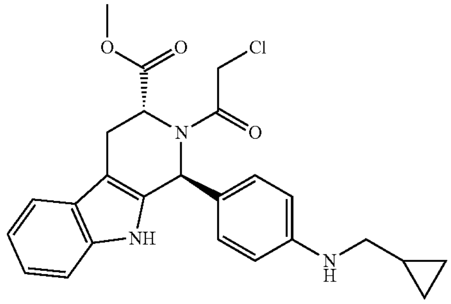 [SMILES: COC(=O)[C@H]1Cc2c([nH]c3ccccc23)[C@H](c2ccc(NCC3CC3)cc2)N1C(=O)CCl] | 83 | 60<br>30<br>0 | 30.0<br>66.1<br>100.0 | 52.9<br>78.5<br>100.0 | A |
| 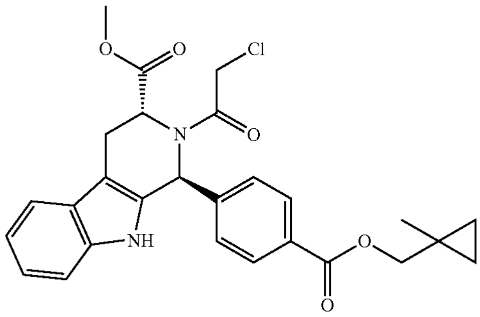 [SMILES: COC(=O)[C@H]1Cc2c([nH]c3ccccc23)[C@H](c2ccc(C(=O)OCC3(C)CC3)cc2)N1C(=O)CCl] | 84 | 60<br>30<br>0 | 0.0<br>0.0<br>100.0 | 58.3<br>87.7<br>100.0 | A |
| 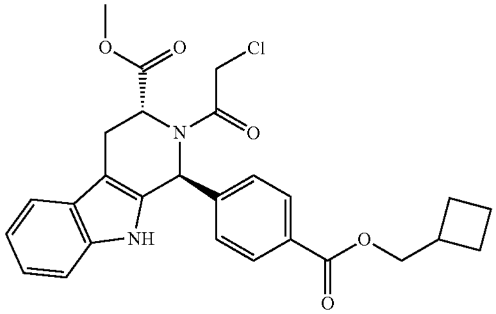 [SMILES: COC(=O)[C@H]1Cc2c([nH]c3ccccc23)[C@H](c2ccc(C(=O)OCC3CCC3)cc2)N1C(=O)CCl] | 85 | 60<br>30<br>0 | 0.0<br>0.0<br>100.0 | 54.4<br>73.5<br>100.0 | A |
| 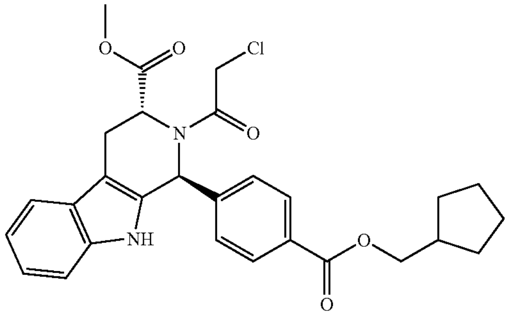 [SMILES: COC(=O)[C@H]1Cc2c([nH]c3ccccc23)[C@H](c2ccc(C(=O)OCC3CCCC3)cc2)N1C(=O)CCl] | 86 | 60<br>30<br>0 | 0.0<br>0.0<br>100.0 | 49.6<br>78.3<br>100.0 | A |

TABLE 24-continued
| Structure | Compound No. | Whole Blood Stability % Remaining at 37° C. Time (min) | Mouse | Human | $IC_{50}$ µM KP4 |
|---|---|---|---|---|---|
| 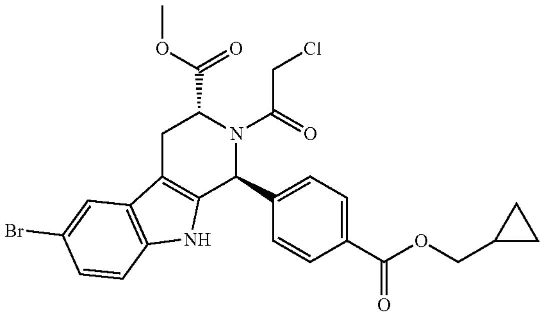 [SMILES: COC(=O)[C@H]1Cc2c([nH]c3ccc(Br)cc23)[C@H](c2ccc(C(=O)OCC3CC3)cc2)N1C(=O)CCl] | 87 | 60<br>30<br>0 | 0.0<br>0.0<br>100.0 | 32.2<br>63.2<br>100.0 | A |
| 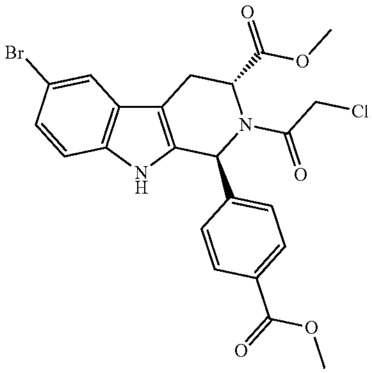 [SMILES: COC(=O)c1ccc([C@H]2c3[nH]c4ccc(Br)cc4c3C[C@H](C(=O)OC)N2C(=O)CCl)cc1] | 88 | 60<br>30<br>0 | 0.0<br>0.0<br>100.0 | 27.0<br>56.4<br>100.0 | A |
| 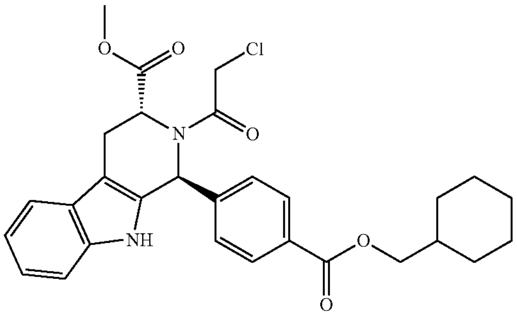 [SMILES: COC(=O)[C@H]1Cc2c([nH]c3ccccc23)[C@H](c2ccc(C(=O)OCC3CCCCC3)cc2)N1C(=O)CCl] | 89 | 60<br>30<br>0 | 0.0<br>0.0<br>100.0 | 91.2<br>84.8<br>100.0 | A |
| 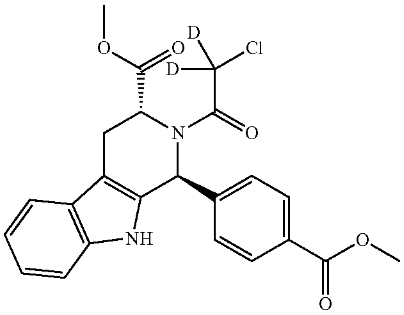 [SMILES: [2H]C([2H])(Cl)C(=O)N1[C@@H](c2ccc(C(=O)OC)cc2)c2[nH]c3ccccc3c2C[C@@H]1C(=O)OC] | 90 | 60<br>30<br>0 | 0.0<br>0.0<br>100.0 | 36.3<br>57.2<br>100.0 | A |

TABLE 24-continued
| Structure | Compound No. | Whole Blood Stability % Remaining at 37° C. Time (min) | Mouse | Human | $IC_{50}$ μM KP4 |
|---|---|---|---|---|---|
| 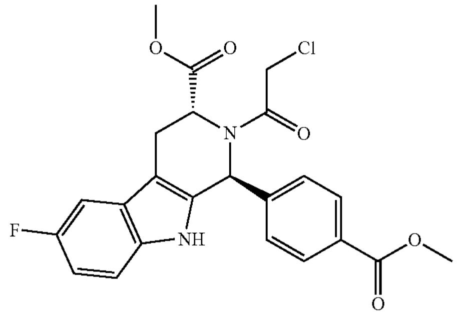 [SMILES: COC(=O)c1ccc([C@H]2c3[nH]c4ccc(F)cc4c3C[C@H](C(=O)OC)N2C(=O)CCl)cc1] | 91 | 60<br>30<br>0 | 0.0<br>0.0<br>100.0 | 47.2<br>65.8<br>100.0 | A |
| 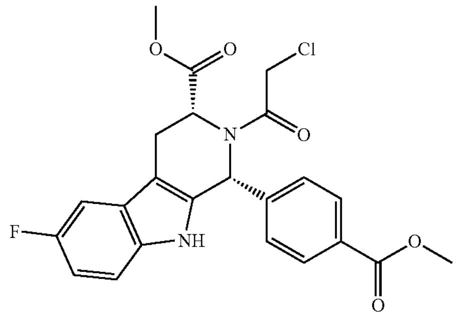 [SMILES: COC(=O)c1ccc([C@@H]2c3[nH]c4ccc(F)cc4c3C[C@H](C(=O)OC)N2C(=O)CCl)cc1] | 92 | 60<br>30<br>0 | 0.0<br>0.0<br>100.0 | 21.0<br>40.2<br>100.0 | C |
| 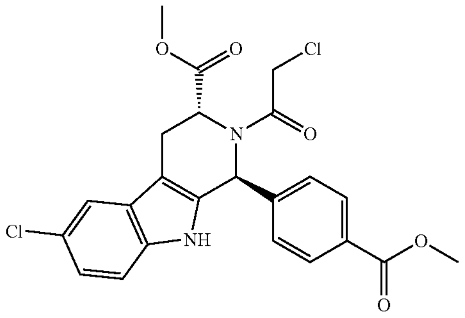 [SMILES: COC(=O)c1ccc([C@H]2c3[nH]c4ccc(Cl)cc4c3C[C@H](C(=O)OC)N2C(=O)CCl)cc1] | 93 | 60<br>30<br>0 | 0.0<br>0.0<br>100.0 | 44.9<br>66.3<br>100.0 | C |
| 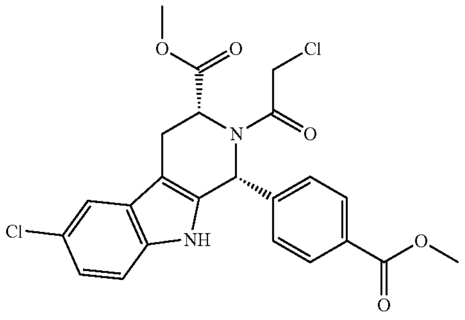 [SMILES: COC(=O)c1ccc([C@@H]2c3[nH]c4ccc(Cl)cc4c3C[C@H](C(=O)OC)N2C(=O)CCl)cc1] | 94 | 60<br>30<br>0 | 0.0<br>0.0<br>100.0 | 27.1<br>50.3<br>100.0 | A |

TABLE 24-continued
| Structure | Compound No. | Whole Blood Stability % Remaining at 37° C. Time (min) | Mouse | Human | $IC_{50}$ μM KP4 |
|---|---|---|---|---|---|
| 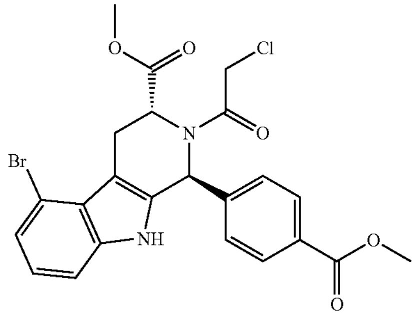 [SMILES: COC(=O)c1ccc([C@H]2c3[nH]c4cccc(Br)c4c3C[C@H](C(=O)OC)N2C(=O)CCl)cc1] | 95 | 60 | 0.0 | 85.6 | B |
| | | 30 | 1.5 | 109.5 | |
| | | 0 | 100.0 | 100.0 | |
| 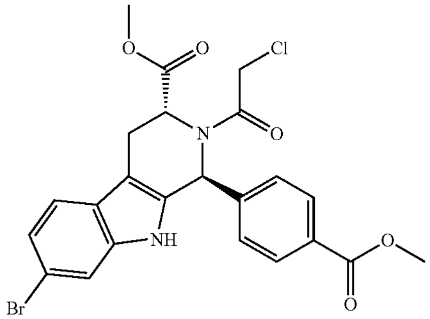 [SMILES: COC(=O)c1ccc([C@H]2c3[nH]c4cc(Br)ccc4c3C[C@H](C(=O)OC)N2C(=O)CCl)cc1] | 96 | 60 | 0.0 | 10.9 | A |
| | | 30 | 0.0 | 29.1 | |
| | | 0 | 100.0 | 100.0 | |
| 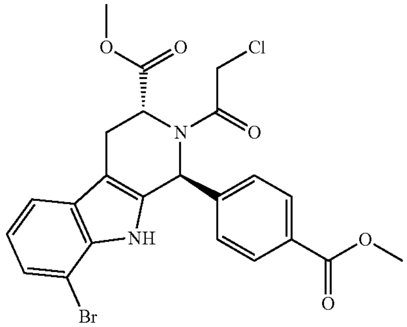 [SMILES: COC(=O)c1ccc([C@H]2c3[nH]c4c(Br)cccc4c3C[C@H](C(=O)OC)N2C(=O)CCl)cc1] | 97 | 60 | 0.0 | 44.1 | A |
| | | 30 | 0.0 | 69.6 | |
| | | 0 | 100.0 | 100.0 | |
| 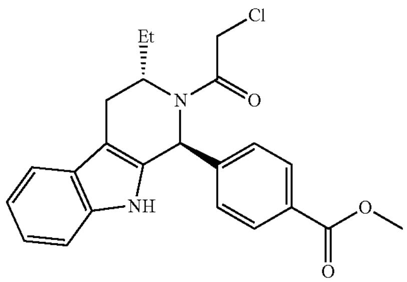 [SMILES: CC[C@H]1Cc2c([nH]c3ccccc23)[C@H](c2ccc(C(=O)OC)cc2)N1C(=O)CCl] | 98 | 60 | 0.0 | 54.8 | A |
| | | 30 | 0.0 | 79.2 | |
| | | 0 | 100.0 | 100.0 | |

TABLE 24-continued
| Structure | Compound No. | Whole Blood Stability % Remaining at 37° C. Time (min) | Mouse | Human | $IC_{50}$ μM KP4 |
|---|---|---|---|---|---|
| 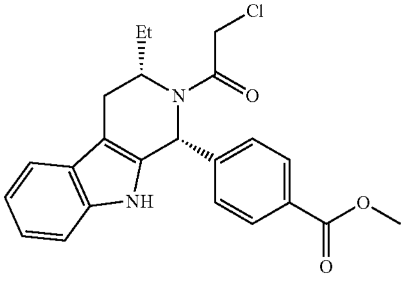 [SMILES: CC[C@H]1Cc2c([nH]c3ccccc23)[C@@H](c2ccc(C(=O)OC)cc2)N1C(=O)CCl] | 99 | 60<br>30<br>0 | 0.0<br>4.0<br>100.0 | 67.9<br>94.5<br>100.0 | E |
| 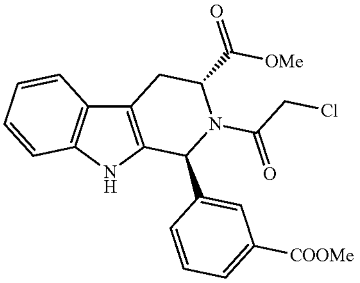 [SMILES: COC(=O)c1cccc([C@H]2c3[nH]c4ccccc4c3C[C@H](C(=O)OC)N2C(=O)CCl)c1] | 100 | 60<br>30<br>0 | 10.8<br>35.8<br>100.0 | 44.3<br>60.9<br>100.0 | A |
| 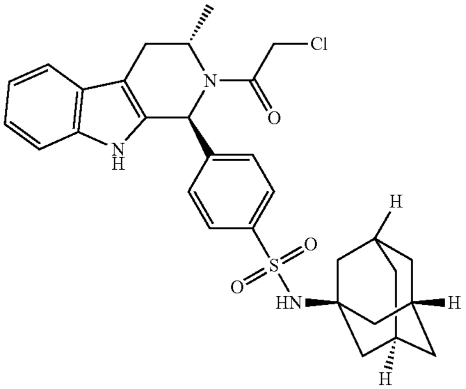 [SMILES: C[C@H]1Cc2c([nH]c3ccccc23)[C@H](c2ccc(S(=O)(=O)N[C@]34CC5C[C@H](C[C@H](C5)C3)C4)cc2)N1C(=O)CCl] | 101 | 60<br>30<br>0 | 113.2<br>82.2<br>100.0 | 29.8<br>46.8<br>100.0 | A |
| 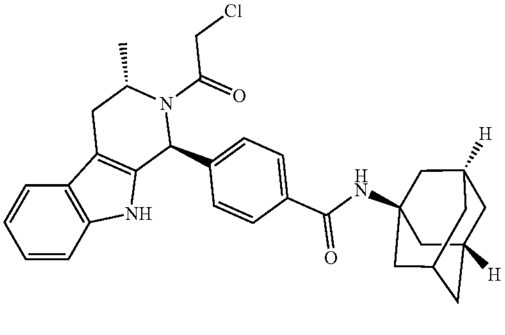 [SMILES: C[C@H]1Cc2c([nH]c3ccccc23)[C@H](c2ccc(C(=O)N[C@]34CC5C[C@H](C[C@H](C5)C3)C4)cc2)N1C(=O)CCl] | 102 | 60<br>30<br>0 | 90.1<br>87.2<br>100.0 | 75.6<br>96.3<br>100.0 | A |

TABLE 24-continued
| Structure | Compound No. | Whole Blood Stability % Remaining at 37° C. Time (min) | Mouse | Human | $IC_{50}$ μM KP4 |
|---|---|---|---|---|---|
| 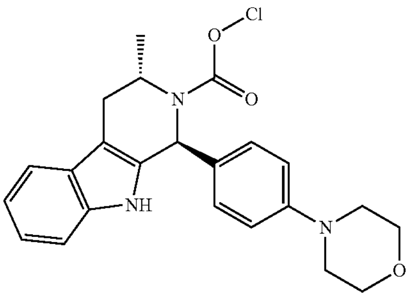 [SMILES: C[C@H]1Cc2c([nH]c3ccccc23)[C@H](c2ccc(N3CCOCC3)cc2)N1C(=O)OCl] | 103 | 60<br>30<br>0 | 56.6<br>87.1<br>100.0 | 75.2<br>98.4<br>100.0 | A |
| 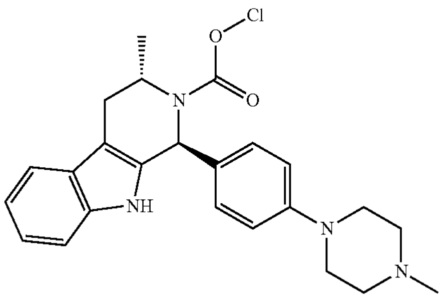 | 104 | 60<br>30<br>0 | 49.1<br>78.9<br>100.0 | 45.9<br>64.9<br>100.0 | B |
| 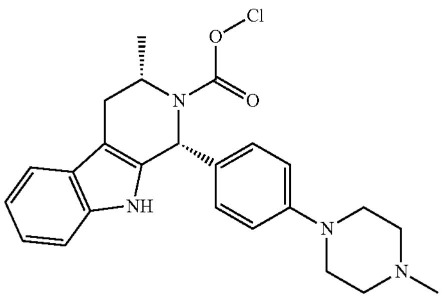 | 105 | 60<br>30<br>0 | 46.6<br>75.1<br>100.0 | 25.3<br>52.3<br>100.0 | D |
| 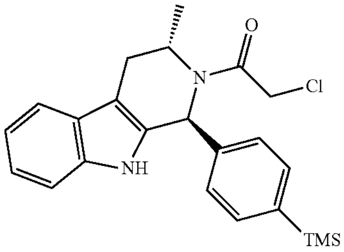 [SMILES: C[C@H]1Cc2c([nH]c3ccccc23)[C@H](c2ccc([Si](C)(C)C)cc2)N1C(=O)CCl] | 106 | 60<br>30<br>0 | 95.5<br>103.6<br>100.0 | 98.6<br>111.8<br>100.0 | A |
| 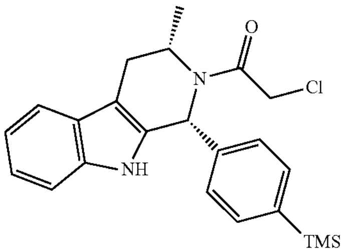 [SMILES: C[C@H]1Cc2c([nH]c3ccccc23)[C@@H](c2ccc([Si](C)(C)C)cc2)N1C(=O)CCl] | 107 | 60<br>30<br>0 | 91.9<br>73.7<br>100.0 | 67.9<br>72.4<br>100.0 | E |

TABLE 24-continued
| Structure | Compound No. | Whole Blood Stability % Remaining at 37° C. Time (min) | Mouse | Human | $IC_{50}$ μM KP4 |
|---|---|---|---|---|---|
| 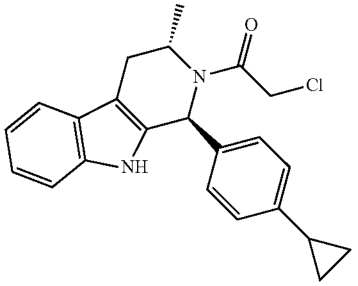 [SMILES: C[C@H]1Cc2c([nH]c3ccccc23)[C@H](c2ccc(C3CC3)cc2)N1C(=O)CCl] | 108 | 60<br>30<br>0 | 58.0<br>64.1<br>100.0 | 51.5<br>58.9<br>100.0 | A |
| 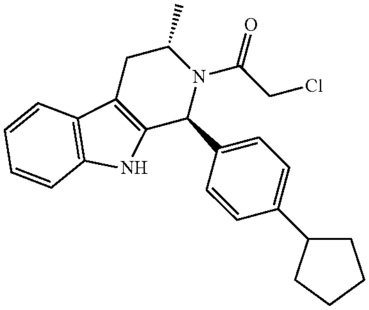 [SMILES: C[C@H]1Cc2c([nH]c3ccccc23)[C@H](c2ccc(C3CCCC3)cc2)N1C(=O)CCl] | 109 | 60<br>30<br>0 | 87.7<br>79.2<br>100.0 | 68.1<br>96.1<br>100.0 | A |
| 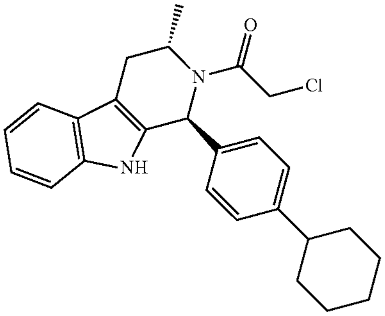 [SMILES: C[C@H]1Cc2c([nH]c3ccccc23)[C@H](c2ccc(C3CCCCC3)cc2)N1C(=O)CCl] | 110 | 60<br>30<br>0 | 111.0<br>127.4<br>100.0 | 51.7<br>68.3<br>100.0 | A |
| 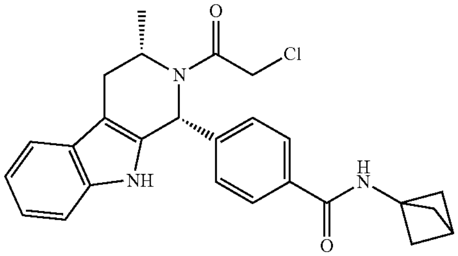 [SMILES: C[C@H]1Cc2c([nH]c3ccccc23)[C@@H](c2ccc(C(=O)NC34CC(C3)C4)cc2)N1C(=O)CCl] | 111 | 60<br>30<br>0 | 87.7<br>79.2<br>100.0 | 68.1<br>96.1<br>100.0 | D |
| 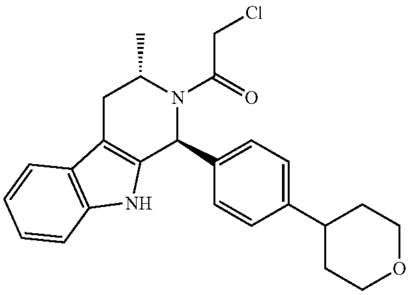 [SMILES: C[C@H]1Cc2c([nH]c3ccccc23)[C@H](c2ccc(C3CCOCC3)cc2)N1C(=O)CCl] | 112 | 60<br>30<br>0 | 69.3<br>68.7<br>100.0 | 44.6<br>58.3<br>100.0 | A |

TABLE 24-continued
| Structure | Compound No. | Whole Blood Stability % Remaining at 37° C. Time (min) | Mouse | Human | IC$_{50}$ μM KP4 |
|---|---|---|---|---|---|
| 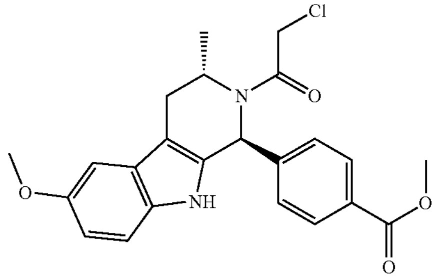 | 113 | 60<br>30<br>0 | 2.4<br>89.5<br>100.0 | 92.7<br>85.1<br>100.0 | A |
| 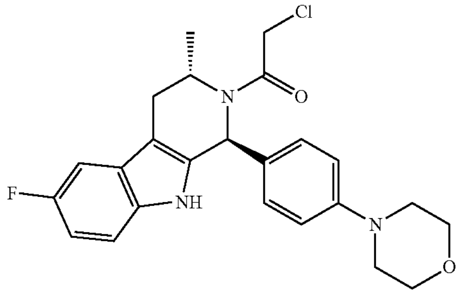 [SMILES: C[C@H]1Cc2c([nH]c3ccc(F)cc23)[C@H](c2ccc(N3CCOCC3)cc2)N1C(=O)CCl] | 114 | 0<br>30<br>60 | 100.0<br>59.3<br>0.0 | 100.0<br>88.1<br>50.8 | A |
| 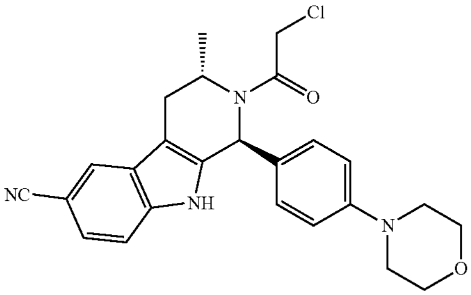 [SMILES: C[C@H]1Cc2c([nH]c3ccc(C#N)cc23)[C@H](c2ccc(N3CCOCC3)cc2)N1C(=O)CCl] | 115 | 0<br>30<br>60 | 100.0<br>34.2<br>0.0 | 100.0<br>72.9<br>44.0 | A |
| 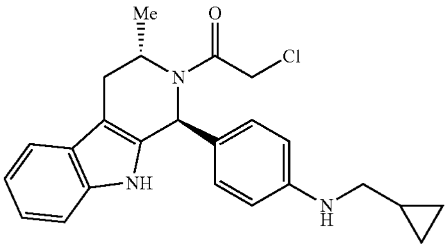 [SMILES: C[C@H]1Cc2c([nH]c3ccccc23)[C@H](c2ccc(NCC3CC3)cc2)N1C(=O)CCl] | 116 | 60<br>30<br>0 | 67.1<br>82.6<br>100.0 | 62.0<br>79.2<br>100.0 | C |
| 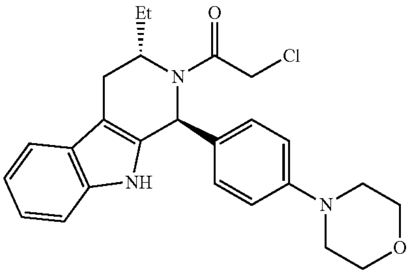 [SMILES: CC[C@H]1Cc2c([nH]c3ccccc23)[C@H](c2ccc(N3CCOCC3)cc2)N1C(=O)CCl] | 117 | 60<br>30<br>0 | 45.8<br>92.3<br>100.0 | 70.3<br>80.5<br>100.0 | A |

TABLE 24-continued

| Structure | Compound No. | Whole Blood Stability % Remaining at 37° C. Time (min) | Mouse | Human | $IC_{50}$ μM KP4 |
|---|---|---|---|---|---|
| 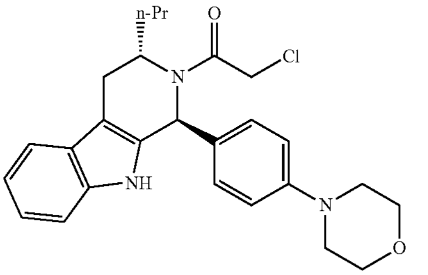 | 118 | 0<br>30<br>60 | 100.0<br>60.7<br>0.0 | 100.0<br>100.2<br>68.8 | A |
| 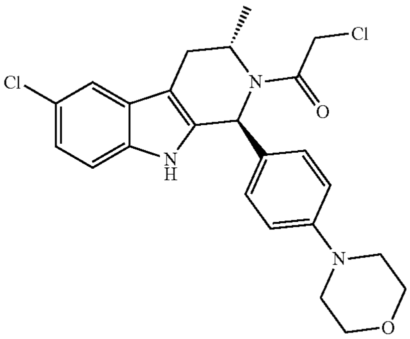 [SMILES: C[C@H]1Cc2c([nH]c3ccc(Cl)cc23)[C@H](c2ccc(N3CCOCC3)cc2)N1C(=O)CCl] | 120 | N/A | N/A | N/A | C |
| 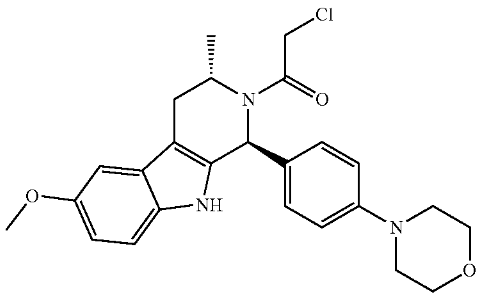 [SMILES: COc1ccc2[nH]c3c(c2c1)C[C@H](C)N(C(=O)CCl)[C@H]3c1ccc(N2CCOCC2)cc1] | 121 | 0<br>30<br>60 | 100.0<br>84.3<br>50.0 | 100.0<br>90.3<br>61.3 | A |

Example 6: Cell Proliferation (Alamar Blue) Assay

Cell viability assay was performed to assess the potency of the compounds in human cancer cell lines 786-O (renal cell carcinoma) and SJSA-1 (osteosarcoma). Additional cell lines, such as those described above in Example 4 as well as various others, e.g., pancreatic cancer cell lines (Panc 02.13, BxPC-3, Panc 12, Panc 02.03, Panc 6.03, PSN-1, HPAC, and Capan-1) and prostate cancer cell lines (PC-3, DU145, 22Rv1, NCI-H660, BPH1, LNCaP, BM-1604, and MDA PCa 2b), were tested for select compounds as shown in Table 25.

Cells (SJSA-1, 786-O and A431) were seeded (5000 cells/100 μL/well) in 96-well tissue culture plate and incubated at 37° C./5% $CO_2$ for 16-24 hours. The cells were then treated with compounds (25 μL of 5×). The compound concentrations were 10-0.0005 μM prepared in 3-fold serial dilutions with final DMSO concentration of 1%. The plates were then incubated for 24 h at 37° C./5% $CO_2$ in a moist environment. Then Alamar Blue™ reagent (final concentration 1×-12.5 μL) was added to each well and incubated for 1.5 hours at 37° C./5% $CO_2$. The plates were read on fluorescence reader at 540 nm excitation and 590 nm emission wavelengths. The $IC_{50}$ values were subsequently determined using a sigmoidal dose-response curve (variable slope) in GraphPad Prism® 5 software.

Table 25 shows cell proliferation data for exemplary compounds as described above. The cell proliferation assays for the compounds shown Table 25 was performed according to the protocols described herein, including Examples 4 and 6.

Table 26 shows that compounds provided herein are GPX4 inhibitors. Studies have shown that lipophilic antioxidants, such as ferrostatin, can rescue cells from GPX4 inhibition-induced ferroptosis. For instance, mesenchymal state GPX4-knockout cells can survive in the presence of ferrostatin, however, when the supply of ferrostatin is terminated, these cells undergo ferroptosis (see, e.g., Viswanathan et al., Nature 547:453-7, 2017). It has also been experimentally determined that that GPX4i can be rescued by blocking other components of the ferroptosis pathways, such as lipid ROS scavengers (Ferrostatin, Liproxstatin), lipoxygenase inhibitors, iron chelators and caspase inhibitors, which an apoptotic inhibitor does not rescue. These findings are suggestive of non-apoptotic, iron-dependent, oxidative cell death (i.e., ferroptosis). Accordingly, the ability of a molecule to induce ferroptotic cancer cell death, and that such ability is admonished by the addition of ferrostatin, is clear indication that the molecule is an GPX4 inhibitor. The data in Table 26 shows that compounds provided herein lost inhibitory activity in the presence of ferrostatin and are thus effective GPX4 inhibitors.

TABLE 25

| Compound No. | Cell Line | $IC_{50}$ μM |
|---|---|---|
| 104 | 786-O | 0.068 |
| | SJSA-1 | 0.147 |
| 122 | A549 | >10.00 |
| | KP4 | 0.3371 |
| 121 | A673 | 0.08848 |
| | KHOS/NP | 0.0632 |
| | MG-63 | 0.5352 |
| | KSK-ES-1 | 0.2153 |
| | U-2 OS | 4.886 |
| | SJSA-1 | 0.1078 |
| | HT1080 | 0.06321 |
| | 143B | 0.06774 |
| | KP4 | 0.2743 |
| | Panc 02.13 | 0.9781 |
| | 143B | 1.058 |
| | H2228 | 0.01662 |
| | AsPC-1 | 0.06934 |
| | BxPC-3 | 1.023 |
| | Mia PaCa-2 | 0.2058 |
| | PSN-1 | 0.1751 |
| | HPAC | 0.2058 |
| | Capan-1 | >1.000 |
| | Panc 10 | 0.05865 |
| | Panc 02.03 | 0.6888 |
| | Panc 6.03 | 0.2247 |
| | A549 | 7.814 |
| | KP4 | 0.015 |
| 120 | A549 | 0.807 |
| | KP4 | 0.362 |
| 119 | A549 | 12.81 |
| | KP4 | 0.102 |
| 118 | A673 | 0.007123 |
| | KHOS/NP | 0.00465 |
| | MG-63 | 0.03926 |
| | KSK-ES-1 | 0.02129 |
| | U-2 OS | 5.02 |
| | SJSA-1 | 0.009377 |
| | A673 | 0.03706 |
| | KHOS/NP | >3.000 |
| | MG-67 | >3.000 |
| | SK-EK-1 | 0.2783 |
| | SJSA-1 | 0.1196 |
| | HT1080 | 0.003806 |
| | 143B | 0.004739 |
| | Panc 02.13 | 0.1026 |
| | H2228 | 0.001381 |
| | AsPC-1 | 0.00734 |
| | BxPC-3 | 0.05444 |
| | Mia PaCa-2 | 0.01643 |
| | PSN-1 | 0.01761 |
| | HPAC | 0.02046 |
| | Capan-1 | 0.1296 |
| | Panc 9 | 0.006384 |
| | Panc 02.03 | 0.04893 |
| | Panc 6.03 | 0.01556 |
| | A549 | 5.369 |
| | KP4 | 0.00092 |
| | KP4 | 0.000569 |
| 117 | A549 | 4.713 |
| | KP4 | 0.003 |
| | A673 | 0.01084 |
| | KHOS/NP | 0.007534 |
| | MG-63 | 0.04359 |
| | KSK-ES-1 | 0.05343 |
| | U-2 OS | 3.596 |
| | SJSA-1 | 0.0197 |

TABLE 25-continued

| Compound No. | Cell Line | $IC_{50}$ μM |
|---|---|---|
| | A673 | 0.07953 |
| | KHOS/NP | >3.000 |
| | MG-66 | >3.000 |
| | SK-EK-1 | 0.4177 |
| | SJSA-1 | 0.2242 |
| | HT1080 | 0.00716 |
| | 143B | 0.01136 |
| | KP4 | 0.0438 |
| | Panc 02.13 | 0.2159 |
| | H2228 | 0.003374 |
| | AsPC-1 | 0.01266 |
| | BxPC-3 | 0.08674 |
| | Mia PaCa-2 | 0.05702 |
| | PSN-1 | 0.04624 |
| | HPAC | 0.04844 |
| | Capan-1 | 0.2609 |
| | Panc 8 | 0.01479 |
| | Panc 02.03 | 0.1479 |
| | Panc 6.03 | 0.03285 |
| 123 | 786-O | 2.4 |
| | SJSA-1 | 4.7 |
| | A431 | 5.4 |
| 124 | 786-O | 0.245 |
| | SJSA-1 | 0.201 |
| 125 | 786-O | 2 |
| | SJSA-1 | 4 |
| 127 | 786-O | >10 |
| | SJSA-1 | >10 |
| | A431 | 2.8 |
| 128 | 786-O | 0.188 |
| | SJSA-1 | 0.184 |
| | A431 | >10 |
| 129 | 786-O | 4.2 |
| | SJSA-1 | 4.4 |
| | A431 | 4.4 |
| 130 | 786-O | 1.8 |
| | SJSA-1 | 2.7 |
| 132 | 786-O | 3.8 |
| | SJSA-1 | 6.8 |
| | A431 | 6 |
| 133 | 786-O | >10 |
| | SJSA-1 | >10 |
| 134 | 786-O | 8.194 |
| | SJSA-1 | 0.1458 |
| | A549 | >30 |
| 143 | 786-O | 0.009 |
| | SJSA-1 | 0.009 |
| | A431 | 2.7 |
| 144 | 786-O | 0.007 |
| | SJSA-1 | 0.025 |
| | A431 | 3.5 |
| 145 | 786-O | 0.003 |
| | SJSA-1 | 0.004 |
| | A431 | 4.6 |
| 146 | 786-O | 0.023 |
| | SJSA-1 | 0.030 |
| | A431 | 2.4 |
| 147 | 786-O | 0.049 |
| | SJSA-1 | 0.159 |
| | A431 | >10 |
| 148 | 786-O | 0.006 |
| | SJSA-1 | 0.008 |
| | A431 | 3.6 |
| 149 | 786-O | 0.001 |
| | SJSA-1 | 0.002 |
| | A431 | 3.8 |
| 150 | 786-O | 0.009 |
| | SJSA-1 | 0.008 |
| 151 | 786-O | 0.018 |
| | SJSA-1 | 0.037 |
| | A431 | 5.22 |
| 152 | 786-O | 0.002 |
| | SJSA-1 | 0.002 |
| 153 | 786-O | 0.009 |
| | SJSA-1 | 0.015 |

TABLE 25-continued

| Compound No. | Cell Line | IC$_{50}$ µM |
|---|---|---|
| 154 | 786-O | 0.1165 |
| | SJSA-1 | 0.1083 |
| | A549 | 7.947 |
| 155 | 786-O | 0.1127 |
| | SJSA-1 | 0.08099 |
| | A549 | 8.518 |
| 156 | 786-O | 0.07511 |
| | SJSA-1 | 0.04224 |
| | A549 | 4.295 |
| 157 | 786-O | >10 |
| | SJSA-1 | >10 |
| | A431 | 2 |
| 158 | 786-O | 0.591 |
| | SJSA-1 | 1.4 |
| | A431 | >10 |
| 159 | 786-O | 4.6 |
| | SJSA-1 | >10 |
| | A431 | 7 |
| 160 | 786-O | 1 |
| | SJSA-1 | 1.3 |
| 161 | 786-O | 2.8 |
| | SJSA-1 | 4.3 |
| 162 | 786-O | 0.060 |
| | SJSA-1 | 0.085 |
| 163 | 786-O | 6.4 |
| | SJSA-1 | >10 |
| | A431 | >10 |
| 164 | 786-O | 0.023 |
| | SJSA-1 | 0.013 |
| | A431 | 9.94 |
| 165 | 786-O | 0.047 |
| | SJSA-1 | 0.119 |
| | A431 | 3.439 |
| 166 | 786-O | 0.008 |
| | SJSA-1 | 0.01 |
| | A431 | >10.00 |
| 167 | 786-O | 0.005 |
| | SJSA-1 | 0.011 |
| | A431 | 1.934 |
| 168 | 786-O | 0.487 |
| | SJSA-1 | 0.56 |
| | A431 | 5.092 |
| 169 | 786-O | 0.003 |
| | SJSA-1 | 0.001 |
| | A431 | 3.898 |
| 170 | 786-O | 0.058 |
| | SJSA-1 | 0.062 |
| | A431 | 4.187 |
| 171 | 786-O | 0.162 |
| | SJSA-1 | 0.254 |
| | A431 | 8.106 |
| 172 | 786-O | 0.023 |
| | SJSA-1 | 0.023 |
| | A431 | 2.109 |
| 173 | 786-O | 0.023 |
| | SJSA-1 | 0.034 |
| | A431 | 3.67 |
| 174 | 786-O | 0.016 |
| | SJSA-1 | 0.091 |
| | A431 | 2.988 |
| 175 | 786-O | >10.00 |
| | SJSA-1 | >10.00 |
| 176 | 786-O | 0.6576 |
| | 786-O | 0.1506 |
| | SJSA-1 | 0.2061 |
| | SJSA-1 | 0.2502 |
| | A549 | 4.104 |
| | A549 | 4.18 |
| 177 | 786-O | 0.07881 |
| | SJSA-1 | 0.06766 |
| | A549 | 3.224 |
| 179 | 786-O | >30 |
| | SJSA-1 | >30 |
| | A549 | 27.41 |
| 180 | 786-O | >30 |
| | SJSA-1 | >30 |
| | A549 | 28.42 |

TABLE 25-continued

| Compound No. | Cell Line | IC$_{50}$ µM |
|---|---|---|
| 182 | 786-O | 0.9616 |
| | SJSA-1 | 0.6674 |
| | A549 | >30 |
| 184 | 786-O | 12.29 |
| | SJSA-1 | 16.25 |
| | A549 | >30 |
| 186 | 786-O | >30 |
| | SJSA-1 | >30 |
| | A549 | >30 |
| 189 | 786-O | 5.15 |
| | SJSA-1 | 4.201 |
| | A549 | 4.107 |
| 190 | 786-O | 1.204 |
| | SJSA-1 | 0.9085 |
| | A549 | 3.054 |
| 192 | 786-O | 0.194 |
| | SJSA-1 | 0.120 |
| | A549 | 14.20 |
| 193 | 786-O | 0.223 |
| | SJSA-1 | 0.175 |
| | A549 | 13.31 |
| 194 | 786-O | 0.286 |
| | SJSA-1 | 0.265 |
| | A549 | 14.32 |
| 195 | 786-O | 0.394 |
| | SJSA-1 | 0.256 |
| | A549 | 16.44 |
| 196 | 786-O | 0.267 |
| | SJSA-1 | 0.133 |
| | A549 | 20.57 |
| 197 | 786-O | 0.133 |
| | SJSA-1 | 0.0102 |
| | A549 | 5.64 |
| 198 | 786-O | 0.181 |
| | SJSA-1 | 0.09 |
| | A549 | 11.25 |
| 199 | 786-O | 0.529 |
| | SJSA-1 | 0.338 |
| | A549 | 19.49 |
| 200 | 786-O | 0.701 |
| | SJSA-1 | 0.448 |
| | A549 | 10.94 |
| 201 | 786-O | 0.642 |
| | SJSA-1 | 0.190 |
| | A549 | 14.82 |
| 202 | 786-O | 1.787 |
| | SJSA-1 | 0.8507 |
| | A549 | 11.35 |
| 205 | 786-O | 0.06189 |
| | SJSA-1 | 0.03241 |
| | A549 | 4.411 |
| 206 | 786-O | 1.099 |
| | SJSA-1 | 0.468 |
| | A549 | 21.8 |
| 207 | 786-O | 0.2141 |
| | SJSA-1 | 0.0868 |
| | A549 | 13.31 |
| 209 | 786-O | 0.022 |
| | SJSA-1 | 0.019 |
| | A431 | 3.279 |
| 210 | 786-O | 0.062 |
| | SJSA-1 | 0.081 |
| | A431 | 1.553 |
| 211 | 786-O | 0.009 |
| | SJSA-1 | 0.011 |
| | A431 | 2.73 |
| 212 | SJSA-1 | 0.011 |
| | 786-O | 0.008 |
| | A431 | 2.511 |
| 213 | SJSA-1 | 0.066 |
| | 786-O | 0.066 |
| | A431 | 1.847 |
| 214 | SJSA-1 | 0.03 |
| | 786-O | 0.019 |
| | A431 | 1.583 |

TABLE 25-continued

| Compound No. | Cell Line | $IC_{50}$ µM |
|---|---|---|
| 215 | SJSA-1 | 0.028 |
| | 786-O | 0.018 |
| | A431 | 8.223 |
| 216 | 786-O | 0.337 |
| | SJSA-1 | 0.163 |
| | A549 | 22.25 |
| 217 | 786-O | 0.022 |
| | SJSA-1 | 0.028 |
| 218 | 786-O | 8.1 |
| | SJSA-1 | 1.4 |
| 219 | 786-O | 0.051 |
| | SJSA-1 | 0.036 |
| | A431 | 1.9 |
| 220 | 786-O | 0.098 |
| | SJSA-1 | 0.093 |
| | A431 | 10 |
| 221 | 786-O | 0.1371 |
| | SJSA-1 | 0.09346 |
| | A549 | 2.815 |
| 222 | 786-O | 0.17 |
| | SJSA-1 | 0.1149 |
| | A549 | 3.353 |
| 223 | 786-O | 0.2745 |
| 224 | SJSA-1 | >3.000 |
| 225 | 786-O | >10 |
| | A549 | >30 |
| 226 | 786-O | 1.262 |
| | SJSA-1 | 1.157 |
| | A549 | 8.62 |
| 227 | SJSA-1 | >3.000 |
| 228 | A549 | >30.00 |
| | KP4 | >30.00 |
| 229 | A549 | >30.00 |
| | KP4 | >30.00 |
| 230 | A549 | 22 |
| | KP4 | >30.00 |
| 231 | 786-O | 0.2699 |
| 232 | 786-O | 0.025 |
| | SJSA-1 | 0.045 |
| | A431 | >10 |
| 233 | 786-O | 0.03369 |
| | SJSA-1 | 0.04433 |
| | A549 | 1.973 |
| | A431 | 4.8 |
| 234 | 786-O | 4.174 |
| | SJSA-1 | 3.915 |
| | A549 | 3.248 |
| | A431 | 8 |
| 235 | A549 | 7.18 |
| | KP4 | 0.041 |
| 236 | A549 | 17.54 |
| | KP4 | 1.204 |
| | A549 | 17.54 |
| | KP4 | >1.000 |
| 237 | A549 | 1.863 |
| | KP4 | 0.458 |
| 238 | KP4 | >10.00 |
| | A549 | >10.00 |
| 239 | A549 | 13.07 |
| | Panc 02.13 | 1.111 |
| | 143B | 1.125 |
| | H2228 | 0.01461 |
| | AsPC-1 | 0.06524 |
| | BxPC-3 | 0.9097 |
| | Mia PaCa-2 | 0.2593 |
| | PSN-1 | 0.1833 |
| | HPAC | 0.3207 |
| | Capan-1 | >1.000 |
| | Panc 12 | 0.05783 |
| | Panc 02.03 | 0.3936 |
| | Panc 6.03 | 0.1655 |
| | A549 | 5.7 |
| | KP4 | 0.004 |
| 240 | A673 | 0.007677 |
| | KHOS/NP | 0.00491 |
| | MG-63 | 0.03973 |
| | KSK-ES-1 | 0.02494 |

TABLE 25-continued

| Compound No. | Cell Line | $IC_{50}$ µM |
|---|---|---|
| | U-2 OS | 4.276 |
| | SJSA-1 | 0.009847 |
| | A673 | 0.05862 |
| | KHOS/NP | >3.000 |
| | MG-68 | >3.000 |
| | SK-EK-1 | 0.3104 |
| | SJSA-1 | 0.1206 |
| | HT1080 | 0.004819 |
| | 143B | 0.005224 |
| | KP4 | 0.04394 |
| | Panc 02.13 | 0.1203 |
| | H2228 | 0.001696 |
| | AsPC-1 | 0.00757 |
| | BxPC-3 | 0.0711 |
| | Mia PaCa-2 | 0.03512 |
| | PSN-1 | 0.01994 |
| | HPAC | 0.0286 |
| | Capan-1 | 0.1691 |
| | Panc 11 | 0.008549 |
| | Panc 02.03 | 0.06414 |
| | Panc 6.03 | 0.01692 |
| | A549 | 5.7 |
| | KP4 | 0.0015 |
| | PC-3 | 0.0039 |
| | DU145 | 0.0062 |
| | 22Rv1 | 0.0229 |
| | NCI-H660 | 0.0317 |
| | BPH1 | 0.2030 |
| | LNCaP | 0.5740 |
| | BM-1604 | >2 |
| | MDA PCa 2b | >2 |
| 250 | A549 | 2.399 |
| 251 | KP4 | 0.0065 |
| 257 | A549 | 8.145 |
| | KP4 | 10.37 |
| 259 | A549 | 7.97 |
| | KP4 | 0.179 |
| | KP4 | 0.212 |
| 263 | A549 | 6.22 |
| | KP4 | 10.41 |
| | Mia PaCa-2 | 5.57 |
| 264 | A549 | 4.45 |
| | KP4 | 8.69 |
| 265 | A549 | 25.4 |
| | KP4 | 0.16 |
| | Mia PaCa-2 | 0.26 |
| 14 | A549 | 1.96 |
| | KP4 | 0.058 |
| | Mia PaCa-2 | 0.14 |
| 272 | A549 | 6.45 |
| | KP4 | 3.99 |
| 273 | A549 | 3.23 |
| | KP4 | 1.71 |
| | Mia PaCa-2 | 0.01 |
| 274 | A549 | 11.78 |
| | KP4 | 4.54 |
| 277 | KP4 | 0.036 |
| 278 | 786-O | 0.22 |
| | SJSA-1 | 0.14 |
| 279 | 786-O | 0.58 |
| | SJSA-1 | 1 |
| 280 | 786-O | 0.21 |
| | SJSA-1 | 0.38 |
| 281 | 786-O | 0.206 |
| | SJSA-1 | 0.261 |
| 282 | 786-O | 0.223 |
| | SJSA-1 | 0.436 |
| 293 | 786-O | 0.067 |
| | SJSA-1 | 0.030 |

TABLE 26

| Compound No. | 786-O (IC$_{50}$, μM) Without Ferrostatin | 2 μM Ferrostatin | SJSA-1 (IC$_{50}$, μM) Without Ferrostatin | 2 μM Ferrostatin |
|---|---|---|---|---|
| 164 | 0.023 | 6.34 | 0.013 | 7.058 |
| 165 | 0.047 | 4.793 | 0.119 | 3.768 |
| 166 | 0.008 | 9.522 | 0.01 | >10.00 |
| 167 | 0.005 | 1.996 | 0.011 | 4.013 |
| 168 | 0.487 | 3.307 | 0.56 | >10.00 |
| 169 | 0.003 | 4.96 | 0.001 | >10.00 |
| 170 | 0.058 | 8.086 | 0.062 | 9.111 |
| 171 | 0.162 | >10.00 | 0.254 | >10.00 |
| 172 | 0.023 | 6.764 | 0.023 | 4.098 |
| 173 | 0.023 | 3.954 | 0.034 | 3.975 |
| 174 | 0.016 | 5.092 | 0.091 | 2.317 |
| 209 | 0.022 | >10.00 | 0.019 | 8.288 |
| 210 | 0.062 | >10.00 | 0.081 | 9.555 |
| 211 | 0.009 | 3.935 | 0.011 | 5.918 |
| 212 | 0.008 | 4.959 | 0.011 | 5.03 |
| 213 | 0.066 | 5.615 | 0.066 | 4.793 |
| 214 | 0.019 | 4.718 | 0.03 | 4.146 |
| 215 | 0.018 | 9.882 | 0.028 | 9.413 |

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. A compound of formula (I):

(I)

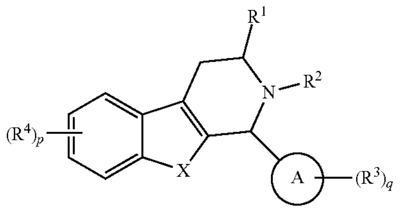

or a tautomer, stereoisomer, mixture of stereoisomers, isotopically enriched analog, or pharmaceutically acceptable salt thereof, wherein:

ring A is $C_4$-$C_{10}$cycloalkyl, heterocyclyl, aryl, or heteroaryl;

X is $NR^5$, O, or S;

p is 0, 1, 2, or 3;

q is 0, 1, 2, or 3;

$R^1$ is $C_1$-$C_6$alkyl, $C_2$-$C_6$alkenyl, $C_2$-$C_6$alkynyl, $C_1$-$C_6$haloalkyl, $C_3$-$C_{10}$cycloalkyl, —CN, —OH, —C(O)$OR^6$, —C(O)$N(R^7)_2$, —OC(O)$R^6$, —$S(O)_2R^8$, —$S(O)_2N(R^7)_2$, —S(O)$N(R^7)_2$, —S(O)$R^8$, —$NH_2$, —$NHR^8$, —$N(R^8)_2$, —$NO_2$, —$OR^8$, —$C_1$-$C_6$alkyl-OH, —$C_1$-$C_6$alkyl-$OR^8$, or —$Si(R^{15})_3$;

$R^2$ is —C(O)$R^9$;

each $R^3$ is independently halo, —CN, —OH, —$OR^8$, —$NH_2$, —$NHR^8$, —$N(R)_2$, —$S(O)_2R^8$, —S(O)$R^8$, —$S(O)_2N(R^7)_2$, —S(O)$N(R^7)_2$, —$NO_2$, —$Si(R^{12})_3$, —$SF_5$, —C(O)$OR^6$, —C(O)$N(R^7)_2$, —$NR^{12}$C(O)$R^8$, —$NR^{12}$C(O)$OR^8$, —OC(O)$N(R^7)_2$, —OC(O)$R^8$, —C(O)$R^6$, —OC(O)$CHR^8N(R^{12})_2$, $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_{10}$cycloalkyl, —$C_2$-$C_6$alkenyl$C_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, $C_1$-$C_6$alkylheteroaryl, or —$C_2$-$C_6$alkenylheteroaryl, wherein each $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_{10}$cycloalkyl, —$C_2$-$C_6$alkenyl$C_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, $C_1$-$C_6$alkylheteroaryl, or —$C_2$-$C_6$alkenylheteroaryl of $R^3$ is independently optionally substituted with one to three $R^{10}$;

each $R^4$ is independently halo, —CN, —OH, —$OR^8$, —$NH_2$, —$NHR^8$, —$N(R)_2$, —$S(O)_2R^8$, —S(O)$R^8$, —$S(O)_2N(R^7)_2$, —S(O)$N(R^7)_2$, —$NO_2$, —$Si(R^{15})_3$, —C(O)$OR^6$, —C(O)$N(R^7)_2$, —$NR^{12}$C(O)$R^8$, —OC(O)$R^8$, —C(O)$R^6$, —$NR^{12}$C(O)$OR^8$, —OC(O)$N(R^7)_2$, —OC(O)$CHR^8N(R^{12})_2$, $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_{10}$cycloalkyl, —$C_2$-$C_6$alkenyl$C_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, $C_1$-$C_6$alkylheteroaryl, or —$C_2$-$C_6$alkenylheteroaryl, wherein each $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_{10}$cycloalkyl, —$C_2$-$C_6$alkenyl$C_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, $C_1$-$C_6$alkylheteroaryl, or —$C_2$-$C_6$alkenylheteroaryl of $R^4$ is independently optionally substituted with one to three $R^{10}$;

$R^5$ is hydrogen or $C_1$-$C_6$alkyl;

each $R^6$ is independently hydrogen, $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_{10}$cycloalkyl, —$C_2$-$C_6$alkenyl$C_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, $C_1$-$C_6$alkylheteroaryl, or —$C_2$-$C_6$alkenylheteroaryl; wherein each $R^6$ is optionally independently further substituted with one to three $R^{11}$;

each $R^7$ is independently hydrogen, $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_6$cycloalkyl, —$C_2$-$C_6$alkenyl$C_3$-$C_6$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, —$C_1$-$C_6$alkylheteroaryl, or —$C_2$-$C_6$alkenylheteroaryl, or two $R^7$ together with the nitrogen atom to which they are attached form a 4- to 7- membered heterocyclyl, wherein each $R^7$ or ring formed thereby is optionally independently further substituted with one to three $R^{11}$;

each $R^8$ is independently $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_{10}$cycloalkyl, —$C_2$-$C_6$alkenyl$C_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, —$C_1$-$C_6$alkylheteroaryl, or —$C_2$-$C_6$alkenylheteroaryl, wherein each $R^8$ is optionally independently further substituted with one to three $R^{11}$;

$R^9$ is $C_2$alkynyl optionally substituted with one —$CH_3$;

each $R^{10}$ is independently halo, —CN, —$OR^{12}$, —$NO_2$, —$N(R^{12})_2$, —$S(O)R^{13}$, —$S(O)_2R^{13}$, —$S(O)N(R^{12})_2$, —$S(O)_2N(R^{12})_2$, —$Si(R^{12})_3$, —$C(O)R^{12}$, —$C(O)OR^{12}$, —$C(O)N(R^{12})_2$, —$NR^{12}C(O)R^{12}$, —$OC(O)R^{12}$, —$OC(O)OR^{12}$, —$OC(O)N(R^{12})_2$, —$NR^{12}C(O)OR^{12}$, —$OC(O)CHR^{12}N(R^{12})_2$, $C_1$-$C_6$alkyl, $C_1$-$C_6$haloalkyl, $C_2$-$C_6$alkenyl, $C_2$-$C_6$alkynyl, $C_3$-$C_{10}$cycloalkyl, heterocyclyl, aryl, or heteroaryl, wherein each $C_1$-$C_6$alkyl, $C_1$-$C_6$haloalkyl, $C_2$-$C_6$alkenyl, $C_2$-$C_6$alkynyl, $C_3$-$C_{10}$cycloalkyl, heterocyclyl, aryl, or heteroaryl of $R^{10}$ is optionally independently substituted with one to three $R^{11}$;

each $R^{11}$ is independently halo, —CN, —$OR^{12}$, —$NO_2$, —$N(R^{12})_2$, —$S(O)R^{13}$, —$S(O)_2R^{13}$, —$S(O)N(R^{12})_2$, —$S(O)_2N(R^{12})_2$, —$Si(R^{12})_3$, —$C(O)R^{12}$, —$C(O)OR^{12}$, —$C(O)N(R^{12})_2$, —$NR^{12}C(O)R^{12}$, —$OC(O)R^{12}$, —$OC(O)OR^{12}$, —$OC(O)N(R^{12})_2$, —$NR^{12}C(O)OR^{12}$, —$OC(O)CHR^{12}N(R^{12})_2$, $C_1$-$C_6$alkyl, $C_1$-$C_6$haloalkyl, $C_2$-$C_6$alkenyl, $C_2$-$C_6$alkynyl, $C_3$-$C_{10}$cycloalkyl, heterocyclyl, aryl, or heteroaryl;

each $R^{12}$ is independently hydrogen, $C_1$-$C_6$alkyl or $C_3$-$C_{10}$cycloalkyl;

each $R^{13}$ is independently $C_1$-$C_6$alkyl, or $C_3$-$C_{10}$cycloalkyl; and each $R^{15}$ is independently $C_1$-$C_6$alkyl, $C_2$-$C_6$alkenyl, aryl, heteroaryl, aryl$C_1$-$C_6$alkyl-, aryl$C_2$-$C_6$alkenyl-, heteroaryl$C_1$-$C_6$alkyl-, and heteroaryl$C_2$-$C_6$alkenyl-.

2. The compound of claim 1, or a tautomer, stereoisomer, mixture of stereoisomers, isotopically enriched analog, or pharmaceutically acceptable salt thereof, represented by formula (II):

(II)

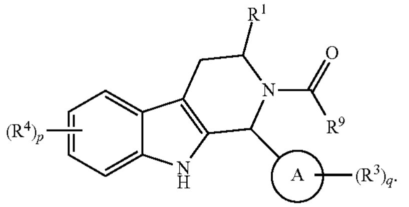

3. The compound of claim 1, or a tautomer, stereoisomer, mixture of stereoisomers, isotopically enriched analog, or pharmaceutically acceptable salt thereof, represented by formula (III):

(III)

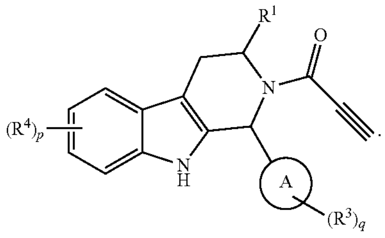

4. The compound of claim 1, wherein ring A is $C_4$-$C_{10}$cycloalkyl.

5. The compound of claim 1, wherein ring A is heterocyclyl.

6. The compound of claim 1, wherein ring A is aryl.

7. The compound of claim 1, wherein ring A is heteroaryl.

8. The compound of claim 1, wherein $R^1$ is $C_1$-$C_6$alkyl, $C_2$-$C_6$alkenyl, $C_2$-$C_6$alkynyl, $C_1$-$C_6$haloalkyl, $C_3$-$C_{10}$cycloalkyl, —CN, —$C(O)OR^6$, —$C(O)N(R^7)_2$, —$NH_2$, —$NHR^8$, —$N(R^8)_2$, —OH, —$OR^8$, —$C_1$-$C_6$alkyl-OH, or —$C_1$-$C_6$alkyl-$OR^8$.

9. The compound of claim 1, wherein $R^1$ is $C_1$-$C_6$alkyl, $C_2$-$C_6$alkenyl, $C_2$-$C_6$alkynyl, $C_1$-$C_6$haloalkyl, $C_3$-$C_{10}$cycloalkyl, —$NH_2$, —$NHR^8$, —$N(R^8)_2$, —OH, —$OR^8$, —$C_1$-$C_6$alkyl-OH, or —$C_1$-$C_6$alkyl-$OR^8$.

10. The compound of claim 1, wherein $R^1$ is $C_1$-$C_6$alkyl.

11. The compound of claim 1, or a tautomer, stereoisomer, mixture of stereoisomers, isotopically enriched analog, or pharmaceutically acceptable salt thereof, represented by formula (IV):

(IV)

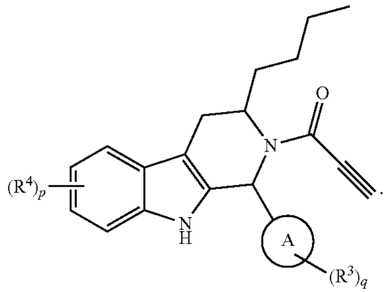

12. The compound of claim 1, wherein each $R^4$ is independently halo, —CN, —OH, —$OR^8$, —$NH_2$, —$NHR^8$, —$N(R)_2$, —$S(O)_2R^8$, —$S(O)R^8$, —$S(O)_2N(R^7)_2$, —$S(O)N(R^7)_2$, —$NO_2$, —$Si(R^{15})_3$, —$C(O)OR^6$, —$C(O)N(R^7)_2$, —$NR^{12}C(O)R^8$, —$OC(O)R^8$, —$C(O)R^6$, $C_1$-$C_6$alkyl, $C_2$-$C_6$alkenyl, $C_2$-$C_6$alkynyl, or $C_3$-$C_{10}$cycloalkyl, wherein each $C_1$-$C_6$alkyl, $C_2$-$C_6$alkenyl, $C_2$-$C_6$alkynyl, or $C_3$-$C_{10}$cycloalkyl of $R^4$ is independently optionally substituted with one to three $R^{10}$.

13. The compound of claim 1, wherein each $R^4$ is independently halo, —CN, —OH, —$OR^8$, $C_1$-$C_6$alkyl, $C_2$-$C_6$alkynyl, or $C_3$-$C_{10}$cycloalkyl, wherein each $C_1$-$C_6$alkyl, $C_2$-$C_6$alkynyl, or $C_3$-$C_{10}$cycloalkyl of $R^4$ is independently optionally substituted with one to three $R^{10}$.

14. The compound of claim 1, wherein p is 0.

15. The compound of claim 1, wherein q is 0.

16. The compound of claim 1, wherein p is 1, 2, or 3.

17. The compound of claim 1, wherein q is 2 or 3.

18. A pharmaceutical composition comprising a compound, or a tautomer, stereoisomer, mixture of stereoisomers, isotopically enriched analog, or pharmaceutically acceptable salt thereof, of claim 1, and a pharmaceutically acceptable carrier.

19. A compound of formula (V):

(V)

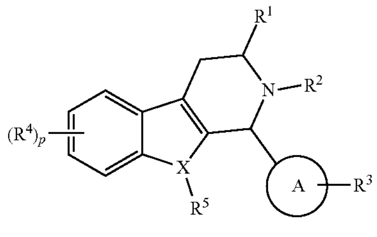

or an enantiomer or pharmaceutically acceptable salt thereof, wherein:

X is N, O, or S;

A is a 4- to 7-membered cycloalkyl, 4- to 7-membered heterocyclyl, aryl, heteroaryl, or bridged bicyclic ring having 0-2 heteroatoms independently selected from nitrogen, oxygen, and sulfur;

$R^1$ is H, $C_1$—$C_6$alkyl, —$C_1$—$C_6$alkylhalo, —C(O)OR$^6$, —C(O)N(R$^7$)$_2$, —OC(O)R$^6$, —SO$_2$R$^8$, —SOR$^8$, NO$_2$, —OR$^8$, —$C_1$—$C_6$alkyl—OR$^{12}$, or —Si(R$^{15}$)$_3$;

$R^2$ is —C(O)R$^9$;

$R^3$ is H, halo, —C(O)OR$^{10}$, —C(O)N(R$^{11}$)$_2$, —OC(O)R$^{10}$, —$C_0$—$C_6$alkyl$C_3$—$C_8$cycloalkyl, —$C_0$-$C_6$alkylheterocyclyl, —N(R$^{11}$)$_2$, —SO$_2$R$^8$, —SOR$^8$, —NO$_2$, or —Si(R$^{15}$)$_3$;

$R^4$ is independently halo, CN, —NH$_2$, —SO$_2$, $C_1$—$C_8$alkyl, —OR$^{12,}$—$C_{1—C6}$alkyl-OR$^{12}$, —$C_1$—$C_6$alkyl—NR$^{12}$, or —OC(O)R$^{12}$;

$R^5$ is H, $C_1$—$C_6$alkyl, or is absent when X is S or O;

p is 0, 1, 2, or 3;

each $R^6$ is independently $C_1$—$C_6$alkyl, $C_3$—$C_6$alkyl, $C_2$—$C_6$alkynyl, $C_2$—$C_6$alkynyl, $C_3$—$C_6$cycloalkyl, heterocyclyl, aryl, heteroaryl, $C_3$—$C_6$cycloalkyl$C_1$—$C_6$alkyl-, $C_3$—$C_6$cycloalkyl$C_2$—$C_6$alkenyl-, heterocyclyl$C_1$—$C_6$alkyl-, heterocyclyl$C_2$—$C_6$alkenyl-, aryl$C_1$—$C_6$alkyl-, aryl$C_2$—$C_6$alkenyl-, heteroaryl$C_{1—C6}$alkyl-, heteroaryl$C_2$—$C_6$alkenyl-, (R$^{11}$)$_2$N$C_1$—$C_6$alkyl—, or (R$^{11}$)$_2$N$C_2$—$C_6$alkenyl-;

each $R^7$ is independently H, $C_1$—$C_6$alkyl, $C_2$—$C_6$alkenyl, $C_3$—$C_6$cycloalkyl, heterocyclyl, aryl, heteroaryl, $C_3$—$C_6$cycloalkyl$C_1$—$C_6$alkyl-, $C_3$—$C_6$cycloalkyl$C_2$—$C_6$alkenyl-, heterocyclyl$C_1$—$C_6$alkyl-, heterocyclyl$C_2$—$C_6$alkenyl-, aryl$C_1$—$C_6$alkyl-, aryl$C_2$—$C_6$alkenyl-, heteroaryl$C_1$—$C_6$alkyl-, heteroaryl$C_2$—$C_6$alkenyl-, (R$^{11}$)$_2$N$C_1$—$C_6$alkyl-, (R$^{11}$)$_2$N$C_2$—$C_6$alkenyl-, R$^{12}$O—$C_1$—$C_6$alkyl-, or R$^{12}$O(O)C—$C_1$—$C_6$alkyl-, or two $R^7$ together with the nitrogen atom to which they are attached form a 4- to 7-membered heterocyclyl, wherein the heterocyclyl formed by the two $R^7$ groups is optionally substituted with OH, halo, $C_1$—$C_6$alkyl, a 4- to 6-membered heterocyclyl, or (R$^{11}$)$_2$N-, wherein the 4- to 6-membered heterocyclyl when containing 2 or more N atoms is optionally substituted with an N-protecting group;

each $R^8$ is independently $C_1$—$C_6$alkyl, $C_3$—$C_6$alkyl, $C_2$—$C_6$alkenyl, $C_2$—$C_6$alkynyl, $C_3$—$C_6$cycloalkyl, heterocyclyl, aryl, heteroaryl, $C_3$—$C_6$cycloalkyl$C_1$—$C_6$alkyl-, $C_3$—$C_6$cycloalkyl$C_{2—C6}$alkenyl-, heterocyclyl$C_1$—$C_6$alkyl-, heterocyclyl$C_2$—$C_6$alkenyl-, aryl$C_1$—$C_6$alkyl-, aryl$C_2$—$C_6$alkenyl-, heteroaryl$C_1$—$C_6$alkyl-, heteroaryl$C_2$—$C_6$alkenyl-, adamantyl, adamantyl$C_1$—$C_6$aliphatic-, (R$^{11}$)$_2$N$C_1$—$C_6$alkyl-, or (R$^{11}$)$_2$N-;

$R^9$ is $C_2$alkynyl;

$R^{10}$ is $C_1$—$C_6$alkyl, $C_2$—$C_6$alkyl, $C_2$—$C_6$alkenyl, $C_2$—$C_6$alkynyl, $C_3$—$C_6$cycloalkyl, heterocyclyl, aryl, heteroaryl, $C_3$—$C_6$cycloalkyl$C_1$—$C_6$alkyl-, $C_3$—$C_6$cycloalkyl$C_2$—$C_6$alkenyl-, heterocyclyl$C_1$—$C_6$alkyl-, heterocyclyl$C_2$—$C_6$alkenyl-, aryl$C_1$—$C_6$alkyl-, aryl$C_2$—$C_6$alkenyl-, heteroaryl$C_1$—$C_6$alkyl-, heteroaryl$C_2$—$C_6$alkenyl-, adamantyl, adamantyl$C_1$—$C_6$aliphatic-, (R$^{11}$)$_2$N$C_1$—$C_6$alkyl-, (R$^{11}$)$_2$N$C_2$—$C_6$alkenyl-, R$^{13}$(NH$_2$)CH-, R$^{14}$$C_0$—$C_6$alkyl-, or (R$^{15}$)$_3$Si$C_0$—$C_6$alkyl-;

each $R^{11}$ is independently H, $C_1$—$C_6$alkyl, $C_2C_6$alkenyl, $C_3$—$C_6$cycloalkyl, heterocyclyl, aryl, heteroaryl, $C_3$—$C_6$cycloalkyl$C_1$—$C_{C6}$alkyl-, $C_3$—$C_6$cycloalkyl$C_2$—$C_6$alkenyl-, heterocyclyl$C_1$—$C_6$alkyl-, heterocyclyl$C_2$—$C_6$alkenyl-, aryl$C_1C_6$alkyl-, aryl$C_2$—$C_6$alkenyl-, heteroaryl$C_1$—$C_6$alkyl-, heteroaryl$C_2$—$C_6$alkenyl-, adamantyl, adamantyl$C_{1—C6}$aliphatic-, R$^{12}$O—$C_1$—$C_6$alkyl-, (R$^{11}$)$_2$N$C_1$—$C_6$alkyl-, (R$^{11}$)$_2$N$C_2$—$C_6$alkenyl-, R$^{12}$O(O)C—$C_1$—$C_6$alkyl—, R$^{13}$(NH$_2$)CH—, R$^{14}$$C_0$—$C_6$alkyl—, (R$^{15}$)$_3$Si$C_0$—$C_6$alkyl-, or an N-protecting group, or two $R^{11}$ together with the nitrogen atom to which they are attached form a 4- to 7-membered heterocyclyl, wherein the heterocyclyl formed by the two $R^{11}$ groups has optionally 0, 1, or 2 additional heteroatoms selected from nitrogen, oxygen, and sulfur, and the heterocyclyl is optionally substituted with OH, halo, $C_1C_6$alkyl, $C_1$—$C_6$alkyl-O(O)C—, (R$^{11}$)$_2$N—, or a 4- to 6-membered heterocyclyl, wherein the 4- to 6-membered heterocyclyl is optionally substituted with OH, halo, —NH$_2$, or $C_1$—$C_6$alkyl, or when containing 2 or more N atoms is optionally substituted with an N- protecting group;

each $R^{12}$ is independently H or $C_1$—$C_6$alkyl;

each $R^{13}$ is independently H, $C_1$—$C_6$alkyl, $C_3$—$C_6$cycloalkyl, heterocyclyl, aryl, heteroaryl, $C_3$—$C_6$cycloalkyl$C_1$—$C_6$alkyl-, $C_3$—$C_6$cycloalkyl$C_2$—$C_6$alkenyl-, heterocyclyl$C_1$—$C_6$alkyl-, heterocyclyl$C_2$—$C_6$alkenyl-, aryl$C_1$—$C_6$alkyl-, aryl$C_2$—$C_6$alkenyl-, heteroaryl$C_1$—$C_6$alkyl-, heteroaryl$C_2$—$C_6$alkenyl-, adamantyl, adamantyl$C_1$—$C_6$aliphatic-, or an N protecting group;

$R^{14}$ is a bridged bicyclic ring having 0-2 heteroatoms independently selected from nitrogen, oxygen, and sulfur; and each $R^{15}$ is independently $C_1$—$C_6$alkyl, $C_2$—$C_6$alkenyl, aryl, heteroaryl, aryl$C_1$—$C_6$alkyl-, aryl$C_2$—$C_6$alkenyl-, heteroaryl$C_1$—$C_6$alkyl-, or heteroaryl$C_2$—$C_6$alkenyl-;

wherein each $C_1$—$C_6$alkyl, —$C_3$—$C_6$cycloalkyl, heterocyclyl, aryl, heteroaryl, or bridged bicyclic ring, by itself or attached to another moiety, are independently optionally substituted with 1-3 substituents selected from the group consisting of OH, halo, —NH$_2$, $C_1$—$C_6$alkyl, $C_1$—$C_6$alkyl—O—, R$^{12}$O—$C_1$—$C_6$alkyl(O)C—, and R$^{12}$O(O)C—.

20. The compound of claim 19, having the structure formula (Va):

(Va)

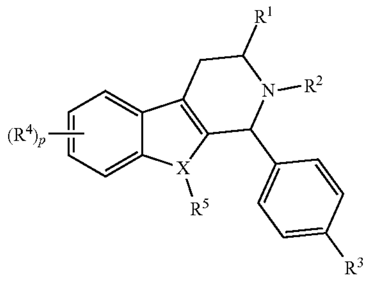

or an enantiomer or pharmaceutically acceptable salt thereof, wherein:

X is N, O, or S;

$R^1$ is $C_1$—$C_6$alkyl, —$C_1$—$C_6$alkylhalo, —C(O)OR$^6$, —C(O)N(R$^7$)$_2$, —OC(O)R$^6$, —SO$_2$R$^8$, —SOR$^8$, NO$_2$, —OR$^8$, —$C_1$—$C_6$alkyl—OR$^{12}$, or —Si(R$^{15}$)$_3$;

$R^2$ is —C(O)$R^9$;

$R^3$ is —C(O)O$R^{10}$, —C(O)N($R^{11}$)$_2$, —OC(O)$R^{10}$, —$C_0$—$C_6$alkyl$C_3$—$C_8$cycloalkyl, —$C_0$—$C_6$alkylheterocyclyl, —N($R^{11}$)$_2$, —$SO_2R^8$, —SO$R^8$, —$NO_2$, or —Si($R^{15}$)$_3$;

$R^4$ is independently halo, CN, —$NH_2$, —$SO_2$, $C_1$—$C_8$alkyl, —O$R^{12}$, —$C_1$—$C_6$alkyl—O$R^{12}$, —$C_1$—$C_6$alkyl—N$R^{12}$, or —OC(O)$R^{12}$;

$R^5$ is H, $C_1$—$C_6$alkyl, or is absent when X is S or O;

p is 0, 1, 2, or 3;

each $R^6$ is independently $C_1$—$C_6$alkyl, $C_3$—$C_6$alkyl, $C_2$—$C_6$alkenyl, $C_2$—$C_6$alkynyl, $C_3$—$C_6$cycloalkyl, heterocyclyl, aryl, heteroaryl, $C_3$—$C_6$cycloalkyl$C_1$—$C_6$alkyl-, $C_3$—$C_6$cycloalkyl$C_2$—$C_6$alkenyl-, heterocyclyl$C_1$—$C_6$alkyl-, heterocyclyl$C_2$—$C_6$alkenyl-, aryl$C_1$—$C_6$alkyl-, aryl$C_2$—$C_6$alkenyl-, heteroaryl$C_1$—$C_6$alkyl-, heteroaryl$C_2$-$C_6$alkenyl-, ($R^{11}$)$_2$N$C_1$—$C_6$alkyl-, or ($R^{11}$)$_2$N$C_2$—$C_6$alkenyl-;

each $R^7$ is independently H, $C_1$—$C_6$alkyl, $C_2$—$C_6$alkenyl, $C_3$—$C_6$cycloalkyl, heterocyclyl, aryl, heteroaryl, $C_3$—$C_6$cycloalkyl$C_1$—$C_6$alkyl-, $C_3$—$C_6$cycloalkyl$C_2$—$C_6$alkenyl-, heterocyclyl$C_1$—$C_6$alkyl-, heterocyclyl$C_2$—$C_6$alkenyl-, aryl$C_1$—$C_6$alkyl-, aryl$C_2$—$C_6$alkenyl-, heteroaryl$C_1$—$C_6$alkyl-, heteroaryl$C_2$—$C_6$alkenyl-, ($R^{11}$)$_2$N$C_1$—$C_6$alkyl-, ($R^{11}$)$_2$N$C_2$—$C_6$alkenyl-, $R^{12}$O—$C_1$—$C_6$alkyl-, or $R^{12}$O(O)C—$C_1$—$C_6$alkyl-, or two $R^7$ together with the nitrogen atom to which they are attached form a 4- to 7-membered heterocyclyl, wherein the heterocyclyl formed by the two $R^7$ groups is optionally substituted with OH, halo, $C_1$—$C_6$alkyl, a 4- to 6-membered heterocyclyl, or ($R^{11}$)$_2$N—, wherein the 4- to 6-membered heterocyclyl when containing 2 or more N atoms is optionally substituted with an N-protecting group;

each $R^8$ is independently $C_1$—$C_6$alkyl, $C_3$—$C_6$alkyl, $C_2$—$C_6$alkenyl, $C_2$—$C_6$alkynyl, $C_3$—$C_6$cycloalkyl, heterocyclyl, aryl, heteroaryl, $C_3$—$C_6$cycloalkyl$C_1$—$C_6$alkyl-, $C_3$—$C_6$cycloalkyl$C_2$—$C_6$alkenyl-, heterocyclyl$C_1$—$C_6$alkyl-, heterocyclyl$C_2$—$C_6$alkenyl-, aryl$C_1$—$C_6$alkyl-, aryl$C_2$—$C_6$alkenyl-, heteroaryl$C_1$—$C_6$alkyl-, heteroaryl$C_2$—$C_6$alkenyl-, adamantyl, adamantyl$C_1$—$C_6$aliphatic-, ($R^{11}$)$_2$N$C_1$—$C_6$alkyl-, or ($R^{11}$)$_2$N-;

$R^9$ is $C_2$alkynyl;

$R^{10}$ is $C_1$—$C_6$alkyl, $C_2$—$C_6$alkyl, $C_2$—$C_6$alkenyl, $C_2$—$C_6$alkynyl, $C_3$—$C_6$cycloalkyl, heterocyclyl, aryl, heteroaryl, $C_3$—$C_6$cycloalkyl$C_1$—$C_6$alkyl-, $C_3$—$C_6$cycloalkyl$C_2$—$C_6$alkenyl-, heterocyclyl$C_1$—$C_6$alkyl-, heterocyclyl$C_2$—$C_6$alkenyl-, aryl$C_1$—$C_6$alkyl-, aryl$C_2$—$C_6$alkenyl-, heteroaryl$C_1$—$C_6$alkyl-, heteroaryl$C_2$—$C_6$alkenyl-, adamantyl, adamantyl$C_1$—$C_6$aliphatic-, ($R^{11}$)$_2$N$C_1$—$C_6$alkyl-, ($R^{11}$)$_2$N$C_2$—$C_6$alkenyl-, $R^{13}$($NH_2$)CH-, $R^{14}C_{C0—C6}$alkyl-, or ($R^{15}$)$_3$Si $C_0$—$C_6$alkyl-;

each $R^{11}$ is independently H, $C_1$—$C_6$alkyl, $C_2$—$C_6$alkenyl, $C_3$—$C_6$cycloalkyl, heterocyclyl, aryl, heteroaryl, $C_3$—$C_6$cycloalkyl$C_1$—$C_6$alkyl-, $C_3$—$C_6$cycloalkyl$C_2$—$C_6$alkenyl-, heterocyclyl$C_1$—$C_6$alkyl-, heterocyclyl$C_2$—$C_6$alkenyl-, aryl$C_1$—$C_6$alkyl-, aryl$C_2$—$C_6$alkenyl-, heteroaryl$C_1$—$C_6$alkyl-, heteroaryl$C_2$—$C_6$alkenyl-, adamantyl, adamantyl$C_1$—$C_6$aliphatic-, $R^{12}$O—$C_1$—$C_6$alkyl-, ($R^{11}$)$_2$N$C_1$—$C_6$alkyl-, ($R^{11}$)$_2$N$C_2$—$C_6$alkenyl-, $R^{12}$O(O)C—$C_1$—$C_6$alkyl- , $R^{13}$($NH_2$)CH—, $R^{14}C_0$—$C_6$alkyl-, ($R^{15}$)$_3$Si$C_0$—$C_6$alkyl-, or an N-protecting group, or two $R^{11}$ together with the nitrogen atom to which they are attached form a 4- to 7-membered heterocyclyl, wherein the heterocyclyl formed by the two $R^{11}$ groups has optionally 0, 1, or 2 additional heteroatoms selected from nitrogen, oxygen, and sulfur, and the heterocyclyl is optionally substituted with OH, halo, $C_1$—$C_6$alkyl, $C_1$—$C_6$alkyl—O(O)C-, ($R^{11}$)$_2$N-, or a 4- to 6-membered heterocyclyl, wherein the 4- to 6-membered heterocyclyl is optionally substituted with OH, halo, —$NH_2$, or $C_1$—$C_6$alkyl, or when containing 2 or more N atoms is optionally substituted with an N-protecting group;

each $R^{12}$ is independently H or $C_1$—$C_6$alkyl;

each $R^{13}$ is independently H, $C_1$—$C_6$alkyl, $C_3$—$C_6$cycloalkyl, heterocyclyl, aryl, heteroaryl, $C_3$—$C_6$cycloalkyl$C_1$—$C_6$alkyl-, $C_3$—$C_6$cycloalkyl$C_2$—$C_6$alkenyl-, heterocyclyl$C_1$—$C_6$alkyl-, heterocyclyl$C_2$—$C_6$alkenyl-, aryl$C_1$—$C_6$alkyl-, aryl$C_2$—$C_6$alkenyl-, heteroaryl$C_1$—$C_6$alkyl-, heteroaryl$C_2$—$C_6$alkenyl-, adamantyl, adamantyl$C_1$—$C_6$aliphatic-, or an N protecting group;

$R^{14}$ is a bridged bicyclic ring having 0-2 heteroatoms independently selected from nitrogen, oxygen, and sulfur; and each $R^{15}$ is independently $C_1$—$C_6$alkyl, $C_2$—$C_6$alkenyl, aryl heteroaryl, aryl$C_1$—$C_6$alkyl-, aryl$C_2$—$C_6$alkenyl-, heteroaryl$C_1$—$C_6$alkyl-, or heteroaryl$C_2$—$C_6$alkenyl-;

wherein each $C_1$—$C_6$alkyl, —$C_3$—$C_6$cycloalkyl, heterocyclyl, aryl, heteroaryl, or bridged bicyclic ring, by itself or attached to another moiety, are independently optionally substituted with 1-3 substituents selected from the group consisting of OH, halo, —$NH_2$, $C_1$—$C_6$alkyl, $C_1$—$C_6$alkyl—O—, $R^{12}$O—$C_1$—$C_6$alkyl(O)C—, and $R^{12}$O(O)C—.

21. The compound of claim 19, having a structure of formula (Vg):

(Vg)

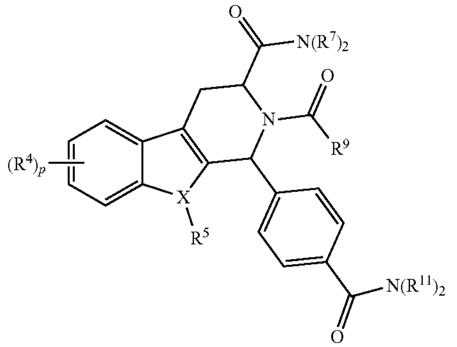

or an enantiomer or pharmaceutically acceptable salt thereof, wherein:

X is N, O, or S;

$R^4$ is independently halo, CN, —$NH_2$, —$SO_2$, $C_1$—$C_8$alkyl, —O$R^{12}$, —$C_1$—$C_6$alkyl-O$R^{12}$, —$C_1$—$C_6$alkyl-N$R^{12}$, or —OC(O)$R^{12}$;

$R^5$ is H, $C_1$—$C_6$alkyl, or is absent when X is S or O;

p is 0, 1, 2, or 3;

each $R^7$ is independently H, $C_1$—$C_6$alkyl, $C_2$—$C_6$alkenyl, $C_3$—$C_6$cycloalkyl, heterocyclyl, aryl, heteroaryl, $C_3$—$C_6$cycloalkyl$C_1$—$C_6$alkyl-, $C_3$—$C_6$cycloalkyl$C_2$—$C_6$alkenyl-, heterocyclyl$C_1$—$C_6$alkyl-, heterocyclyl$C_2$—$C_6$alkenyl-, aryl$C_1$—$C_6$alkyl-, aryl$C_2$—$C_6$alkenyl-, heteroaryl$C_1$—$C_6$alkyl-, heteroaryl$C_2$—$C_6$alkenyl-, ($R^{11}$)$_2$N$C_1$—$C_6$alkyl-, $(R^{11})_2NC_2$—$C_6$alkenyl-, $R^{12}O$—$C_1$—$C_6$alkyl-, or $R^{12}O(O)C$—$C_1$—$C_6$alkyl-, or two $R^7$ together with the nitrogen atom to which they are attached form a 4- to 7-membered heterocyclyl, wherein the heterocyclyl formed by the two $R^7$ groups is optionally substituted with OH, halo, $C_1$—$C_6$alkyl, a 4- to 6-membered heterocyclyl, or $(R^{11})_2N$—, wherein the 4- to 6-membered heterocyclyl when containing 2 or more N atoms is optionally substituted with an N-protecting group;

$R^9$ is $C_2$alkynyl;

each $R^{11}$ is independently H, $C_1$—$C_6$alkyl, $C_2$—$C_6$alkenyl, $C_3$—$C_6$cycloalkyl, heterocyclyl, aryl, heteroaryl, $C_3$—$C_6$cycloalkyl$C_1$—$C_6$alkyl-, $C_3$—$C_6$cycloalkyl$C_2$—$C_6$alkenyl-, heterocyclyl$C_1$—$C_6$alkyl-, heterocyclyl$C_2$—$C_6$alkenyl-, aryl$C_1$—$C_6$alkyl-, aryl$C_2$—$C_6$alkenyl-, heteroaryl$C_1$—$C_6$alkyl-, heteroaryl$C_2$—$C_6$alkenyl-, adamantyl, adamantyl$C_1$—$C_6$aliphatic-, $R^{12}O$—$C_1$—$C_6$alkyl-, $(R^{11})_2NC_1$—$C_6$alkyl-, $(R^{11})_2NC_2$—$C_6$alkenyl-, $R^{12}O(O)C$—$C_1$—$C_6$alkyl- , $R^{13}(NH_2)CH$—, $R^{14}C_0$—$C_6$alkyl-, $(R^{15})_3SiC_0$—$C_6$alkyl-, or an N-protecting group, or two $R^{11}$ together with the nitrogen atom to which they are attached form a 4- to 7-membered heterocyclyl, wherein the heterocyclyl formed by the two $R^{11}$ groups has optionally 0, 1, or 2 additional heteroatoms selected from nitrogen, oxygen, and sulfur, and the heterocyclyl is optionally substituted with OH, halo, $C_1$—$C_6$alkyl, $C_1$—$C_6$alkyl—O(O)C—, $(R^{11})_2N$—, or a 4- to 6-membered heterocyclyl, wherein the 4- to 6-membered heterocyclyl is optionally substituted with OH, halo, —$NH_2$, or $C_1$—$C_6$alkyl, or when containing 2 or more N atoms is optionally substituted with an N-protecting group;

each $R^{12}$ is independently H or $C_1$—$C_6$alkyl;

each $R^{13}$ is independently H, $C_1$—$C_6$alkyl, $C_3$—$C_6$cycloalkyl, heterocyclyl, aryl, heteroaryl, $C_3$—$C_6$cycloalkyl$C_1$—$C_6$alkyl-, $C_3$—$C_6$cycloalkyl$C_2$—$C_6$alkenyl-, heterocyclyl$C_1$—$C_6$alkyl-, heterocyclyl$C_2$—$C_6$alkenyl-, aryl$C_1$—$C_6$alkyl-, aryl$C_2$—$C_6$alkenyl-, heteroaryl$C_1$—$C_6$alkyl-, heteroaryl$C_2$—$C_6$alkenyl-, adamantyl, adamantyl$C_1$—$C_6$aliphatic-, or an N protecting group;

$R^{14}$ is a bridged bicyclic ring having 0-2 heteroatoms independently selected from nitrogen, oxygen, and sulfur; and each $R^{15}$ is independently $C_1$—$C_6$alkyl, $C_2$—$C_6$alkenyl, aryl, heteroaryl, aryl$C_1$—$C_6$alkyl-, aryl$C_2$—$C_6$alkenyl-, heteroaryl$C_1$—$C_6$alkyl-, or heteroaryl$C_2$—$C_6$alkenyl-;

wherein each $C_1$—$C_6$alkyl, —$C_3$—$C_6$cycloalkyl, heterocyclyl, aryl, heteroaryl, or bridged bicyclic ring, by itself or attached to another moiety, are independently optionally substituted with 1-3 substituents selected from the group consisting of OH, halo, —$NH_2$, $C_1$—$C_6$alkyl, $C_1$—$C_6$alkyl—O—, $R^{12}O$—$C_1$—$C_6$alkyl(O)C—, and $R^{12}O(O)C$—.

22. The compound of claim 19, having as structure of formula (Vi):

(Vi)

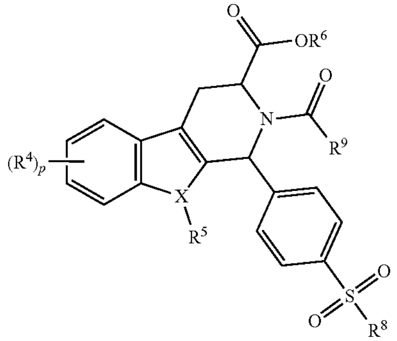

or an enantiomer or pharmaceutically acceptable salt thereof, wherein:

X is N, O, or S;

$R^4$ is independently halo, CN, —$NH_2$, —$SO_2$, $C_1$—$C_8$alkyl, —$OR^{12}$, —$C_1$—$C_6$alkyl-$OR^{12}$, —$C_1$—$C_6$alkyl-$NR^{12}$, or —$OC(O)R^{12}$;

$R^5$ is H, $C_1$—$C_6$alkyl, or is absent when X is S or O;

p is 0, 1, 2, or 3;

$R^6$ is independently $C_1$—$C_6$alkyl, $C_3$—$C_6$alkyl, $C_2$—$C_6$alkenyl, $C_2$—$C_6$alkynyl, $C_3$—$C_6$cycloalkyl, heterocyclyl, aryl, heteroaryl, $C_3$—$C_6$cycloalkyl$C_1$—$C_6$alkyl-, $C_3$—$C_6$cycloalkyl$C_2$—$C_6$alkenyl-, heterocyclyl$C_1$—$C_6$alkyl-, heterocyclyl$C_2$—$C_6$alkenyl-, aryl$C_1$—$C_6$alkyl-, aryl$C_2$—$C_6$alkenyl-, heteroaryl$C_1$—$C_6$alkyl-, heteroaryl$C_2$—$C_6$alkenyl-, $(R^{11})_2NC_{1-C6}$alkyl-, or $(R^{11})_2NC_2$—$C_6$alkenyl-;

$R^8$ is independently $C_1$—$C_6$alkyl, $C_3$—$C_6$alkyl, $C_2$—$C_6$alkenyl, $C_2$—$C_6$alkynyl, $C_3$—$C_6$cycloalkyl, heterocyclyl, aryl, heteroaryl, $C_3$—$C_6$cycloalkyl$C_1$—$C_6$alkyl-, $C_3$—$C_6$cycloalkyl$C_2$—$C_6$alkenyl-, heterocyclyl$C_1$—$C_6$alkyl-, heterocyclyl$C_2$—$C_6$alkenyl-, aryl$C_1$—$C_6$alkyl-, aryl$C_2$—$C_6$alkenyl-, heteroaryl$C_1$—$C_6$alkyl-, heteroaryl$C_2$—$C_6$alkenyl-, adamantyl, adamantyl$C_1$—$C_6$aliphatic-, $(R^{11})_2NC_1$—$C_6$alkyl-, or $(R^{11})_2N$—;

$R^9$ is $C_2$alkynyl;

each $R^{11}$ is independently H, $C_1$—$C_6$alkyl, $C_2$—$C_6$alkenyl, $C_3$—$C_6$cycloalkyl, heterocyclyl, aryl, heteroaryl, $C_3$—$C_6$cycloalkyl$C_1$—$C_6$alkyl-, $C_3$—$C_6$cycloalkyl$C_2$—$C_6$alkenyl-, heterocyclyl$C_1$—$C_6$alkyl-, heterocyclyl$C_2$—$C_6$alkenyl-, aryl$C_1$—$C_6$alkyl-, aryl$C_2$—$C_6$alkenyl-, heteroaryl$C_1$—$C_6$alkyl-, heteroaryl$C_2$—$C_6$alkenyl-, adamantyl, adamantyl$C_1$—$C_6$aliphatic-, $R^{12}O$—$C_1$—$C_6$alkyl-, $(R^{11})_2NC_1$—$C_6$alkyl-, $(R^{11})_2NC_2$—$C_6$alkenyl-, $R^{12}O(O)C$—$C_1$—$C_6$alkyl- , $R^{13}(NH_2)CH$—, $R^{14}C_0$—$C_6$alkyl-, $(R^{15})_3SiC_0$—$C_6$alkyl-, or an N-protecting group, or two $R^{11}$ together with the nitrogen atom to which they are attached form a 4- to 7-membered heterocyclyl, wherein the heterocyclyl formed by the two $R^{11}$ groups has optionally 0, 1, or 2 additional heteroatoms selected from nitrogen, oxygen, and sulfur, and the heterocyclyl is optionally substituted with OH, halo, $C_1$—$C_6$alkyl, $C_1$—$C_6$alkyl-O(O)C—, $(R^{11})_2N$—, or a 4- to 6-membered heterocyclyl, wherein the 4- to 6-membered heterocyclyl is optionally substituted with OH, halo, —$NH_2$, or $C_1$—$C_6$alkyl, or when containing 2 or more N atoms is optionally substituted with an N-protecting group;

each $R^{12}$ is independently H or $C_1$—$C_6$alkyl;

each $R^{13}$ is independently H, $C_1$—$C_6$alkyl, $C_3$—$C_6$cycloalkyl, heterocyclyl, aryl, heteroaryl, $C_3$—$C_6$cycloalkyl$C_1$—$C_6$alkyl, $C_3$—$C_6$cycloalkyl$C_2$—$C_6$alkenyl-, heterocyclyl$C_1$—$C_6$alkyl-, heterocyclyl$C_2$—$C_6$alkenyl-, aryl$C_1$—$C_6$alkyl-, aryl$C_2$—$C_6$alkenyl-, heteroaryl$C_1$—$C_6$alkyl-, heteroaryl$C_2$—$C_6$alkenyl-, adamantyl, adamantyl$C_1$—$C_6$aliphatic-, or an N protecting group;

$R^{14}$ is a bridged bicyclic ring having 0-2 heteroatoms independently selected from nitrogen, oxygen, and sulfur; and $R^{15}$ is independently $C_1$—$C_6$alkyl, $C_2$—$C_6$alkenyl, aryl, heteroaryl, aryl$C_1$—$C_6$alkyl-, aryl$C_2$—$C_6$alkenyl-, heteroaryl$C_1$—$C_6$alkyl-, or heteroaryl$C_2$—$C_6$alkenyl-;

wherein each $C_1$—$C_6$alkyl, —$C_3$—$C_6$cycloalkyl, heterocyclyl, aryl, heteroaryl, or bridged bicyclic ring, by itself or attached to another moiety, are independently optionally substituted with 1-3 substituents selected from the group consisting of OH, halo, —$NH_2$, $C_1$—$C_6$alkyl, $C_1$—$C_6$alkyl—O—, $R^{12}$O—$C_1$—$C_6$alkyl(O)C—, and $R^{12}$O(O)C—.

23. The compound of claim 19, having a structure of formula (Vj):

(Vj)

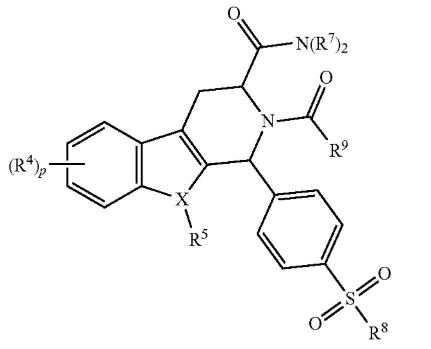

or an enantiomer or pharmaceutically acceptable salt thereof, wherein:

X is N, O, or S;

$R^4$ is independently halo, CN, —$NH_2$, —$SO_2$, $C_1$—$C_8$alkyl, —$OR^{12}$, —$C_1$—$C_6$alkyl-$OR^{12}$, —$C_1$—$C_6$alkyl-$NR^{12}$, or —OC(O)$R^{12}$;

$R^5$ is H, $C_1$—$C_6$alkyl, or is absent when X is S or O;

P is 0, 1, 2, or 3;

each $R^7$ is independently H, $C_1$—$C_6$alkyl, $C_2$—$C_6$alkenyl, $C_3$—$C_6$cycloalkyl, heterocyclyl, aryl, heteroaryl, $C_3$—$C_6$cycloalkyl$C_1$—$C_6$alkyl-, $C_3$—$C_6$cycloalkyl$C_2$—$C_6$alkenyl-, heterocyclyl$C_1$—$C_6$alkyl-, heterocyclyl$C_2$—$C_6$alkenyl-, aryl$C_1$—$C_6$alkyl-, aryl$C_2$—$C_6$alkenyl-, heteroaryl$C_1$—$C_6$alkyl-, heteroaryl$C_2$—$C_6$alkenyl-, $(R^{11})_2$N$C_1$—$C_6$alkyl-, $(R^{11})_2$N$C_2$—$C_6$alkenyl-, $R^{12}$O—$C_1$—$C_6$alkyl-, or $R^{12}$O(O)C—$C_1$—$C_6$alkyl-, or two $R^7$ together with the nitrogen atom to which they are attached form a 4- to 7-membered heterocyclyl, wherein the heterocyclyl formed by the two $R^7$ groups is optionally substituted with OH, halo, $C_1$—$C_6$alkyl, a 4- to 6-membered heterocyclyl, or $(R^{11})_2$N—, wherein the 4- to 6-membered heterocyclyl when containing 2 or more N atoms is optionally substituted with an N-protecting group;

$R^8$ is independently $C_1$—$C_6$alkyl, $C_3$—$C_6$, $C_2$—$C_6$alkenyl, $C_2$—$C_6$alkynyl, $C_3$—$C_6$cycloalkyl, heterocyclyl, aryl, heteroaryl, $C_3$—$C_6$cycloalkyl$C_1$—$C_6$alkyl-, $C_3$—$C_6$cycloalkyl$C_2$—$C_6$alkenyl-, heterocyclyl$C_1$—$C_6$alkyl-, heterocyclyl$C_2$—$C_6$alkenyl-, aryl$C_1$—$C_6$alkyl-, aryl$C_2$—$C_6$alkenyl-, heteroaryl$C_1$—$C_6$alkyl-, heteroaryl$C_2$—$C_6$alkenyl-, adamantyl, adamantyl$C_1$—$C_6$aliphatic-, $(R^{11})_2$N$C_1$—$C_6$alkyl-, or $(R^{11})_2$N-;

$R^9$ is $C_2$alkynyl;

each $R^{11}$ is independently H, $C_1$—$C_6$alkyl, $C_2$—$C_6$alkenyl, $C_3$—$C_6$cycloalkyl, heterocyclyl, aryl, heteroaryl, $C_3$—$C_6$cycloalkyl$C_1$—$C_6$alkyl-, $C_3$—$C_6$cycloalkyl$C_2$—$C_6$alkenyl-, heterocyclyl$C_1$—$C_6$alkyl-, heterocyclyl$C_2$—$C_6$alkenyl-, aryl$C_1$—$C_6$alkyl-, aryl$C_2$—$C_6$alkenyl-, heteroaryl$C_1$—$C_6$alkyl-, heteroaryl$C_2$—$C_6$alkenyl-, adamantyl, adamantyl$C_1$—$C_6$aliphatic-, $R^{12}$O—$C_1$—$C_6$alkyl-, $(R^{11})_2$N$C_1$—$C_6$alkyl-, $(R^{11})_2$N$C_2$—$C_6$alkenyl-, $R^{12}$O(O)C—$C_1$—$C_6$alkyl- , $R^{13}(NH_2)$CH—, $R^{14}C_0$—$C_6$alkyl-, $(R^{15})_3$Si$C_0$—$C_6$alkyl-, or an N-protecting group, or two $R^{11}$ together with the nitrogen atom to which they are attached form a 4- to 7-membered heterocyclyl, wherein the heterocyclyl formed by the two $R^{11}$ groups has optionally 0, 1, or 2 additional heteroatoms selected from nitrogen oxygen, and sulfur, and the heterocyclyl is optionally substituted with OH, halo, $C_1$—$C_6$alkyl, $C_1$—$C_6$alkyl-O(O)C—, $(R^{11})_2$N—, or a 4- to 6-membered heterocyclyl, wherein the 4- to 6-membered heterocyclyl is optionally substituted with OH, halo, —$NH_2$, or $C_1$—$C_6$alkyl, or when containing 2 or more N atoms is optionally substituted with an N-protecting group;

each $R^{12}$ is independently H or $C_1$—$C_6$alkyl;

each $R^{13}$ is independently H, $C_1$—$C_6$alkyl, $C_3$—$C_6$cycloalkyl, heterocyclyl, aryl, heteroaryl, $C_3$—$C_6$cycloalkyl$C_1$—$C_6$alkyl-, $C_3$—$C_6$cycloalkyl$C_2$—$C_6$alkenyl-, heterocyclyl$C_1$—$C_6$alkyl-, heterocyclyl$C_2$—$C_6$alkenyl-, aryl$C_1$—$C_6$alkyl-, aryl$C_2$—$C_6$alkenyl-, heteroaryl$C_1$—$C_6$alkyl-, heteroaryl$C_2$—$C_6$alkenyl—, adamantyl, adamantyl$C_1$—$C_6$aliphatic-, or an N protecting group;

$R^{14}$ is a bridged bicyclic ring having 0-2 heteroatoms independently selected from nitrogen, oxygen, and sulfur; and each $R^{15}$ *is independently* $C_1$—$C_6$alkyl, $C_2$—$C_6$alkenyl, aryl, heteroaryl, aryl$C_1$—$C_6$alkyl-, aryl$C_2$—$C_6$alkenyl-, heteroaryl$C_1$—$C_6$alkyl-, or heteroaryl$C_2$—$C_6$alkenyl-;

wherein each $C_1$—$C_6$alkyl, —$C_3$—$C_6$cycloalkyl, heterocyclyl, aryl, heteroaryl, or bridged bicyclic ring, by itself or attached to another moiety, are independently optionally substituted with 1-3 substituents selected from the group consisting of OH, halo, —$NH_2$, $C_1$—$C_6$alkyl, $C_1$—$C_6$alkyl-O—, $R^{12}$O—$C_1$—$C_6$alkyl(O)C—, and $R^{12}$O(O)C—.

24. The compound of claim 19, having a structure of formula (Vn):

(Vn)

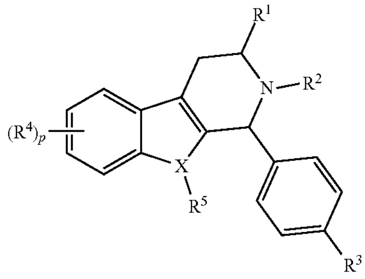

, or an enantiomer or pharmaceutically acceptable salt thereof, wherein:

X is N, O, or S;

$R^1$ is $C_1$—$C_6$alkyl, —$C_1$—$C_6$alkylhalo, or —$C_1$—$C_6$alkyl-$OR^{12}$;

$R^2$ is —C(O)$R^9$;

$R^3$ is —C(O)$OR^{10}$, —C(O)N($R^{11}$)$_2$, —OC(O)$R^{10}$, —$C_0$—$C_6$alkyl$C_3$—$C_8$cycloalkyl, —$C_0$—$C_6$alkylheterocyclyl, —N($R^{11}$)$_2$, —$SO_2R^8$, —$SOR^8$, —$NO_2$, or —Si($R^{15}$)$_3$;

$R^4$ is independently halo, CN, —$NH_2$, —$NH_2$, —$SO_2$, $C_1$—$C_8$alkyl, —$OR^{12}$, —$C_1$—$C_6$alkyl-$OR^{12}$, —$C_1$—$C_6$alkyl-$NR^{12}$, or —OC(O)$R^{12}$;

$R^5$ is H, $C_1$—$C_6$alkyl, or is absent when X is S or O;

p is 0, 1, 2, or 3;

$R^8$ *is independently* $C_1$—$C_6$alkyl, $C_3$—$C_6$alkyl, $C_2$—$C_6$alkenyl, $C_2$—$C_6$alkynyl, $C_3$—$C_6$cycloalkyl, heterocyclyl, aryl, heteroaryl, $C_3$—$C_6$cycloalkyl$C_1$—$C_6$alkyl-, $C_3$—$C_6$cycloalkyl$C_2$—$C_6$alkenyl-, heterocyclyl$C_1$—$C_6$alkyl-, heterocyclyl$C_2$—$C_6$alkenyl-, aryl$C_1$—$C_6$alkyl-, aryl$C_2$—$C_6$alkenyl-, heteroaryl$C_1$—$C_6$alkyl-, heteroaryl$C_2$—$C_6$alkenyl-, adamantyl, adamantyl$C_1$—$C_6$aliphatic-, ($R^{11}$)$_2$N$C_1$—$C_6$alkyl-, ($R^{11}$)$_2$N—, or $R^{14}C_0$—$C_6$alkyl-;

$R^9$ is $C_2$alkynyl;

$R^{10}$ is $C_1$—$C_6$alkyl, $C_2$—$C_6$alkyl, $C_2$—$C_6$alkenyl, $C_2$—$C_6$alkynyl, $C_3$—$C_6$cycloalkyl, heterocyclyl, aryl, heteroaryl, $C_3$—$C_6$cycloalkyl$C_1$—$C_6$alkyl-, $C_3$—$C_6$cycloalkyl$C_2$—$C_6$alkenyl-, heterocyclyl$C_1$—$C_6$alkyl-, heterocyclyl$C_2$—$C_6$alkenyl-, aryl$C_1$—$C_6$alkyl-, aryl$C_2$—$C_6$alkenyl-, heteroaryl$C_1$—$C_6$alkyl-, heteroaryl$C_2$—$C_6$alkenyl-, adamantyl, adamantyl$C_1$—$C_6$aliphatic-, ($R^{11}$)$_2$N$C_1$—$C_6$alkyl-, ($R^{11}$)$_2$N$C_2$—$C_6$alkenyl-, $R^{13}$($NH_2$)CH—, $R^{14}C_0$—$C_6$alkyl-, or ($R^{15}$)$_3$Si$C_0$—$C_6$alkyl-;

each $R^{11}$ is independently H, $C_1$—$C_6$alkyl, $C_2$—$C_6$alkenyl, $C_3$—$C_6$cycloalkyl, heterocyclyl, aryl, heteroaryl, $C_3$—$C_6$cycloalkyl$C_1$—$C_6$alkyl-, $C_3$—$C_6$cycloalkyl$C_3$—$C_6$cycloalkyl$C_2$—$C_6$alkenyl-, heterocyclyl$C_1$—$C_6$alkyl-, heterocyclyl$C_2$—$C_6$alkenyl-, aryl$C_1$—$C_6$alkyl-, aryl$C_2$—$C_6$alkenyl-, heteroaryl$C_1$—$C_6$alkyl-, heteroaryl$C_2$—$C_6$alkenyl-, adamantyl, adamantyl$C_1$—$C_6$aliphatic-, $R^{12}$O—$C_1$—$C_6$alkyl-, ($R^{11}$)$_2$N$C_1$—$C_6$alkyl-, ($R^{11}$)$_2$N$C_2$—$C_6$alkenyl-, $R^{12}$O(O)C—$C_1$—$C_6$alkyl- , $R^{13}$($NH_2$)CH—, $R^{14}C_0$—$C_6$alkyl-, ($R^{15}$)$_3$Si$C_0$—$C_6$alkyl-, or an N-protecting group, or two $R^{11}$ together with the nitrogen atom to which they are attached form a 4- to 7-membered heterocyclyl, wherein the heterocyclyl formed by the two $R^{11}$ groups has optionally 0, 1, or 2 additional heteroatoms selected from nitrogen, oxygen, and sulfur, and the heterocyclyl is optionally substituted with OH, halo, $C_1$—$C_6$alkyl, $C_1$—$C_6$alkyl-O(O)C—, ($R^{11}$)$_2$N—, or a 4- to 6-membered heterocyclyl, wherein the 4- to 6-membered heterocyclyl is optionally substituted with OH, halo, —$NH_2$, or $C_1$—$C_6$alkyl, or when containing 2 or more N atoms is optionally substituted with an N-protecting group;

each $R^{12}$ is independently H or $C_1$—$C_6$alkyl;

each $R^{13}$ *is independently H,* $C_3$—$C_6$alkyl, $C_3$—$C_6$cycloalkyl, heterocyclyl, aryl, heteroaryl, heterocyclyl$C_2$—$C_6$alkenyl-, aryl$C_1$—$C_6$alkyl-, aryl$C_2$—$C_6$alkenyl-, heteroaryl$C_1$—$C_6$alkyl-, heteroaryl$C_2$—$C_6$alkenyl-, adamantyl, adamantyl$C_1$—$C_6$aliphatic-, or an N protecting group;

$R^{14}$ is a bridged bicyclic ring having 0-2 heteroatoms independently selected from nitrogen, oxygen, and sulfur; and each $R^{15}$ is independently $C_1$—$C_6$alkyl, $C_2$—$C_6$alkenyl, aryl, heteroaryl, aryl$C_1$—$C_6$alkyl-, aryl$C_2$—$C_6$alkenyl-, heteroaryl$C_1$—$C_6$alkyl-, or heteroaryl$C_2$—$C_6$alkenyl-;

wherein each $C_1$—$C_6$alkyl, —$C_3$—$C_6$cycloalkyl, heterocyclyl, aryl, heteroaryl, or bridged bicyclic ring, by itself or attached to another moiety, are independently optionally substituted with 1-3 substituents selected from the group consisting of OH, halo, —$NH_2$, $C_1$—$C_6$alkyl, $C_1$—$C_6$alkyl-O—, $R^{12}$O—$C_1$—$C_6$alkyl(O)C—, and $R^{12}$O(O)C—.

25. The compound of claim 19, having a structure of formula (Vp):

(Vp)

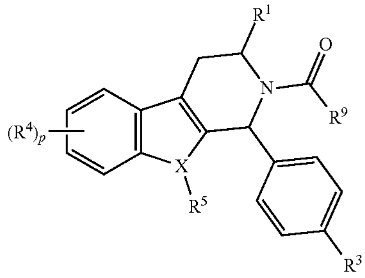

or an enantiomer or pharmaceutically acceptable salt thereof, wherein:

X is N, O, or S;

$R^1$ is $C_1$—$C_6$alkyl, —$C_1$—$C_6$alkylhalo, or —$C_1$—$C_6$alkyl-$OR^{12}$;

$R^3$ is —$C_0$—$C_6$alkyl$C_3$—$C_8$cycloalkyl, or —$C_0$—$C_6$alkylheterocyclyl;

$R^4$ is independently halo, CN, —$NH_2$ , —$SO_2$, $C_1$—$C_8$alkyl, —$OR^{12}$, —$C_1$—$C_6$alkyl-$OR^{12}$, —$C_1$—$C_6$alkyl-$NR^{12}$, or —OC(O)$R^{12}$;

$R^5$ is H, $C_1$—$C_6$alkyl, or is absent when X is S or O;

0, 1, 2, or 3;

$R^9$ is $C_2$alkynyl;

$R^{12}$ independently H or $C_1$—$C_6$alkyl;

wherein each $C_0$—$C_6$alkyl or —$C_3$—$C_8$cycloalkyl are independently optionally substituted with 1-3 substituents selected from the group consisting of OH, halo, —$NH_2$, $C_1$—$C_6$alkyl, $C_1$—$C_6$alkyl-O—, $R^{12}$O—$C_1$—$C_6$alkyl(O)C—, and $R^{12}$O(O)C—.

26. A compound, or a tautomer, stereoisomer, mixture of stereoisomers, isotopically enriched analog, or pharmaceutically acceptable salt thereof, selected from:

Compound 134

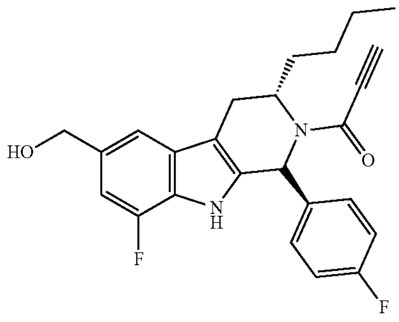

,

-continued
Compound 135
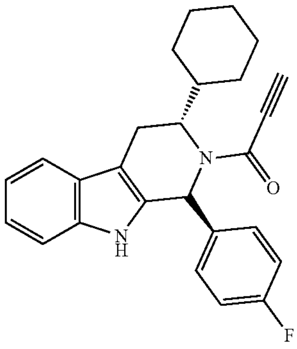
,
Compound 136
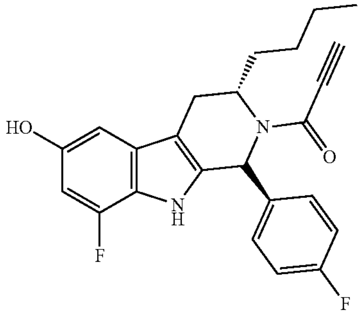
,
Compound 137
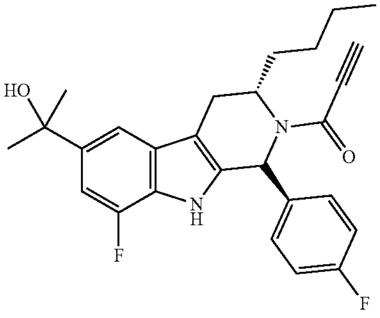
,
Compound 138
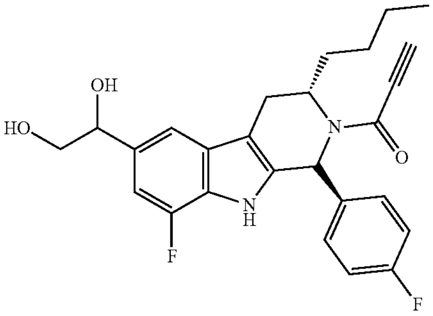
,
-continued
Compound 139
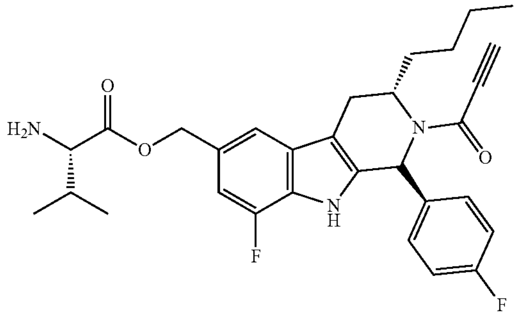
,
Compound 140
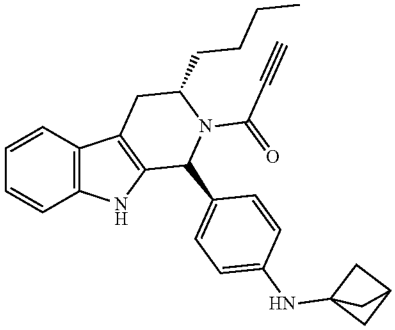
,
Compound 143
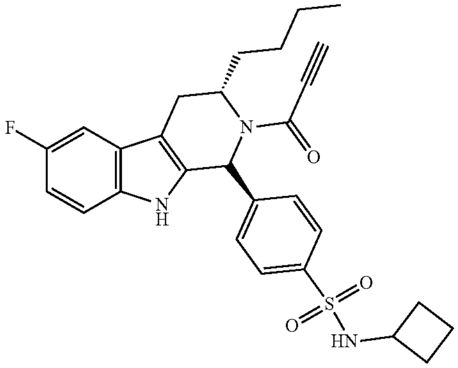
,
Compound 144
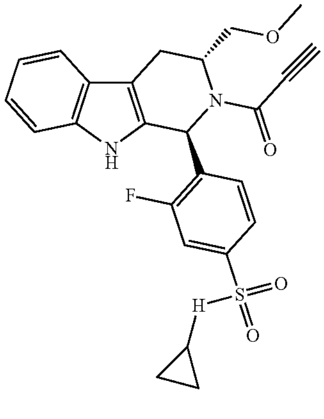
, -continued
Compound 146
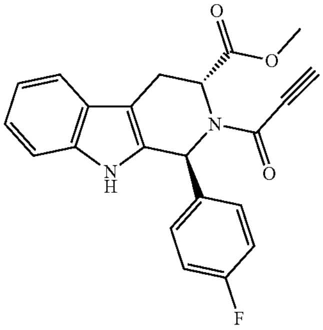
,
Compound 148
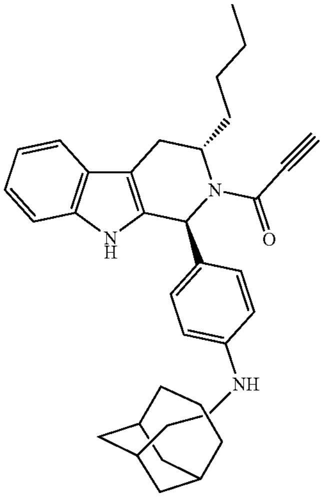
,
Compound 151
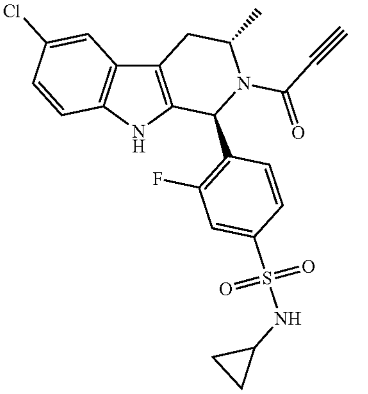
,
Compound 153
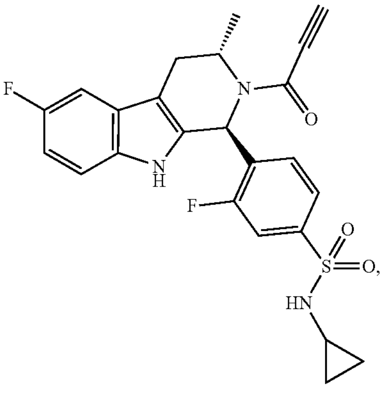
-continued
Compound 154
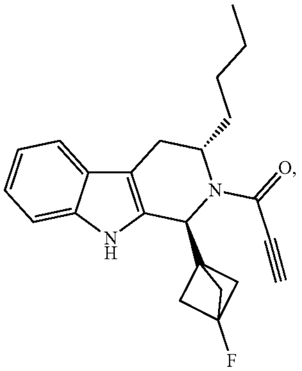
Compound 155
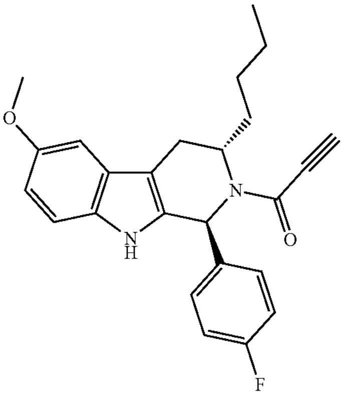
,
Compound 156
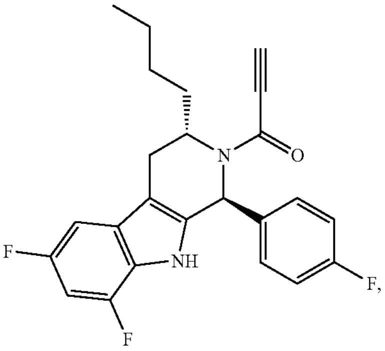
Compound 165
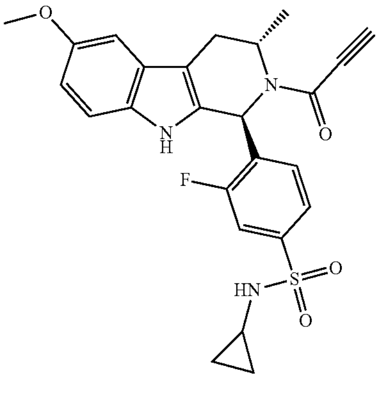
, -continued
Compound 167
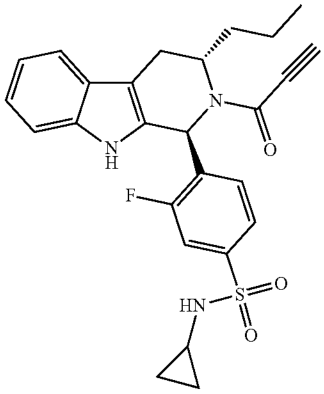
,
Compound 174
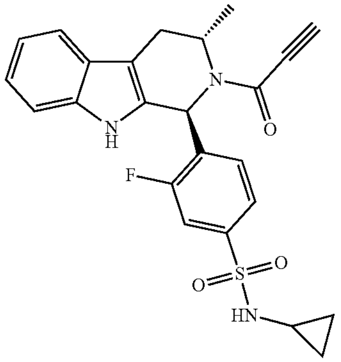
,
Compound 176
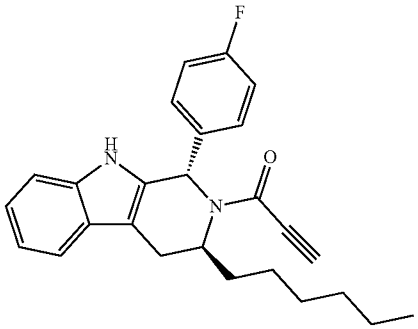
,
Compound 177
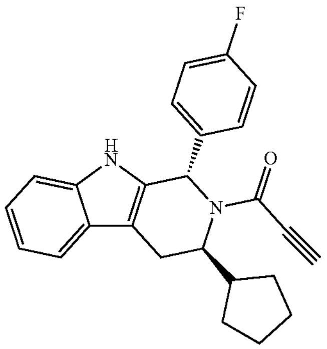
,
Compound 178
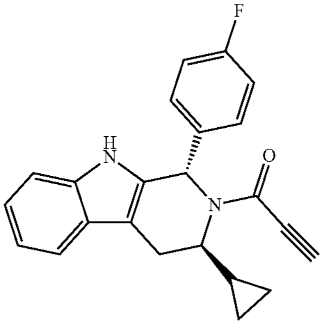
,
Compound 180
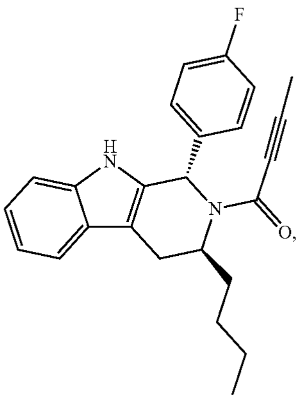
,
Compound 182
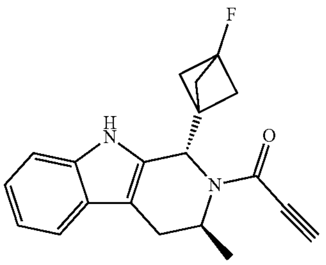
,
Compound 190
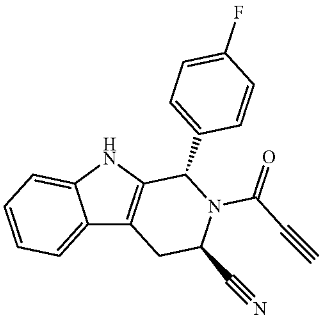
,
Compound 191
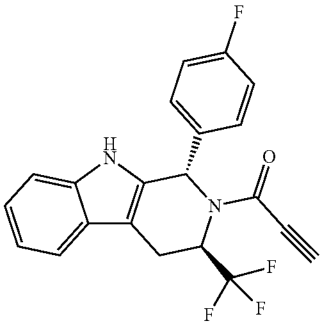
, -continued
Compound 192
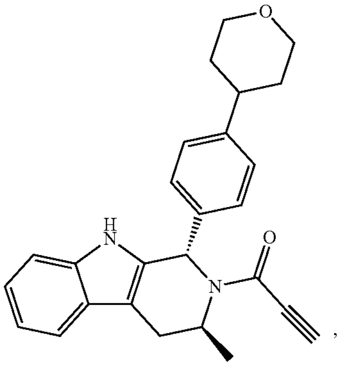
Compound 193
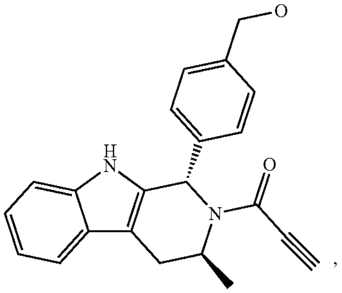
Compound 194
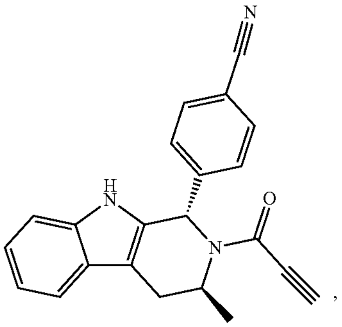
Compound 195
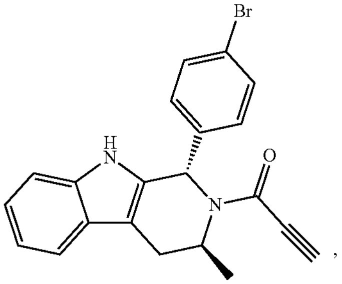
Compound 196
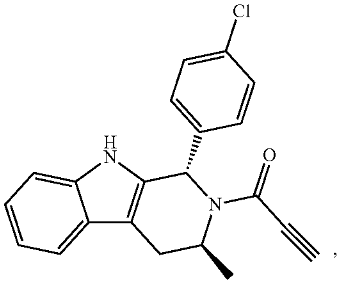
-continued
Compound 197
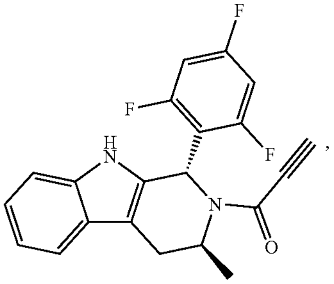
Compound 198
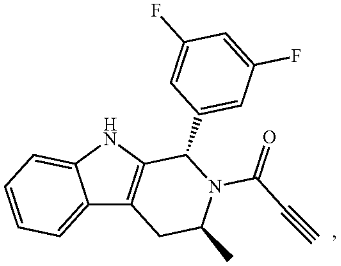
Compound 199
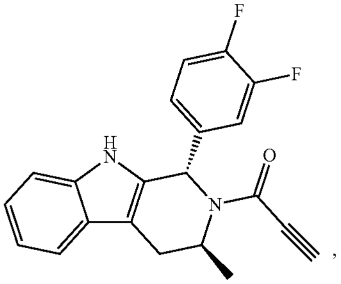
Compound 200
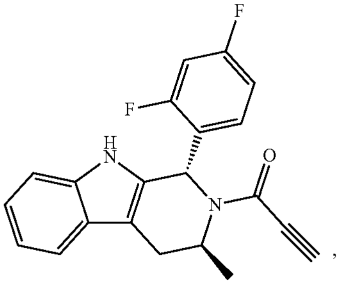
Compound 201
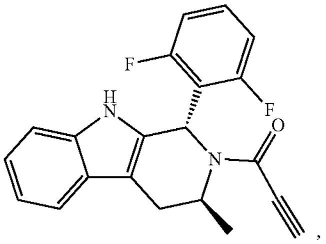

-continued
Compound 202
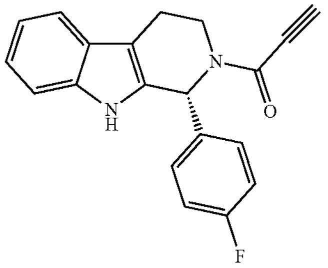
,
Compound 205
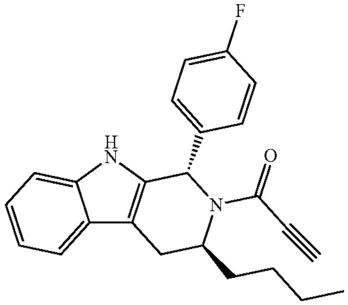
,
Compound 206
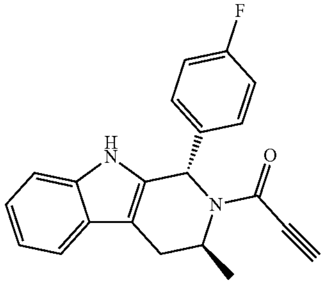
,
Compound 216
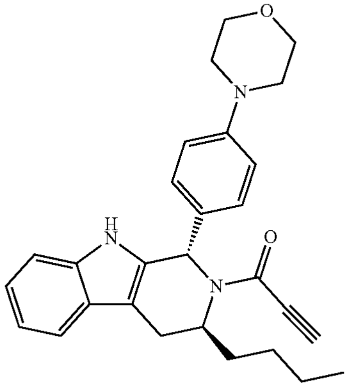
,
Compound 224
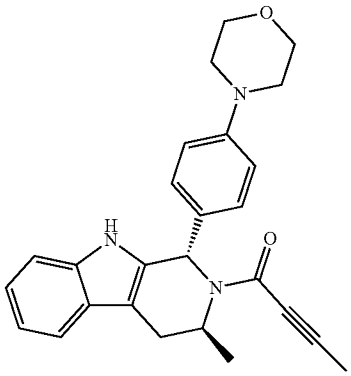
,
-continued
Compound 231
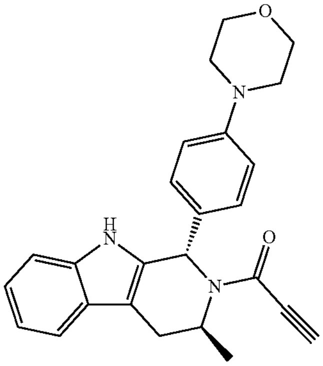
,
Compound 271
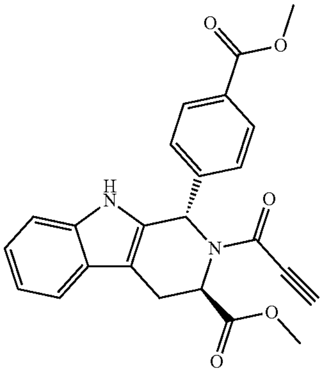
,
Compound 272
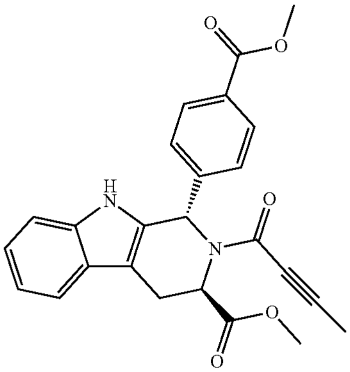
,
Compound 275
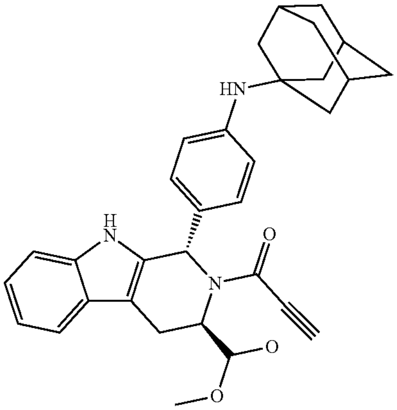
, and -continued
Compound 282
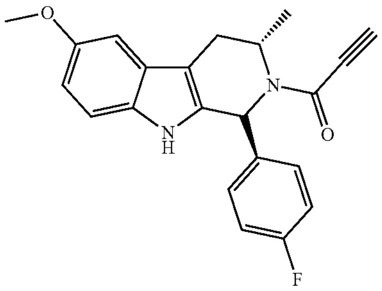
.
* * * * *